(12) United States Patent
　　　Han

(10) Patent No.: US 12,134,631 B2
(45) Date of Patent: Nov. 5, 2024

(54) HYDROPHILIC LINKERS FOR ANTIBODY DRUG CONJUGATES

(71) Applicant: REGENERON PHARMACEUTICALS, INC., Tarrytown, NY (US)

(72) Inventor: Amy Han, Hockessin, DE (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 689 days.

(21) Appl. No.: 16/761,493

(22) PCT Filed: Nov. 6, 2018

(86) PCT No.: PCT/US2018/059495
§ 371 (c)(1),
(2) Date: May 4, 2020

(87) PCT Pub. No.: WO2019/094395
PCT Pub. Date: May 16, 2019

(65) Prior Publication Data
US 2021/0332080 A1　Oct. 28, 2021

Related U.S. Application Data

(63) Continuation-in-part of application No. PCT/US2017/060434, filed on Nov. 7, 2017, and a continuation-in-part of application No. 15/806,197, filed on Nov. 7, 2017, now Pat. No. 10,711,032.

(60) Provisional application No. 62/669,034, filed on May 9, 2018.

(51) Int. Cl.
　　*A61K 31/566* (2006.01)
　　*A61K 31/58* (2006.01)
　　*A61K 47/61* (2017.01)
　　*A61K 47/68* (2017.01)
　　*A61K 47/69* (2017.01)
　　*A61P 29/00* (2006.01)
　　*C07J 41/00* (2006.01)
　　*C07J 71/00* (2006.01)

(52) U.S. Cl.
CPC ......... *C07J 71/0026* (2013.01); *A61K 31/566* (2013.01); *A61K 31/58* (2013.01); *A61K 47/61* (2017.08); *A61K 47/6801* (2017.08); *A61K 47/6803* (2017.08); *A61K 47/6849* (2017.08); *A61K 47/6889* (2017.08); *A61K 47/6951* (2017.08); *A61P 29/00* (2018.01); *C07J 41/005* (2013.01); *C07J 41/0088* (2013.01); *C07J 71/0031* (2013.01)

(58) Field of Classification Search
None
See application file for complete search history.

(56) References Cited

U.S. PATENT DOCUMENTS

| | | | |
|---|---|---|---|
| 2,920,999 | A | 1/1960 | Agnello et al. |
| 3,007,923 | A | 11/1961 | Muller et al. |
| 3,020,275 | A | 2/1962 | Marx et al. |
| 3,033,873 | A | 5/1962 | Pinson et al. |
| 3,033,874 | A | 5/1962 | Pinson et al. |
| 3,047,468 | A | 7/1962 | Origoni et al. |
| 3,197,469 | A | 7/1965 | Fried |
| 3,232,839 | A | 2/1966 | Kieslich et al. |
| 3,383,394 | A | 5/1968 | Weber et al. |
| 3,723,484 | A | 3/1973 | Laurant et al. |
| 3,798,216 | A | 3/1974 | Boissier et al. |
| 3,886,145 | A | 5/1975 | Diamanti |
| 3,928,326 | A | 12/1975 | Brattsand et al. |
| 3,929,768 | A | 12/1975 | Brattsand et al. |
| 4,076,737 | A | 2/1978 | Anner et al. |
| 4,925,933 | A | 5/1990 | Jakupovic et al. |
| 5,116,829 | A | 5/1992 | Hori et al. |
| 5,183,815 | A | 2/1993 | Saari et al. |
| 5,208,020 | A | 5/1993 | Chari et al. |
| 5,500,362 | A | 3/1996 | Robinson et al. |
| 5,714,586 | A | 2/1998 | Kunstmann et al. |
| 5,821,337 | A | 10/1998 | Carter et al. |
| 5,837,698 | A | 11/1998 | Tjoeng et al. |
| 5,908,833 | A | 6/1999 | Brattsand et al. |
| 6,596,541 | B2 | 7/2003 | Murphy et al. |

(Continued)

FOREIGN PATENT DOCUMENTS

| | | |
|---|---|---|
| CN | 1414008 A | 4/2003 |
| CN | 101397328 A | 4/2009 |

(Continued)

OTHER PUBLICATIONS

Lhospice et al (Molecular Pharmaceutics, 12:1863-1871, 2015) (Year: 2015).*

(Continued)

*Primary Examiner* — Craig D Ricci
(74) *Attorney, Agent, or Firm* — SQUIRE PATTON BOGGS (US)

(57) ABSTRACT

Described herein protein drug conjugates and compositions thereof that are useful, for example, for the target-specific delivery of drugs to cells. By administering these compounds, compositions, and conjugates as described herein to specific target cells, side-effects due to non-specific binding phenomena, for example, to non-target cells are reduced. In certain embodiments, compounds, compositions, and conjugates are provided, which include hydrophilic residues in linker-payloads and protein conjugates thereof.

29 Claims, 35 Drawing Sheets

(56) References Cited

U.S. PATENT DOCUMENTS

| | | |
|---|---|---|
| 6,908,934 B2 | 6/2005 | Adams et al. |
| 7,750,116 B1 | 7/2010 | Doronina et al. |
| 8,524,697 B2 | 9/2013 | Anthes et al. |
| 8,703,714 B2 | 4/2014 | Doronina et al. |
| 9,375,473 B2 | 6/2016 | Latov et al. |
| 10,711,032 B2 | 7/2020 | Han et al. |
| 11,129,903 B2 | 9/2021 | Andreev et al. |
| 11,491,237 B2 | 11/2022 | Han et al. |
| 11,578,135 B2 | 2/2023 | Papadopoulos et al. |
| 11,760,775 B2 | 9/2023 | Han et al. |
| 2003/0125357 A1 | 7/2003 | Adams et al. |
| 2003/0199529 A1 | 10/2003 | Garvey et al. |
| 2004/0077595 A1 | 4/2004 | Cheng et al. |
| 2004/0157810 A1 | 8/2004 | Teicher et al. |
| 2004/0192778 A1 | 9/2004 | Jardien et al. |
| 2005/0009798 A1 | 1/2005 | Currie et al. |
| 2005/0192257 A1 | 9/2005 | Peyman |
| 2005/0287155 A1 | 12/2005 | Santi et al. |
| 2006/0046967 A1 | 3/2006 | Satyam |
| 2006/0074008 A1 | 4/2006 | Senter et al. |
| 2007/0258987 A1 | 11/2007 | Francisco et al. |
| 2008/0171040 A1 | 7/2008 | Ebens et al. |
| 2008/0305044 A1 | 12/2008 | McDonagh et al. |
| 2008/0305497 A1 | 12/2008 | Kosmeder et al. |
| 2009/0221543 A1 | 9/2009 | Soldato et al. |
| 2009/0318396 A1 | 12/2009 | Baker et al. |
| 2010/0041633 A1 | 2/2010 | Benedini et al. |
| 2010/0093685 A1 | 4/2010 | Benedini et al. |
| 2010/0129314 A1 | 5/2010 | Singh et al. |
| 2010/0209508 A1 | 8/2010 | Baker et al. |
| 2010/0226987 A1 | 9/2010 | Gnaim et al. |
| 2010/0323973 A1 | 12/2010 | Leamon et al. |
| 2011/0178287 A1 | 7/2011 | Glucksmann et al. |
| 2011/0182828 A1 | 7/2011 | Anthes et al. |
| 2011/0262368 A1 | 10/2011 | Anthes et al. |
| 2012/0058892 A1 | 3/2012 | Braun et al. |
| 2012/0059158 A1 | 3/2012 | Ishii |
| 2012/0096572 A1 | 4/2012 | Macdonald et al. |
| 2012/0258107 A1 | 10/2012 | Graversen et al. |
| 2012/0276193 A1 | 11/2012 | Graversen et al. |
| 2012/0302505 A1 | 11/2012 | Fetzer et al. |
| 2013/0101546 A1 | 4/2013 | Yurkovetskiy et al. |
| 2014/0227294 A1 | 8/2014 | Anderson et al. |
| 2015/0152187 A1 | 6/2015 | Sun et al. |
| 2015/0165064 A1 | 6/2015 | Bregeon et al. |
| 2015/0258203 A1 | 9/2015 | Vlahov et al. |
| 2015/0290337 A1 | 10/2015 | Vetter et al. |
| 2015/0291563 A1 | 10/2015 | Park et al. |
| 2016/0082119 A1 | 3/2016 | Gonzalez et al. |
| 2016/0158369 A1 | 6/2016 | Sato et al. |
| 2016/0279054 A1 | 9/2016 | Rangaramanujam et al. |
| 2016/0310612 A1 | 10/2016 | Lyon et al. |
| 2016/0340445 A1 | 11/2016 | Bouckaert et al. |
| 2017/0182181 A1 | 6/2017 | Garbaccio et al. |
| 2018/0002372 A1 | 1/2018 | Tripathi et al. |
| 2018/0126000 A1 | 5/2018 | Mcpherson et al. |
| 2018/0155389 A1 | 6/2018 | Han et al. |
| 2018/0333504 A1 | 11/2018 | Han et al. |
| 2018/0334426 A1 | 11/2018 | Han et al. |
| 2018/0360979 A1 | 12/2018 | Mejia Oneto et al. |
| 2019/0030171 A1 | 1/2019 | Garbaccio et al. |
| 2019/0134220 A1 | 5/2019 | Godwin |
| 2019/0209702 A1 | 7/2019 | Han |
| 2019/0367631 A1 | 12/2019 | Gromada et al. |
| 2020/0115326 A1 | 4/2020 | Tsuchikama et al. |
| 2020/0368361 A1 | 11/2020 | Nittoli et al. |
| 2021/0040144 A1 | 2/2021 | Han et al. |
| 2023/0079407 A1 | 3/2023 | Gromada et al. |
| 2023/0119539 A1 | 4/2023 | Han |

FOREIGN PATENT DOCUMENTS

| | | |
|---|---|---|
| CN | 103694375 A | 4/2014 |
| CN | 104302664 A | 1/2015 |
| CN | 107849131 A | 3/2018 |
| CN | 108853514 A | 11/2018 |
| CN | 109106951 A | 1/2019 |
| DE | 1165595 B | 3/1964 |
| EP | 1625854 A1 | 2/2006 |
| ES | 544825 A1 | 7/1985 |
| GB | 889766 A | 2/1962 |
| GB | 898295 A | 6/1962 |
| GB | 1428416 | 3/1976 |
| IL | 73337 A | 9/1988 |
| WO | WO 94/22898 A1 | 10/1994 |
| WO | WO 2000/049993 A2 | 8/2000 |
| WO | WO 2002/080931 A1 | 10/2002 |
| WO | WO 2004/017904 A2 | 3/2004 |
| WO | WO 2004/022099 A2 | 3/2004 |
| WO | WO 2005/063777 A1 | 7/2005 |
| WO | WO 2005/079523 A2 | 9/2005 |
| WO | WO 2005/089808 | 9/2005 |
| WO | WO 2005/119266 A1 | 12/2005 |
| WO | WO 2006/135371 A1 | 12/2006 |
| WO | WO 2008/122039 | 10/2008 |
| WO | WO 2008/127347 A1 | 10/2008 |
| WO | WO 2009/085879 A2 | 7/2009 |
| WO | WO 2009/085880 A2 | 7/2009 |
| WO | WO 2010/010119 A1 | 1/2010 |
| WO | WO 2010/010324 | 1/2010 |
| WO | WO 2010/126953 A1 | 11/2010 |
| WO | WO 2010/132743 A1 | 11/2010 |
| WO | WO 2011/018611 A1 | 2/2011 |
| WO | WO 2011/020107 A2 | 2/2011 |
| WO | WO 2011/039511 A2 | 4/2011 |
| WO | WO 2011/081937 A1 | 7/2011 |
| WO | WO 2011/103389 A1 | 8/2011 |
| WO | WO 2011/130598 | 10/2011 |
| WO | WO 2012/011591 A1 | 1/2012 |
| WO | WO 2012/058592 | 5/2012 |
| WO | WO 2012/166559 | 12/2012 |
| WO | WO 2013/053872 | 4/2013 |
| WO | WO 2013/053873 | 4/2013 |
| WO | WO 2013/055990 | 4/2013 |
| WO | WO 2013/055993 | 4/2013 |
| WO | WO 2013/068874 | 5/2013 |
| WO | WO 2013/085925 | 6/2013 |
| WO | WO 2013/093465 A2 | 6/2013 |
| WO | WO 2014/065661 | 5/2014 |
| WO | WO 2014/165119 | 10/2014 |
| WO | WO 2014/197854 | 12/2014 |
| WO | WO 2015/026907 | 2/2015 |
| WO | WO 2015/153401 A1 | 10/2015 |
| WO | WO 2015/155998 A1 | 10/2015 |
| WO | WO 2015/189478 A1 | 12/2015 |
| WO | WO 2016/090038 A1 | 6/2016 |
| WO | WO 2016/090040 A1 | 6/2016 |
| WO | WO 2016/094509 A1 | 6/2016 |
| WO | WO 2016/094517 A1 | 6/2016 |
| WO | WO 2016127081 A1 | 8/2016 |
| WO | WO 2017006279 A1 | 1/2017 |
| WO | WO 2017/062271 A1 | 4/2017 |
| WO | WO 2017/132103 A2 | 8/2017 |
| WO | WO 2017/147542 | 8/2017 |
| WO | WO 2017/165851 A1 | 9/2017 |
| WO | WO 2017/199046 A1 | 11/2017 |
| WO | WO 2017/210471 A1 | 12/2017 |
| WO | WO 2017/214458 A2 | 12/2017 |
| WO | WO 2018/058001 | 3/2018 |
| WO | WO 2018/089373 A2 | 5/2018 |
| WO | WO 2018/160539 A1 | 9/2018 |
| WO | WO 2018/213077 A1 | 11/2018 |
| WO | WO 2018/213082 A1 | 11/2018 |
| WO | WO 2019/094395 A2 | 5/2019 |
| WO | WO 2019/136487 A2 | 7/2019 |
| WO | WO 2019/195665 A1 | 10/2019 |
| WO | WO 2020/146541 A2 | 7/2020 |

OTHER PUBLICATIONS

International Search Report and Written Opinion for PCT Application No. PCT/US2018/059495 dated Jul. 23, 2019, 23 pages.

(56) References Cited

OTHER PUBLICATIONS

Jasbir Singh et al., "Polymer Drug Conjugates: Recent Advancements in Various Diseases", Current Pharmaceutical design, vol. 22, No. 19, May 10, 2016, pp. 2821-2843; XP055490895.

Mark Frigerio et al., "The Chemical Design and Synthesis of Linkers Used in Antibody Drug Conjugates", Current Topics in Medicinal Chemistry, 2017, 17(32), pp. 3393-3424.

Agarwal et al., "Site-Specific Antibody-Drug Conjugates: The Nexus of Bioorthogonal Chemistry, Protein Engineering, and Drug Development", Bioconjugate Chem., 2015, 26, pp. 176-192.

Dai et al., "Regulation of MSR-1 and CD36 in macrophages by LOX-1 mediated through PPAR-γ", Biochemical and Biophysical Research Communications, 431, pp. 496-500, Publication Date: Jan. 16, 2013.

Database Registry [Online] Chemical Abstracts Service Retrieved from STN on Aug. 11, 2020; Compounds with CAS Registry No. of 23640-98-4 (Entered STN: Nov. 16, 1984); 23640-97-3 (Entered STN: Nov. 16, 1984); 6477-56-1 (Entered STN: Nov. 16, 1984); 5514-61-4 (Entered STN: Nov. 16, 1984); 2353-16-4 (Entered STN: Nov. 16, 1984).

Dennler et al., "Antibody Conjugates: From Heterogeneous Populations to Defined Reagents", Antibodies 2015, 4, pp. 197-224; doi:10.3390/antib4030197.

Lemke et al., Foye's Principles of Medicinal Chemistry, Chapter 44, p. 1253, Publication Year: 2008.

Miller-Larsson et al., "Reversible Fatty Acid Conjugation of Budesonide—Novel Mechanism for Prolonged Retention of Topically Applied Steroid in Airway Tissue", Drug Metab. Dispos. 1998, vol. 26, pp. 623-630.

Tunek et al., "Reversible Formation of Fatty Acid Esters of Budesonide, an Antiasthma Glucgcorticoid, In Human Lung and Liver Microsomes", Drug Metab. Dispos. 1997, vol. 25, No. 11, pp. 1311-1317.

CAS Registry No. 803648-23-9; STN Entry Date Dec. 29, 2004; 21-(Diethylamino)-11,17-dihydroxy-(11B)-(9Cl)pregna-1,4-diene-3,20-dione [2] Category: X Claims: 1, 2, 4, 14; SciFinder"®.

Peng, J., et al. "Chemoselective reduction of 21-azidocorticosteroids to primary 21-primary aminocorticoster-oids." Chemical Research In Chinese Universities (2004), 25(5), pp. 866-869. Abstract in English.

Zoltan, T., et al., "Synthesis of biologically active amino and aza steroids and some of their new chemical reactions", Int. Conf. Chem. Biotechnol. Biol. Act. Nat. Prod., 1981, 2, pp. 135-149.

Cannon et al., "The liver X receptor agonist AZ876 protects against pathological cardiac hypertrophy and fibrosis without lipogenic side effects", European Journal of Heart Failure, 2015, vol. 17, pp. 273-282.

Doi et al., "The Histidine Interruption of An α-Helical Coiled Coil Allosterically Mediates A pH-Dependent Ligand Dissociation From Macrophage Scavenger Receptors", The Journal of Biological Chemistry, vol. 269, No. 41, Oct. 14, 1994, pp. 25598-25604.

Mori et al., "Endocytic Pathway of Scavenger Receptors Via Trans-Golgi System In Bovine Alveolar Macrophages", Laboratory Investigation, vol. 71, No. 3, 1994, pp. 409-417.

Diamantis et al., "Antibody-drug conjugates an emerging class of cancer treatment", British Journal Of Cancer, 2016, vol. 114, pp. 362-367; D01:10.1038/bjc.2015.435.

Friedman et al., "The Smart Targeting of Nanoparticles", Current Pharmaceutical Design, 2013, vol. 19, pp. 6315-6329.

Sagar S., et al., Bifidobacterium breve and Lactobacillus rhamnosus treatment is as effective as budesonide at reducing inflammation in a murine model for chronic asthma, Respiratory Research, Apr. 16, 2014, vol. 15, No. 1, article No. 46; Abstract.

Romero-Hernández et al., "Diosgenin-based thio(seleno)ureas and triazolyl glycoconjugates as hybrid drugs, Antioxidant and antiproliferative profile", European Journal of Medicinal Chemistry, May 14, 2015, vol. 99, pp. 67-81.

Jain et al., "Current ADC Linker Chemistry", Pharm Res, 2015, vol. 32, pp. 3526-3540; DOI 10.1007/s11095-015-1657-7.

Tang et al., "One-pot N-glycosylation remodeling of igG with non-natural sialyiglycopeptides enables glycosite-specific and dual-payload antibody—drug conjugates", Org Biomol Chem 14:9501-9518, Oct. 28, 2016.

Williams et al., (Foye's Principles of Medicinal Chemistry, 5th Ed, pp. 59-63, 2002).

Gonzales et al., "Minimizing the Immunogenicity of Antibodies for Clinical Application", Tumor Biol. 2005; vol. 26, pp. 31-43; doi: 10.1159/000084184.

Kunik, Vered et al: "Structural consensus among antibodies defines the antigen binding site", PLoS Comput Biol 8(2): e1002388. https://doi.org/10.1371/journal.pcbi.1002388; Published Feb. 23, 2012.

Kussie et al., "A Single Engineered Amino Acid Substitution Changes Antibody Fine Specificity", Journal of Immunology, 1994, pp. 146-152.

Opalinski et al., "High Affinity Promotes Internalization of Engineered Antibodies Targeting FGFR1", International Journal of Molecular Sciences, 2018, vol. 19, 1435; Published online May 10, 2018. doi: 10.3390/ijms19051435.

Panka et al., "Variable region framework differences result in decreased or increased affinity of variant anti-digoxin antibodies", Proc. Natl. Acad. Sci. USA, vol. 85, May 1988, pp. 3080-30844, Immunology; doi: 10.1073/pnas.85.9.3080.

Rudikoff, Stuart el al., "Single amino acid substitution altering antigen-binding specificity", Proc. Nat. Acad. Sci., USA, vol. 79, Mar. 1982, pp. 1979-1983; DOI: 10.1073/pnas.79.6.1979.

Sela-Culang et al., "The Structural Basis of Antibody-Antigen Recognition", Frontiers in Immunology, vol. 4, article 302, Oct. 2013; doi: 10.3389/fimmu.2013.00302.

Wark et al., "Latest technologies for the enhancement of antibody affinity", Advanced Drug Delivery Reviews, 2006, vol. 58, pp. 657-670; doi:10.1016/j.addr.2006.01.025.

Simons S S JR et al., "Alpha Keto Mesylate: a Reactive Thiol Specific Functional Group", Journal of Organic Chemistry, American Chemical Society, Washington, vol. 45, No. 15, Jan. 1, 1980, pp. 3084-3088.

Agard et al., "A Strain-Promoted [3+2] Azide-Alkyne Cycloaddition for Covalent Modification of Biomolecules in Living Systems", J. Am. Chem. Soc., Nov. 24, 2004, vol. 126, No. 46, pp. 15046-15047.

Agarwal et al., "A Pictet-Spengler ligation for protein chemical modification", PNAS, Jan. 2, 2013, vol. 110, No. 1, pp. 46-51.

Aherne et al., "A sensitive radioimmunoassay for budesonide in plasma", Journal of Steroid Biochemistry, vol. 17, No. 5, Nov. 1982, pp. 559-565.

Angal et al., "A Single Amino Acid Substitution Abolishes the Heterogeneity of Chimeric Mouse/Human (IgG4) Antibody", Molecular Immunology, Jan. 1993, vol. 30, No. 1, pp. 105-108.

Bajaj et al., "Topochemical model for prediction of anti-HIV activity of HEPT analogs", Bioorganic & Medicinal Chemistry Letters, vol. 15, No. 2, Jan. 17, 2005, pp. 467-469.

Baskin et al., "Copper-free click chemistry for dynamic in vivo imaging", PNAS, Oct. 23, 2007, vol. 104, No. 43, pp. 16793-16797.

Beck et al., "Strategies and challenges for the next generation of antibody-drug conjugates", Nature Reviews, Drug Discovery, vol. 16, May 2017, pp. 315-337.

Berge et al., "Pharmaceutical Salts", Review Article, Jan. 1977, vol. 66, No. 1, pp. 1-19.

Berlin M., "Recent advances in the development of novel glucocorticoid receptor modulators", Review, Expert Opinion on Therapeutic Patents (2010) 20(7), pp. 855-873; DOI: 10.1517/13543776.2010. 493876.

Biju et al., "Synthesis of novel anti-inflammatory steroidal macrocycles using ring closing metathesis reaction", Tetrahedron Letters, Jan. 2015, vol. 56, issue 4, pp. 636-638.

Boersma et al., "DARPins and other repeat protein scaffolds: advances in engineering and applications", 2011, Current Opinion in Biotechnology, 2011, vol. 22, pp. 849-857.

Bogan et al., "Liver X Receptor Modulation of Gene Expression Leading to Proluteolytic Effects in Primate Luteal Cells", Biology Of Reproduction, (2012) 86(3):89, pp. 1-9.

(56) References Cited

OTHER PUBLICATIONS

Carrico et al., "Introducing genetically enclosed aldehydes into proteins", Nature Chemical Biology, Jun. 2007, vol. 3, No. 6, pp. 321-322.
CAS Registry Compounds, accessed Jul. 16, 2019; 355 pages.
CAS RN 2341-08-4, 1984 (entered into STN Nov. 16, 1984).
CAS RN 3859-14-1, 1984 (entered into STN Nov. 16, 1984).
CAS RN 57-86-3, 1984 (entered into STN Nov. 16, 1984).
Casati et al., "Unraveling Unidirectional Threading of α-Cyclodextrin in a [2]Rotaxane through Spin Labeling Approach", Journal of the American Chemical Society, Oct. 29, 2012, vol. 134, pp. 19108-19117.
Cho et al., "Regioselective Synthesis of Heterocycles Containing Nitrogen Neighboring an Aromatic Ring by Reductive Ring Expansion Using Diisobutylaluminum Hydride and Studies on the Reaction Mechanism", J. Org. Chem., 2010, vol. 75, pp. 627-636; published online Dec. 29, 2009.
Cho et al., "The first preparation of alpha-functionalized benzylamine", Tetrahedron Letters, vol. 40, 1999, pp. 8215-8217.
Chuu, "Modulation of liver X receptor signaling as a prevention and therapy for colon cancer", Medical Hypotheses, 2011, vol. 76, pp. 697-699.
Clynes et al., "Fc receptors are required in passive and active immunity to melanoma", Proc. Natl. Acad. Sci. USA, Jan. 1998, vol. 95, pp. 652-656.
Compounds from CAS Registry database, accessed May 20, 2019; 16 pages.
Compounds retrieved on Nov. 18, 2017 from SciFinder, Set 1; 4 pages.
Compounds retrieved on Nov. 18, 2017 from SciFinder, Set 2; 1 page.
Compounds retrieved on Nov. 18, 2017 from SciFinder, Set 3; 3 pages.
Czerkies et al., "An interplay between scavenger receptor A and CD14 during activation of J774 cells by high concentrations of LPS", Immunobiology, Apr. 12, 2013, vol. 218, pp. 1217-1226.
Database Registry: Compounds with CAS Registry No. of 23640-98-4; 23640-97-3; 6477-56-1; 5514-61-4; 2353-16-4.
Dennler et al., "Transglutaminase-Based Chemo-Enzymatic Conjugation Approach Yields Homogeneous Antibody-Drug Conjugates", Bioconjugate Chem., Feb. 3, 2014, vol. 25, pp. 569-578.
Doronina et al., "Novel Peptide Linkers for Highly Potent Antibody-Auristatin Conjugate", Bioconjugate Chem., 2008, vol. 19, No. 10, pp. 1960-1963.
Doronina et al., "Development of potent monoclonal antibody auristatin conjugates for cancer therapy", Nature Biotechnology, Jul. 2003, vol. 21, No. 7, pp. 778-941.
Dubois-Camacho et al., "Glucocorticosteroid therapy in inflammatory bowel diseases: From clinical practiceto molecular biology", World J Gastroenterol, Sep. 28, 2017, vol. 23(36), pp. 6628-6638; DOI: 10.3748/wjg.v23.i36.6628.
Fellier et al., "Bindung von Cortisol, Fluocortolon und Difluocortolon a Humanplasmaproteine", J. Clin. Chem. Clin. Biochem., 1977, vol. 15, pp. 545-548.
Ferraboschi et al., "Estimation and characterisation of budesonide tablets impurities", Journal of Pharmaceutical and Biomedical Analysis, 2008, 47(3), pp. 636-640.
Effenberger et al., "Trifluormethansulfonate von [alpha]-Hydroxycarbonsaureestern—Edukte zur racemisierungsfreien Synthese N-substituierter [alpha]-Aminosauren", Angewandte Chemie, vol. 95, No. 1, Jan. 1, 1983, p. 50.
Gidwani et al., "A Comprehensive Review on Cyclodextrin-Based Carriers for Delivery of Chemotherapeutic Cytotoxic Anticancer Drugs", Hindawi Publishing Corporation, BioMed Research International, vol. 2015, article ID 198268,15 pages.
Graversen et al., "Targeting the Hemoglobin Scavenger receptor CD163 in Macrophages Highly Increases the Anti-inflammatory Potency of Dexamethasone", Molecular Therapy, vol. 20, No. 8, Aug. 2012, pp. 1550-1558.
Hamasaki et al., "Fluorescent sensors of molecular recognition. Modified cyclodextrins capable of exhibitingguest-responsive twisted intramolecular charge transfer fluorescence", J. Am. Chem. Soc., Jun. 1993, vol. 115, No. 12, pp. 5035-5040.
Hein et al., "The Synthesis of a Multiblock Osteotropic Polyrotaxane by Copper(I)-Catalyzed Huisgen 1,3-Dipolar Cycloaddition", Macromolecular Bioscience, Dec. 8, 2010, vol. 10, No. 12, pp. 1544-1556.
Hofer et al., "An engineered selenocysteine defines a unique class of antibody derivatives", PNAS, Aug. 26, 2008, vol. 105, No. 34, pp. 12451-12456.
Hollander et al., "Selection of Reaction Additives Used in the Preparetion of Monomeric Antibody-Calicheamicin Conjugates", Bioconjugate Chem., 2008, vol. 19, pp. 358-361; published online Nov. 10, 2007.
Huisgen, "1,3-Dipolar Cycloadditions", Proceedings of the Chemical Society, Oct. 1961, pp. 357-369.
Jain R. A., "The manufacturing techniques of various drug loaded biodegradable poly(lactide-co-glycolide) (PLGA) devices", Biomaterials 21(23), 2000, pp. 2475-2490.
Kapp et al., "Studies on the Pharmacology of 6alpha, 9-difluoro-11beta-hydroxy-16alpha-methyl-21-valeryloxy-1,4-pregnadiene-3,20-dione", Arzneimittel-Forschung Drug Reserch. 1976;26(7b):1463-1475; with an English abstract.
Kern et al., "Discovery of Pyrophosphate Diesters as Tunable, Soluble, and Bioorthogonal Linkers for Site-Specific Antibody-Drug Conjugates", J. Am. Chem. Soc. (JACS), Jan. 25, 2016, vol. 138, No. 4, pp. 1430-1445.
Kern et al., "Novel Phosphate Modified Cathepsin B Linkers: Improving Aqueous Solubility and Enhancing Payload Scope of ADCs", Bioconjugate Chem. Bioconjugate Chem., Jul. 28, 2016, vol. 27, No. 9, pp. 2081-2088.
Kovtun et al., "Antibody-Maytansinoid Conjugates Designed to Bypass Multidrug Resistance", Cancer Research, vol. 70, No. 6, Mar. 15, 2010, pp. 2528-2537.
Krajcsi et al., "Novel Synthesis of 21-Aminopregnanes", J. Chem. Research (S), Nov. 1987, issue 11, pp. 382-383.
Kronkvist et al., "Determination of Drugs in Biosamples at Picomolar Concentrations Using Competitive Elisa With Electrochemical Detection: Application to Steroids", Journal of Pharmaceutical and Biomedical Analysis, vol. 11, No. 6, 1993, pp. 459-463.
Lehar et al., "Novel antibody-antibiotic conjugate eliminates intracellular *S. aureus*", Nature, Nov. 19, 2015, vol. 527, No. 7578, pp. 323-328.
Lhospice et al. "Site-Specific Conjugation of Monomethyl Auristatin E to Anti-CD30 Antibodies Improves Their Pharmacokinetics and Therapeutic Index in Rodent Models", Mol. Pharmaceutics, 2015, vol. 12, pp. 1863-1871.
Lichtenecker R. J., "Synthesis of aromatic $^{13}C/^{2}H$-α-ketoacid precursors to be used in selective phenylalanine and tyrosine protein labelling", Organic & Biomolecular Chemistry, Jul. 31, 2014, vol. 12, pp. 7551-7560.
Lim et al., "Targeted Delivery of LXR Agonist Using a Site-Specific Antibody-Drug Conjugate", Bioconjugate Chemistry, 2015, vol. 26, No. 11, pp. 2216-2222.
Lu et al., "Linkers Having a Crucial Role in Antibody-Drug Conjugates", Int. J. Mol. Sci., Apr. 14, 2016, vol. 17, No. 561, 22 pages.
Lyon et al., Reducing hydrophobicity of homogeneous antibody-drug conjugates improves pharmacokinetics and therapeutic index, Nature Biotechnology, Jul. 2015, vol. 33, No. 7, pp. 733-735.
McCombs et al., "Antibody Drug Conjugates: Design and Selection of Linker, Payload and Conjugation Chemistry", The AAPS Journal, Mar. 2015, vol. 17, No. 2, pp. 339-351.
Muck et al., "High pressure liquid chromatography of some triamcinolone derivatives", Bollettino chimico farmaceutica, Italy, Apr. 1981, 120(4), pp. 240-247; with an English abstract.
Papachristos et al., "Antibody-drug conjugates: a mini-review. The synopsis of two approved medicines", Drug Delivery, 2016, vol. 23, No. 5, pp. 1662-1666; published online Jan. 27, 2015.
Park T. G., "Degradation of poly(lactic-co-glycolic acid) microspheres: effect of copolymer composition", Biomaterials 16(15), 1995, pp. 1123-1130.

(56) References Cited

OTHER PUBLICATIONS

Paul-Clark et al., "Glucocorticoid Receptor Nitration Leads to Enhanced Anti-Inflammatory Effects of Novel Steroid Ligands", The Journal of Immunology, 2003, vol. 171, pp. 3245-3252; doi: 10.4049/jimmunol.171.6.3245.
Pufall "Glucocorticoids and Cancer", Adv Exp Med Biol., 2015, vol. 872, pp. 315-333.
Rabuka et al., "Site-specific chemical protein conjugation using genetically encoded aldehyde tags", Nat Protoc., vol. 7, No. 6, pp. 1052-1067, Dec. 1, 2012, doi:10.1038/nprot.2012.04.
Reggelin et al., "Asymmetric Synthesis of Highly Substituted Azapolycyclic Compounds via 2-Alkenyl Sulfoximines: Potential Scaffolds for Peptide Mimetics", J. American Chemical Society, Mar. 8, 2006, vol. 128, pp. 4023-4034.
Romero-Hernandez et al., "Diosgenin-based thio (seleno) ureas and triazolyl glycoconjugates as hybrid drugs. Antioxidant and antiproliferative profile", European Journal Of Medicinal Chemistry, Editions Scientifique Elsevier, Paris, FR, May 14, 2015, vol. 99, pp. 67-81, XP029222662.
Ryan et al., "Polyclonal Antibody Production Against Chito-Oligosaccharides", Food and Agricultural Immunology, 2001, vol. 13, pp. 127-130.
Samal et al., "The First Synthesis of Water-Soluble Cyclodextrinazafullerenes", Synthetic Communications, 2002, vol. 32, No. 21, pp. 3367-3372.
Samant et al., "Synthesis of 3-hydroxypyrid-2-ones from furfural for treatment against iron overload and iron deficiency", European Journal Of Medicinal Chemistry, vol. 43 , No. 9 , Sep. 1, 2008, pp. 1978-1982.
Sehgal et al., "Desoxymethasone: a new topical corticosteroid", International Journal of Dermatology, Dec. 1976, vol. 15, pp. 770-773; with an English abstract.
Shaunak et al., "Site-specific PEGylation of native disulfide bonds in therapeutic proteins", Nature Chemical Biology, Jun. 2006, vol. 2, No. 6, pp. 312-313.
Jeger, "Site-specific conjugation of tumour-targeting, antibodies using transglutaminase", Ph.D. thesis, 2009, XP055208841, ETH Zurich, CH; 140 pages.
Jeger, "Site-specific conjugation of tumour-targeting, antibodies using transglutaminase", Angew. Chem. Int. Ed. 2010, 49, pp. 9995-9997; DOI: 10.3929/ethz-a-005963273, and supporting Information 46 pages.
Singh et al., "Polymer Drug Conjugates: Recent Advancements in Various Diseases", Current Pharmaceutical Design, May 10, 2016, vol. 22, No. 19, pp. 2821-2843, XP055490895.
Svendsen et al., "Antibody-Directed Glucocorticoid Targeting to CD163 M2-type Macrophages AttenuatesFructose-Induced Liver Inflammatory Changes", Molecular Therapy—Methods & Clinical Develop, vol. 4, Mar. 2017, pp. 50-61.
Taylor et al., "A transgenic mouse that expresses a diversity of human sequence heavy and light chain immunoglobulins", Nucleic Acids Research, 1992, vol. 20, No. 23, pp. 6287-6295.
Thalen et al., "Epimers of budesonide and related corticosteroids. I. Preparative resolution by chromatography on Sephadex LH-20", Acta Pharmaceutica Suecica, 1982, 19(4), pp. 247-266.
Thalen et al., "Synthesis and pharmacological properties of some 16α, 17α-acetals of 16α hydroxyhydrocortisone, 16α-hydroxyprednisolone and fluorinated 16α-hydroxyprednisolones", Acta Pharmaceutica Suecica, 1984, 21(2), pp. 109-124.
Thalen, "Epimers of budesonide and related corticosteroids. II. Structure elucidation by mass spectrometry", Acta Pharmaceutica Suecica, 1982, 19(5), pp. 327-354.
Tian et al., "Inhibition of influenza virus infection by multivalent pentacyclic triterpene-functionalized per-0-methylated cyclodextrin conjugates", European Journal Of Medicinal Chemistry, Editions Scientifique Elsevier, Paris, FR, Apr. 2, 2017, vol. 134, pp. 133-139, XP029995979.
Toth et al., "Amino-derivatives of 11,17,21-Trihydroxy-3,20-Dioxo-1,4-Pregnadiene", Nature 191, Aug. 5, 1961, p. 607.
Tumey et al., "ADME Considerations for the Development of Biopharmaceutical Conjugates Using Cleavable Linkers", Current Topics In Medicinal Chemistry, vol. 17, No. 32, 2017, pp. 3444-3462.
Uekama et al., "$6^A$-O-[(4-Biphenylyl)acetyl]-α-, -β-, and -γ-cyclodextrins and 6 $^A$-Deoxy-6 $^A$-[[(4-biphenylyl)acetyl]amino]- α-, -β-, and -γ-cyclodextrins: Potential Prodrugs for Colon-Specific Delivery", J. Med. Chem., 1997, vol. 40, pp. 2755-2761.
Uhrich et al., "Polymeric Systems for Controlled Drug Release", Chemical Reviews, 1999, vol. 11, pp. 3181-3198.
Vert et al., "Something new in the field of PLA/GA bioresorbable polymers?" Journal of Controlled Release 53, 1998, pp. 85-92.
Wang et al., "Bioconjugation by Copper(I)-Catalyzed Azide-Alkyne [3+2] Cycloaddition", J. Am. Chem. Soc. 2003, vol. 125, pp. 3192-3193.
Wikby et al., "Separation of epimers of budesonide and related corticosteroids by high-performance liquid chromatography. A comparison between straight- and reversed-phase systems", Journal of Chromatography, 1978, 157(1), pp. 65-74.
Wikby et al., "Separation of epimers of budesonide and related corticosteroids by reversed bonded-phase liquid chromatography", Journal of Chromatography, 1978, 157(1), pp. 51-64.
Xiao et al., "Synthesis and biological evaluation of novel pentacyclic triterpene [alpha]—cyclodextrin conjugates as HCV entry inhibitors", European Journal Of Medicinal Chemistry, Nov. 1, 2016, vol. 124, pp. 1-9, XP055490888.
Yano et al., "Preparation of prednisolone-appended [alpha]-, [beta]- and [gamma]-cyclodextrins: Substitution at secondary hydroxyl groups and in vitro hydrolysis behavior", Journal of Pharmaceutical Sciences, American Chemical Society and American Pharmaceutical Association, US, Apr. 1, 2001, vol. 90, No. 4, pp. 493-503.
Besret et al., "Thiocarbamate-Linked Polysulfonate-Peptide Conjugates as Selective Hepatocyte Growth Factor Receptor Binders", dx.doi.org/10.1021/bc500137j | Bioconjugate Chem. 2014, 25, pp. 1000-1010.
Patani et al., "Bioisosterism: A Rational Approach in Drug Design", Chem. Rev. 96, 1996, pp. 3147-3176.
Thalen et al., "6a-Fluoro- and 6a, 9a-difluoro-11b,21-dihydroxy-16a, 17a-propylmethylenedioxypregn-4-ene-3,20-dione: Synthesis and evaluation of activity and kinetics of their C-22 epimers", Steroids, vol. 63, 1998, pp. 37-43.
Makinen et al., "Silencing of either SR-A or CD36 reduces at herosclerosis in hyperlipidaemic mice and reveals reciprocal upregulation of these receptors", Cardiovascular Research, 2010, vol. 88, No. 3, pp. 530-538.
Ozment et al., "Blood Monocyte Scavenger Receptor A (Cd204) Expression Is Increased in Septic Patients", Shock, 2016, vol. 45, No. 6S, p. 129.
Everts et al., "Selective Intracellular Delivery of Dexamethasone into Activated Endothelial Cells Using an E-Selectin-Directed Immunoconjugate", J Immunol (2002) 168 (2): 883-889; https://doi.org/10.4049/jimmunol.168.2.883.
Han et al., "Development of Novel Glucocorticoids for Use in Antibody-Drug Conjugates for the Treatment of Inflammatory Diseases", J. Med. Chem. 2021, 64, pp. 11958-11971.
Pang et al., "Synthesis of an enzyme-dependent prodrug and evaluation of its potential for colon targeting", World J Gastroenterol., Oct. 15, 2002; 8(5): 913-917; doi: 10.3748/wjg.v8.i5.913.
Varshosaz et al. "Synthesis and evaluation of dextran-budesonide conjugates as colon specific prodrugs for treatment of ulcerative colitis", International Journal of Pharmaceutics, Jan. 5, 2009;365(1-2):69-76; doi:10.1016/j.ijpharm.2008.08.034.
Reyna et al., "Targeted Delivery of LXR Agonist Using a Site-Specific Antibody—Drug Conjugate", Bioconjugate Chem. 2015, 26, pp. 2216-2222; DOI: 10.1021/acs.bioconjchem.5b00203.

\* cited by examiner

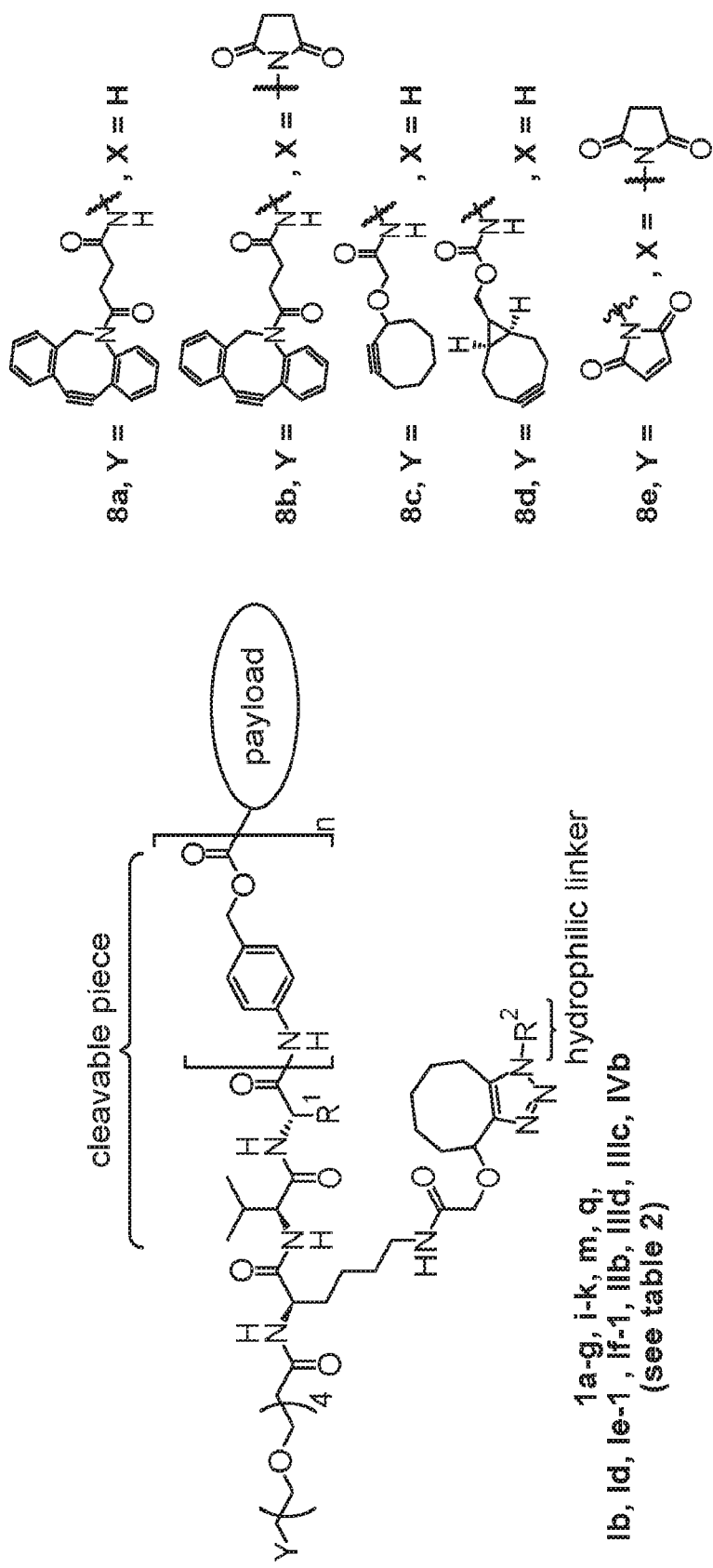
FIG. 2 (Cont. 1)

| Amine 3 | Product 5 | Payload | n | R¹ |
|---|---|---|---|---|
| 3a | 5a | A | 1 | $(CH_2)_3NHCONH_2$ |
| 3b | 5b | B | 1 | $(CH_2)_3NHCONH_2$ |
| 3c | 5c | C | 1 | $(CH_2)_3NHCONH_2$ |
| 3d | 5d | C | 0 | $CH_3$ |
| 3e | 5e | C | 0 | $(CH_2)_3NHCONH_2$ |
| 3f | 5f | D | 0 | $CH_3$ |
| 3g | 5g | E | 0 | $(CH_2)_3NHCONH_2$ |

| Amine 3 | Product 10 | Payload | n | R$^1$ |
|---|---|---|---|---|
| 3a | 10d | A | 1 | (CH$_2$)$_3$NHCONH$_2$ |
| 3b | 10a | B | 1 | (CH$_2$)$_3$NHCONH$_2$ |
| 3c | 10c | C | 1 | (CH$_2$)$_3$NHCONH$_2$ |
| 3f | 10b | D | 0 | CH$_3$ |

| | | | | |
|---|---|---|---|---|
| 5a | 6e | 7ae | A | 1 | (CH$_2$)$_3$NHCONH$_2$ |
| 5b | 6c | 7ba | B | 1 | (CH$_2$)$_3$NHCONH$_2$ |
| 5b | 6b | 7bb | B | 1 | (CH$_2$)$_3$NHCONH$_2$ |
| 5b | 6d | 7f | B | 1 | (CH$_2$)$_3$NHCONH$_2$ |
| 5c | 6c | 7i | C | 1 | (CH$_2$)$_3$NHCONH$_2$ |
| 5d | 6c | 7j | C | 0 | CH$_3$ |
| 5e | 6c | 7k | C | 0 | (CH$_2$)$_3$NHCONH$_2$ |

FIG. 14 (Cont.)

| 5c | 6b | 7cb | C | 1 | (CH₂)₃NHCONH₂ | structure |
|----|----|-----|---|---|---------------|-----------|
| 5f | 6c | 7m  | D | 0 | CH₃ | structure |
| 5f | 6b | 7fb | D | 0 | CH₃ | structure |
| 5g | 6c | 7q  | E | 1 | (CH₂)₃NHCONH₂ | structure |

FIG. 14 (Cont. 1)

| 3 | 7 | Payload | n |
|---|---|---------|---|
| 3b | 7h | B | 1 |
| 3e | 7l | C | 0 |

| Amine 7 | Product 1 | Payload | R² |
|---|---|---|---|
| 7a | 1a | A | ⤳(O)₅OH |

FIG. 17 (Cont.1)

| | A | | 1 | (CH$_2$)$_3$NHCONH$_2$ | |
|---|---|---|---|---|---|
| 7ab | 1b | A | [DBCO-amide] | 1 | (CH$_2$)$_3$NHCONH$_2$ | [triazole-trimethylammonium] |
| 7c | 1c | A | [DBCO-amide] | 1 | (CH$_2$)$_3$NHCONH$_2$ | [triazole-sulfonate] |
| 7ad | 1d | A | [DBCO-amide] | 1 | (CH$_2$)$_3$NHCONH$_2$ | [triazole-phosphonate] |
| 7ae | 1e-1 | A | [DBCO-amide] | 1 | (CH$_2$)$_3$NHCONH$_2$ | [triazole-sugar] |
| 7ae | 1f-1 | A | [maleimide] | 1 | (CH$_2$)$_3$NHCONH$_2$ | [triazole-sugar] |

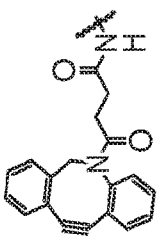
FIG. 17 (Cont.2)

FIG. 17 (Cont.3)

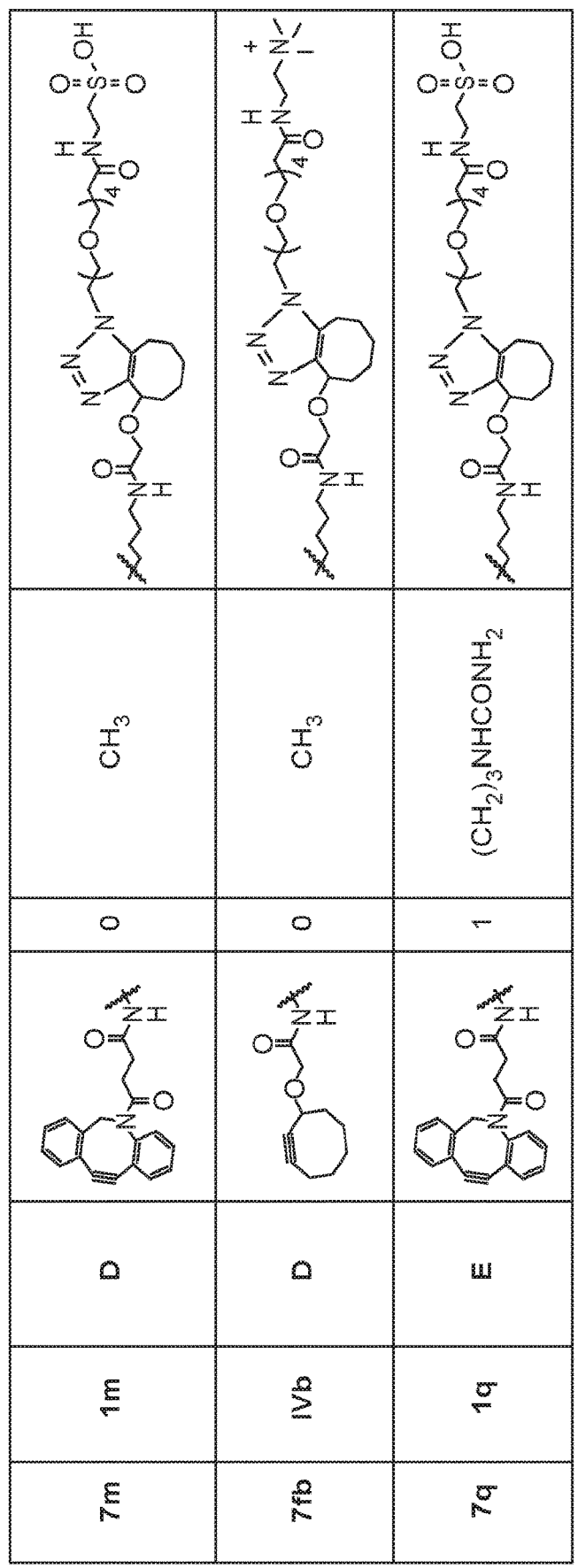
FIG. 17 (Cont.4)

HYDROPHILIC LINKERS FOR ANTIBODY DRUG CONJUGATES

This PCT International application claims the benefit of priority to U.S. Provisional Application No. 62/669,034, filed on May 9, 2018; PCT International Application PCT/US17/60434 (published as WO 2018/089373), filed on Nov. 7, 2017; and U.S. Nonprovisional application Ser. No. 15/806,197 (published as US 2018/0155389), filed on Nov. 7, 2017; the content of all said applications is incorporated herein by reference in its entirety for all purposes.

FIELD

Provided herein are novel protein, e.g., antibody, drug conjugates comprising hydrophilic solubilizing groups and/or linkers comprising hydrophilic solubilizing groups, and methods for treating diseases, disorders, and conditions comprising administering the protein drug conjugates comprising hydrophilic solubilizing groups and/or linkers thereof.

BACKGROUND

Antibody-drug conjugates (ADCs) are antibodies that are conjugated to a biologically active small molecule. ADCs deliver a potent drug selectively to target-expressing cells, leading to a potential reduction of off-target side effects and/or toxicity and improved therapeutic index. The lipophilic nature of many payloads (i.e., drugs) can adversely affect the properties of the ADC to the extent that the payloads are not efficiently delivered to the target cells. Low bioavailability of lipophilic payloads can narrow therapeutic windows for ADC treatment. Furthermore, the hydropobic nature of payloads can present challenges to their conjugation to antibodies, a reaction performed in aqueous conditions. Thus there is an ongoing need for development of hydrophilic linkers for protein conjugates, e.g., ADCs, which would allow for the feasibility of conjugating lipophilc payloads, improved modulation of biological targets, improved bioavailability, and improved therapeutic window.

SUMMARY

Provided herein are compounds useful, for example, for the treatment of diseases, conditions, and disorders including, without limitation, metabolic diseases, proliferative diseases, and other diseases and conditions.

In one embodiment, set forth herein, is a compound or a pharmaceutically acceptable salt thereof, including: a protein binding agent linked to at least one payload moiety and linked to at least one hydrophilic moiety via a covalent linker, wherein said covalent linker is bonded directly or indirectly to each of the binding agent, the payload moiety, and the hydrophilic moiety.

In another embodiment, set forth herein, is a compound, including: a reactive group linked to at least one payload moiety and linked to at least one hydrophilic moiety via a covalent linker, wherein said covalent linker is bonded directly or indirectly to each of the reactive group, the payload moiety, and the hydrophilic moiety.

In another embodiment, set forth herein is an antibody-drug conjugate having a compound, described above and herein, bonded to an antibody or an antigen binding fragment thereof.

In another embodiment, set forth herein is a method of treating a disease, condition, or disorder in a patient in need thereof including administering to the patient a compound set forth herein. Also provided is the use of a compound set forth herein for treating a disease, condition, or disorder set forth herein. Further provided is the use of a compound set forth herein for the manufacture of a medicament for treating a disease, condition, or disorder set forth herein. In some embodiments, the compound is an antibody-drug conjugate.

In another embodiment, set forth herein is a method of preparing an antibody-drug conjugate including the step of contacting a binding agent with a linker-payload compound set forth herein under conditions suitable for forming a bond between the binding agent and the linker-payload compound.

BRIEF DESCRIPTIONS OF THE DRAWINGS

FIG. 9 shows a synthetic process for preparation of intermediate 4a.

FIG. 11A shows a synthetic process for preparation of intermediate 10a.

FIG. 16 shows a general synthetic procedure G for preparing compound 1a.

DETAILED DESCRIPTION

Figure 1:
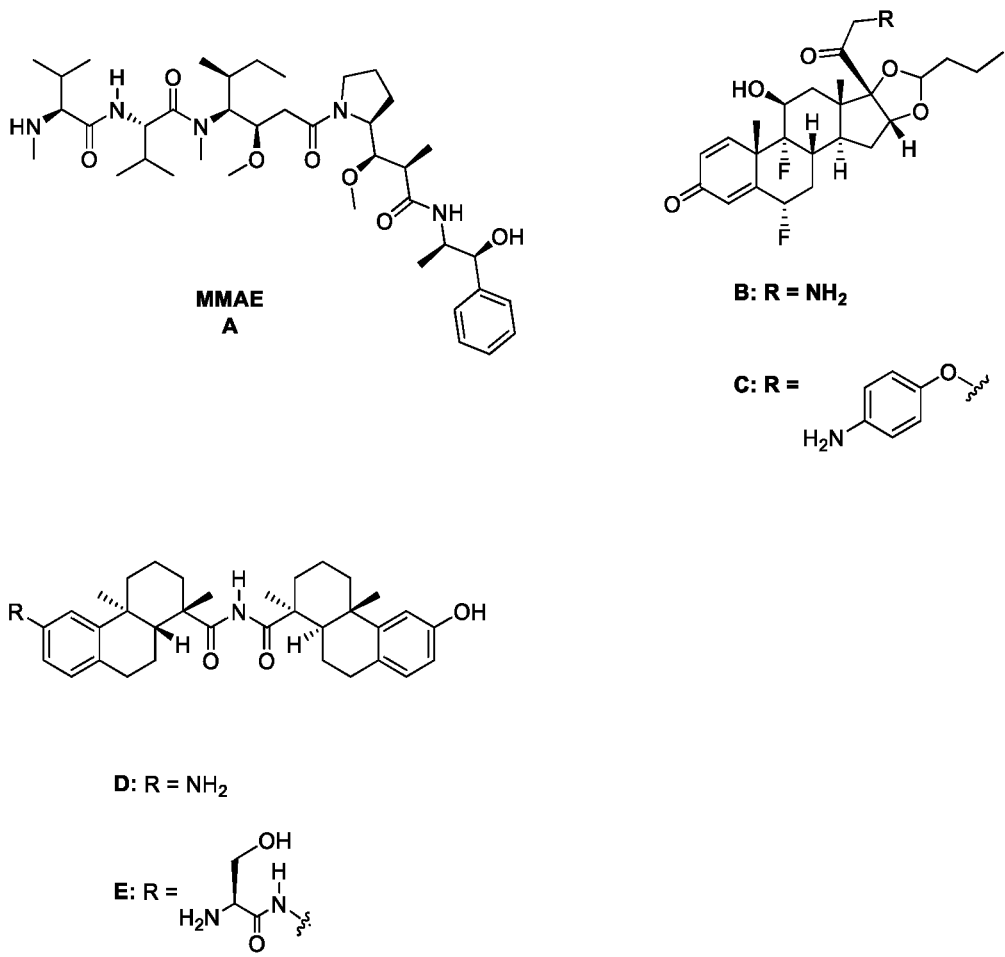
FIG. 1 shows three different types of payload compounds.

Provided herein are compounds, compositions, and methods useful for treating, for example, dyslipidemia, a metabolic disease, inflammation, or a neurodegenerative disease, in a subject.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term provided herein, these Definitions prevail unless stated otherwise.

As used herein, "alkyl" refers to a monovalent and saturated hydrocarbon radical moiety. Alkyl is optionally substituted and can be linear, branched, or cyclic, i.e., cycloalkyl. Alkyl includes, but is not limited to, those radicals having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to methyl, ethyl, n-propyl, i-propyl, n-butyl, s-butyl, t-butyl, i-butyl, a pentyl moiety, a hexyl moiety, cyclopropyl, cyclobutyl, cyclopentyl, and cyclohexyl. A pentyl moiety includes, but is not limited to, n-pentyl and i-pentyl. A hexyl moiety includes, but is not limited to, n-hexyl.

As used herein, "alkylene" refers to a divalent alkyl group. Unless specified otherwise, alkylene includes, but is not limited to, 1-20 carbon atoms. The alkylene group is optionally substituted as described herein for alkyl. In some embodiments, alkylene is unsubstituted.

Designation of an amino acid or amino acid residue without specifying its stereochemistry is intended to encompass the L form of the amino acid, the D form of the amino acid, or a racemic mixture thereof.

As used herein, "haloalkyl" refers to alkyl, as defined above, wherein the alkyl includes at least one substituent selected from a halogen, for example, fluorine (F), chlorine (Cl), bromine (Br), or iodine (I). Examples of haloalkyl include, but are not limited to, —$CF_3$, —$CH_2CF_3$, —$CCl_2F$, and —$CCl_3$.

As used herein, "alkenyl" refers to a monovalent hydrocarbon radical moiety containing at least two carbon atoms and one or more non-aromatic carbon-carbon double bonds. Alkenyl is optionally substituted and can be linear, branched, or cyclic. Alkenyl includes, but is not limited to, those radicals having 2-20 carbon atoms, i.e., $C_{2-20}$ alkenyl; 2-12 carbon atoms, i.e., $C_{2-12}$ alkenyl; 2-8 carbon atoms, i.e., $C_{2-8}$ alkenyl; 2-6 carbon atoms, i.e., $C_{2-6}$ alkenyl; and 2-4 carbon atoms, i.e., $C_{2-4}$ alkenyl. Examples of alkenyl moieties include, but are not limited to vinyl, propenyl, butenyl, and cyclohexenyl.

As used herein, "alkynyl" refers to a monovalent hydrocarbon radical moiety containing at least two carbon atoms and one or more carbon-carbon triple bonds. Alkynyl is optionally substituted and can be linear, branched, or cyclic. Alkynyl includes, but is not limited to, those radicals having 2-20 carbon atoms, i.e., $C_{2-20}$ alkynyl; 2-12 carbon atoms, i.e., $C_{2-12}$ alkynyl; 2-8 carbon atoms, i.e., $C_{2-8}$ alkynyl; 2-6 carbon atoms, i.e., $C_{2-6}$ alkynyl; and 2-4 carbon atoms, i.e., $C_{2-4}$ alkynyl. Examples of alkynyl moieties include, but are not limited to ethynyl, propynyl, and butynyl.

As used herein, "alkoxy" refers to a monovalent and saturated hydrocarbon radical moiety wherein the hydrocarbon includes a single bond to an oxygen atom and wherein the radical is localized on the oxygen atom, e.g., $CH_3CH_2$—O· for ethoxy. Alkoxy substituents bond to the compound which they substitute through this oxygen atom of the alkoxy substituent. Alkoxy is optionally substituted and can be linear, branched, or cyclic, i.e., cycloalkoxy. Alkoxy includes, but is not limited to, those having 1-20 carbon atoms, i.e., $C_{1-20}$ alkoxy; 1-12 carbon atoms, i.e., $C_{1-12}$ alkoxy; 1-8 carbon atoms, i.e., $C_{1-8}$ alkoxy; 1-6 carbon atoms, i.e., $C_{1-6}$ alkoxy; and 1-3 carbon atoms, i.e., $C_{1-3}$ alkoxy. Examples of alkoxy moieties include, but are not limited to methoxy, ethoxy, n-propoxy, i-propoxy, n-butoxy, s-butoxy, t-butoxy, i-butoxy, a pentoxy moiety, a hexoxy moiety, cyclopropoxy, cyclobutoxy, cyclopentoxy, and cyclohexoxy.

As used herein, "haloalkoxy" refers to alkoxy, as defined above, wherein the alkoxy includes at least one substituent selected from a halogen, e.g., F, Cl, Br, or I.

As used herein, "aryl" refers to a monovalent moiety that is a radical of an aromatic compound wherein the ring atoms are carbon atoms. Aryl is optionally substituted and can be monocyclic or polycyclic, e.g., bicyclic or tricyclic. Examples of aryl moieties include, but are not limited to, those having 6 to 20 ring carbon atoms, i.e., $C_{6-20}$ aryl; 6 to 15 ring carbon atoms, i.e., $C_{6-15}$ aryl, and 6 to 10 ring carbon atoms, i.e., $C_{6-10}$ aryl. Examples of aryl moieties include, but are not limited to phenyl, naphthyl, fluorenyl, azulenyl, anthryl, phenanthryl, and pyrenyl.

As used herein, "arylalkyl" refers to a monovalent moiety that is a radical of an alkyl compound, wherein the alkyl compound is substituted with an aromatic substituent, i.e., the aromatic compound includes a single bond to an alkyl group and wherein the radical is localized on the alkyl group. An arylalkyl group bonds to the illustrated chemical structure via the alkyl group. An arylalkyl can be represented by the structure, e.g.,

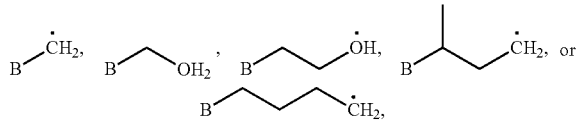

wherein B is an aromatic moiety, e.g., phenyl. Arylalkyl is optionally substituted, i.e., the aryl group and/or the alkyl group, can be substituted as disclosed herein. Examples of arylalkyl include, but are not limited to, benzyl.

As used herein, "alkylaryl" refers to a monovalent moiety that is a radical of an aryl compound, wherein the aryl compound is substituted with an alkyl substituent, i.e., the aryl compound includes a single bond to an alkyl group and wherein the radical is localized on the aryl group. An alkylaryl group bonds to the illustrated chemical structure via the aryl group.

An alkylaryl can be represented by the structure, e.g.,

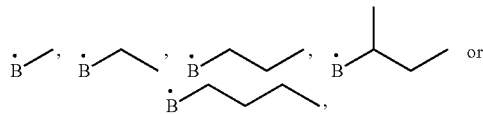

wherein B is an aromatic moiety, e.g., phenyl. Alkylaryl is optionally substituted, i.e., the aryl group and/or the alkyl group, can be substituted as disclosed herein. Examples of alkylaryl include, but are not limited to, toluyl.

As used herein, "aryloxy" refers to a monovalent moiety that is a radical of an aromatic compound wherein the ring atoms are carbon atoms and wherein the ring is substituted with an oxygen radical, i.e., the aromatic compound includes a single bond to an oxygen atom and wherein the radical is localized on the oxygen atom, e.g

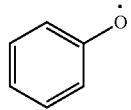

for phenoxy. Aryloxy substituents bond to the compound which they substitute through this oxygen atom. Aryloxy is optionally substituted. Aryloxy includes, but is not limited to, those radicals having 6 to 20 ring carbon atoms, i.e., $C_{6-20}$ aryloxy; 6 to 15 ring carbon atoms, i.e., $C_{6-15}$ aryloxy, and 6 to 10 ring carbon atoms, i.e., $C_{6-10}$ aryloxy. Examples of aryloxy moieties include, but are not limited to phenoxy, naphthoxy, and anthroxy.

As used herein, "$R^aR^bN$-aryloxy" refers to a monovalent moiety that is a radical of an aromatic compound wherein the ring atoms are carbon atoms and wherein the ring is substituted with at least one $R^aR^b$N-substituent and at least one oxygen radical, i.e., the aromatic compound includes a single bond to an $R^aR^b$N-substituent and a single bond to an oxygen atom and wherein the radical is localized on the oxygen atom, e.g.,

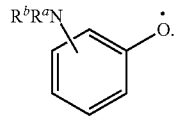

$R^aR^b$N-aryloxy substituents bond to the compound which they substitute through this oxygen atom. $R^aR^b$N-aryloxy is optionally substituted. $R^aR^b$N-aryloxy includes, but is not limited to, those having 6 to 20 ring carbon atoms, for example, $C_{6-20}$ ($R^aR^b$N)n-aryloxy, 6 to 15 ring carbon atoms, for example, $C_{6-15}$ ($R^aR^b$N)n-aryloxy, and 6 to 10 ring carbon atoms, for example, $C_{6-10}$ ($R^aR^b$N)n-aryloxy, wherein n represents the number of $R^aR^b$N-substituents. An example of an $R^aR^b$N-aryloxy moiety includes, but is not limited to 4-(dimethylamino)-phenoxy,

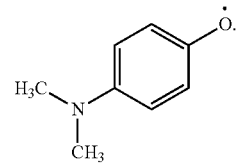

As used herein, "arylene" refers to a divalent moiety of an aromatic compound wherein the ring atoms are only carbon atoms. Arylene is optionally substituted and can be monocyclic or polycyclic, e.g., bicyclic or tricyclic. Examples of arylene moieties include, but are not limited to those having 6 to 20 ring carbon atoms, i.e., $C_{6-20}$ arylene; 6 to 15 ring carbon atoms, i.e., $C_{6-15}$ arylene, and 6 to 10 ring carbon atoms, i.e., $C_{6-10}$ arylene.

As used herein, "heteroalkyl" refers to an alkyl in which one or more carbon atoms are replaced by heteroatoms. As used herein, "heteroalkenyl" refers to an alkenyl in which one or more carbon atoms are replaced by heteroatoms. As used herein, "heteroalkynyl" refers to an alkynyl in which one or more carbon atoms are replaced by heteroatoms. Suitable heteroatoms include, but are not limited to, nitrogen, oxygen, and sulfur atoms. Heteroalkyl is optionally substituted. Examples of heteroalkyl moieties include, but are not limited to, aminoalkyl, sulfonylalkyl, and sulfinylalkyl. Examples of heteroalkyl moieties also include, but are not limited to, methylamino, methylsulfonyl, and methylsulfinyl.

As used herein, "heteroaryl" refers to a monovalent moiety that is a radical of an aromatic compound wherein the ring atoms contain carbon atoms and at least one oxygen, sulfur, nitrogen, or phosphorus atom. Examples of heteroaryl moieties include, but are not limited to those having 5 to 20 ring atoms; 5 to 15 ring atoms; and 5 to 10 ring atoms. Heteroaryl is optionally substituted.

As used herein, "heteroarylene" refers to an arylene in which one or more ring atoms of the aromatic ring are replaced with an oxygen, sulfur, nitrogen, or phosphorus atom. Heteroarylene is optionally substituted.

As used herein, "heterocycloalkyl" refers to a cycloalkyl in which one or more carbon atoms are replaced by heteroatoms. Suitable heteroatoms include, but are not limited to, nitrogen, oxygen, and sulfur atoms. Heterocycloalkyl is optionally substituted. Examples of heterocycloalkyl moieties include, but are not limited to, morpholinyl, piperidinyl, tetrahydropyranyl, pyrrolidinyl, imidazolidinyl, oxazolidinyl, thiazolidinyl, dioxolanyl, dithiolanyl, oxanyl, or thianyl.

As used herein, "N-containing heterocycloalkyl," refers to a cycloalkyl in which one or more carbon atoms are replaced by heteroatoms and wherein at least one heteroatom is a nitrogen atom. Suitable heteroatoms in addition to nitrogen, include, but are not limited to oxygen and sulfur atoms. N-containing heterocycloalkyl is optionally substituted. Examples of N-containing heterocycloalkyl moieties include, but are not limited to, morpholinyl, piperidinyl, pyrrolidinyl, imidazolidinyl, oxazolidinyl, or thiazolidinyl.

As used herein, "optionally substituted," when used to describe a radical moiety, for example, optionally substituted alkyl, means that such moiety is optionally bonded to one or more substituents. Examples of such substituents include, but are not limited to, halo, cyano, nitro, optionally substituted haloalkyl, azido, epoxy, optionally substituted heteroaryl, optionally substituted heterocycloalkyl,

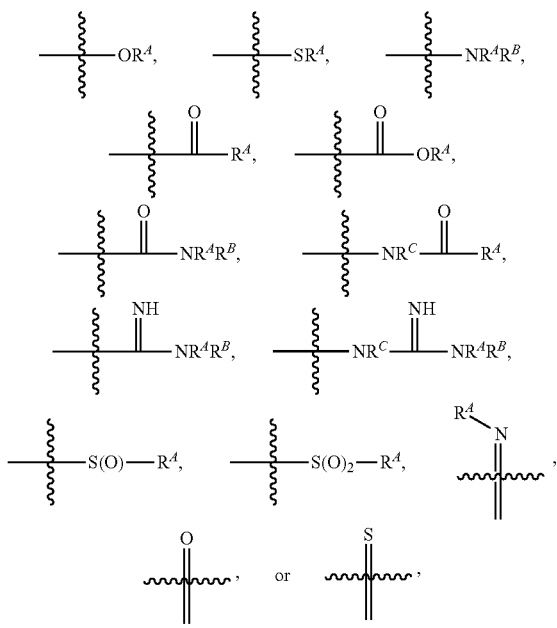

wherein $R^A$, $R^B$, and $R^C$ are, independently at each occurrence, a hydrogen atom, alkyl, alkenyl, alkynyl, aryl, alkylaryl, arylalkyl, heteroalkyl, heteroaryl, or heterocycloalkyl, or $R^A$ and $R^B$ together with the atoms to which they are bonded, form a saturated or unsaturated carbocyclic ring, wherein the ring is optionally substituted, and wherein one or more ring atoms is optionally replaced with a heteroatom. In certain embodiments, when a radical moiety is optionally substituted with an optionally substituted heteroaryl, optionally substituted heterocycloalkyl, or optionally substituted saturated or unsaturated carbocyclic ring, the substituents on the optionally substituted heteroaryl, optionally substituted heterocycloalkyl, or optionally substituted saturated or unsaturated carbocyclic ring, if they are substituted, are not substituted with substituents which are further optionally substituted with additional substituents. In some embodiments, when a group described herein is optionally substituted, the substituent bonded to the group is unsubstituted unless otherwise specified.

As used herein, "binding agent" refers to any molecule, e.g., protein, capable of binding with specificity to a given binding partner, e.g., antigen.

As used herein, "linker" refers to a divalent, trivalent, or multivalent moiety that covalently links the binding agent to one or more compounds described herein, for instance payload compounds and a hydrophilic group, as described herein.

As used herein, "amide synthesis conditions" refers to reaction conditions suitable to effect the formation of an amide, e.g., by the reaction of a carboxylic acid, activated carboxylic acid, or acyl halide with an amine. In some examples, amide synthesis conditions refer to reaction conditions suitable to effect the formation of an amide bond between a carboxylic acid and an amine. In some of these examples, the carboxylic acid is first converted to an activated carboxylic acid before the activated carboxylic acid reacts with an amine to form an amide. Suitable conditions to effect the formation of an amide include, but are not limited to, those utilizing reagents to effect the reaction between a carboxylic acid and an amine, including, but not limited to, dicyclohexylcarbodiimide (DCC), diisopropylcarbodiimide (DIC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-azabenzotriazol-1-yloxy) tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[Bis(dimethylamino)methylene]-1H-1,2,3-triazolo[4,5-b]pyridinium 3-oxid hexafluorophosphate (HATU), N-ethoxycarbonyl-2-ethoxy-1,2-dihydroquinoline (EEDQ), N-ethyl-N'-(3-dimethylaminopropyl)carbodiimide (EDC), 2-chloro-1,3-dimethylimidazolidinium hexafluorophosphate (CIP), 2-chloro-4,6-dimethoxy-1,3,5-triazine (CDMT), and carbonyldiimidazole (CDI). In some examples, a carboxylic acid is first converted to an activated carboxylic ester before treating the activated carboxylic ester with an amine to form an amide bond. In certain embodiments, the carboxylic acid is treated with a reagent. The reagent activates the carboxylic acid by deprotonating the carboxylic acid and then forming a product complex with the deprotonated carboxylic acid as a result of nucleophilic attack by the deprotonated carboxylic acid onto the protonated reagent. The activated carboxylic esters for certain carboxylic acids are subsequently more susceptible to nucleophilic attack by an amine than the carboxylic acid is before it is activated. This results in amide bond formation. As such, the carboxylic acid is described as activated. Exemplary reagents include DCC and DIC.

As used herein, "taurine" refers to the reagent

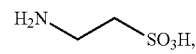

or the group

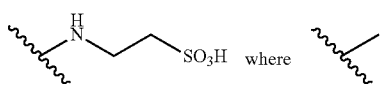

where indicates the atom through which the taurine is bonded to the adjacent groups in the formula. As used herein, "dualtaurine" refers to the group

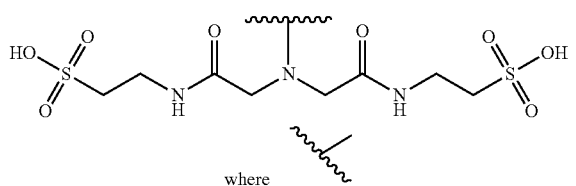

where 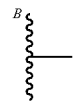 indicates the atom through which the dualtaurine is bonded to the adjacent groups in the formula.

As used herein, "stereoisomeric form" refers to the relative spatial orientation of different groups in a compound. Stereoisomeric forms include enantiomers, diasteromers, and/or mixtures thereof.

As used herein, "regioisomer," "regioisomers," or "mixture of regioisomers" refers to the product(s) of 1,3-cycloadditions or strain-promoted alkyne-azide cycloadditions (SPAACs)—otherwise known as click reactions—that derive from suitable azides (e.g., —$N_3$, or PEG-$N_3$ derivatized antibodies) treated with suitable alkynes. In certain embodiments, for example, regioisomers and mixtures of regioisomers are characterized by the click reaction products shown below:

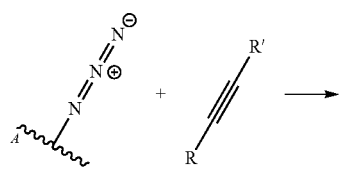

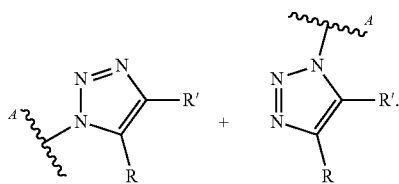

By way of example only, regioisomers of compound A1', i.e., compounds A2', A3', A4', are shown below, wherein each

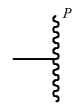

is a bond to the binding agent; and each

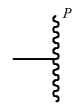

is a bond to the payload:

compound A1'
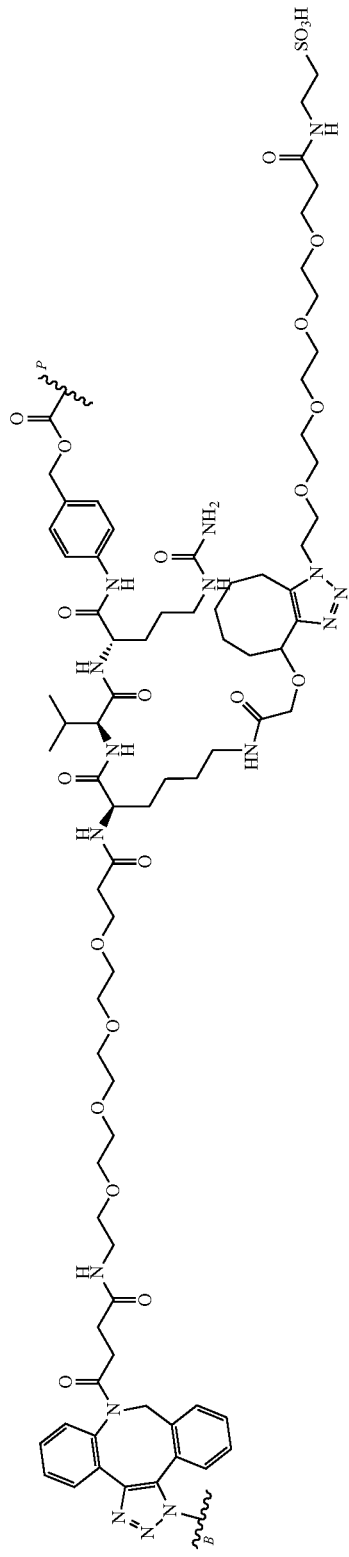
compound A2'
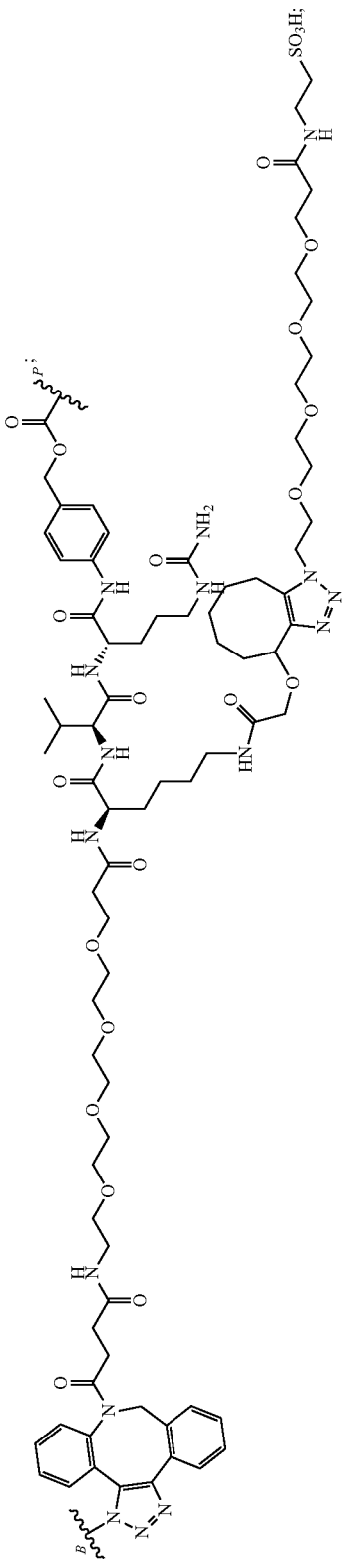

-continued
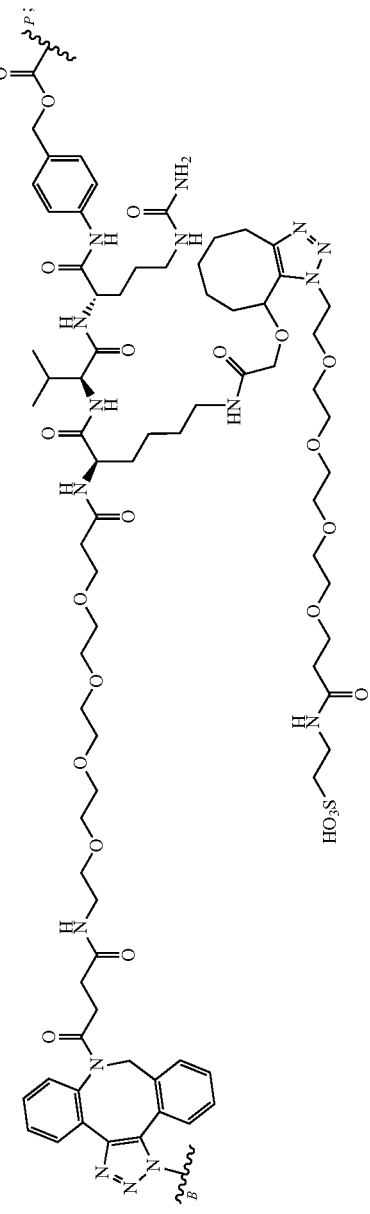
compound A3'
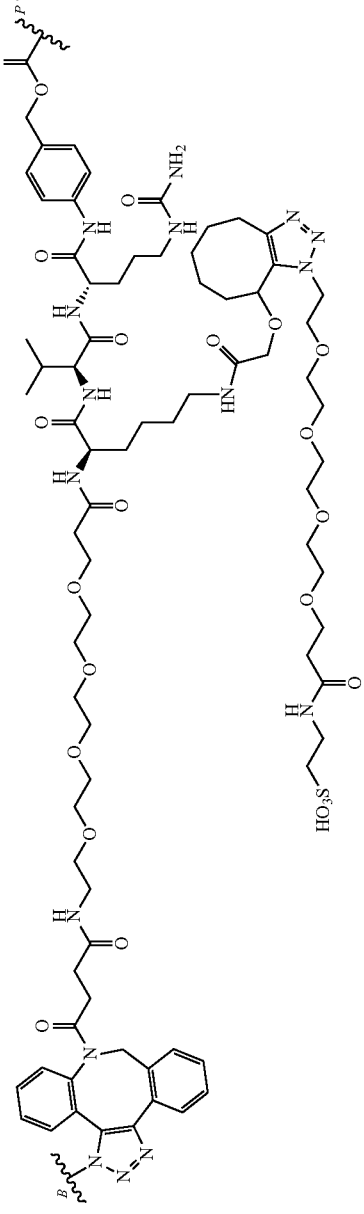
compound A4'

In certain embodiments, more than one suitable azide and more than one suitable alkyne can be utilized within a synthetic process en route to a product, where each pair of azide-alkyne can participate in one or more independent click reactions to generate a mixture of regioisomeric click reaction products. For example, a person of skill will recognize that a first suitable azide may independently react with a first suitable alkyne, and a second suitable azide may independently react with a second suitable alkyne, en route to a product, resulting in the generation of four possible click reaction regioisomers or a mixture of the four possible click reaction regioisomers in a sample of an ADC described herein. For example, a person of skill will recognize that a first suitable azide may independently react with a first suitable alkyne, en route to a product, resulting in the generation of two possible click reaction regioisomers or a mixture of the two possible click reaction regioisomers in a sample of a linker-payload described herein.

As used herein, the term "residue" refers to the chemical moiety within a compound that remains after a chemical reaction. For example, the term "amino acid residue" or "N-alkyl amino acid residue" refers to the product of an amide coupling or peptide coupling of an amino acid or a N-alkyl amino acid to a suitable coupling partner; wherein, for example, a water molecule is expelled after the amide or peptide coupling of the amino acid or the N-alkylamino acid, resulting in the product having the amino acid residue or N-alkyl amino acid residue incorporated therein.

As used herein, "therapeutically effective amount" refers to an amount (e.g., of a compound) that is sufficient to provide a therapeutic benefit to a patient in the treatment or management of a disease or disorder, or to delay or minimize one or more symptoms associated with the disease or disorder.

As used herein, "sugar" or "sugar group" or "sugar residue" refers to a carbohydrate moiety which may comprise 3-carbon (triose) units, 4-carbon (tetrose) units, 5-carbon (pentose) units, 6-carbon (hexose) units, 7-carbon (heptose) units, or combinations thereof, and may be a monosaccharide, a disaccharide, a trisaccharide, a tetrasaccharide, a pentasaccharide, an oligosaccharide, or any other polysaccharide. In some instances, a "sugar" or "sugar group" or "sugar residue" comprises furanoses (e.g., ribofuranose, fructofuranose) or pyranoses (e.g., glucopyranose, galactopyranose), or a combination thereof. In some instances, a "sugar" or "sugar group" or "sugar residue" comprises aldoses or ketoses, or a combination thereof. Non-limiting examples of monosaccharides include ribose, deoxyribose, xylose, arabinose, glucose, mannose, galactose, and fructose. Non-limiting examples of disaccharides include sucrose, maltose, lactose, lactulose, and trehalose. Other "sugars" or "sugar groups" or "sugar residues" include polysaccharides and/or oligosaccharides, including, and not limited to, amylose, amylopectin, glycogen, inulin, and cellulose. In some instances a "sugar" or "sugar group" or "sugar residue" is an amino-sugar. In some instances a "sugar" or "sugar group" or "sugar residue" is a glucamine residue (1-amino-1-deoxy-D-glucitol) linked to the rest of molecule via its amino group to form an amide linkage with the rest of the molecule (i.e., a glucamide).

Certain groups, moieties, substituents, and atoms are depicted with a wiggly line that intersects a bond or bonds to indicate the atom through which the groups, moieties, substituents, atoms are bonded. For example, a phenyl group that is substituted with a propyl group depicted as:

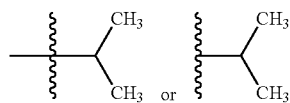

has the following structure:

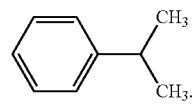

As used herein, illustrations showing substituents bonded to a cyclic group (e.g., aromatic, heteroaromatic, fused ring, and saturated or unsaturated cycloalkyl or heterocycloalkyl) through a bond between ring atoms are meant to indicate, unless specified otherwise, that the cyclic group may be substituted with that substituent at any ring position in the cyclic group or on any ring in the fused ring group, according to techniques set forth herein or which are known in the field to which the instant disclosure pertains. For example, the group,

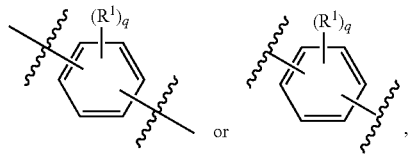

wherein subscript q is an integer from 0 to 4 and in which the positions of substituent $R^1$ are described generically, i.e., not directly attached to any vertex of the bond line structure, i.e., specific ring carbon atom, includes the following, non-limiting examples of groups in which the substituent $R^1$ is bonded to a specific ring carbon atom:

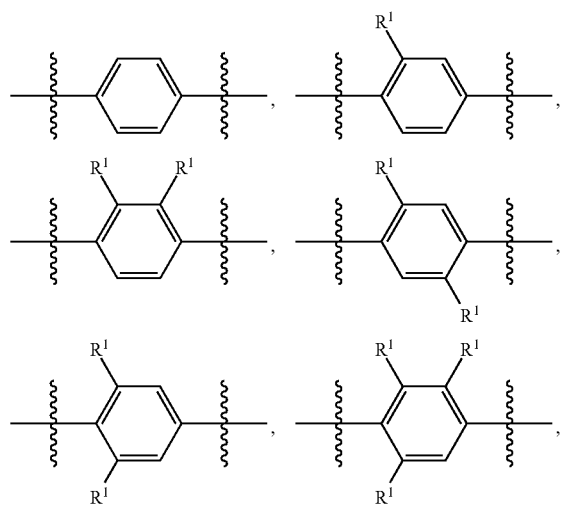

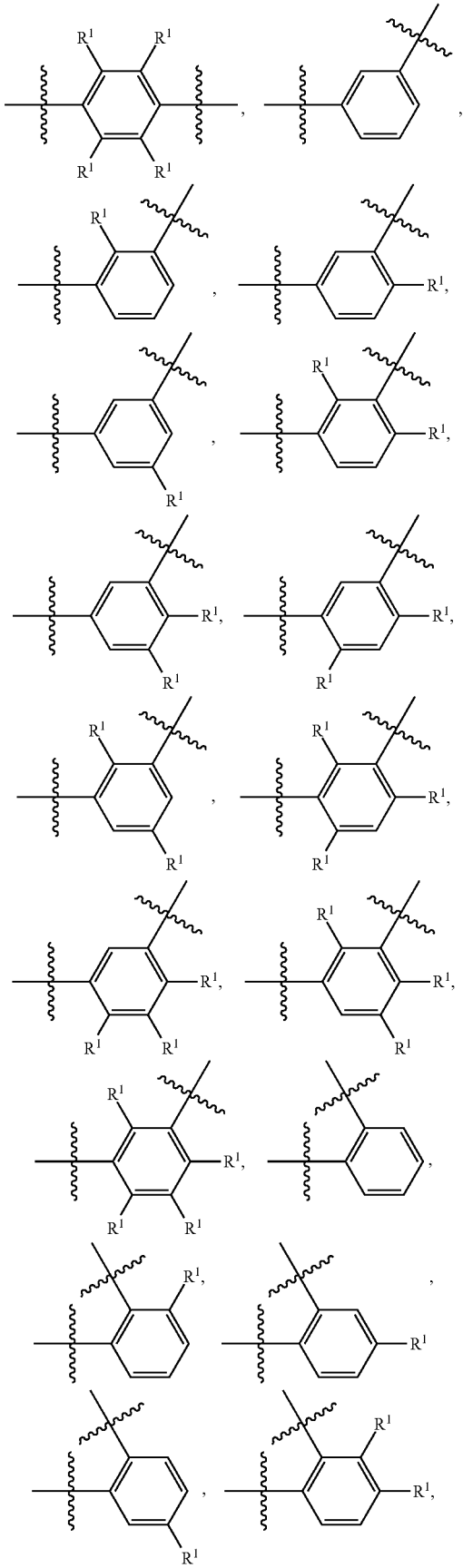

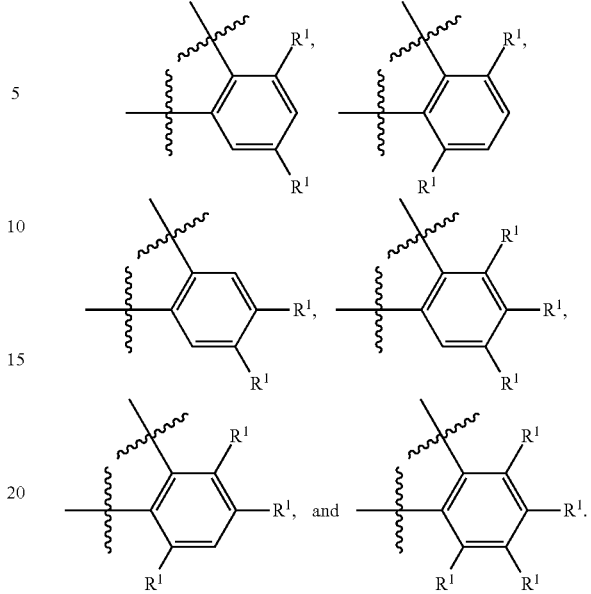

As used herein, the phrase "hydrophilic linker (HL)" refers to a moiety comprising a hydrophilic group (HG) as defined herein, and a spacer $SP^2$ as defined herein.

As used herein, the phrase "reactive linker" refers to a monovalent group that includes a reactive group and spacer group, depicted for example as

wherein RG' is the reactive group and $SP^1$ is the spacer group. As described herein, a reactive linker may include more than one reactive group and more than one spacer group. The spacer group is any divalent or trivalent moiety that bridges the reactive group to another group, such as a payload or also to a binding agent. The reactive linkers (L, LL), together with the payloads to which they are bonded, provide intermediates ("linker-payloads") useful as synthetic precursors for the preparation of the antibody conjugates described herein. The reactive linker contains one or more than one reactive group RG ($RG^1$, $RG^2$, or RG'), which is a functional group or moiety that is capable of reacting with a reactive portion of another group, for instance, an antibody, modified antibody, or antigen binding fragment thereof, or a hydrophilic group, as described herein. The moiety resulting from the reaction of the reactive group with the antibody, modified antibody, or antigen binding fragment thereof, together with the linking group, includes the "binding agent linker" ("BL") portion of the conjugate, described herein. In certain embodiments, the "reactive group" is a functional group or moiety (e.g., maleimide or N-hydroxysuccinimide (NHS) ester) that reacts with a cysteine or lysine residue of an antibody or antigen-binding fragment thereof.

In certain embodiments, the "reactive group" is a functional group or moiety that is capable of undergoing a click chemistry reaction (see, e.g., click chemistry, Huisgen Proc. Chem. Soc. 1961, Wang et al. J. Am. Chem. Soc. 2003, and Agard et al. J. Am. Chem. Soc. 2004). In some embodiments of said click chemistry reaction, the reactive group is an alkyne that is capable of undergoing a 1,3-cycloaddition reaction with an azide. An alkyne that is capable of undergoing a 1,3-cycloaddition reaction with an azide is also referred to herein as a "click chemistry residue". Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3-cycloaddition reactions with alkynes in the absence of copper catalysts. Suitable alkynes also include, but are not limited to, dibenzoazacyclooctyne or

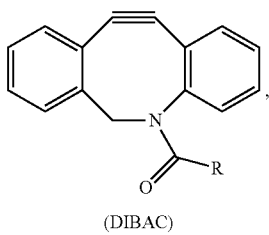

(DIBAC)

for example,

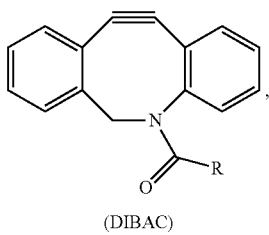

dibenzocyclooctyne or

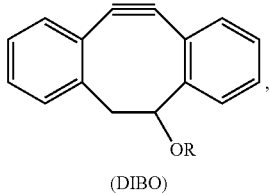

(DIBO)

for example,

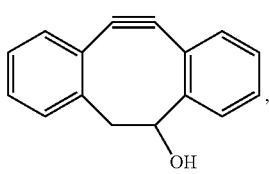 [SMILES: OC1Cc2ccccc2C#Cc2ccccc21]

biarylazacyclooctynone or

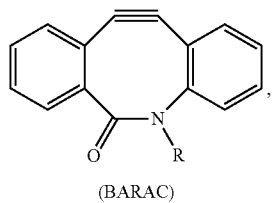

(BARAC)

for example,

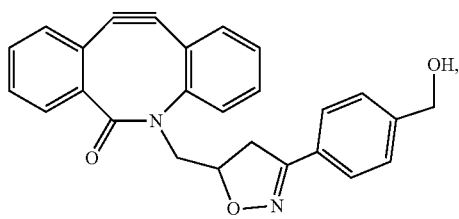 [SMILES: O=C1c2ccccc2C#Cc2ccccc2N1CC1CC(c2ccc(CO)cc2)=NO1]

difluorinated cyclooctyne or

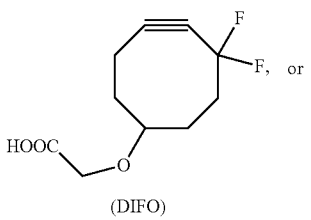

(DIFO)

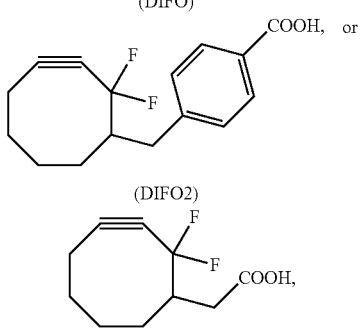

(DIFO2)

(DIFO3)

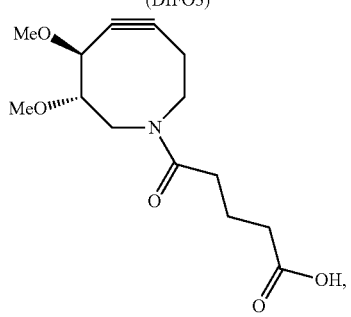

(DIMAC)

(ALO)

-continued

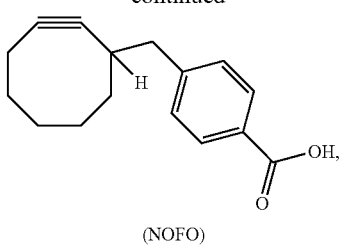
(NOFO)

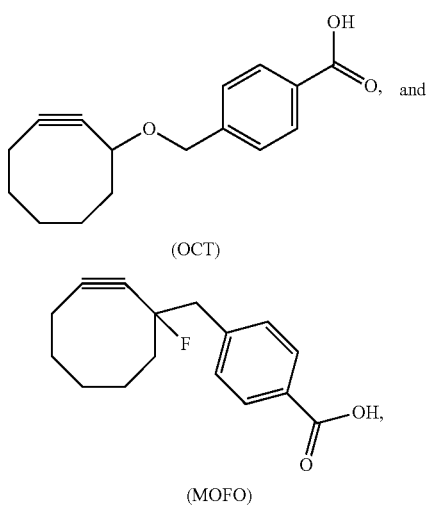
(OCT)

(MOFO)

substituted, e.g., fluorinated alkynes, aza-cycloalkynes, bicycle[6.1.0]nonyne or

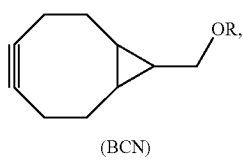
(BCN)

where R is alkyl, alkoxy, or acyl, and derivatives thereof, for example,

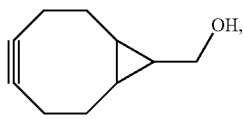

Particularly useful alkynes include

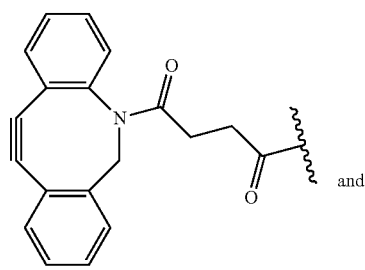
and

-continued

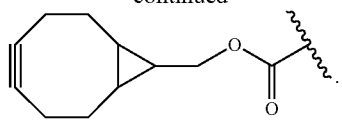

Additional alkynes include

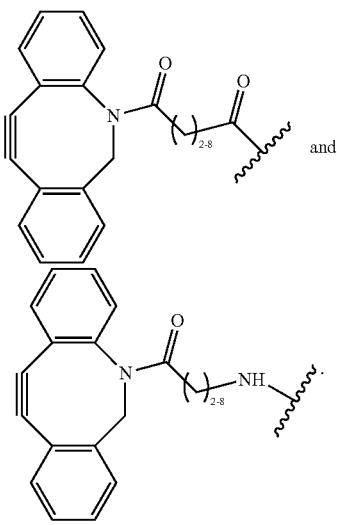
and

Linker-payloads including such reactive groups are useful for conjugating antibodies that have been functionalized with azido groups. Such functionalized antibodies include antibodies functionalized with azido-polyethylene glycol groups. In certain embodiments, such a functionalized antibody is derived by treating an antibody having at least one glutamine residue, e.g., a heavy chain Gln295, with a compound bearing an amino group and an azide group, in the presence of the enzyme transglutaminase.

In certain embodiments, the antibody or a glutaminyl-modified antibody or antigen binding molecule comprises at least one glutamine residue in at least one polypeptide chain sequence. In certain embodiments, the antibody or a glutaminyl-modified antibody or antigen binding molecule comprises two heavy chain polypeptides, each with one Gln295 residue. In further embodiments, the antibody or a glutaminyl-modified antibody or antigen binding molecule comprises one or more glutamine residues at a site other than a heavy chain Gln 295. Included herein are antibodies bearing N297Q mutation(s) described herein. Briefly, in some embodiments, an antibody including a glutamine residue is treated with a primary amine compound, described in more detail below, in the presence of the enzyme transglutaminase. In some embodiments, an antibody including a Asn297Gln (N297Q) residue is treated with a primary amine compound, described in more detail below, in the presence of the enzyme transglutaminase. In some embodiments, an antibody including Gln295 (Q295) residue is treated with a primary amine compound, described in more detail below, in the presence of the enzyme transglutaminase. In some embodiments, an antibody including Gln55 (Q55) residue is treated with a primary amine compound, described in more detail below, in the presence of the enzyme transglutaminase. For example, in some embodiments, such an antibody can be prepared by site-directed mutagenesis to remove or disable a sequence or to insert a glutamine residue at a site apart from any interfering structure. Such an antibody also can be isolated from natural or artificial sources.

The amino acid sequence of an antibody can be numbered using any known numbering schemes, including those described by Kabat et al., ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme). Unless otherwise specified, the numbering scheme used herein is the Kabat numbering scheme. However, selection of a numbering scheme is not intended to imply differences in sequences where they do not exist, and one of skill in the art can readily confirm a sequence position by examining the amino acid sequence of one or more antibodies. Unless stated otherwise, the "EU numbering scheme" is generally used when referring to a residue in an antibody heavy chain constant region (e.g., as reported in Kabat et al., supra).

The term "aglycosylated antibody" refers to an antibody that does not comprise a glycosylation sequence that might interfere with a transglutamination reaction, for instance an antibody that does not have saccharide group at N297 on one or more heavy chains. In particular embodiments, an antibody heavy chain has an N297 mutation. In other words, the antibody is mutated to no longer have an asparagine residue at position 297 according to the EU numbering system as disclosed by Kabat et al. In particular embodiments, an antibody heavy chain has an N297Q or an N297D mutation. Such an antibody can be prepared by site-directed mutagenesis to remove or disable a glycosylation sequence or by site-directed mutagenesis to insert a glutamine residue at site apart from any interfering glycosylation site or any other interfering structure. Such an antibody also can be isolated from natural or artificial sources.

The term "deglyosylated antibody" refers to an antibody in which a saccharide group at N297 was removed, thereby opening Q295 to transglutamination. In particular embodiments, provided herein are processes that encompass an additional step of deglycosylating an antibody, for instance an N297 antibody.

In some examples, the alkyne used in the bioconjugation reaction is useful for Cu(I) click-chemistry conjugation reaction. In some examples, the alkyne used in the conjugation reaction reacts with 1,2 aminothiol in the 2-Cyanobenzothiazole (CBT) reaction. In some examples, the alkyne used is BCN, derivative of BCN, or trans-cyclooctene (TCOs) in an inverse electron demand Diels Alder reactions. See, for example, Wang et al., J. Am. Chem. Soc.; (Article), 2012, 134 (6), 2950-2953.

In some examples, the reactive group is an alkyne, e.g.,

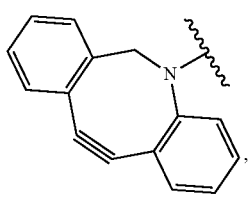 [SMILES: *N1Cc2ccccc2C#Cc2ccccc21]

which can react via click chemistry with an azide, e.g.,

to form a click chemistry product, e.g.,

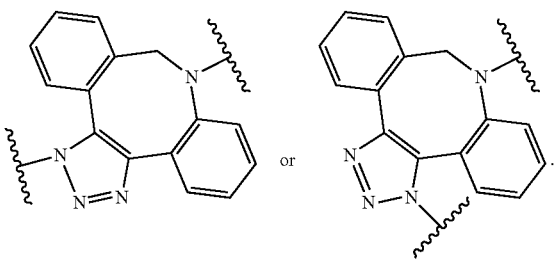 [SMILES: *N1Cc2ccccc2-c2c(nnn2*)-c2ccccc21 ; *N1Cc2ccccc2-c2nnn(*)c2-c2ccccc21]

In some examples, the group reacts with an azide on a modified antibody or antigen binding fragment thereof. In some examples, the reactive group is an alkyne, e.g.,

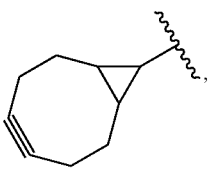 [SMILES: *C1C2CCC#CCCC12]

which can react via click chemistry with an azide, e.g.,

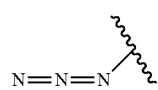

to form a click chemistry product, e.g.,

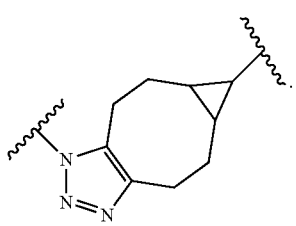 [SMILES: *C1C2CCc3nnn(*)c3CCC12]

In some examples, the reactive group is an alkyne, e.g.,

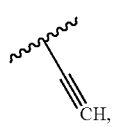

which can react via click chemistry with an azide, e.g.,

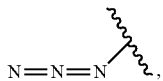

to form a click chemistry product, e.g.,

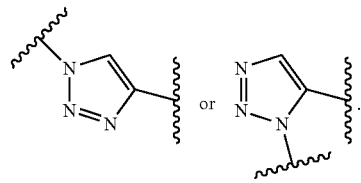 [SMILES: *c1cn(*)nn1 ; *c1cnnn1*]

In some examples, the reactive group is a functional group, e.g.,

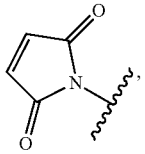 [SMILES: *N1C(=O)C=CC1=O]

which reacts with a cysteine residue on an antibody or antigen-binding fragment thereof, to form a bond thereto, e.g.,

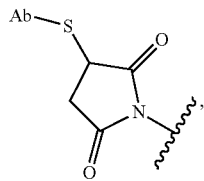

wherein Ab refers to an antibody or antigen-binding fragment thereof and S refers to the S atom on a cysteine residue through which the functional group bonds to the Ab. In some examples, the reactive group is a functional group, e.g.,

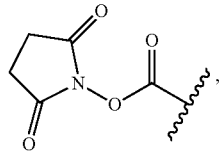 [SMILES: *C(=O)ON1C(=O)CCC1=O]

which reacts with a lysine residue on an antibody or antigen-binding fragment thereof, to form a bond thereto, e.g.,

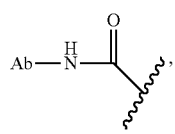

wherein Ab refers to an antibody or antigen-binding fragment thereof and NH refers to the NH atom on a lysine side chain residue through which the functional group bonds to the Ab.

As used herein, the phrase "binding agent linker," or "BL" refers to any divalent, trivalent, or multi-valent group or moiety that links, connects, or bonds a binding agent (e.g., an antibody or an antigen-binding fragment thereof) with a payload compound set forth herein (e.g., MMAE, bis-octahydrophenanthrene carboxamides, steroids) and, optionally, with one or more side chain compounds. Generally, suitable binding agent linkers for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers are linkers that are cleaved by intracellular metabolism following internalization, e.g., cleavage via hydrolysis, reduction, or enzymatic reaction. Non-cleavable linkers are linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citrulline units, and para-aminobenzyl (PAB) units. In some embodiments, the binding agent linker (BL) includes a moiety that is formed by the reaction of the reactive group (RG) of a reactive linker (RL) and reactive portion of the binding agent, e.g., antibody, modified antibody, or antigen binding fragment thereof.

In some examples, the BL includes the following moiety:

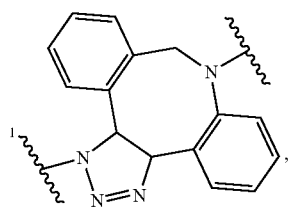 [SMILES: *N1Cc2ccccc2C2C(N=NN2*)c2ccccc21]

wherein $\overset{1}{\xi}$ is the bond to the binding agent. In some examples, the BL includes the following moiety:

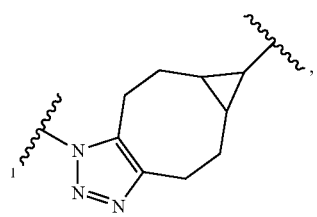 [SMILES: *C1C2CCc3nnn(*)c3CCC12]

wherein $\overset{1}{\xi}$ is the bond to the binding agent. In some examples, the BL includes the following moiety:

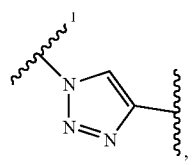

wherein $\overset{1}{\vdots}$ is the bond to the binding agent. In some examples, the BL includes the following moiety:

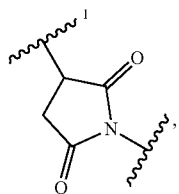 [SMILES: *C1CC(=O)N(*)C1=O]

wherein $\overset{1}{\vdots}$ is the bond to the cysteine of the antibody or antigen-binding fragment thereof. In some examples, the BL includes the following moiety:

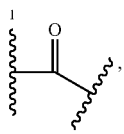

wherein $\overset{1}{\vdots}$ is the bond to the lysine of the antibody or antigen-binding fragment thereof.

Conjugates and Payloads

In some examples, set forth herein is a compound, or a pharmaceutically acceptable salt thereof, comprising: a binding agent linked to at least one payload moiety and linked to at least one hydrophilic moiety via a covalent linker, wherein said covalent linker is bonded directly or indirectly to each of the binding agent, the payload moiety, and the hydrophilic moiety.

In some other examples, set forth herein is a compound, or a pharmaceutically acceptable salt thereof, comprising: a protein linked to at least one payload moiety and linked to at least one hydrophilic moiety via a covalent linker, wherein said covalent linker is bonded directly or indirectly to each of the protein, the payload moiety, and the hydrophilic moiety. In some embodiments, the protein is an antibody or antigen binding fragment thereof.

As illustrated herein, in some examples, the binding agent is bonded directly to a covalent linker, such as a lysine amino acid. This means that the binding agent is one bond position away from the lysine amino acid covalent linker. In some of these examples, the covalent linker is also bonded directly to a payload moiety. This means that the covalent linker is one bond position away from a payload such as, but not limited to, a maytansinoid, MMAE, MMAF, a steroid, an LXR modulator, or any payload set forth herein. In some of these examples, the covalent linker is also bonded directly to a hydrophilic moiety. This means that the covalent linker is one bond position away from a hydrophilic residue, such as the hydrophilic residues set forth herein. In some of these examples, the covalent linker is a lysine amino acid or a derivative thereof.

In other examples, the binding agent is bonded indirectly to a covalent linker. This means that the binding agent is more than one bond position away from the covalent linker. This also means that the binding agent is bonded through another moiety to the covalent linker. For example, the binding agent may be bonded to a maleimide group which is bonded to a polyethylene glycol group which is bonded to the covalent linker. In some of these examples, the covalent linker is also bonded indirectly to a payload moiety. This means that the covalent linker is more than one bond position away from a payload such as, but not limited to, MMAE, a steroid, an LXR modulator, or any payload set forth herein. This also means that the covalent linker is bonded through another moiety to the payload. For example, the covalent linker may be bonded to a dipeptide, such as but not limited to Val-Ala or Val-Cit, which may be bonded to PAB which may be bonded to the payload. In some of these examples, the covalent linker is also bonded indirectly to a hydrophilic moiety. This means that the covalent linker is more than one bond position away from a hydrophilic moiety, such as the hydrophilic residues set forth herein. This also means that the covalent linker is bonded through another moiety to the hydrophilic moiety. For example, the covalent linker may be bonded to a polyethylene glycol group which may be bonded to reactive group which may be bonded to the hydrophilic residue. In some of these examples, the covalent linker is a lysine amino acid or a derivative thereof.

In certain instances, the hydrophilic residue comprises a terminal hydrophilic group. In some instances, the hydrophilic residue comprises at least one taurine group. In some instances, the hydrophilic residue comprises a sulfonic acid group. In some cases, the hydrophilic reside comprises a terminal sulfonic acid group. In further instances, the hydrophilic residue comprises more than one sulfonic acid groups. In some cases, the hydrophilic reside comprises more than one terminal sulfonic acid groups.

Described herein are compounds according to Formula (I):

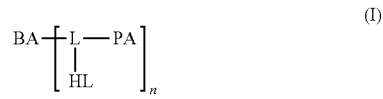

or pharmaceutically acceptable salts, solvates, stereoisomers, or derivatives thereof, wherein, in Formula (I), BA is a binding agent; L is a trivalent linker; HL is a hydrophilic residue; PA is a payload residue; and subscript n is an integer from 1 to 30. In some instances more than one trivalent linker L may be present. In some instances, n is an integer from 1 to 4. In some instances n is 1. In some instances n is 2. In some instances n is 3. In some instances n is 4.

In one example, a compound of Formula (I) is according to Formula (II):

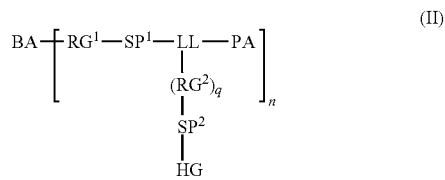

wherein, in Formula (II), BA is a binding agent; LL is a trivalent linker; $RG^1$ and $RG^2$ are reactive group residues; $SP^1$ and $SP^2$ are independently, in each instance, absent, or a spacer group residue; HG is a hydrophilic residue; PA is a payload residue; subscript n is an integer from 1 to 30; and subscript q is 0 or 1. In some instances more than one trivalent linker LL may be present. In some instances, n is an integer from 1 to 4. In some instances n is 1. In some instances n is 2. In some instances n is 3. In some instances n is 4. In some instances, HG is a terminal hydrophilic group. In some instances, HG comprises one terminal sulfonic acid group ($SO_3H$), or salts thereof. In other instances, HG comprises more than one terminal sulfonic acid groups, or salts thereof. In some instances, HG comprises one terminal taurine group or salts thereof. In other instances, HG comprises more than one terminal taurine groups or salts thereof. In some instances, HG comprises one terminal phosphonic acid group ($PO_3H$), or salt thereof. In other instances, HG comprises more than one terminal phosphonic acid groups, or salts thereof. In some instances, HG comprises one terminal amine group, or salt thereof. In other instances, HG comprises more than one terminal amine group, or salts thereof. In further instances, HG comprises one terminal quarternary amine group, or salts thereof. In further instances, HG comprises more than one terminal quarternary amine group, or salts thereof. In some instances, HG comprises one terminal sugar group, or salt thereof. In other instances, HG comprises more than one terminal sugar groups, or salts thereof.

In some instances, the compound of Formula (I) or Formula (II) comprises a mixture of compounds wherein subscript n is 1, 2, 3 or 4. In some instances, the compound of Formula (I) or Formula (II) comprises a mixture of compounds wherein subscript n is 2. In some instances, the compound of Formula (I) or Formula (II) comprises a mixture of compounds wherein subscript n is 4.

In one example, the compound of Formula (I) is according to Formula (III):

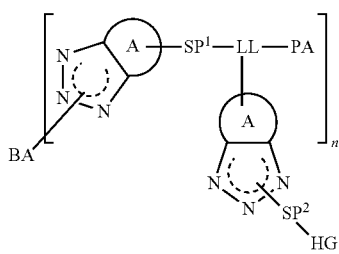

(III)

wherein
  ring A is fused to the triazole and is selected from the group consisting of cycloalkyl, cycloalkenyl, heterocycloalkyl, and heterocycloalkenyl;
  wherein cycloalkyl, cycloalkenyl, heterocycloalkyl, and heterocycloalkenyl are optionally substituted with alkyl, —OH, or —$NR^aR^b$, where each of $R^a$ and $R^b$ is alkyl or H.

In another example, the compound of Formula (I) is according to Formula (IV):

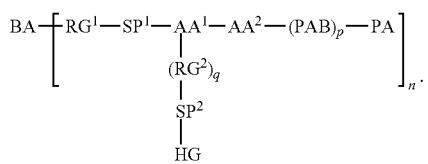

(IV)

In Formula (IV), BA, $RG^1$, $SP^1$, $RG^2$, $SP^2$ and HG are as defined above, $AA^1$ is a trivalent linker comprising an amino acid residue and is directly or indirectly linked to an antibody, a payload and a hydrophilic group; $AA^2$ is a dipeptide, tripeptide or tetrapeptide residue; and PAB is

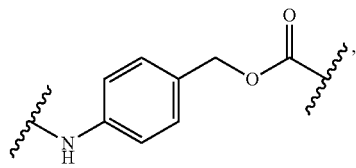 [SMILES: *Nc1ccc(COC(*)=O)cc1]

wherein the

indicates the atom through which the PAB is bonded to the adjacent groups in the formula; subscript p is 0 or 1; and subscript q is 0 or 1. In some instances, subscript p is 0 and subscript q is 0. In some instances, subscript p is 1; and subscript q is 0. In some instances, subscript p is 0; and subscript q is 1. In some instances, subscript p is 1; and subscript q is 1. In some instances $SP^1$ comprises from 0-5 polyethylene glycol (PEG) residues. In some instances $SP^2$ comprises from 0-5 PEG residues. In some examples, $SP^1$ is independently in each instance, selected from the group consisting of $C_{1-6}$ alkylene, —NH—, —C(O)—, (—$CH_2$—$CH_2$—O)$_e$, —NH—$CH_2$—$CH_2$—(—O—$CH_2$—$CH_2$)$_e$—C(O)—, —C(O)—($CH_2$)$_u$—C(O)—, —C(O)—NH—($CH_2$)$_v$—, polyglycine (e.g., ((glycine)$_4$-serine)$_f$ wherein subscript f is an integer from 1 to 6), and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, (—$CH_2$—$CH_2$—O)$_e$, —NH—$CH_2$—$CH_2$—(—O—$CH_2$—$CH_2$)$_e$—C(O)—, —C(O)—($CH_2$)$_u$—C(O)—, —C(O)—NH—($CH_2$)$_v$—, polyglycine (e.g., ((glycine)$_4$-serine)$_f$ wherein subscript f is an integer from 1 to 6), and combinations thereof, wherein subscript e is an integer from 0 to 4, subscript u is an integer from 1 to 8, and subscript v is an integer from 1 to 8. In some examples, any one of $AA^1$ or $AA^2$ comprises, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, $AA^1$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, $AA^1$ is an amino acid with three functional groups to link to a payload, to a binding agent (e.g., antibody or antigen binding fragment thereof), and to a linker comprising a hydrophilic group, e.g., lysine, aspargine, glutamic acid, aspartic acid, glutamine, cysteine, threonine, serine, or tyrosine. In certain embodiments, $AA^1$ is lysine. In certain embodiments, $AA^1$ is lysine or a derivative of lysine. In certain embodiments, $AA^1$ is L-lysine. In certain embodiments, the $AA^1$ is D-lysine. In certain embodiments, $AA^1$ is glutamine. In certain embodiments, $AA^1$ is glutamic acid. In certain embodiments, $AA^1$ is aspartic acid. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In some embodiments, the $AA^1$-$AA^2$ is glutamine-valine-citrulline. In some embodiments, the $AA^1$-$AA^2$ is lysine-valine-citrulline. In some embodiments, the $AA^1$-$AA^2$ is lysine-valine-alanine. In some embodiments, the $AA^1$-$AA^2$ is glutamine-valine-alanine. In certain embodiments, ((glycine)$_4$-serine)$_f$ is (glycine)$_4$-serine.

In some examples, the compound of Formula (I) or Formula (II) or Formula (III) or Formula (IV) is according to Formula (IVa), Formula (IVb) or Formula (IVc):

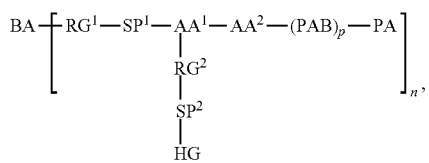

(IVa)

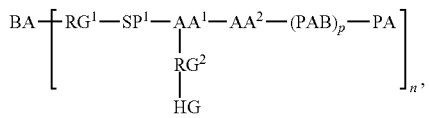

(IVb)

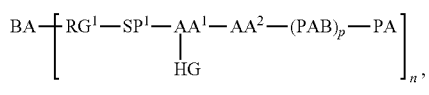

(IVc)

In Formulae (IVa), (IVb), and (IVc), BA, $RG^1$, $SP^1$, $RG^2$, $SP^2$, HG and subscript p are as defined above, $AA^1$ is a trivalent linker comprising an amino acid residue and is directly or indirectly linked to an antibody, a payload and a hydrophilic group; $AA^2$ is a dipeptide, tripeptide, or tetrapeptide residue; and PAB is

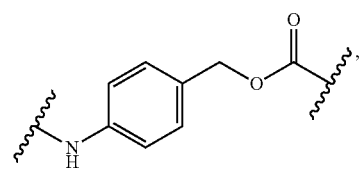 [SMILES: *Nc1ccc(COC(*)=O)cc1]

wherein the

indicates the atom through which the PAB is bonded to the adjacent groups in the formula. In some instances, subscript p is 0. In some instances, subscript p is 1. In some instances $SP^1$ comprises from 0-5 polyethylene glycol (PEG) residues. In some instances $SP^2$ comprises from 0-5 PEG residues. In some examples, $SP^1$ is independently in each instance, selected from the group consisting of $C_{1-6}$ alkylene, —NH—, —C(O)—, (—CH$_2$—CH$_2$—O)$_e$, —NH—CH$_2$—CH$_2$—(—O—CH$_2$—CH$_2$)$_e$—C(O)—, —C(O)—(CH$_2$)$_u$—C(O)—, —C(O)—NH—(CH$_2$)$_v$—, polyglycine (e.g., ((glycine)$_4$-serine)$_f$ wherein subscript f is an integer from 1 to 6), and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, (—CH$_2$—CH$_2$—O)$_e$, —NH—CH$_2$—CH$_2$—(—O—CH$_2$—CH$_2$)$_e$—C(O)—, —C(O)—(CH$_2$)$_u$—C(O)—, —C(O)—NH—(CH$_2$)$_v$—, polyglycine (e.g., ((glycine)$_4$-serine)$_f$ wherein subscript f is an integer from 1 to 6), and combinations thereof, wherein subscript e is an integer from 0 to 4, subscript u is an integer from 1 to 8, and subscript v is an integer from 1 to 8. In some examples, any one of $AA^1$ or $AA^2$ comprises, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, $AA^1$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, $AA^1$ is lysine. In certain embodiments, $AA^1$ is an amino acid with three functional groups to link to a payload, to a binding agent (e.g., antibody or antigen binding fragment thereof), and to a linker comprising a hydrophilic group, e.g., lysine, aspargine, glutamic acid, aspartic acid, glutamine, cysteine, threonine, serine, or tyrosine. In certain embodiments, $AA^1$ is lysine or a derivative of lysine. In certain embodiments, $AA^1$ is L-lysine. In certain embodiments, the $AA^1$ is D-lysine. In certain embodiments, $AA^1$ is glutamine. In certain embodiments, $AA^1$ is glutamic acid. In certain embodiments, $AA^1$ is aspartic acid. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In some embodiments, the $AA^1$-$AA^2$ is glutamine-valine-citrulline. In some embodiments, the $AA^1$-$AA^2$ is lysine-valine-citrulline. In some embodiments, the $AA^1$-$AA^2$ is lysine-valine-alanine. In some embodiments, the $AA^1$-$AA^2$ is glutamine-valine-alanine. In certain embodiments, ((glycine)$_4$-serine)$_f$ is (glycine)$_4$-serine.

In some examples, the compound of Formula (I) or Formula (II) or Formula (III) or Formula (IV) is according to to Formula (Va), (Vb), (Vc) or (Vd) respectively:

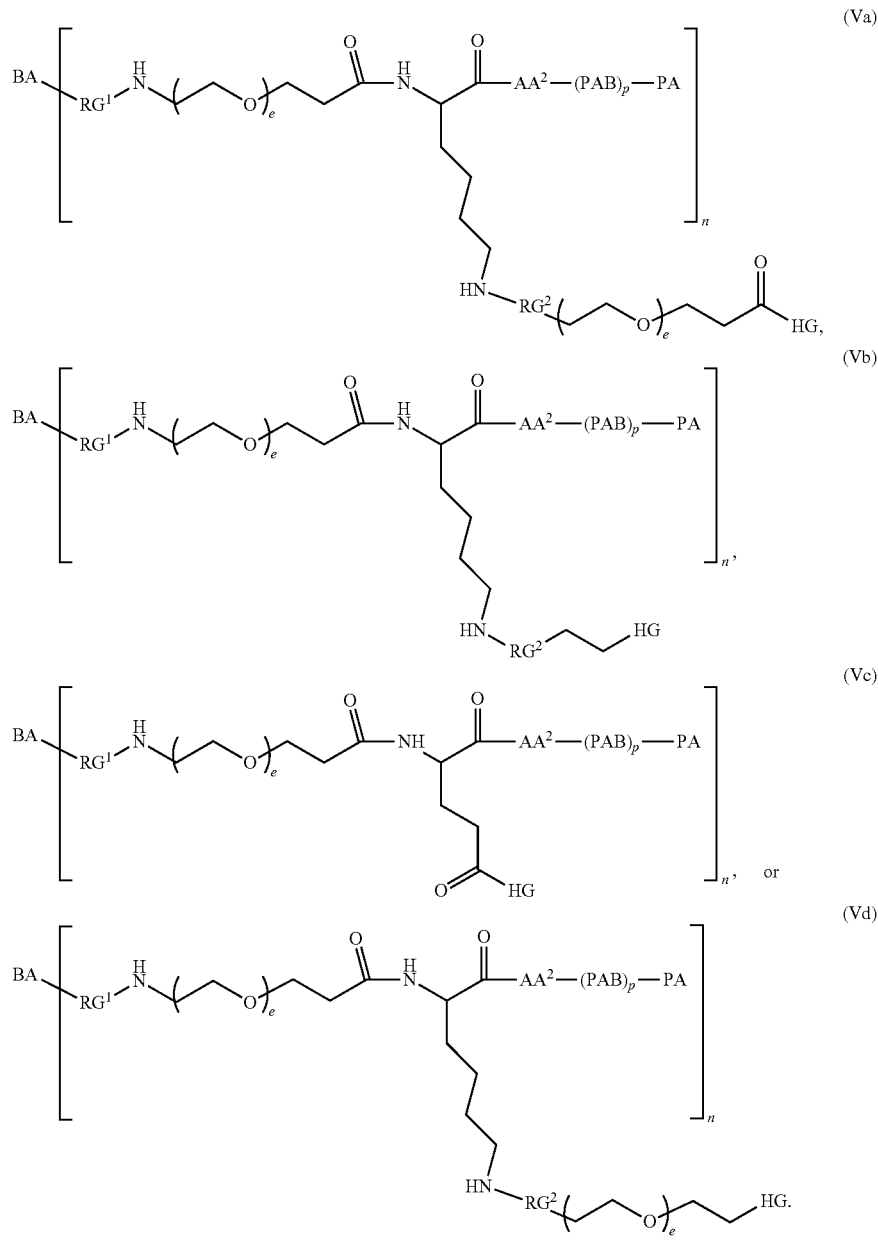

In Formulae (Va), (Vb), (Vc), and (Vd) BA, $RG^1$, $SP^1$, $RG^2$, $SP^2$ and HG are as defined above, $AA^2$ is a dipeptide, tripeptide or tetrapeptide residue; and PAB is

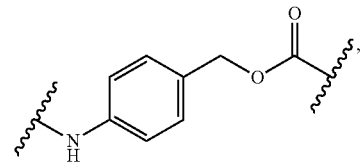 [SMILES: *Nc1ccc(COC(*)=O)cc1]

wherein the

indicates the atom through which the PAB is bonded to the adjacent groups in the formula; subscript p is 0 or 1; and subscript e is independently, in each instance, an integer from 0 to 6, or an integer from 0 to 5. In some instances, subscript p is 0. In some instances, subscript p is 1. In any of these examples, subscript e is 1, 2, 3, or 4. In some examples, subscript e is 1. In some examples, subscript e is 2. In some examples, subscript e is 3. In some examples, subscript e is 4. In some examples, subscript e is 5. In some examples, subscript e is 6. In some examples, $SP^1$ is independently in each instance, selected from the group consisting of $C_{1-6}$ alkylene, —NH—, —C(O)—, (—CH$_2$—CH$_2$—O)$_e$, —NH—CH$_2$—CH$_2$—(—O—CH$_2$—CH$_2$)$_e$—C(O)—, —C(O)—(CH$_2$)$_u$—C(O)—, —C(O)—NH—(CH$_2$)$_v$—, polyglycine (e.g., ((glycine)$_4$-serine)$_f$ wherein subscript f is an integer from 1 to 6), and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, (—CH$_2$—CH$_2$—O)$_e$, —NH—CH$_2$—CH$_2$—(—O—CH$_2$—CH$_2$)$_e$—C(O)—, —C(O)—(CH$_2$)$_u$—C(O)—, —C(O)—NH—(CH$_2$)$_v$—, polyglycine (e.g., ((glycine)$_4$-serine)$_f$ wherein subscript f is an integer from 1 to 6), and combinations thereof, wherein subscript e is an integer from 0 to 4, subscript u is an integer from 1 to 8, and subscript v is an integer from 1 to 8. In some examples, any $AA^2$ comprises, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In certain embodiments, ((glycine)$_4$-serine)$_f$ is (glycine)$_4$-serine.

In any compound of Formula (I), Formula (II), Formula (III), Formula (IV), Formula (IVa), Formula (IVb), Formula (IVc), Formula (Va), Formula (Vb), Formula (Vc), Formula (Vd), $RG^1$ and $RG^2$ are independently in each instance, a click chemistry residue. In some examples, $RG^1$ and $RG^2$ independently in each instance, comprise a triazaole or a fused triazole. In some instances, $RG^1$ and $RG^2$ are independently, in each instance, selected from the group consisting of

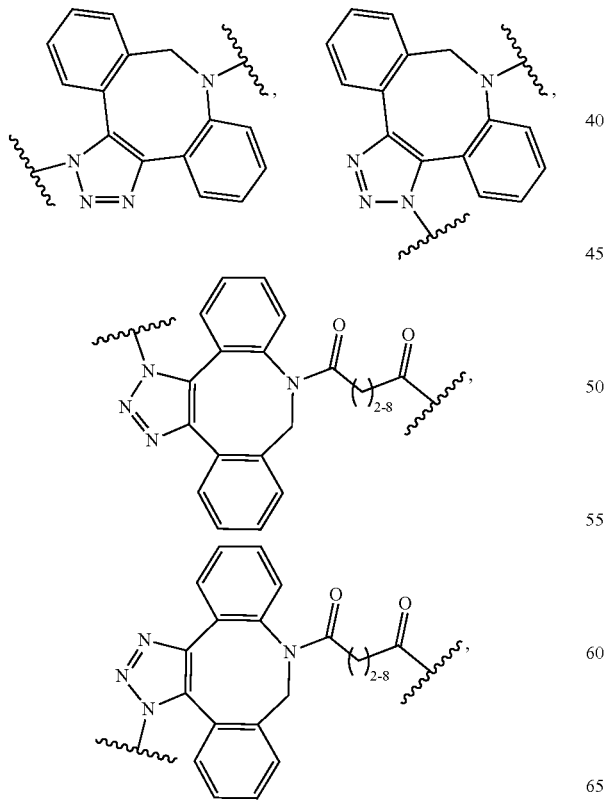

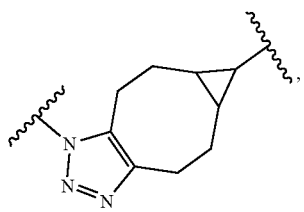

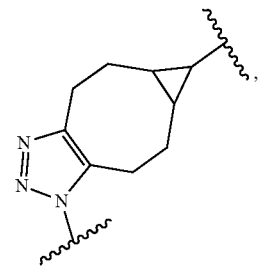

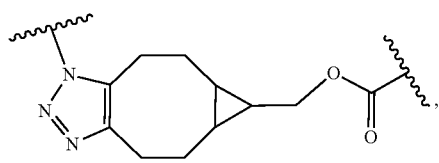

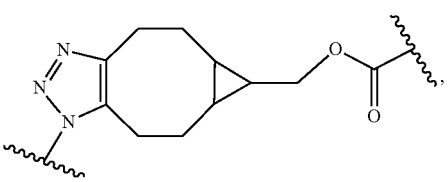

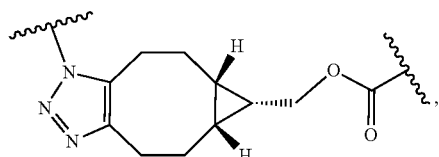

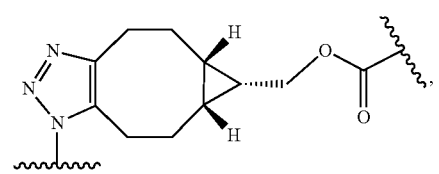

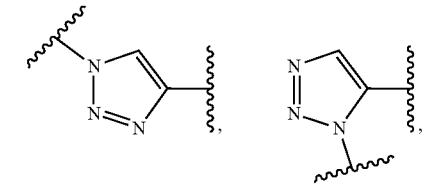

-continued
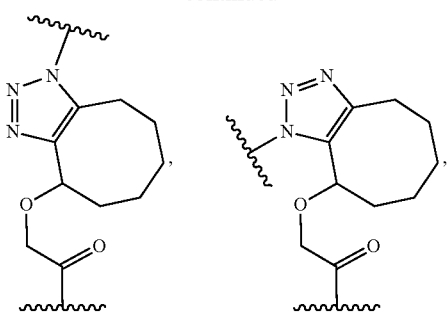
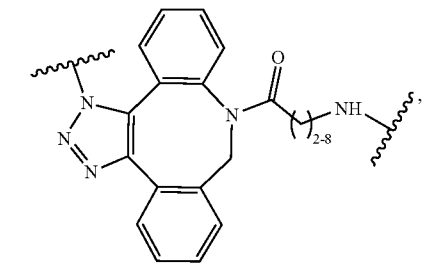
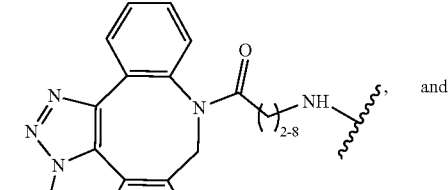
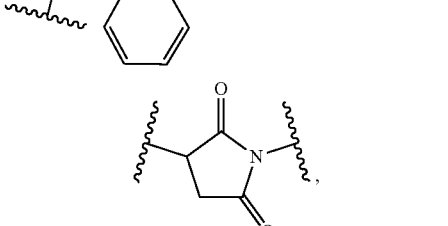
wherein the
indicates the atom through which the RG$^1$ or RG$^2$ is bonded to the adjacent groups in the formula.
In certain embodiments,
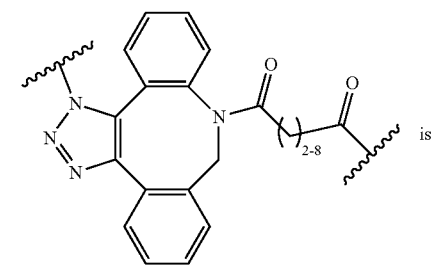 is
-continued
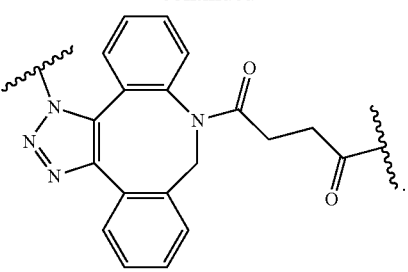
In certain embodiments,
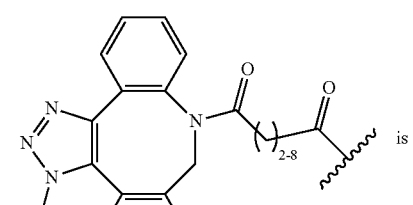 is
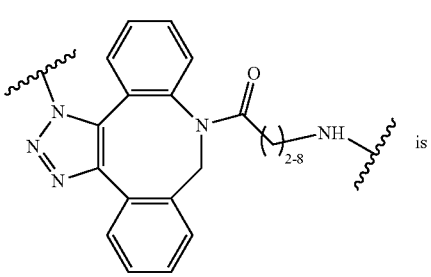
In certain embodiments,
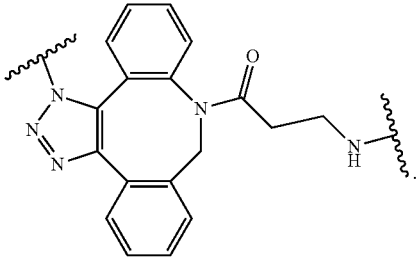

In some embodiments, 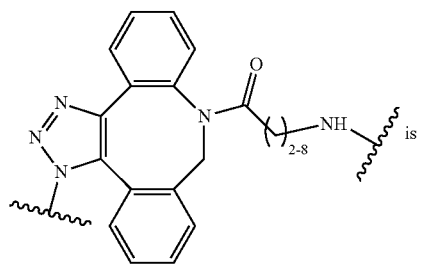 is
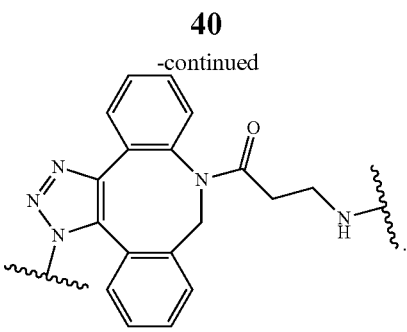
In certain instances, $RG^1$ and $RG^2$ are independently, in each instance, as shown in Table R.
TABLE R
| $RG^1$ | $RG^2$ |
|---|---|
| , or | , or |
| , | , |
| , or | , or |
| , | , |

TABLE R-continued
| RG¹ | RG² |
|---|---|
| 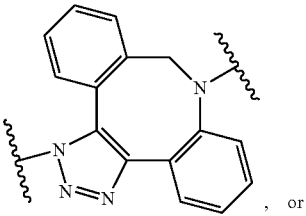 [SMILES: *N1Cc2ccccc2-c2c(nnn2*)-c2ccccc21], or | 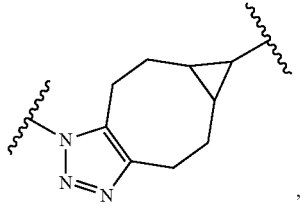 [SMILES: *C1C2CCc3nnn(*)c3CCC12], |
| 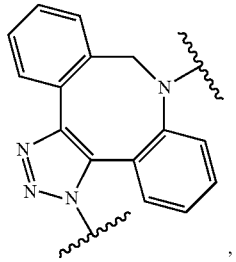 [SMILES: *N1Cc2ccccc2-c2nnn(*)c2-c2ccccc21], | 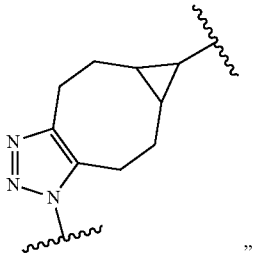 [SMILES: *C1C2CCc3nnn(*)c3CCC12], |
| 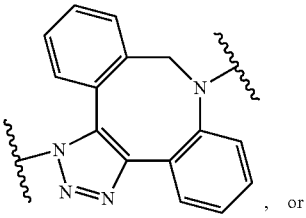 [SMILES: *N1Cc2ccccc2-c2c(nnn2*)-c2ccccc21], or | 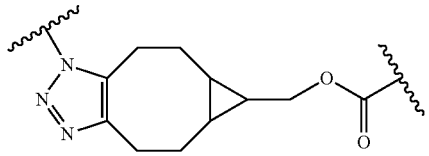, |
| 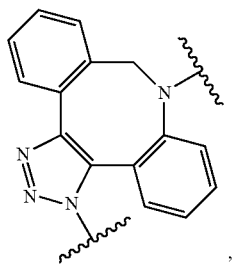 [SMILES: *N1Cc2ccccc2-c2nnn(*)c2-c2ccccc21], | 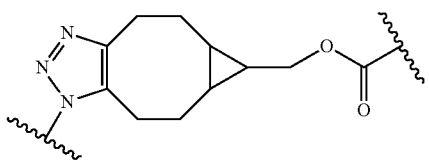, |
|  | 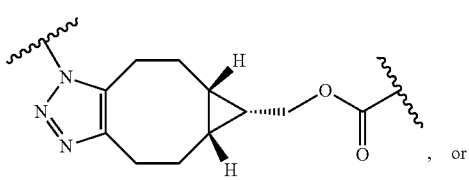 [SMILES: *C(=O)OC[C@@H]1[C@@H]2CCc3nnn(*)c3CC[C@@H]21], or |
|  | 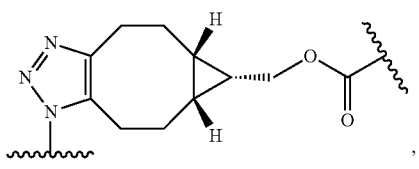 [SMILES: *C(=O)OC[C@@H]1[C@@H]2CCc3c(nnn3*)CC[C@@H]21], |

TABLE R-continued
| RG¹ | RG² |
|---|---|
| 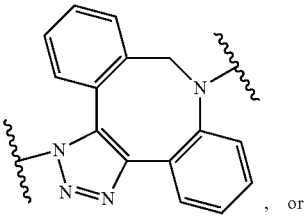 [SMILES: *N1Cc2ccccc2-c2c(nnn2*)-c2ccccc21], or | 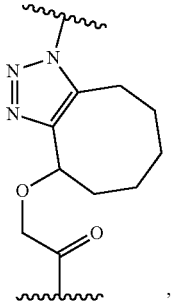, or |
| 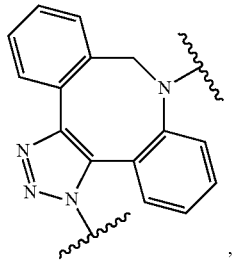 [SMILES: *N1Cc2ccccc2-c2nnn(*)c2-c2ccccc21], | 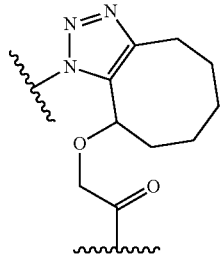 [SMILES: *C(=O)COC1CCCCCc2nnn(*)c21] |
| 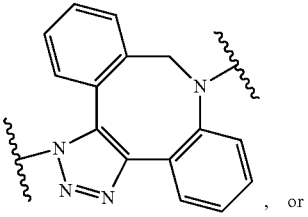 [SMILES: *N1Cc2ccccc2-c2c(nnn2*)-c2ccccc21], or | 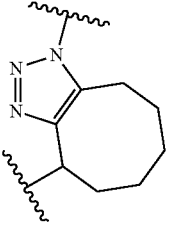, or |
| 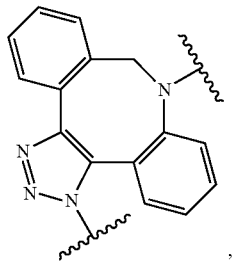 [SMILES: *N1Cc2ccccc2-c2nnn(*)c2-c2ccccc21], | 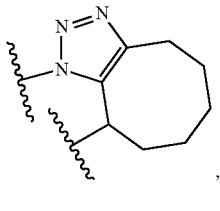 [SMILES: *C1CCCCCc2nnn(*)c21], |
| 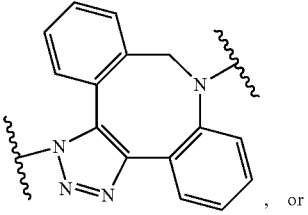 [SMILES: *N1Cc2ccccc2-c2c(nnn2*)-c2ccccc21], or | 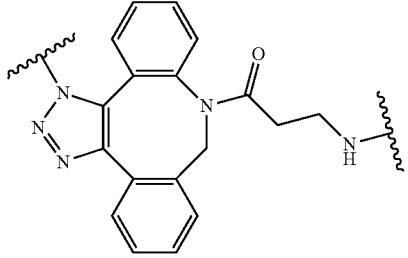, or |

TABLE R-continued
| RG¹ | RG² |
|---|---|
| 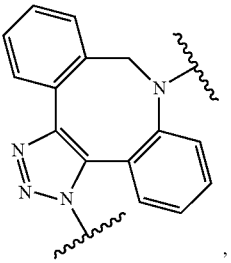 [SMILES: *N1Cc2ccccc2-c2nnn(*)c2-c2ccccc21] , | 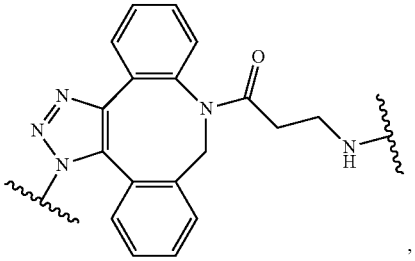 [SMILES: *NCCC(=O)N1Cc2ccccc2-c2c(nnn2*)-c2ccccc21] , |
| 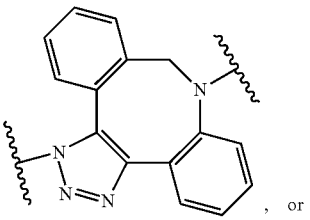 [SMILES: *N1Cc2ccccc2-c2c(nnn2*)-c2ccccc21] , or | 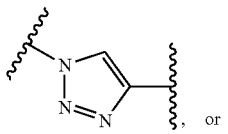 , or |
| 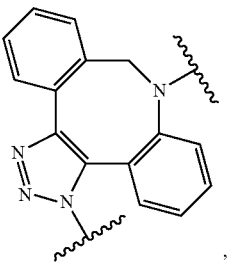 [SMILES: *N1Cc2ccccc2-c2nnn(*)c2-c2ccccc21] , | 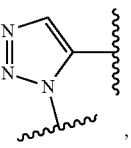 , |
| 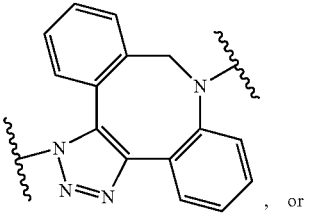 [SMILES: *N1Cc2ccccc2-c2c(nnn2*)-c2ccccc21] , or | 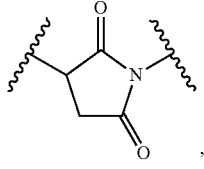 [SMILES: *C1CC(=O)N(*)C1=O] , |
| 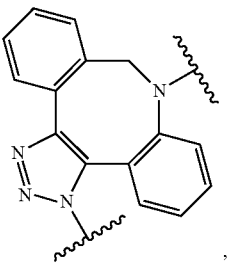 [SMILES: *N1Cc2ccccc2-c2nnn(*)c2-c2ccccc21] , | |
| 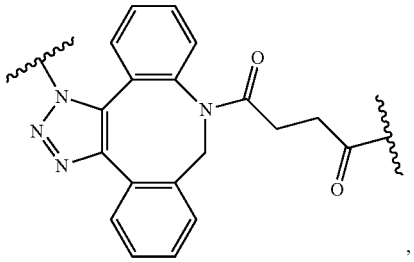 , or | 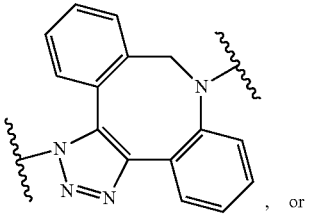 [SMILES: *N1Cc2ccccc2-c2c(nnn2*)-c2ccccc21] , or |

TABLE R-continued
| RG¹ | RG² |
|---|---|
| 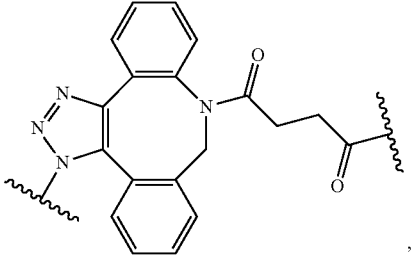 [SMILES: *C(=O)CCC(=O)N1Cc2ccccc2-c2c(nnn2*)-c2ccccc21] | 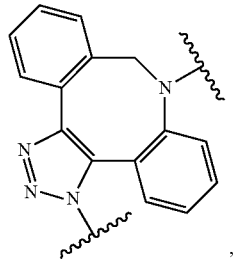 [SMILES: *N1Cc2ccccc2-c2nnn(*)c2-c2ccccc21] |
| 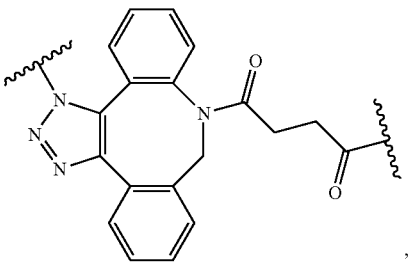, or | 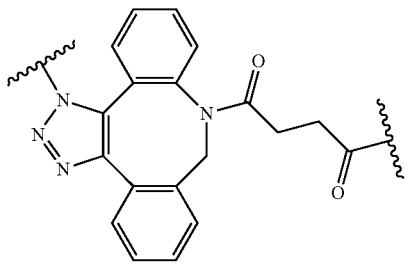, or |
| 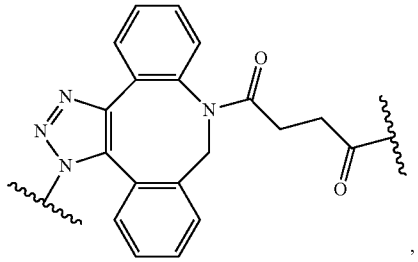 [SMILES: *C(=O)CCC(=O)N1Cc2ccccc2-c2c(nnn2*)-c2ccccc21] | 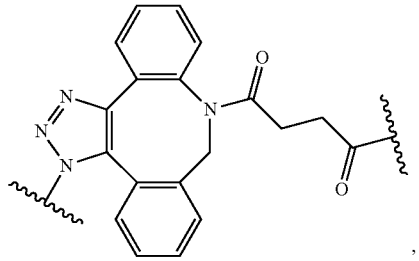 [SMILES: *C(=O)CCC(=O)N1Cc2ccccc2-c2c(nnn2*)-c2ccccc21], |
| 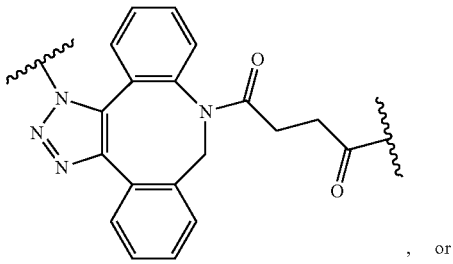 [SMILES: *C(=O)CCC(=O)N1Cc2ccccc2-c2nnn(*)c2-c2ccccc21], or | 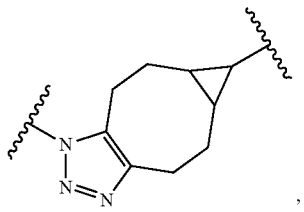 [SMILES: *C1C2CCc3nnn(*)c3CCC12], |
| 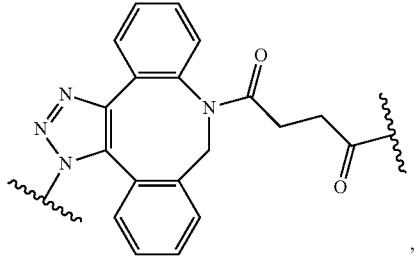 [SMILES: *C(=O)CCC(=O)N1Cc2ccccc2-c2c(nnn2*)-c2ccccc21], | 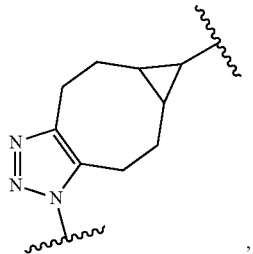 [SMILES: *C1C2CCc3nnn(*)c3CCC12], |

TABLE R-continued

| RG¹ | RG² |
|---|---|
| [structure], or | [structure], |
| [structure], | [structure], |
| | [structure], or |
| | [structure], |
| [structure], or | [structure], or |
| [structure], | [structure], |

TABLE R-continued
| RG¹ | RG² |
|---|---|
| 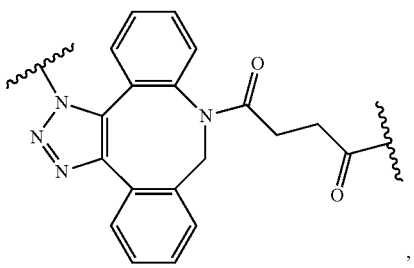, or | 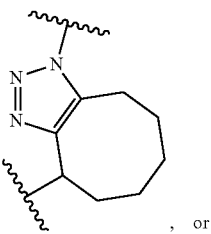 [SMILES: *C1CCCCCc2c1nnn2*], or |
| 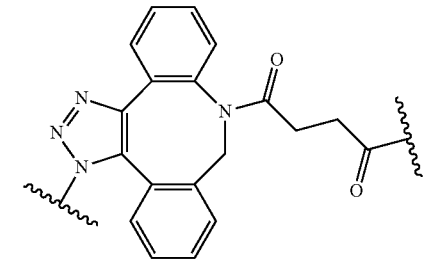, | 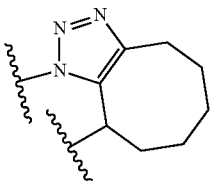, |
| 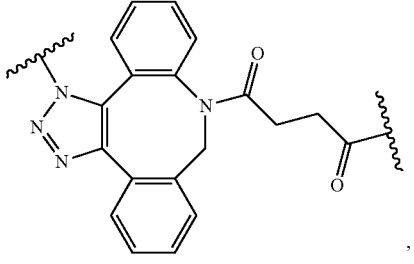, or | 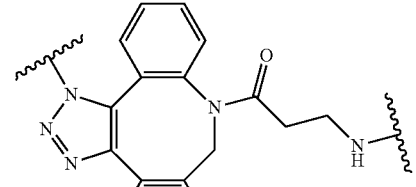, or |
| 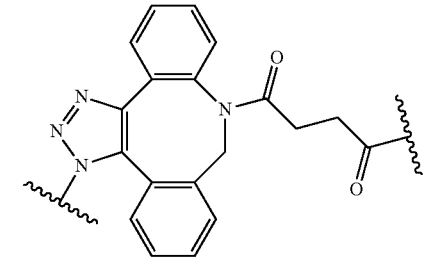, | 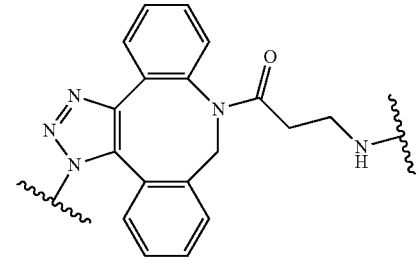, |
| 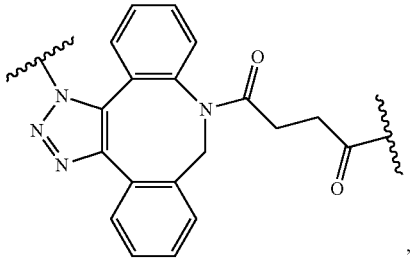, or | 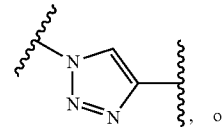, or |
| 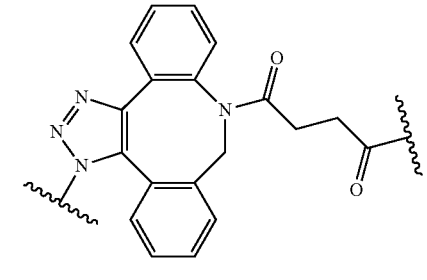, | 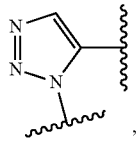, |

TABLE R-continued

| RG¹ | RG² |
|---|---|
| [structure: dibenzocyclooctyne-triazole with amide-ketone linker] , or [structure: dibenzocyclooctyne-triazole isomer with amide-ketone linker] , | [structure: succinimide (maleimide adduct)] , |
| [structure: BCN-triazole (bicyclo[6.1.0]nonyne-triazole)] , | [structure: benzocyclooctyne-triazole] , or [structure: benzocyclooctyne-triazole isomer] , |
| [structure: BCN-triazole isomer] , | [structure: dibenzocyclooctyne-triazole with amide-ketone linker] , or [structure: dibenzocyclooctyne-triazole isomer with amide-ketone linker] , |

TABLE R-continued
| RG¹ | RG² |
|---|---|
| 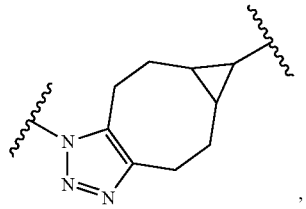 [SMILES: *C1C2CCc3nnn(*)c3CCC12], | 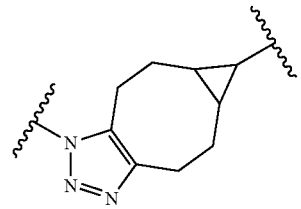, |
| 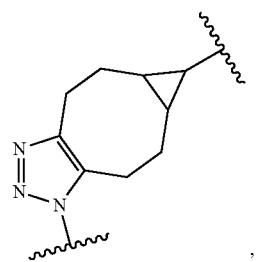 [SMILES: *C1C2CCc3nnn(*)c3CCC12], | 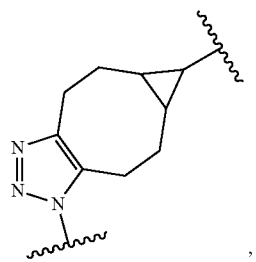 [SMILES: *C1C2CCc3nnn(*)c3CCC12], |
| 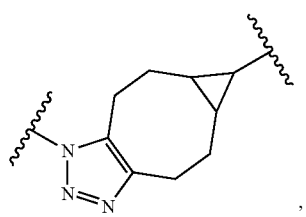 [SMILES: *C1C2CCc3nnn(*)c3CCC12], | 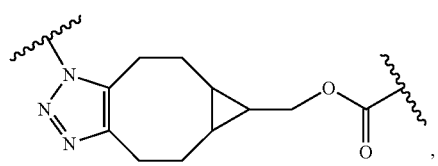 [SMILES: *C(=O)OCC1C2CCc3nnn(*)c3CCC21], |
| 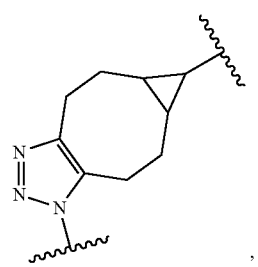 [SMILES: *C1C2CCc3nnn(*)c3CCC12], | 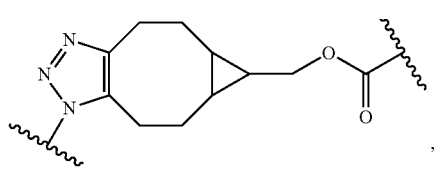 [SMILES: *C(=O)OCC1C2CCc3nnn(*)c3CCC21], |
| | 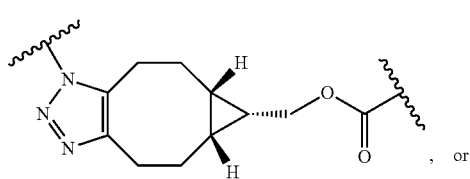 [SMILES: *C(=O)OC[C@@H]1[C@@H]2CCc3nnn(*)c3CC[C@@H]21], or |
| | 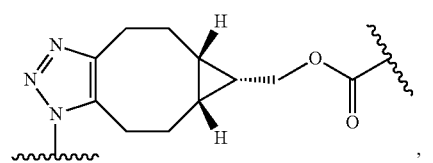 [SMILES: *C(=O)OC[C@@H]1[C@@H]2CCc3c(nnn3*)CC[C@@H]21], |

TABLE R-continued

| RG¹ | RG² |
|---|---|
| (structure) | (structure), or |
| (structure) | (structure) |
| (structure) | (structure), or |
| (structure) | (structure), |
| (structure) | (structure), or |

TABLE R-continued

| RG¹ | RG² |
|---|---|

TABLE R-continued

| RG¹ | RG² |
|---|---|
| (structure: triazole-fused cyclooctane with cyclopropane-CH₂-O-C(=O)- linker) | (structure: dibenzazocine fused with triazole) , |
| (structure: triazole-fused cyclooctane with cyclopropane (H,H stereochem)-CH₂-O-C(=O)- linker) , or | |
| (structure: triazole-fused cyclooctane with cyclopropane (H,H stereochem)-CH₂-O-C(=O)- linker) , | |
| (structure: triazole-fused cyclooctane with cyclopropane-CH₂-O-C(=O)- linker) , | (structure: dibenzazocine-triazole with N-C(=O)-CH₂CH₂-C(=O)- linker) , or |
| (structure: triazole-fused cyclooctane with cyclopropane-CH₂-O-C(=O)- linker) , | (structure: dibenzazocine-triazole with N-C(=O)-CH₂CH₂-C(=O)- linker) , |
| (structure: triazole-fused cyclooctane with cyclopropane (H,H stereochem)-CH₂-O-C(=O)- linker) , or | |
| (structure: triazole-fused cyclooctane with cyclopropane (H,H stereochem)-CH₂-O-C(=O)- linker) , | |

TABLE R-continued

| RG¹ | RG² |
|---|---|

TABLE R-continued
| RG[1] | RG[2] |
|---|---|
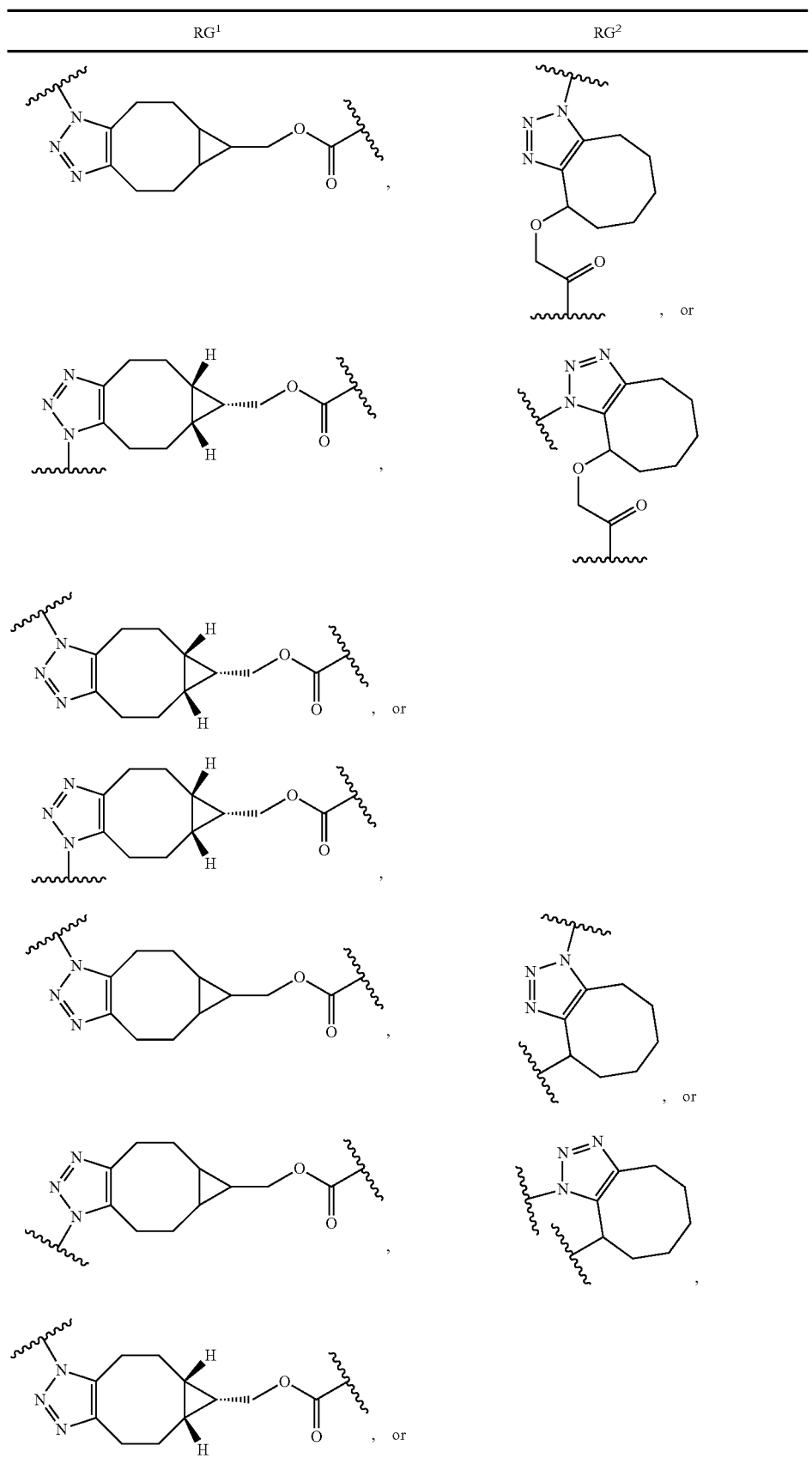

TABLE R-continued

| RG¹ | RG² |
|---|---|
| (structure) | |
| (structure) | (structure), or |
| (structure) | (structure), |
| (structure), or | |
| (structure), | |
| (structure) | (structure), or |
| (structure) | (structure), |
| (structure), or | |

TABLE R-continued

| RG¹ | RG² |
|---|---|
| (structure) | |
| (structure) | (structure) |
| (structure) | |
| (structure), or | |
| (structure) | |
| (structure), or | (structure), or |
| (structure) | (structure), |

TABLE R-continued

| RG¹ | RG² |
|---|---|
| (structure), or | (structure), or |
| (structure) | (structure), |
| (structure), or | (structure), |
| (structure) | (structure), |
| (structure), or | (structure), |

TABLE R-continued

| RG¹ | RG² |
|---|---|

TABLE R-continued

| RG¹ | RG² |
|---|---|

TABLE R-continued

| RG¹ | RG² |
|---|---|
| [triazole fused cyclooctane with -O-CH2-C(O)- linker], or | [succinimide (pyrrolidine-2,5-dione)], |
| [triazole fused cyclooctane with -O-CH2-C(O)- linker] | |
| [triazole fused cyclooctane], or | [dibenzo-triazole-azocine], or |
| [triazole fused cyclooctane], | [benzo-pyridо-triazole-azocine], |
| [triazole fused cyclooctane], or | [dibenzo-triazole-azocine with -C(O)-CH2CH2-C(O)- linker], or |

TABLE R-continued

| RG¹ | RG² |
|---|---|

TABLE R-continued

| RG¹ | RG² |
|---|---|

TABLE R-continued
| RG¹ | RG² |
|---|---|
| 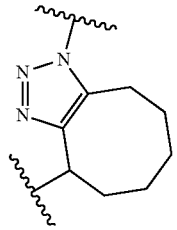 , or 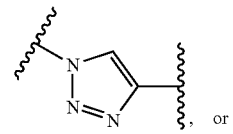 [SMILES: *c1cn(*)nn1] , | 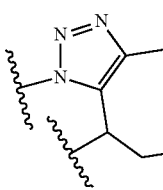 , or 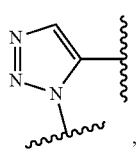 , |
| 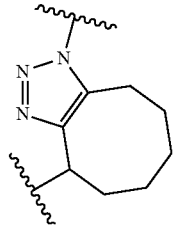 , or 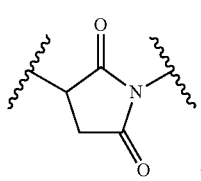 , | 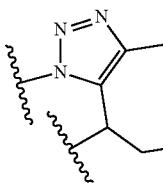 , |
| 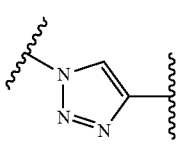 , or 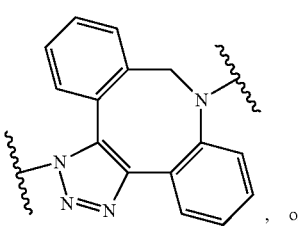 | 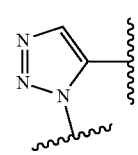 , or 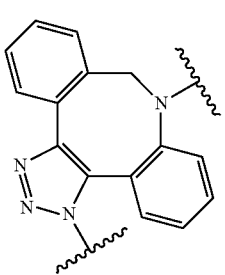 , |

TABLE R-continued

| RG¹ | RG² |
|---|---|
| [1,2,3-triazole linker] , or | [dibenzocyclooctyne-triazole with succinyl linker] , or |
| [1,2,3-triazole linker] | [dibenzocyclooctyne-triazole with succinyl linker] , |
| [1,2,3-triazole linker] , or | [bicyclononyne-triazole] , |
| [1,2,3-triazole linker] | [bicyclononyne-triazole] , |
| [1,2,3-triazole linker] , or | [bicyclononyne-triazole with methylene ester linker] , |
| [1,2,3-triazole linker] | [bicyclononyne-triazole with methylene ester linker] , |
|  | [bicyclononyne-triazole with methylene ester linker, stereochemistry shown] , or |

TABLE R-continued
| RG¹ | RG² |
|---|---|
| | 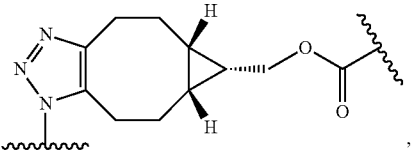 [SMILES: *C(=O)OC[C@@H]1[C@@H]2CCc3c(nnn3*)CC[C@@H]21] , |
| 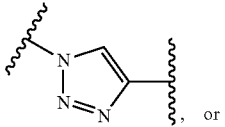 [SMILES: *c1cn(*)nn1] , or |  , or |
|  , | 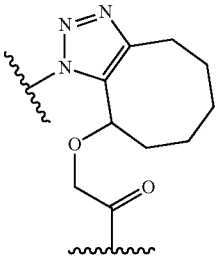 [SMILES: *C(=O)COC1CCCCCc2nnn(*)c21] , |
| 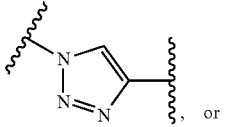 [SMILES: *c1cn(*)nn1] , or | 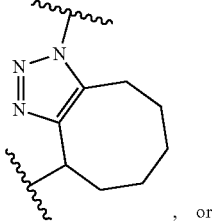 [SMILES: *C1CCCCCc2c1nnn2*] , or |
| 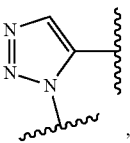 , | 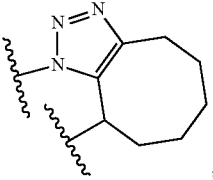 , |
| 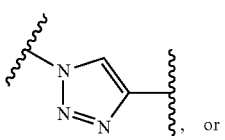 [SMILES: *c1cn(*)nn1] , or | 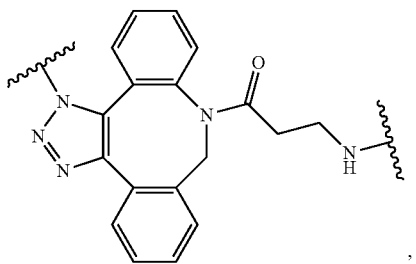 , or |

TABLE R-continued

| RG¹ | RG² |
|---|---|
| (triazole) | (dibenzotriazocine-propanamide-NH) |
| (triazole) , or | (triazole) , or |
| (triazole) | (triazole) |
| (triazole) , or | (succinimide) |
| (triazole) | |
| (succinimide) | (dibenzotriazocine) , or |
| | (dibenzotriazocine) |

TABLE R-continued

| RG¹ | RG² |
|---|---|
| [structure: succinimide] | [structure: dibenzocyclooctyne-triazole with amide-ketone linker], or [structure: isomeric dibenzocyclooctyne-triazole with amide-ketone linker], |
| [structure: succinimide] | [structure: bicyclononyne-triazole], [structure: bicyclononyne-triazole isomer], |
| [structure: succinimide] | [structure: bicyclononyne-triazole with methylene ester], [structure: bicyclononyne-triazole with methylene ester isomer], [structure: bicyclononyne-triazole with methylene ester, stereochemistry shown with H], or |

TABLE R-continued

| RG¹ | RG² |
|---|---|
| (structure) | (triazole-fused bicyclic with cyclopropane and ester linker) |
| succinimide | triazole-fused cyclooctane with O-CH₂-C(=O)- linker, or triazole-fused cyclooctane with O-CH₂-C(=O)- linker (isomer) |
| succinimide | triazole-fused cyclooctane, or triazole-fused cyclooctane (isomer) |
| succinimide | dibenzocyclooctyne-triazole with amide-NH linker, or |

TABLE R-continued
| RG¹ | RG² |
|---|---|
| 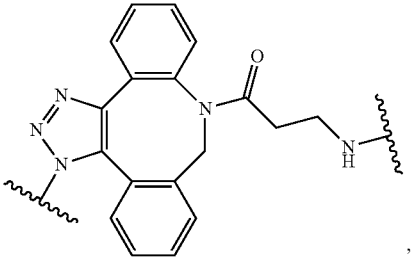 [SMILES: *NCCC(=O)N1Cc2ccccc2-c2c(nnn2*)-c2ccccc21] | 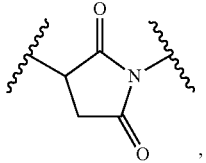 [SMILES: *C1CC(=O)N(*)C1=O] , |
| 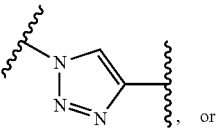 [SMILES: *c1cn(*)nn1] , | 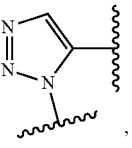 , or 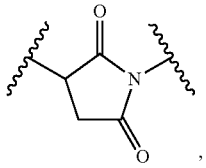 [SMILES: *C1CC(=O)N(*)C1=O] , |
| 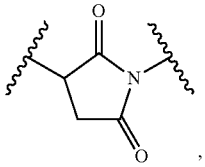 [SMILES: *C1CC(=O)N(*)C1=O] , | 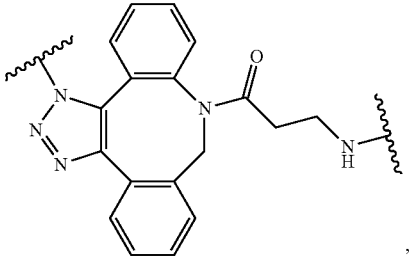 , |
| 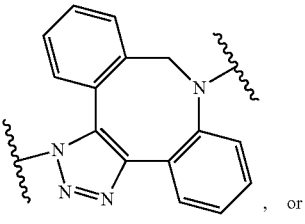 [SMILES: *N1Cc2ccccc2-c2c(nnn2*)-c2ccccc21] , or | 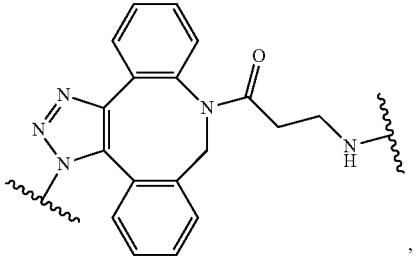 [SMILES: *NCCC(=O)N1Cc2ccccc2-c2c(nnn2*)-c2ccccc21] , or |
| 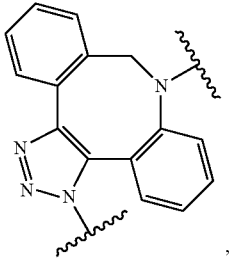 [SMILES: *N1Cc2ccccc2-c2nnn(*)c2-c2ccccc21] , or | 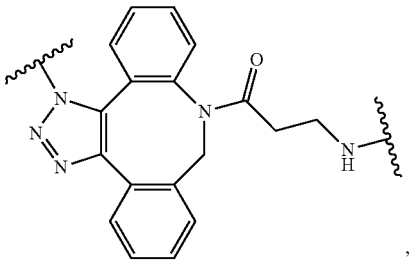 , or |
| 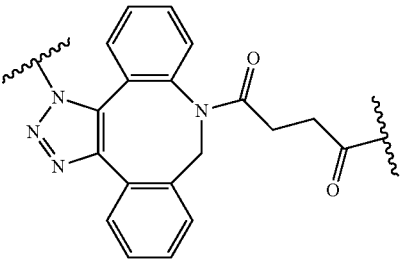 , or | |

TABLE R-continued

| RG¹ | RG² |
|---|---|

TABLE R-continued

| RG¹ | RG² |
|---|---|
| | (chemical structure), |
| (chemical structure), | (chemical structure), or |
| (chemical structure), | (chemical structure), or |
| (chemical structure), or | (chemical structure), or |
| (chemical structure), | |
| (chemical structure), or | (chemical structure), or |

TABLE R-continued

| RG¹ | RG² |
|---|---|

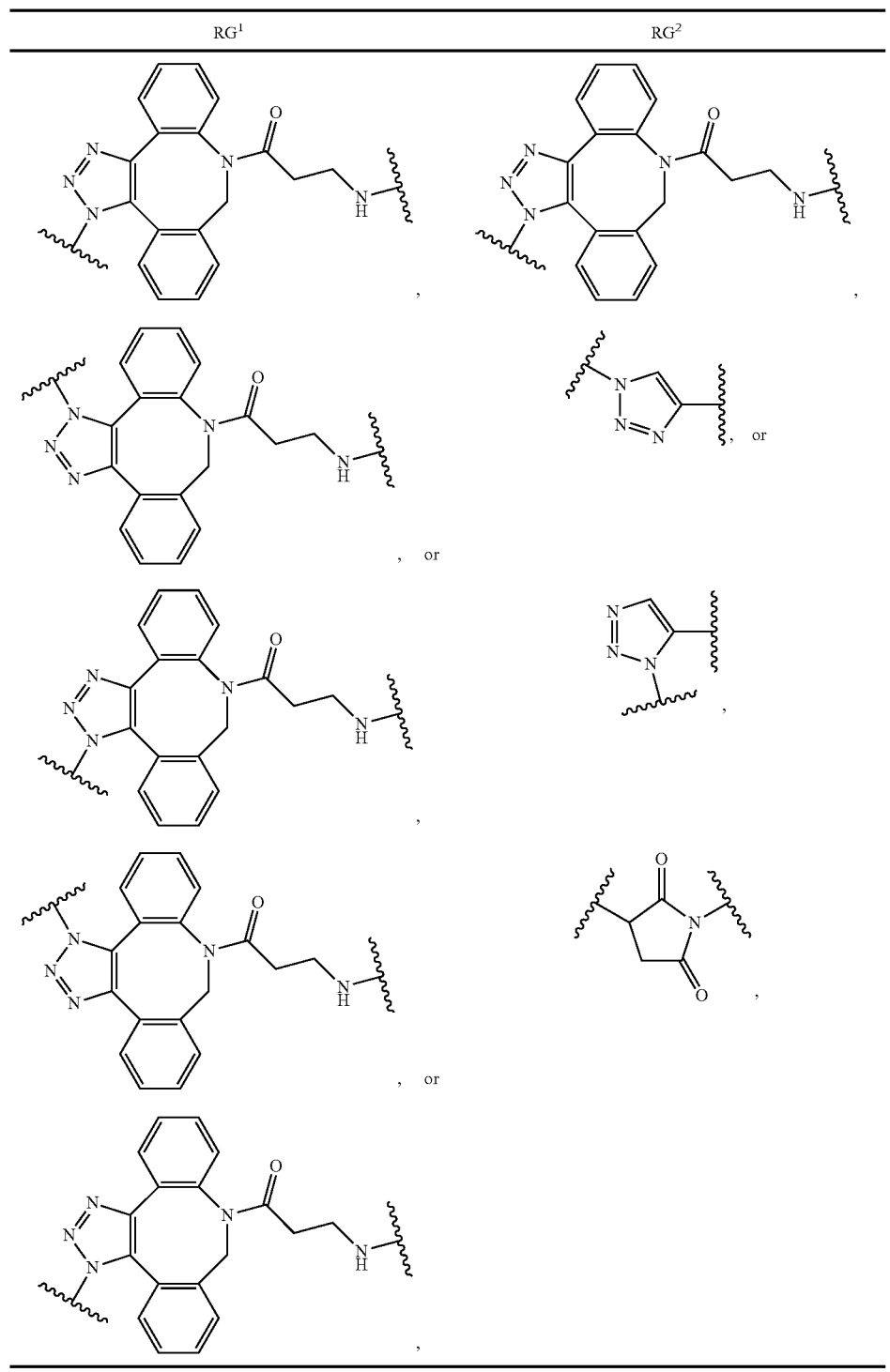

wherein the

indicates the atom through which the RG¹ or RG² is bonded to the adjacent groups in the formula.

In some instances, for any compound of Formula (I), Formula (II), Formula (III), Formula (IV), Formula (IVa), Formula (IVb), Formula (IVc), Formula (Va), Formula (Vb), Formula (Vc), or Formula (Vd), HG is is —$(CH_2)_{1-5}SO_3H$, —$(CH_2)_n$—NH—$(CH_2)_{1-5}SO_3H$, —$(CH_2)_n$—C(O)NH—$(CH_2)_{1-5}SO_3H$, —$(CH_2CH_2O)_m$—C(O)NH—$(CH_2)_{1-5}SO_3H$, —$(CH_2)_n$—N($(CH_2)_{1-5}C(O)NH(CH_2)_{1-5}SO_3H)_2$, —$(CH_2)_n$—C(O)N($(CH_2)_{1-5}C(O)NH(CH_2)_{1-5}SO_3H)_2$, or —$(CH_2CH_2O)_m$—C(O)N($(CH_2)_{1-5}C(O)NH(CH_2)_{1-5}$ $SO_3H)_2$, wherein n is 1, 2, 3, 4, or 5, and m is 1, 2, 3, 4, or 5. In one embodiment, HG is —$(CH_2)_{1-5}SO_3H$. In another embodiment, HG is —$(CH_2)_n$—NH—$(CH_2)_{1-5}SO_3H$, wherein n is 1, 2, 3, 4, or 5. In another embodiment, HG is —$(CH_2)_n$—C(O)NH—$(CH_2)_{1-5}SO_3H$, wherein n is 1, 2, 3, 4, or 5. In another embodiment, HG is —$(CH_2CH_2O)_m$—C(O)NH—$(CH_2)_{1-5}SO_3H$, wherein m is 1, 2, 3, 4, or 5. In another embodiment, HG is —$(CH_2)_n$—N($(CH_2)_{1-5}C(O)NH(CH_2)_{1-5}SO_3H)_2$, wherein n is 1, 2, 3, 4, or 5. In another embodiment, HG is —$(CH_2)_n$—C(O)N($(CH_2)_{1-5}C(O)NH(CH_2)_{1-5}SO_3H)_2$, wherein n is 1, 2, 3, 4, or 5. In another embodiment, HG is —$(CH_2CH_2O)_m$—C(O)N($(CH_2)_{1-5}C(O)NH(CH_2)_{1-5}SO_3H)_2$, wherein m is 1, 2, 3, 4, or 5.

In some instances, for any compound of Formula (I), Formula (II), Formula (III), Formula (IV), Formula (IVa), Formula (IVb), Formula (IVc), Formula (Va), Formula (Vb), Formula (Vc), or Formula (Vd), HG is is —$(CH_2)_{1-5}PO_3H$, —$(CH_2)_n$—NH—$(CH_2)_{1-5}PO_3H$, —$(CH_2)_n$—C(O)NH—$(CH_2)_{1-5}PO_3H$, —$(CH_2CH_2O)_m$—C(O)NH—$(CH_2)_{1-5}PO_3H$, —$(CH_2)_n$—N($(CH_2)_{1-5}C(O)NH(CH_2)_{1-5}PO_3H)_2$, —$(CH_2)_n$—C(O)N($(CH_2)_{1-5}C(O)NH(CH_2)_{1-5}PO_3H)_2$, or —$(CH_2CH_2O)_m$—C(O)N($(CH_2)_{1-5}C(O)NH(CH_2)_{1-5}PO_3H)_2$, wherein n is 1, 2, 3, 4, or 5, and m is 1, 2, 3, 4, or 5. In one embodiment, HG is —$(CH_2)_{1-5}PO_3H$. In another embodiment, HG is —$(CH_2)_n$—NH—$(CH_2)_{1-5}PO_3H$, wherein n is 1, 2, 3, 4, or 5. In another embodiment, HG is —$(CH_2)_n$—C(O)NH—$(CH_2)_{1-5}PO_3H$, wherein n is 1, 2, 3, 4, or 5. In another embodiment, HG is —$(CH_2CH_2O)_m$—C(O)NH—$(CH_2)_{1-5}PO_3H$, wherein m is 1, 2, 3, 4, or 5. In another embodiment, HG is —$(CH_2)_n$—N($(CH_2)_{1-5}C(O)NH(CH_2)_{1-5}PO_3H)_2$, wherein n is 1, 2, 3, 4, or 5. In another embodiment, HG is —$(CH_2)_n$—C(O)N($(CH_2)_{1-5}C(O)NH(CH_2)_{1-5}PO_3H)_2$, wherein n is 1, 2, 3, 4, or 5. In another embodiment, HG is —$(CH_2CH_2O)_m$—C(O)N($(CH_2)_{1-5}C(O)NH(CH_2)_{1-5}PO_3H)_2$, wherein m is 1, 2, 3, 4, or 5.

In some instances, for any compound of Formula (I), Formula (II), Formula (III), Formula (IV), Formula (IVa), Formula (IVb), Formula (IVc), Formula (Va), Formula (Vb), Formula (Vc), or Formula (Vd), HG is is —$(CH_2)_{1-5}N^+(R^M)_3$, —$(CH_2)_n$—NH—$(CH_2)_{1-5}N^+(R^M)_3$, —$(CH_2)_n$—C(O)NH—$(CH_2)_{1-5}N^+(R^M)_3$, —$(CH_2CH_2O)_m$—C(O)NH—$(CH_2)_{1-5}N^+(R^M)_3$, —$(CH_2)_n$—N($(CH_2)_{1-5}C(O)NH(CH_2)_{1-5}N^+(R^M)_3)_2$, —$(CH_2)_n$—C(O)N($(CH_2)_{1-5}C(O)NH(CH_2)_{1-5}N^+(R^M)_3)_2$, or —$(CH_2CH_2O)_m$—C(O)N($(CH_2)_{1-5}C(O)NH(CH_2)_{1-5}N^+(R^M)_3)_2$, wherein n is 1, 2, 3, 4, or 5, m is 1, 2, 3, 4, or 5, and $R^M$, at each occurrence, is independently H, $C_{1-6}$alkyl, $C_{3-7}$cycloalkyl or $C_{1-6}$alkyl-$C_{3-7}$cycloalkyl or, two $R^M$ together with the nitrogen atom to which they are attached, form a 3-7-membered heterocycloalkyl ring. In one embodiment, HG is —$(CH_2)_{1-5}N^+(R^M)_3$. In another embodiment, HG is —$(CH_2)_n$—NH—$(CH_2)_{1-5}N^+(R^M)_3$, wherein n is 1, 2, 3, 4, or 5. In another embodiment, HG is —$(CH_2)_n$—C(O)NH—$(CH_2)_{1-5}N^+(R^M)_3$, wherein n is 1, 2, 3, 4, or 5. In another embodiment, HG is —$(CH_2CH_2O)_m$—C(O)NH—$(CH_2)_{1-5}N^+(R^M)_3$, wherein m is 1, 2, 3, 4, or 5. In another embodiment, HG is —$(CH_2)_n$—N($(CH_2)_{1-5}C(O)NH(CH_2)_{1-5}N^+(R^M)_3)_2$, wherein n is 1, 2, 3, 4, or 5. In another embodiment, HG is —$(CH_2)_n$—C(O)N($(CH_2)_{1-5}C(O)NH(CH_2)_{1-5}N^+(R^M)_3)_2$, wherein n is 1, 2, 3, 4, or 5. In another embodiment, HG is —$(CH_2CH_2O)_m$—C(O)N($(CH_2)_{1-5}C(O)NH(CH_2)_{1-5}N^+(R^M)_3)_2$, wherein m is 1, 2, 3, 4, or 5.

In some instances, for any compound of Formula (I), Formula (II), Formula (III), Formula (IV), Formula (IVa), Formula (IVb), Formula (IVc), Formula (Va), Formula (Vb), Formula (Vc), or Formula (Vd), HG is is —$(CH_2)_{1-5}N^+Me_3$, —$(CH_2)_n$—NH—$(CH_2)_{1-5}N^+Me_3$, —$(CH_2)_n$—C(O)NH—$(CH_2)_{1-5}N^+Me_3$, —$(CH_2CH_2O)_m$—C(O)NH—$(CH_2)_{1-5}N^+Me_3$, —$(CH_2)_n$—N($(CH_2)_{1-5}C(O)NH(CH_2)_{1-5}N^+Me_3)_2$, —$(CH_2)_n$—C(O)N($(CH_2)_{1-5}C(O)NH(CH_2)_{1-5}N^+Me_3)_2$, or —$(CH_2CH_2O)_m$—C(O)N($(CH_2)_{1-5}C(O)NH(CH_2)_{1-5}N^+Me_3)_2$, wherein n is 1, 2, 3, 4, or 5, and m is 1, 2, 3, 4, or 5. In one embodiment, HG is —$(CH_2)_{1-5}N^+Me_3$. In another embodiment, HG is —$(CH_2)_n$—NH—$(CH_2)_{1-5}N^+Me_3$, wherein n is 1, 2, 3, 4, or 5. In another embodiment, HG is —$(CH_2)_n$—C(O)NH—$(CH_2)_{1-5}N^+Me_3$, wherein n is 1, 2, 3, 4, or 5. In another embodiment, HG is —$(CH_2CH_2O)_m$—C(O)NH—$(CH_2)_{1-5}N^+Me_3$, wherein m is 1, 2, 3, 4, or 5. In another embodiment, HG is —$(CH_2)_n$—N($(CH_2)_{1-5}C(O)NH(CH_2)_{1-5}N^+Me_3)_2$, wherein n is 1, 2, 3, 4, or 5. In another embodiment, HG is —$(CH_2)_n$—C(O)N($(CH_2)_{1-5}C(O)NH(CH_2)_{1-5}N^+Me_3)_2$, wherein n is 1, 2, 3, 4, or 5. In another embodiment, HG is —$(CH_2CH_2O)_m$—C(O)N($(CH_2)_{1-5}C(O)NH(CH_2)_{1-5}N^+Me_3)_2$, wherein m is 1, 2, 3, 4, or 5.

In some instances, for any compound of Formula (I), Formula (II), Formula (III), Formula (IV), Formula (IVa), Formula (IVb), Formula (IVc), Formula (Va), Formula (Vb), Formula (Vc), or Formula (Vd), HG is

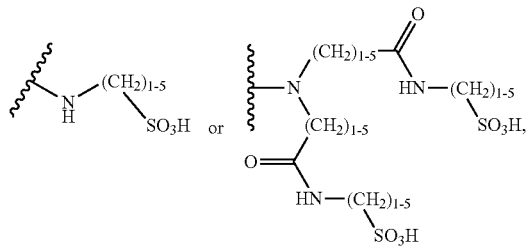 [SMILES: *NCS(=O)(=O)O ; *N(CC(=O)NCS(=O)(=O)O)CC(=O)NCS(=O)(=O)O]

or salts thereof, wherein the

indicates the atom through which the HG is bonded to the adjacent groups in the formula. In one instance HG is

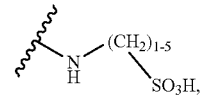

or salts thereof. In another instance, HG is

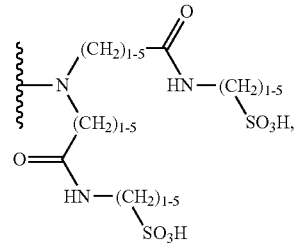 [SMILES: *N(CC(=O)NCS(=O)(=O)O)CC(=O)NCS(=O)(=O)O]

or salts thereof. In one instance HG is

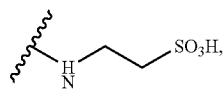 [SMILES: *NCCS(=O)(=O)O]

or salts thereof. In another instance, HG is

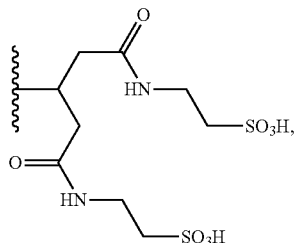

or salts thereof.

In some examples, for any compound of Formula (I), Formula (II), Formula (III), Formula (IV), Formula (IVa), Formula (IVb), Formula (IVc), Formula (Va), Formula (Vb), Formula (Vc), or Formula (Vd), HG is an amine, or salts thereof, for instance, a quarternary amine, e.g.,

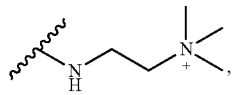

wherein the

indicates the atom through which the HG is bonded to the adjacent groups in the formula.

In other examples, for any compound of Formula (I), Formula (II), Formula (III), Formula (IV), Formula (IVa), Formula (IVb), Formula (IVc), Formula (Va), Formula (Vb), Formula (Vc), or Formula (Vd), HG is a phosphonic acid, or salts thereof, e.g.,

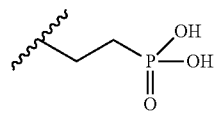 [SMILES: *CCP(=O)(O)O]

wherein the

indicates the atom through which the HG is bonded to the adjacent groups in the formula. In other examples, for any compound of Formula (I), Formula (II), Formula (III), Formula (IV), Formula (IVa), Formula (IVb), Formula (IVc), Formula (Va), Formula (Vb), Formula (Vc), or Formula (Vd), HG is a phosphonic acid, or salts thereof, e.g.,

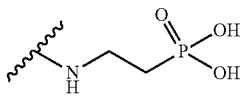 [SMILES: *NCCP(=O)(O)O]

wherein the

indicates the atom through which the HG is bonded to the adjacent groups in the formula.

In yet other examples, for any compound of Formula (I), Formula (II), Formula (III), Formula (IV), Formula (IVa), Formula (IVb), Formula (IVc), Formula (Va), Formula (Vb), Formula (Vc), or Formula (Vd), HG is a sugar residue, e.g.,

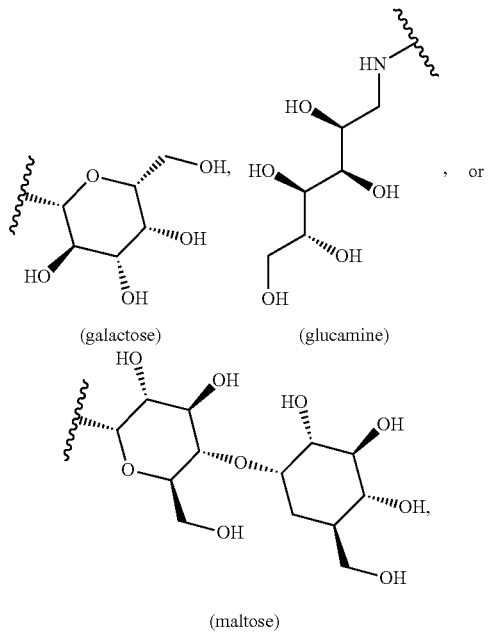

(galactose) (glucamine)

(maltose)

wherein the

indicates the atom through which the HG is bonded to the adjacent groups in the formula.

In some cases, for any compound of Formula (I), Formula (II), Formula (III), Formula (IV), Formula (IVa), Formula (IVb), Formula (IVc), Formula (Va), Formula (Vb), Formula (Vc), or Formula (Vd), $SP^1$ and $SP^2$ are independently, in each instance, absent, or selected from the group consisting of $C_{1-6}$ alkylene, —NH—, —C(O)—, (—CH$_2$—CH$_2$—O)$_e$, —NH—CH$_2$—CH$_2$—(—O—CH$_2$—CH$_2$)$_e$—C(O)—, —C(O)—(CH$_2$)$_u$—C(O)—, —C(O)—NH—(CH$_2$)$_v$—, polyglycine (e.g., ((glycine)$_4$-serine)$_f$, wherein subscript f is an integer from 1 to 6), and combinations thereof, wherein subscript e is an integer from 0 to 4, subscript u is an integer from 1 to 8, and subscript v is an integer from 1 to 8. In some instances, $SP^1$ and $SP^2$ are independently, in each instance, as shown in Table S.

TABLE S

| SP$^1$ | SP$^2$ |
|---|---|
| absent | absent |
| absent | C$_{1-6}$ alkylene, |
| absent | —NH—, |
| absent | —C(O)—, |
| absent | (—CH$_2$—CH$_2$—O)$_e$, |
| absent | —NH—CH$_2$—CH$_2$—(—O—CH$_2$—CH$_2$)$_e$-C(O)—, |
| absent | —C(O)—(CH$_2$)$_u$-C(O)—, |
| absent | —C(O)—NH—(CH$_2$)$_v$-, |
| absent | (glycine)$_4$-serine |
| C$_{1-6}$ alkylene, | absent |
| C$_{1-6}$ alkylene, | C$_{1-6}$ alkylene, |
| C$_{1-6}$ alkylene, | —NH—, |
| C$_{1-6}$ alkylene, | —C(O)—, |
| C$_{1-6}$ alkylene, | (—CH$_2$—CH$_2$—O)$_e$, |
| C$_{1-6}$ alkylene, | —NH—CH$_2$—CH$_2$—(—O—CH$_2$—CH$_2$)$_e$-C(O)—, |
| C$_{1-6}$ alkylene, | —C(O)—(CH$_2$)$_u$-C(O)—, |
| C$_{1-6}$ alkylene, | —C(O)—NH—(CH$_2$)$_v$-, |
| C$_{1-6}$ alkylene, | (glycine)$_4$-serine |
| NH—, | absent |
| NH—, | C$_{1-6}$ alkylene, |
| NH—, | —NH—, |
| NH—, | —C(O)—, |
| NH—, | (—CH$_2$—CH$_2$—O)$_e$, |
| NH—, | —NH—CH$_2$—CH$_2$—(—O—CH$_2$—CH$_2$)$_e$-C(O)—, |
| NH—, | —C(O—(CH$_2$)$_u$-C(O)—, |
| NH—, | —C(O)—NH—(CH$_2$)$_v$-, |
| NH—, | (glycine)$_4$-serine |
| —C(O)—, | absent |
| —C(O)—, | C$_{1-6}$ alkylene, |
| —C(O)—, | —NH—, |
| —C(O)—, | —C(O)—, |
| —C(O)—, | (—CH$_2$—CH$_2$—O)$_e$, |
| —C(O)—, | —NH—CH$_2$—CH$_2$—(—O—CH$_2$—CH$_2$)$_e$-C(O)—, |
| —C(O)—, | —C(O) —(CH$_2$)$_u$-C(O)—, |
| —C(O)—, | —C(O)—NH—(CH$_2$)$_v$-, |
| —C(O)—, | (glycine)$_4$-serine |
| (—CH$_2$—CH$_2$—O)$_e$, | absent |
| (—CH$_2$—CH$_2$—O)$_e$, | C$_{1-6}$ alkylene, |
| (—CH$_2$—CH$_2$—O)$_e$, | —NH—, |
| (—CH$_2$—CH$_2$—O)$_e$, | —C(O)—, |
| (—CH$_2$—CH$_2$—O)$_e$, | (—CH$_2$—CH$_2$—O)$_e$, |
| (—CH$_2$—CH$_2$—O)$_e$, | —NH—CH$_2$—CH$_2$—(—O—CH$_2$—CH$_2$)$_e$-C(O)—, |
| (—CH$_2$—CH$_2$—O)$_e$, | —C(O)—(CH$_2$)$_u$-C(O)—, |
| (—CH$_2$—CH$_2$—O)$_e$, | —C(O)—NH—(CH$_2$)$_v$-, |
| (—CH$_2$—CH$_2$—O)$_e$, | (glycine)$_4$-serine |
| —N—HCH$_2$—CH$_2$—(—O—CH$_2$—CH$_2$)$_e$-C(O)—, | absent |
| —N—HCH$_2$—CH$_2$—(—O—CH$_2$—CH$_2$)$_e$-C(O)—, | C$_{1-6}$ alkylene, |
| —N—HCH$_2$—CH$_2$—(—O—CH$_2$—CH$_2$)$_e$-C(O)—, | —NH—, |
| —N—HCH$_2$—CH$_2$—(—O—CH$_2$—CH$_2$)$_e$-C(O)—, | —C(O) —, |
| —N—HCH$_2$—CH$_2$—(—O—CH$_2$—CH$_2$)$_e$-C(O)—, | (—CH$_2$—CH$_2$—O)$_e$, |
| —N—HCH$_2$—CH$_2$—(—O—CH$_2$—CH$_2$)$_e$-C(O)—, | —NH—CH$_2$—CH$_2$—(—O—CH$_2$—CH$_2$)$_e$-C(O)—, |
| —N—HCH$_2$—CH$_2$—(—O—CH$_2$—CH$_2$)$_e$-C(O)—, | —C(O)—(CH$_2$)$_u$-C(O)—, |
| —N—HCH$_2$—CH$_2$—(—O—CH$_2$—CH$_2$)$_e$-C(O)—, | —C(O)—NH—(CH$_2$)$_v$-, |
| —N—HCH$_2$—CH$_2$—(—O—CH$_2$—CH$_2$)$_e$-C(O)—, | (glycine)$_4$-serine |
| —C(O)—(CH$_2$)$_u$-C(O)—, | absent |
| —C(O)—(CH$_2$)$_u$-C(O)—, | C$_{1-6}$ alkylene, |
| —C(O)—(CH$_2$)$_u$-C(O)—, | —NH—, |
| —C(O)—(CH$_2$)$_u$-C(O)—, | —C(O)—, |
| —C(O)—(CH$_2$)$_u$-C(O)—, | (—CH$_2$—CH$_2$—O)$_e$, |
| —C(O)—(CH$_2$)$_u$-C(O)—, | —NH—CH$_2$—CH$_2$—(—O—CH$_2$—CH$_2$)$_e$-C(O) —, |
| —C(O)—(CH$_2$)$_u$-C(O)—, | —C(O)—(CH$_2$)$_u$-C(O)—, |
| —C(O)—(CH$_2$)$_u$-C(O)—, | —C(O)—NH—(CH$_2$)$_v$-, |
| —C(O)—(CH$_2$)$_u$-C(O)—, | (glycine)$_4$-serine |
| —C(O)—NH—(CH$_2$)$_v$-, | absent |
| —C(O)—NH—(CH$_2$)$_v$-, | C$_{1-6}$ alkylene, |
| —C(O)—NH—(CH$_2$)$_v$-, | —NH—, |
| —C(O)—NH—(CH$_2$)$_v$-, | —C(O)—, |
| —C(O)—NH—(CH$_2$)$_v$-, | (—CH$_2$—CH$_2$—O)$_e$, |
| —C(O)—NH—(CH$_2$)$_v$-, | —NH—CH$_2$—CH$_2$—(—O—CH$_2$—CH$_2$)$_e$-C(O)—, |
| —C(O)—NH—(CH$_2$)$_v$-, | —C(O)—(CH$_2$)$_u$-C(O)—, |
| —C(O)—NH—(CH$_2$)$_v$-, | —C(O—NH—(CH$_2$)$_v$-, |
| —C(O)—NH—(CH$_2$)$_v$-, | (glycine)$_4$-serine |

Any combination of a row from Table R and a row from Table S may be present in a compound of Formula (I) described herein.
In some examples, for any compound of Formula (I), Formula (II), Formula (III), Formula (IV), Formula (IVa), Formula (IVb), Formula (IVc), Formula (Va), Formula (Vb), Formula (Vc), or Formula (Vd),
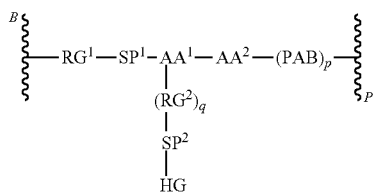
is selected from the group consisting of:
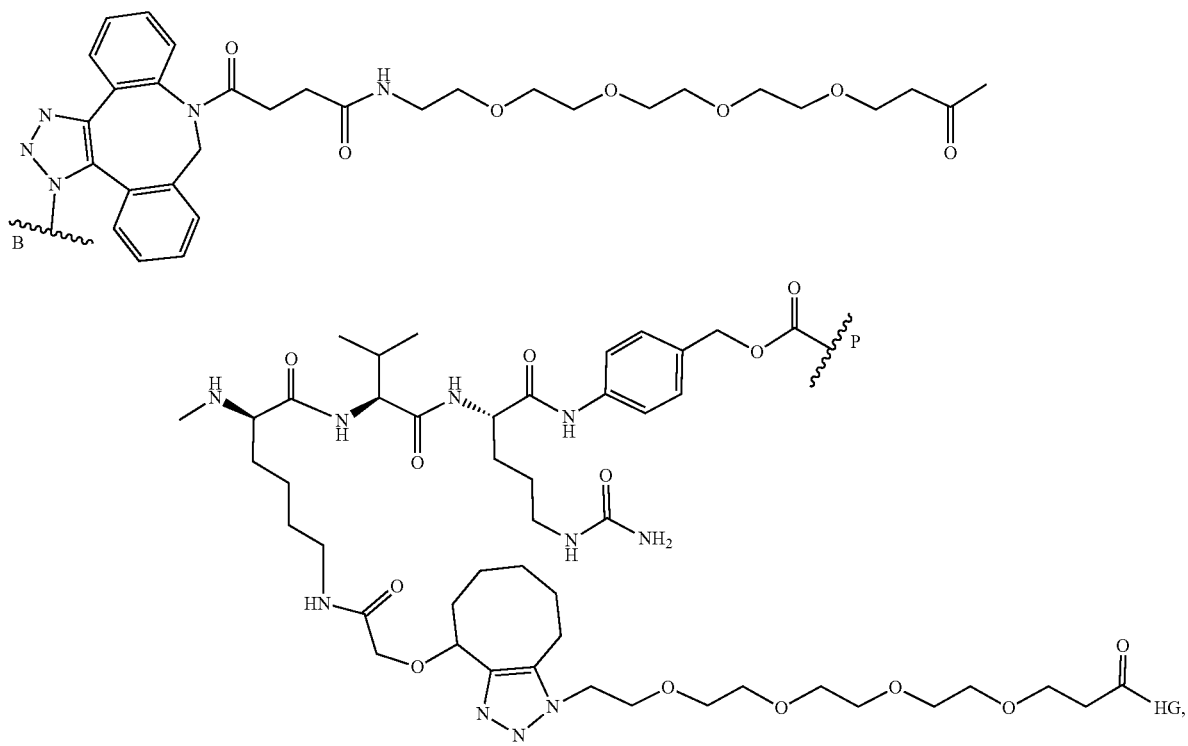

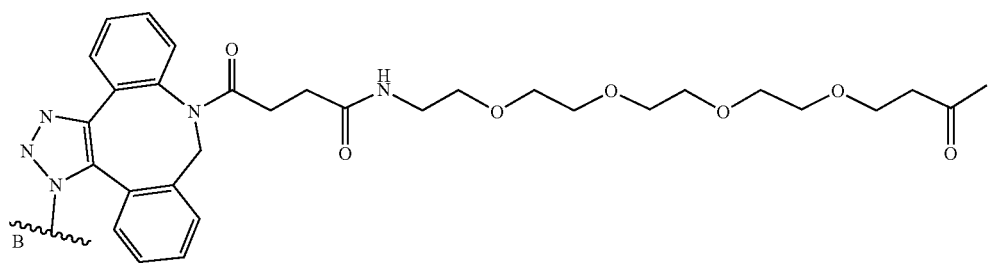
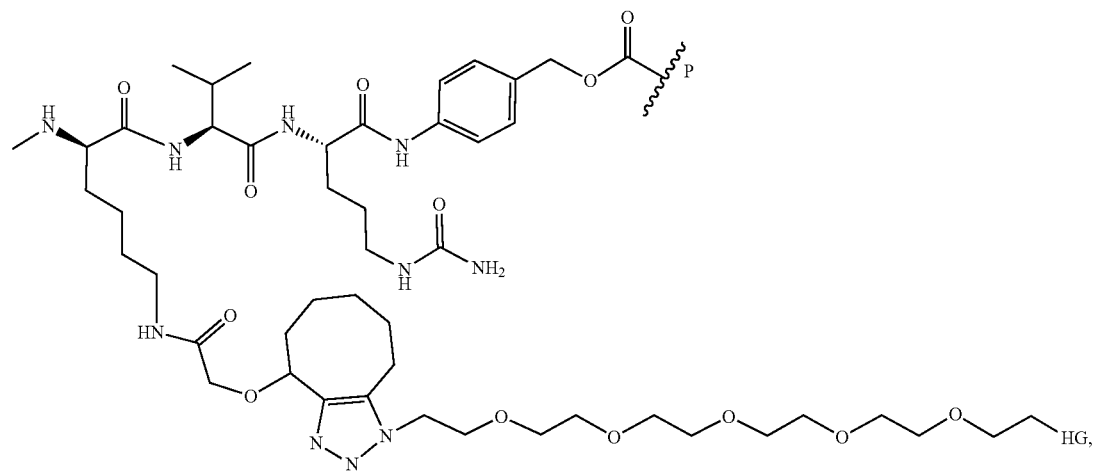
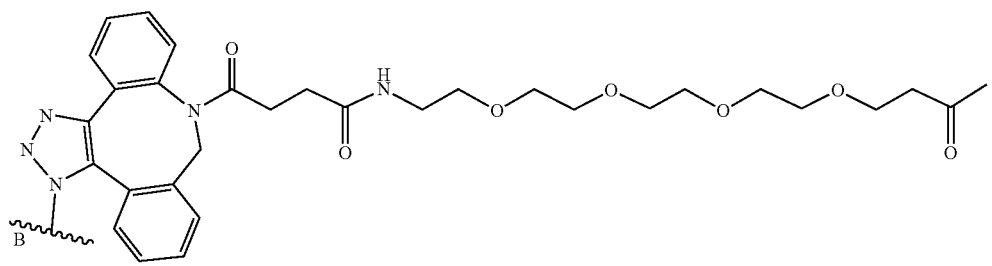
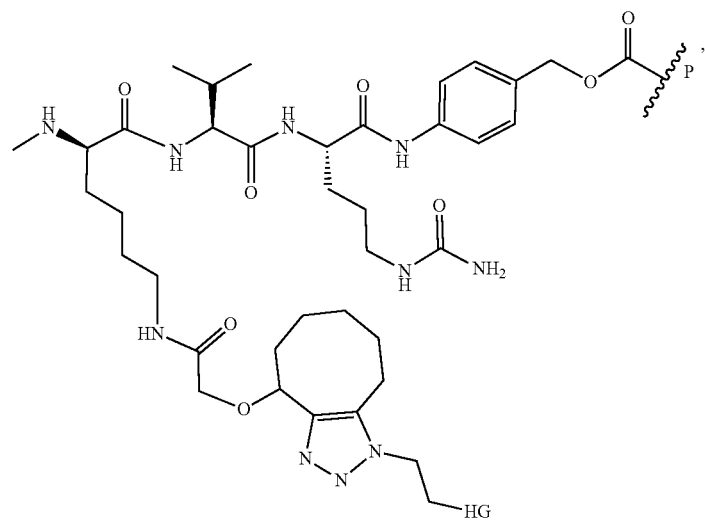

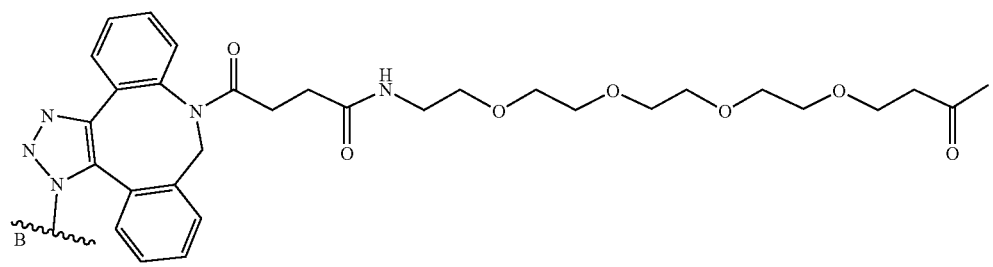
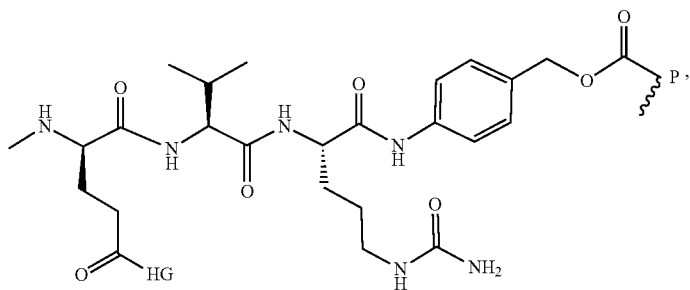
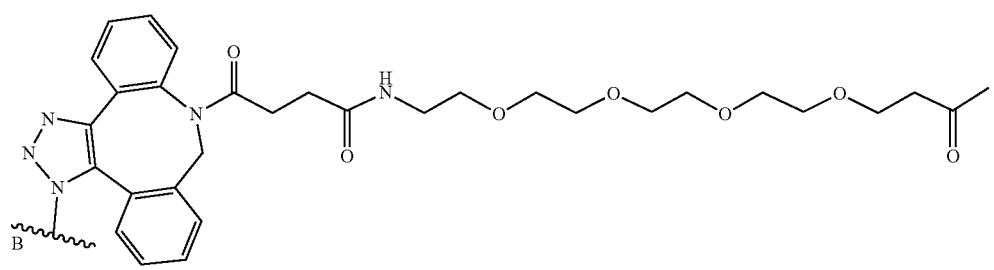
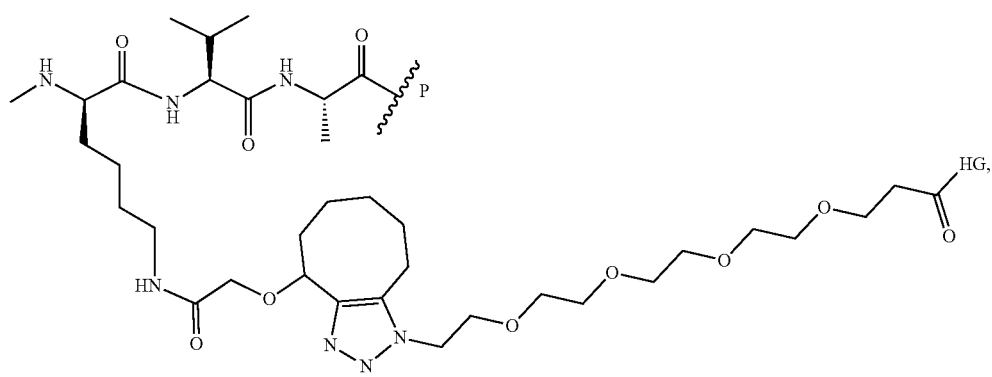

-continued
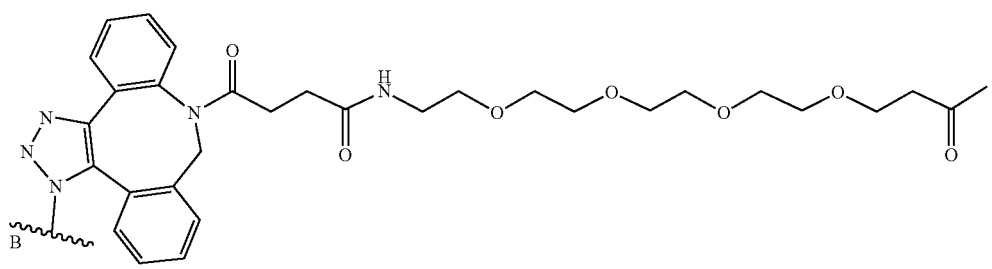
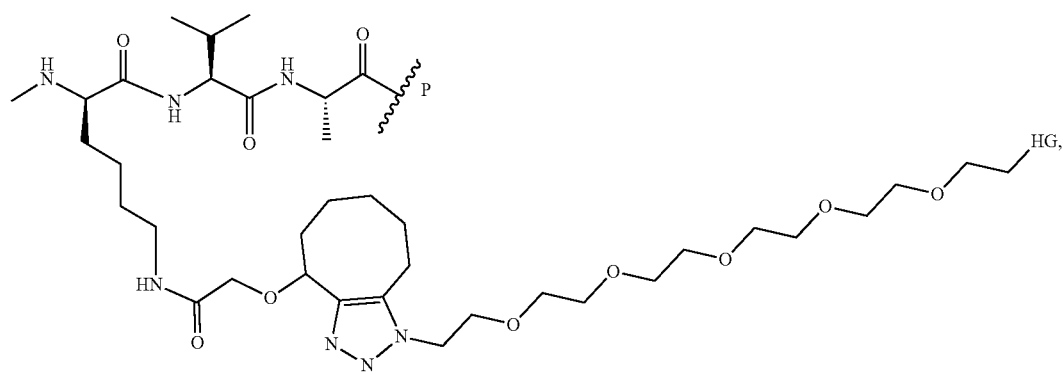
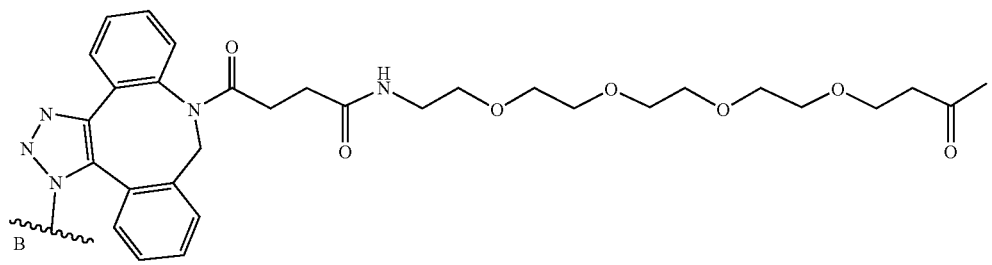
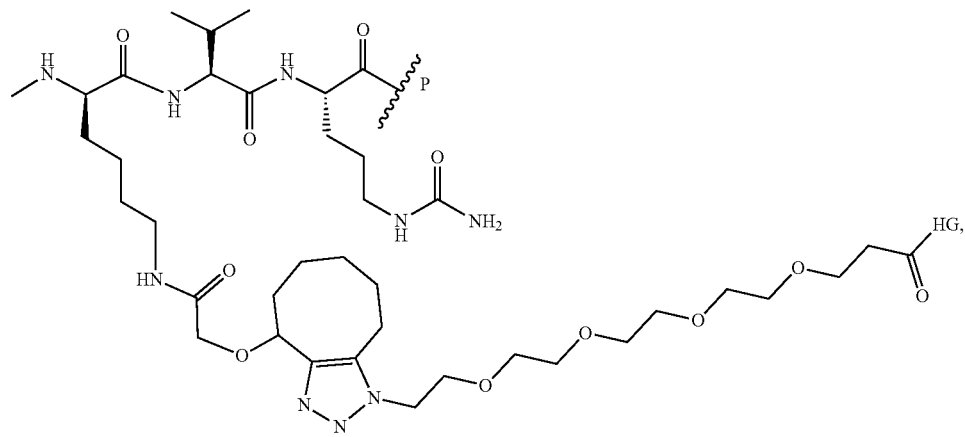

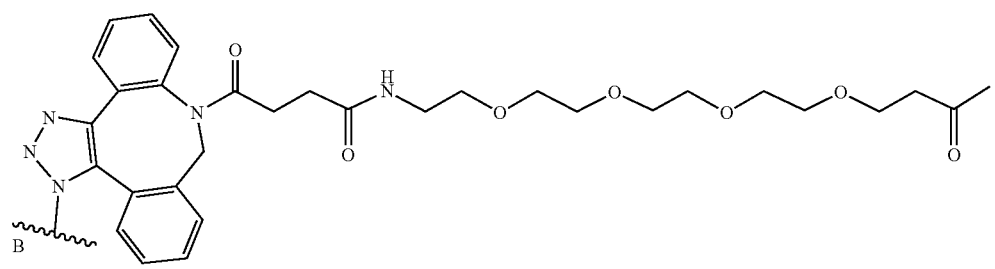
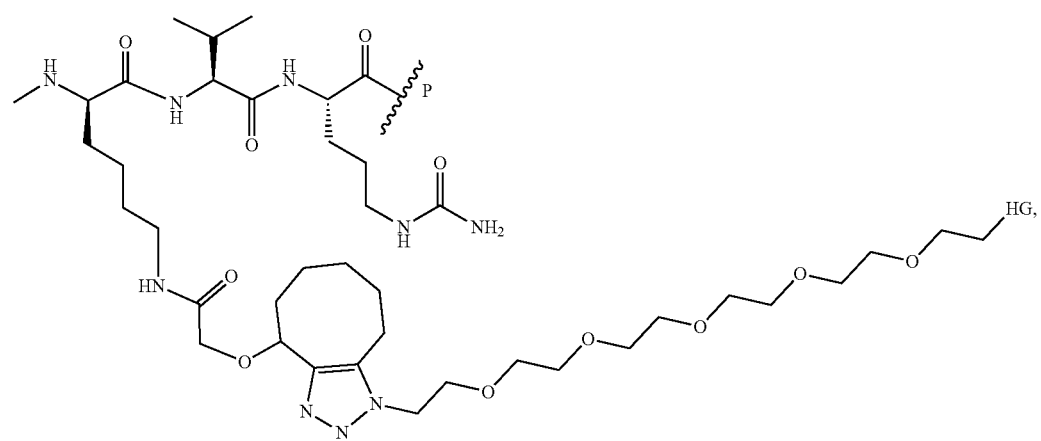
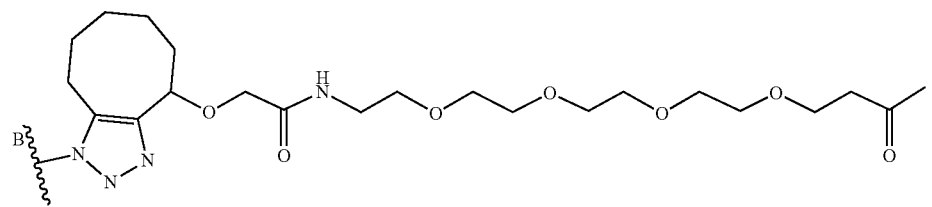
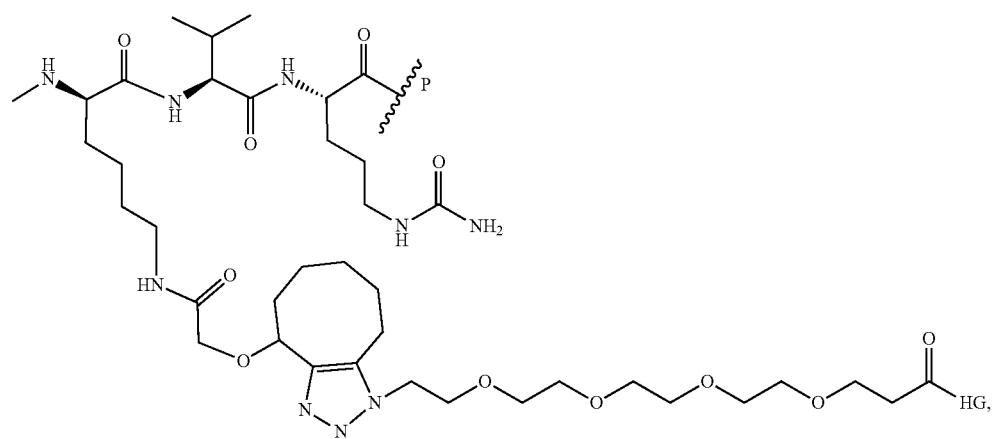

119
-continued
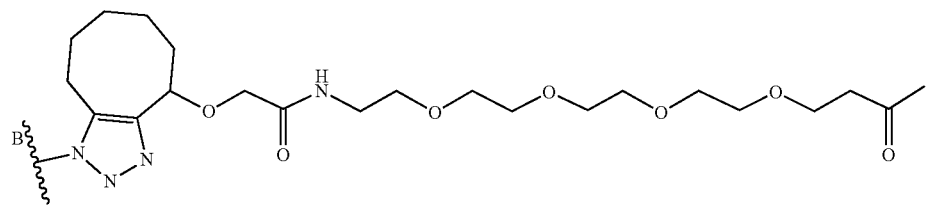
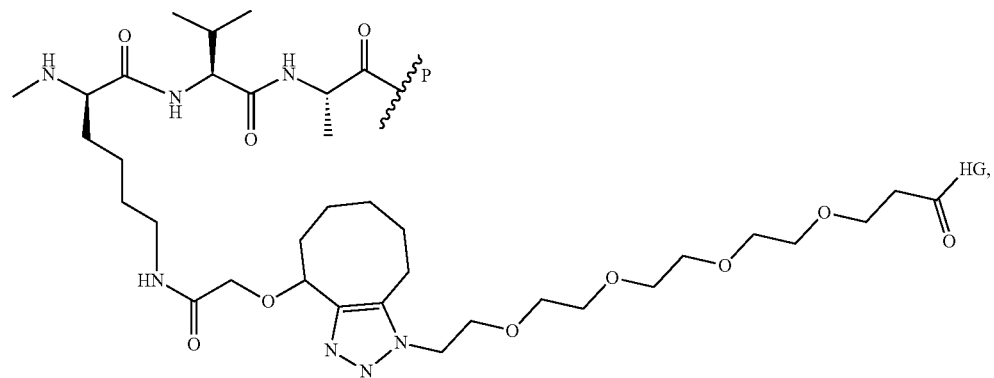
120
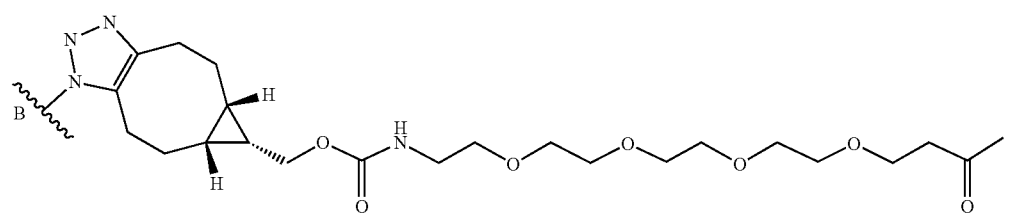
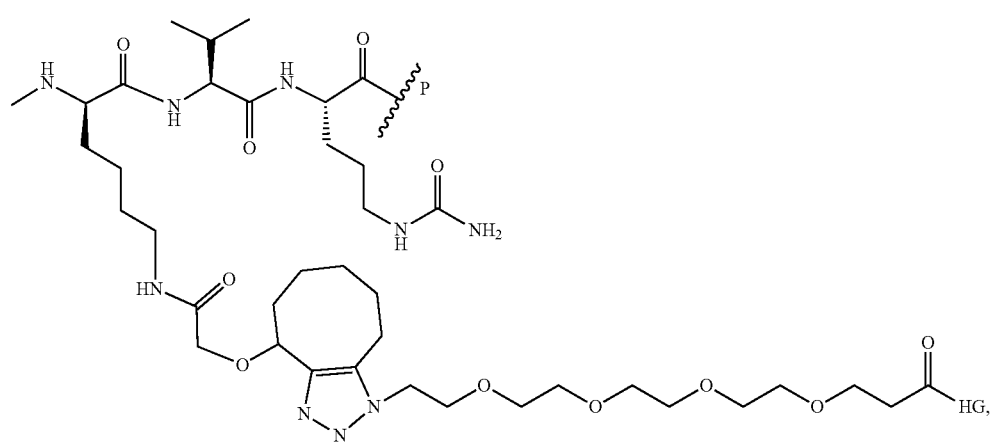

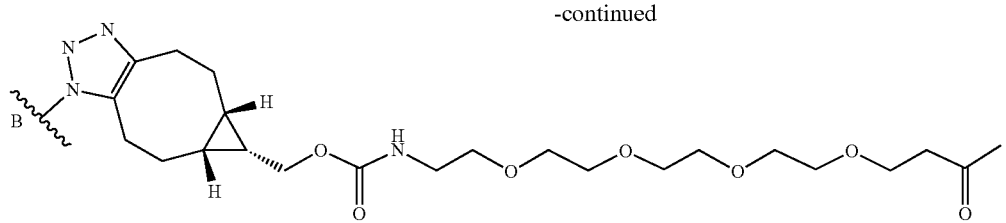
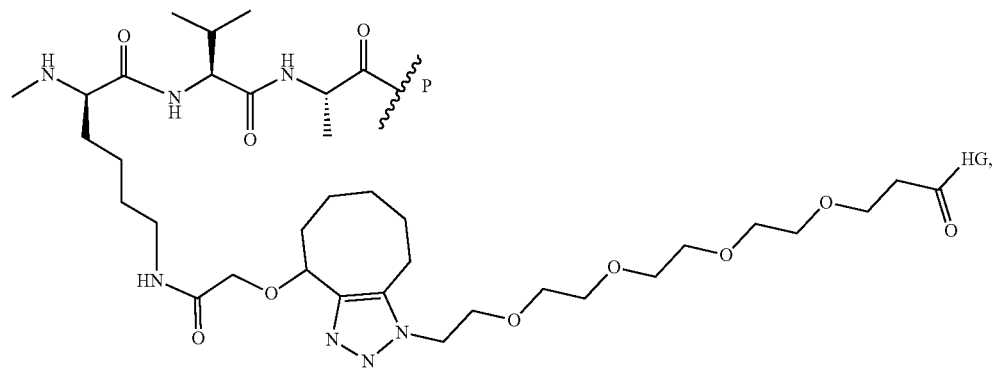
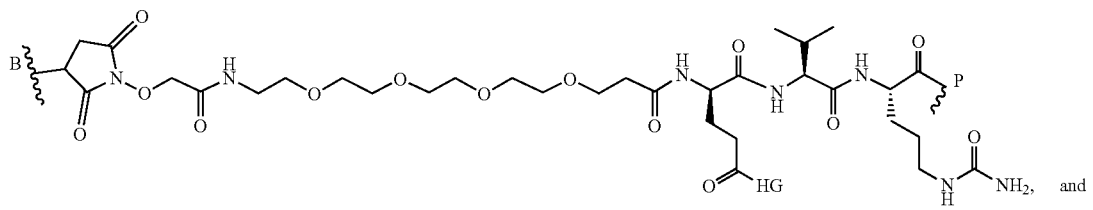
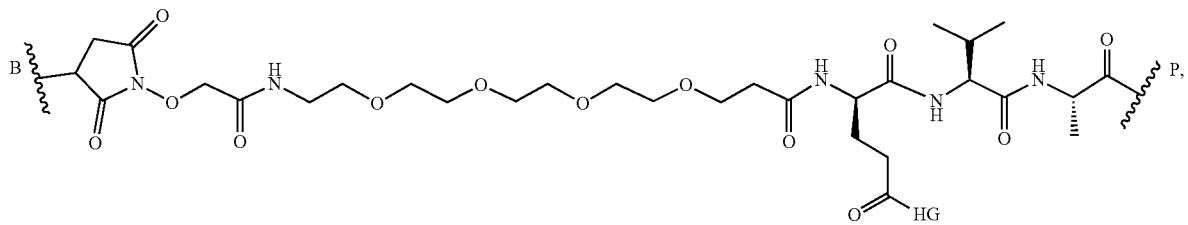
or a stereoisomeric form thereof, or a regioisomer thereof, or a mixture of regioisomers thereof, wherein each
is a bond to the binding agent; and each
is a bond to the payload residue.
In some examples, for any compound of Formula (I), Formula (II), Formula (III), Formula (IV), Formula (IVa), Formula (IVb), Formula (IVc), Formula (Va), Formula (Vb), Formula (Vc), or Formula (Vd),
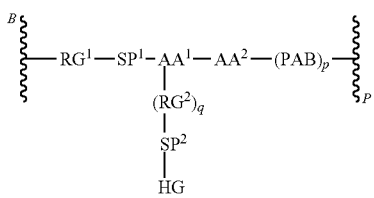

is selected from the group consisting of:
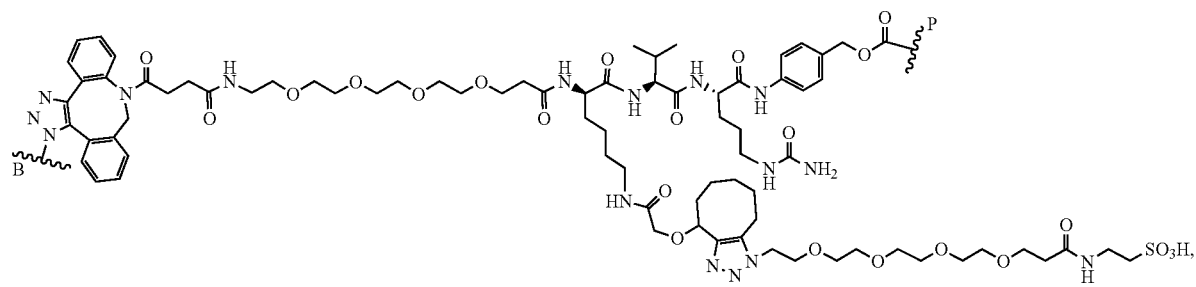
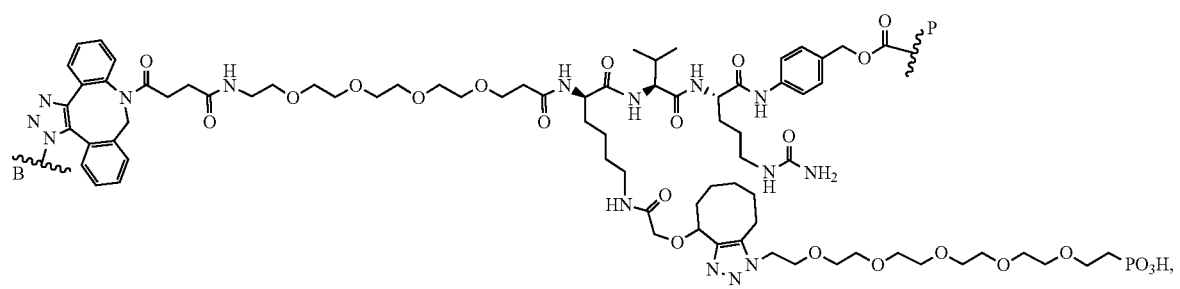
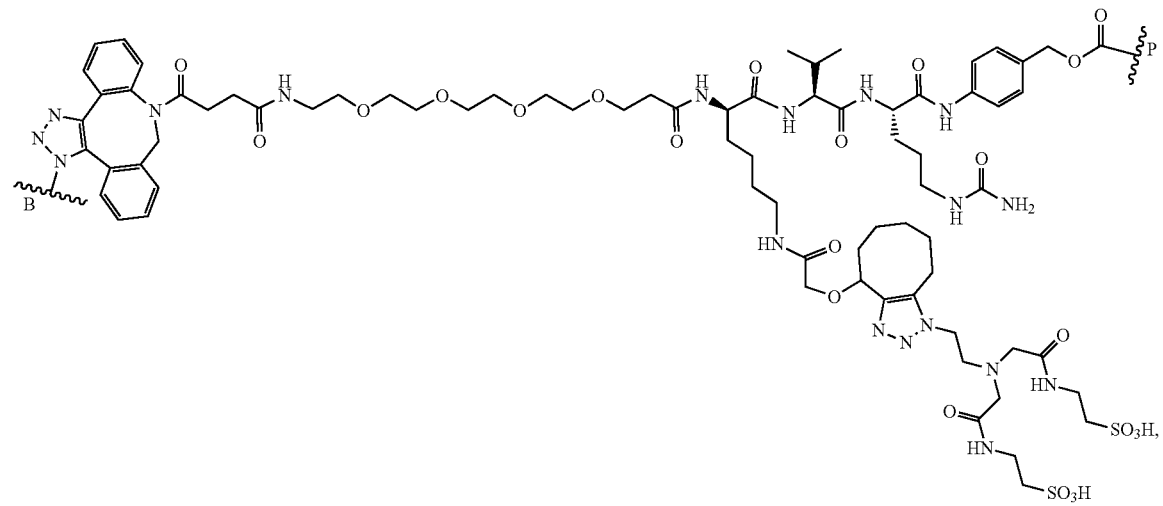
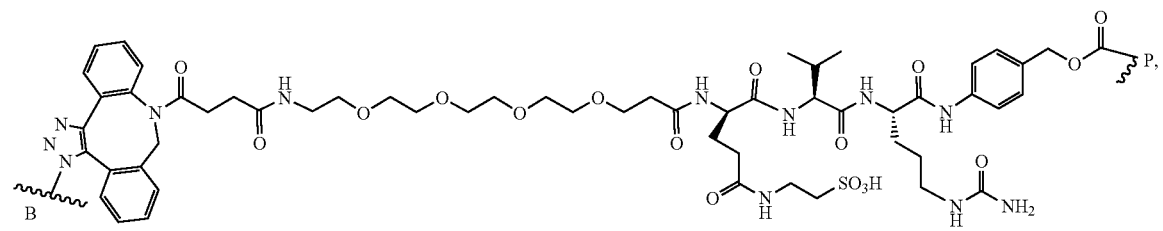

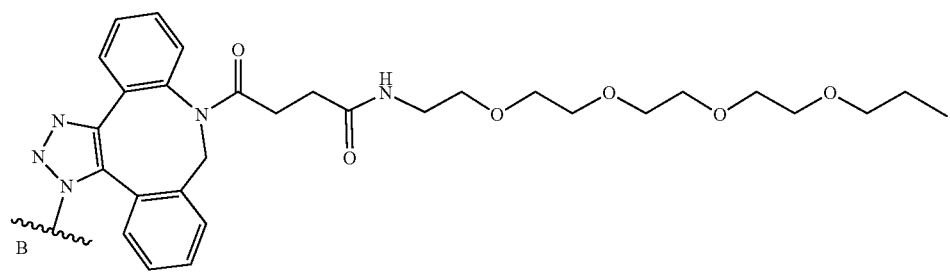
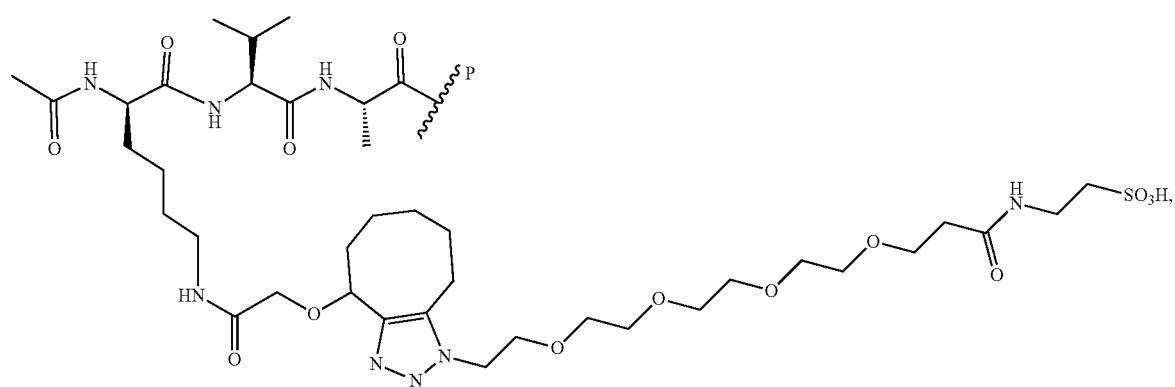
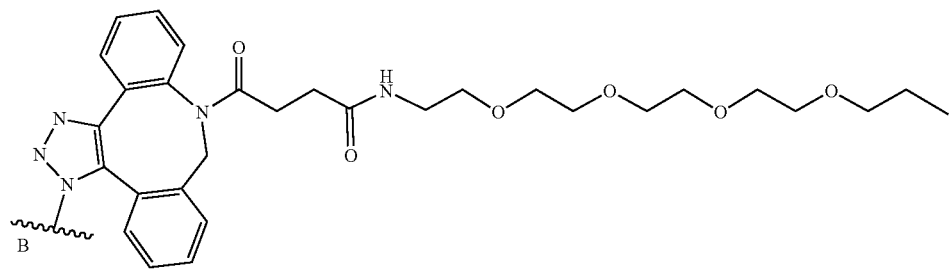
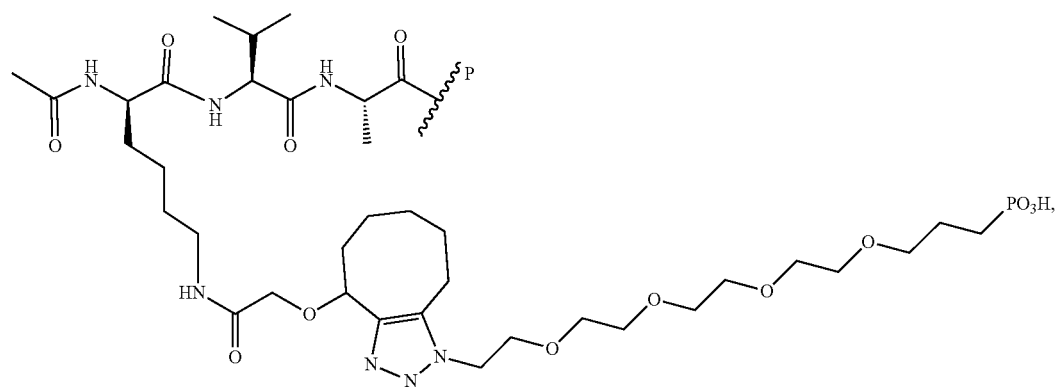

-continued
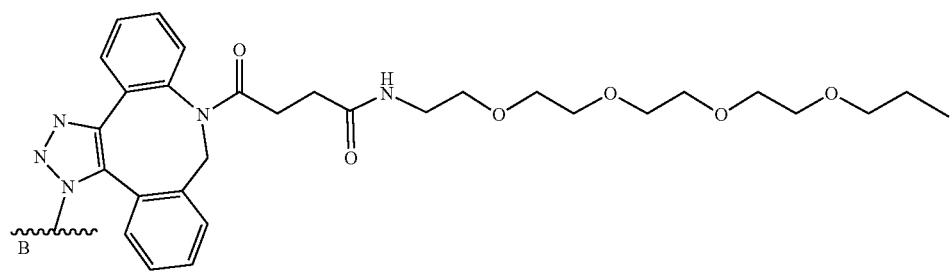
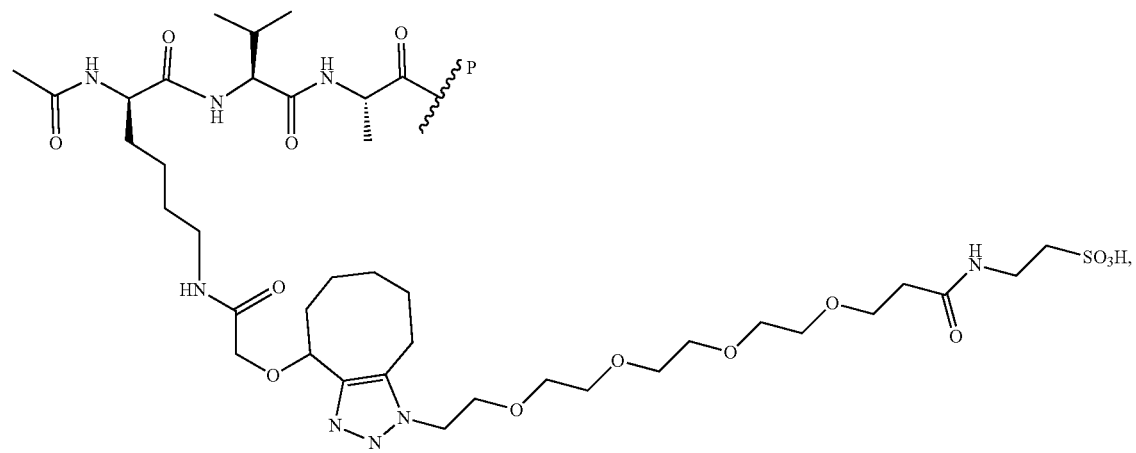
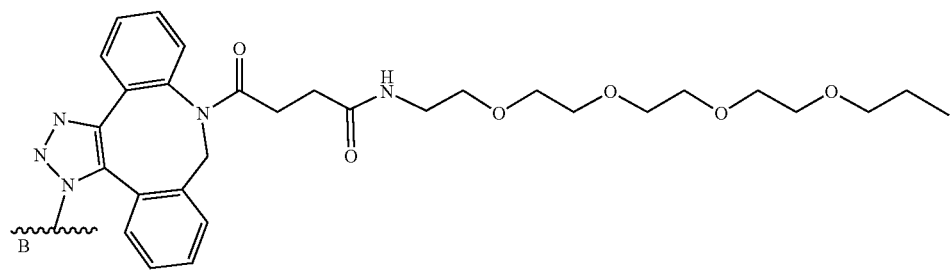
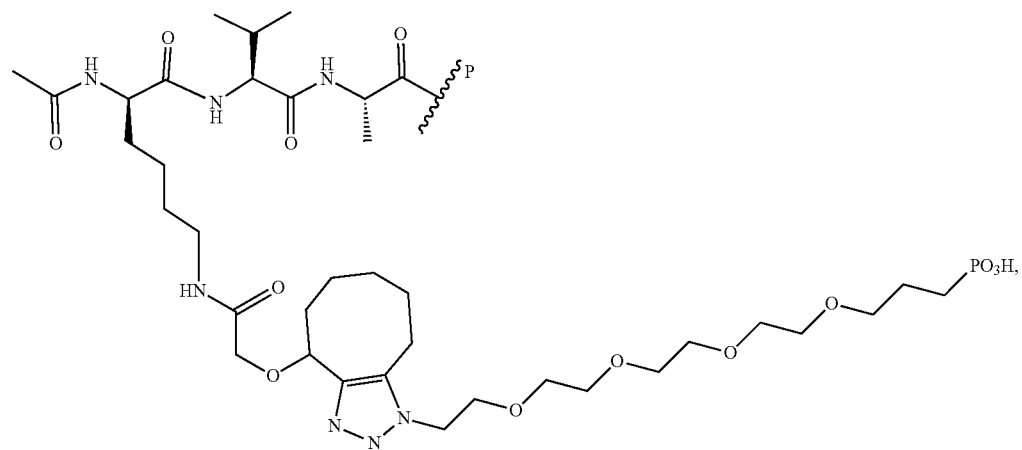

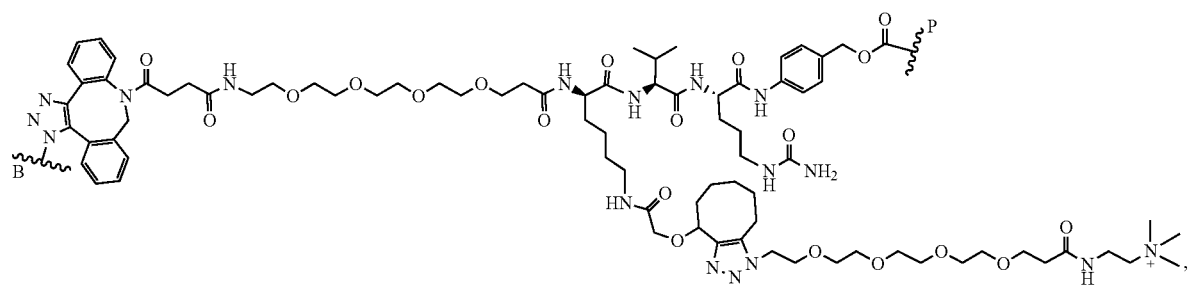
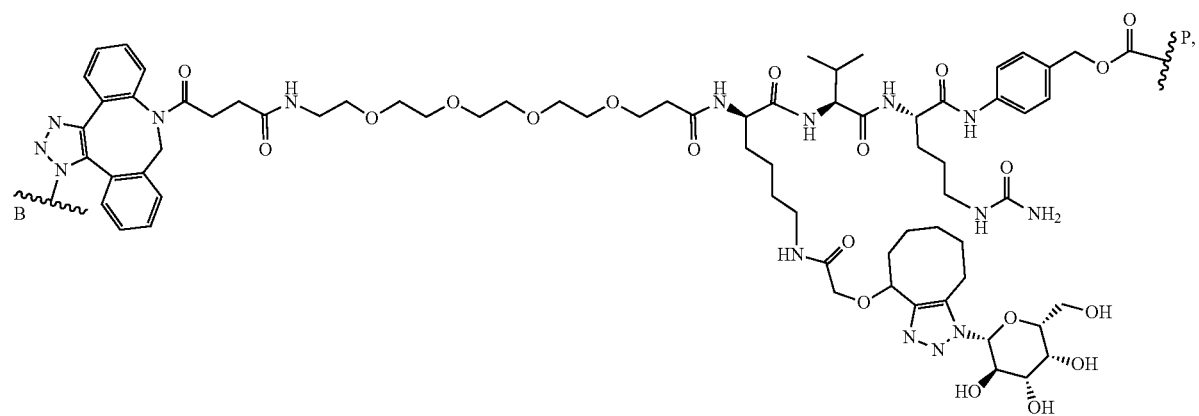
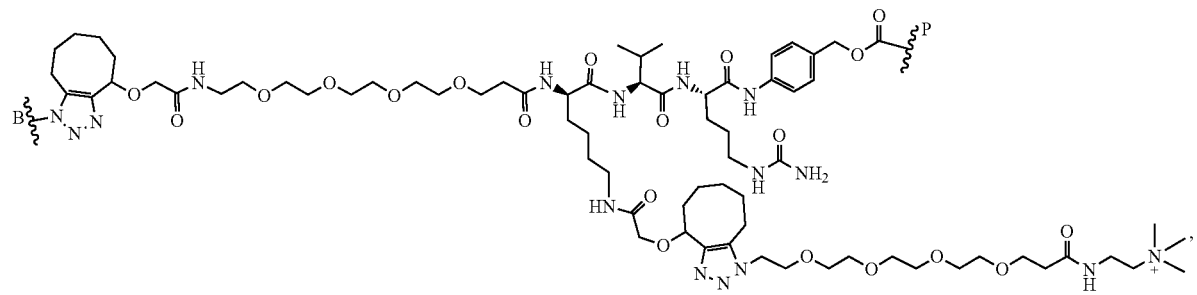
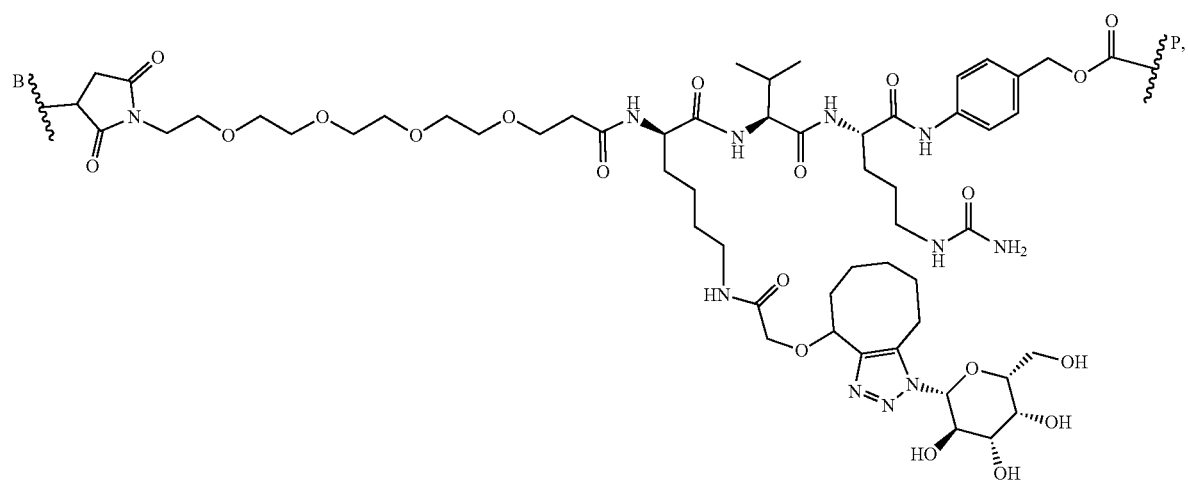

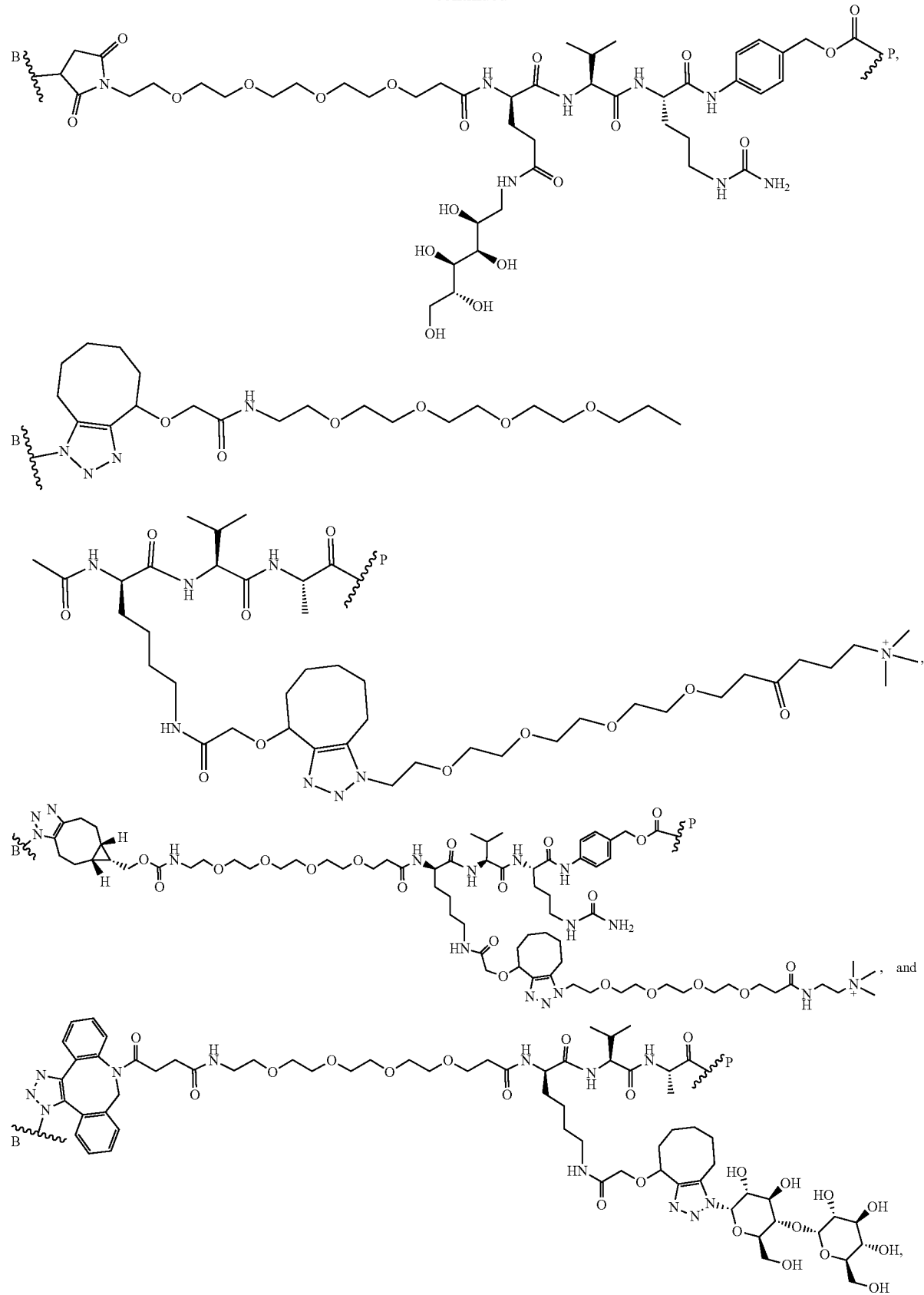

or a stereoisomeric form thereof, or a regioisomer thereof, or a mixture of regioisomers thereof, wherein
each

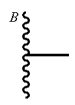

is a bond to the binding agent; and
each

is a bond to the payload residue.

In some examples, for any compound of Formula (I), Formula (II), Formula (III), Formula (IV), Formula (IVa), Formula (IVb), Formula (IVc), Formula (Va), Formula (Vb), Formula (Vc), or Formula (Vd), in the structure

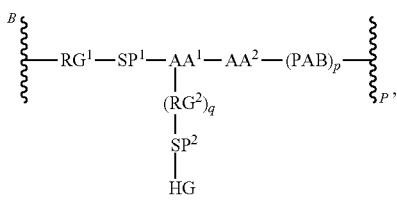

or a stereoisomeric form thereof, or a regioisomer thereof, or a mixture of regioisomers thereof, $RG^1$ is

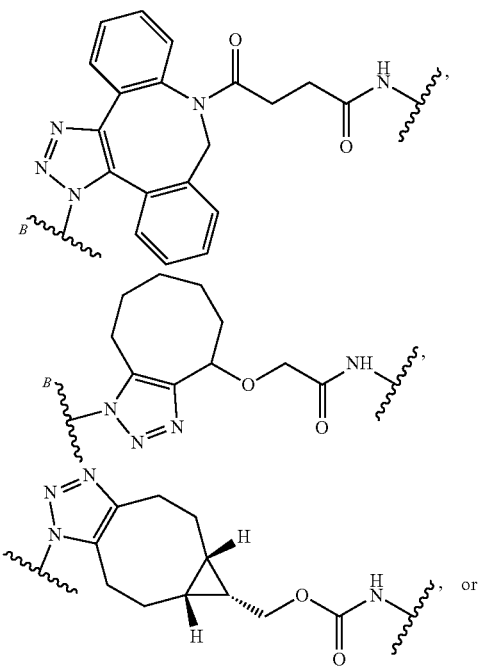

-continued

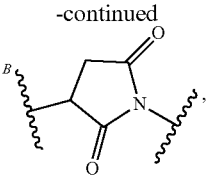

HG is

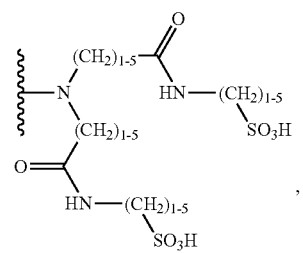

or
HG is

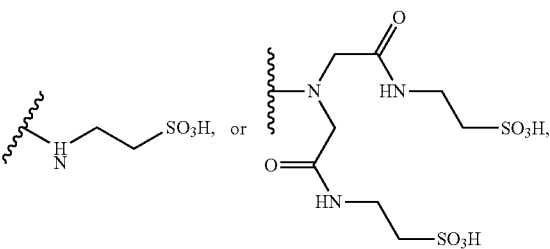 [SMILES: *NCCS(=O)(=O)O ; *N(CC(=O)NCCS(=O)(=O)O)CC(=O)NCCS(=O)(=O)O]

each

is a bond to the binding agent;
each

is a bond to the payload residue; and
each

indicates the atom through which the group is attached to the rest of the molecule.

In some examples, for any compound of Formula (I), Formula (II), Formula (III), Formula (IV), Formula (IVa), Formula (IVb), Formula (IVc), Formula (Va), Formula (Vb), Formula (Vc), or Formula (Vd), LL is according to Formula (LL1):

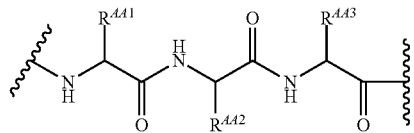

(LL1)

wherein $R^{AA1}$, $R^{AA2}$, and $R^{AA3}$ are each, independently, amino acid side chains, at least one of which is bonded directly or indirectly to —(RG²)$_q$-SP²-HG In some cases, for Formula LL1, $R^{AA1}$ is a lysine, glutamine, glutamic acid, or aspartic acid side chain bonded directly or indirectly to HG, and $R^{AA2}$ and $R^{AA3}$ are either valine and alanine or valine and citrulline sidechains respectively.

In some cases, for any compound of Formula (I), Formula (II), Formula (III), Formula (IV), Formula (IVa), Formula (IVb), Formula (IVc), Formula (Va), Formula (Vb), Formula (Vc), or Formula (Vd), AA² is

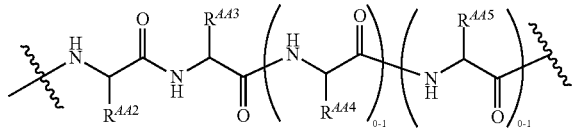

wherein $R^{AA2}$, $R^{AA3}$, $R^{AA4}$, and $R^{AA5}$ are each, independently, amino acid side chains, at least one of which is bonded directly or indirectly to —(RG²)$_q$-SP²-HG, wherein the

indicates the atom through which AA² is bonded to the adjacent groups in the formula. In some examples, $R^{AA2}$, $R^{AA3}$, $R^{AA4}$, and $R^{AA5}$, are independently in each instance, an amino acid side chain selected from the sidechains of alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof.

In some cases, for any compound of Formula (I), Formula (II), Formula (III), Formula (IV), Formula (IVa), Formula (IVb), Formula (IVc), Formula (Va), Formula (Vb), Formula (Vc), or Formula (Vd), AA² is

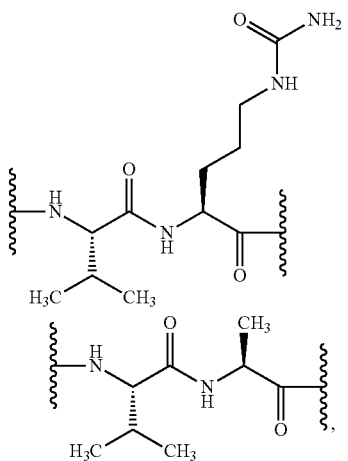

or wherein the

indicates the atom through which AA² is bonded to the adjacent groups in the formula.

In one instance AA² is

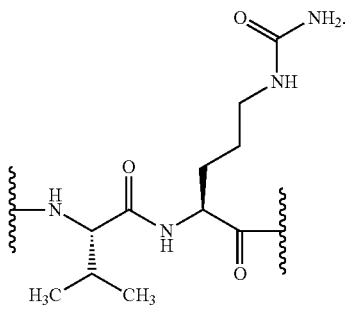 [SMILES: *N[C@H](C(=O)N[C@@H](CCCNC(N)=O)C(*)=O)C(C)C]

In another instance, AA² is

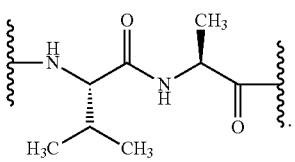 [SMILES: *N[C@H](C(=O)N[C@@H](C)C(*)=O)C(C)C]

In some cases, for any compound of Formula (Va), Formula (Vb), Formula (Vc), or Formula (Vd), subscript e is 4. In some cases, for any compound of Formula (Va), Formula (Vb), Formula (Vc), or Formula (Vd), subscript e is 5.

In some embodiments, for any compound of Formula (I), Formula (II), Formula (III), Formula (IV), Formula (IVa), Formula (IVb), Formula (IVc), Formula (Va), Formula (Vb), Formula (Vc), or Formula (Vd), the binding agent (BA) is an antibody or antigen-binding fragment thereof. In some instances, the antibody or antigen-binding fragment thereof binds a tumor-expressed antigen. In some instances, the antibody or antigen-binding fragment thereof binds a macrophage expressed antigen. In some instances, the binding agent (BA) is an antibody, or an antigen-binding fragment thereof, selective for an antigen selected from the group consisting of AXL, BAFFR, BCMA, BCR-list components, BDCA2, BDCA4, BTLA, BTNL2, BTNL3, BTNL8, BTNL9, C10 or f54, CCR1, CCR3, CCR4, CCR5, CCR6, CCR7, CCR9, CCR10, CD11c, CD137, CD138, CD14, CD168, CD177, CD19, CD20, CD209, CD209L, CD22, CD226, CD248, CD25, CD27, CD274, CD276, CD28, CD30, CD300A, CD33, CD37, CD38, CD4, CD40, CD44, CD45, CD46, CD48, CD5, CD52, CD55, CD56, CD59, CD62E, CD68, CD69, CD70, CD74, CD79a, CD79b, CD8, CD80, CD86, CD90.2, CD96, CLEC12A, CLEC12B, CLEC7A, CLEC9A, CR1, CR3, CRTAM, CSF1R, CTLA4, CXCR1/2, CXCR4, CXCR5, DDR1, DDR2, DEC-205, DLL4, DR6, FAP, EGFR, EGFRVIII, FCamR, FCMR, FcR's, Fire, GITR, HHLA2, HLA class II, HVEM, ICO-SLG, IFNLR1, IL10R1, IL10R2, IL12R, IL13RA1, IL13RA2, IL15R, IL17RA, IL17RB, IL17RC, IL17RE, IL20R1, IL20R2, IL21R, IL22R1, IL22RA, IL23R, IL27R, IL29R, IL2Rg, IL31R, IL36R, IL3RA, IL4R, IL6R, IL5R, IL7R, IL9R, Integrins, LAG3, LIFR, MAG/Siglec-4, MET, MMR, MSR1, NCR3LG1, NKG2D, NKp30, NKp46, PDCD1, PRLR, PROKR1, PVR, PVRIG, PVRL2, PVRL3, RELT, SIGIRR, Siglec-1, Siglec-10, Siglec-5, Siglec-6, Siglec-7, Siglec-8, Siglec-9, SIRPA, SLAMF7, TACI, TCR-list components/assoc, PTCRA, TCRb, CD3z, CD3, TEK, TGFBR1, TGFBR2, TGFBR3, TIGIT, TLR2, TLR4, TROY, TSLPR, TYRO, VLDLR, VSIG4, and VTCN1.

In some instances, for any compound of Formula (I), Formula (II), Formula (III), Formula (IV), Formula (IVa), Formula (IVb), Formula (IVc), Formula (Va), Formula (Vb), Formula (Vc), or Formula (Vd), PA is the residue of a group selected from the group consisting of a dolastatin, an auristatin, a maytansinoid, a plant alkaloid, a taxane, a vinca alkaloid, a steroid, and a liver X receptor (LXR) modulator. In some cases, PA is a dolastatin. In some cases, PA is an auristatin. In some cases, PA is a maytansinoid. In some cases, PA is a plant alkaloid. In some cases, PA is a taxane. In some cases, PA is a vinca alkaloid. In some cases, PA is a steroid. In some cases, PA is a LXR modulator. In some cases, a LXR modulator is a LXR agonist. In some embodiments, a LXR modulator is a LXR antagonist. In some examples, PA is any compound set forth in FIG. 1. In some cases PA is a steroid, e.g., a glucocorticoid. Other suitable payloads include those that are highly hydrophobic, e.g., those that are not amenable to Ab conjugation conditions due to their hydrophilic nature, e.g., payloads such as pyrrolobenzodiazepines (PBDs), SN38 (7-Ethyl-10-hydroxy-camptothecin), etc. In certain embodiments, provided herein are antibody-drug conjugates according to any formula herein wherein PA is a hydrophobic payload moiety.

In some embodiments a payload in Formula (I) is a dolastatin or a synthetic analog thereof. In certain embodiments, the payloads in compounds of Formula (I) are auristatins that have the structure of monomethyl auristatin D (MMAD), (MMAE monomethyl auristatin E (MMAE), or monomethyl auristatin F (MMAF), or stereoisomers thereof.

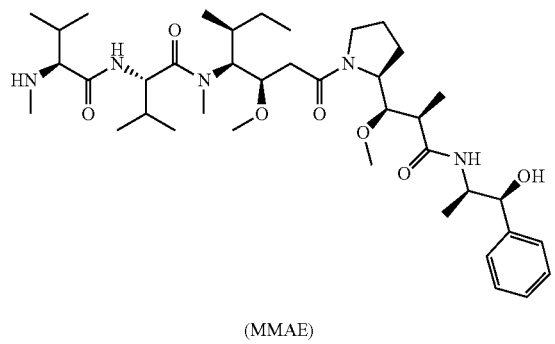

(MMAE)

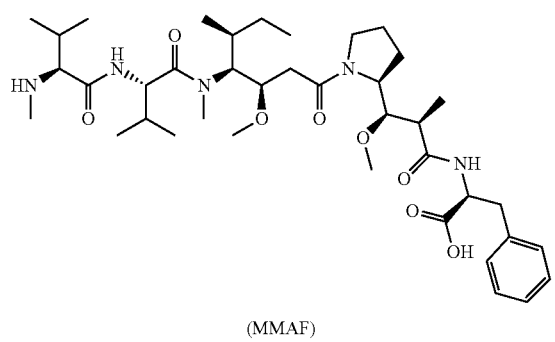

(MMAF)

In certain aspects, the compounds of Formula (I) described herein are protein-drug conjugates, e.g., antibody-drug conjugates, comprising an antigen-binding protein, e.g., antibody, an auristatin payload, and a hydrophilic moiety.

In certain embodiments, the payloads in compounds of Formula (I) are maytansinoids. Maytansinoid payloads disclosed in U.S. Non-Provisional application Ser. No. 15/081,759 filed on Mar. 25, 2016, titled "MAYTANSINOID DERIVATIVES, CONJUGATES THEREOF, AND METHODS OF USE," published as U.S. Patent Application Publication No. 2016/0375147, and in U.S. Non-Provisional application Ser. No. 15/414,537 filed on Jan. 24, 2017, titled "MAYTANSINOID DERIVATIVES, CONJUGATES THEREOF, AND METHODS OF USE," issued as U.S. Pat. No. 9,950,076, are incorporated herein by reference. In certain embodiments, PA is DM1, DM3, or DM4. In certain embodiments, PA is

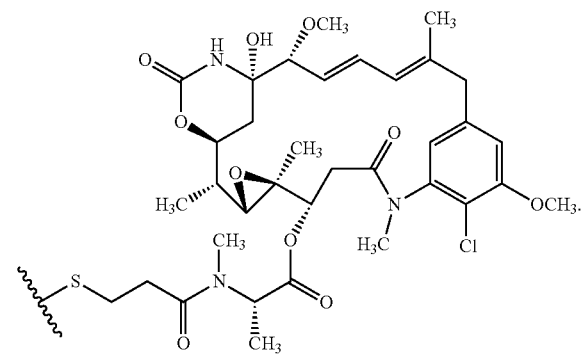 [SMILES: *SCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In certain embodiments, PA is

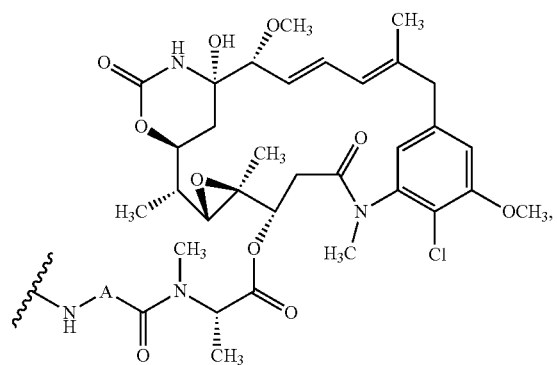

where A is optionally substituted arylene or heteroarylene.
In certain embodiments, PA is

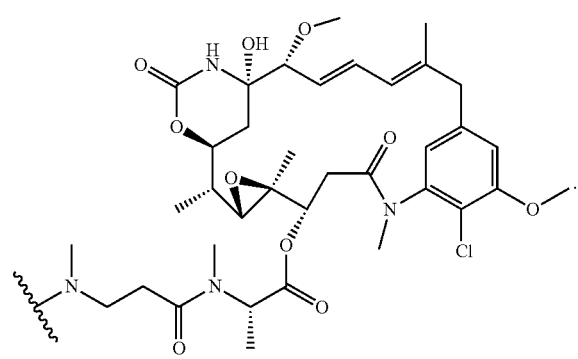 [SMILES: *N(C)CCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In particular embodiments, the wavy line indicates a bond to LL.

In certain aspects, the compounds of Formula (I) described herein are protein-drug conjugates, e.g., antibody-drug conjugates, comprising an antigen-binding protein, e.g., antibody, a maytansinoid payload, and a hydrophilic moiety.

In certain embodiments, the payloads in compounds of Formula (I) are glucocorticoids according to Formula (A):

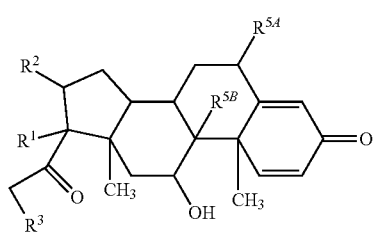

wherein
$R^1$ and $R^2$ are, independently, —H, alkyl, alkyl-C(O)—O—, —OH, or halo; or $R^1$ and $R^2$ together form

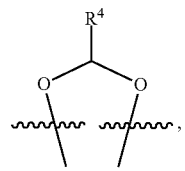

wherein $R^4$ is alkyl, aryl, arylalkyl, or an N-containing heterocycloalkyl, wherein the alkyl, aryl, arylalkyl, and N-containing heterocycloalkyl are, independently in each instance, optionally substituted with —$NR^{Aa}R^{Ab}$;

$R^3$ is —OH, $R^Z$—C(O)—X—, heteroalkyl, piperidinyl, —$NR^{Aa}R^{Ab}$, -oxyaryl-$NR^{Aa}R^{Ab}$ or —Z-A'$(R^P)_t$;

$R^Z$ is alkyl;

X is O or $NR^{Aa}$;

Z is S, S(O), S(O)$_2$, SO$_2NR^{Aa}$, O, C(O)$NR^{Aa}$, C(O), or $NR^{Aa}$;

A' is aryl, arylalkyl, or heteroaryl;

$R^P$ is, independently in each instance, halo, optionally substituted alkyl, —OH, or —$NR^{Aa}R^{Ab}$;

$R^{Aa}$ and $R^{Ab}$ are, independently in each instance, —H, optionally substituted alkyl, or optionally substituted aryl;

subscript a is an integer from 0-19; and t is an integer from 1-3;

with the proviso that:
(1) $R^3$ is not —OH (a) when $R^1$ is —OH or (b) when $R^1$ and $R^2$ together form

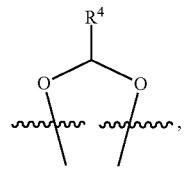

wherein $R^4$ is C$_{1-9}$alkyl or

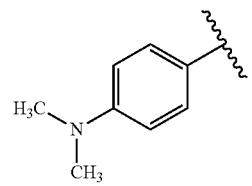 [SMILES: *c1ccc(N(C)C)cc1]

and
(2) $R^3$ is not

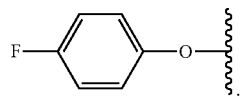

and
$R^{5A}$ and $R^{5B}$ are each, independently, halo or a hydrogen atom.

In some of such embodiments, $R^3$ is NH$_2$. In some of such embodiments, $R^3$ is

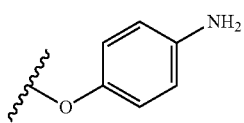 [SMILES: *Oc1ccc(N)cc1]

wherein

indicates the atom through which $R^3$ is attached to the adjacent groups in Formula (I).

In certain embodiments, PA is selected from

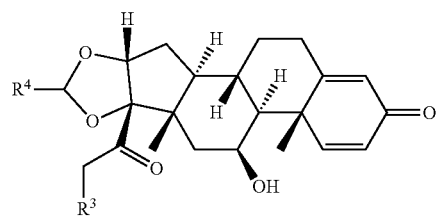

1110

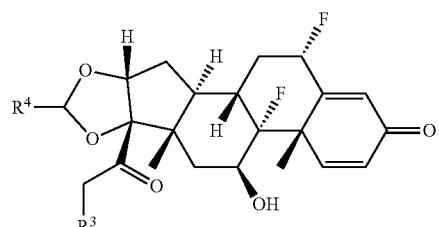

1120

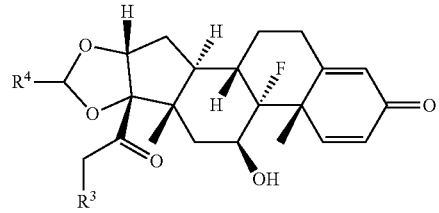

1130

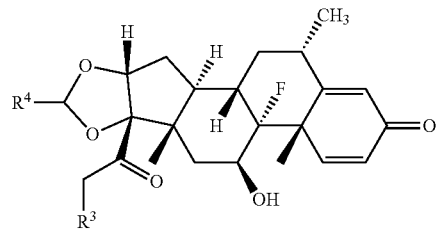

1140 or a pharmaceutically acceptable salt, solvate, or stereoisomer thereof. In certain embodiments according to any of Formulas 1110-1140, $R^3$ is —O-aryl, —NR$^{Aa}$R$^{Ab}$, -alkylene-NR$^{Aa}$R$^{Ab}$, —X-arylene-Y—NR$^{Aa}$R$^{Ab}$, —X-heteroarylene-Y—NR$^{Aa}$R$^{Ab}$, or N-containing heterocycloalkyl; wherein X is absent, —N—, —CH$_2$—, or —O—; wherein Y is absent or —CH$_2$—; and $R^4$ is alkyl, aryl, alkylaryl, or arylalkyl. In certain embodiments, $R^3$ is —O-arylene-NR$^{Aa}$R$^{Ab}$, —O-heteroarylene-NR$^{Aa}$R$^{Ab}$; wherein aryl or heteroaryl is optionally substituted with halogen, deuterium, hydroxyl, or methoxyl. In certain embodiments, $R^3$ is —O-phenyl-NR$^{Aa}$R$^{Ab}$, —O-heteroarylene-NR$^{Aa}$R$^{Ab}$; wherein phenyl or heteroaryl is optionally substituted with halogen or deuterium. In certain embodiments, $R^4$ is n-propyl. In certain embodiments, R$^{Aa}$ and R$^{Ab}$ are each independently hydrogen or alkyl. In particular embodiments, one of R$^{Aa}$ and R$^{Ab}$ is substituted with a bond to LL. In certain embodiments, PA is

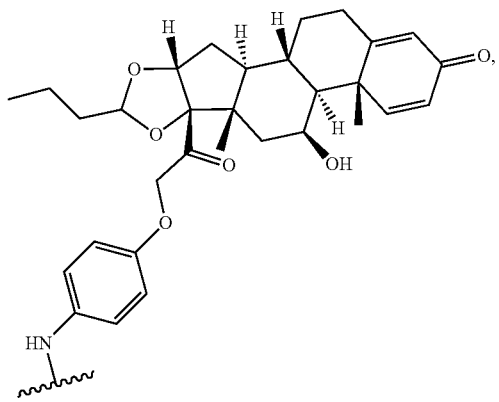 [SMILES: *Nc1ccc(OCC(=O)[C@@]23OC(CCC)O[C@@H]2C[C@H]2[C@@H]4CCC5=CC(=O)C=C[C@]5(C)[C@H]4[C@@H](O)C[C@@]23C)cc1]

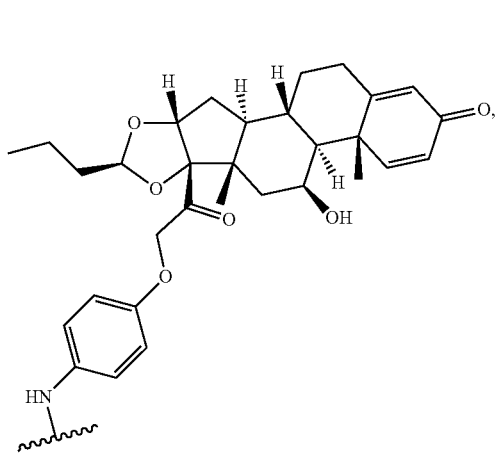 [SMILES: *Nc1ccc(OCC(=O)[C@@]23O[C@@H](CCC)O[C@@H]2C[C@H]2[C@@H]4CCC5=CC(=O)C=C[C@]5(C)[C@H]4[C@@H](O)C[C@@]23C)cc1]

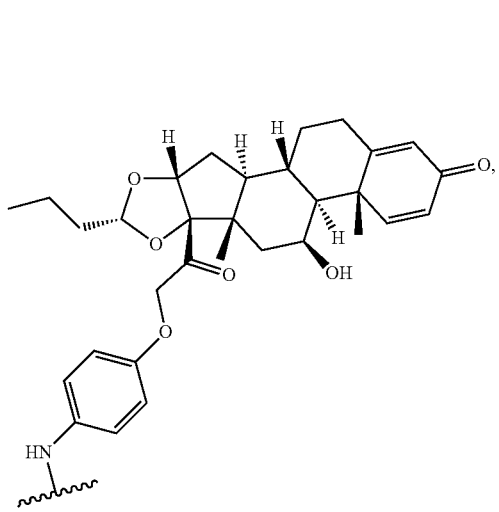

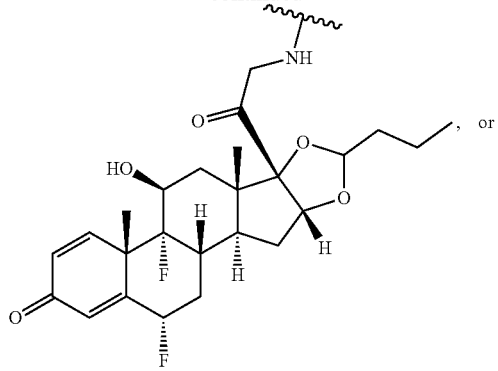

, or

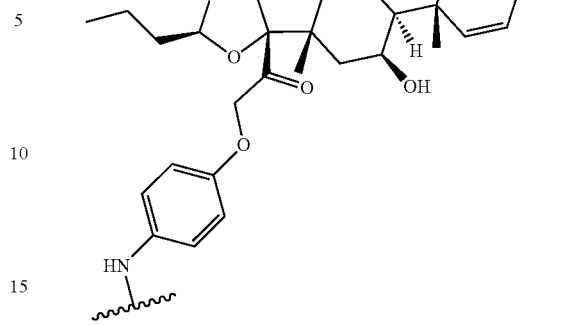

or a pharmaceutically acceptable salt, solvate, or stereoisomer thereof. In certain embodiments, PA is

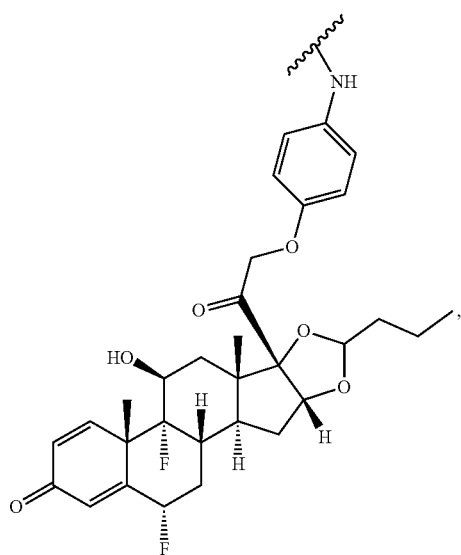

,

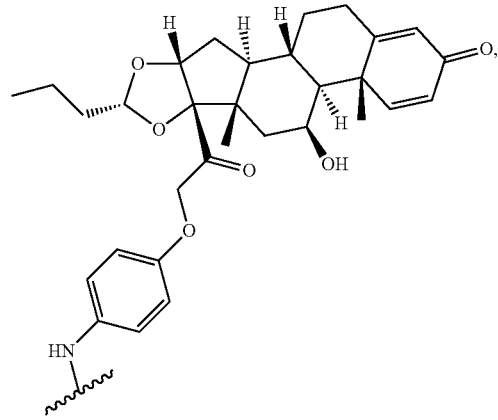 [SMILES: *Nc1ccc(OCC(=O)[C@@]23O[C@H](CCC)O[C@@H]2C[C@H]2[C@@H]4CCC5=CC(=O)C=C[C@]5(C)[C@H]4[C@@H](O)C[C@@]23C)cc1]

, or a pharmaceutically acceptable salt, solvate, or stereoisomer thereof. In certain embodiments, PA is or a pharmaceutically acceptable salt, solvate, or stereoisomer thereof. In certain embodiments, PA is

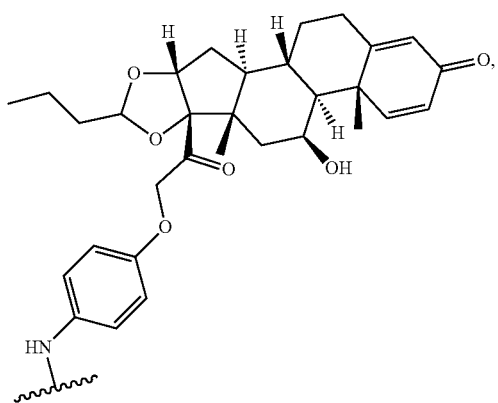

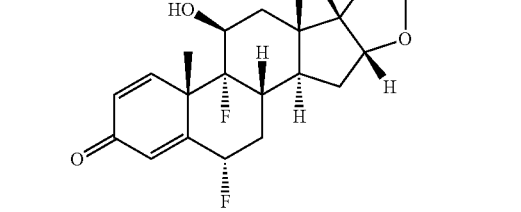

, or a pharmaceutically acceptable salt, solvate, or stereoisomer thereof. In certain embodiments, PA is or a pharmaceutically acceptable salt, solvate, or stereoisomer thereof. In certain embodiments, PA is

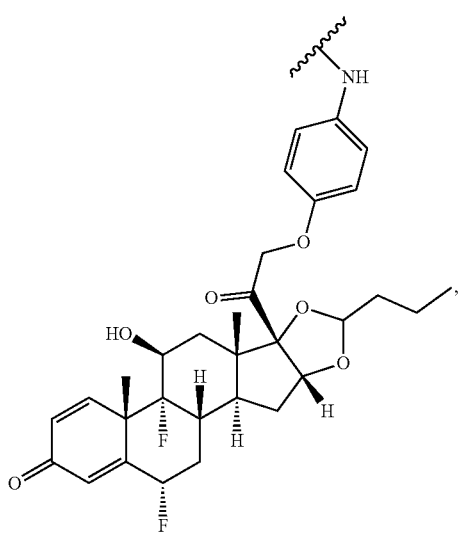
or a pharmaceutically acceptable salt, solvate, or stereoisomer thereof. In such embodiments, the wavy line indicates a bond to LL.
In some embodiments, PA is selected from the group consisting of:
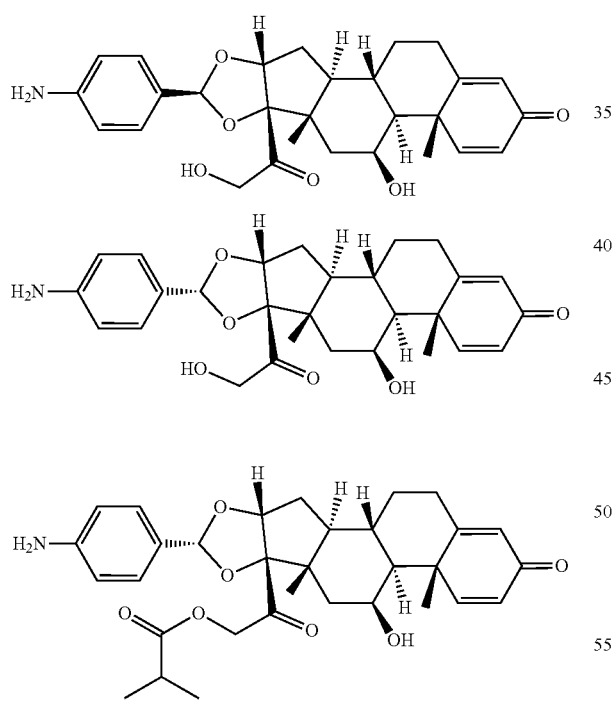
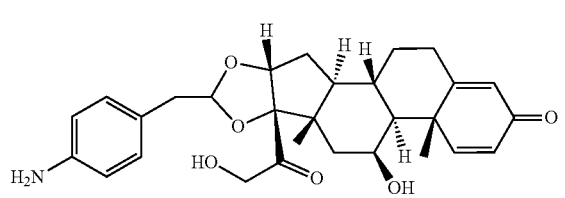
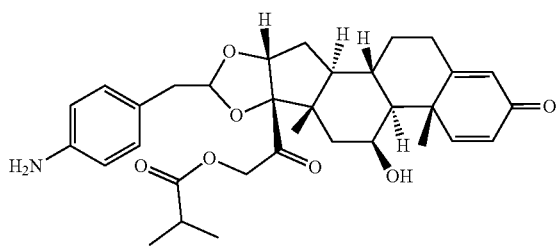
-continued
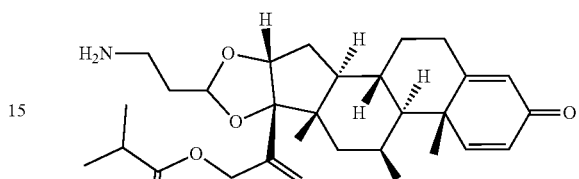
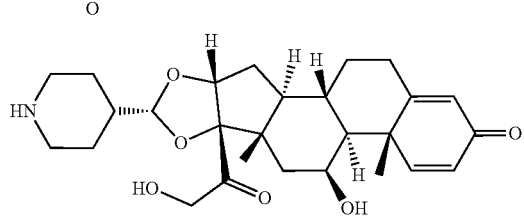
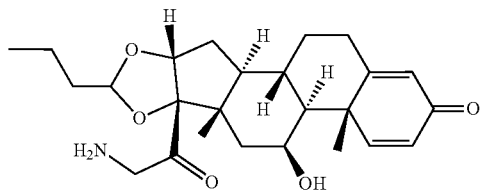
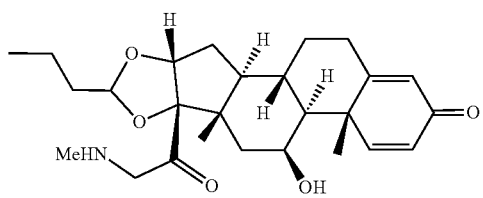
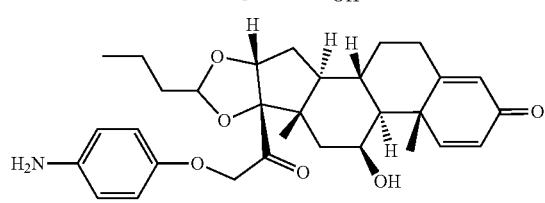
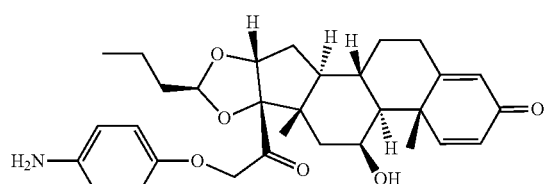
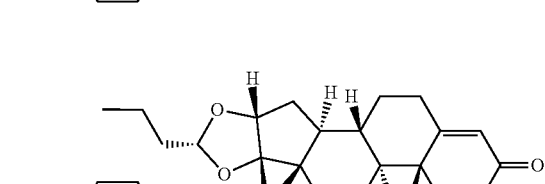
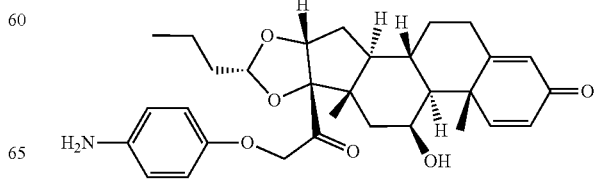

147
-continued
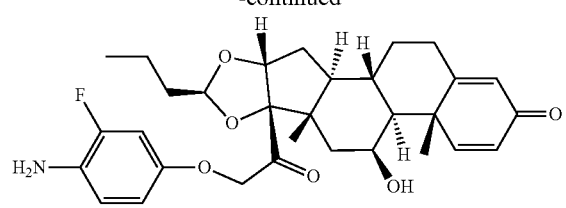
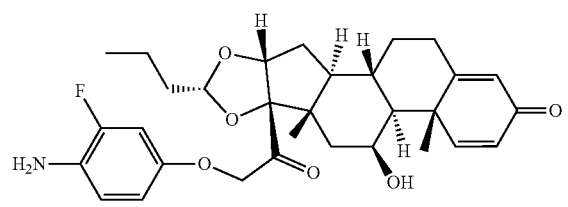
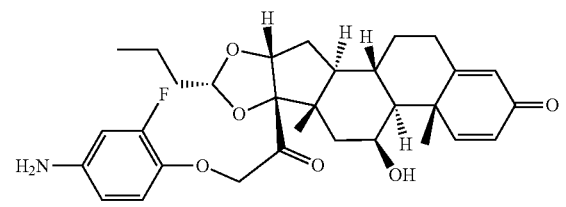
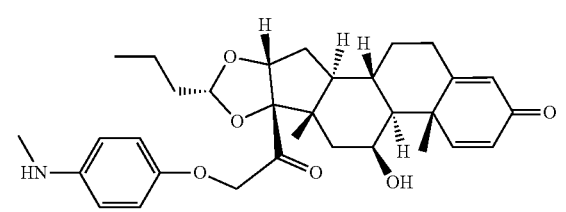
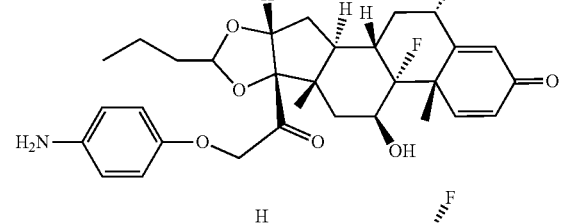
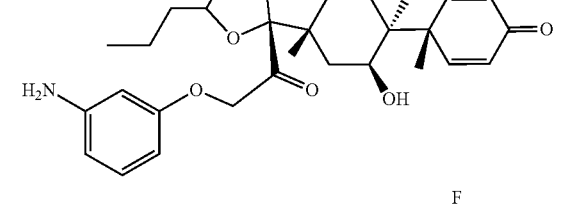
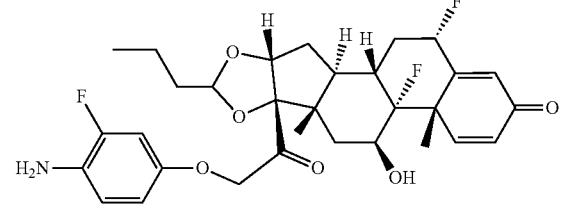
148
-continued
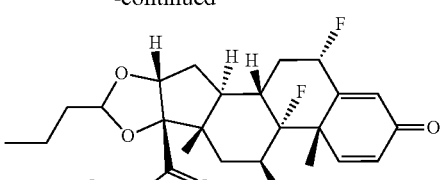
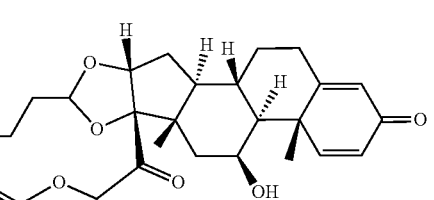
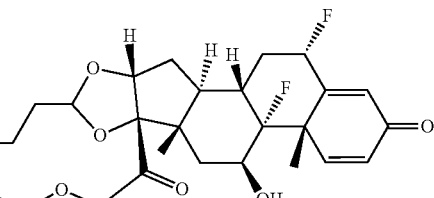
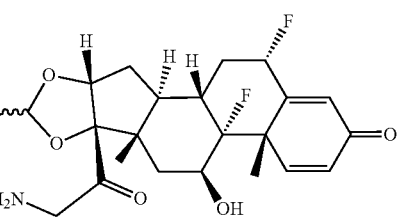
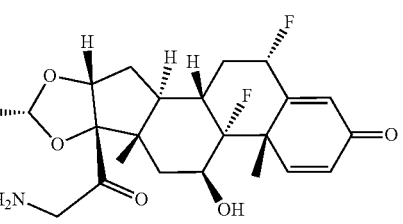
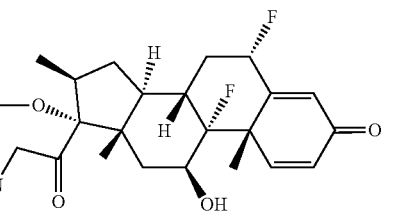
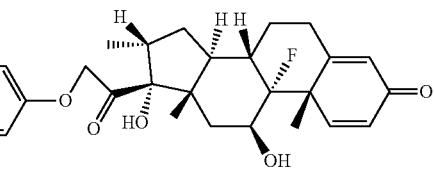

149
-continued
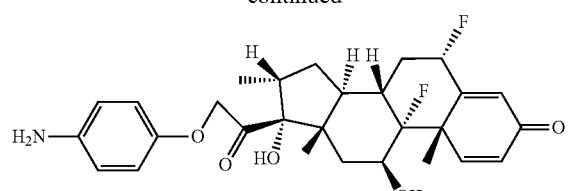
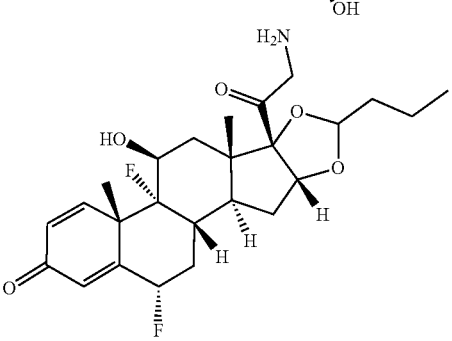
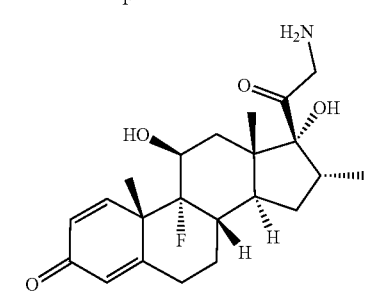
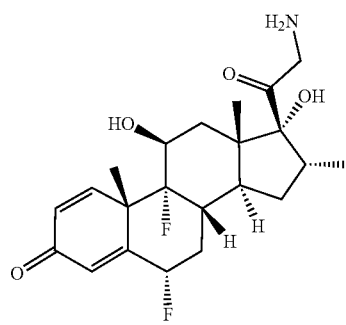
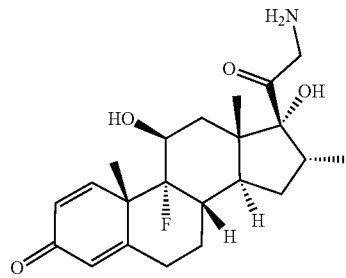
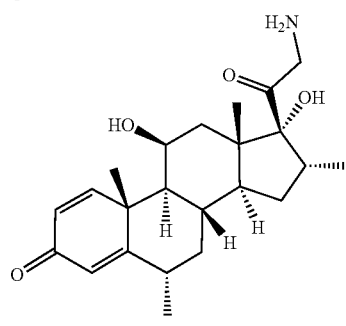
150
-continued
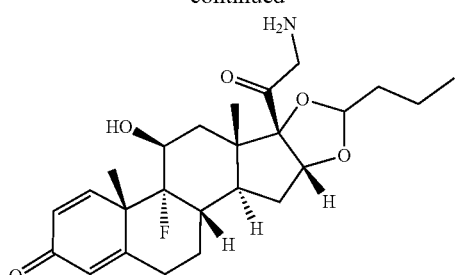
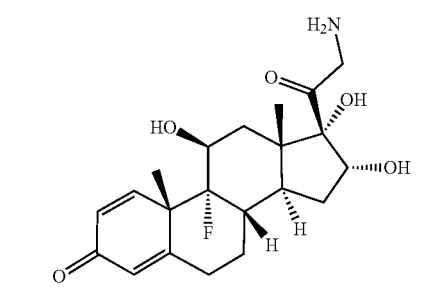
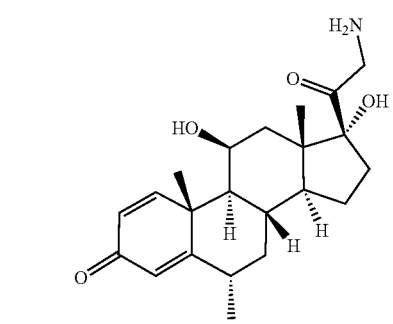
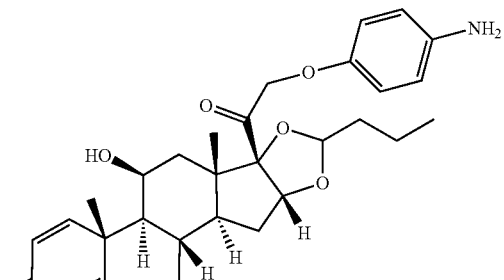
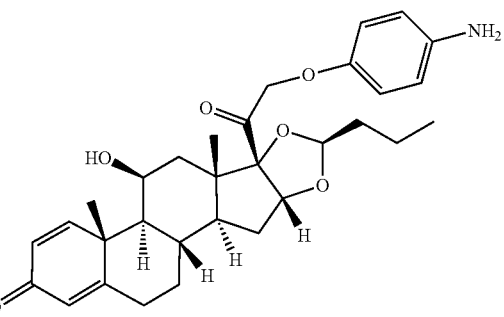

151
-continued

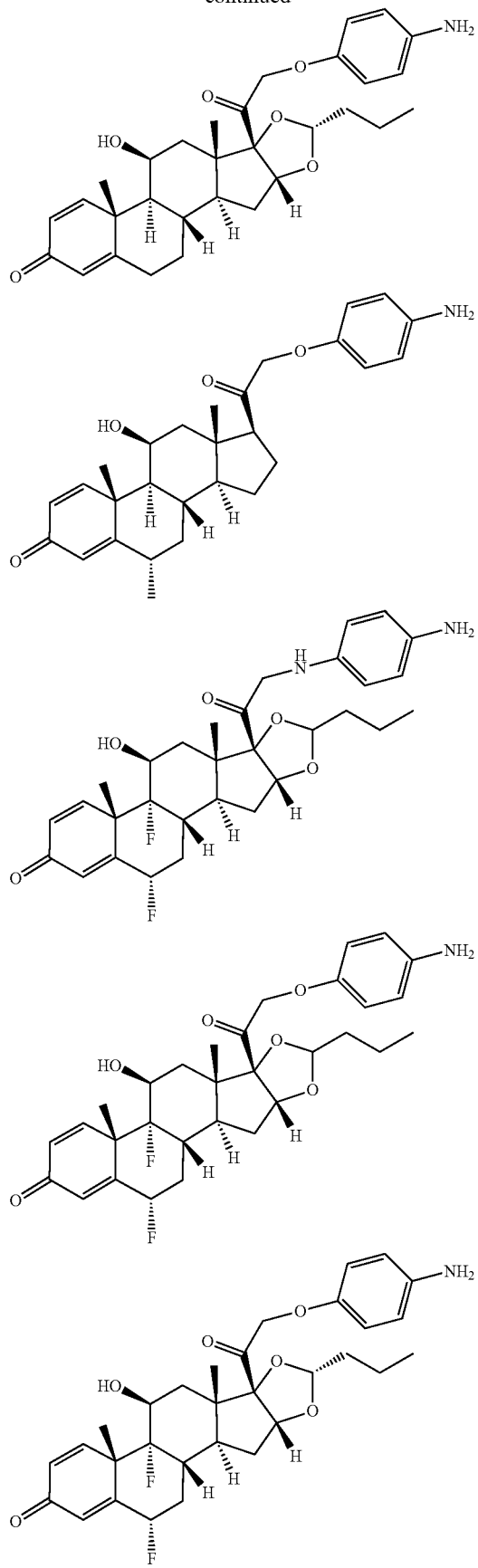

152
-continued

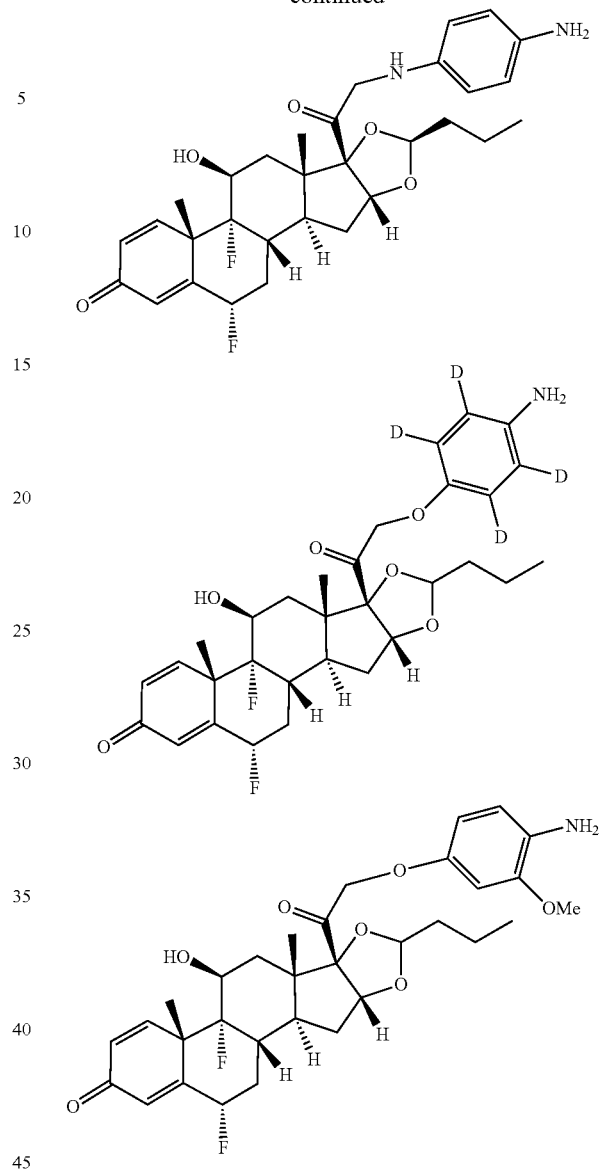

or a pharmaceutically acceptable stereoisomer thereof, wherein the PA is linked as a residue through the $R^3$ group, e.g., the conjugates comprise a payload described above linked to a linker via a bond to a residue of a primary or secondary amine of the payload.

In certain aspects, the compounds of Formula (I) described herein are protein-drug conjugates, e.g., antibody-drug conjugates, comprising an antigen-binding protein, e.g., antibody, a payload of Formula (A), and a hydrophilic moiety.

Steroid payloads disclosed in U.S. Provisional Application No. 62/614,905 filed on Jan. 8, 2018, titled "STEROIDS AND ANTIBODY CONJUGATES THEREOF," and in U.S. Non-Provisional application Ser. No. 15/806,197 filed on Nov. 7, 2017, titled "STEROIDS AND PROTEIN-CONJUGATES THEREOF" are incorporated herein by reference.

In certain embodiments, the payloads in compounds of Formula (I) are LXR modulators that have the structure according to Formula (B):

Formula (B)

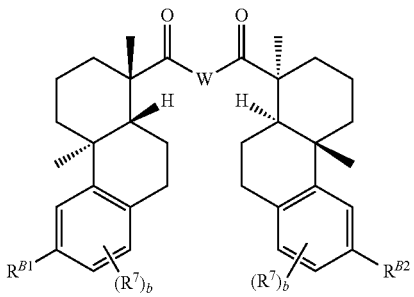

or a pharmaceutically acceptable stereoisomeric form thereof, wherein

W is —CH$_2$—, —N(H)—, or —O—;

R$^{B1}$ is —H, —OH, —NH$_2$, alkyl, or —OP(O)(OR$^6$)(OH)—OP(O)(OR$^6$)$_2$;

R$^{B2}$ is —H, —OH, —CH$_2$NH$_2$, R$^{B3}$, R$^{B4}$, R$^{B5}$, or —O—R$^{B5}$, wherein R$^{B1}$ and R$^{B2}$ are not simultaneously —H;

R$^{B3}$ is —N(R$^6$)$_2$;

R$^{B4}$ is —X—Y—Z;

X is selected from the group consisting of —O— and —N(H)—;

Y is selected from the group consisting of alkylene, substituted alkylene (including, without limitation, oxo substitution, i.e., =O), heteroalkylene, and substituted heteroalkylene (including, without limitation, oxo substitution (i.e., =O));

Z is selected from the group consisting of —OH and —NH$_2$;

R$^{B5}$ is alkyl, heterocycloalkyl, or substituted heterocycloalkyl, wherein each heterocycloalkyl or substituted heterocycloalkyl includes one, two, or three heteroatoms selected from nitrogen and oxygen, and includes at least one —OH and —CH$_2$OH substituent, or at least one primary or secondary nitrogen, for instance, O-glucose;

each R$^6$ is in each instance, —H, an amino acid residue, an N-alkyl amino acid residue, a peptide, or alkyl; and each R$^7$ is, independently, halo, C$_{1-6}$ alkyl, C$_{1-6}$ alkoxy, —CN, O-glucose, O-amino acid residue, and O-PEG$_b$, wherein each subscript b is an integer from 0-3.

In particular embodiments, R$^{B1}$ or R$^{B2}$ is substituted with a bond to LL. In certain embodiments, PA is selected from:

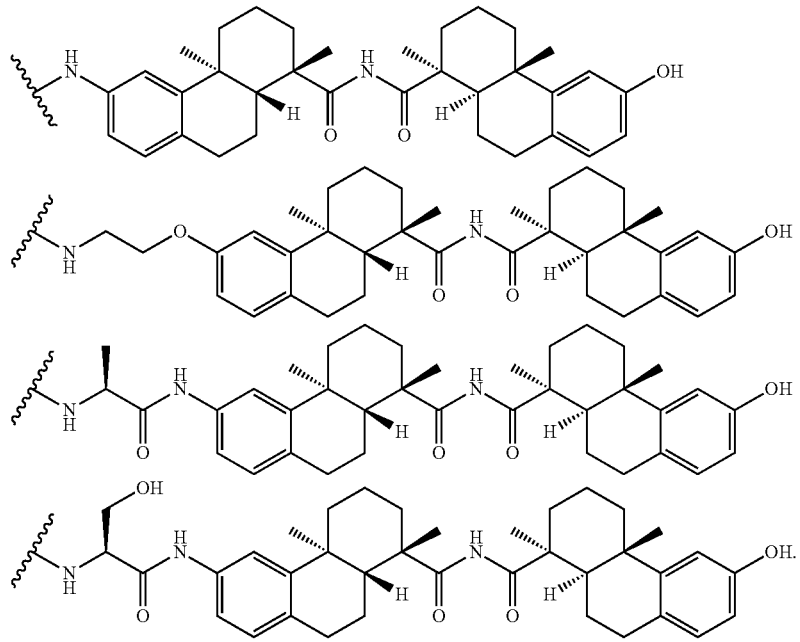

In particular embodiments, the wavy line indicates a bond to LL.

In certain embodiments, PA is selected from the group consisting of:

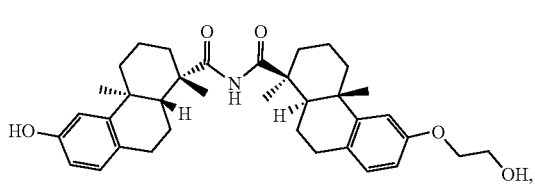

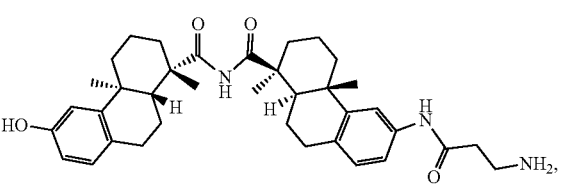

-continued

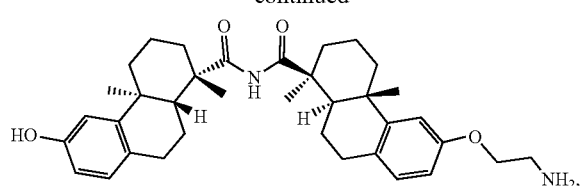
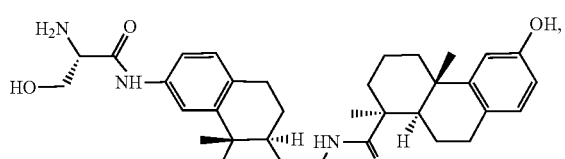
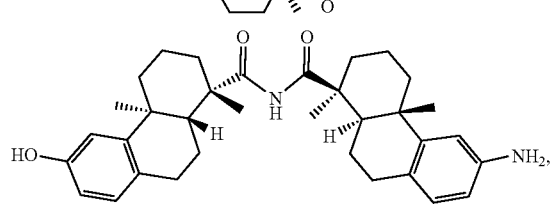
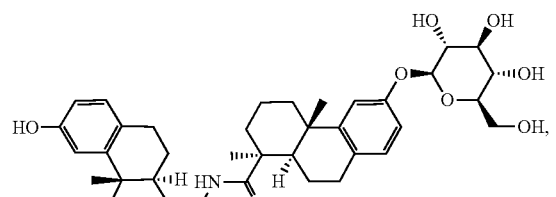
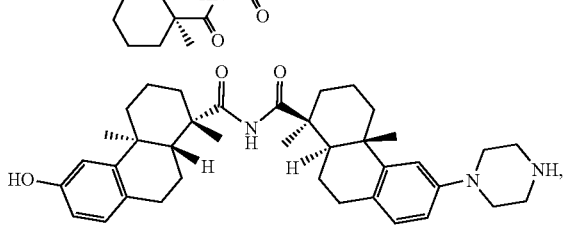
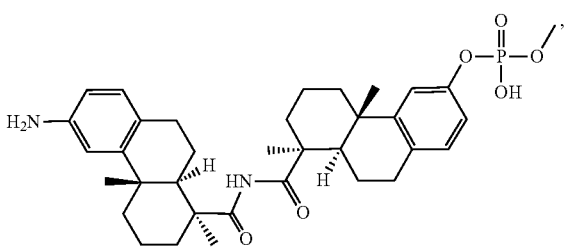
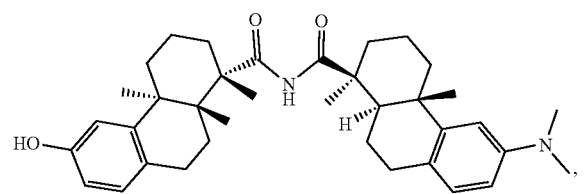
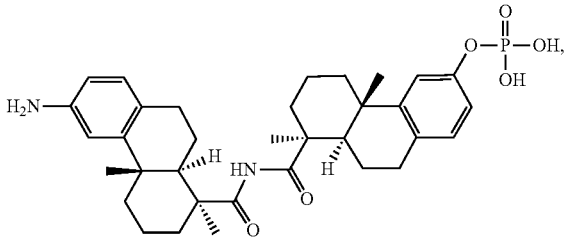

-continued

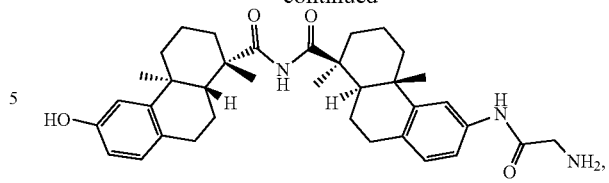
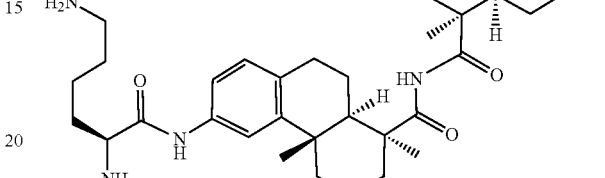
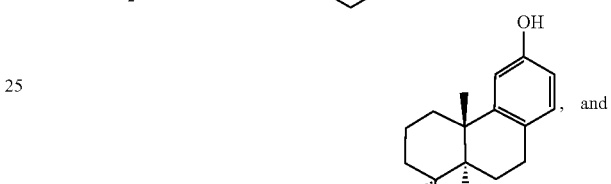
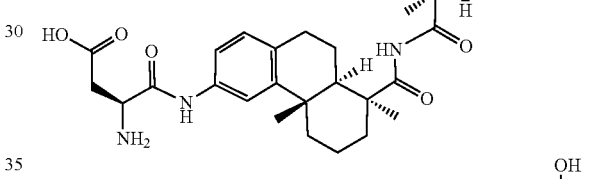

or a pharmaceutically acceptable stereoisomeric form thereof, wherein the PA is linked as a residue through the $R^{B1}$ or $R^{B2}$ group, e.g., the conjugates comprise a payload described above linked to a linker via a bond to a residue of a primary or secondary amine of the payload.

In certain aspects, the compounds of Formula (I) described herein are protein-drug conjugates, e.g., antibody-drug conjugates, comprising an antigen-binding protein, e.g., antibody, a payload of Formula (B), and a hydrophilic moiety.

LXR modulator payloads disclosed in U.S. Provisional Application No. 62/508,327 filed on May 18, 2017, titled "BIS-OCTAHYDROPHENANTHRENE CARBOXAMIDES AND PROTEIN CONJUGATES THEREOF" are incorporated herein by reference.

Also contemplated within the scope of embodiments presented herein are payloads disclosed in U.S. Non-Provisional application Ser. No. 14/776,668 filed on Sep. 14, 2015, titled "BIOLOGICALLY ACTIVE MOLECULES, CONJUGATES THEREOF, AND THERAPEUTIC USES," published as U.S. Patent Application Publication No. 2016/0030591, and U.S. Non-Provisional application Ser. No. 14/913,965 filed on Feb. 23, 2016, titled "PHARMACEUTICAL COMPOSITIONS COMPRISING MACROLIDE DIASTEREOMERS, METHODS OF THEIR SYNTHESIS AND THERAPEUTIC USES," published as U.S. Patent Application Publication No. 2016/0354482, the disclosure of said payloads is incorporated herein by reference.

In some instances, a compound of Formula (I), Formula (II), Formula (III), Formula (IV), Formula (IVa), Formula (IVb), Formula (IVc), Formula (Va), Formula (Vb), Formula (Vc), or Formula (Vd), is an antibody drug conjugate (ADC) wherein BA is Ab, and Ab is an antibody or antigen-binding fragment thereof. In some instances, a compound of Formula (I), Formula (II), Formula (III), Formula (IV), Formula (IVa), Formula (IVb), Formula (IVc), Formula (Va), Formula (Vb), Formula (Vc), or Formula (Vd), is a conjugate selected from the group consisting of:

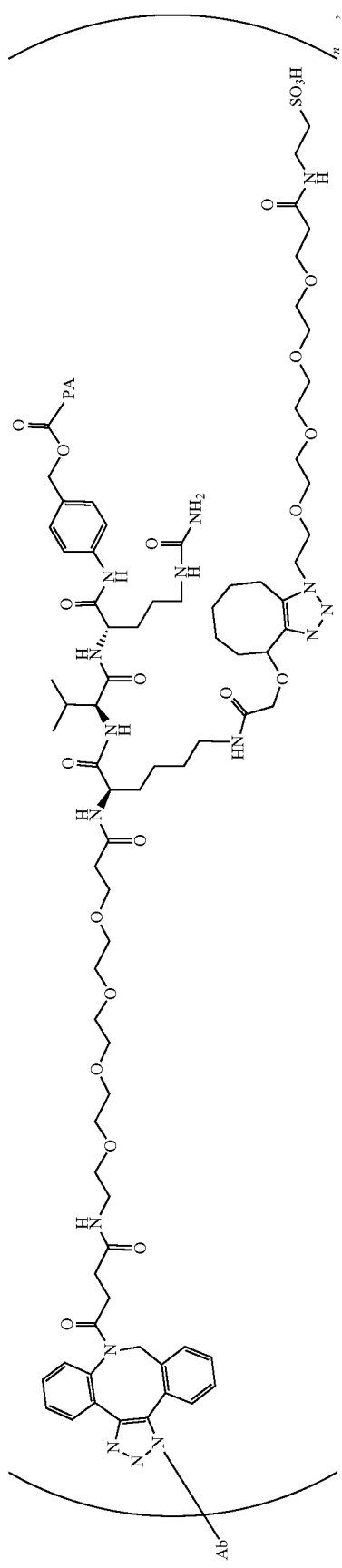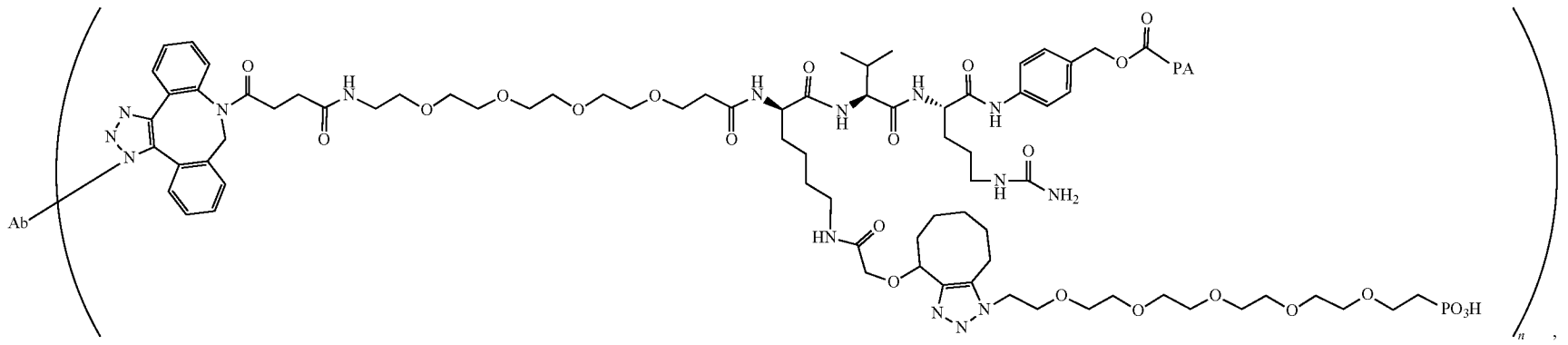

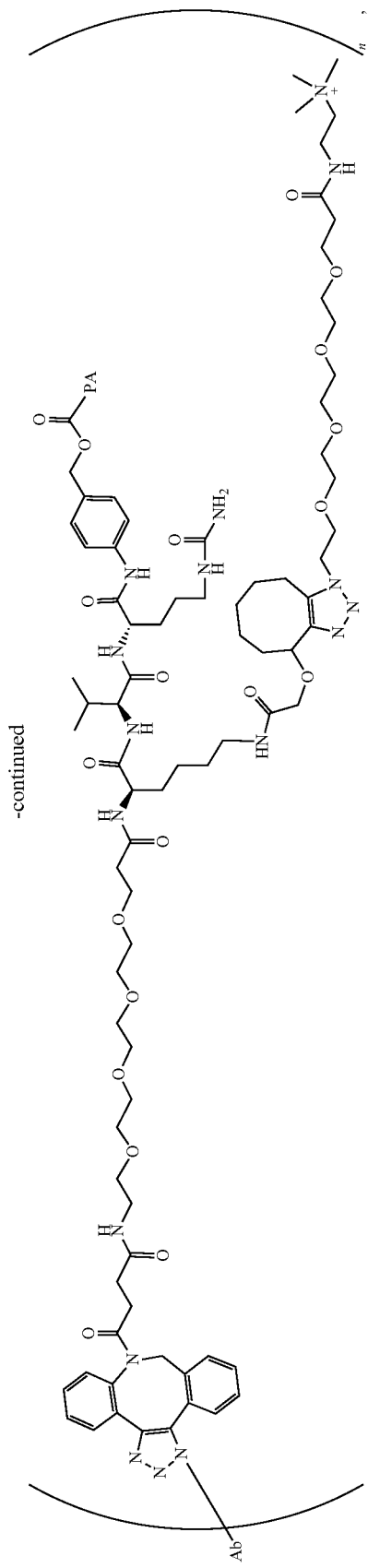

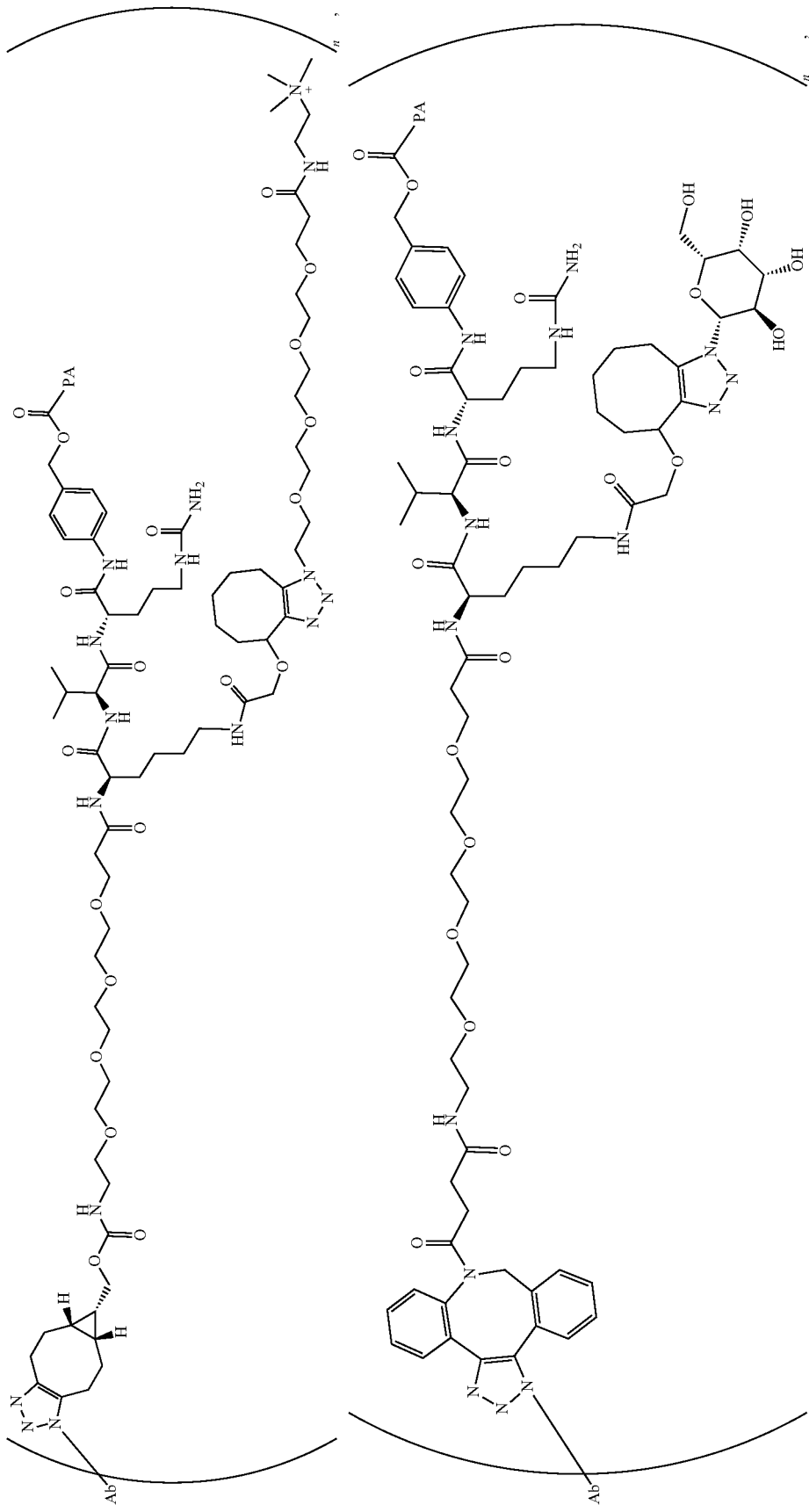

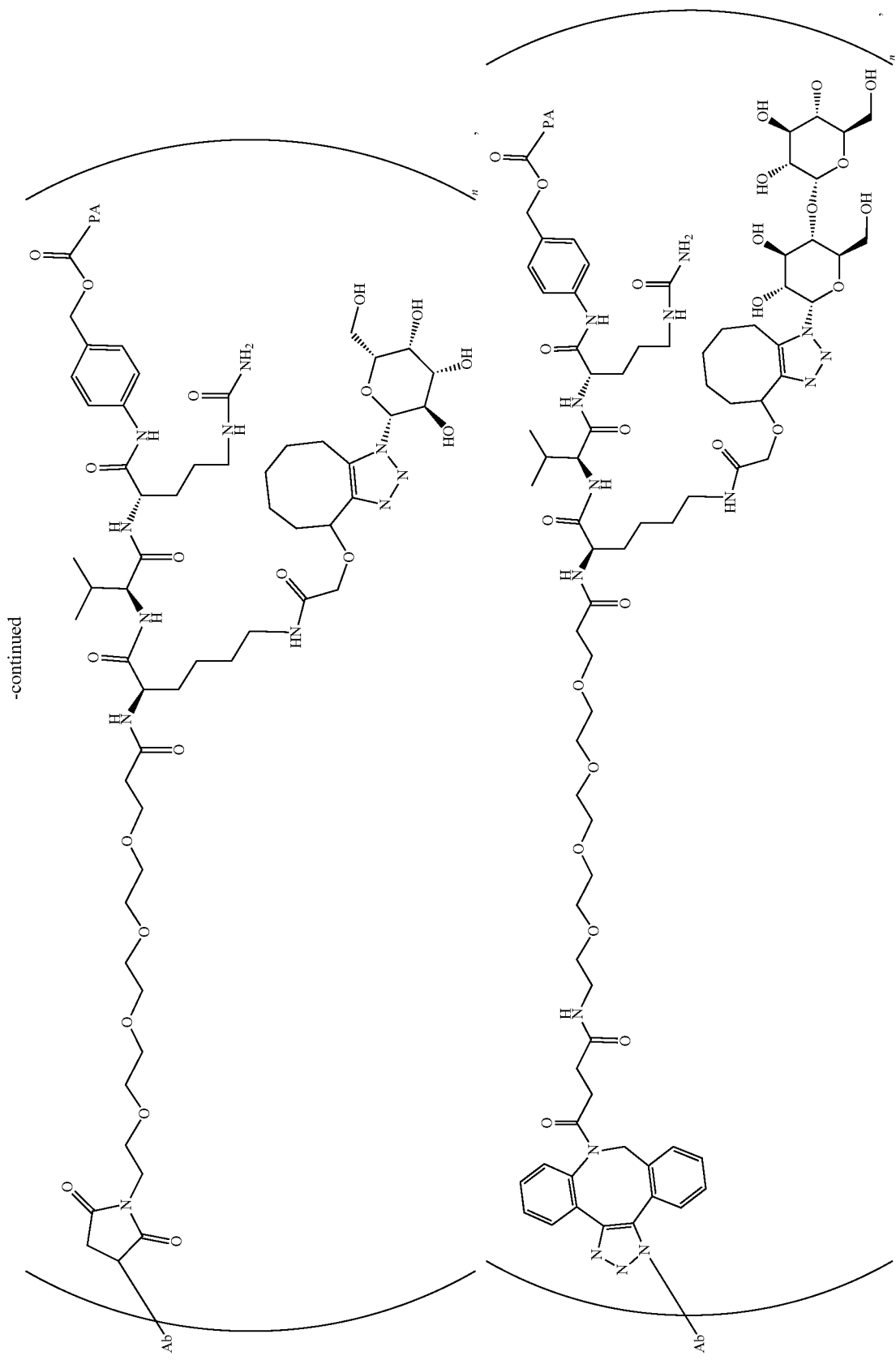

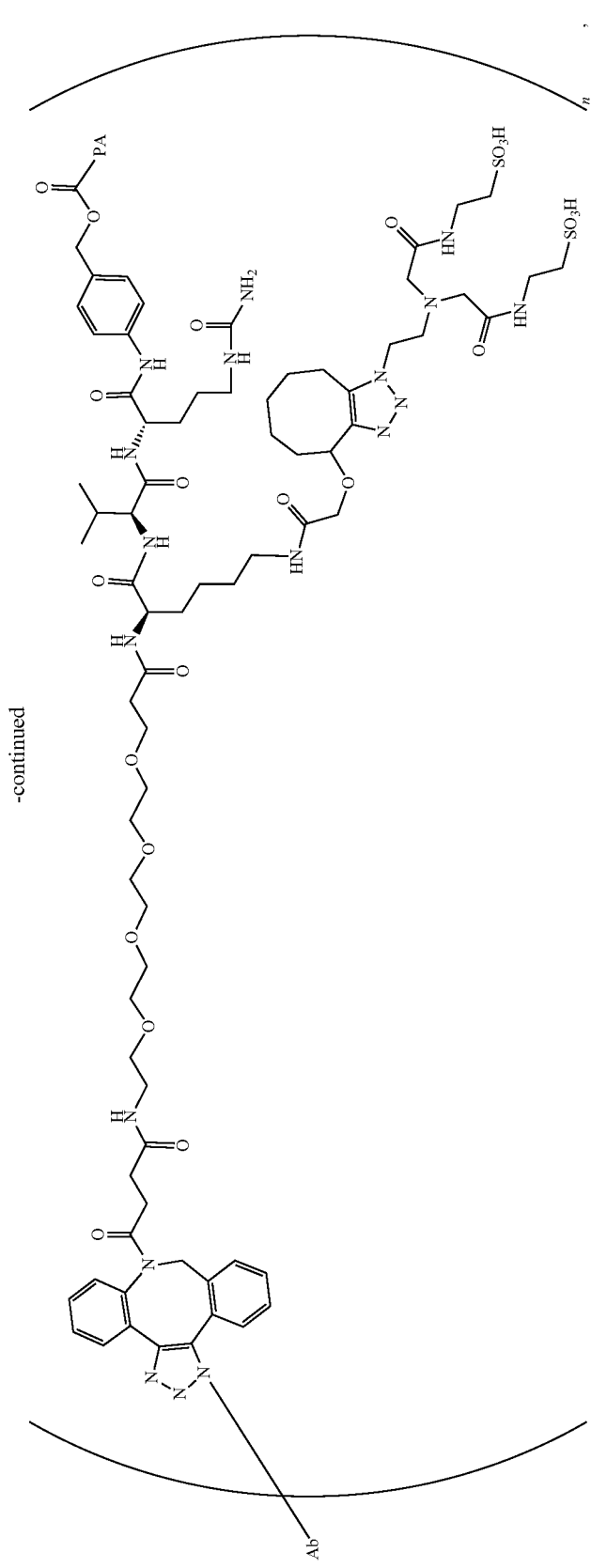
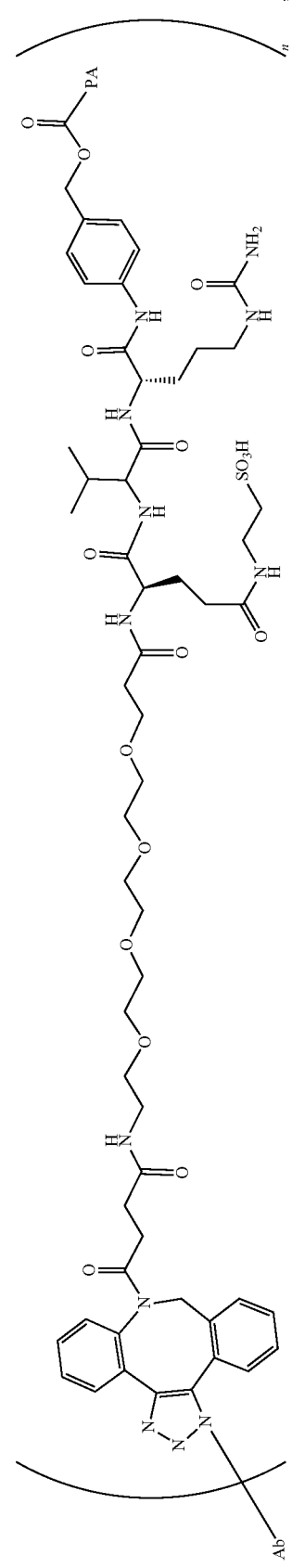

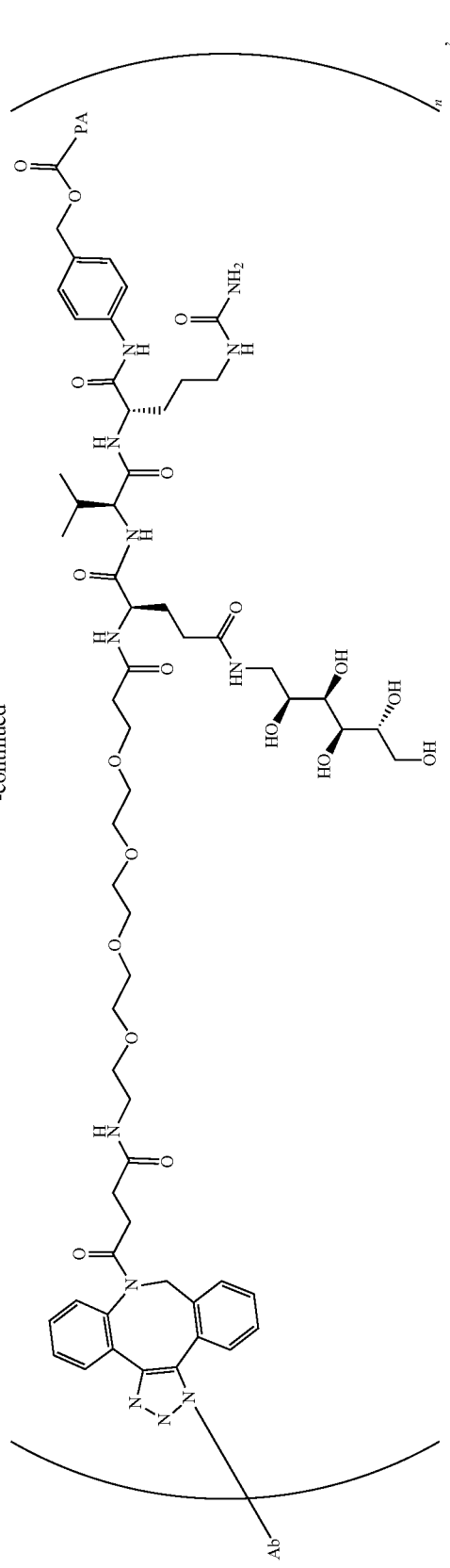
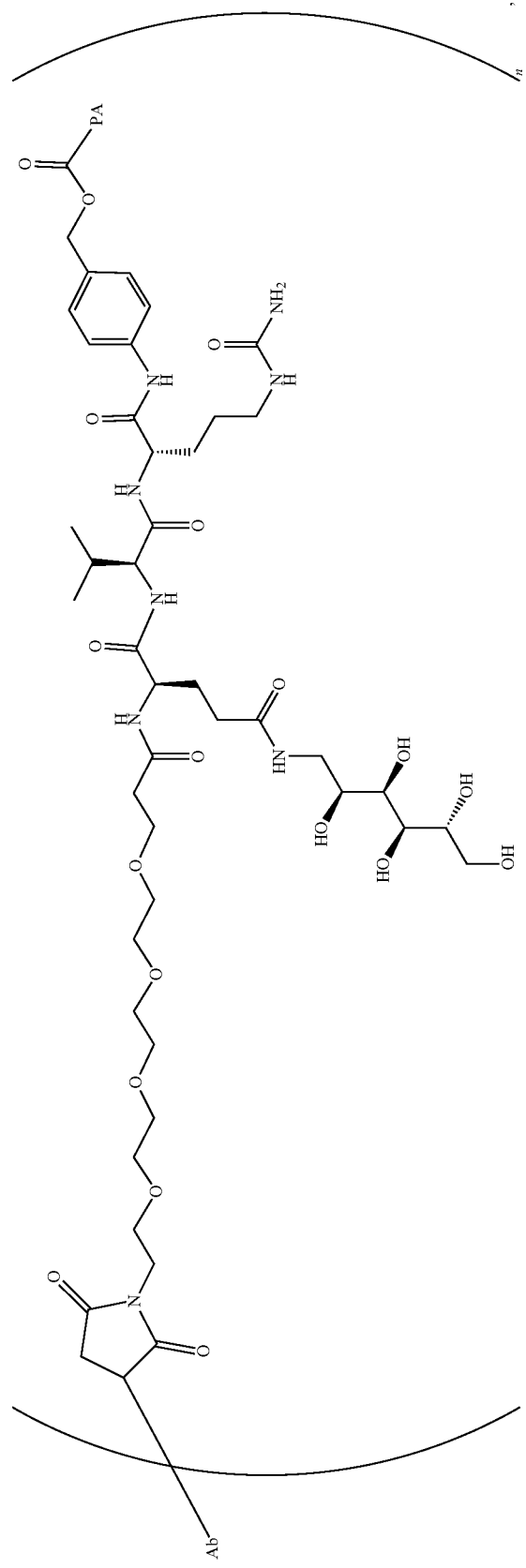

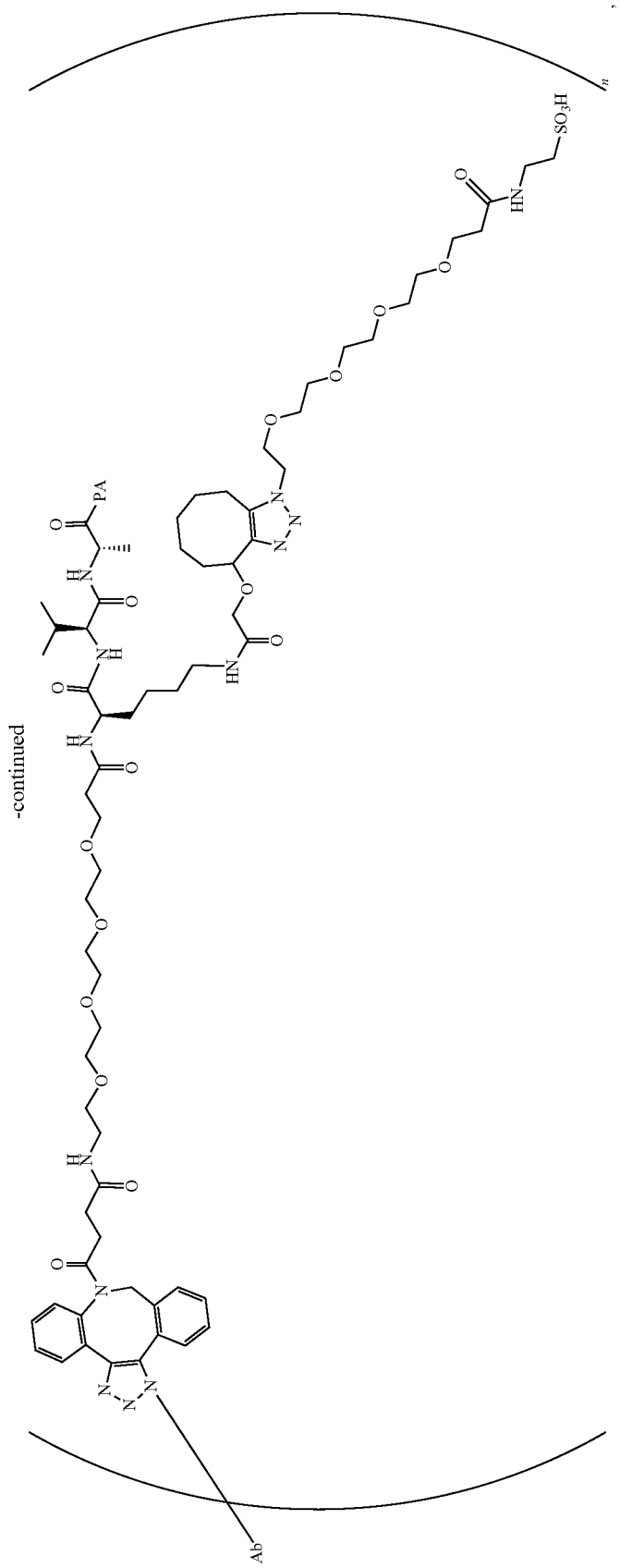

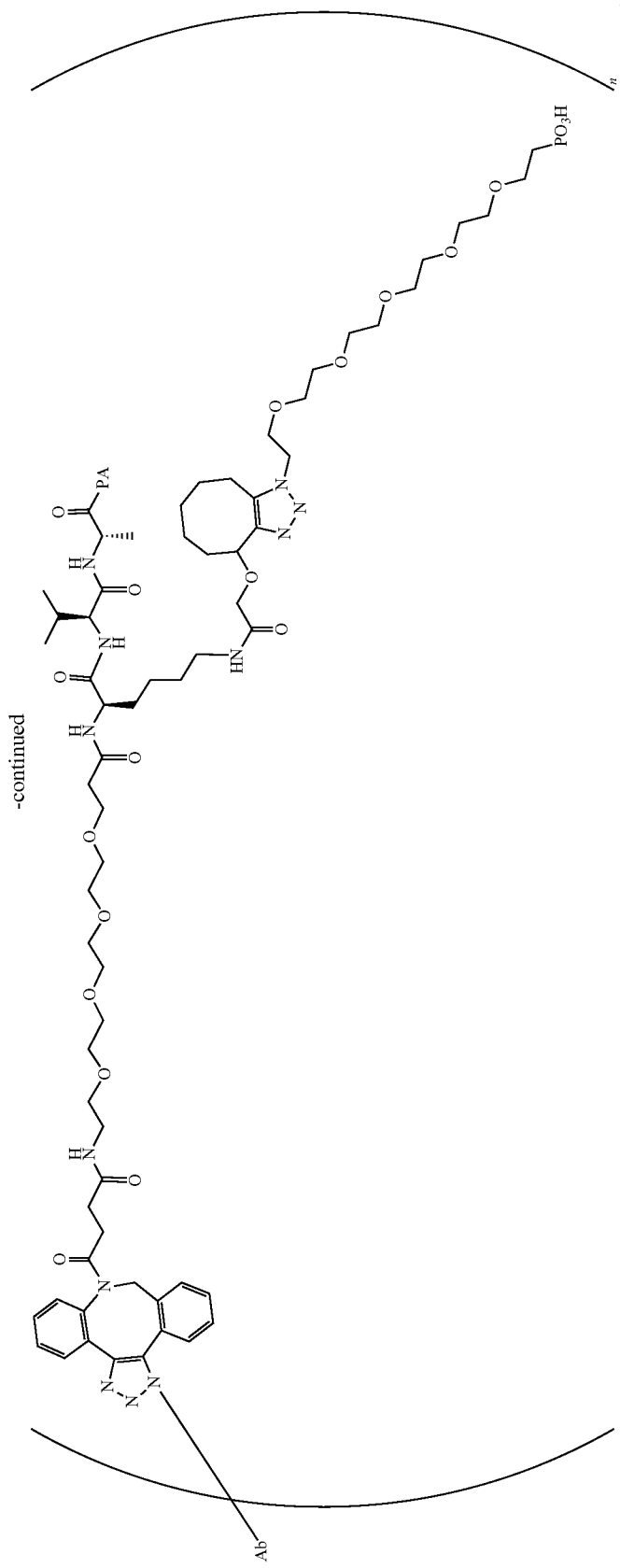

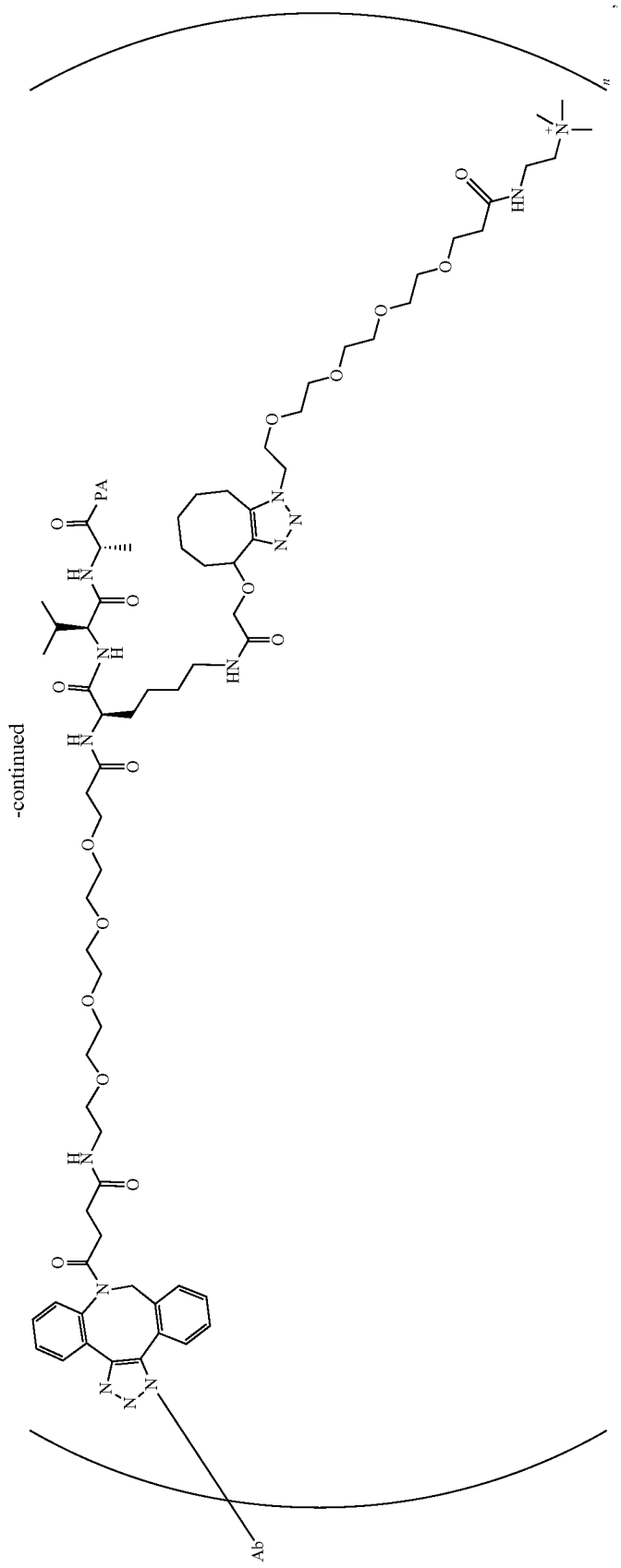

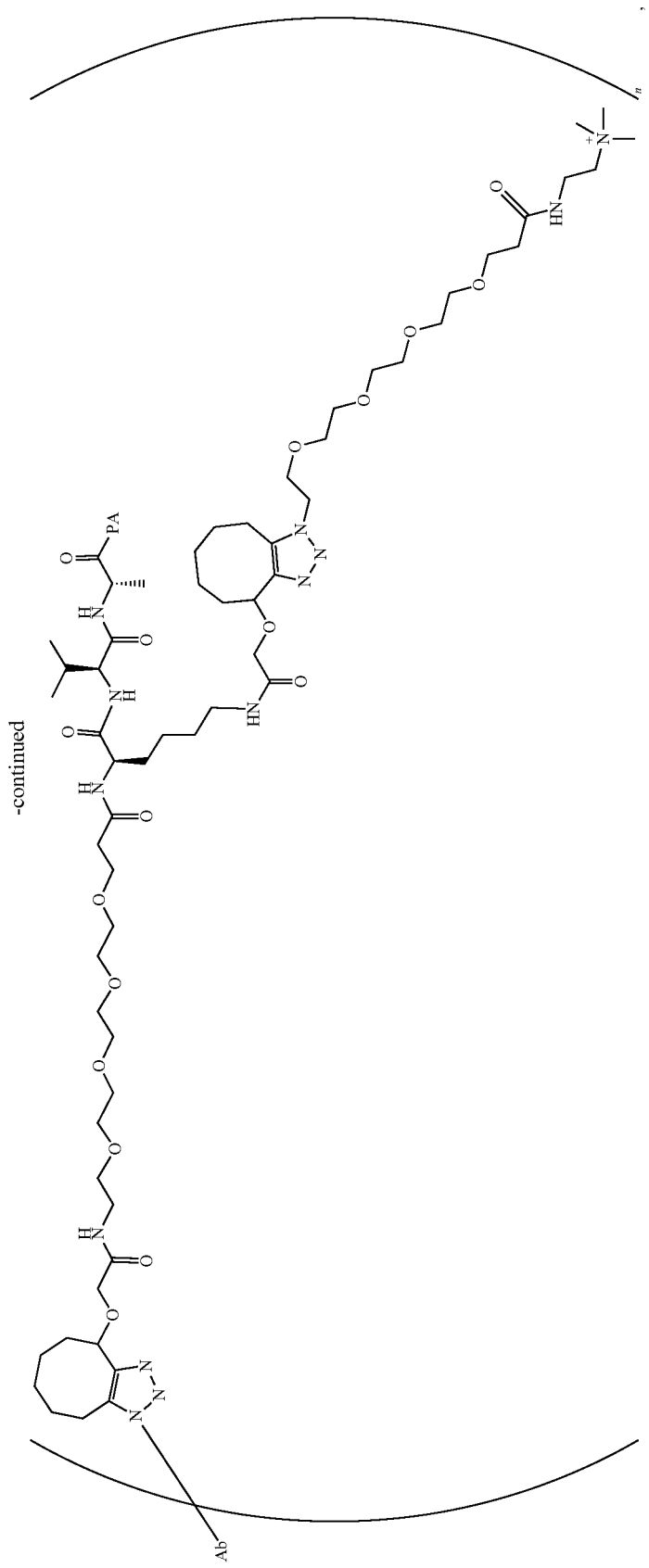

-continued
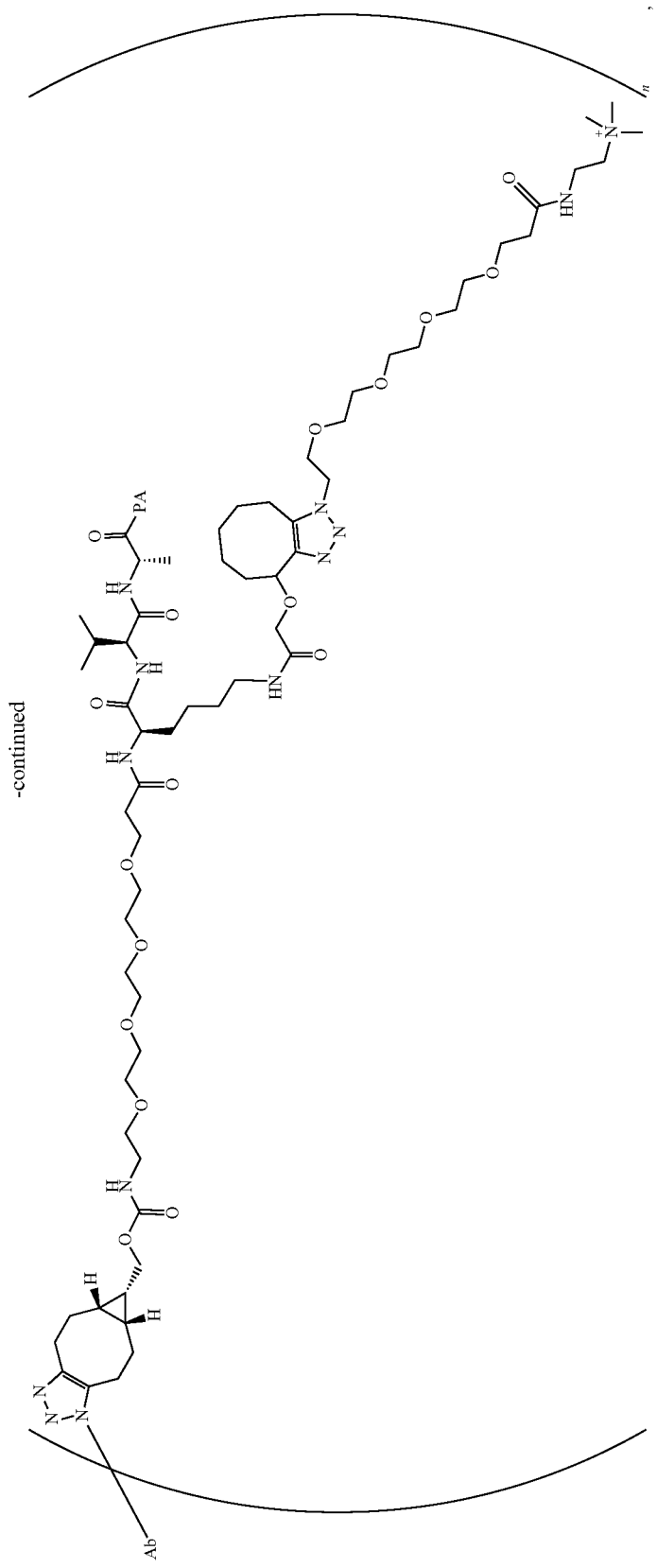

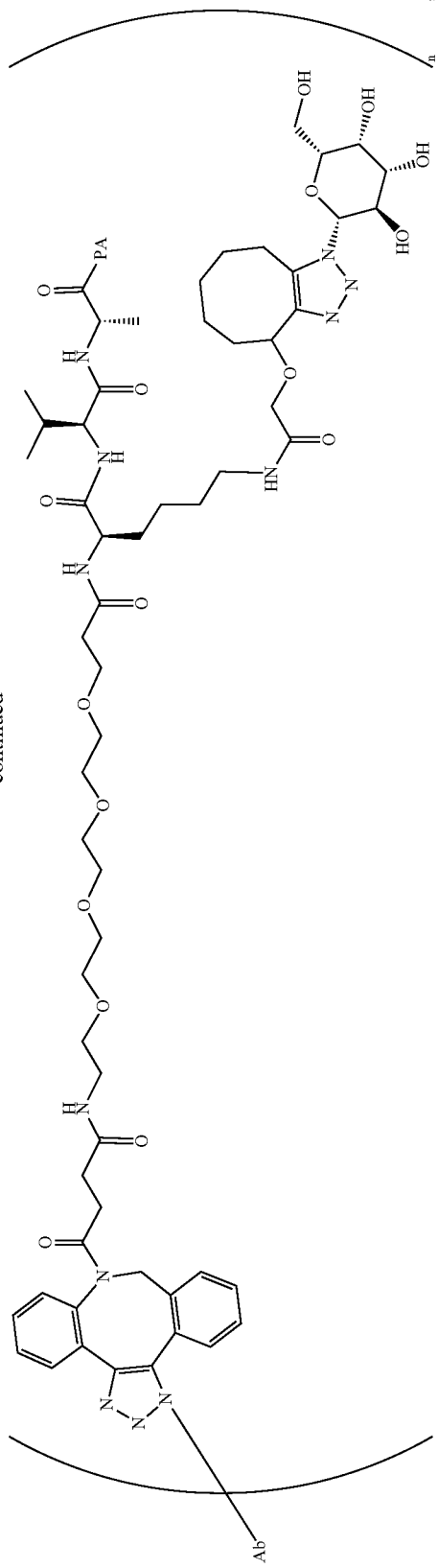
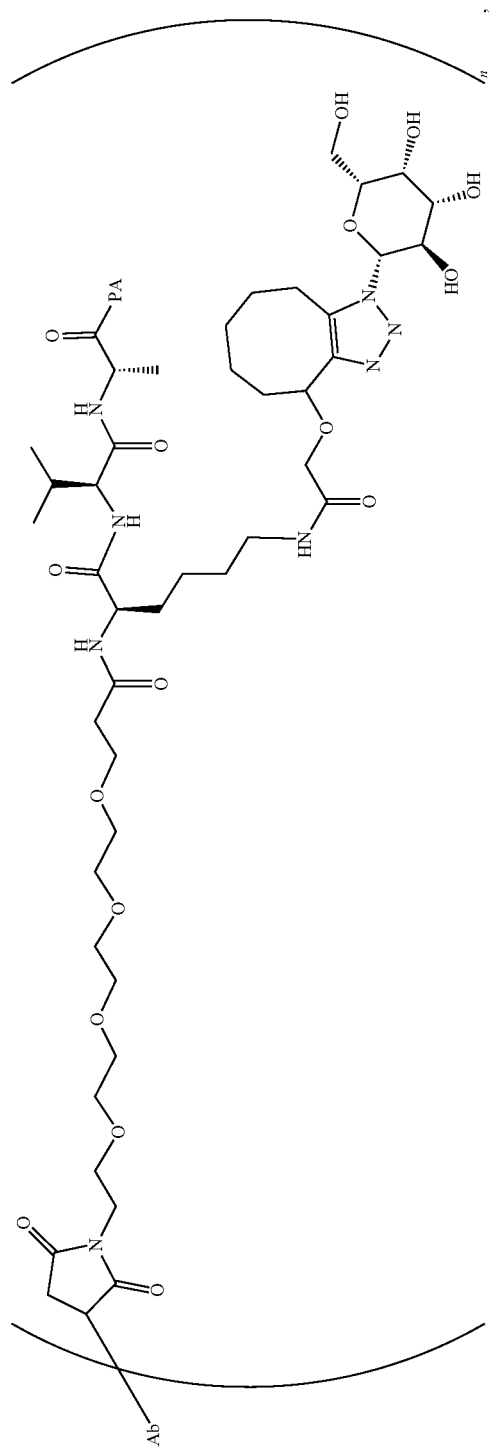

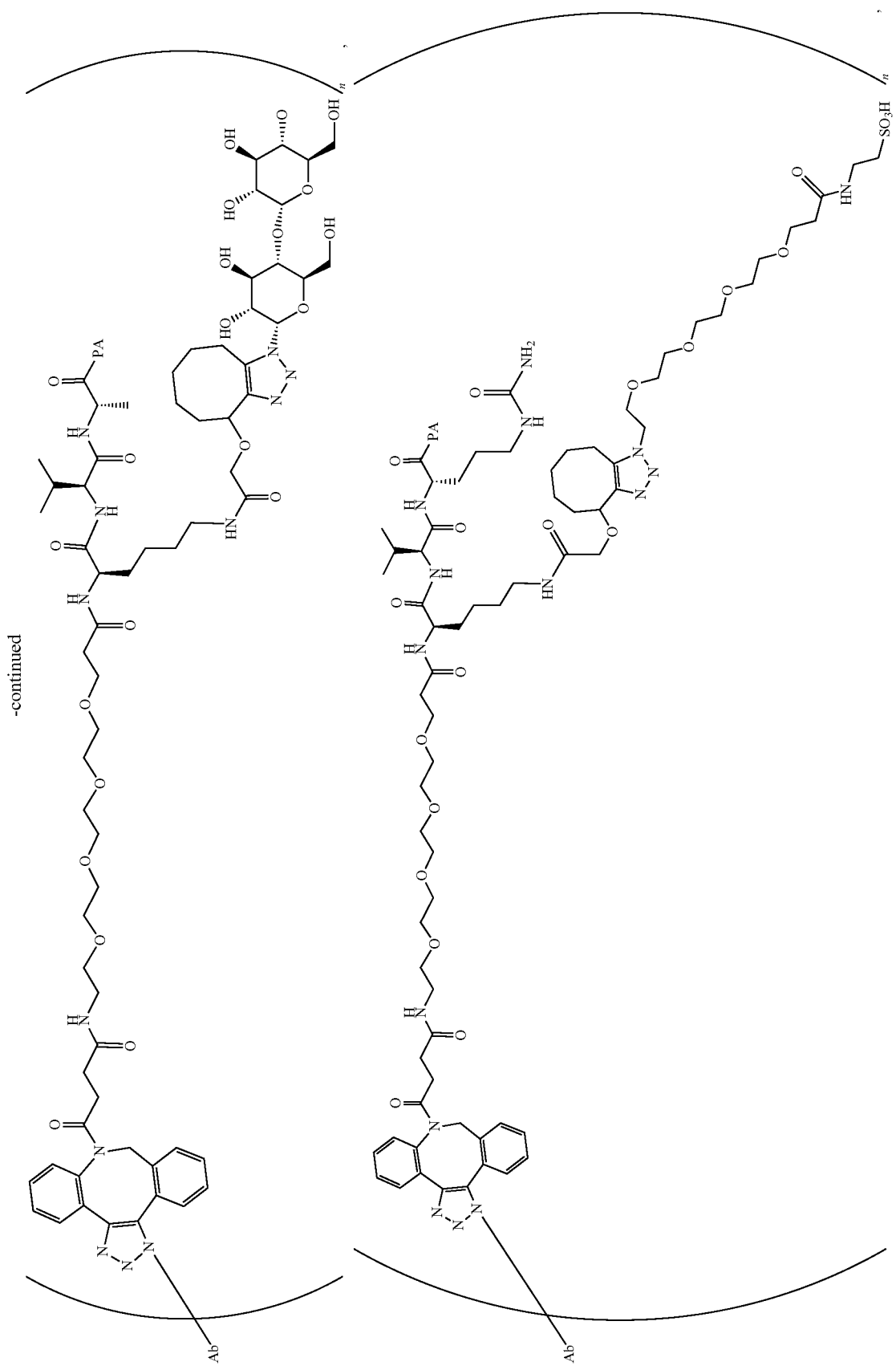

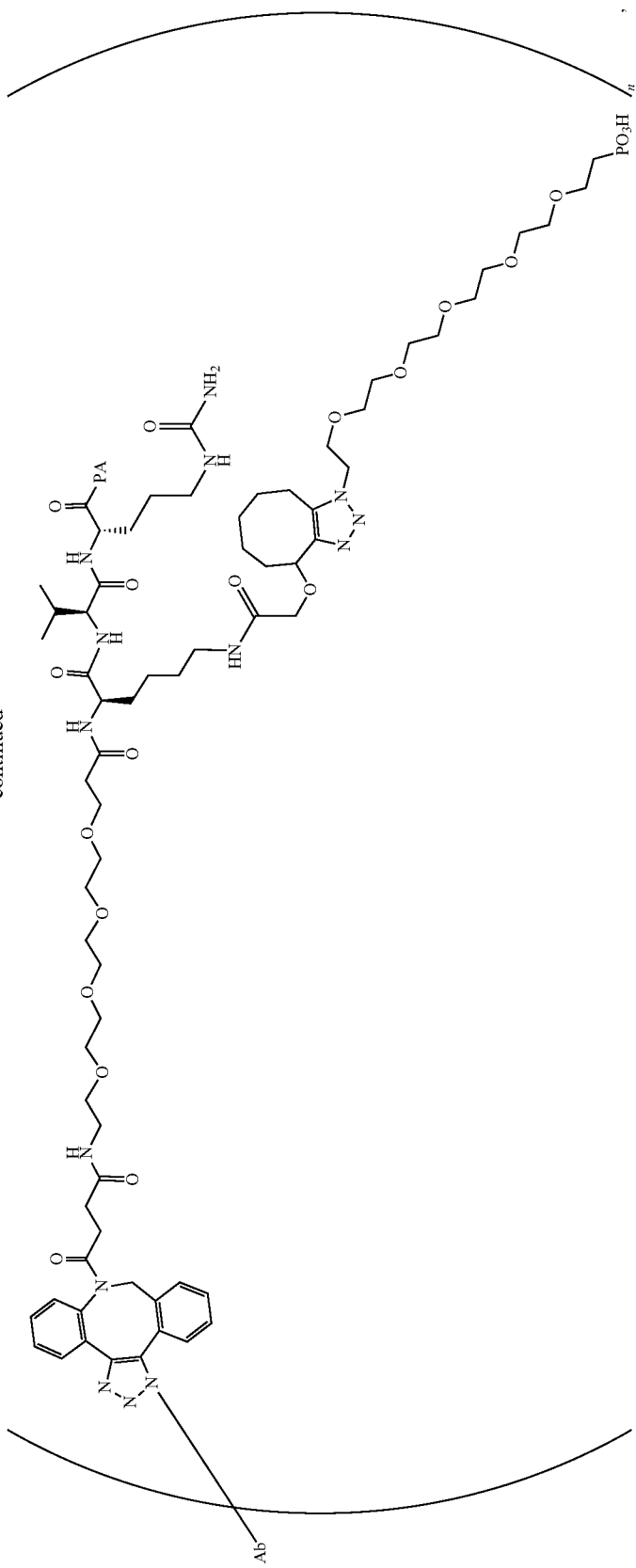

-continued
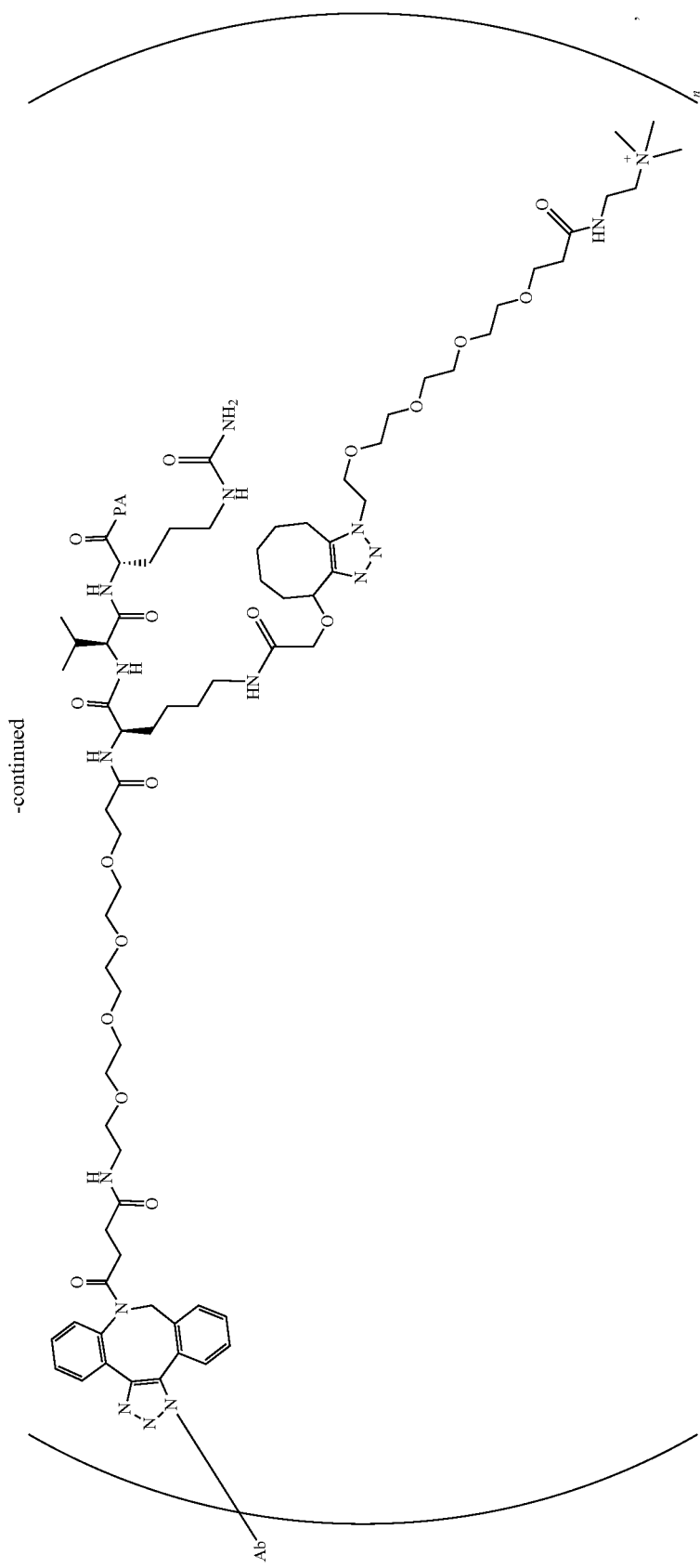

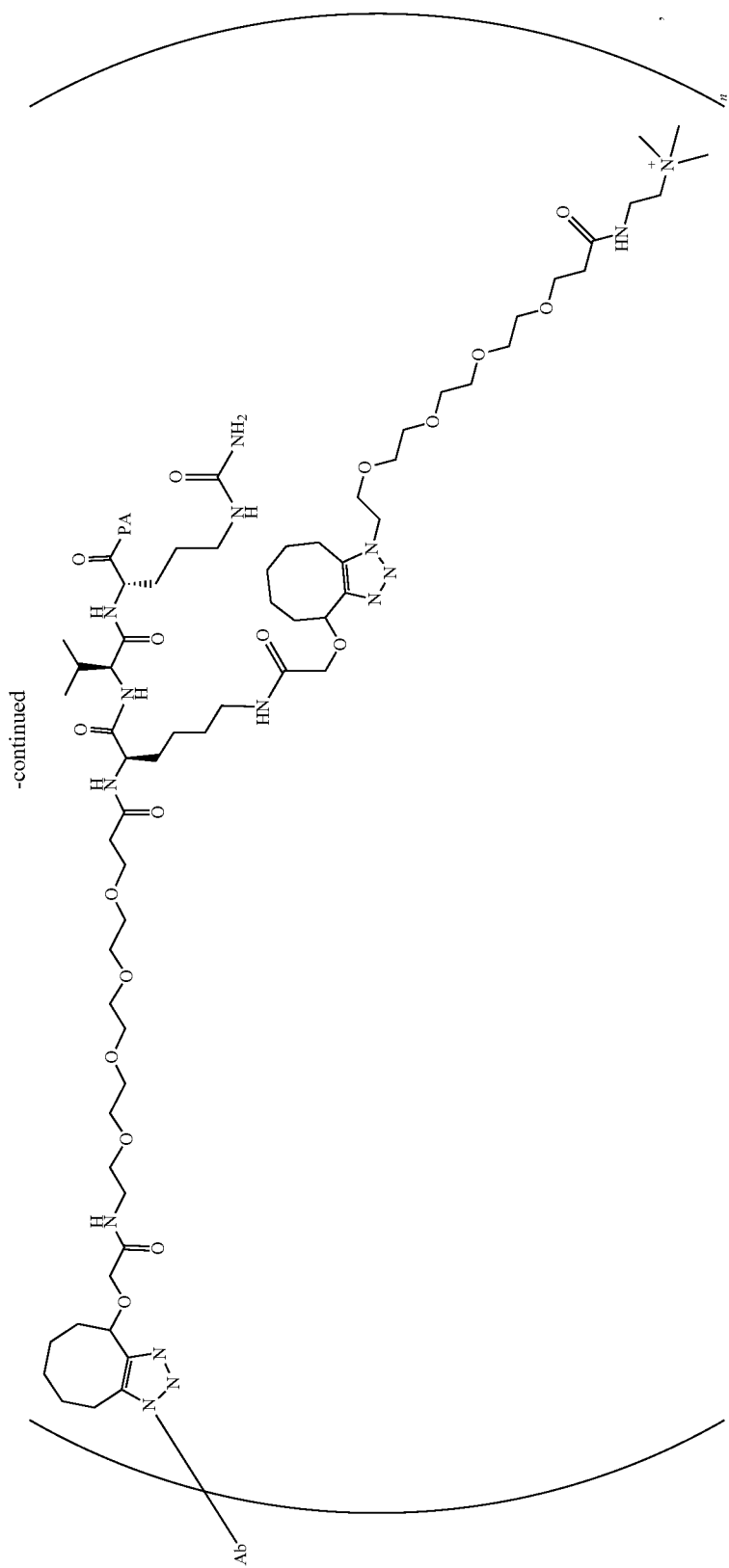

-continued
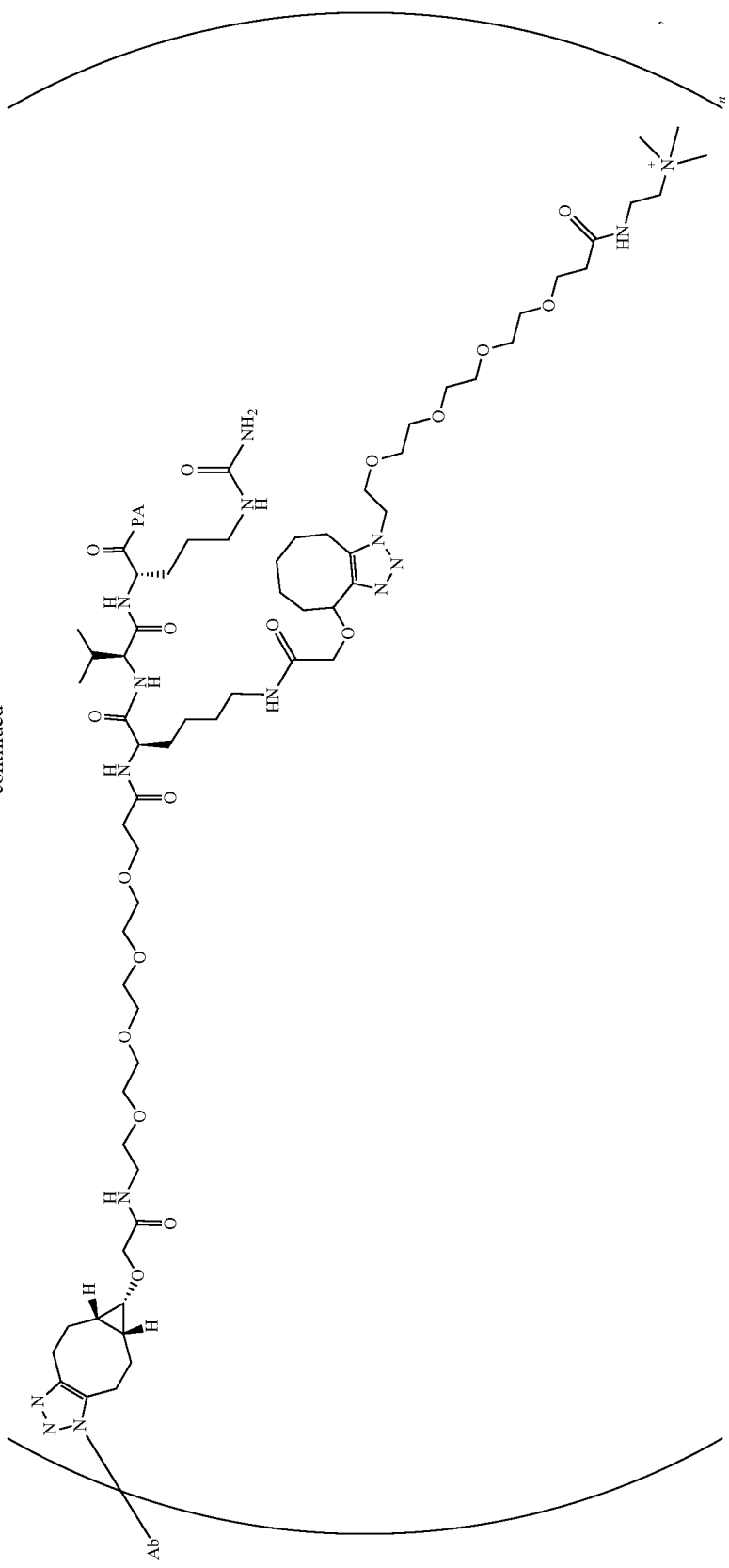

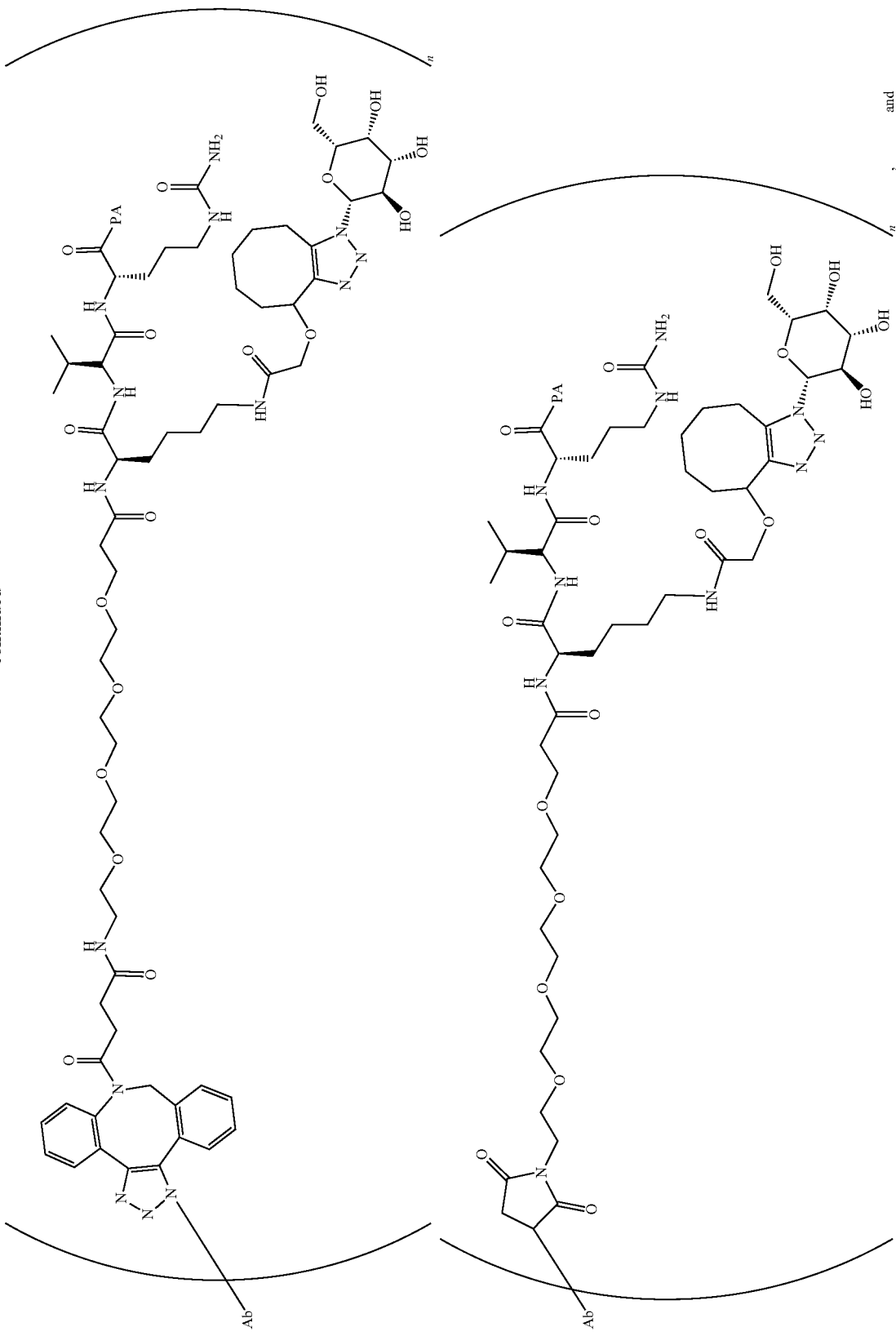

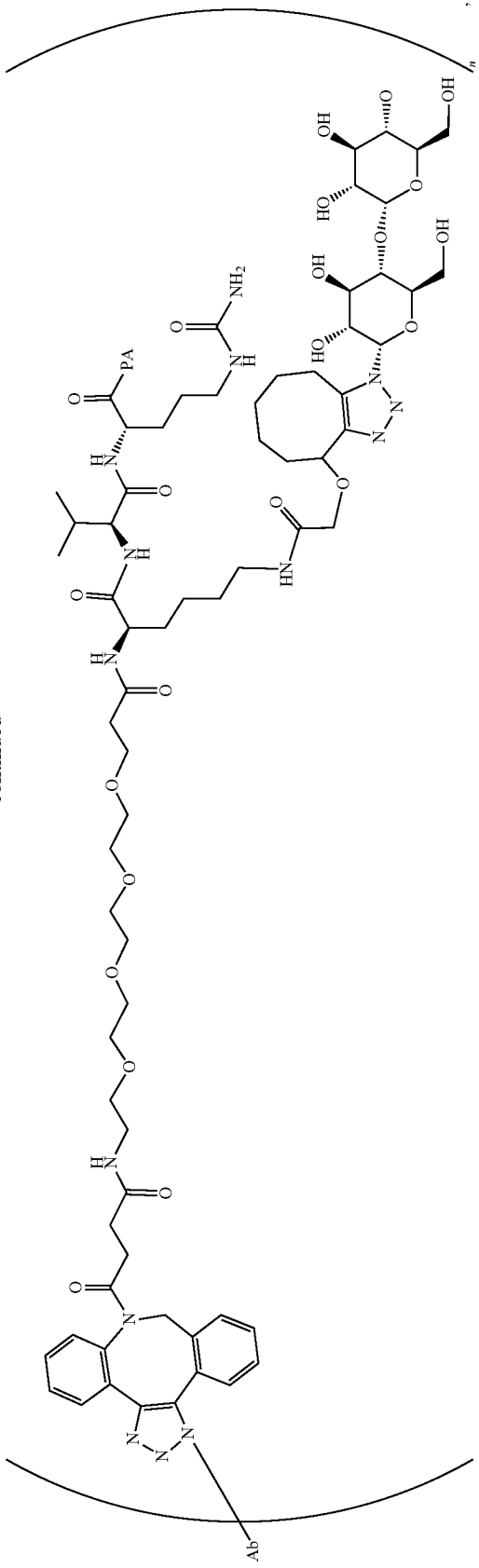

or a stereoisomeric form thereof, or a regioisomer thereof, or a mixture of regioisomers thereof, wherein each Ab is an antibody, or an antigen-binding fragment thereof;

PA is a payload residue; and subscript n is an integer from 1 to 30.

In some instances, a compound of Formula (I), Formula (II), Formula (III), Formula (IV), Formula (IVa), Formula (IVb), Formula (IVc), Formula (Va), Formula (Vb), Formula (Vc), or Formula (Vd), is an antibody drug conjugate (ADC), wherein BA is Ab and Ab is an antigen or antigen-binding fragment thereof, selected from the group consisting of:

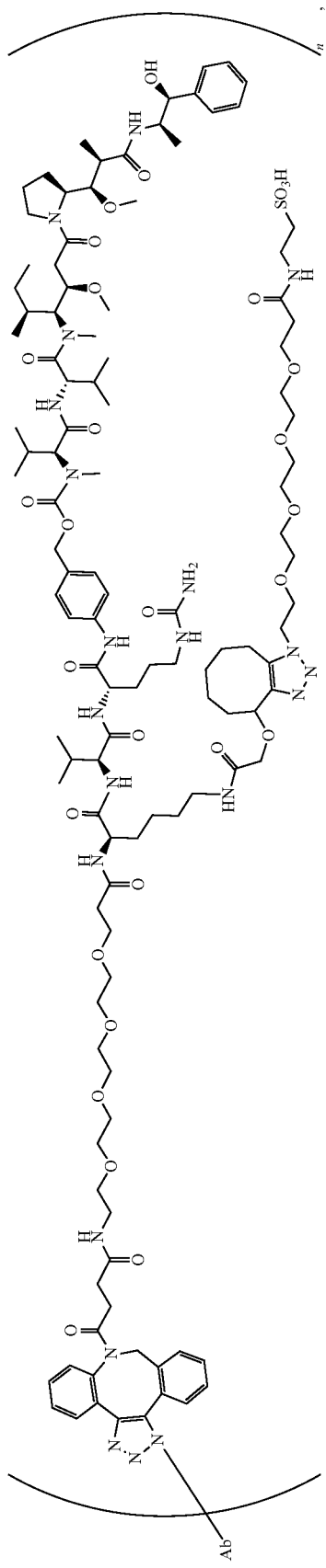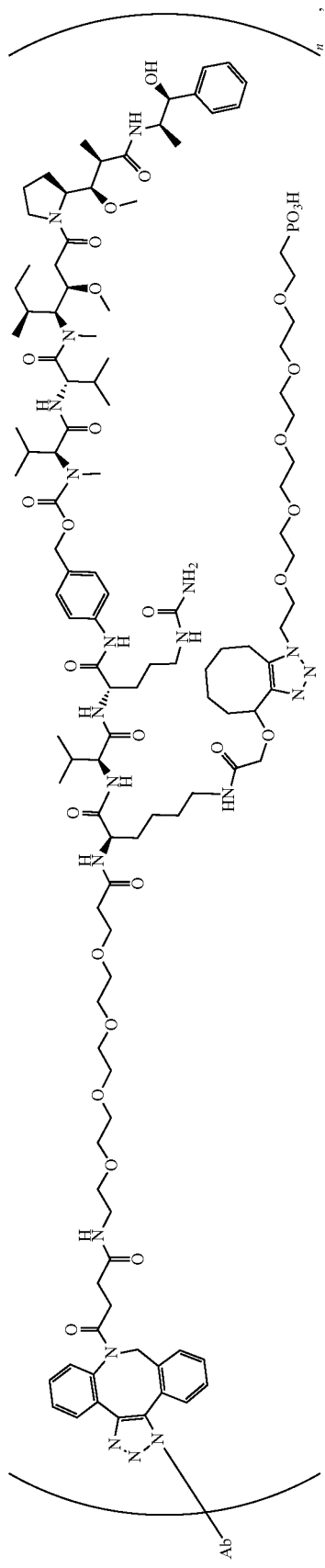

-continued
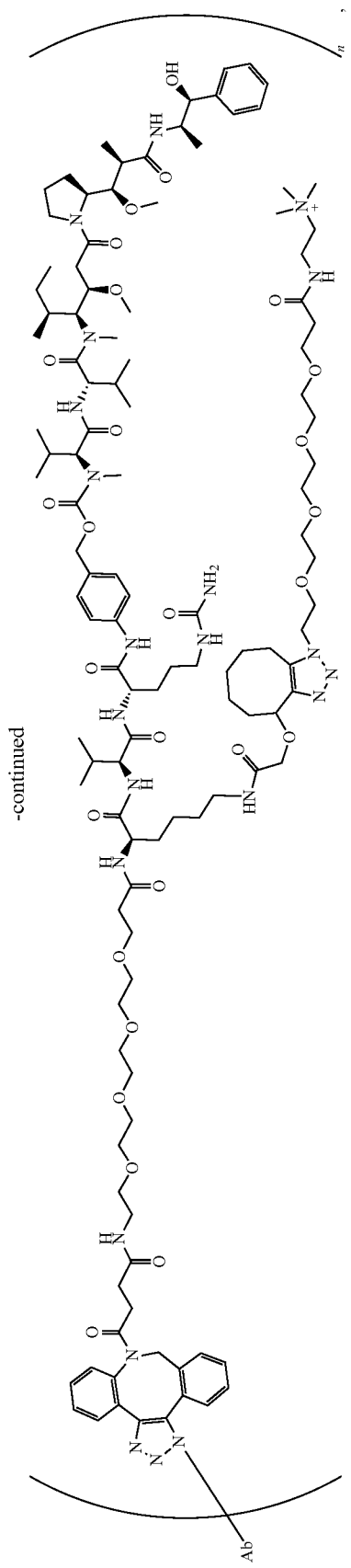
201
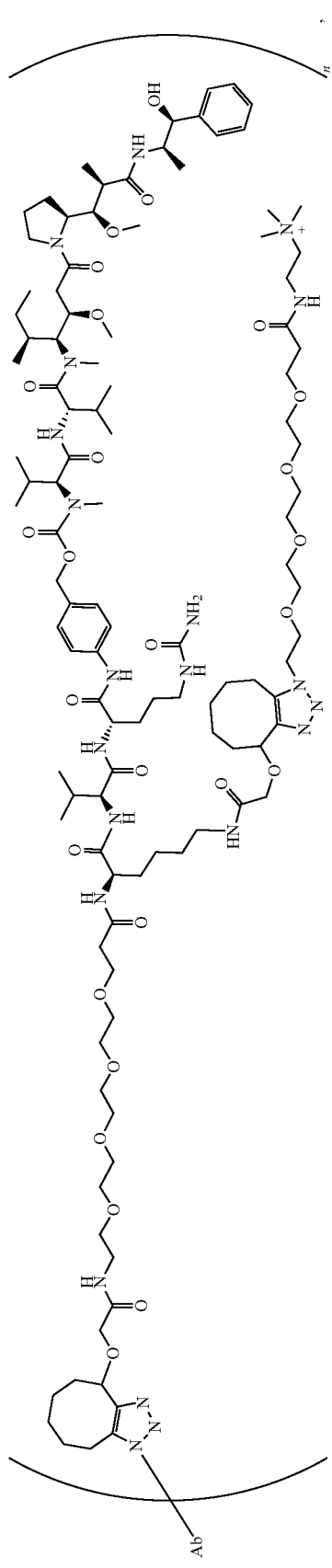
202

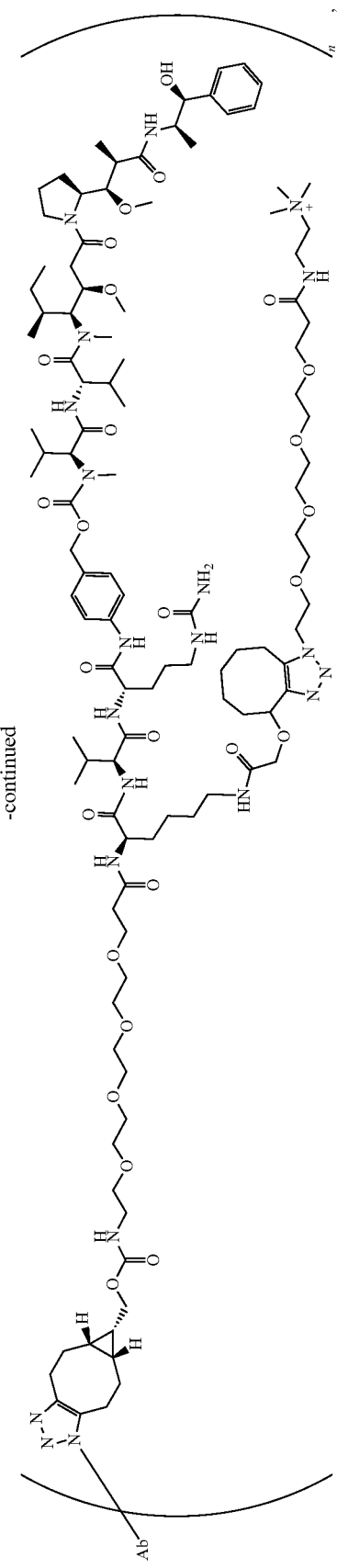
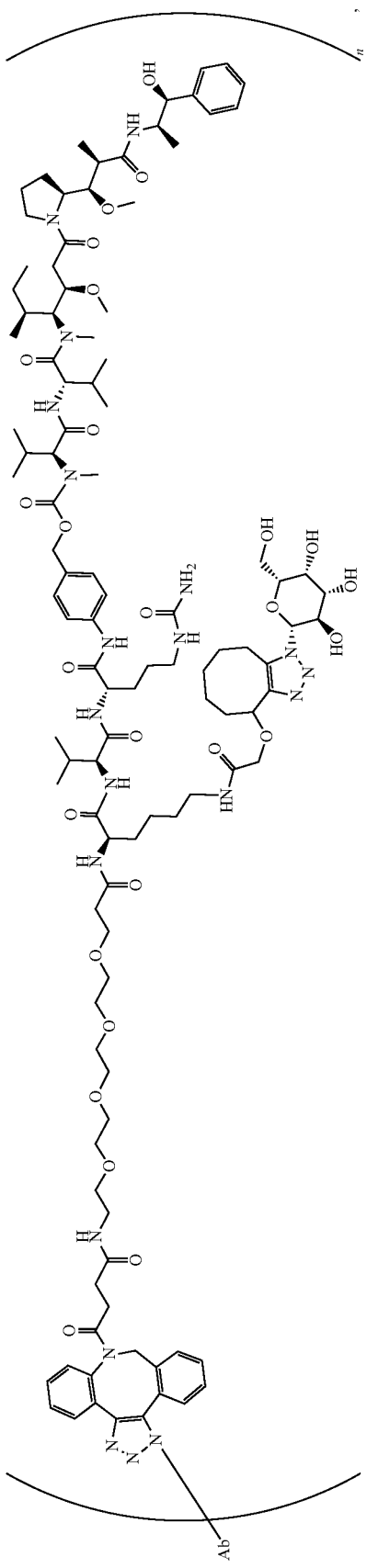

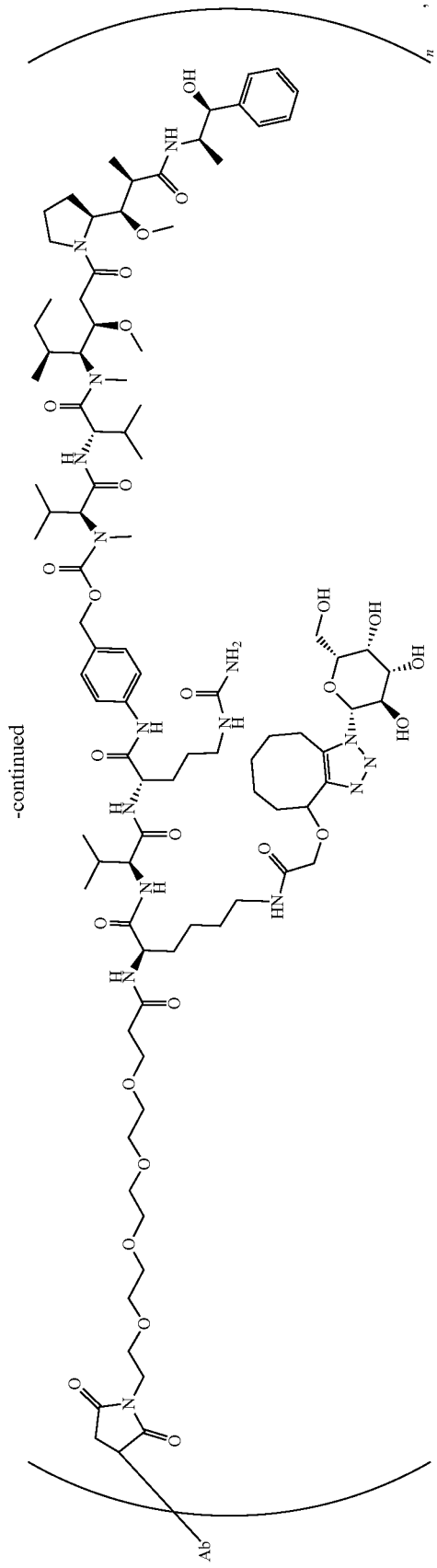

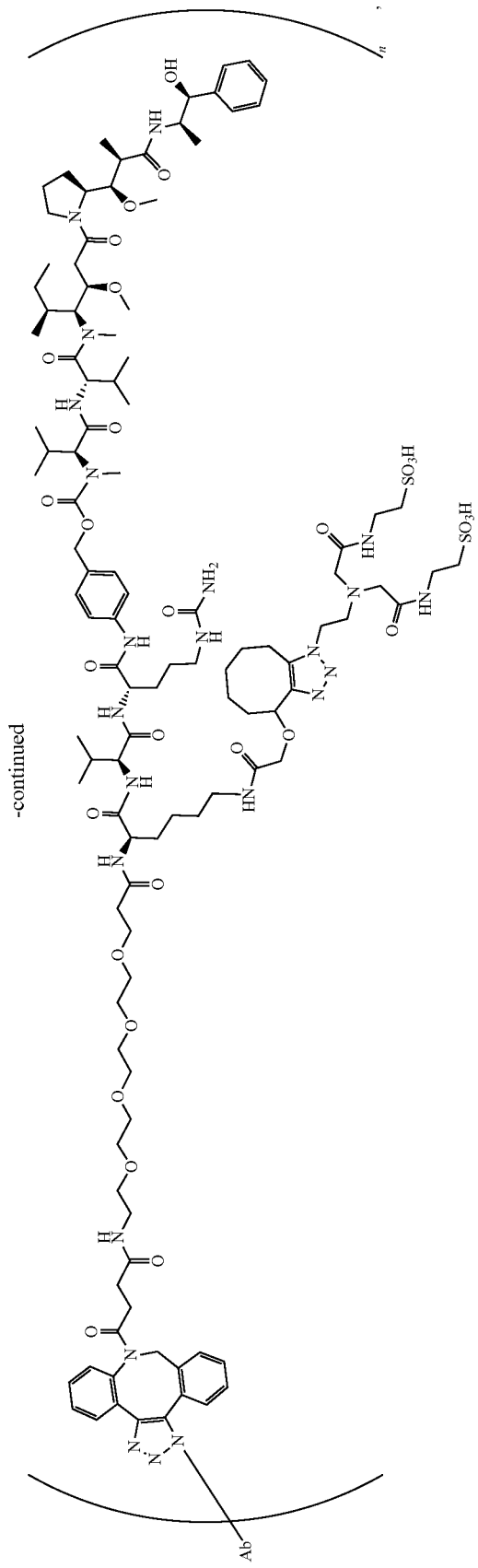
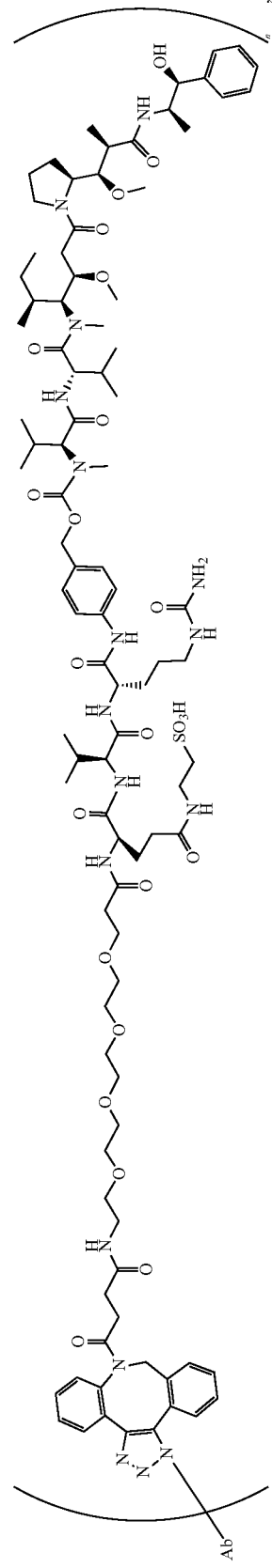

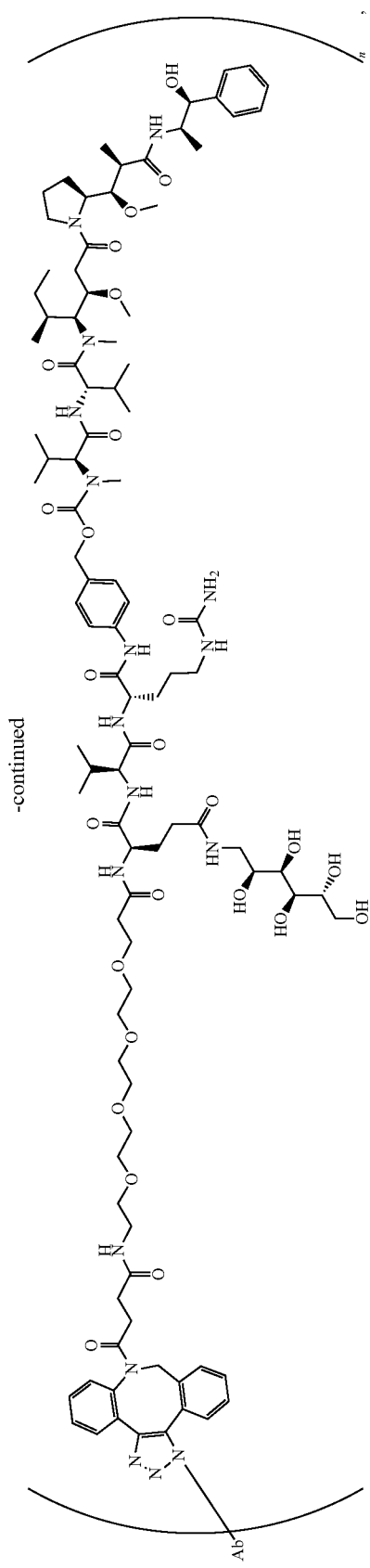

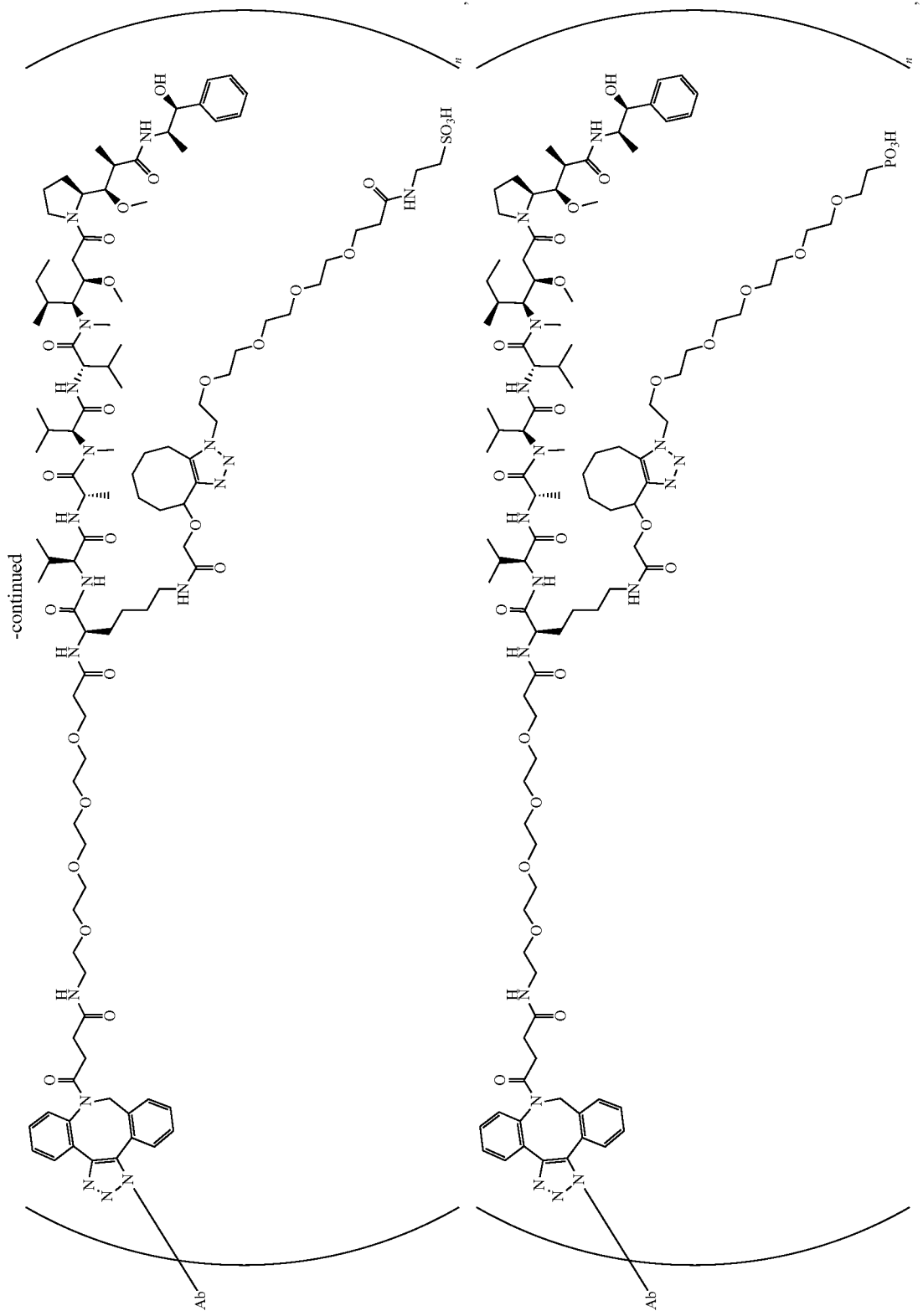

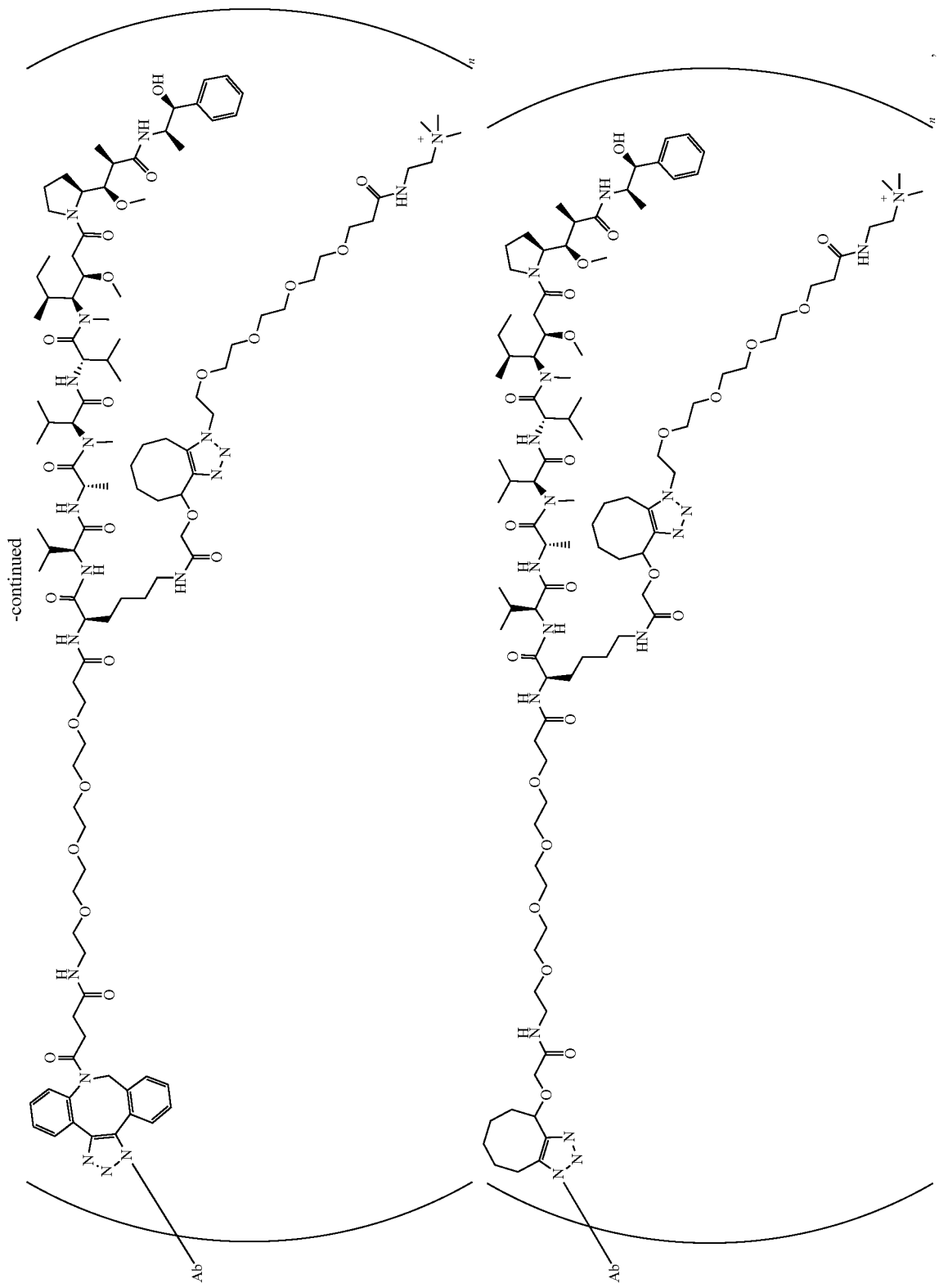

-continued
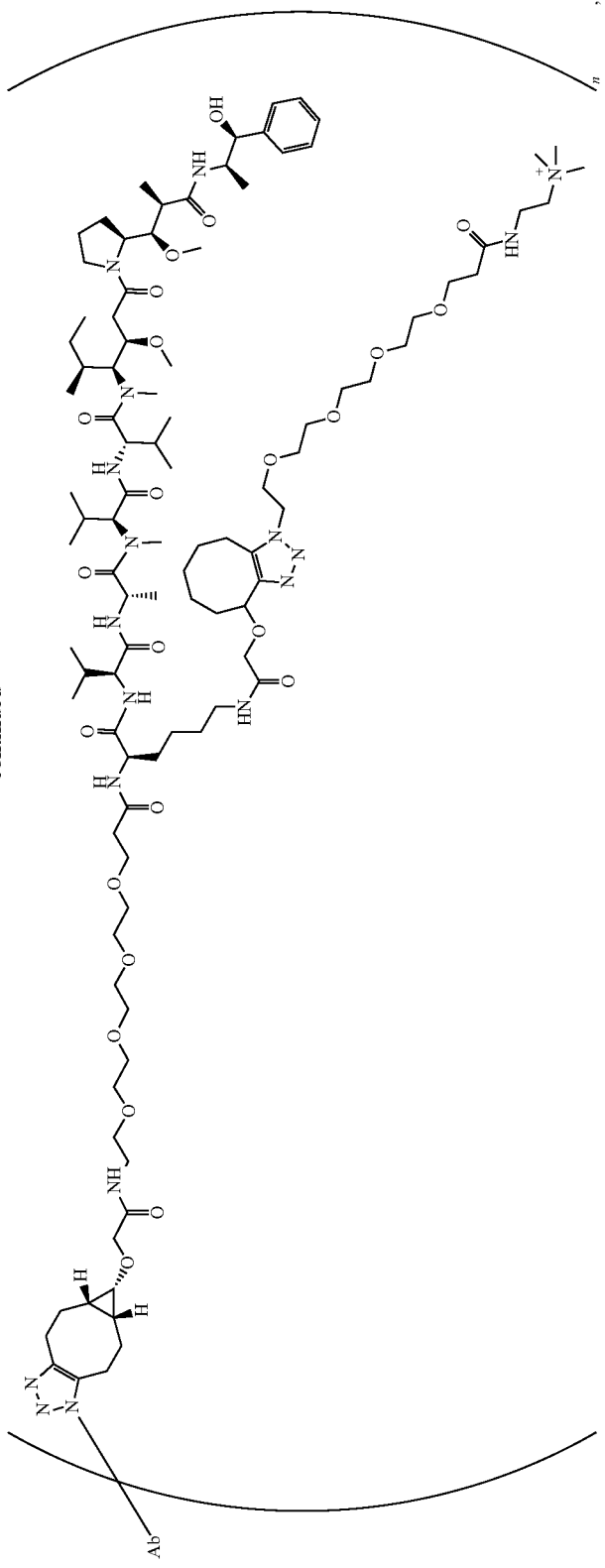

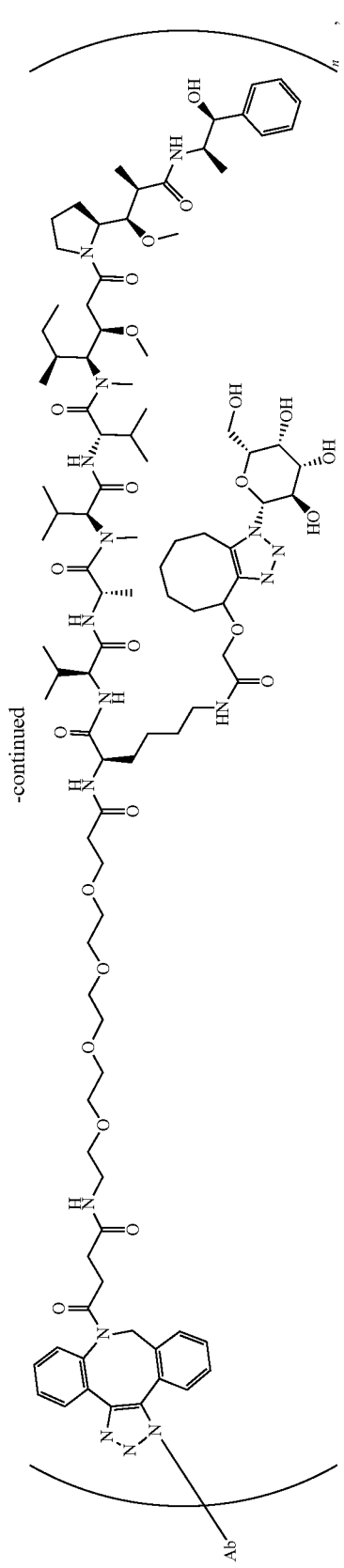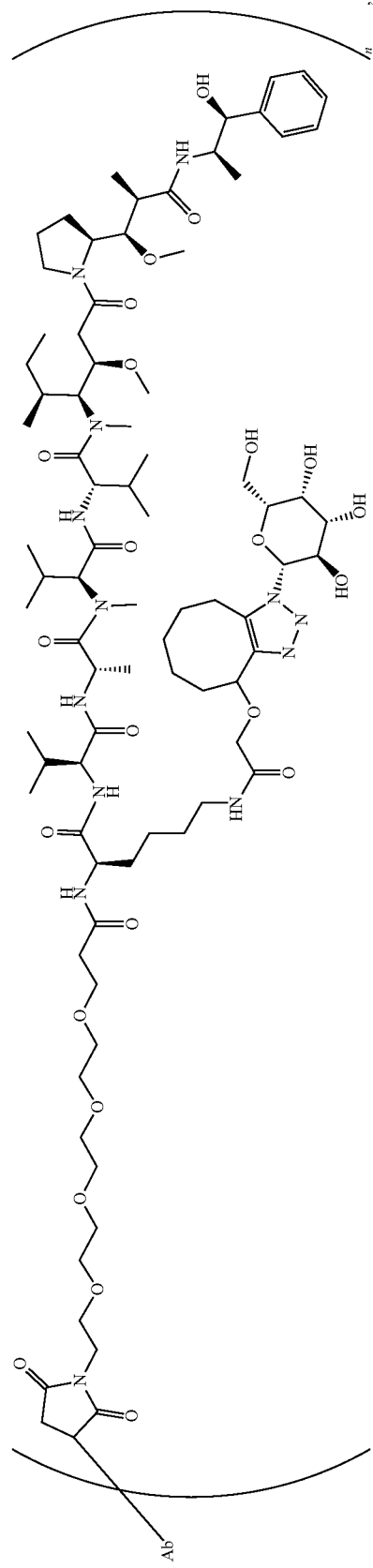

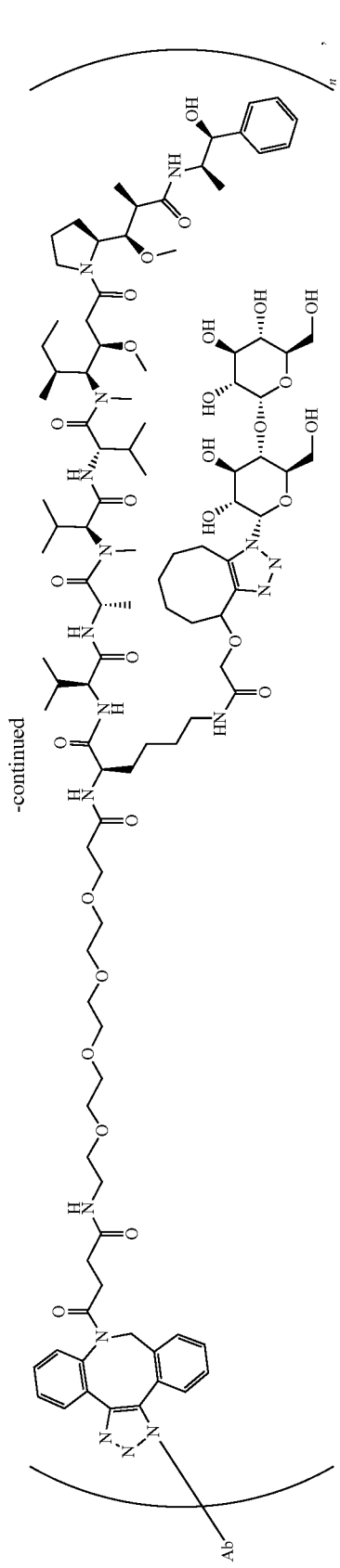
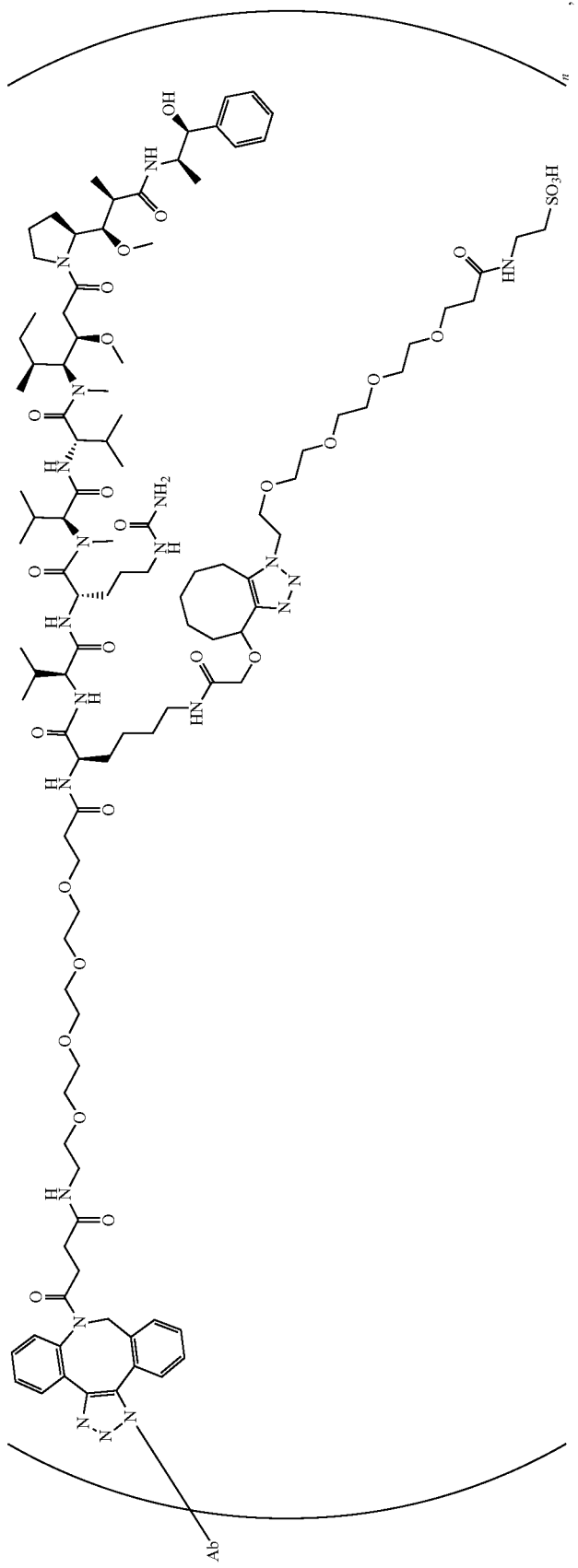

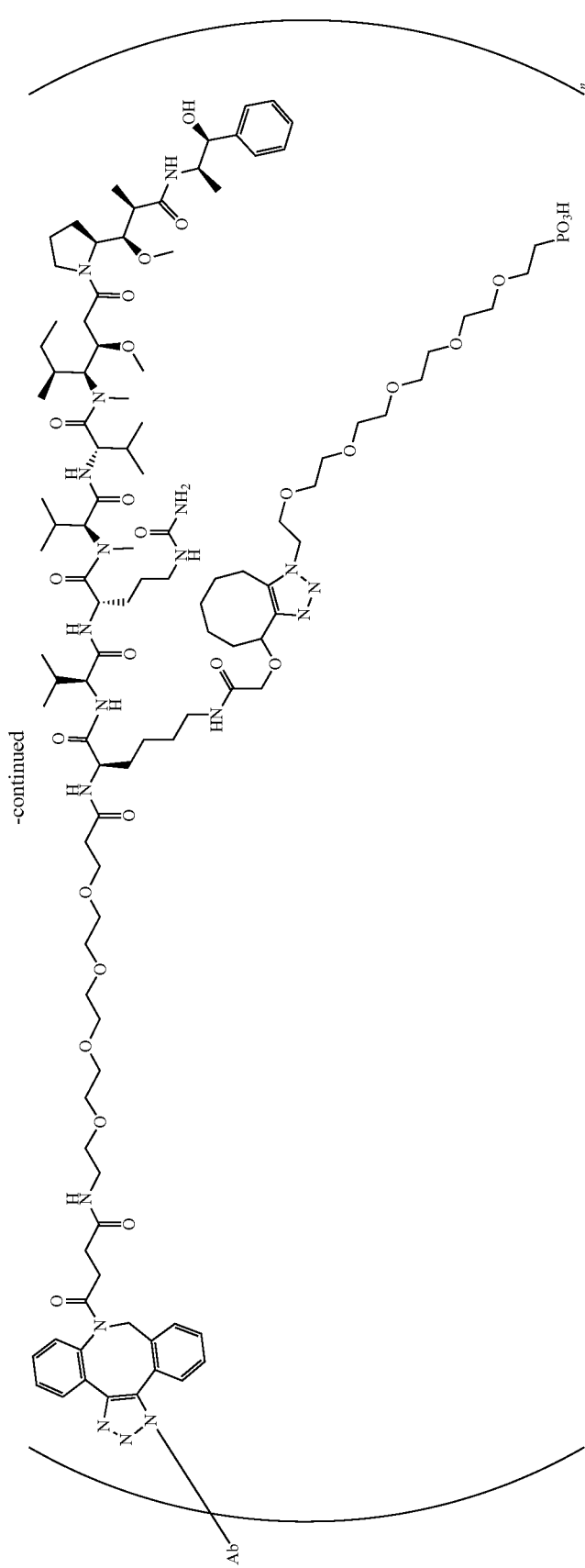

-continued
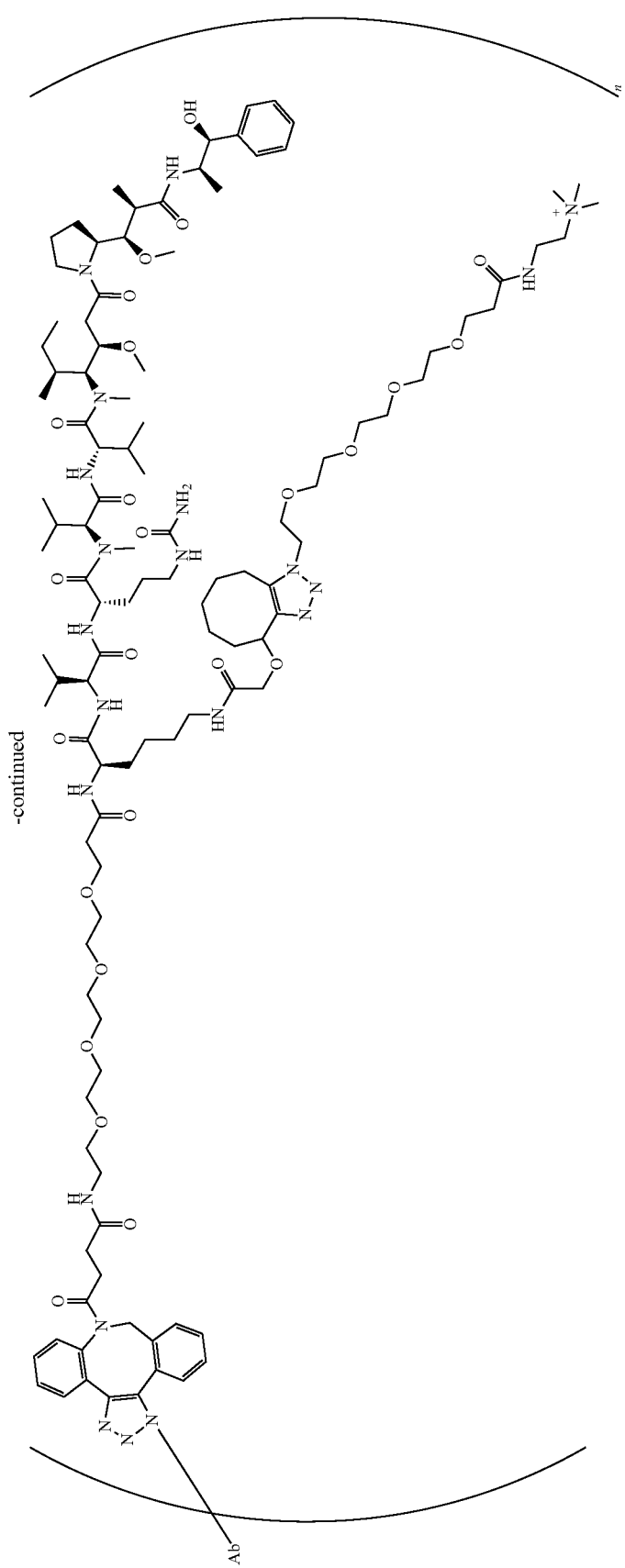

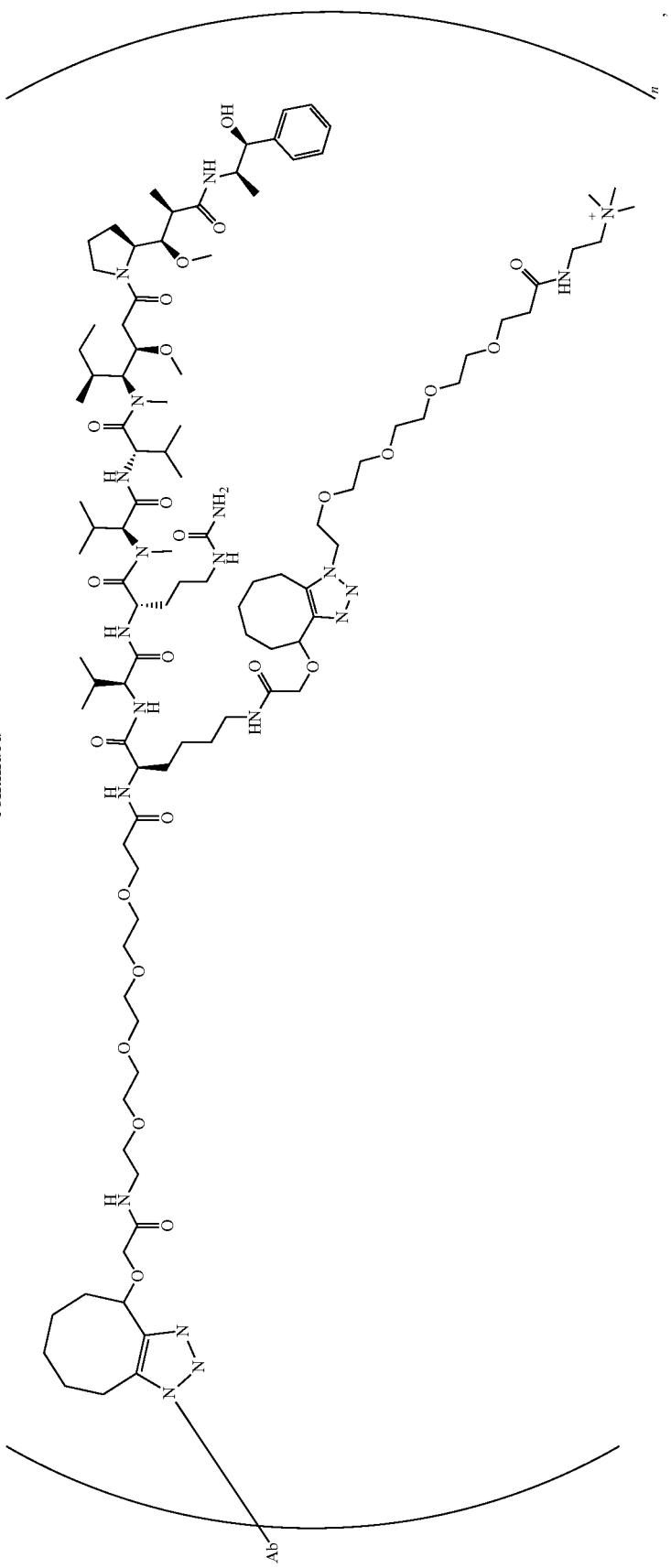

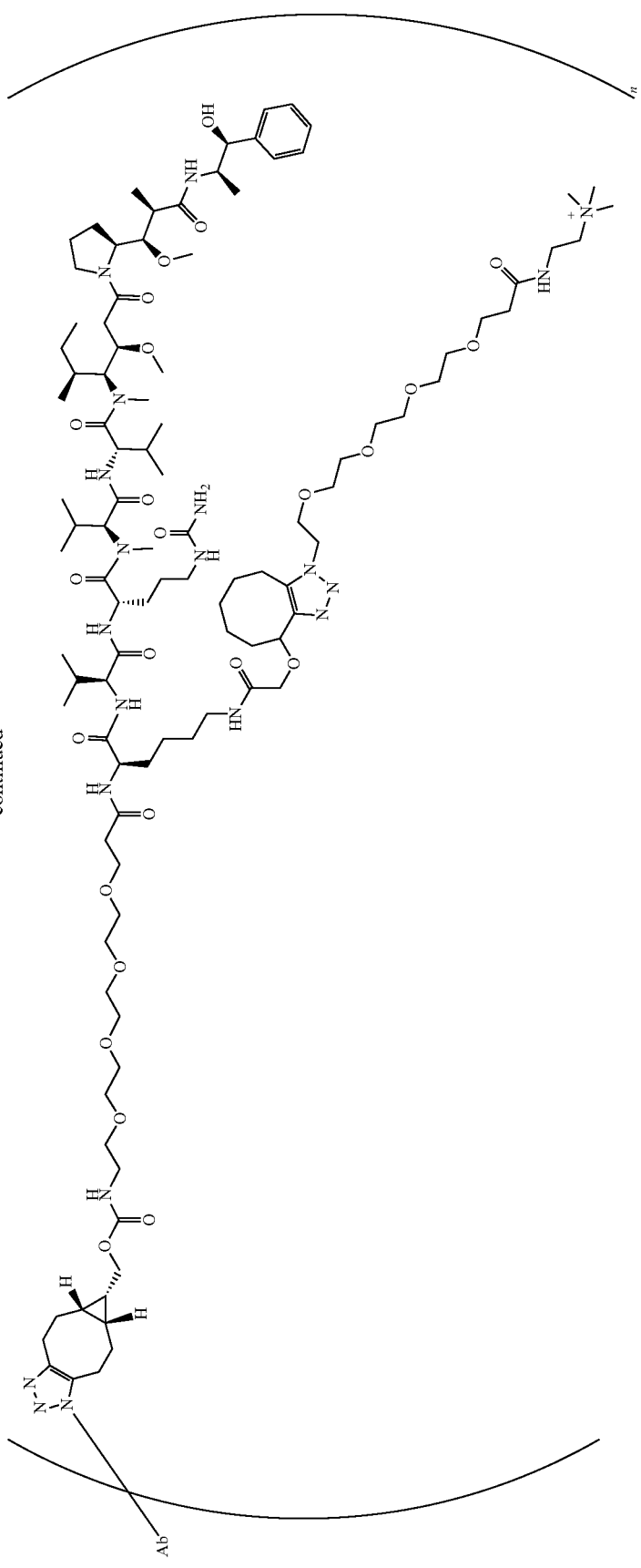

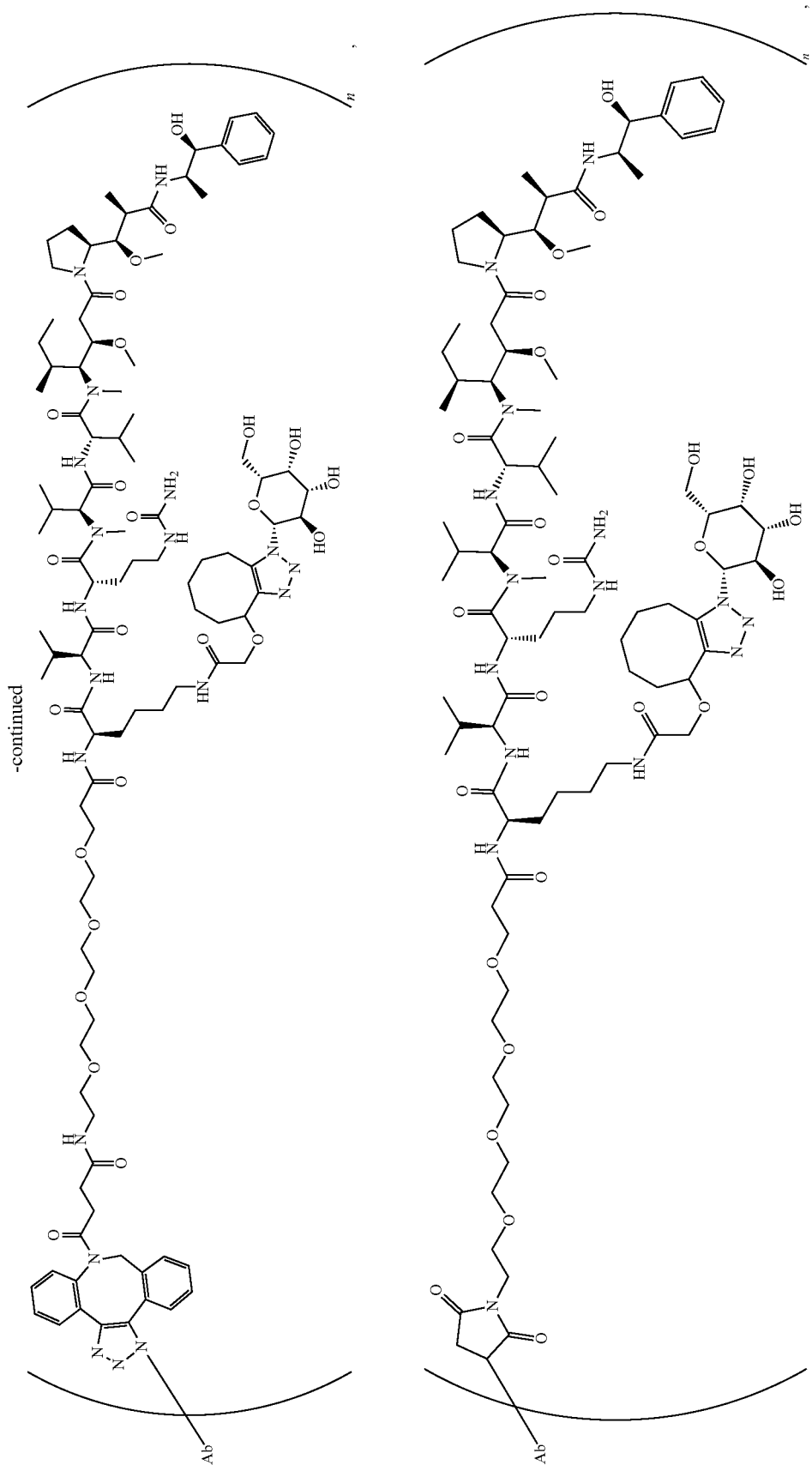

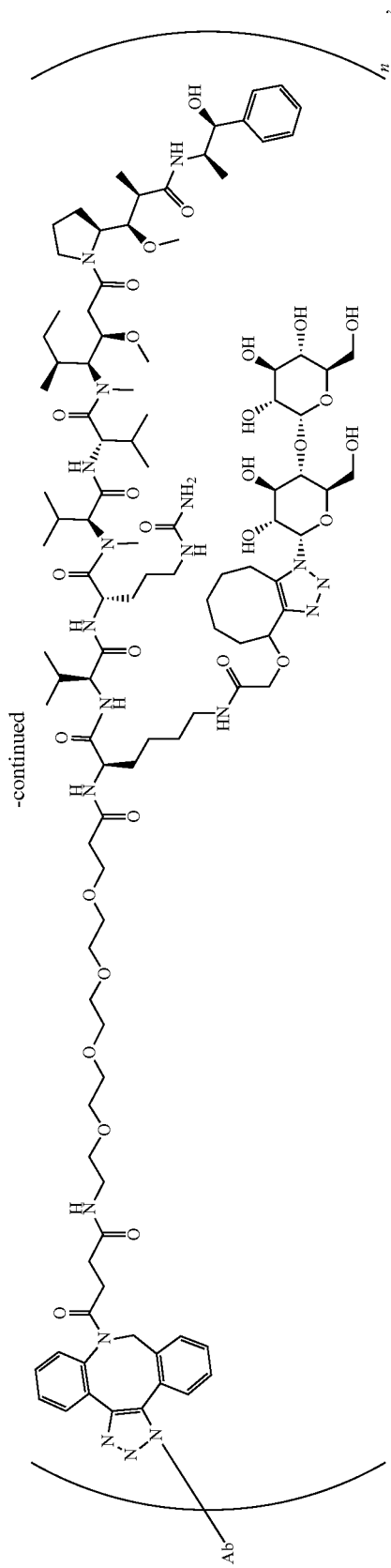

233
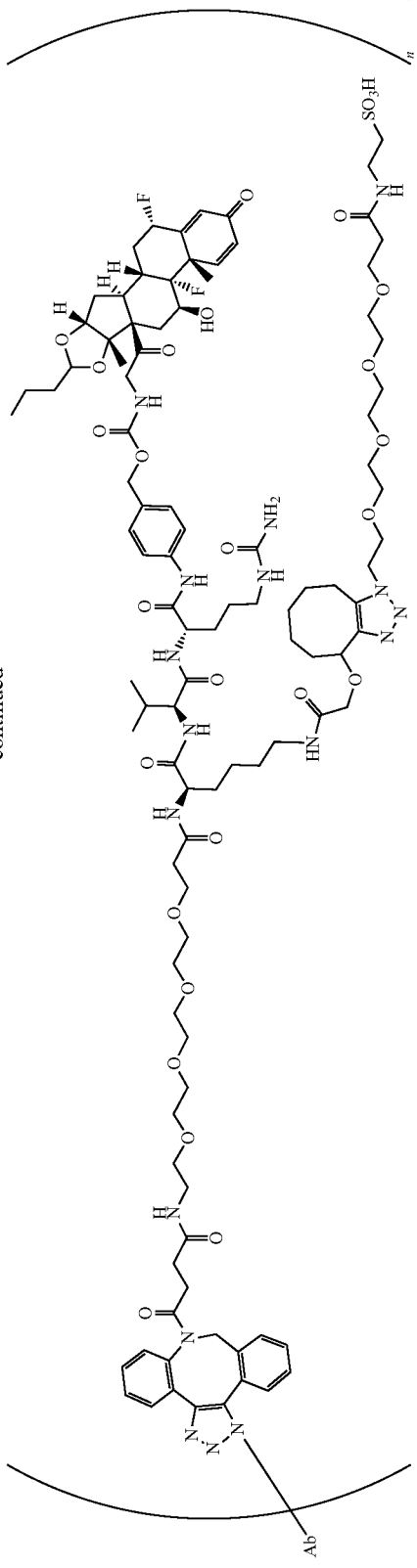
234
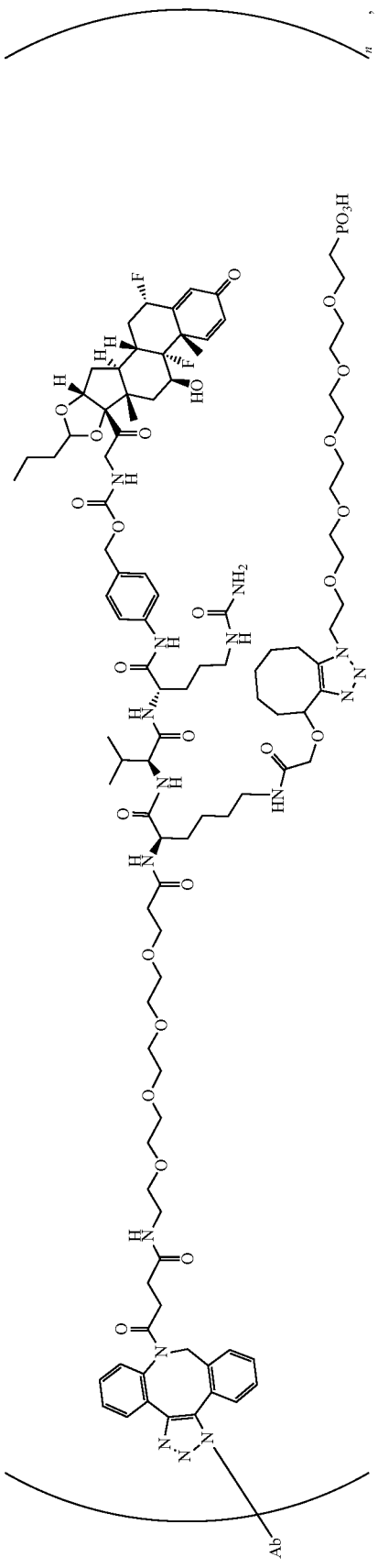

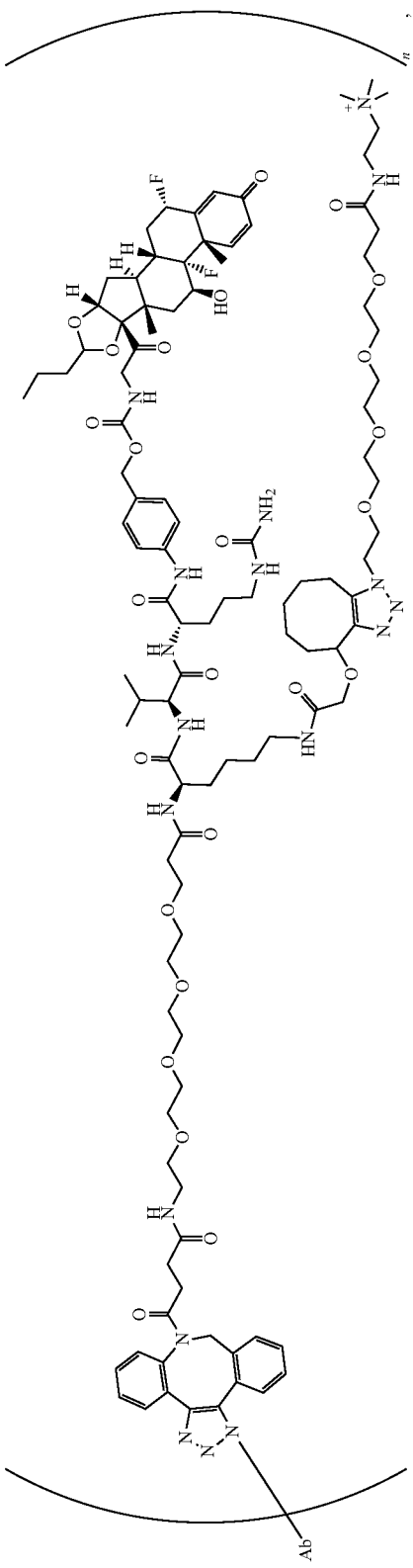
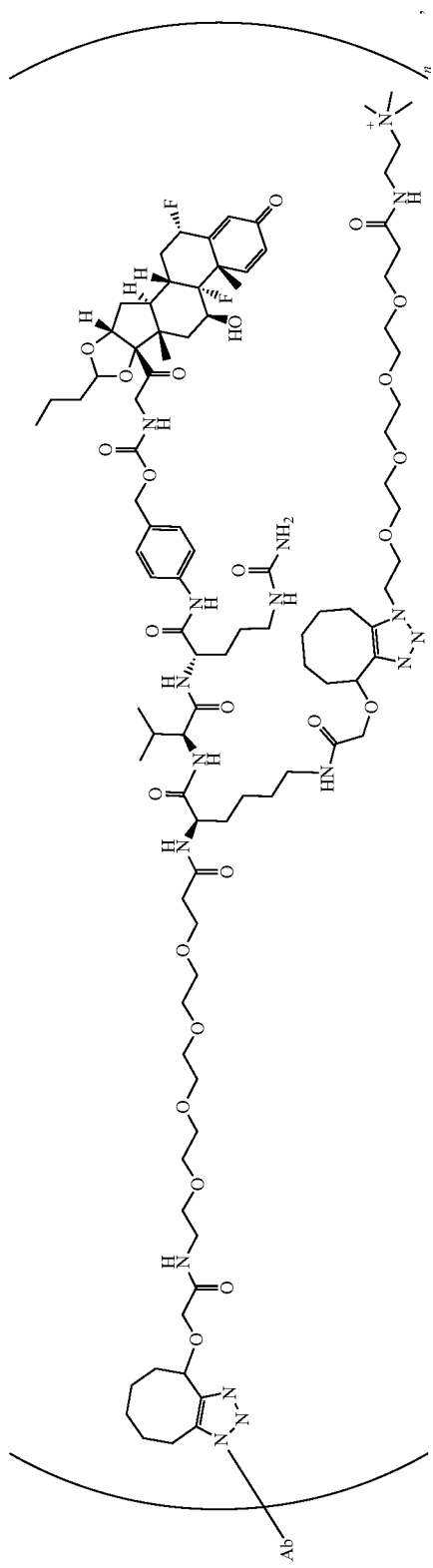

-continued
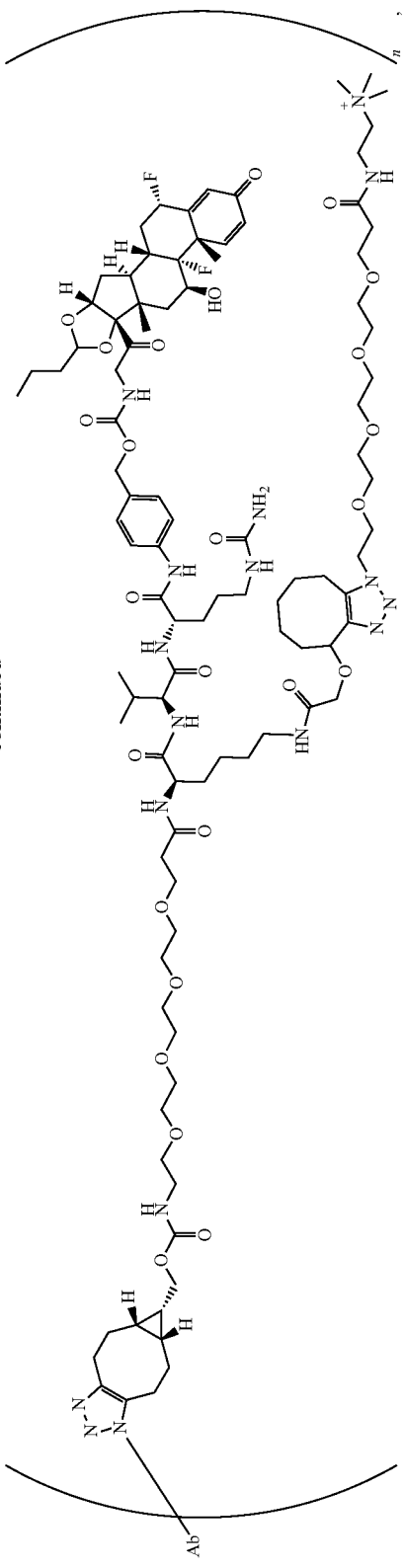 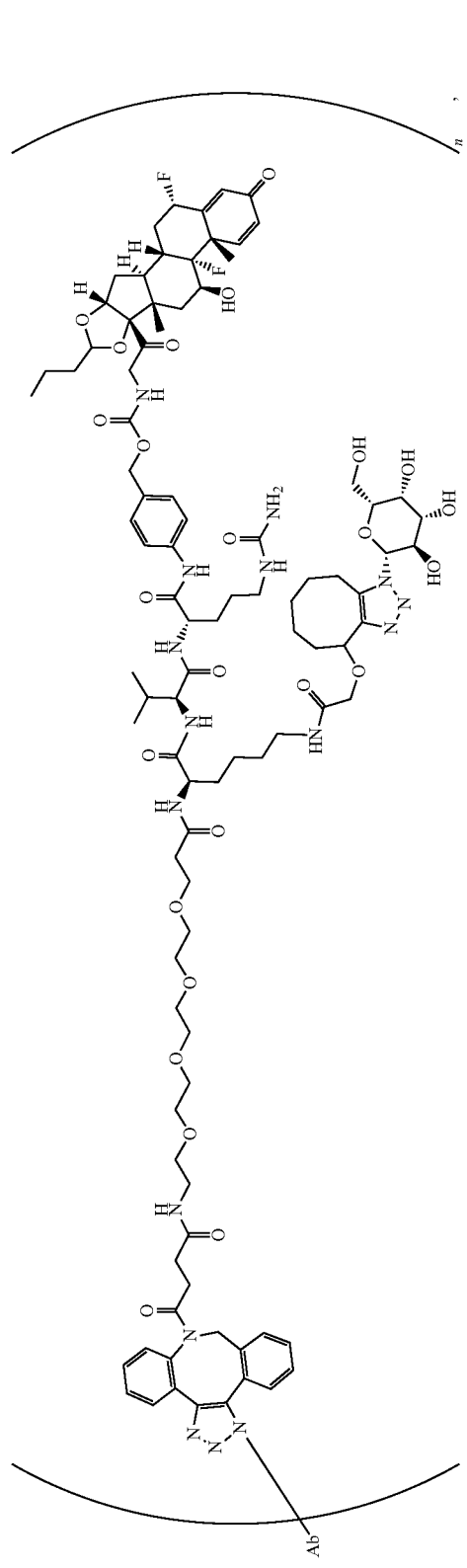

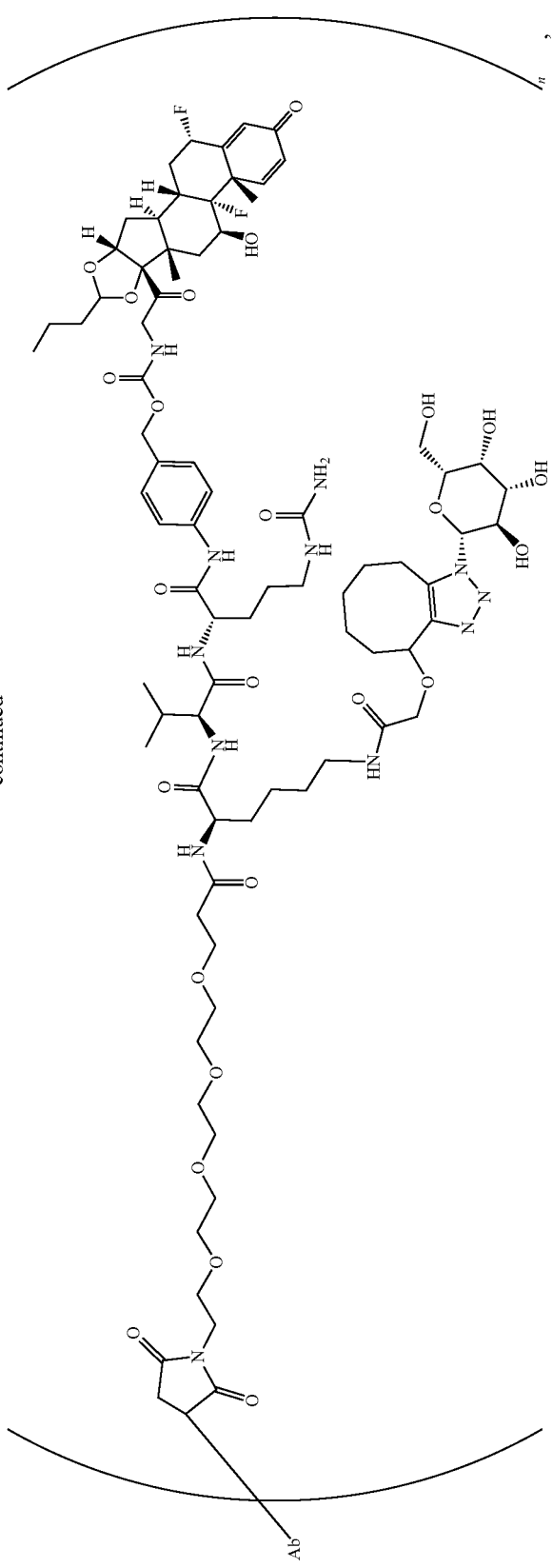
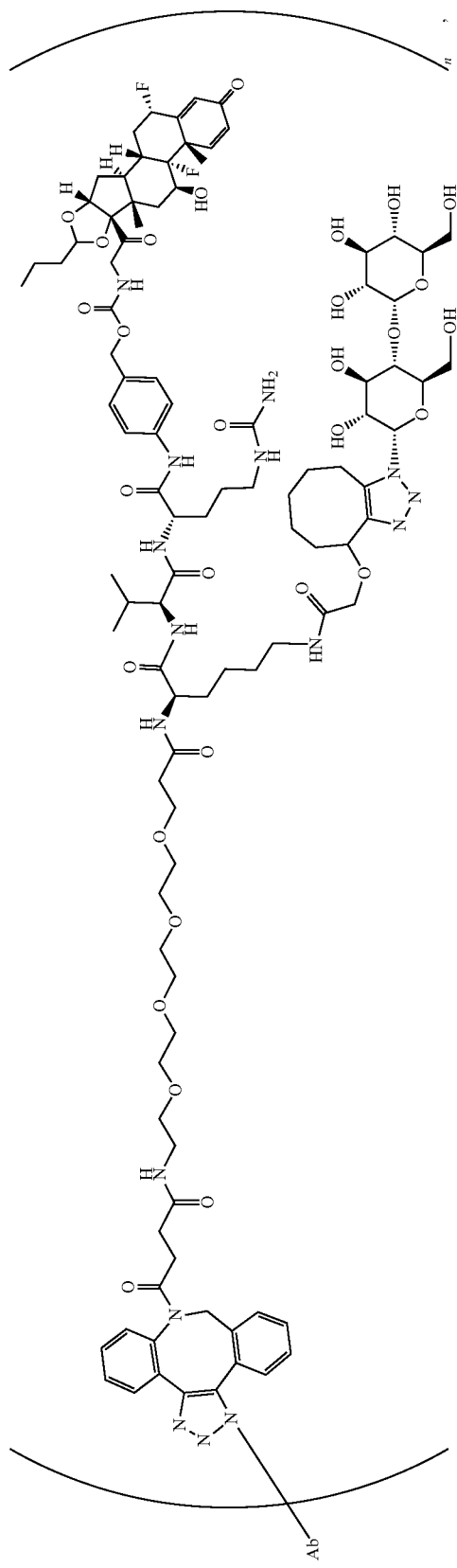

241
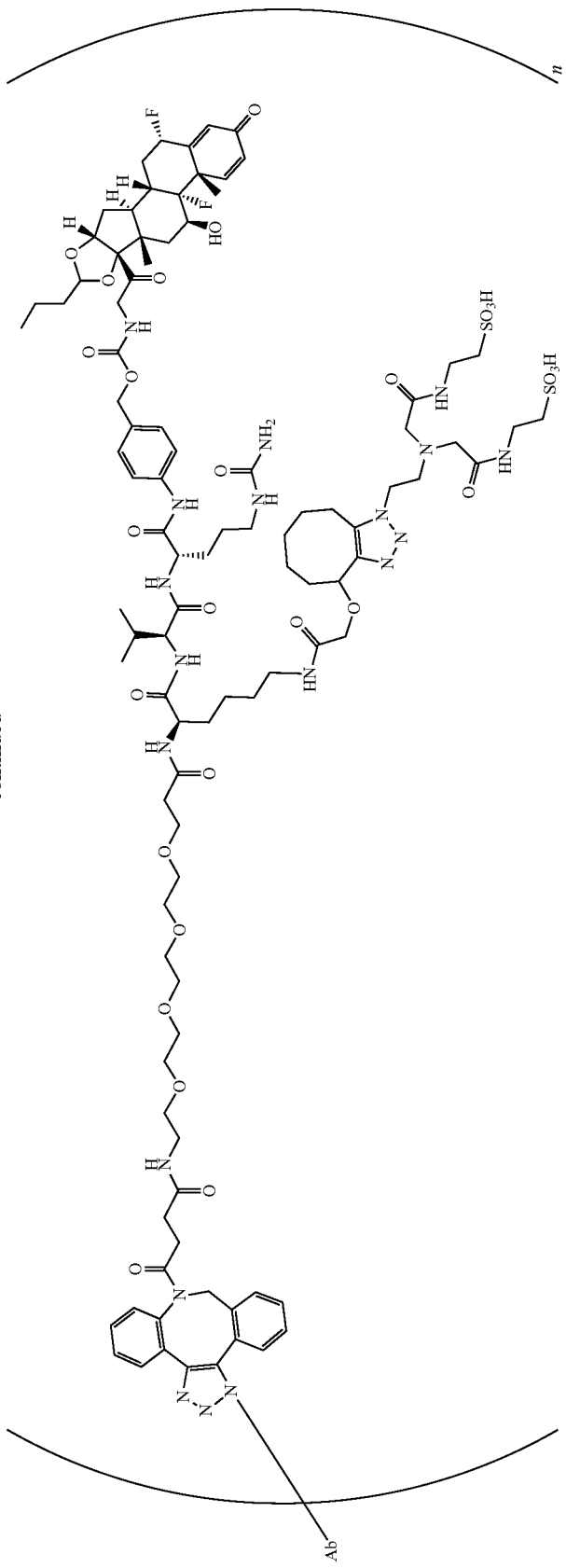
242
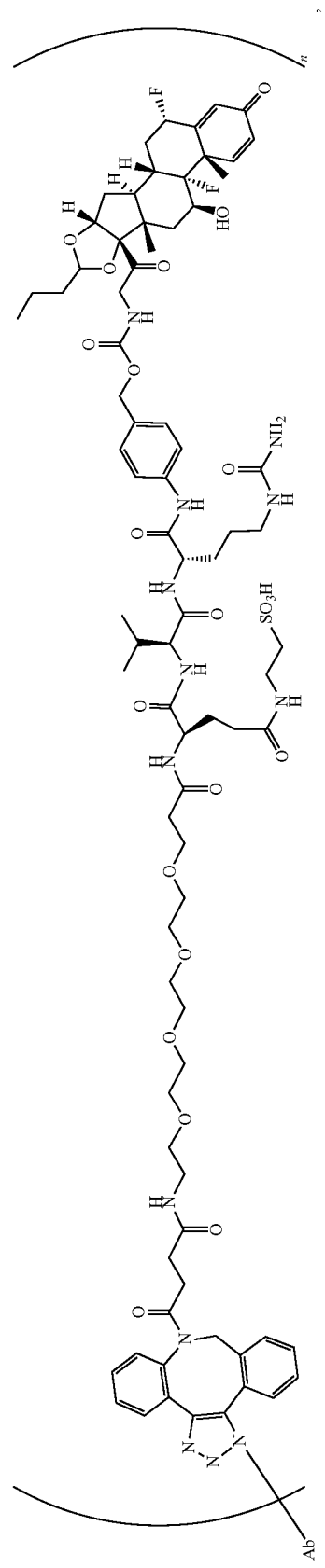

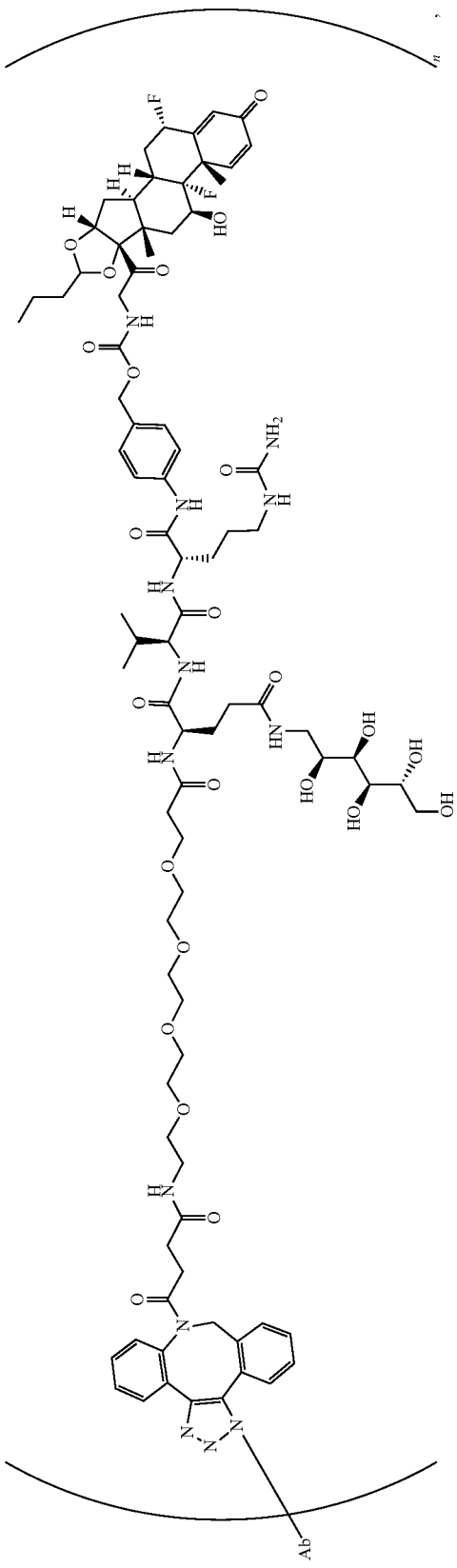
,
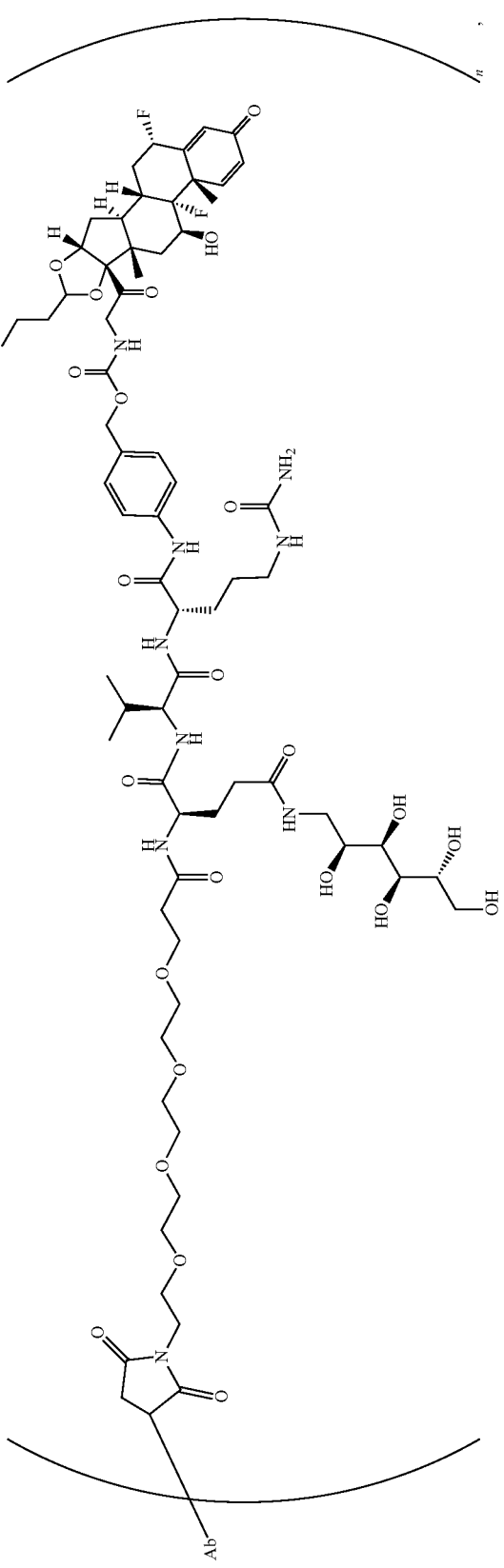
,

-continued
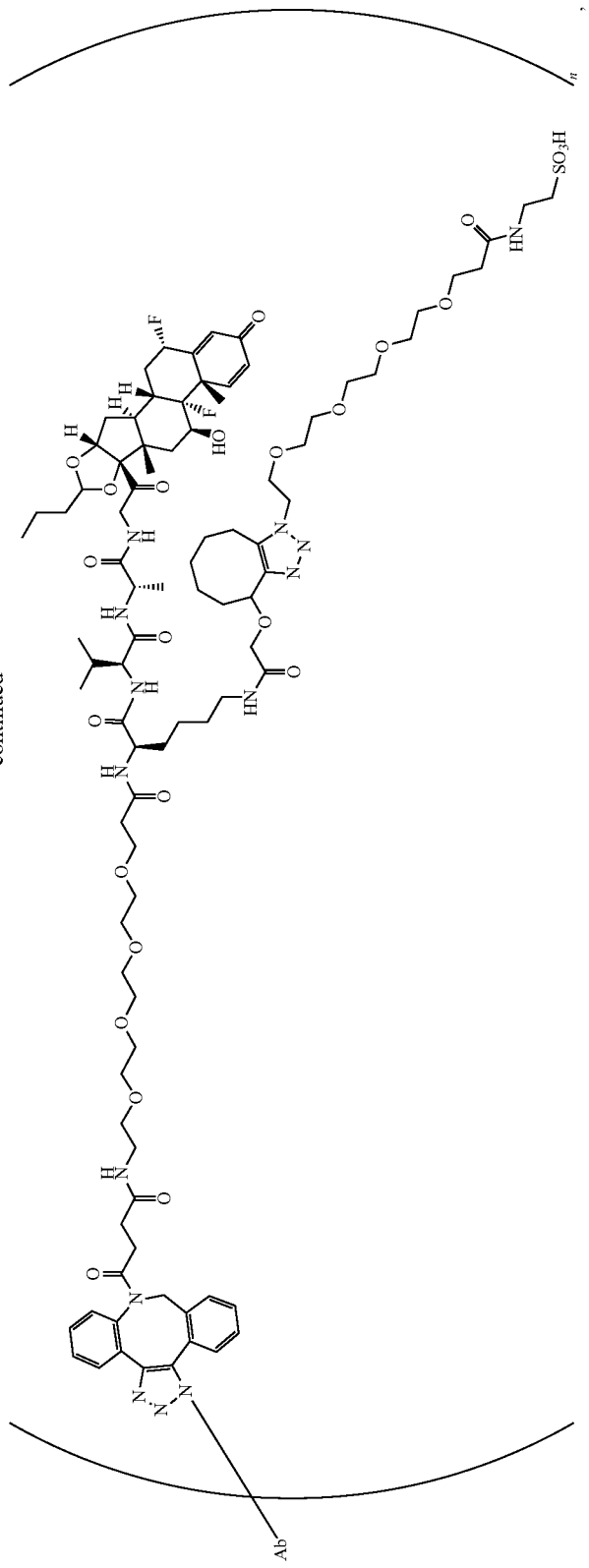

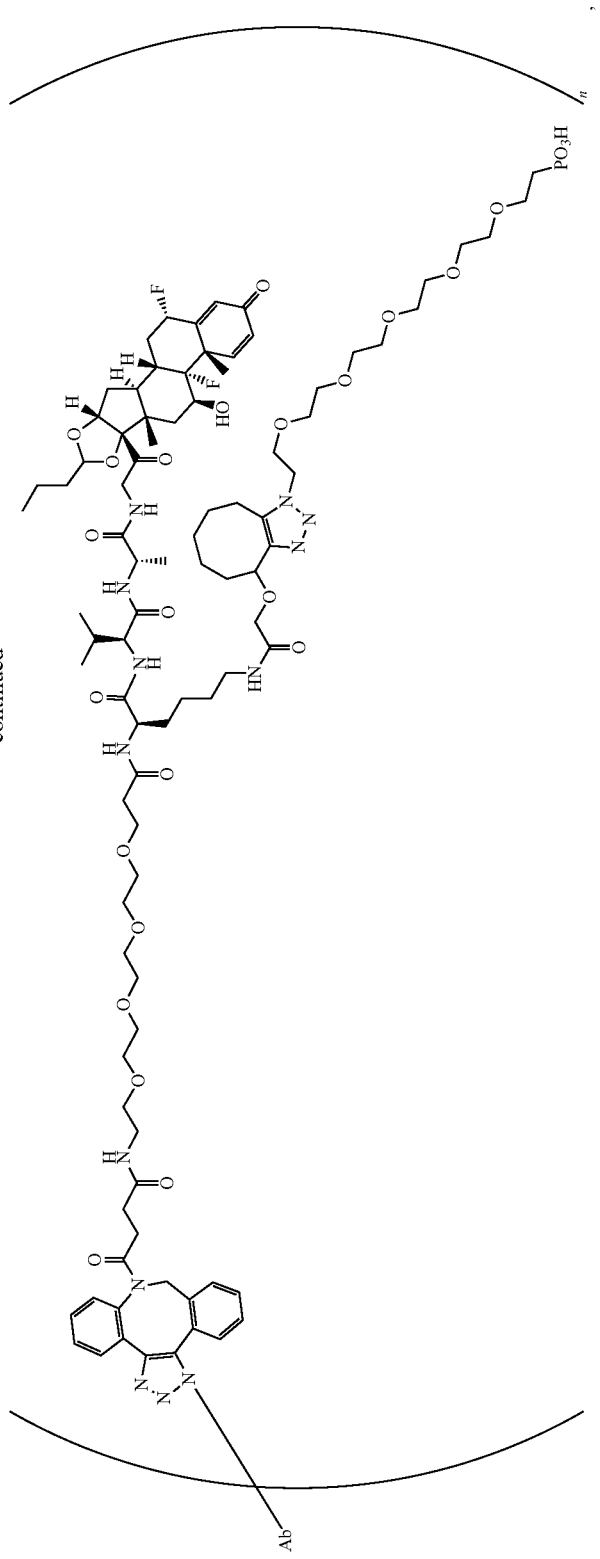

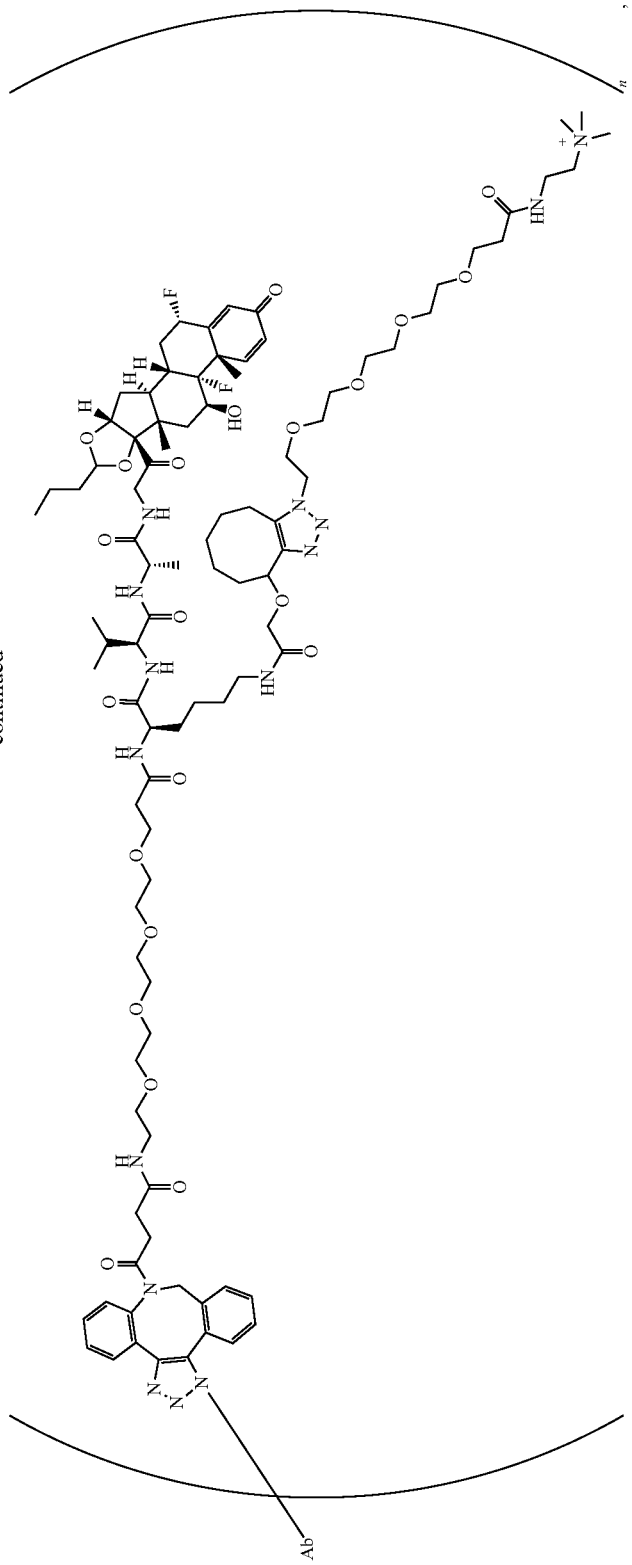

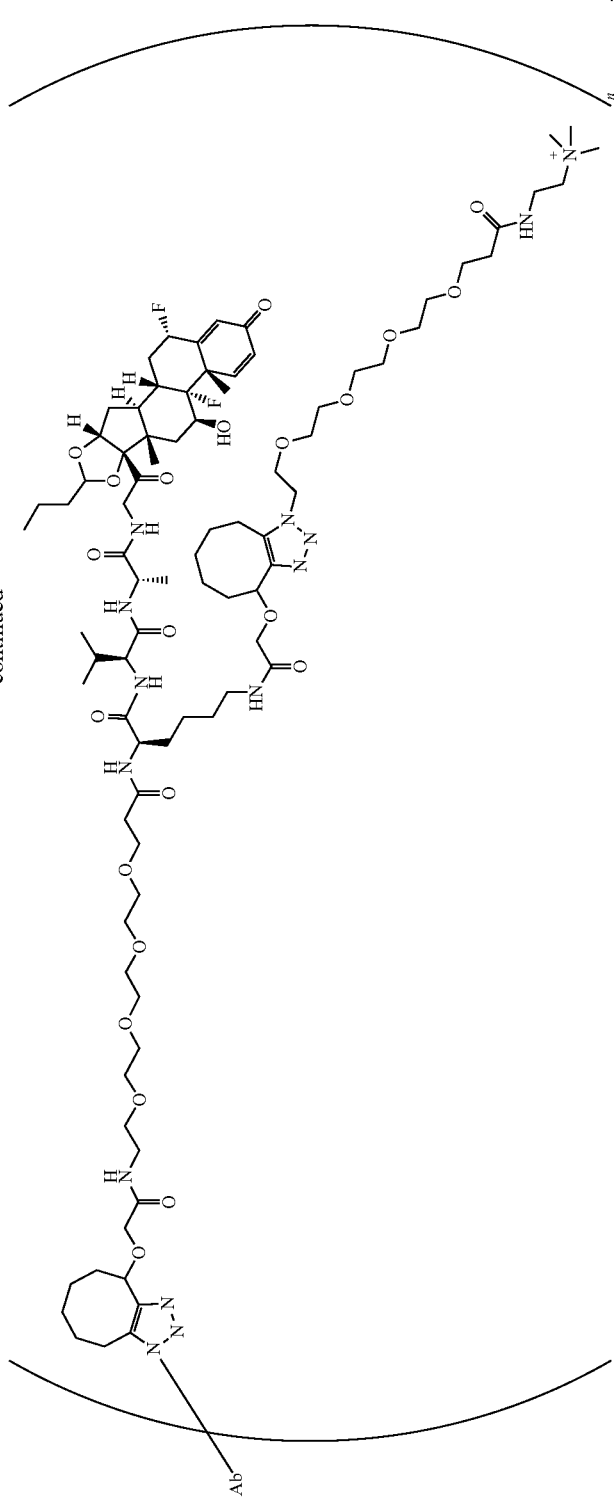

-continued
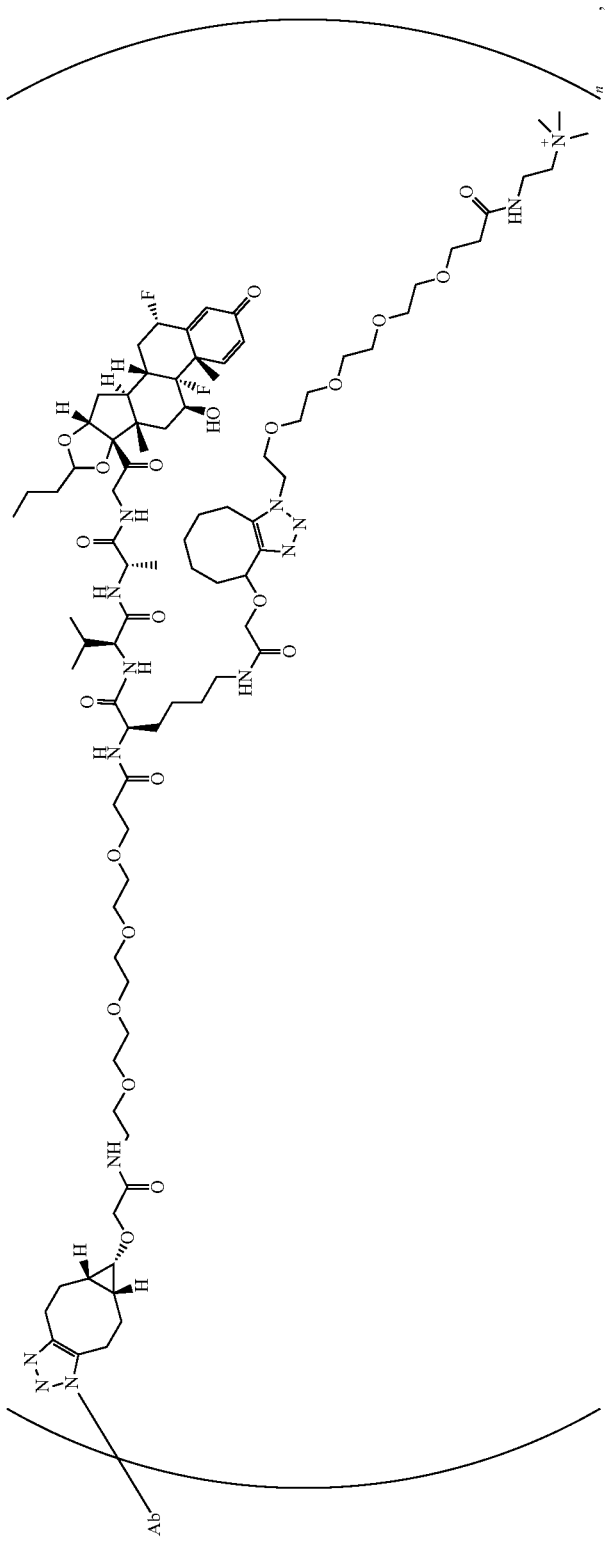

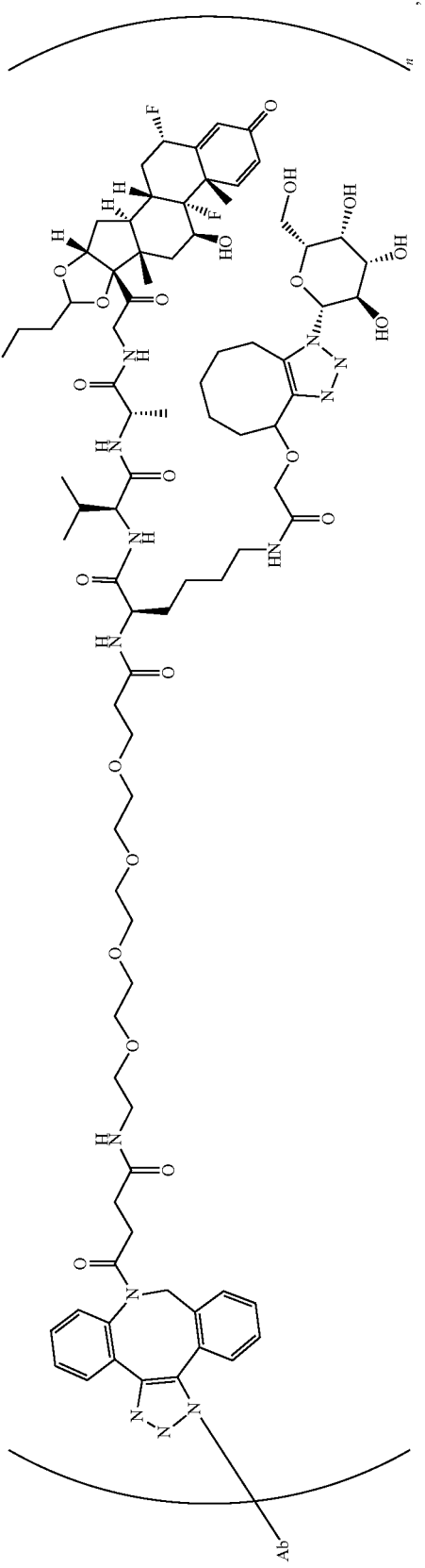
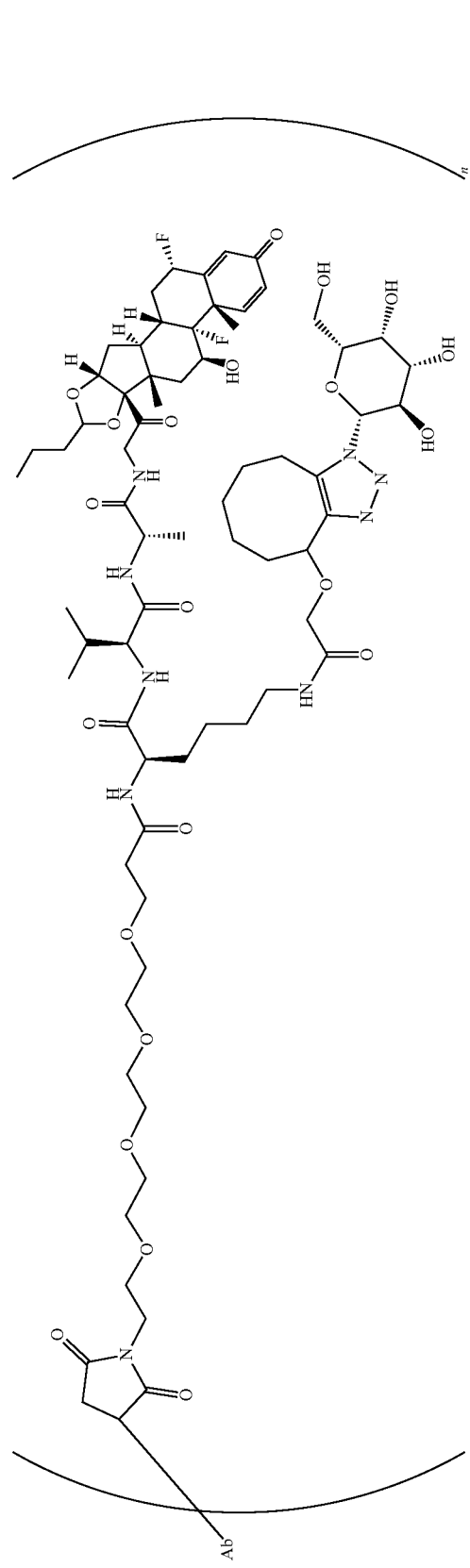

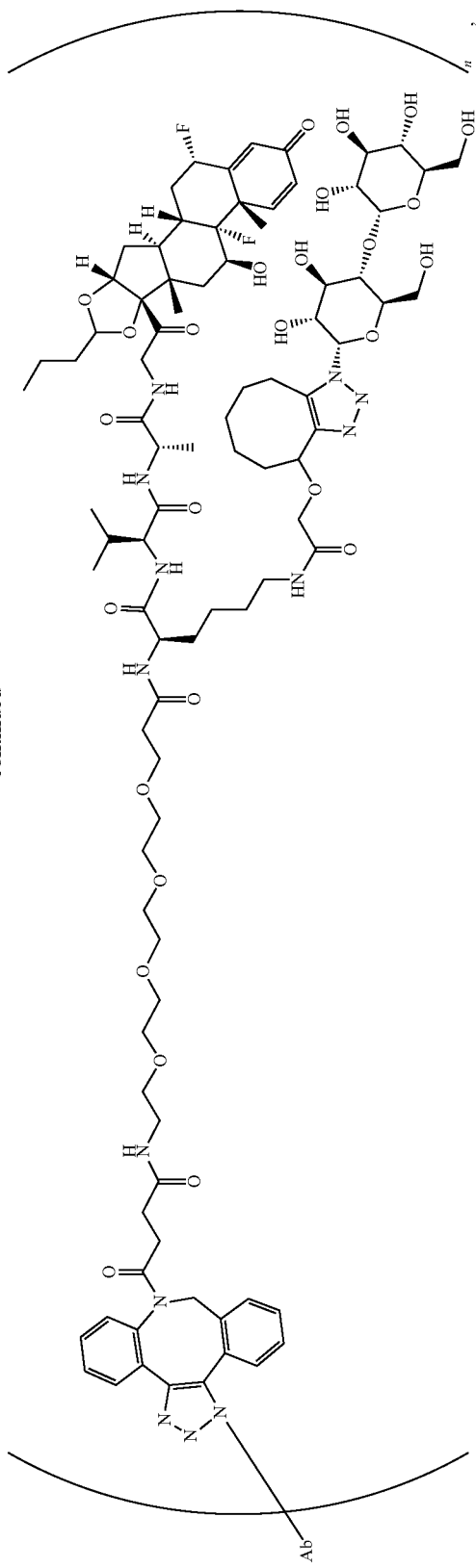

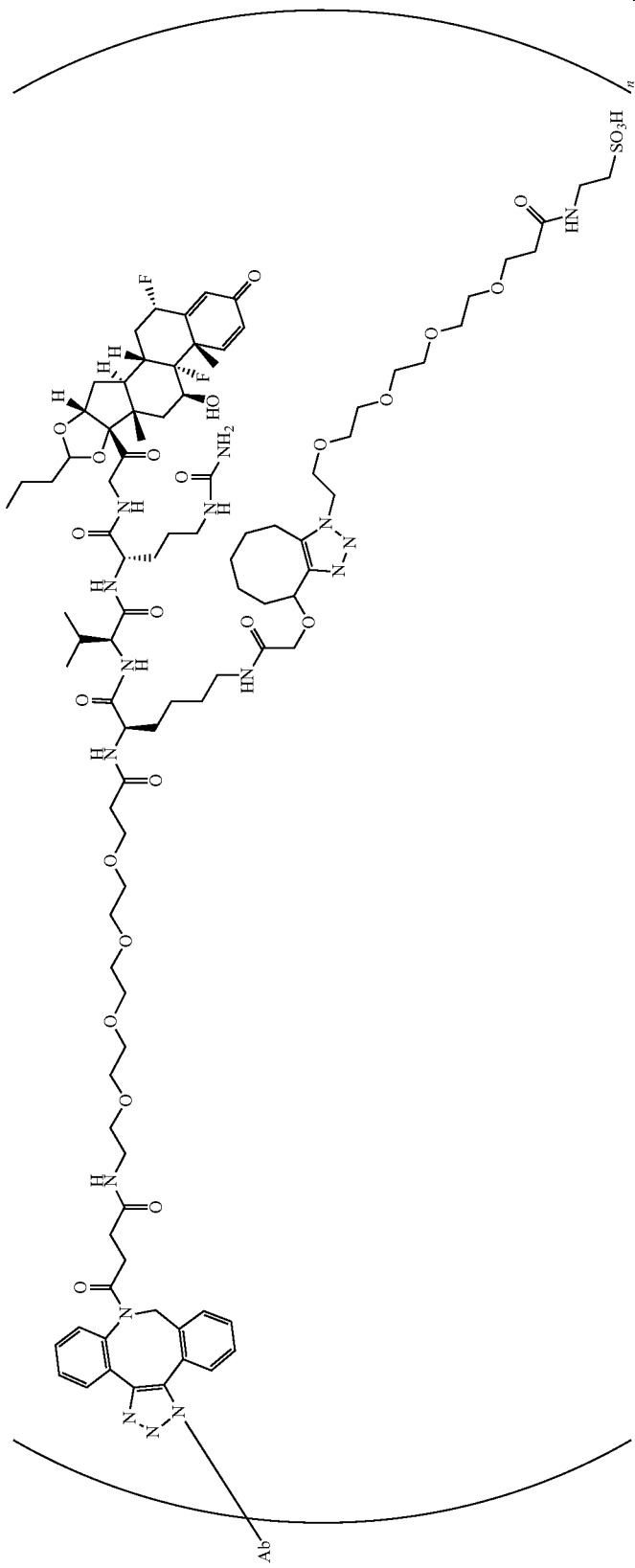

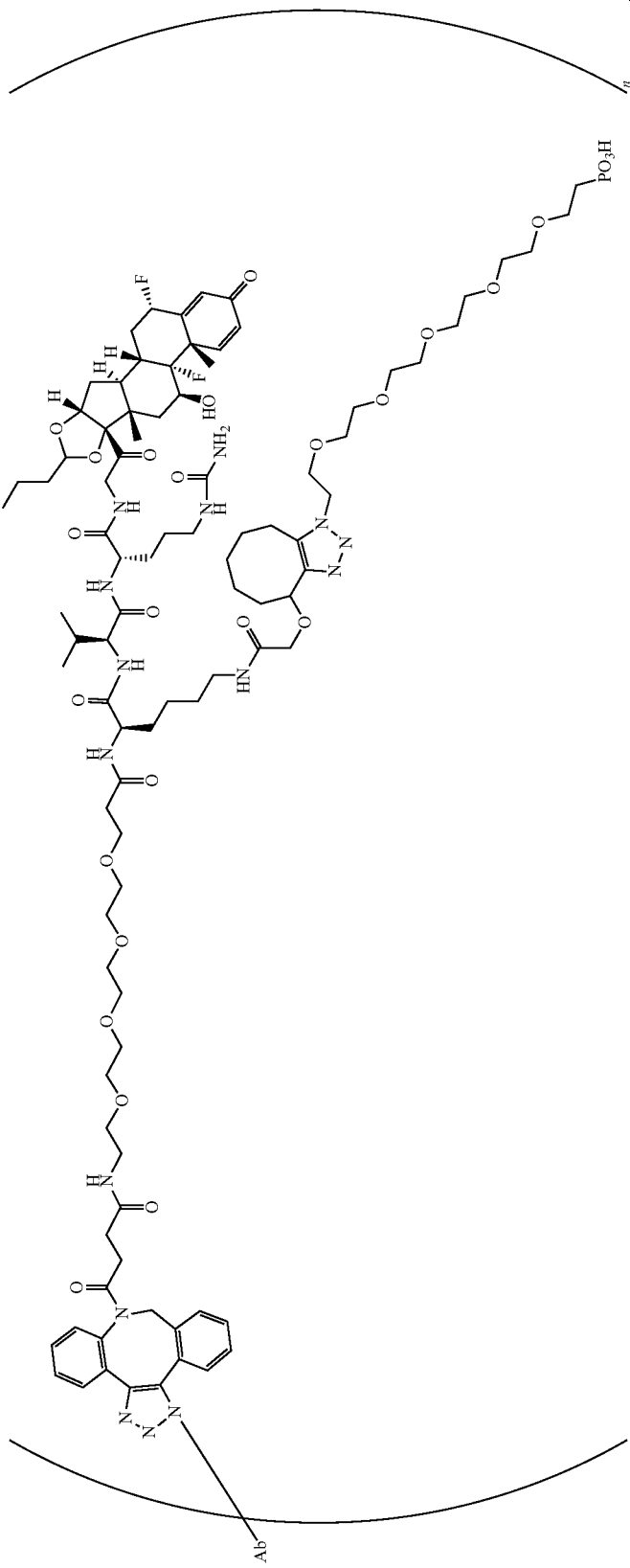

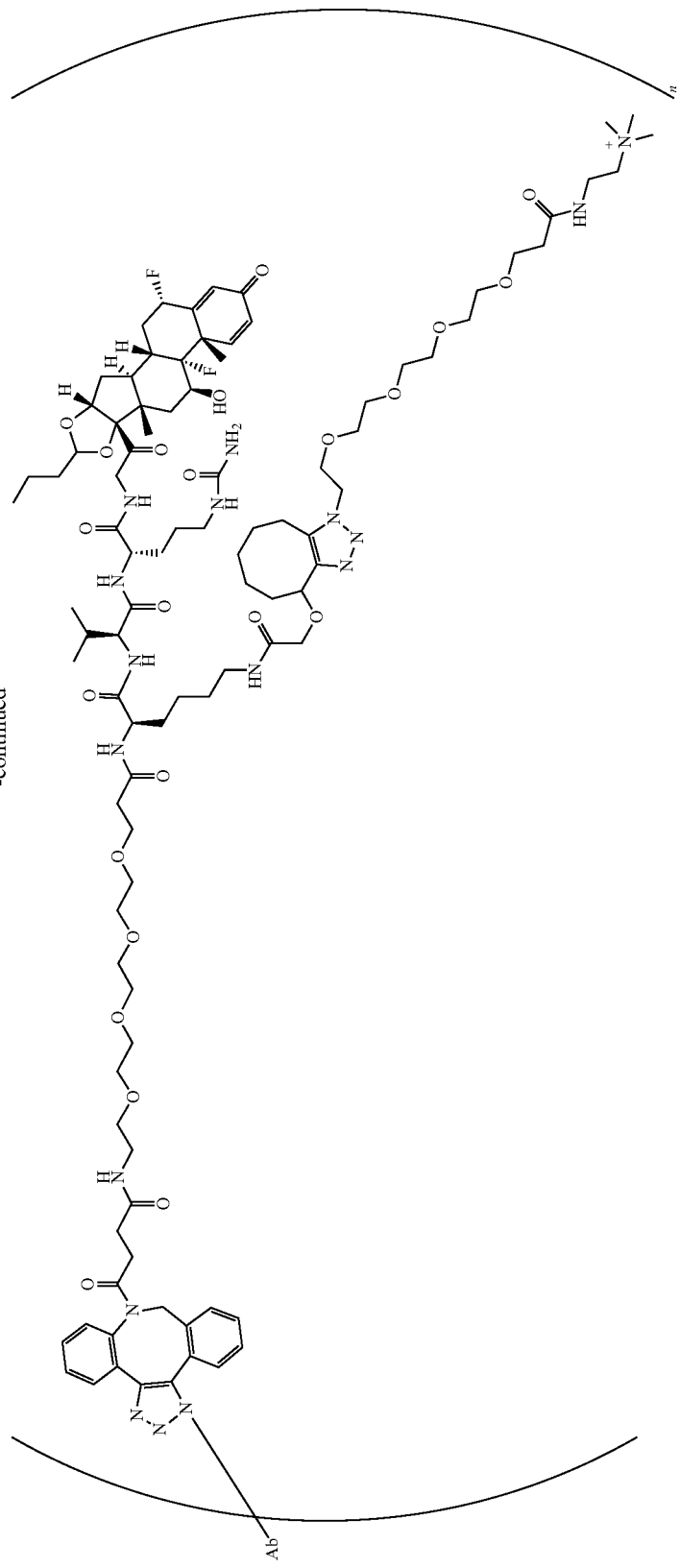

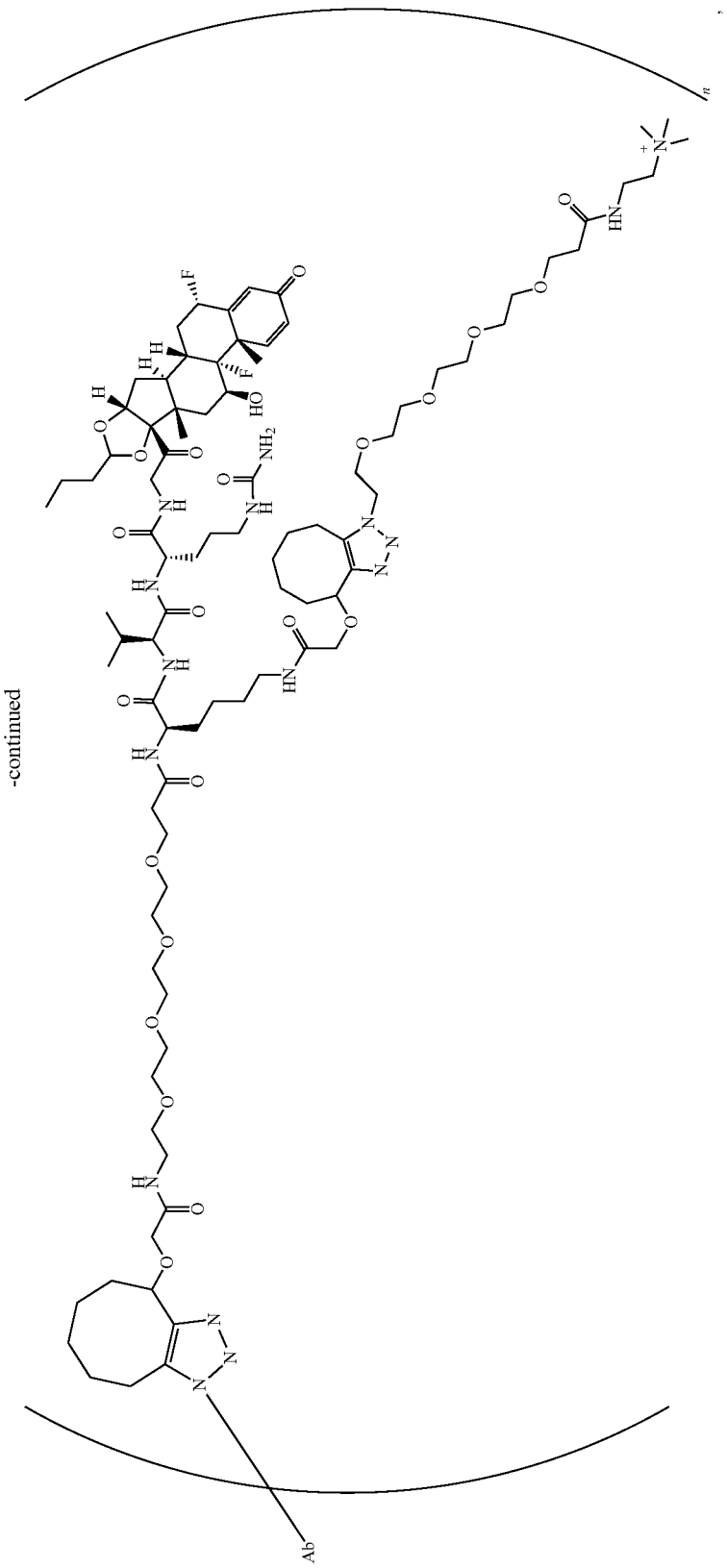

-continued
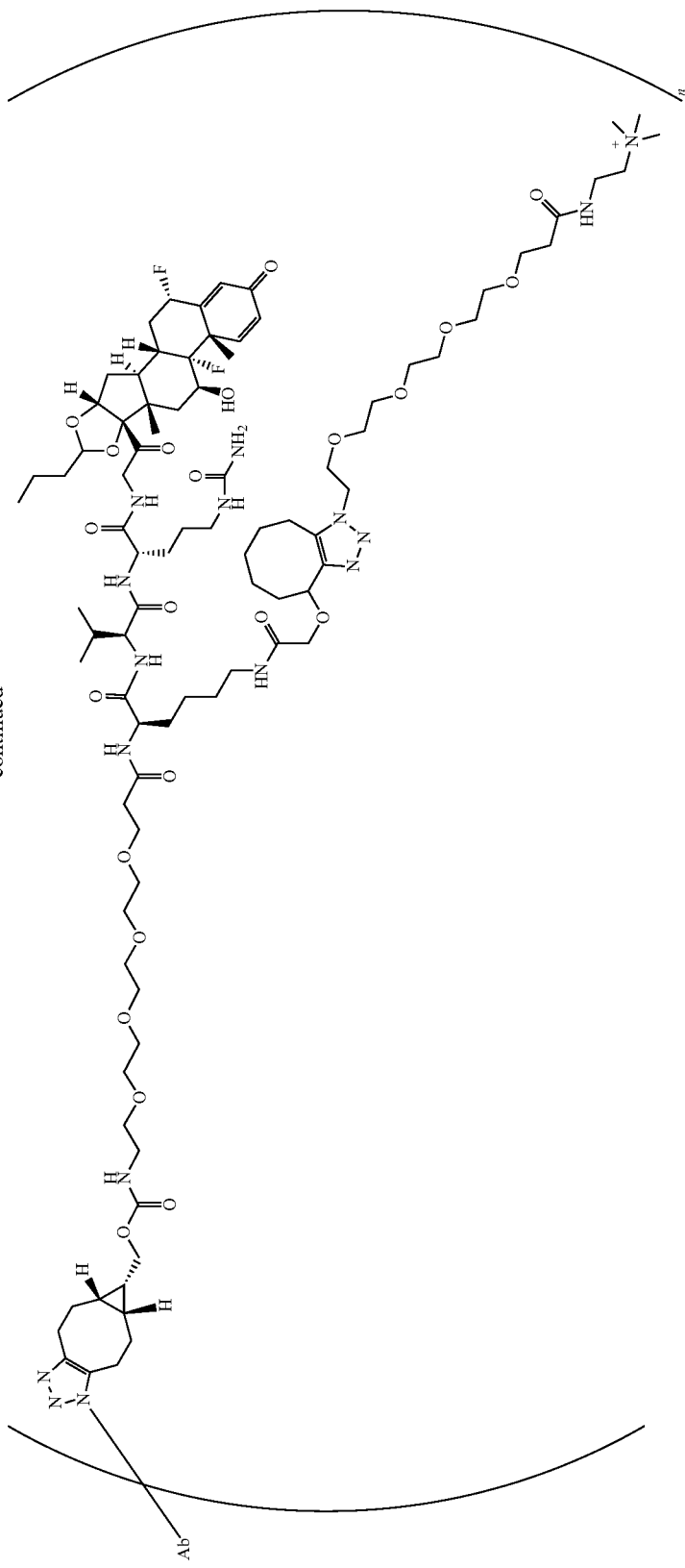

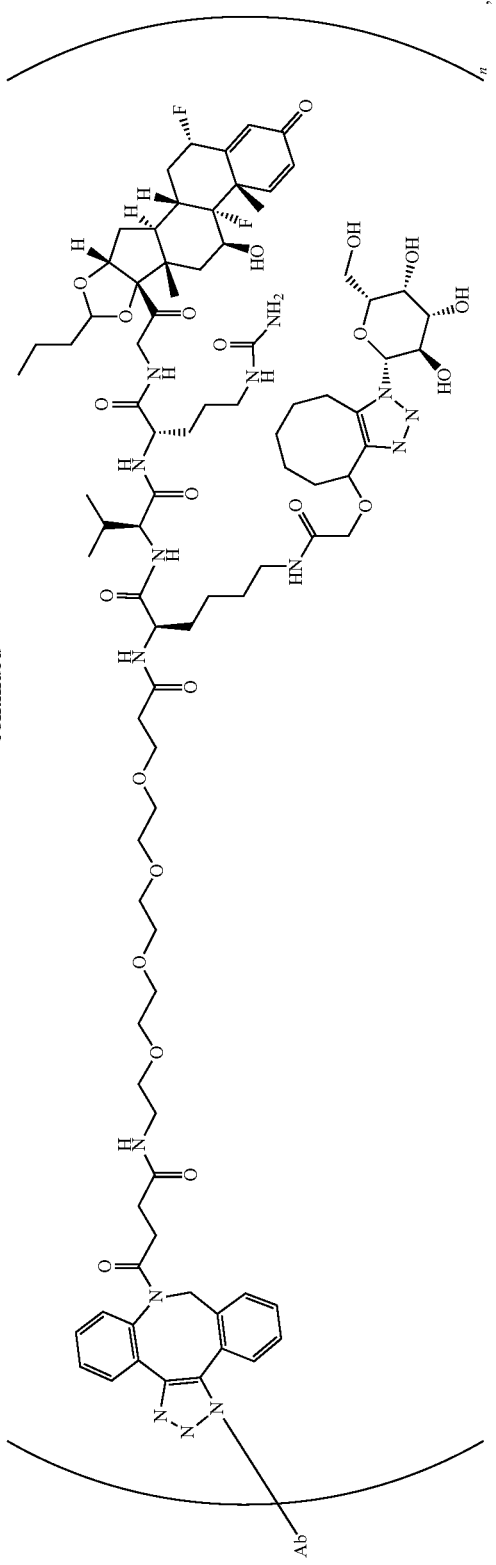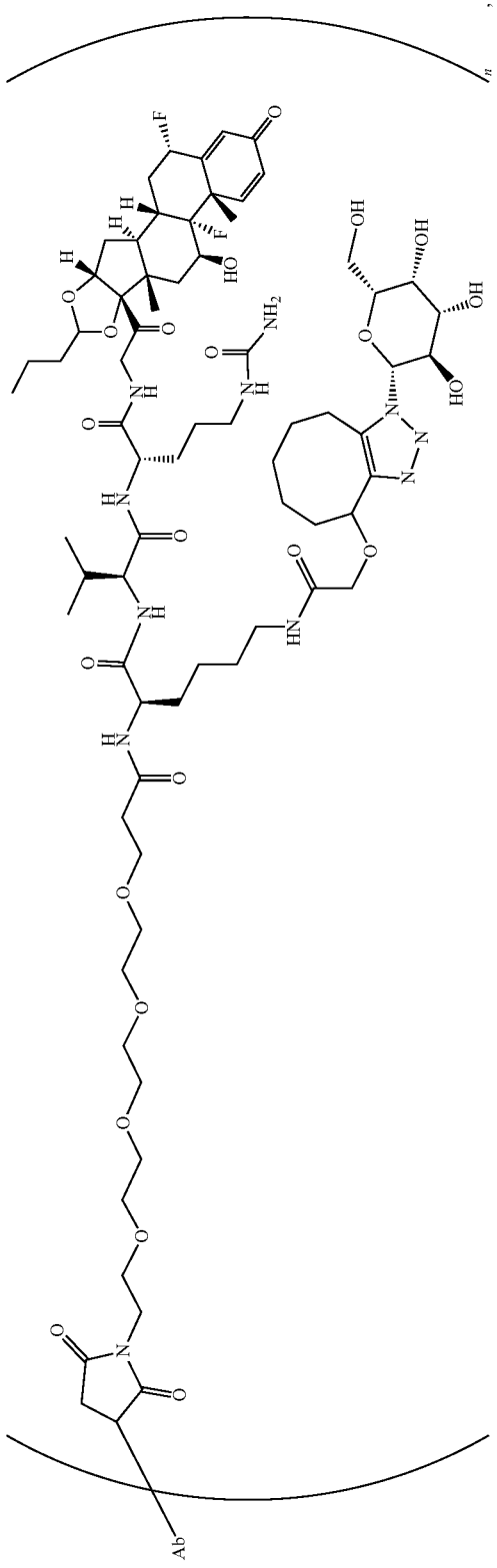

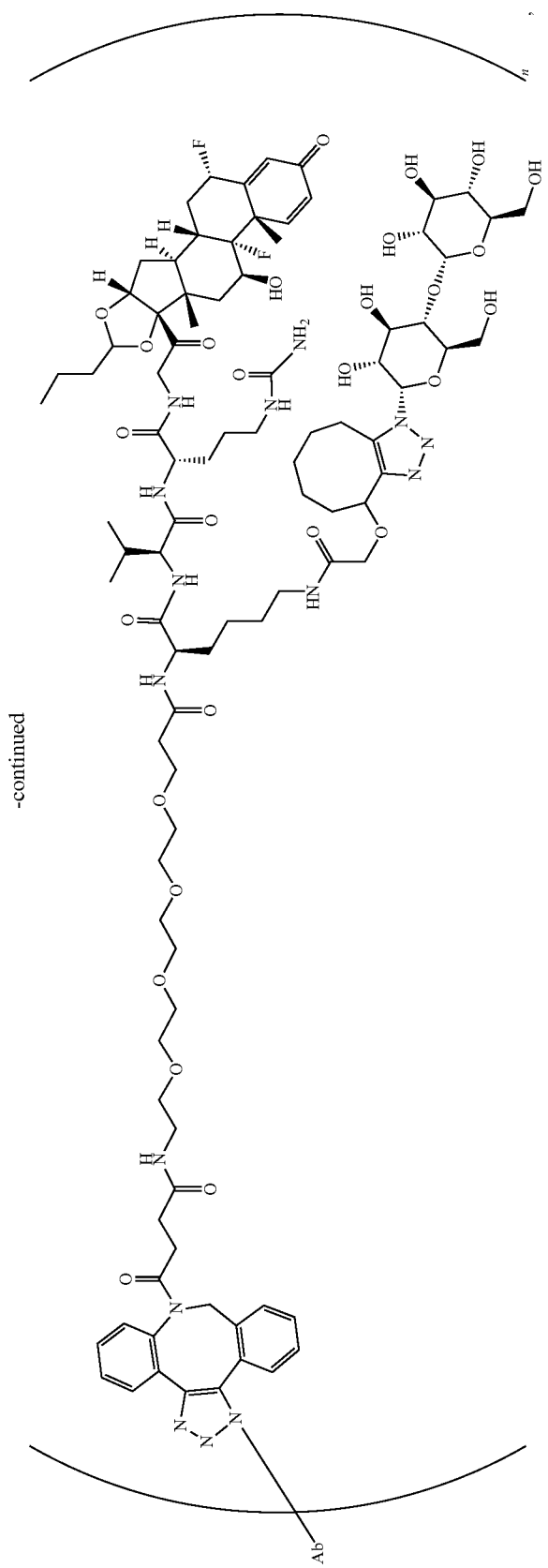

273
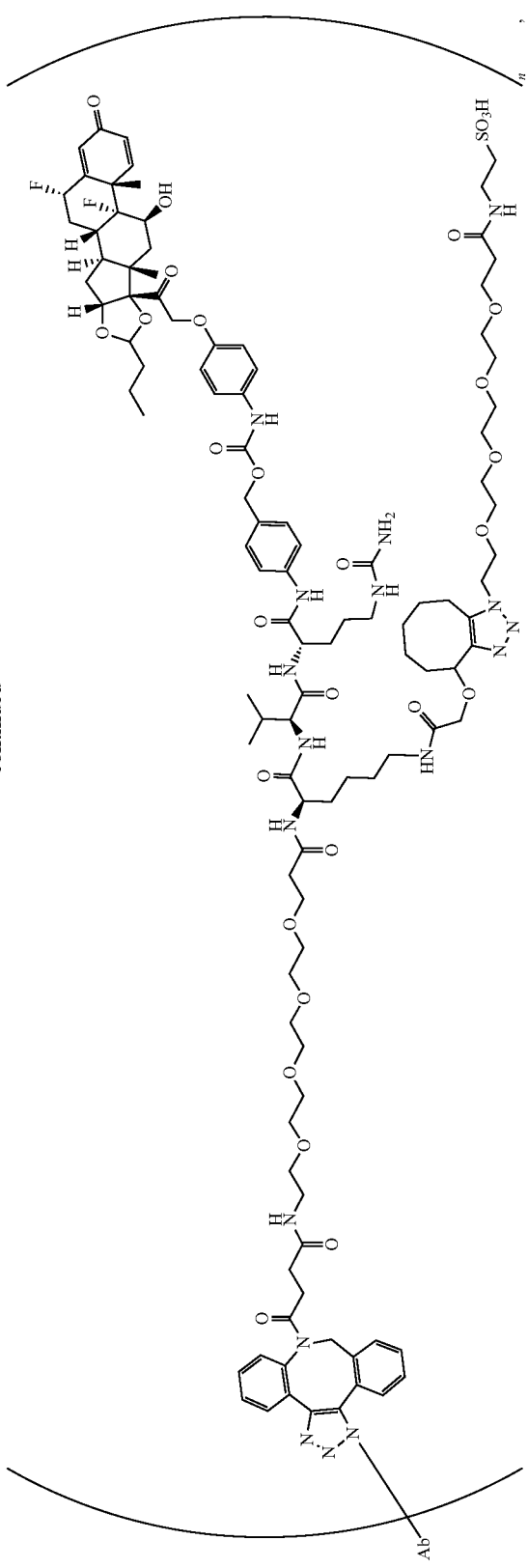
274
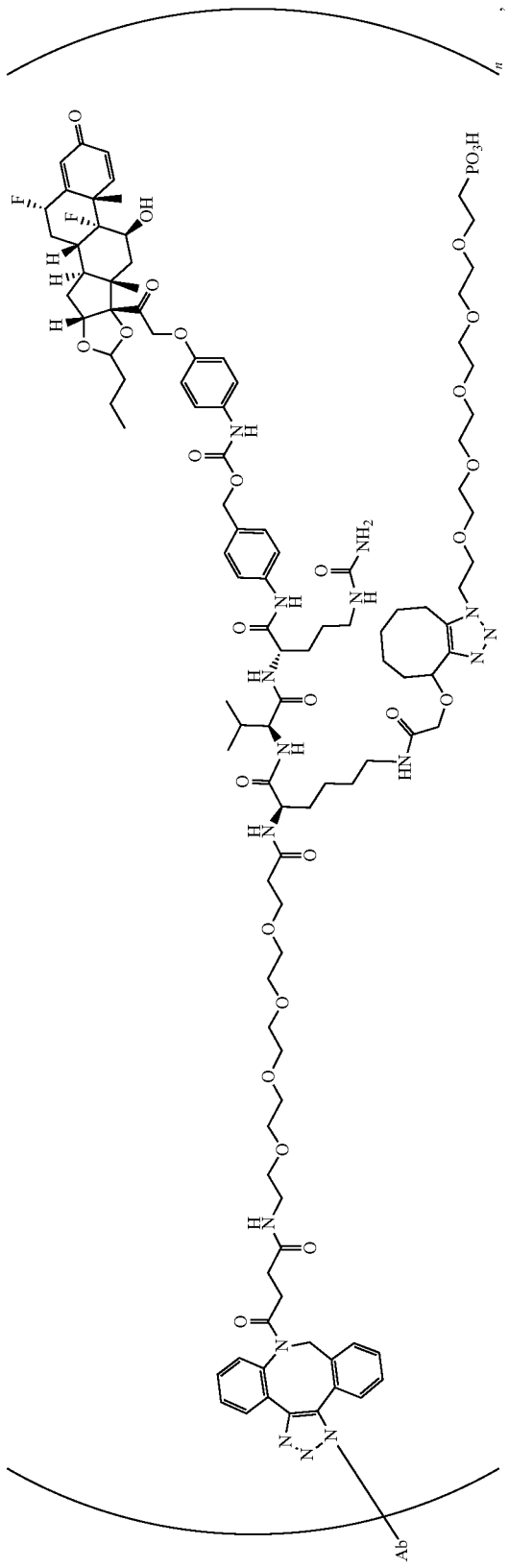

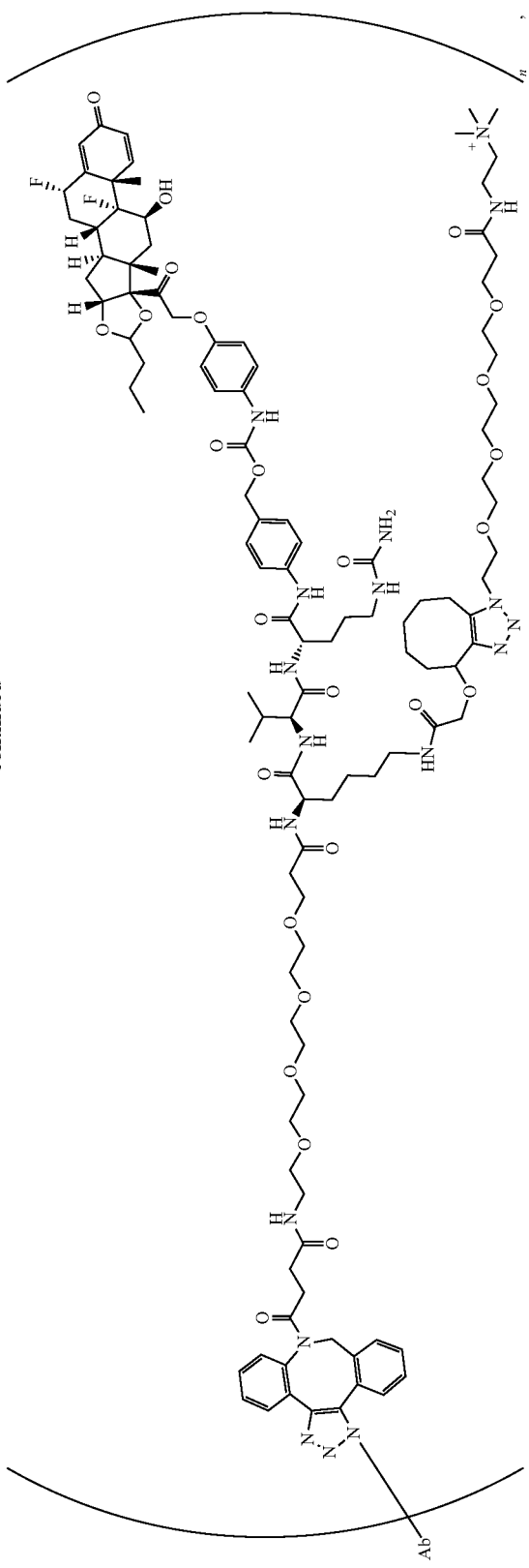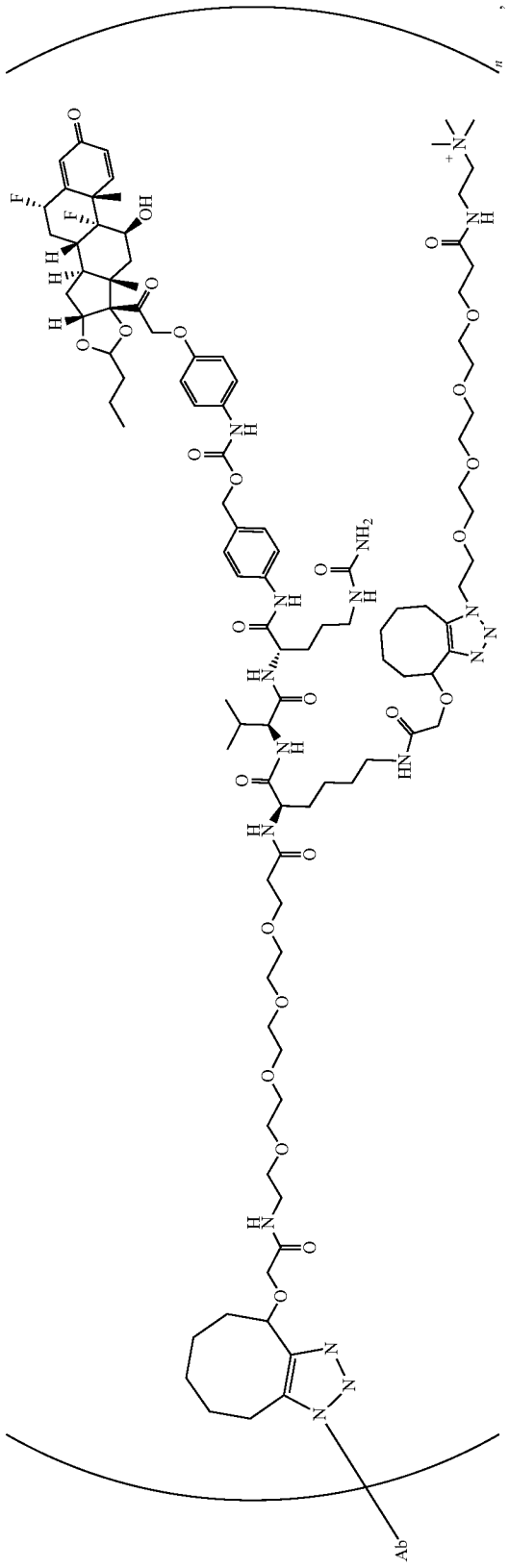

277
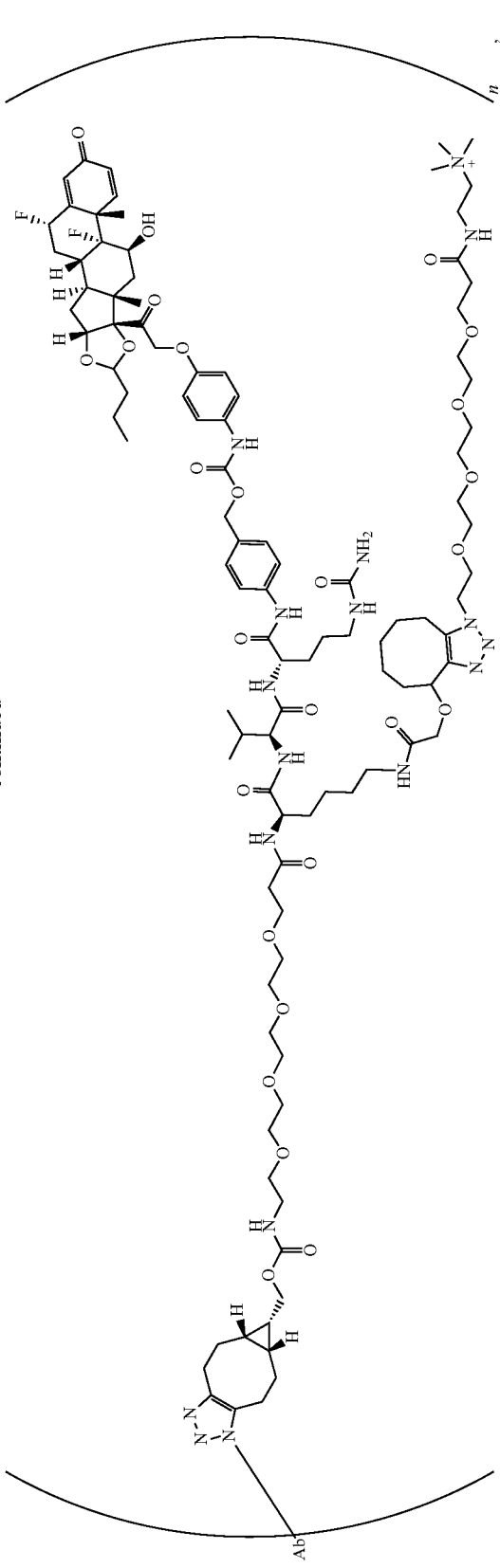
278
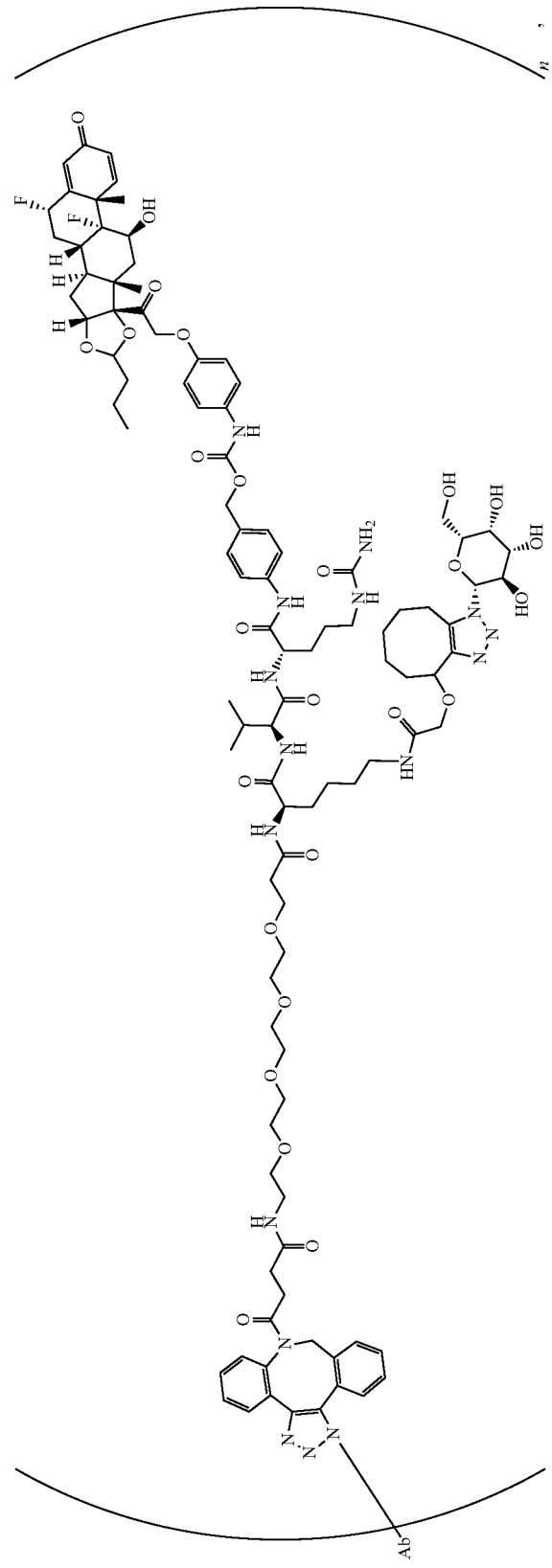

-continued
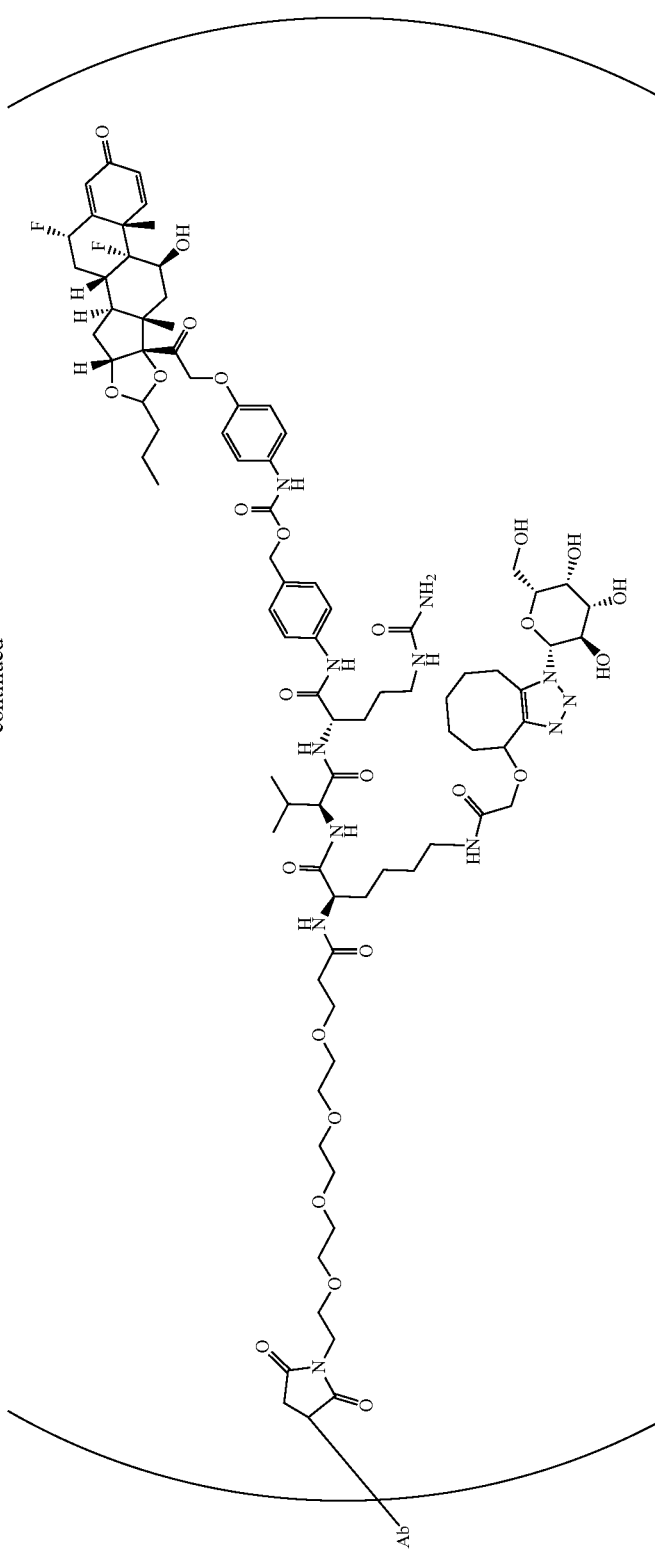

-continued
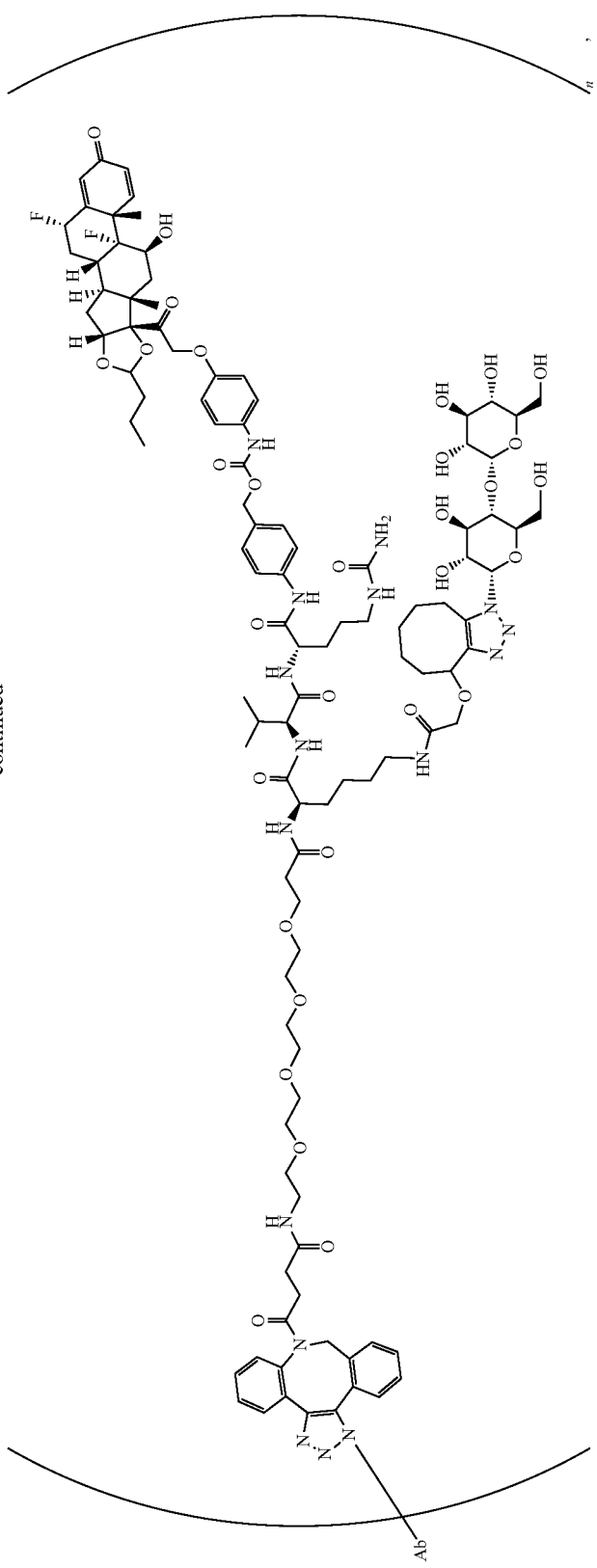

283 284
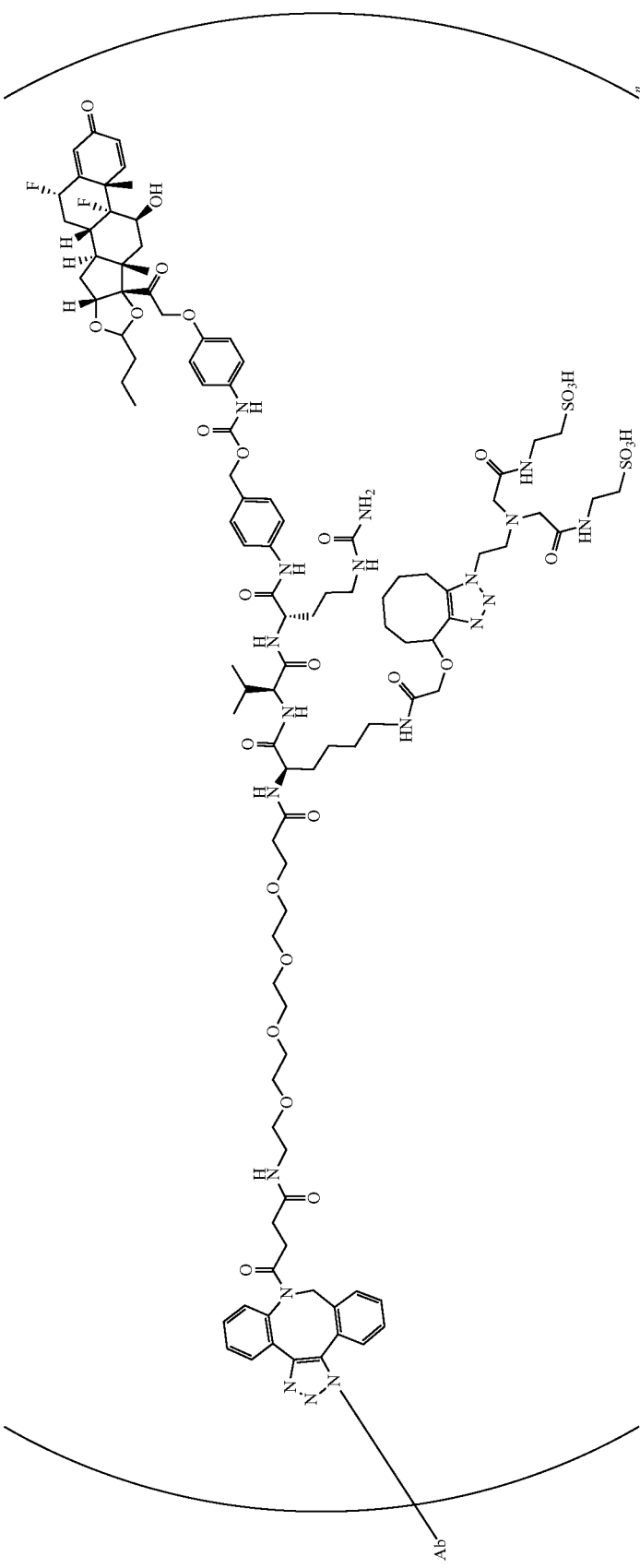
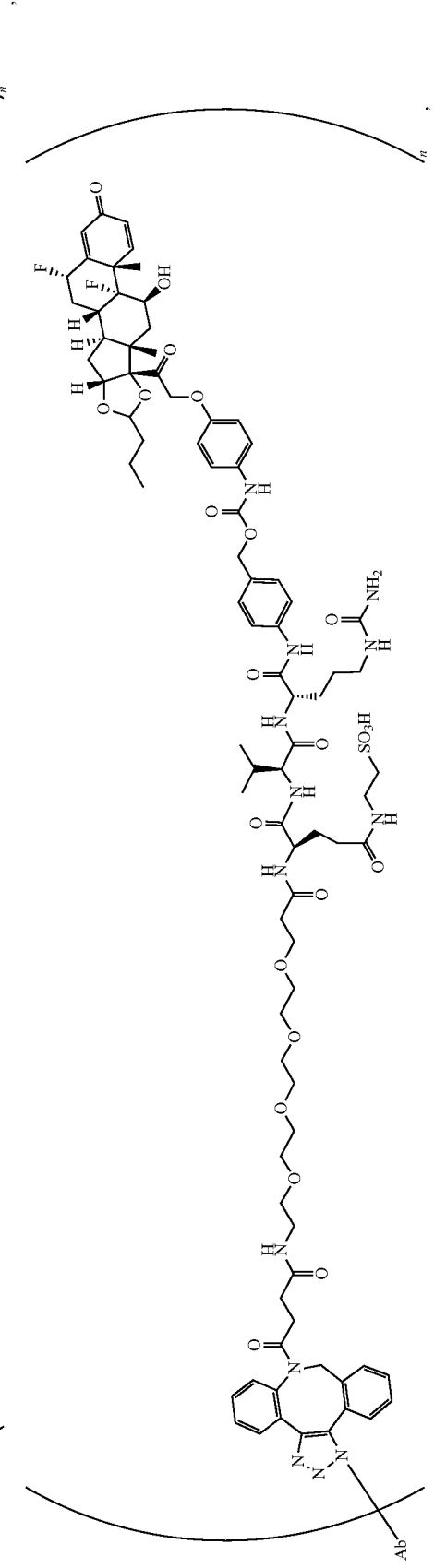

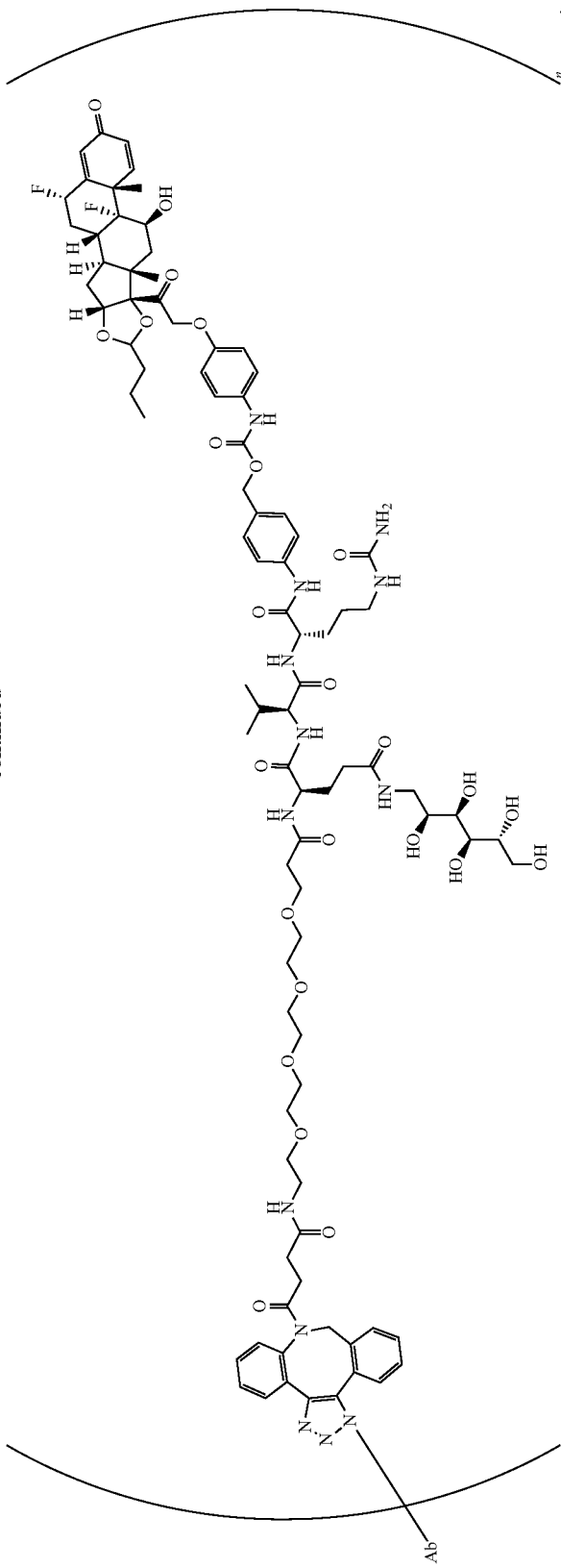

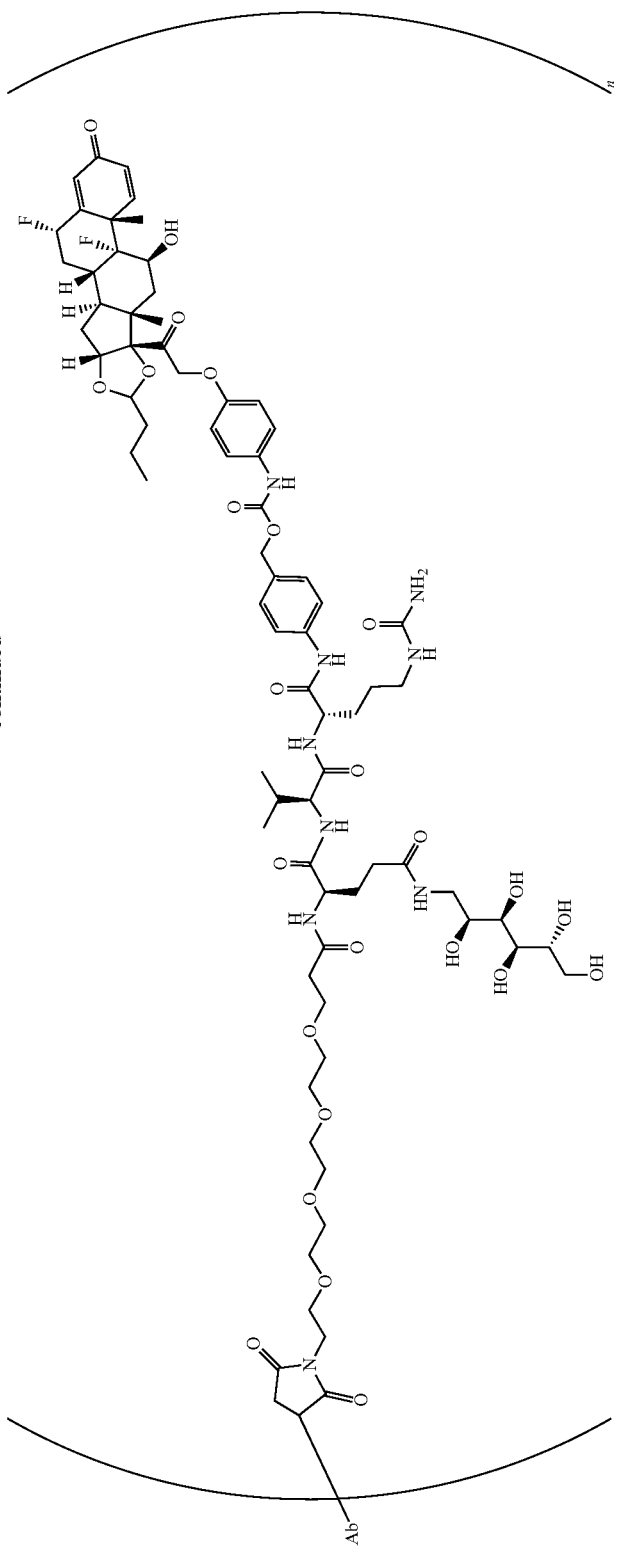

-continued
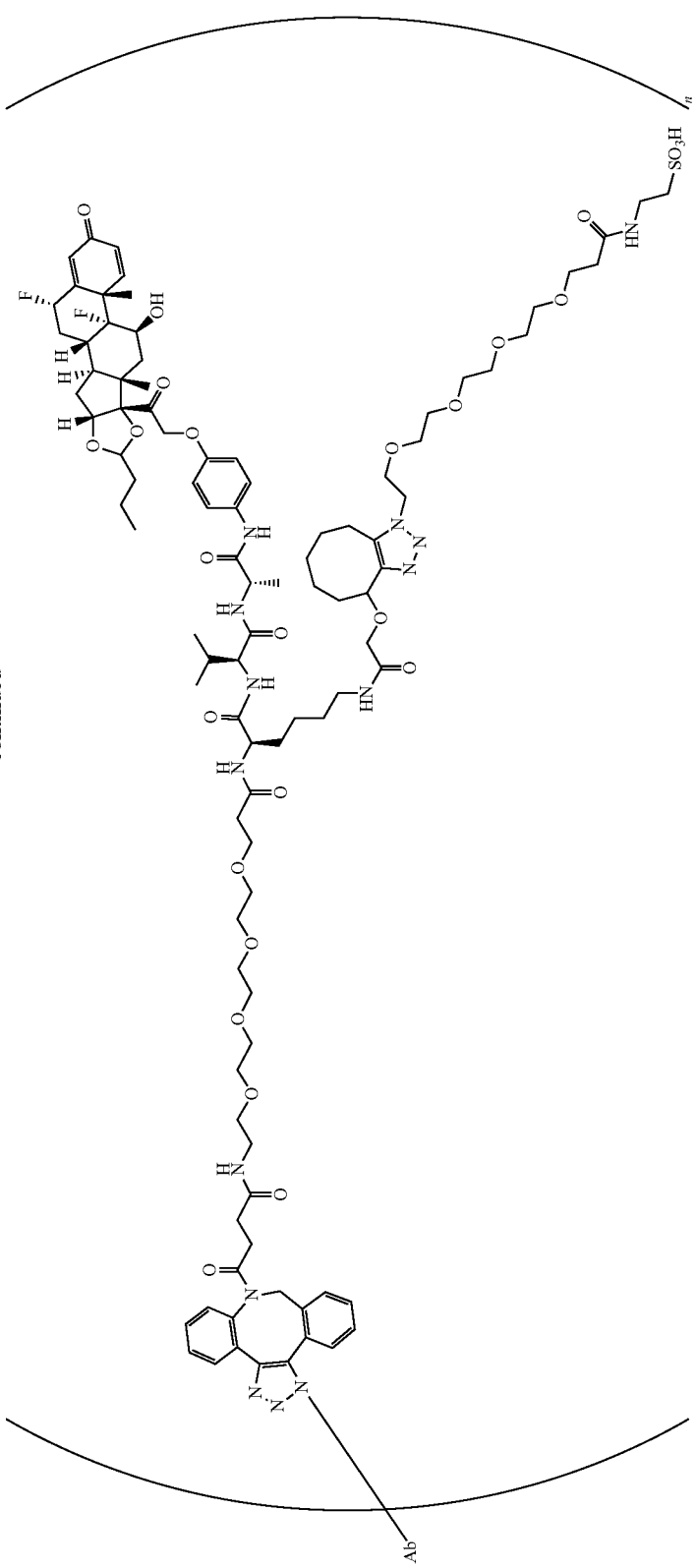

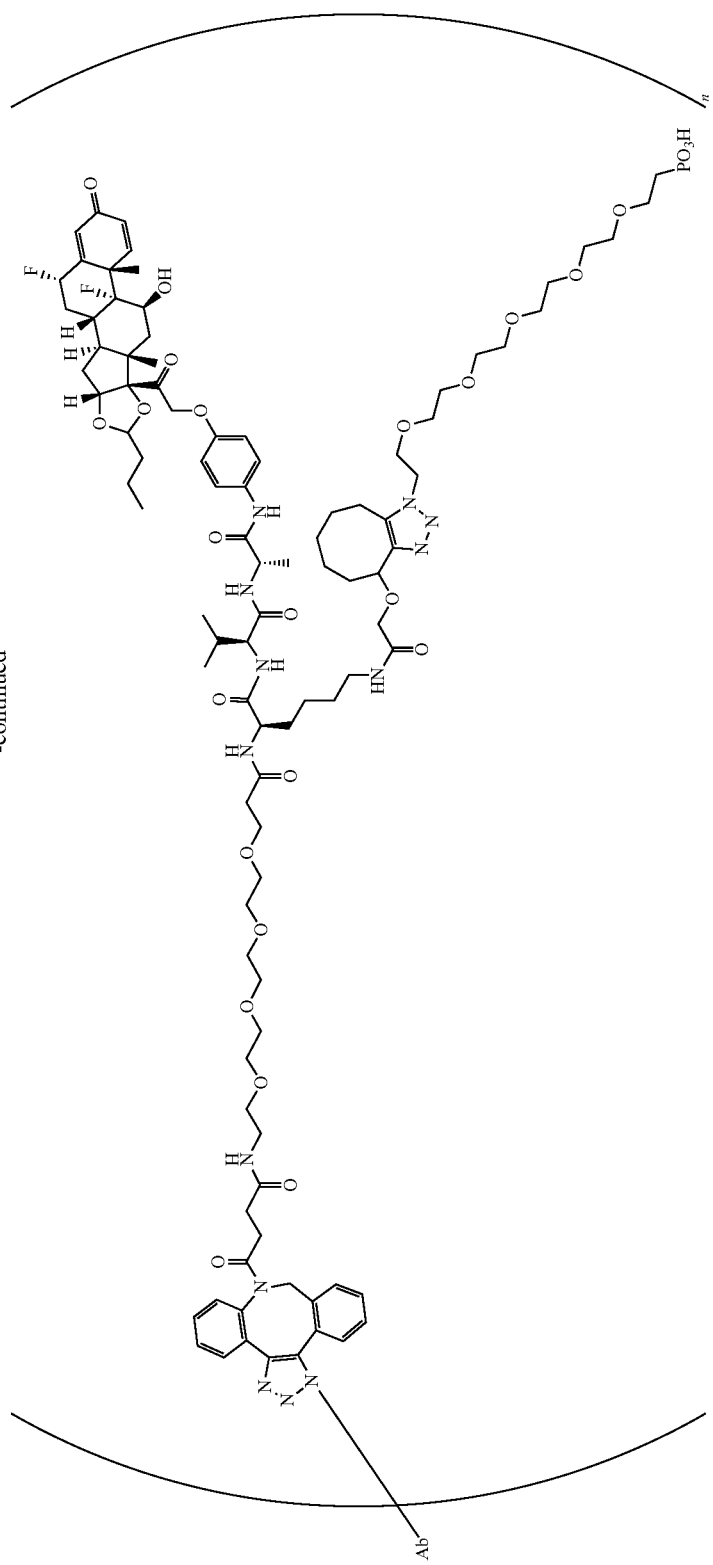

-continued
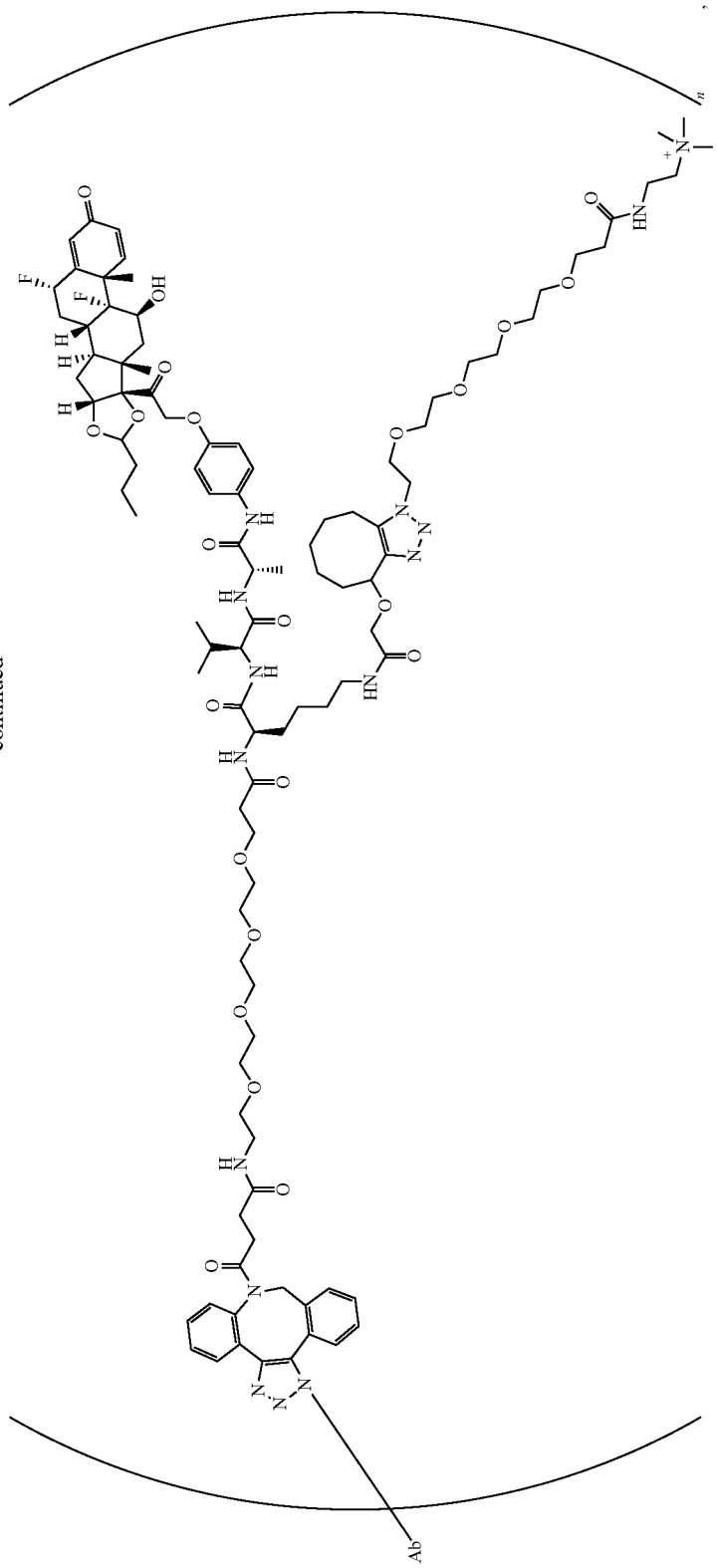

-continued
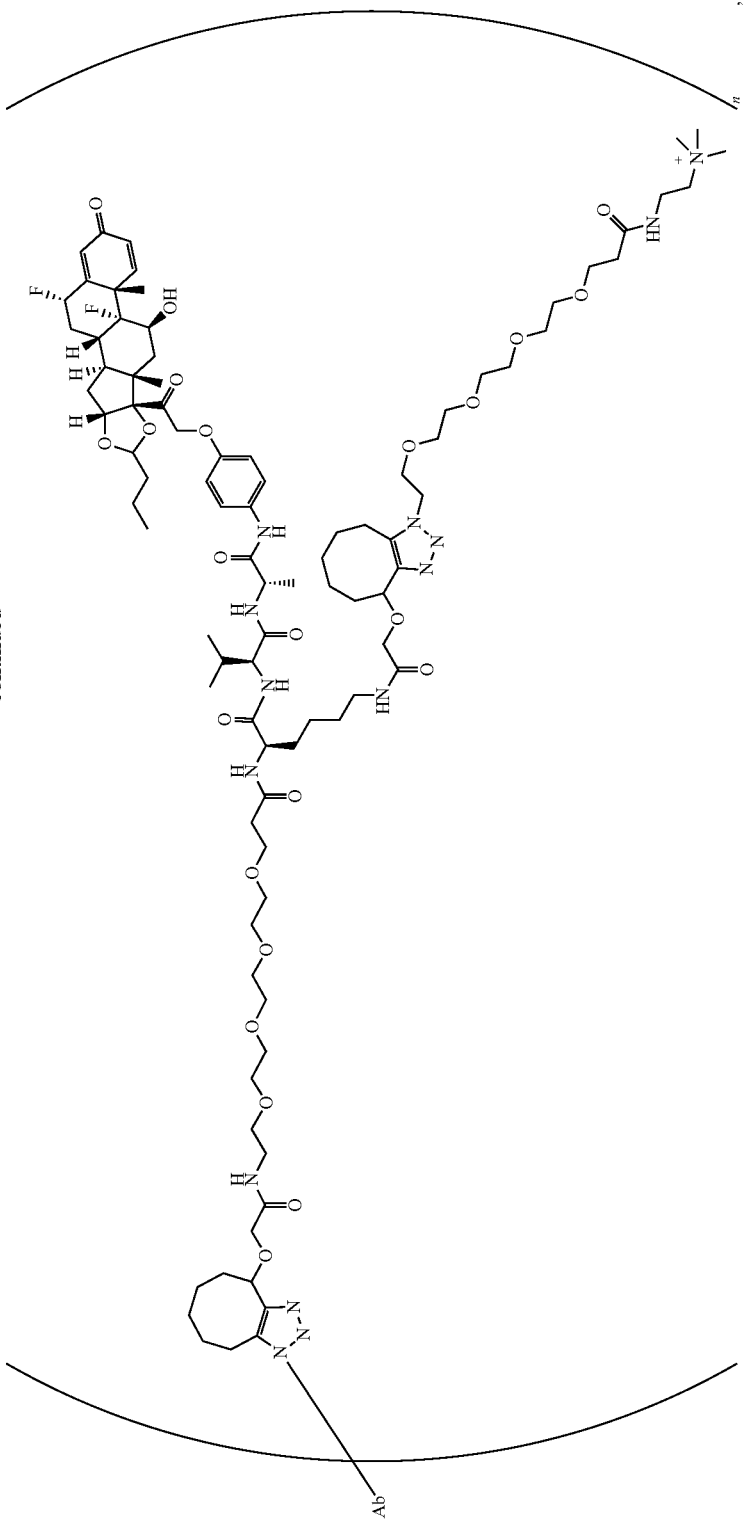

-continued
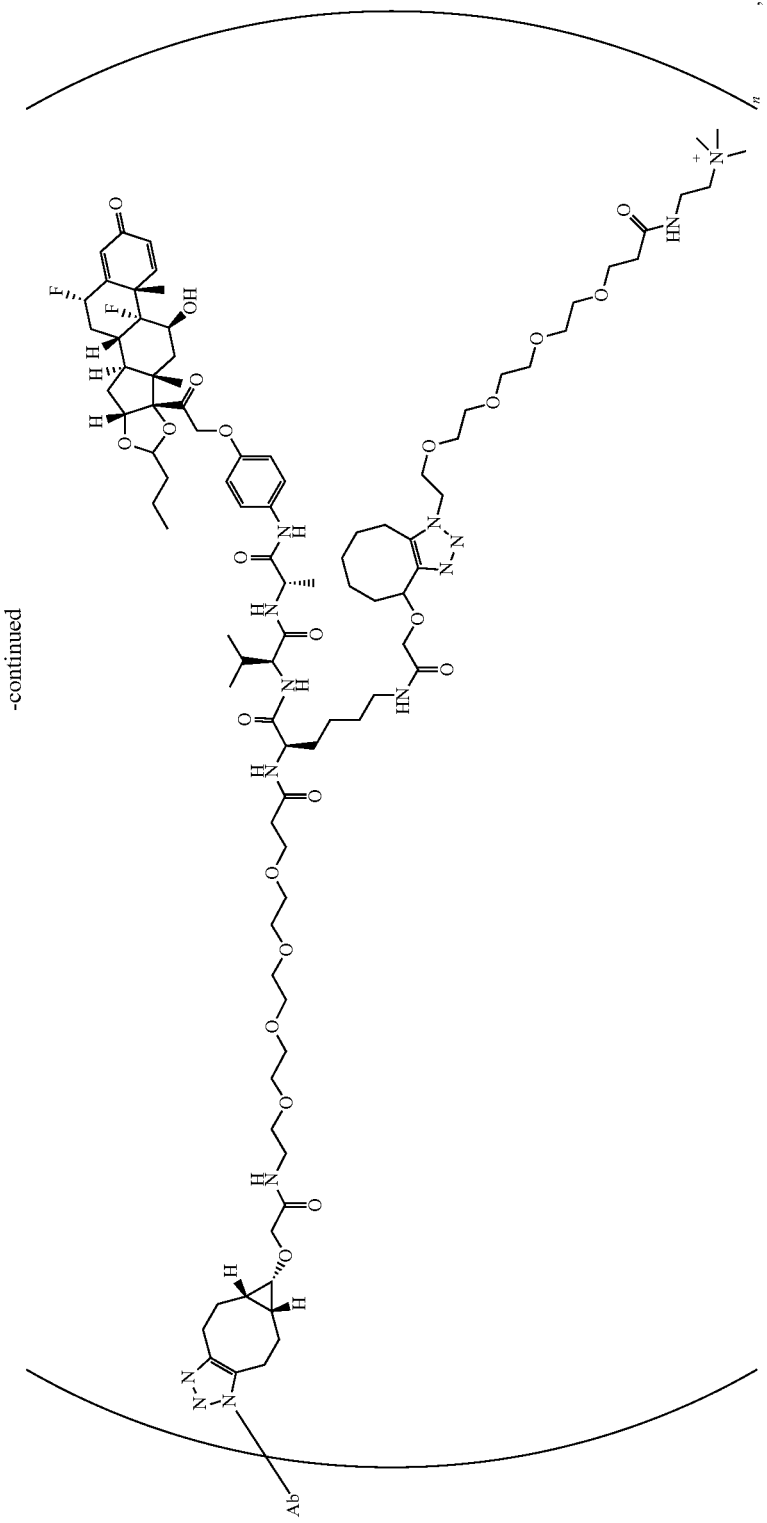

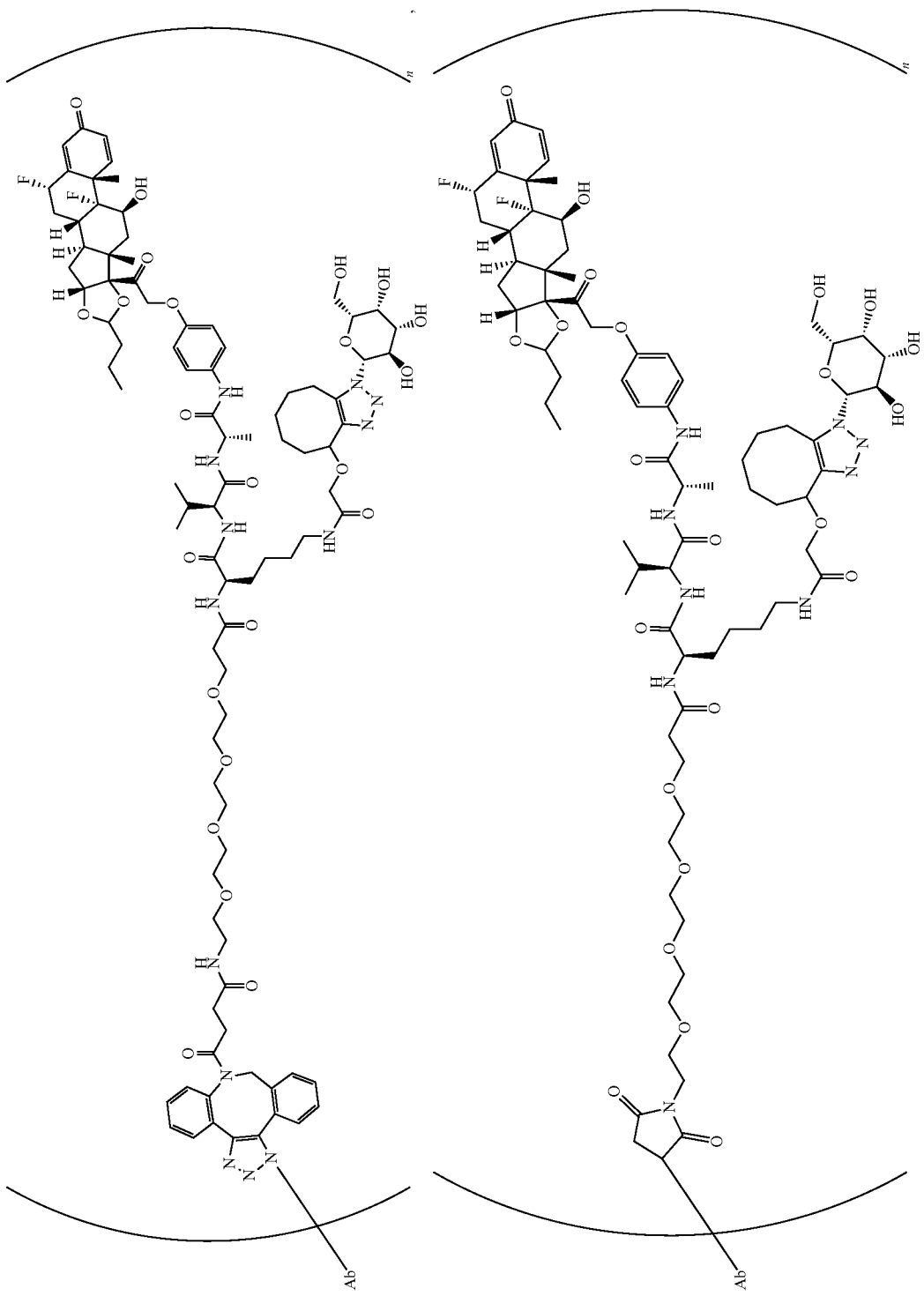

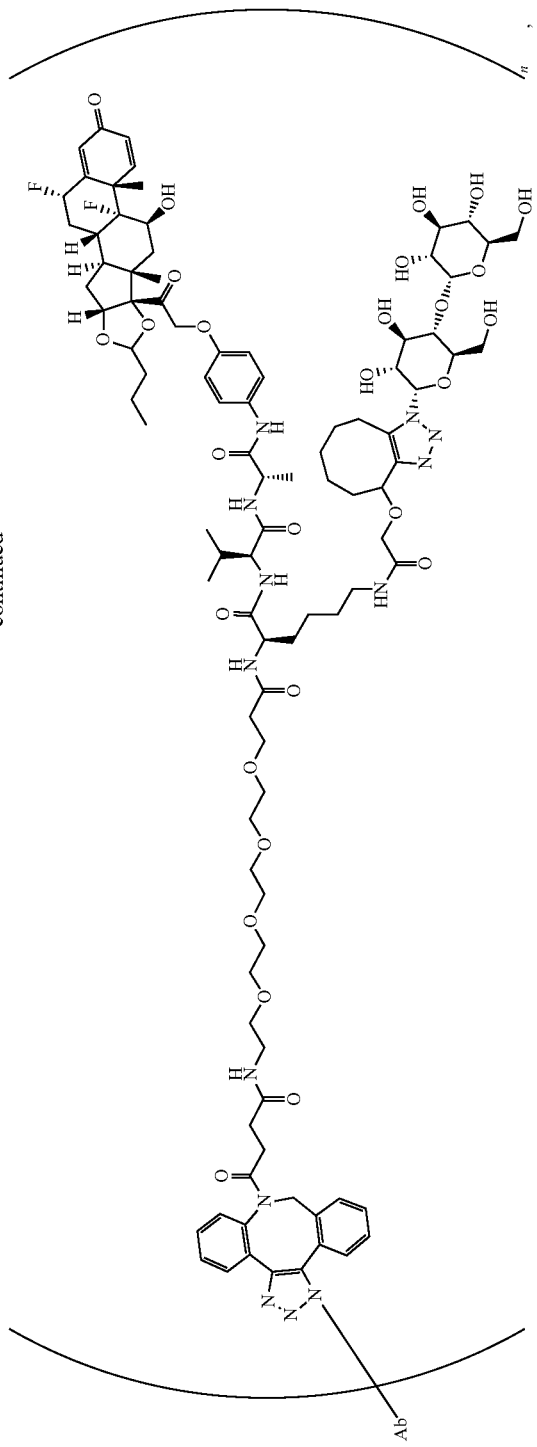

-continued
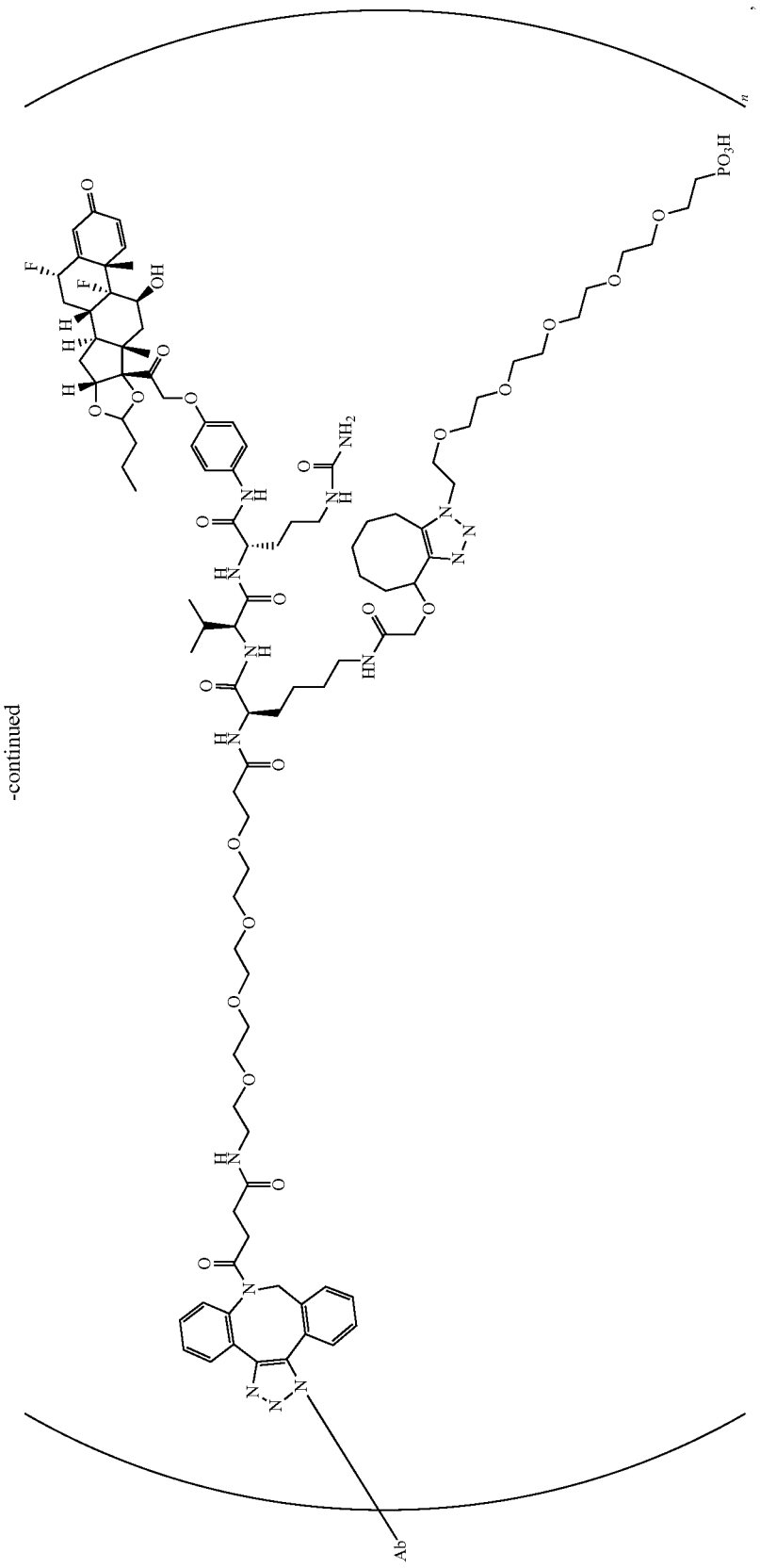

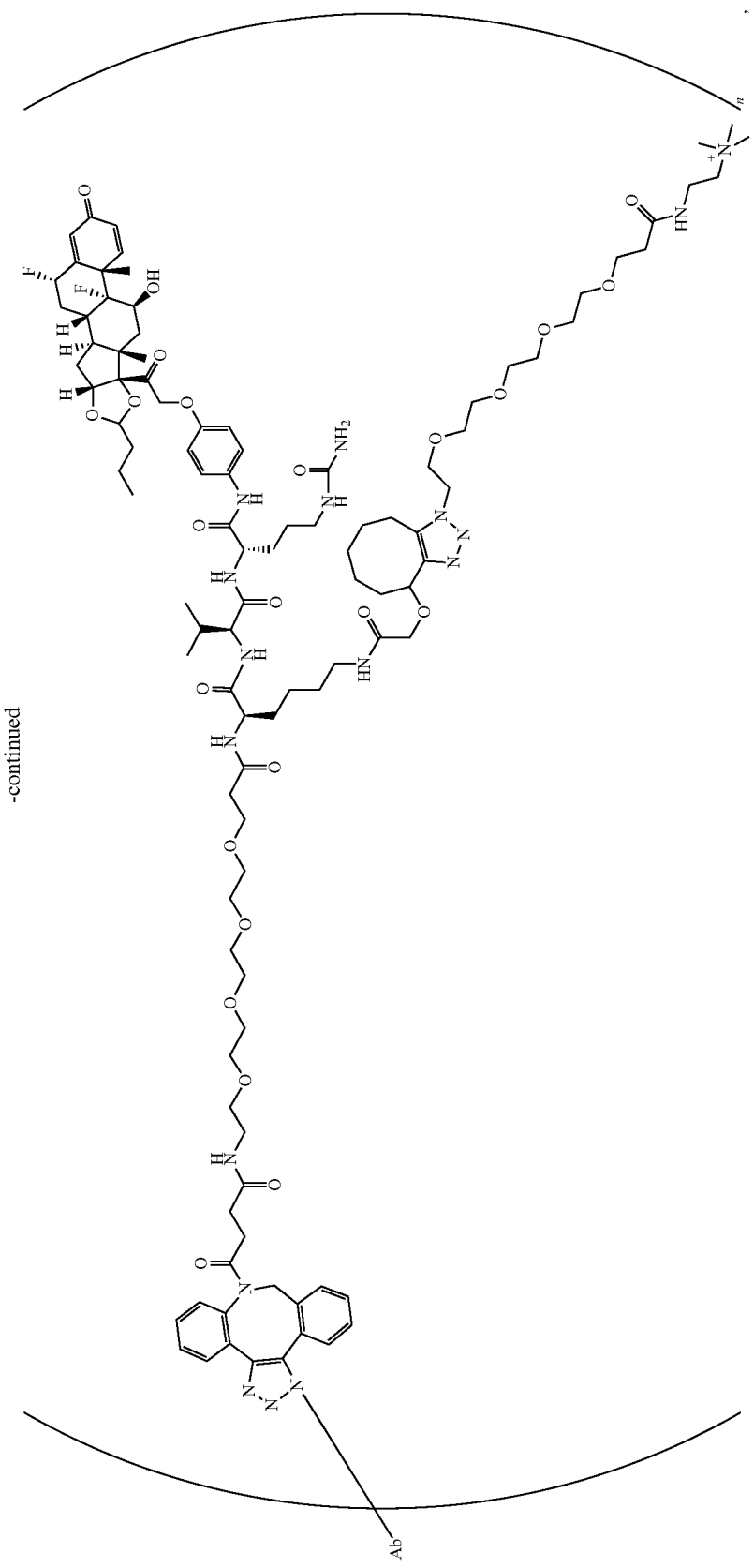

-continued
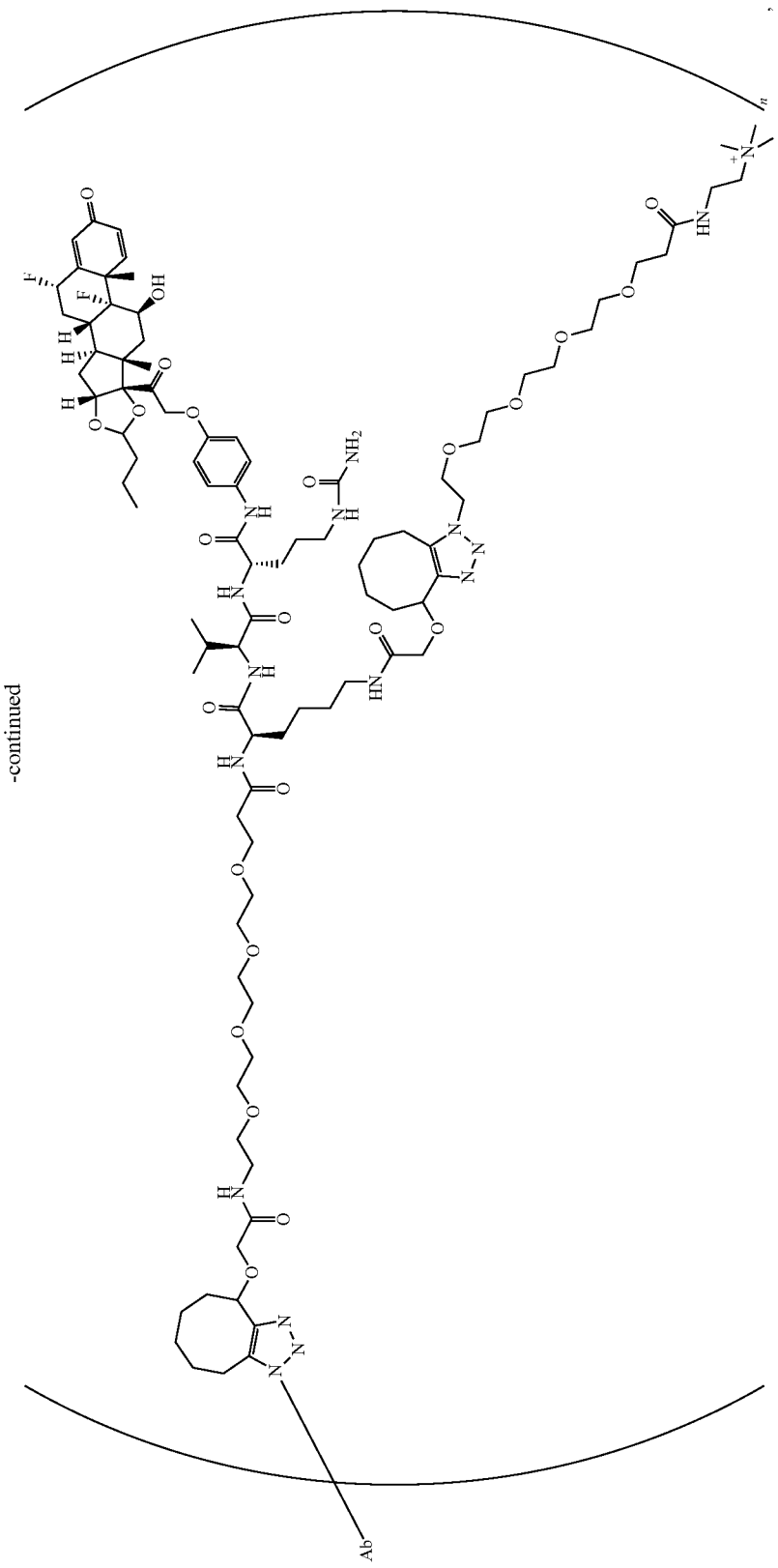

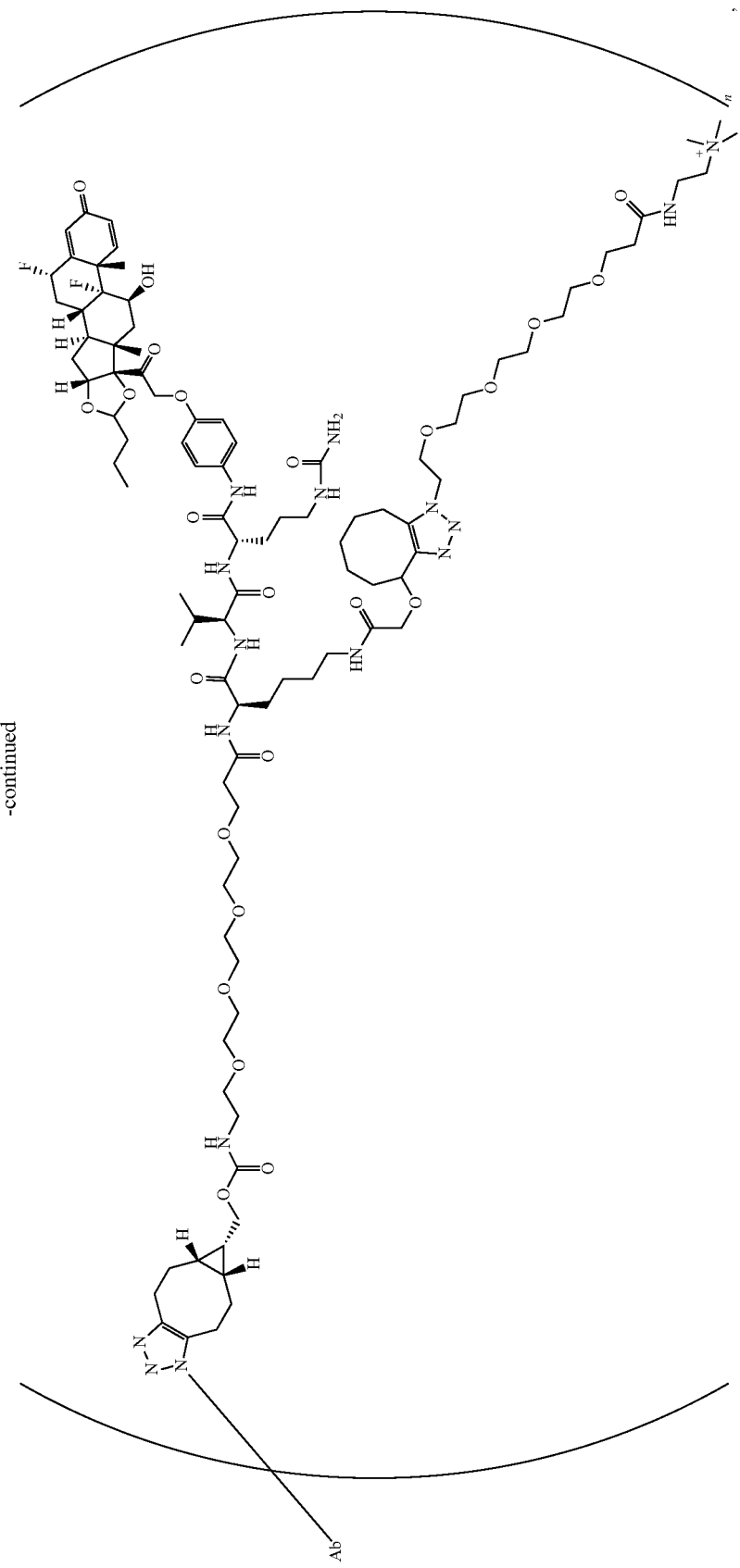

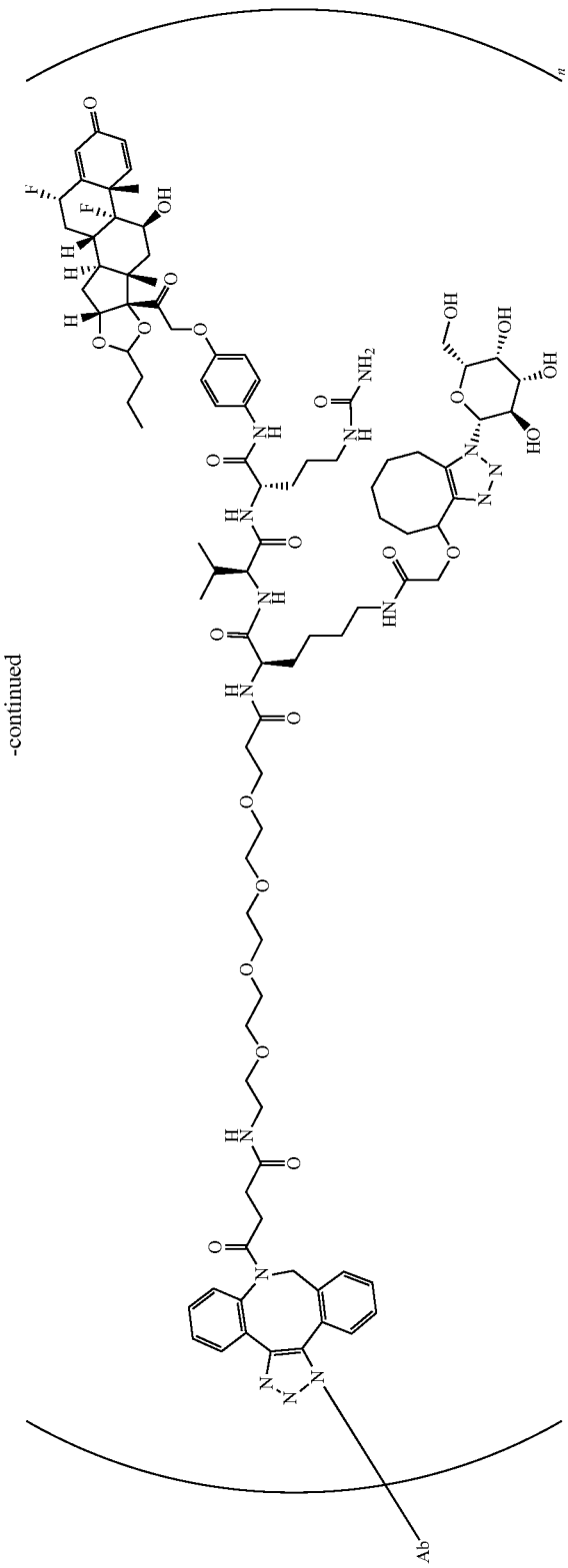

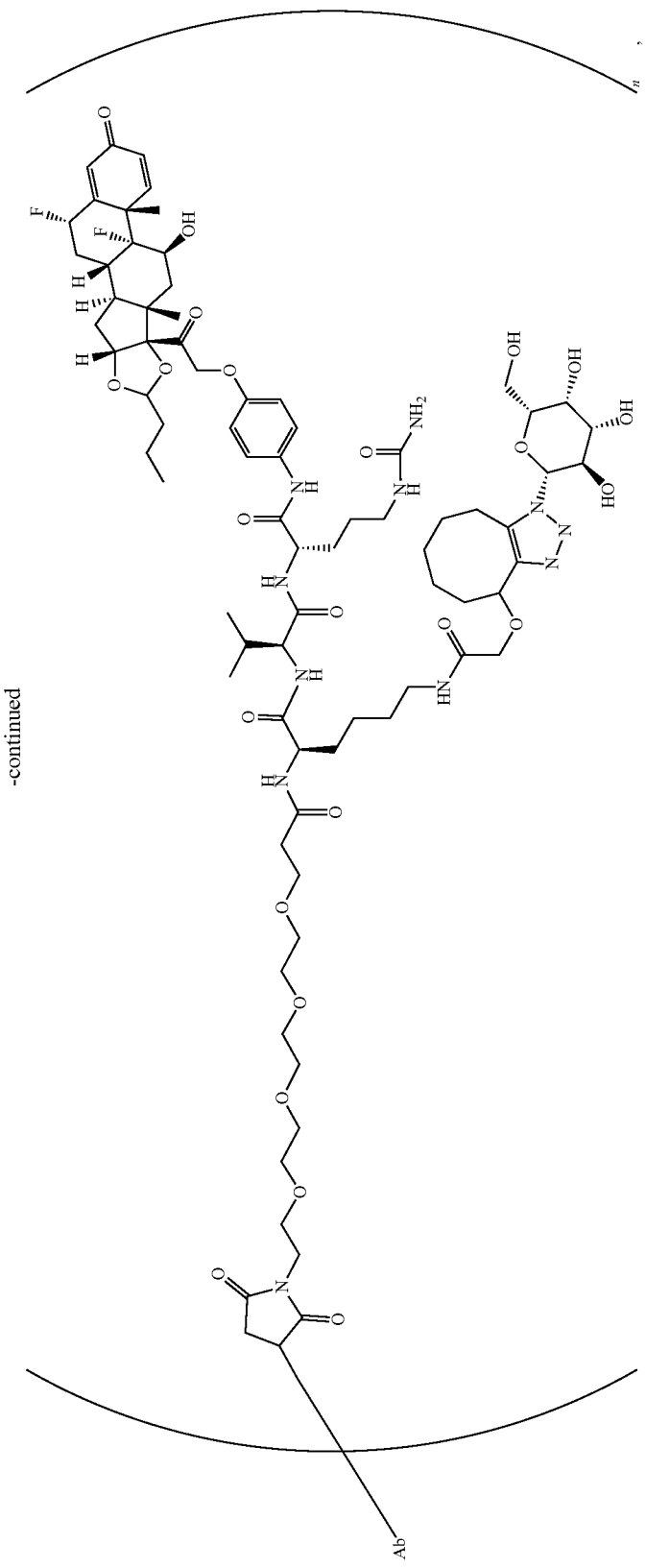

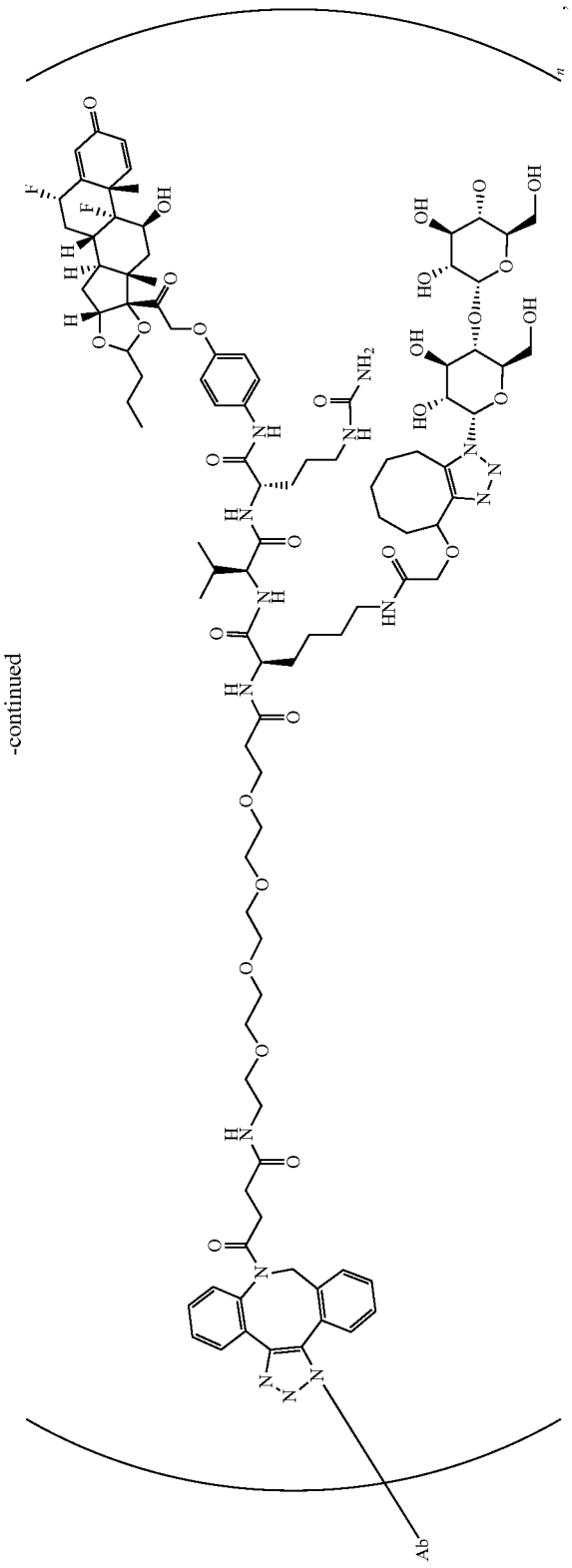

-continued
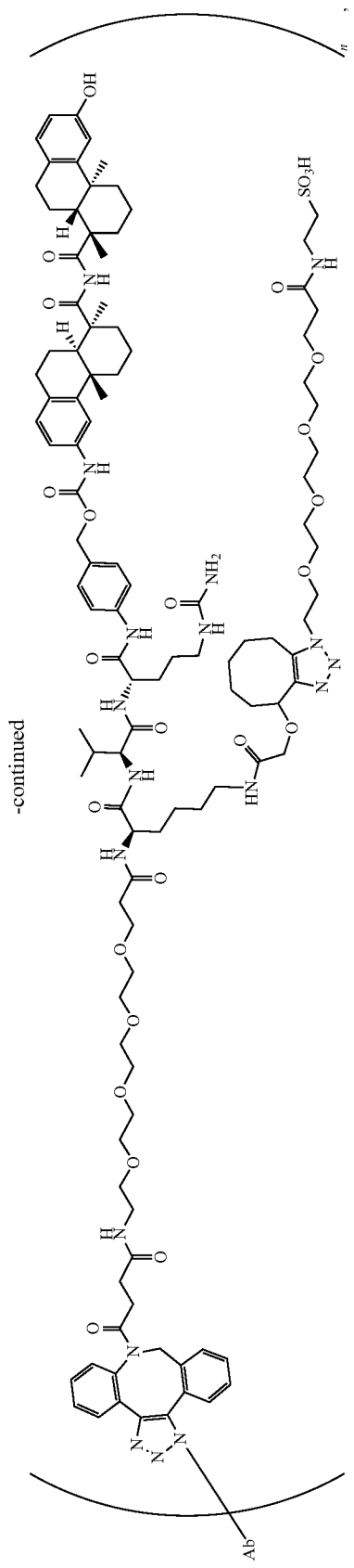
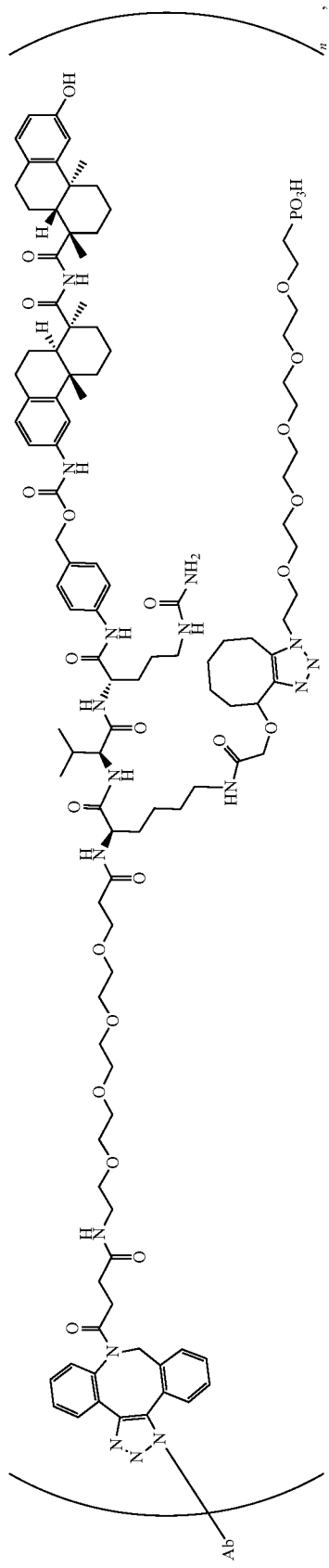

-continued
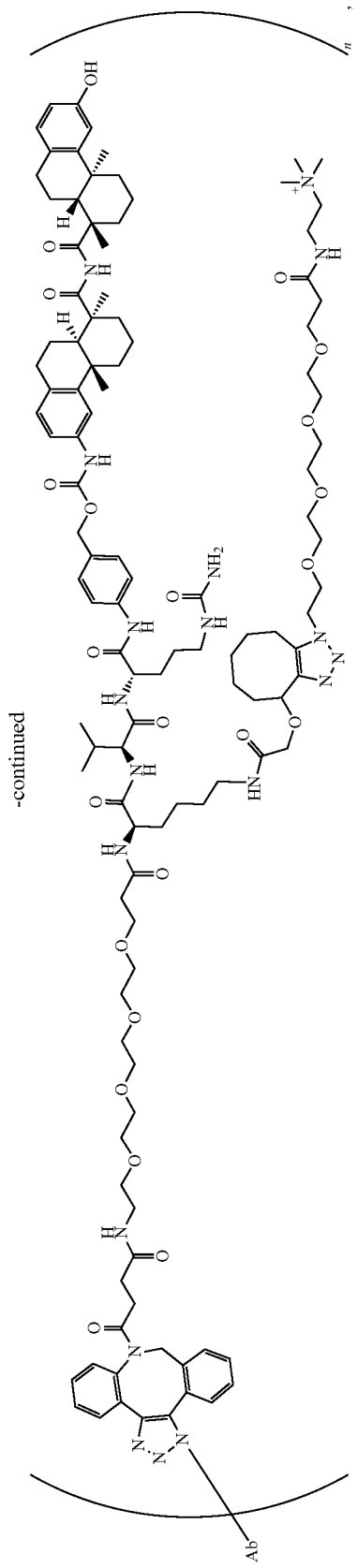
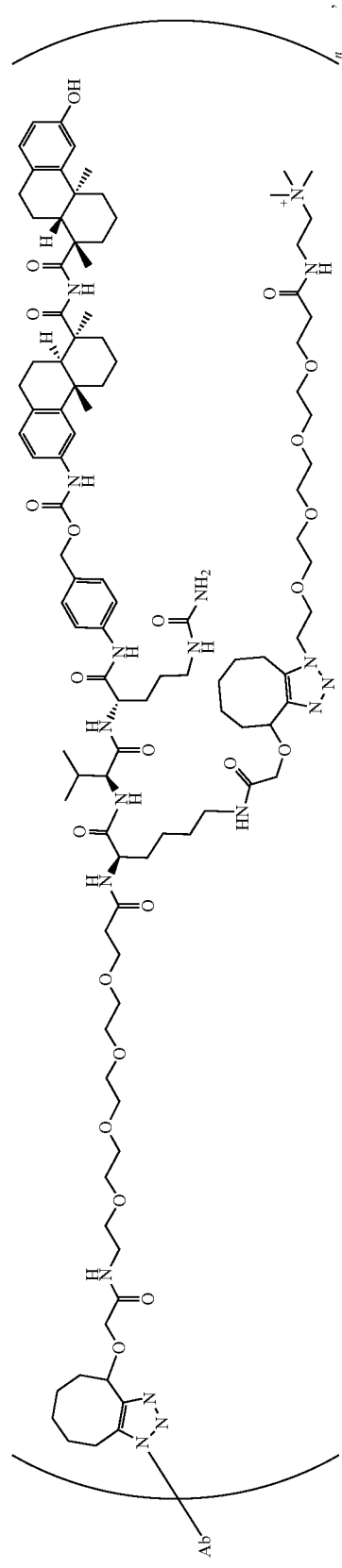

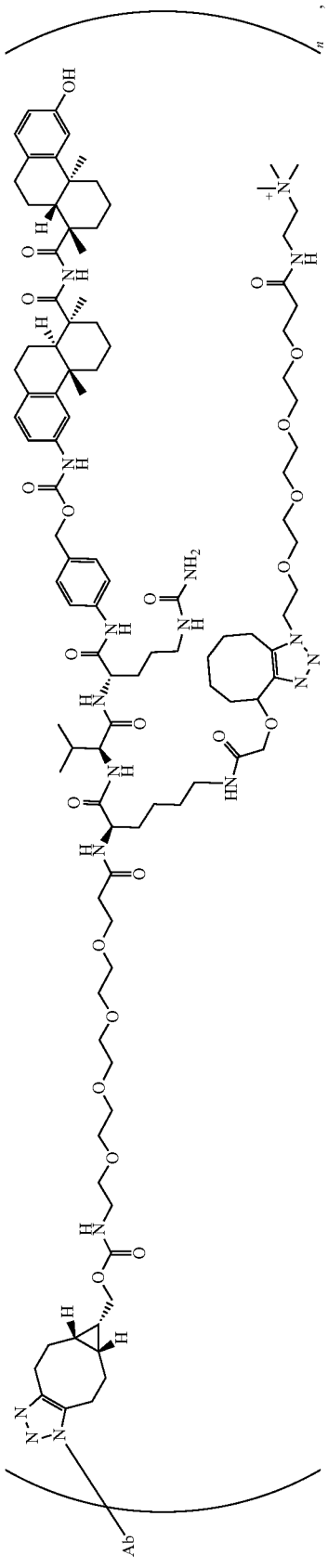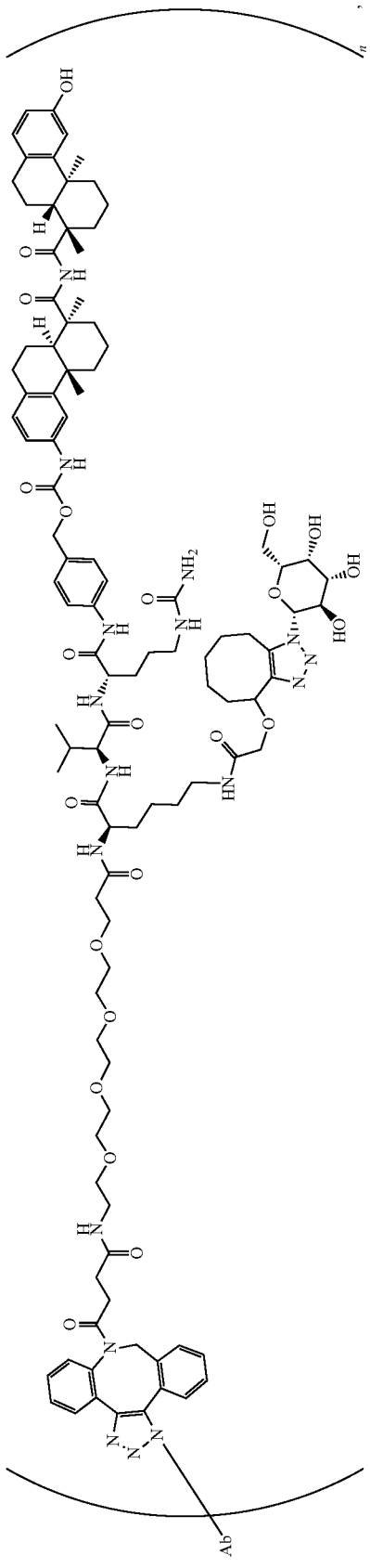

323
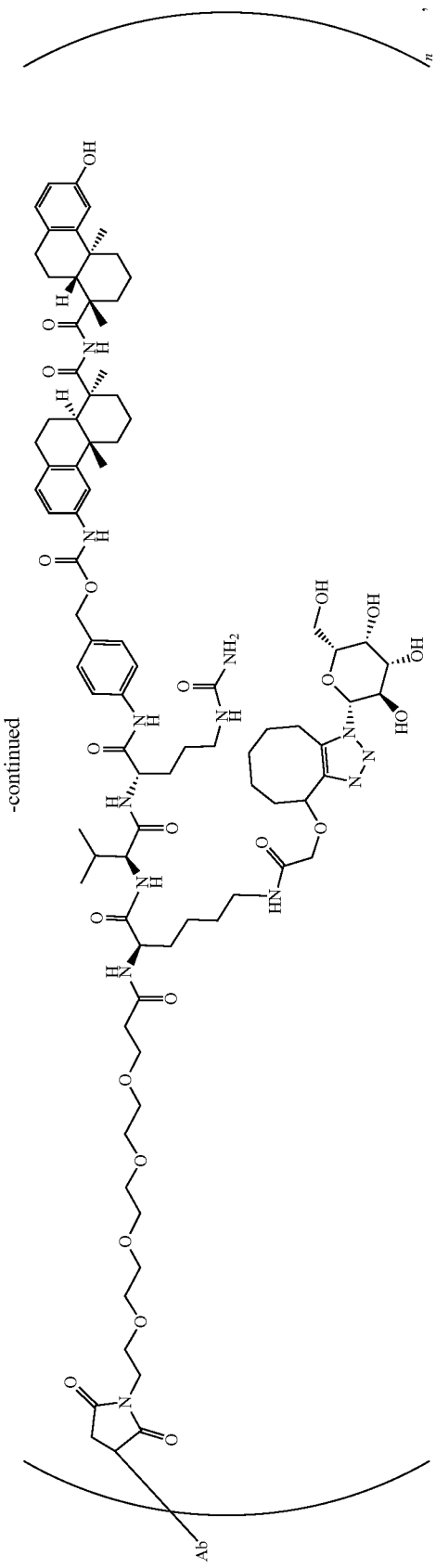
324
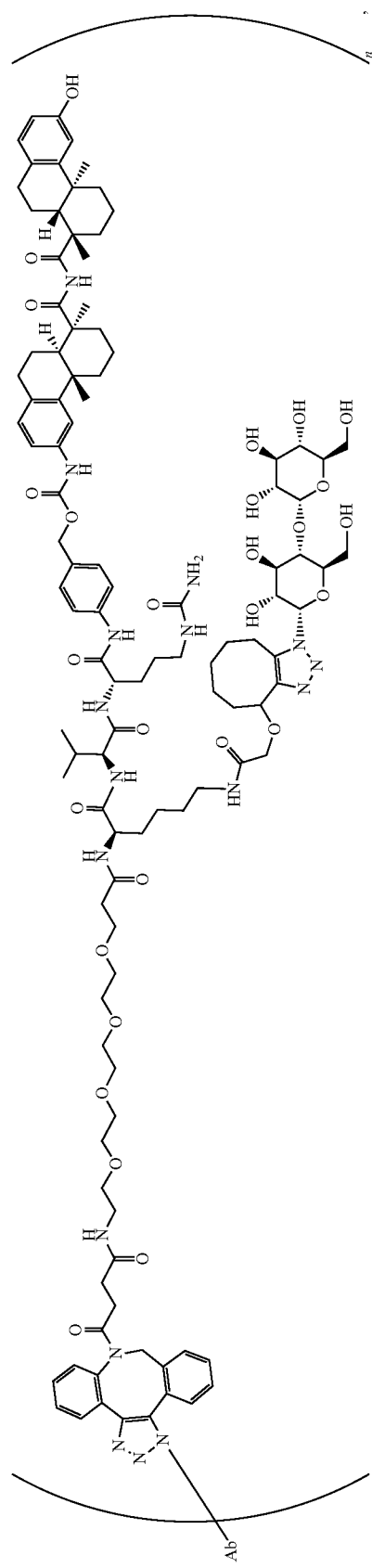

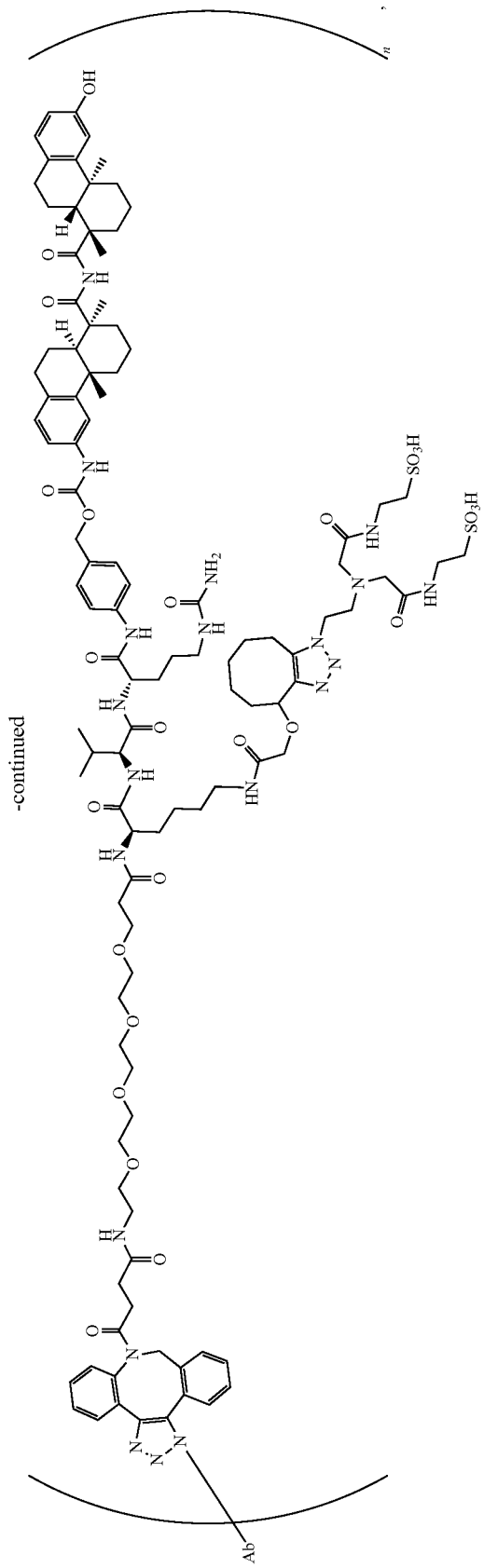
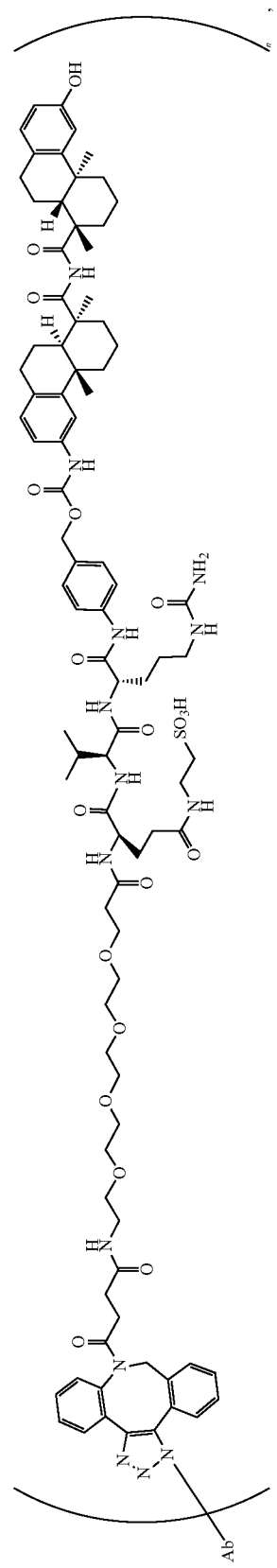

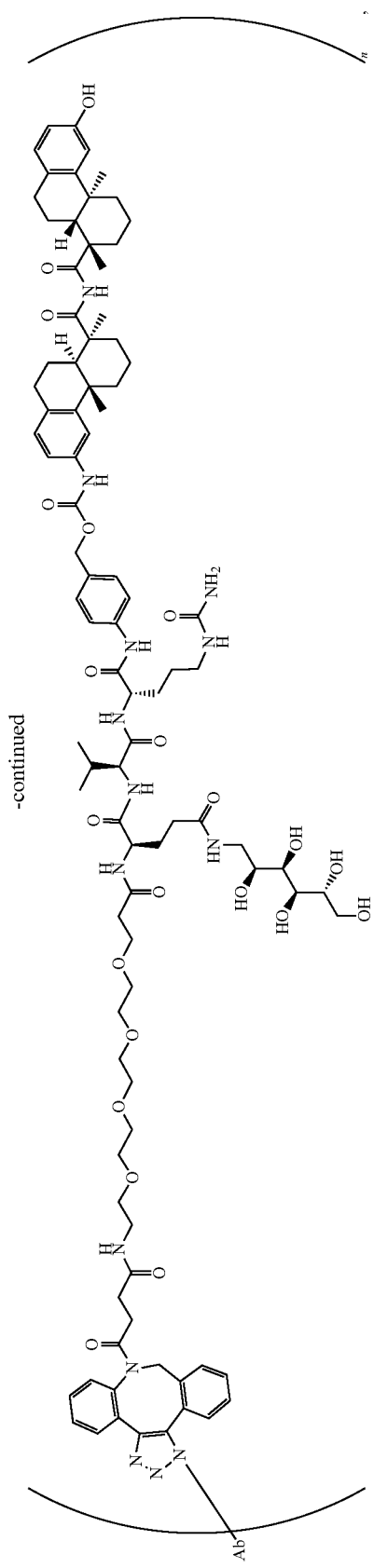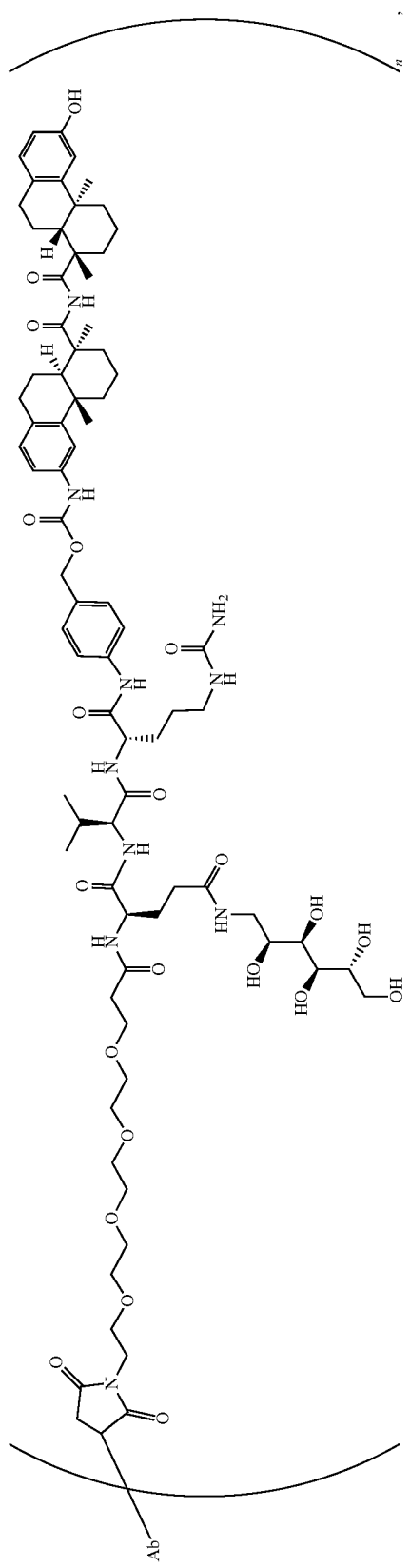

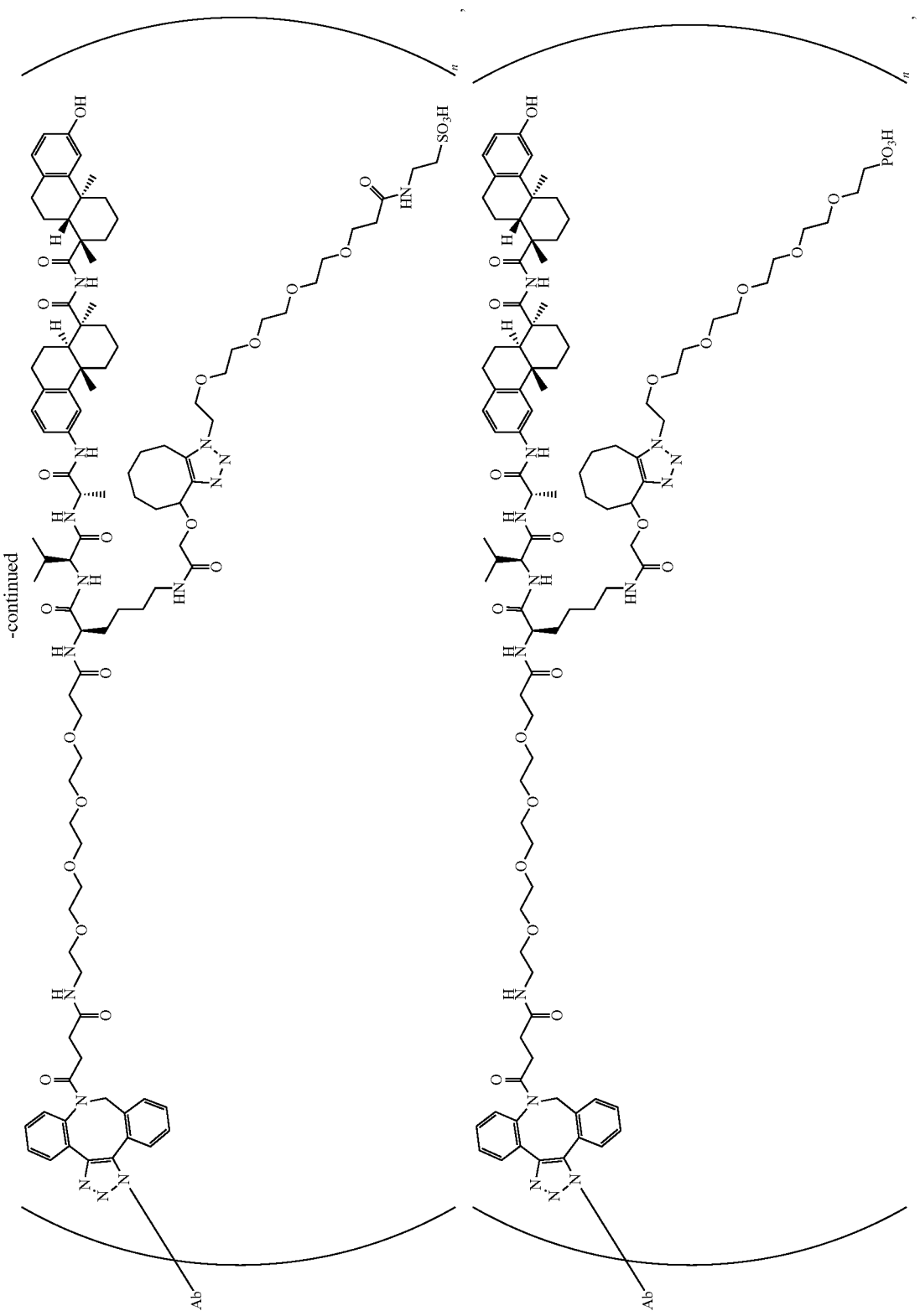

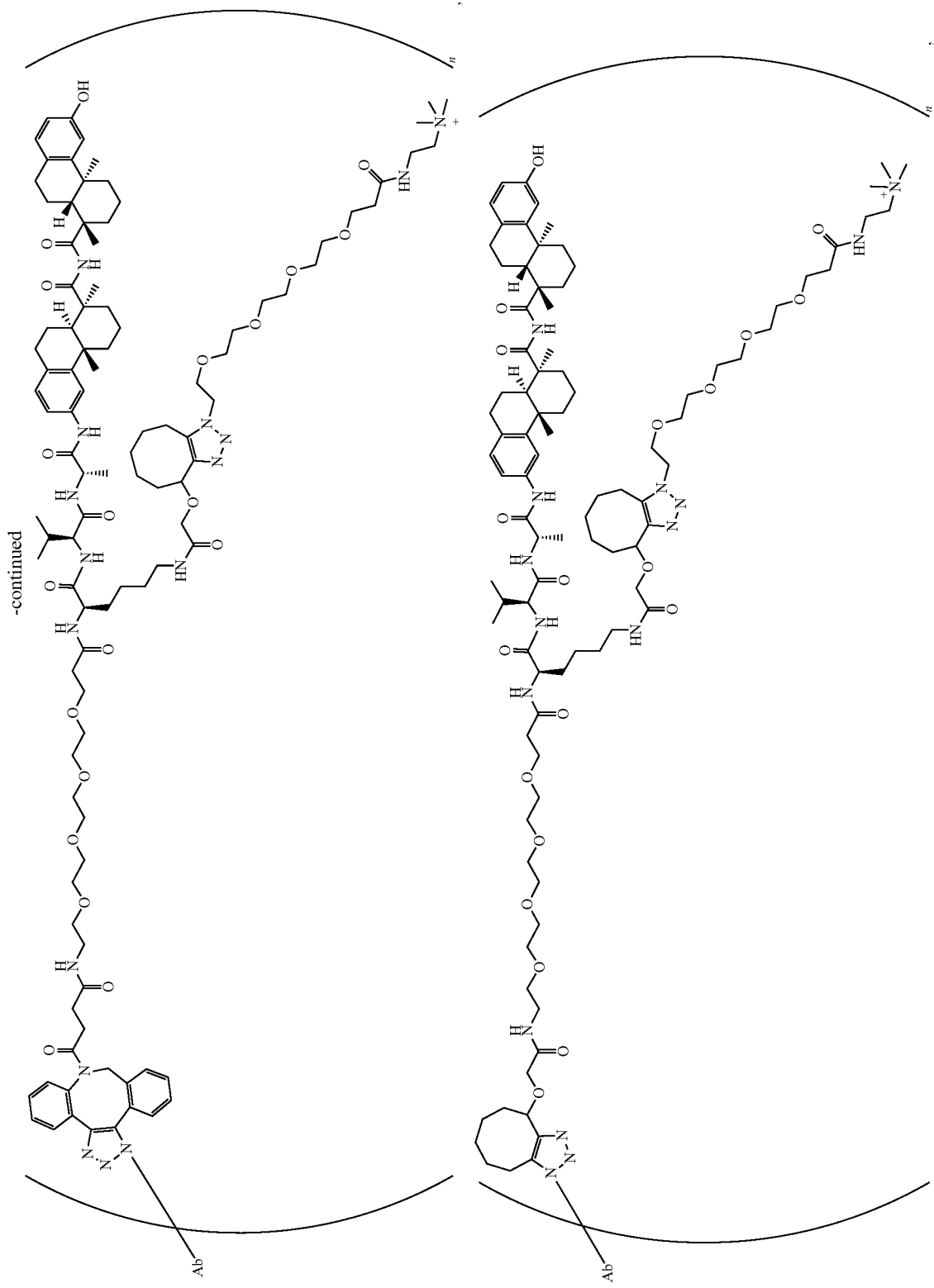

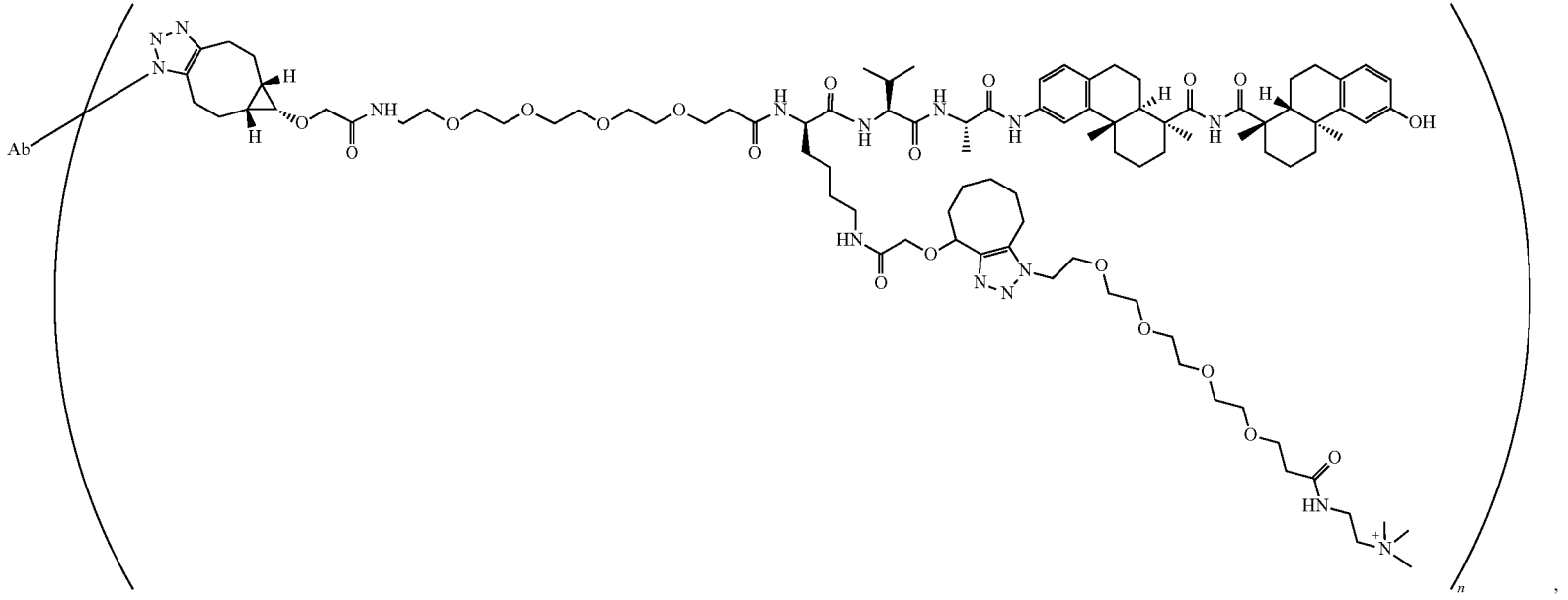

-continued
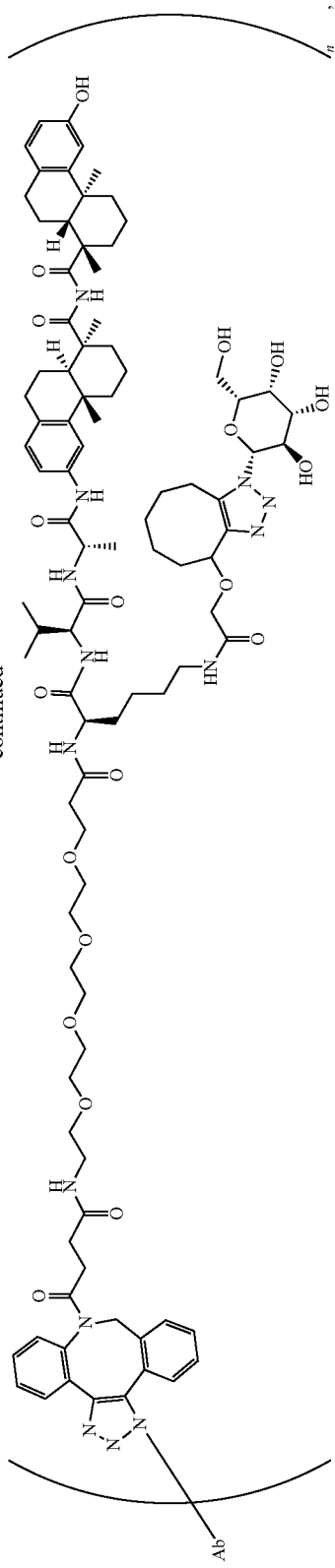
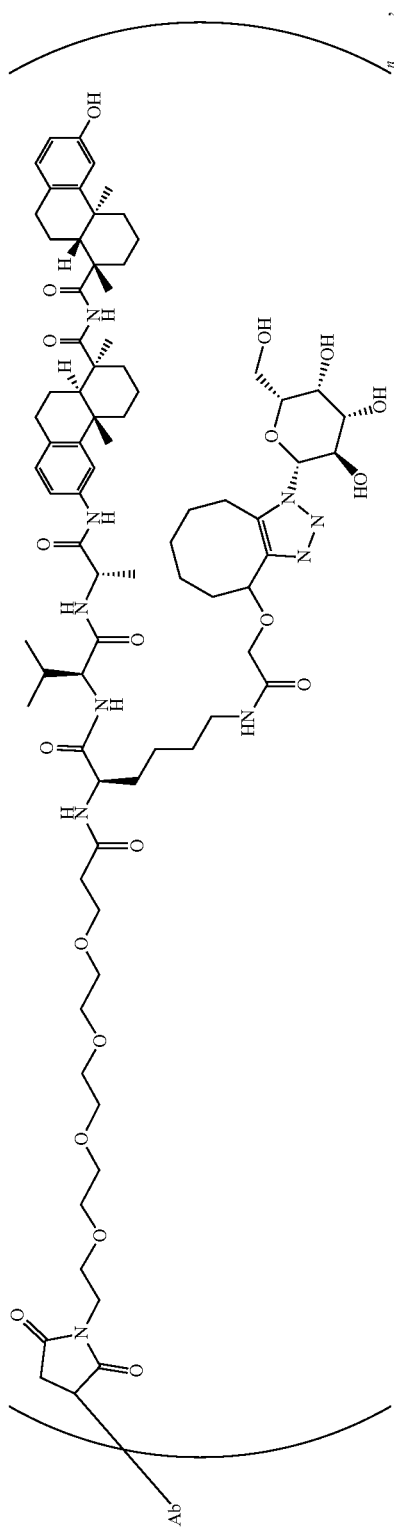

-continued
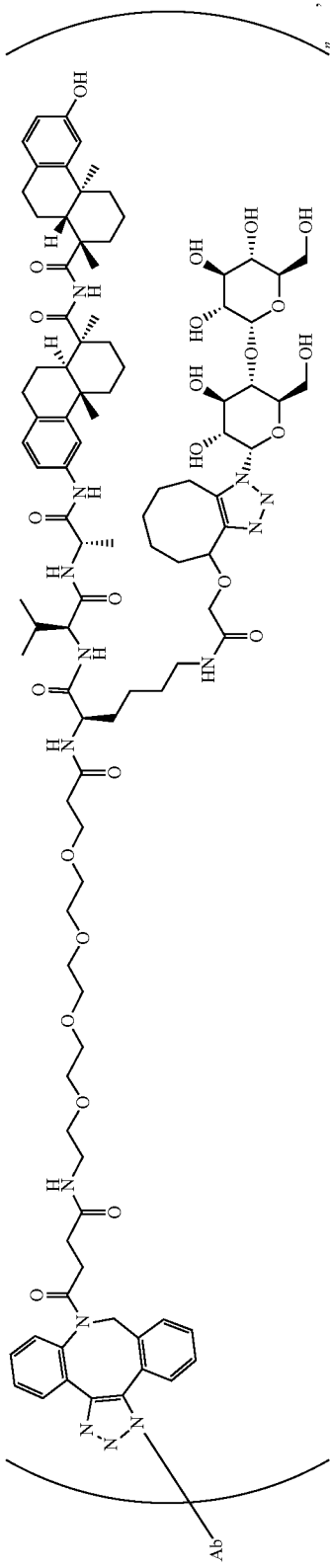
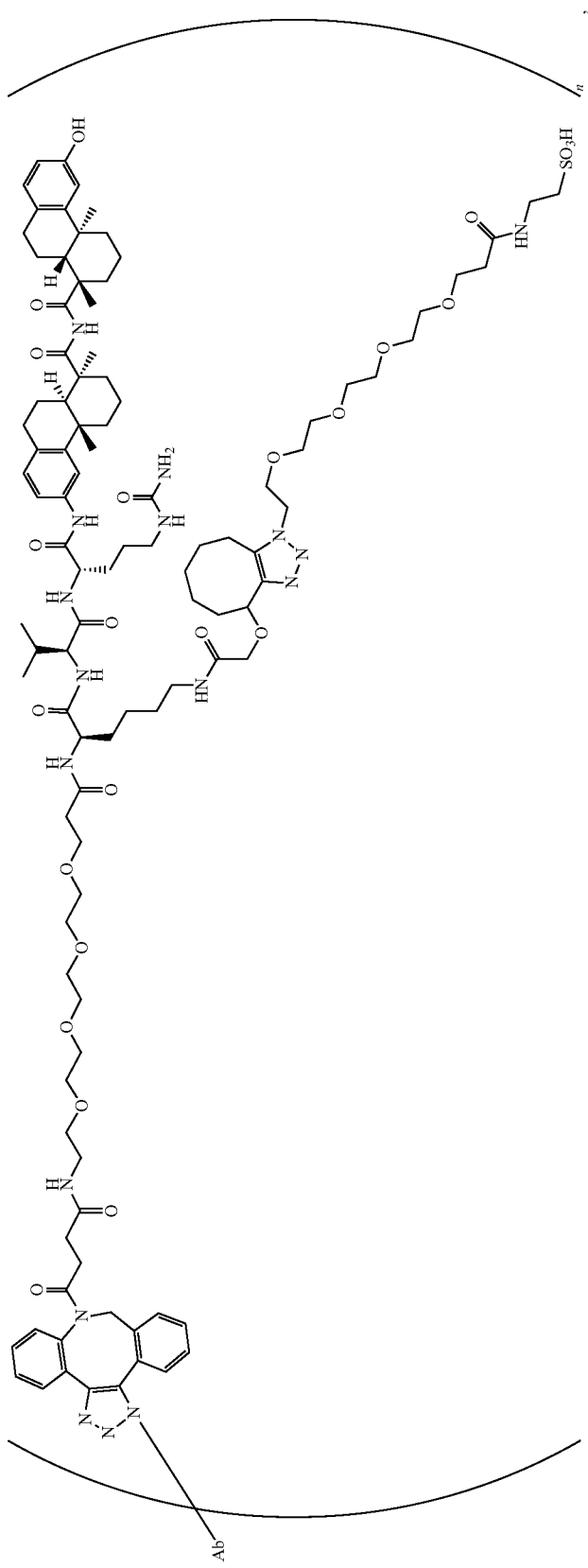

-continued
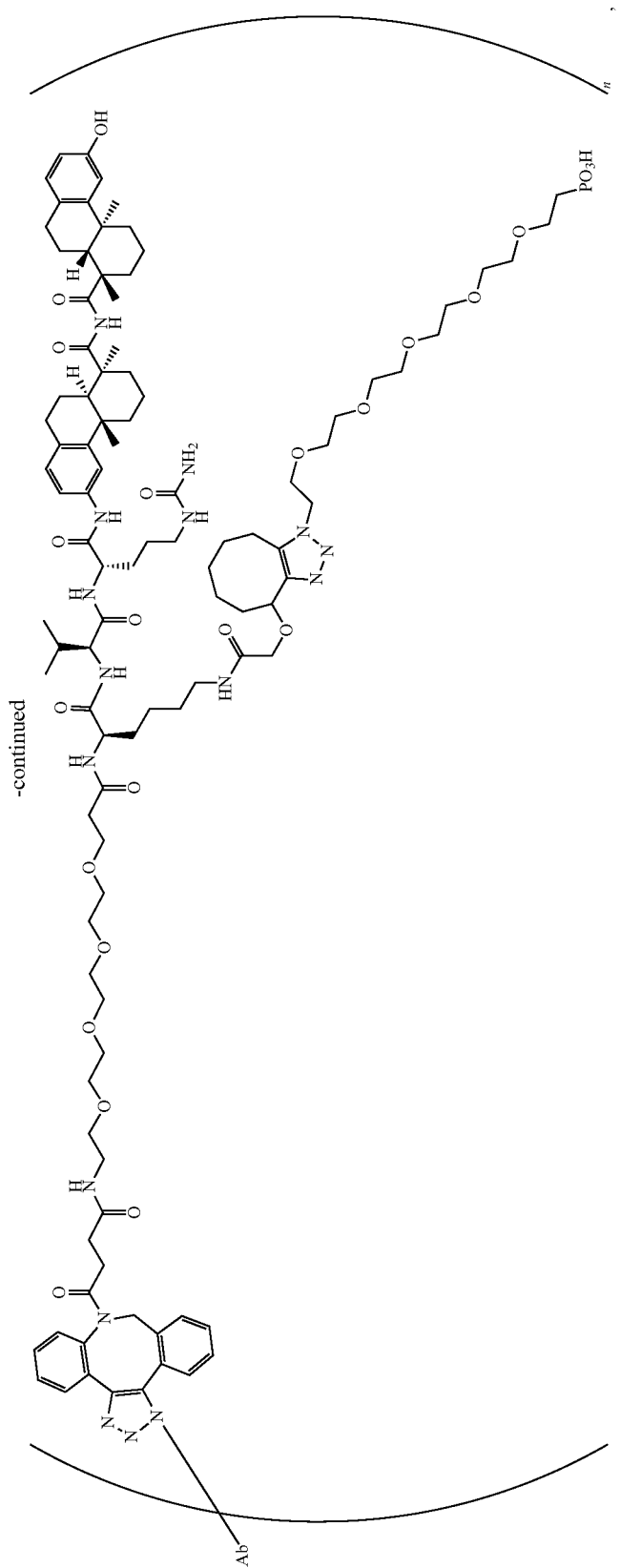

-continued
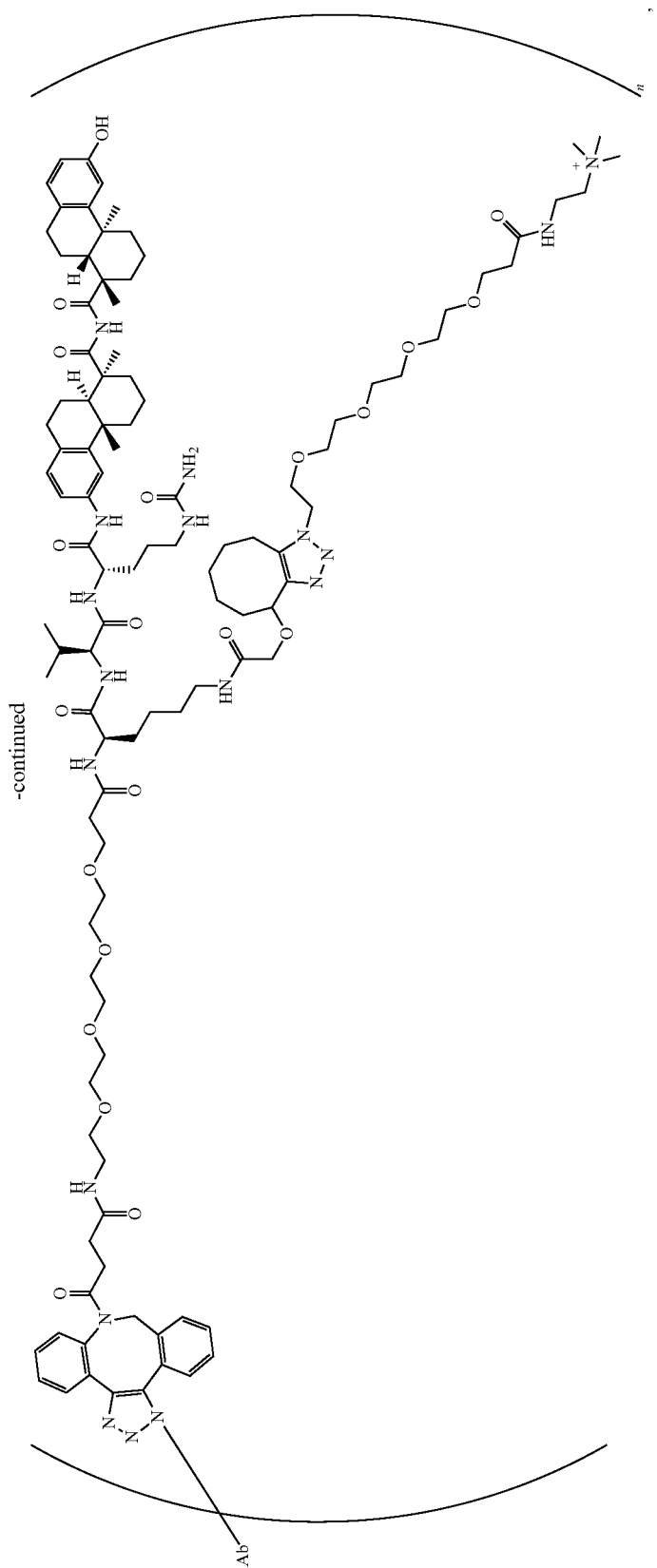

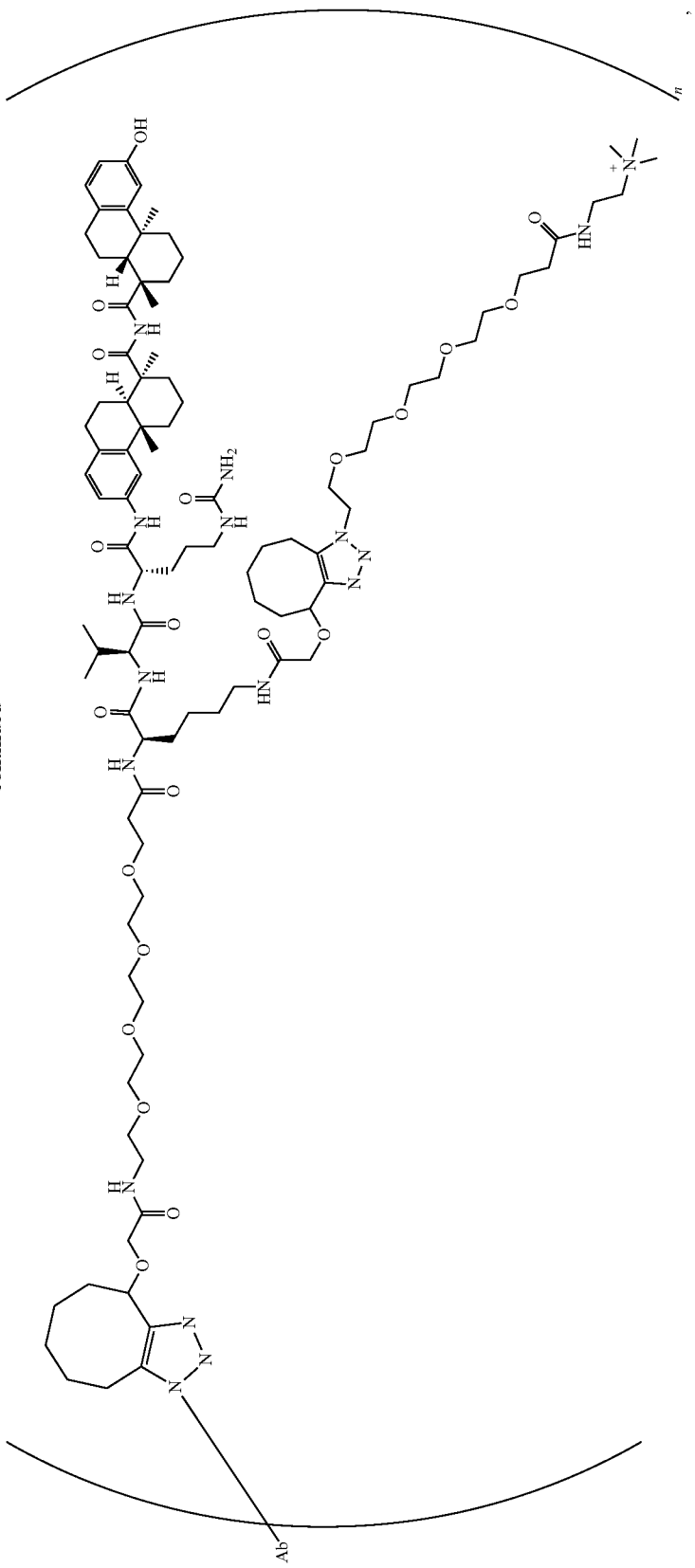

-continued
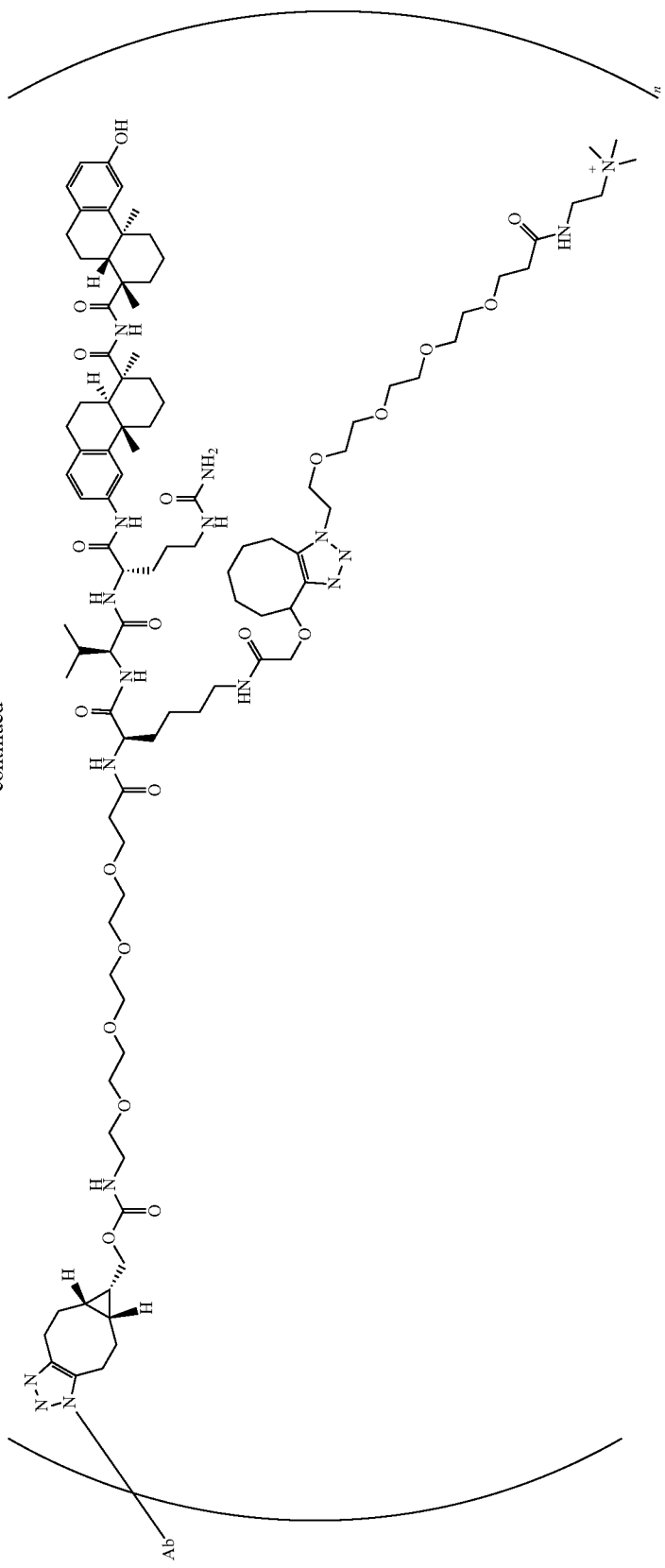

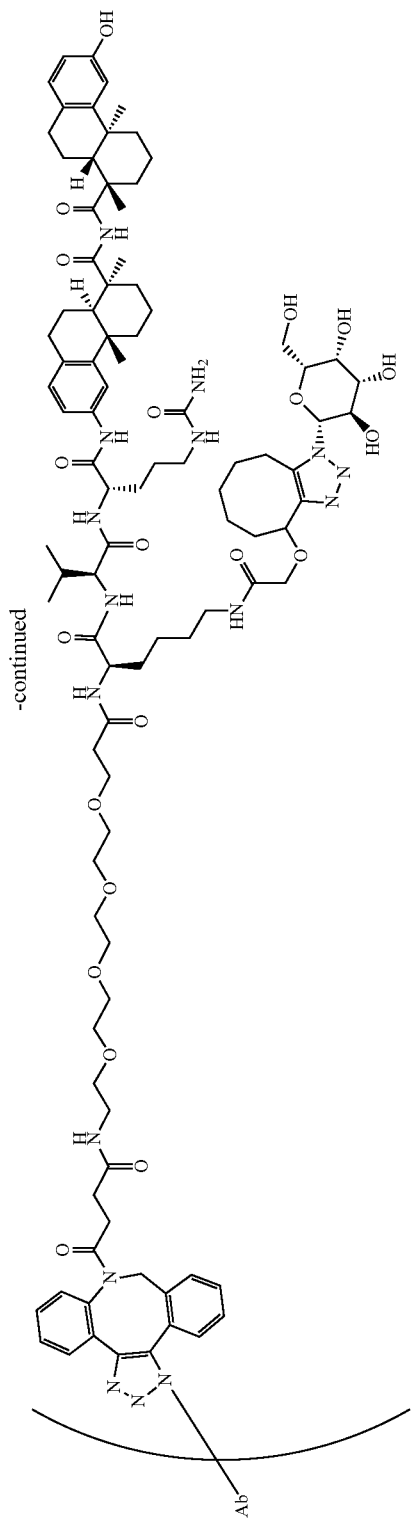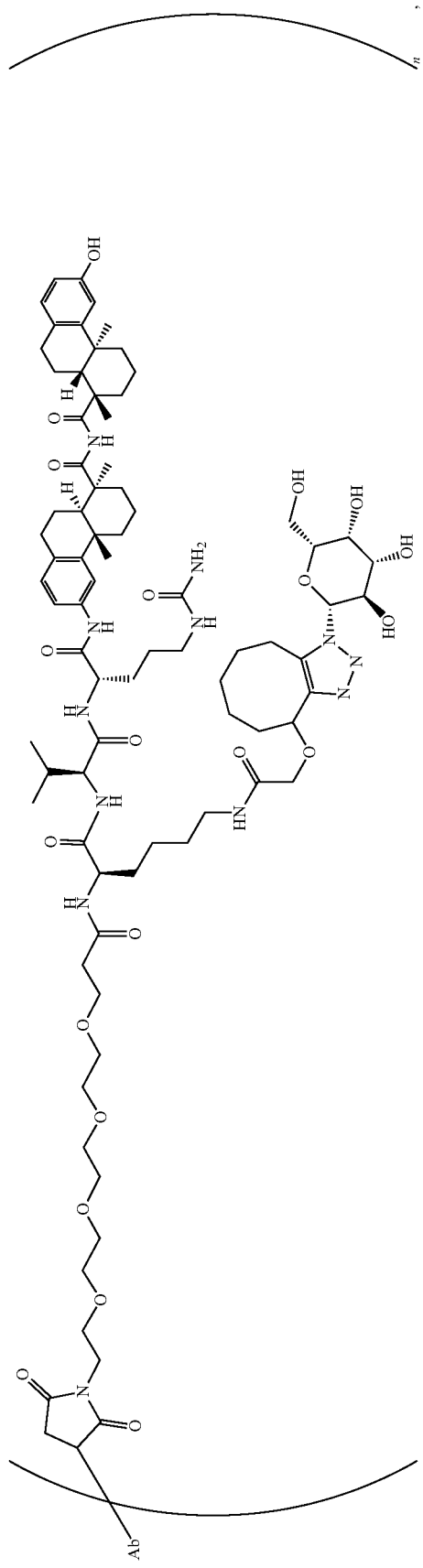

-continued
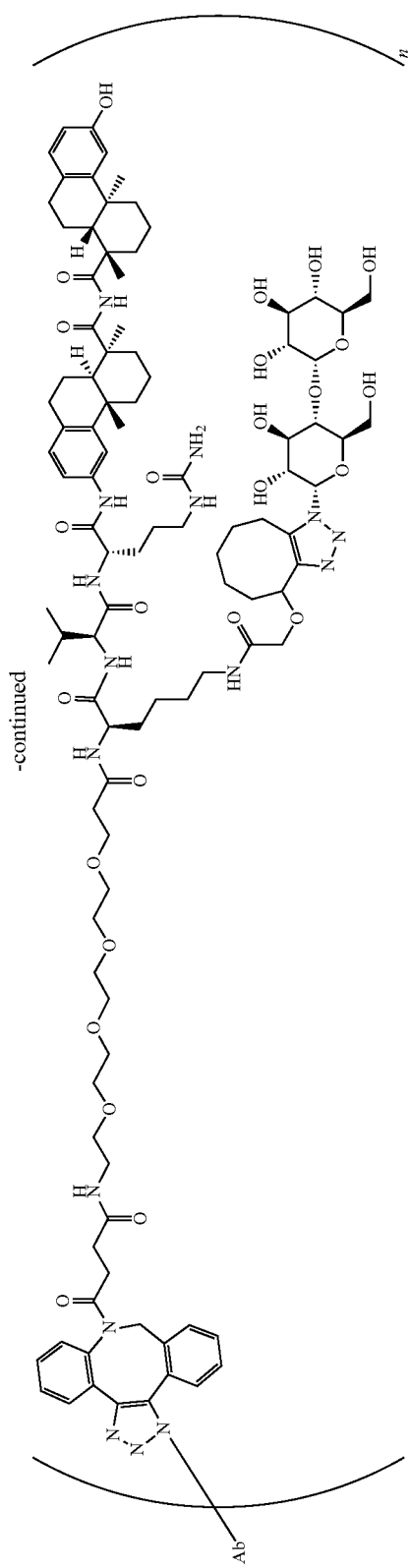

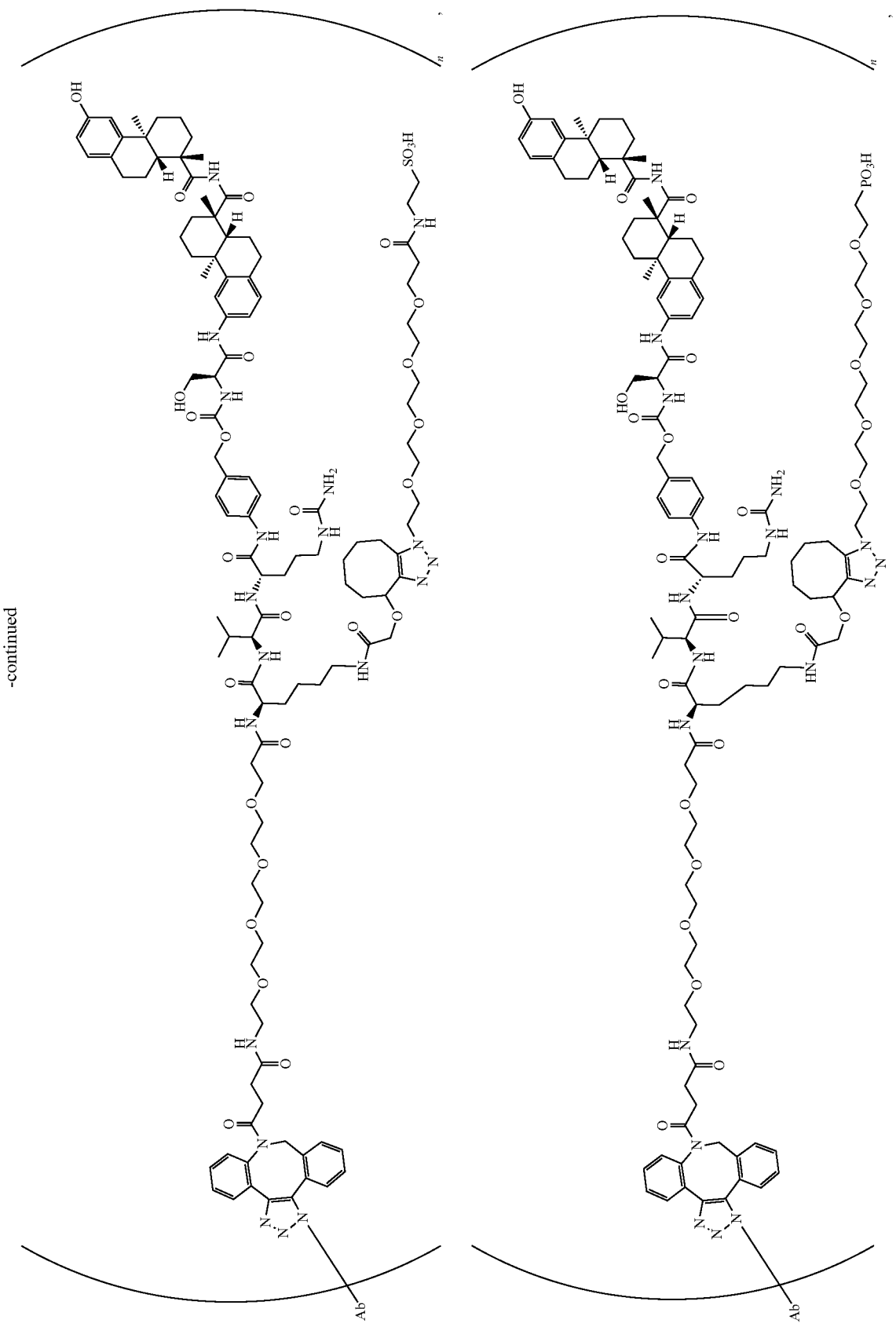

353 354
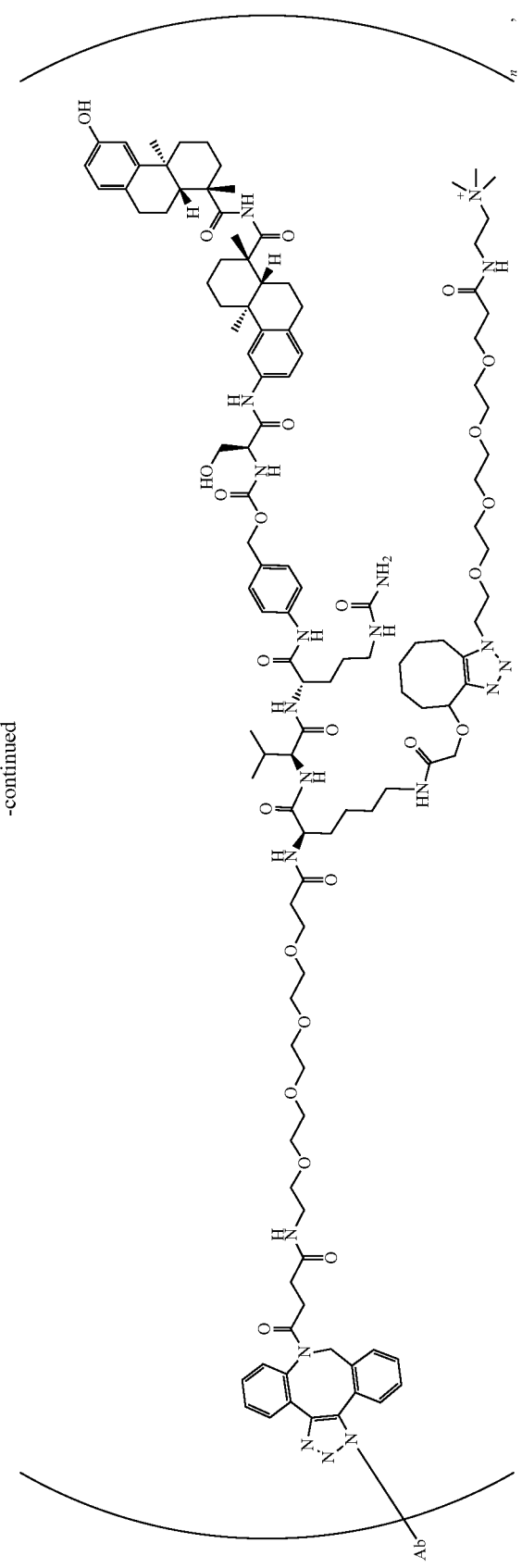
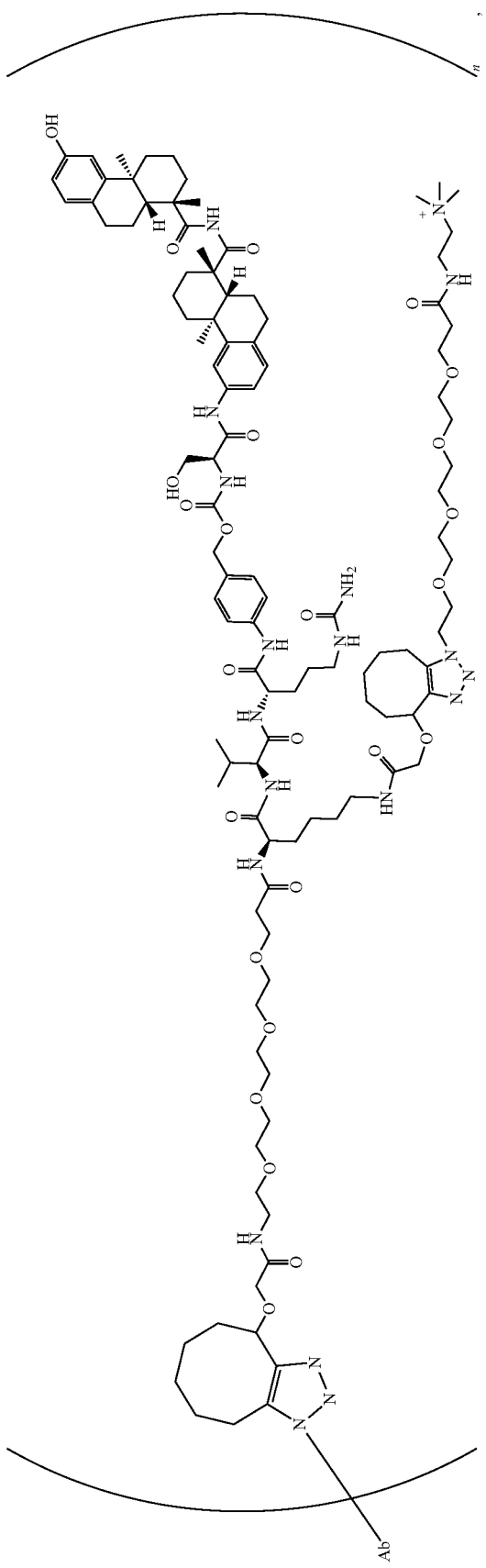

355 356
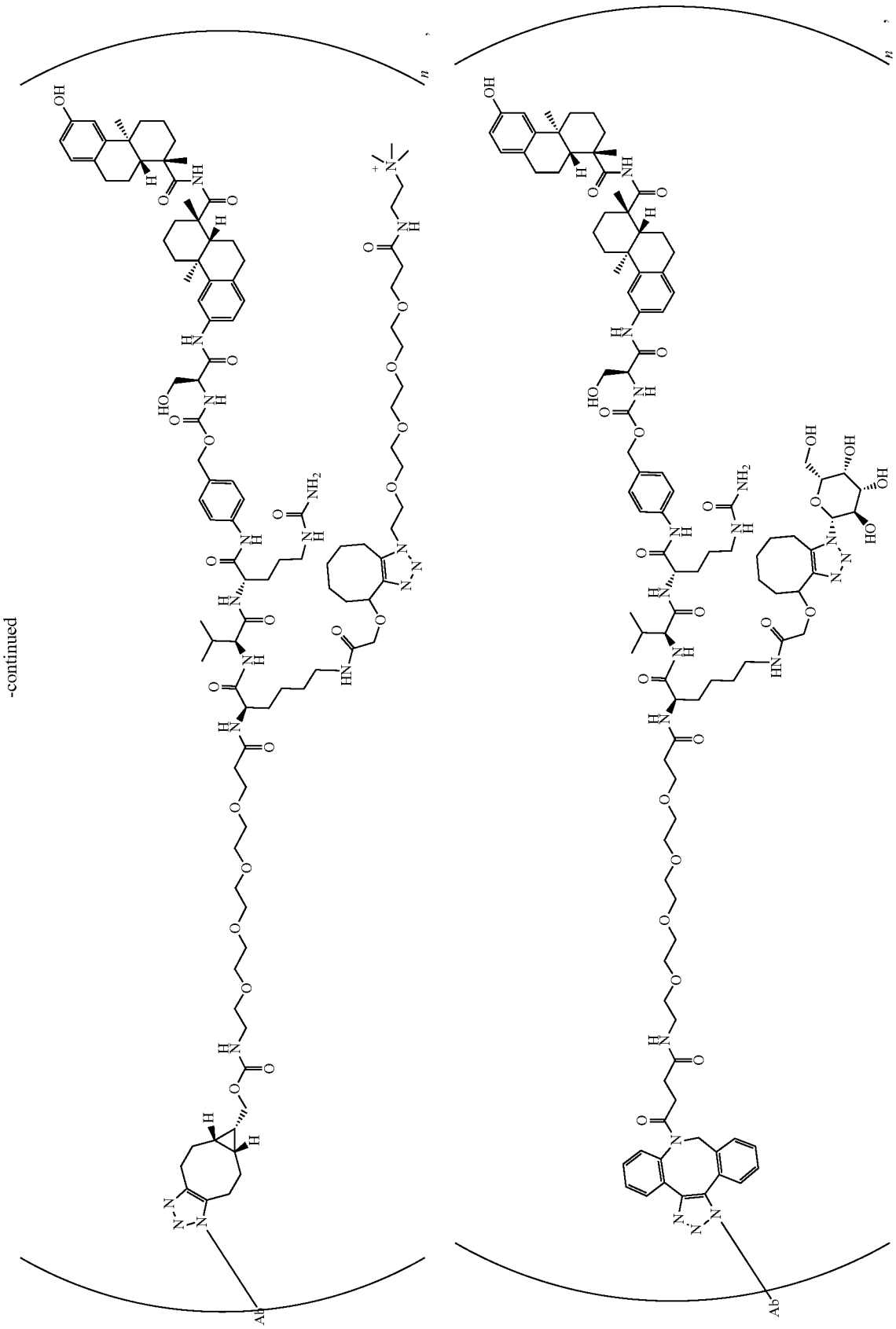

-continued
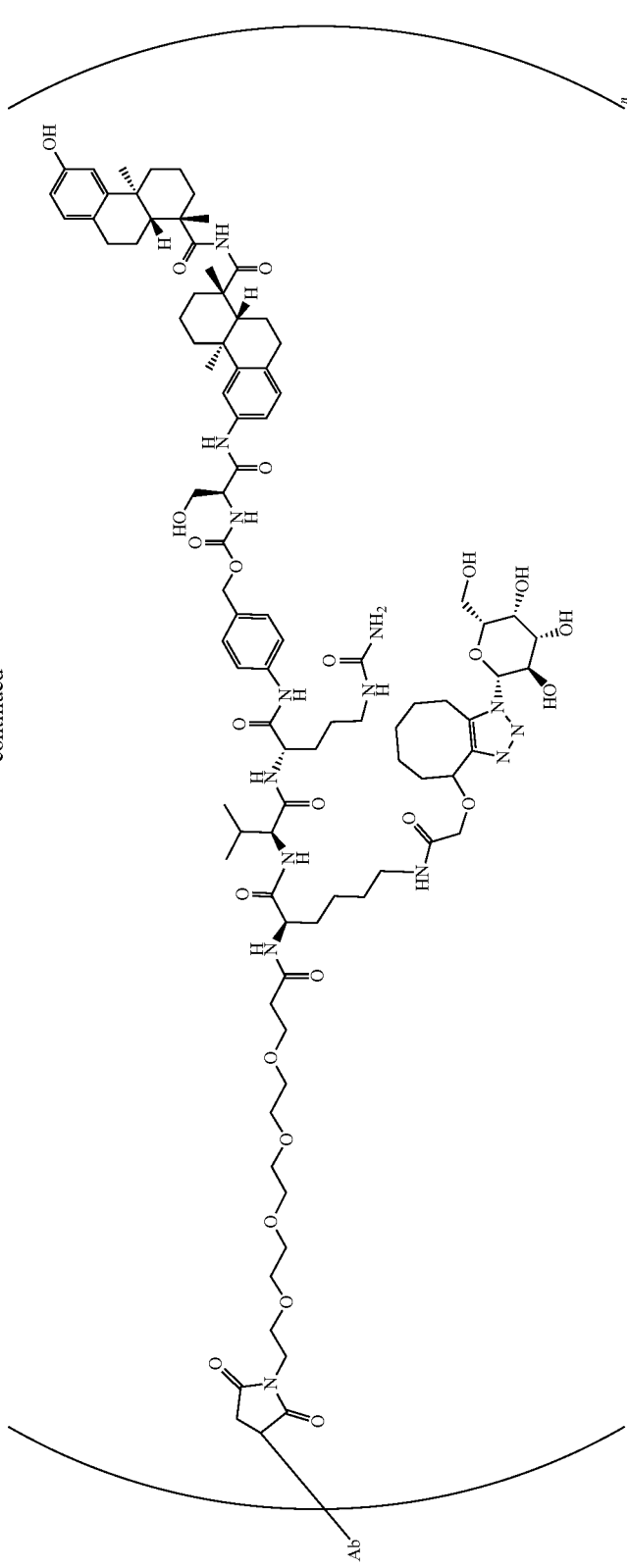

-continued
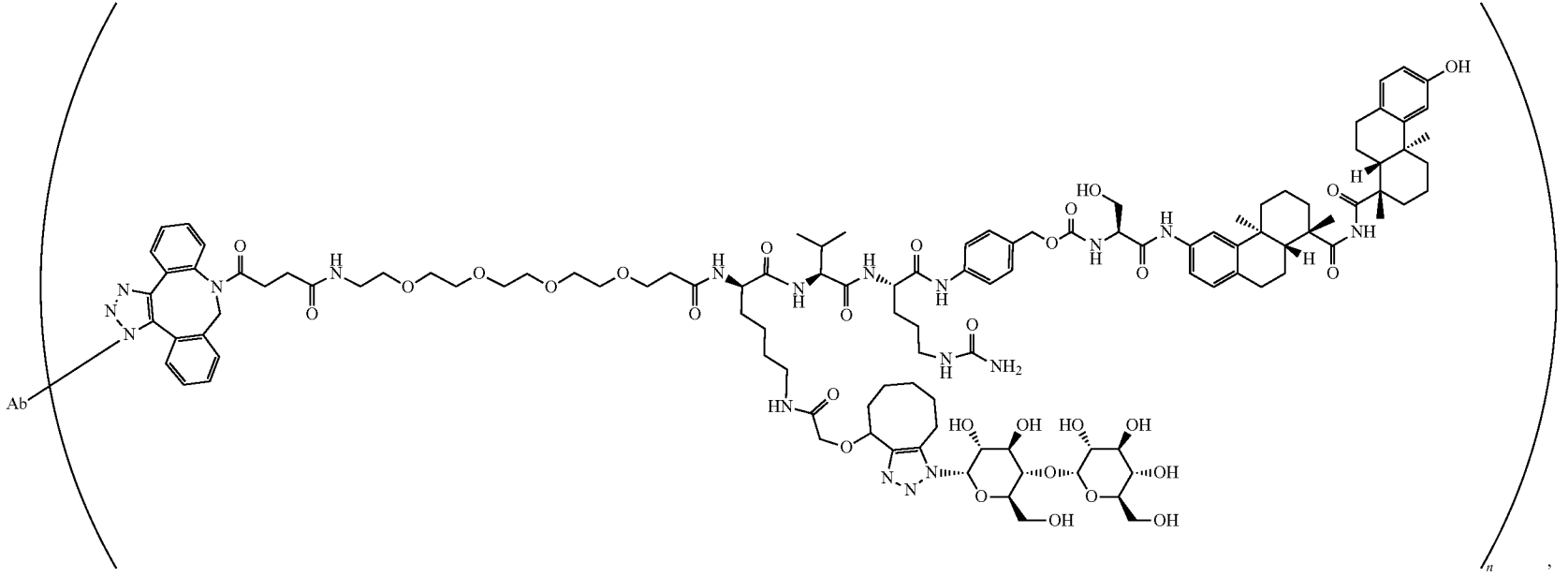

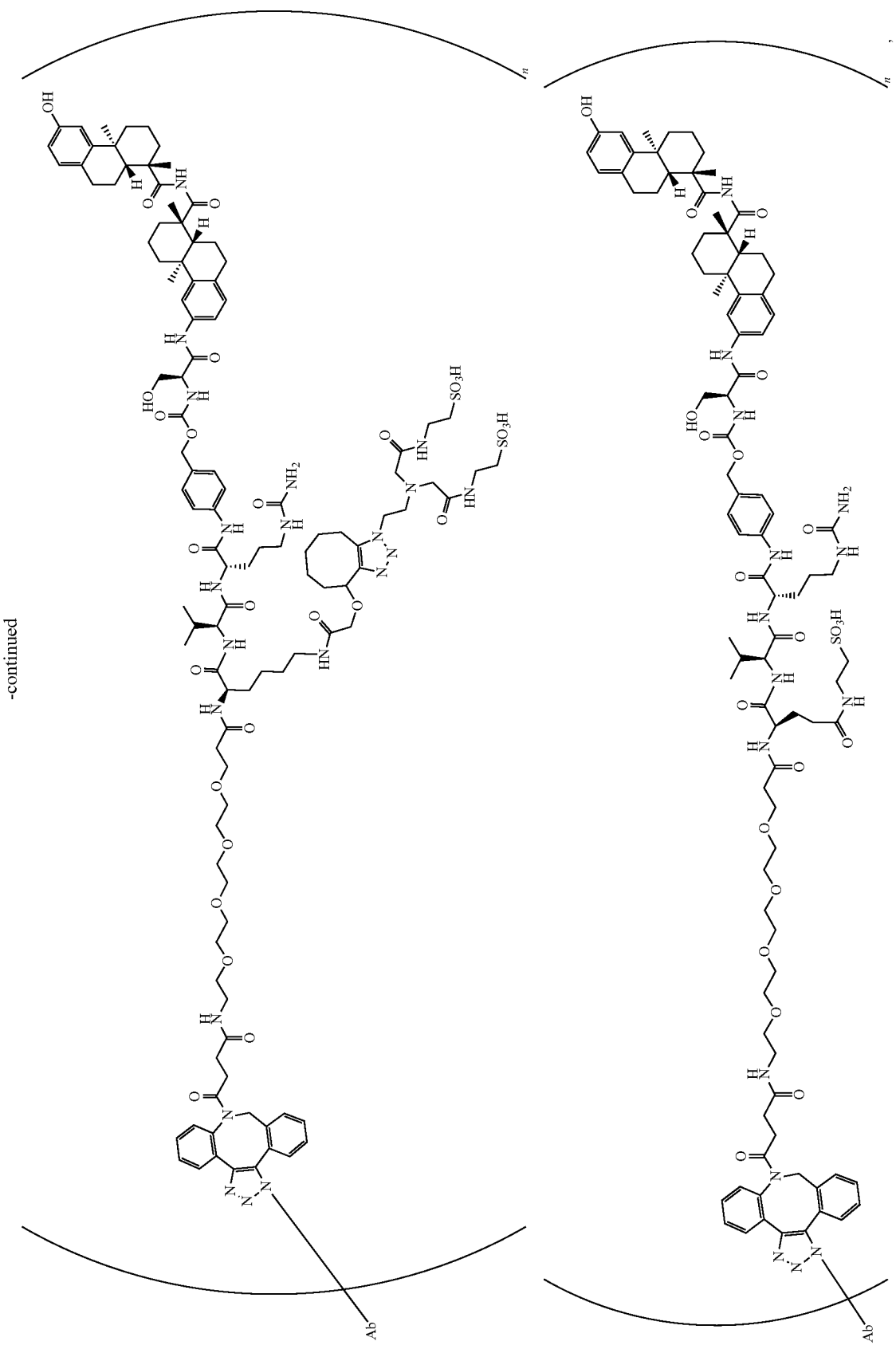

-continued
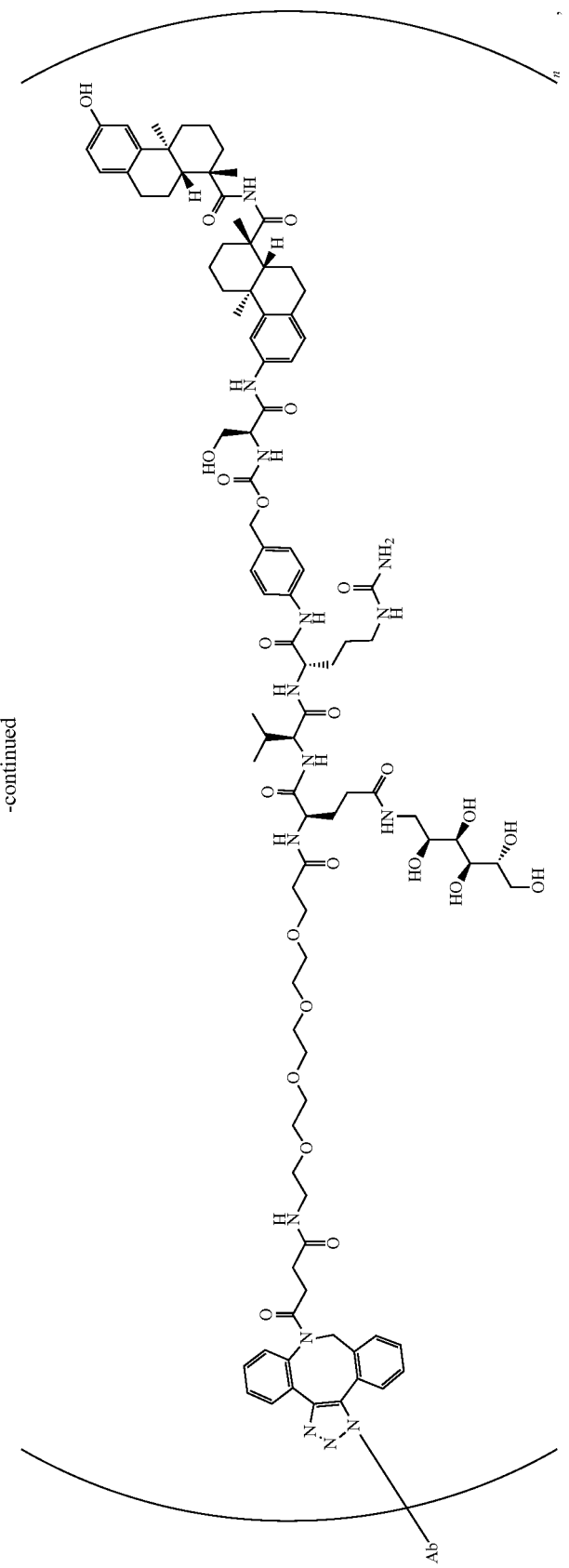

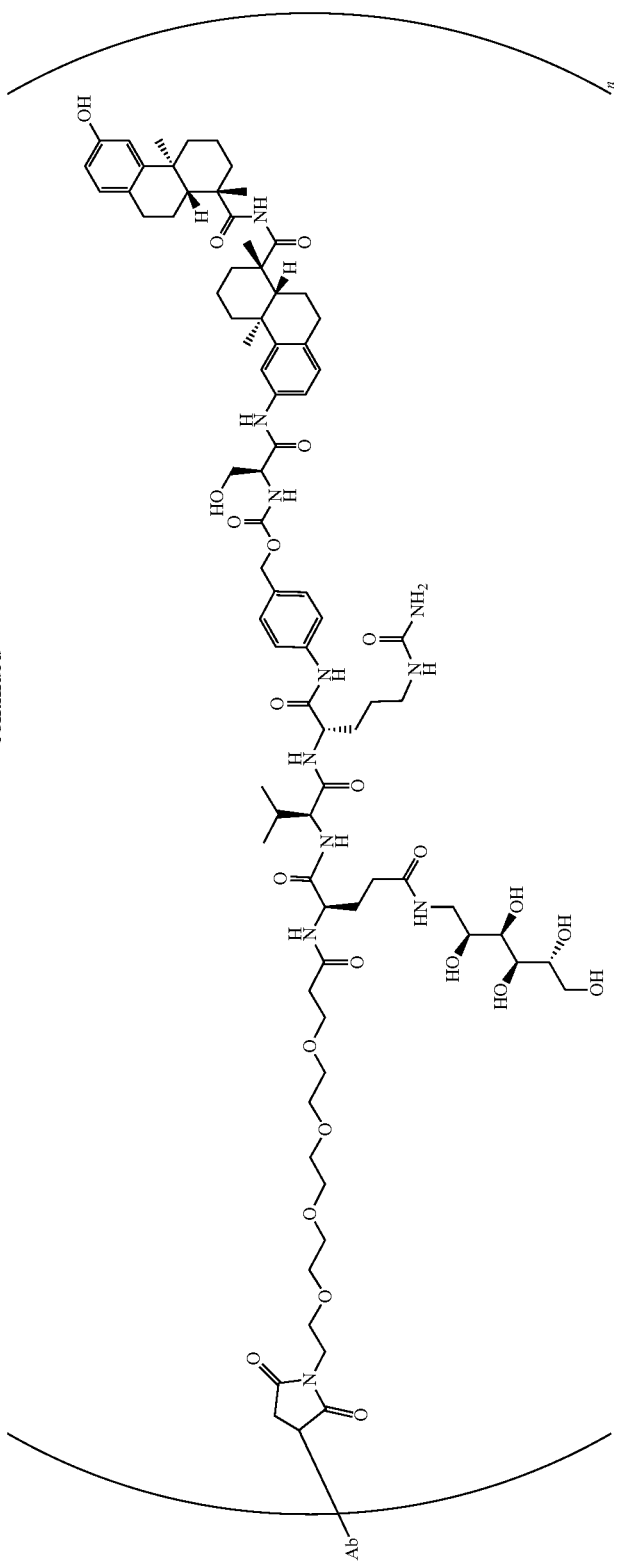

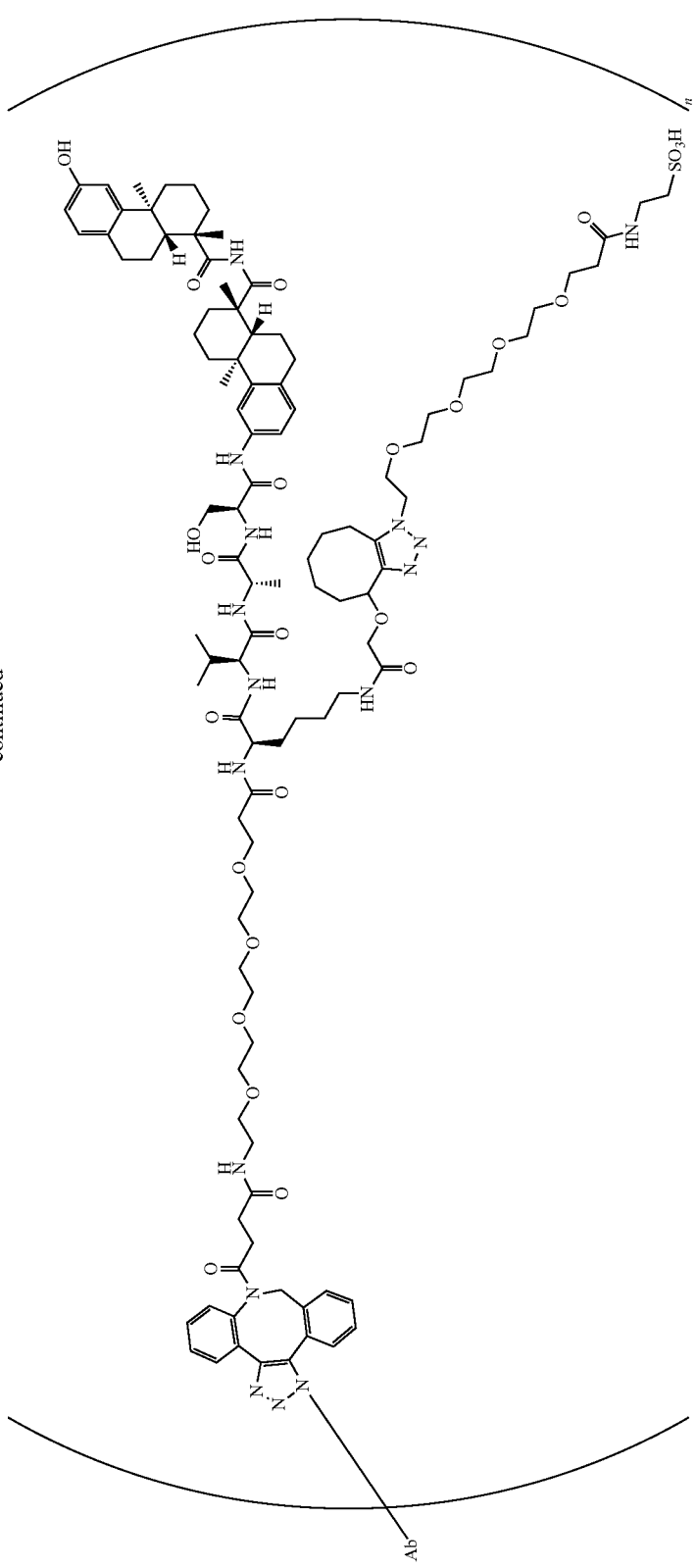

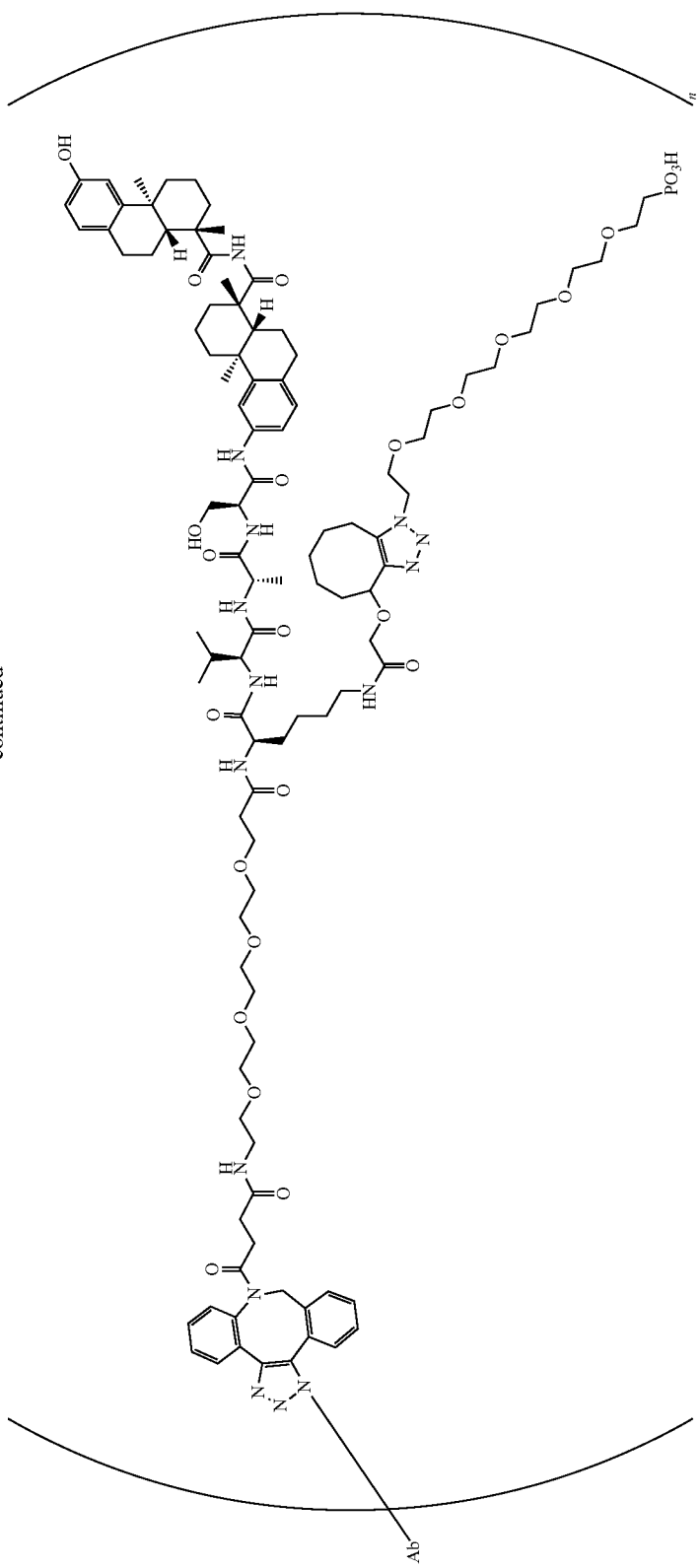

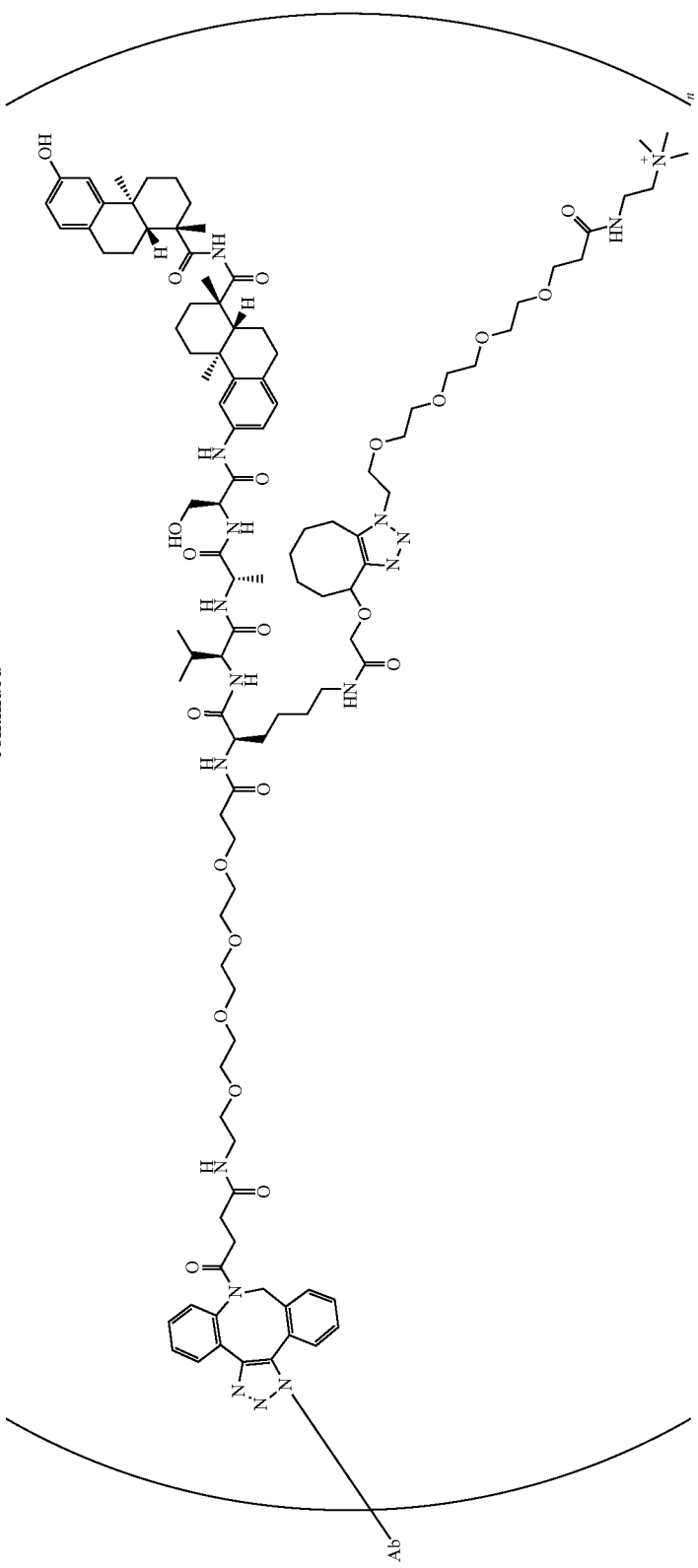
-continued

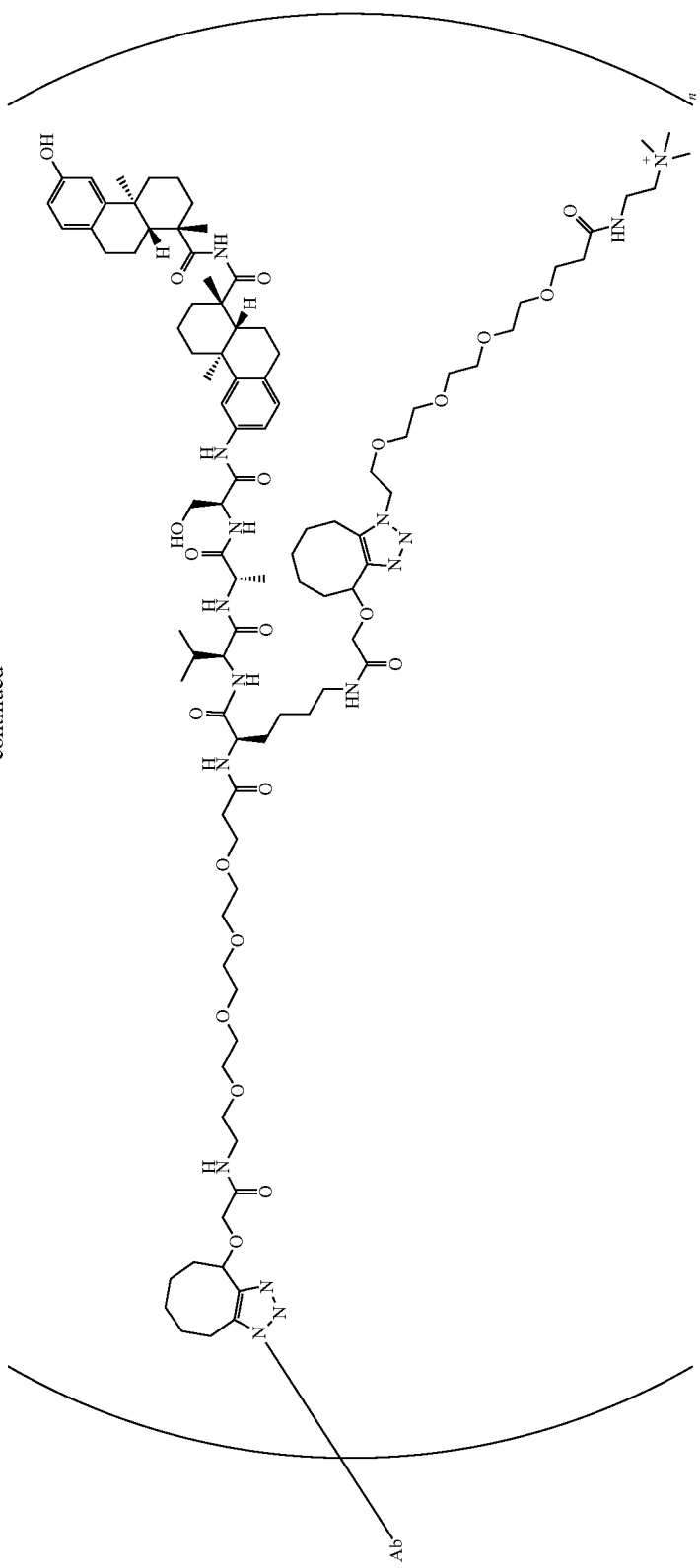

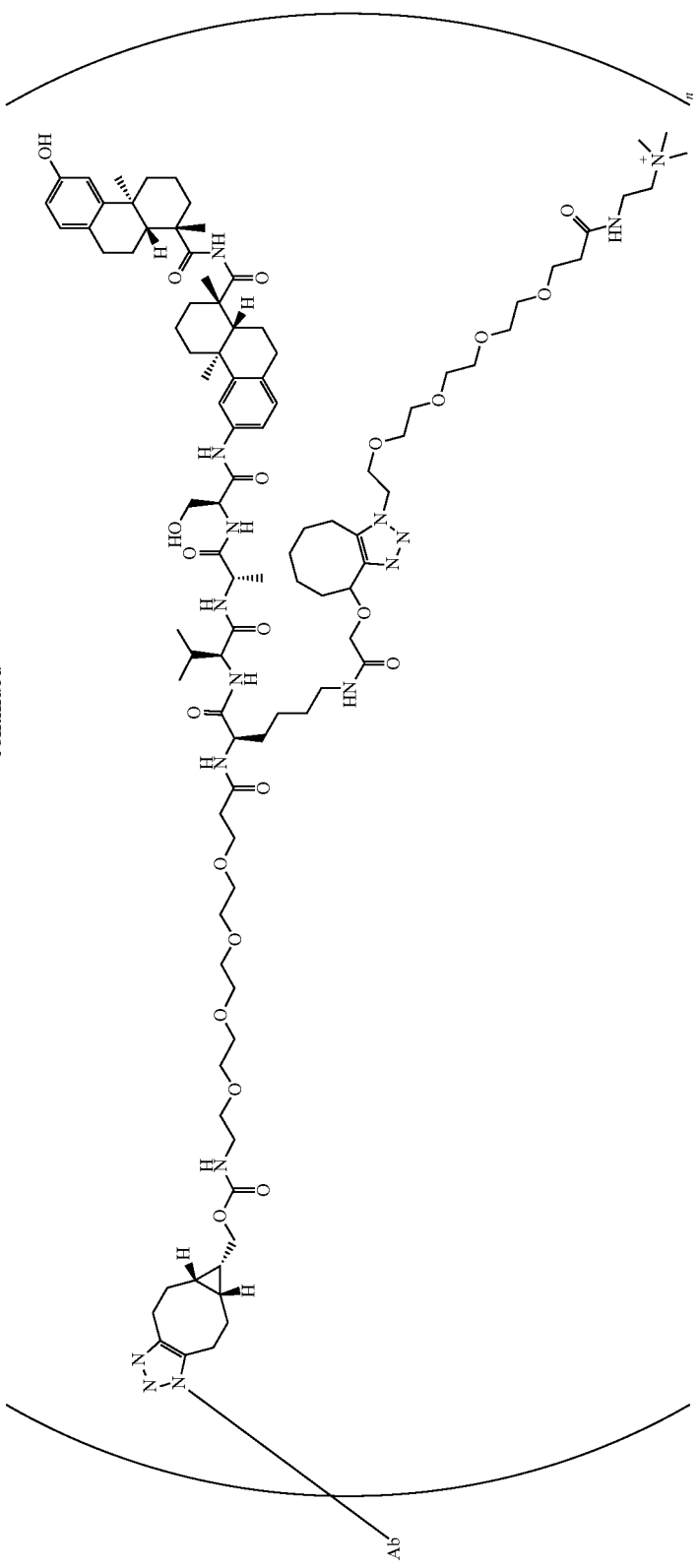

-continued
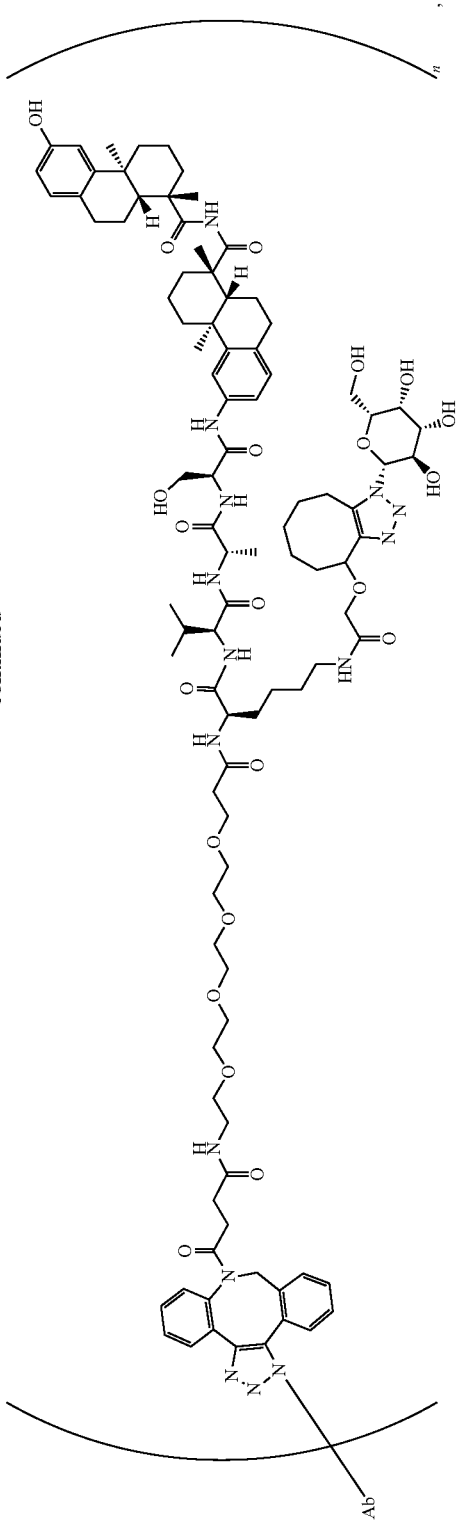
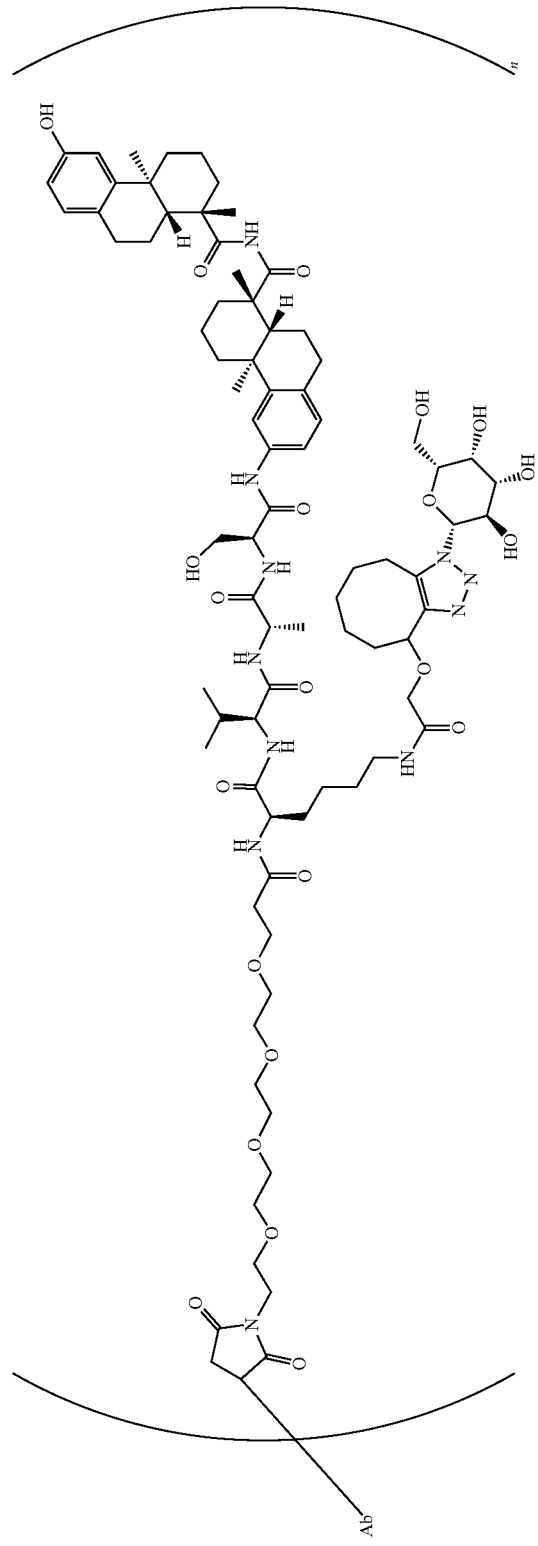

-continued
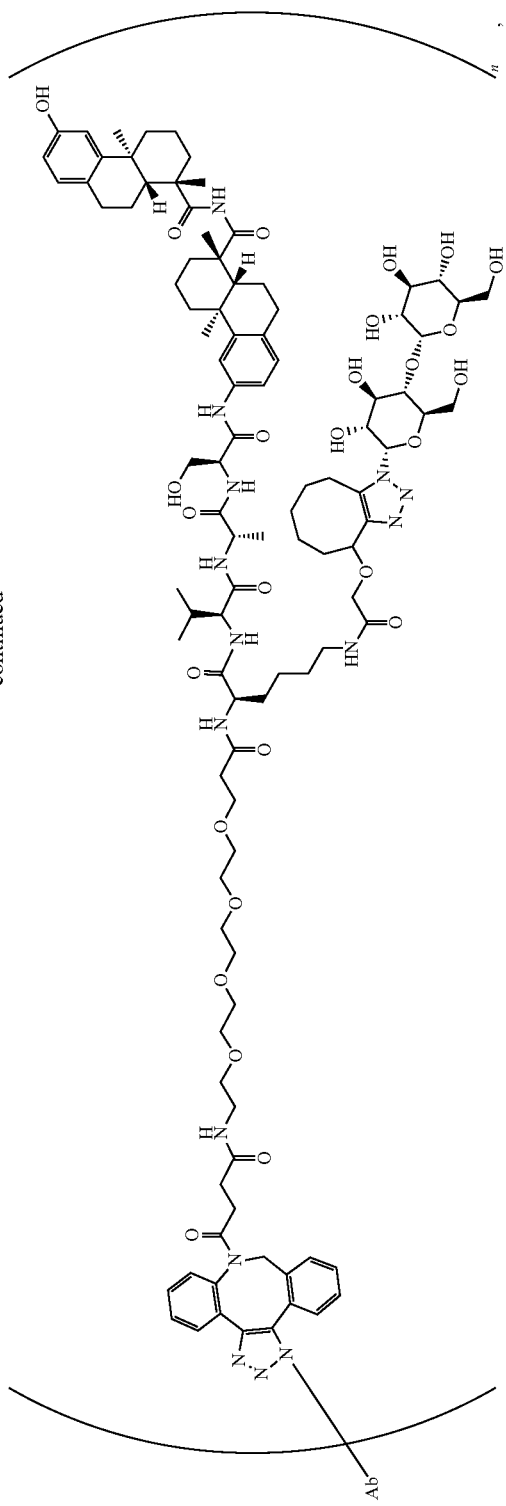

-continued
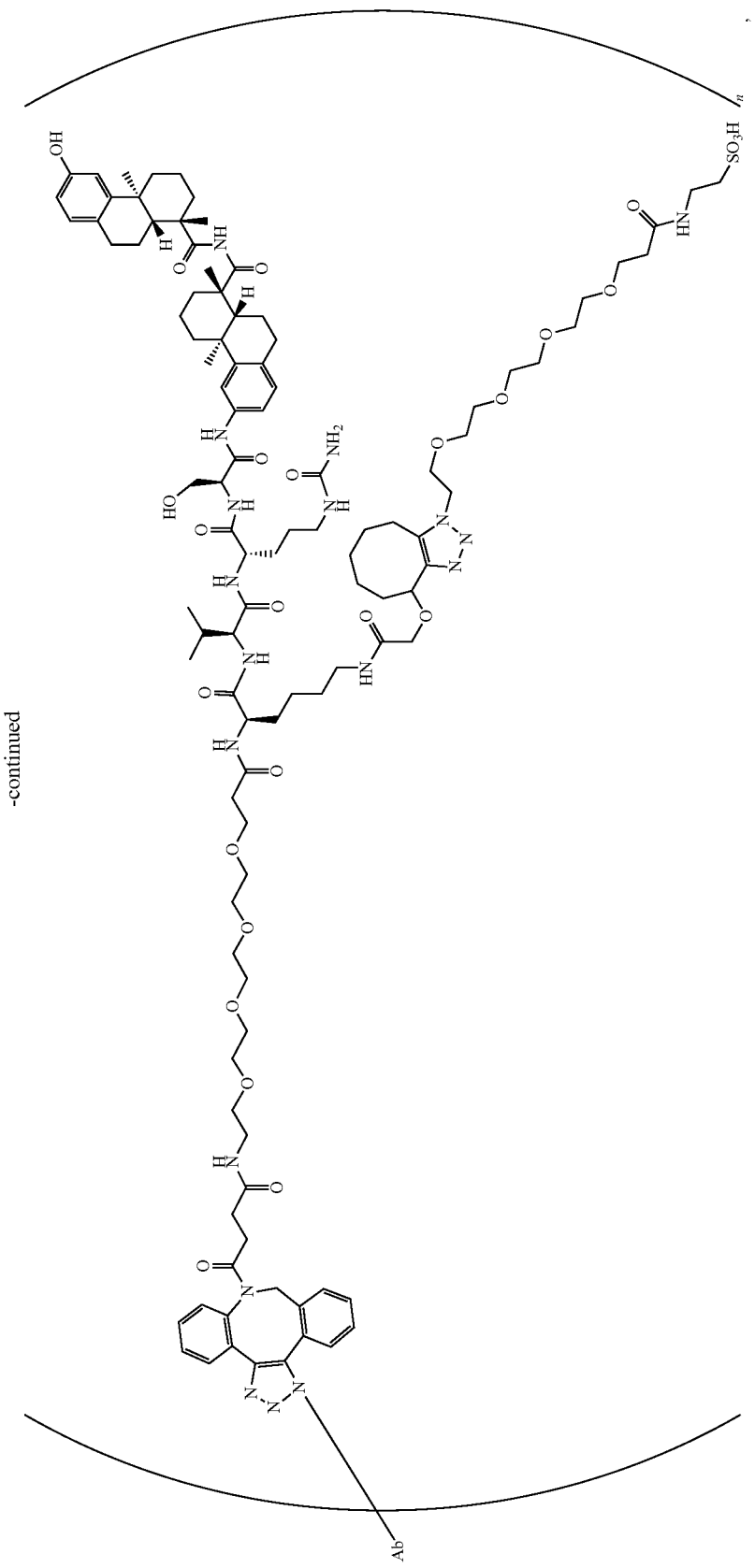

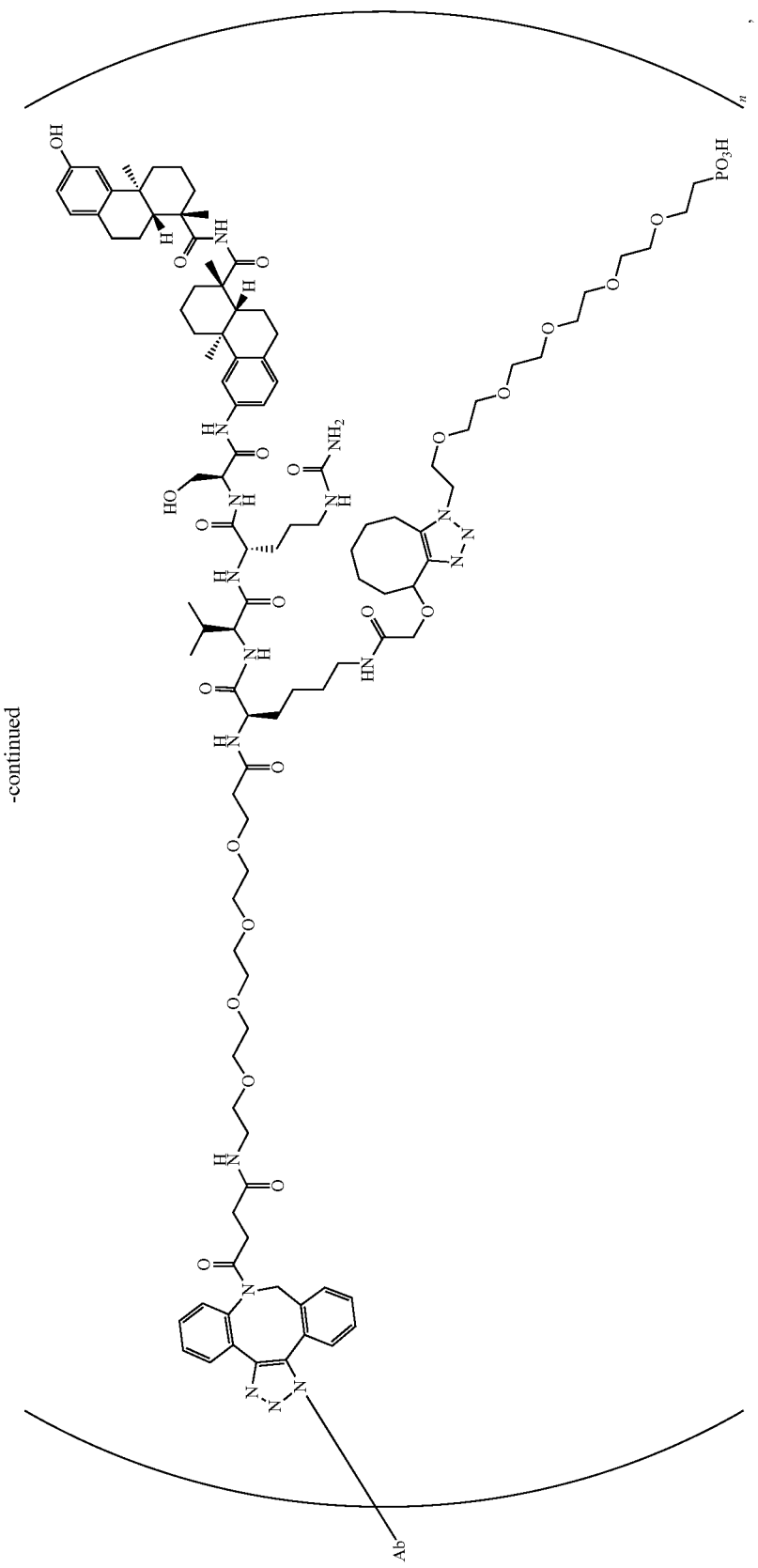

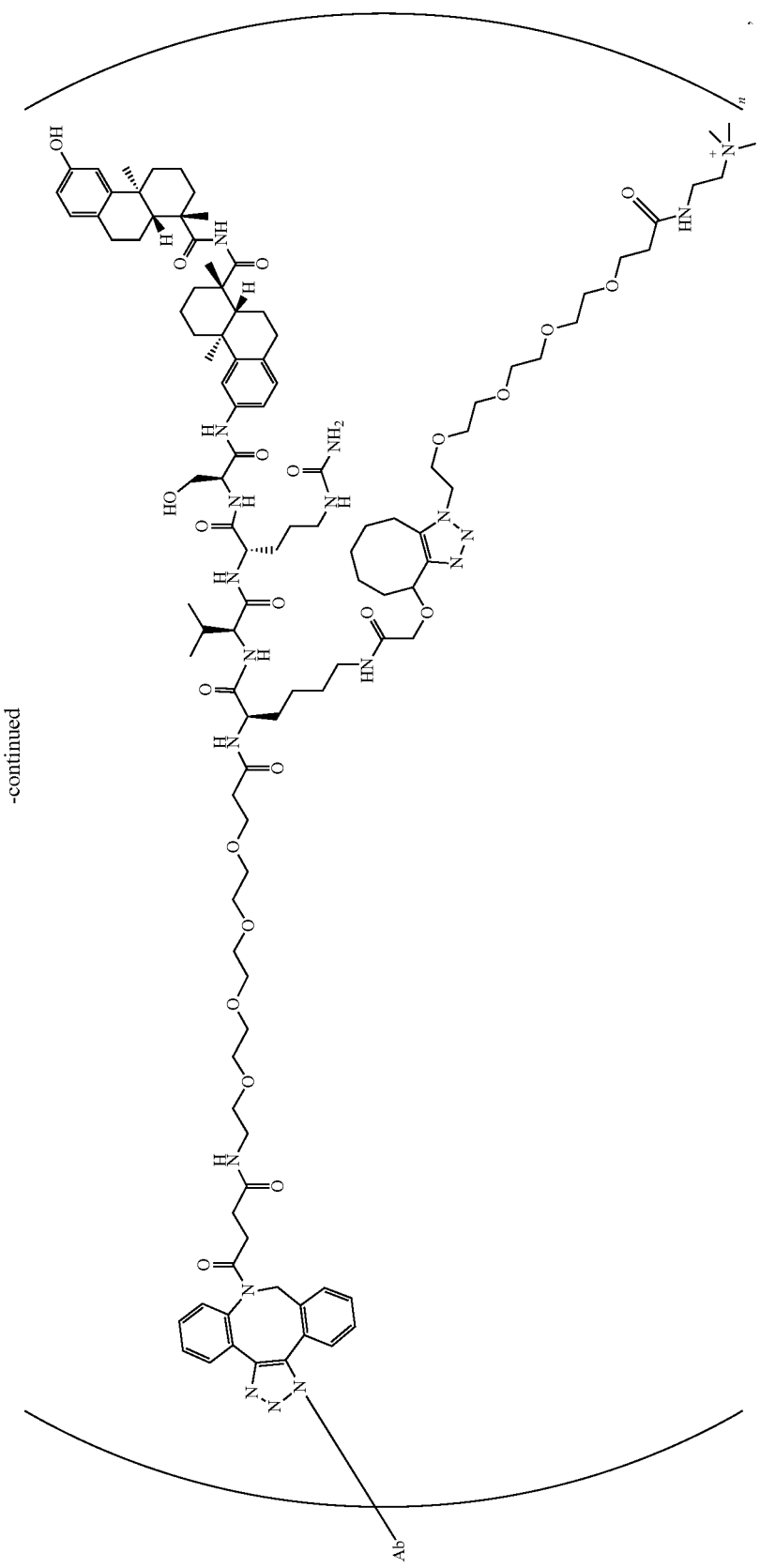

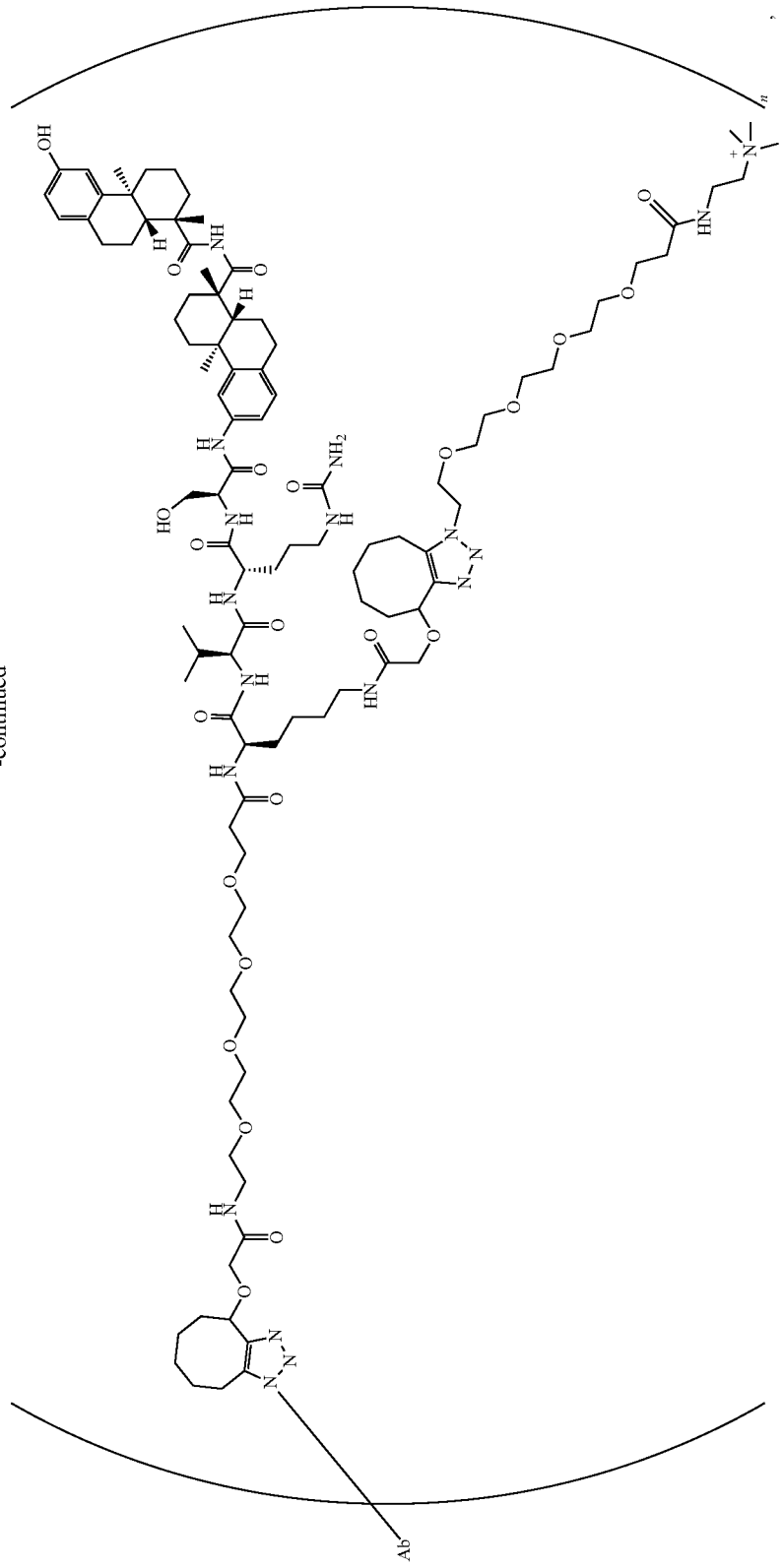

-continued
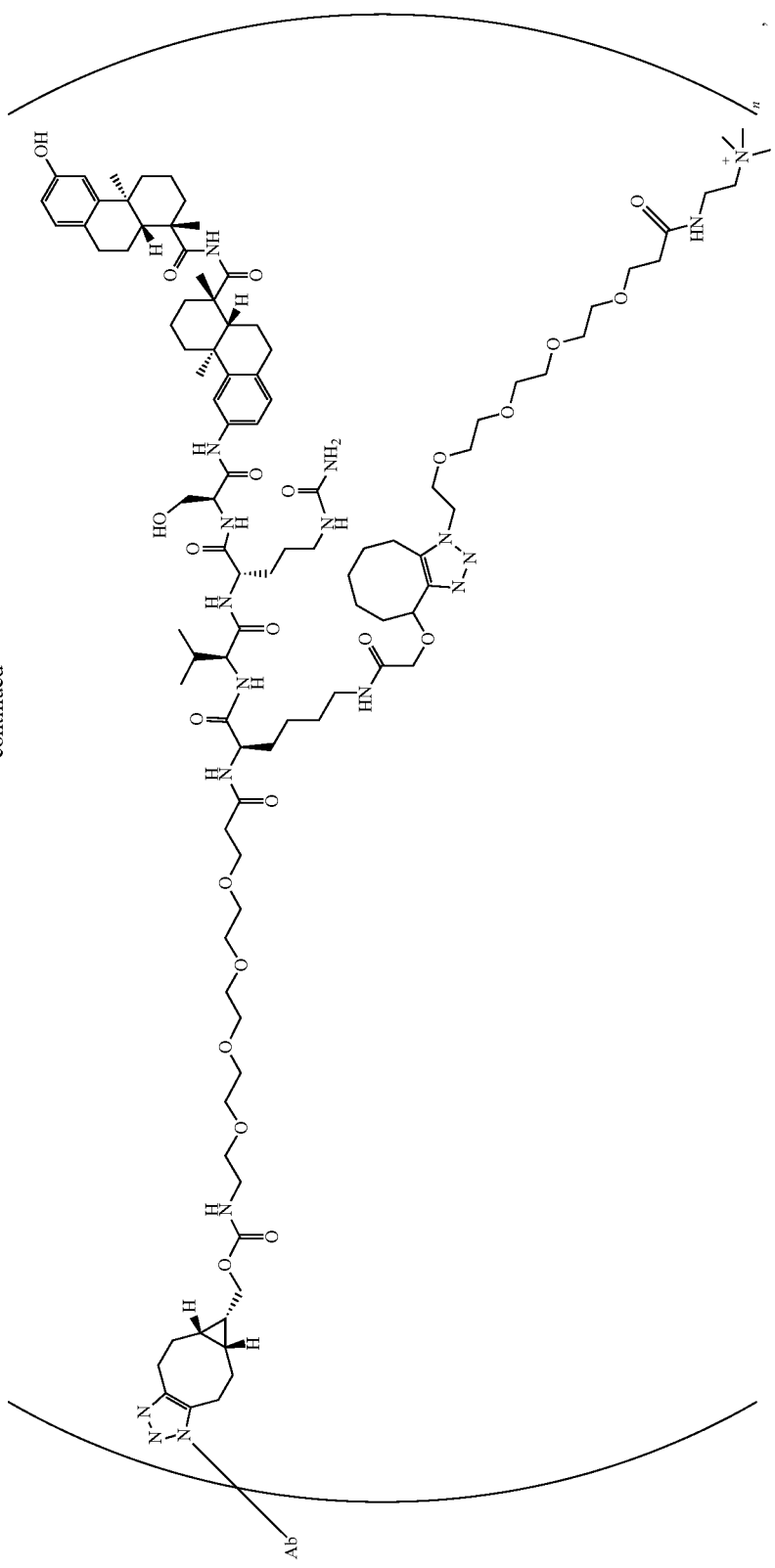

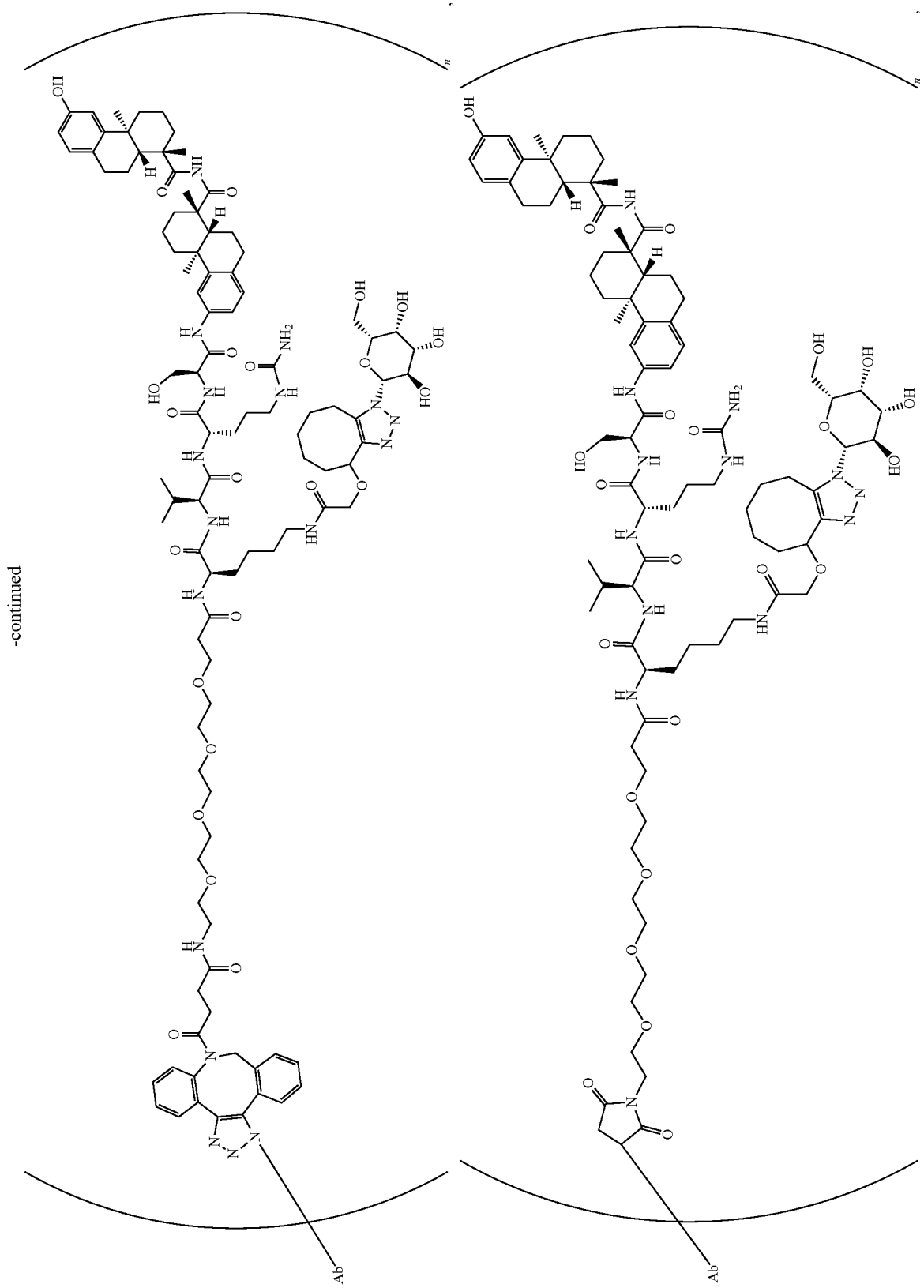

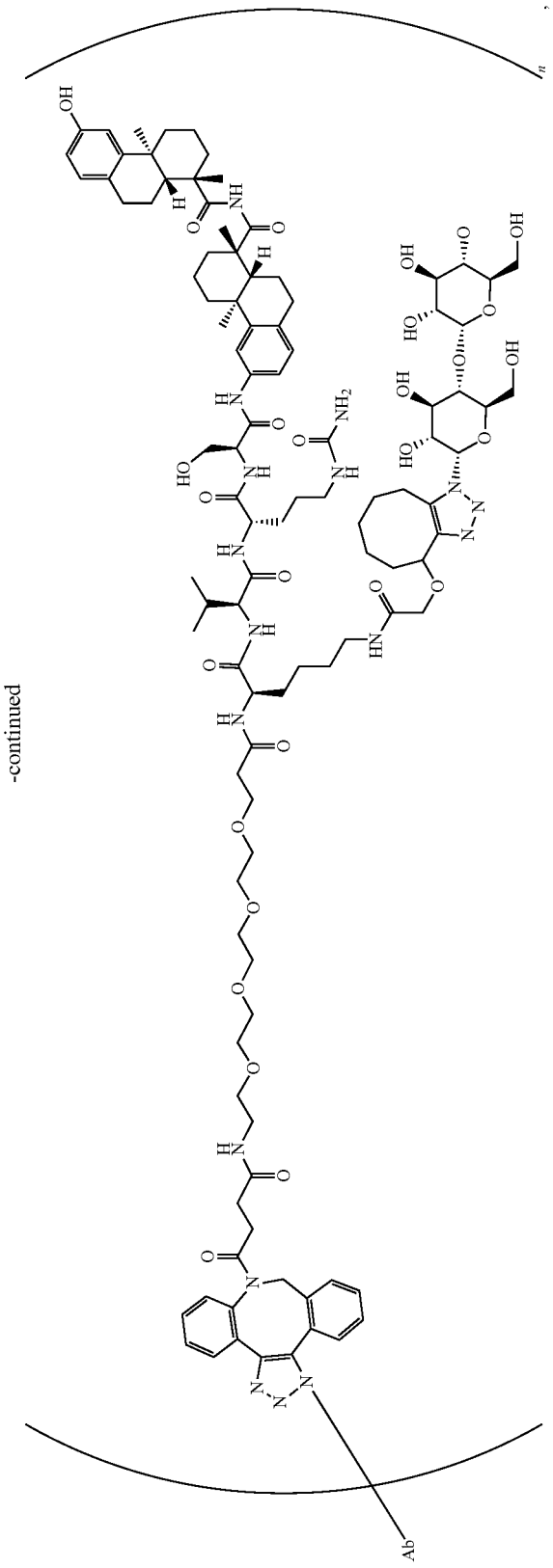

or a stereoisomeric form thereof, or a regioisomer thereof, or a mixture of regioisomers thereof, wherein each Ab is an antibody, or an antigen-binding fragment thereof, and subscript n is an integer from 1 to 30. In some embodiments, n is an integer from 1 to 4. In some embodiments n is 2. In some embodiments, n is 4.

In some instances, BA is a modified antibody of formula (Ab-1)

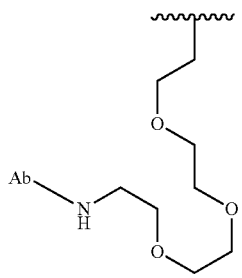

(Ab-1)

wherein the

indicates the atom through which Ab-1 is bonded to the adjacent groups in the formula.

In some instances, a compound of Formula (I), Formula (II), Formula (III), Formula (IV), Formula (IVa), Formula (IVb), Formula (IVc), Formula (Va), Formula (Vb), Formula (Vc), or Formula (Vd), is an antibody drug conjugate (ADC), wherein BA is Ab-1 as defined herein, where Ab is an antigen or antigen-binding fragment thereof, selected from the group consisting of:

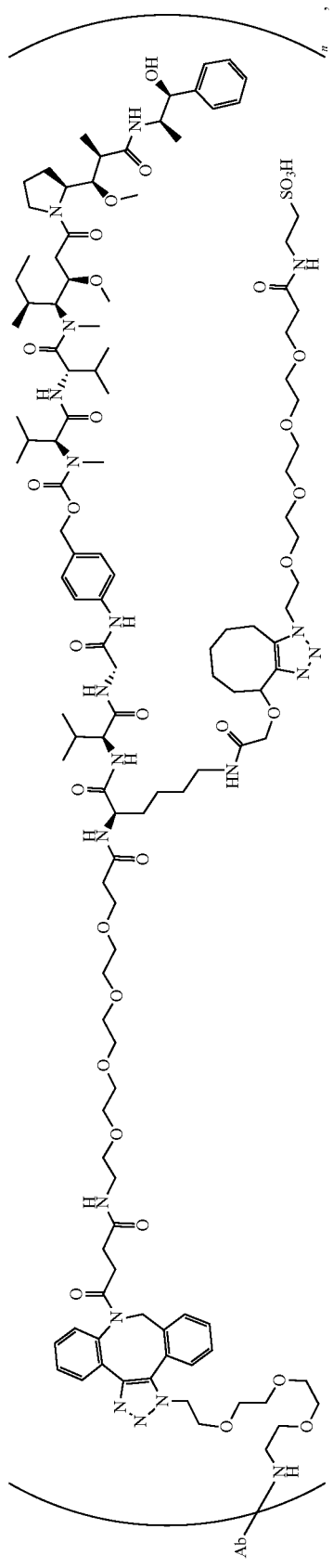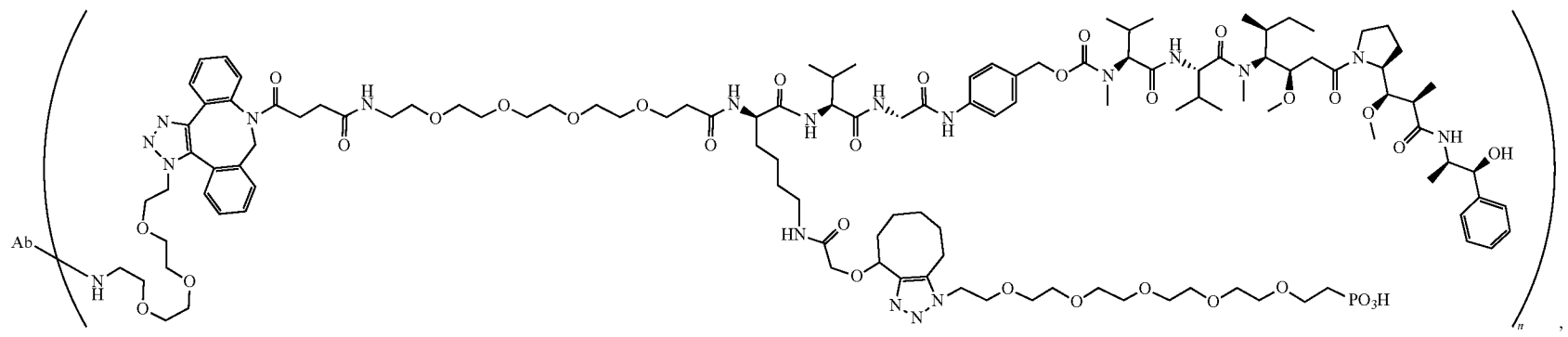

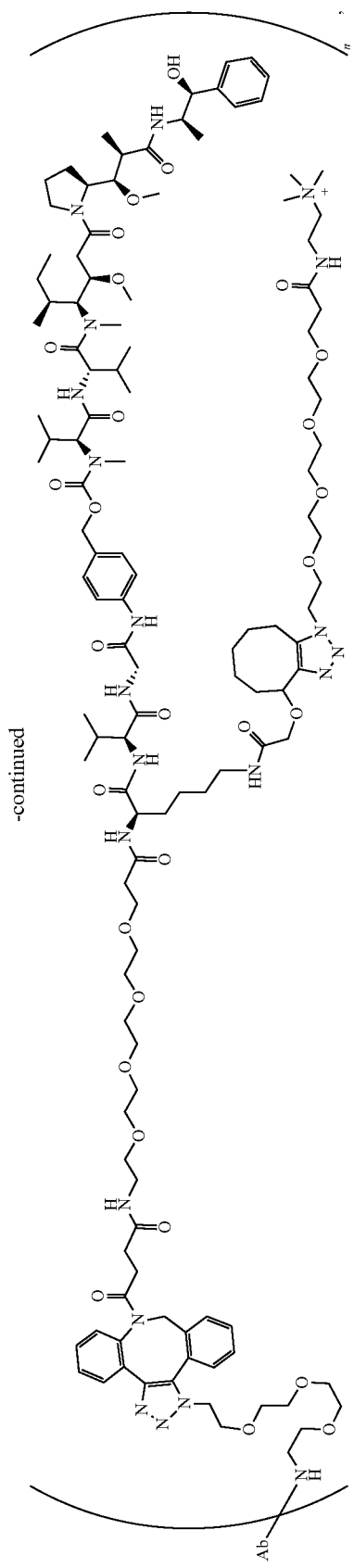

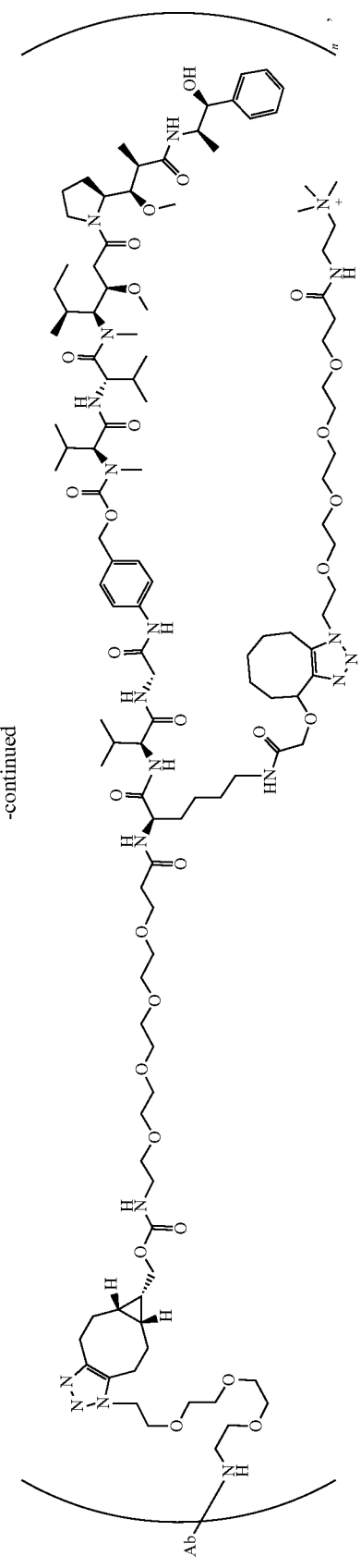
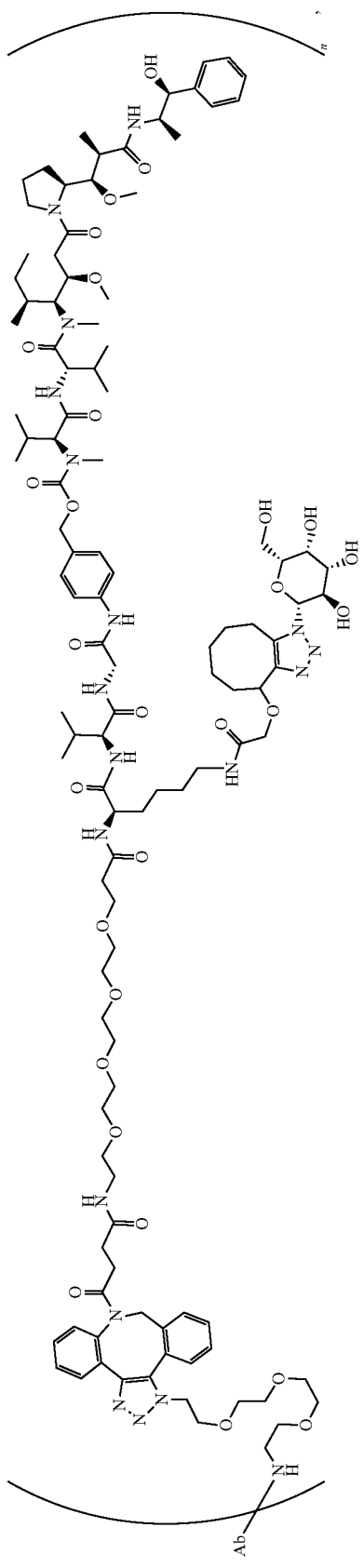

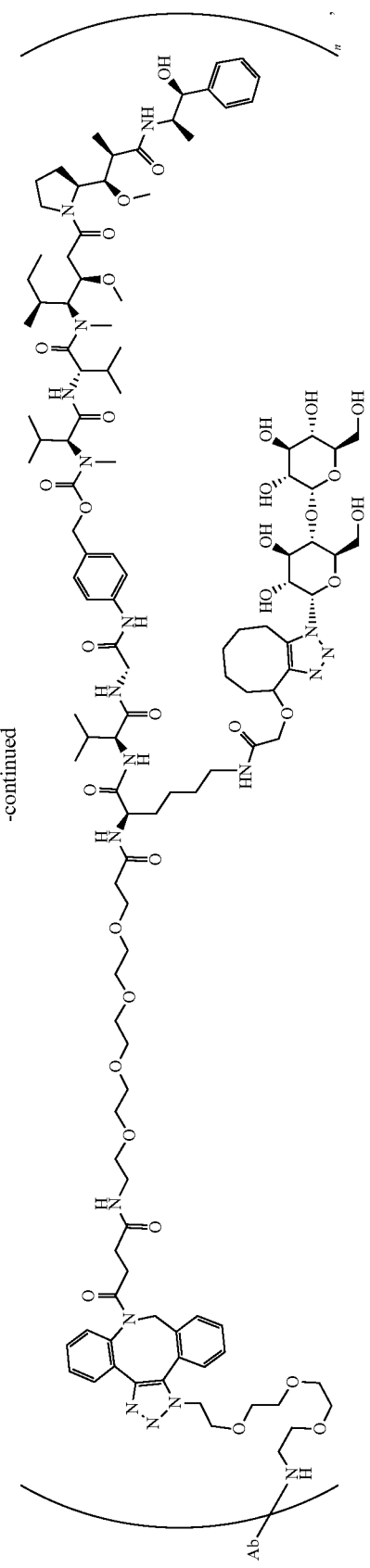
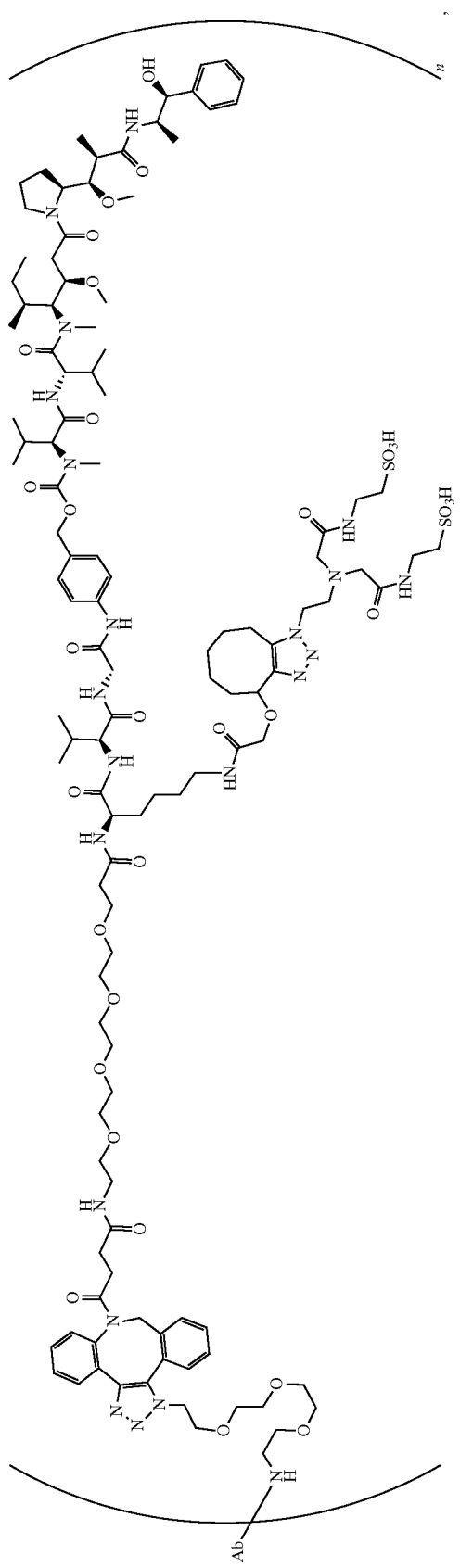

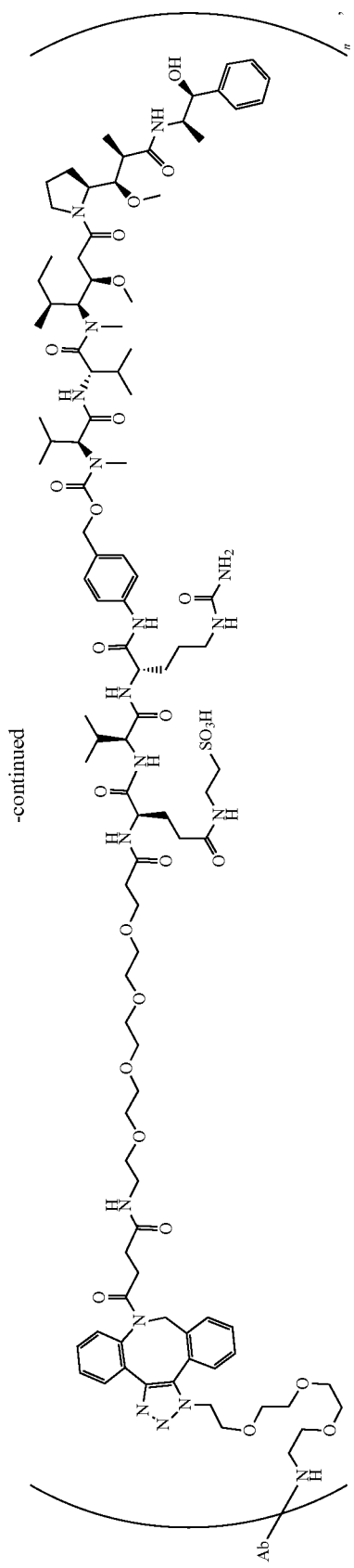

407
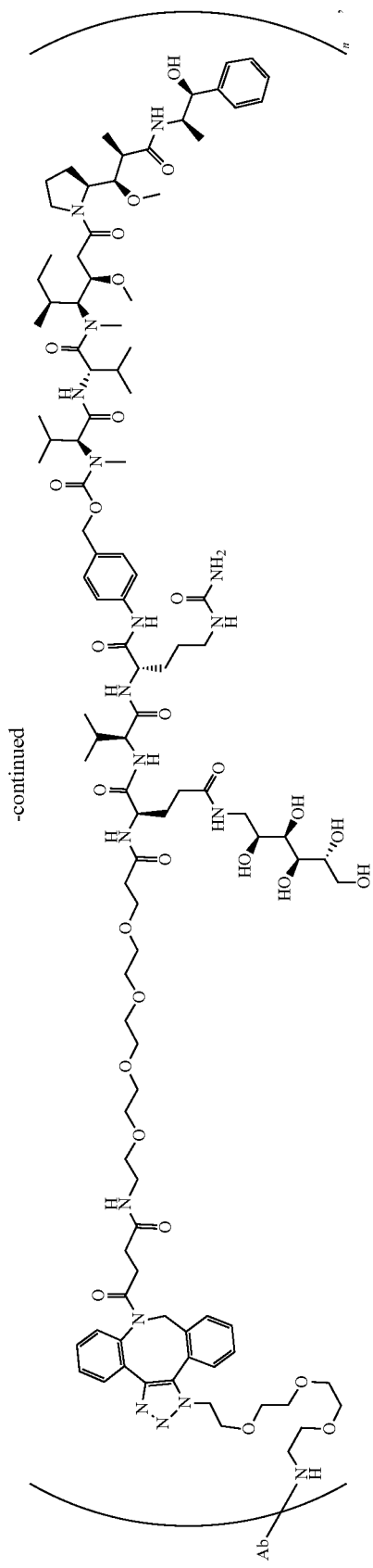
408
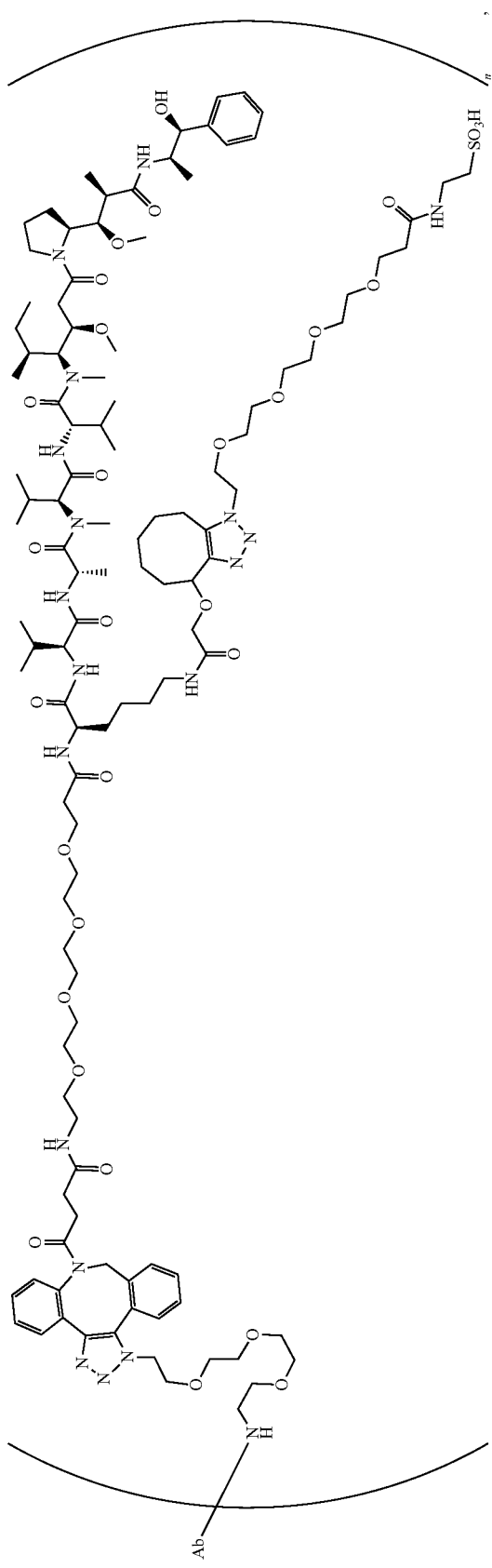

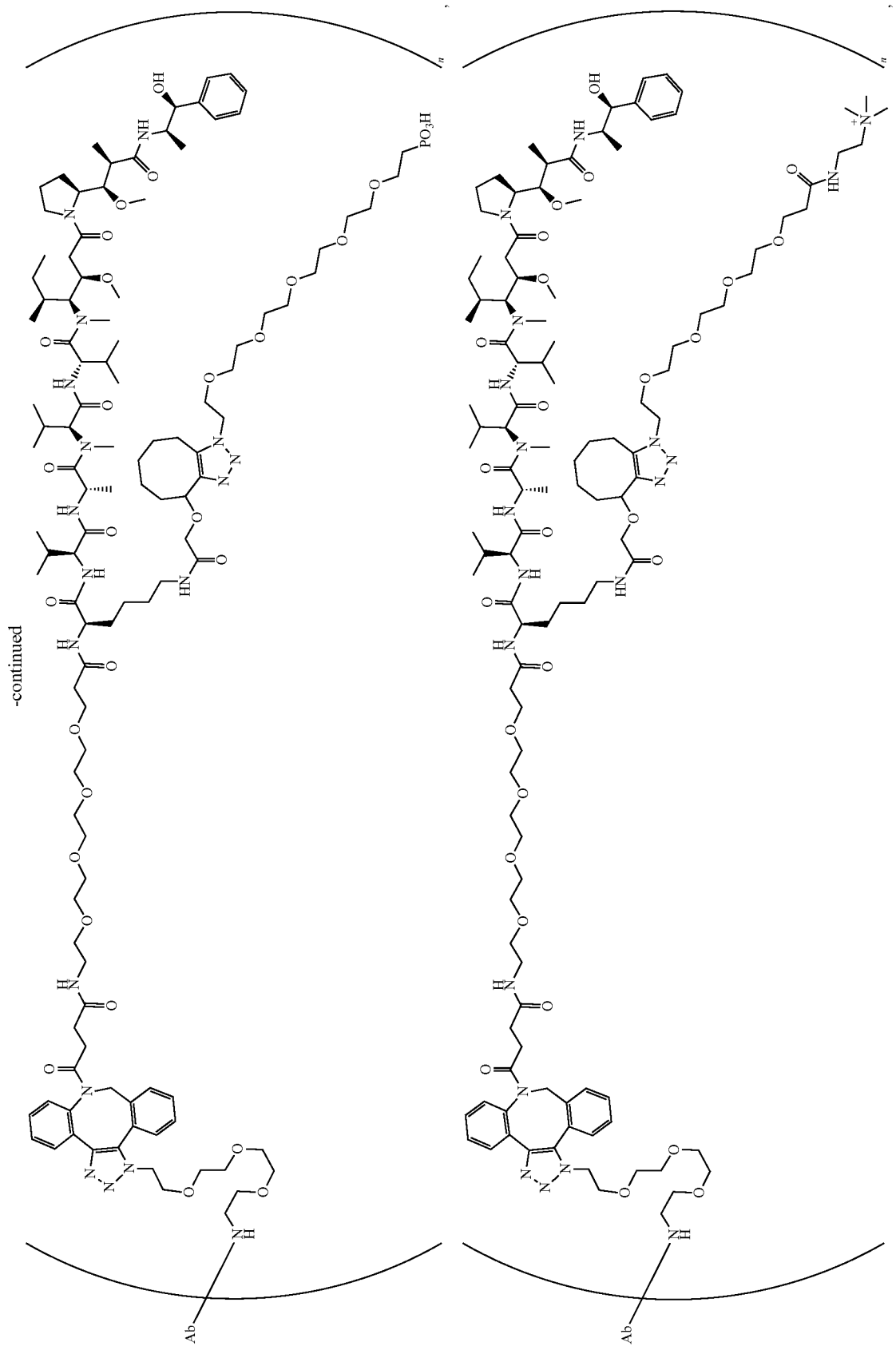

411                    412
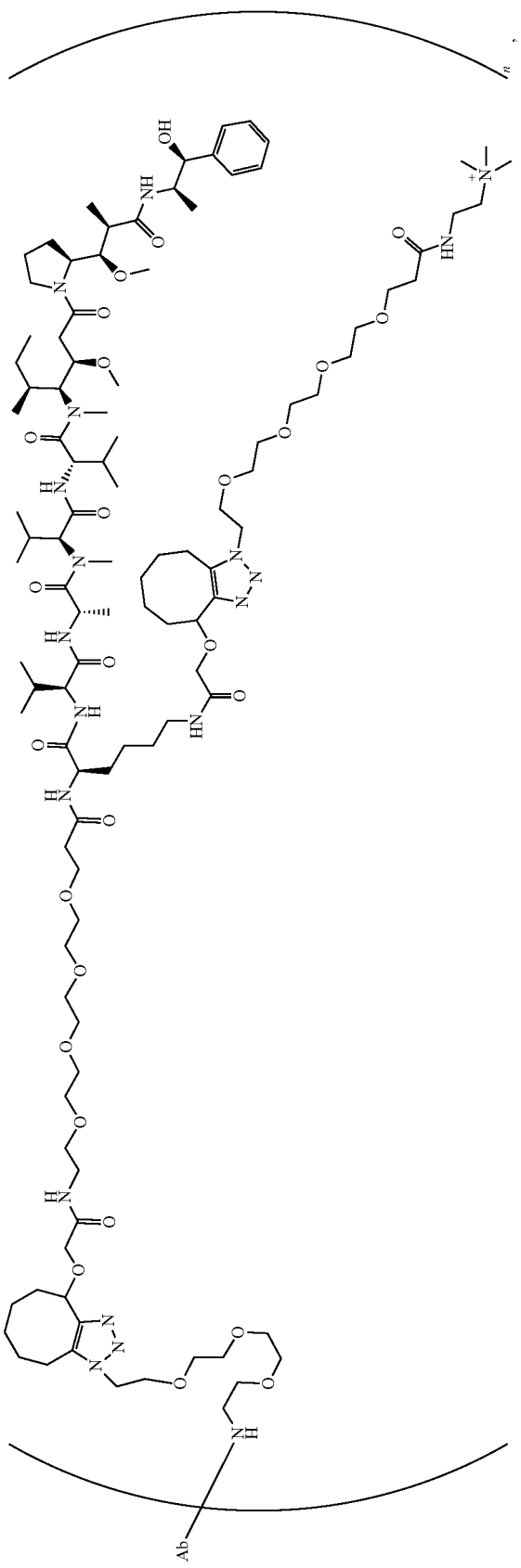
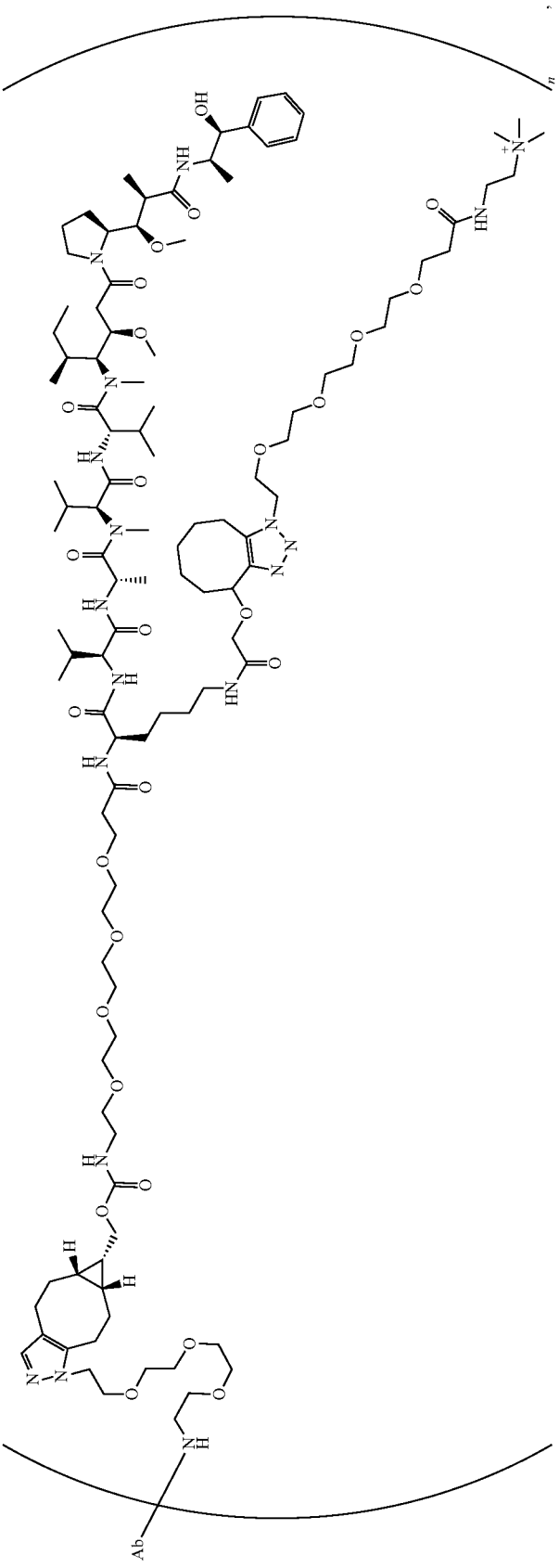

-continued
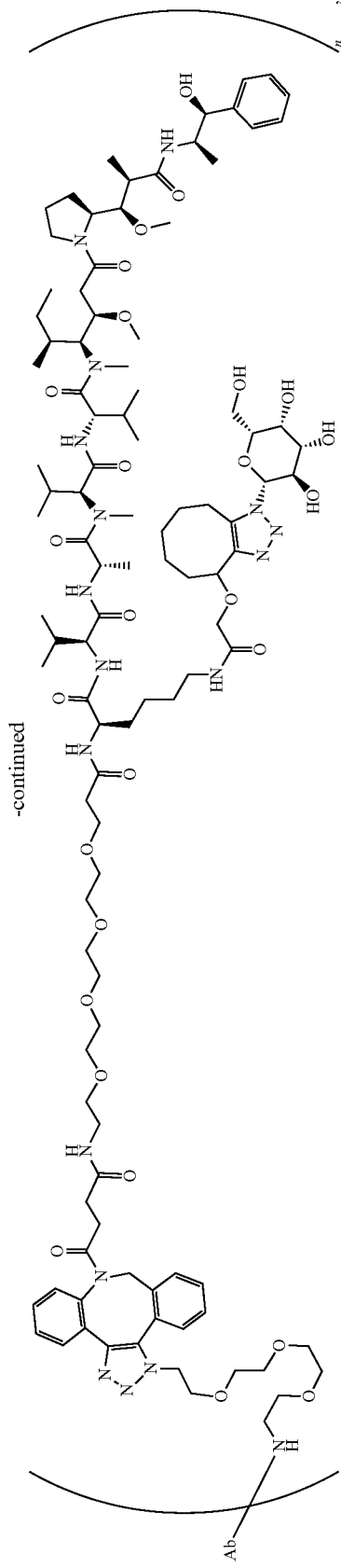
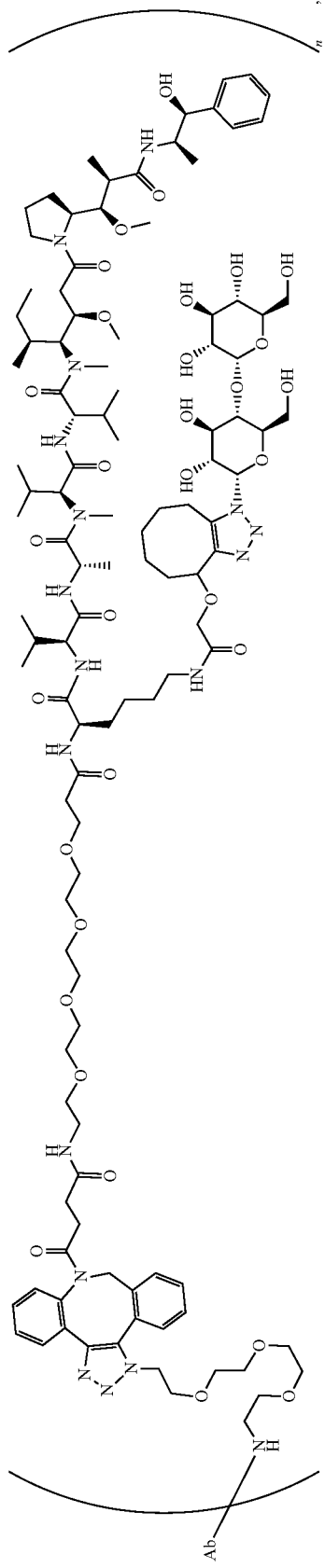

-continued
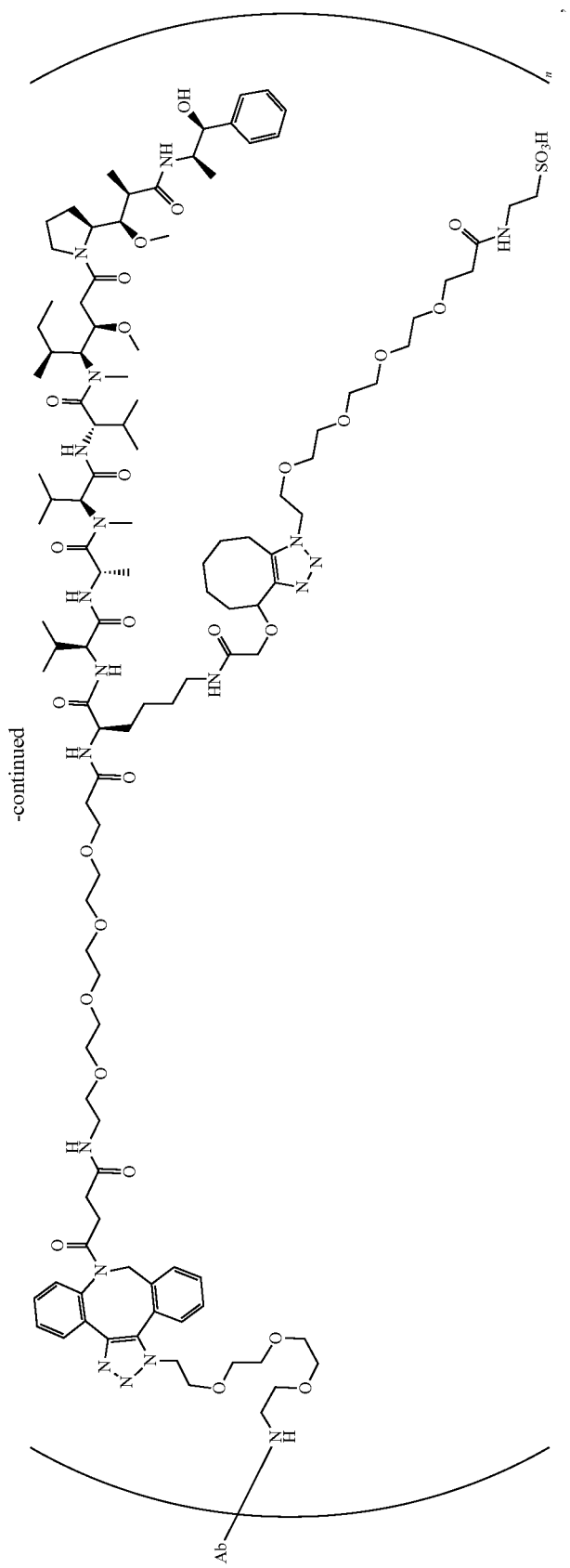

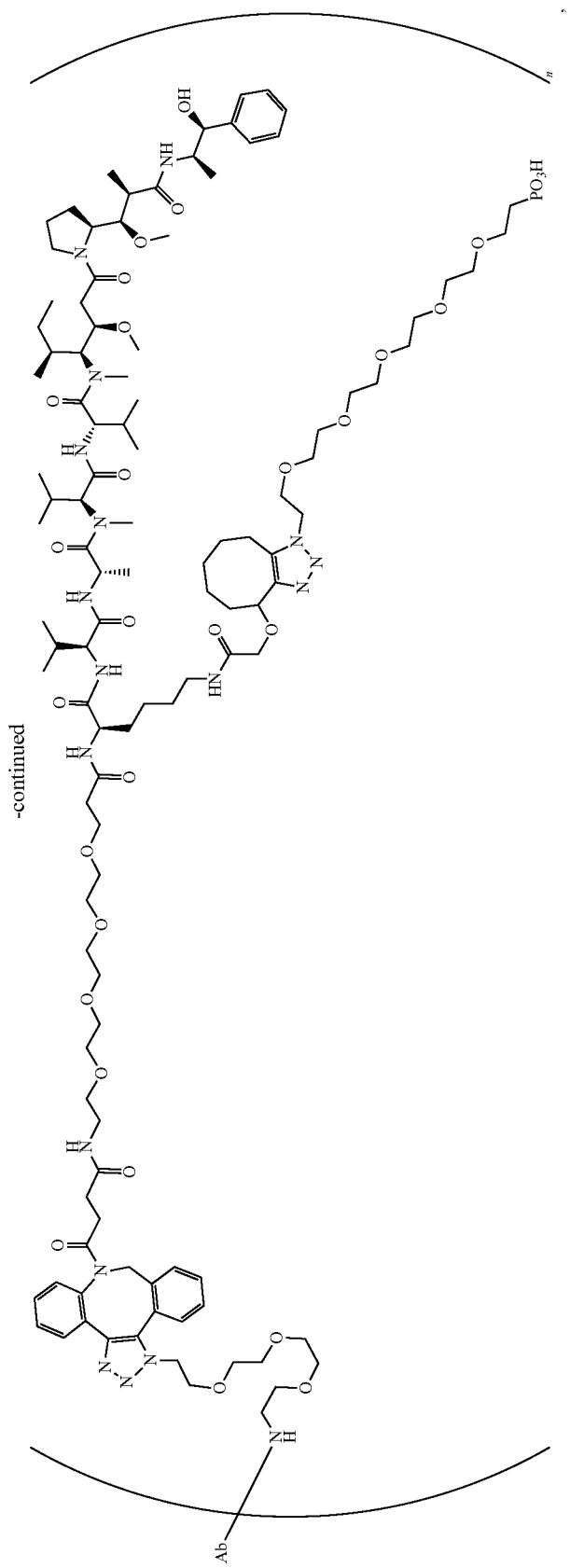

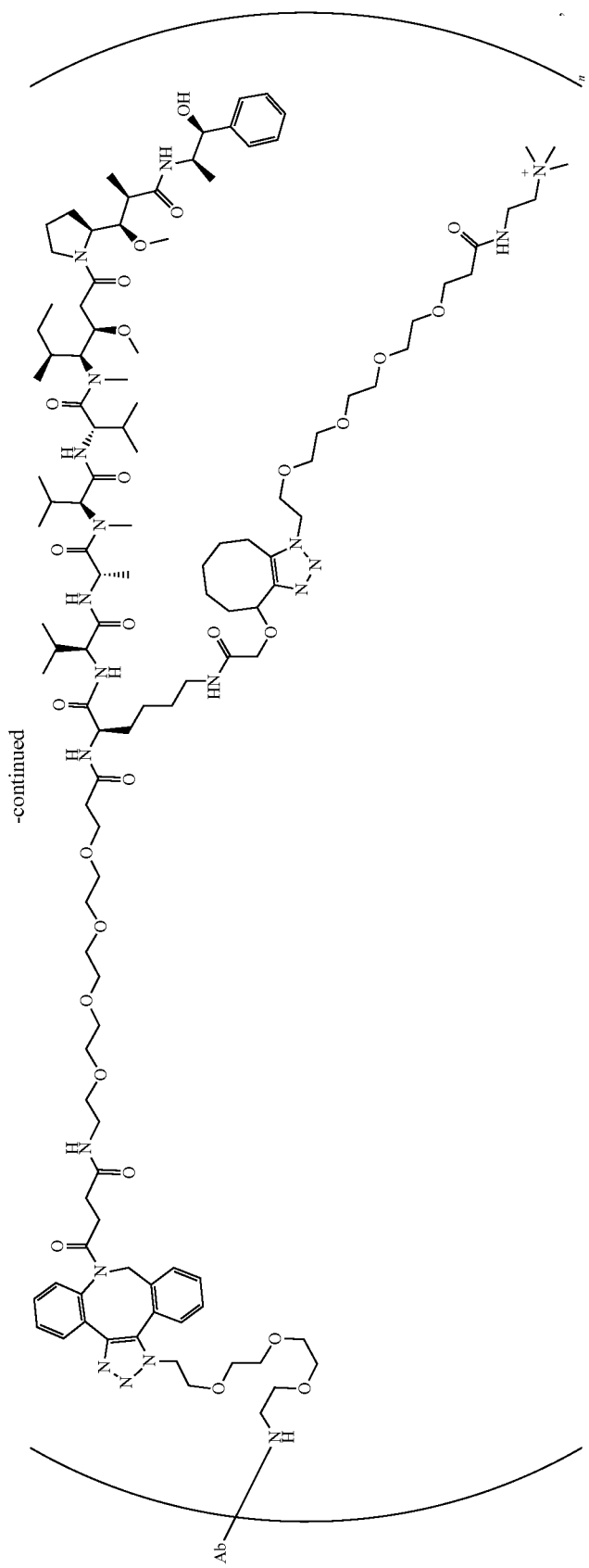

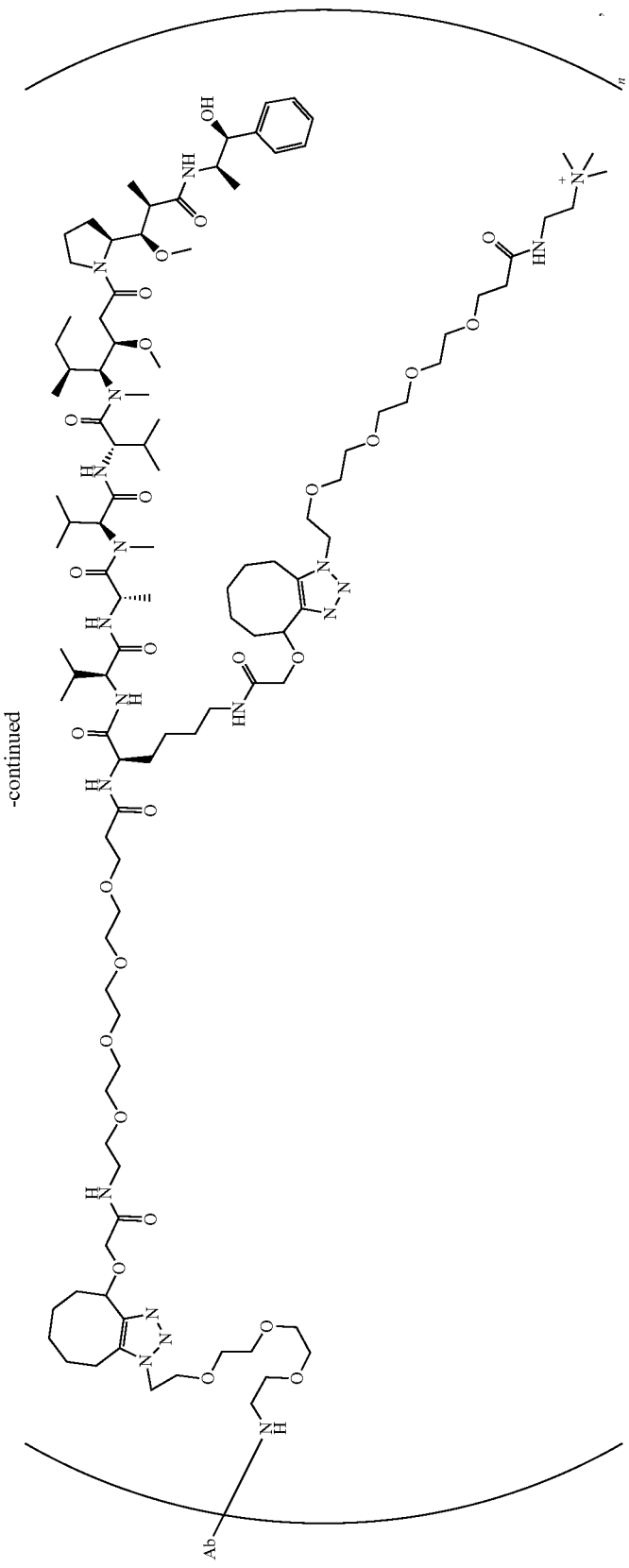

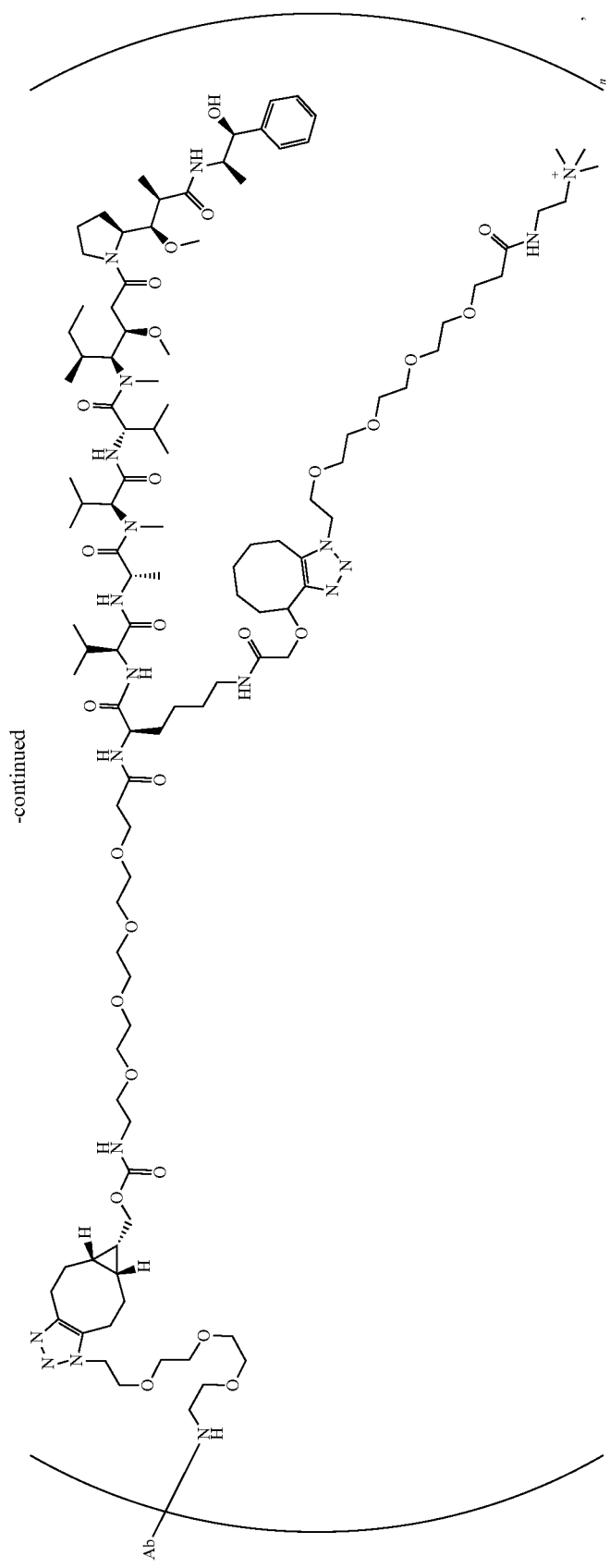

-continued
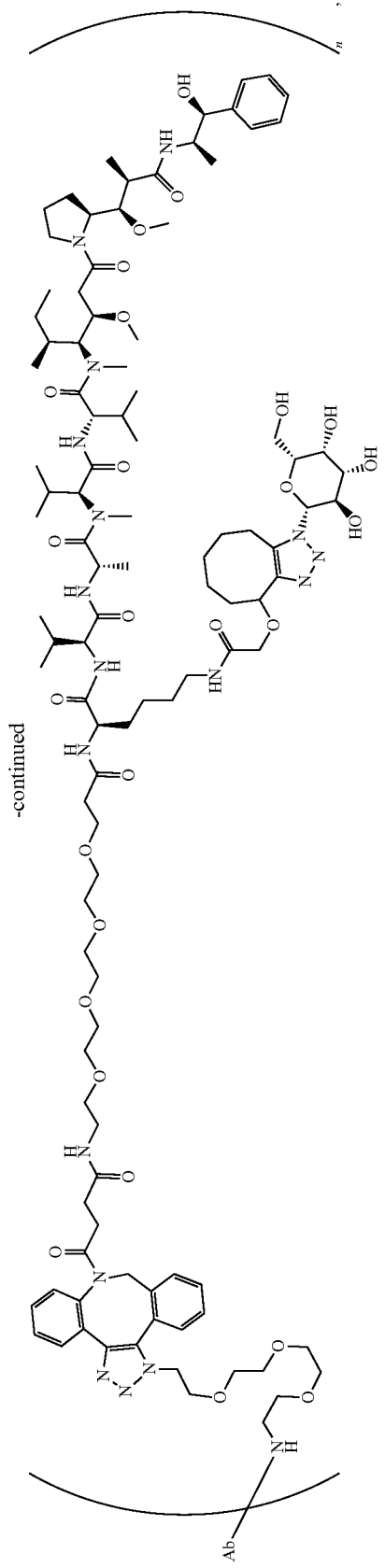
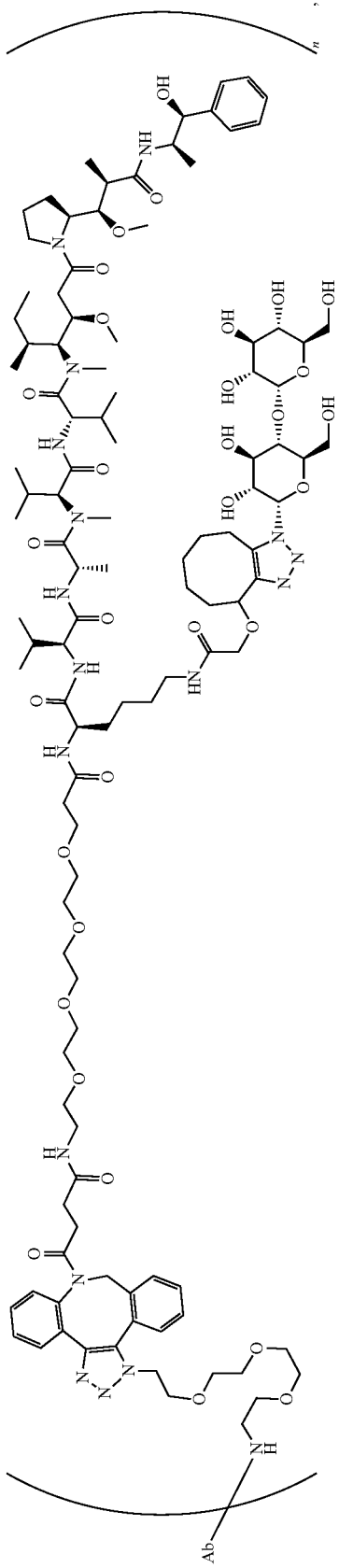

427
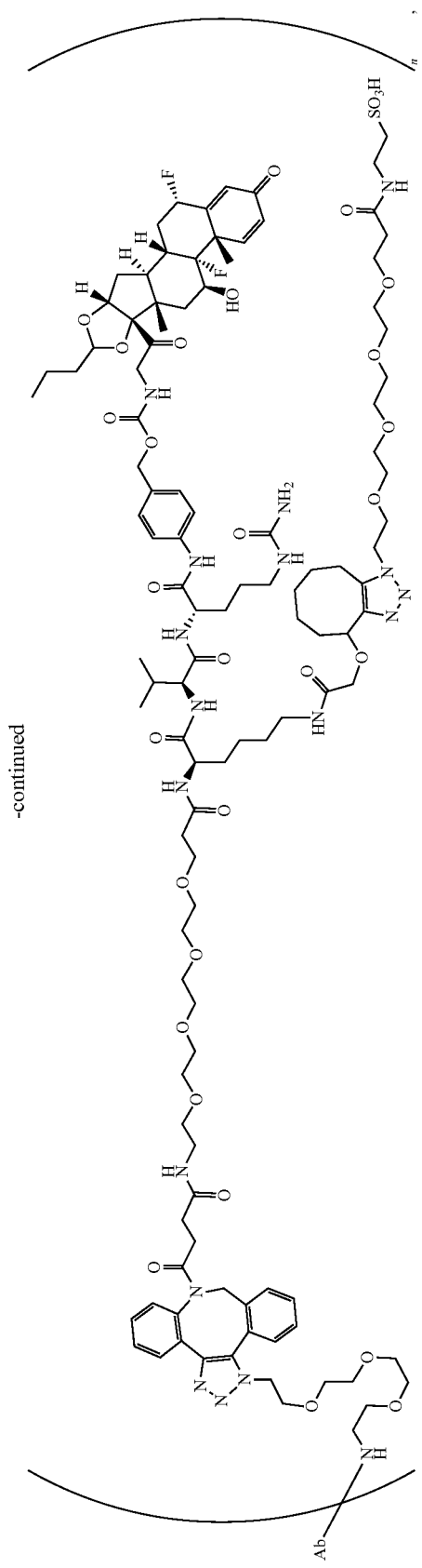
428
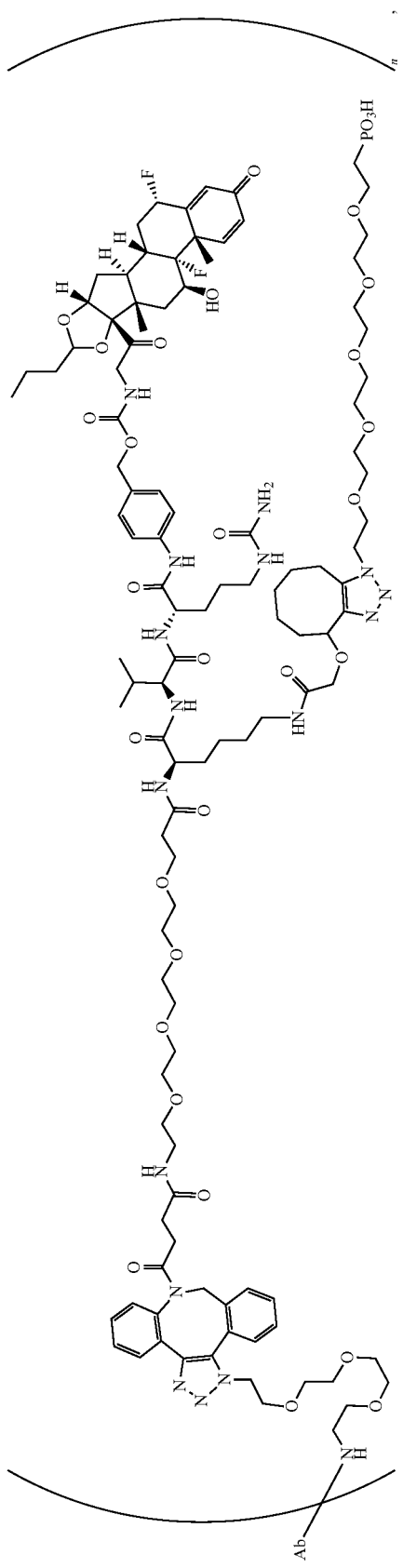

429
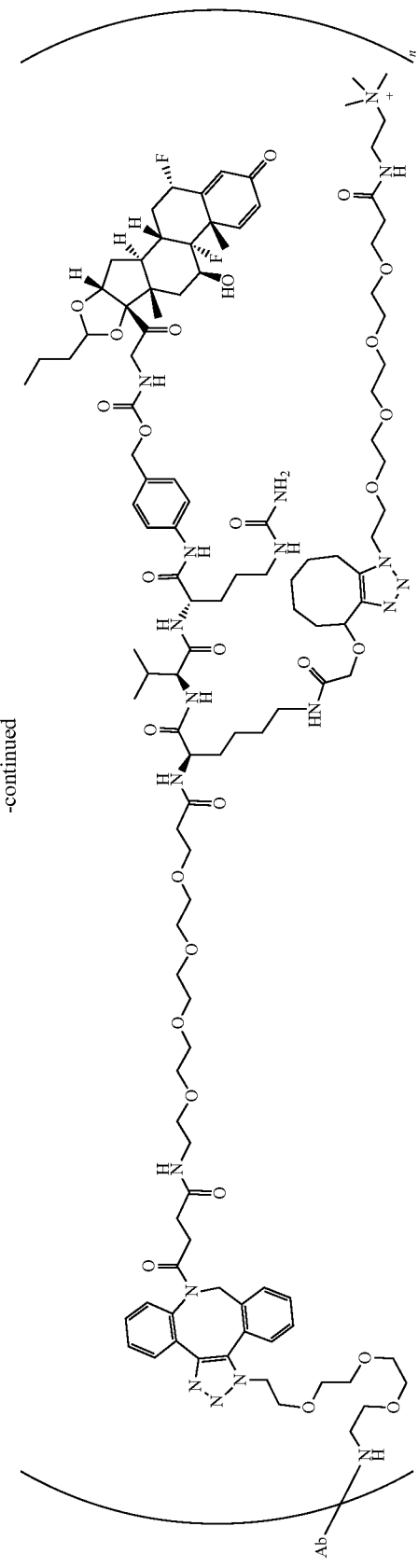
430
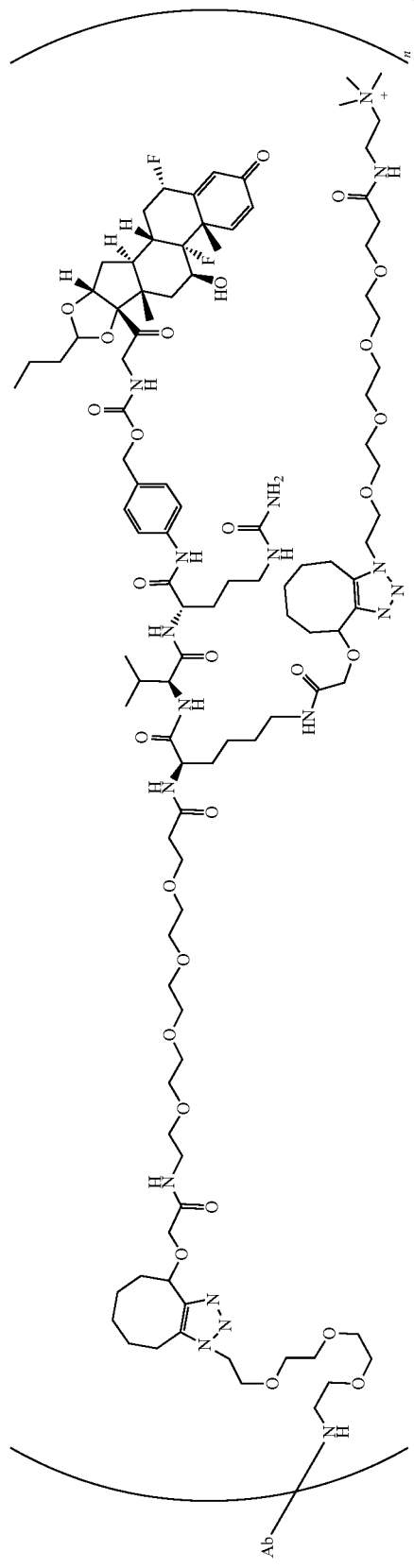

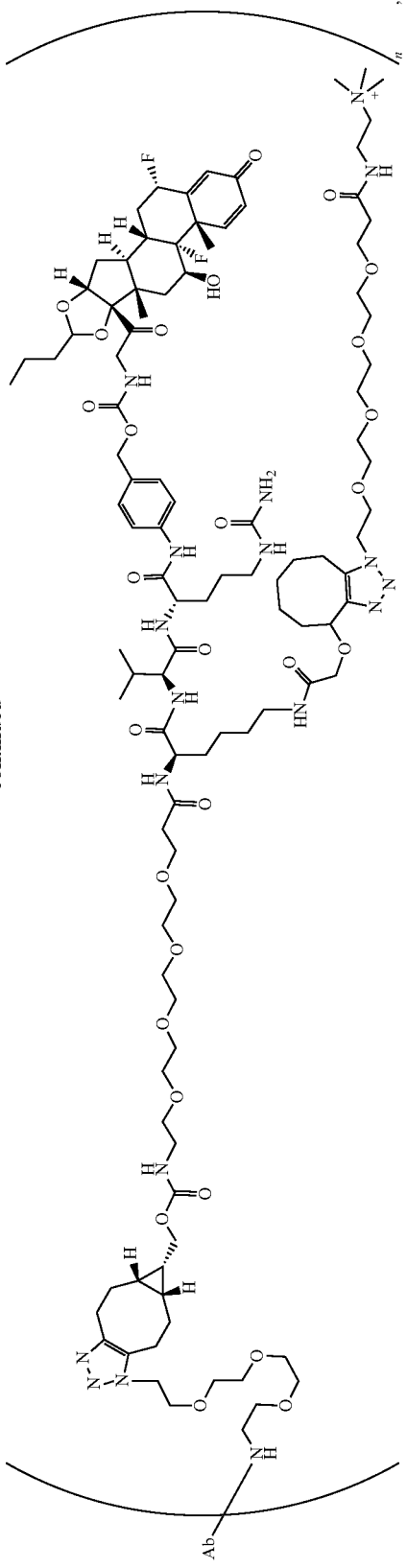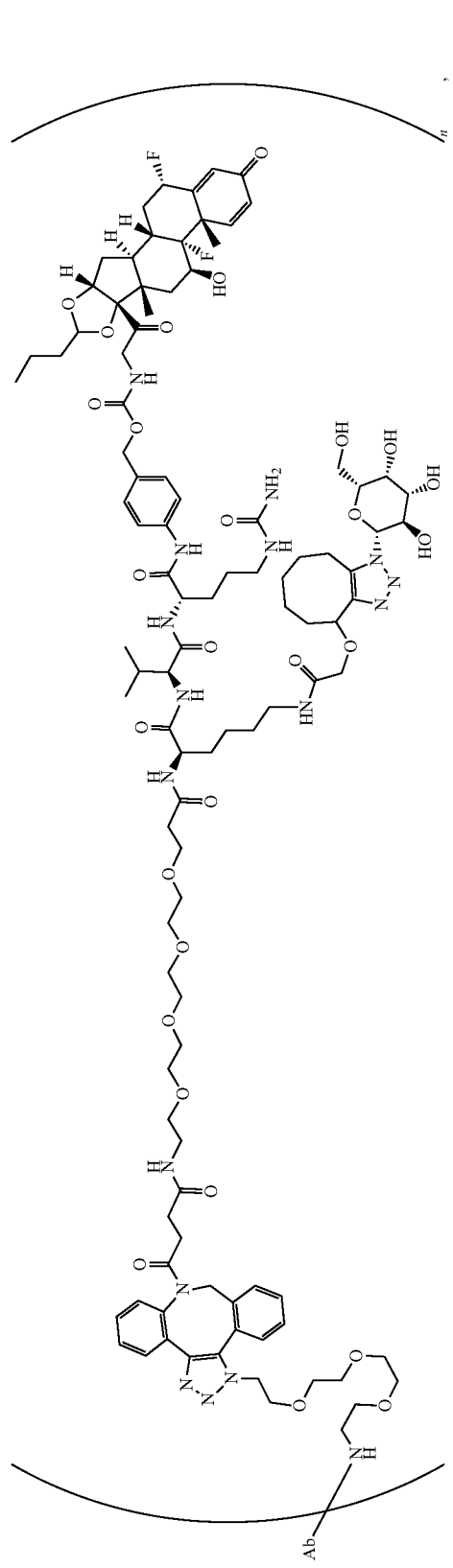

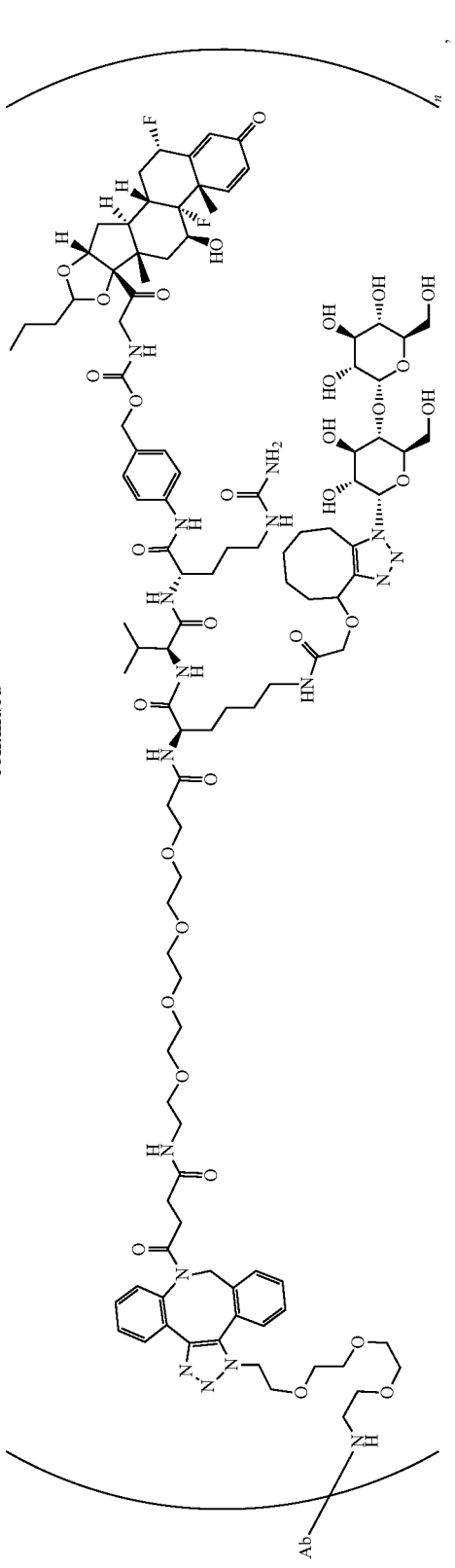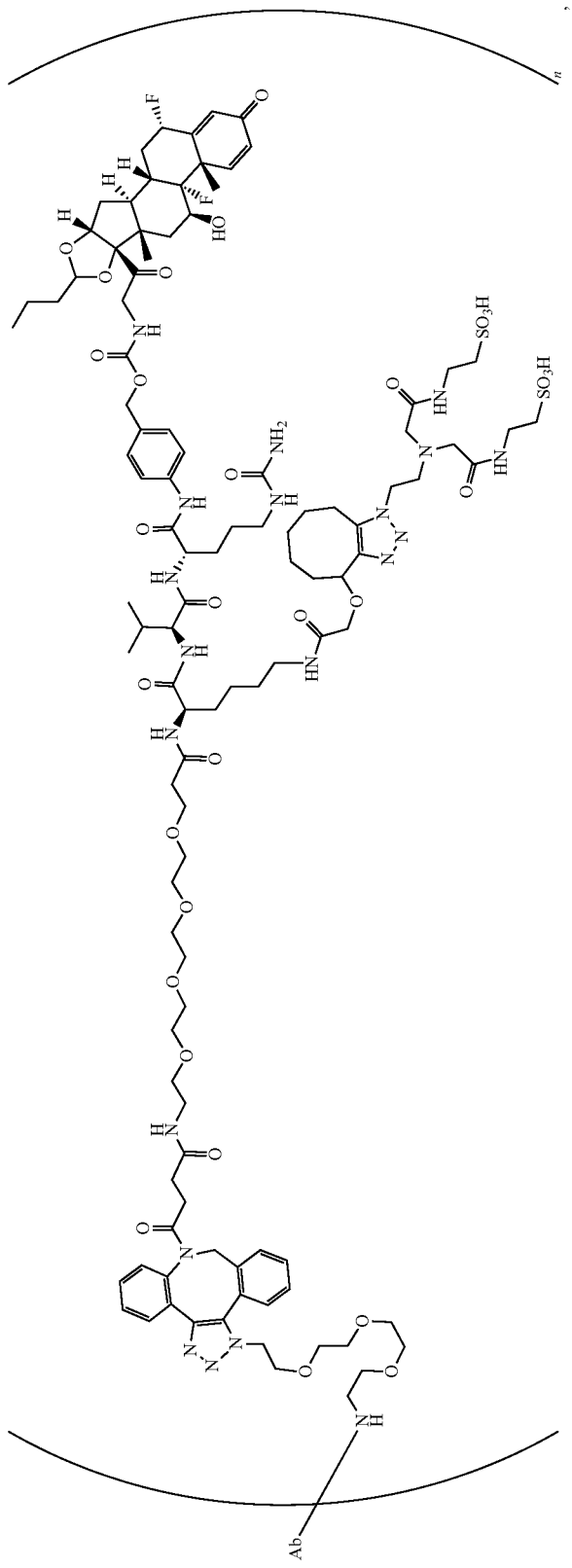

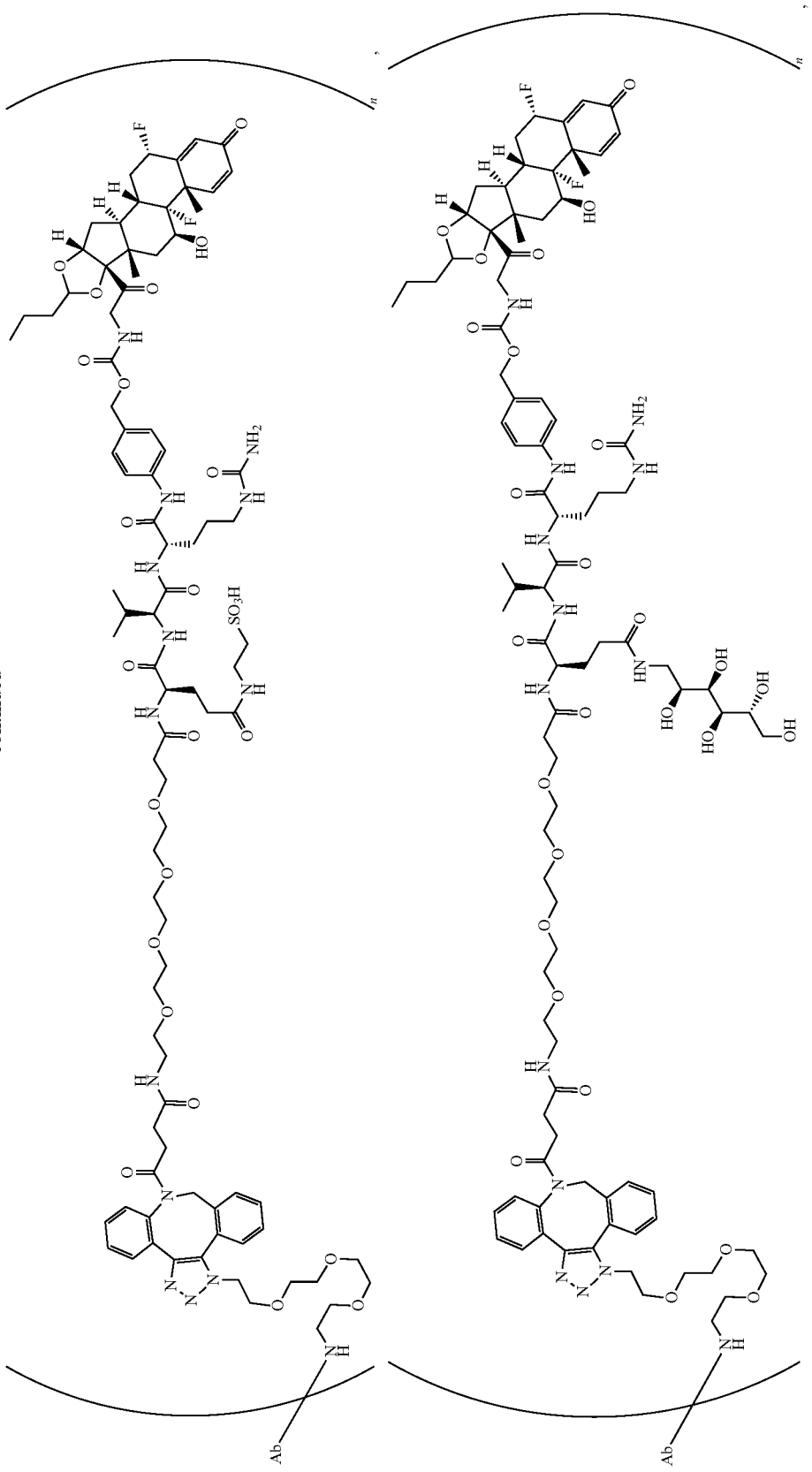

-continued
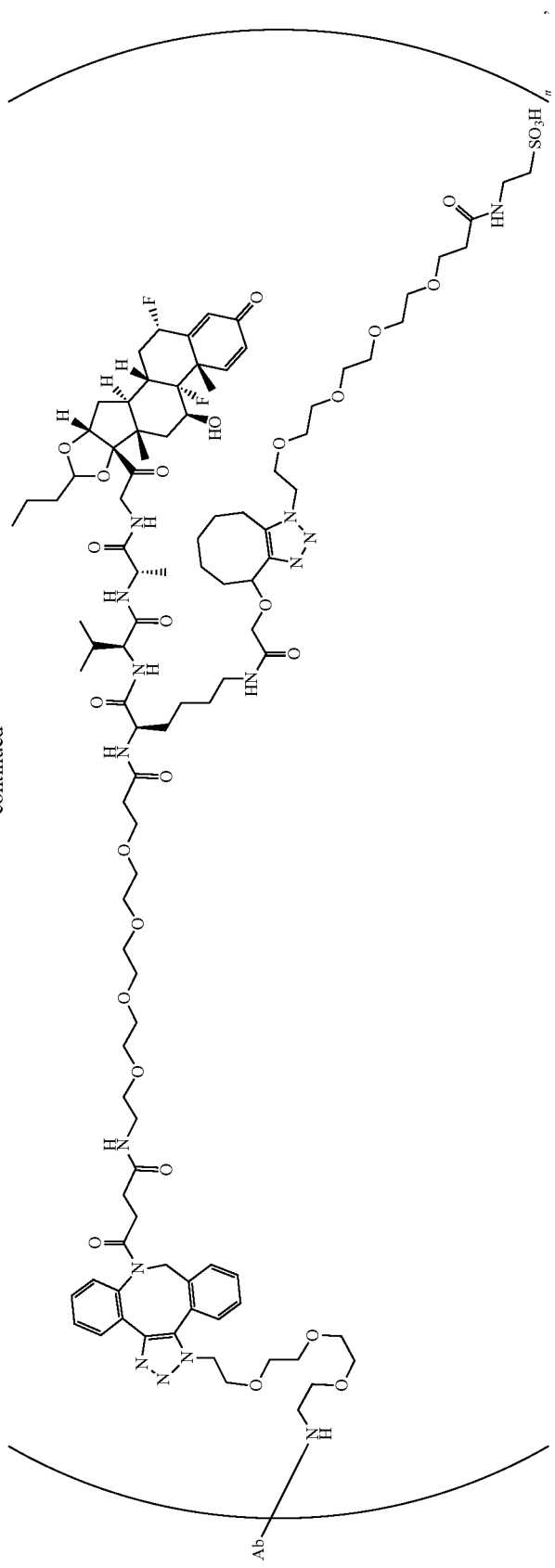

-continued
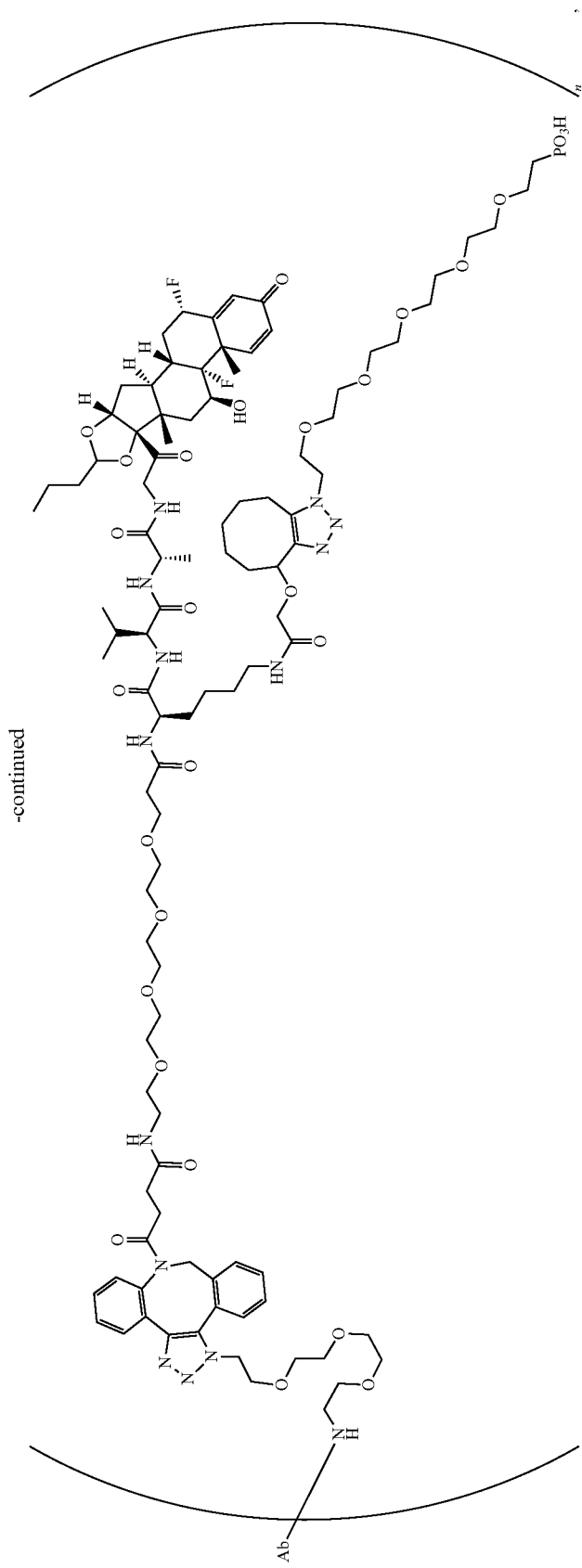

-continued
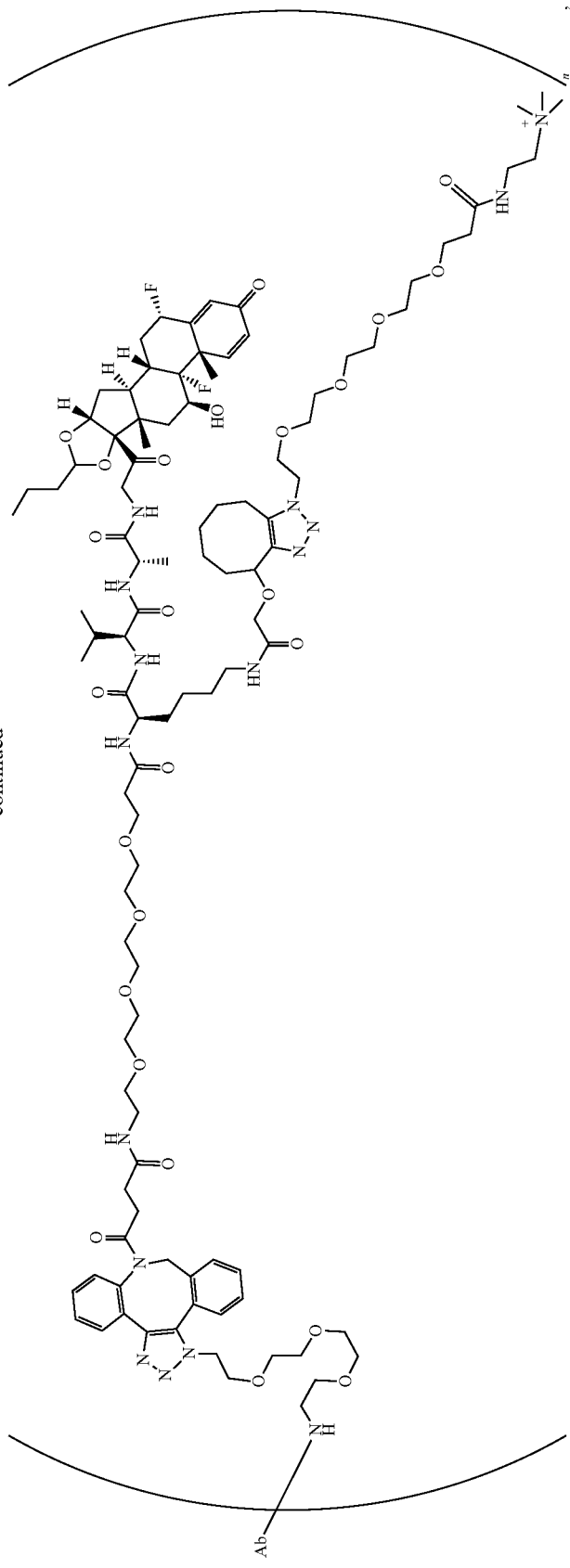

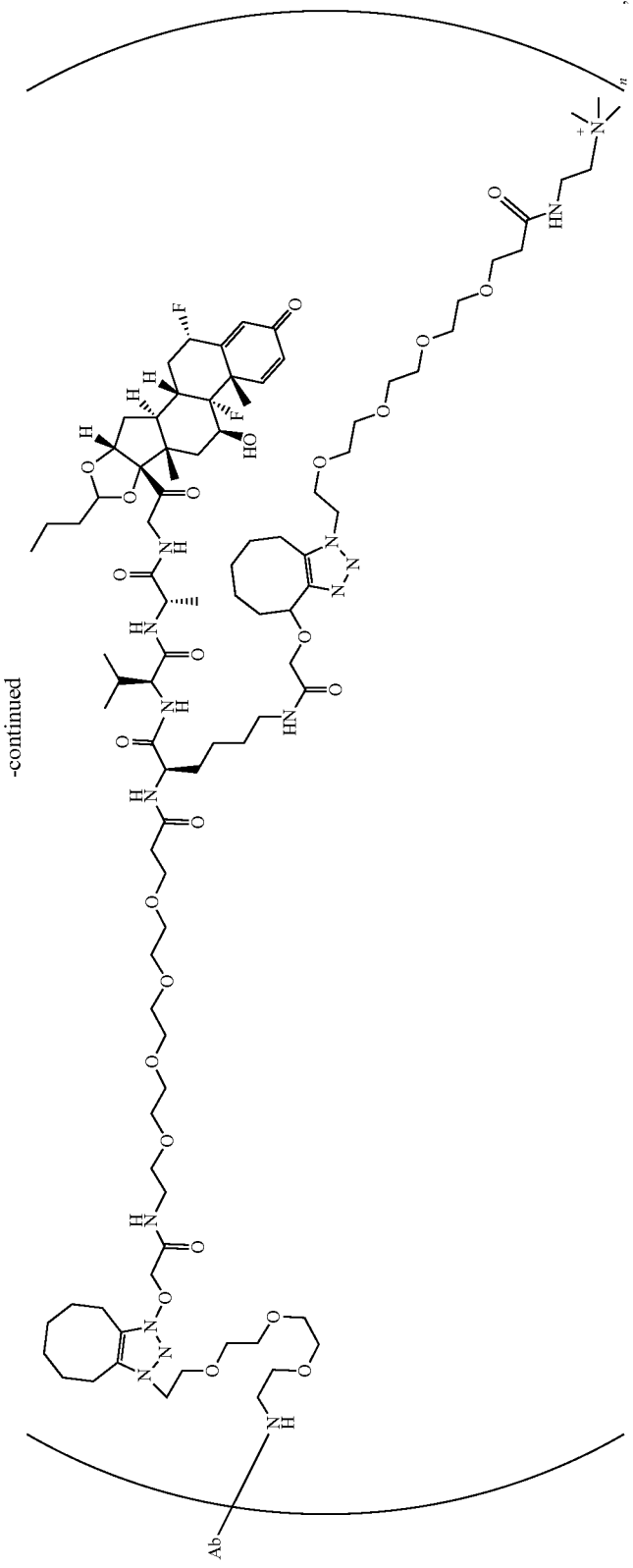

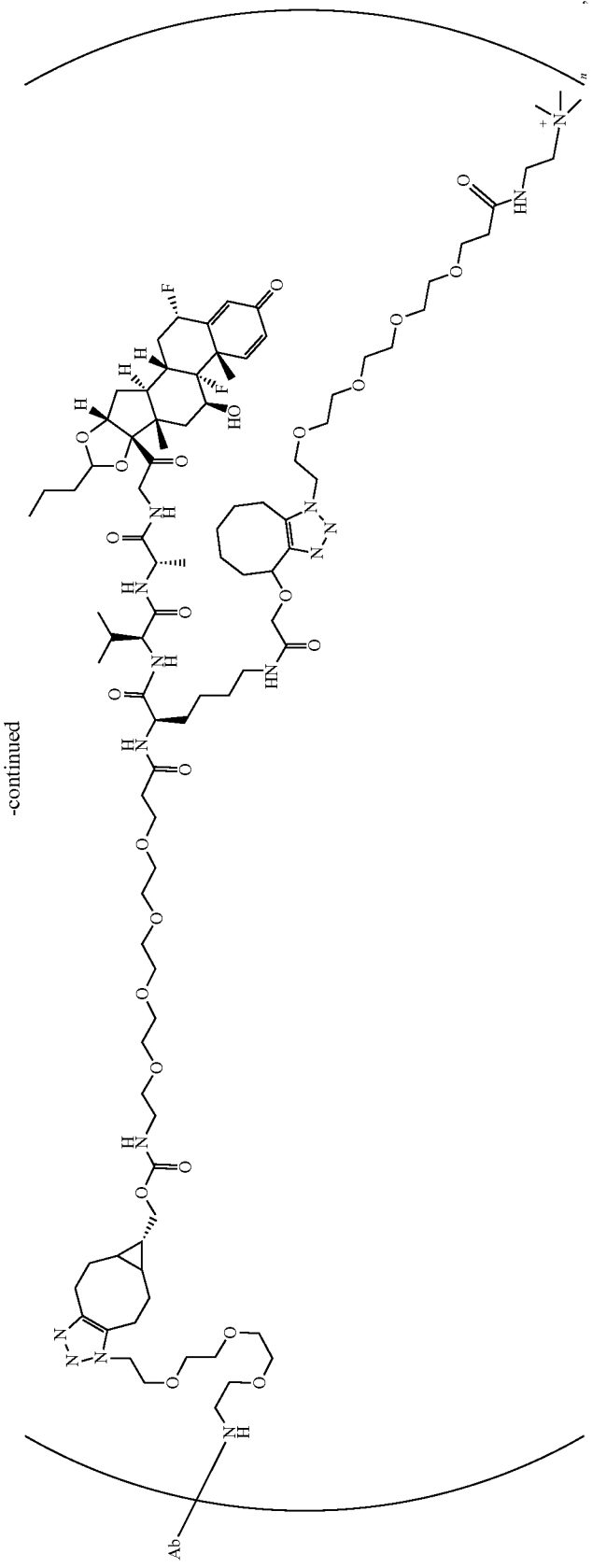

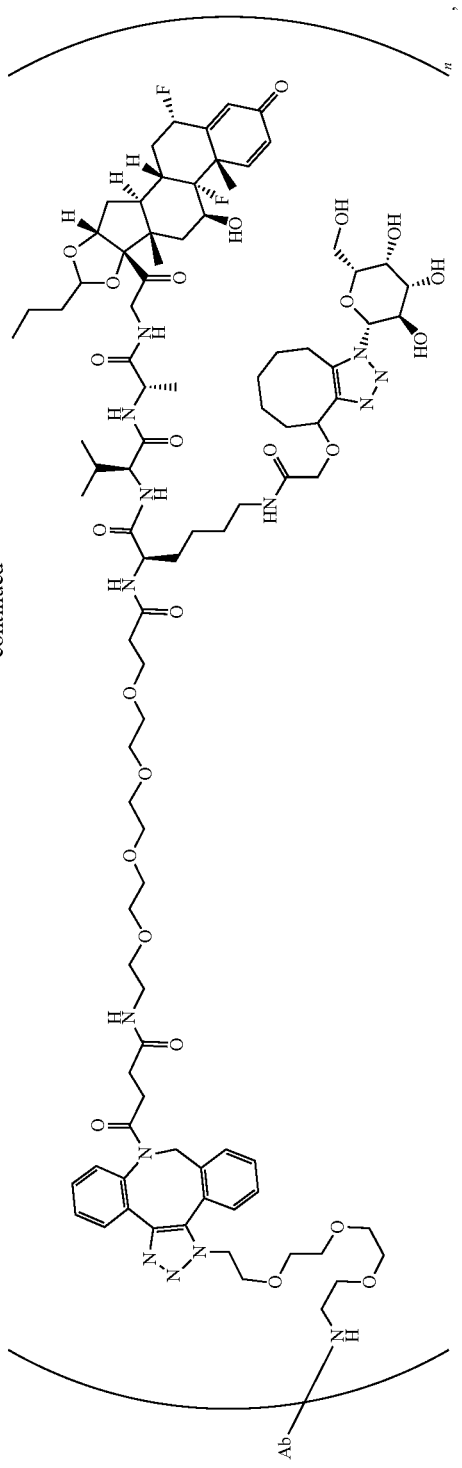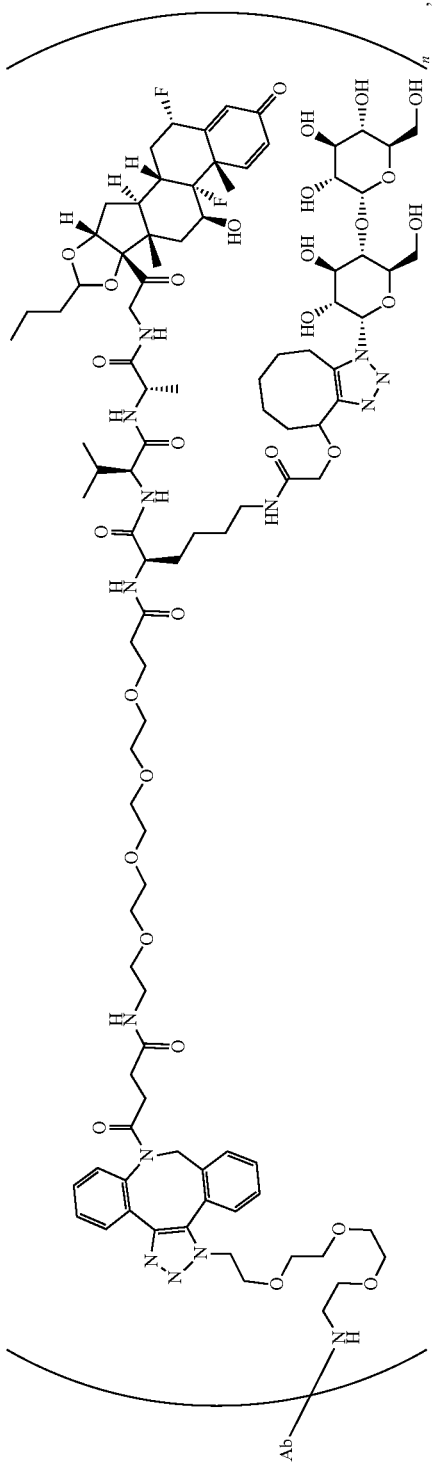

-continued
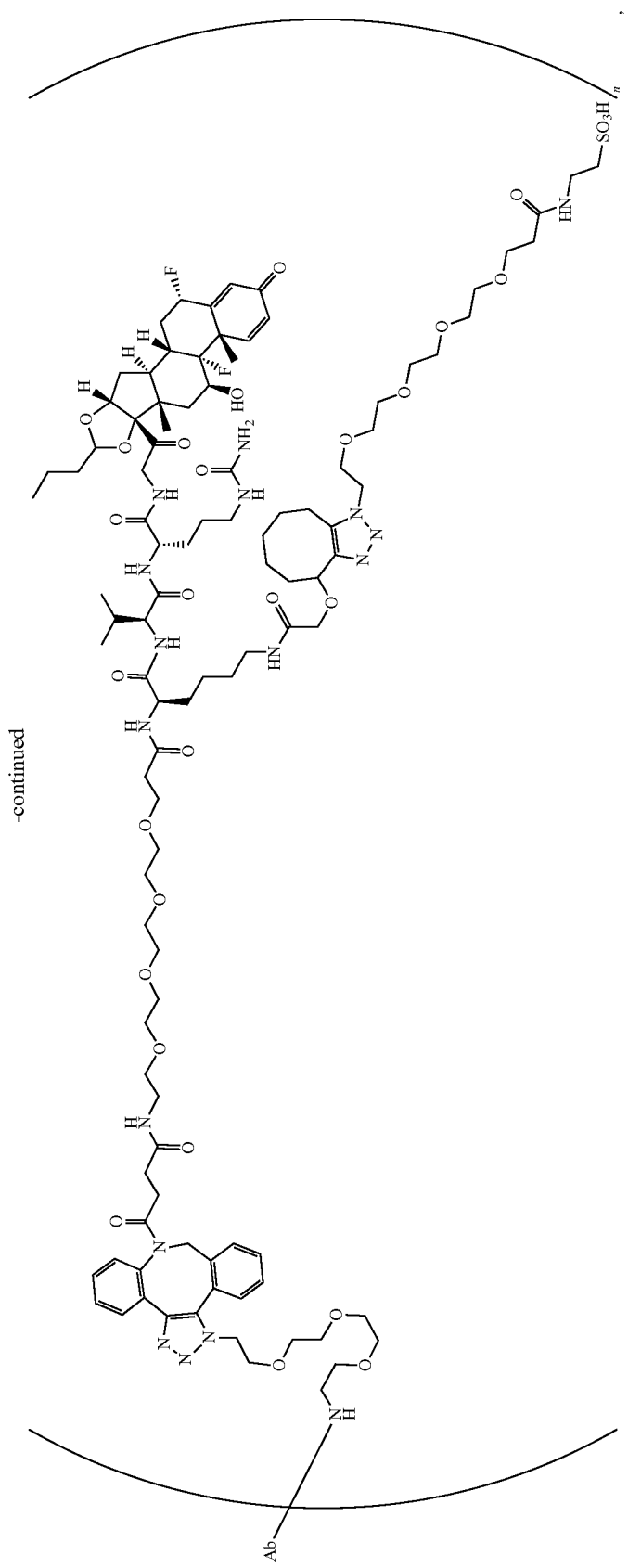

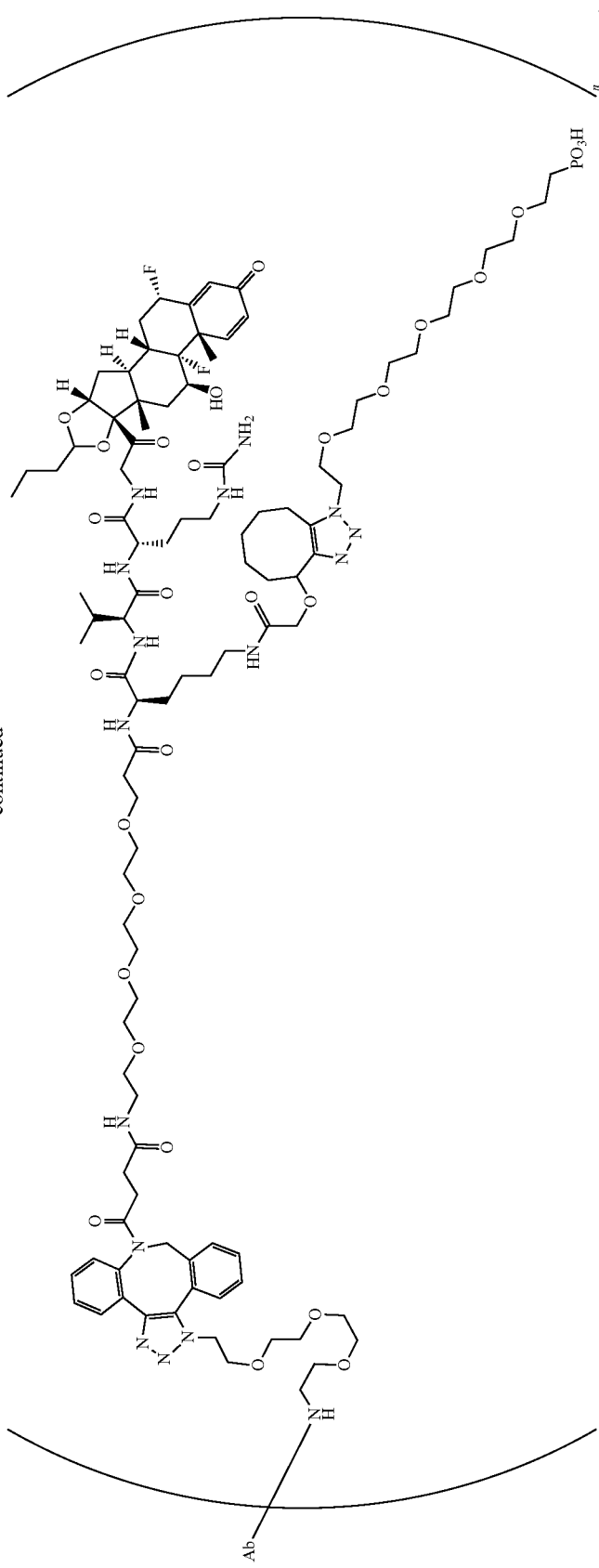

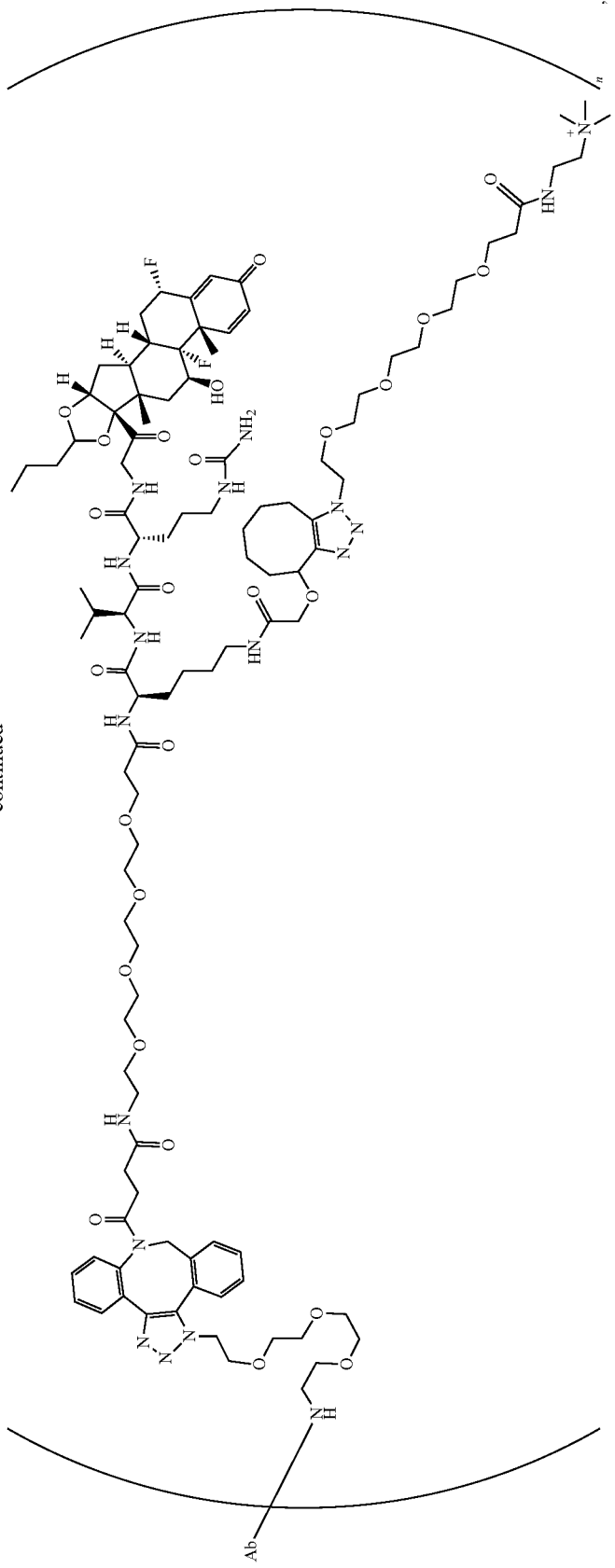

-continued
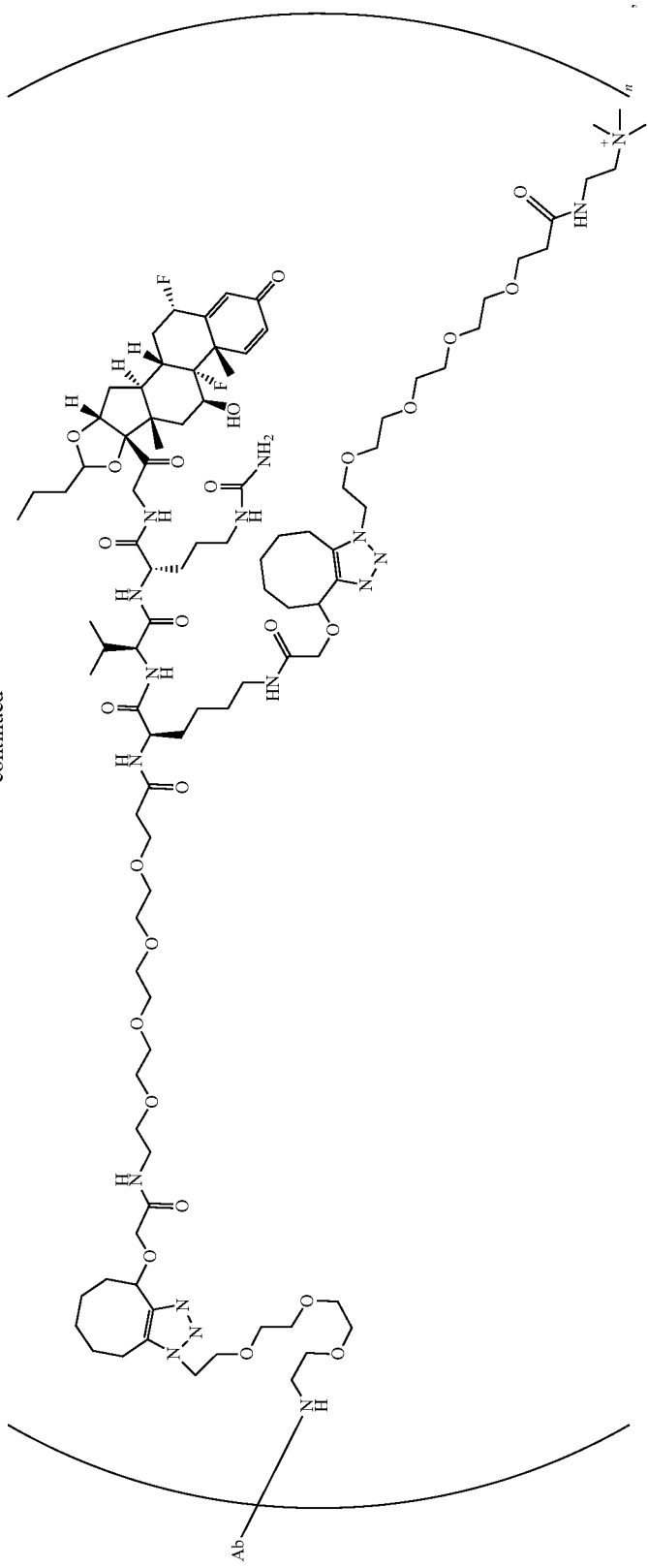

457
458
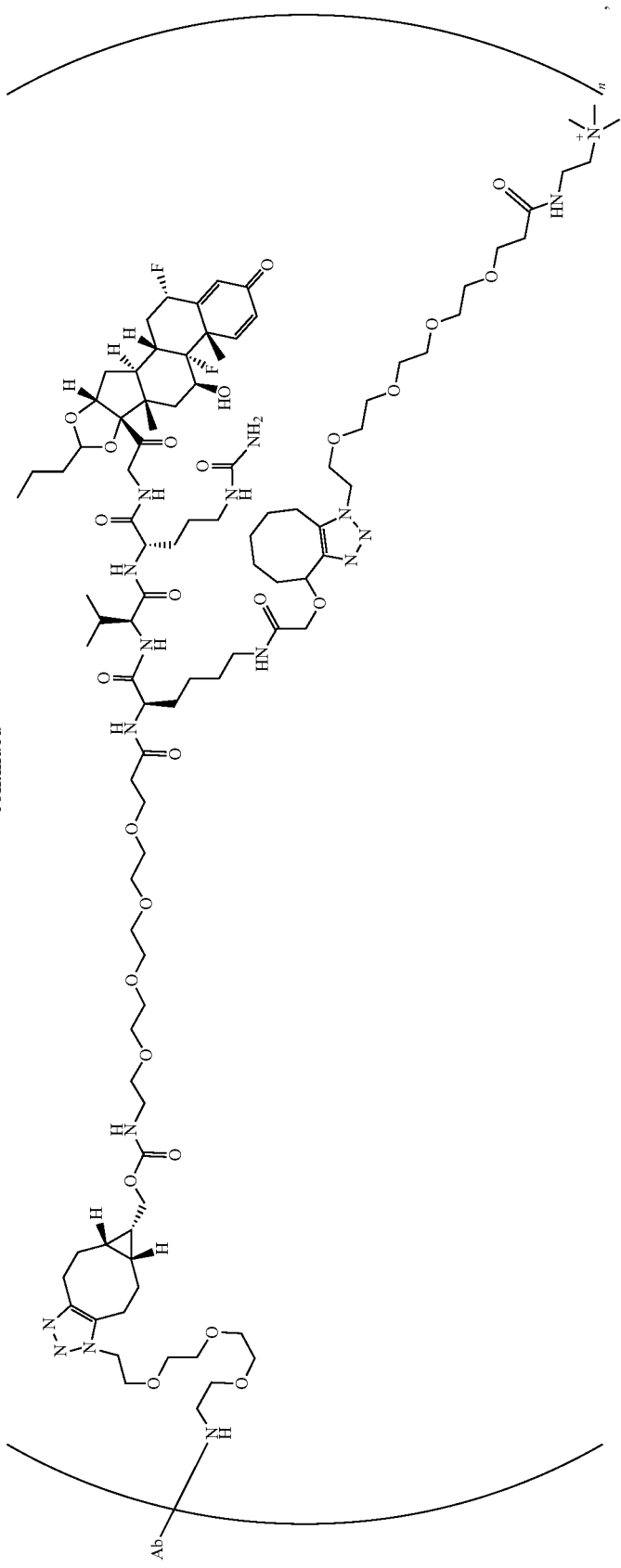
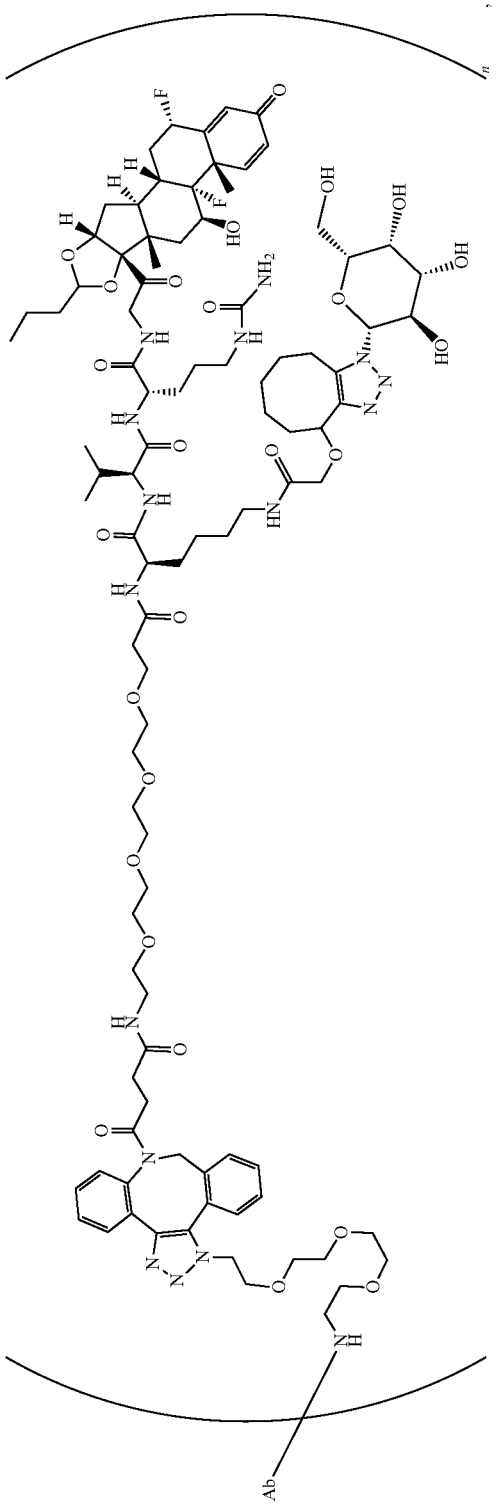

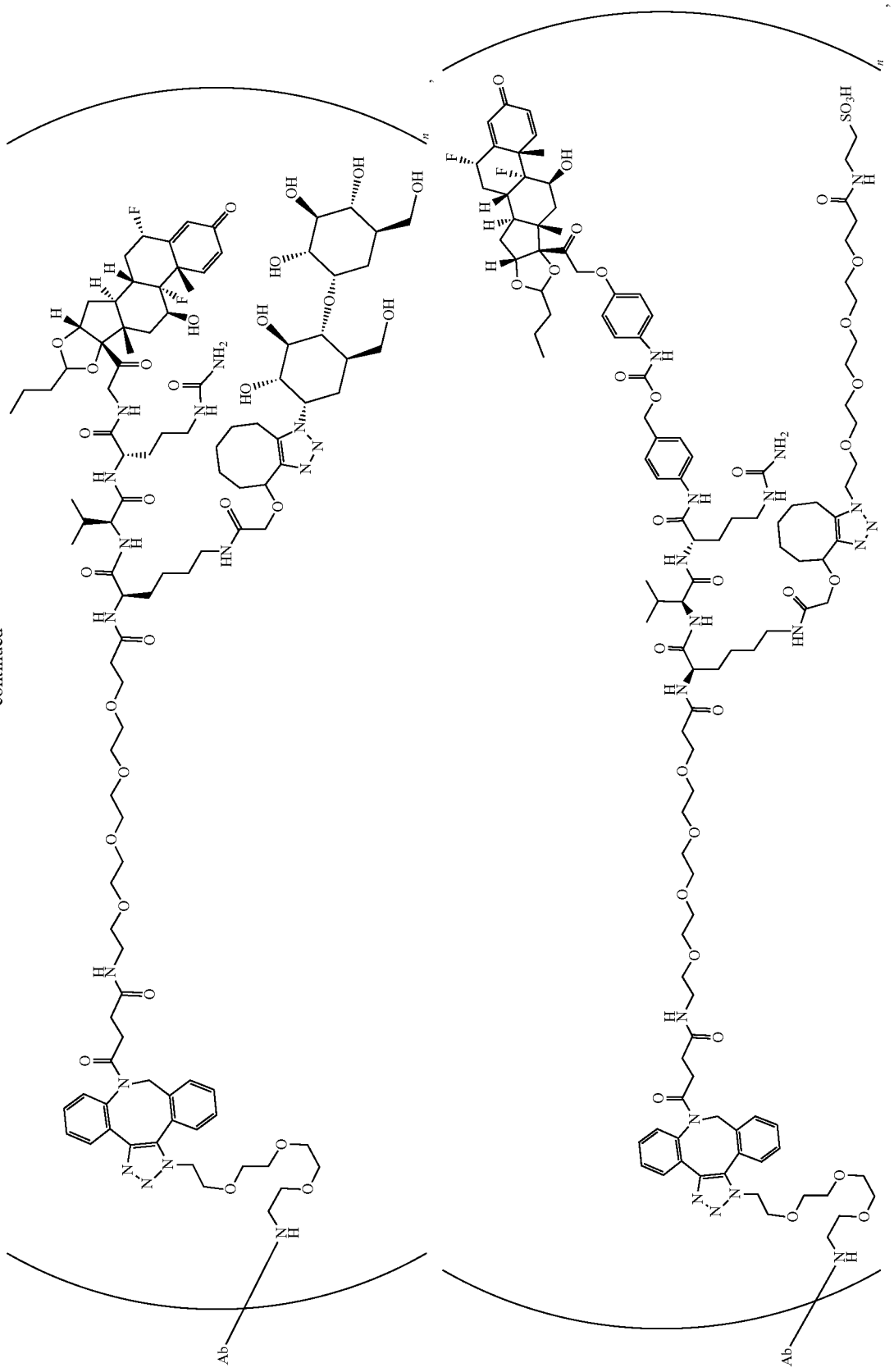

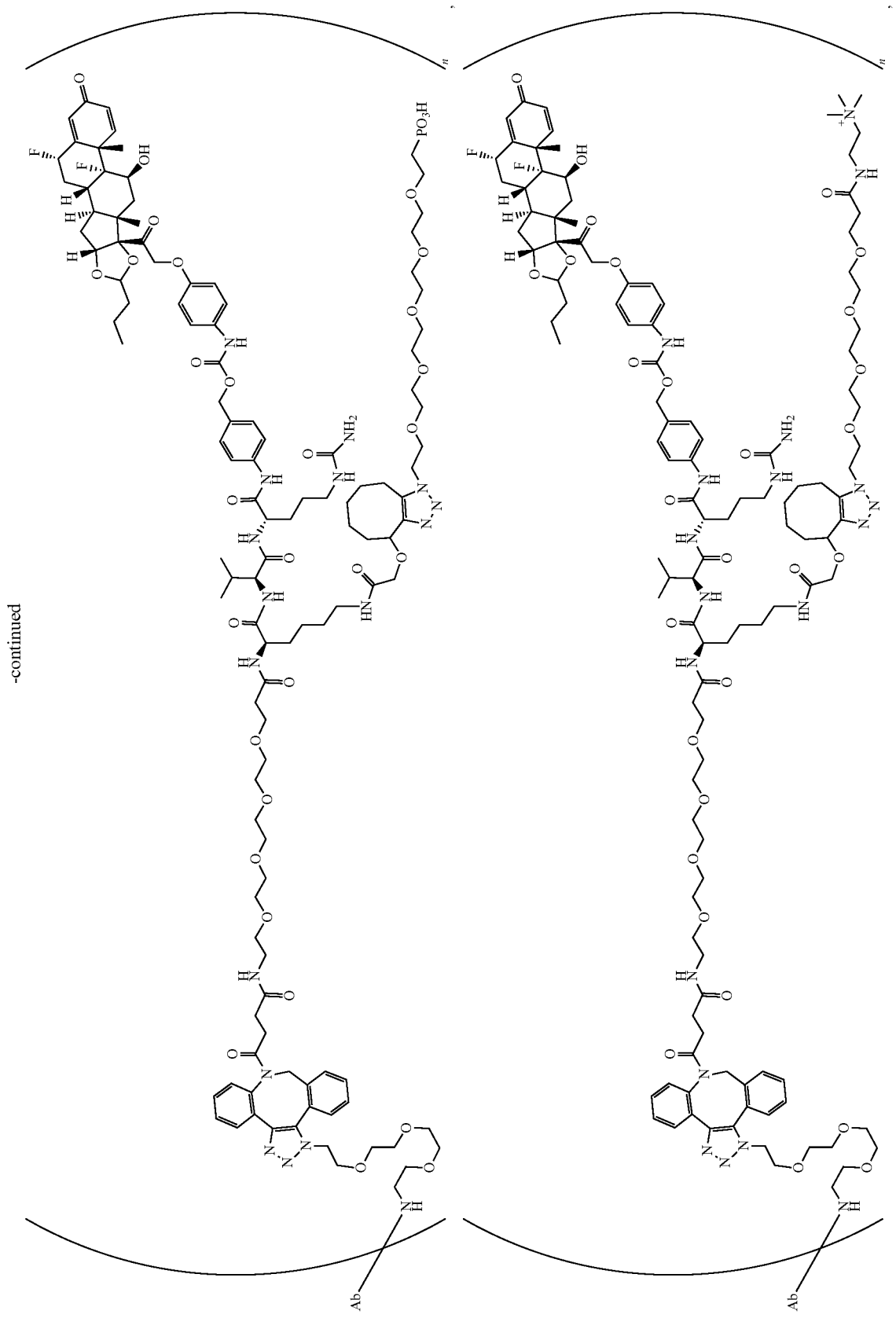

463
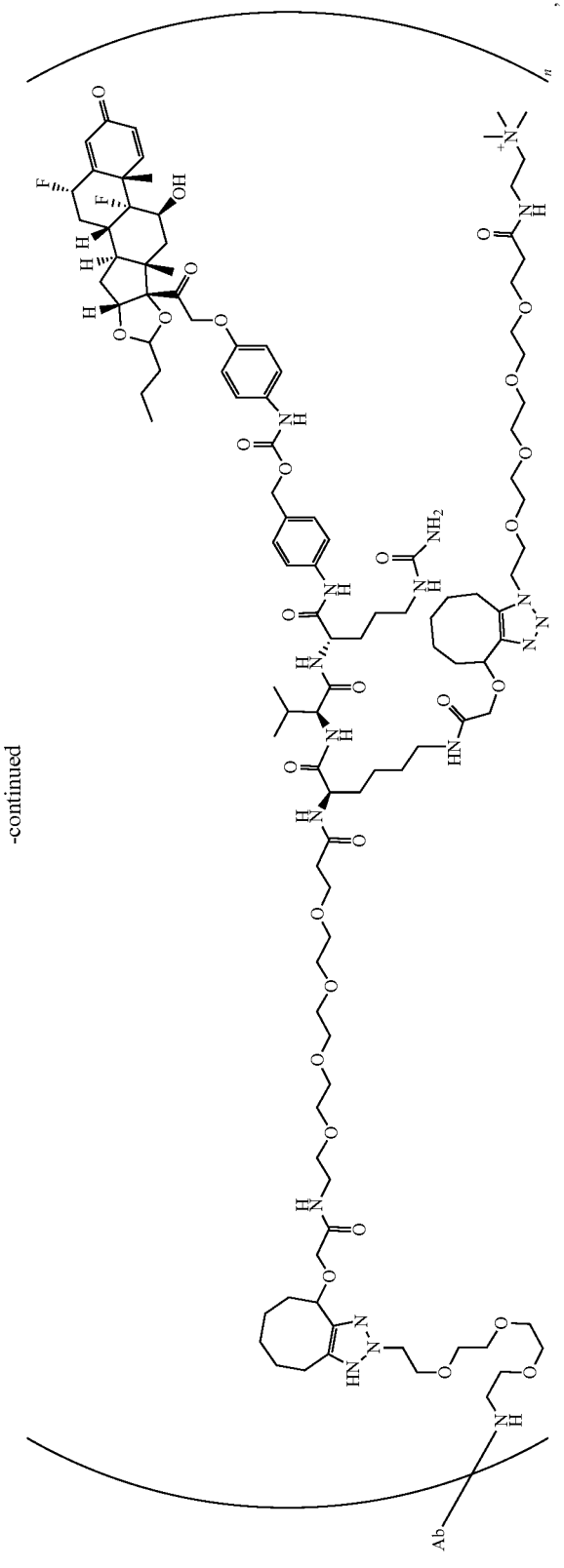
464
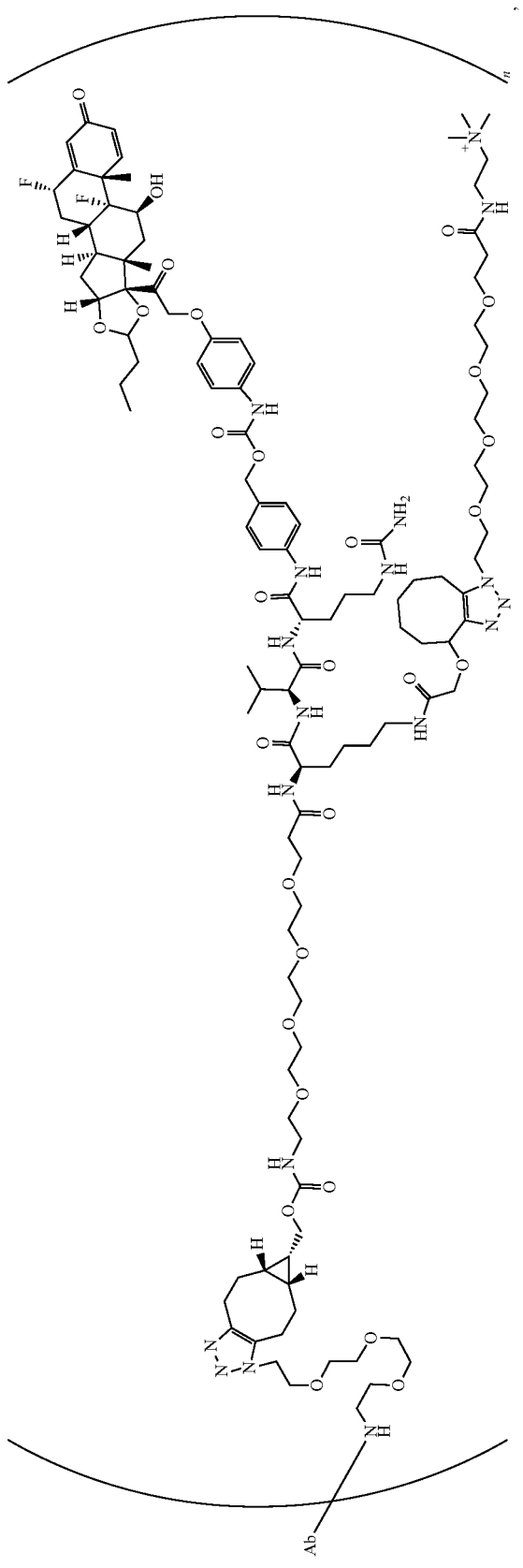

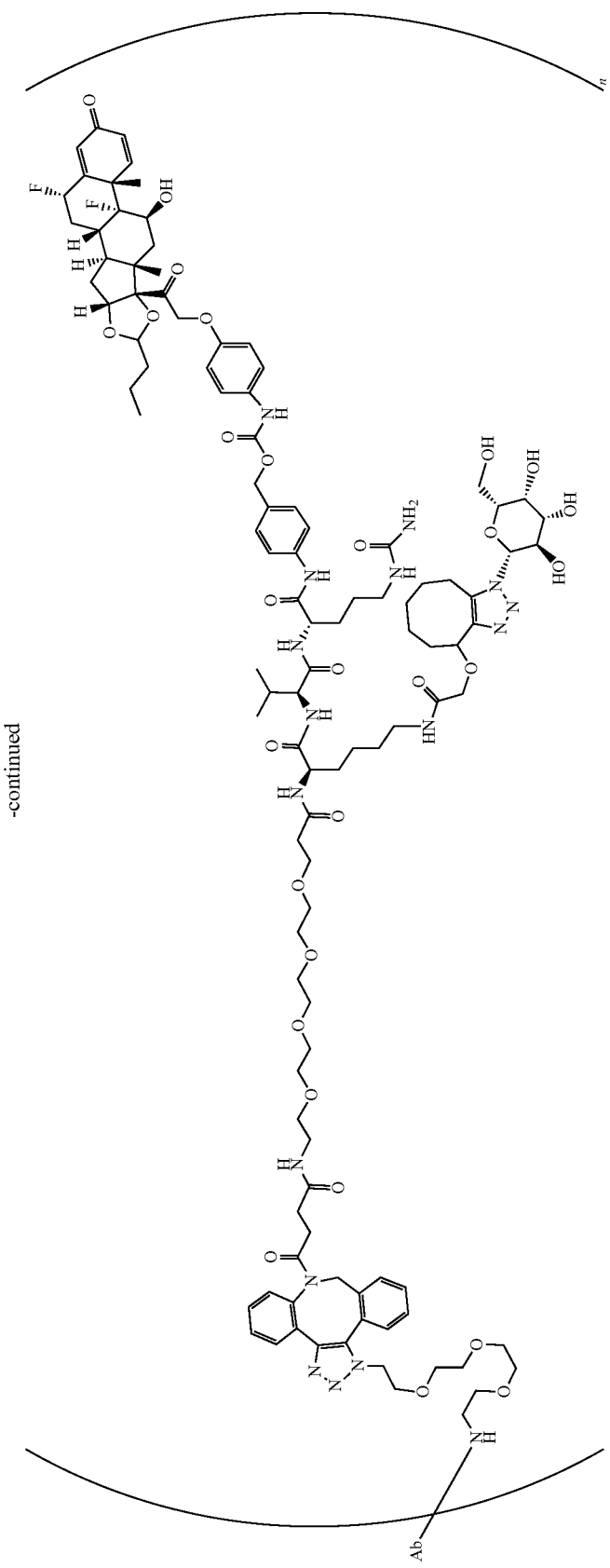
-continued

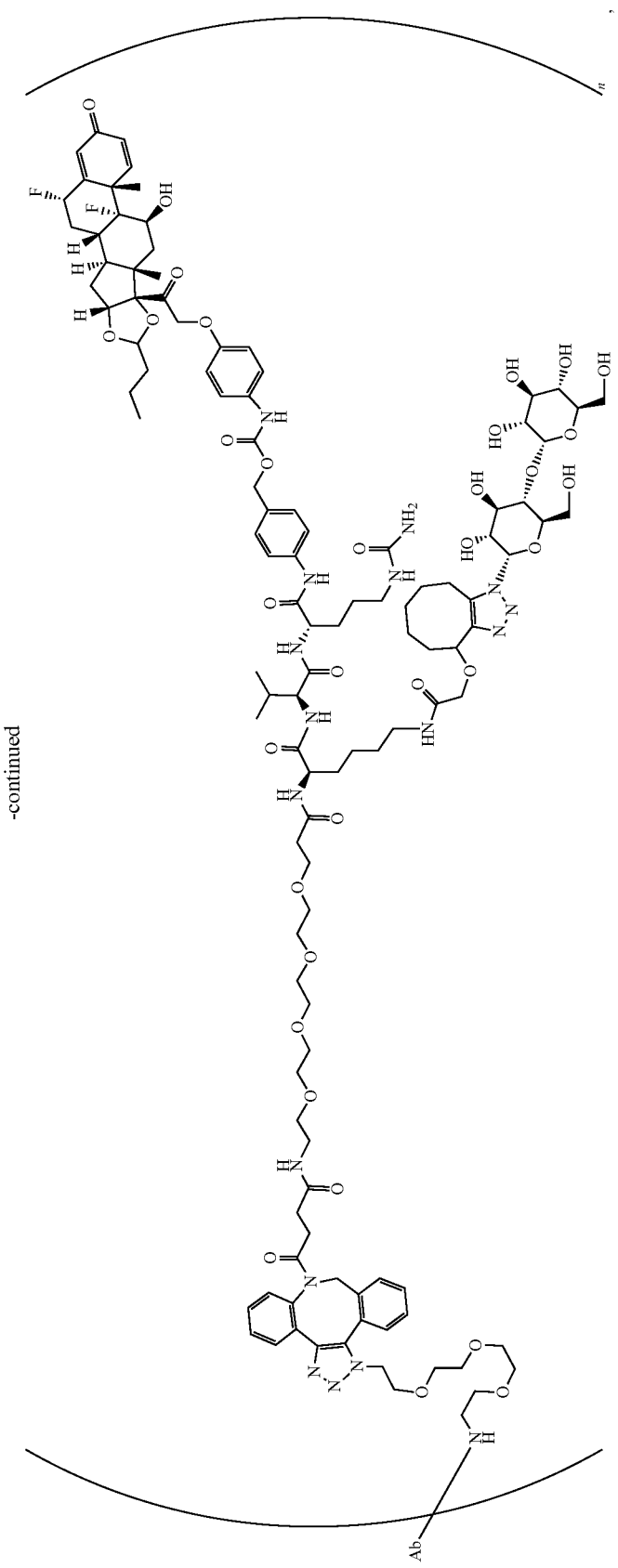

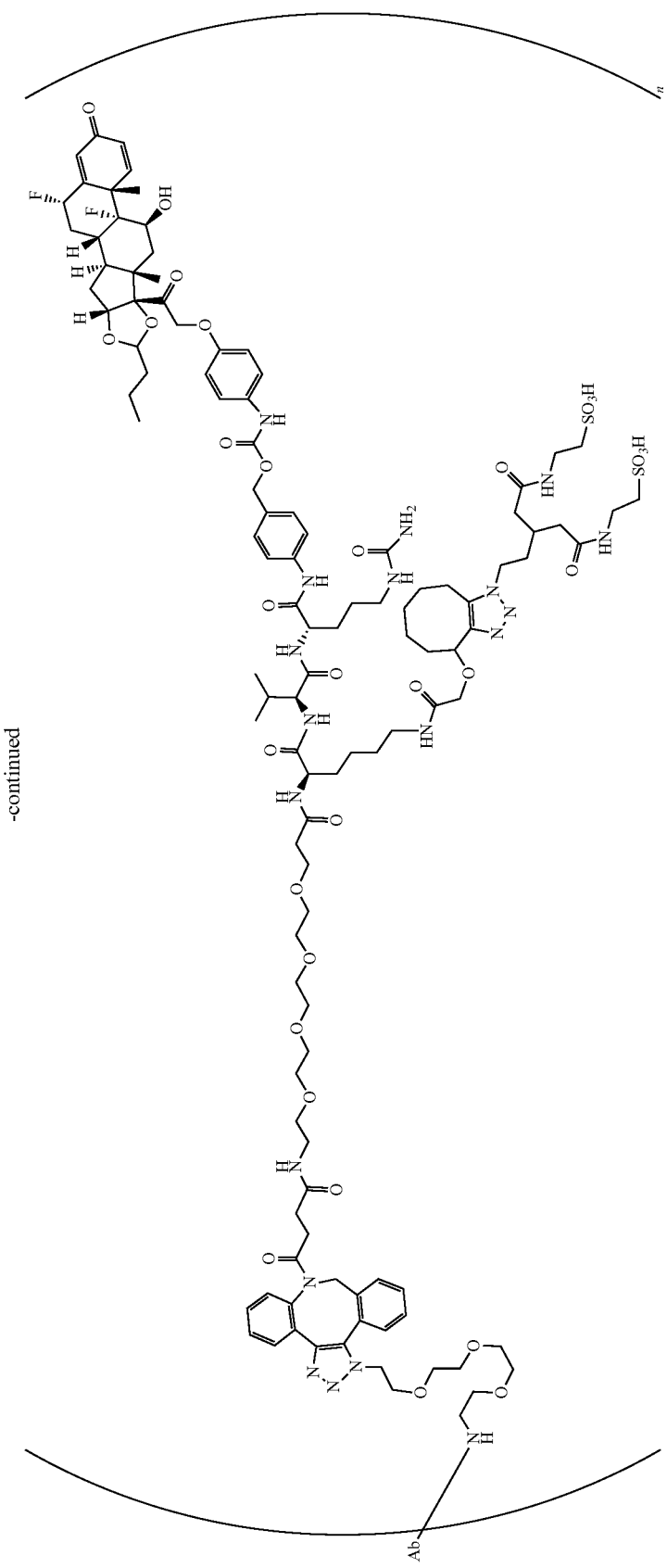

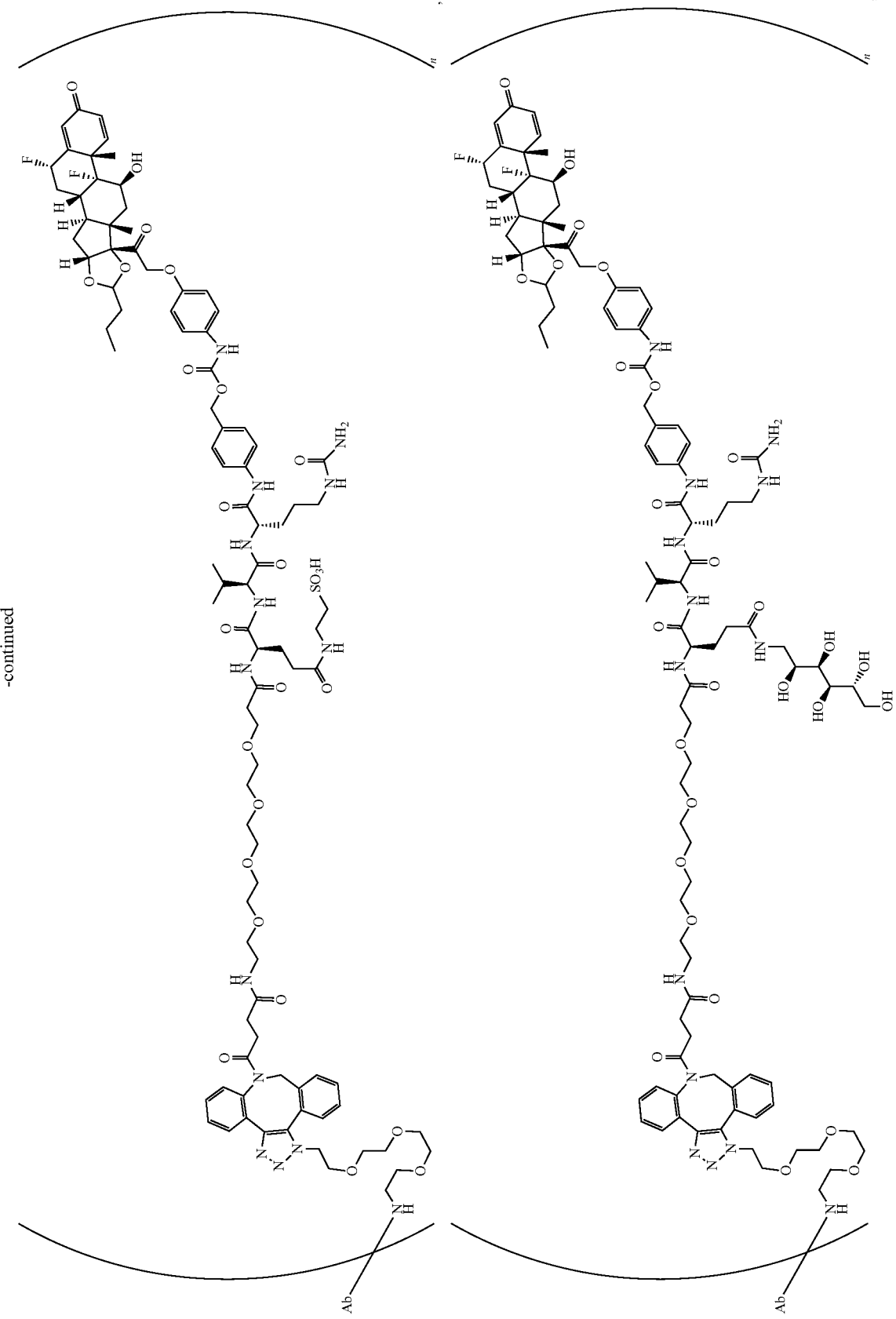


-continued
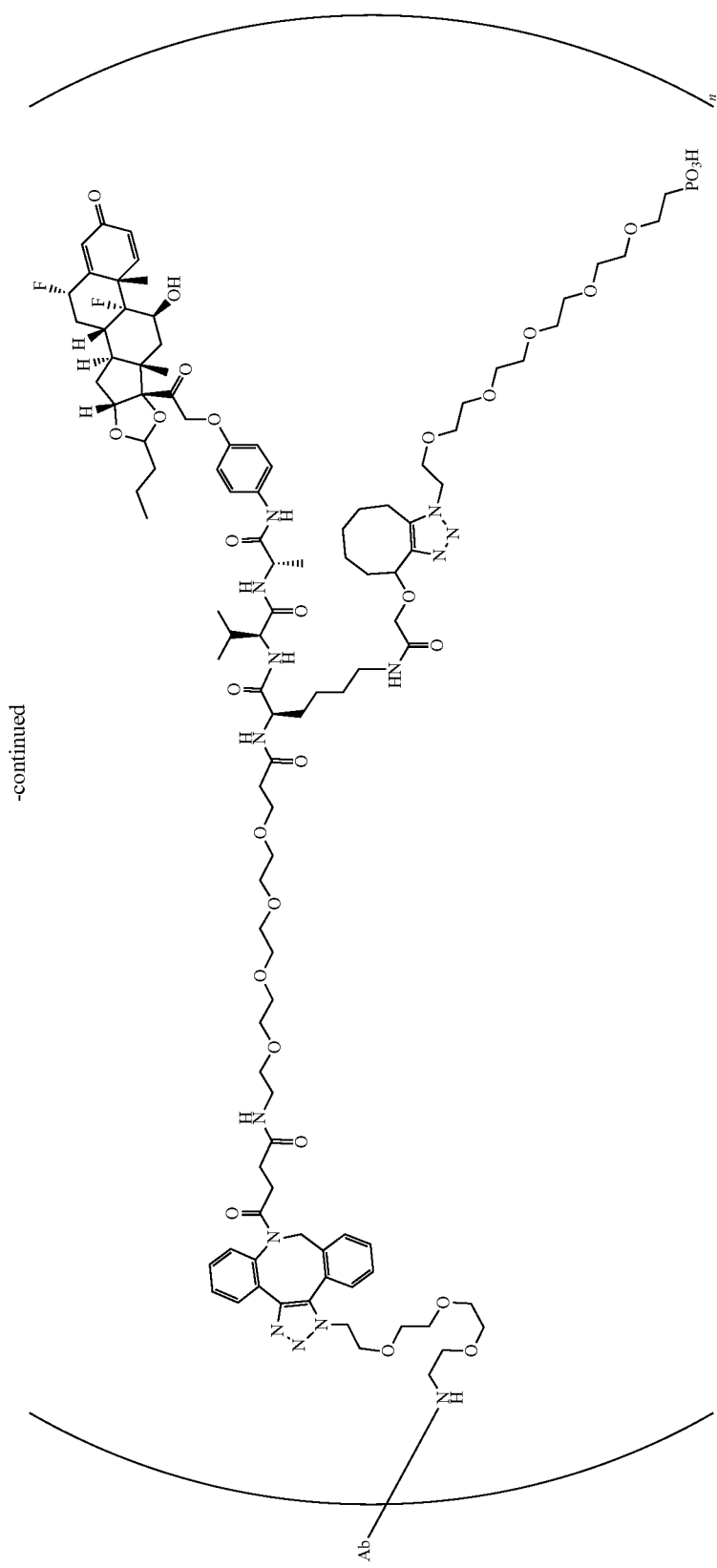

-continued
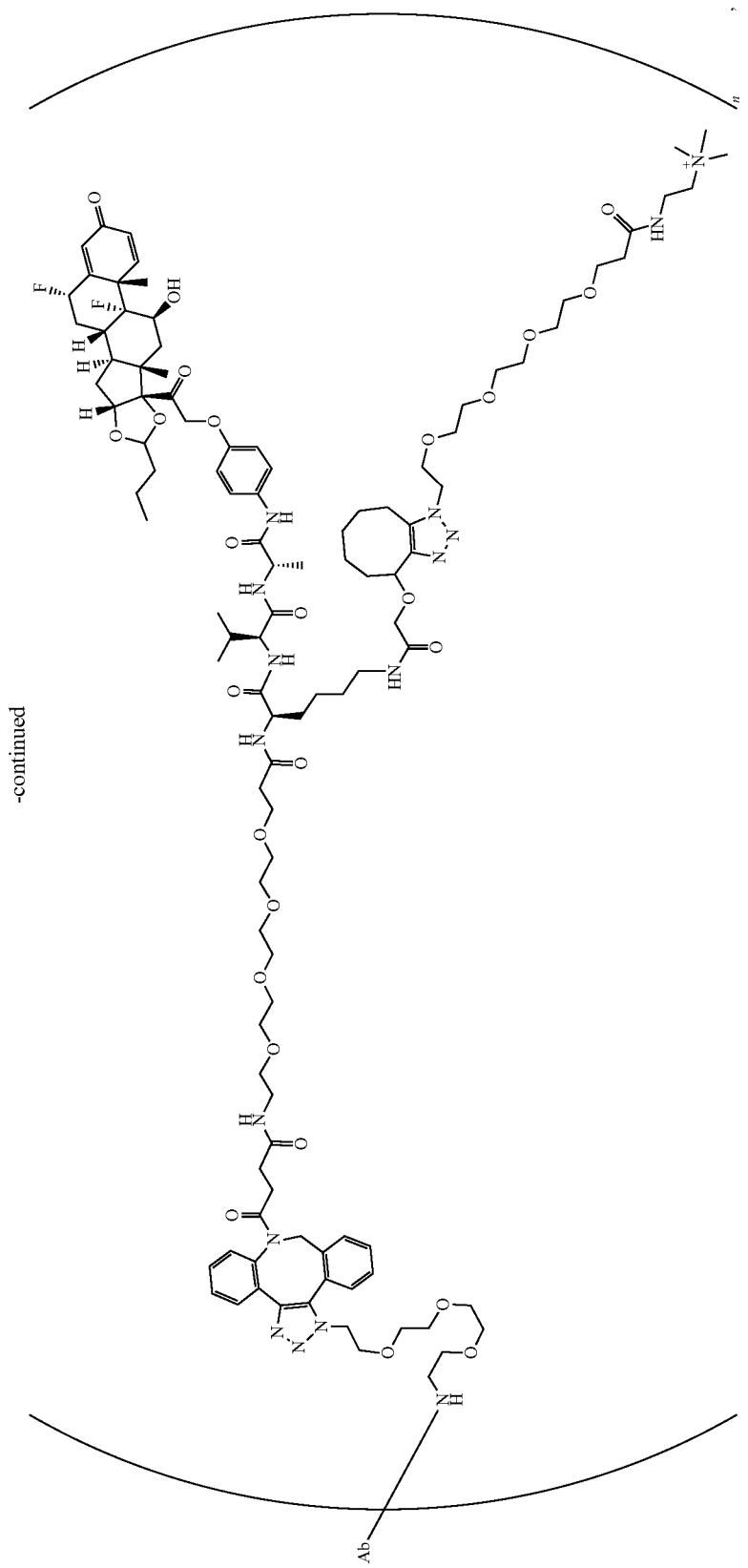

-continued
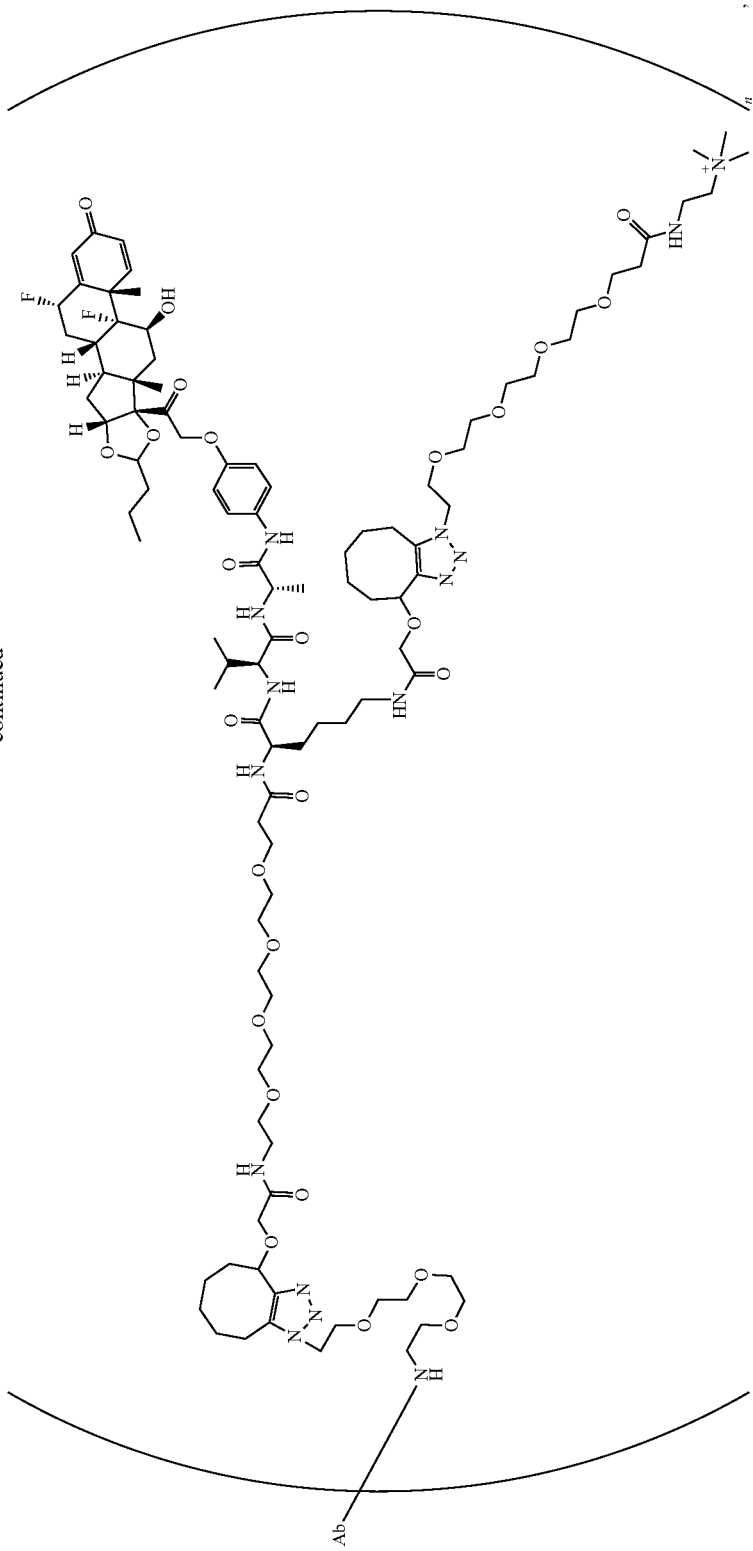

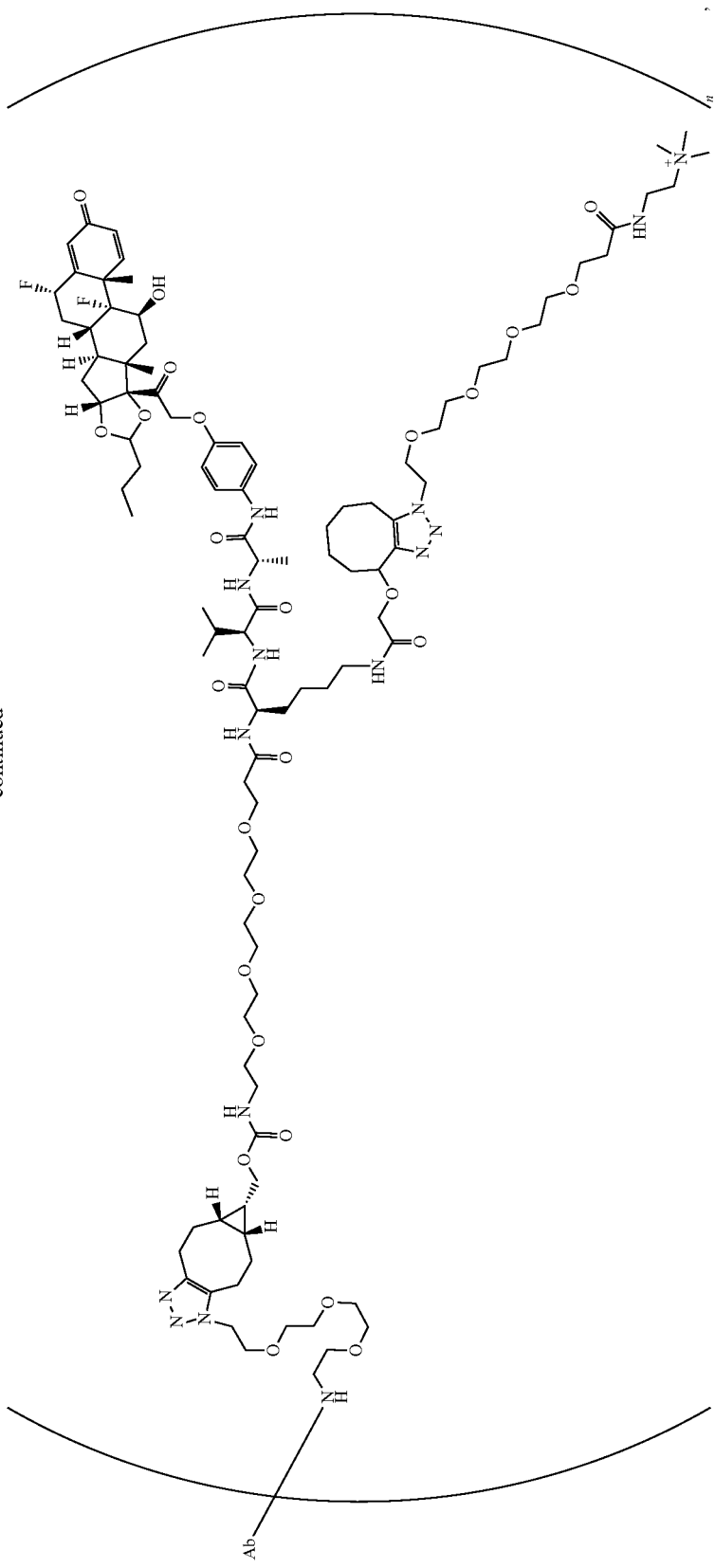

483
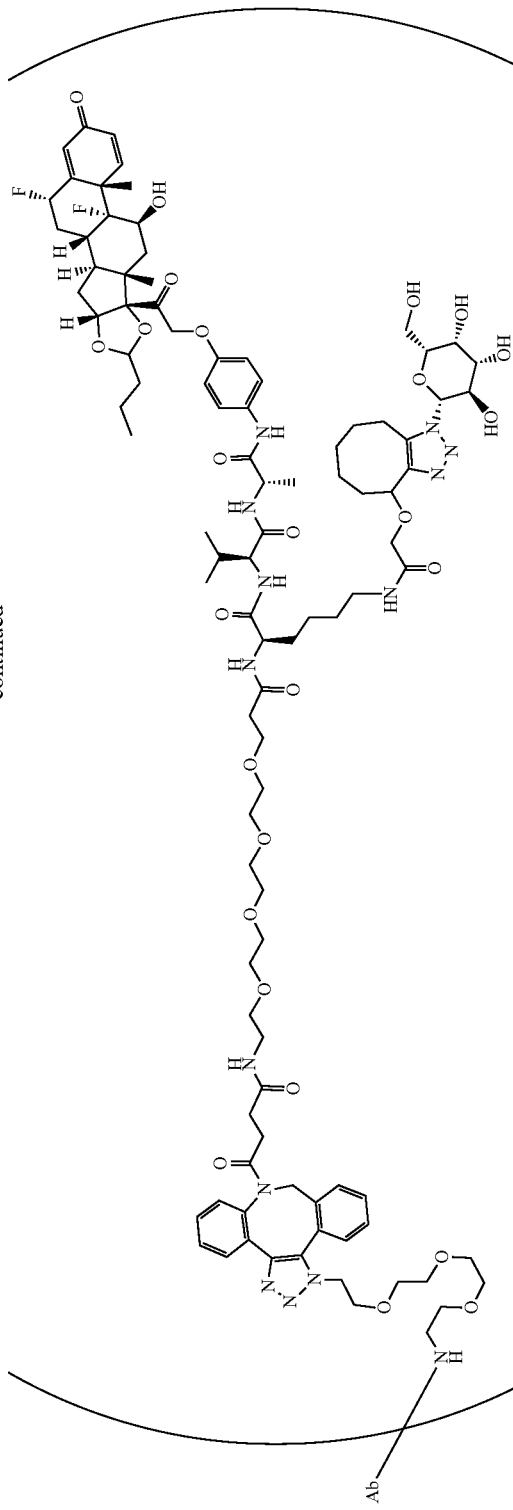
484
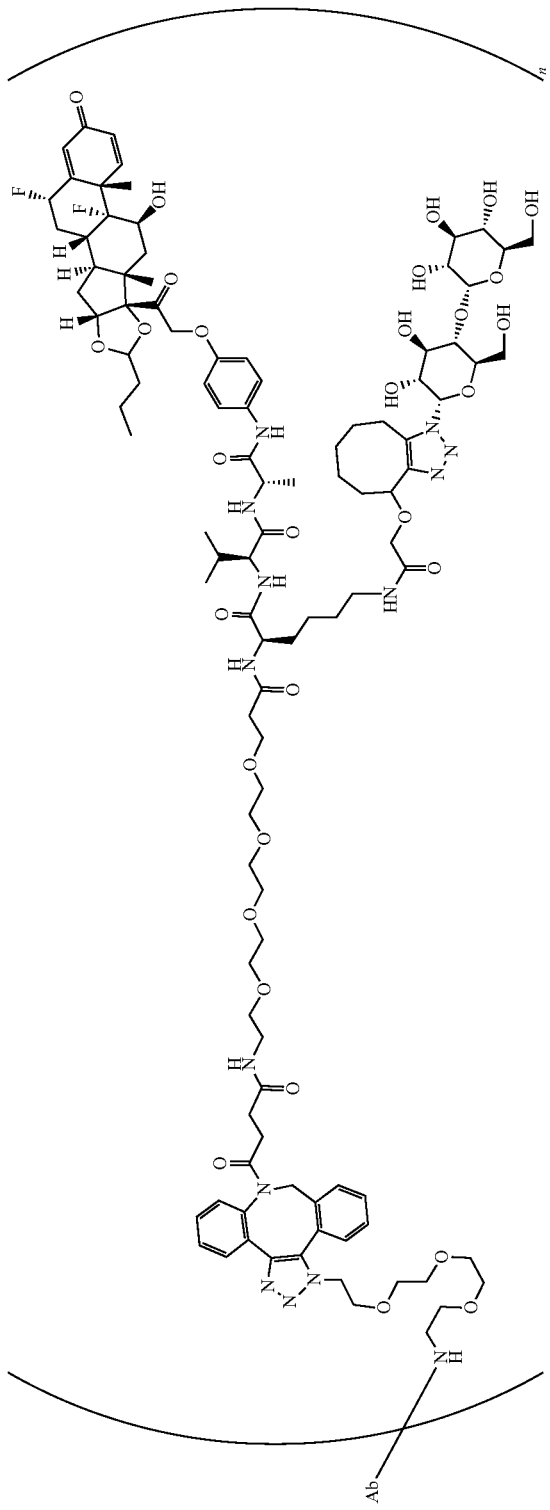

-continued
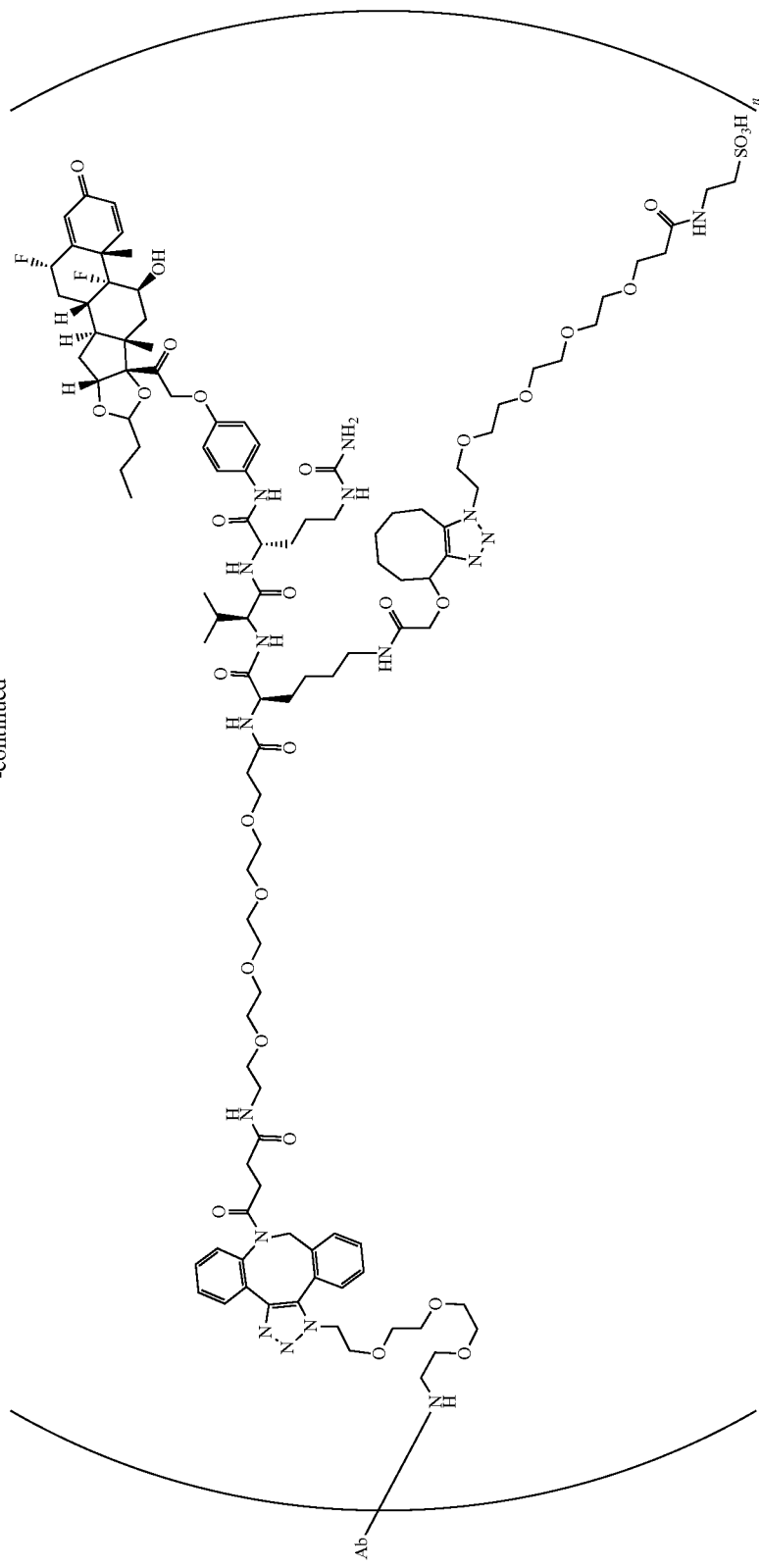

-continued
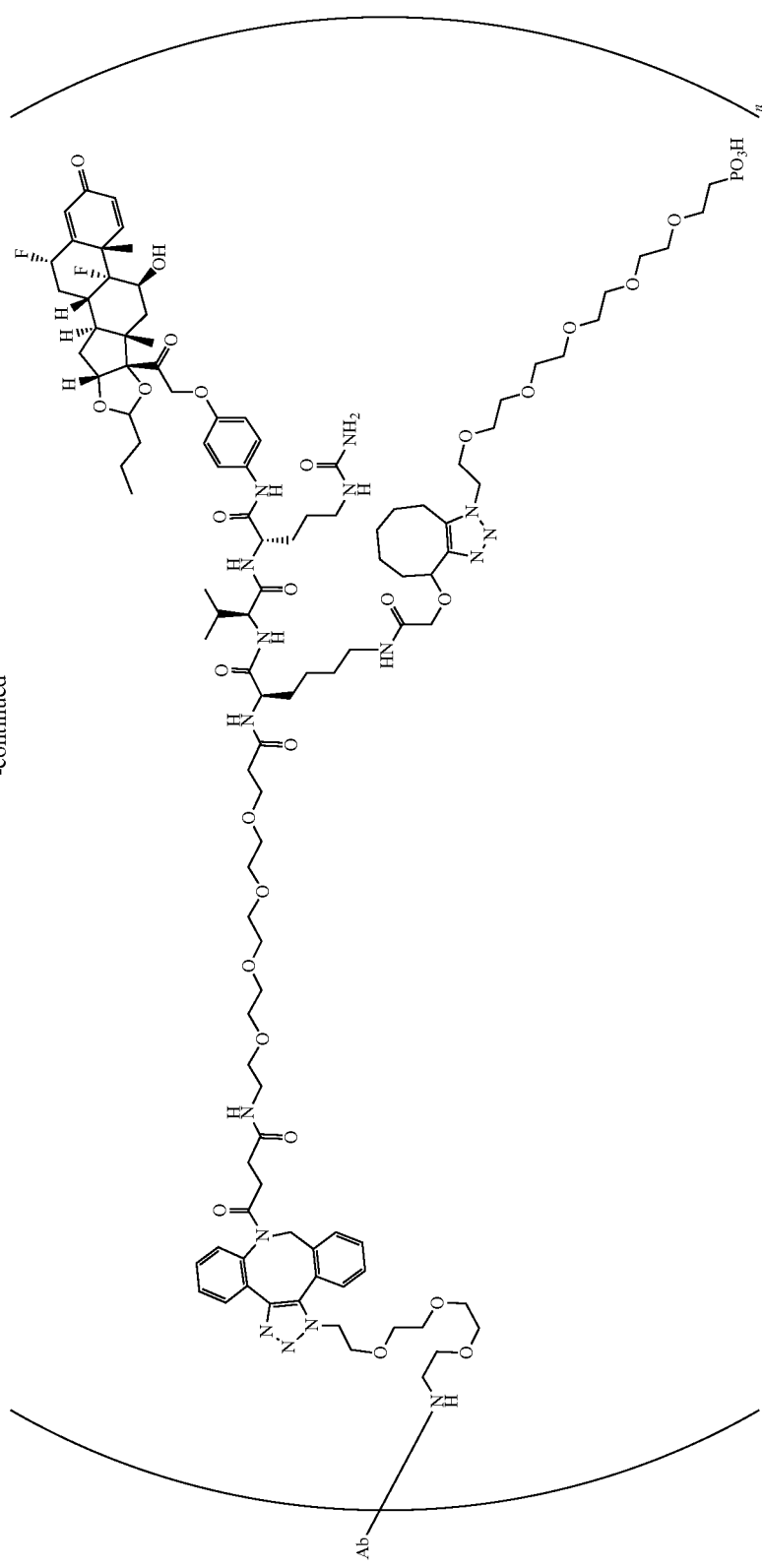

-continued
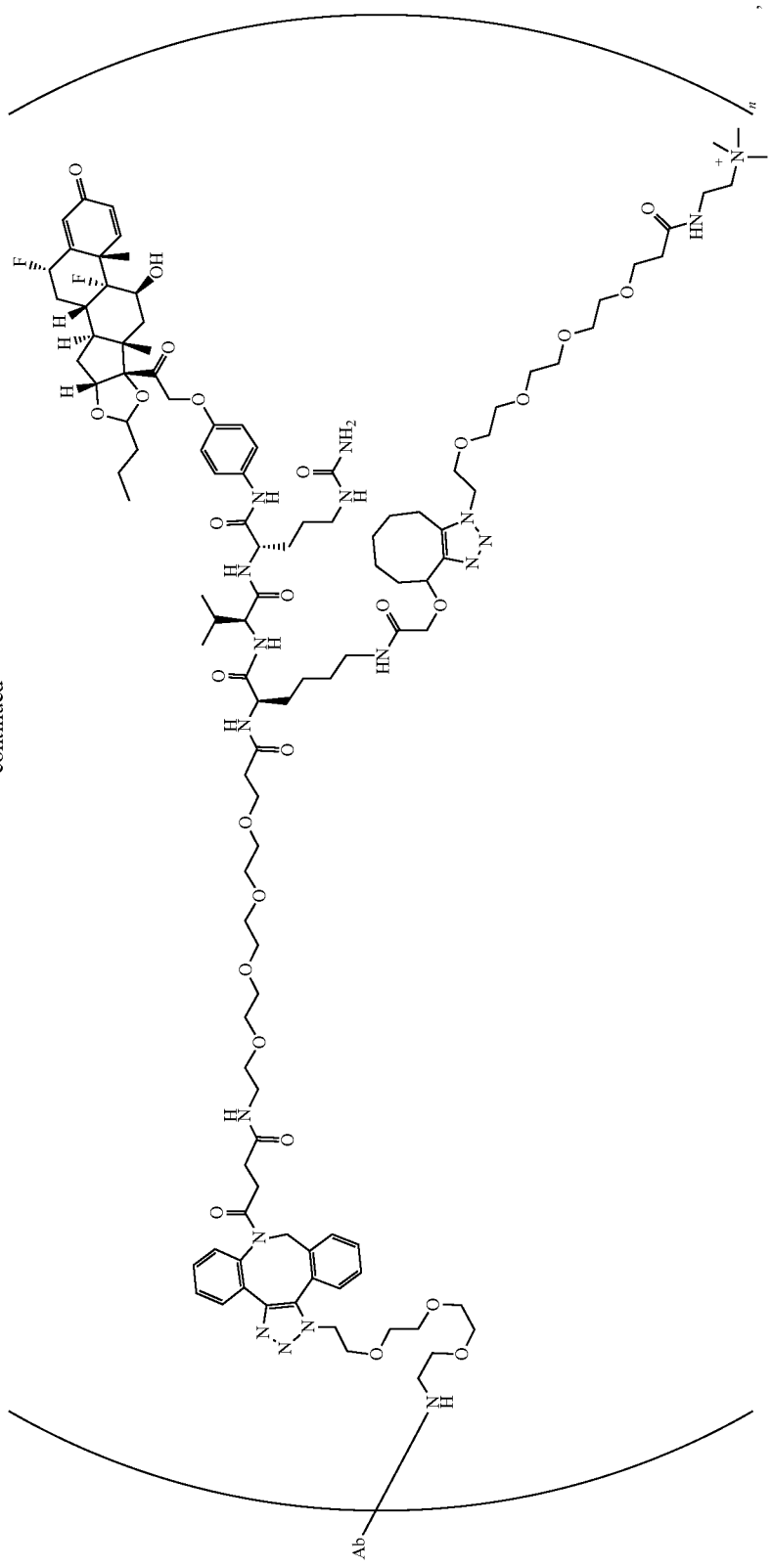

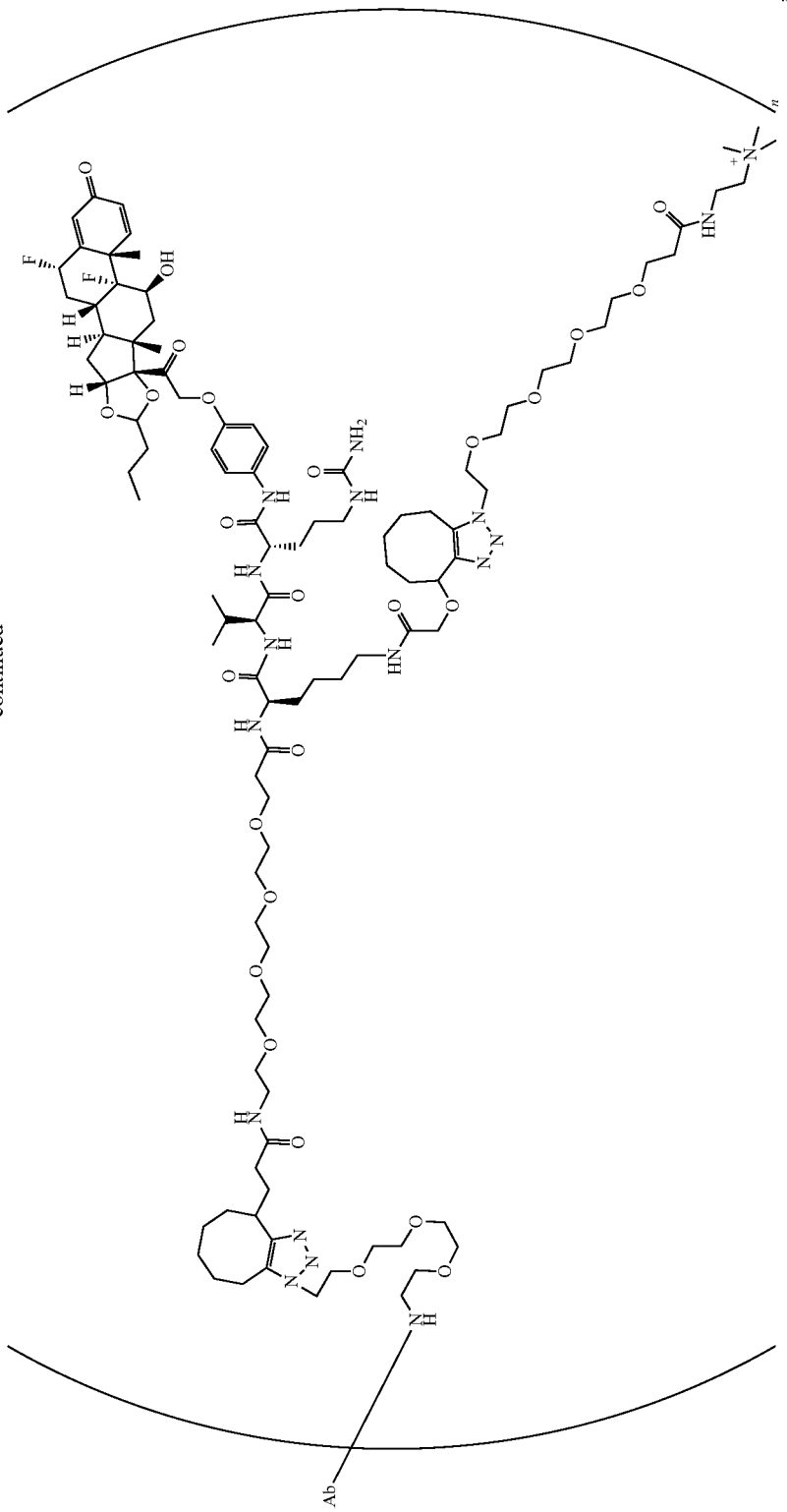

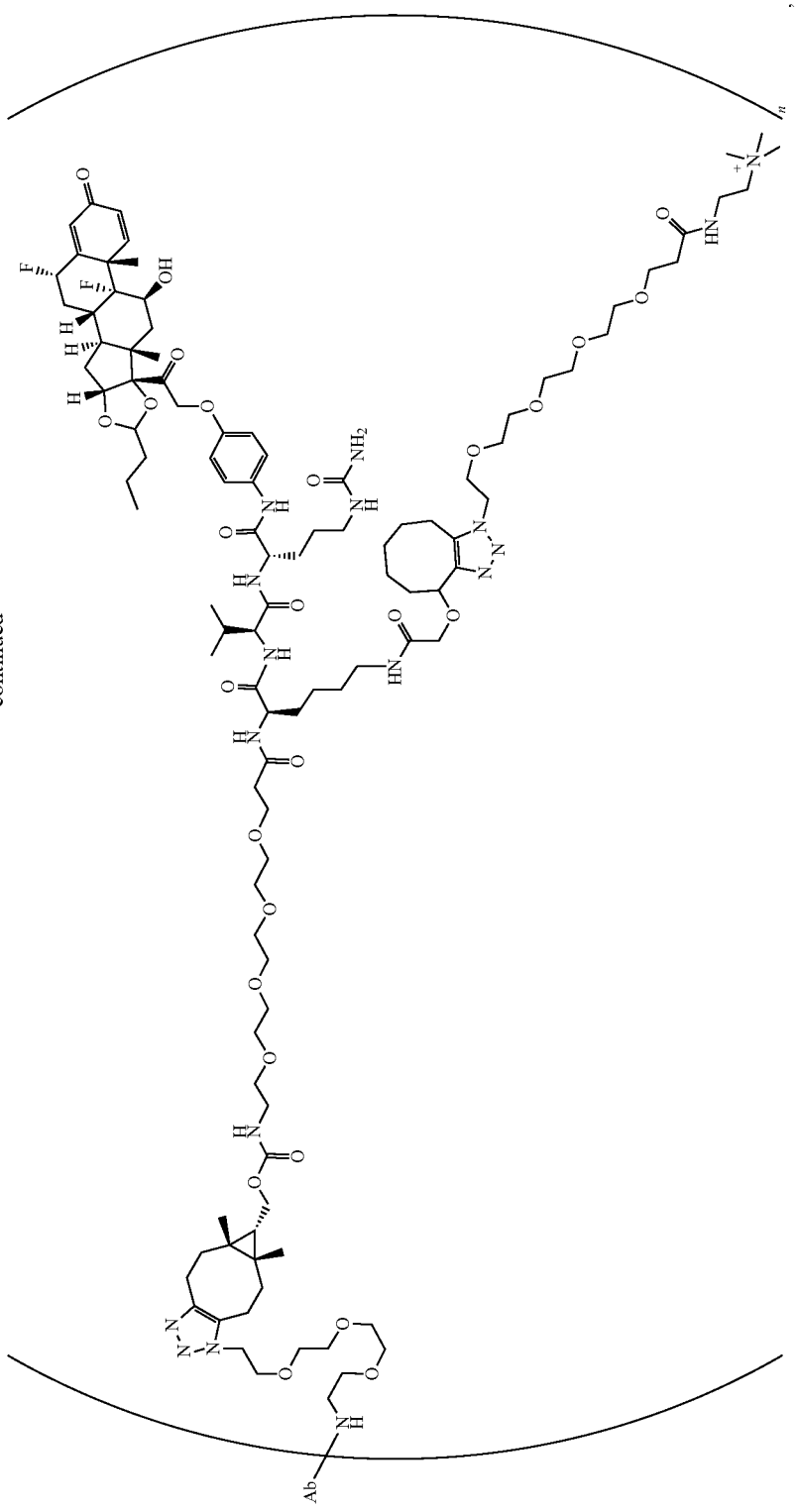

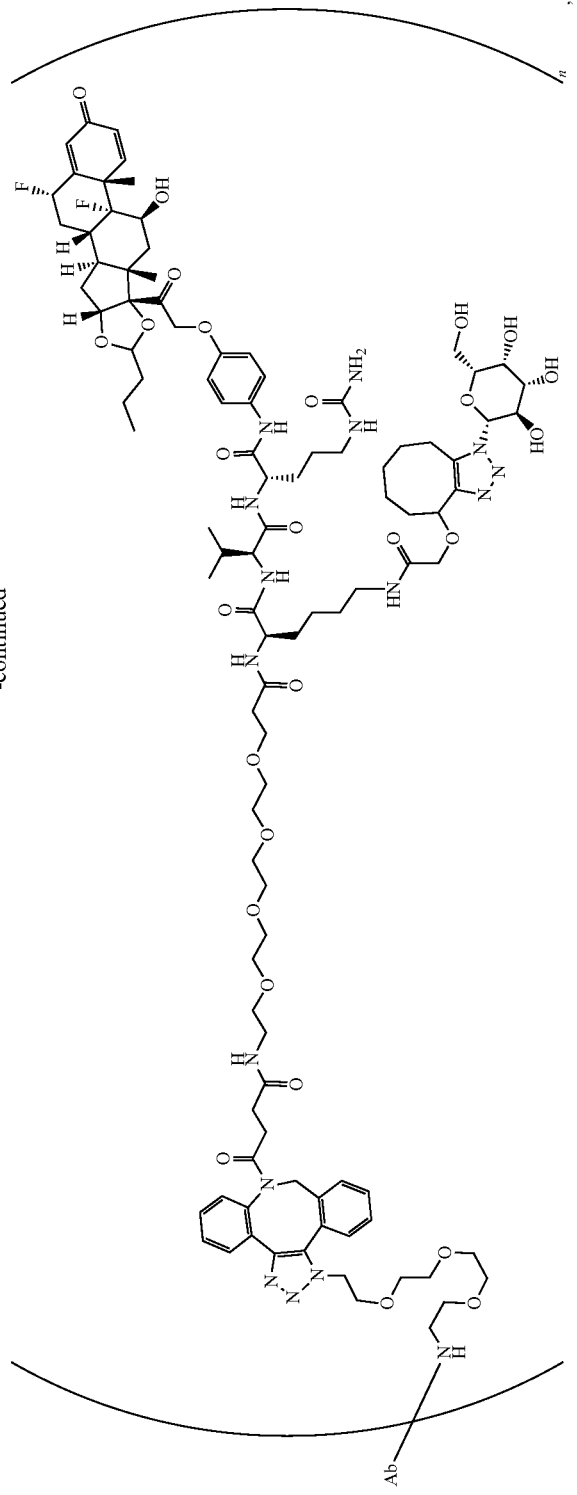

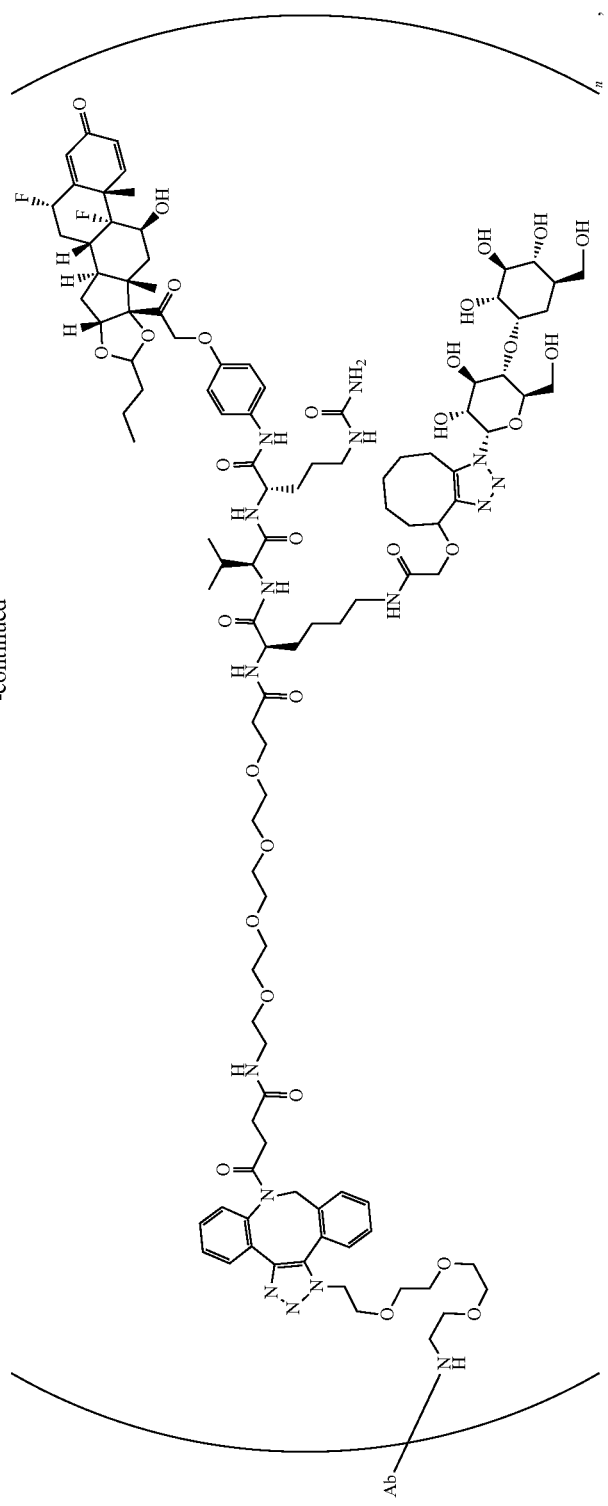

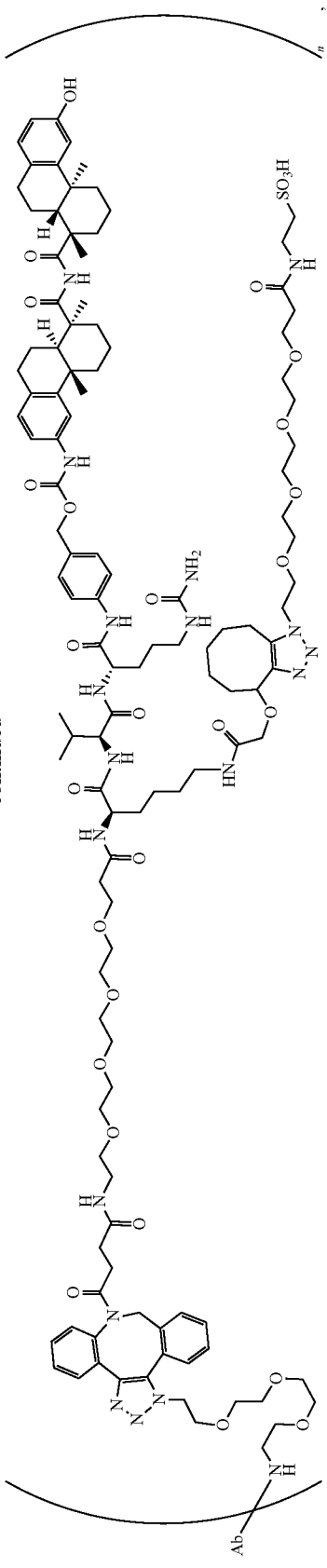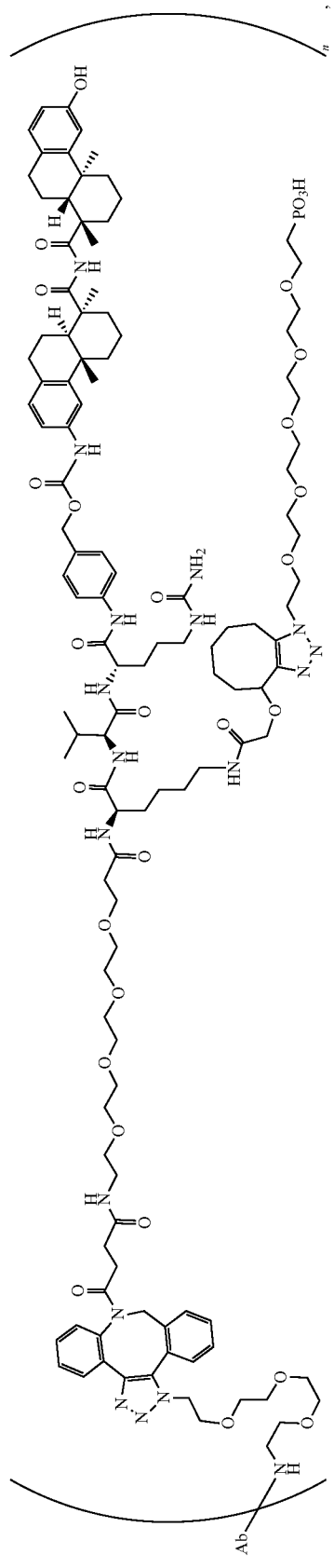

-continued
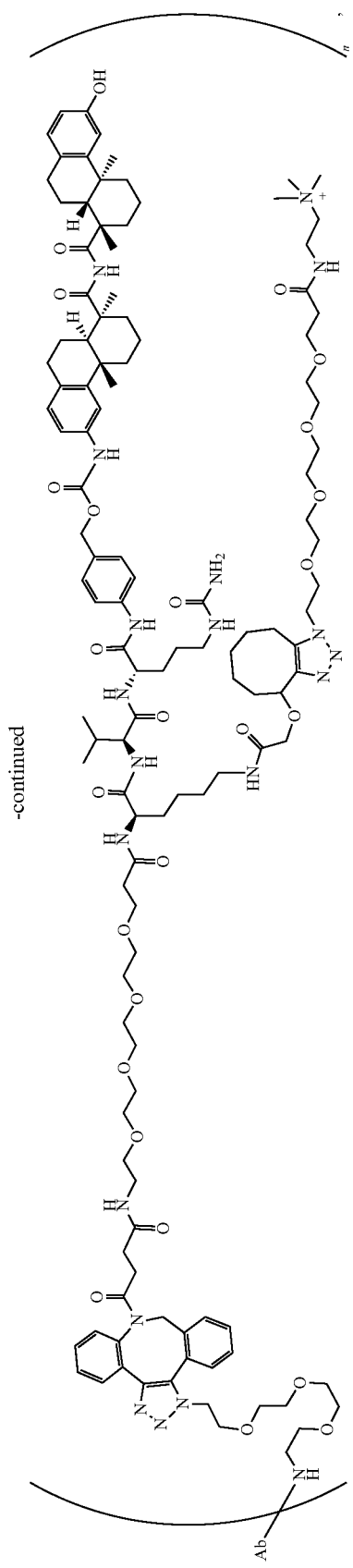
501
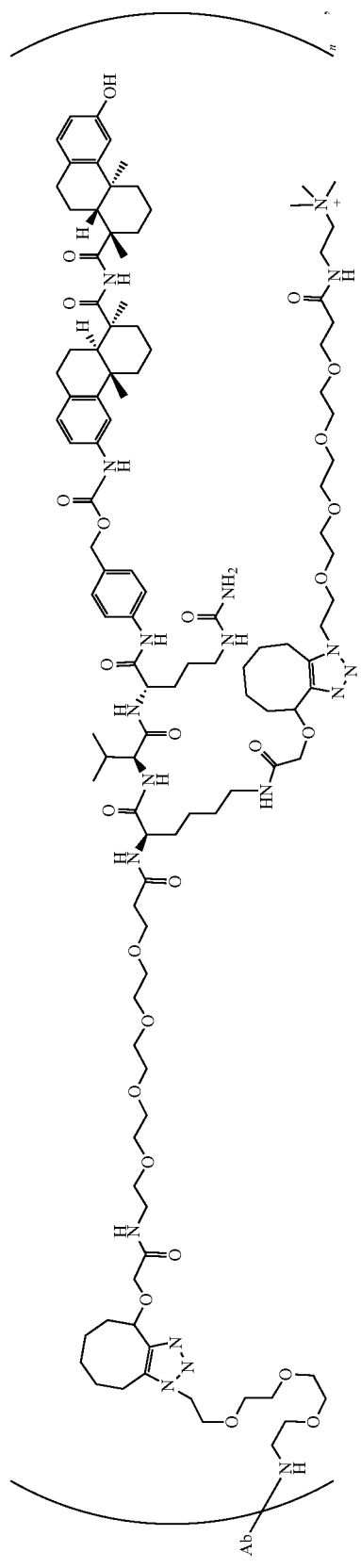
502

-continued
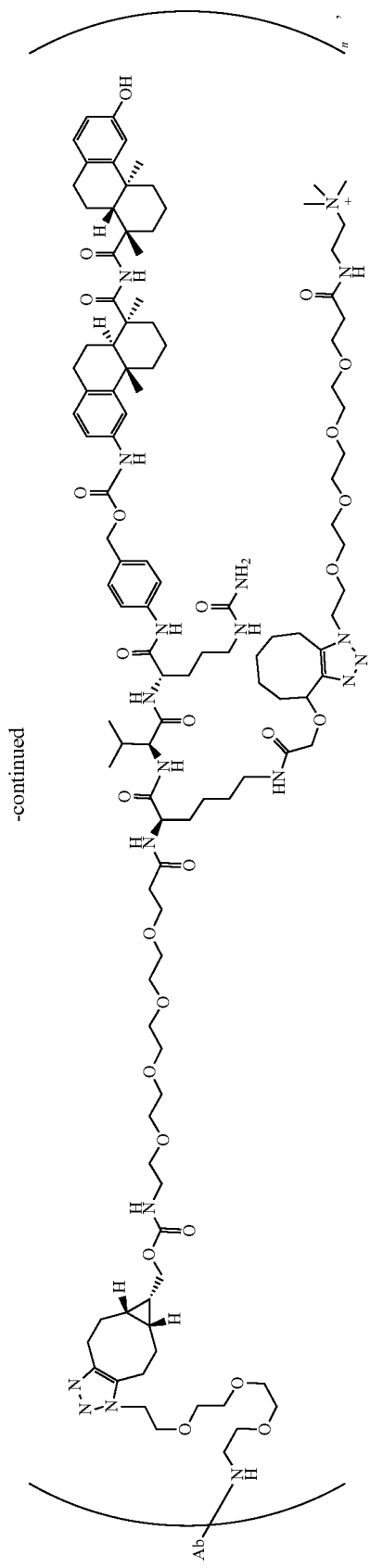
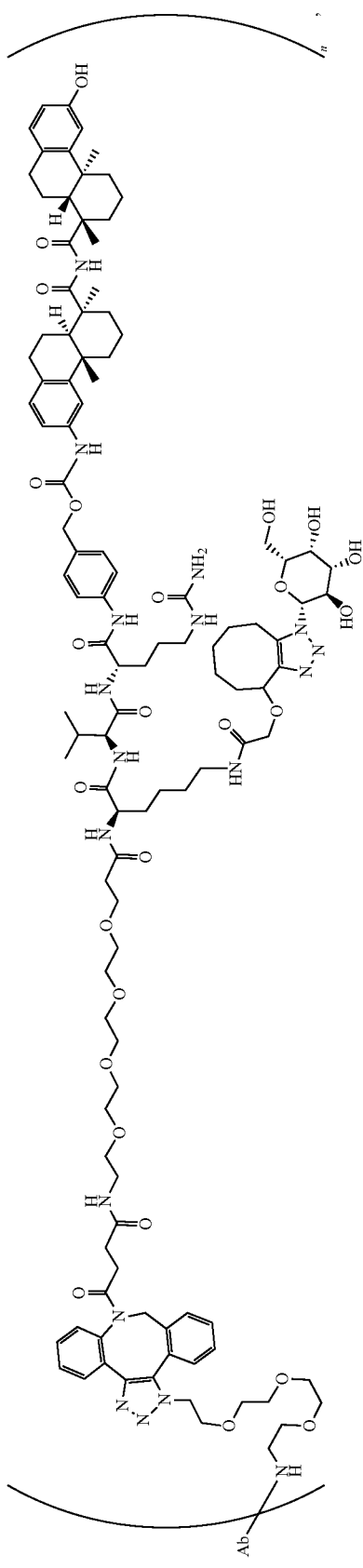

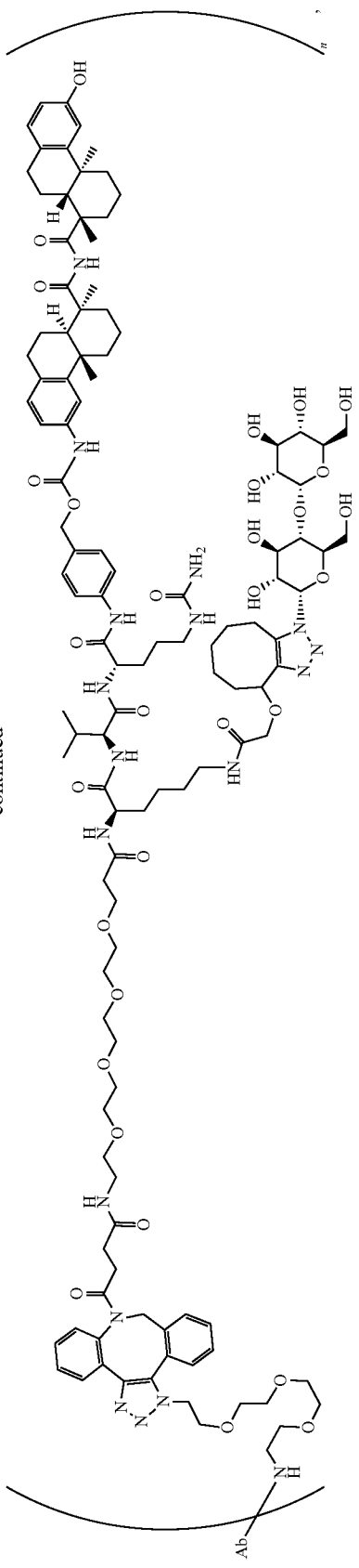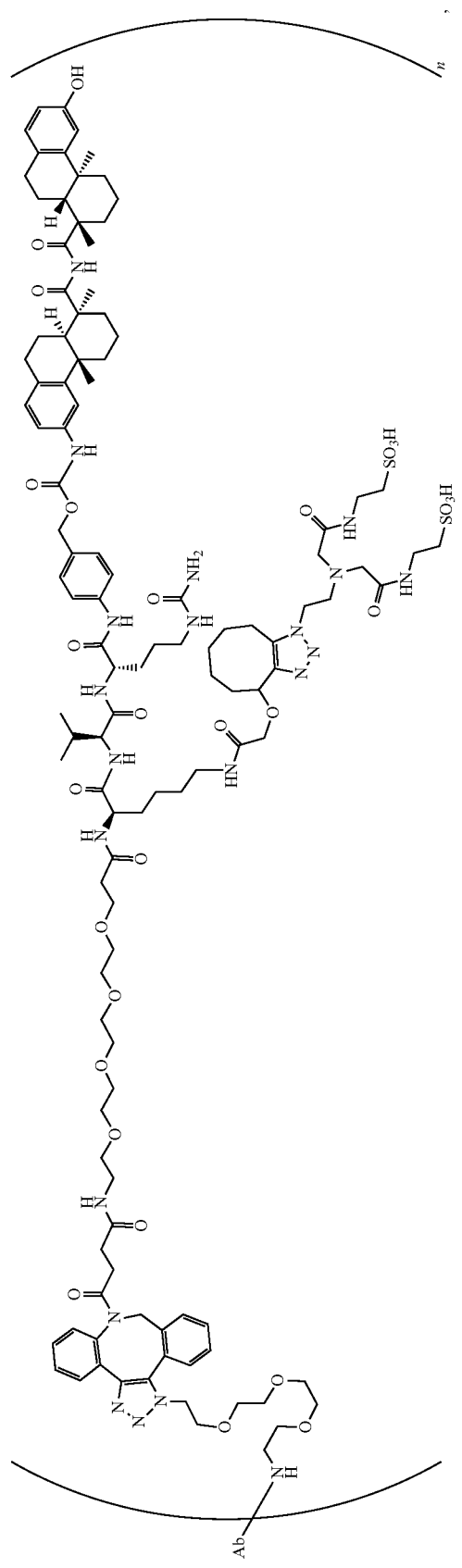

-continued
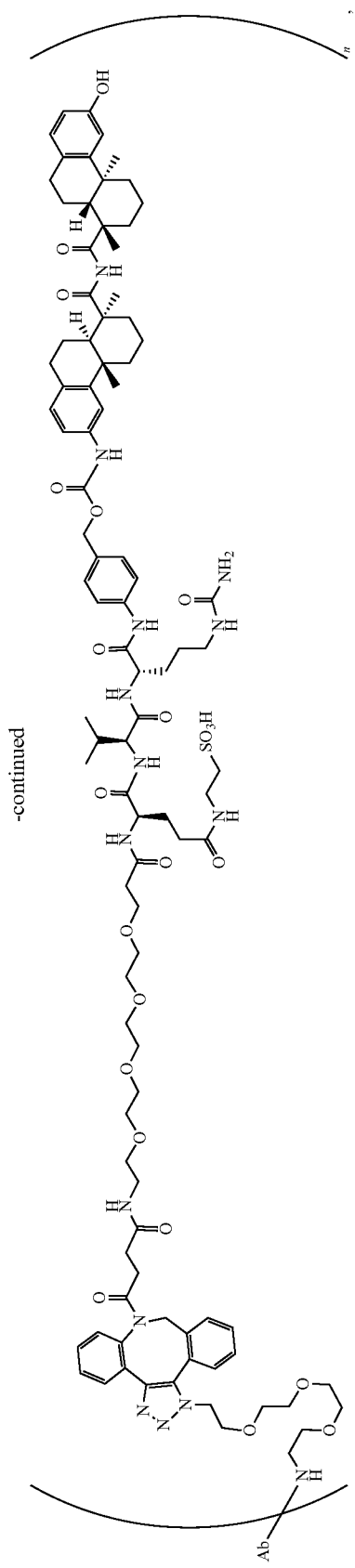

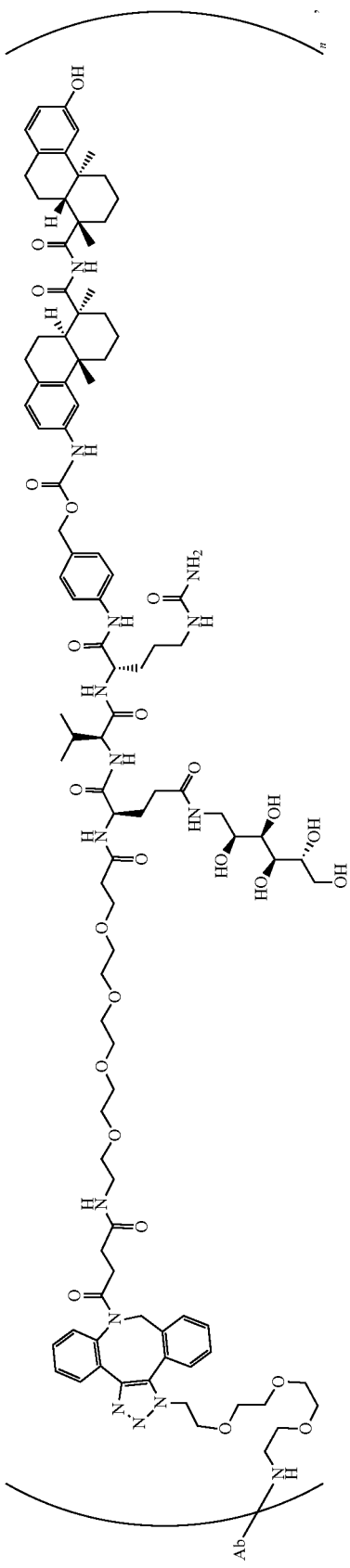
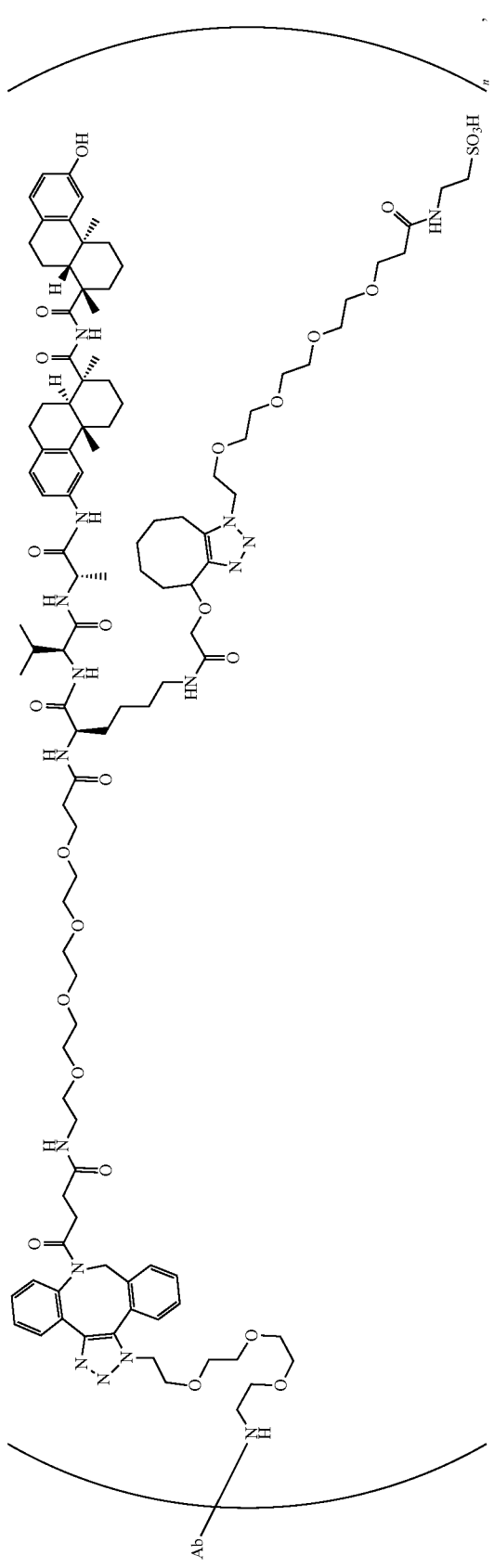

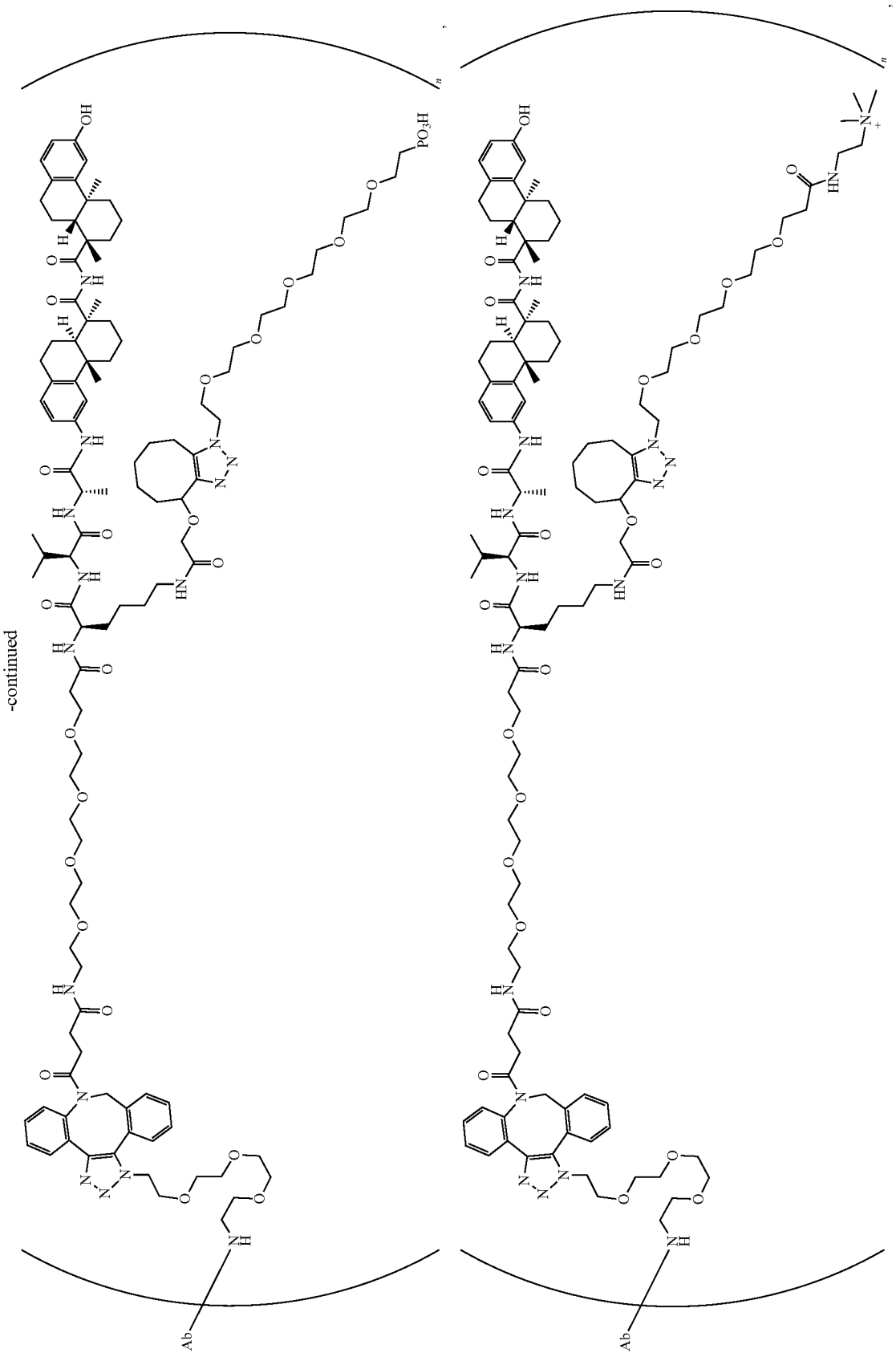

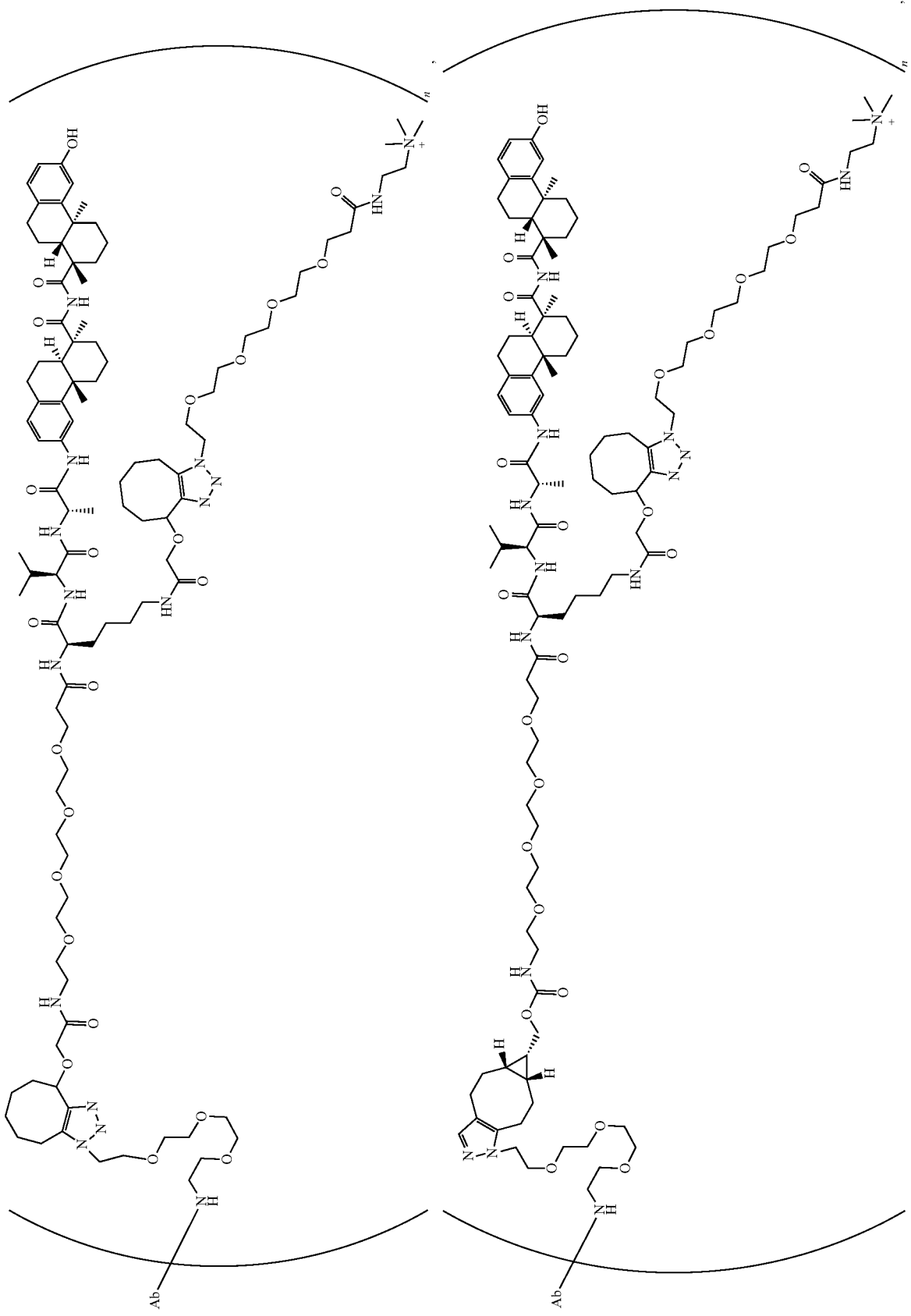

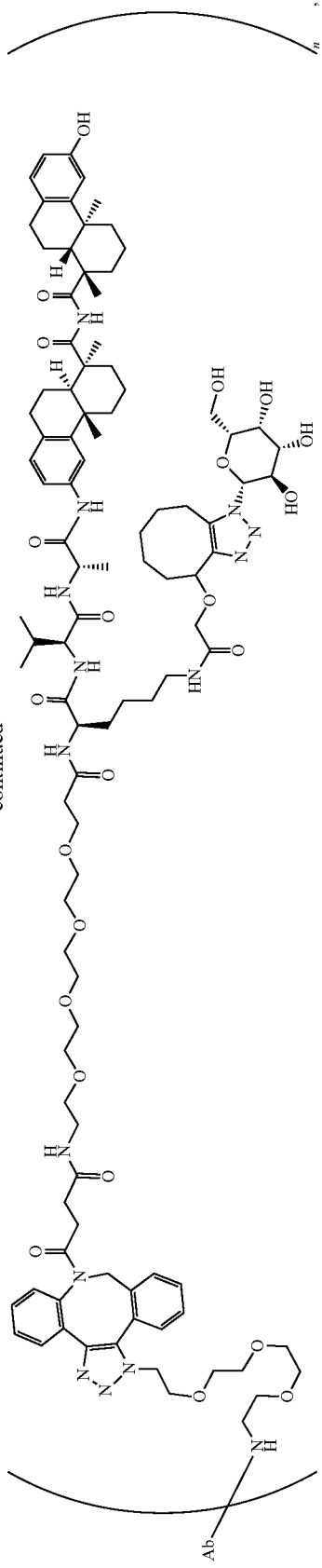
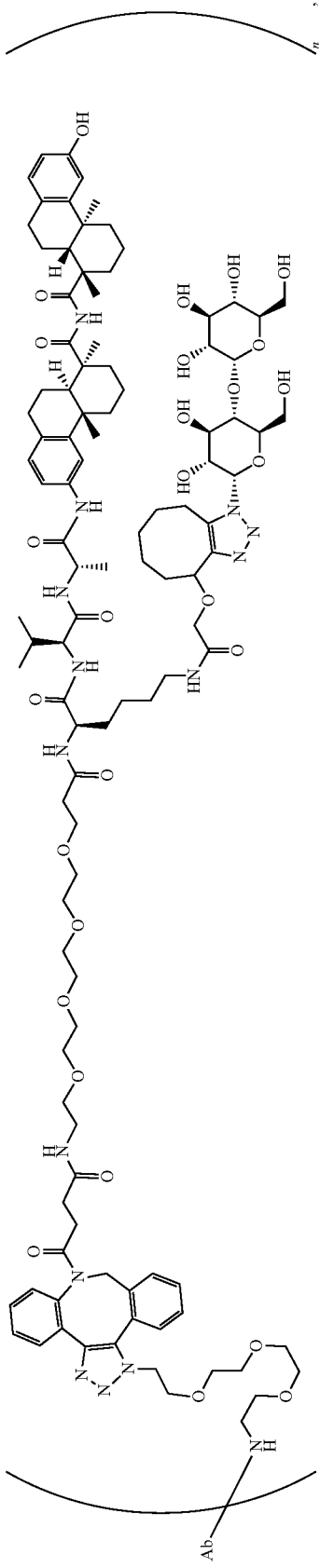

-continued
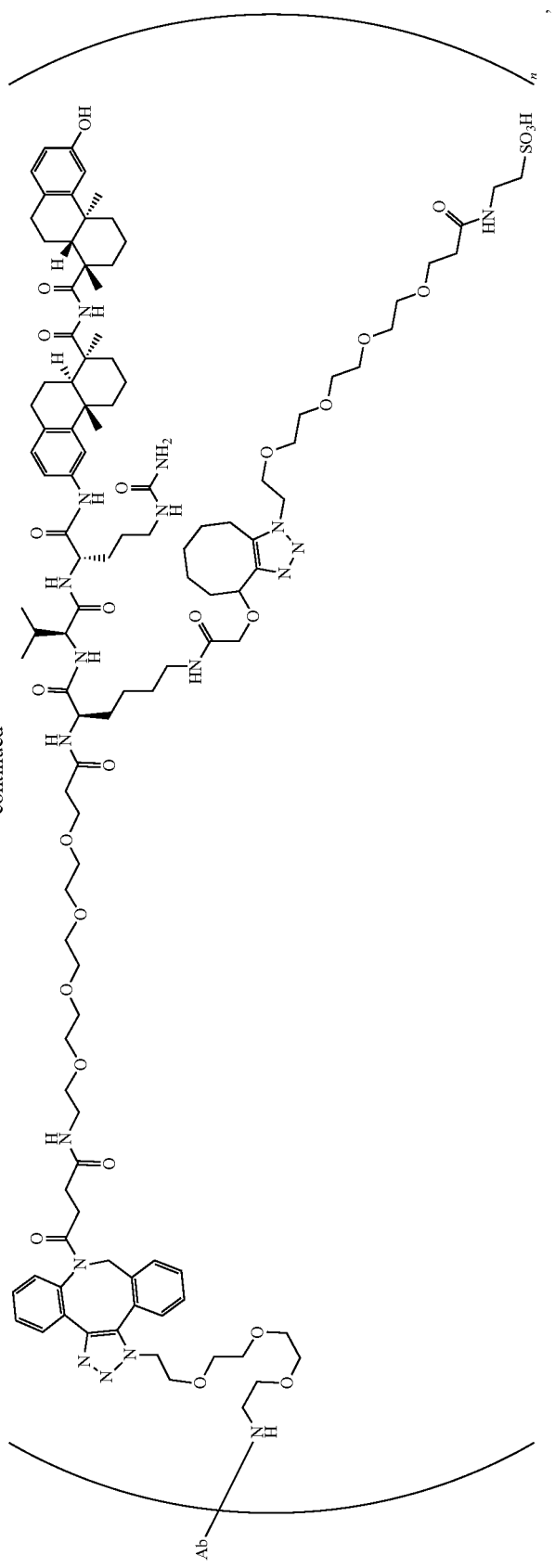

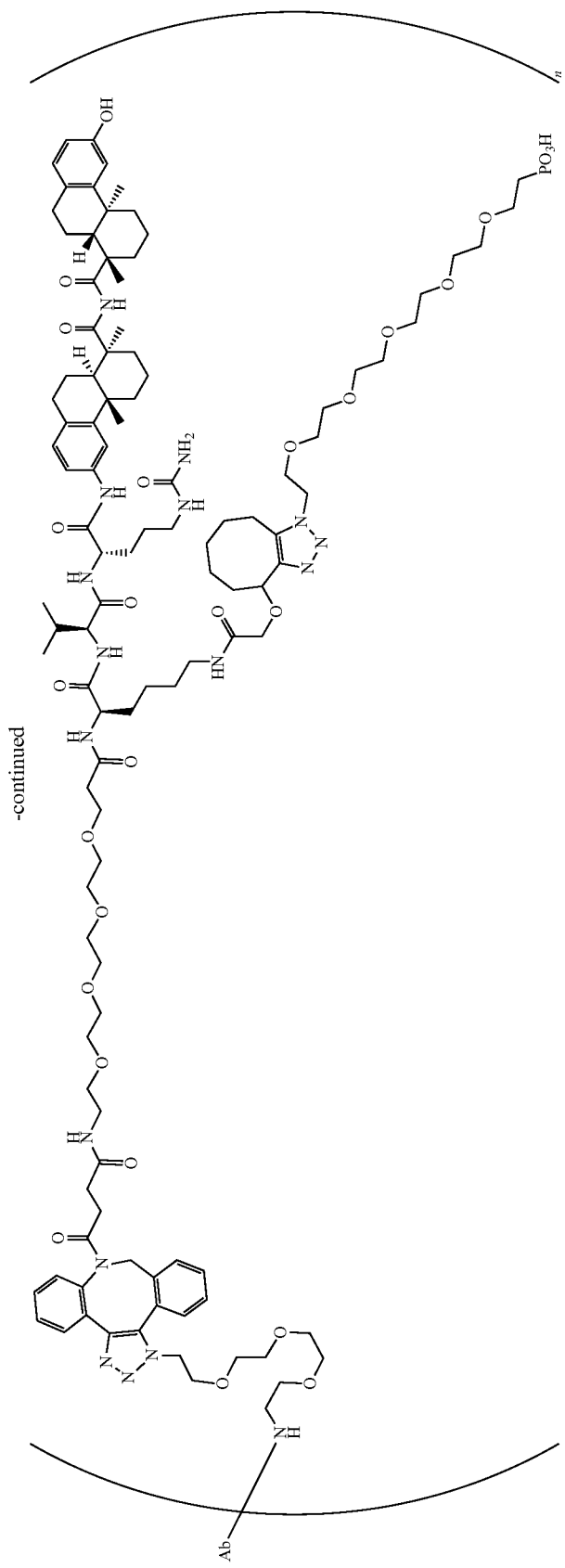

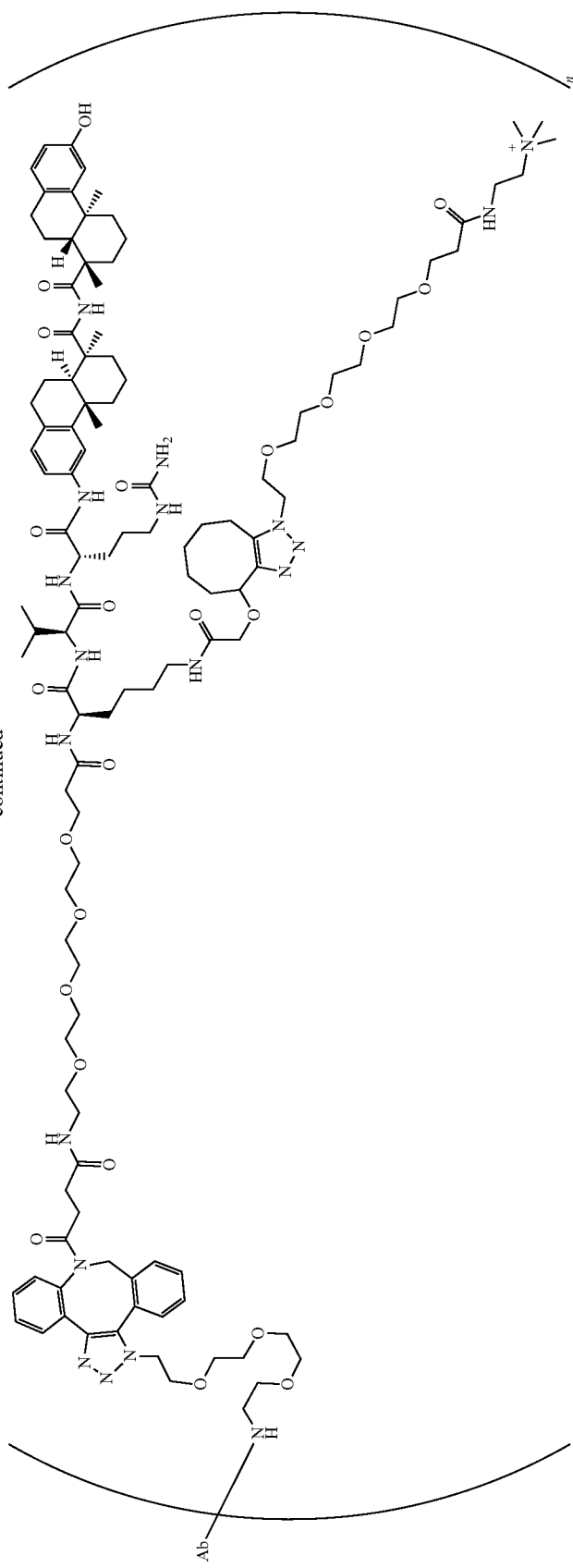

-continued
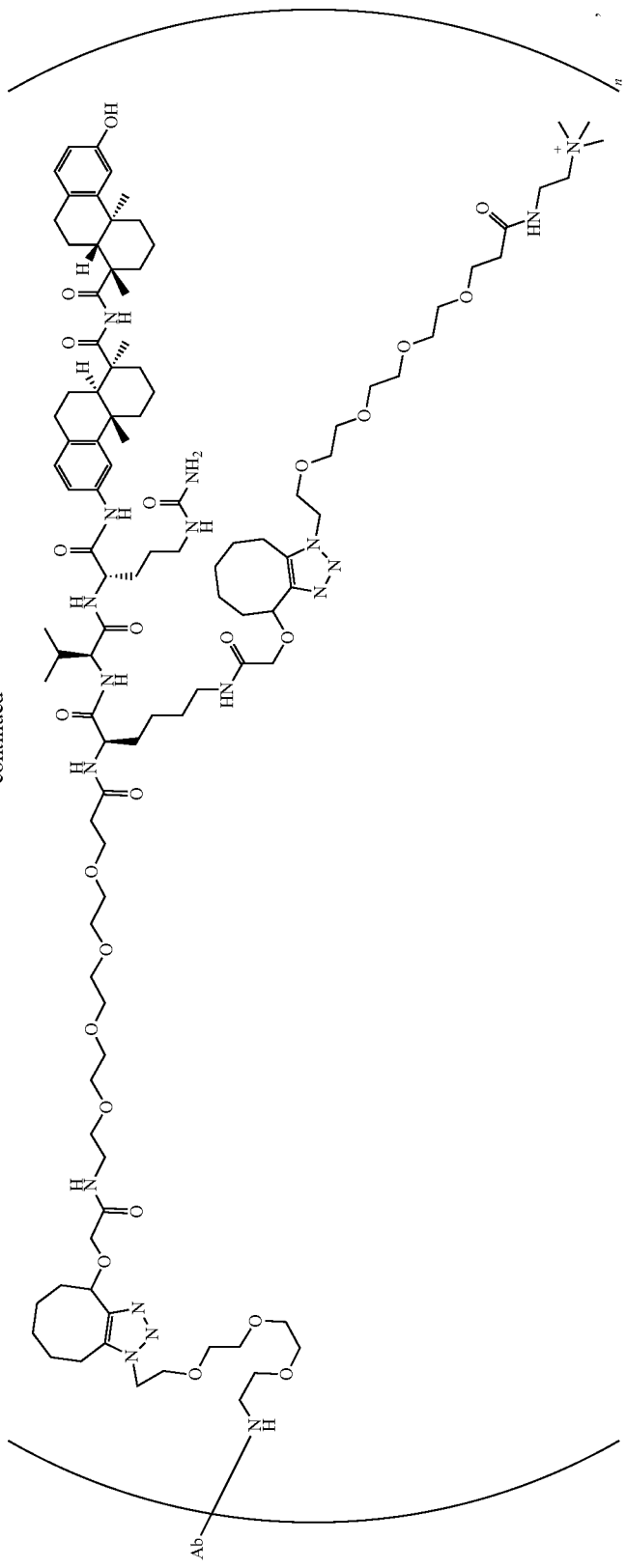

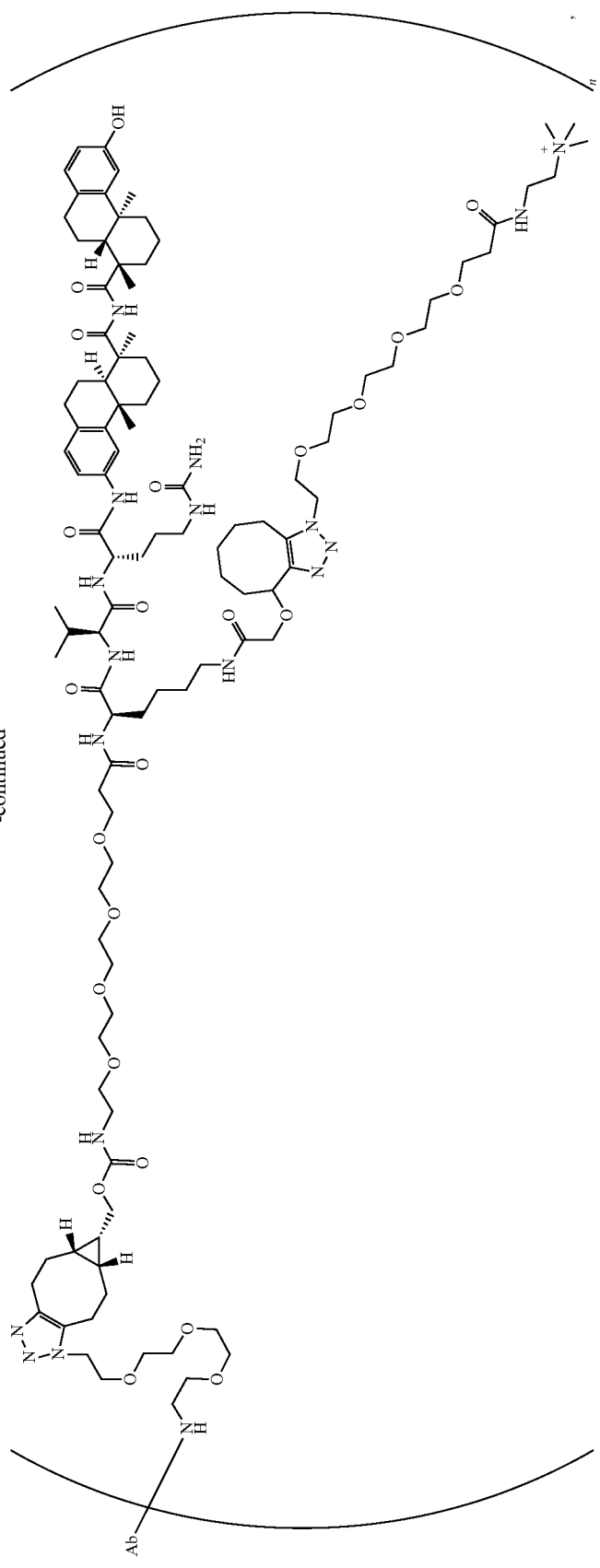

-continued
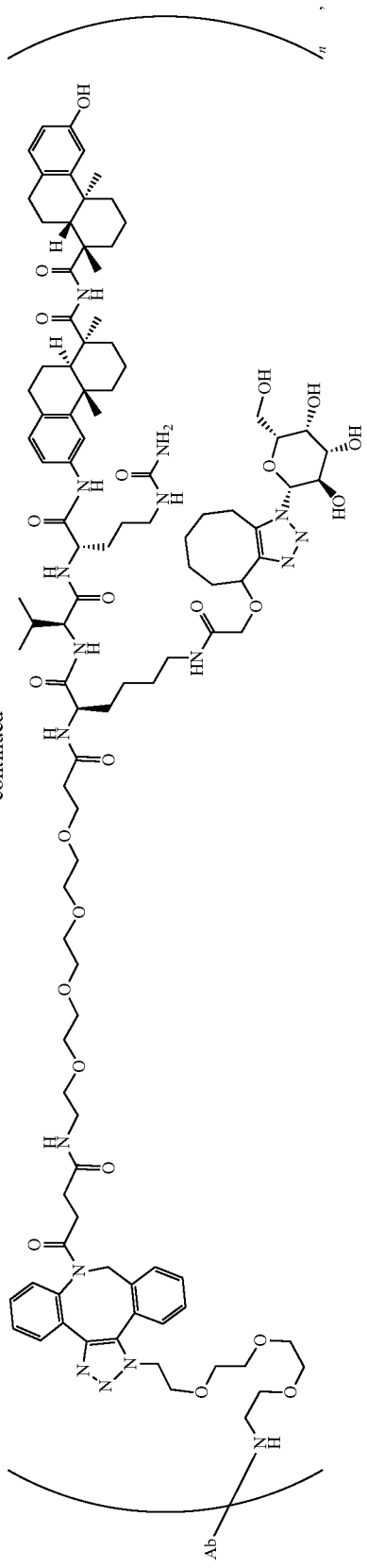
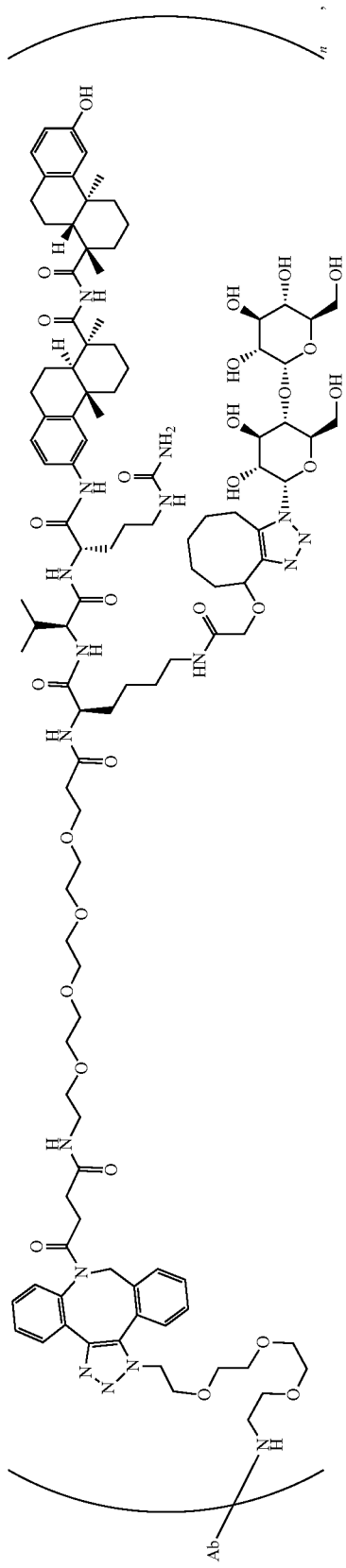

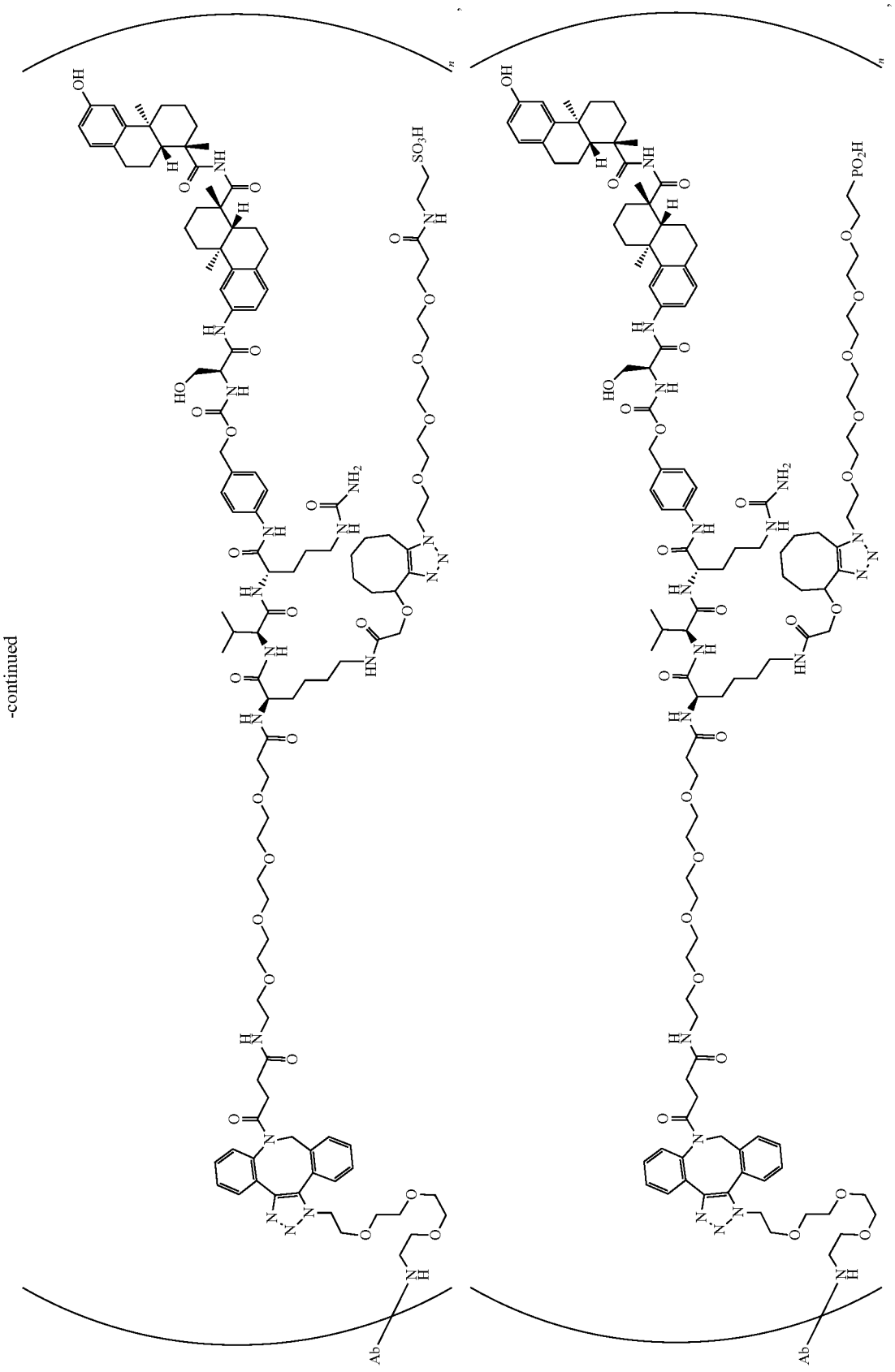

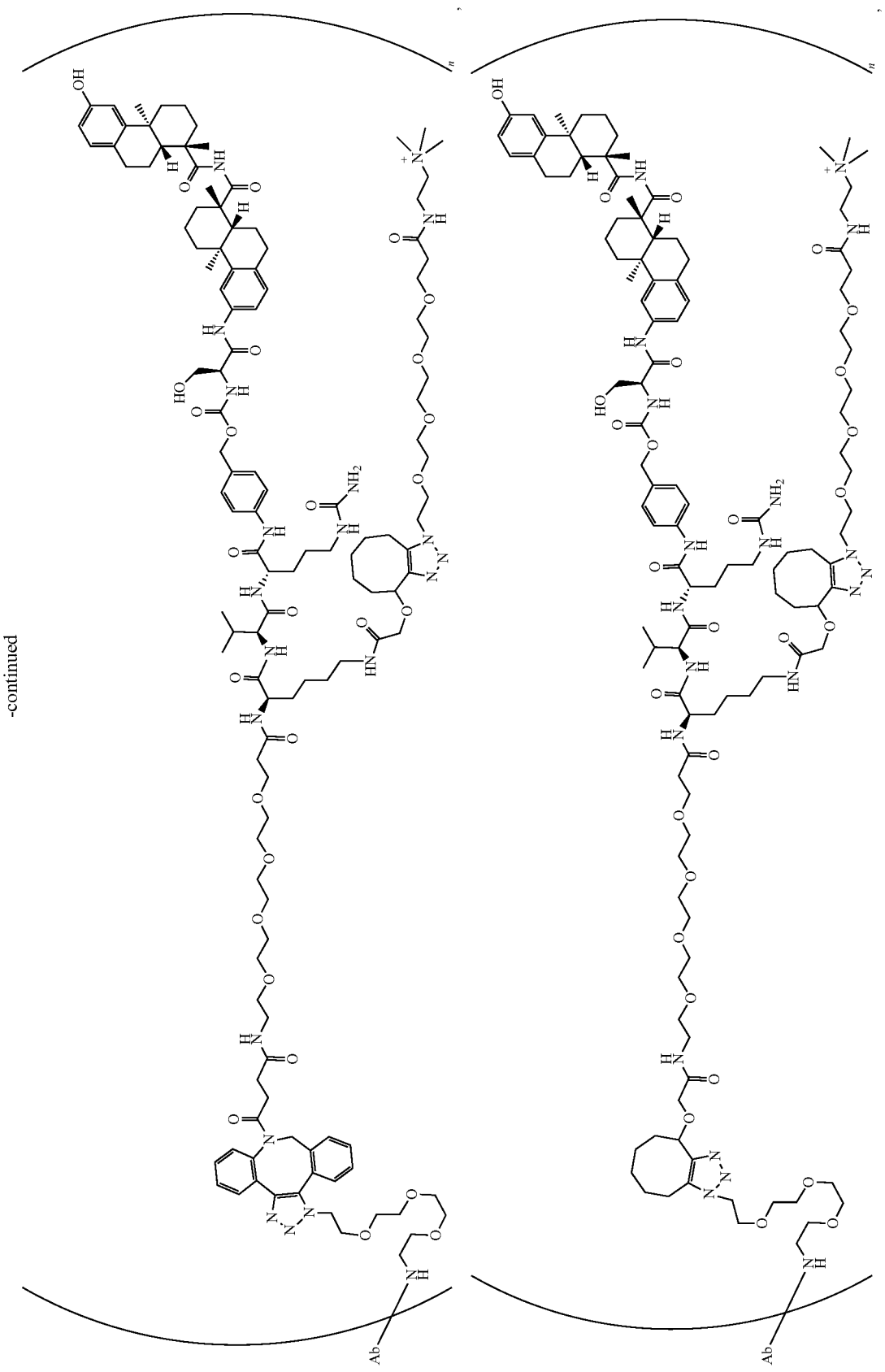

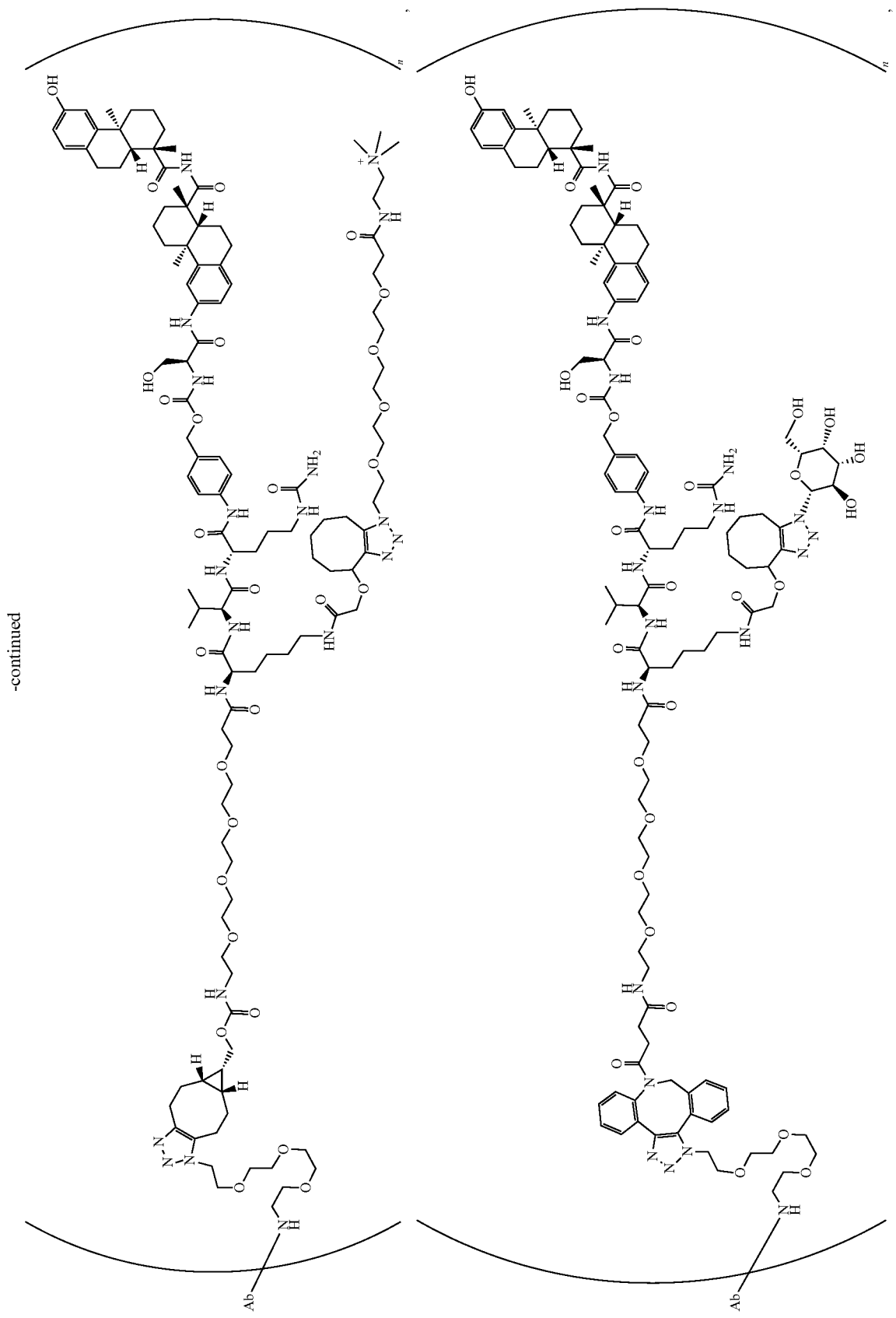

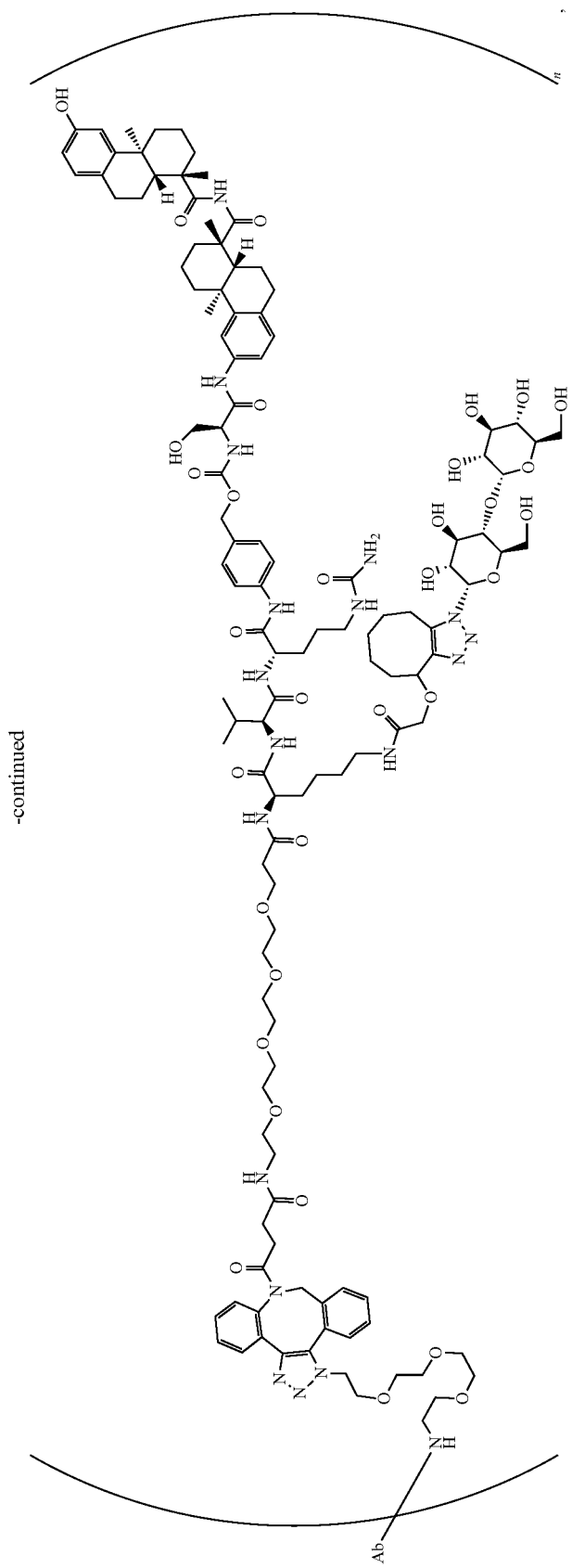

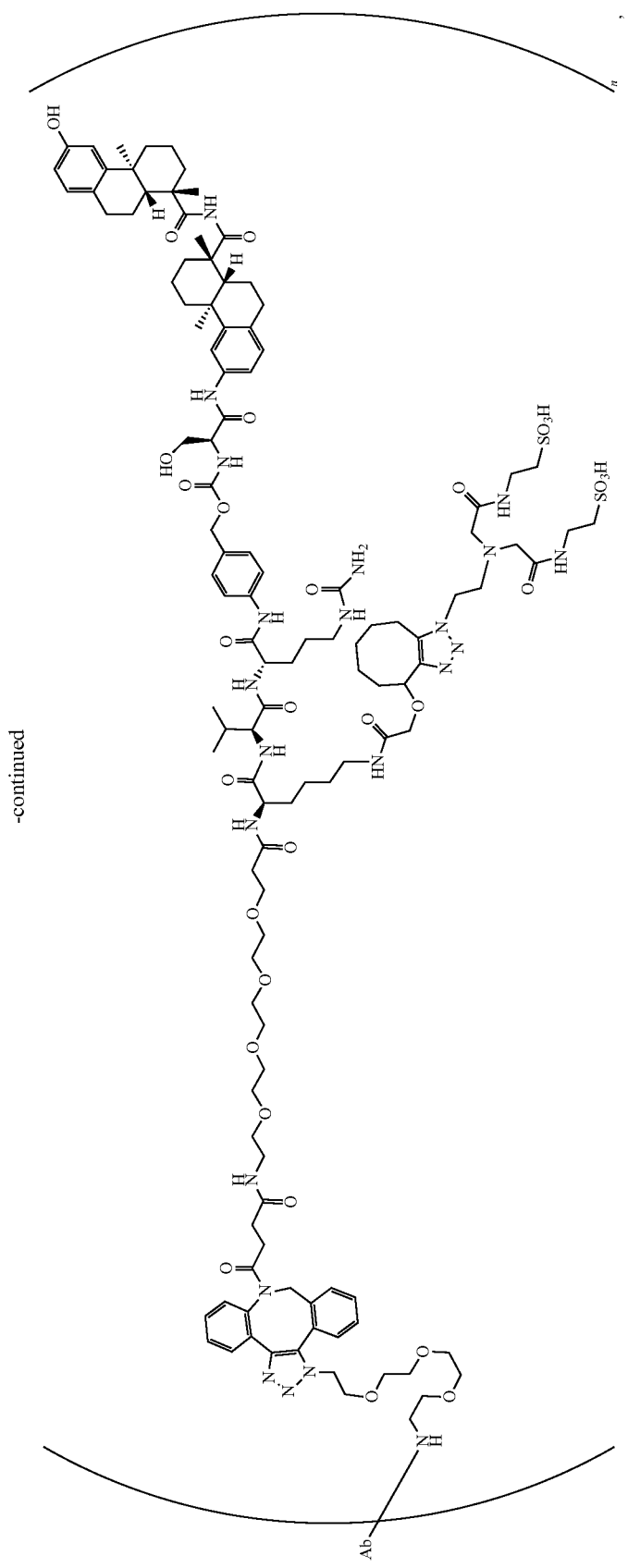

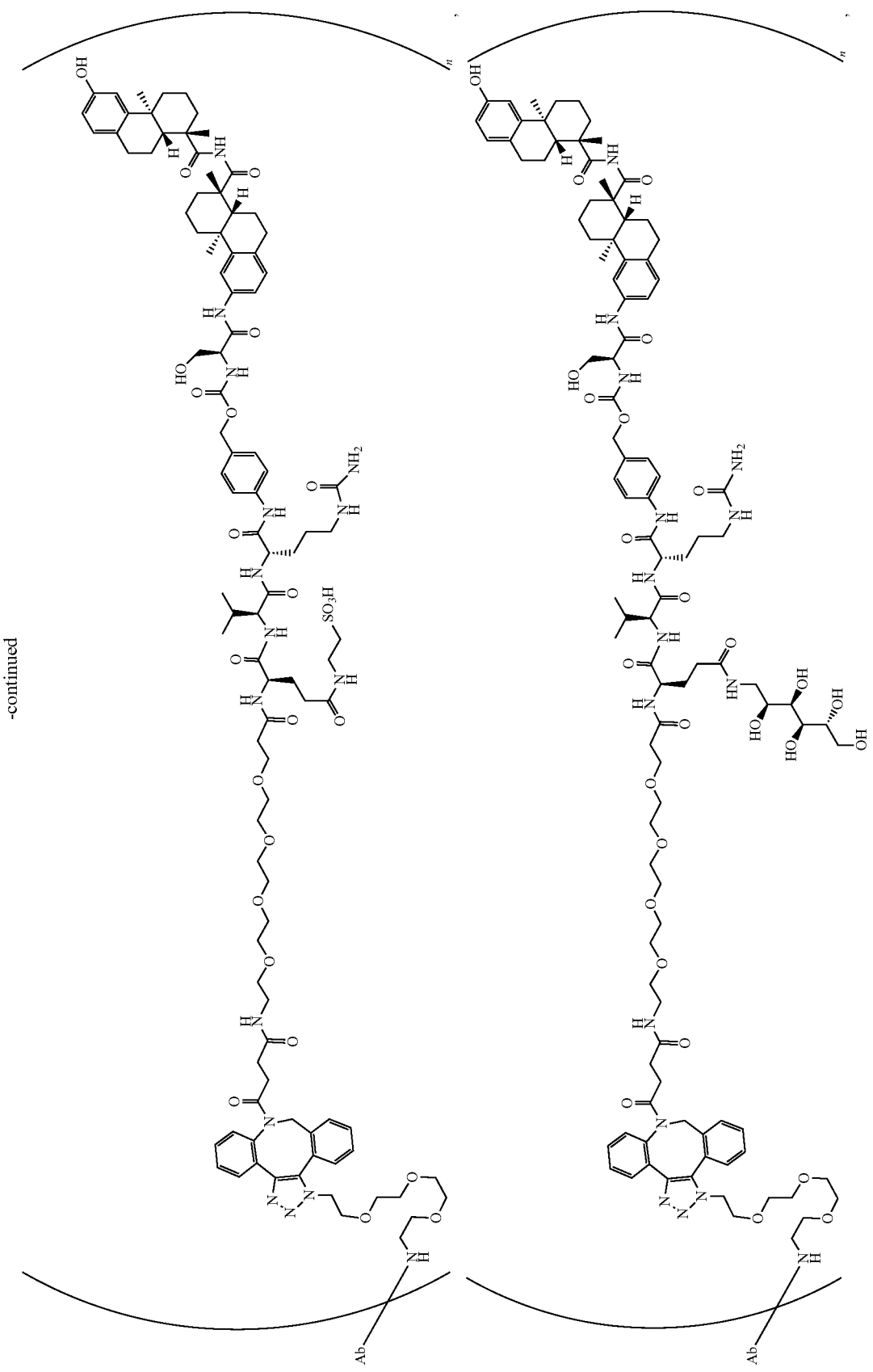

-continued

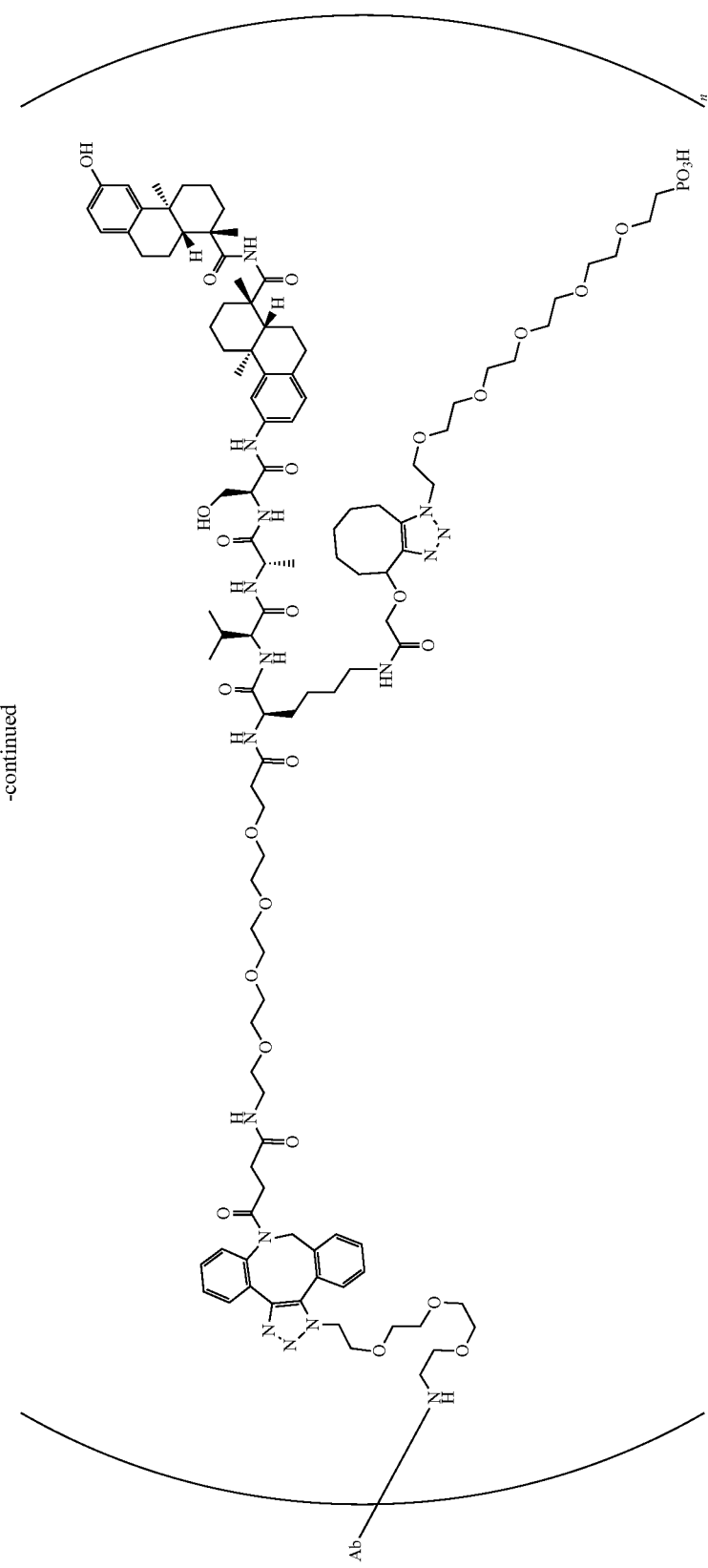

-continued
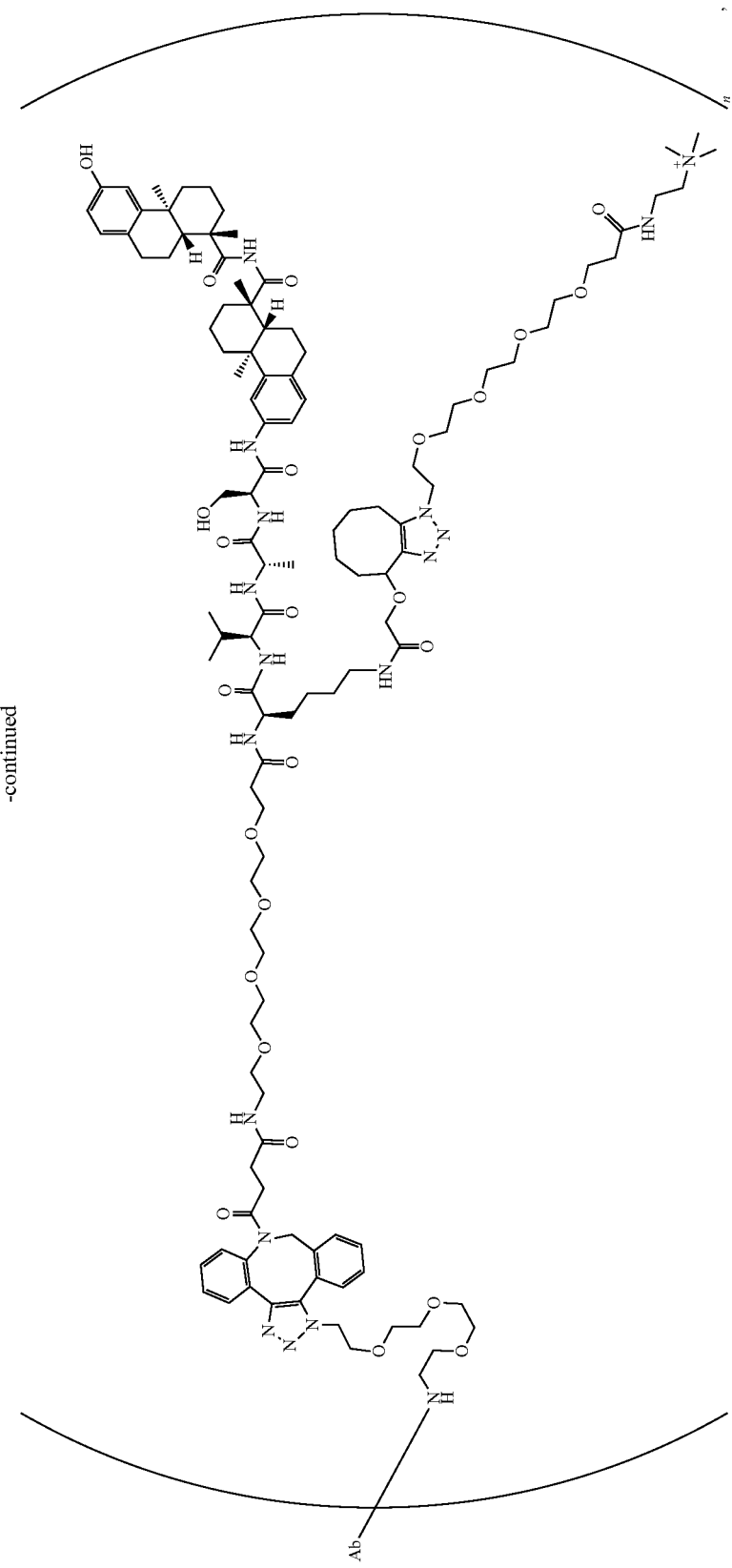

-continued
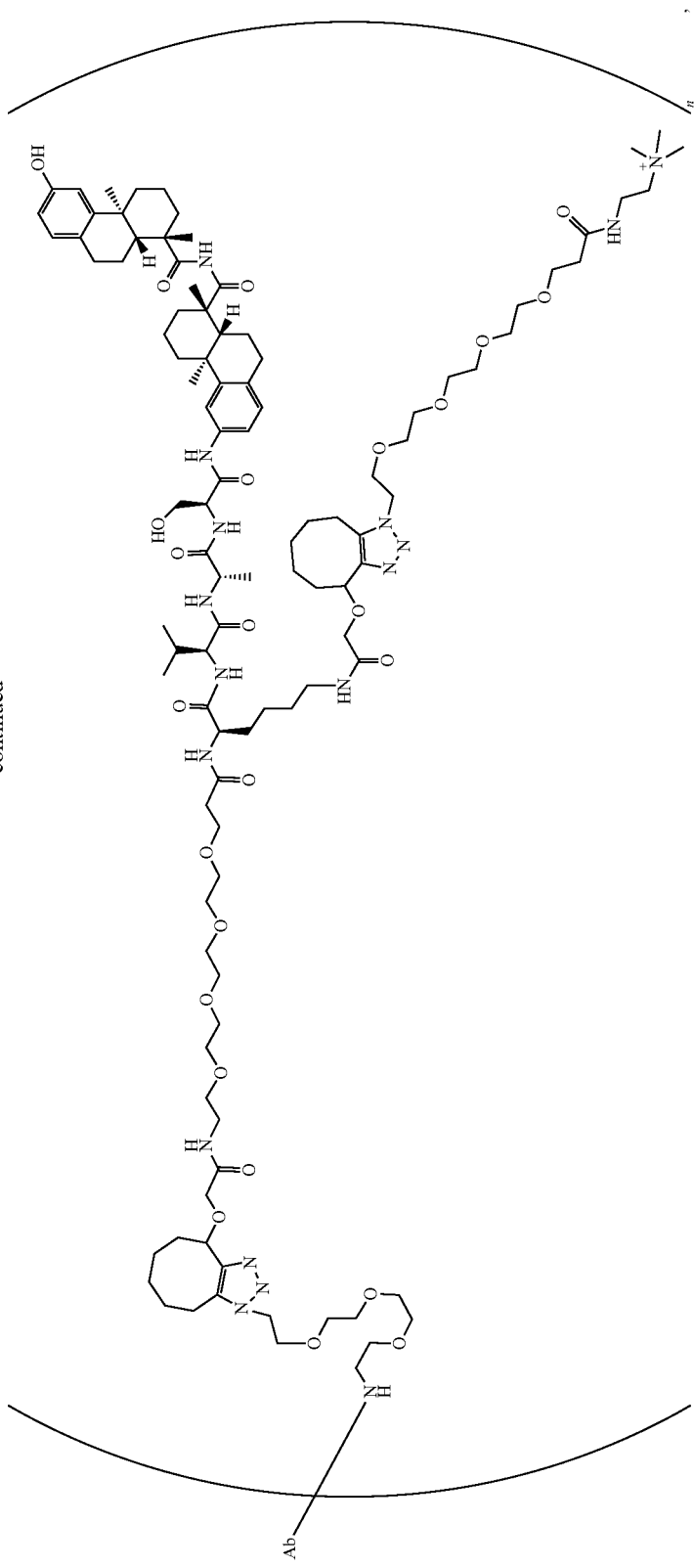

-continued
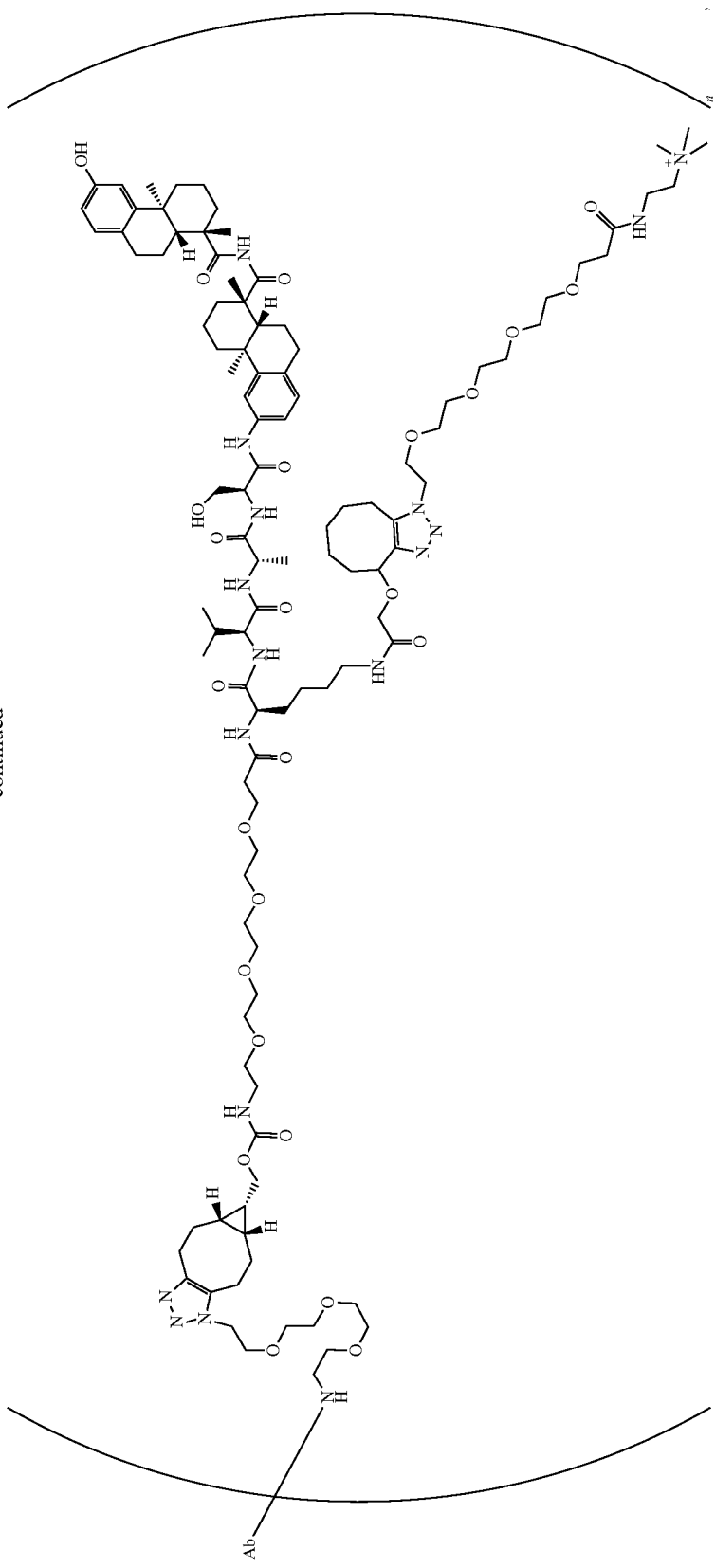

-continued
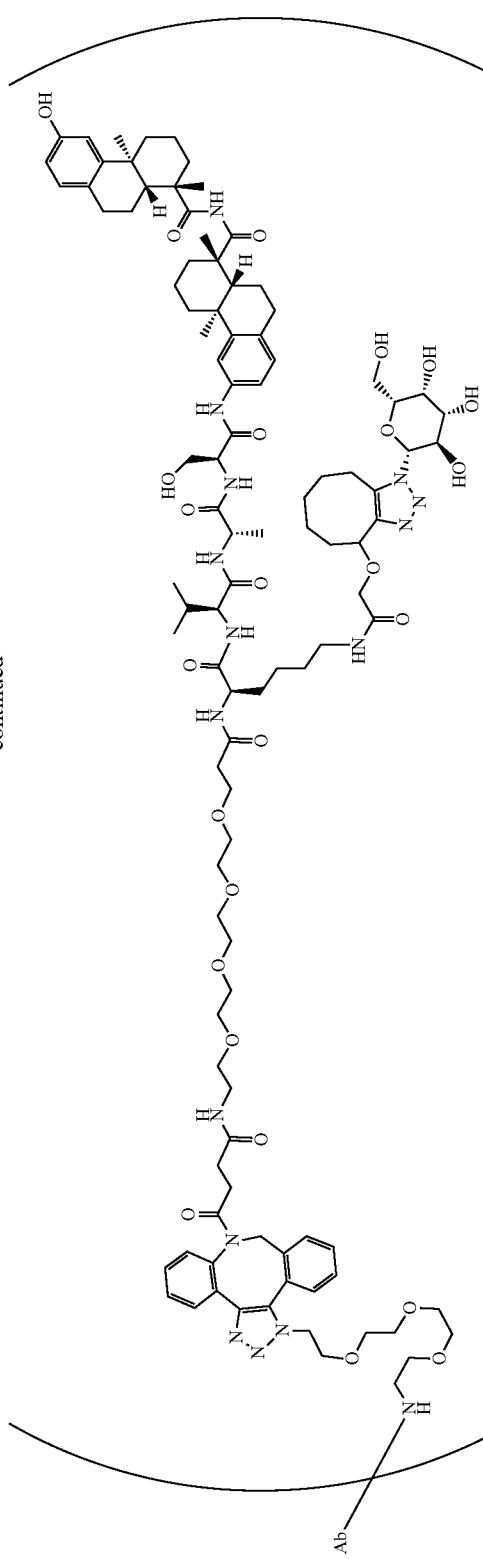
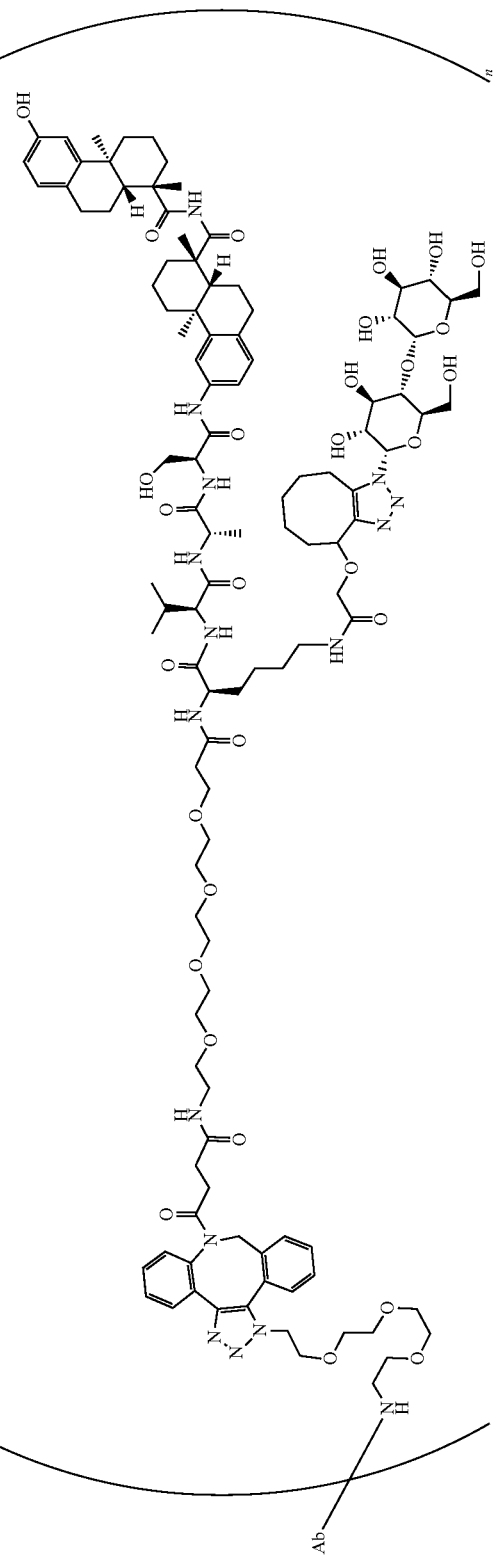

-continued
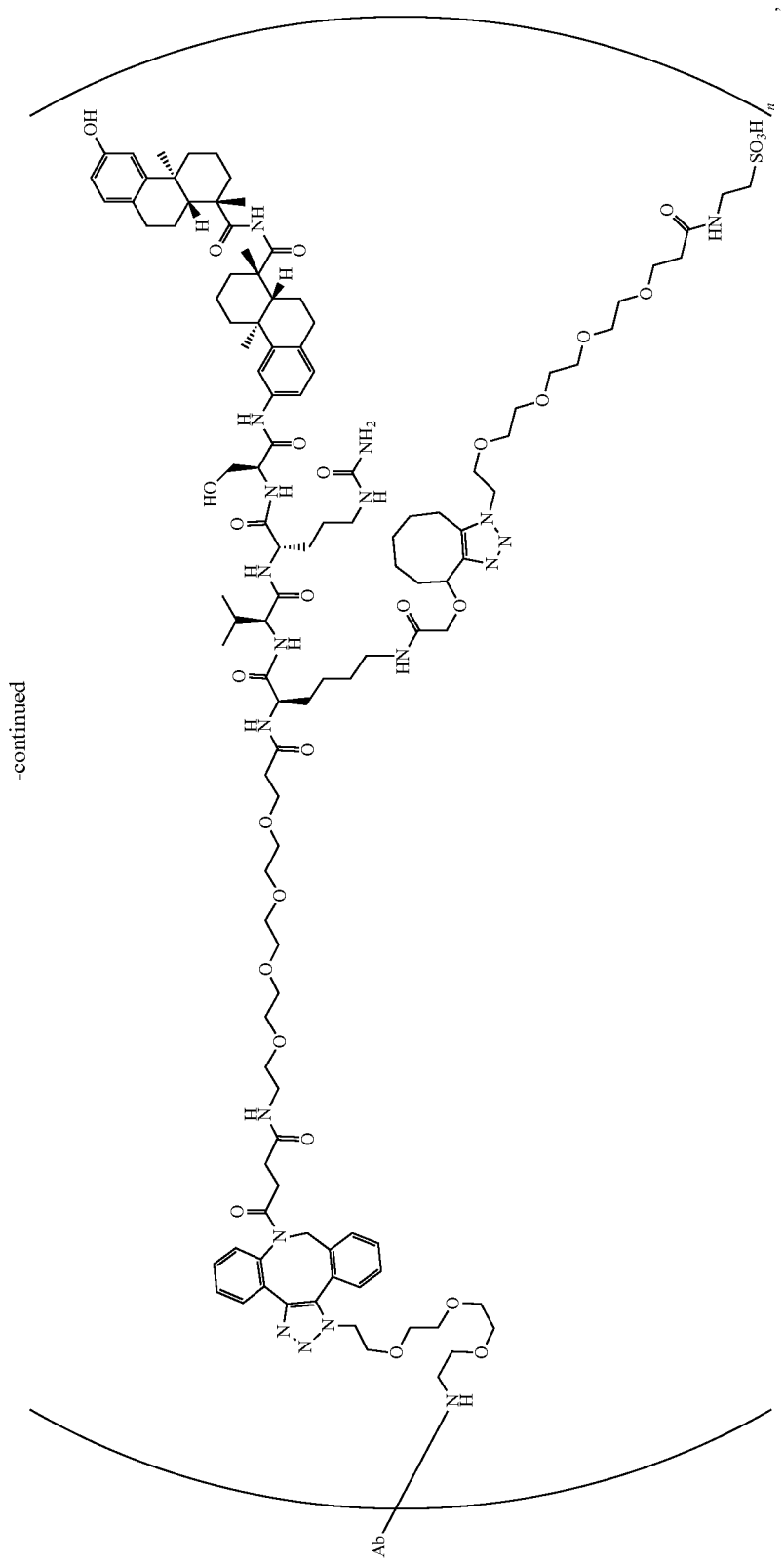

-continued
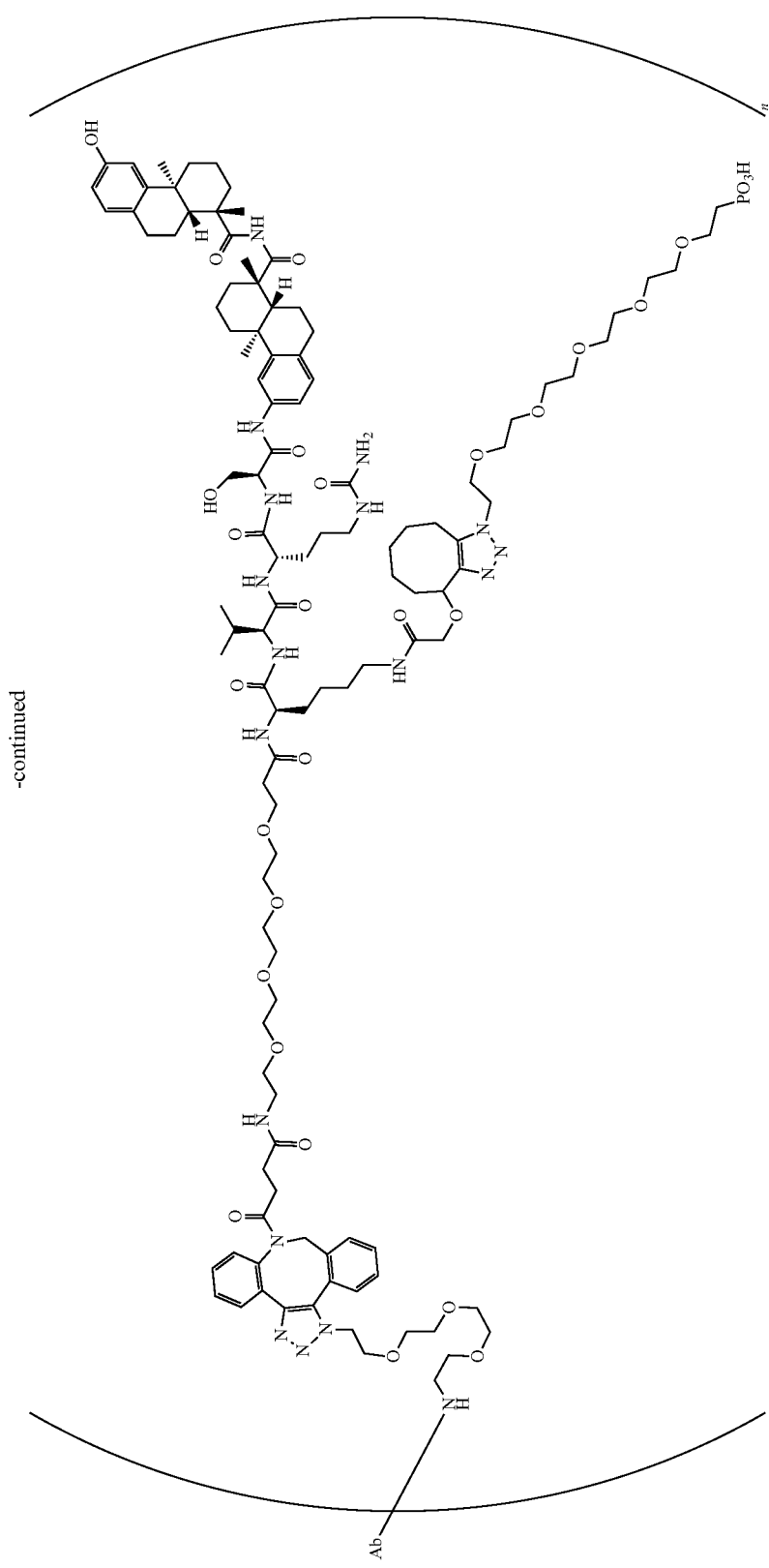

-continued
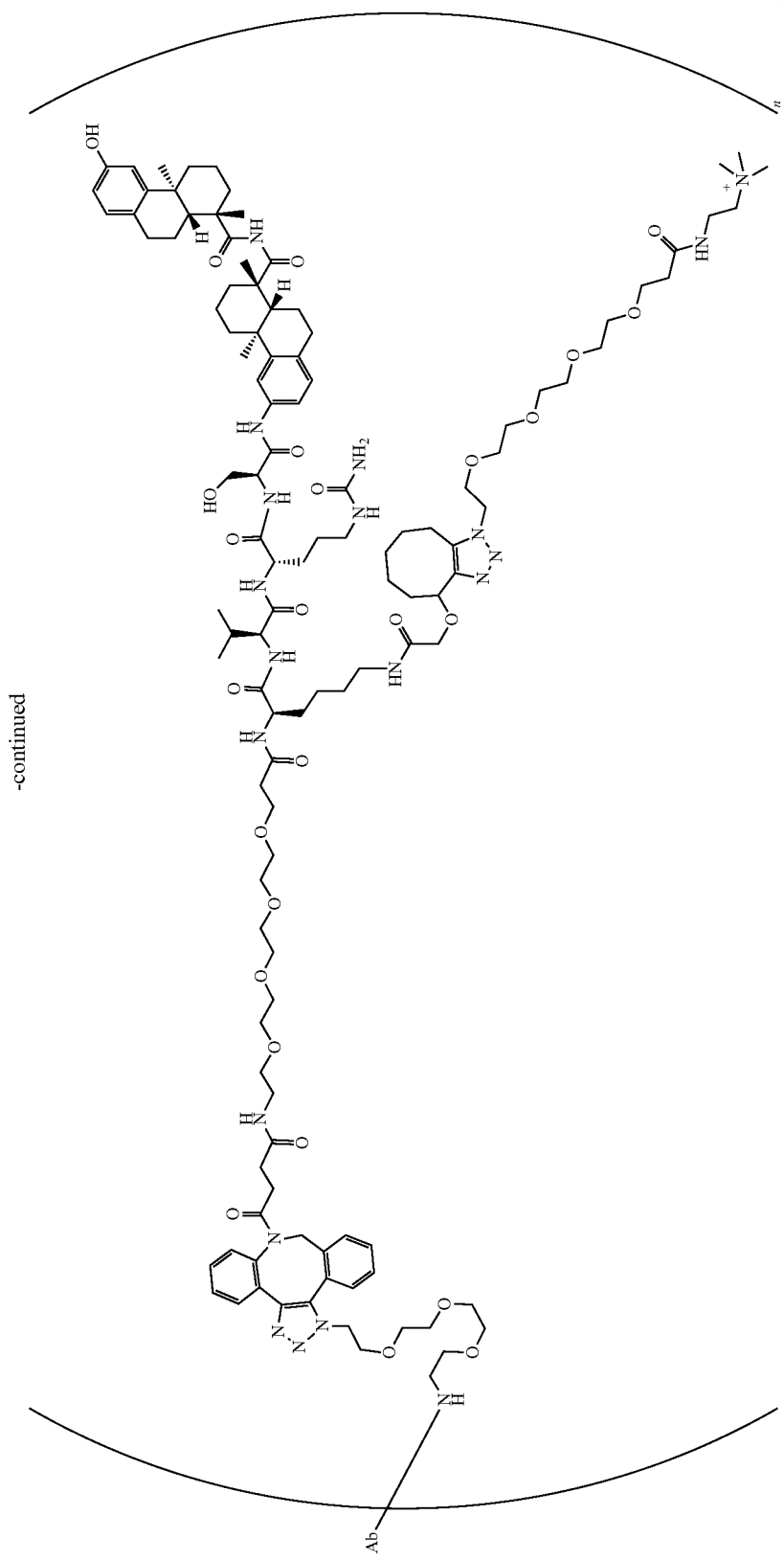

-continued
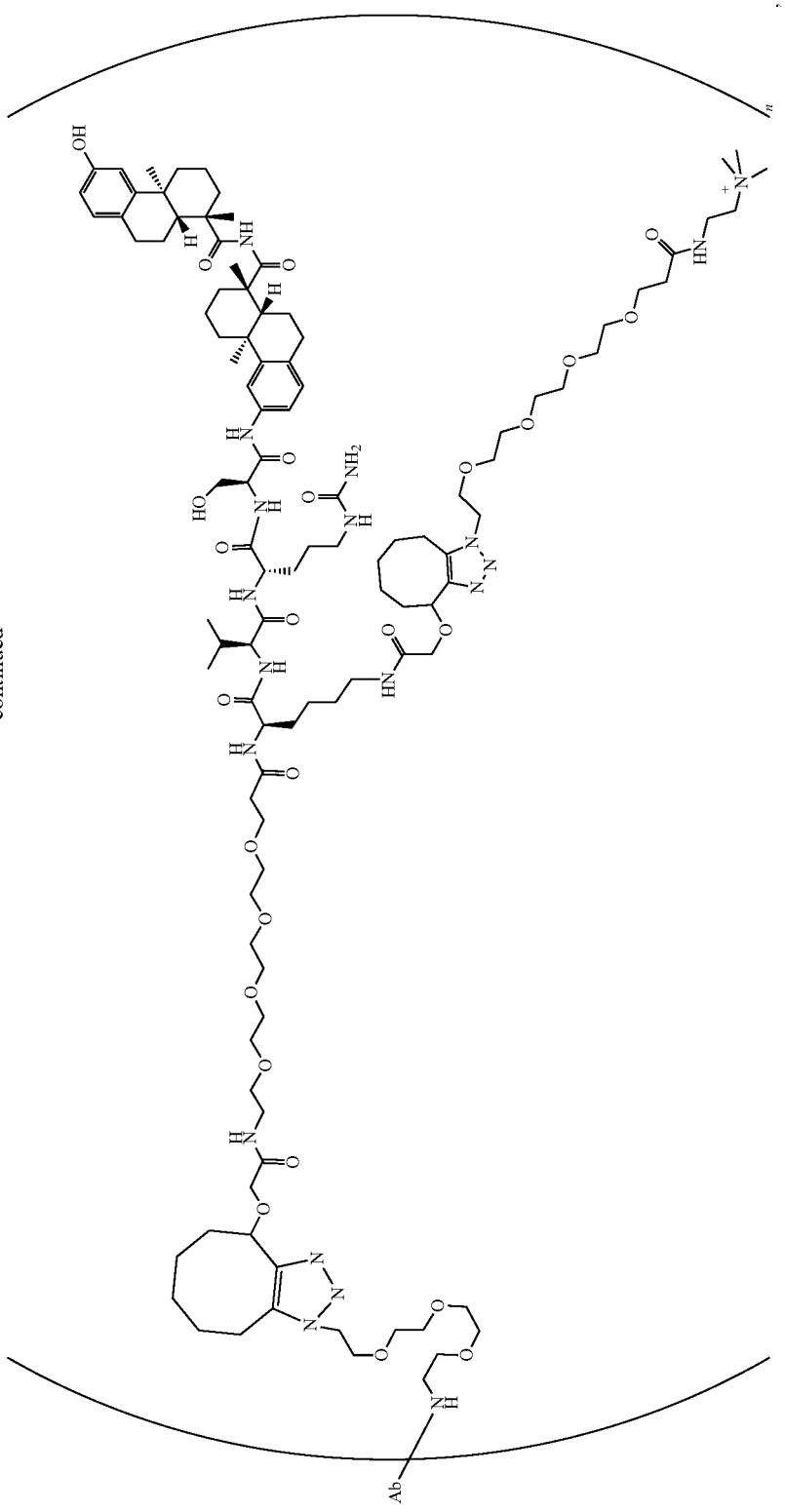

-continued
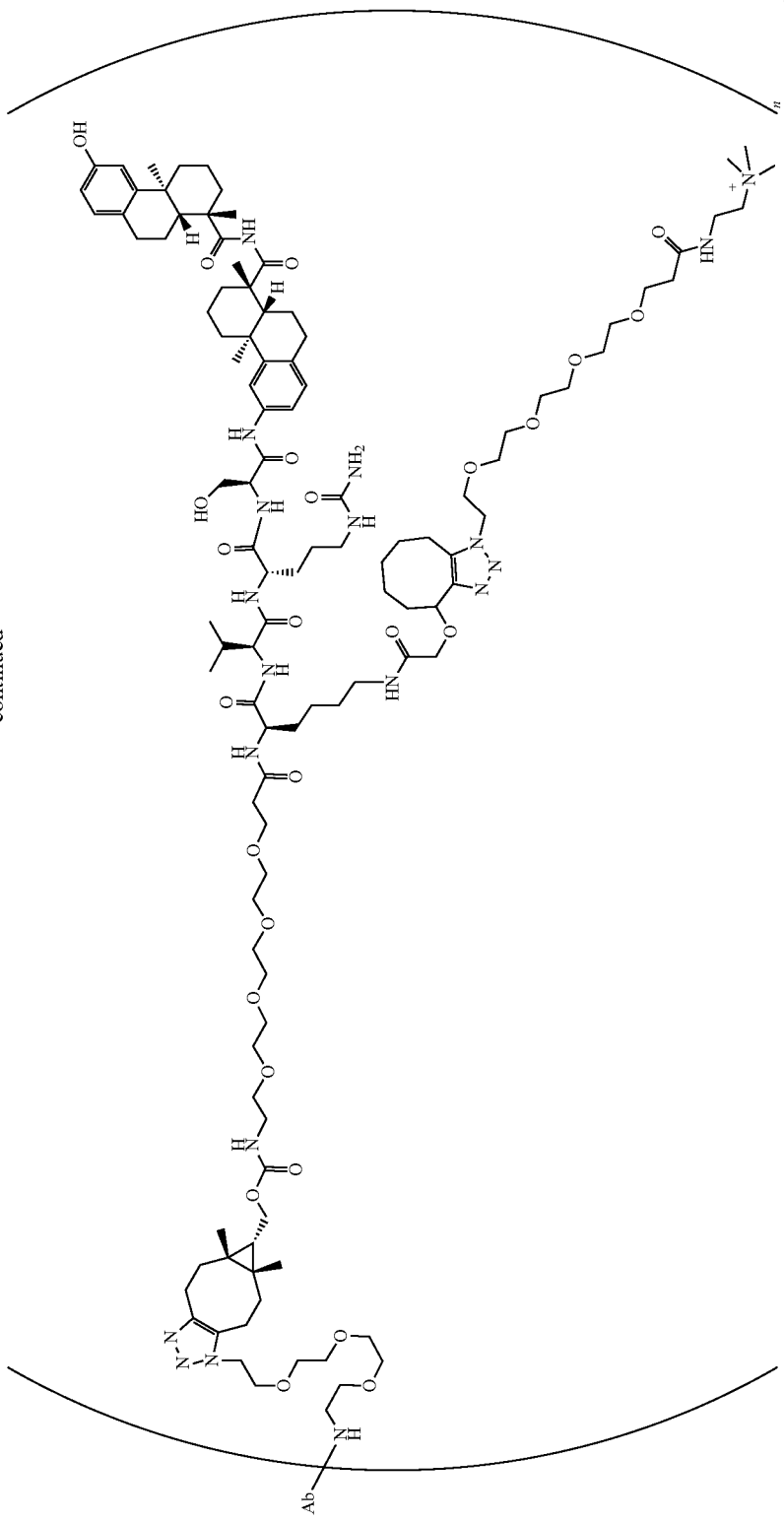

-continued
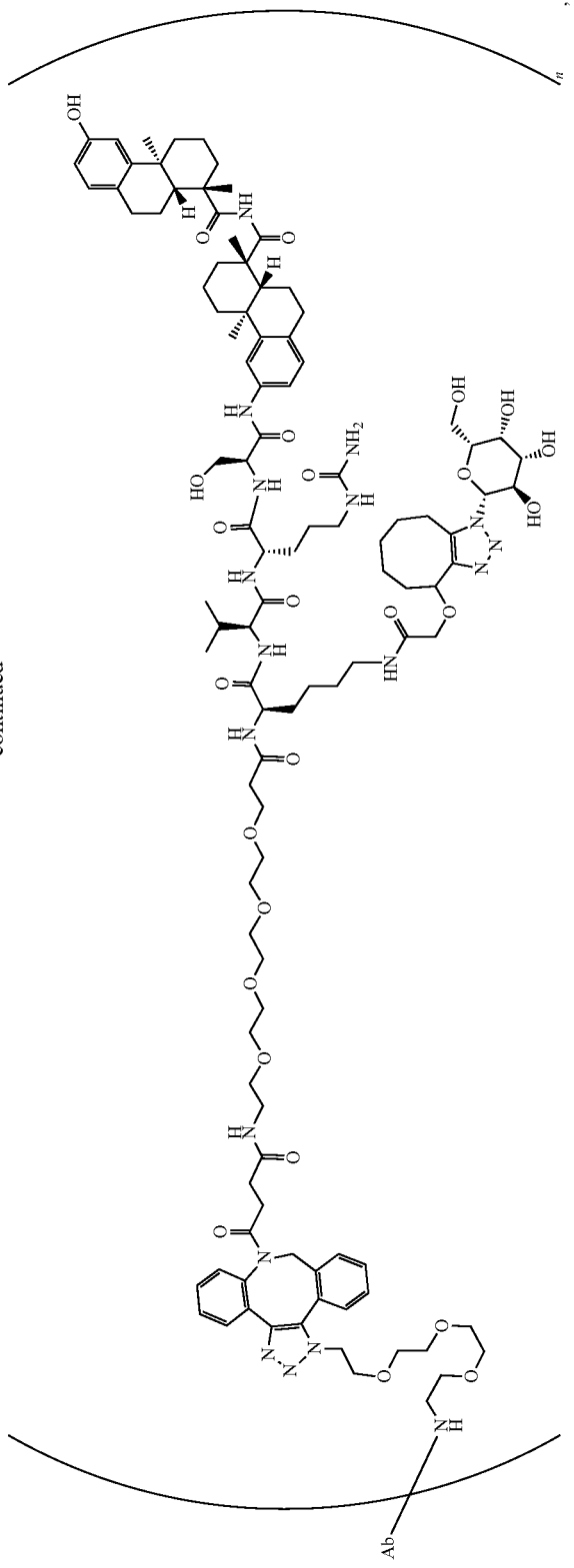

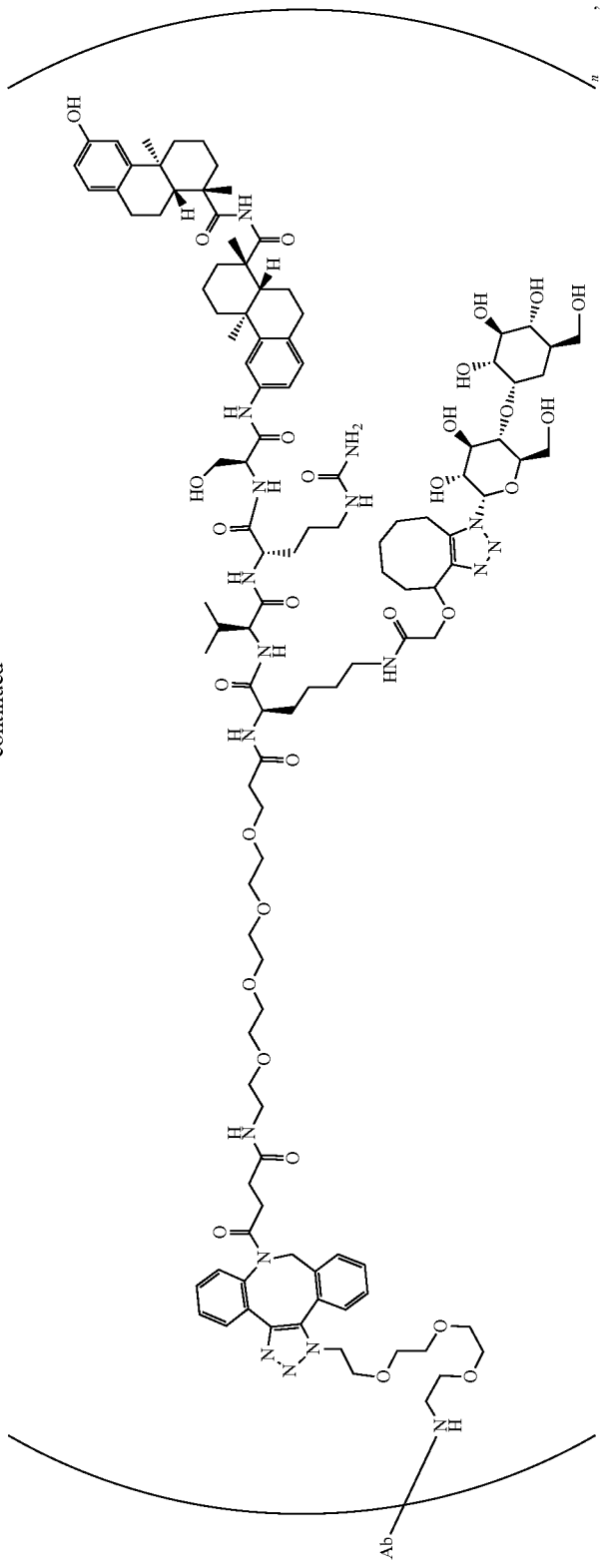

or a stereoisomeric form thereof, or a regioisomer thereof, or a mixture of regioisomers thereof, wherein each Ab is an antibody, or an antigen-binding fragment thereof, and subscript n is an integer from 1 to 30. In some embodiments, n is an integer from 1 to 4. In some embodiments, n is 2. In some embodiments, n is 4.

Provided herein is a pharmaceutical composition comprising a compound of Formula (I), Formula (II), Formula (III), Formula (IV), Formula (IVa), Formula (IVb), Formula (IVc), Formula (Va), Formula (Vb), Formula (Vc), or Formula (Vd), or pharmaceutically acceptable salt thereof, and a pharmaceutically acceptable excipient.

Also provided herein is a method of treating a disease or disorder in a patient in need thereof comprising administering to the patient a compound of any one of Formula (I), Formula (II), Formula (III), Formula (IV), Formula (IVa), Formula (IVb), Formula (IVc), Formula (Va), Formula (Vb), Formula (Vc), or Formula (Vd), or a composition comprising a compound of Formula (I), Formula (II), Formula (III), Formula (IV), Formula (IVa), Formula (IVb), Formula (IVc), Formula (Va), Formula (Vb), Formula (Vc), or Formula (Vd).

In another aspect is provided a compound comprising a reactive linker bonded to at least one payload moiety and bonded to at least one hydrophilic residue via a covalent linker, wherein said covalent linker is bonded directly or indirectly to each of the reactive linker, the payload moiety, and the hydrophilic residue.

In a further aspect is provided a compound according to Formula (VI):

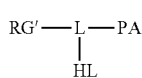

(VI)

or a pharmaceutically acceptable salt, solvate, stereoisomer, or derivative thereof, wherein:
RG' is a reactive group;
L is a trivalent linker;
HL is a hydrophilic residue; and
PA is a payload residue.

In one instance, a compound of Formula (VI) is according to Formula (VII):

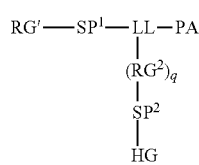

(VII)

wherein:
LL is a trivalent linker;
RG' is a reactive group;
RG$^2$ is a reactive group residue;
SP$^1$ and SP$^2$ are independently, in each instance, absent, or a spacer group residue;
HG is a hydrophilic residue;
PA is a payload residue; and
subscript q is 0 or 1.

In one instance, a compound of Formula (VII) is according to Formula (VIII):

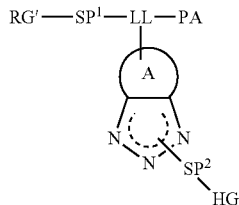

(VIII)

wherein
ring A is fused to the triazole and is selected from the group consisting of cycloalkyl, cycloalkenyl, heterocycloalkyl, and heterocycloalkenyl;
wherein cycloalkyl, cycloalkenyl, heterocycloalkyl, and heterocycloalkenyl are optionally substituted with alkyl, —OH, or —NR$^a$R$^b$, where each of R$^a$ and R$^b$ is alkyl or —H.

In another instance, a compound of Formula (VII) is according to Formula (IX):

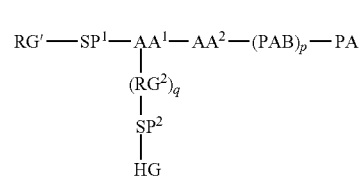

(IX)

wherein:
AA$^1$ is a trivalent linker comprising an amino acid residue;
AA$^2$ is a dipeptide, tripeptide or tetrapeptide residue; and
PAB is

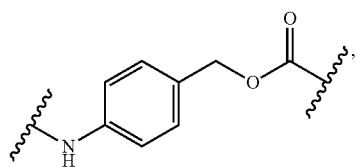 [SMILES: *Nc1ccc(COC(*)=O)cc1]

wherein the

indicates the atom through which the PAB is bonded to the adjacent groups in the formula;
subscript p is 0 or 1; and
subscript q is 0 or 1.

In certain instances, a compound of Formula (IX) is according to Formula (IX):according to Formula (IXa), Formula (IXb) or Formula (IXc):

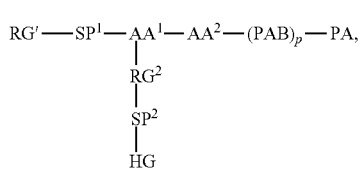

(IXa)

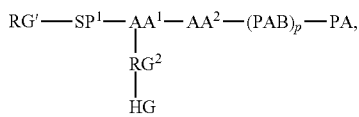

(IXb)

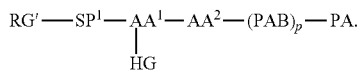

(IXc)

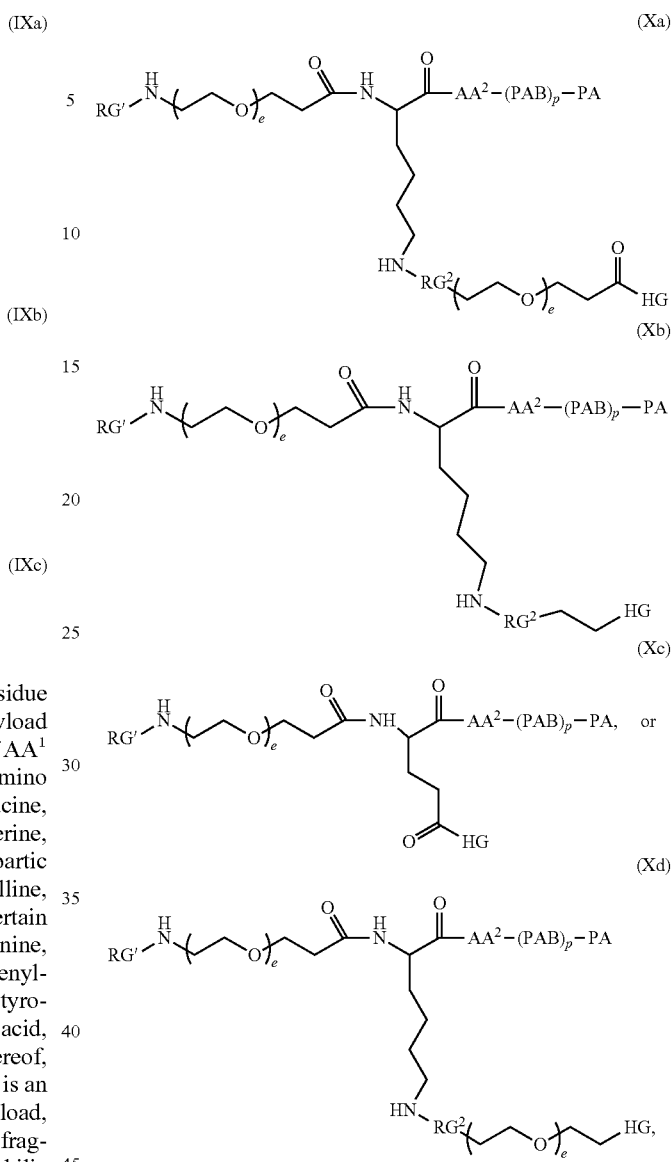

AA¹ is a trivalent linker comprising an amino acid residue and is directly or indirectly linked to an antibody, a payload and a hydrophilic group. In some examples, any one of AA¹ or AA² comprises, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, AA¹ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, AA¹ is an amino acid with three functional groups to link to a payload, to a binding agent (e.g., antibody or antigen binding fragment thereof), and to a linker comprising a hydrophilic group, e.g., lysine, aspargine, glutamic acid, aspartic acid, glutamine, cysteine, threonine, serine, or tyrosine. In certain embodiments, AA¹ is lysine. In certain embodiments AA¹ is glutamine. In certain embodiments, AA¹ is lysine or a derivative of lysine. In certain embodiments, AA¹ is L-lysine. In certain embodiments, the AA¹ is D-lysine. In certain embodiments, AA¹ is glutamic acid. In certain embodiments, AA¹ is aspartic acid. In certain embodiments, the AA² is valine-citrulline. In some embodiments, the AA² is citrulline-valine. In some embodiments, the AA² is valine-alanine. In some embodiments, the AA² is alanine-valine. In some embodiments, the AA² is valine-glycine. In some embodiments, the AA² is glycine-valine. In some embodiments, the AA¹-AA² is glutamine-valine-citrulline. In some embodiments, the AA¹-AA² is lysine-valine-citrulline. In some embodiments, the AA¹-AA² is lysine-valine-alanine. In some embodiments, the AA¹-AA² is glutamine-valine-alanine.

In certain instances, a compound of Formula (IXa), Formula (IXb) or Formula (IXc) is according to according to Formula (Xa), (Xb), (Xc) or (Xd):

wherein:
subscript e is independently, in each instance, an integer from 0 to 6, or an integer from 0 to 5. In some instances, subscript p is 0. In some instances, subscript p is 1. In any of these examples, subscript e is 1, 2, 3, or 4. In some examples, subscript e is 1. In some examples, subscript e is 2. In some examples, subscript e is 3. In some examples, subscript e is 4. In some examples, subscript e is 5. In some examples, subscript e is 6. In certain embodiments, the AA² is valine-citrulline. In some embodiments, the AA² is citrulline-valine. In some embodiments, the AA² is valine-alanine. In some embodiments, the AA² is alanine-valine. In some embodiments, the AA² is valine-glycine. In some embodiments, the AA² is glycine-valine. In some embodiments, the AA¹-AA² is glutamine-valine-citrulline. In certain embodiments, the lysine is L-lysine. In certain embodiments, the lysine is D-lysine.

In certain embodiments, RG' is, independently in each instance, a click chemistry residue. In some instances, RG' is, independently in each instance, selected from the group consisting of

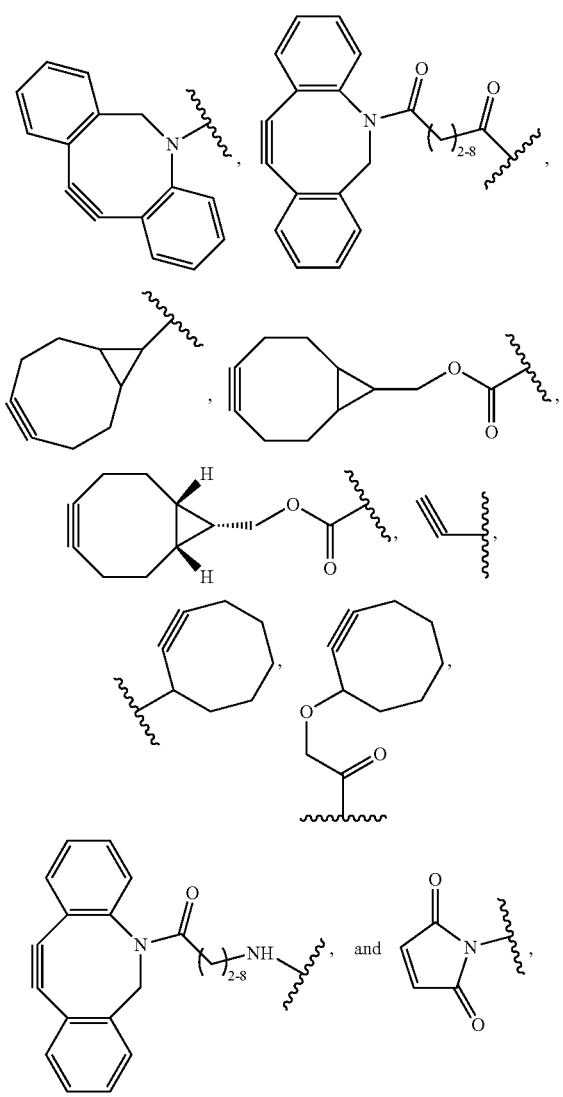
wherein the
indicates the atom through which the RG' is bonded to the adjacent groups in the formula. In one case, RG' is
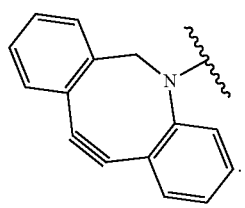 [SMILES: *N1Cc2ccccc2C#Cc2ccccc21]
In another case, RG' is
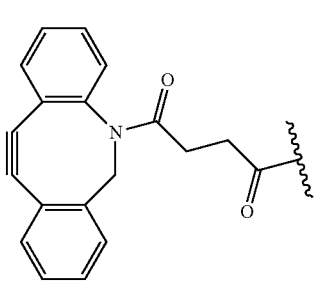
In some instances, RG' is
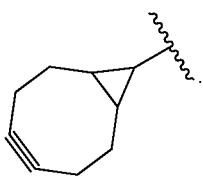 [SMILES: *C1C2CCC#CCCC12]
In some instances, RG' is
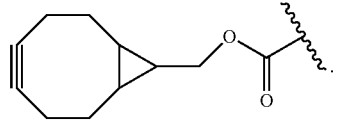 [SMILES: *C(=O)OCC1C2CCC#CCCC21]
In some instances, RG' is
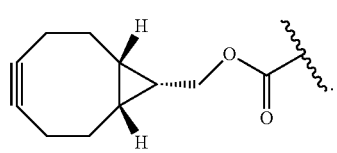 [SMILES: *C(=O)OC[C@@H]1[C@@H]2CCC#CCC[C@@H]21]
In some instances, RG' is
In some instances, RG' is
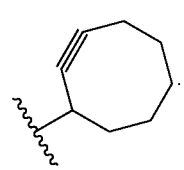 [SMILES: *C1C#CCCCCC1]

In some instances, RG' is
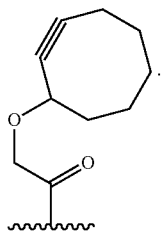 [SMILES: *C(=O)COC1C#CCCCCC1]
In some instances, RG' is
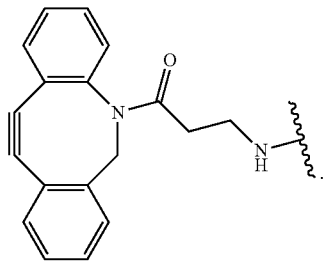 [SMILES: *NCCC(=O)N1Cc2ccccc2C#Cc2ccccc21]
In some instances, RG' is
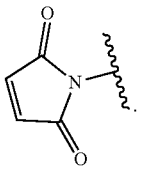 [SMILES: *N1C(=O)C=CC1=O]
In some instances, RG² is independently, in each instance, selected from the group consisting of
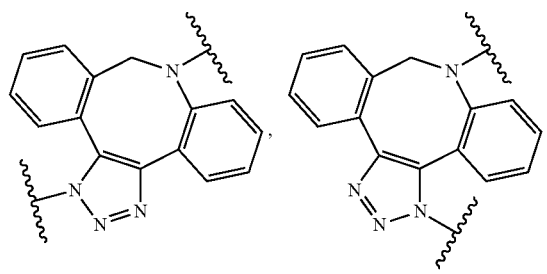
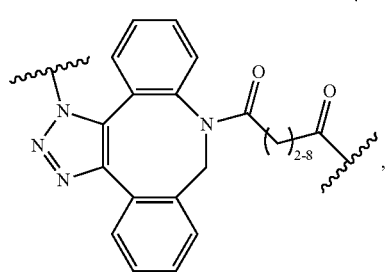
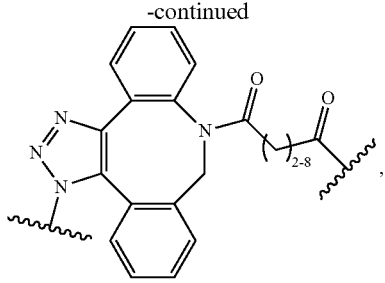
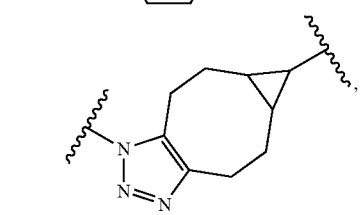
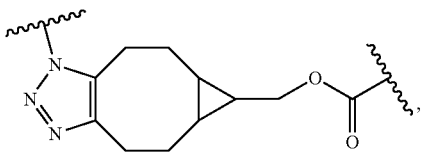
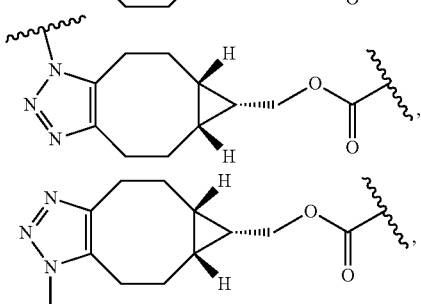
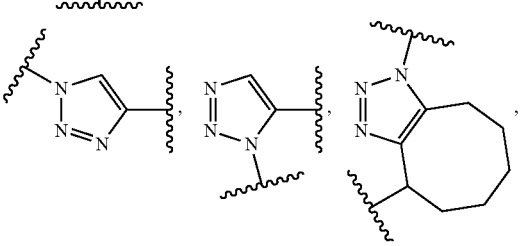
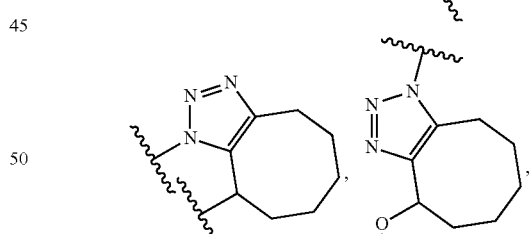
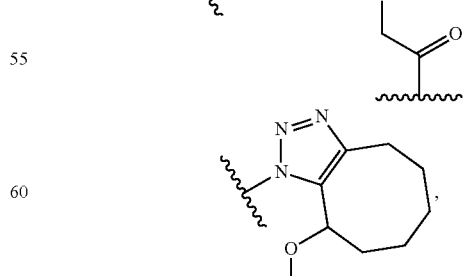

-continued
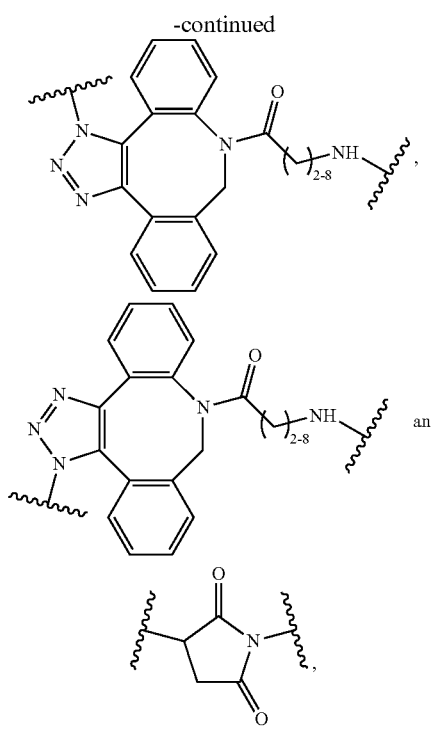
wherein the
indicates the atom through which the RG² is bonded to the adjacent groups in the formula.
In certain embodiments,
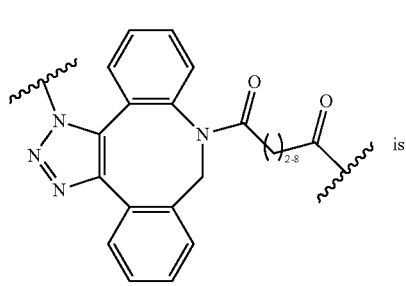
is
In certain embodiments,
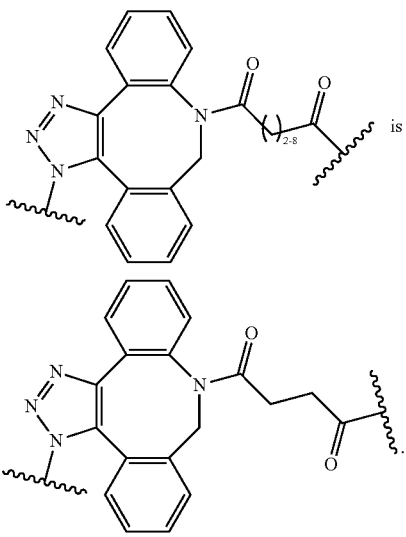
is
In certain embodiments,
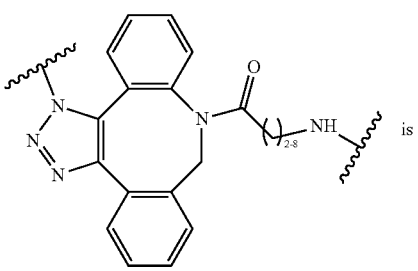
In some embodiments,
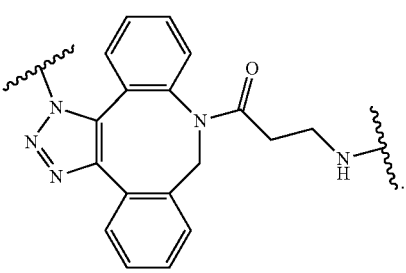
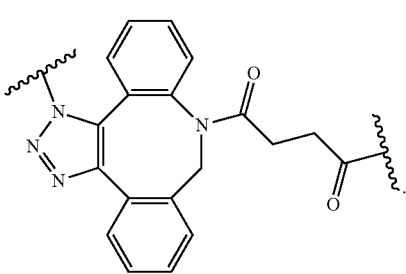
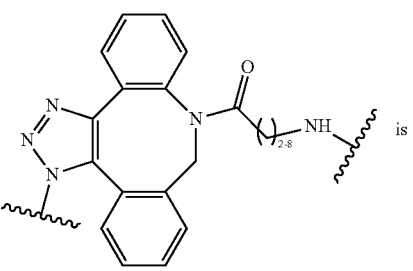 is

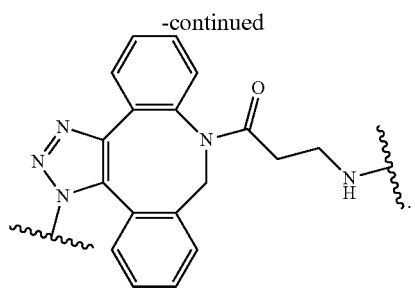
In certain instances, $RG^1$ and $RG^2$ are independently, in each instance, as shown in Table R'.

TABLE R'-continued

| RG¹ | RG² |
|---|---|

TABLE R'-continued
| RG¹ | RG² |
|---|---|
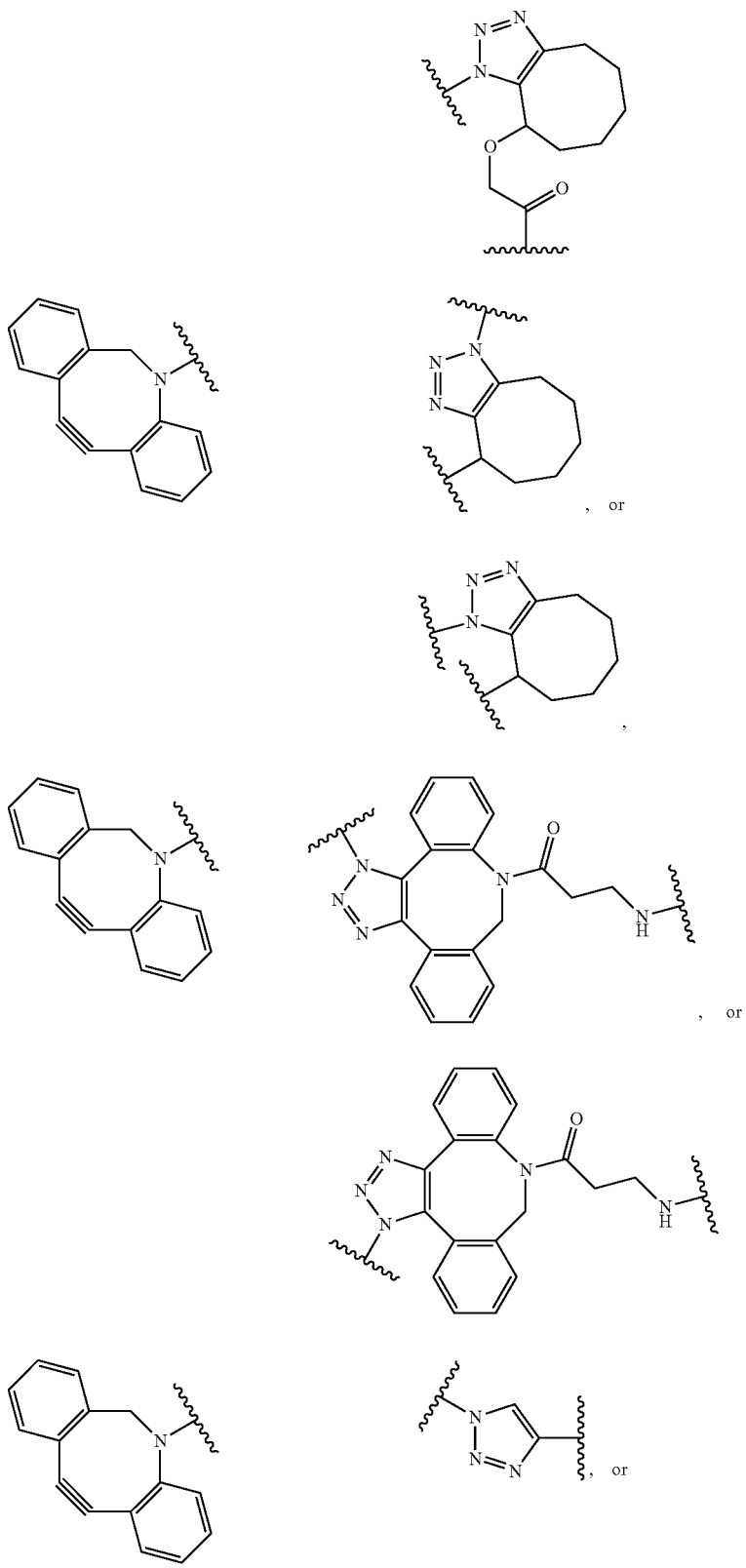

TABLE R'-continued
| RG¹ | RG² |
|---|---|
| 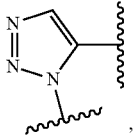 | 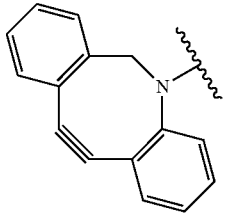 [SMILES: *N1Cc2ccccc2C#Cc2ccccc21], |
| 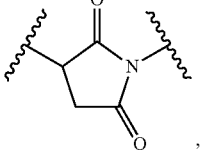 | 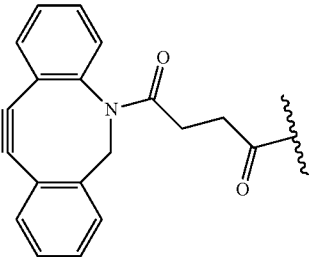 [SMILES: *C(=O)CCC(=O)N1Cc2ccccc2C#Cc2ccccc21], or 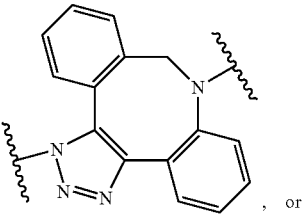 [SMILES: *N1Cc2ccccc2-c2c(nnn2*)-c2ccccc21] , |
| 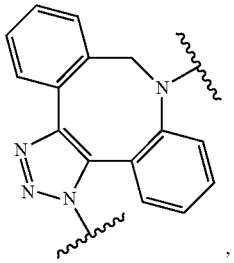 [SMILES: *N1Cc2ccccc2-c2nnn(*)c2-c2ccccc21] | 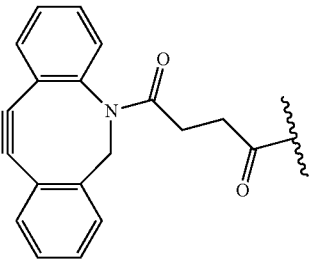 [SMILES: *C(=O)CCC(=O)N1Cc2ccccc2C#Cc2ccccc21], or 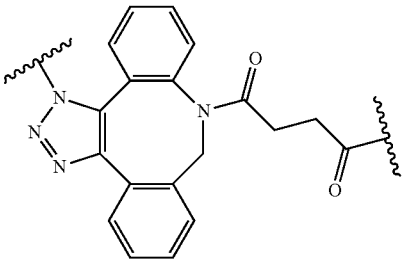 , |

TABLE R'-continued

| RG¹ | RG² |
|---|---|
| (dibenzocyclooctyne-amide-ketone structure) | (bicyclic triazole-cyclopropane structure) |
| | (bicyclic triazole-cyclopropane structure, alternate regiochemistry) |
| (dibenzocyclooctyne-amide-ketone structure) | (triazole-cyclooctane-cyclopropane-methylene ester structure) |
| | (triazole-cyclooctane-cyclopropane-methylene ester structure, alternate regiochemistry) |
| | (triazole-cyclooctane-cyclopropane-methylene ester structure with defined H stereochemistry), or |
| | (triazole-cyclooctane-cyclopropane-methylene ester structure with opposite H stereochemistry) |

TABLE R'-continued
| RG¹ | RG² |
|---|---|
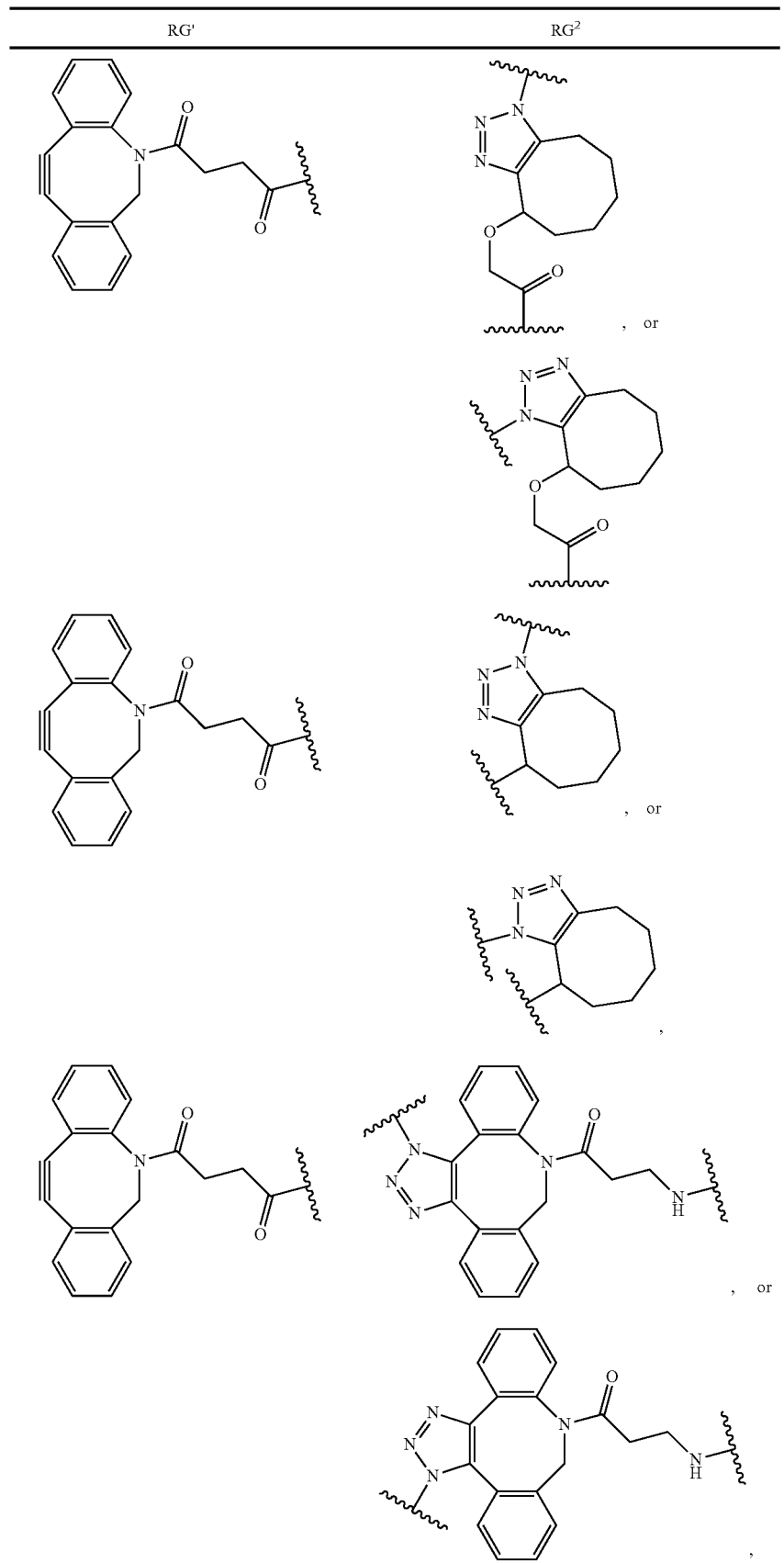

TABLE R'-continued
| RG¹ | RG² |
|---|---|
| 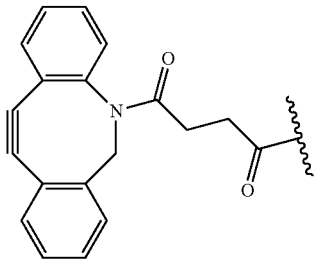 [SMILES: *C(=O)CCC(=O)N1Cc2ccccc2C#Cc2ccccc21] | 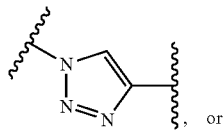, or |
|  | 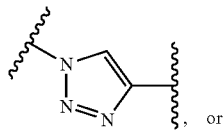, |
| 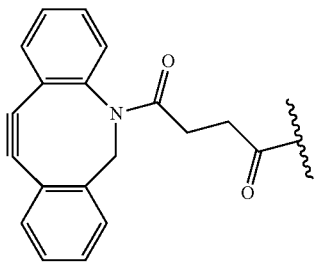 [SMILES: *C(=O)CCC(=O)N1Cc2ccccc2C#Cc2ccccc21] | 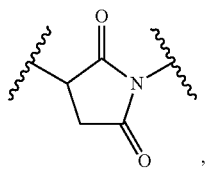 [SMILES: *C1CC(=O)N(*)C1=O], |
| 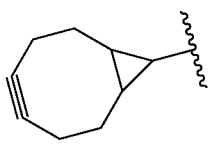 [SMILES: *C1C2CCC#CCCC12] | 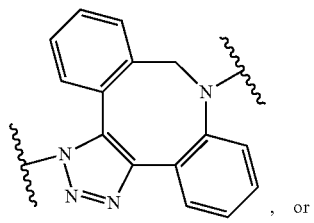 [SMILES: *N1Cc2ccccc2-c2c(nnn2*)-c2ccccc21], or |
|  | 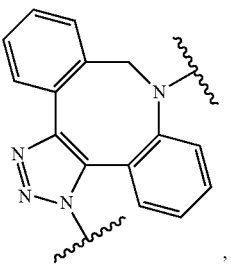 [SMILES: *N1Cc2ccccc2-c2nnn(*)c2-c2ccccc21], |
| 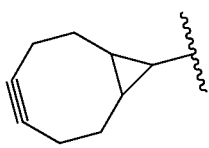 [SMILES: *C1C2CCC#CCCC12] | 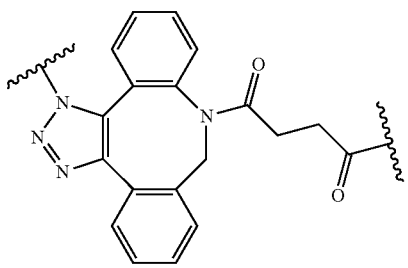, or |

TABLE R'-continued
| RG¹ | RG² |
|---|---|
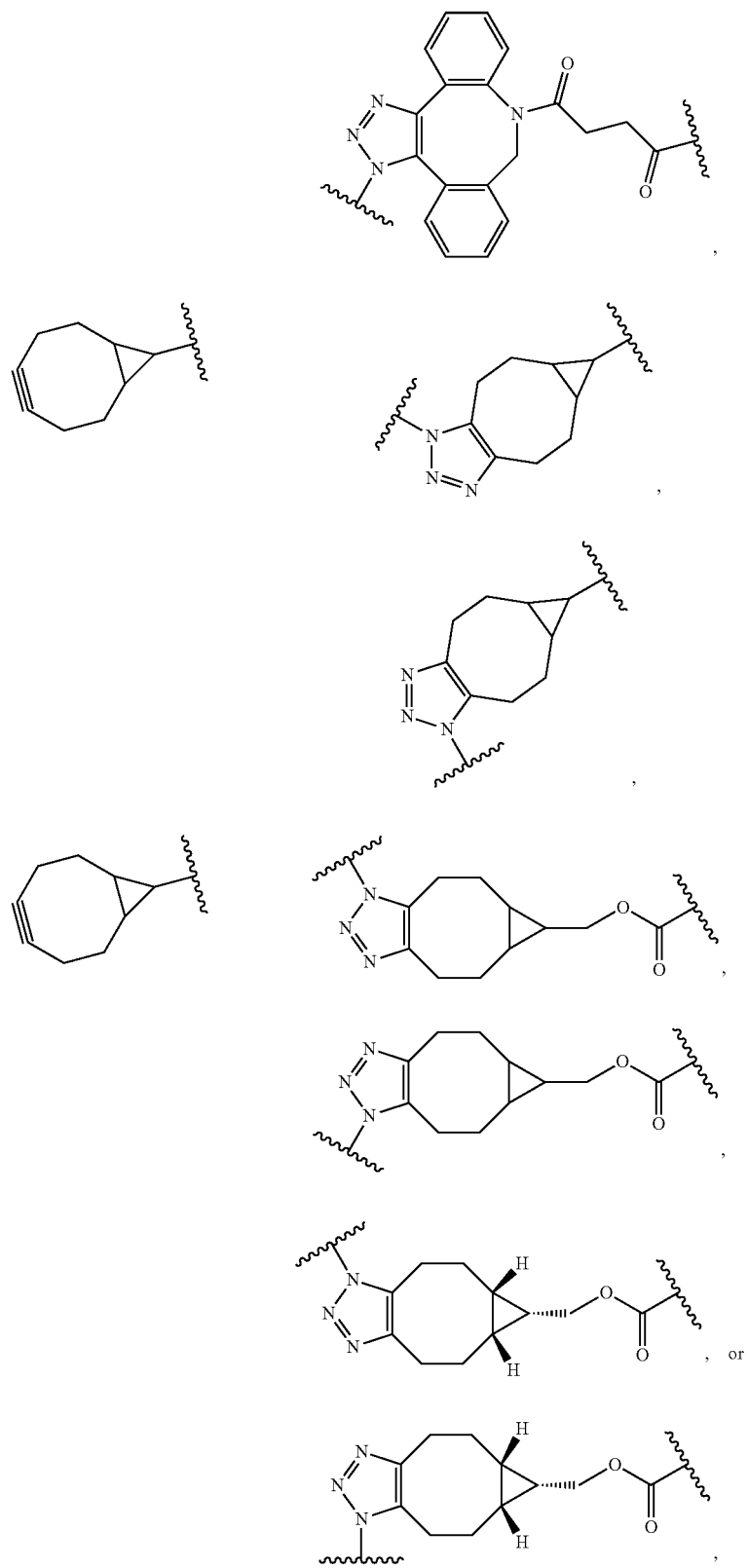

TABLE R'-continued

| RG¹ | RG² |
|---|---|
| (BCN alkyne structure) | (triazole-fused cyclooctane with -O-CH₂-C(=O)- linker), or (triazole-fused cyclooctane with -O-CH₂-C(=O)- linker, alternate regiochemistry) |
| (BCN alkyne structure) | (triazole-fused cyclooctane), or (triazole-fused cyclooctane, alternate regiochemistry) |
| (BCN alkyne structure) | (dibenzo-triazole-fused azocine with -C(=O)-CH₂-CH₂-NH- linker), or (dibenzo-triazole-fused azocine with -C(=O)-CH₂-CH₂-NH- linker, alternate regiochemistry) |

TABLE R'-continued
| RG¹ | RG² |
|---|---|
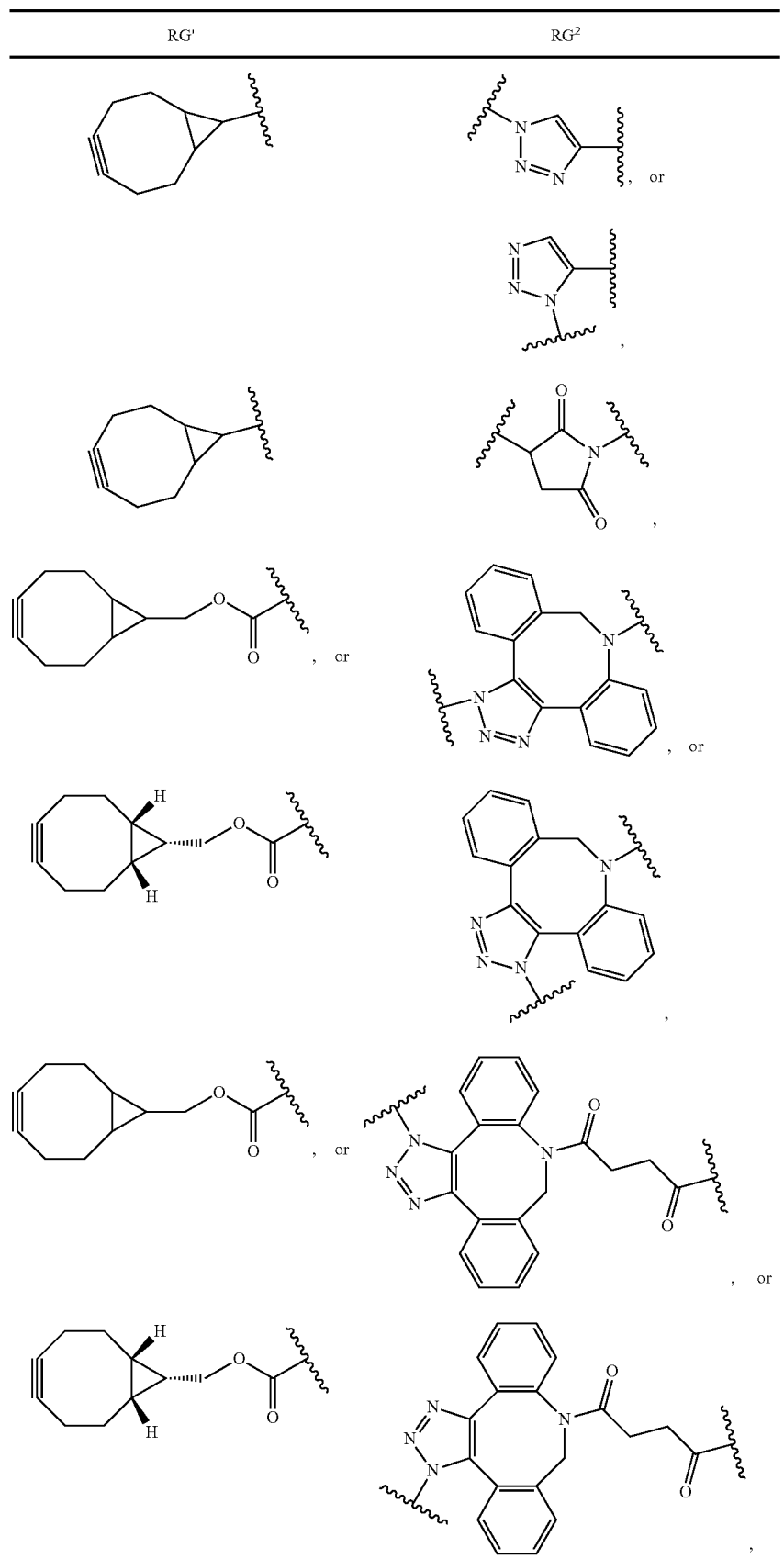

TABLE R'-continued
| RG¹ | RG² |
|---|---|
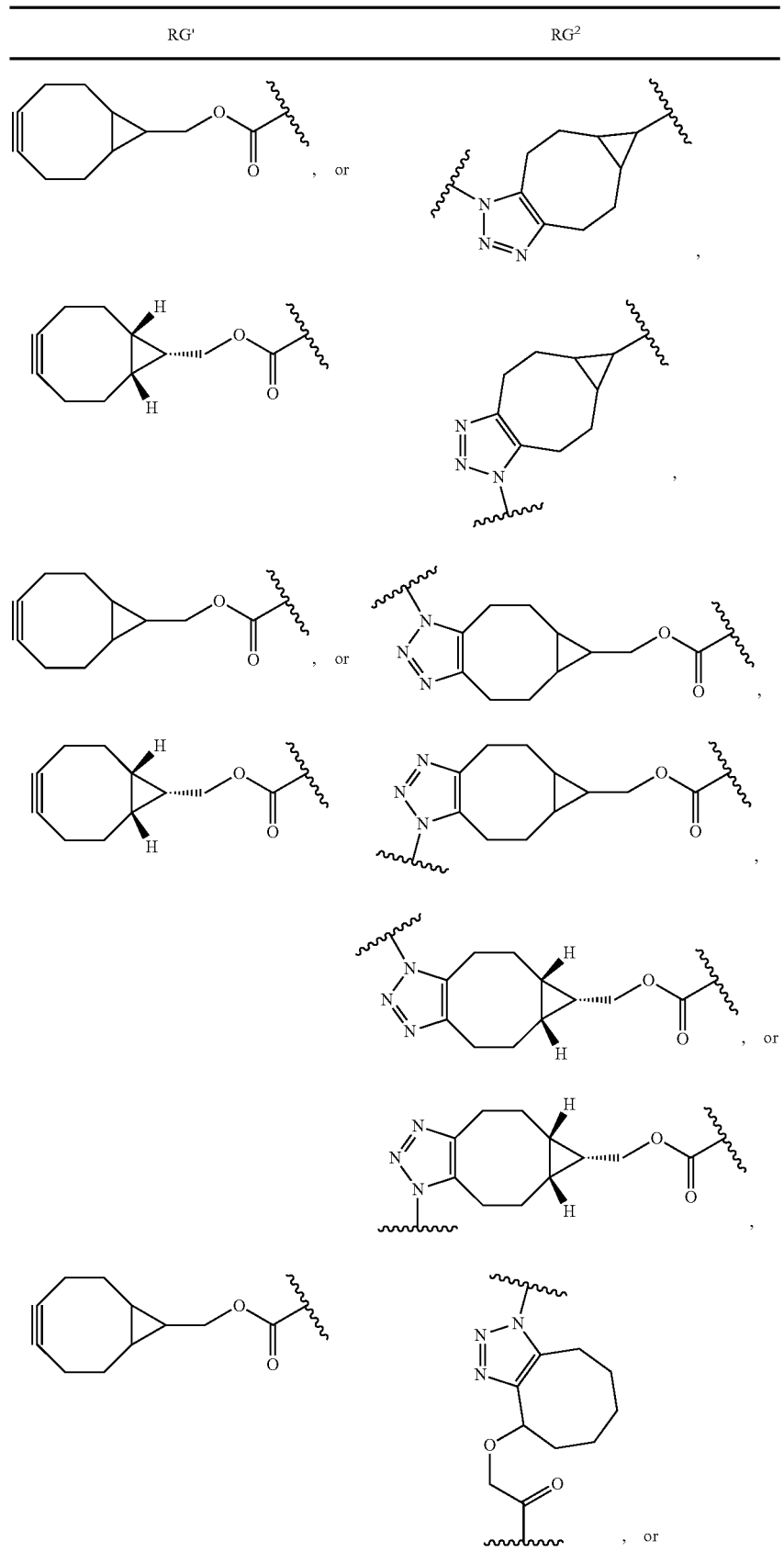

TABLE R'-continued
| RG¹ | RG² |
|---|---|
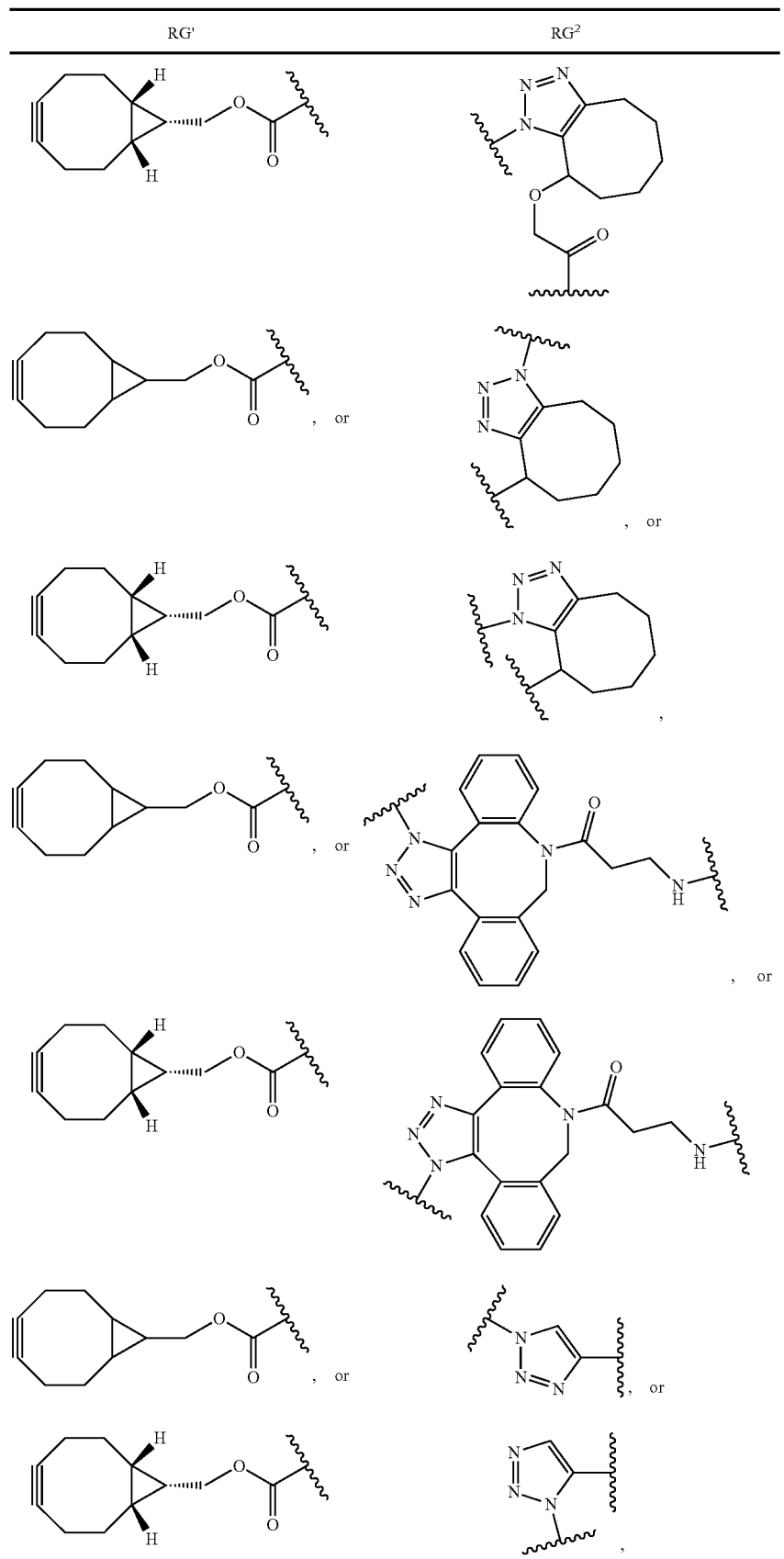

TABLE R'-continued
| RG¹ | RG² |
|---|---|
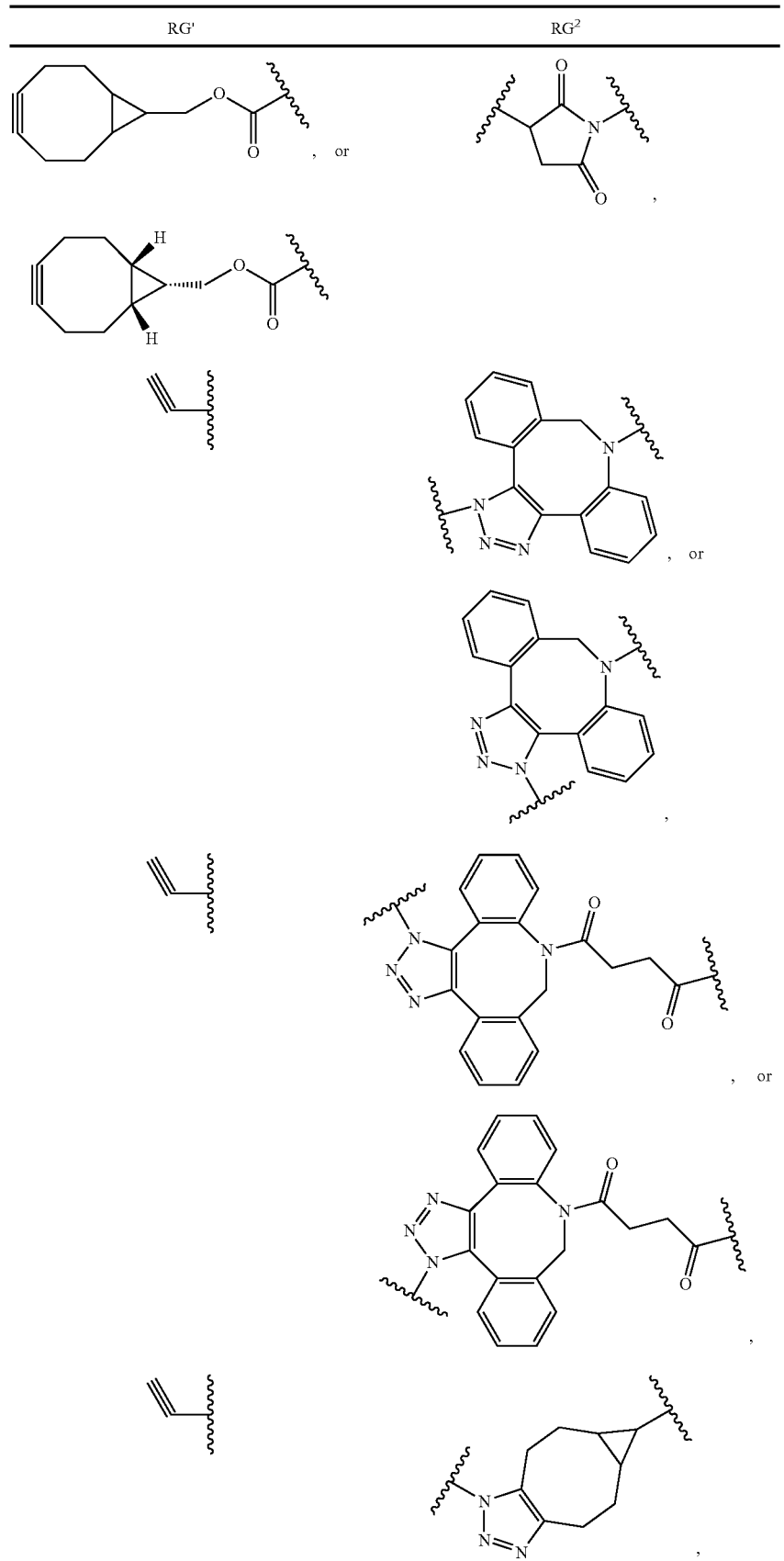

TABLE R'-continued
| RG¹ | RG² |
|---|---|
| | 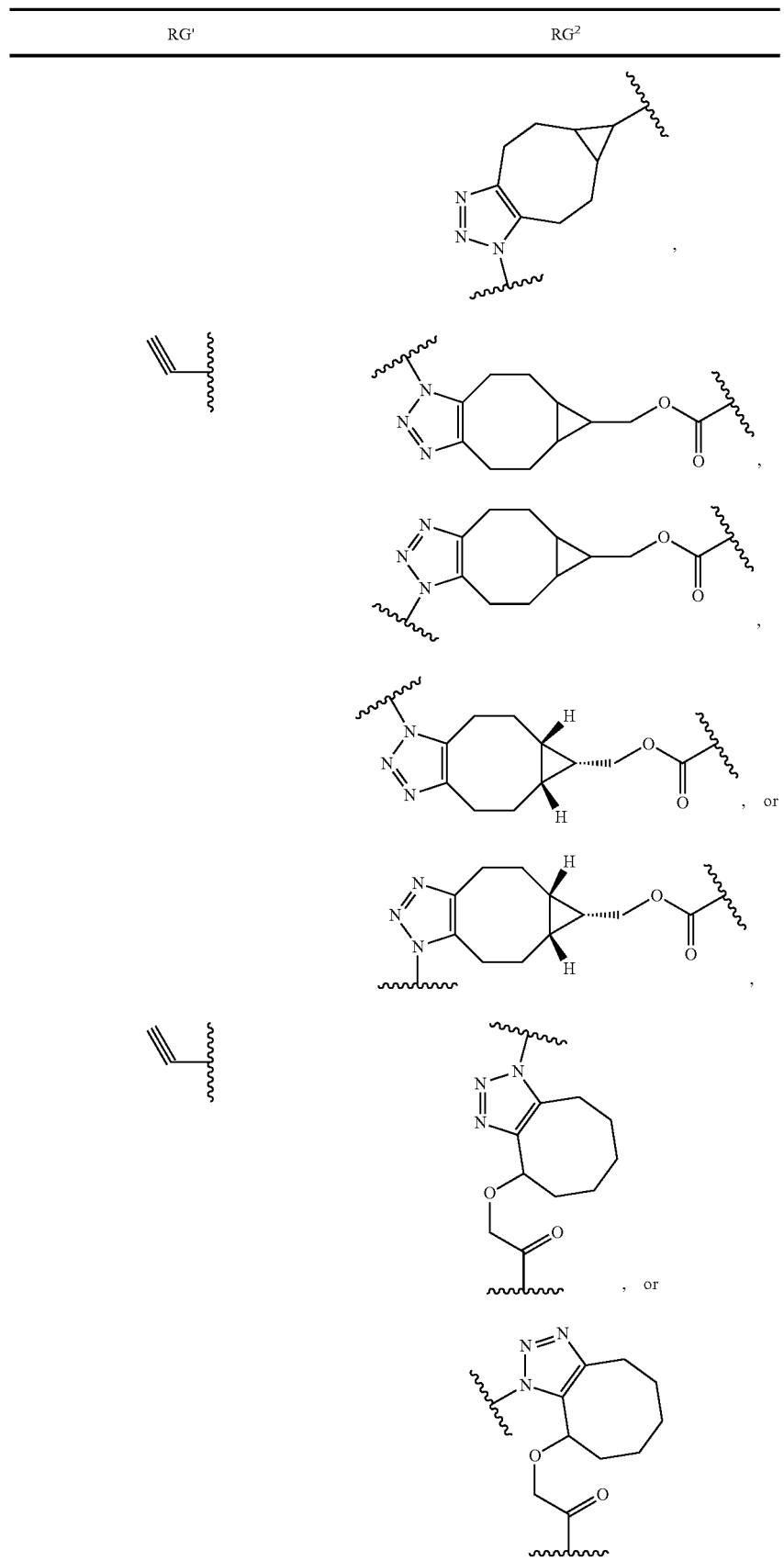 |

TABLE R'-continued

| RG¹ | RG² |
|---|---|
| (alkyne) | (triazole fused cyclooctane), or (triazole fused azocane) |
| (alkyne) | (dibenzotriazocine-propanamide), or (dibenzotriazocine-propanamide isomer) |
| (alkyne) | (1,4-triazole), or (1,5-triazole) |
| (alkyne) | (succinimide) |

TABLE R'-continued
| RG¹ | RG² |
|---|---|
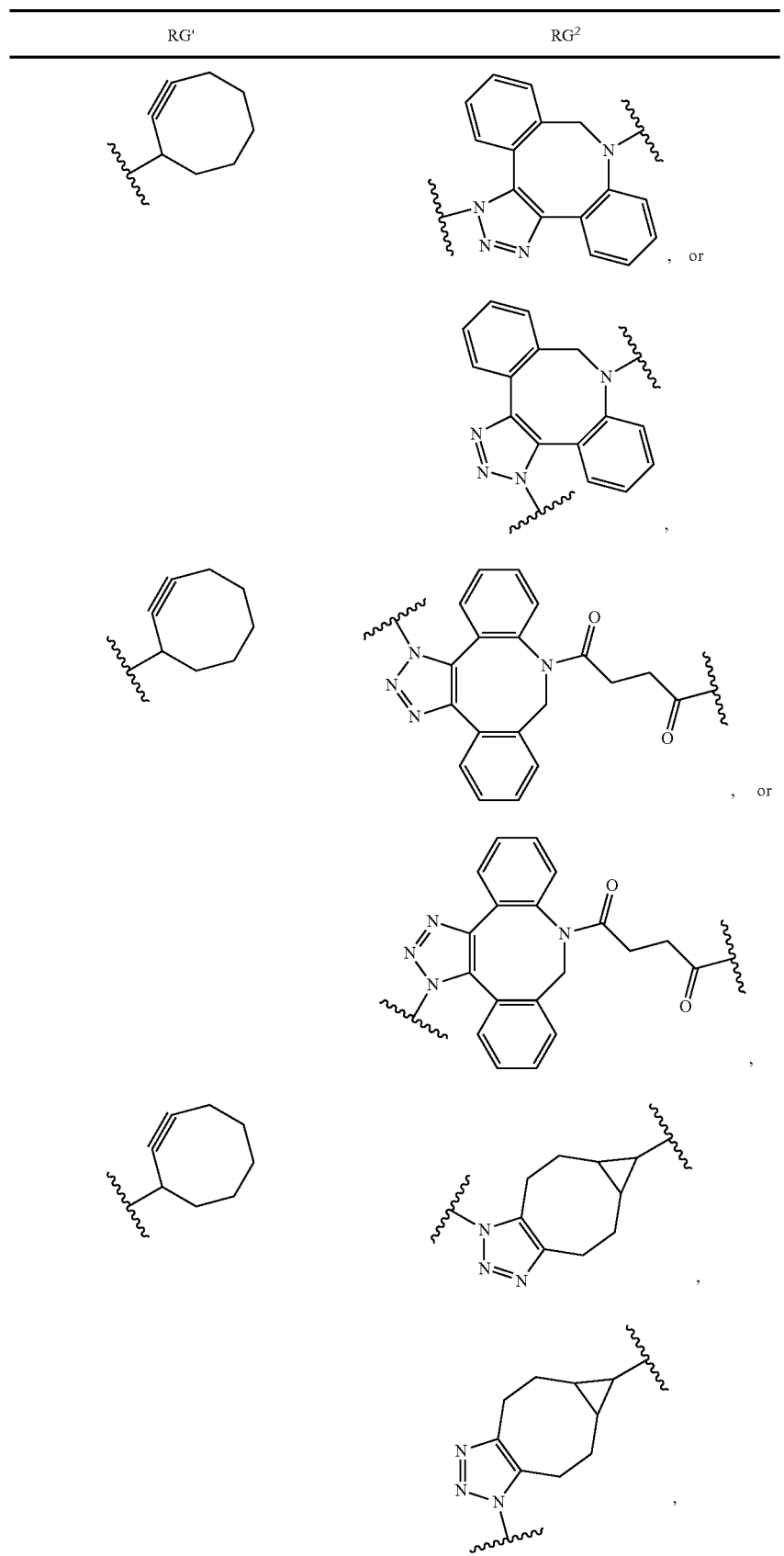

TABLE R'-continued

| RG¹ | RG² |
|---|---|
| (cyclooctyne structure) | (triazole-fused bicyclic with cyclopropane and -CH₂-O-C(=O)- linker) |
| | (triazole-fused bicyclic with cyclopropane and -CH₂-O-C(=O)- linker, alternate regiochemistry) |
| | (triazole-fused bicyclic with cyclopropane, H stereochemistry indicated, -CH₂-O-C(=O)- linker), or |
| | (triazole-fused bicyclic with cyclopropane, H stereochemistry indicated, -CH₂-O-C(=O)- linker, alternate regiochemistry) |
| (cyclooctyne structure) | (triazole fused to cyclooctane with -O-CH₂-C(=O)- linker), or |
| | (triazole fused to cyclooctane with -O-CH₂-C(=O)- linker, alternate regiochemistry) |
| (cyclooctyne structure) | (triazole fused to cyclooctane), or |

TABLE R'-continued
| RG¹ | RG² |
|---|---|
| | 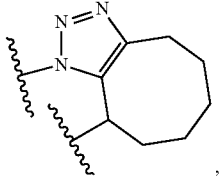 [SMILES: *C1CCCCCc2nnn(*)c21] , |
| 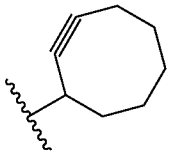 [SMILES: *C1C#CCCCCC1] | 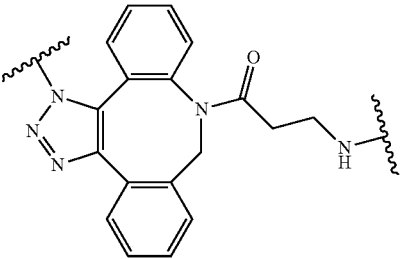 , or 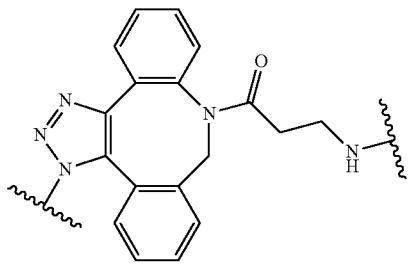 [SMILES: *NCCC(=O)N1Cc2ccccc2-c2c(nnn2*)-c2ccccc21] |
| 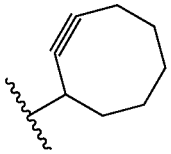 [SMILES: *C1C#CCCCCC1] | 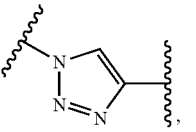 , or 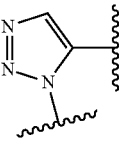 , |
| 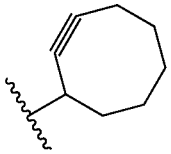 [SMILES: *C1C#CCCCCC1] | 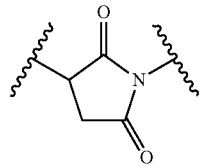 , |
| 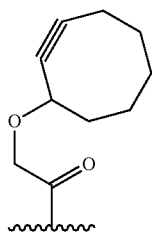 [SMILES: *C(=O)COC1C#CCCCCC1] | 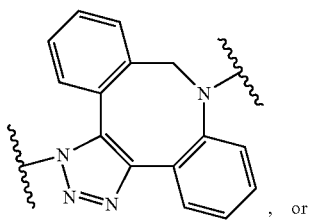 [SMILES: *N1Cc2ccccc2-c2c(nnn2*)-c2ccccc21] , or |

TABLE R'-continued
| RG¹ | RG² |
|---|---|

TABLE R'-continued
| RG' | RG² |
|---|---|
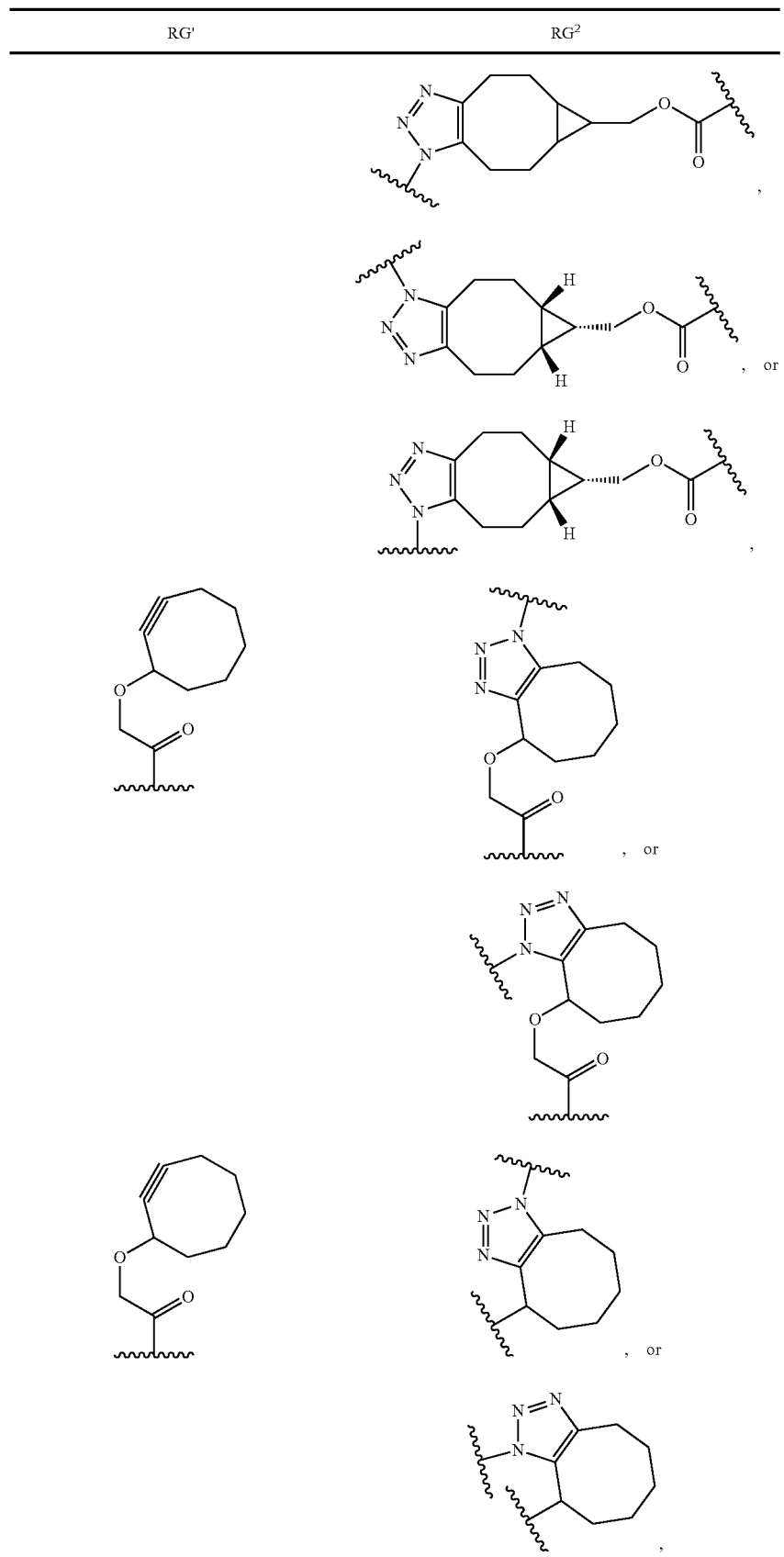

TABLE R'-continued

| RG¹ | RG² |
|---|---|
| (cyclooctyne-O-CH₂-C(=O)-) | (dibenzocyclooctyne-triazole with N-C(=O)-CH₂-CH₂-NH-), or |
| | (dibenzocyclooctyne-triazole isomer with N-C(=O)-CH₂-CH₂-NH-) |
| (cyclooctyne-O-CH₂-C(=O)-) | (1,4-triazole), or |
| | (1,5-triazole) |
| (cyclooctyne-O-CH₂-C(=O)-) | (succinimide) |
| (maleimide) | (dibenzocyclooctyne-triazole), or |

TABLE R'-continued
| RG' | RG² |
|---|---|
| | 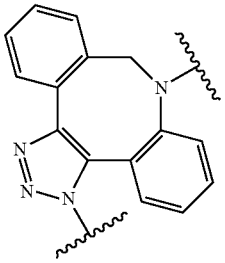 |
| 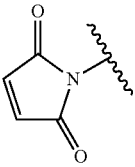 | 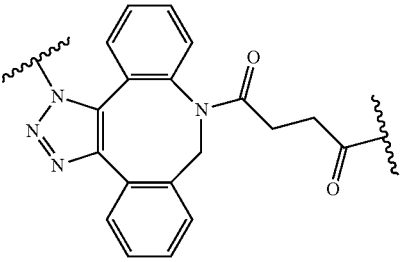, or |
| | 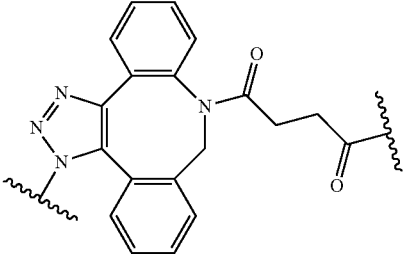 [SMILES: *NCCC(=O)N1Cc2ccccc2-c2c(nnn2*)-c2ccccc21], |
| 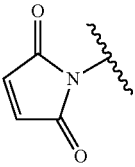 [SMILES: *N1C(=O)C=CC1=O] | 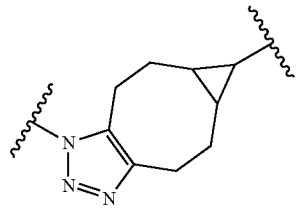, |
| | 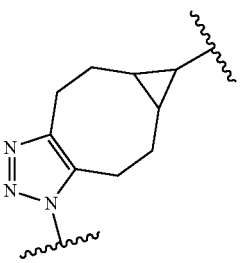, |
| 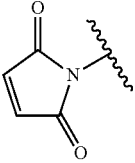 [SMILES: *N1C(=O)C=CC1=O] | 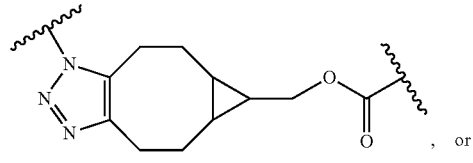 [SMILES: *C(=O)OCC1C2CCc3nnn(*)c3CCC21], or |

TABLE R'-continued
| RG' | RG² |
|---|---|
| 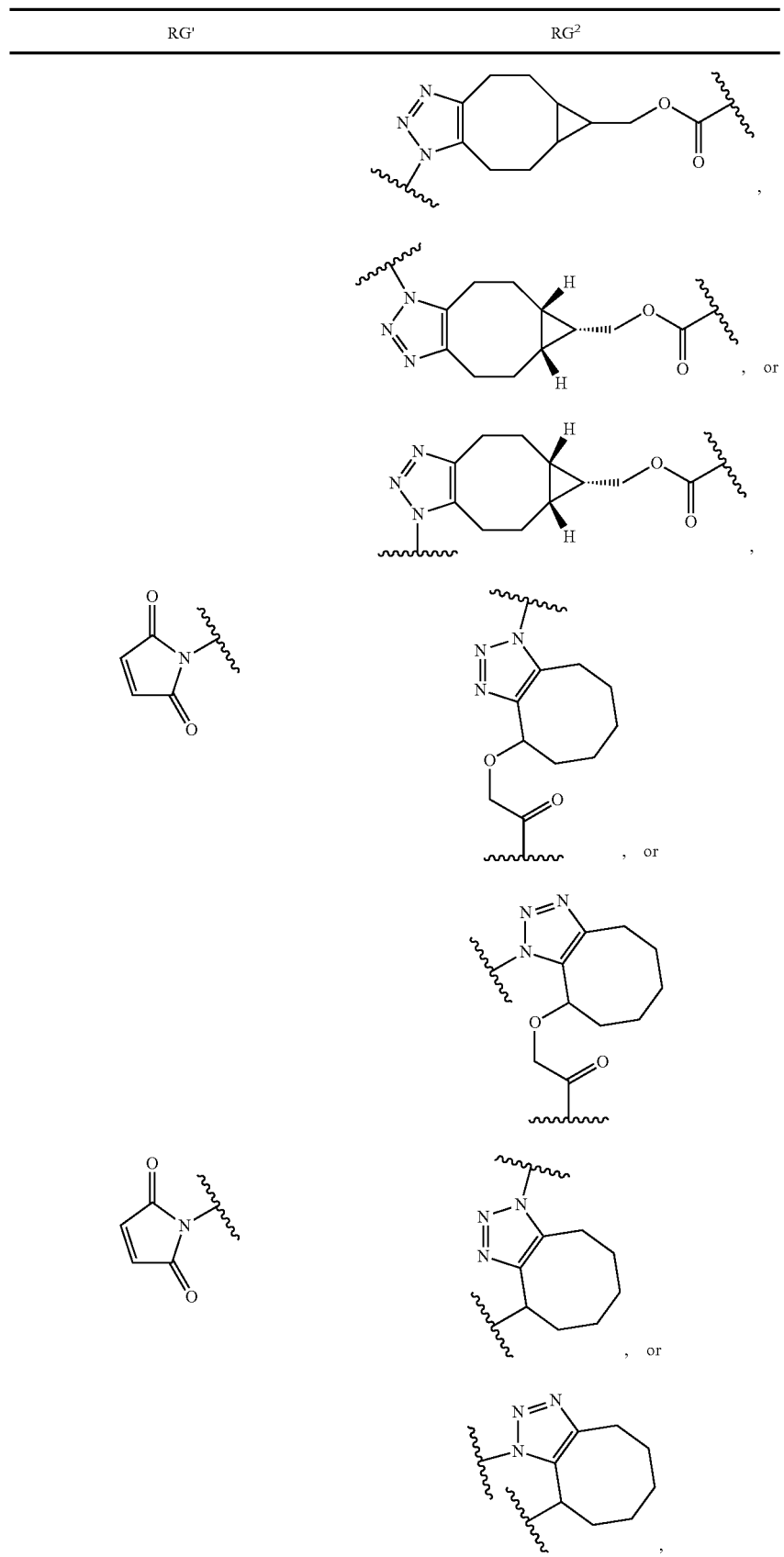 | |

TABLE R'-continued

| RG' | RG² |
|---|---|

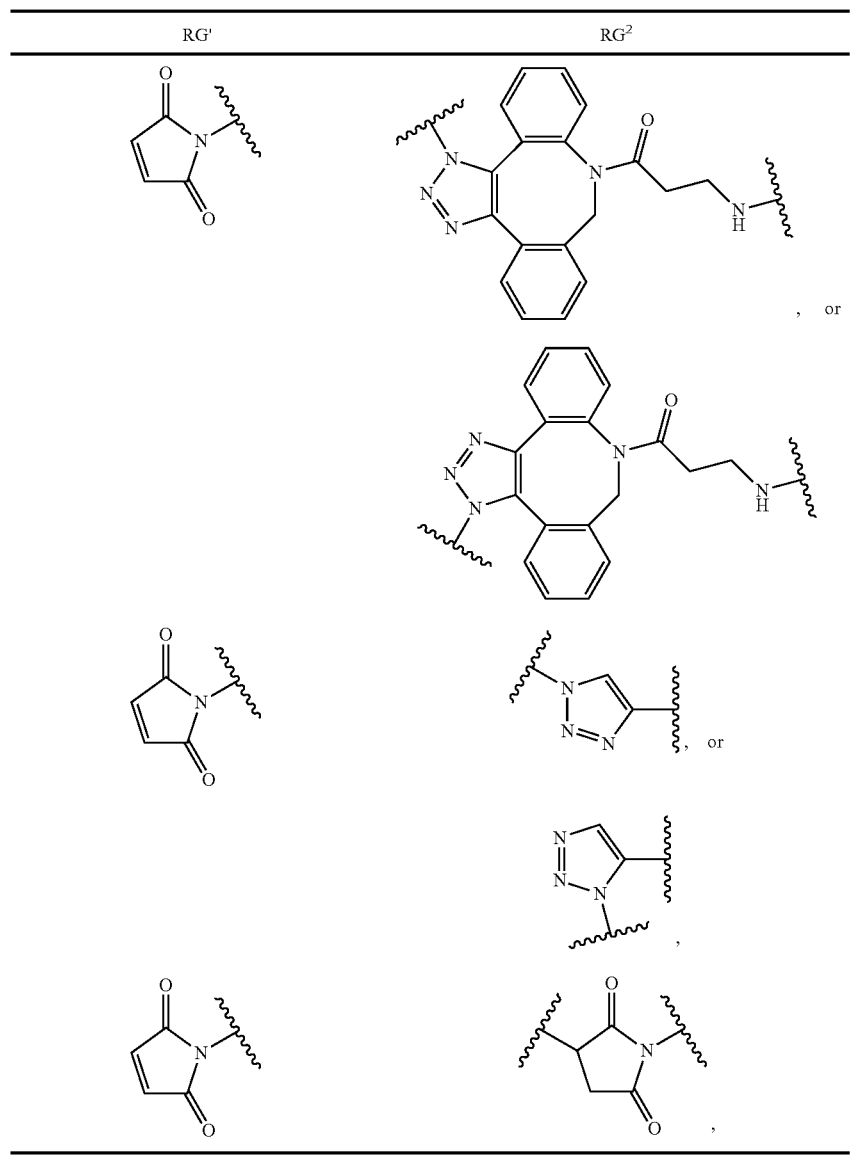

wherein the

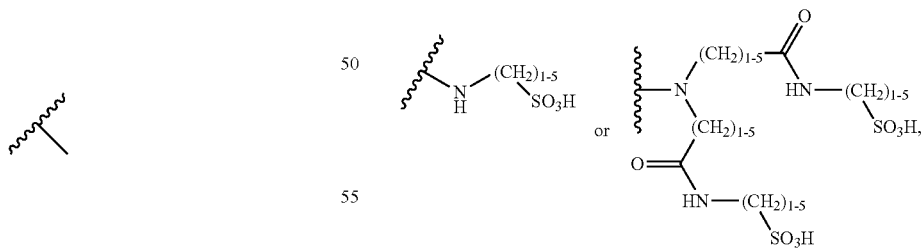

indicates the atom through which the RG' or RG² is bonded to the adjacent groups in the formula.

Any combination of a row from Table R' and a spacer SP² as described herein may be present in a compound of Formula (VI) described herein.

In certain instances, for any compound of Formula (VI), Formula (VII), Formula (VIII), Formula (IX), Formula (IXa), Formula (IXb), Formula (IXc), Formula (Xa), Formula (Xb), Formula (Xc), or Formula (Xd), HG is wherein the

indicates the atom through which the HG is bonded to the adjacent groups in the formula.

In some instances, for any compound of Formula (VI), Formula (VII), Formula (VIII), Formula (IX), Formula (IXa), Formula (IXb), Formula (IXc), Formula (Xa), Formula (Xb), Formula (Xc) or Formula (Xd), HG is —$(CH_2)_{1-5}SO_3H$, —$(CH_2)_{n''}$—NH—$(CH_2)_{1-5}SO_3H$, —$(CH_2)_{n''}$—C(O)NH—$(CH_2)_{1-5}SO_3H$, —$(CH_2CH_2O)_{m''}$—C(O)NH—$(CH_2)_{1-5}SO_3H$, —$(CH_2)_{n''}$—N$((CH_2)_{1-5}C(O)NH(CH_2)_{1-5}SO_3H)_2$, —$(CH_2)_{n''}$—C(O)N$((CH_2)_{1-5}C(O)NH(CH_2)_{1-5}SO_3H)_2$, or —$(CH_2CH_2O)_{m''}$—C(O)N$((CH_2)_{1-5}C(O)NH(CH_2)_{1-5}SO_3H)_2$, wherein subscript n'' is 1, 2, 3, 4, or 5, and subscript m'' is 1, 2, 3, 4, or 5. In one embodiment, HG is —$(CH_2)_{1-5}SO_3H$. In another embodiment, HG is —$(CH_2)_{n''}$—NH—$(CH_2)_{1-5}SO_3H$, wherein subscript n'' is 1, 2, 3, 4, or 5. In another embodiment, HG is —$(CH_2)_{n''}$—C(O)NH—$(CH_2)_{1-5}SO_3H$, wherein n'' is 1, 2, 3, 4, or 5. In another embodiment, HG is —$(CH_2CH_2O)_{m''}$—C(O)NH—$(CH_2)_{1-5}SO_3H$, wherein subscript m'' is 1, 2, 3, 4, or 5. In another embodiment, HG is —$(CH_2)_{n''}$—N$((CH_2)_{1-5}C(O)NH(CH_2)_{1-5}SO_3H)_2$, wherein subscript n'' is 1, 2, 3, 4, or 5. In another embodiment, HG is —$(CH_2)_{n''}$—C(O)N$((CH_2)_{1-5}C(O)NH(CH_2)_{1-5}SO_3H)_2$, wherein subscript n'' is 1, 2, 3, 4, or 5. In another embodiment, HG is —$(CH_2CH_2O)_{m''}$—C(O)N$((CH_2)_{1-5}C(O)NH(CH_2)_{1-5}SO_3H)_2$, wherein subscript m'' is 1, 2, 3, 4, or 5.

In some instances, for any compound of Formula (VI), Formula (VII), Formula (VIII), Formula (IX), Formula (IXa), Formula (IXb), Formula (IXc), Formula (Xa), Formula (Xb), Formula (Xc), or Formula (Xd), HG is —$(CH_2)_{1-5}PO_3H$, —$(CH_2)_n$—NH—$(CH_2)_{1-5}PO_3H$, —$(CH_2)_n$—C(O)NH—$(CH_2)_{1-5}PO_3H$, —$(CH_2CH_2O)_m$—C(O)NH—$(CH_2)_{1-5}PO_3H$, —$(CH_2)_n$—N$((CH_2)_{1-5}C(O)NH(CH_2)_{1-5}PO_3H)_2$, —$(CH_2)_n$—C(O)N$((CH_2)_{1-5}C(O)NH(CH_2)_{1-5}PO_3H)_2$, or —$(CH_2CH_2O)_m$—C(O)N$((CH_2)_{1-5}C(O)NH(CH_2)_{1-5}PO_3H)_2$, wherein n is 1, 2, 3, 4, or 5, and m is 1, 2, 3, 4, or 5. In one embodiment, HG is —$(CH_2)_{1-5}PO_3H$. In another embodiment, HG is —$(CH_2)_n$—NH—$(CH_2)_{1-5}PO_3H$, wherein n is 1, 2, 3, 4, or 5. In another embodiment, HG is —$(CH_2)_n$—C(O)NH—$(CH_2)_{1-5}PO_3H$, wherein n is 1, 2, 3, 4, or 5. In another embodiment, HG is —$(CH_2CH_2O)_m$—C(O)NH—$(CH_2)_{1-5}PO_3H$, wherein m is 1, 2, 3, 4, or 5. In another embodiment, HG is —$(CH_2)_n$—N$((CH_2)_{1-5}C(O)NH(CH_2)_{1-5}PO_3H)_2$, wherein n is 1, 2, 3, 4, or 5. In another embodiment, HG is —$(CH_2)_n$—C(O)N$((CH_2)_{1-5}C(O)NH(CH_2)_{1-5}PO_3H)_2$, wherein n is 1, 2, 3, 4, or 5. In another embodiment, HG is —$(CH_2CH_2O)_m$—C(O)N$((CH_2)_{1-5}C(O)NH(CH_2)_{1-5}PO_3H)_2$, wherein m is 1, 2, 3, 4, or 5.

In some instances, for any compound of Formula (VI), Formula (VII), Formula (VIII), Formula (IX), Formula (IXa), Formula (IXb), Formula (IXc), Formula (Xa), Formula (Xb), Formula (Xc) or Formula (Xd), HG is —$(CH_2)_{1-5}N^+(R^M)_3$, —$(CH_2)_n$—NH—$(CH_2)_{1-5}N^+(R^M)_3$, —$(CH_2)_n$—C(O)NH—$(CH_2)_{1-5}N^+(R^M)_3$, —$(CH_2CH_2O)_m$—C(O)NH—$(CH_2)_{1-5}N^+(R^M)_3$, —$(CH_2)_n$—N$((CH_2)_{1-5}C(O)NH(CH_2)_{1-5}N^+(R^M)_3)_2$, —$(CH_2)_n$—C(O)N$((CH_2)_{1-5}C(O)NH(CH_2)_{1-5}N^+(R^M)_3)_2$, or —$(CH_2CH_2O)_m$—C(O)N$((CH_2)_{1-5}C(O)NH(CH_2)_{1-5}N^+(R^M)_3)_2$, wherein n is 1, 2, 3, 4, or 5, m is 1, 2, 3, 4, or 5, and $R^M$, at each occurrence, is independently H, $C_{1-6}$alkyl, $C_{3-7}$cycloalkyl or $C_{1-6}$alkyl-$C_{3-7}$ cycloalkyl, or, two $R^M$ together with the nitrogen atom to which they are attached, form a 3-7-membered heterocycloalkyl ring. In one embodiment, HG is —$(CH_2)_{1-5}N^+(R^M)_3$. In another embodiment, HG is —$(CH_2)_n$—NH—$(CH_2)_{1-5}N^+(R^M)_3$, wherein n is 1, 2, 3, 4, or 5. In another embodiment, HG is —$(CH_2)_{n''}$—C(O)NH—$(CH_2)_{1-5}N^+(R^M)_3$, wherein n is 1, 2, 3, 4, or 5. In another embodiment, HG is —$(CH_2CH_2O)_m$—C(O)NH—$(CH_2)_{1-5}N^+(R^M)_3$, wherein m is 1, 2, 3, 4, or 5. In another embodiment, HG is —$(CH_2)_n$—N$((CH_2)_{1-5}C(O)NH(CH_2)_{1-5}N^+(R^M)_3)_2$, wherein n is 1, 2, 3, 4, or 5. In another embodiment, HG is —$(CH_2)_n$—C(O)N$((CH_2)_{1-5}C(O)NH(CH_2)_{1-5}N^+(R^M)_3)_2$, wherein n is 1, 2, 3, 4, or 5. In another embodiment, HG is —$(CH_2CH_2O)_m$—C(O)N$((CH_2)_{1-5}C(O)NH(CH_2)_{1-5}N^+(R^M)_3)_2$, wherein m is 1, 2, 3, 4, or 5.

In some instances, for any compound of Formula (VI), Formula (VII), Formula (VIII), Formula (IX), Formula (IXa), Formula (IXb), Formula (IXc), Formula (Xa), Formula (Xb), Formula (Xc), or Formula (Xd), HG is —$(CH_2)_{1-5}N^+Me_3$, —$(CH_2)_n$—NH—$(CH_2)_{1-5}N^+Me_3$, —$(CH_2)_n$—C(O)NH—$(CH_2)_{1-5}N^+Me_3$, —$(CH_2CH_2O)_m$—C(O)NH—$(CH_2)_{1-5}N^+Me_3$, —$(CH_2)_n$—N$((CH_2)_{1-5}C(O)NH(CH_2)_{1-5}N^+Me_3)_2$, —$(CH_2)_n$—C(O)N$((CH_2)_{1-5}C(O)NH(CH_2)_{1-5}N^+Me_3)_2$, or —$(CH_2CH_2O)_m$—C(O)N$((CH_2)_{1-5}C(O)NH(CH_2)_{1-5}N^+Me_3)_2$, wherein n is 1, 2, 3, 4, or 5, and m is 1, 2, 3, 4, or 5. In one embodiment, HG is —$(CH_2)_{1-5}N^+Me_3$. In another embodiment, HG is —$(CH_2)_n$—NH—$(CH_2)_{1-5}N^+Me_3$, wherein n is 1, 2, 3, 4, or 5. In another embodiment, HG is —$(CH_2)_n$—C(O)NH—$(CH_2)_{1-5}N^+Me_3$, wherein n is 1, 2, 3, 4, or 5. In another embodiment, HG is —$(CH_2CH_2O)_m$—C(O)NH—$(CH_2)_{1-5}N^+Me_3$, wherein m is 1, 2, 3, 4, or 5. In another embodiment, HG is —$(CH_2)_n$—N$((CH_2)_{1-5}C(O)NH(CH_2)_{1-5}N^+Me_3)_2$, wherein n is 1, 2, 3, 4, or 5. In another embodiment, HG is —$(CH_2)_n$—C(O)N$((CH_2)_{1-5}C(O)NH(CH_2)_{1-5}N^+Me_3)_2$, wherein n is 1, 2, 3, 4, or 5. In another embodiment, HG is —$(CH_2CH_2O)_m$—C(O)N$((CH_2)_{1-5}C(O)NH(CH_2)_{1-5}N^+Me_3)_2$, wherein m is 1, 2, 3, 4, or 5.

In certain instances, for any compound of Formula (VI), Formula (VII), Formula (VIII), Formula (IX), Formula (IXa), Formula (IXb), Formula (IXc), Formula (Xa), Formula (Xb), Formula (Xc), or Formula (Xd), HG is

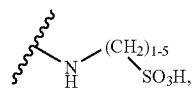

or salts thereof. In certain instances, for any compound of Formula (VI), Formula (VII), Formula (VIII), Formula (IX), Formula (IXa), Formula (IXb), Formula (IXc), Formula (Xa), Formula (Xb), Formula (Xc), or Formula (Xd), HG is

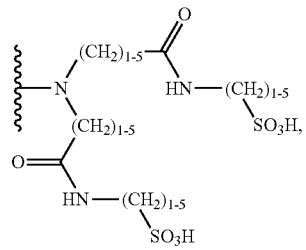 [SMILES: *N(CC(=O)NCS(=O)(=O)O)CC(=O)NCS(=O)(=O)O]

or salts thereof. In one instance HG is

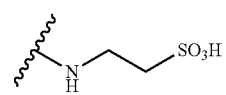 [SMILES: *NCCS(=O)(=O)O]

or salts thereof. In another instance, HG is

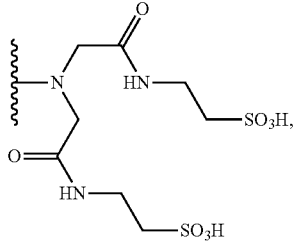

or salts thereof.

In some examples, for any compound of Formula (VI), Formula (VII), Formula (VIII), Formula (IX), Formula (IXa), Formula (IXb), Formula (IXc), Formula (Xa), Formula (Xb), Formula (Xc), or Formula (Xd), HG is an amine, or salts thereof, for instance a quarternary amine, e.g.,

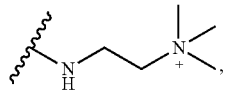

wherein the

indicates the atom through which the HG is bonded to the adjacent groups in the formula.

In other examples, for any compound of Formula (I), Formula (II), Formula (III), Formula (IV), Formula (IVa), Formula (IVb), Formula (IVc), Formula (Va), Formula (Vb), Formula (Vc), or Formula (Vd), HG is a phosphonic acid, or salts thereof, e.g.,

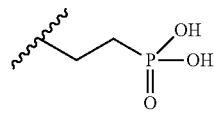 [SMILES: *CCP(=O)(O)O]

wherein the

indicates the atom through which the HG is bonded to the adjacent groups in the formula. In other examples, for any compound of Formula (I), Formula (II), Formula (III), Formula (IV), Formula (IVa), Formula (IVb), Formula (IVc), Formula (Va), Formula (Vb), Formula (Vc), or Formula (Vd), HG is a phosphonic acid, or salts thereof, e.g.,

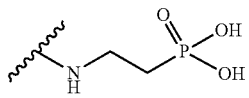 [SMILES: *NCCP(=O)(O)O]

wherein the

indicates the atom through which the HG is bonded to the adjacent groups in the formula.

In yet other examples, for any compound of Formula (VI), Formula (VII), Formula (VIII), Formula (IX), Formula (IXa), Formula (IXb), Formula (IXc), Formula (Xa), Formula (Xb), Formula (Xc), or Formula (Xd), HG is a sugar residue, e.g.,

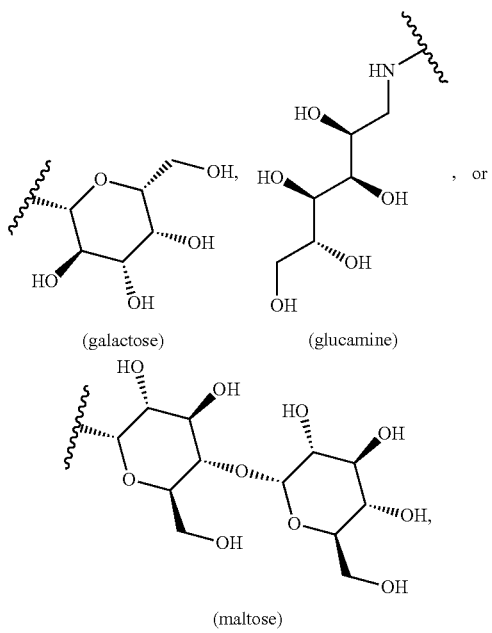

(galactose)   (glucamine)

(maltose)

wherein the

indicates the atom through which the HG is bonded to the adjacent groups in the formula.

In certain instances, for any compound of Formula (VI), Formula (VII), Formula (VIII), Formula (IX), Formula (IXa), Formula (IXb), Formula (IXc), Formula (Xa), Formula (Xb), Formula (Xc), or Formula (Xd), $SP^1$ and $SP^2$ are independently, in each instance, absent, or selected from the group consisting of $C_{1-6}$ alkylene, —NH—, —C(O)—, (—CH$_2$—CH$_2$—O)$_e$, —NH—CH$_2$—CH$_2$—(—O—CH$_2$—CH$_2$)$_e$—C(O)—, —C(O)—(CH$_2$)$_e$—C(O)—, —C(O)—NH—(CH$_2$)$_v$—, polyglycine (e.g., ((glycine)$_4$-serine)$_f$, wherein subscript f is an integer from 1 to 6), and combinations thereof, wherein subscript e is an integer from 0 to 4, subscript u is an integer from 1 to 8, and subscript v is an integer from 1 to 8. In certain instances, for any compound of Formula (VI), Formula (VII), Formula (VIII), Formula (IX), Formula (IXa), Formula (IXb), Formula (IXc), Formula (Xa), Formula (Xb), Formula (Xc), or Formula (Xd), $SP^1$ and $SP^2$ are independently, in each instance, as shown in Table S. In certain embodiments, ((glycine)$_4$-serine)$_f$ is (glycine)$_4$-serine.

In some instances, for any compound of Formula (VI), Formula (VII), Formula (VIII), Formula (IX), Formula (IXa), Formula (IXb), Formula (IXc), Formula (Xa), Formula (Xb), Formula (Xc), or Formula (Xd),

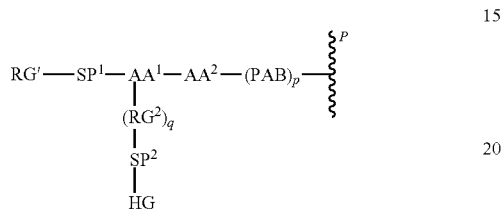

is selected from the group consisting of:

631 632
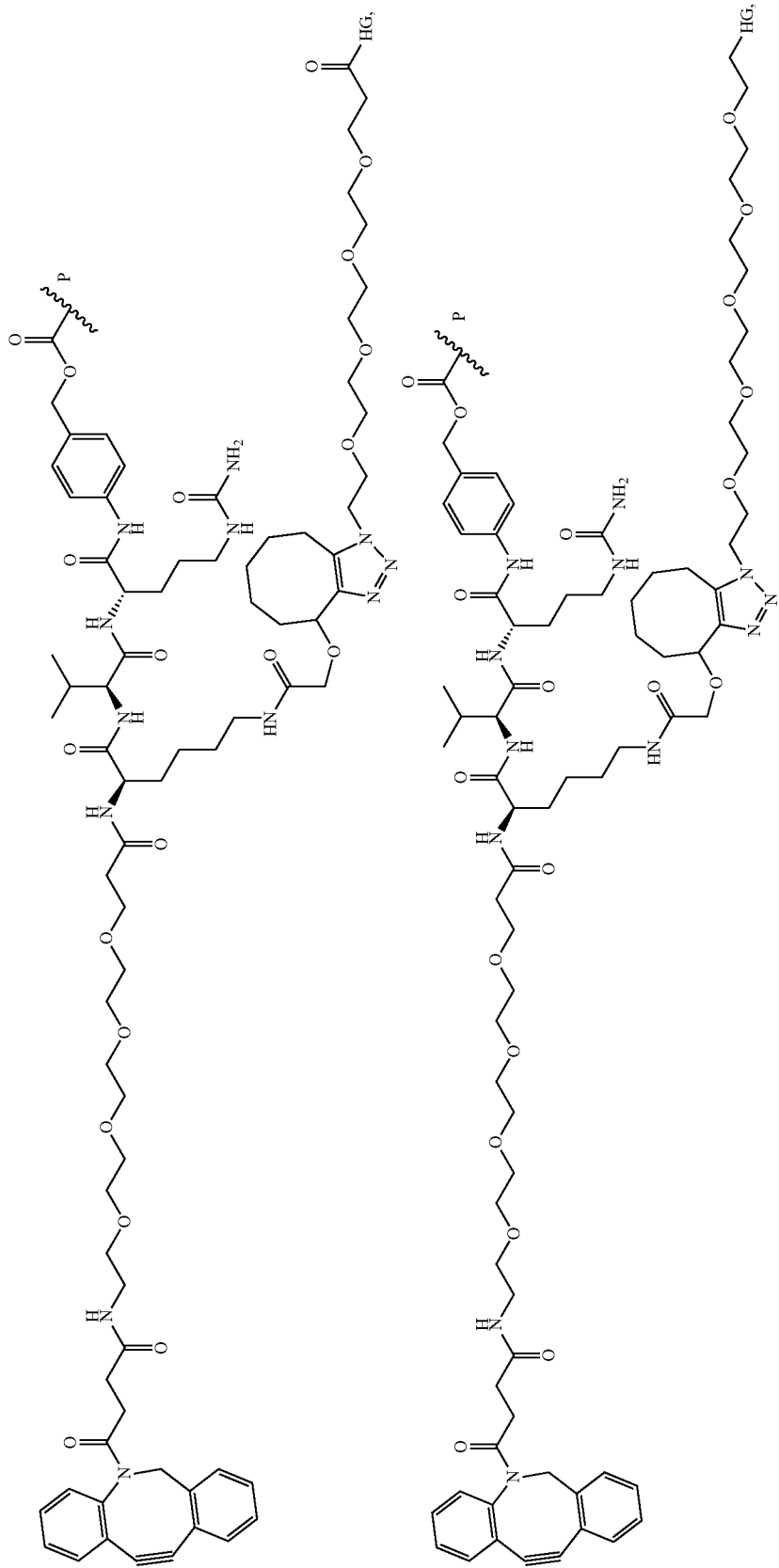

633
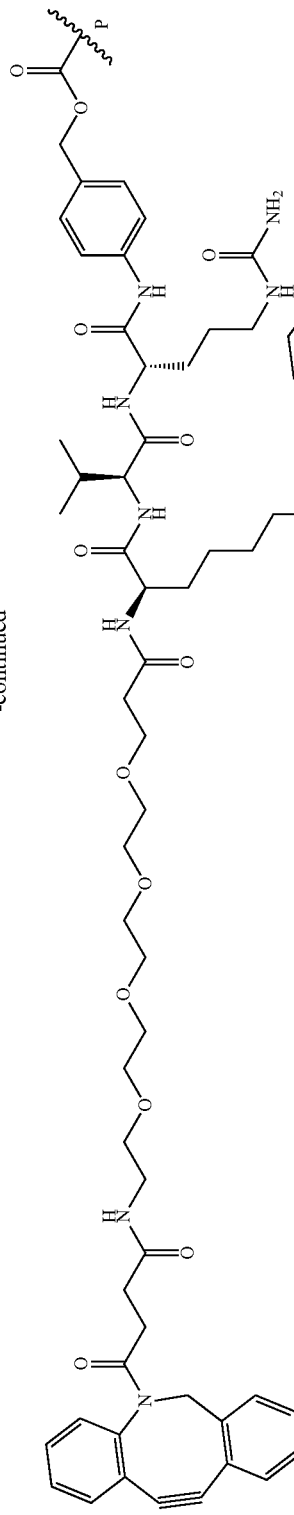
634
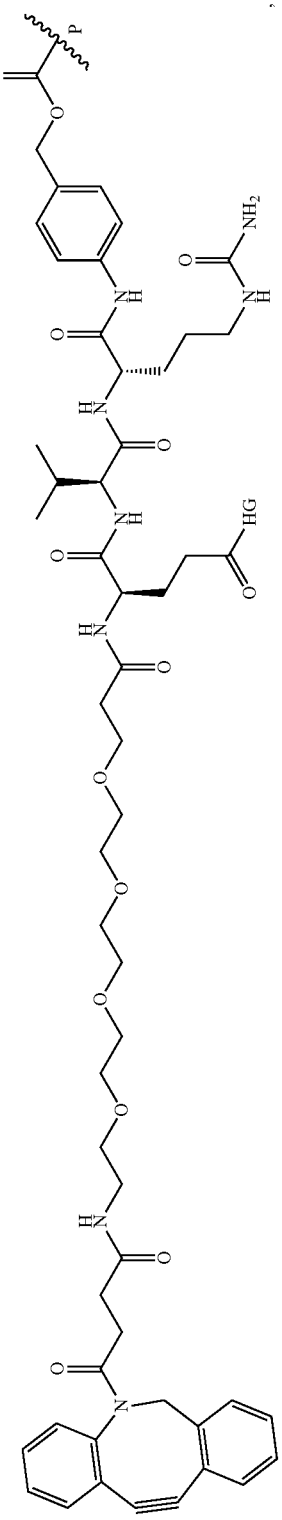
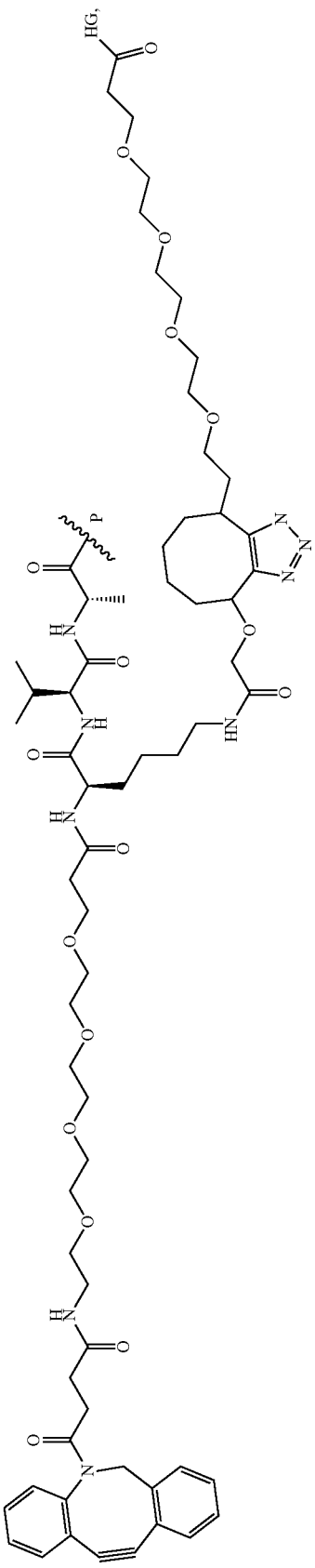

635
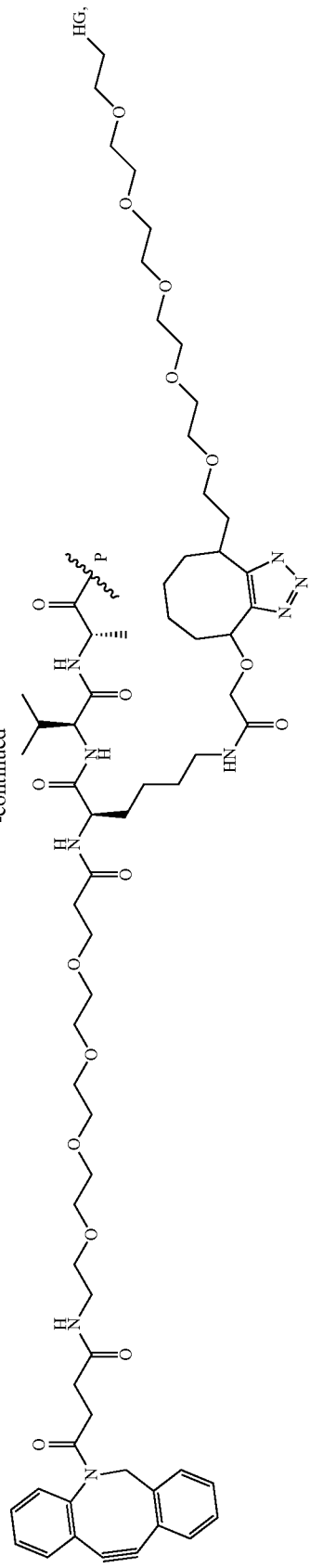
636
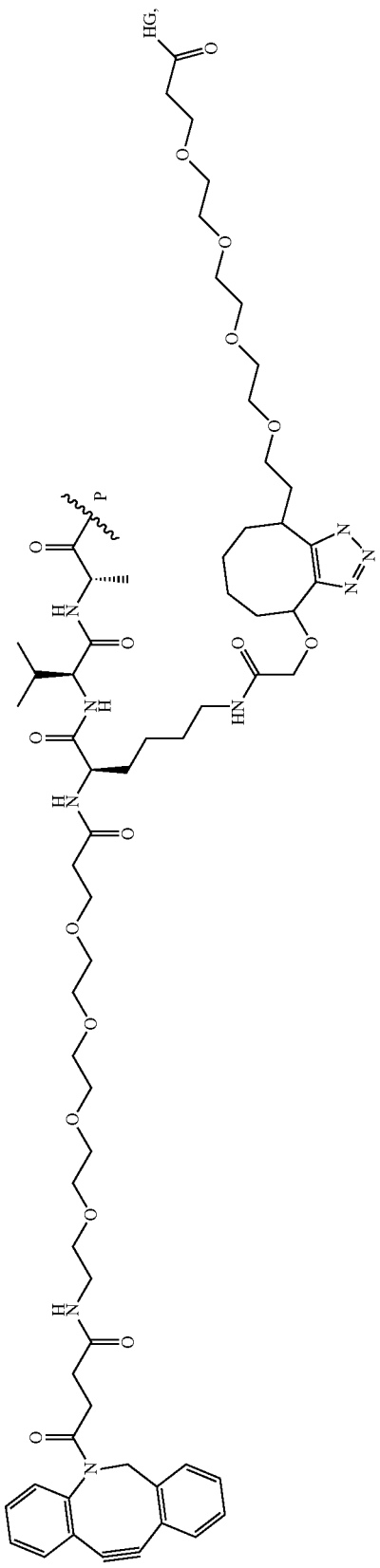
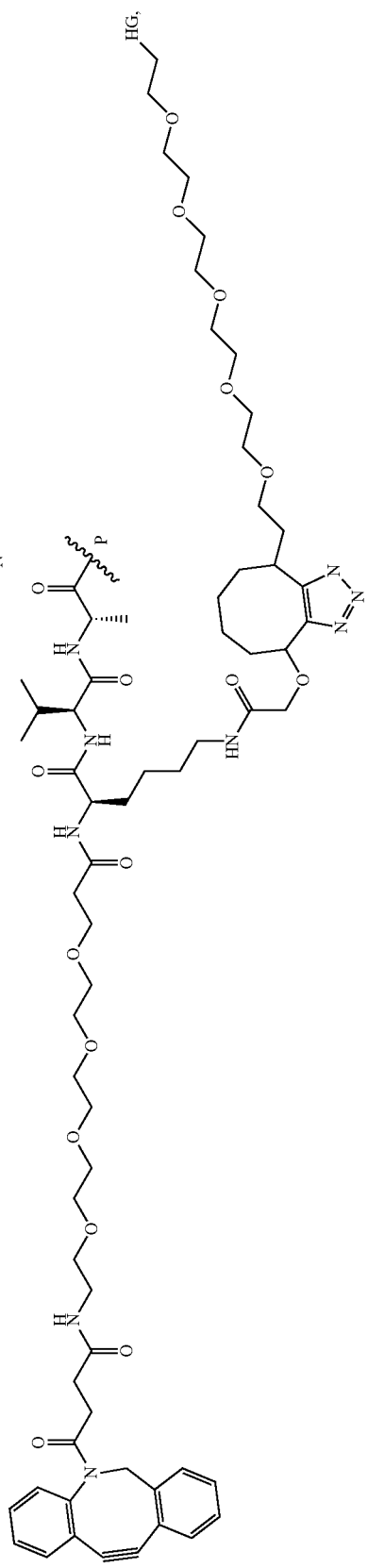

-continued
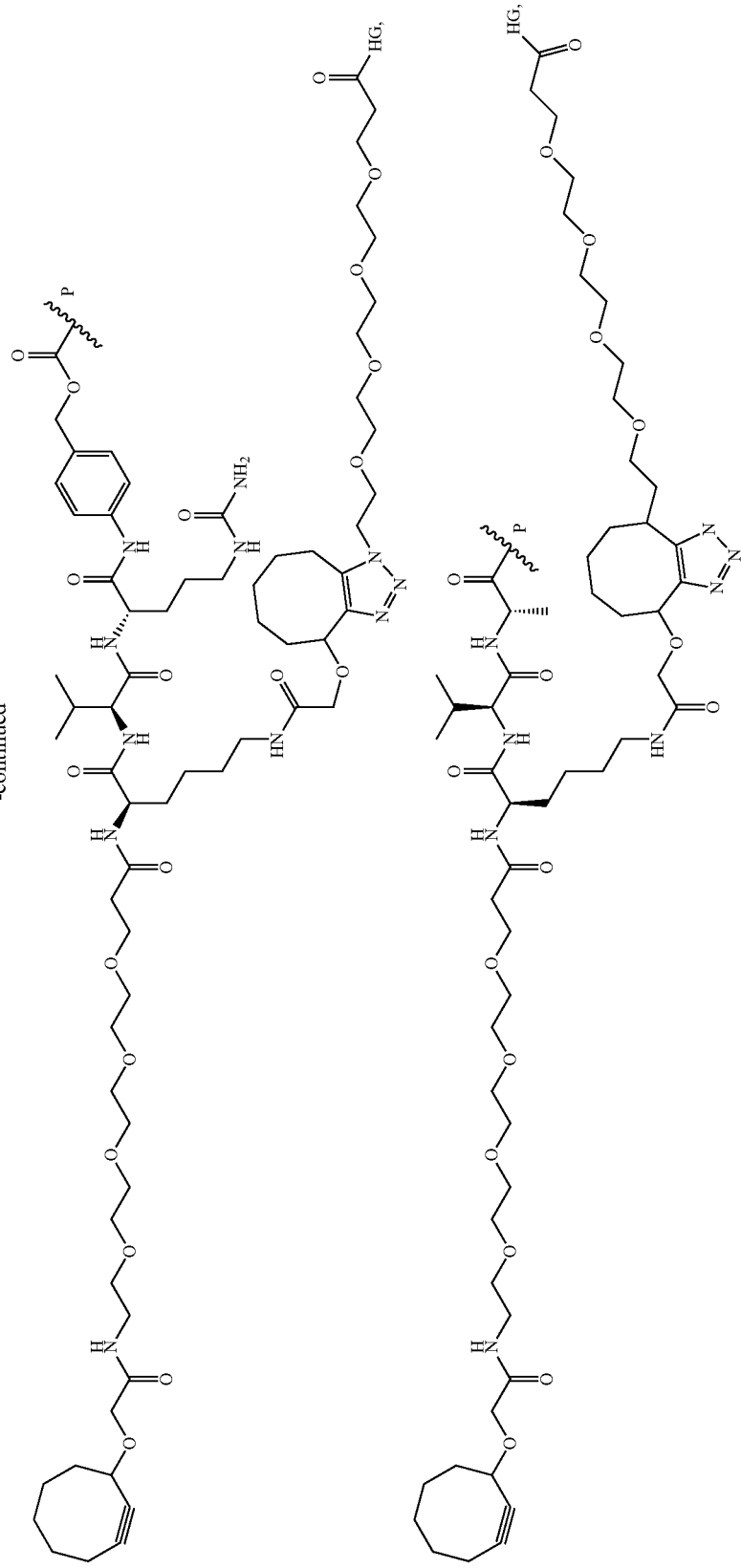

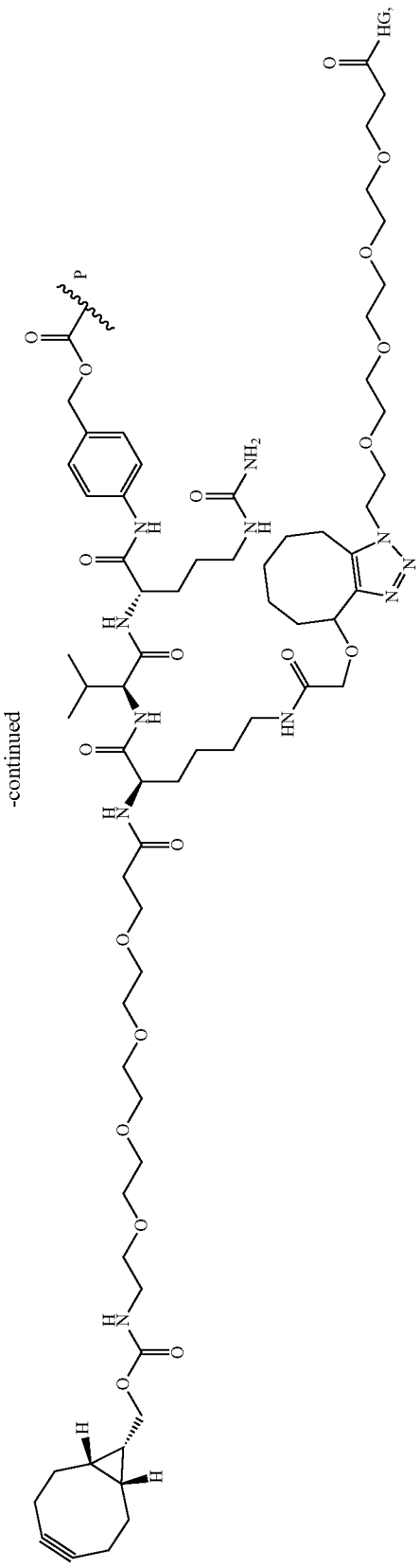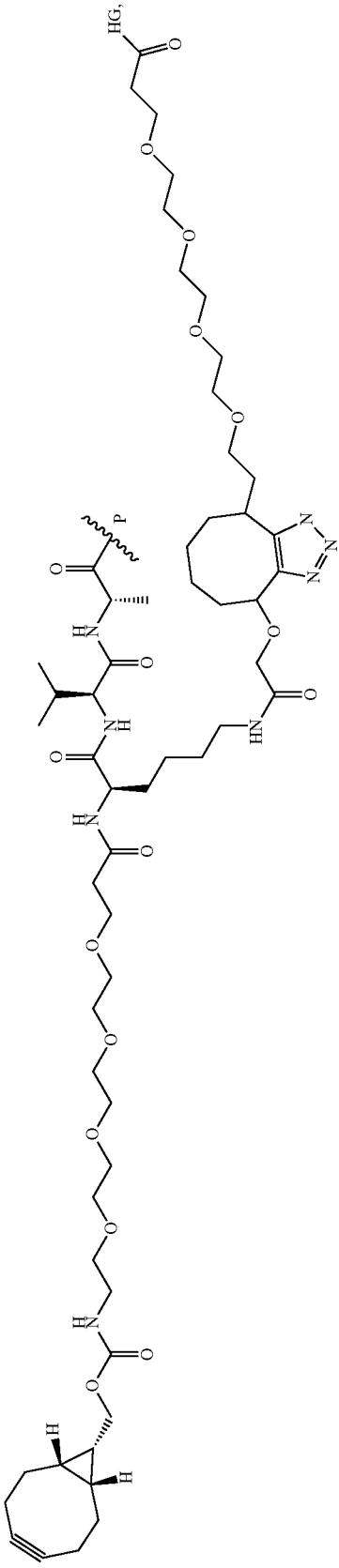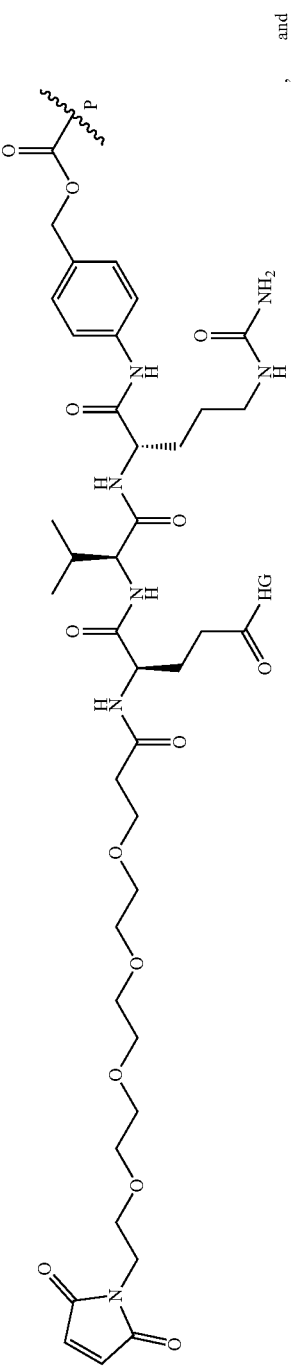

-continued
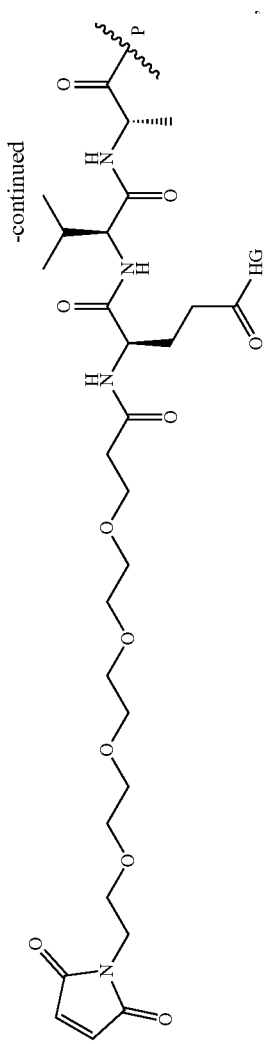

or a stereoisomeric form thereof, or a regioisomer thereof, or a mixture of regioisomers thereof, wherein
each

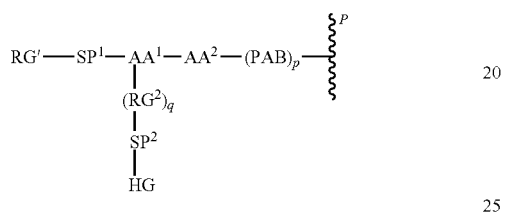

is a bond to the payload residue.

In some instances, for any compound of Formula (VI), Formula (VII), Formula (VIII), Formula (IX), Formula (IXa), Formula (IXb), Formula (IXc), Formula (Xa), Formula (Xb), Formula (Xc), or Formula (Xd), $$RG'-SP^1-\underset{\underset{\underset{HG}{|}}{\underset{SP^2}{|}}}{\underset{(RG^2)_q}{\overset{|}{AA^1}}}-AA^2-(PAB)_p-\overset{P}{\xi}$$

is selected from the group consisting of:

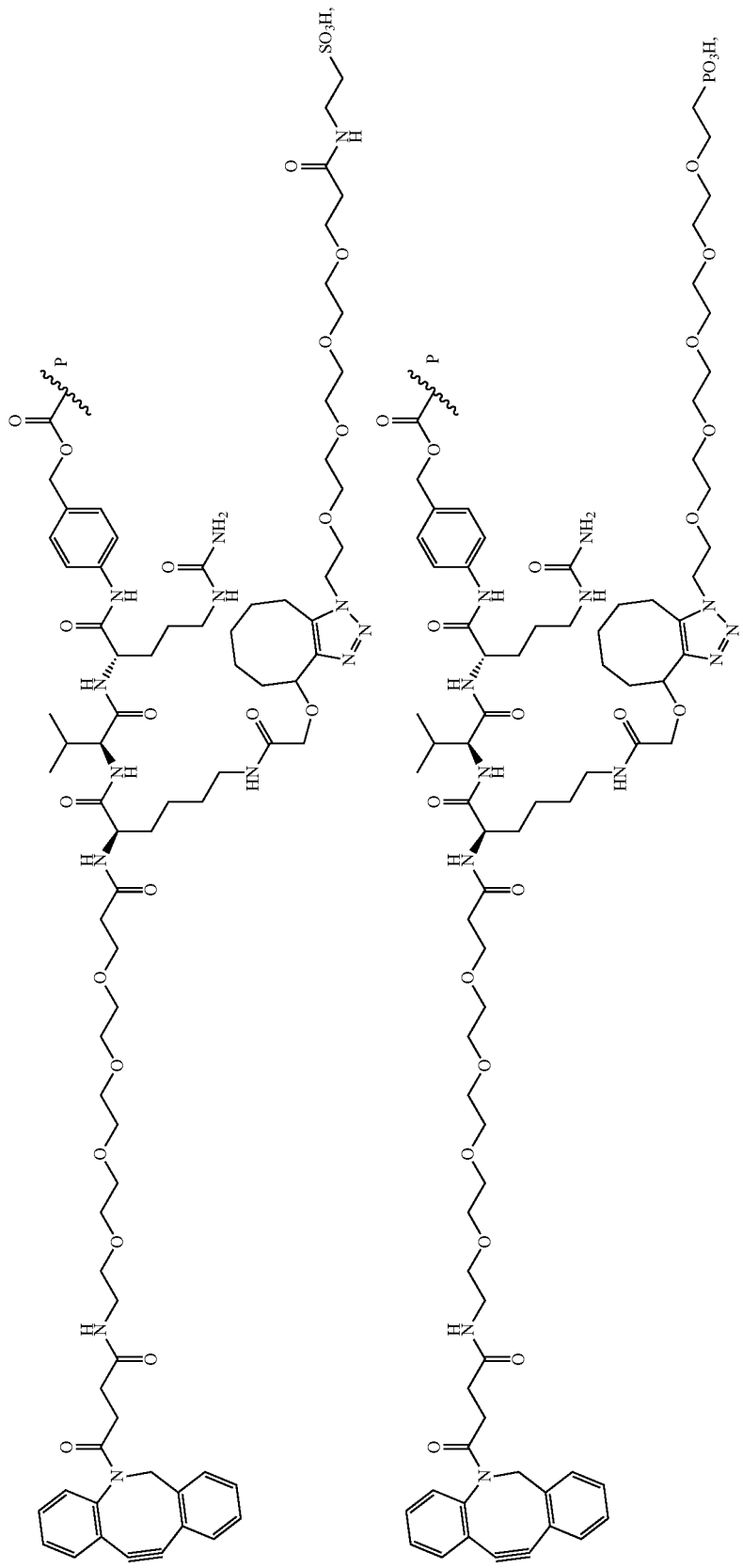

647
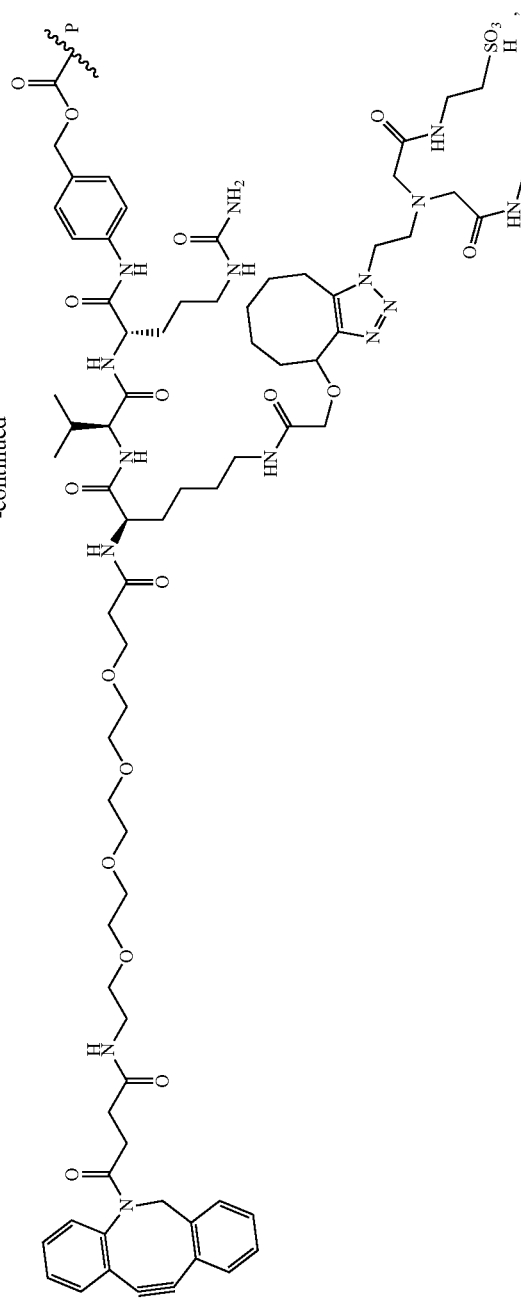
648
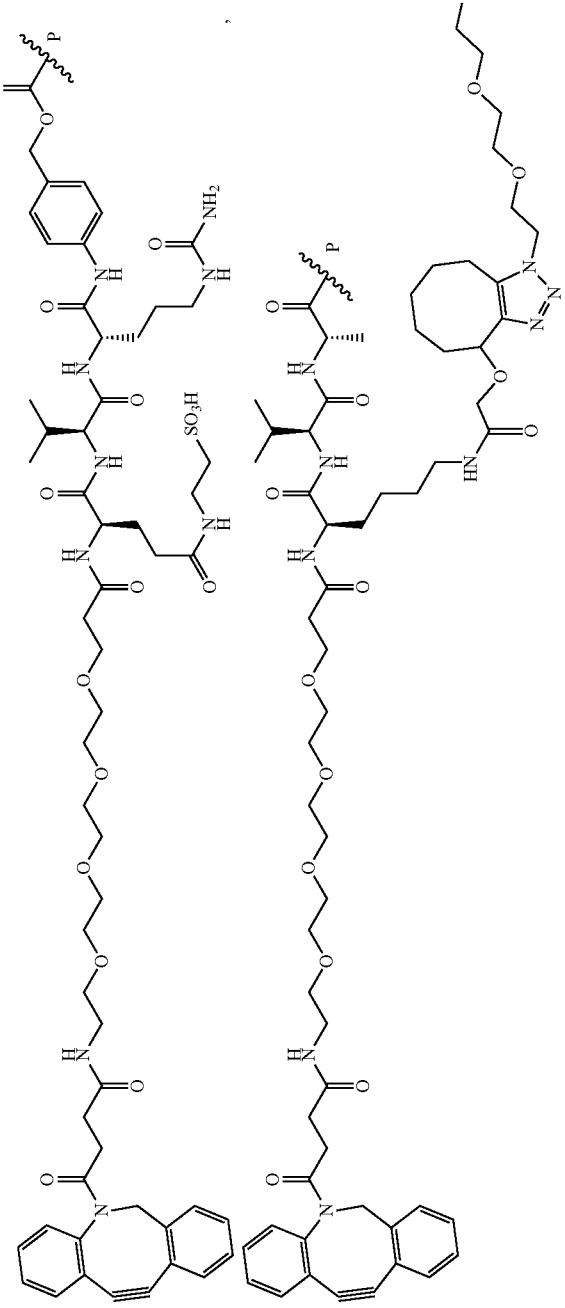
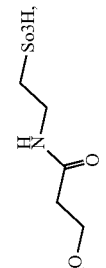

-continued
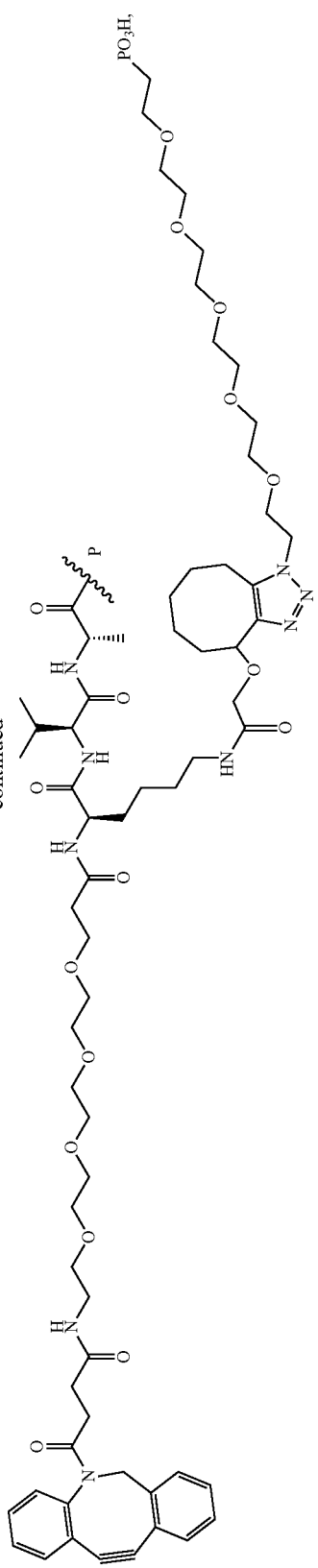
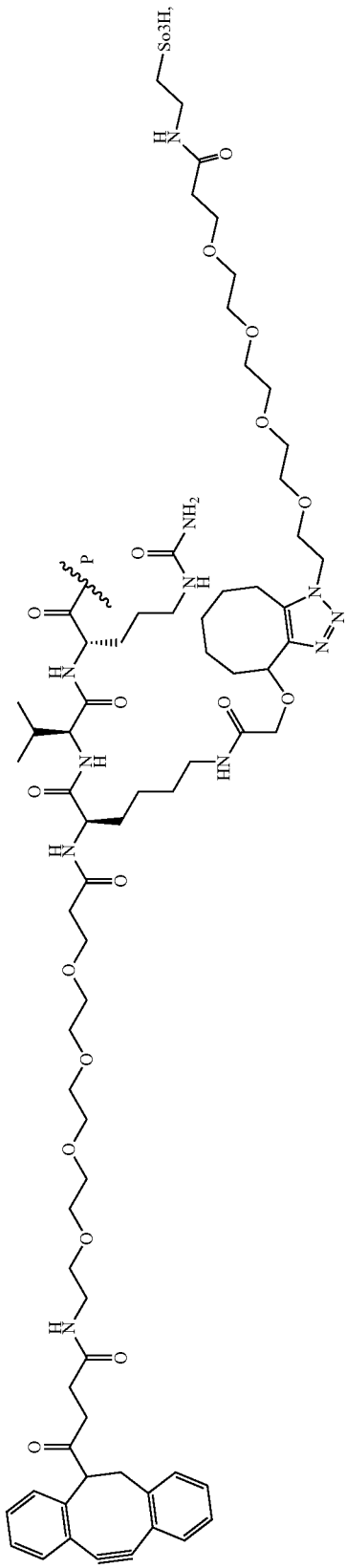
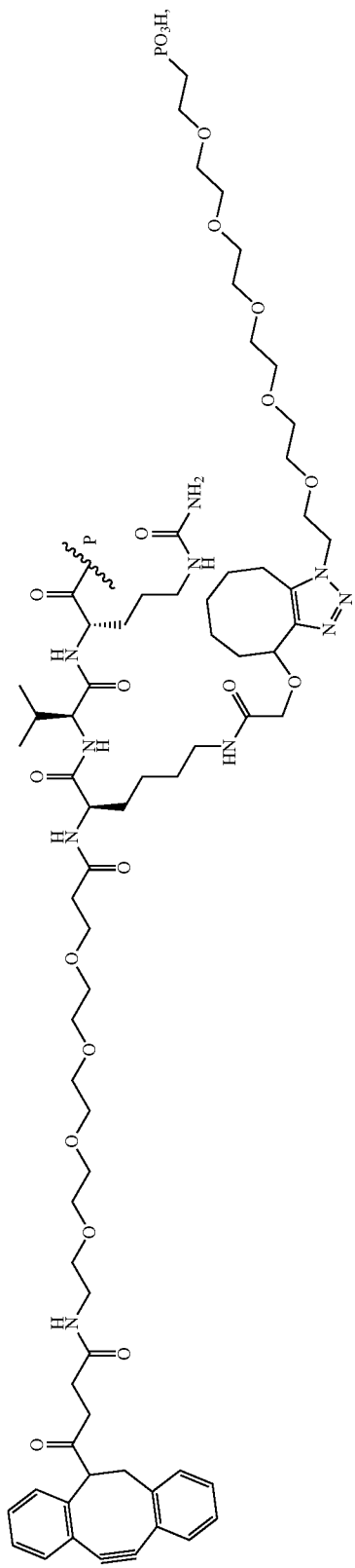

651
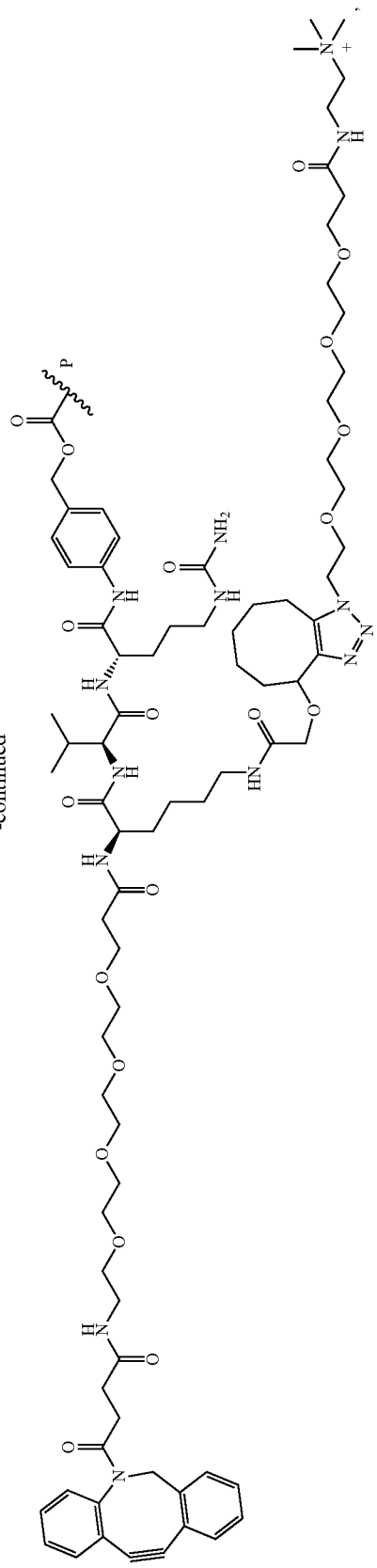
-continued
652
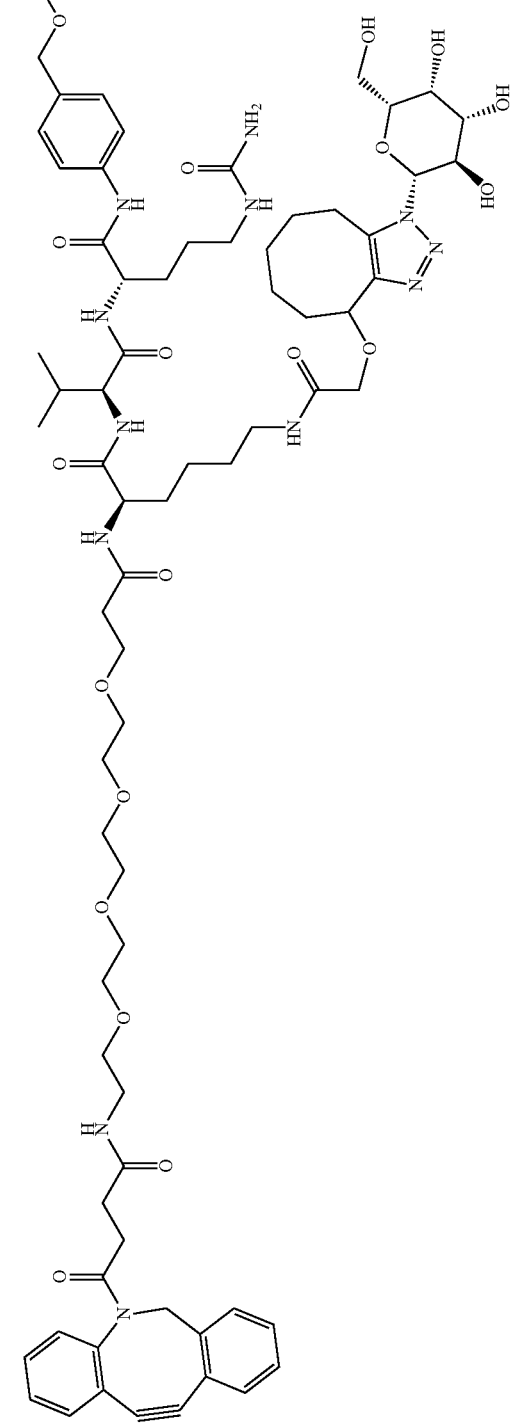

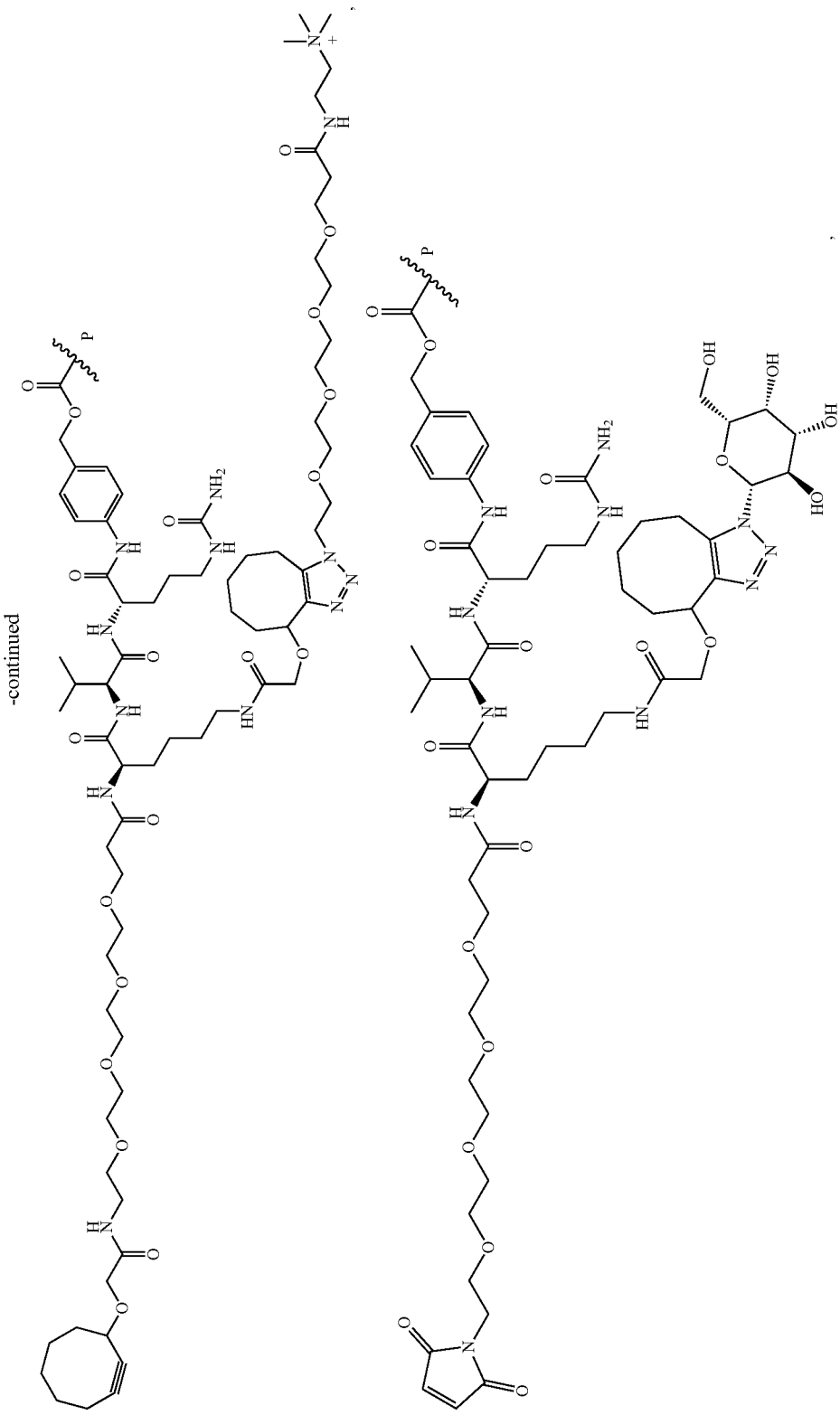

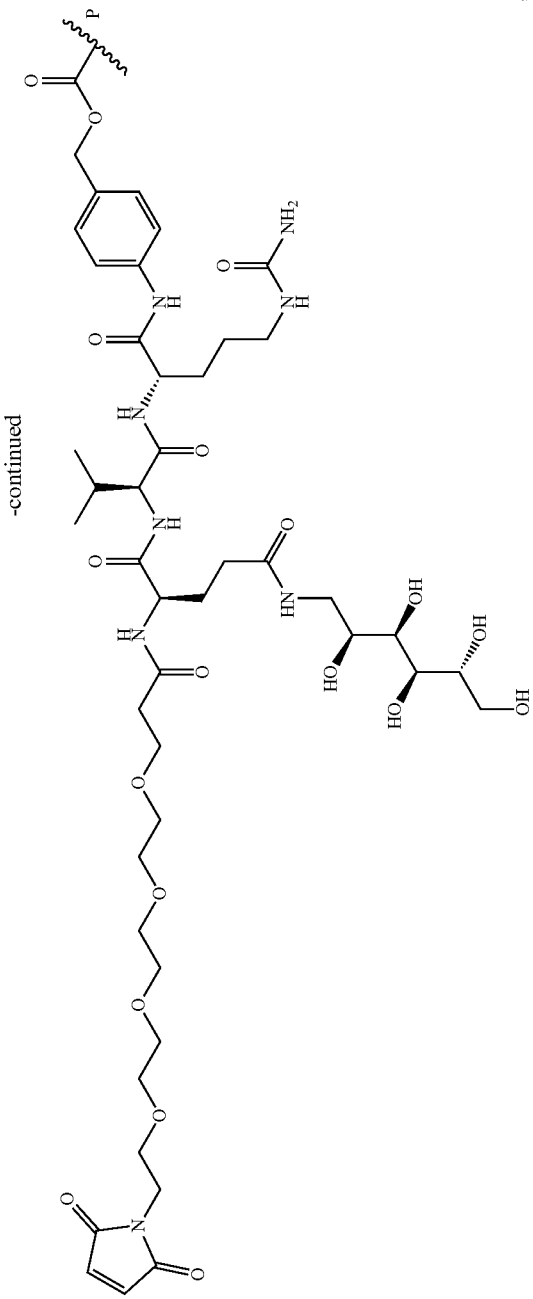
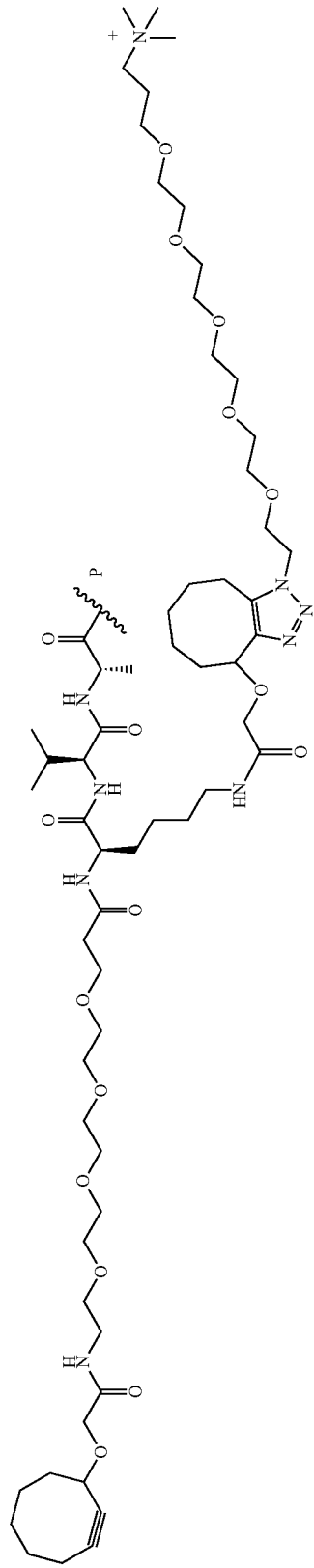

-continued
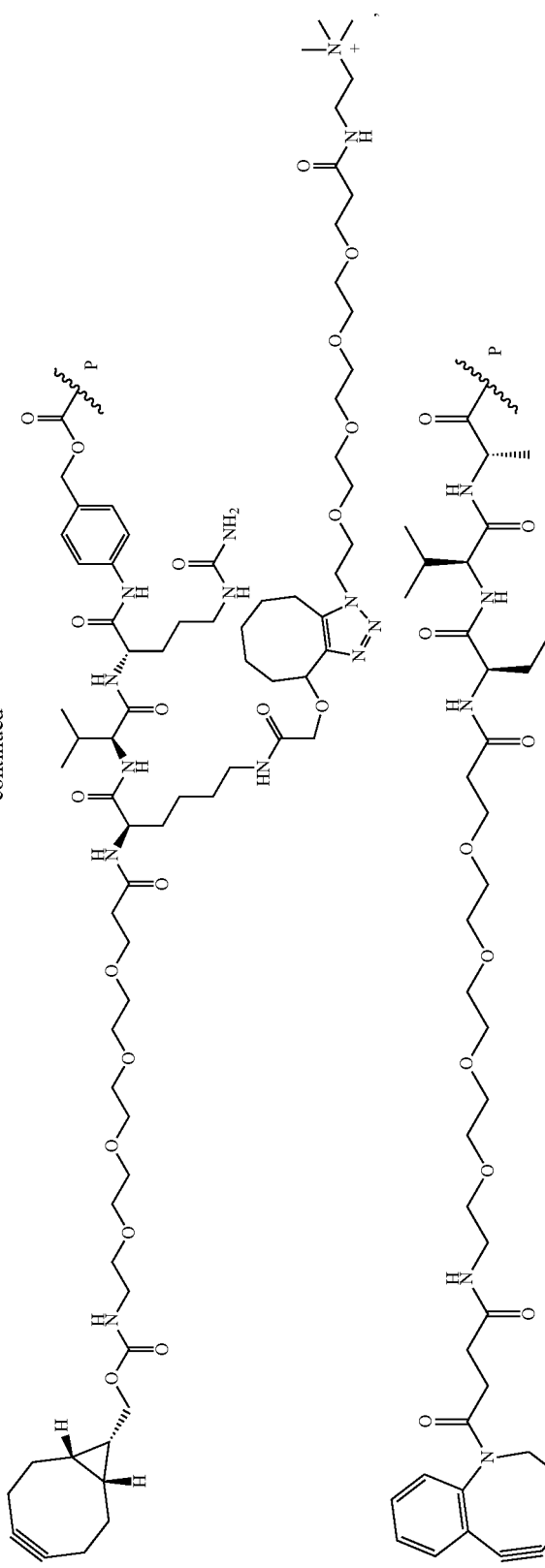
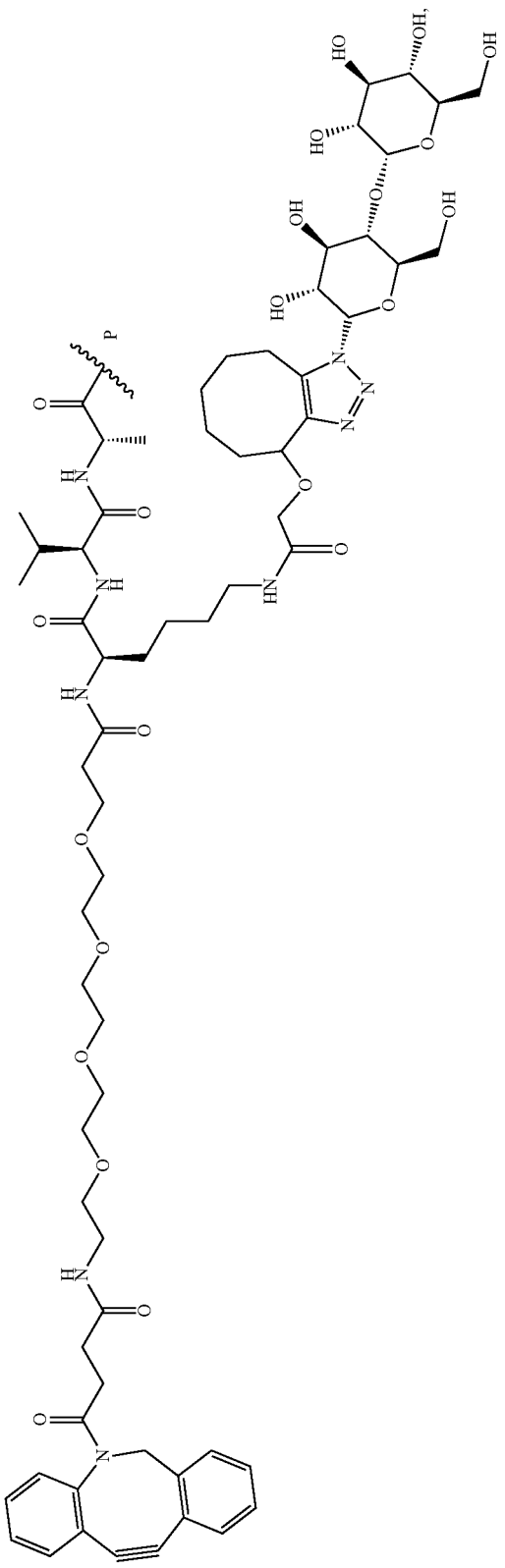

or a stereoisomeric form thereof, or a regioisomer thereof, or a mixture of regioisomers thereof, wherein each

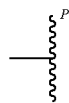

is a bond to the payload residue.

In some instances, for any compound of Formula (VI), Formula (VII), Formula (VIII), Formula (IX), Formula (IXa), Formula (IXb), Formula (IXc), Formula (Xa), Formula (Xb), Formula (Xc), or Formula (Xd), LL is according to Formula (LL1):

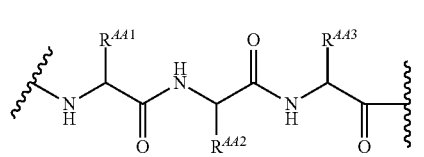

(LL1)

wherein $R^{AA1}$, $R^{AA2}$, and $R^{AA3}$ are each, independently, amino acid side chains, at least one of which is bonded directly or indirectly to —$(RG^2)_q$-$SP^2$-HG. In some cases, $R^{AA1}$ is a lysine, glutamine, glutamic acid or aspartic acid side chain bonded directly or indirectly to HG, and $R^{AA2}$ and $R^{AA3}$ are either valine and alanine or valine and citrulline sidechains respectively.

In some instances, for any compound of Formula (IX), Formula (IXa), Formula (IXb), Formula (IXc), Formula (Xa), Formula (Xb), Formula (Xc), or Formula (Xd), $AA^2$ is

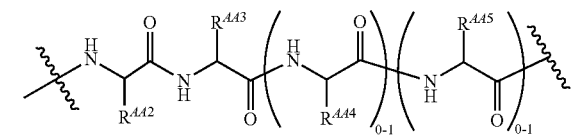

wherein $R^{AA2}$, $R^{AA3}$, $R^{AA4}$, and $R^{AA5}$ are each, independently, amino acid side chains, at least one of which is bonded directly or indirectly to —$(RG^2)_q$-$SP^2$-HG, wherein the

indicates the atom through which $AA^2$ is bonded to the adjacent groups in the formula. In some examples, $R^{AA2}$, $R^{AA3}$, $R^{AA4}$, and $R^{AA5}$, are independently in each instance, an amino acid side chain selected from the side chains of alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof.

In some instances, for any compound of Formula (IX), Formula (IXa), Formula (IXb), Formula (IXc), Formula (Xa), Formula (Xb), Formula (Xc), or Formula (Xd), $AA^2$ is

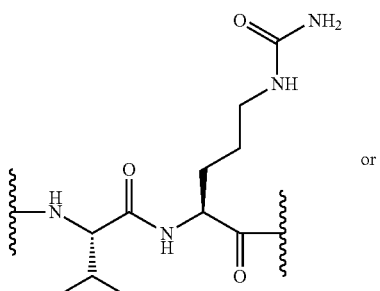

or

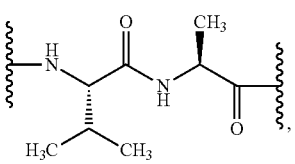

wherein the

indicates the atom through which $AA^2$ is bonded to the adjacent groups in the formula.

In some instances, for any compound of Formula (Xa), Formula (Xb), Formula (Xc), or Formula (Xd), subscript e is 4. In some instances, for any compound of Formula (Xa), Formula (Xb), Formula (Xc), or Formula (Xd), subscript e is 5.

In some instances, for any compound of Formula (IX), Formula (IXa), Formula (IXb), Formula (IXc), Formula (Xa), Formula (Xb), Formula (Xc), or Formula (Xd), PA is the residue of a group selected from the group consisting of a dolastatin, an auristatin, a maytansinoid, a plant alkaloid, a taxane, a vinca alkaloid, a steroid, and a liver X receptor (LXR) modulator. In some cases, PA is a dolastatin. In some cases, PA is a dolastatin. In some cases, PA is an auristatin. In some cases, PA is a maytansinoid. In some cases, PA is a dopant alkaloid. In some cases, PA is a taxane. In some cases, PA is a vinca alkaloid. In some cases, PA is a steroid. In some cases, PA is a LXR modulator. In some cases, a LXR modulator is a LXR agonist. In some cases, a LXR modulator is a LXR antagonist.

In certain instances, any compound of Formula (IX), Formula (IXa), Formula (IXb), Formula (IXc), Formula (Xa), Formula (Xb), Formula (Xc), or Formula (Xd), is selected from the group consisting of:

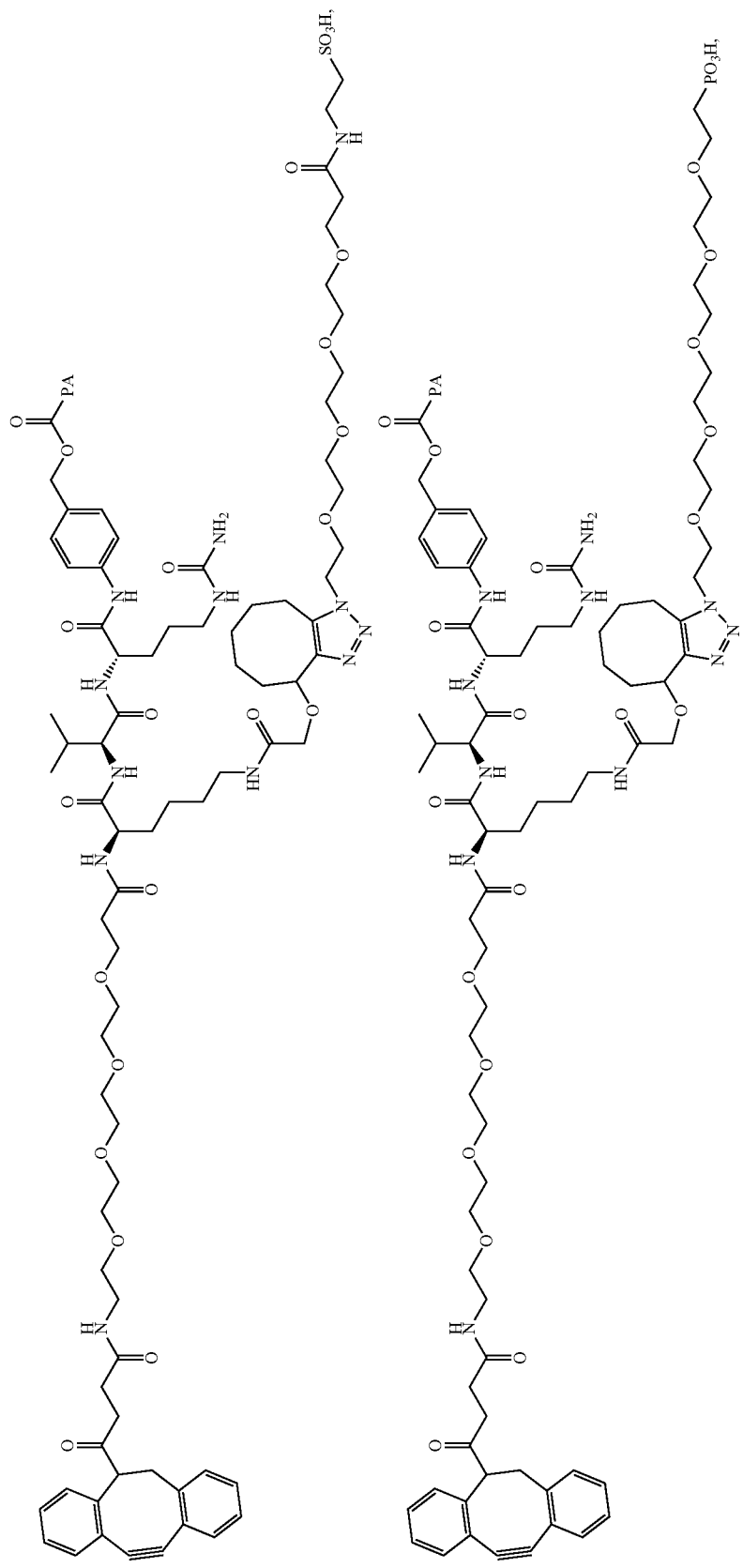

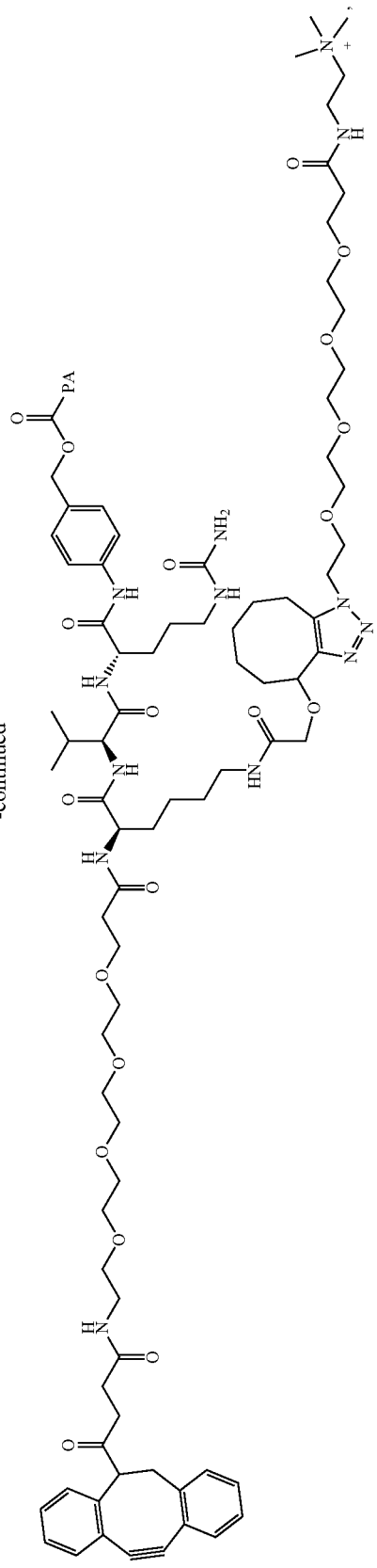
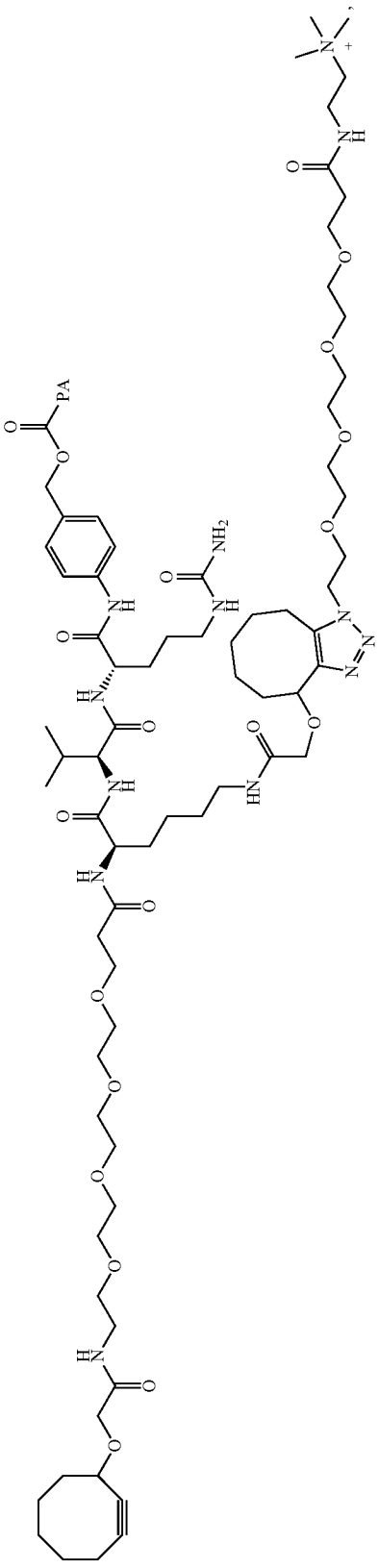

-continued
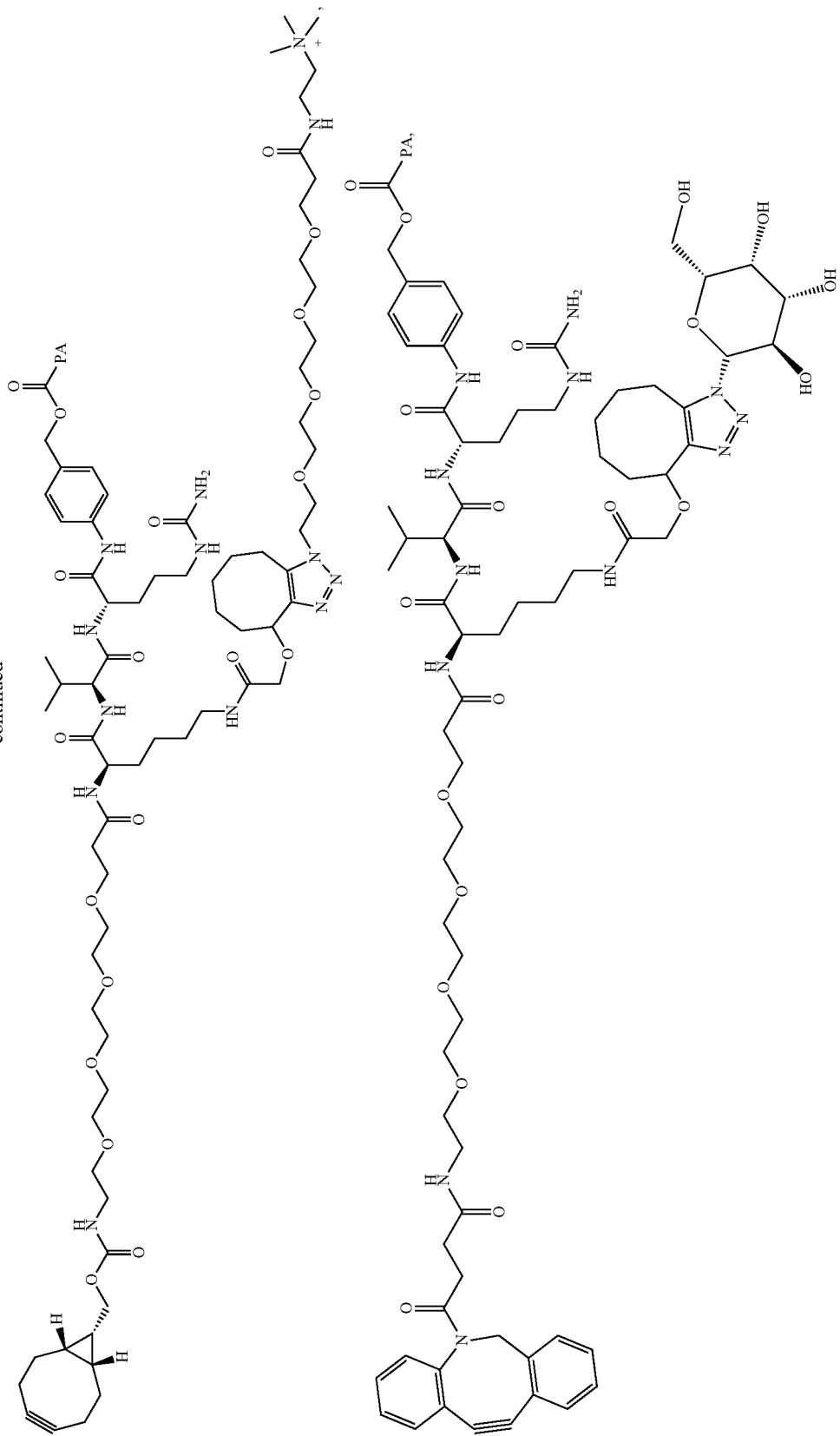

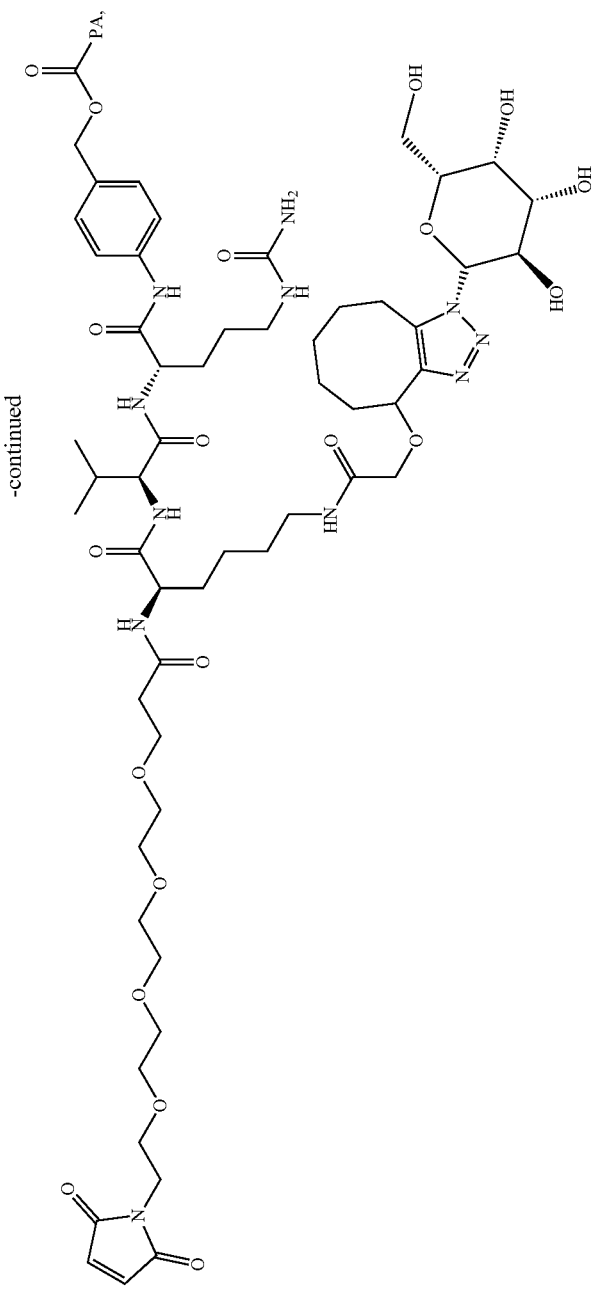
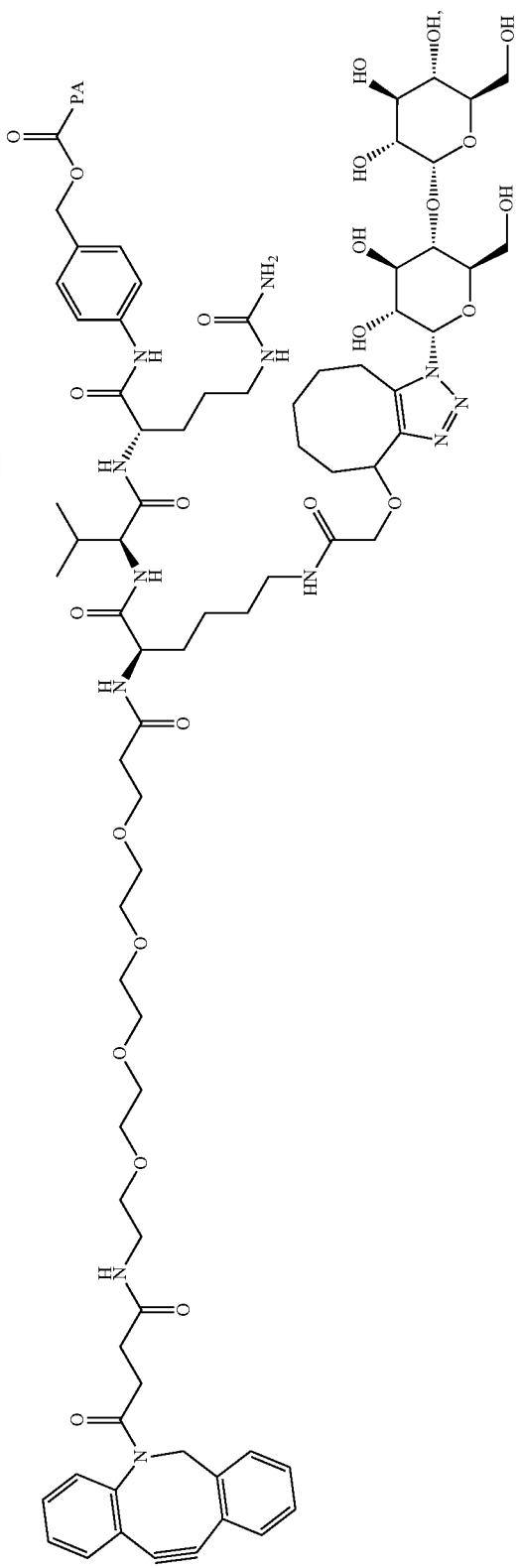

-continued
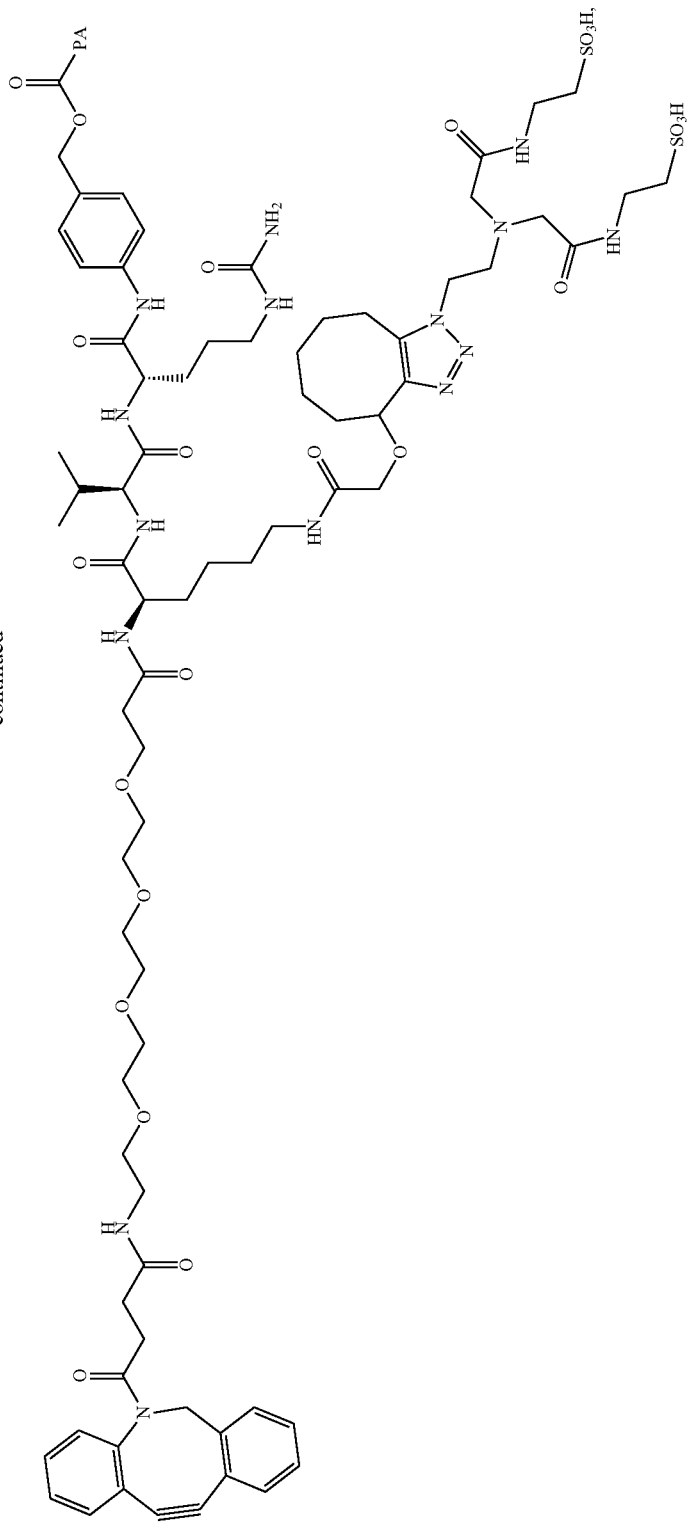

-continued
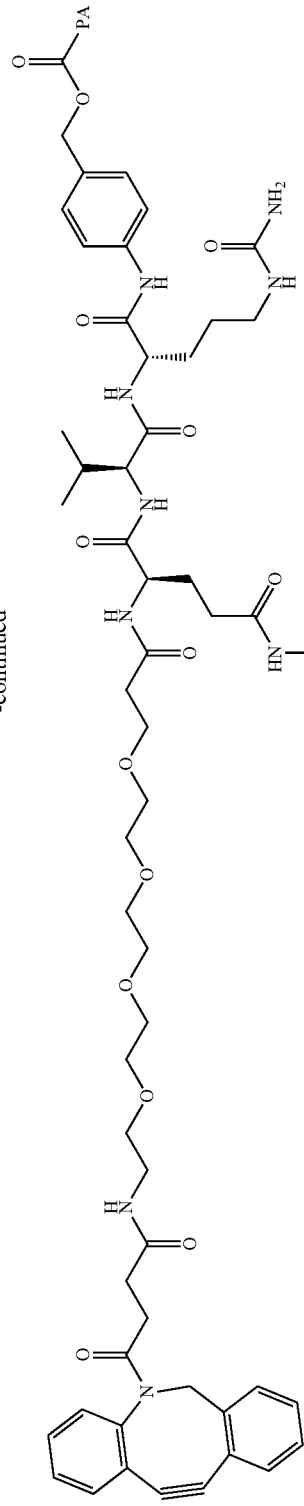
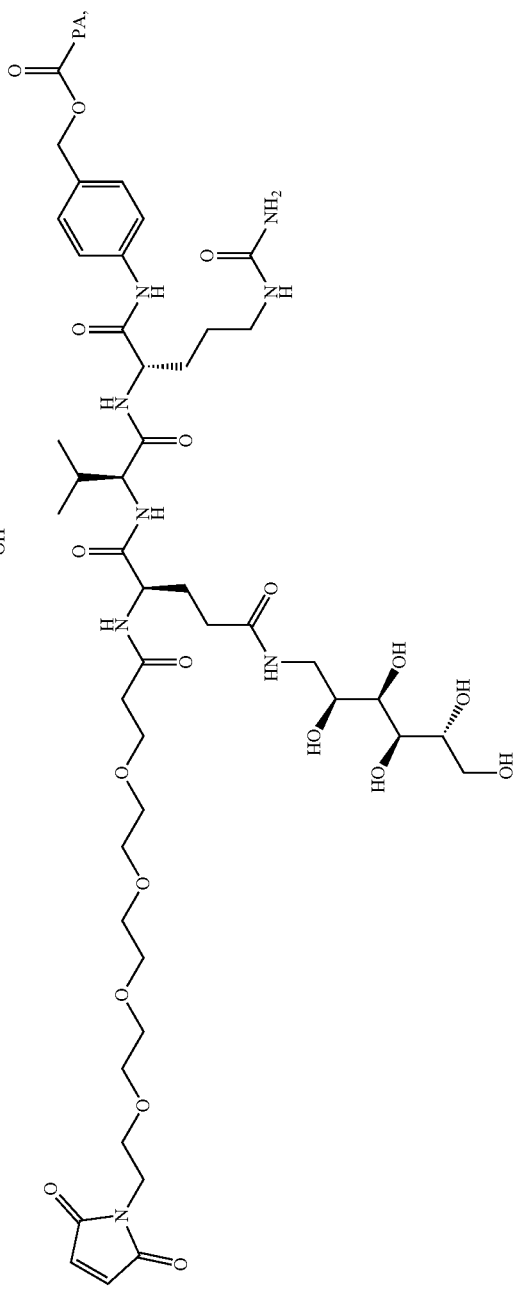

-continued
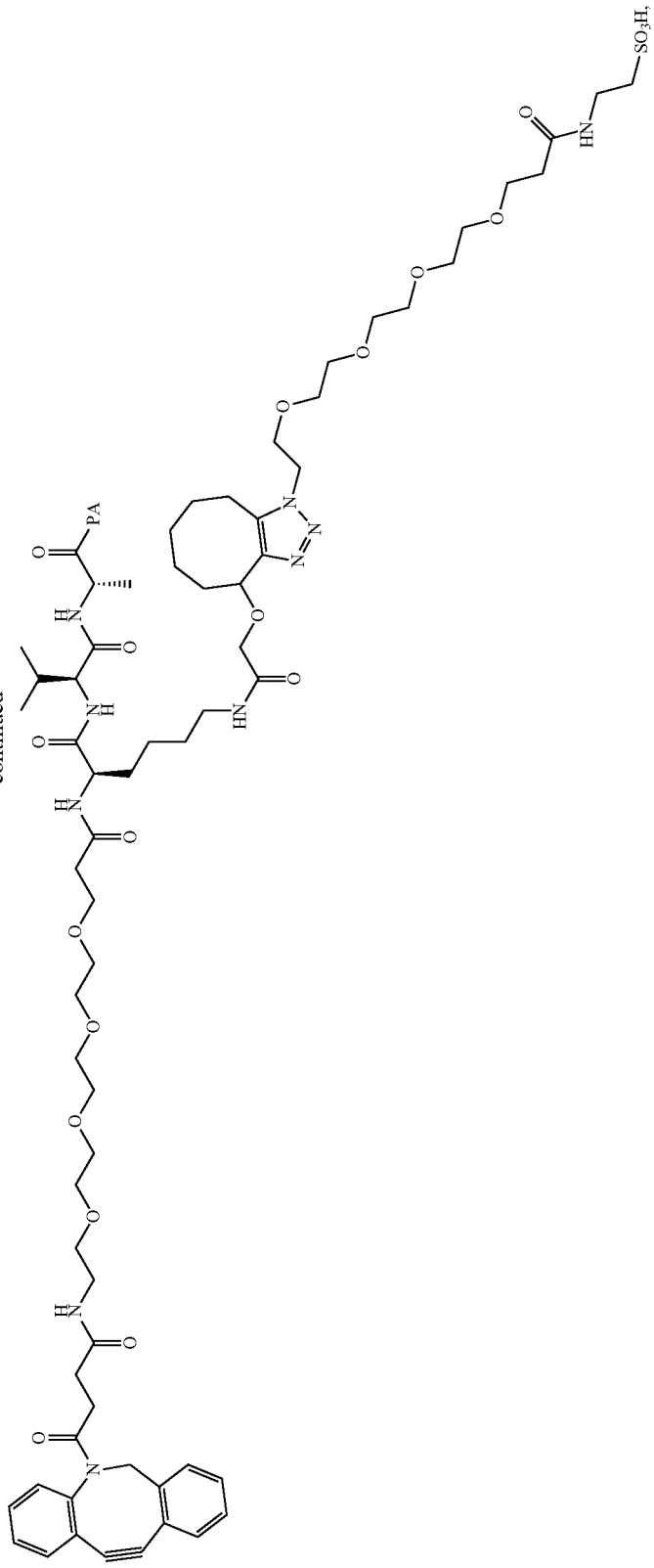

-continued
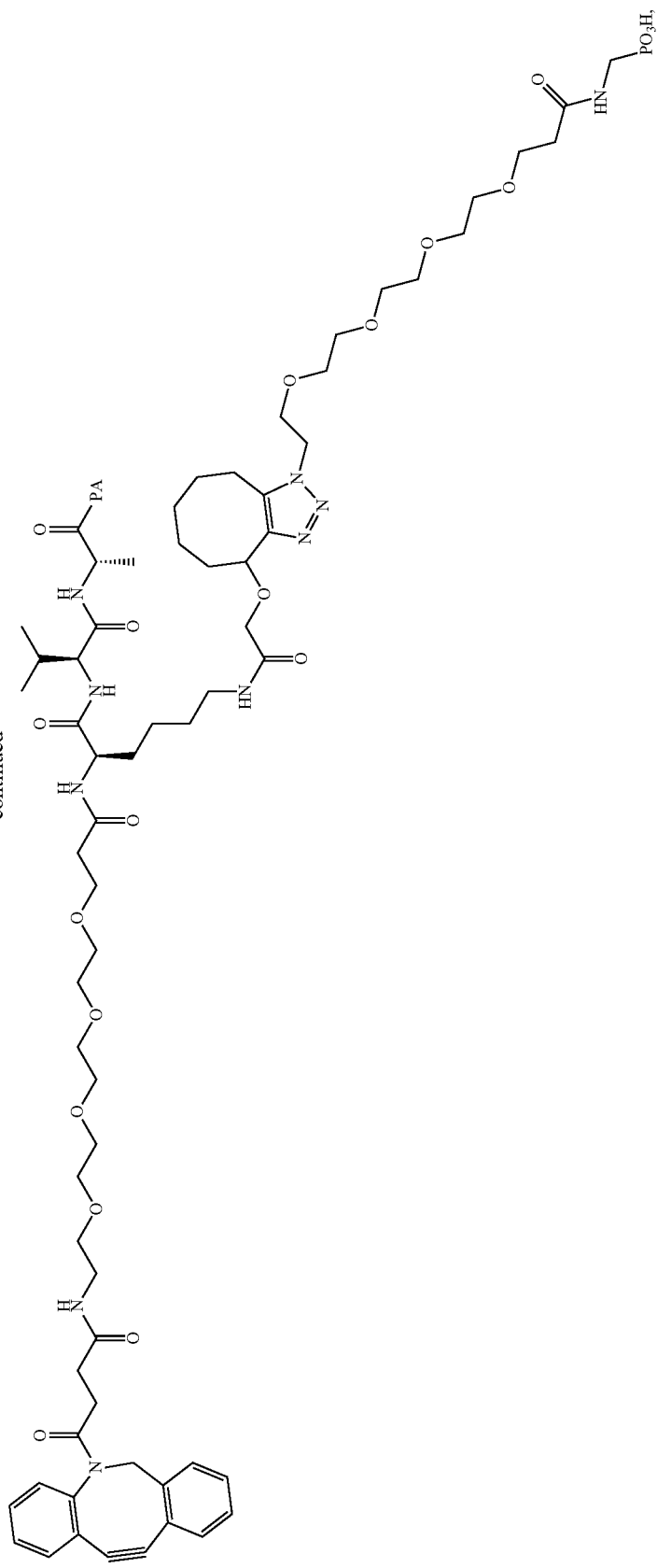

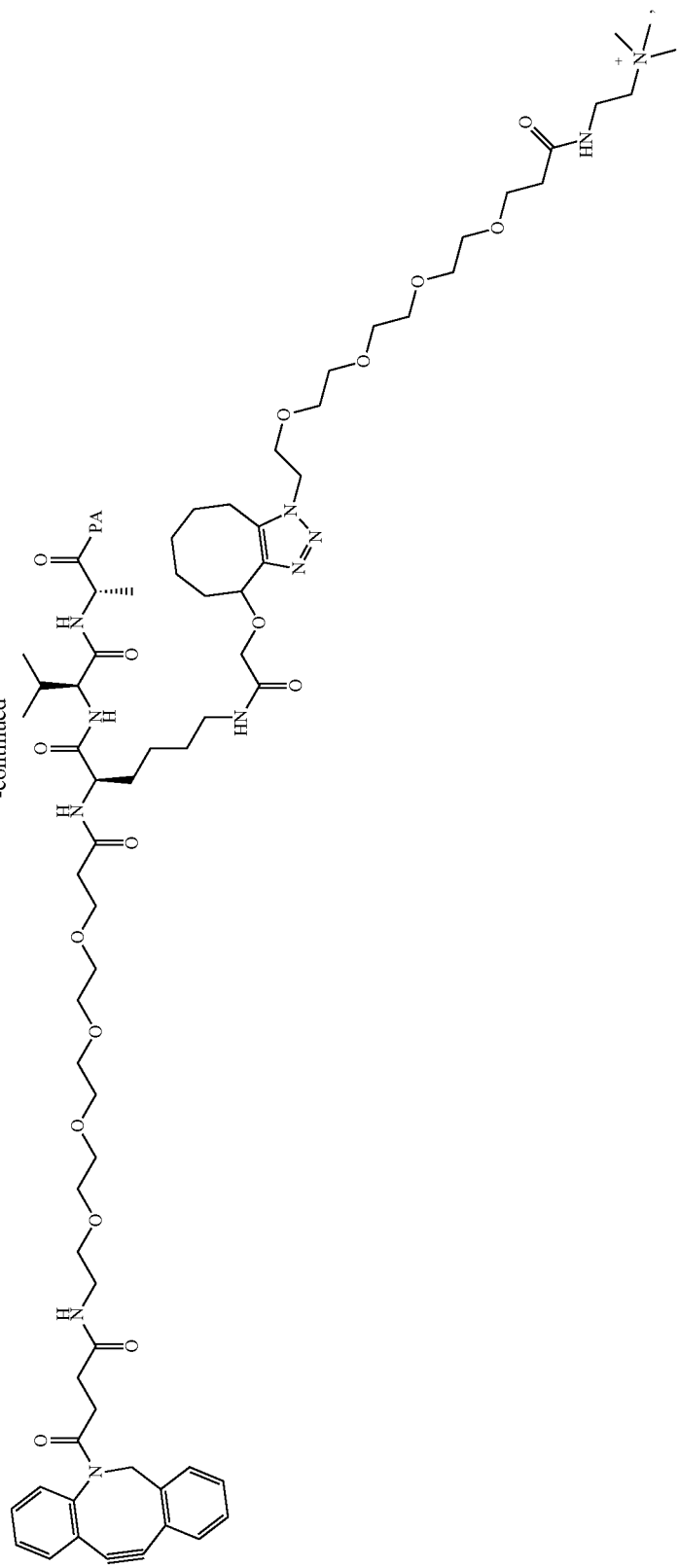

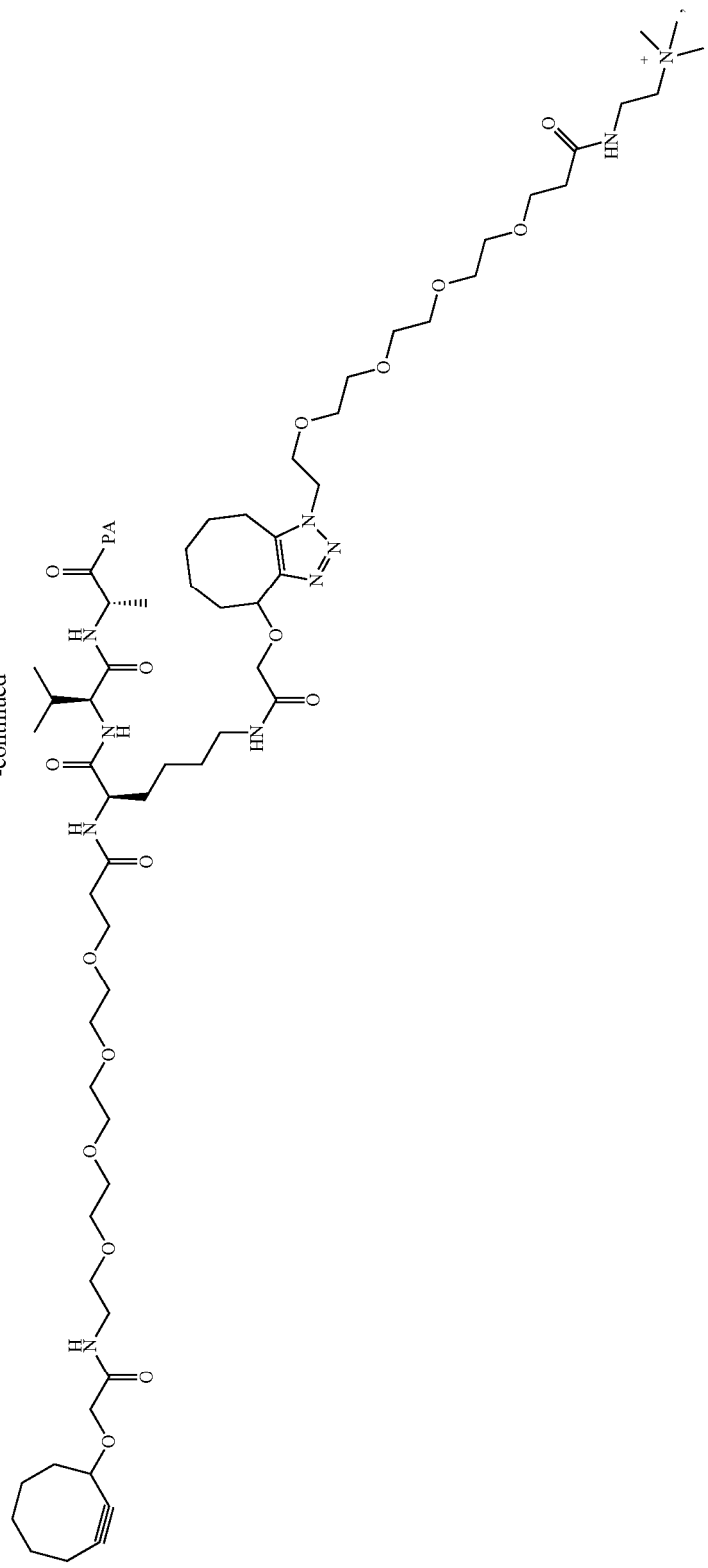

681 682
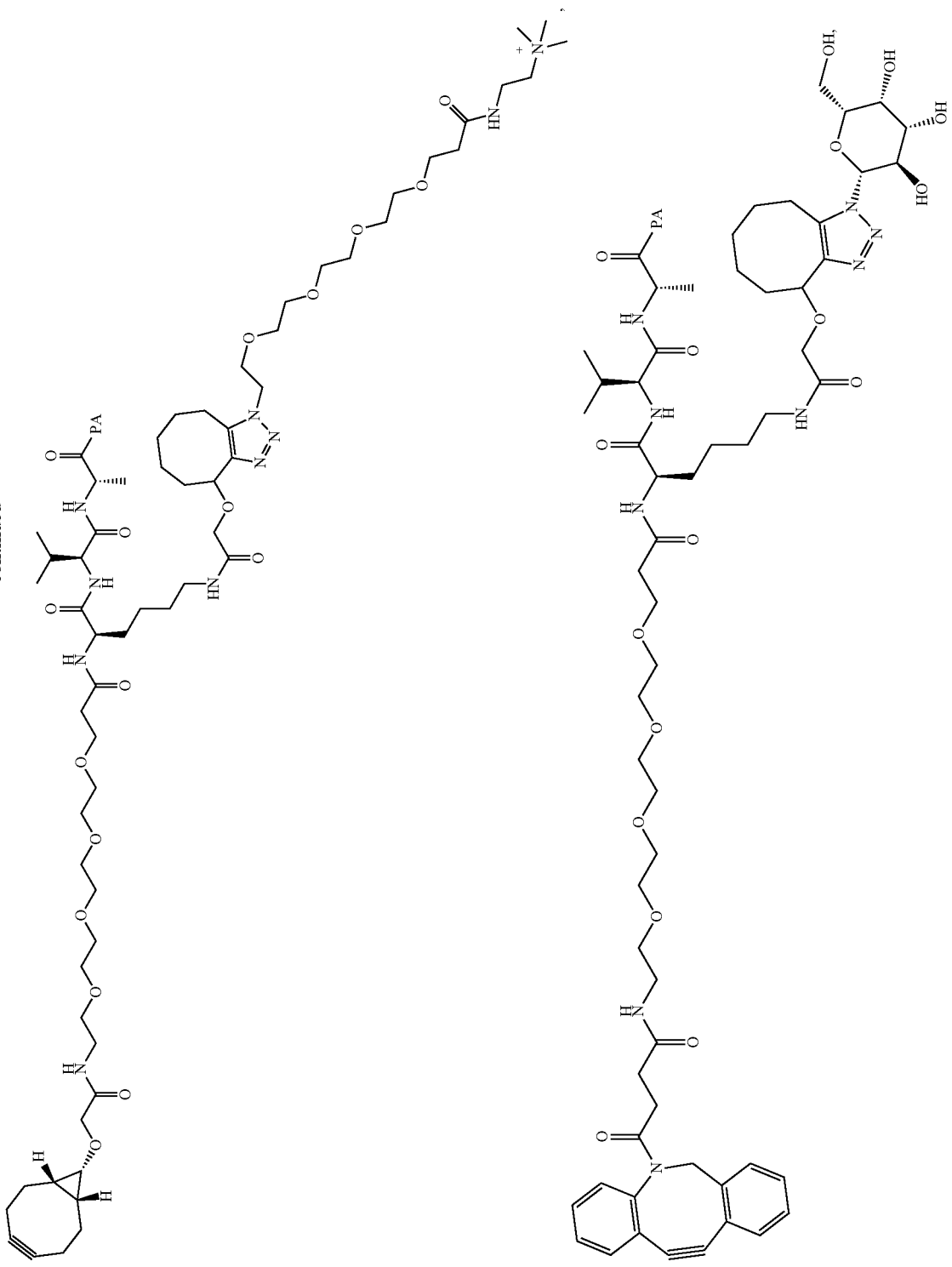
-continued

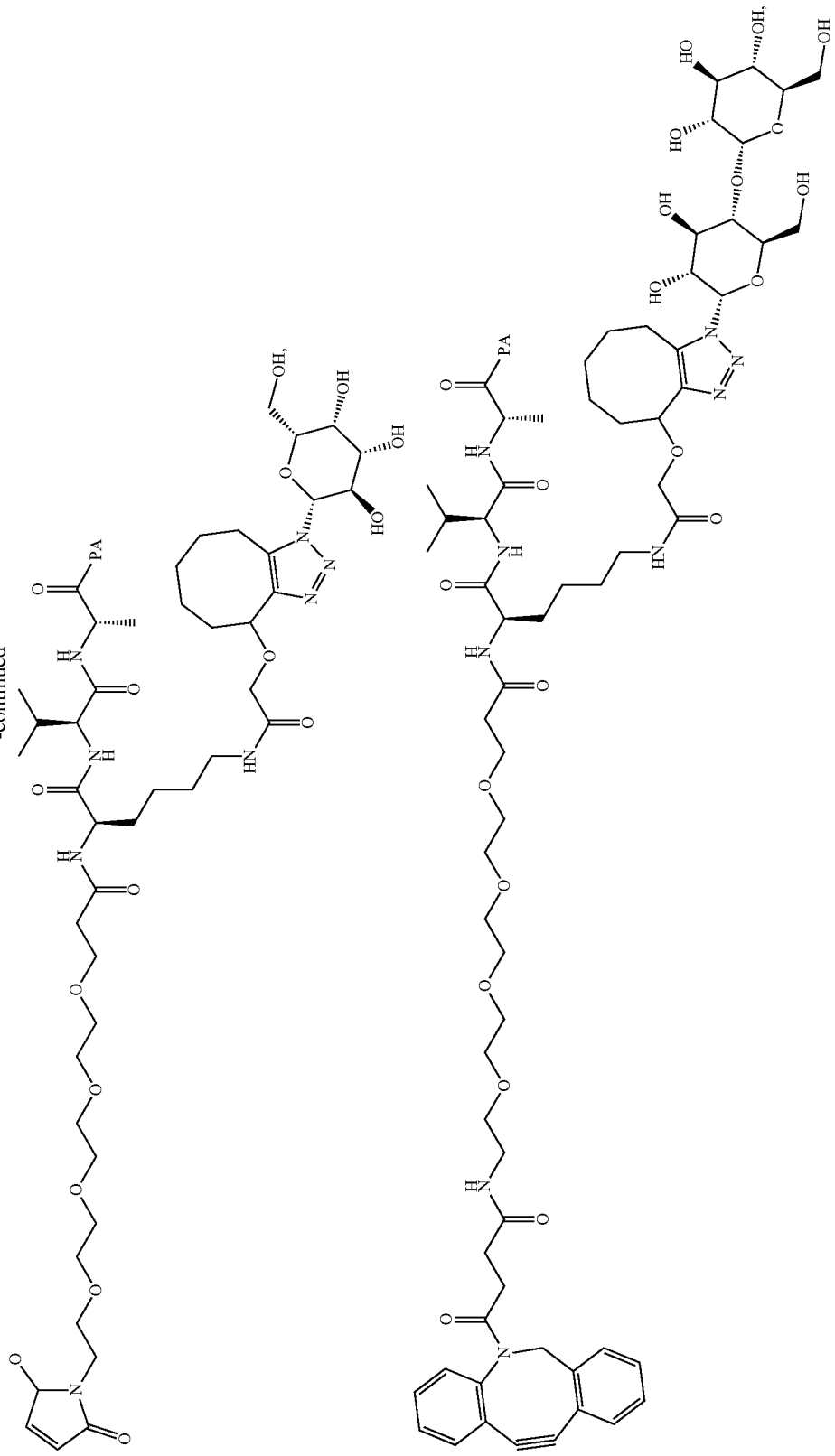

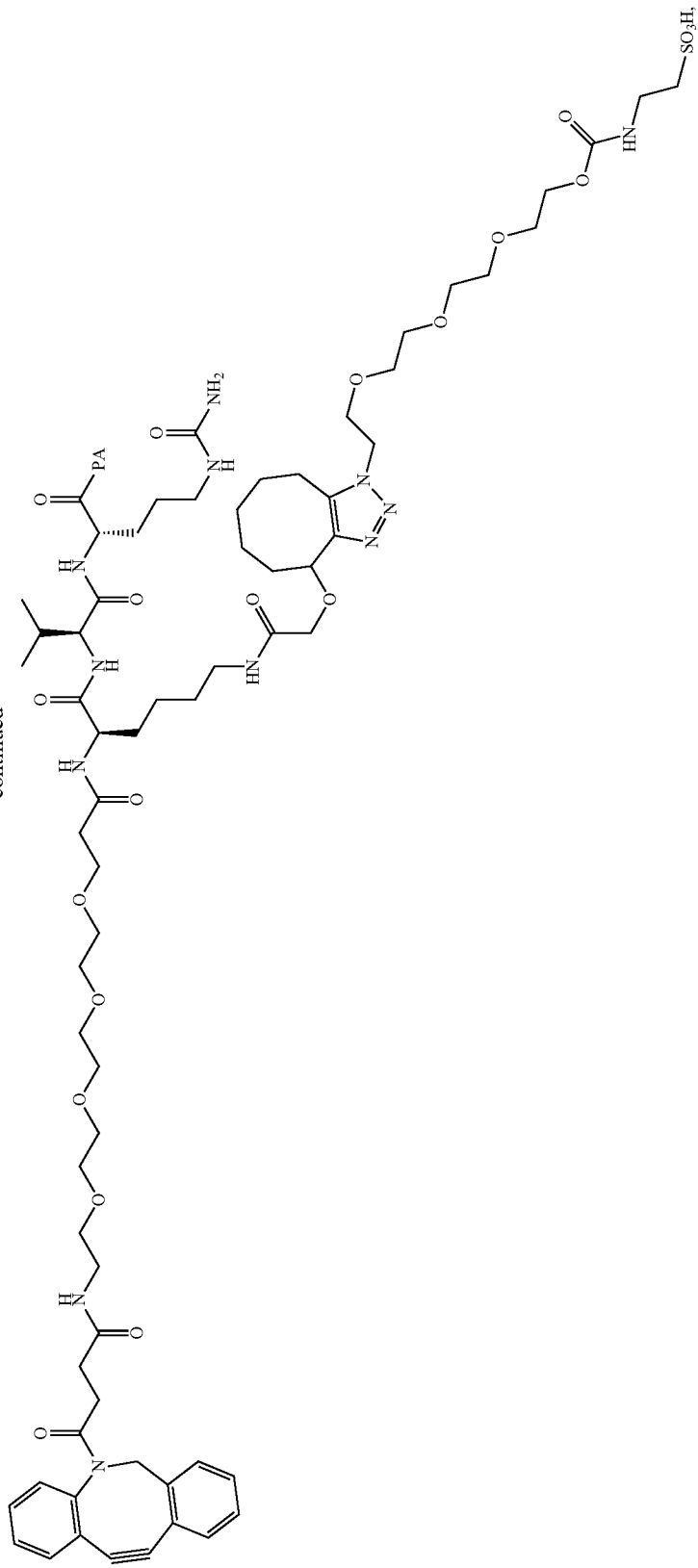

-continued
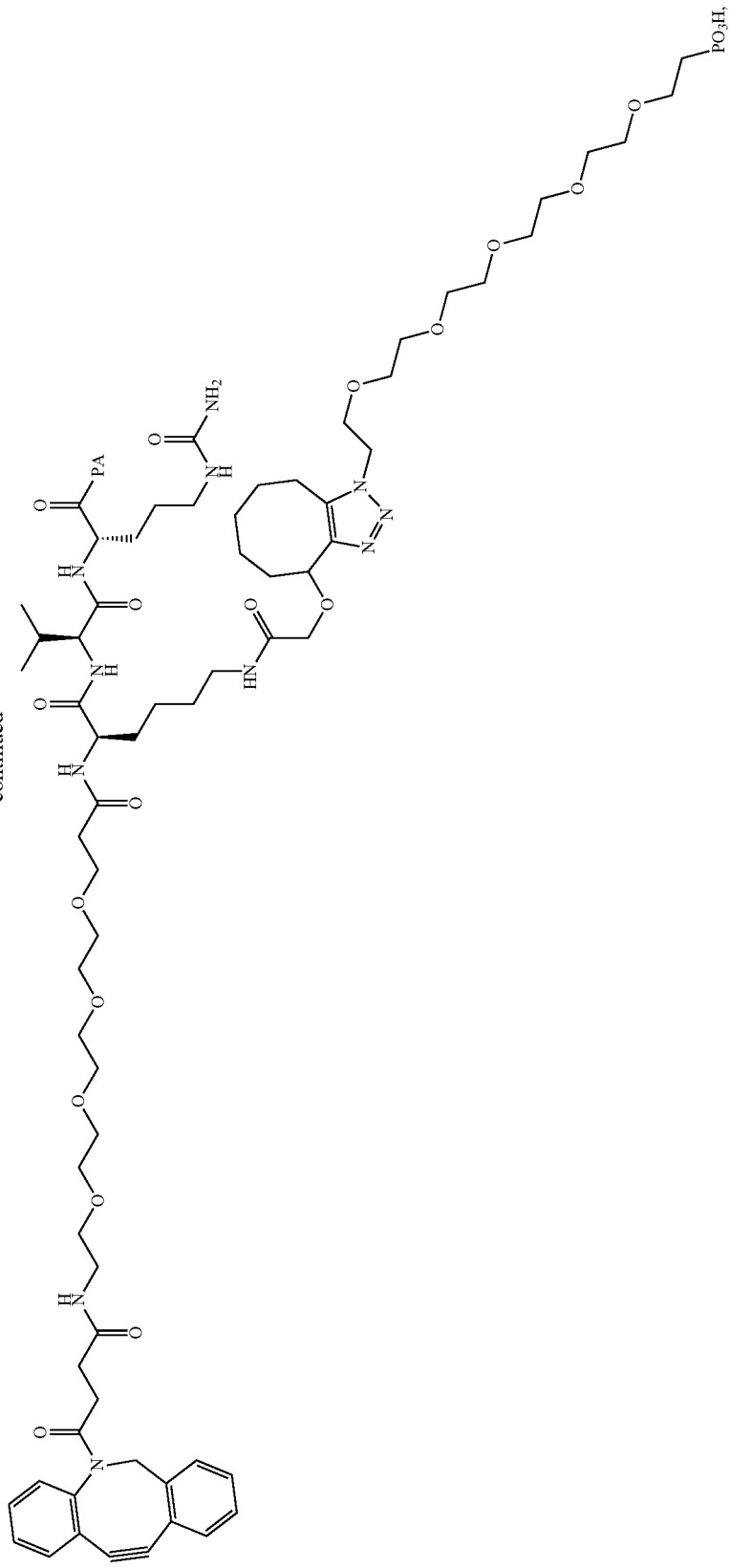

-continued
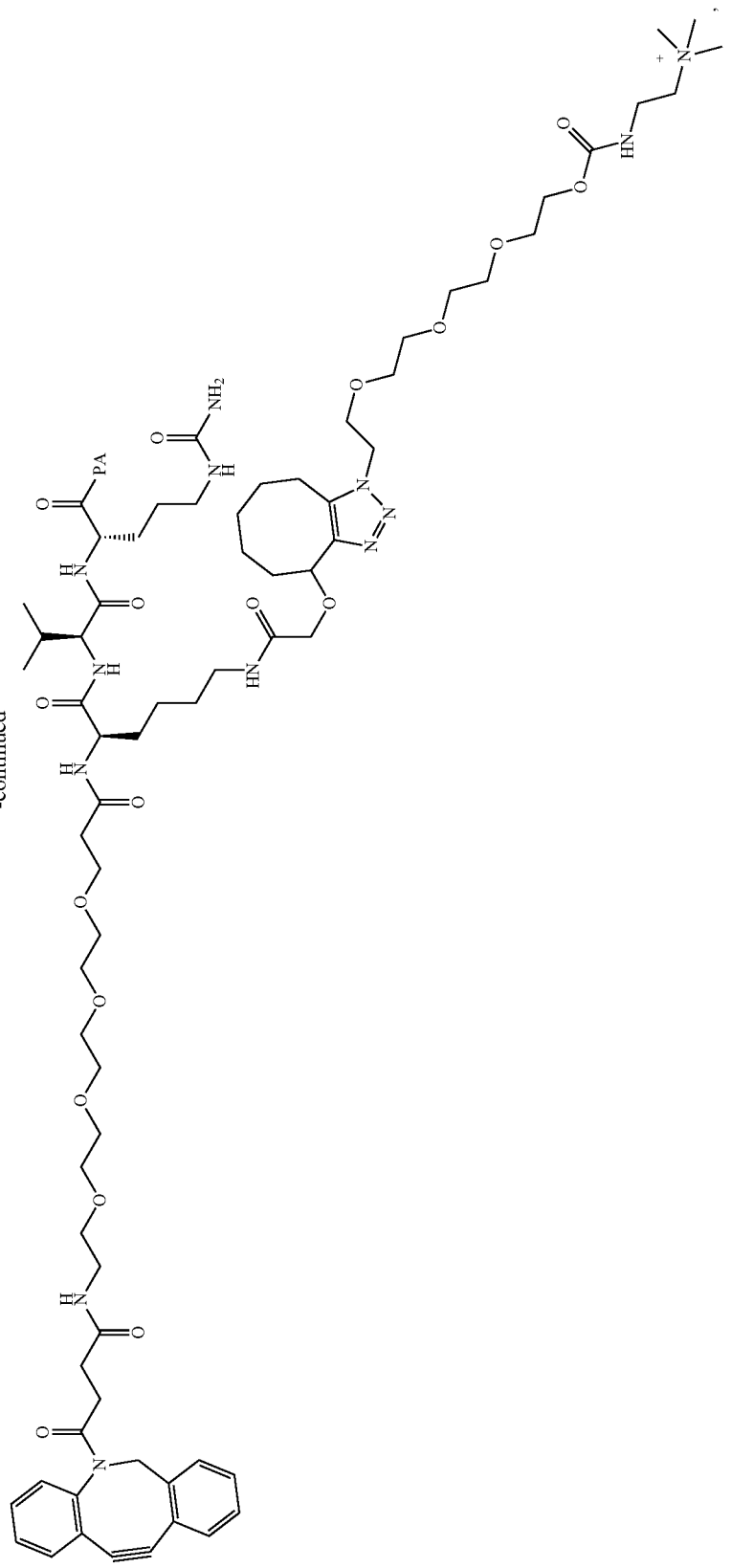

-continued
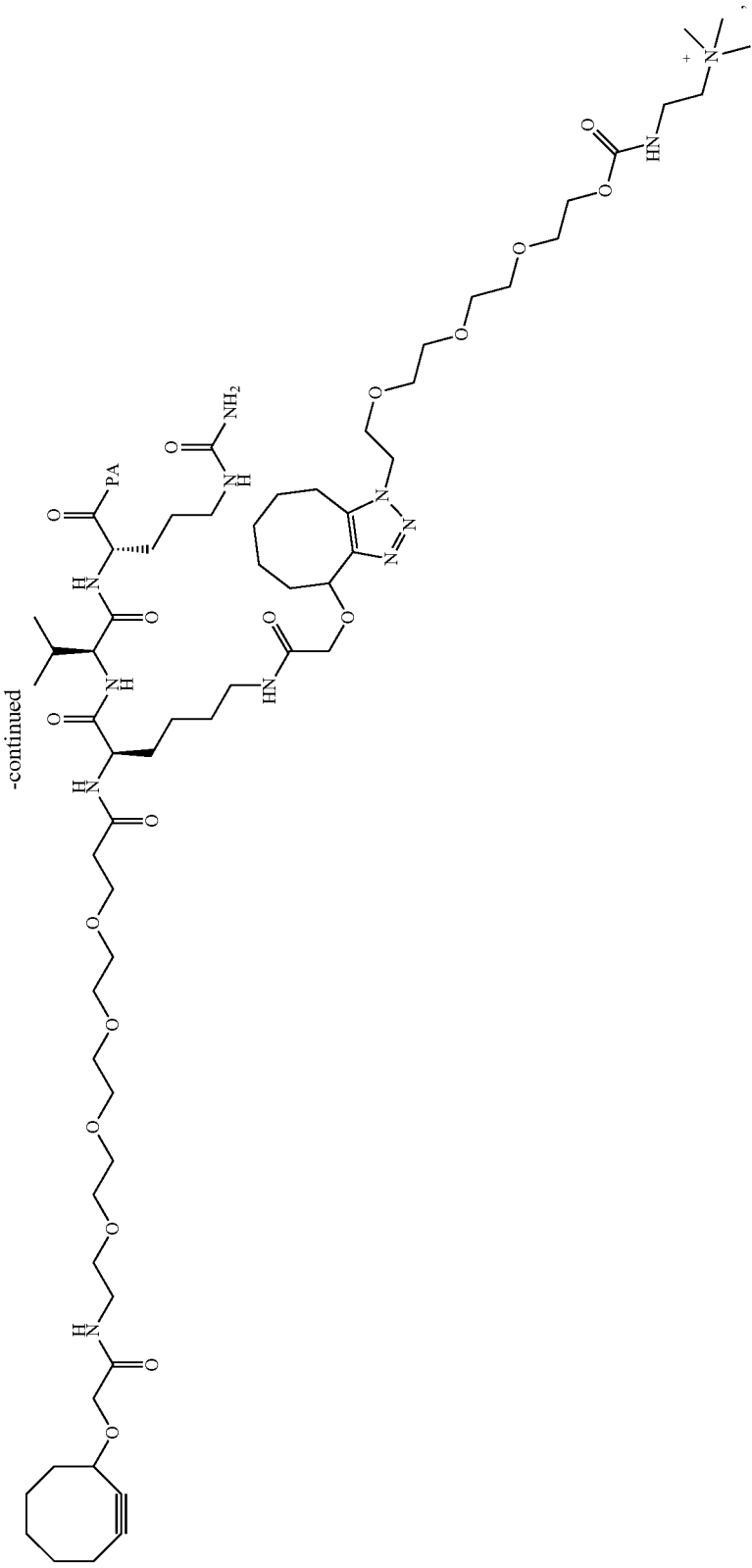

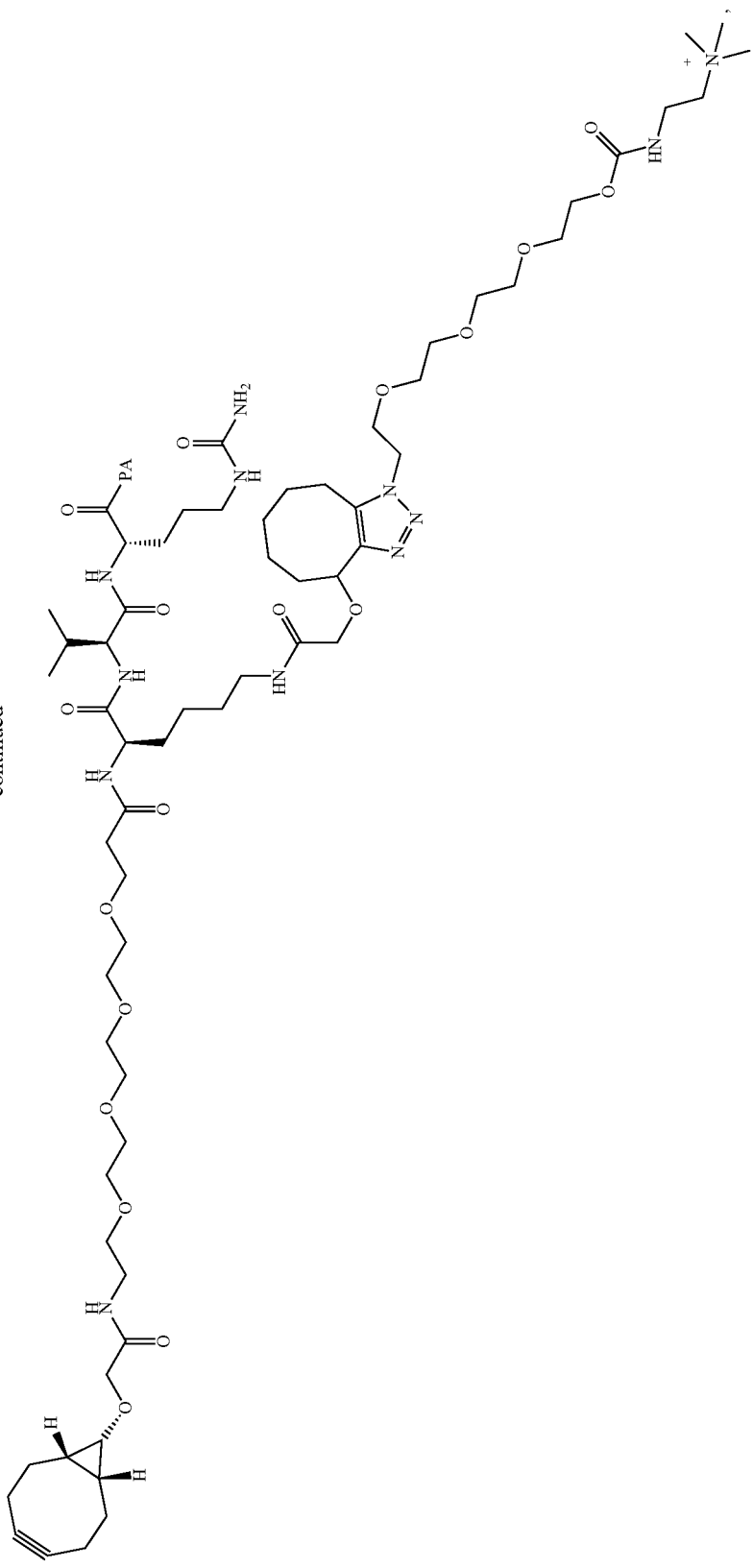

-continued
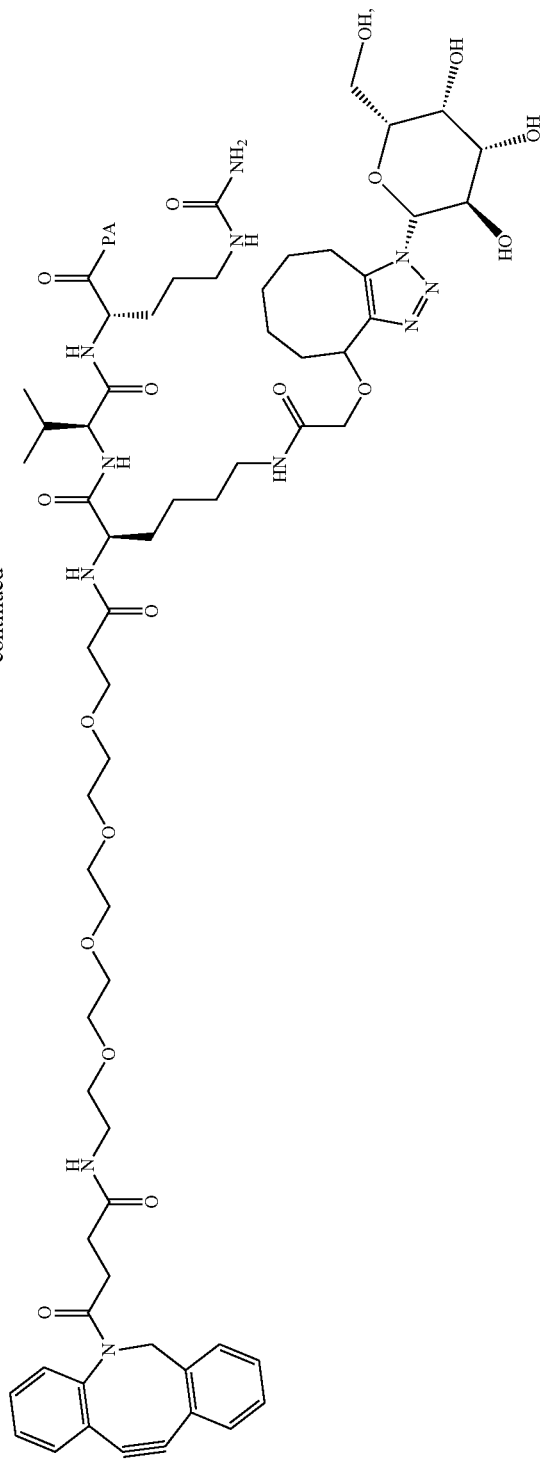
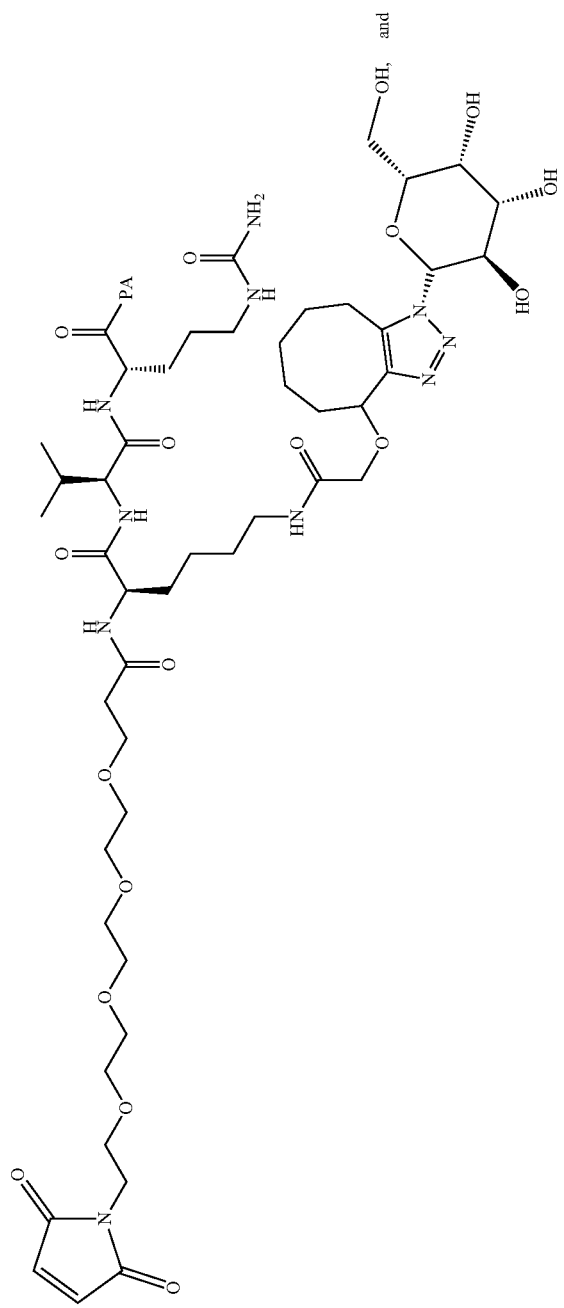

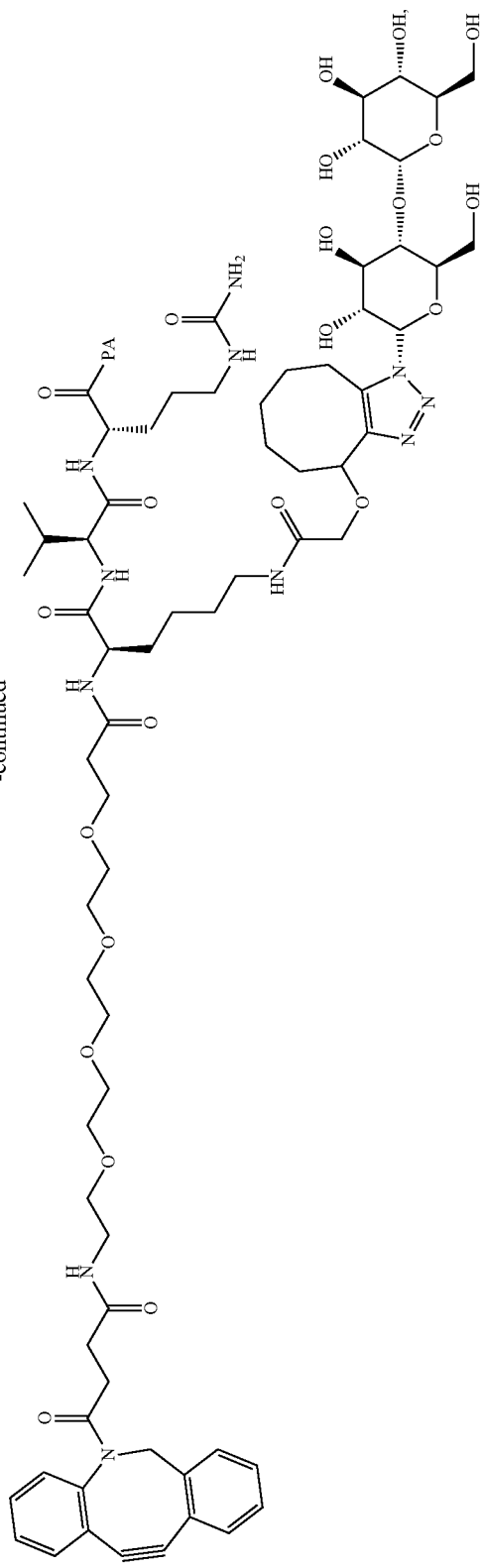

or a stereoisomeric form thereof, or a regioisomer thereof, or a mixture of regioisomers thereof, wherein PA is a payload residue.

In some instances, any compound of Formula (IX), Formula (IXa), Formula (IXb), Formula (IXc), Formula (Xa), Formula (Xb), Formula (Xc), or Formula (Xd), is selected from the group consisting of:

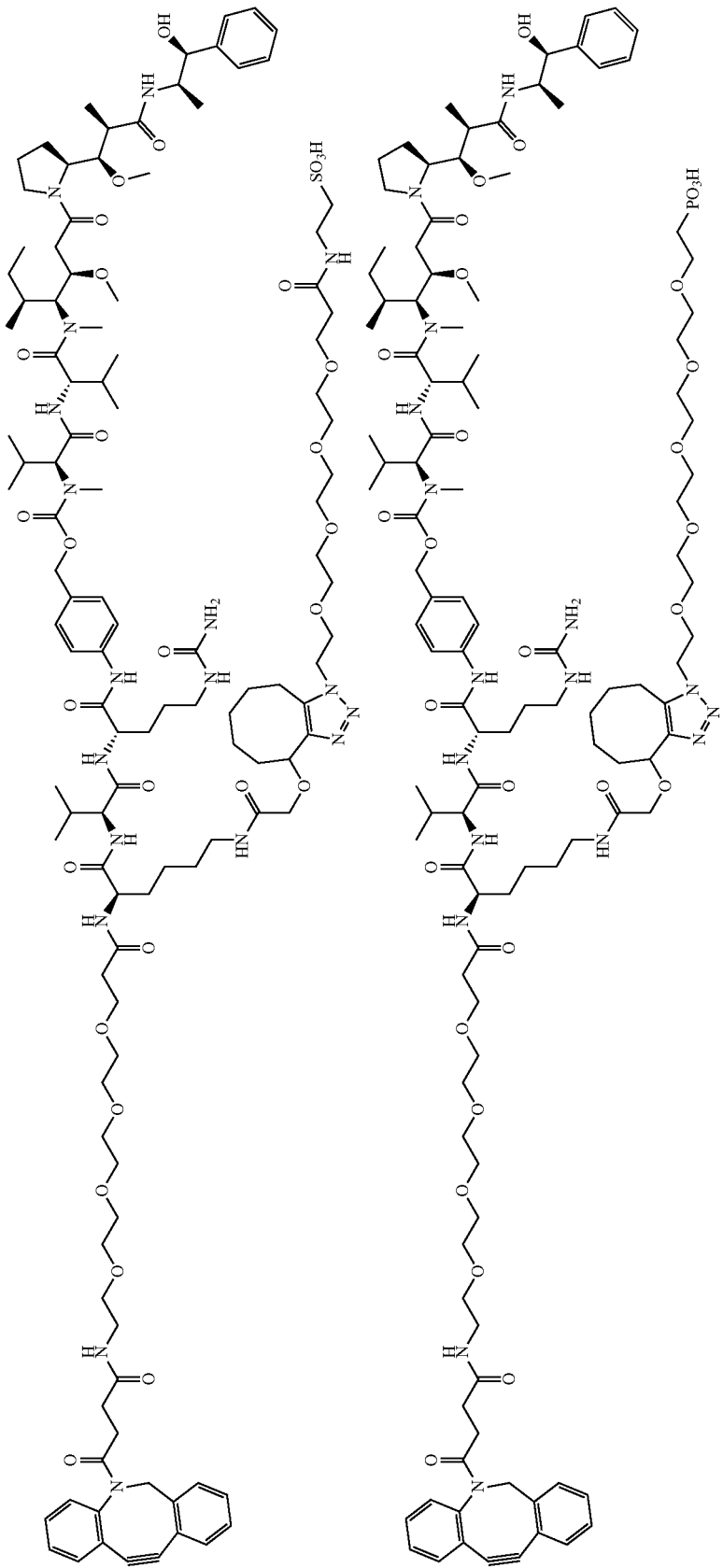

703
-continued
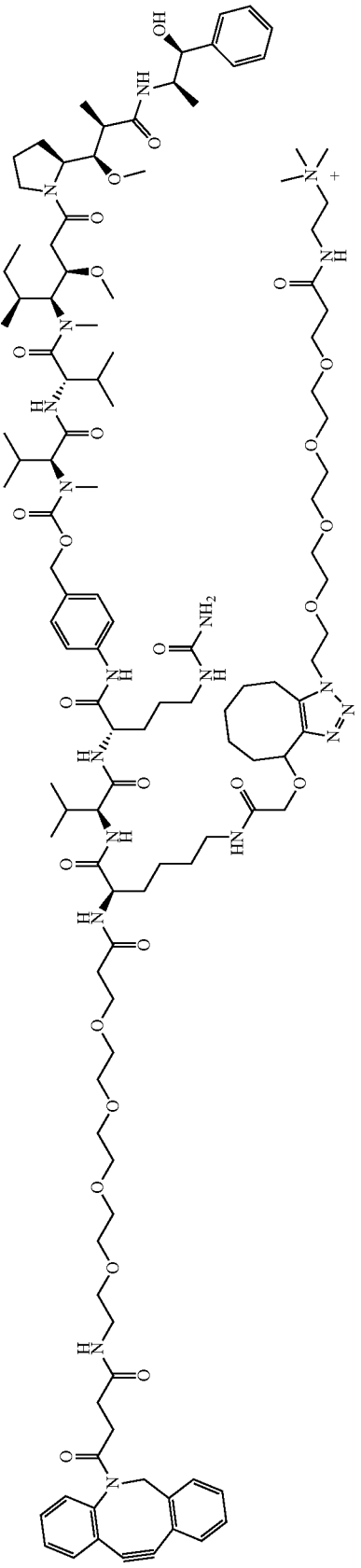
704
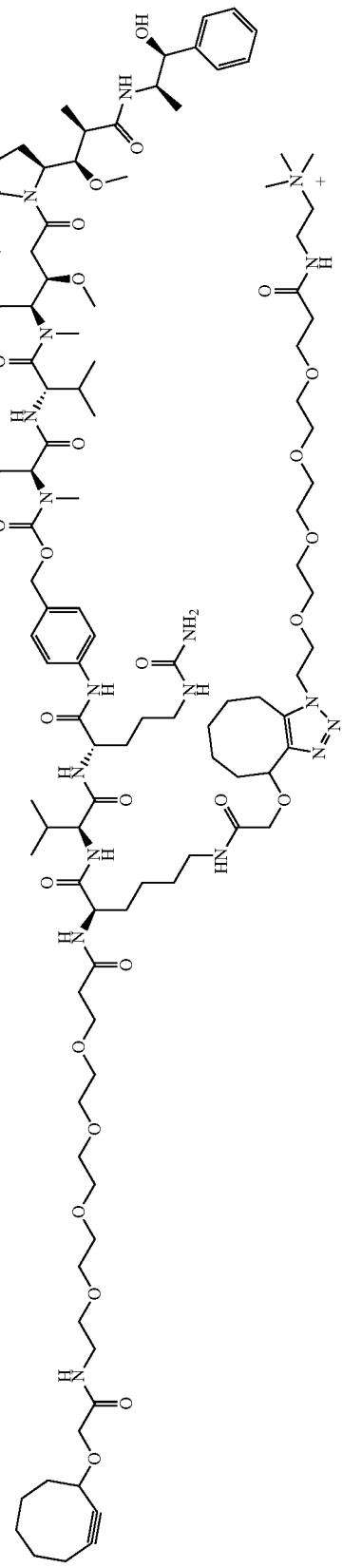

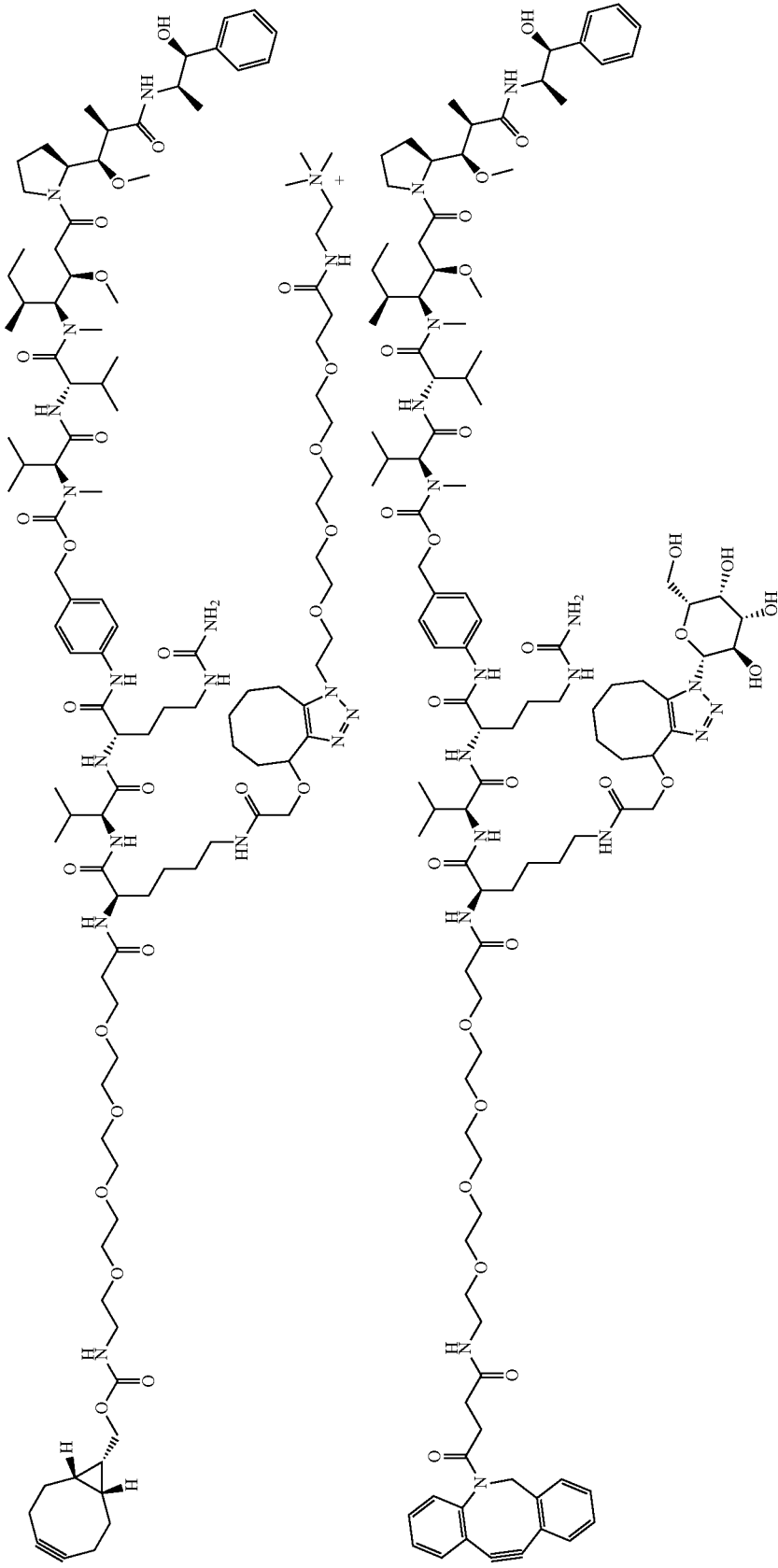

-continued
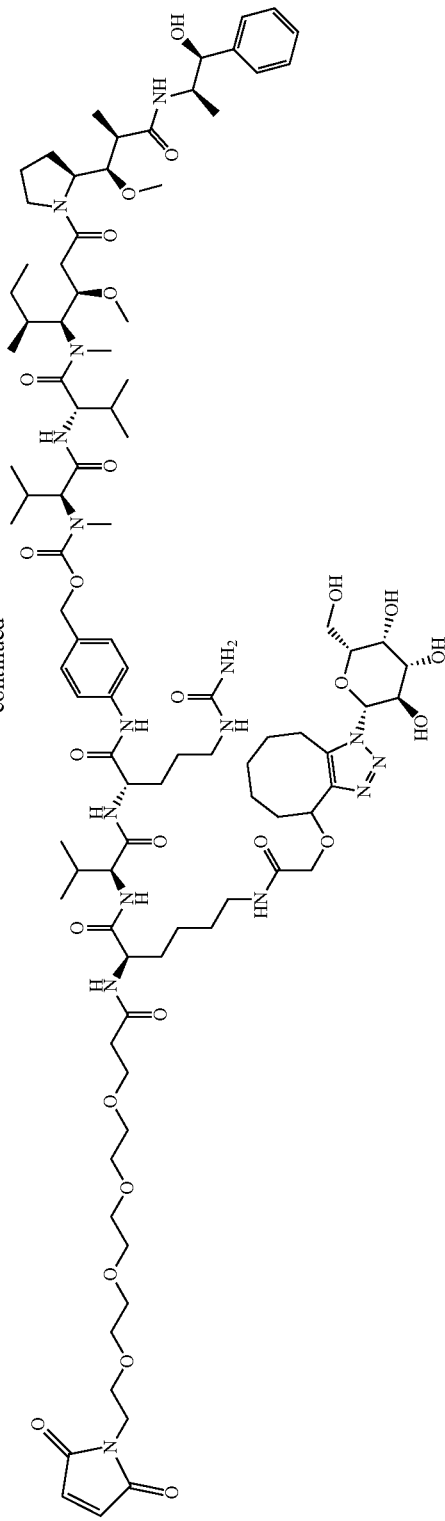 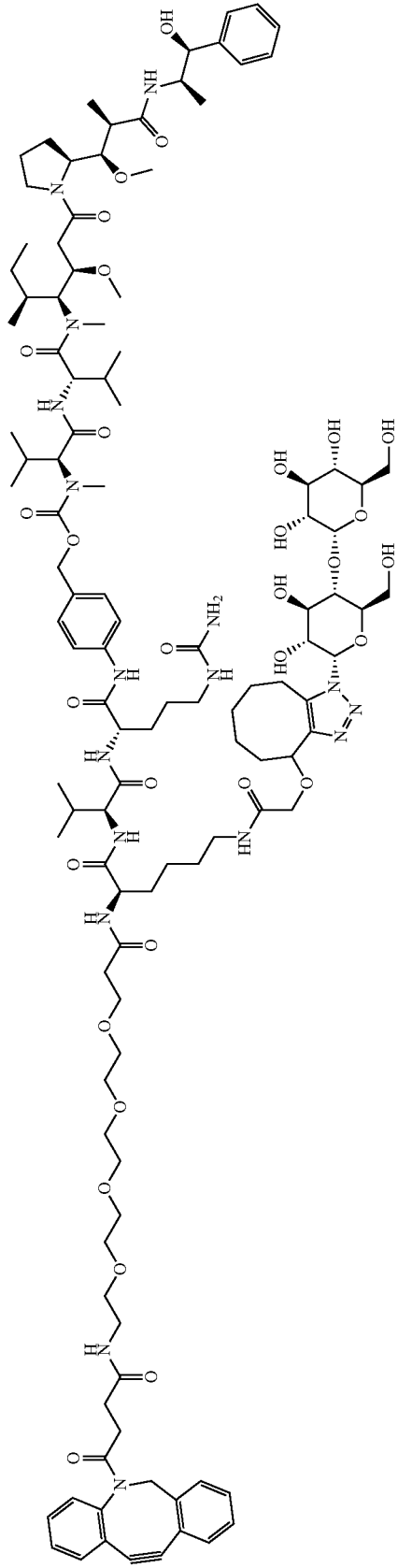

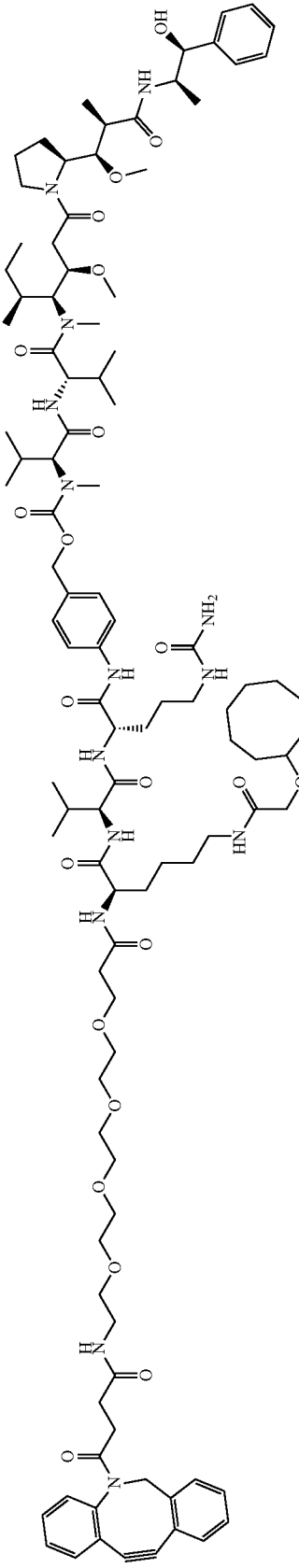
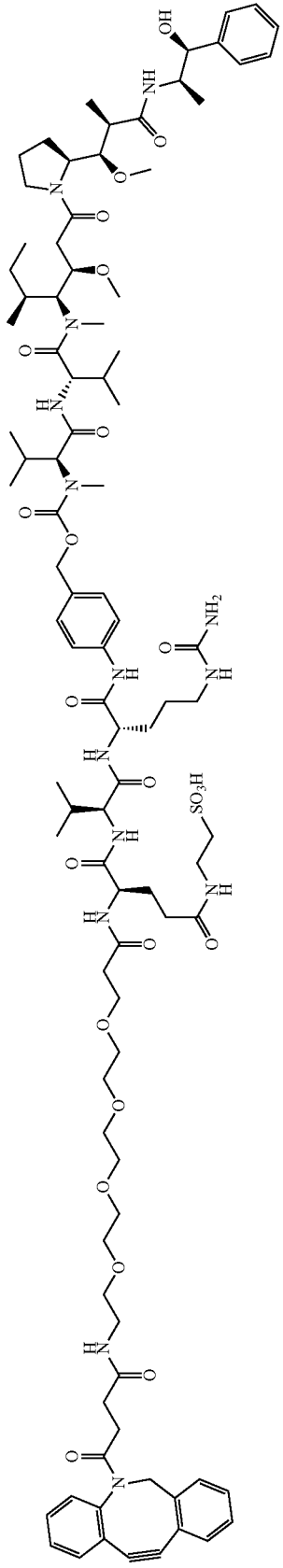

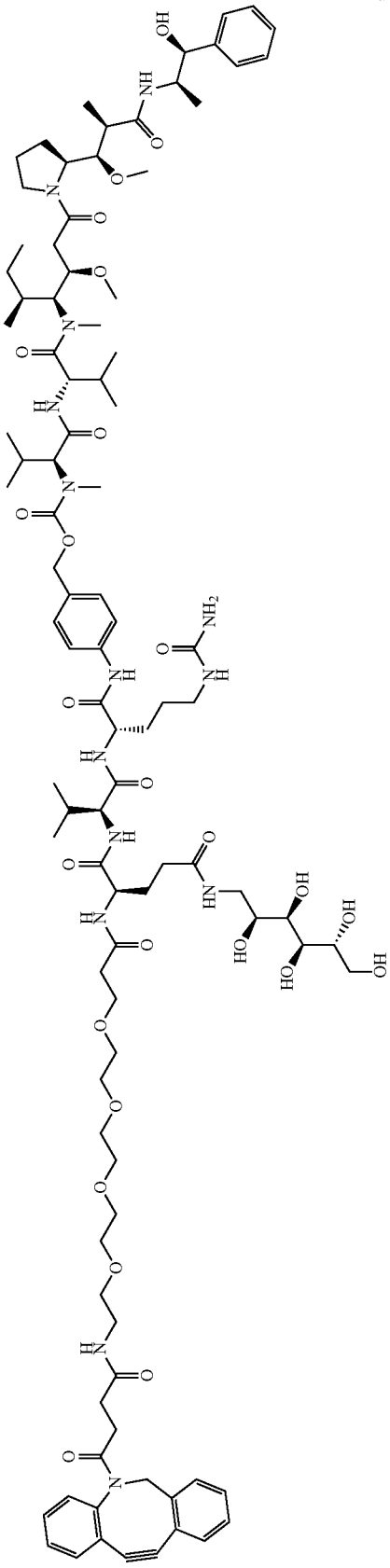
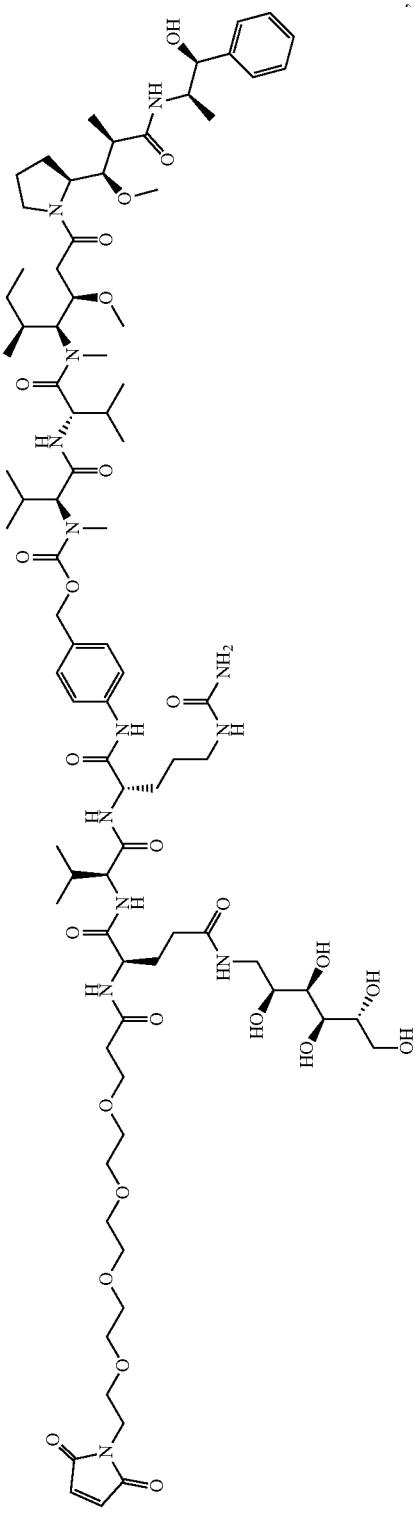

-continued
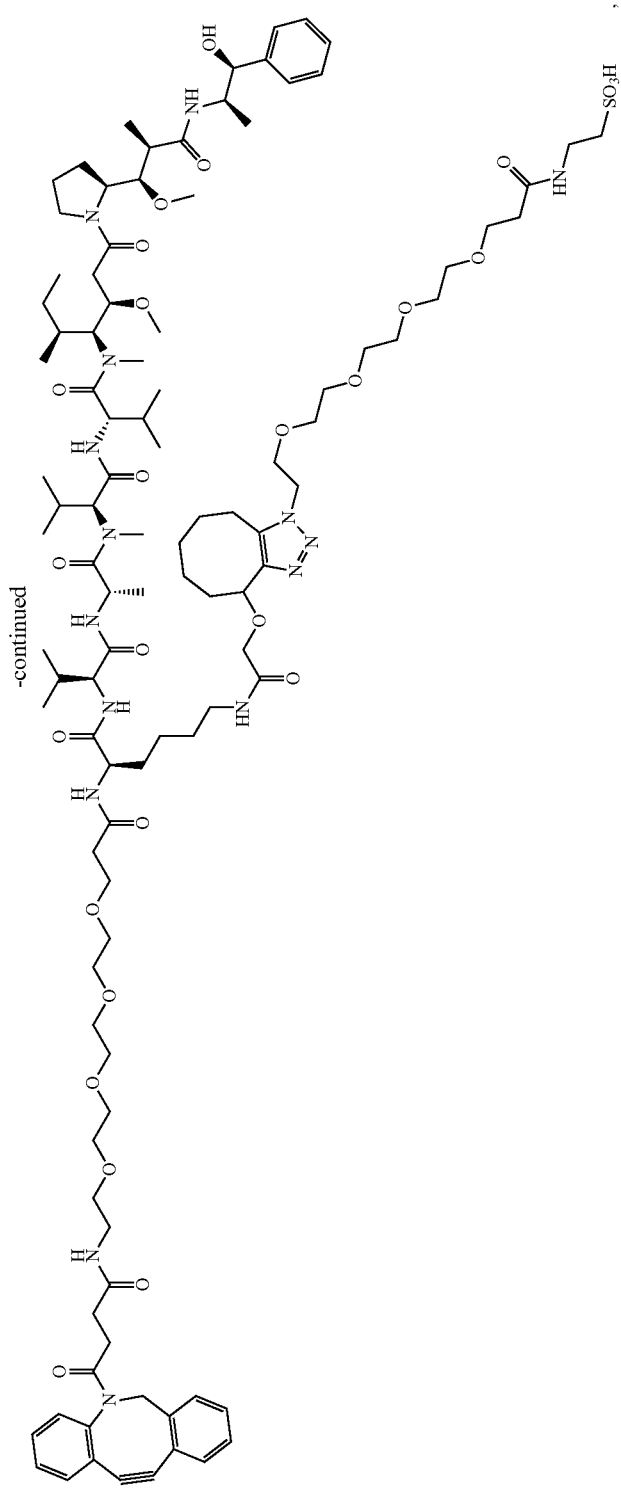

-continued
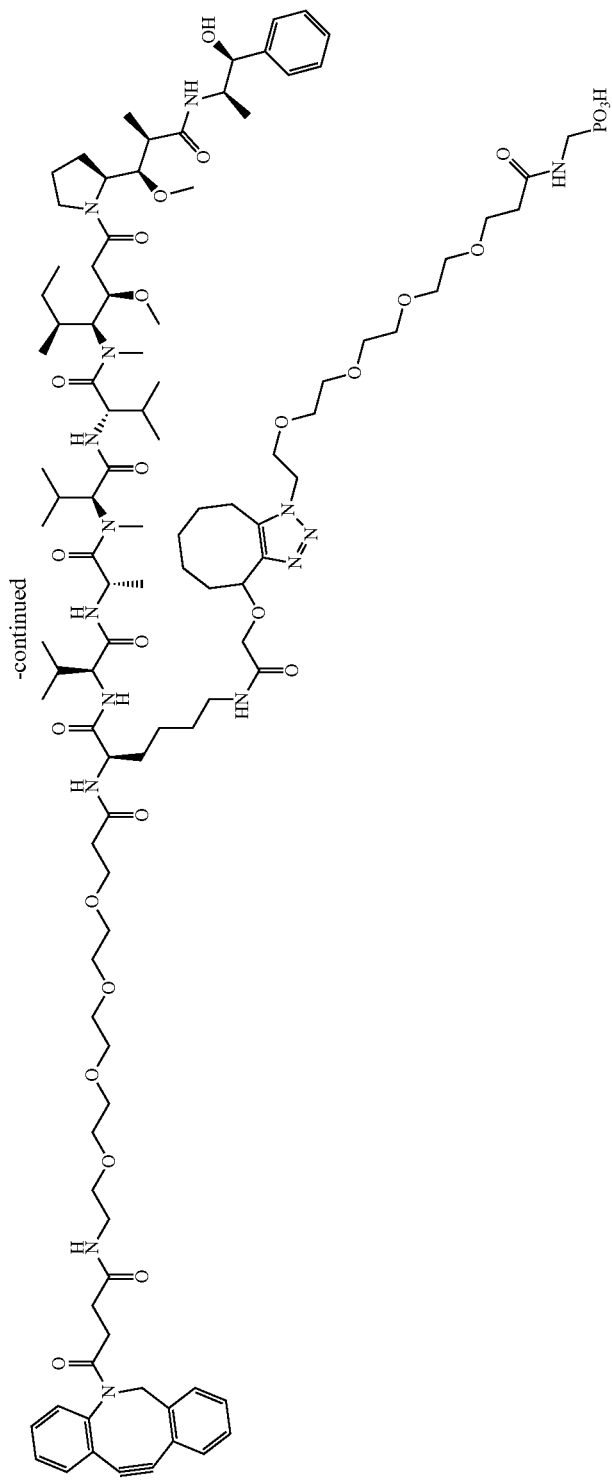

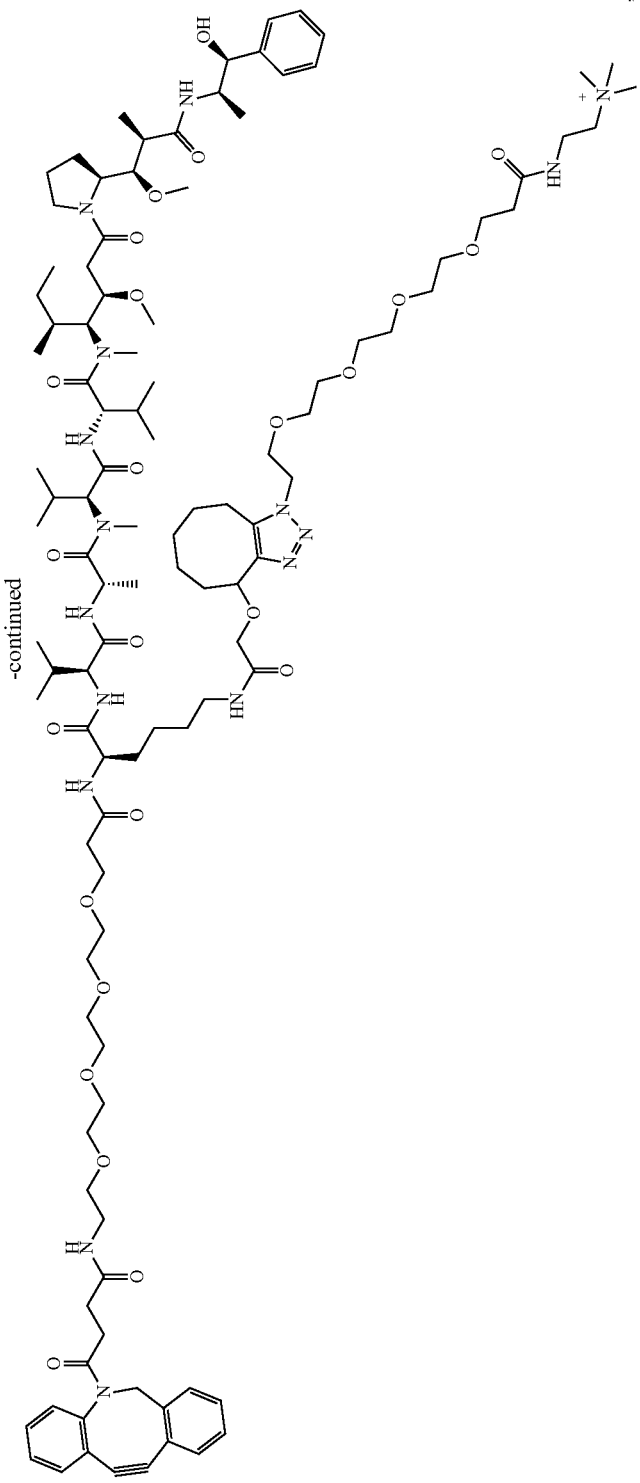

-continued
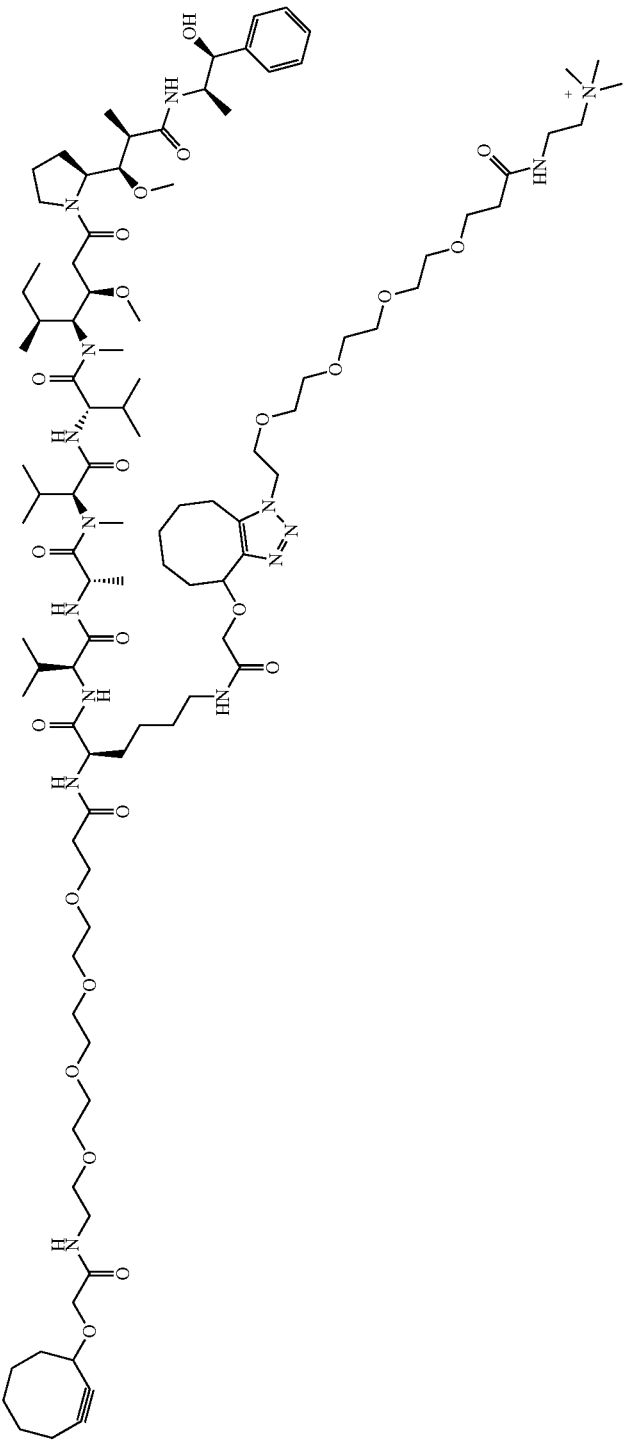

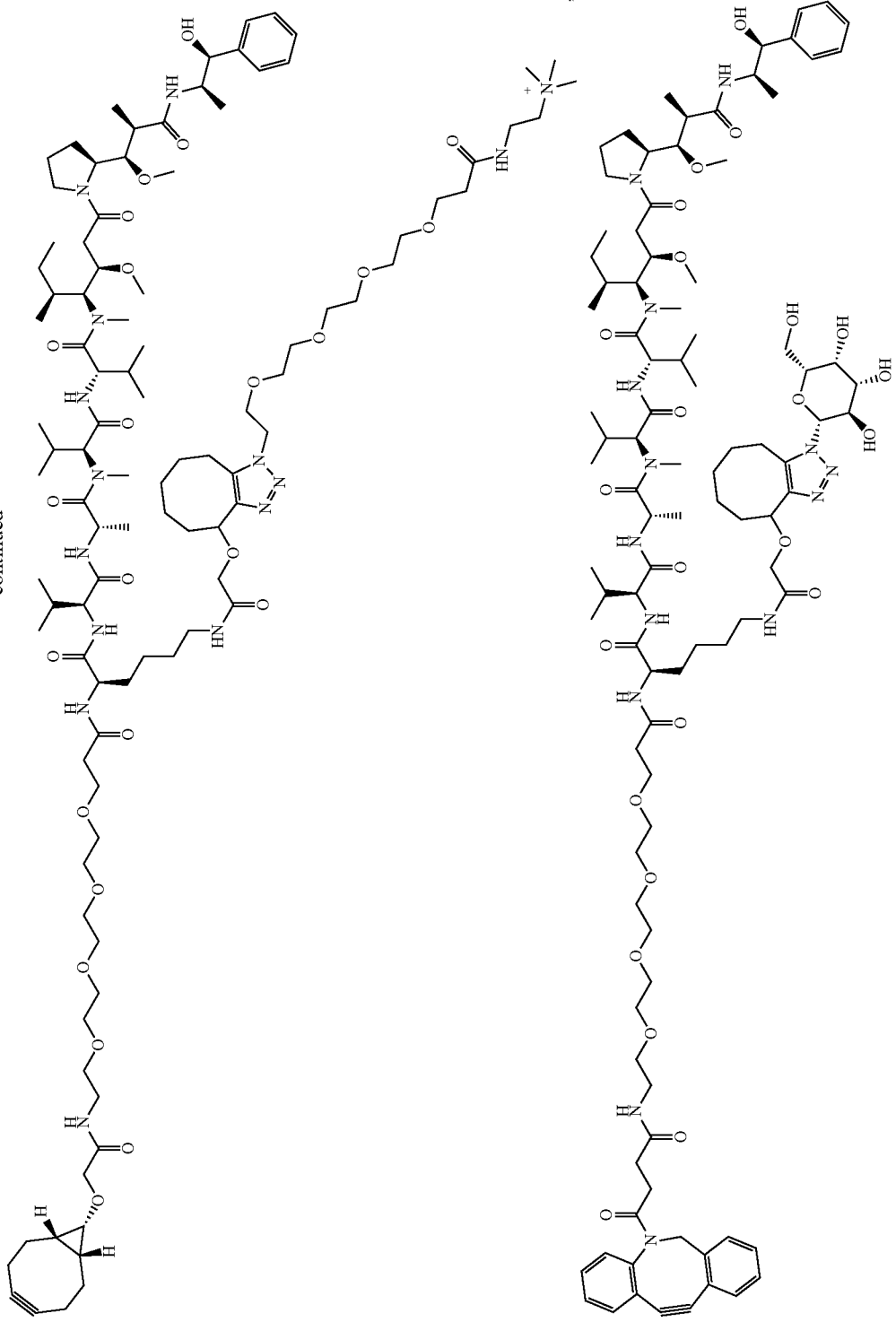

-continued
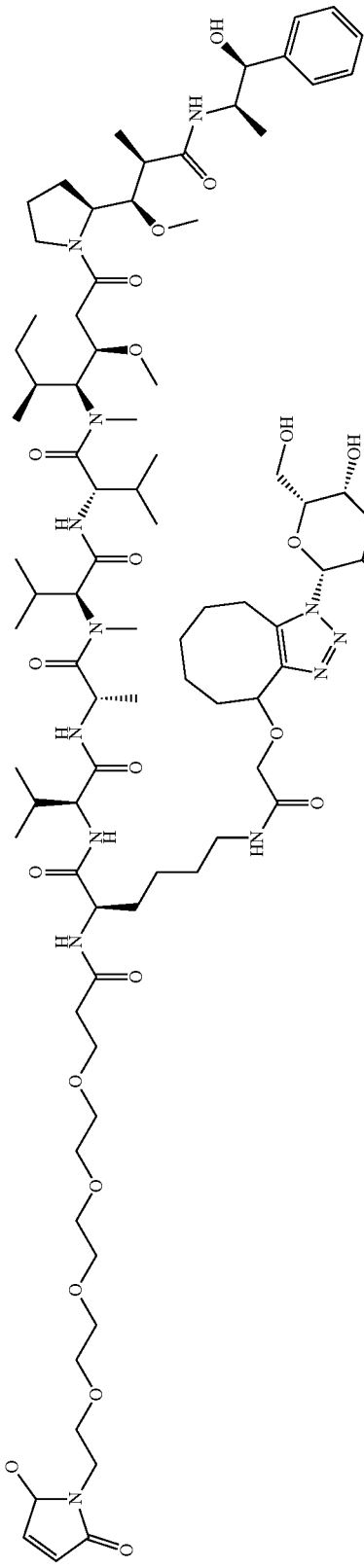
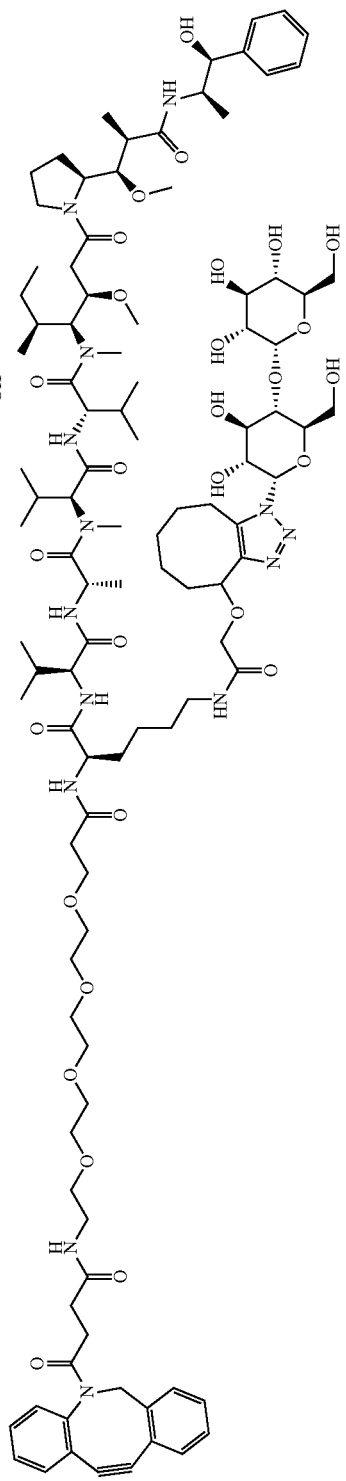

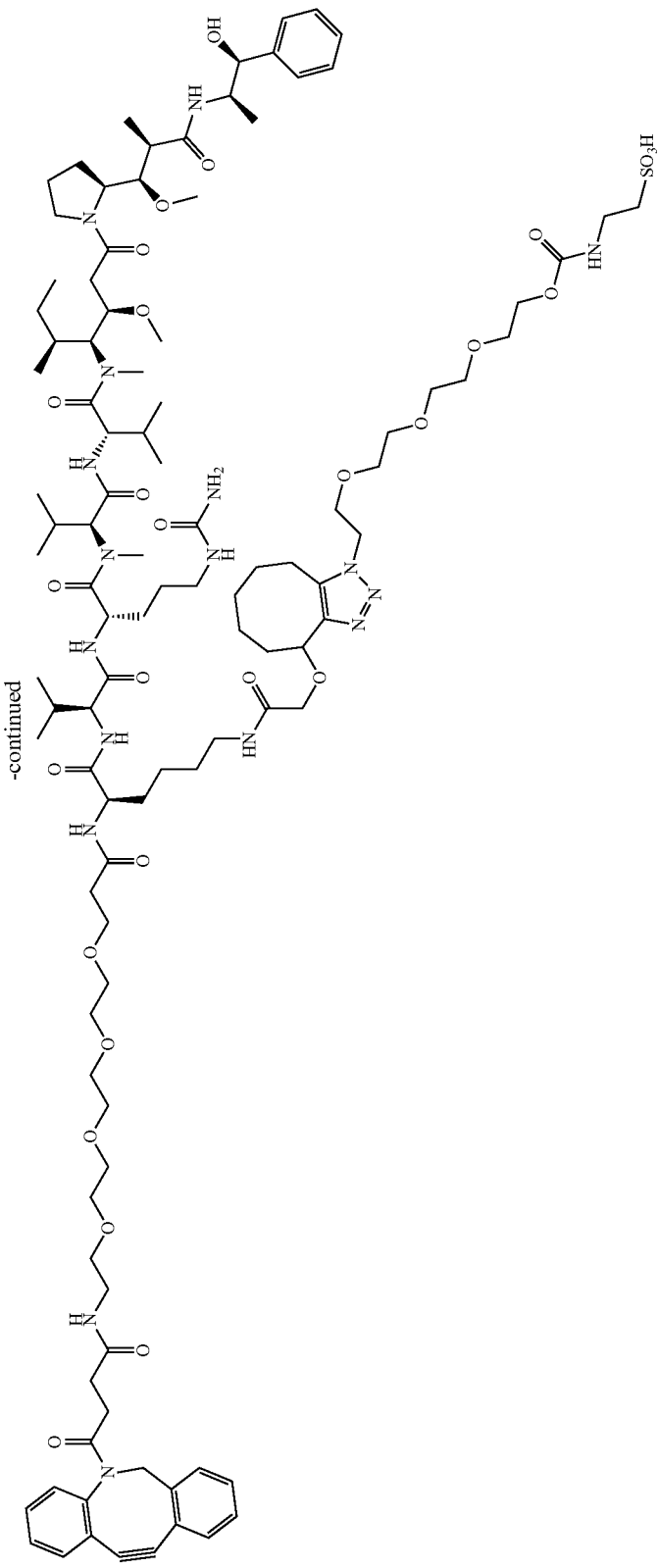

-continued
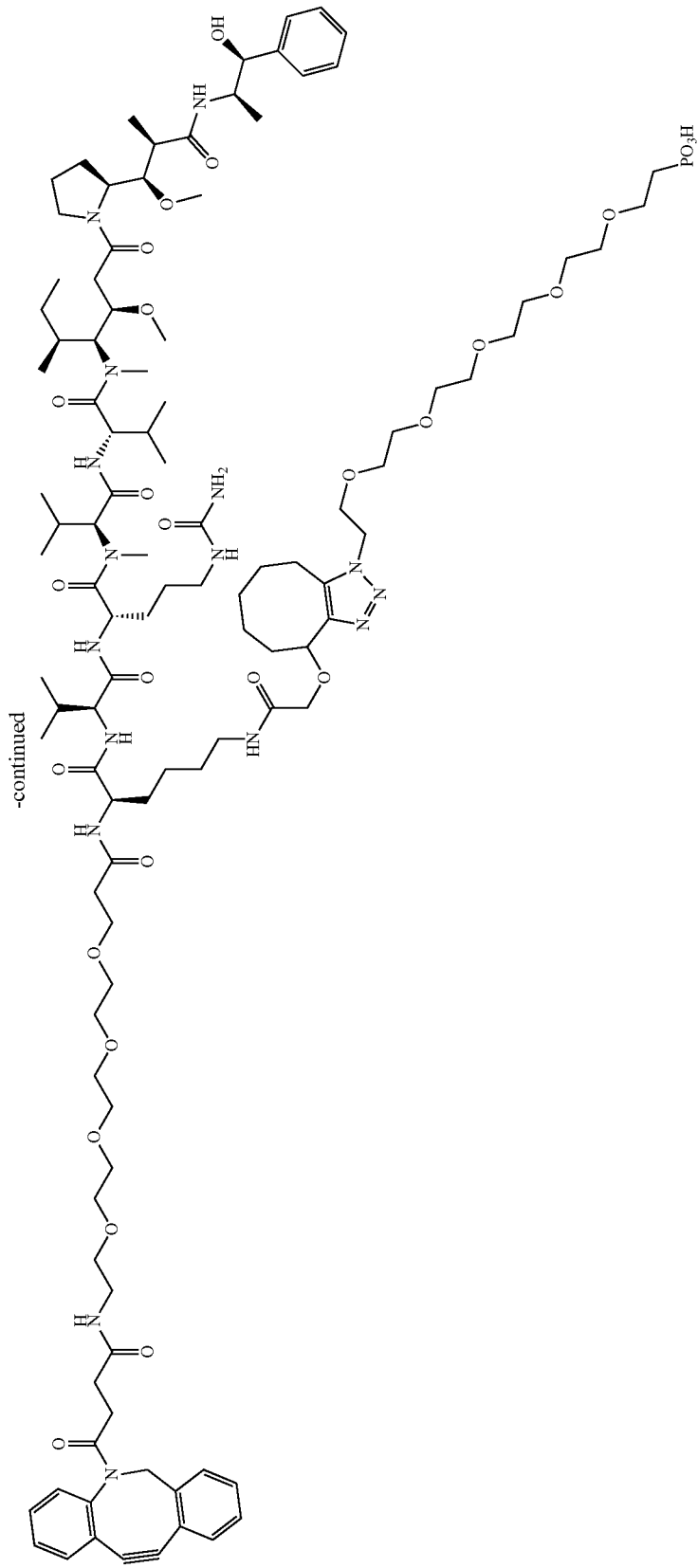

-continued
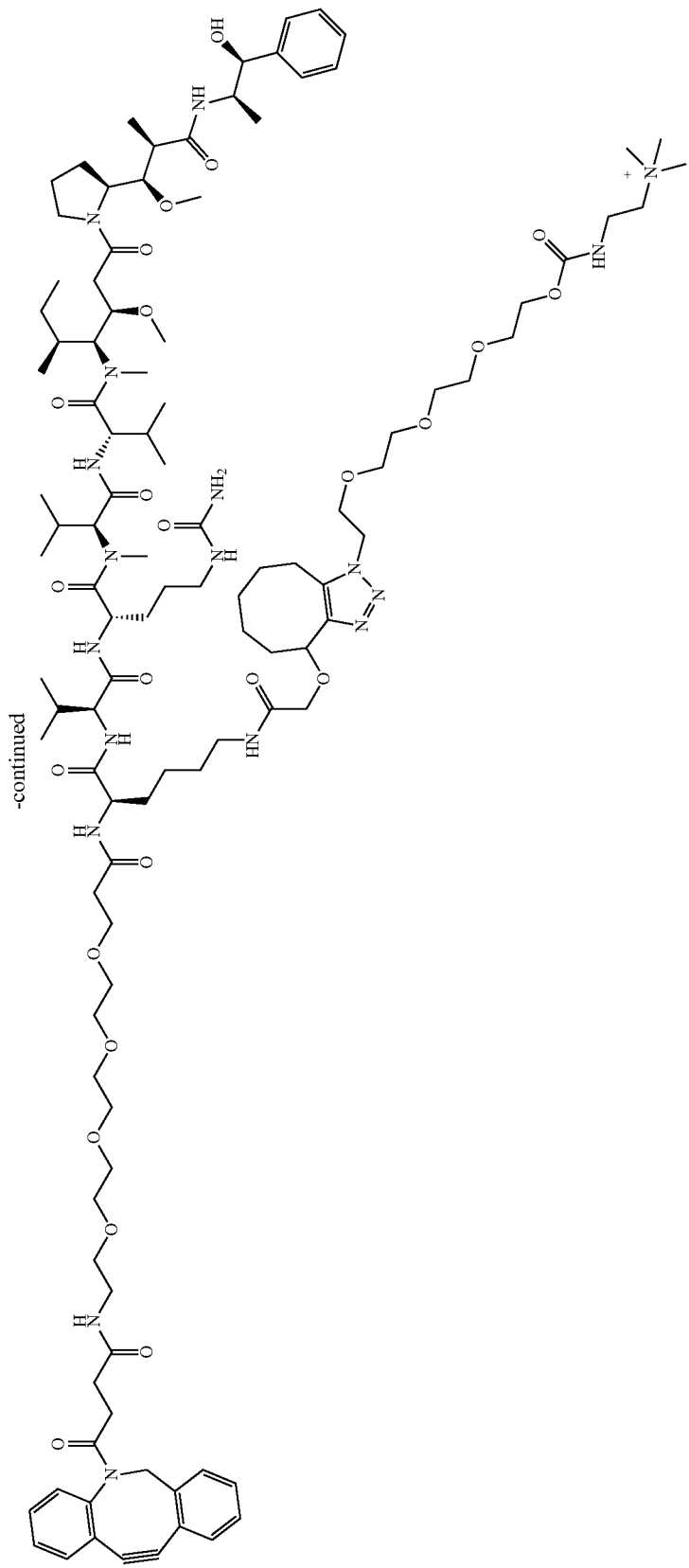

-continued
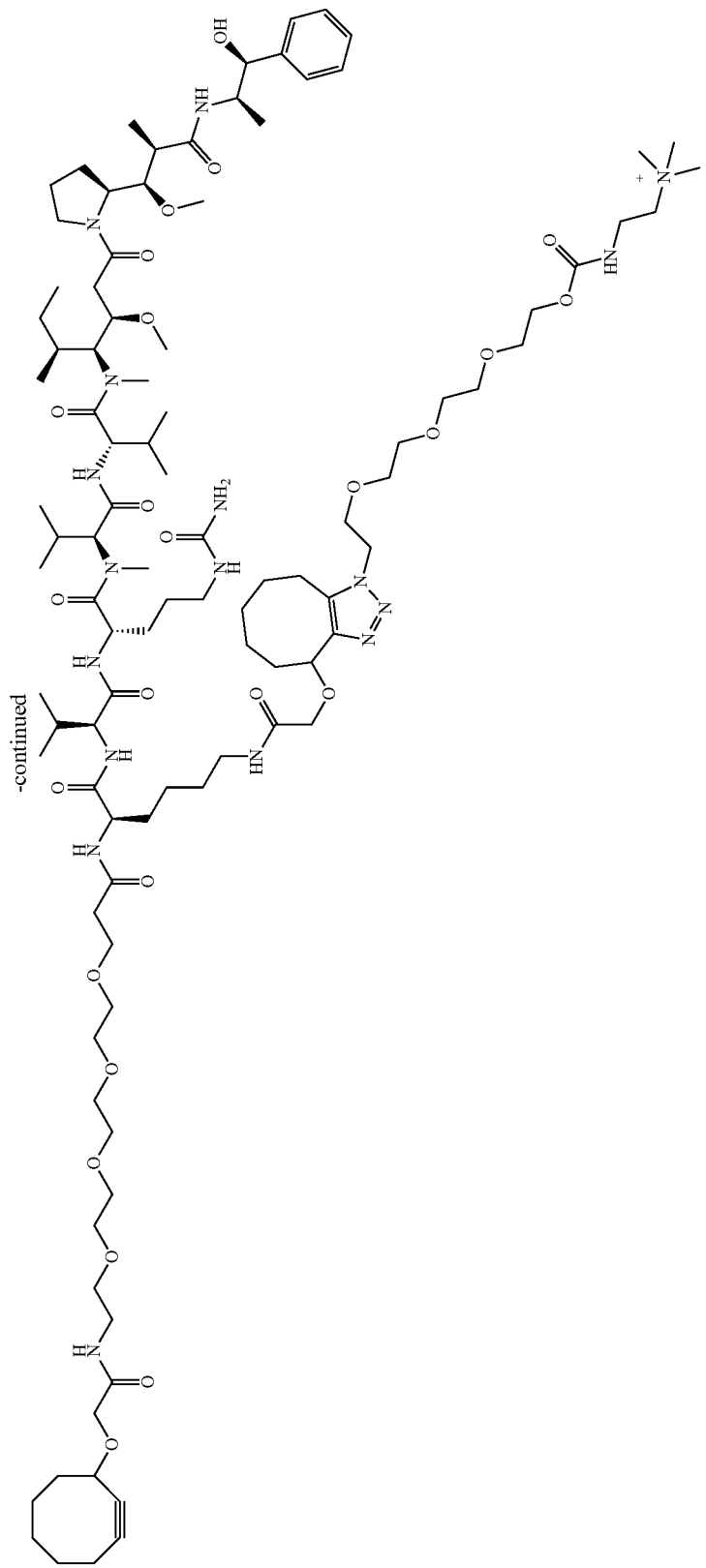

733
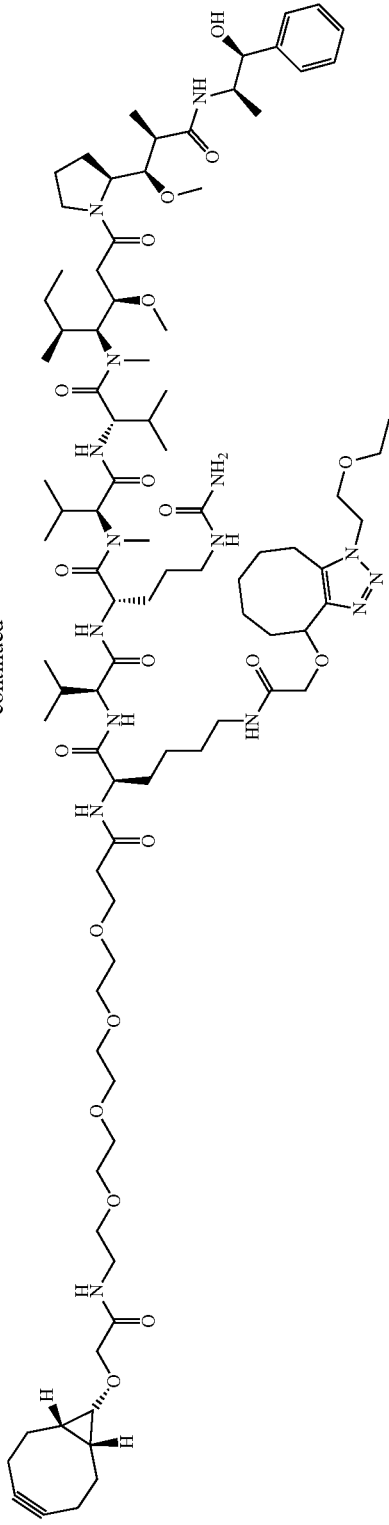
-continued
734
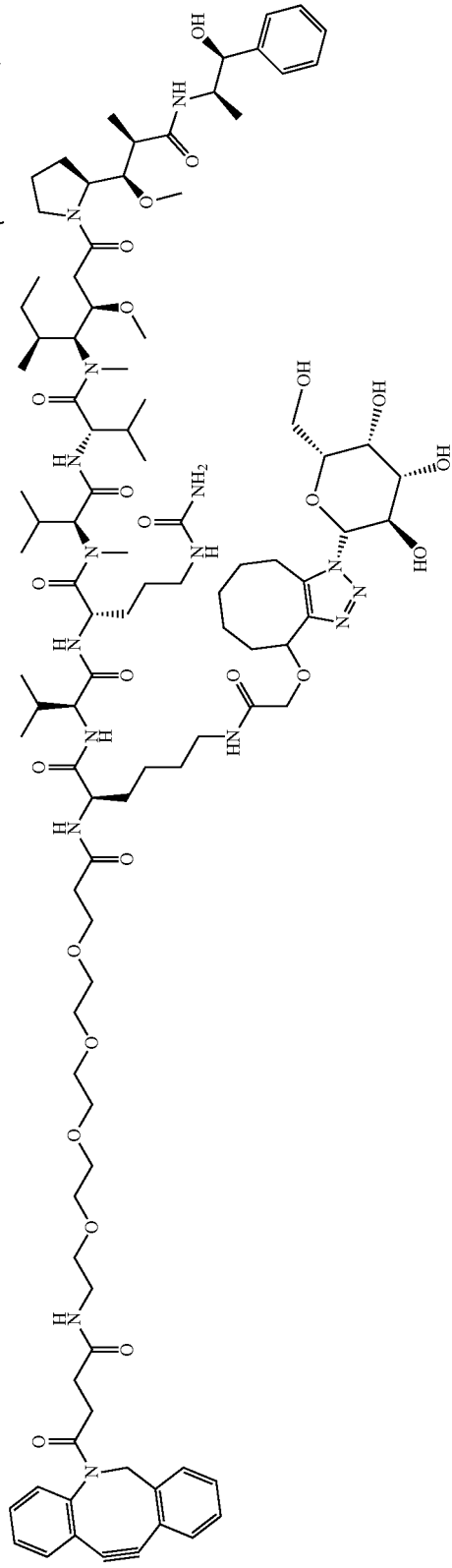

735
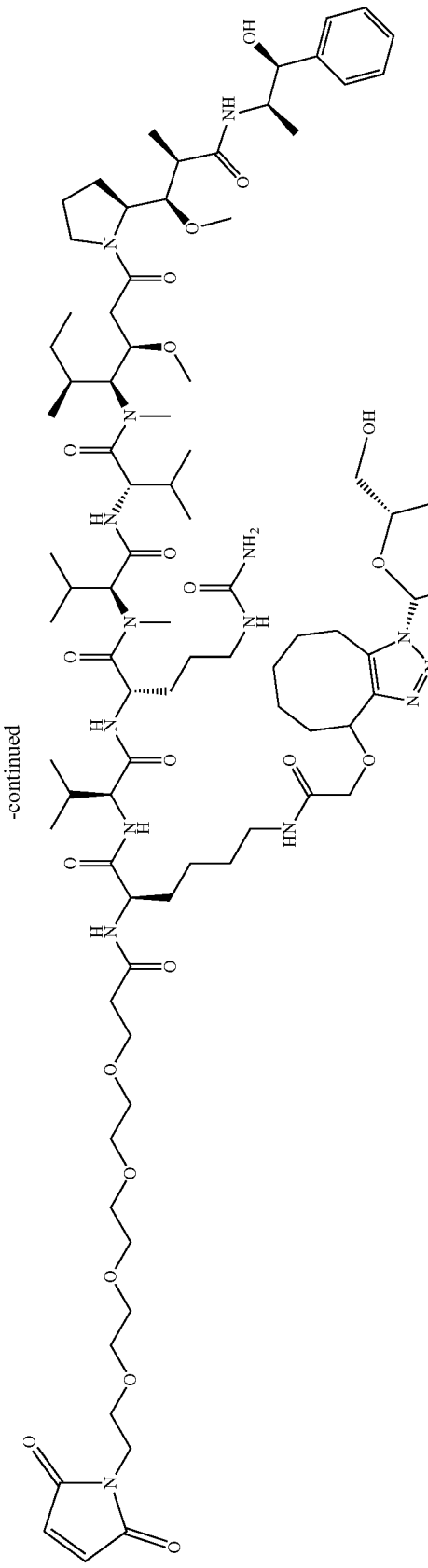
-continued
736
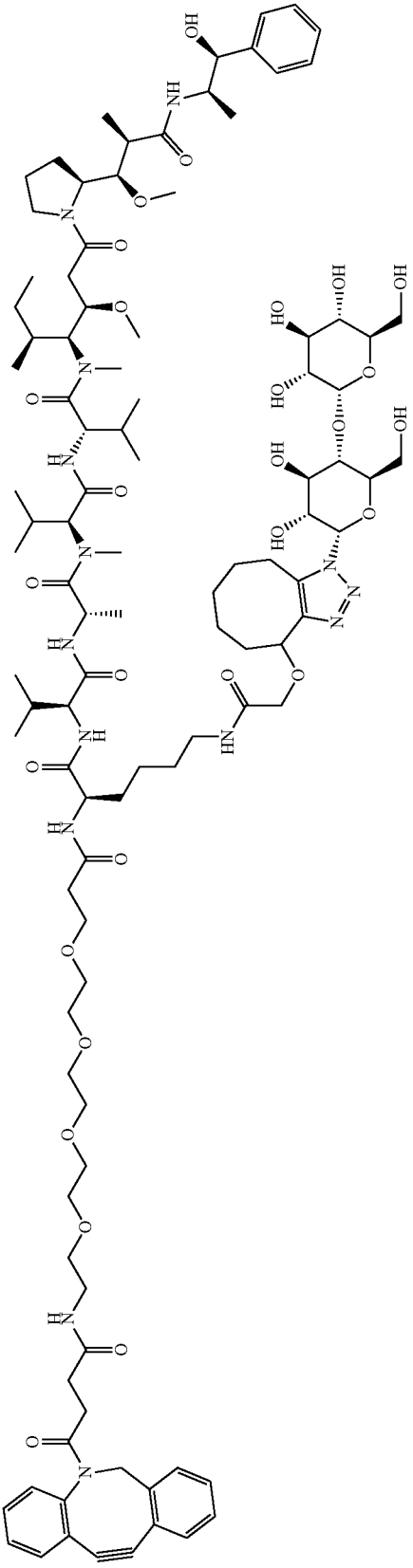

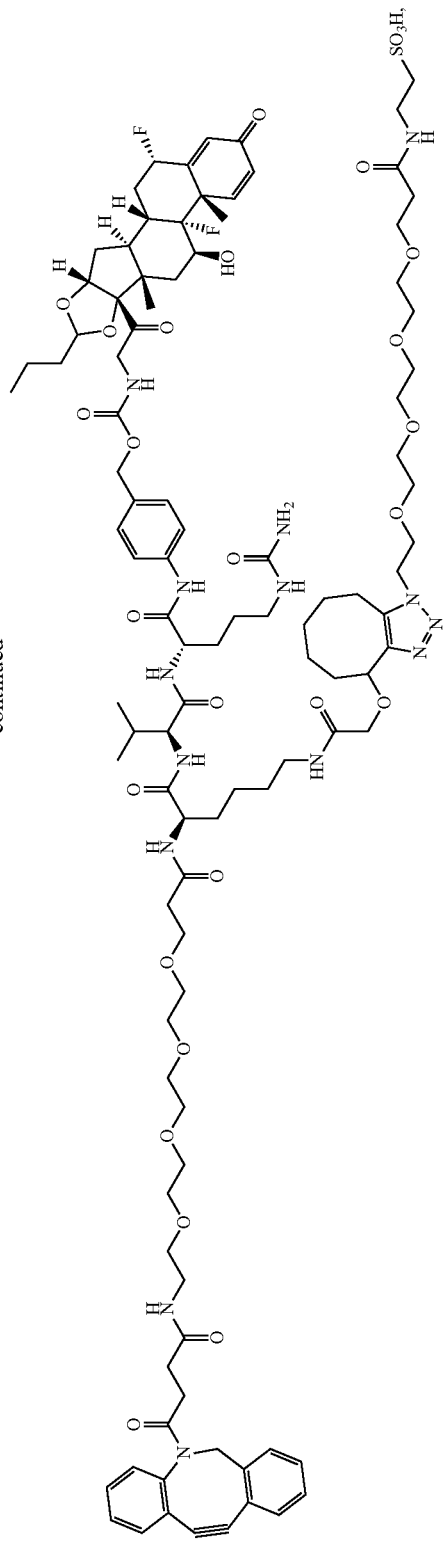
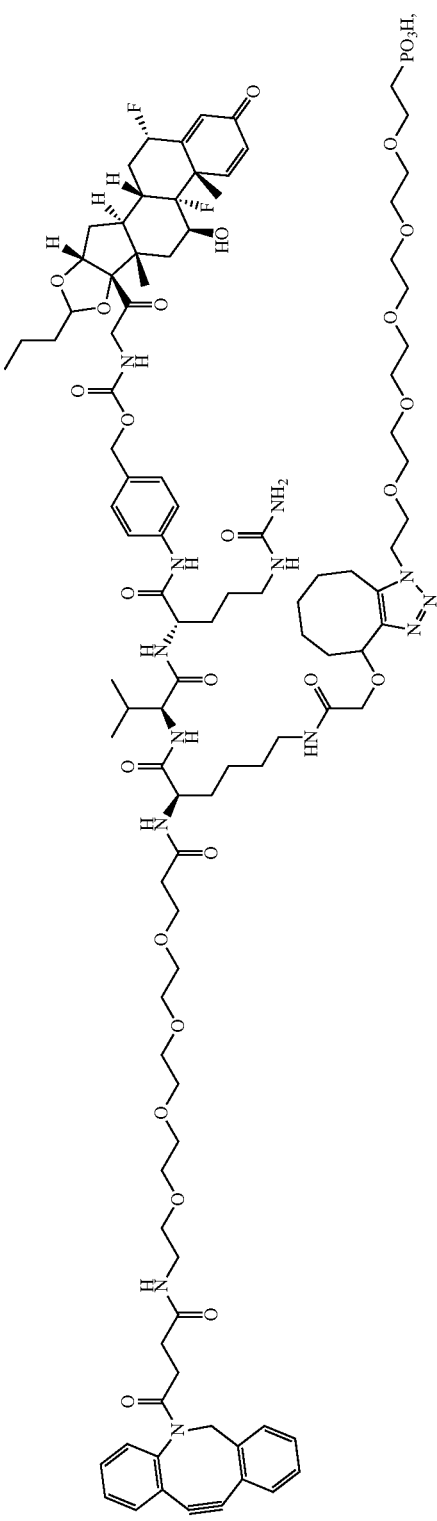

-continued
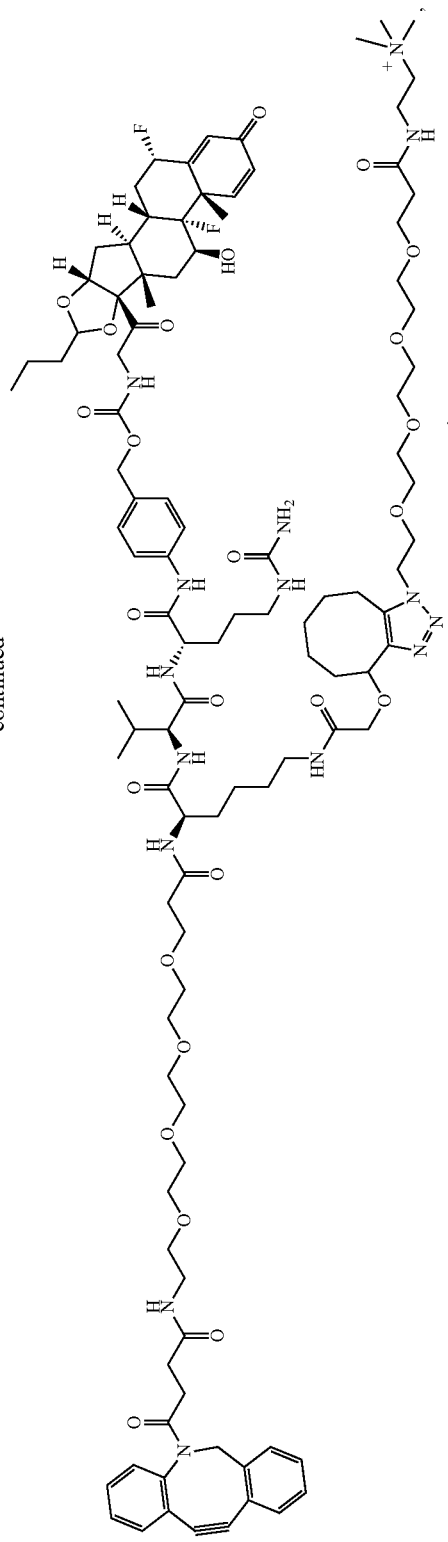
739
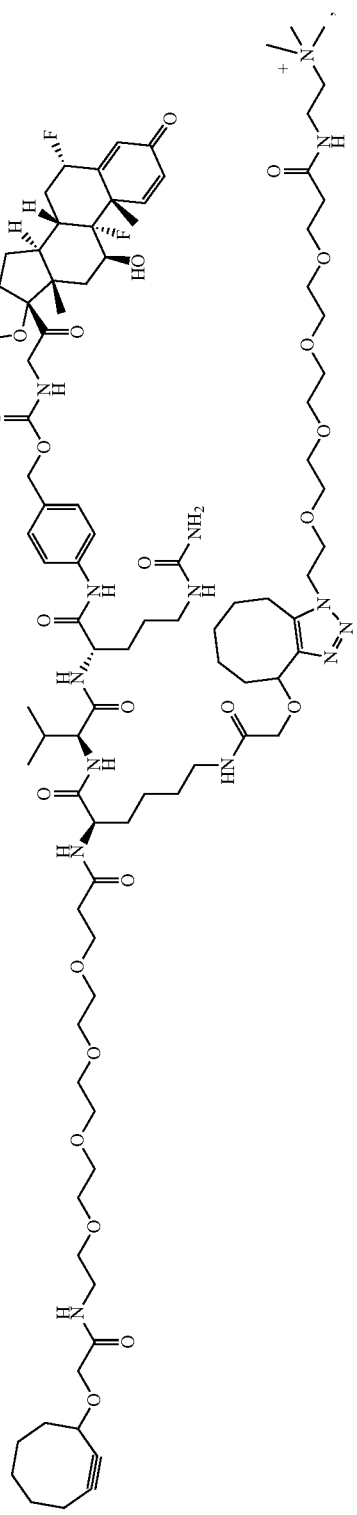
740

741 742
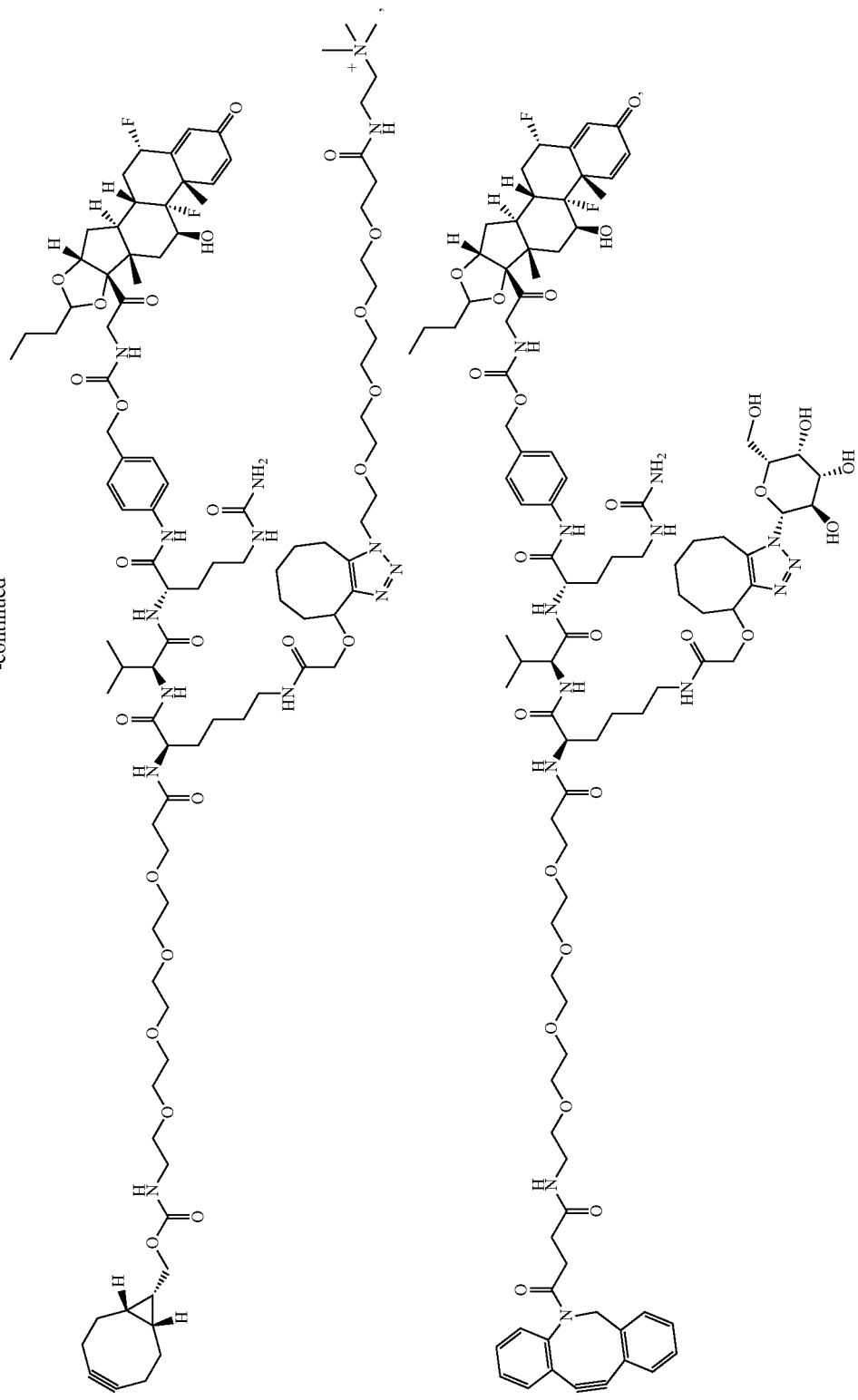

743
-continued
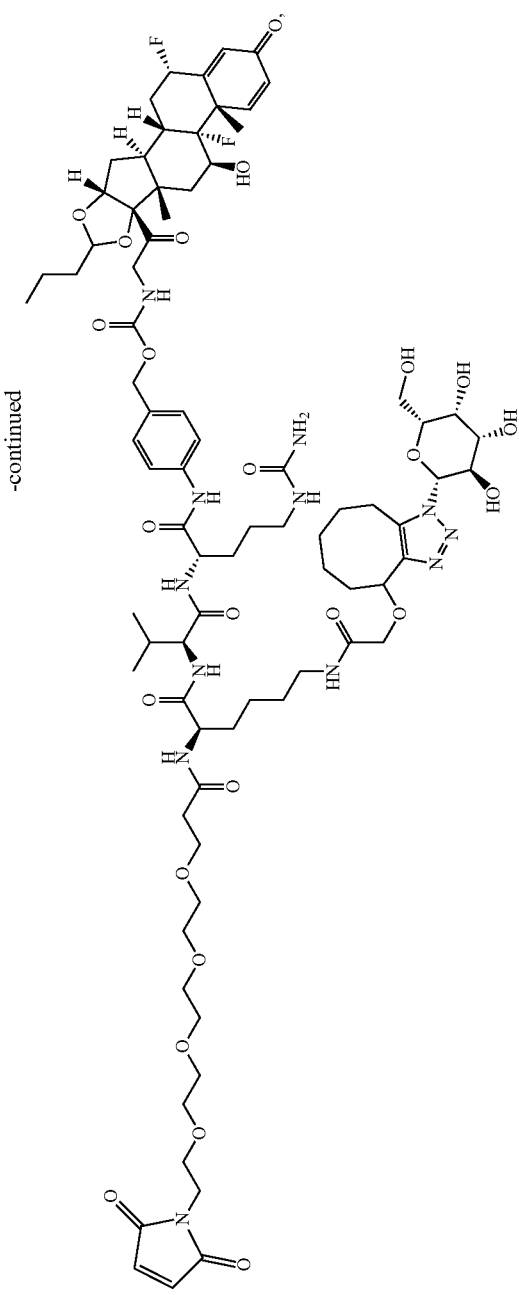
744
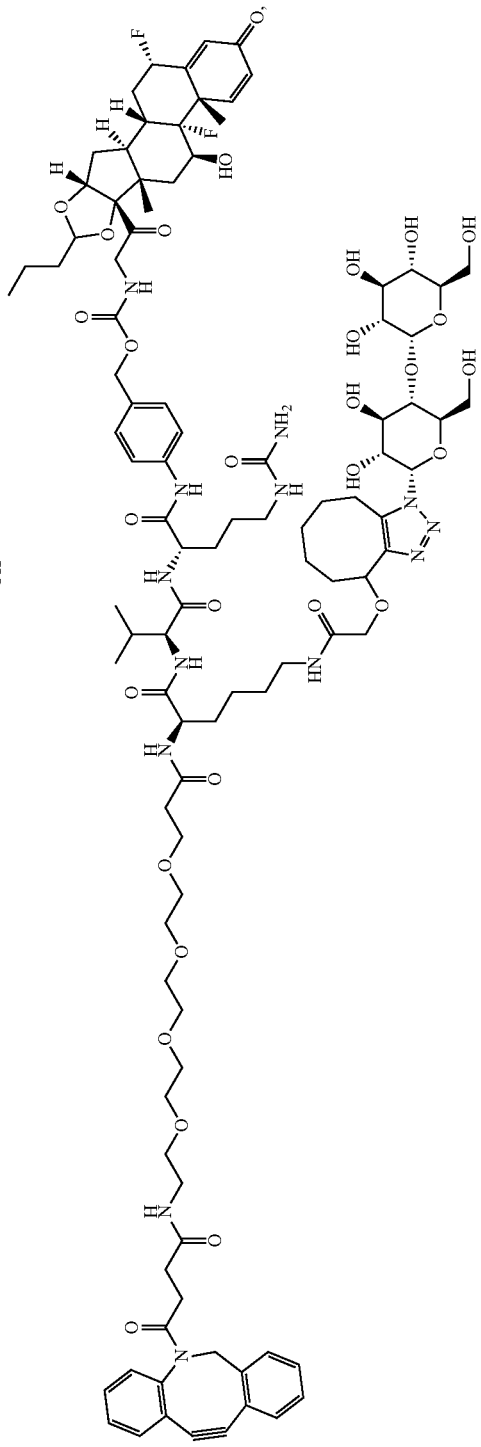

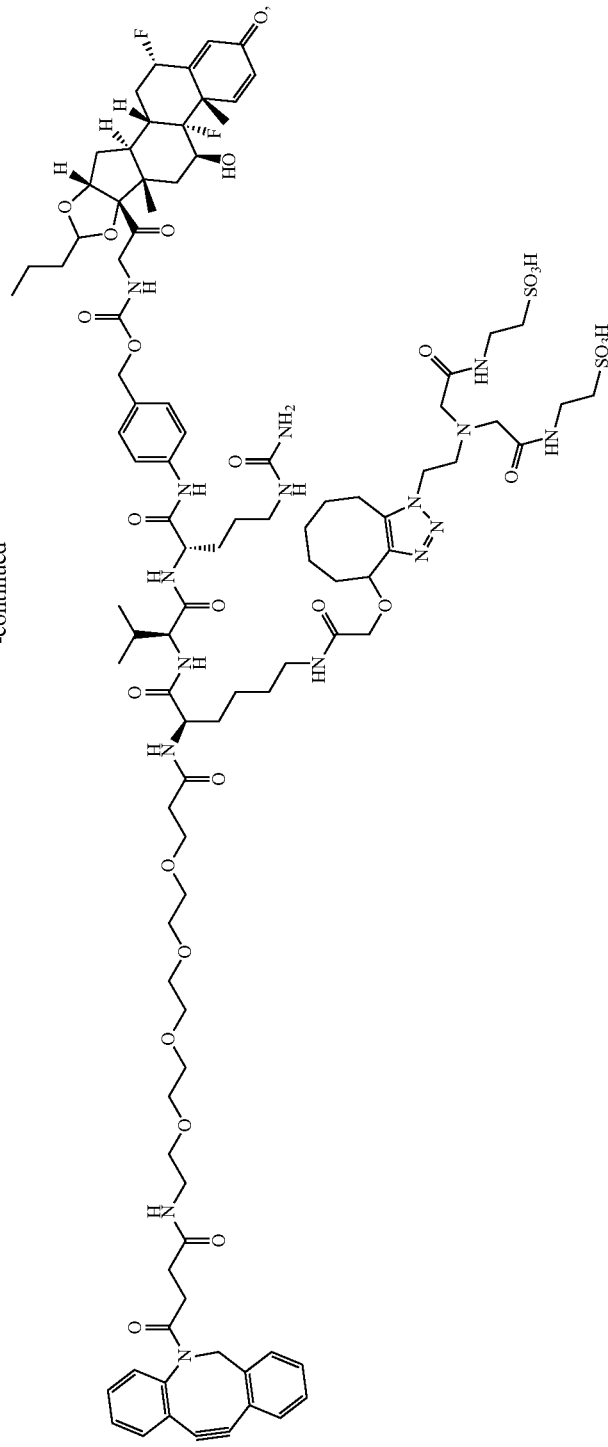
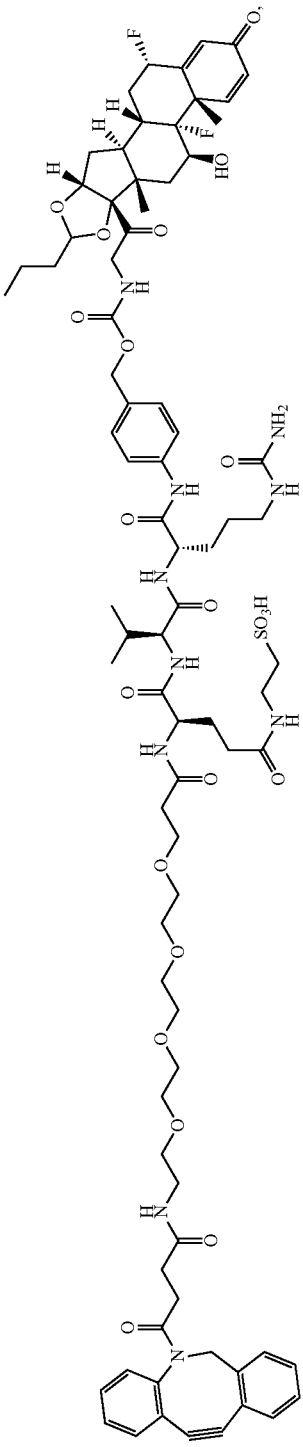

747
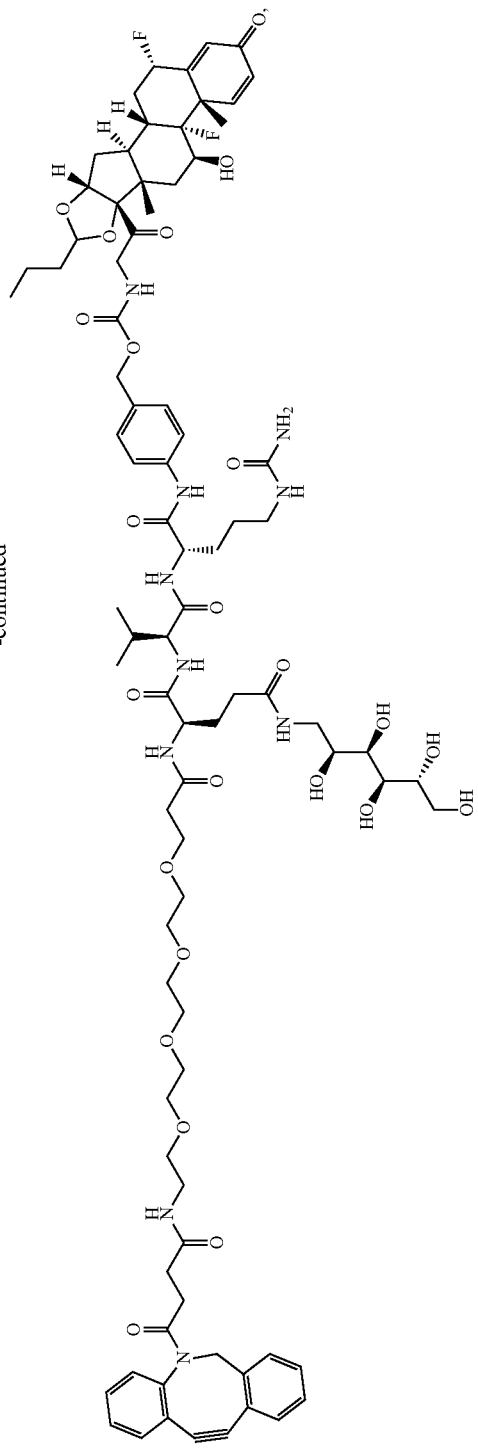
748
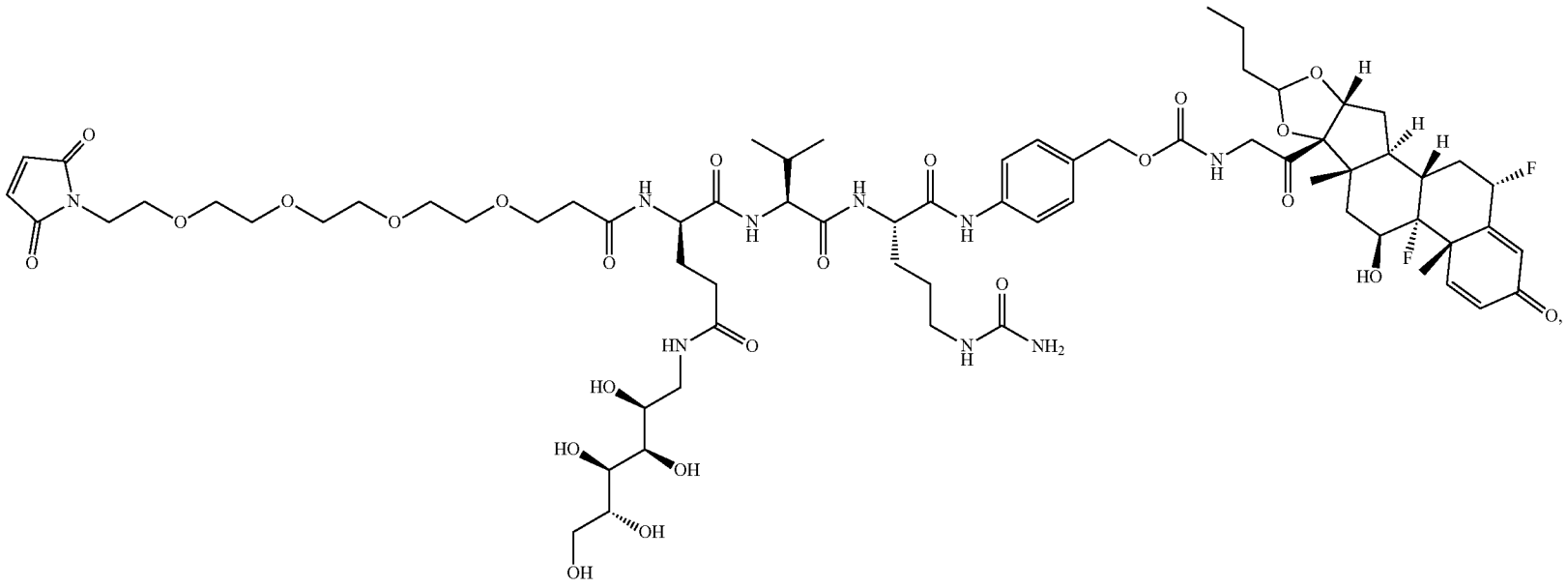 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@@H](CCC(=O)NC[C@H](O)[C@@H](O)[C@H](O)[C@H](O)CO)NC(=O)CCOCCOCCOCCOCCN3C(=O)C=CC3=O)C(C)C)cc2)O1]

-continued
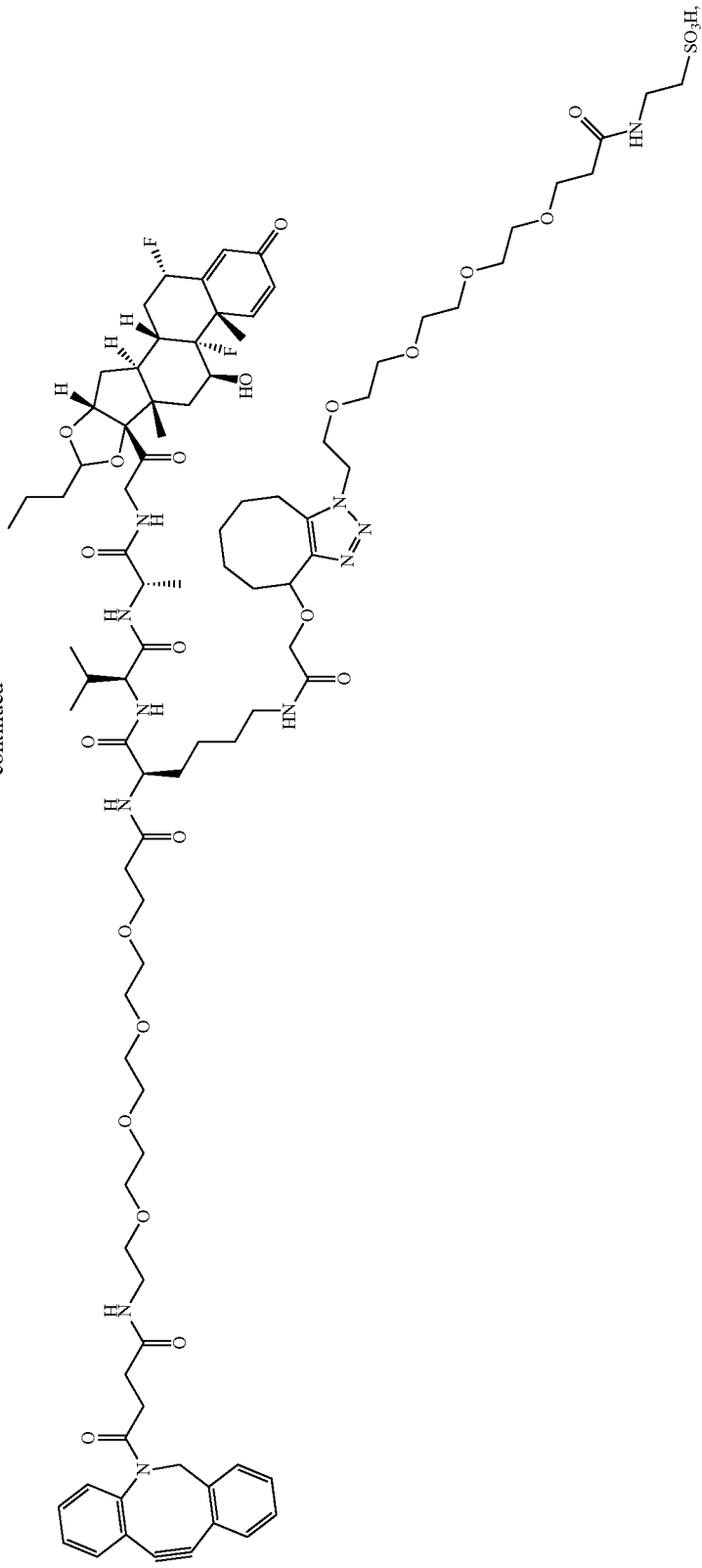

-continued
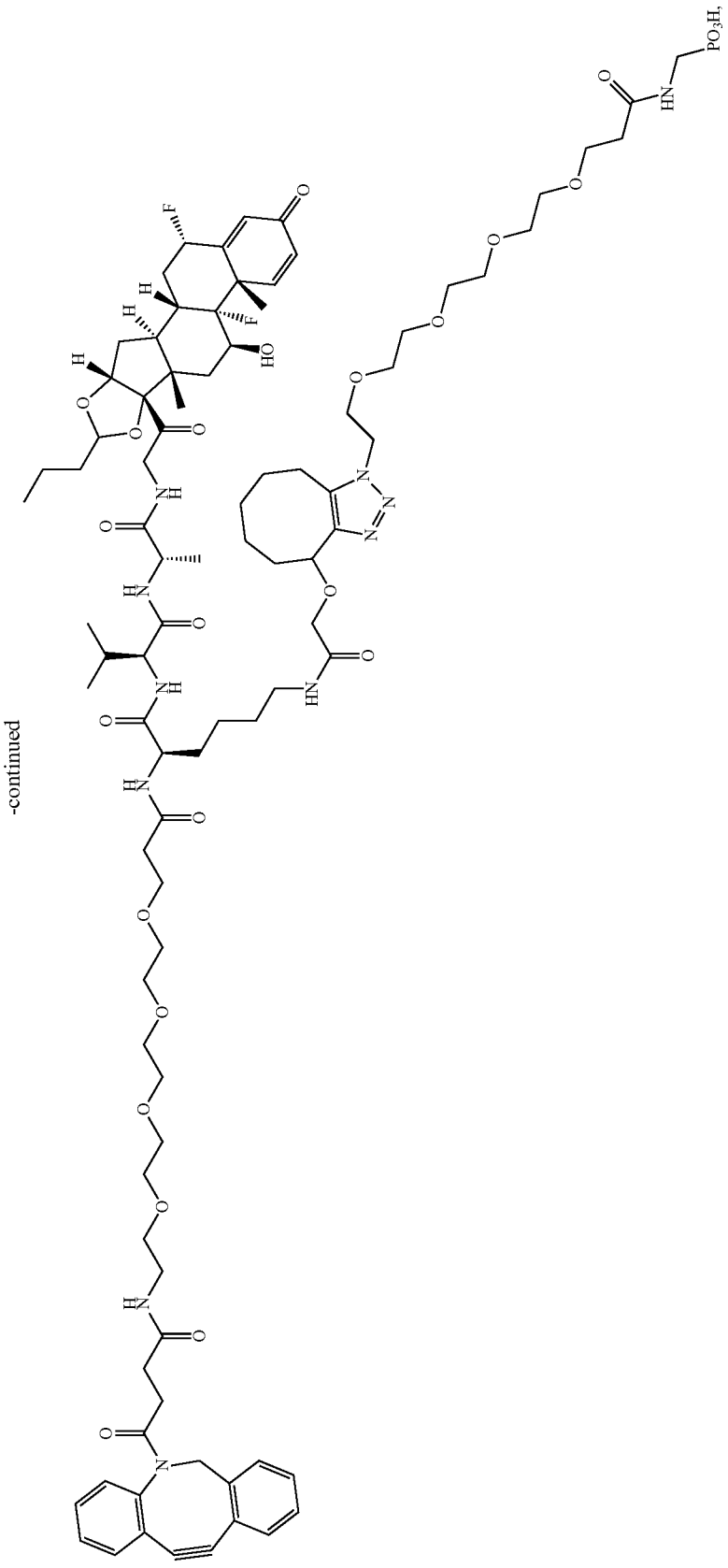

-continued
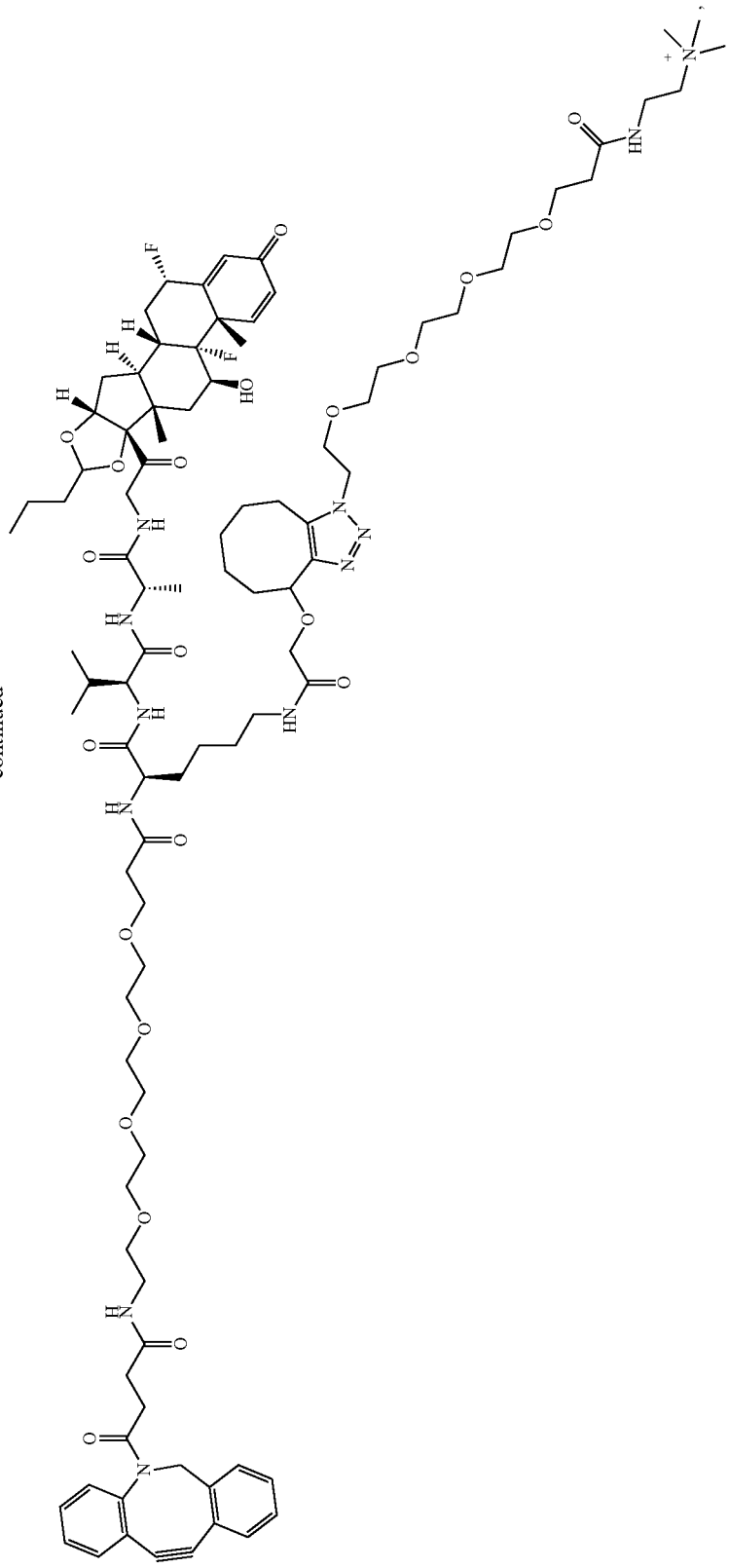

-continued
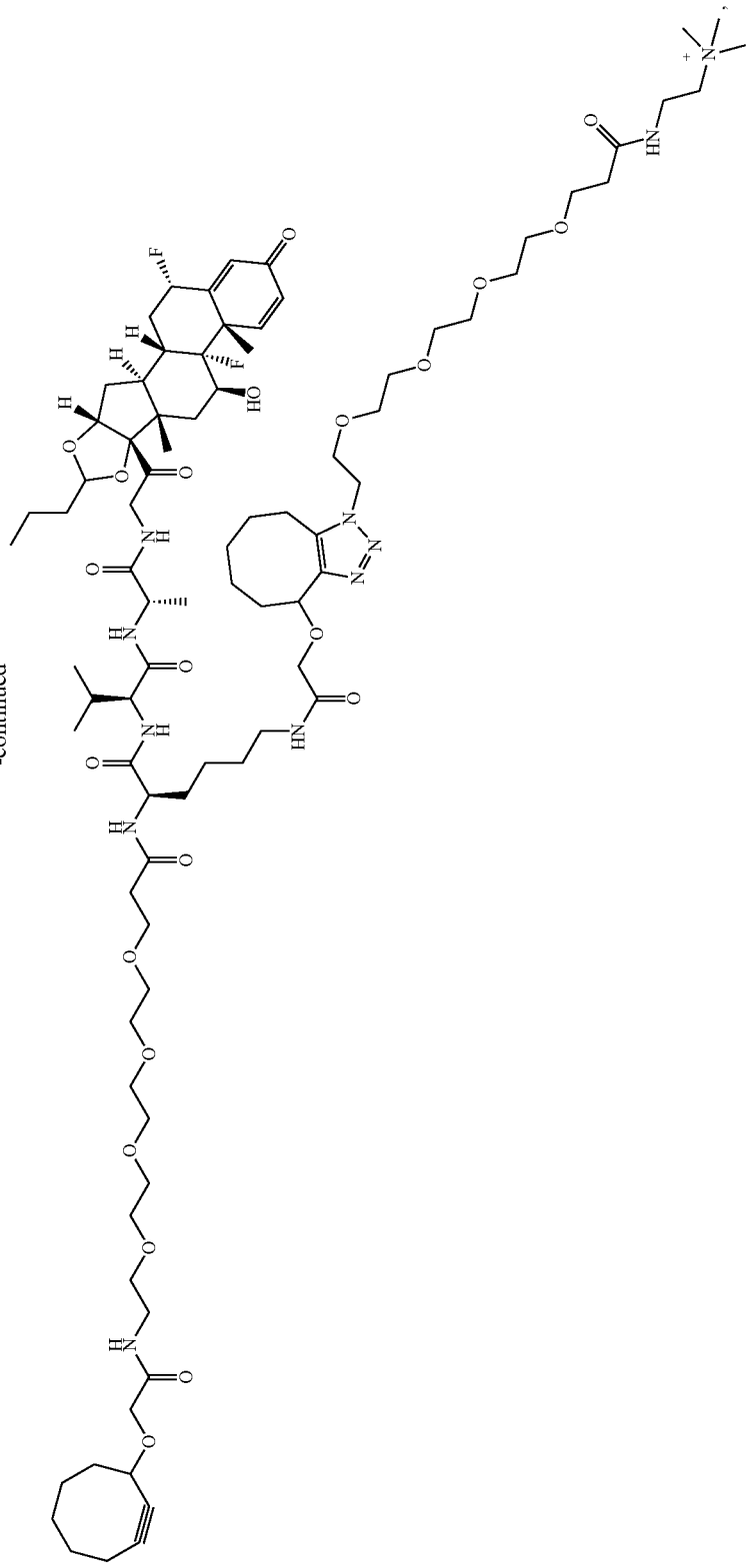

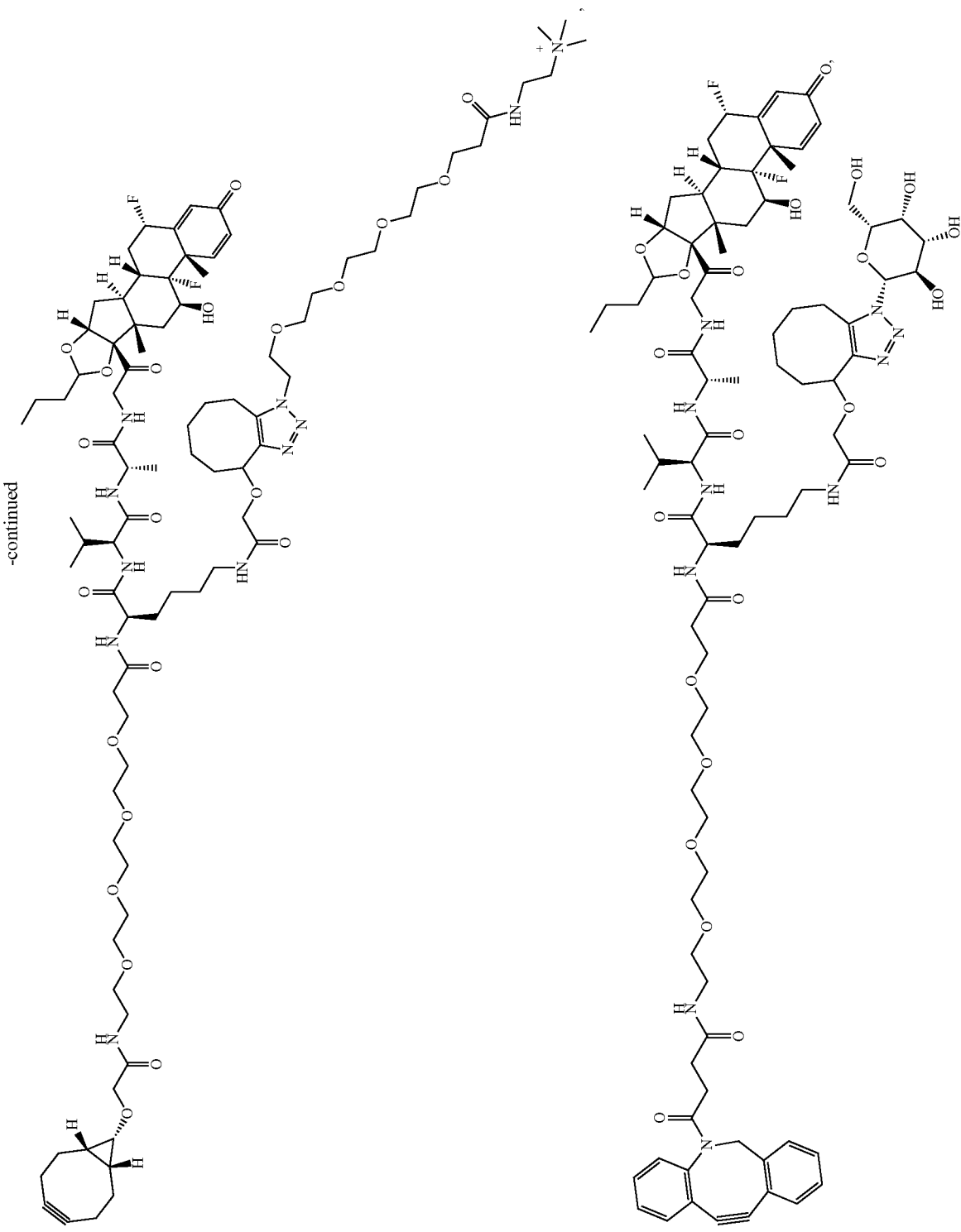

-continued
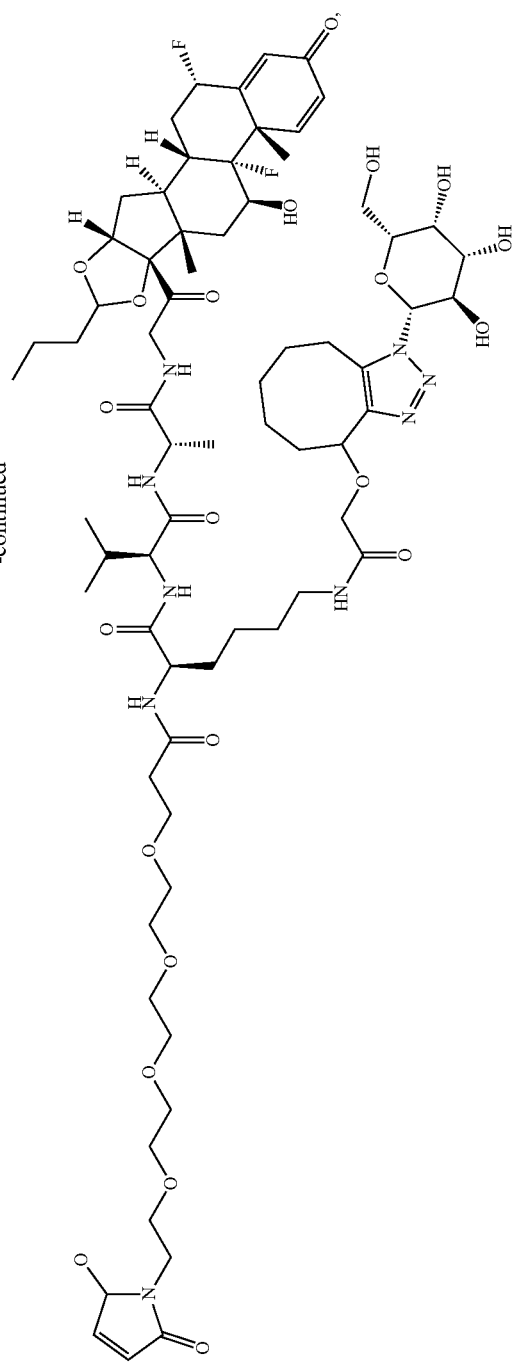
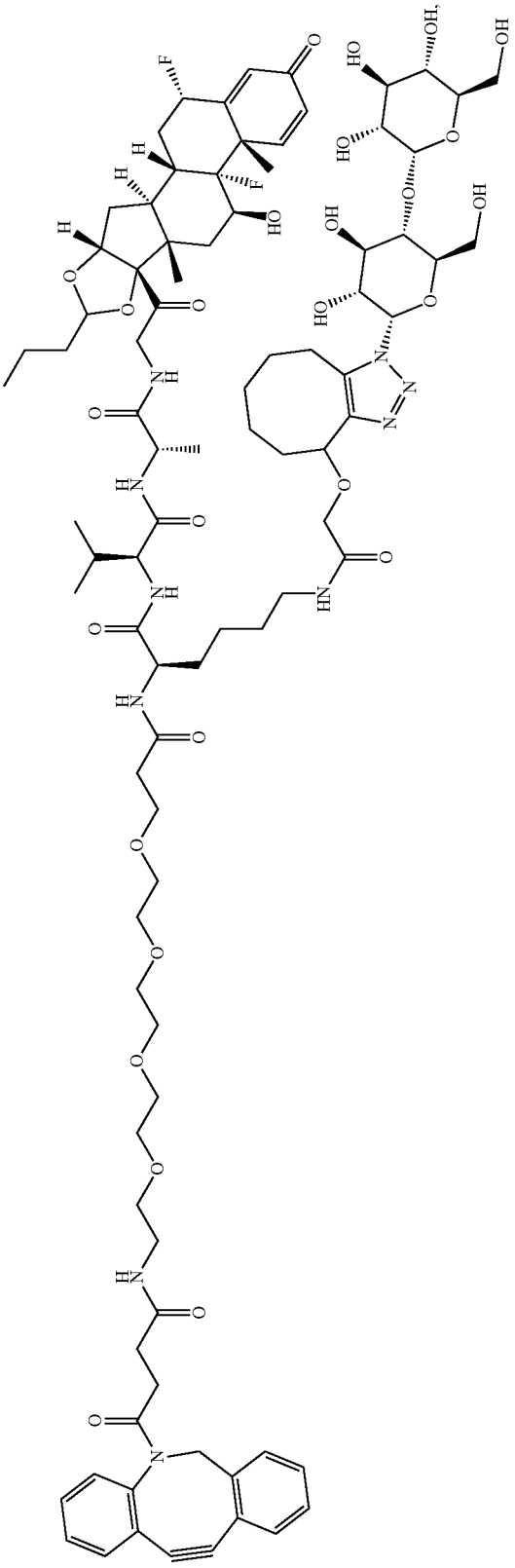

-continued
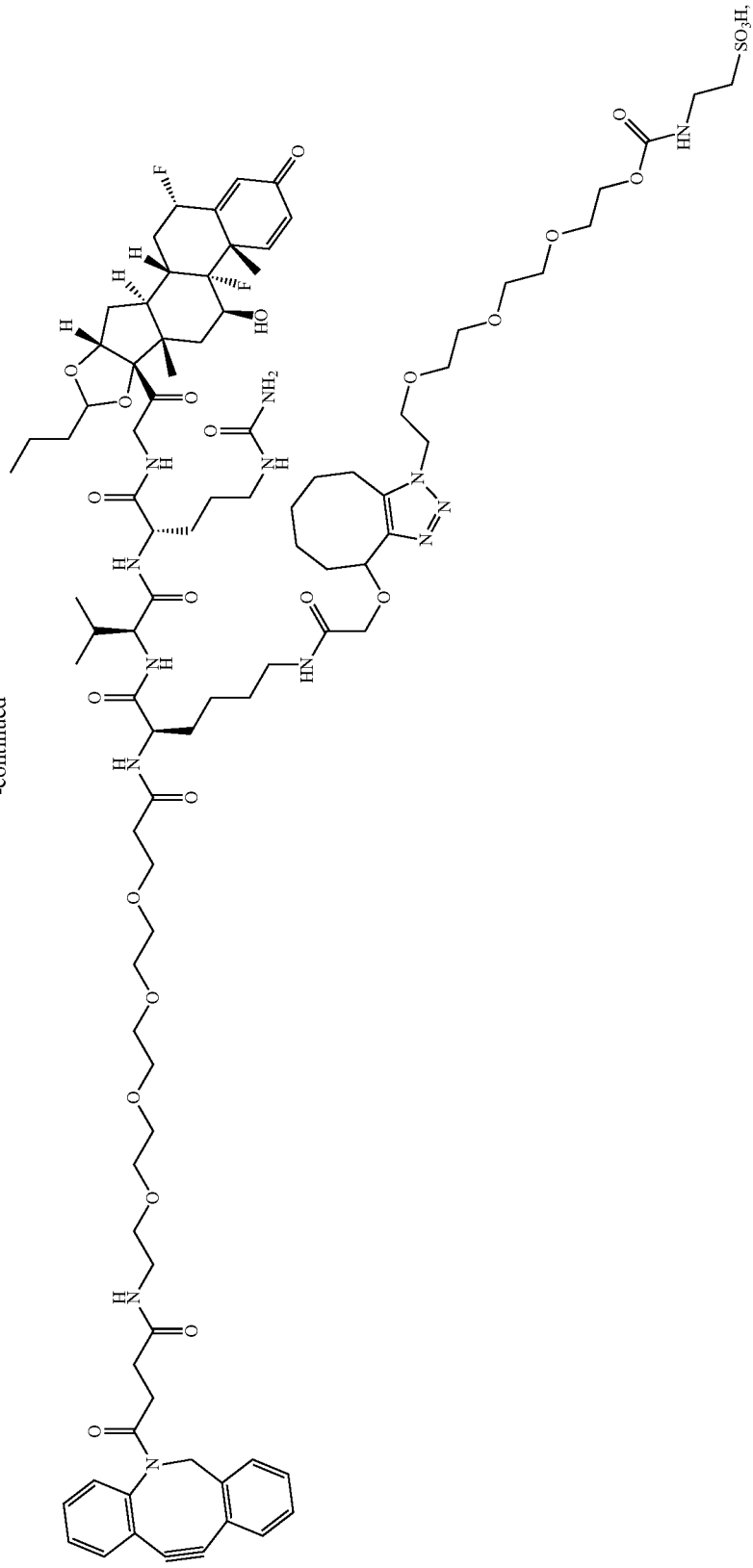

-continued
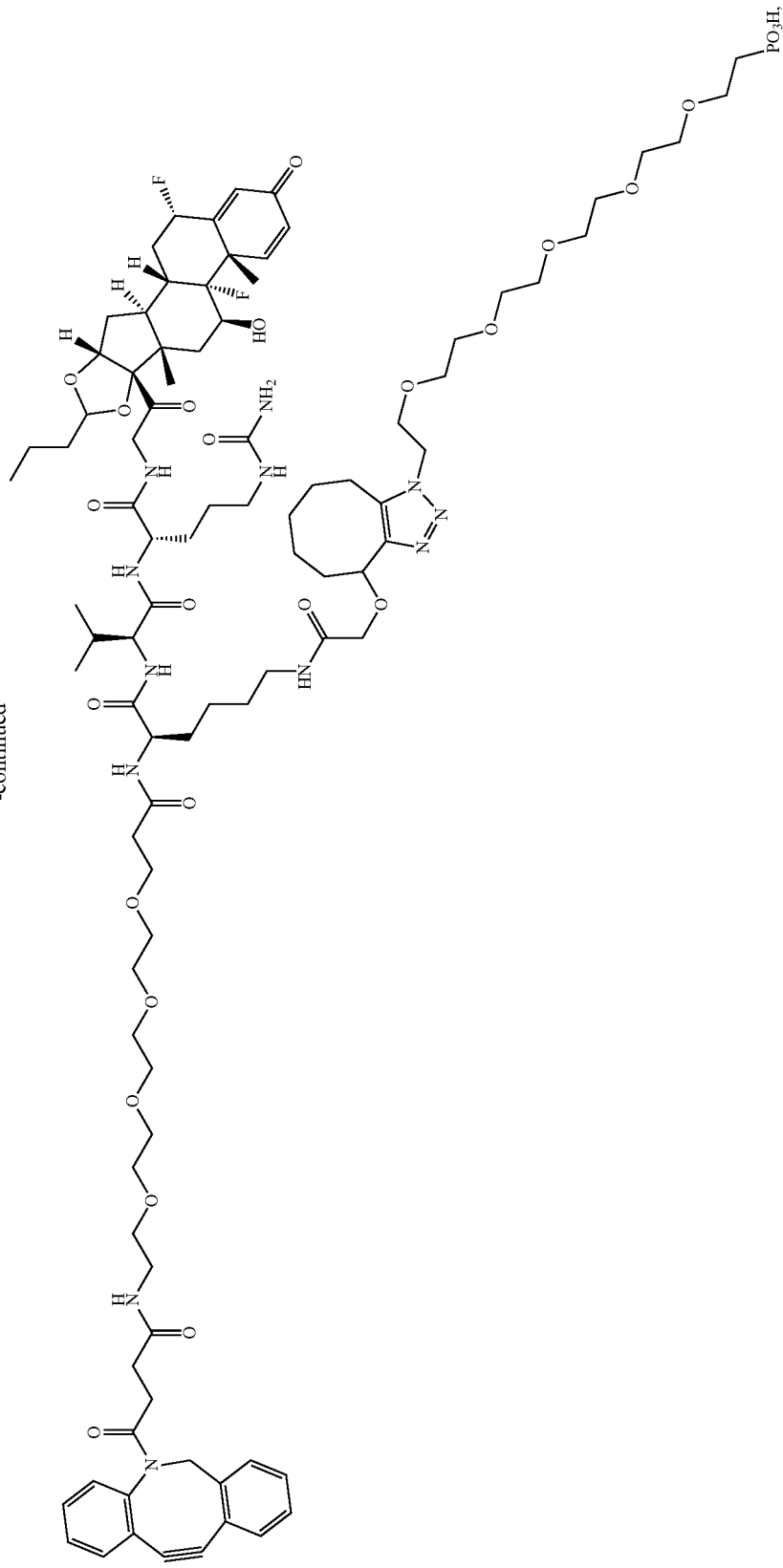

-continued
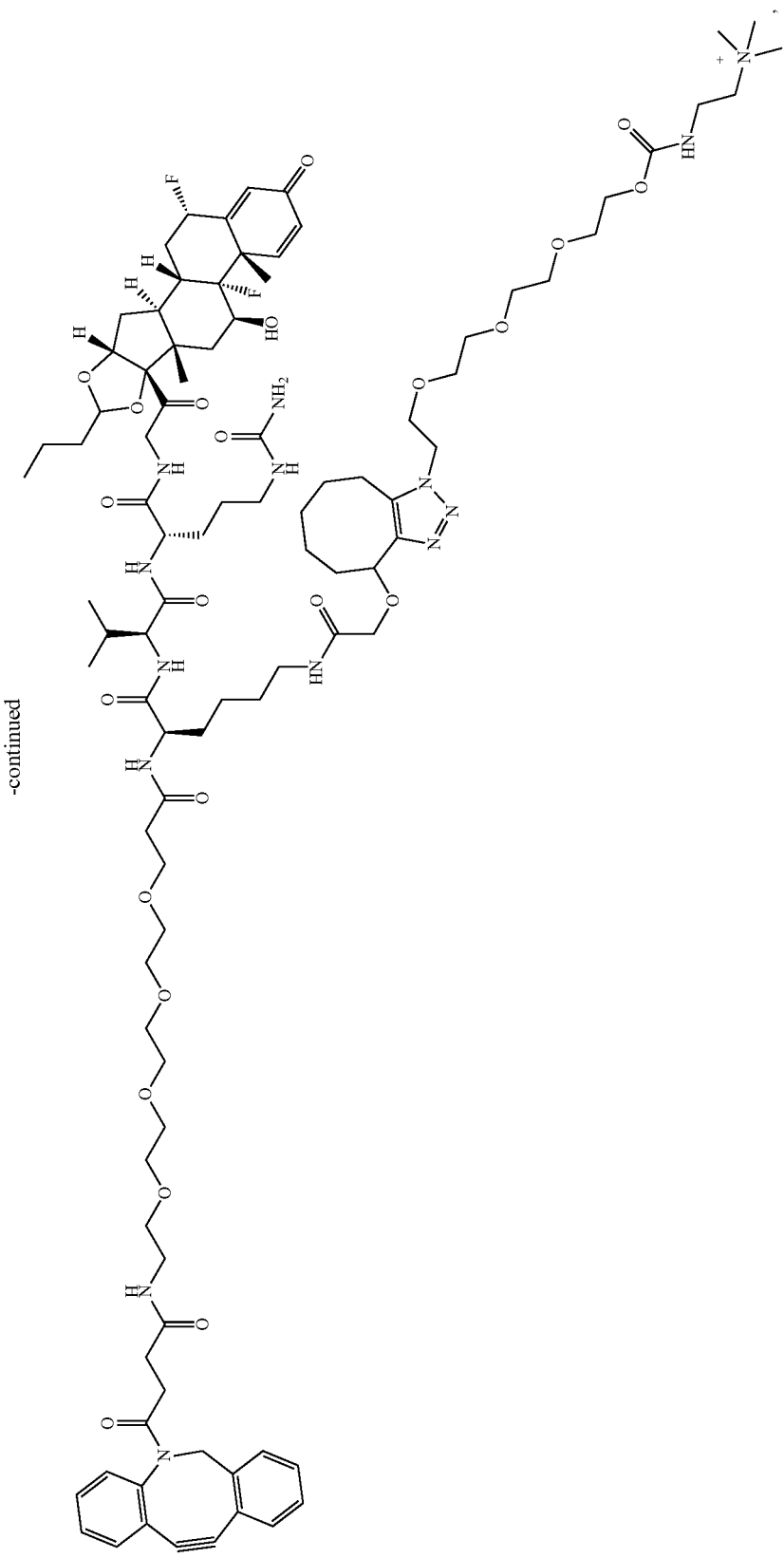

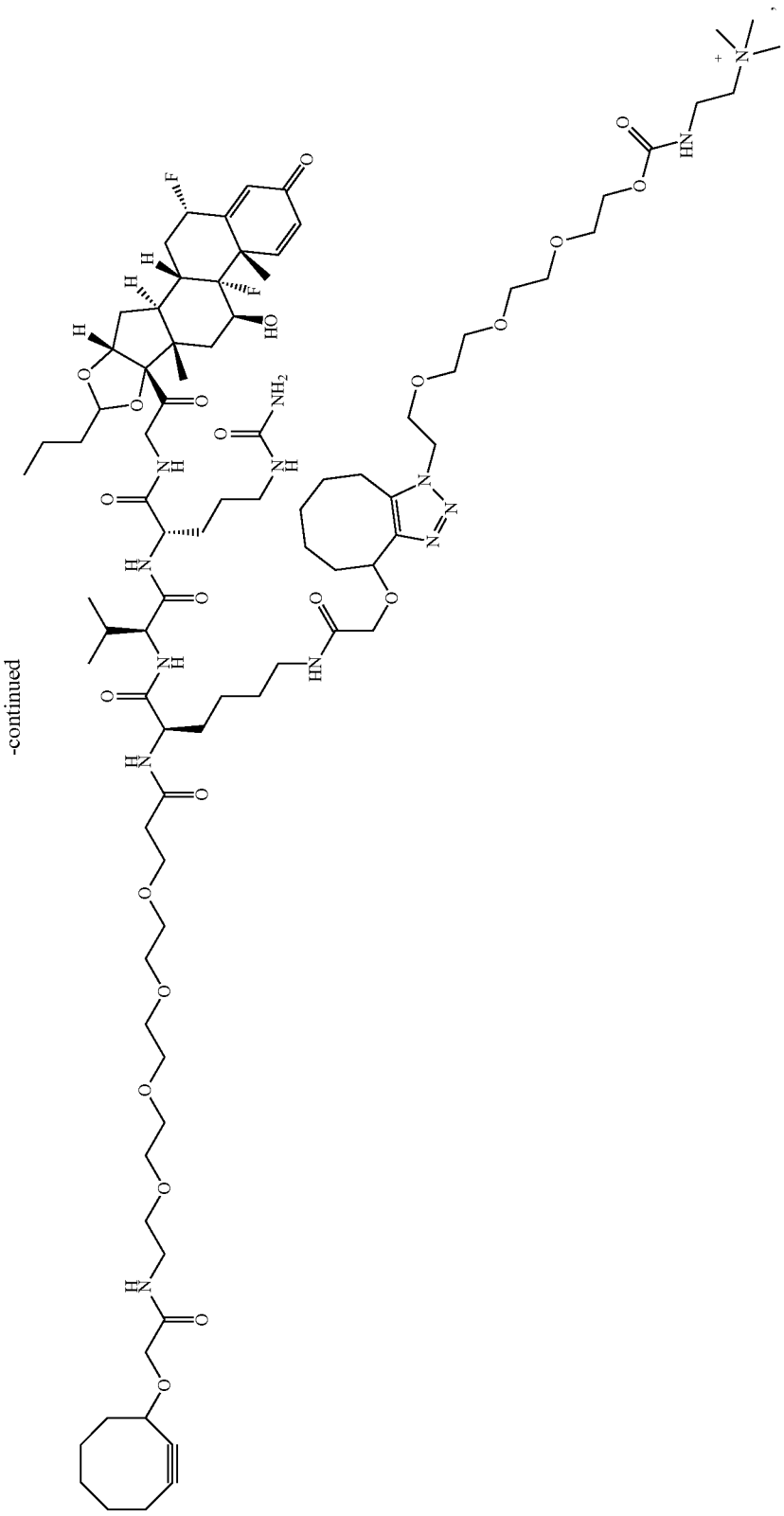

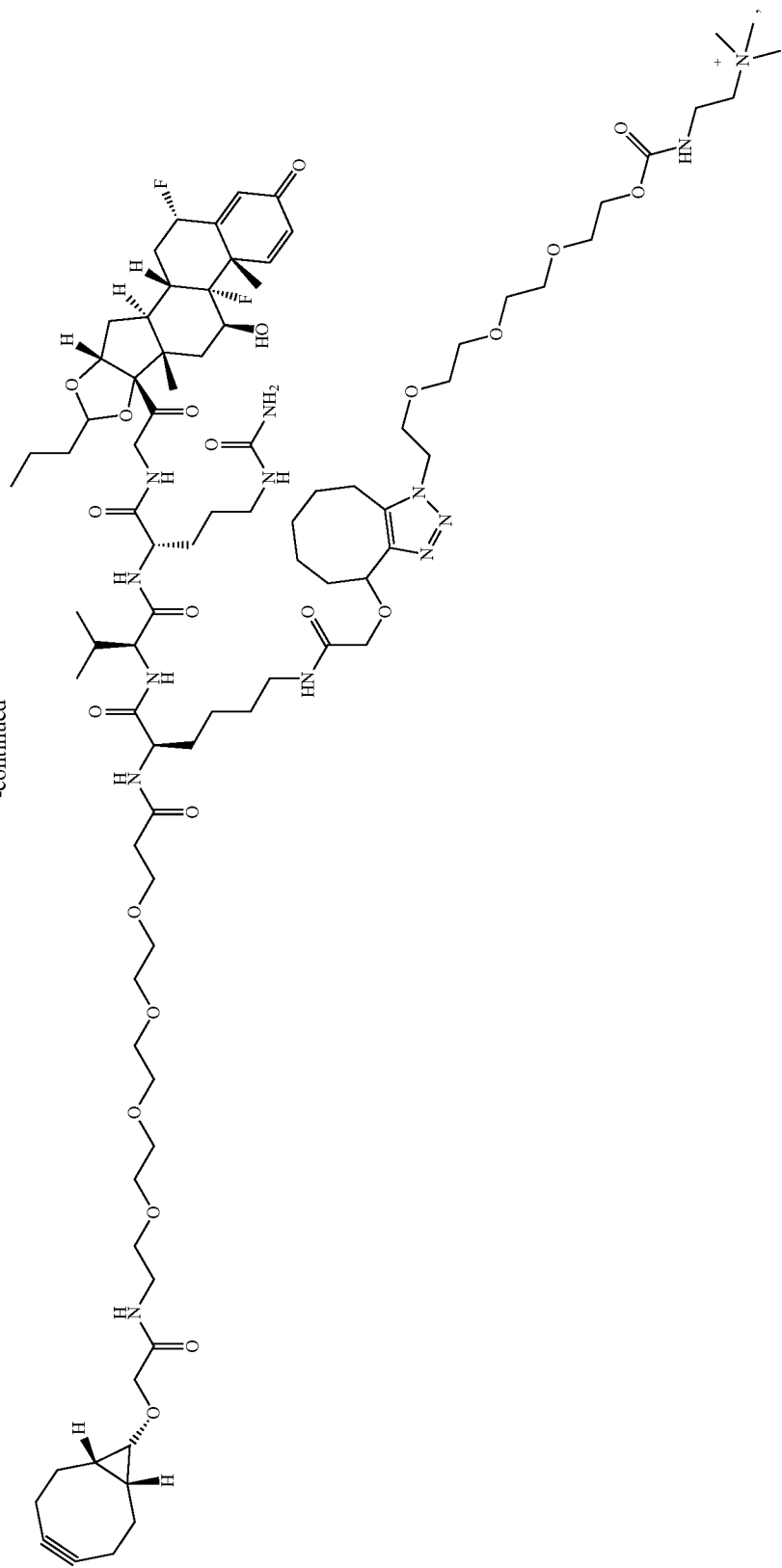

-continued
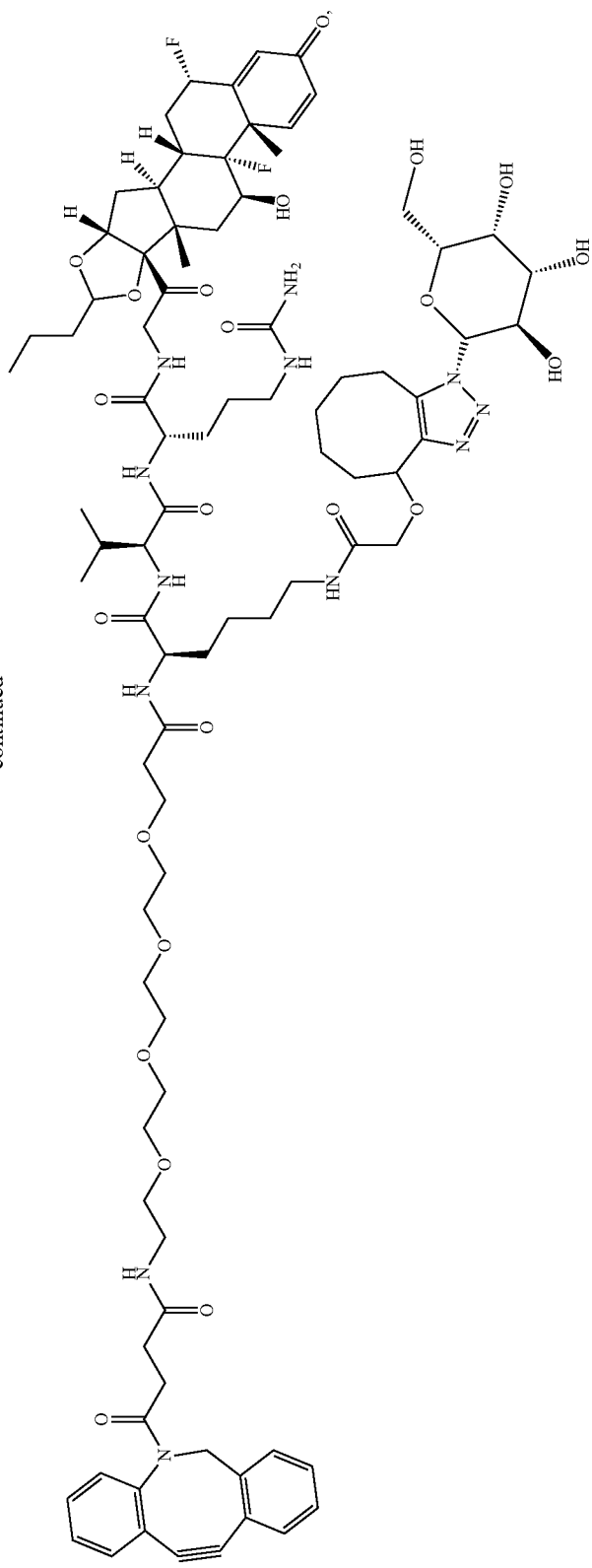

-continued
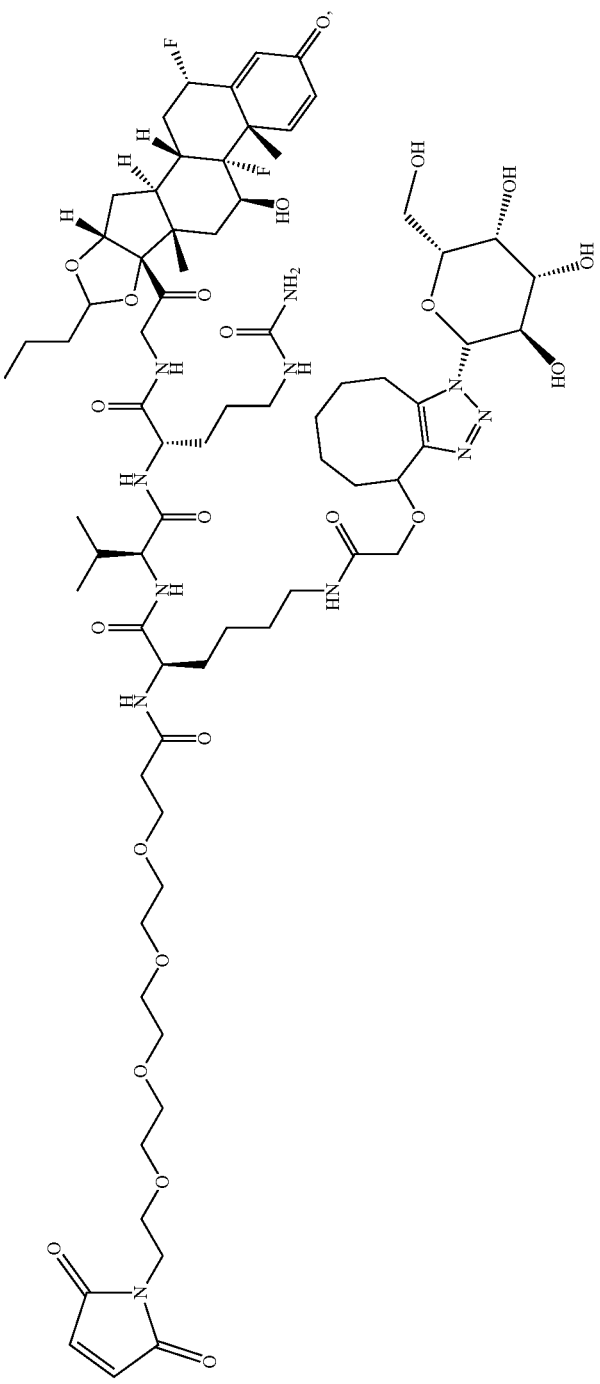

775
776
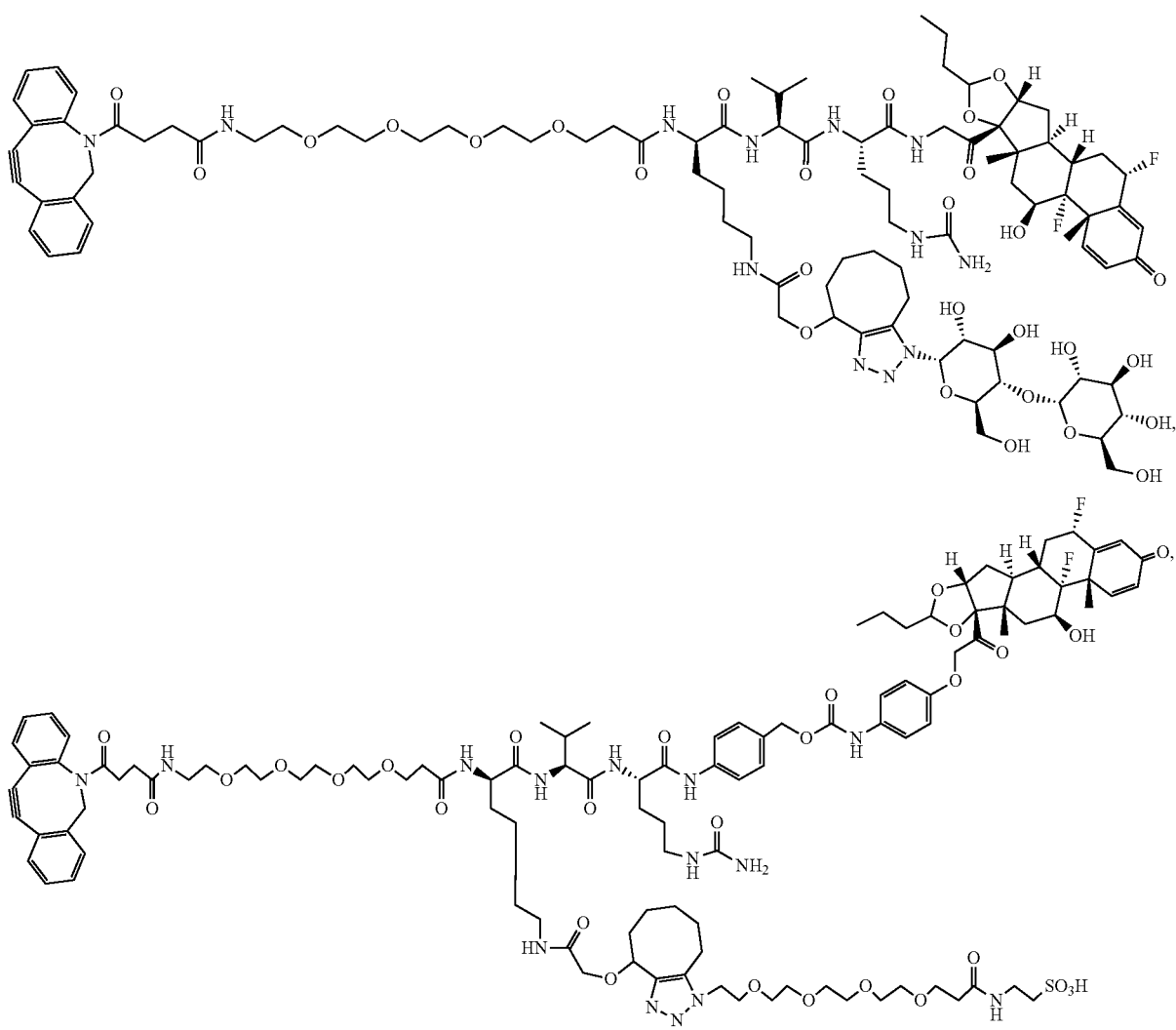
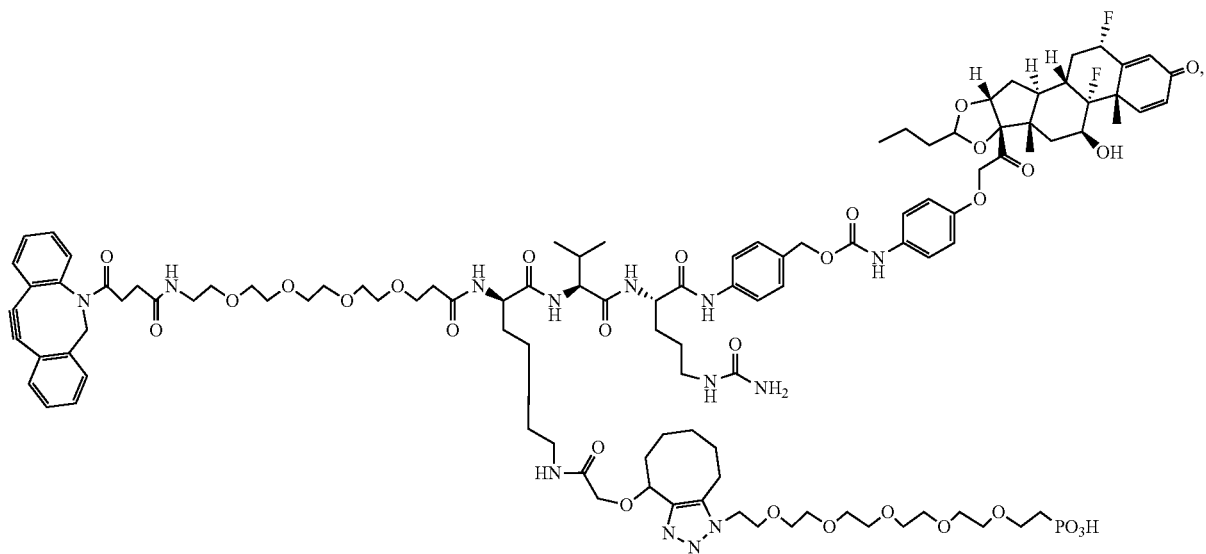

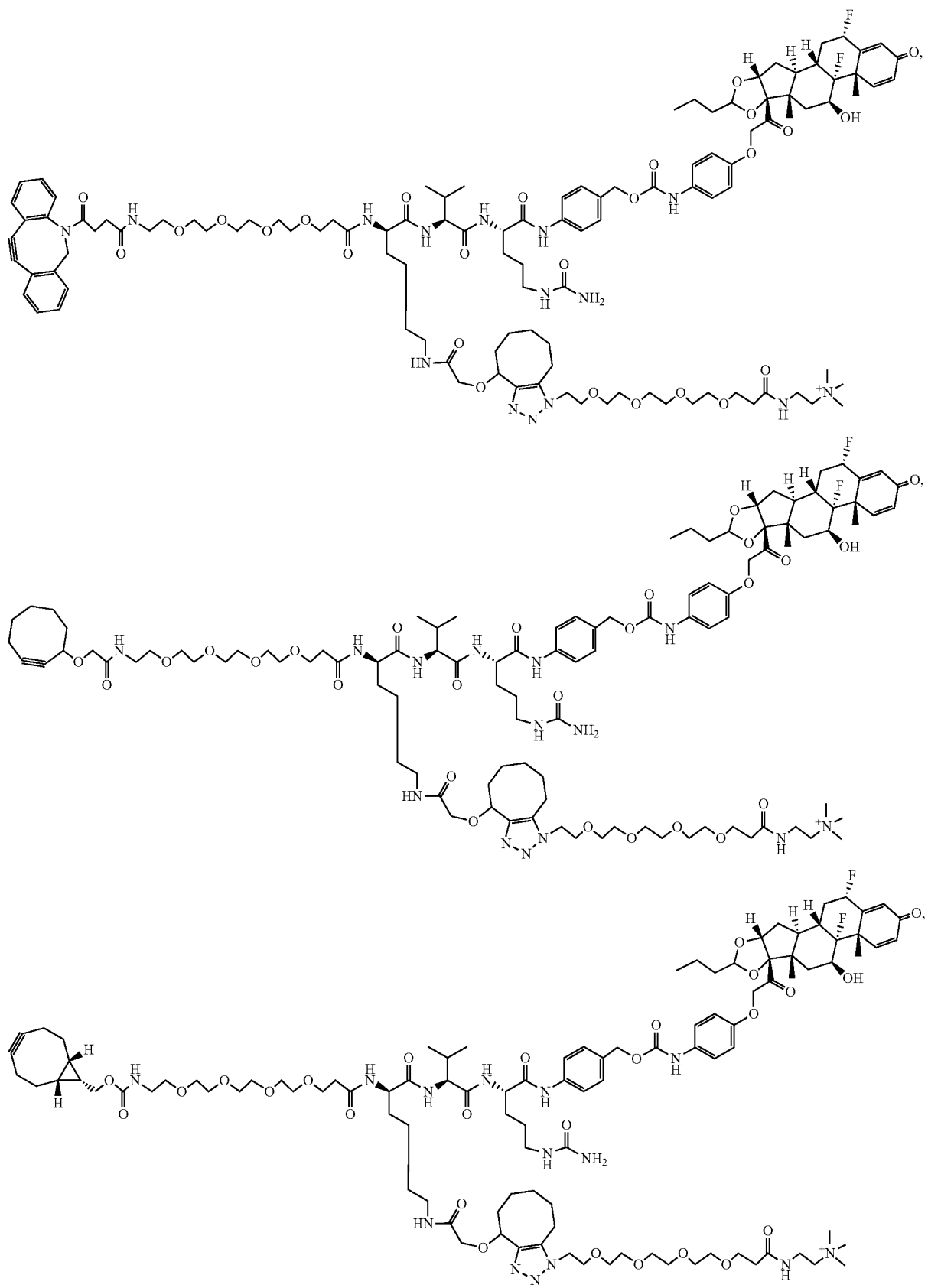

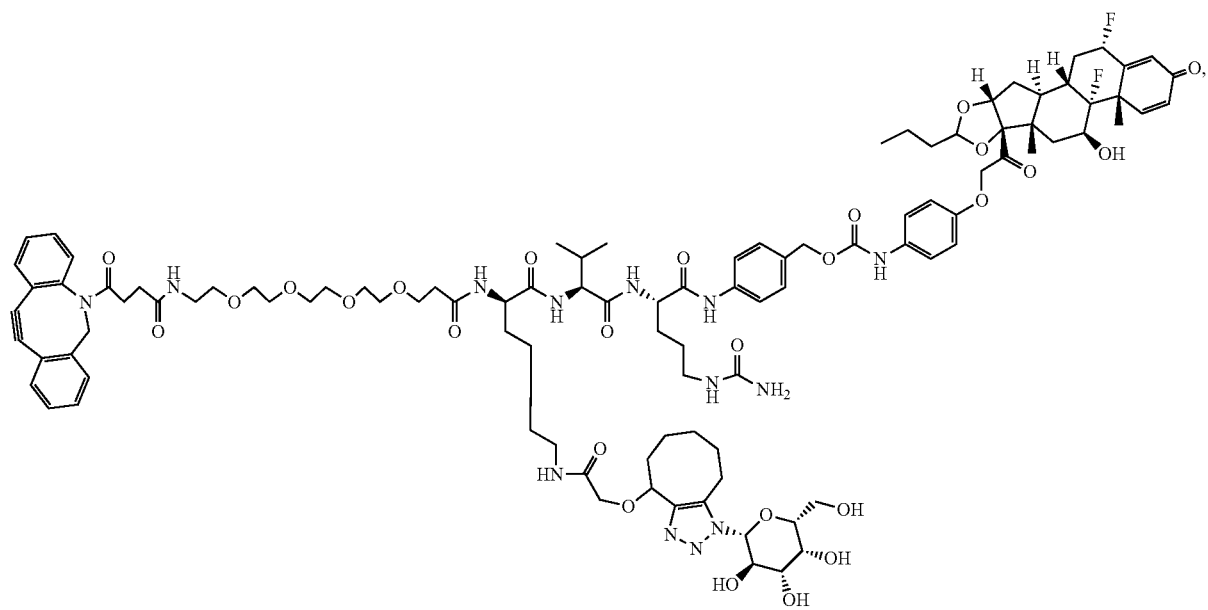
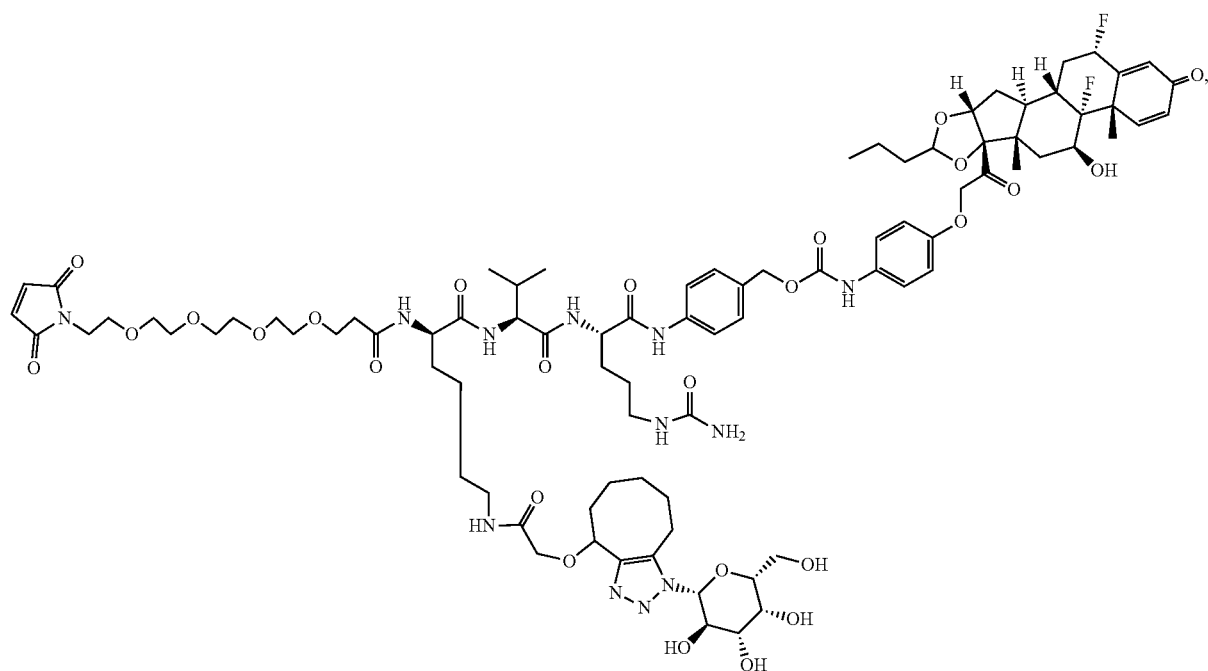

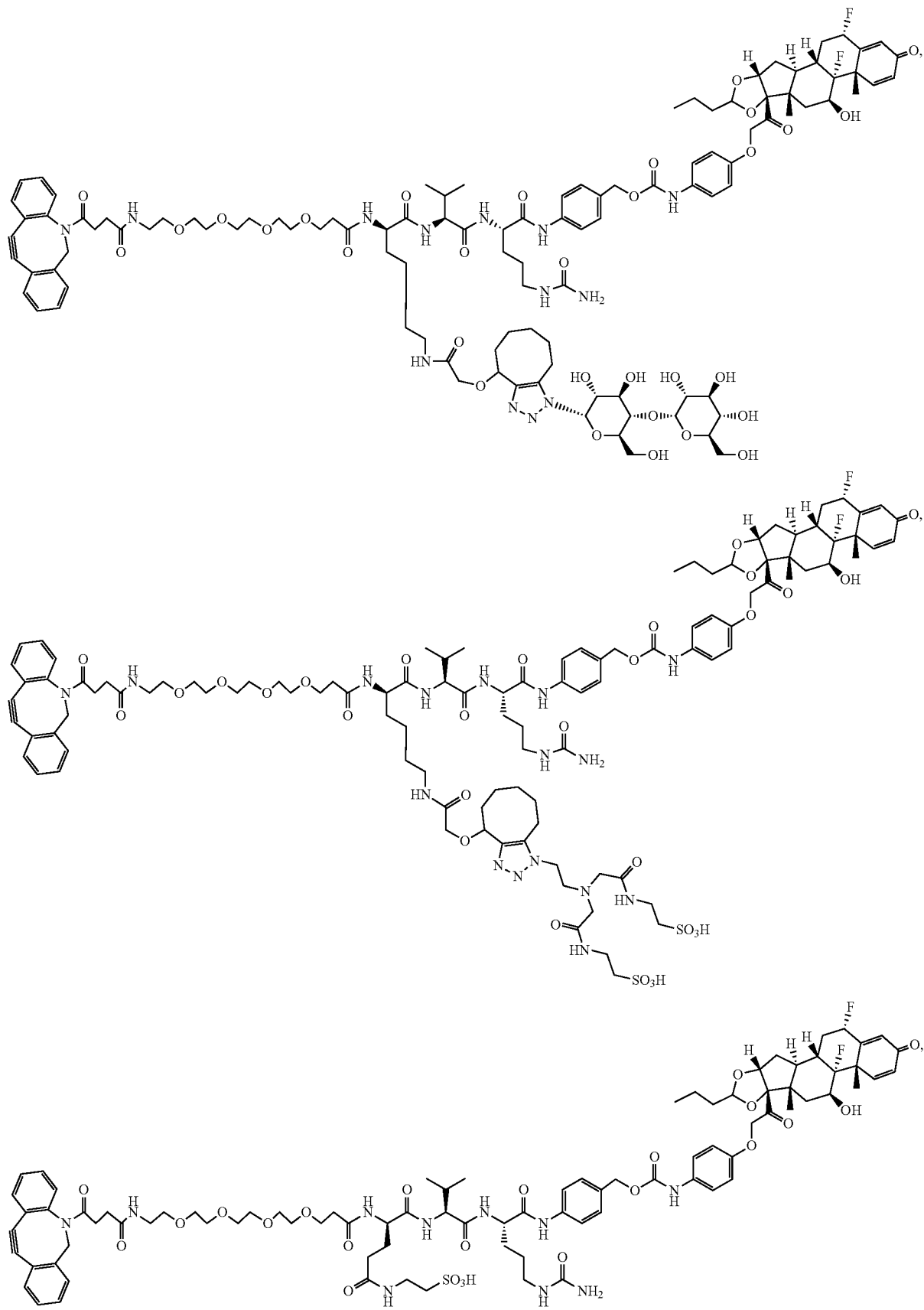

783
784
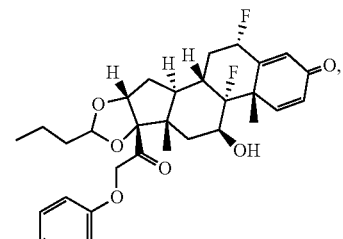
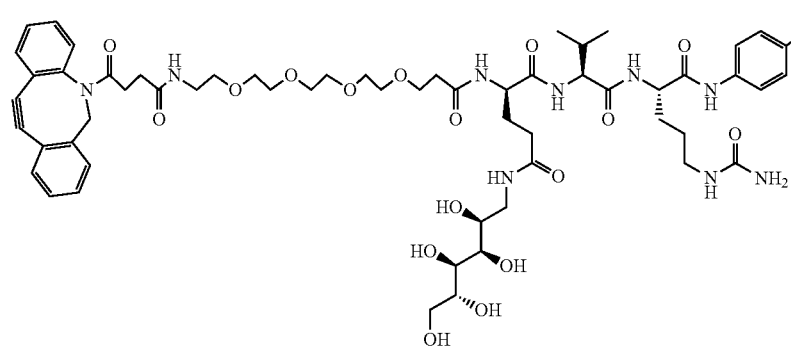
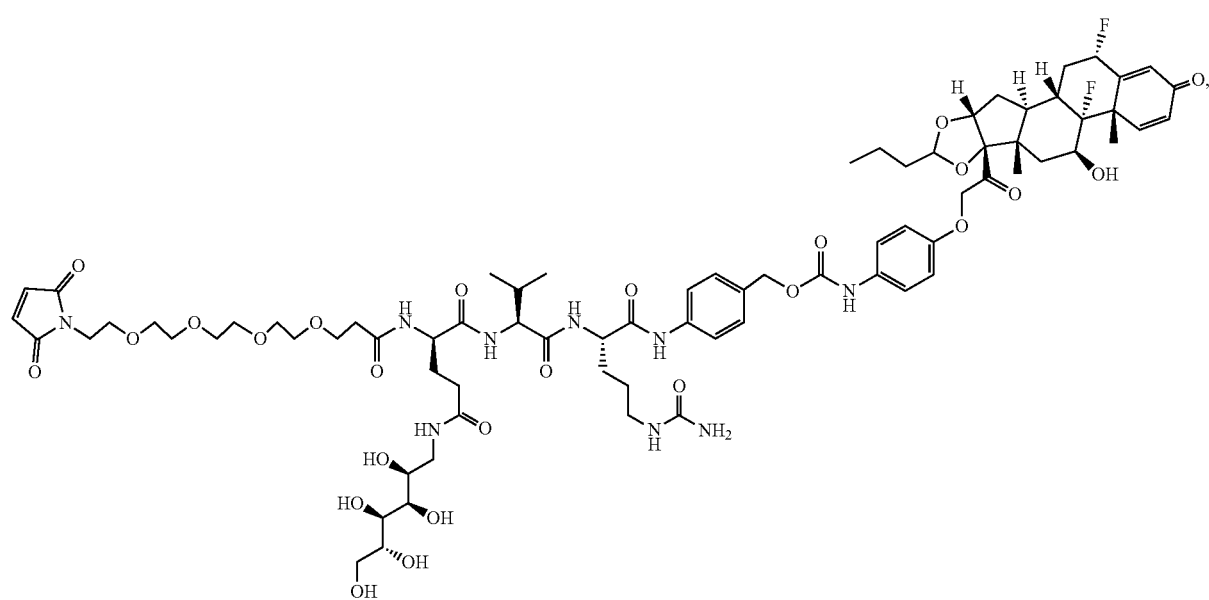

785
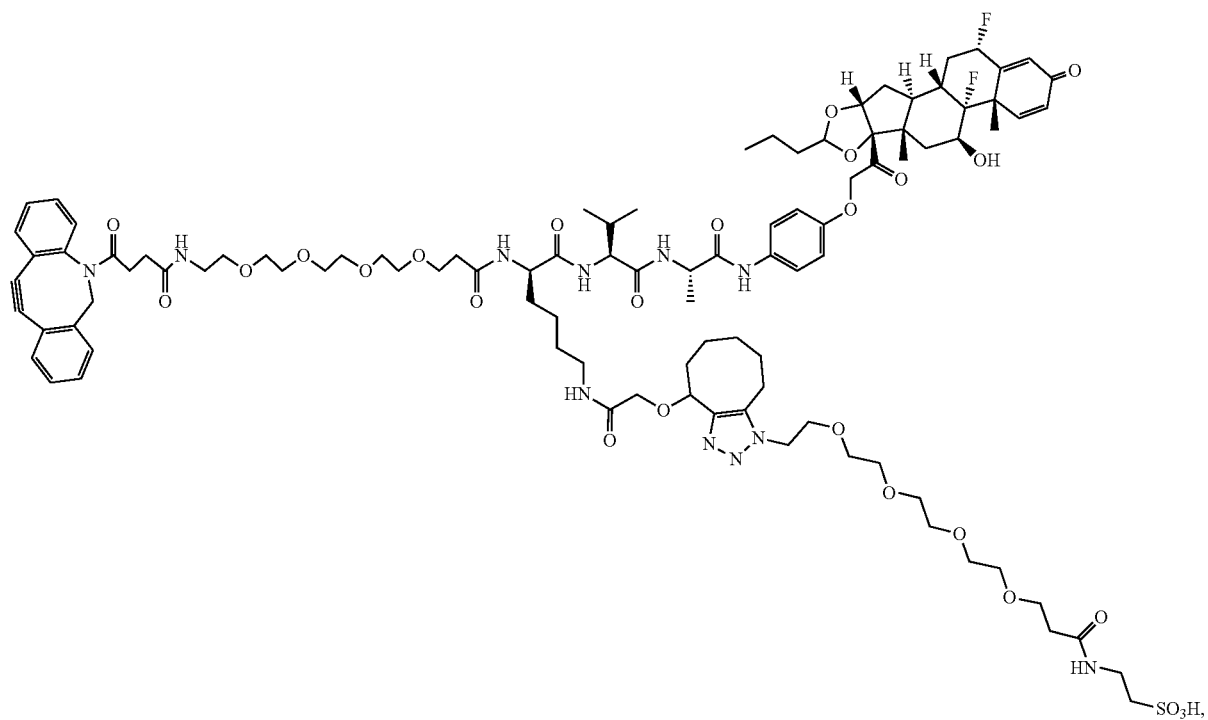
786
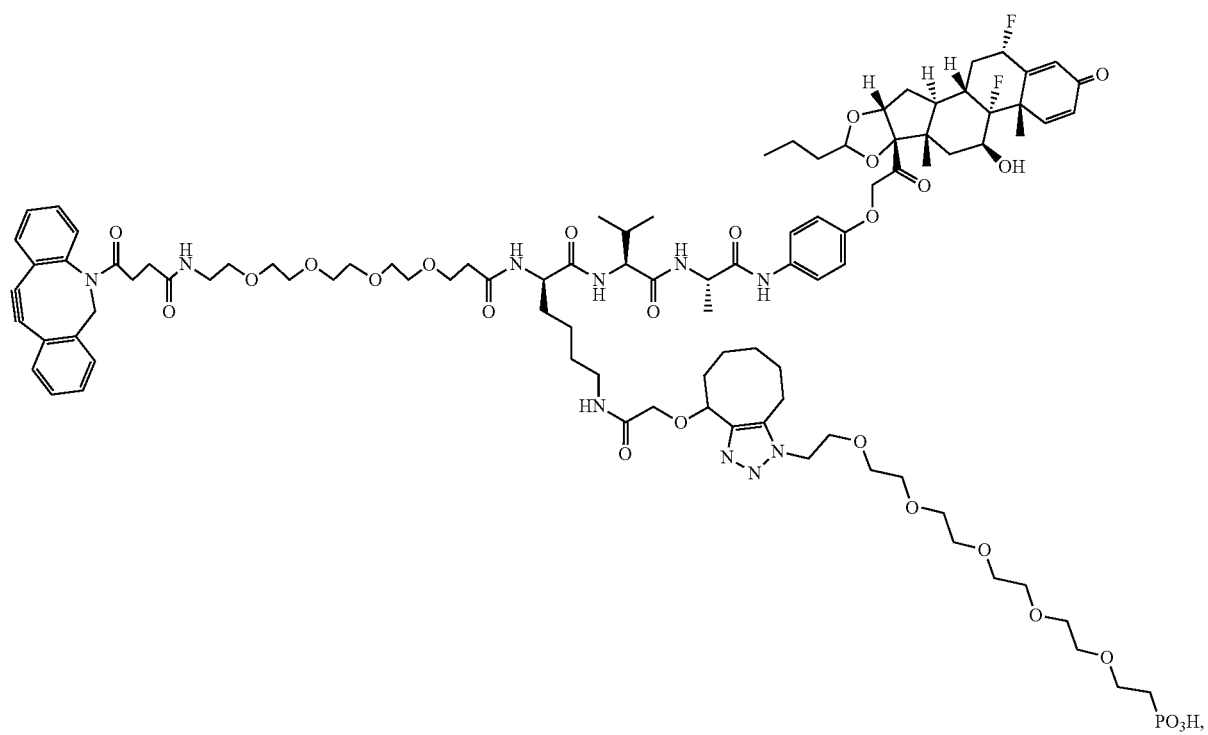

787
788
-continued
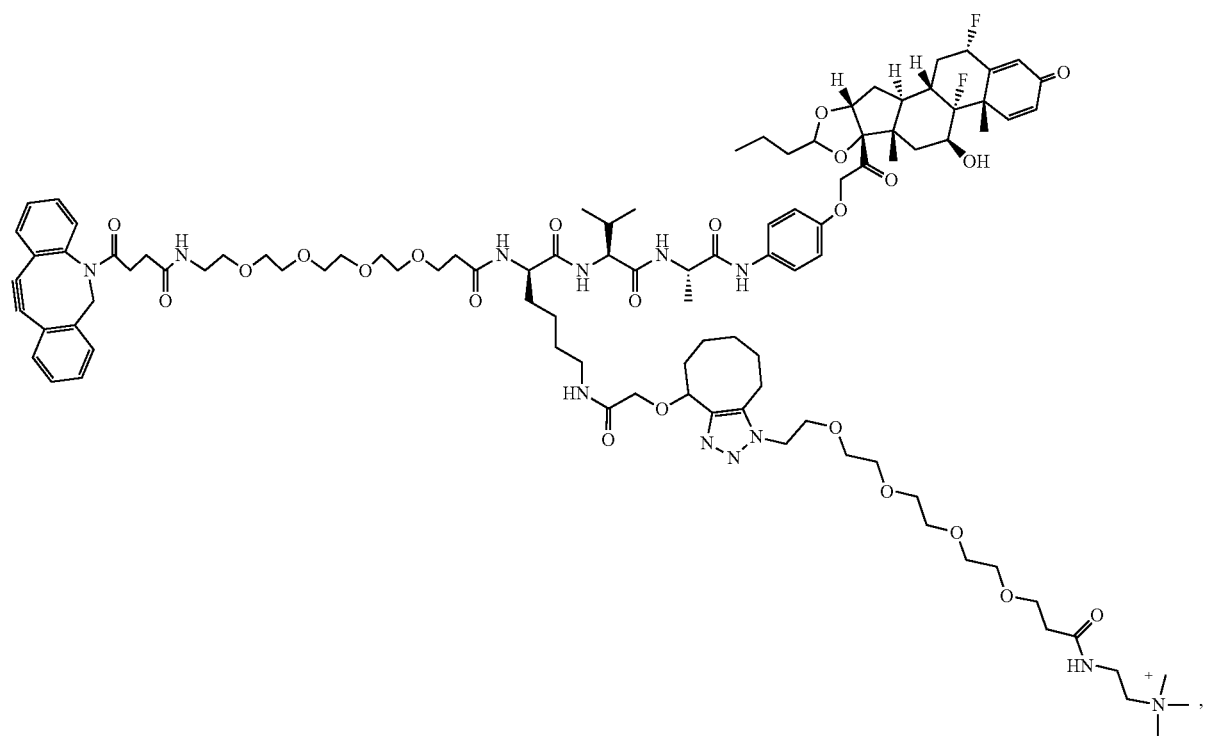
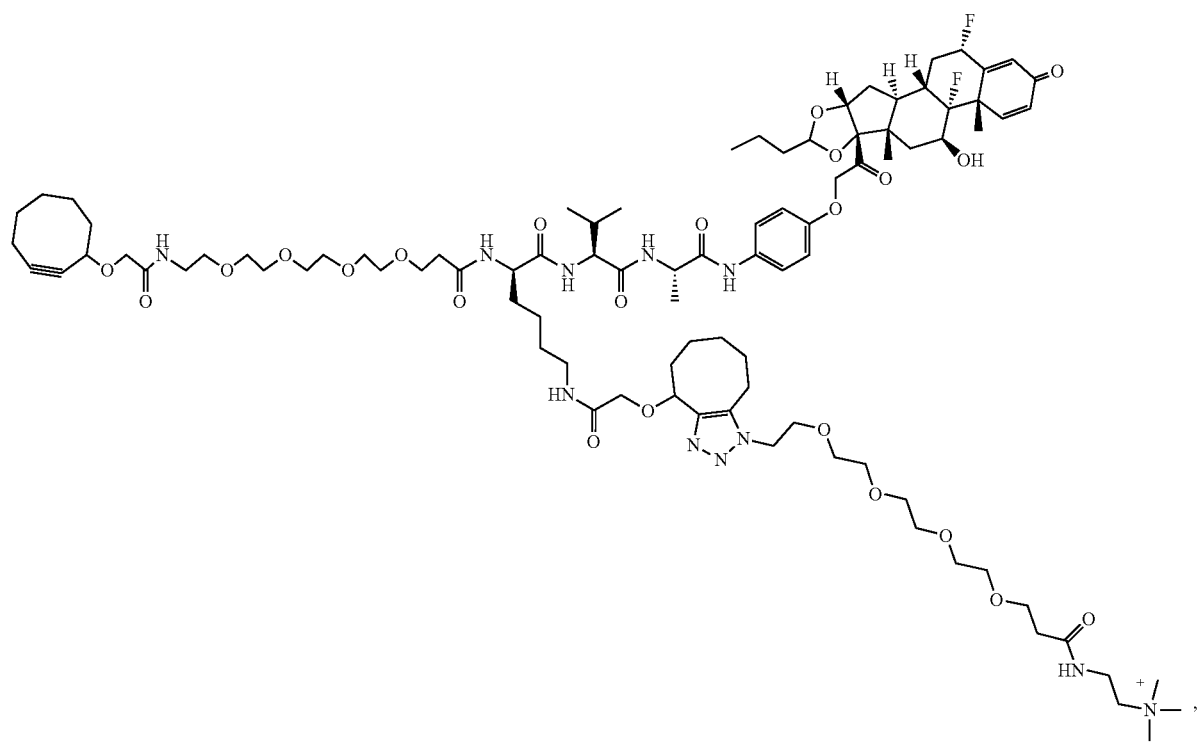

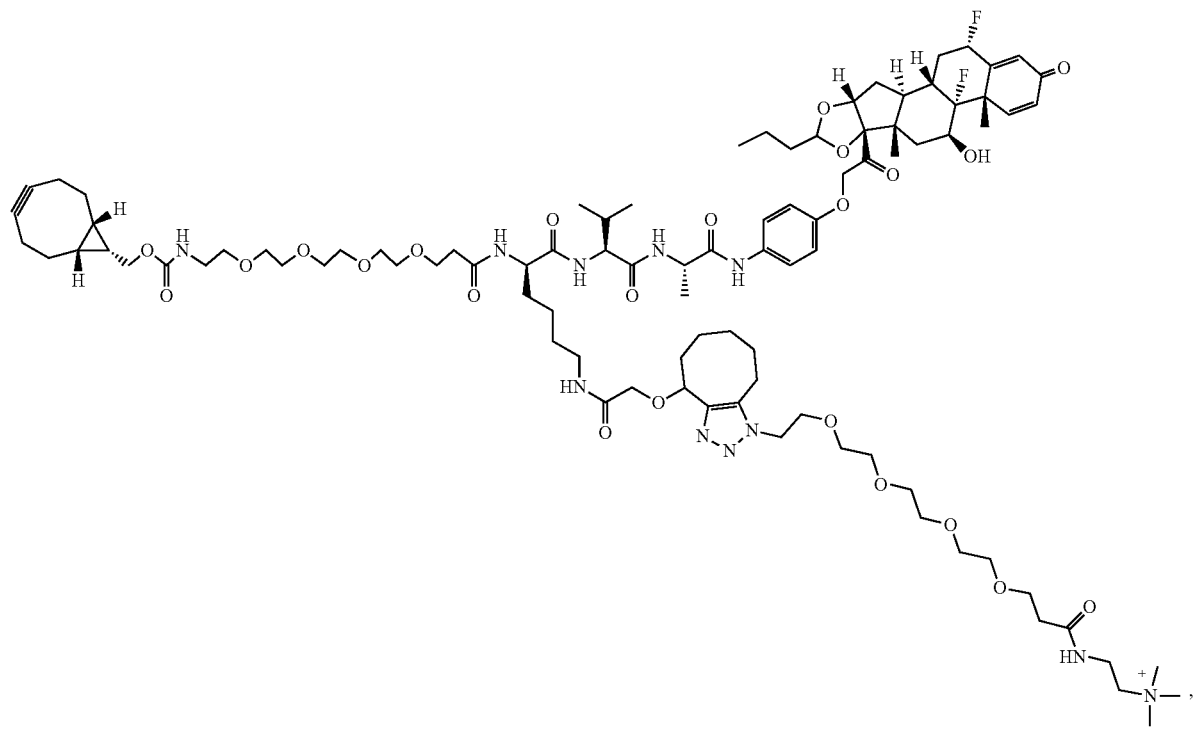
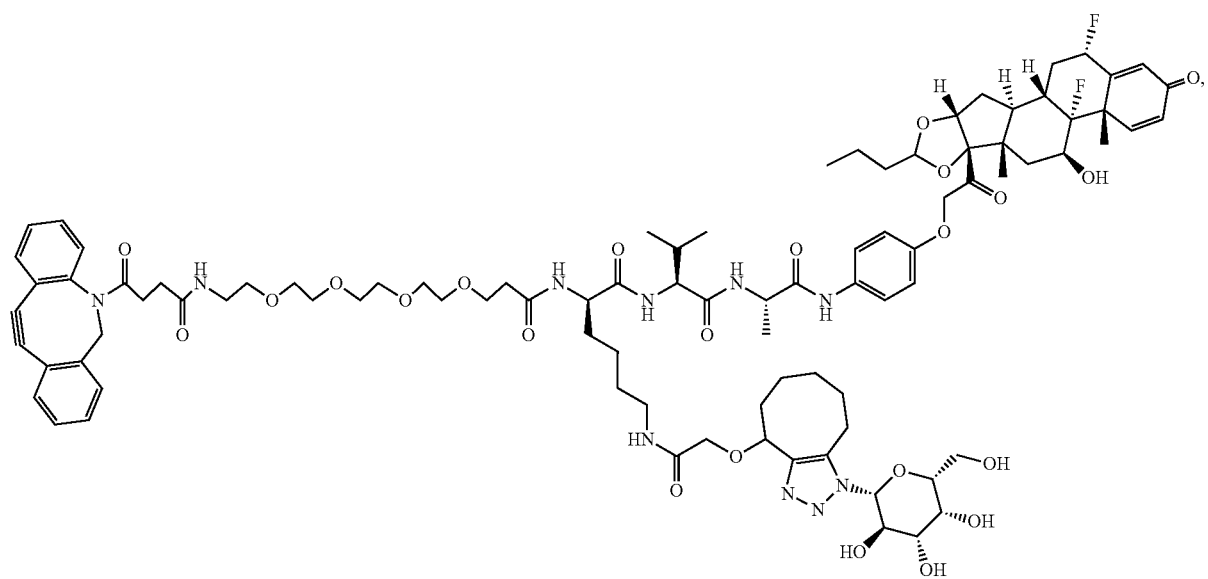

791
792
-continued
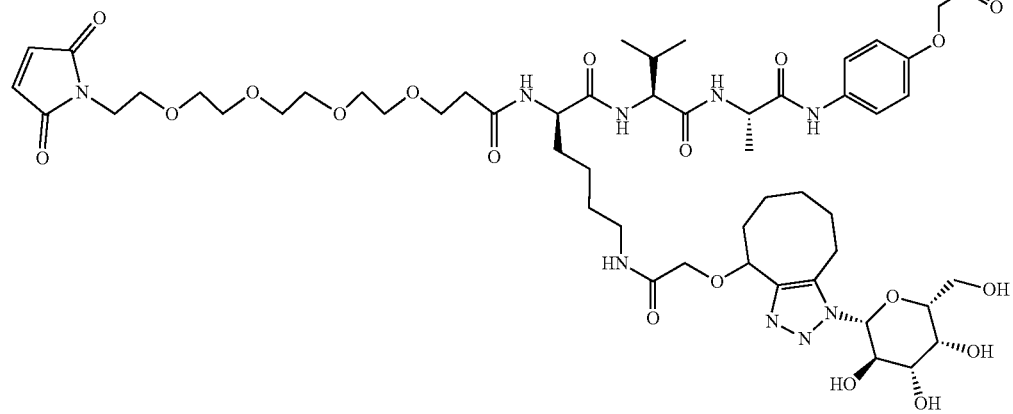
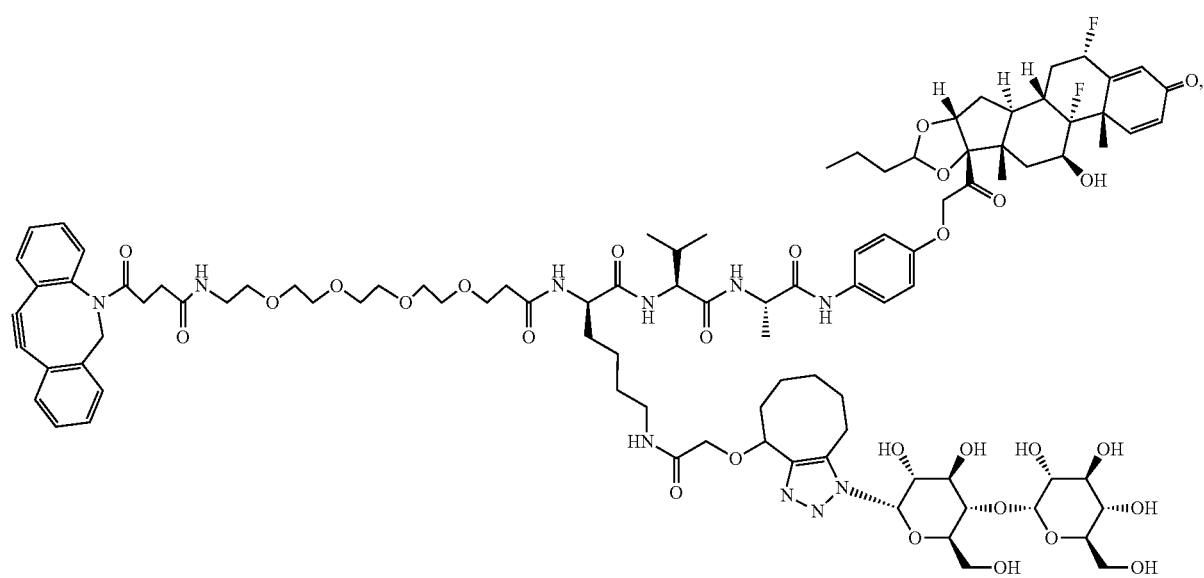

793 794
-continued
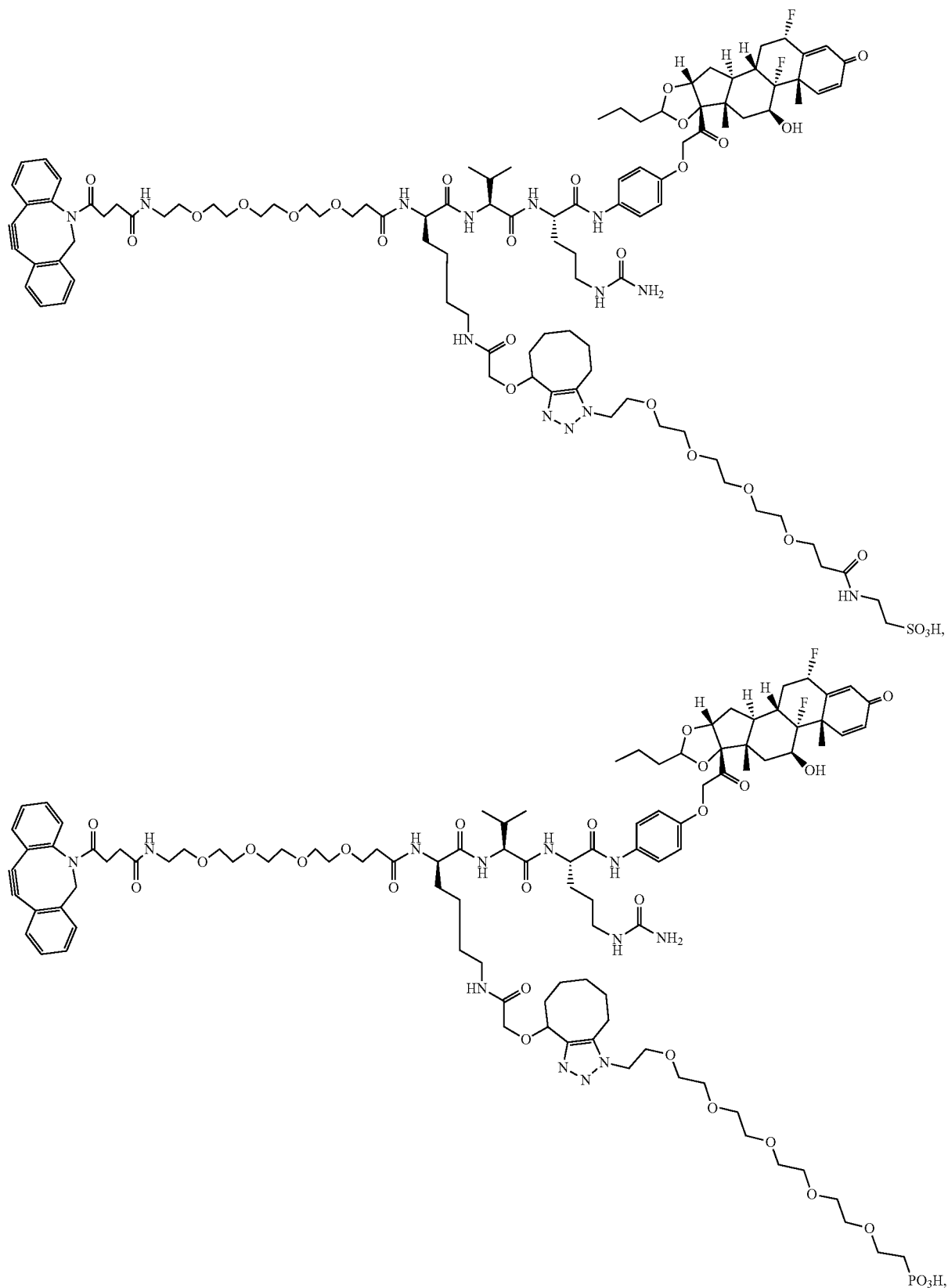

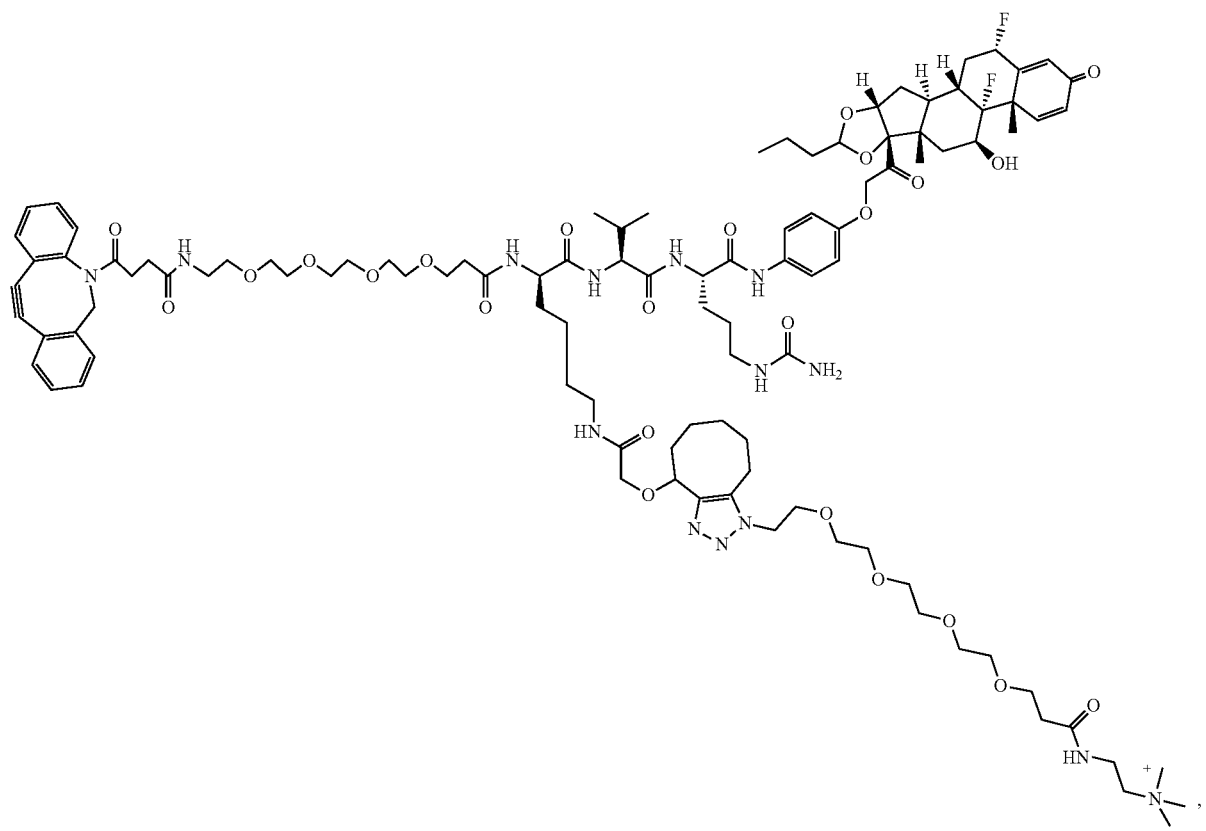
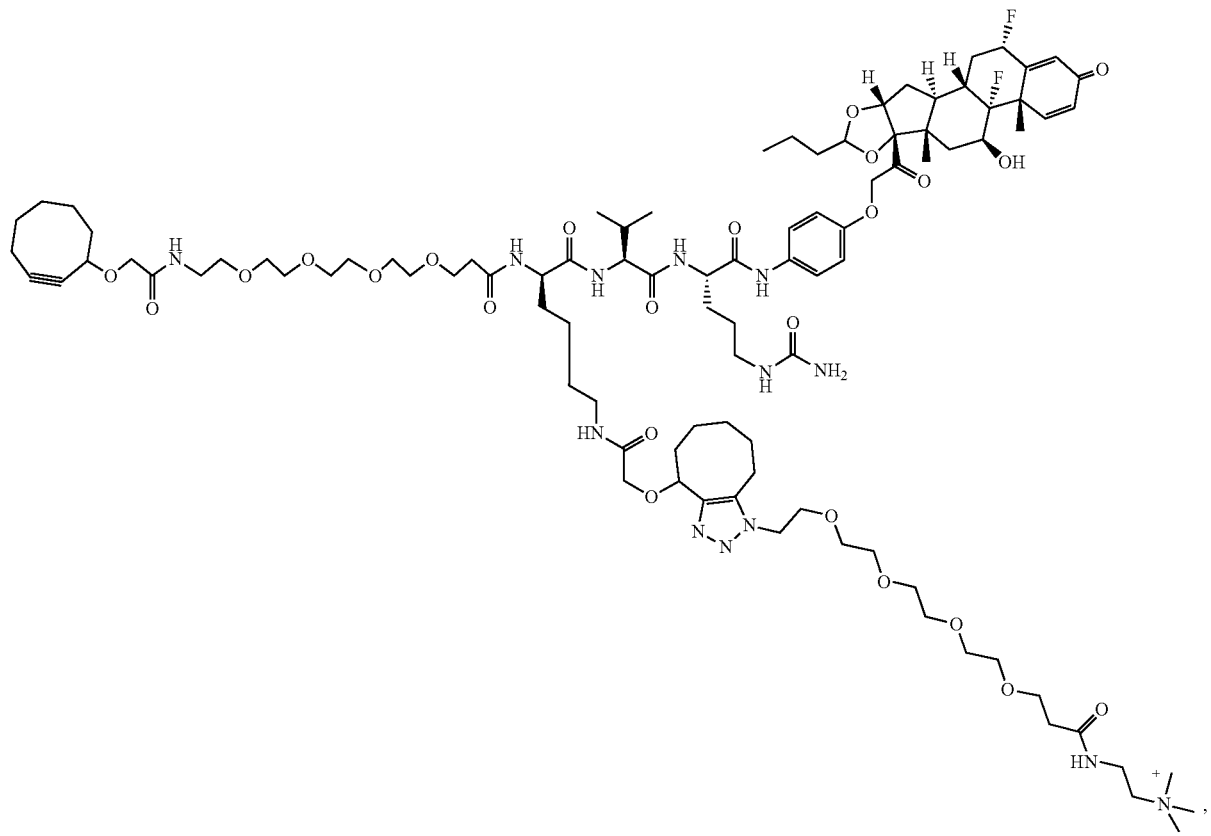

797
798
-continued
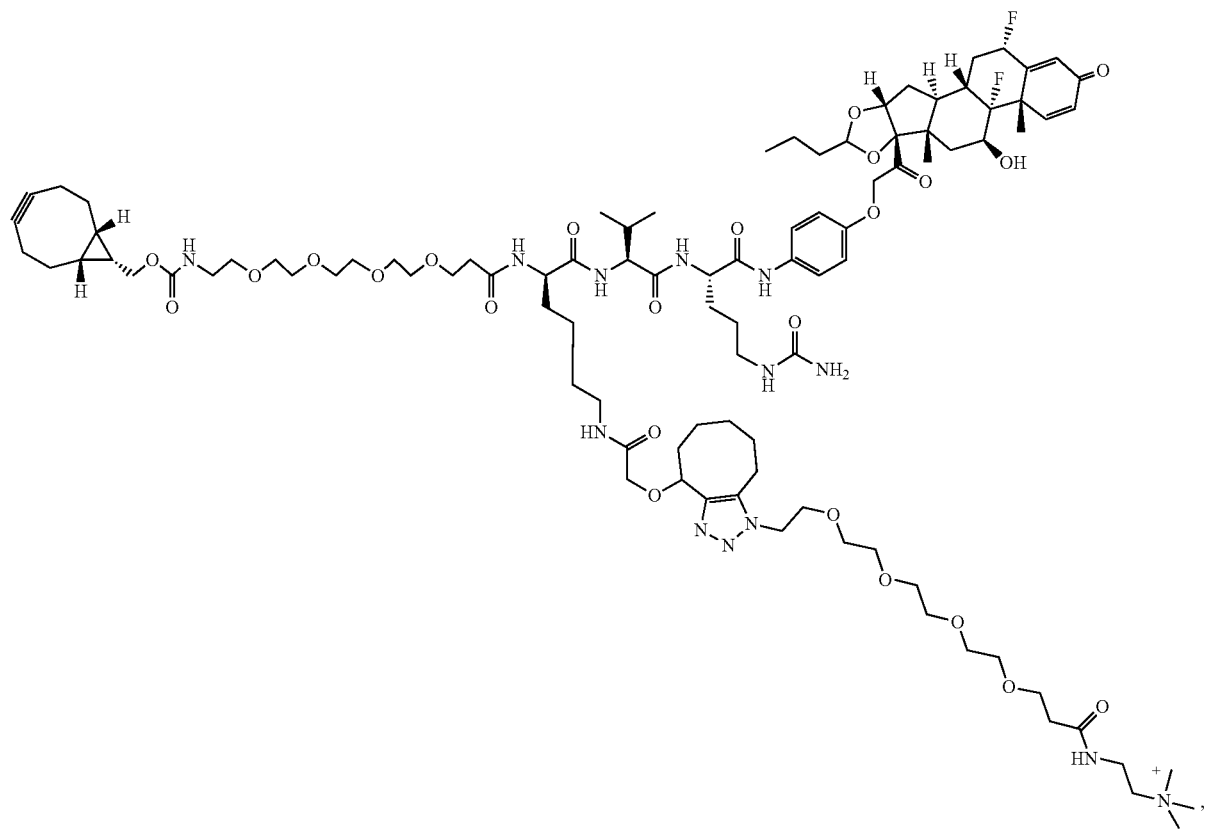
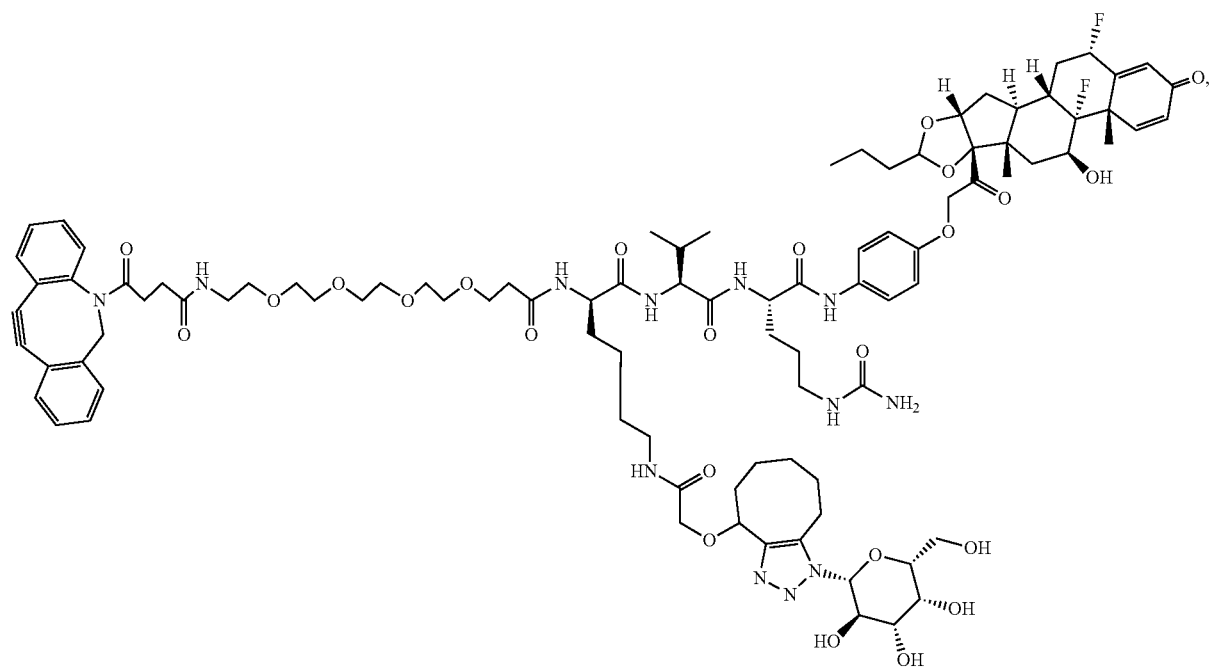

799
800
-continued
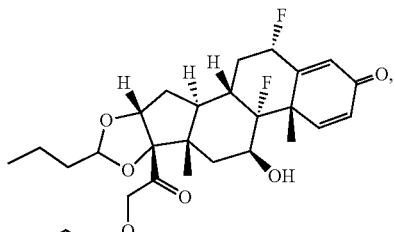
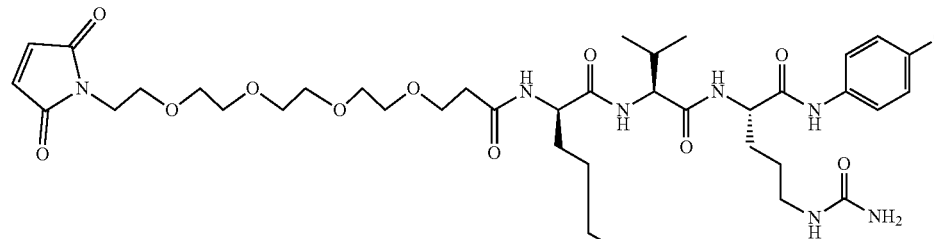
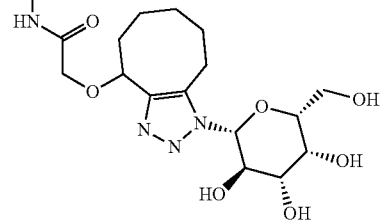
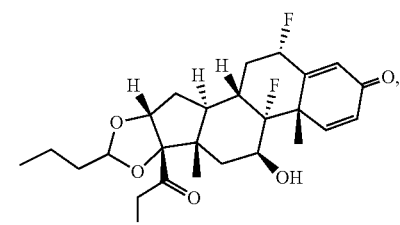
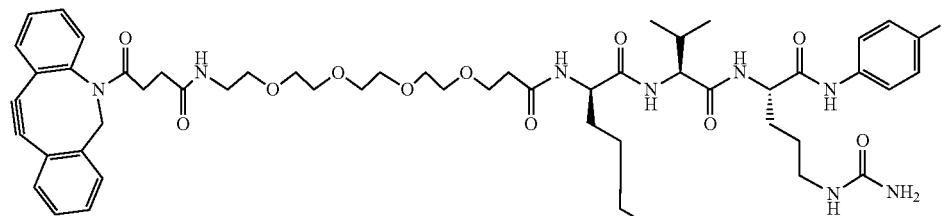
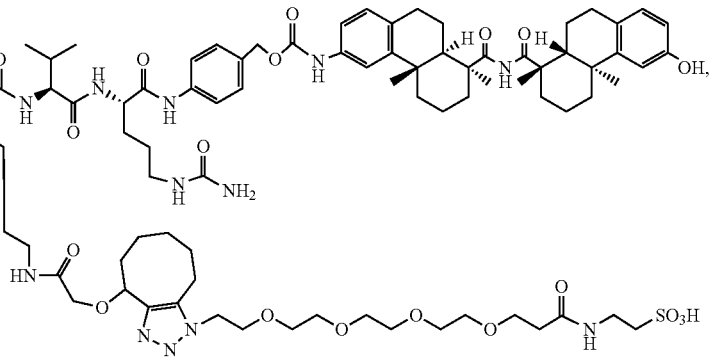
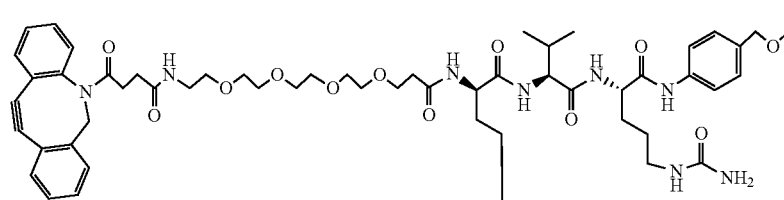

801 802
-continued
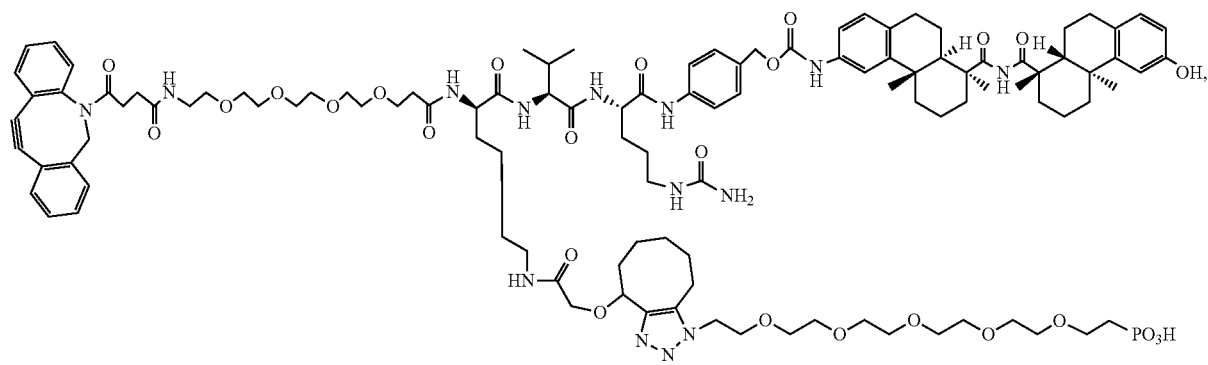
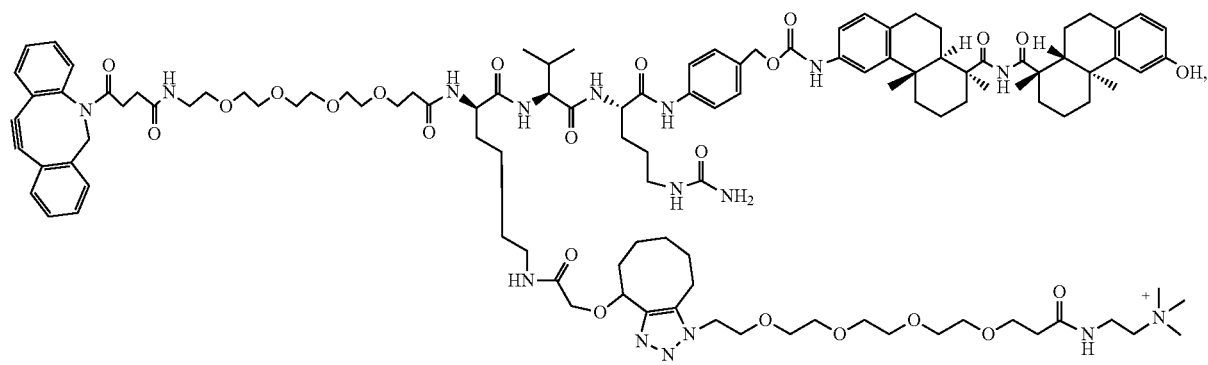
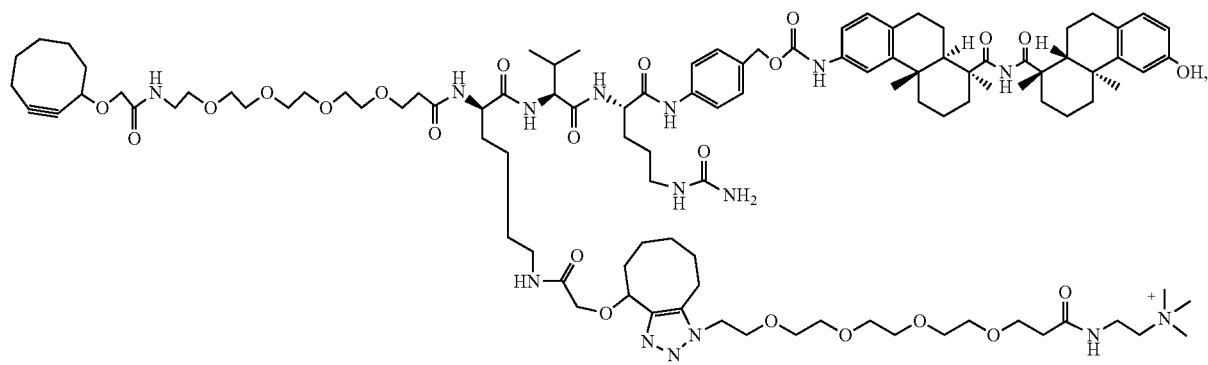
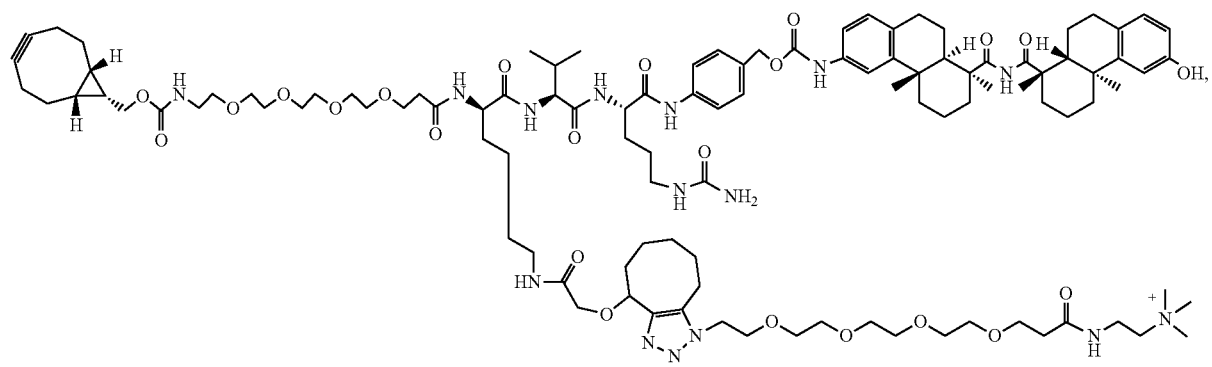

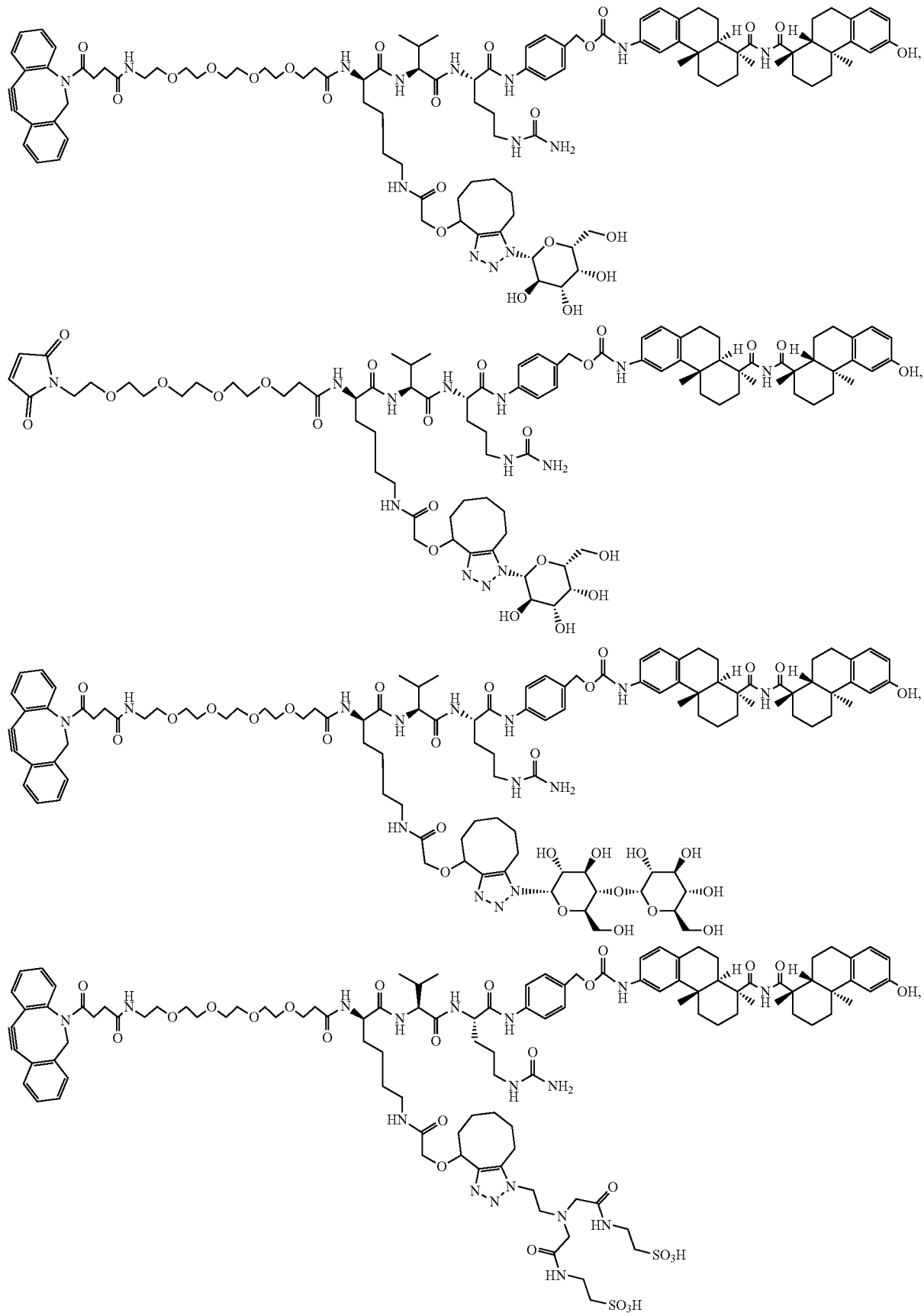

805 806
-continued
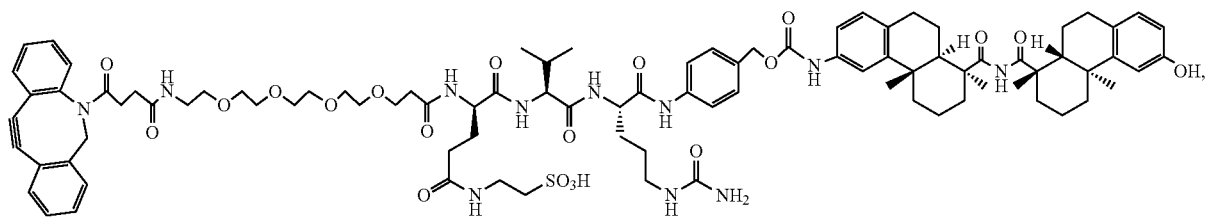
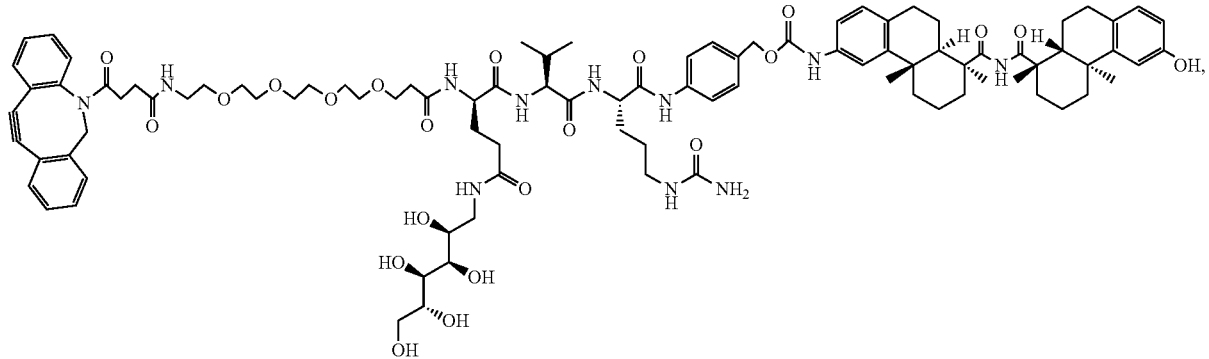
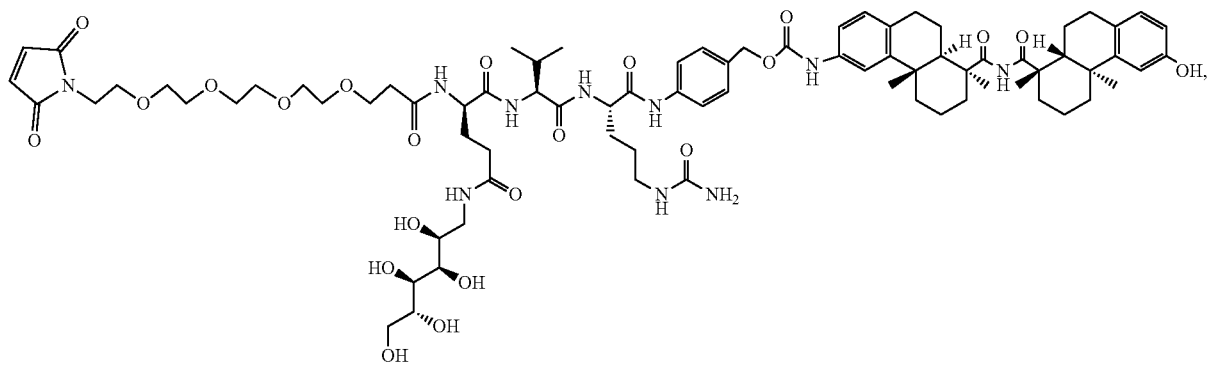
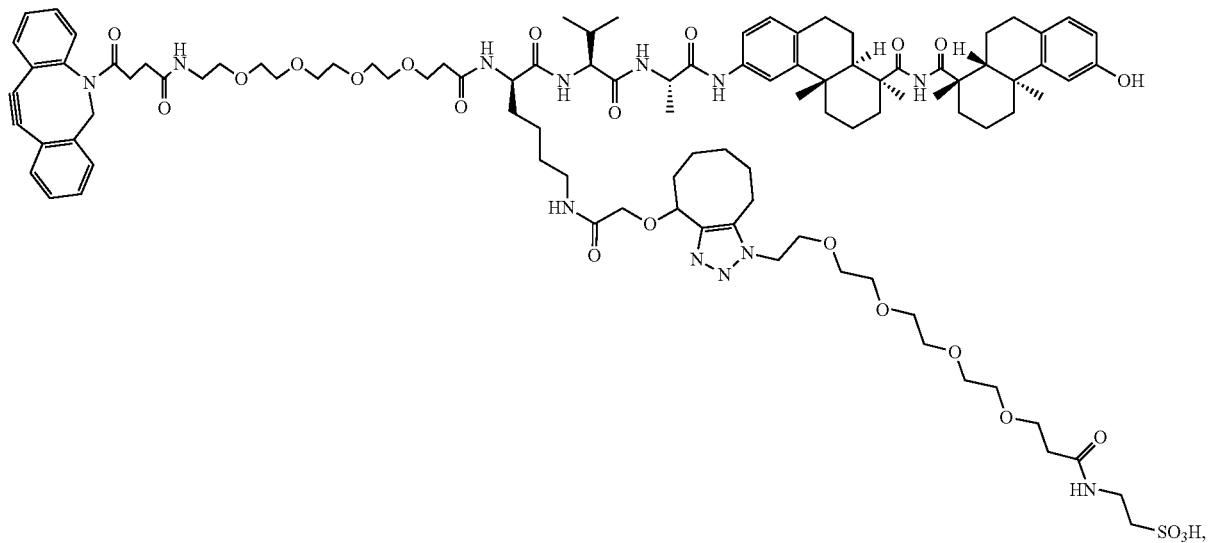

-continued
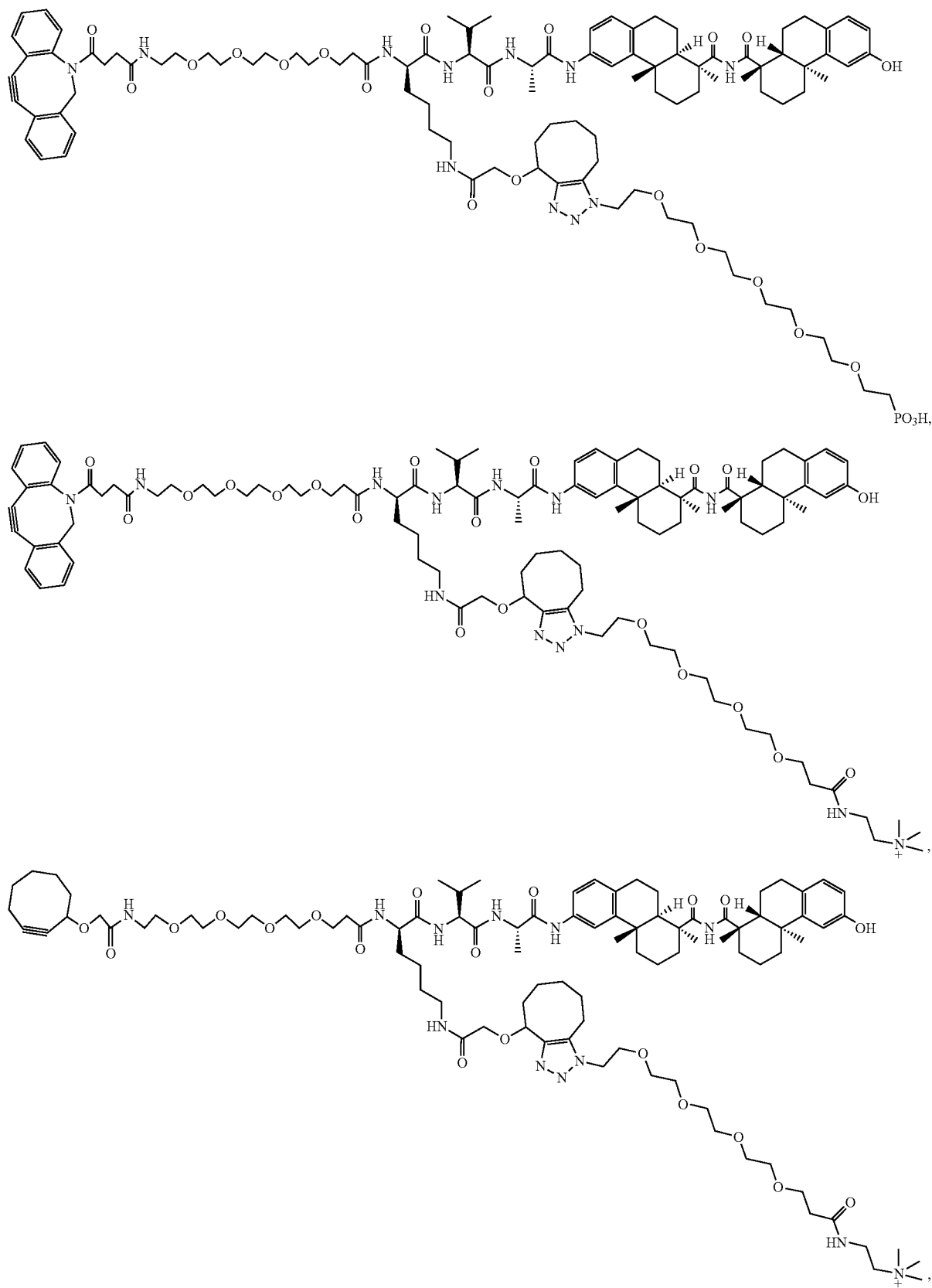

809 810
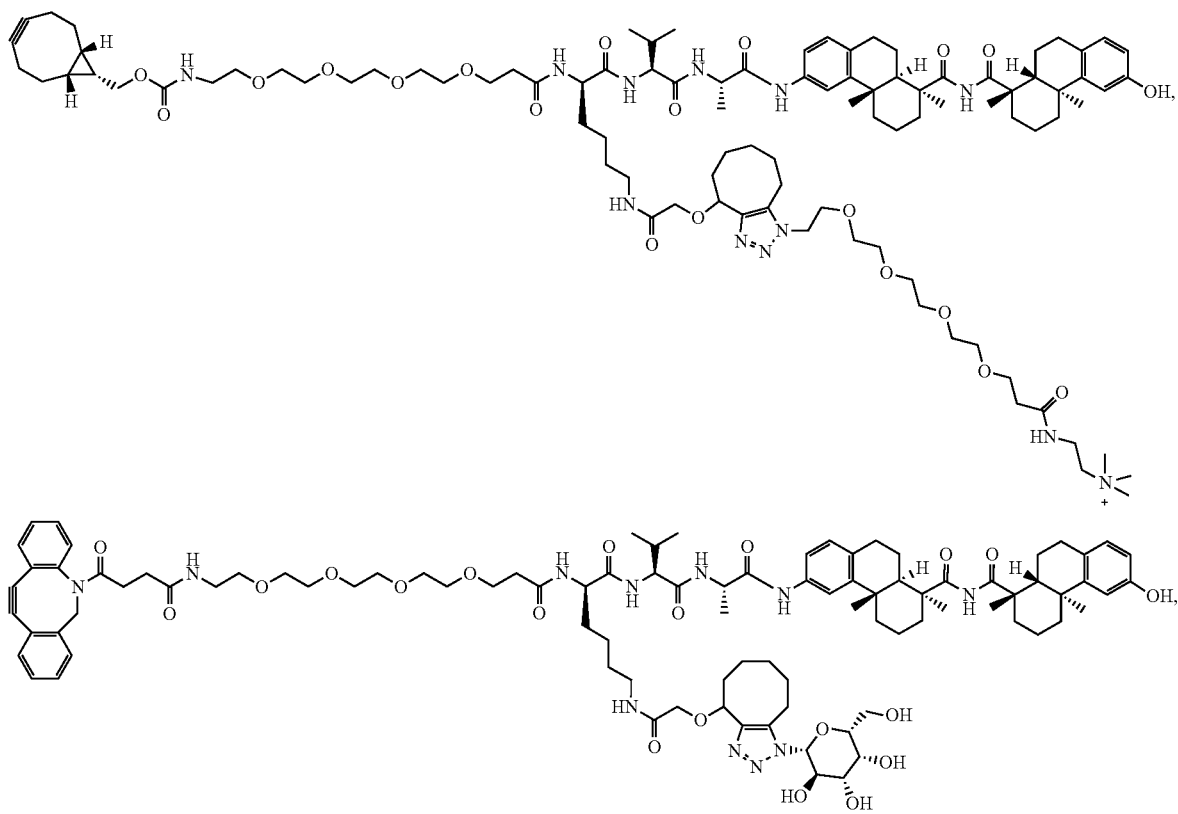
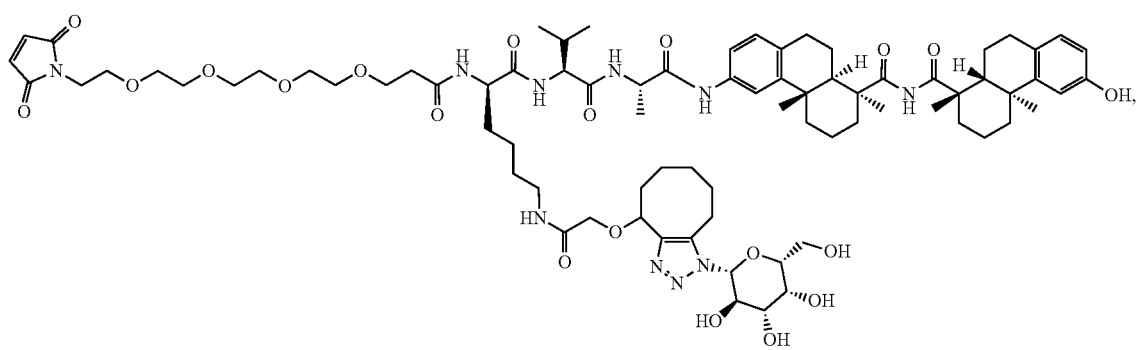
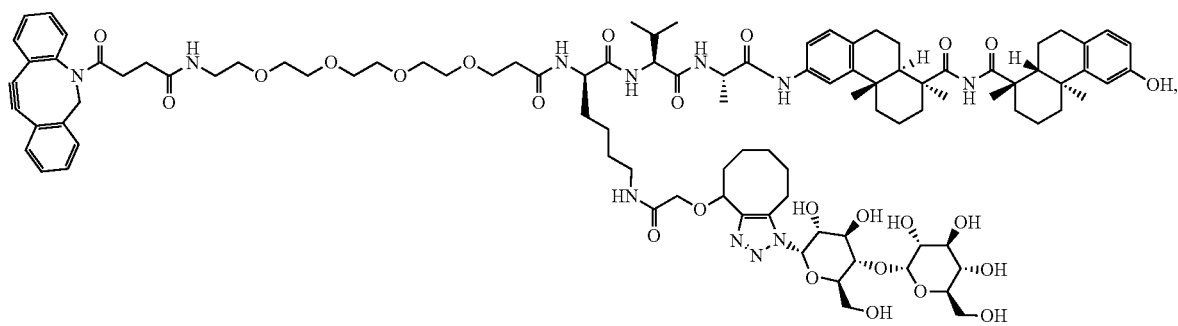

-continued
811
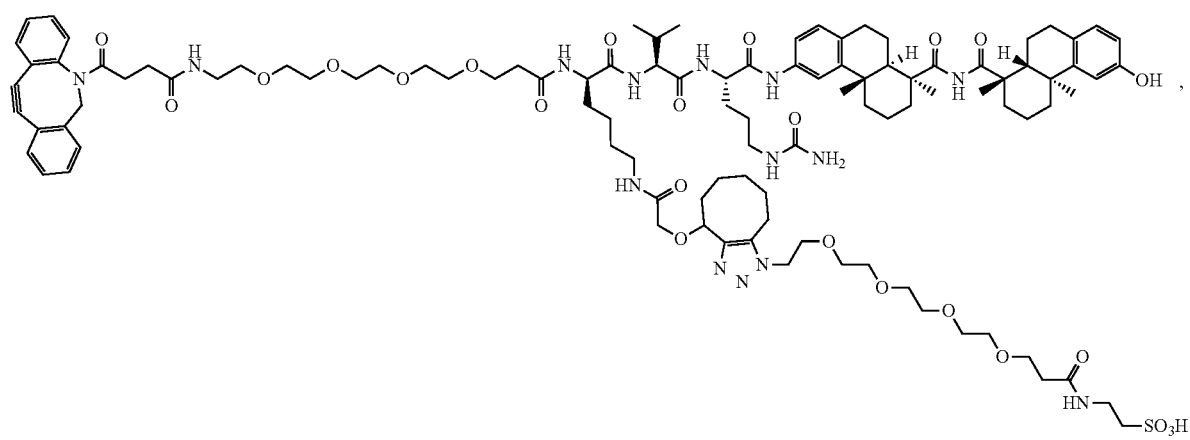
812
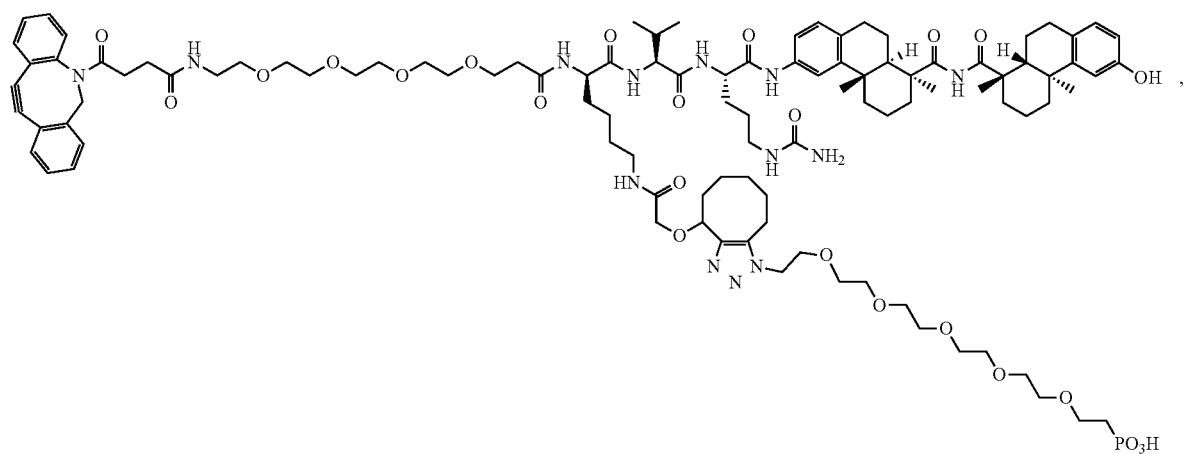
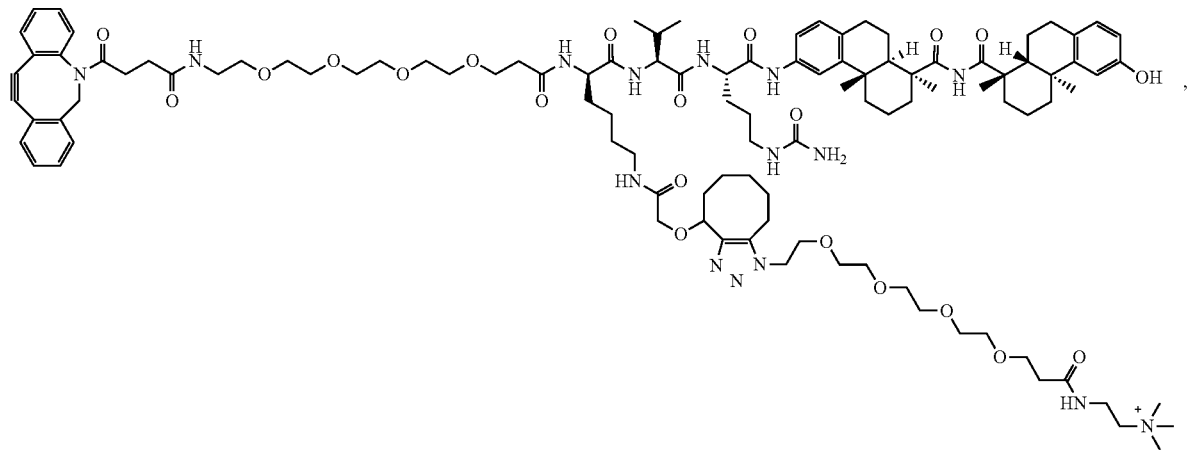

813 814
-continued
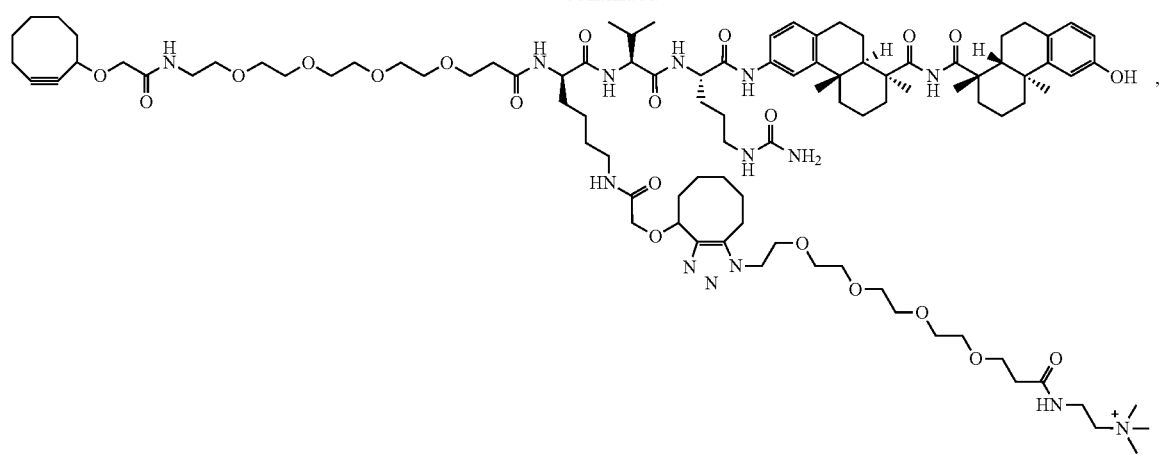
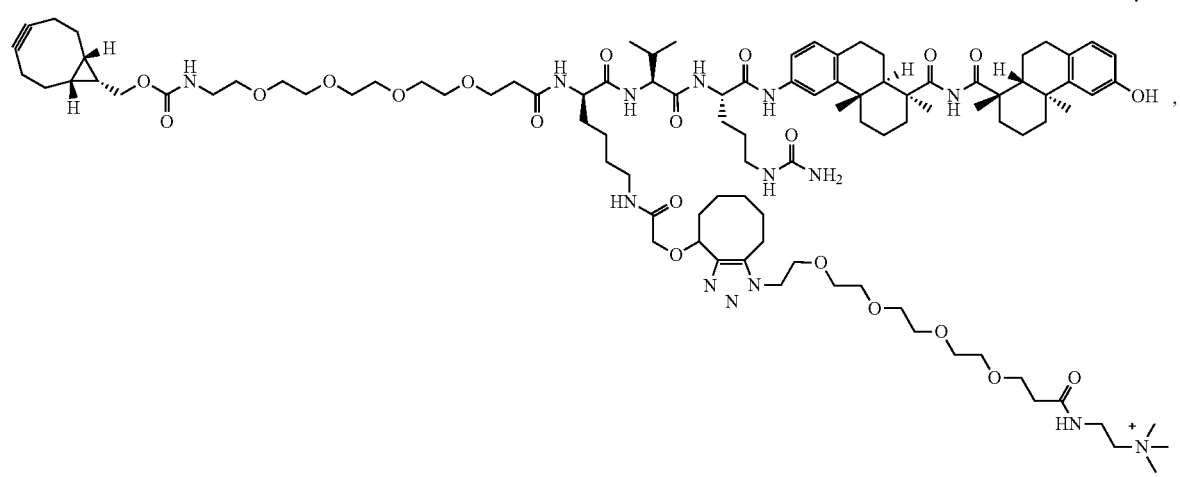
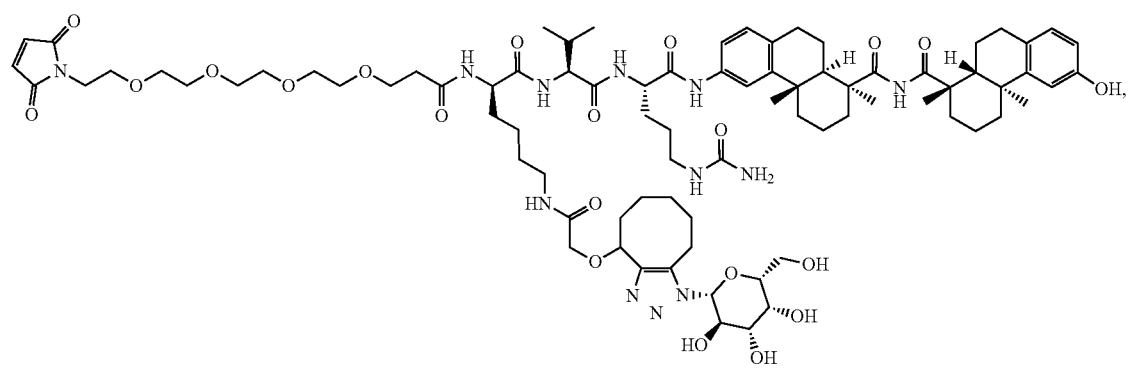

-continued
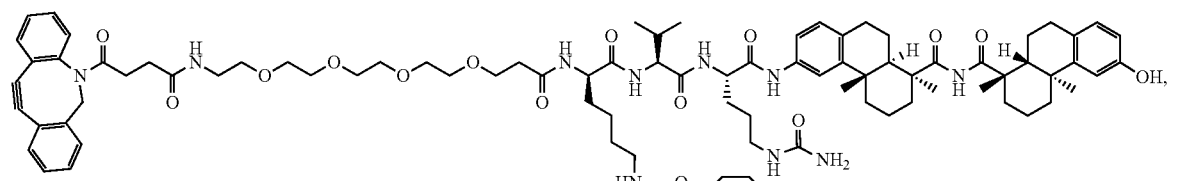
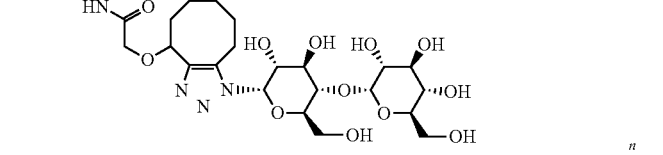
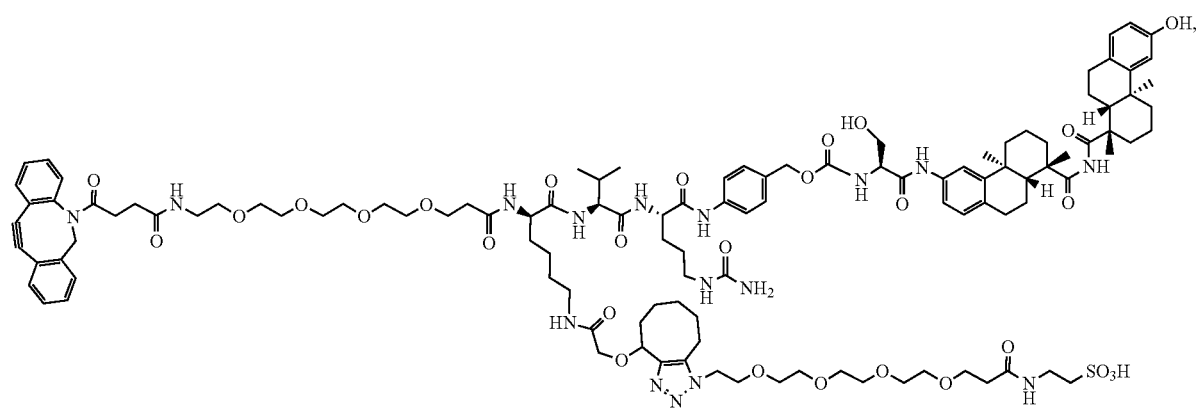
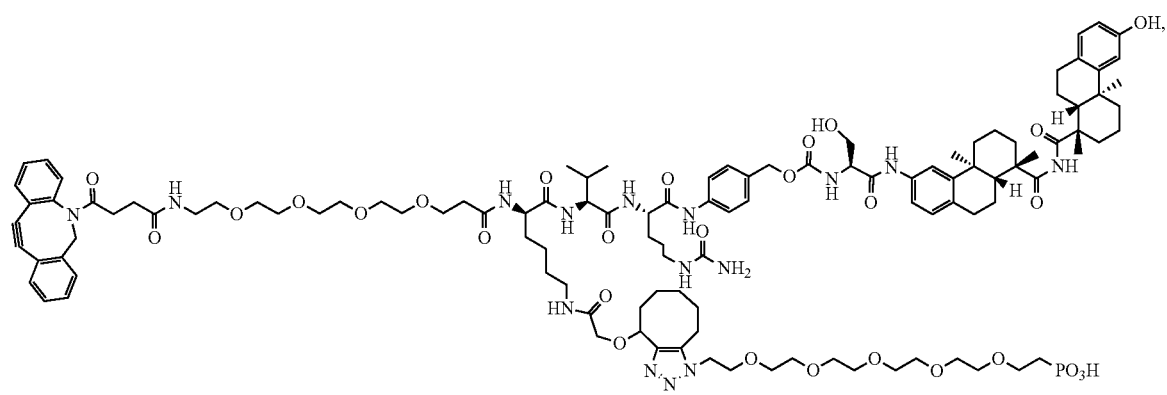
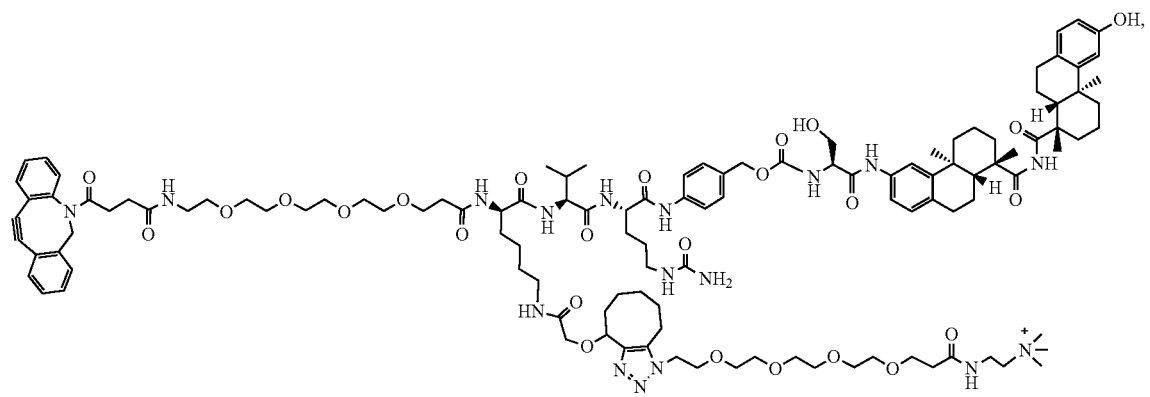

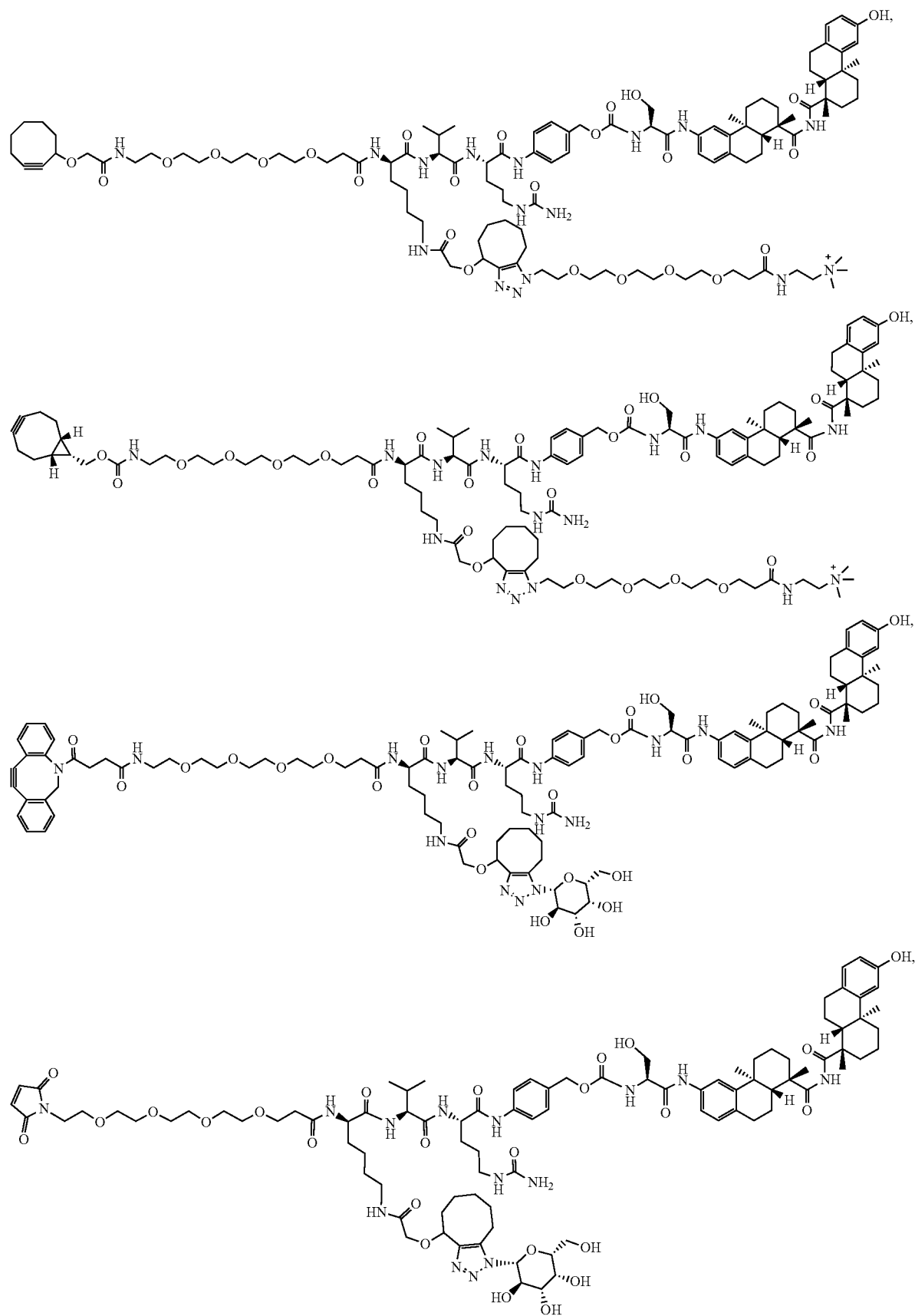

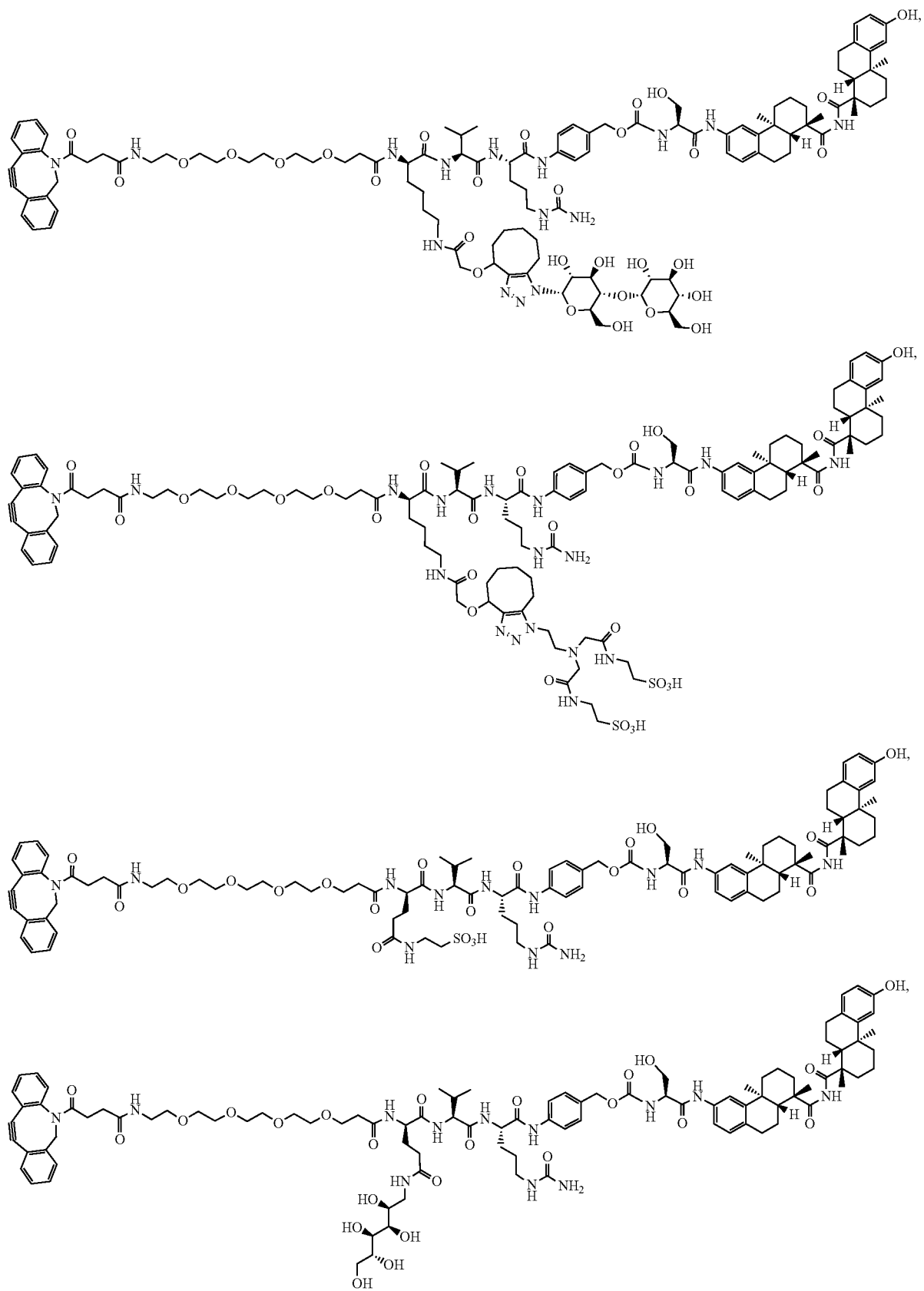

821 822
-continued
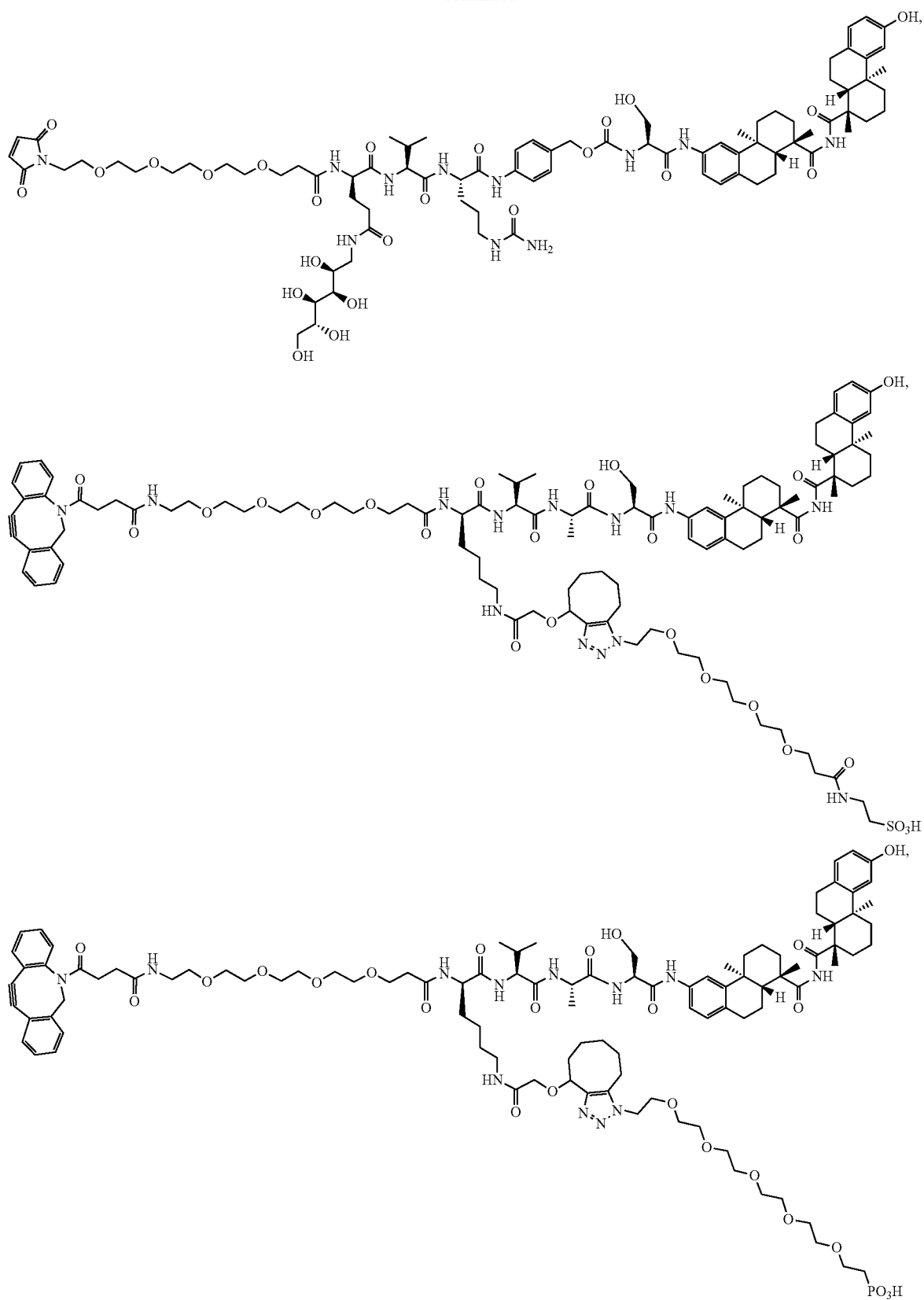

823
824
-continued
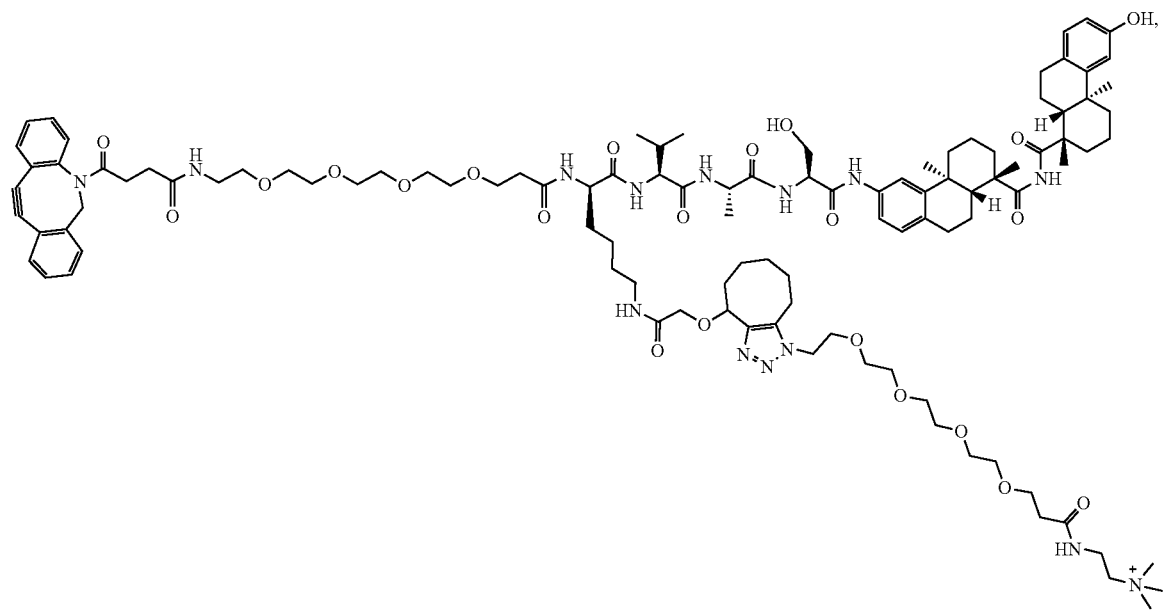
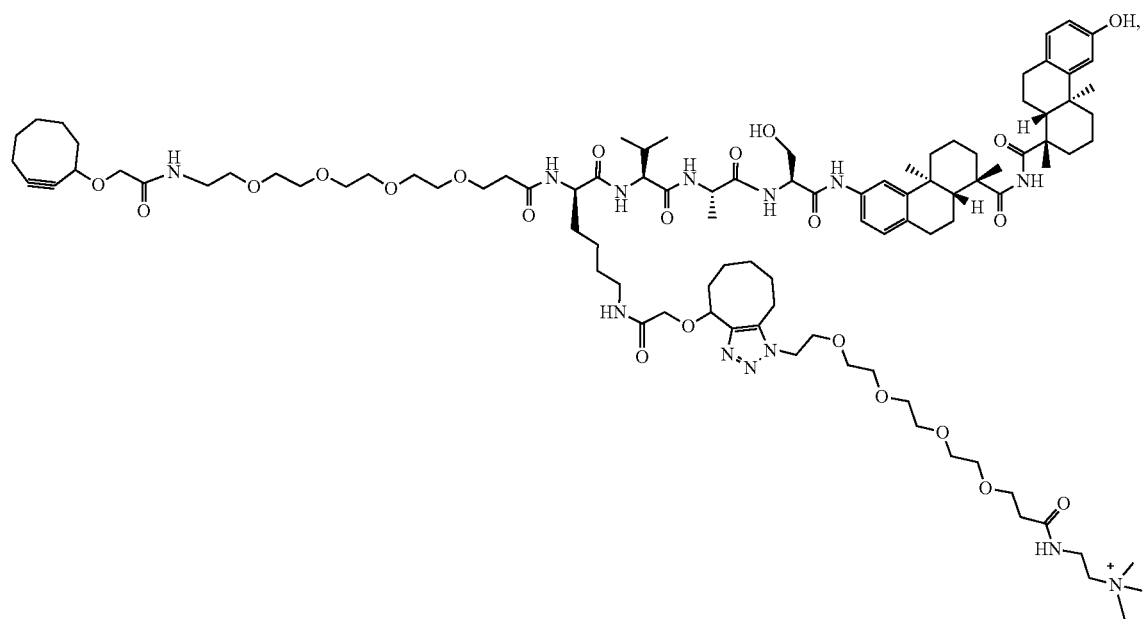

825
826
-continued
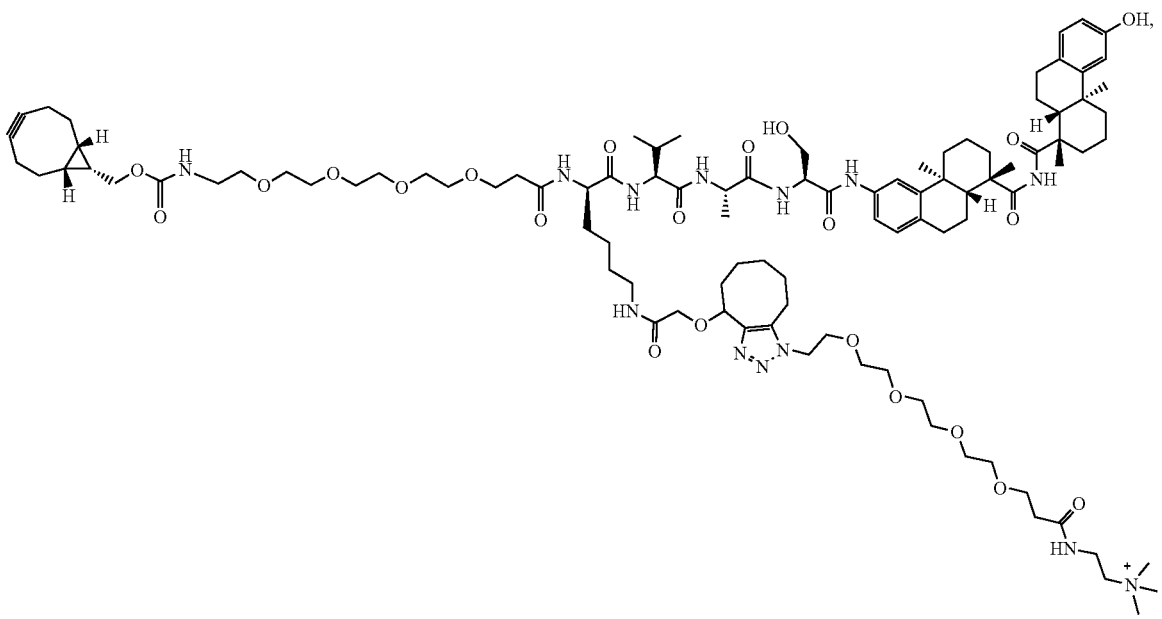
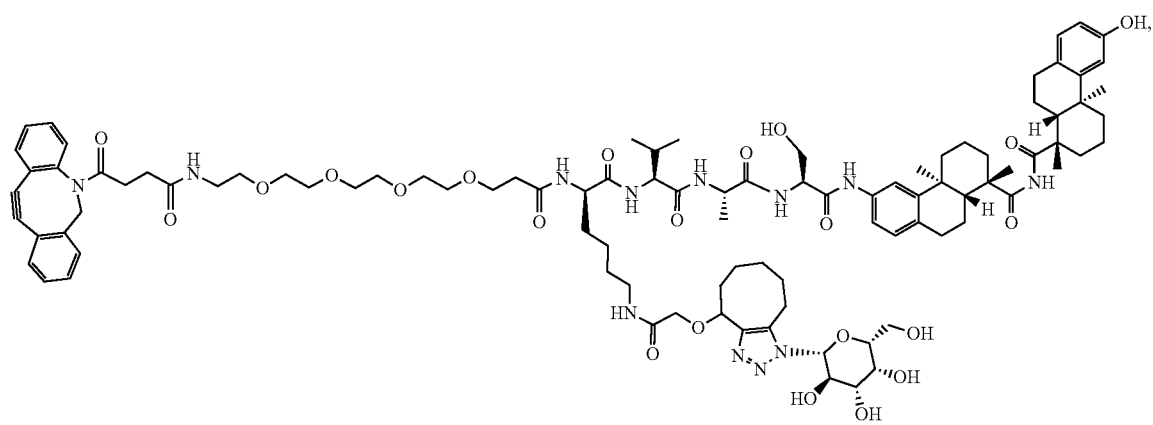
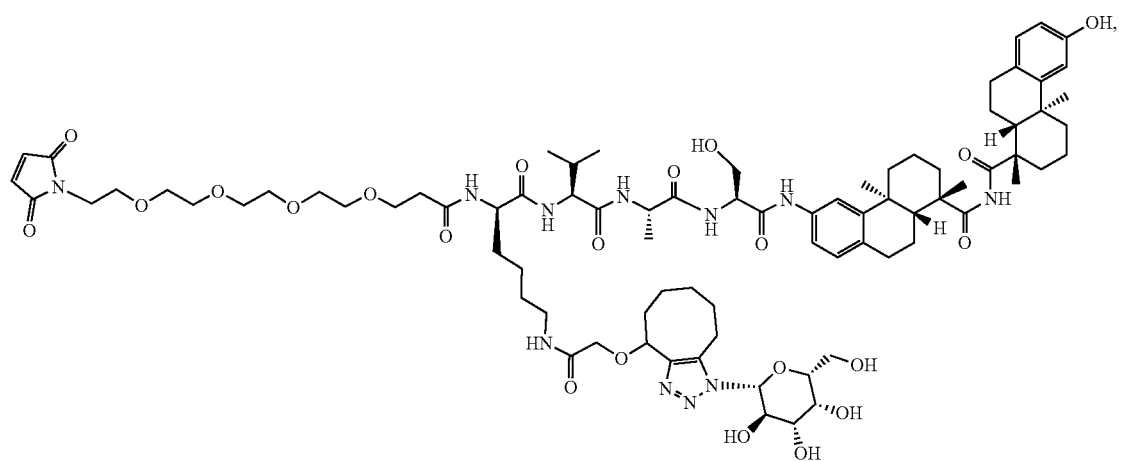

827 828
-continued
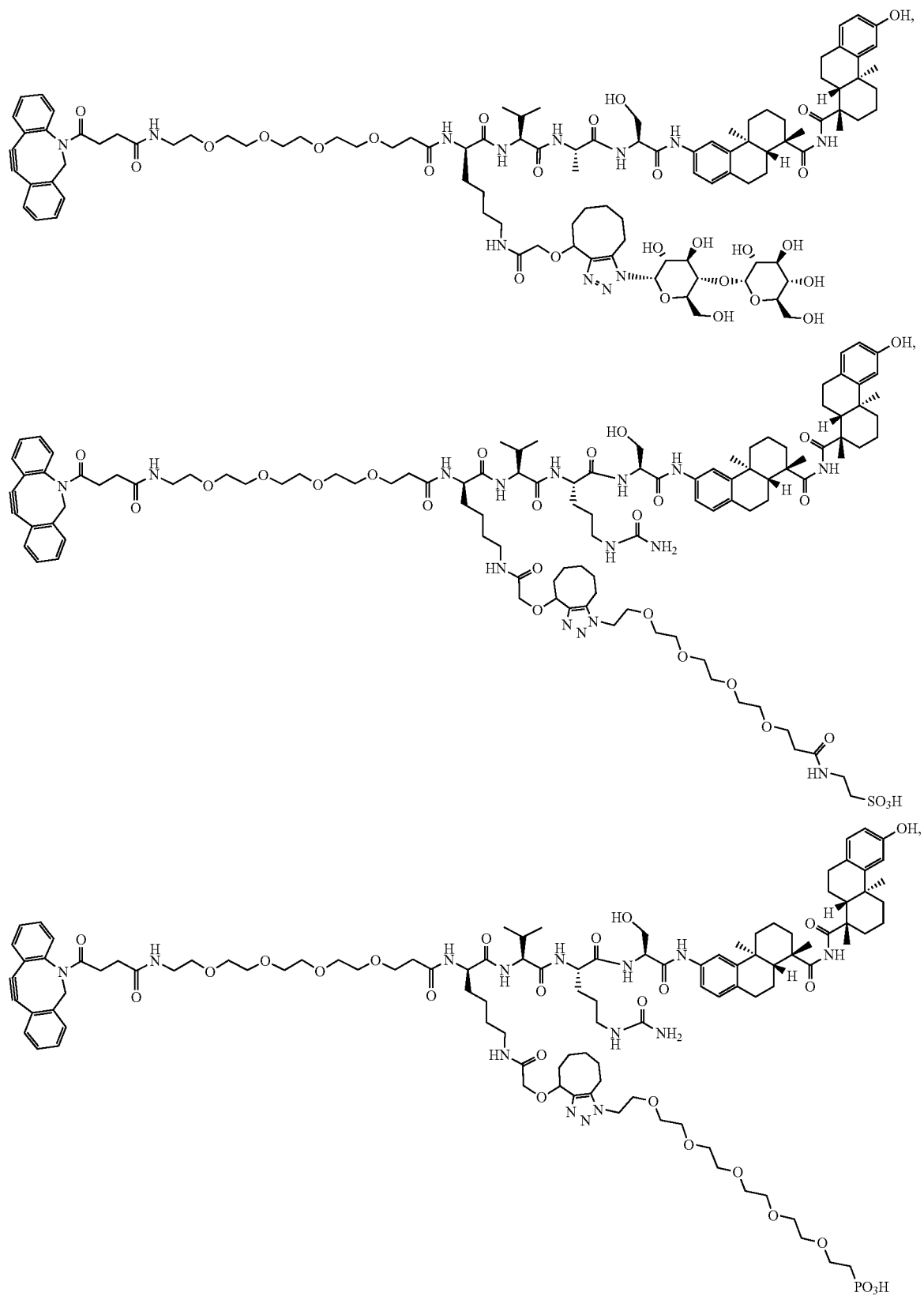

829 830
-continued
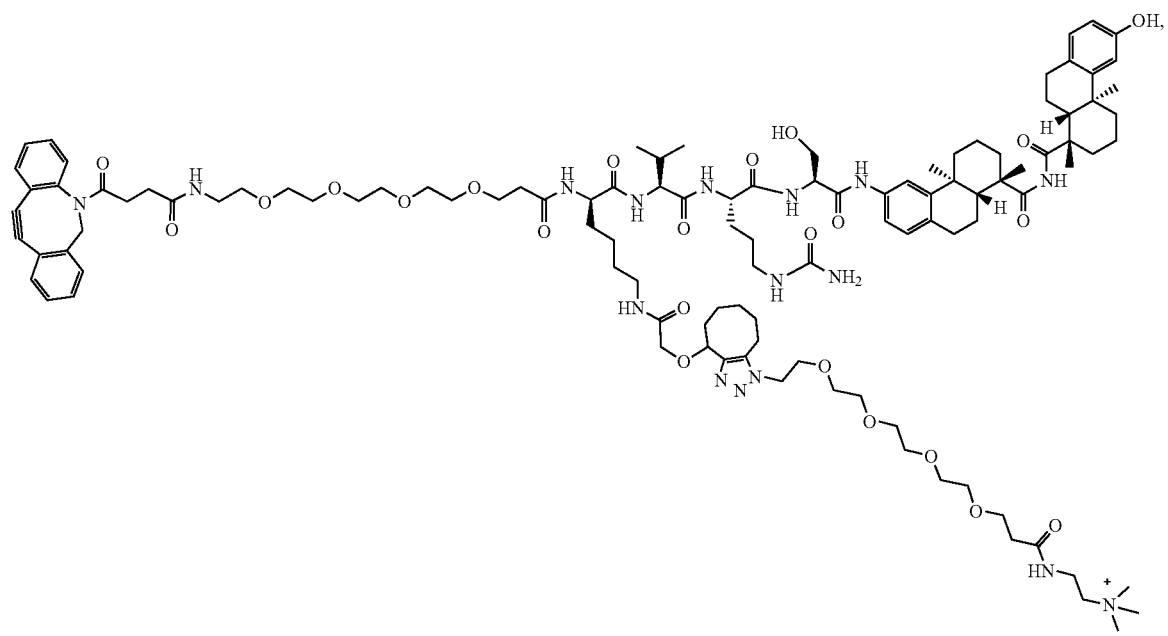
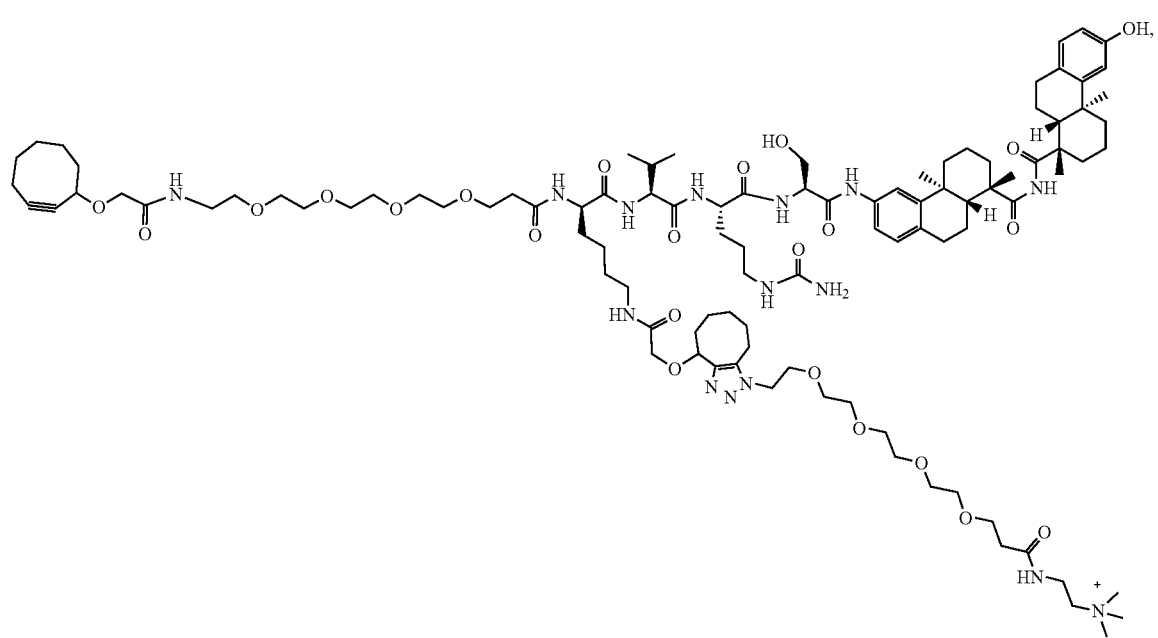

831
832
-continued
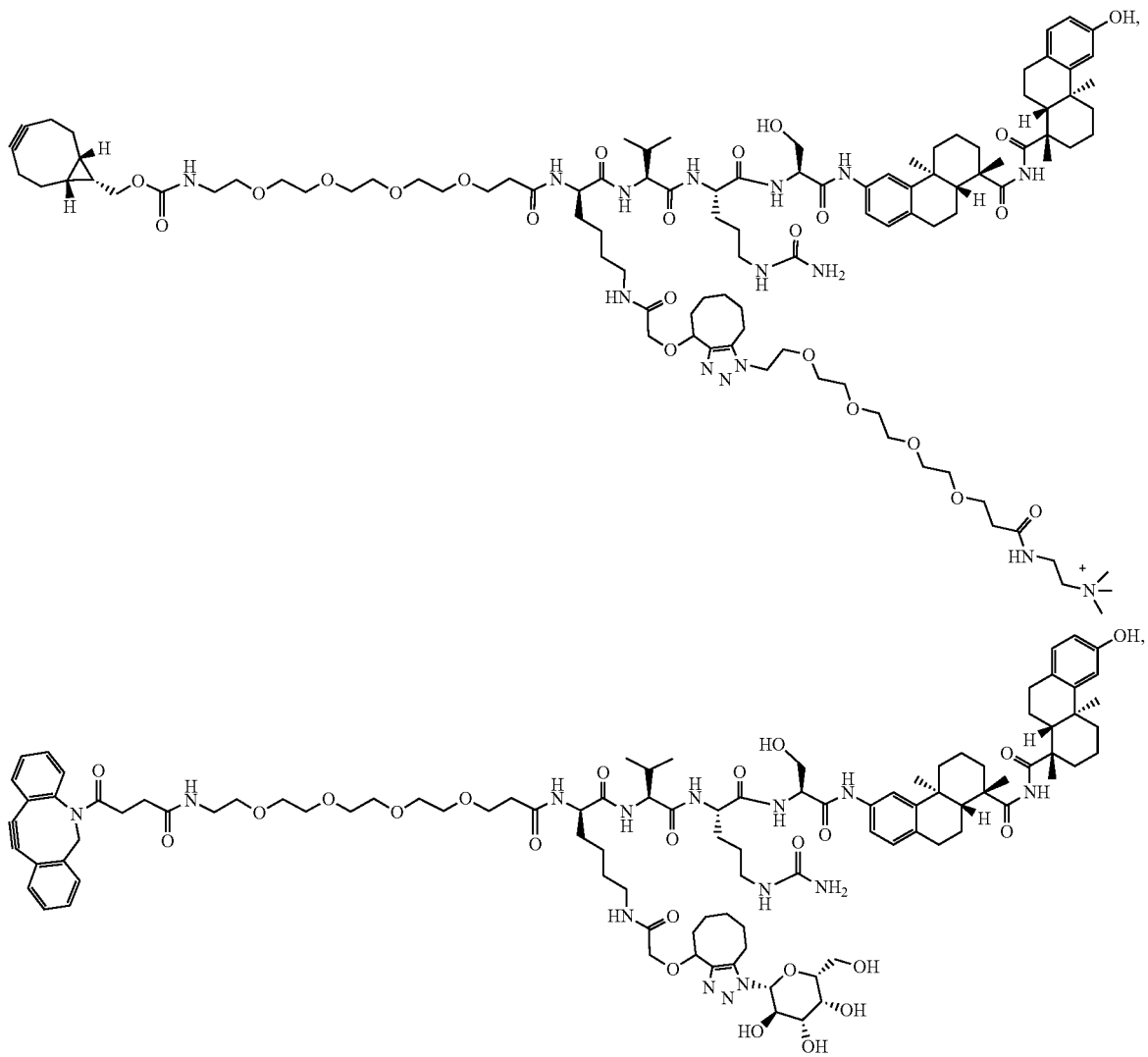
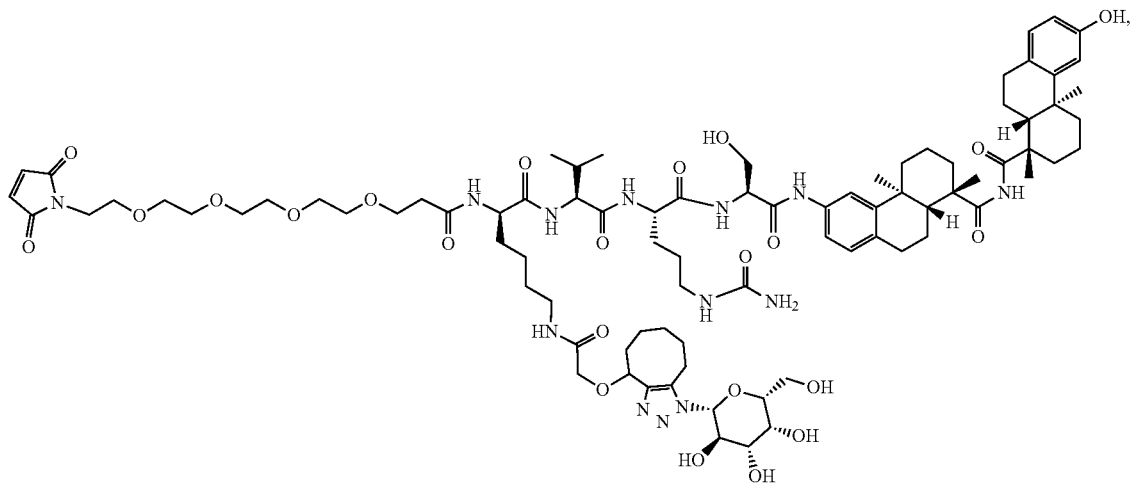

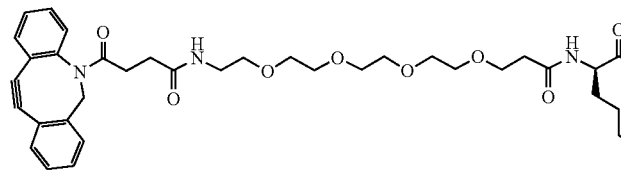
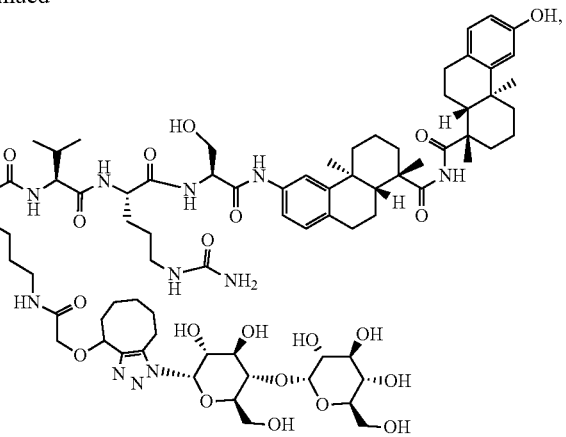

or a stereoisomeric form thereof, or a regioisomer thereof, or a mixture of regioisomers thereof.

Also provided is a method of preparing a compound of Formula (I), Formula (II), Formula (III), Formula (IV), Formula (IVa), Formula (IVb), Formula (IVc), Formula (Va), Formula (Vb), Formula (Vc), or Formula (Vd), comprising the step of contacting a binding agent (BA) with a compound according to Formula (VI), Formula (VII), Formula (VIII), Formula (IX), Formula (IXa), Formula (IXb), Formula (IXc), Formula (Xa), Formula (Xb), Formula (Xc), or Formula (Xd), under conditions suitable for forming a bond between the binding agent and the compound. In one instance, the binding agent is a modified binding agent comprising an azido group

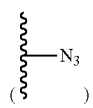

wherein the

indicates the atom through which the azido group is bonded to the adjacent groups in the formula.

Provided herein is a linker-payload comprising the compound of any of Formula (VI), Formula (VII), Formula (VIII), Formula (IX), Formula (IXa), Formula (IXb), Formula (IXc), Formula (Xa), Formula (Xb), Formula (Xc) or Formula (Xd), bonded to a linker.

Provided is a linker-payload comprising the compound of any of Formula (VI), Formula (VII), Formula (VIII), Formula (IX), Formula (IXa), Formula (IXb), Formula (IXc), Formula (Xa), Formula (Xb), Formula (Xc), or Formula (Xd), bonded to an oxygen or a primary or secondary nitrogen of the payload.

Further provided herein is an antibody-drug-conjugate comprising a compound or linker-payload described above bonded to an antibody, or an antigen binding fragment thereof.

In one aspect is provided a method of treating a proliferative disease, a metabolic disease, inflammation, or a neurodegenerative disease in a subject comprising administering to the subject an effective treatment amount of a compound according Formula (I), Formula (II), Formula (III), Formula (IV), Formula (IVa), Formula (IVb), Formula (IVc), Formula (Va), Formula (Vb), Formula (Vc), or Formula (Vd), or a pharmaceutical composition comprising a compound of Formula (I), Formula (II), Formula (III), Formula (IV), Formula (IVa), Formula (IVb), Formula (IVc), Formula (Va), Formula (Vb), Formula (Vc) or Formula (Vd).

In one aspect is provided a method for the treatment of a disease, disorder, or condition in a subject comprising administering to the subject an effective treatment amount of a compound according Formula (I), Formula (II), Formula (III), Formula (IV), Formula (IVa), Formula (IVb), Formula (IVc), Formula (Va), Formula (Vb), Formula (Vc), or Formula (Vd), or a pharmaceutical composition comprising a compound of Formula (I), Formula (II), Formula (III), Formula (IV), Formula (IVa), Formula (IVb), Formula (IVc), Formula (Va), Formula (Vb), Formula (Vc), or Formula (Vd).

In one aspect is provided a method for the treatment of a proliferatice disease in a subject comprising administering to the subject an effective treatment amount of a compound according Formula (I), Formula (II), Formula (III), Formula (IV), Formula (IVa), Formula (IVb), Formula (IVc), Formula (Va), Formula (Vb), Formula (Vc), or Formula (Vd), or a pharmaceutical composition comprising a compound of Formula (I), Formula (II), Formula (III), Formula (IV), Formula (IVa), Formula (IVb), Formula (IVc), Formula (Va), Formula (Vb), Formula (Vc), or Formula (Vd).

In one aspect is provided a method for the treatment of a metabolic disease in a subject comprising administering to the subject an effective treatment amount of a compound according Formula (I), Formula (II), Formula (III), Formula (IV), Formula (IVa), Formula (IVb), Formula (IVc), Formula (Va), Formula (Vb), Formula (Vc), or Formula (Vd), or a pharmaceutical composition comprising a compound of Formula (I), Formula (II), Formula (III), Formula (IV), Formula (IVa), Formula (IVb), Formula (IVc), Formula (Va), Formula (Vb), Formula (Vc), or Formula (Vd).

In one aspect is provided a method for the treatment of inflammation in a subject comprising administering to the subject an effective treatment amount of a compound according Formula (I), Formula (II), Formula (III), Formula (IV), Formula (IVa), Formula (IVb), Formula (IVc), Formula (Va), Formula (Vb), Formula (Vc), or Formula (Vd), or a pharmaceutical composition comprising a compound of Formula (I), Formula (II), Formula (III), Formula (IV), Formula (IVa), Formula (IVb), Formula (IVc), Formula (Va), Formula (Vb), Formula (Vc) or Formula (Vd).

In one aspect is provided a method for the treatment of a neurodegenerative disease in a subject comprising administering to the subject an effective treatment amount of a compound according Formula (I), Formula (II), Formula (III), Formula (IV), Formula (IVa), Formula (IVb), Formula (IVc), Formula (Va), Formula (Vb), Formula (Vc), or Formula (Vd), or a pharmaceutical composition comprising a compound of Formula (I), Formula (II), Formula (III), Formula (IV), Formula (IVa), Formula (IVb), Formula (IVc), Formula (Va), Formula (Vb), Formula (Vc), or Formula (Vd).

In some examples, set forth herein is a pharmaceutical composition comprising a compound set forth herein, including any of the foregoing compounds, or a pharmaceutically acceptable salt thereof, and a pharmaceutically acceptable excipient.

Those of skill in the art will recognize that the amino acid residue may be achiral or chiral, for example, an L-amino acid or D-amino acid. The amino acids generally include an amino acid side chain. The side chain can be the side chain of any amino acids known to those of skill. In certain embodiments, the side chain is the side chain of histidine, alanine, isoleucine, arginine, leucine, asparagine, lysine, aspartic acid, methionine, cysteine, phenylalanine, glutamic acid, threonine, glutamine, tryptophan, valine, ornithine, selenocysteine, serine, glycine, homoglycine (e.g., β-homoglycine), or tyrosine. Those of skill in the art will recognize that the peptide may be achiral or chiral, for example, including racemic DL-amino acids or non-racemic D- or L-amino acids and diastereomeric mixtures thereof. The side chains of the peptides are as described in the context of amino acids, above. Those of skill in the art will recognize that the N-alkyl amino acid residue includes an alkyl substituent, as defined herein, at the terminal amino group of the amino acid or the terminal amino group of the peptide.

In some examples, including any of the foregoing, subscript n is an integer from 1 to 30. In some examples, including any of the foregoing, subscript n is 1. In some examples, including any of the foregoing, subscript n is 2. In some examples, including any of the foregoing, subscript n is 3. In some examples, including any of the foregoing, subscript n is 4. In some examples, including any of the foregoing, subscript n is 5. In some examples, including any of the foregoing, subscript n is 6. In some examples, including any of the foregoing, subscript n is 7. In some examples, including any of the foregoing, subscript n is 8. In some examples, including any of the foregoing, subscript n is 9. In some examples, including any of the foregoing, subscript n is 10. In some examples, including any of the foregoing, subscript n is 11. In some examples, including any of the foregoing, subscript n is 12. In some examples, including any of the foregoing, subscript n is 13. In some examples, including any of the foregoing, subscript n is 14. In some examples, including any of the foregoing, subscript n is 15. In some examples, including any of the foregoing, subscript n is 16. In some examples, including any of the foregoing, subscript n is 17. In some examples, including any of the foregoing, subscript n is 18. In some examples, including any of the foregoing, subscript n is 19. In some examples, including any of the foregoing, subscript n is 20. In some examples, including any of the foregoing, subscript n is 21. In some examples, including any of the foregoing, subscript n is 22. In some examples, including any of the foregoing, subscript n is 23. In some examples, including any of the foregoing, subscript n is 24. In some examples, including any of the foregoing, subscript n is 25. In some examples, including any of the foregoing, subscript n is 26. In some examples, including any of the foregoing, subscript n is 27. In some examples, including any of the foregoing, subscript n is 28. In some examples, including any of the foregoing, subscript n is 29. In some examples, including any of the foregoing, subscript n is 30.

Binding Agents (BA)

Suitable binding agents for any of the conjugates provided in the instant disclosure include, but are not limited to, antibodies, lymphokines, hormones, growth factors, viral receptors, interleukins, or any other cell binding or peptide binding molecules or substances. Suitable binding agents also include polypeptides.

In some examples, including any of the foregoing, the binding agent (BA) is selected from any polypeptide. Example polypeptides include, but are not limited to, natural polypeptides and unnatural polypeptides. Example polypeptides include, but are not limited to, those produced from genetically modified organisms.

In some examples, including any of the foregoing, the BA is selected from receptors, cytokines, proteins, enzymes, binding agents, milk peptides, ribosomal peptides, nonribosomal peptides, peptones, and peptide fragments. In some examples, including any of the foregoing, the BA is selected selected from antimicrobial peptides, tachykinin peptides, vasoactive intestinal peptides, pancreatic polypeptide-related peptides, opiod peptides, and calcitonin peptides. In some examples, including any of the foregoing, the BA is selected B-type natriuretic peptide (BNP), lactotripeptides, neuropeptides, lipopeptides, proteoses, or hormones.

In some examples, including any of the foregoing, the BA is selected from short amino acid chains comprising two or more amino acids bonded together. In some examples, including any of the foregoing, the BA is selected from dipeptides (Val-Cit), tripeptides, and tetrapeptides (e.g., Val-Gly-Ser-Ala) having two, three, or four amino acids bonded together, respectively. In some examples, including any of the foregoing, the BA is selected from dipeptides, tripeptides, tetrapeptides, pentapeptides, hexapeptides, heptapeptides, octapeptides, nonapeptides, decapeptides, undecapeptides, and icosapeptides.

In some examples, including any of the foregoing, the BA is selected from any proteins. In some examples, the proteins include only natural amino acids. In some examples, the proteins further include non-natural amino acids. In some embodiments, the binding agent is an antibody of an antigen-binding fragment thereof. The antibody can be in any form known to those of skill in the art. The term "antibody", as used herein, means any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the antibodies suitable for the compounds herein (or antigen-binding portion thereof) may be identical to the human germline sequences, or may be naturally or artificially modified. An amino acid consensus sequence may be defined based on a side-by-side analysis of two or more CDRs. The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc. Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein. An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain. In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$CH_1$; (ii) $V_H$-$CH_2$; (iii) $V_H$-$CH_3$; (iv) $V_H$-$CH_1$—$CH_2$; (v) $V_H$-$CH_1$—$CH_2$—$CH_3$; (vi) $V_H$-$CH_2$—$CH_3$; (vii) $V_H$-$C_L$; (viii) $V_L$-$CH_1$; (ix) $V_L$-$C_H2$; (x) $V_L$-$C_H3$; (xi) $V_L$-$CH_1$—$CH_2$; (xii) $V_L$-$CH_1$—$CH_2$—$CH_3$; (xiii) $V_L$-$CH_2$—$CH_3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art. In certain embodiments of the invention, antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences. The term "human antibody" does not include naturally occurring molecules that normally exist without modification or human intervention/manipulation, in a naturally occurring, unmodified living organism. The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification. The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form. The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals. The antibodies used herein can comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention. Antibodies useful for the compounds herein also include antibodies comprising variants of any of the HCVR, LCVR, and/or CDR amino acid sequences disclosed herein having one or more conservative substitutions. The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

In certain embodiments, the antibody comprises a light chain. In certain embodiments, the light chain is a kappa light chain. In certain embodiments, the light chain is a lambda light chain. In certain embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a $F(ab')_2$ fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

The antibody can have binding specificity for any antigen deemed suitable to those of skill in the art. In certain embodiments, the antigen is a transmembrane molecule (e.g., receptor) or a growth factor. Exemplary antigens include, but are not limited to, molecules such as renin; a growth hormone, including human growth hormone and bovine growth hormone; growth hormone releasing factor; parathyroid hormone; thyroid stimulating hormone; lipoproteins; alpha1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-I-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; 19E; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; fibroblast growth factor receptor 2 (FGFR2), epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(I-3)-IGF-I (brain IGF-I), insulin-like growth factor binding proteins, EpCAM, GD3, FLT3, PSMA, PSCA, MUCI, MUCI6, STEAP, CEA, TENB2, EphA receptors, EphB receptors, folate receptor, FOLRI, mesothelin, cripto, alphavbeta6, integrins, VEGF, VEGFR, EGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CDI52, or an antibody which binds to one or more tumor-associated antigens or cell-surface receptors disclosed in US Publication No. 2008/0171040 or US Publication No. 2008/0305044 and incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CDIIa, CDIIb, CDIIc, CD18, an ICAM, VLA-4 and VCAM; a tumor associated antigen such as AFP, ALK, B7H4, BAGE proteins, β-catenin, brc-abl, BRCA1, BORIS, CA9 (carbonic anhydrase IX), caspase-8, CD20, CD40, CD123, CDK4, CEA, CLEC12A, c-kit, cMET, CTLA4, cyclin-B1, CYP1B1, EGFR, EGFRvIII, endoglin, Epcam, EphA2, ErbB2/Her2, ErbB3/Her3, ErbB4/Her4, ETV6-AML, Fra-1, FOLR1, GAGE proteins (e.g., GAGE-1, -2), GD2, GD3, GloboH, glypican-3, GM3, gp100, Her2, HLA/B-raf, HLA/EBNA1, HLA/k-ras, HLA/MAGE-A3, hTERT, IGF1R, LGR5, LMP2, MAGE proteins (e.g., MAGE-1, -2, -3, -6, and -12), MART-1, mesothelin, ML-IAP, Muc1, Muc16 (CA-125), MUM1, NA17, NGEP, NY-BR1, NY-BR62, NY-BR85, NY-ESO1, OX40, p15, p53, PAP, PAX3, PAX5, PCTA-1, PDGFR-α, PDGFR-β, PDGF-A, PDGF-B, PDGF-C, PDGF-D, PLAC1, PRLR, PRAME, PSCA, PSGR, PSMA (FOLH1), RAGE proteins, Ras, RGS5, Rho, SART-1, SART-3, Steap-1, Steap-2, STn, survivin, TAG-72, TGF-β, TMPRSS2, Tn, TNFRSF17, TRP-1, TRP-2, tyrosinase, and uroplakin-3, and fragments of any of the above-listed polypeptides. In some embodiments, the antigen is a tumor antigen, including antigens specific for a type of tumor or antigens that are shared, overexpressed or modified on a particular type of tumor. Examples include, but are not limited to: alpha-actinin-4 with lung cancer, ARTC1 with melanoma, BCR-ABL fusion protein with chronic myeloid leukemia, B-RAF, CLPP or Cdc27 with melanoma, CASP-8 with squamous cell carcinoma, and hsp70-2 with renal cell carcinoma as well as the following shared tumor-specific antigens, for example: BAGE-1, GAGE, GnTV, KK-LC-1, MAGE-A2, NA88-A, TRP2-INT2. In some embodiments, the antigen is PRLR or HER2. In some embodiments, the antibody is an anti-PRLR or anti HER2 antibody.

The binding agent linkers can be bonded to the binding agent, e.g., antibody or antigen-binding molecule, through an attachment at a particular amino acid within the antibody or antigen-binding molecule. Exemplary amino acid attachments that can be used in the context of this aspect of the disclosure include, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA,* 2008, 105:12451-12456), formyl glycine (see, e.g., Carrico et al., *Nat. Chem. Biol.*, 2007, 3:321-322; Agarwal et al., *Proc. Natl. Acad. Sci., USA,* 2013, 110:46-51, and Rabuka et al., *Nat. Protocols,* 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, and Ryan et al., *Food & Agriculture Immunol.,* 2001, 13:127-130).

In some examples, the binding agent is an antibody or antigen binding molecule, and the antibody is bonded to the linker through a lysine residue. In some embodiments, the antibody or antigen binding molecule is bonded to the linker through a cysteine residue.

Linkers can also be conjugated to one or more glutamine residues via transglutaminase-based chemo-enzymatic conjugation (see, e.g., Dennler et al., *Bioconjugate Chem.* 2014, 25, 569-578). For example, in the presence of transglutaminase, one or more glutamine residues of an antibody can coupled to a primary amine compound. Primary amine compounds include payloads or linker-payloads, which directly provide antibody drug conjugates via transglutaminase-mediated coupling. Primary amine compounds also include linkers and spacers that are functionalized with reactive groups that can be subsequently reacted with further compounds towards the synthesis of antibody drug conjugates. Antibodies comprising glutamine residues can be isolated from natural sources or engineered to comprise one or more glutamine residues. Techniques for engineering glutamine residues into an antibody polypeptide chain (glutaminyl-modified antibodies or antigen binding molecules)

are within the skill of the practitioners in the art. In certain embodiments, the antibody is aglycosylated.

In certain embodiments, the antibody or a glutaminyl-modified antibody or antigen binding molecule comprises at least one glutamine residue in at least one polypeptide chain sequence. Site specific conjugation techniques can also be employed to direct conjugation to particular residues of the antibody or antigen binding protein (see, e.g., Schumacher et al. *J Clin Immunol* (2016) 36(Suppl 1): 100). Site specific conjugation techniques, include, but are not limited to glutamine conjugation via transglutaminase (see e.g., Schibli, *Angew Chemie Inter Ed.* 2010, 49, 9995). In certain embodiments, the antibody or a glutaminyl-modified antibody or antigen binding molecule comprises two heavy chain polypeptides, each with one Gln295 residue. In further embodiments, the antibody or a glutaminyl-modified antibody or antigen binding molecule comprises one or more glutamine residues at a site other than a heavy chain 295, for instance at Gln55 (Q55). Included herein are antibodies of this section bearing N297Q mutation(s) described herein. Briefly, in some embodiments, an antibody including a glutamine residue is treated with a primary amine compound, described in more detail below, in the presence of the enzyme transglutaminase. An exemplary N297 mutant is Asn297Gln (N297Q) mutant. For example, in some embodiments, such an antibody can be prepared by site-directed mutagenesis to remove or disable a sequence or to insert a glutamine residue at a site apart from any interfering structure. Such an antibody can also be isolated from natural or artificial sources. The amide groups in the inserted glutamine residues can be linked to azido groups which are suitable for the click chemistry reactions described herein. Advantageously, the number of inserted glutamine residues can be controlled and consequently, the number of azido groups in the antibody or a glutaminyl-modified antibody or antigen binding molecule can also be controlled, thereby allowing for improved control of Antibody-Drug ratios (ADR), see, for instance, Example 29 and Table 5.

In a specific instance, for a compound of Formula (I), Formula (II), Formula (III), Formula (IV), Formula (IVa), Formula (IVb), Formula (IVc), Formula (Va), Formula (Vb), Formula (Vc), or Formula (Vd), described herein, the Drug Antibody Ratio (DAR) in any antibody drug conjugate sample described herein is about 2 (i.e., n is 2). In such instances, the antibody or antigen binding molecule comprises two heavy chain polypeptides, each with one Gln295 residue, and each Gln295 residue is linked to an azido group which is suitable for click chemistry reactions described herein, allowing a DAR of about 2.

In another specific instance, for a compound of Formula (I), Formula (II), Formula (III), Formula (IV), Formula (IVa), Formula (IVb), Formula (IVc), Formula (Va), Formula (Vb), Formula (Vc) or Formula (Vd), described herein, the Drug Antibody Ratio in any antibody drug conjugate sample described herein is about 4 (i.e., n is 4). In such instances, the antibody or antigen binding molecule comprises two heavy chain polypeptides, each with one Gln295 residue, and each Gln295 residue is linked to an azido group which is suitable for click chemistry reactions described herein. In addition, the antibody or antigen binding molecule is further modified prior to conjugation by site-directed mutagenesis to remove or disable a sequence or to insert a glutamine residue at a site apart from any interfering structure. For example, an N297 mutant, Asn297Gln (N297Q) mutant, in each heavy chain is linked to an azido group. Thus the glutaminyl-modified antibody or antigen binding molecule comprises 4 azido groups suitable for click chemistry reactions described herein, allowing a DAR of about 4. See FIG. 19.

In another specific instance, for a compound of Formula (I), Formula (II), Formula (III), Formula (IV), Formula (IVa), Formula (IVb), Formula (IVc), Formula (Va), Formula (Vb), Formula (Vc) or Formula (Vd), described herein, the Drug Antibody Ratio in any antibody drug conjugate sample described herein is about 5 or about 6 (i.e., n is 5 or 6). In such instances, the antibody or antigen binding molecule comprises two heavy chain polypeptides, each with one Gln295 residue, and each Gln295 residue is linked to an azido group which is suitable for click chemistry reactions described herein. In addition, the antibody or antigen binding molecule is further modified prior to conjugation by site-directed mutagenesis to remove or disable a sequence or to insert a glutamine residue at a site apart from any interfering structure. For example, an N297 mutant, Asn297Gln (N297Q) mutant, in each heavy chain is linked to an azido group. In certain instances, antibodies to be conjugated contain one or more additional naturally occurring glutamine residues in their variable regions, which can be accessible to transglutaminase and therefore are able to be conjugated, for instance Gln55 (Q55). In these instances, the antibodies after conjugation via transglutaminase will have a DAR value higher than 4. Thus, the glutaminyl-modified antibody or antigen binding molecule may comprise 5 or 6 azido groups suitable for click chemistry reactions described herein, allowing a DAR of about 5 or about 6.

In some embodiments, BA of the conjugates described herein is an antibody or an antigen-binding fragment thereof. In some examples, the binding agent that reacts with a compound of Formula (VI), Formula (VII), Formula (VIII), Formula (IX), Formula (IXa), Formula (IXb), Formula (IXc), Formula (Xa), Formula (Xb), Formula (Xc), or Formula (Xd), as described herein, is an antibody or an antigen binding fragment thereof. In such instances, the binding agent is an antibody or an antigen-binding fragment thereof, is optionally modified with azido groups, or the binding agent is a modified antibody or antigen-binding fragment thereof of Formula Ab-1 described herein, or a combination thereof. In some embodiments, the conjugates described herein are derived from azido-functionalized antibodies or antigen binding fragments thereof. In some embodiments, the conjugates described herein are derived from PEG-functionalized antibodies or antigen-binding fragments thereof. In some embodiments, the conjugates described herein are derived from azido and PEG-functionalized antibodies or antigen binding fragments thereof where the PEG is attached on a first end to the antibody or antigen binding fragments thereof and the PEG is attached on the second end to an azido group which is suitable for click chemistry reactions described herein. In certain embodiments, BA of the conjugates described herein is:

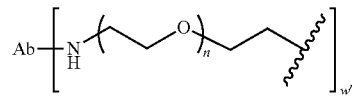

where w' is an integer from 1 to 10.

Figure 20:
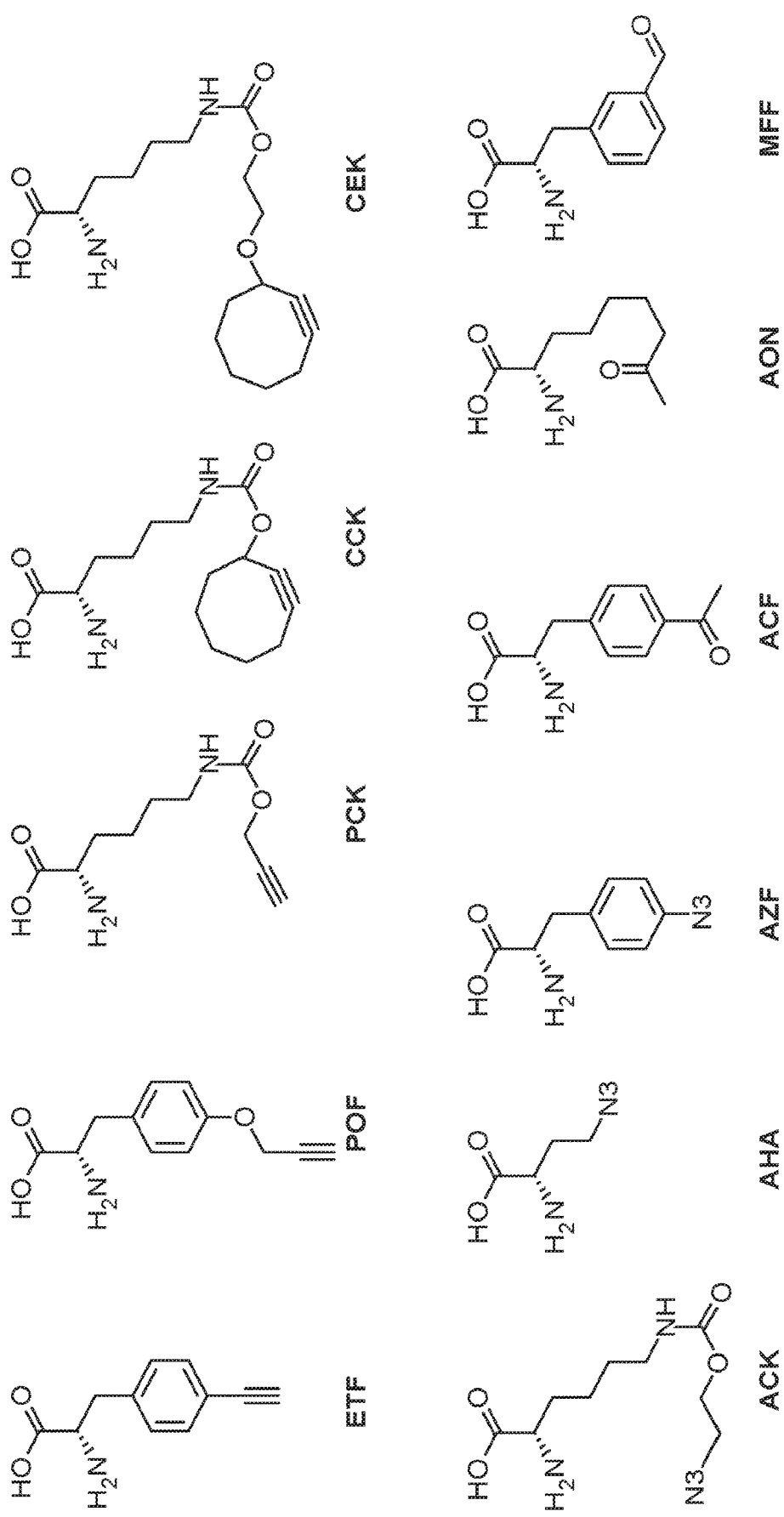
FIG. 20 shows reagents that may be used in place of d-Lys in the methods set forth herein.
Figure 20:
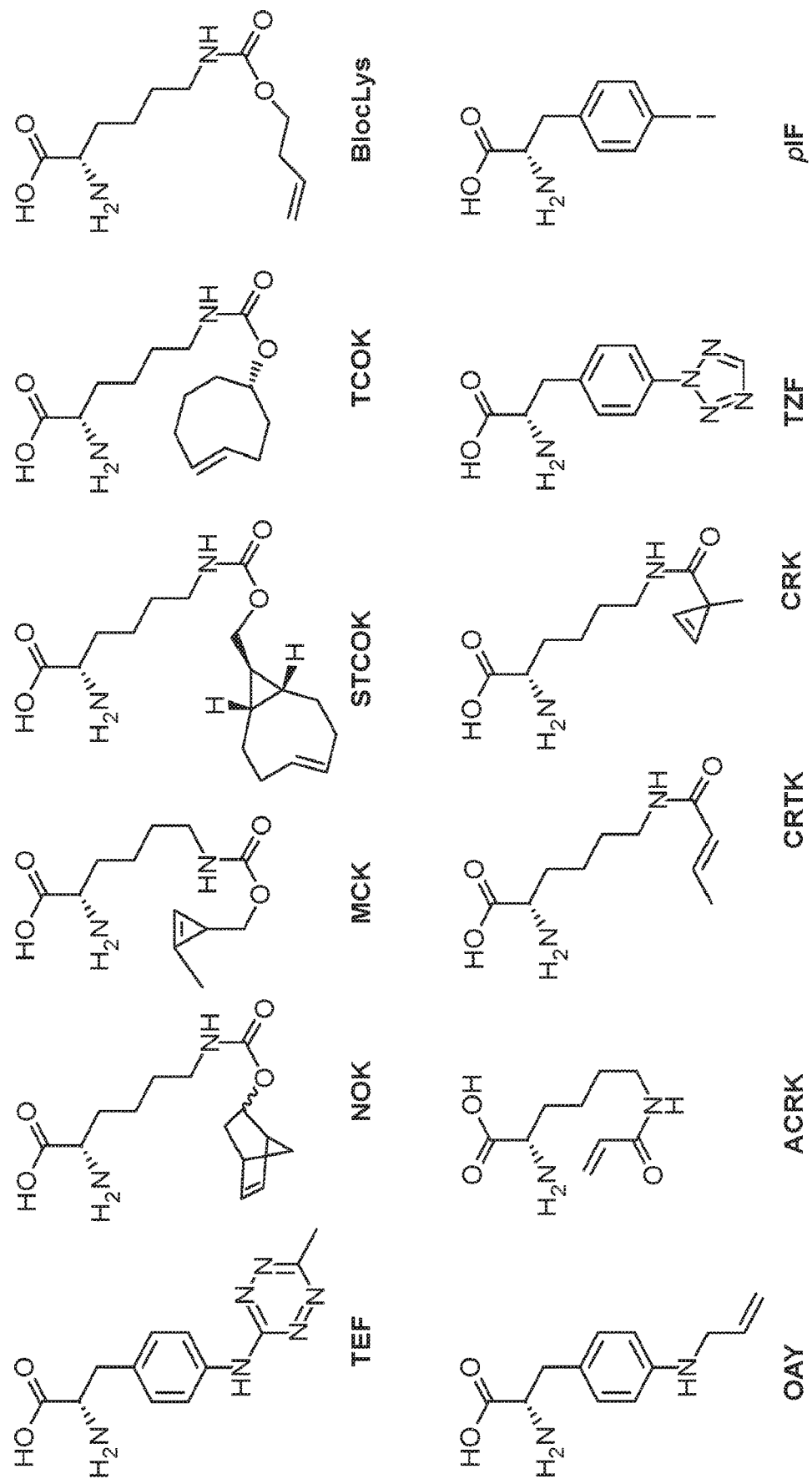

In some examples, herein, the d-Lys can be replaced with a reagent set forth in FIG. 20.

Primary Amine Compounds

The primary amine compound useful for the transglutaminase mediated coupling of an antibody (or antigen binding compound) comprising a glutamine can be any primary amine compound deemed useful by the practitioner of ordinary skill. Generally, the primary amine compound has the formula H$_2$N—R, where R can be any group compatible with the antibody and reaction conditions. In certain embodiments, R is alkyl, substituted alkyl, heteroalkyl, or substituted heteroalkyl.

In some embodiments, the primary amine compound comprises a reactive group or protected reactive group. Useful reactive groups include azides, alkynes, cycloalkynes, thiols, alcohols, ketones, aldehydes, acids, esters, hydrozides, analines, and amines. In certain embodiments, the reactive group is selected from the group consisting of azide, alkyne, sulfhydryl, cycloalkyne, aldehyde, and carboxyl.

In certain embodiments, the primary amine compound is according to the formula H$_2$N-LL-X, where LL is a divalent spacer and X is a reactive group or protected reactive group. In particular embodiments, LL is a divalent polyethylene glycol (PEG) group. In certain embodiments, X is selected from the group consisting of —SH, —N$_3$, alkyne, aldehyde, and tetrazole. In particular embodiments, X is —N$_3$.

In certain embodiments, the primary amine compound is according to one of the following formulas:

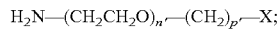

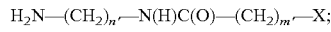

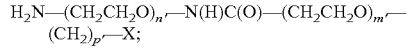

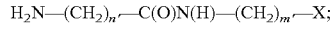

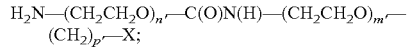

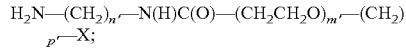

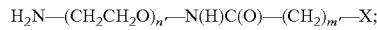

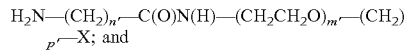

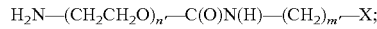

where subscript n' is an integer selected from 1 to 12;
subscript m' is an integer selected from 0 to 12;
subscript p' is an integer selected from 0 to 2;
and X is selected from the group consisting of —SH, —N$_3$, —C≡CH, —C(O)H, tetrazole, and any of

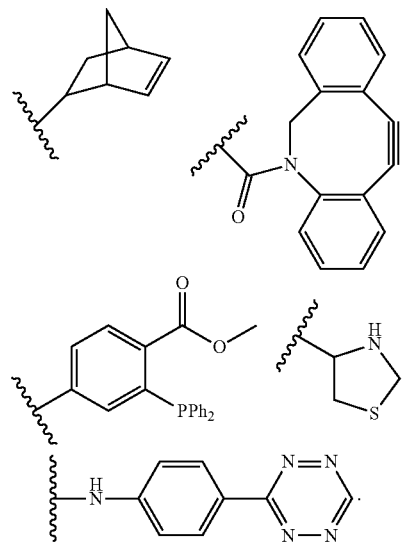

In the above, any of the alkyl or alkylene (i.e., —CH$_2$—) groups can optionally be substituted, for example with C$_{1-8}$alkyl, methylformyl, or —SO$_3$H. In certain embodiments, the alkyl groups are unsubstituted.

In certain embodiments, the primary amine compound is selected from the group consisting of:

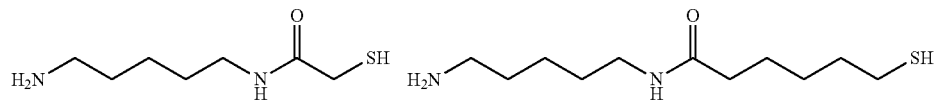

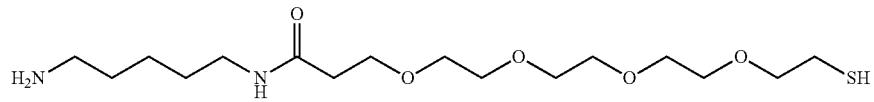

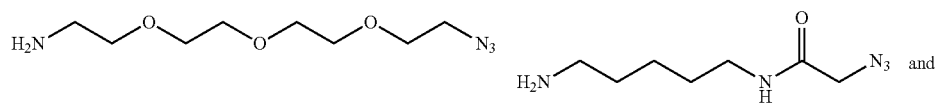

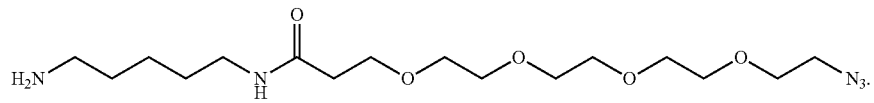

In particular embodiments, the primary amine compound is

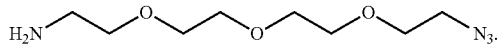

Exemplary conditions for the above reactions are provided in the Examples below.

Linkers

The linker LL portion of the conjugates described herein is a moiety, for instance a divalent moiety, that covalently links a binding agent to a payload compound described herein. In other instances, the linker LL is a trivalent or multivalent moiety that covalently links a binding agent to a payload compound described herein. Suitable linkers may be found, for example, in *Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. Payload compounds include compounds of FIG. 1, and their residues following bonding or incorporation with linker LL. Those of skill in the art will recognize that certain functional groups of the payload moieties are convenient for linking or bonding to linkers and/or binding agents. Those groups include amines, hydroxyls, phosphates, and sugars.

In certain embodiments, the linkers are stable in physiological conditions. In certain embodiments, the linkers are cleavable, for instance, able to release at least the payload portion in the presence of an enzyme or at a particular pH range or value. In some embodiments, a linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the linker comprises a non-cleavable moiety. In some embodiments, the non-cleavable linker is derived from

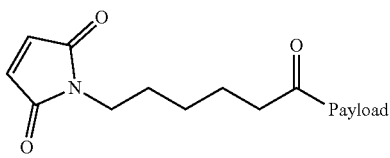

or a residue thereof. In some embodiments, the non-cleavable linker-payload is

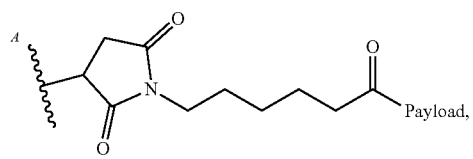

or a regioisomer thereof. In some embodiments, the non-cleavable linker is derived from

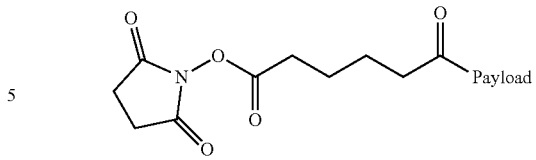

or a residue thereof. In some embodiments, the non-cleavable linker-payload is

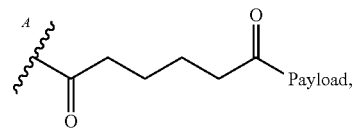

or a regioisomer thereof. In one embodiment, the linker is maleimide cyclohexane carboxylate or 4-(N-maleimidomethyl)cyclohexanecarboxylic acid (MCC). In the structures,

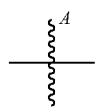

indicates a bond to a binding agent. In the structures, in some examples,

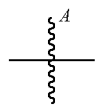

indicates a click chemistry residue which results from the reaction of, for example, a binding agent and a linker payload.

In some embodiments, suitable linkers include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. Suitable amino acids include natural, non-natural, standard, non-standard, proteinogenic, non-proteinogenic, and L-, or D-α-amino acids. In some embodiments, the linker comprises alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or combination thereof. In certain embodiments, one or more side chains of the amino acids is linked to a side chain group, described below. In some embodiments, the linker comprises valine and citrulline. In some embodiments, the linker comprises lysine, valine, and citrulline. In some embodiments, the linker comprises lysine, valine, and alanine. In some embodiments, the linker comprises valine and alanine.

In some embodiments, the linker comprises a self-immolative group. The self-immolative group can be any such group known to those of skill. In particular embodiments, the self-immolative group is p-aminobenzyl (PAB), or a derivative thereof. Useful derivatives include p-aminobenzyloxycarbonyl (PABC). Those of skill will recognize that a self-immolative group is capable of carrying out a chemical reaction which releases the remaining atoms of a linker from a payload.

In certain embodiments, reactive groups include, but are not limited to, alkynes. In certain embodiments, the alkynes are alkynes capable of undergoing 1,3-cycloaddition reactions with alkynes in the absence of copper catalysts such as strained alkynes. Strained alkynes are suitable for strain-promoted alkyne-azide cycloadditions (SPAAC), cycloalkynes, e.g., cyclooctynes, and benzannulated alkynes. Suitable alkynes include, but are not limited to, dibenzoazacyclooctyne or

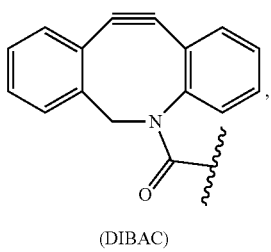 [SMILES: *C(=O)N1Cc2ccccc2C#Cc2ccccc21]

(DIBAC)

dibenzocyclooctyne or

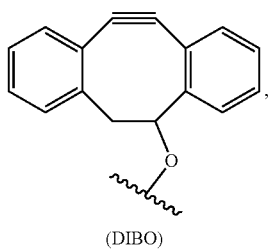 [SMILES: *OC1Cc2ccccc2C#Cc2ccccc21 ; "(DIBO)"]

(DIBO)

biarylazacyclooctynone or

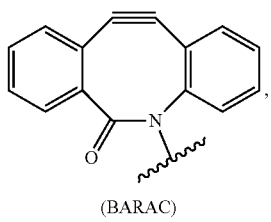

(BARAC)

difluorinated cyclooctyne or

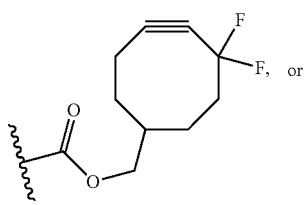

, or

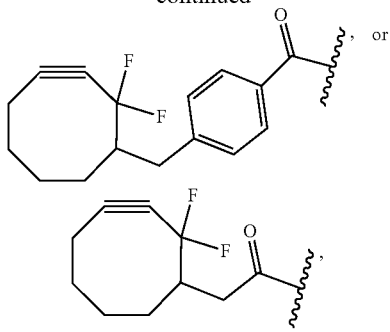

(DIFO)

substituted, e.g., fluorinated alkynes, aza-cycloalkynes, bicycle[6.1.0]nonyne or

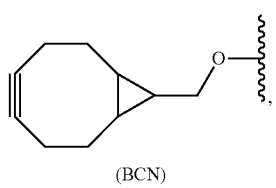

(BCN)

and derivatives thereof. Particularly useful alkynes include

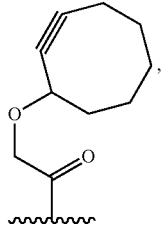

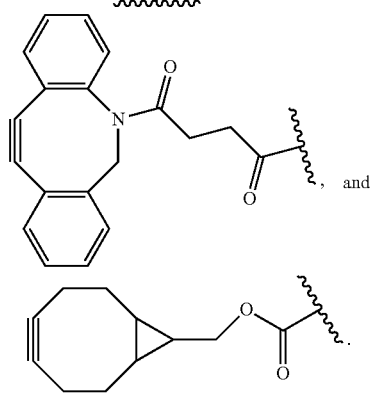

, and

In certain embodiments, the binding agent is bonded directly to a reactive group RG. In certain embodiments, the binding agent is bonded to a reactive group RG via a spacer. In particular embodiments, the binding agent is bonded to a reactive group. via a PEG spacer. In certain embodiments, the binding agent is prepared by functionalizing with one or more azido groups. Each azido group is capable of reacting with an alkyne in RG to form $RG^1$ or RG'. In particular embodiments, the binding agent is derivatized with -PEG-$N_3$ linked to a glutamine residue. Exemplary —$N_3$ derivatized binding agents, methods for their preparation, and methods for their use in reacting with RG are provided herein. In certain embodiments, RG is an alkyne suitable for participation in 1,3-cycloadditions, and $RG^1$ or RG' is a 1,2,3-triazolyl moiety formed from the reaction of RG with an azido-functionalized binding agent. By way of further example, in certain embodiments, RG is linked to the binding agent as shown in

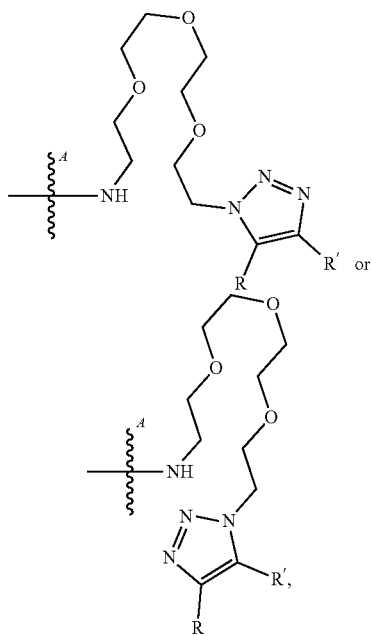

or a mixture of each regioisomer. Each R and R' is as described herein.

In an analogous manner, each HG described herein may be an azido-functionalized hydrophilic group which reacts with an alkyne in RG to form $RG^2$.

In certain embodiments, $RG^1$, or RG' is derived from the reaction of a reactive group with a cysteine or lysine residue of an antibody or antigen-binding fragment thereof. In certain embodiments, $RG^1$, or RG' is derived from a click chemistry reaction. In some embodiments of said click chemistry reaction, $RG^1$, or RG' is derived from a 1,3 cycloaddition reaction between an alkyne and an azide. Non-limiting examples of such $RG^1$, or RG' include those derived from strained alkynes, e.g., those suitable for strain-promoted alkyne-azide cycloadditions (SPAAC), cycloalkynes, e.g., cyclooctynes, benzannulated alkynes, and alkynes capable of undergoing 1,3 cycloaddition reactions with azides in the absence of copper catalysts. Suitable $RG^1$, or RG' also include, but are not limited to those derived from DIBAC, DIBO, BARAC, substituted, e.g., fluorinated alkynes, aza-cycloalkynes, BCN, and derivatives thereof. Conjugates containing such $RG^1$, or RG' groups can be derived from antibodies that have been functionalized with azido groups. Such functionalized antibodies include antibodies functionalized with azido-polyethylene glycol groups. In certain embodiments, such functionalized antibody is derived by reacting an antibody comprising at least one glutamine residue with a compound according to the formula $H_2N$-LL'-$N_3$, wherein LL' is a divalent polyethylene glycol group, in the presence of the enzyme transglutaminase, e.g., microbial transglutaminase. Suitable glutamine residues of an antibody include Q295 or Q55, or those derived by insertion or mutation, e.g., N297Q mutation.

Those of skill will recognize PAB and PABC as residues of p-aminobenzyloxycarbonyl and p-aminobenzylcarbamate with the following structures respectively:

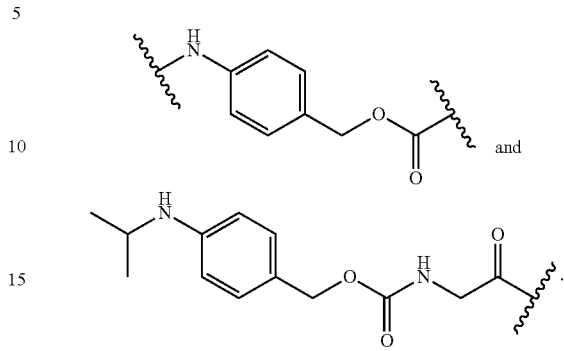

The PAB and PABC residues have been shown to facilitate cleavage of certain linkers in vitro and in vivo.

In some embodiments, the linker is DIBAC-$PEG_e$-dLys ($COT$-$PEG_6$)-VC-PAB. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-$PEG_e$-dLys ($COT$-$PEG_e$-taurine)-VC-PAB. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-$PEG_e$-dLys ($COT$-$PEG_e$-taurine)-VC-PAB. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-$PEG_4$-dLys (COT-dualtaurine)-VC-PAB. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-$PEG_e$-dGlu (taurine)-VC-PAB. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-$PEG_e$-dLys ($COT$-$PEG_4$-taurine)-VC-PAB. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-$PEG_e$-dLys ($COT$-$PEG_4$-taurine)-VA. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-$PEG_e$-dLys ($COT$-$PEG_4$-taurine)-VC. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-PEG$_e$-dGlu (taurine)-VC. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-PEG$_e$-dLys (COT-PEG$_e$-taurine)-VA. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-PEG$_e$-dLys (COT-PEG$_e$-taurine)-VC. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-PEG$_e$-dLys (COT-PEG$_e$-N$^+$Me$_3$)-vcPAB. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-PEG$_e$-dLys (COT-PEG$_e$-phosphate)-vcPAB. Subscript e is an integer from 0 to 4. In some examples subscript e is 0. In some examples subscript e is 1. In some examples subscript e is 2. In some examples subscript e is 3. In some examples subscript e is 4. In some examples subscript e is 3. In some examples subscript e is 5.

In some embodiments, the linker is DIBAC-PEG$_e$-dLys (COT-galactose)-vcPAB. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is MAL-PEG$_e$-dLys (COT-galactose)-vcPAB. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-PEG$_e$-dGlu (glucamide)-vcPAB. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is MAL-PEG$_e$-dGlu (glucamide)-vcPAB. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-PEG$_e$-dLys (COT-PEG$_e$-N$^+$Me$_3$)-vcPAB. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is COT-PEG$_e$-dLys (COT-PEG$_e$-N$^+$Me$_3$)-vcPAB. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is BCN-PEG$_e$-dLys (COT-PEG$_e$-N$^+$Me$_3$)-vcPAB. Subscript e is an integer from 0 to 5. In some examples subscript e is 0. In some examples subscript e is 1. In some examples subscript e is 2. In some examples subscript e is 3. In some examples subscript e is 4. In some examples subscript e is 5.

In some embodiments, the linker is DIBAC-PEG$_e$-dLys (COT-PEG$_e$-N$^+$Me$_3$)-VA. Subscript e is an integer from 0 to 4. In some examples subscript e is 0. In some examples subscript e is 1. In some examples subscript e is 2. In some examples subscript e is 3. In some examples subscript e is 4.

In some embodiments, the linker is DIBAC-PEG$_4$-dLys (COT-PEG$_6$)-VC-PAB.

In some embodiments, the linker is DIBAC-PEG$_4$-dLys (COT-PEG$_4$-taurine)-VC-PAB.

In some embodiments, the linker is DIBAC-PEG$_4$-dLys (COT-PEG$_4$-taurine)-VC-PAB.

In some embodiments, the linker is DIBAC-PEG$_4$-dLys (COT-dualtaurine)-VC-PAB.

In some embodiments, the linker is DIBAC-PEG$_4$-dGlu (taurine)-VC-PAB.

In some embodiments, the linker is DIBAC-PEG$_4$-dLys (COT-PEG$_4$-taurine)-VC-PAB.

In some embodiments, the linker is DIBAC-PEG$_4$-dLys (COT-PEG$_4$-taurine)-VA.

In some embodiments, the linker is DIBAC-PEG$_4$-dLys (COT-PEG$_4$-taurine)-VC.

In some embodiments, the linker is DIBAC-PEG$_4$-dGlu (taurine)-VC.

In some embodiments, the linker is DIBAC-PEG$_4$-dLys (COT-PEG$_4$-taurine)-VA.

In some embodiments, the linker is DIBAC-PEG$_4$-dLys (COT-PEG$_4$-taurine)-VC.

In some embodiments, the linker is DIBAC-PEG$_4$-dLys (COT-PEG$_4$-N$^+$Me$_3$)-vcPAB In some embodiments, the linker is DIBAC-PEG$_4$-dLys (COT-PEG$_5$-phosphate)-vcPAB In some embodiments, the linker is DIBAC-PEG$_4$-dLys (COT-galactose)-vcPAB In some embodiments, the linker is MAL-PEG$_4$-dLys (COT-galactose)-vcPAB In some embodiments, the linker is DIBAC-PEG$_4$-dGlu (glucamide)-vcPAB In some embodiments, the linker is MAL-PEG$_4$-dGlu (glucamide)-vcPAB In some embodiments, the linker is DIBAC-PEG$_4$-dLys (COT-PEG$_4$-N$^+$Me$_3$)-vcPAB In some embodiments, the linker is COT-PEG$_4$-dLys (COT-PEG$_4$-N$^+$Me$_3$)-vcPAB In some embodiments, the linker is BCN-PEG$_4$-dLys (COT-PEG$_4$-N$^+$Me$_3$)-vcPAB In some embodiments, the linker is DIBAC-PEG$_4$-dLys (COT-PEG$_4$-N$^+$Me$_3$)-VA Reactive Linker-Payloads Conjugates provided herein can be prepared from reactive linker-payloads comprising reactive groups RG$^1$ or RG', or RG$^2$, as described above. The reactive linker payloads can be linked to hydrophilic groups, as described herein, and/or binding agents according to the methods described below.

In some embodiments, set forth herein is a reactive linker-payload which comprises a reactive group linked to at least one payload moiety and linked to at least one hydrophilic moiety via a covalent linker, wherein said covalent linker is bonded directly or indirectly to each of the reactive group, the payload moiety, the hydrophilic moiety.

As illustrated herein, in some examples, the reactive group is bonded directly to a covalent linker, such as a lysine amino acid. This means that the reactive group is one bond position away from the covalent linker. In some of these examples, the covalent linker is also bonded directly to a payload moiety. This means that the covalent linker is one bond position away from a payload such as, but not limited to, MMAE, a steroid, an LXR modulator, or any payload set forth herein. In some of these examples, the covalent linker is also bonded directly to a hydrophilic moiety. This means that the covalent linker is one bond position away from a hydrophilic residue, such as the hydrophilic residues set forth herein. In some of these examples, the covalent linker is a lysine amino acid or a derivative thereof.

In other examples, the reactive group is bonded indirectly to a covalent linker. This means that the reactive group is more than one bond position away from the covalent linker. This also means that the reactive group is bonded through another moiety to the covalent linker. For example, the reactive group may be bonded to a polyethylene glycol group which is bonded to the covalent linker. In some of these examples, the covalent linker is also bonded indirectly to a payload moiety. This means that the covalent linker is more than one bond position away from a payload such as, but not limited to, MMAE, or a steroid, or any payload set forth herein. This also means that the covalent linker is bonded through another moiety to the payload. For example, the covalent linker may be bonded to a dipeptide, such as but not limited to Val-Ala or Val-Cit, which may be bonded to PAB which may be bonded to the payload. In some of these examples, the covalent linker is also bonded indirectly to a hydrophilic moiety. This means that the covalent linker is more than one bond position away from a hydrophilic moiety, such as the hydrophilic residues set forth herein. This also means that the covalent linker is bonded through another moiety to the hydrophilic residue. For example, the covalent linker may be bonded to a polyethylene glycol group which may be bonded to a reactive group which may be bonded to the hydrophilic residue. In some of these examples, the covalent linker is a lysine amino acid or a derivative thereof.

In the formulas, herein, each $AA^1$ is an amino acid. In some examples in the formulas, herein, each $AA^2$ is an amino acid. In some examples in the formulas, herein, each $AA^2$ is a di-peptide. In some examples in the formulas, herein, each $AA^2$ is a tri-peptide. Suitable amino acids for each $AA^1$ or $AA^2$ include natural, non-natural, standard, non-standard, proteinogenic, non-proteinogenic, and L-, or D-amino acids. In some embodiments, the linker comprises alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, one or more side chains of the amino acids are linked to a side chain group, described below. In certain embodiments, $AA^1$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, $AA^1$ is an amino acid with three functional groups to link to a payload, to a binding agent (e.g., antibody or antigen binding fragment thereof), and to a linker comprising a hydrophilic group, e.g., lysine, asparagine, glutamic acid, aspartic acid, glutamine, cysteine, threonine, serine, or tyrosine. In certain embodiments, $AA^1$ is lysine. In certain embodiments, $AA^1$ is glutamine. In certain embodiments, $AA^1$ is lysine or a derivative of lysine. In certain embodiments, $AA^1$ is L-lysine. In certain embodiments, the $AA^1$ is D-lysine. In certain embodiments, $AA^1$ is glutamic acid. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In some embodiments, the $AA^1$-$AA^2$ is glutamine-valine-citrulline. In some embodiments, the $AA^1$-$AA^2$ is lysine-valine-citrulline. In some embodiments, the $AA^1$-$AA^2$ is lysine-valine-alanine. In some embodiments, the $AA^1$-$AA^2$ is glutamine-valine-alanine.

In some embodiments, $AA^2$ is a dipeptide selected from valine-citrulline, citrulline-valine, lysine-phenylalanine, phenylalanine-lysine, valine-asparagine, asparagine-valine, threonine-asparagine, asparagine-threonine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, or asparagine-alanine.

In some examples, $AA^1$-$AA^2$ is lysine-valine-alanine or alanine-valine-lysine.

In some examples, $AA^1$-$AA^2$ is lysine-valine-citrulline or citrulline-valine-lysine.

In some examples, $AA^2$ is valine-citrulline or citrulline-valine.

In some examples, $AA^2$ is valine-alanine or alanine-valine.

In some examples, $AA^1$-$AA^2$ is

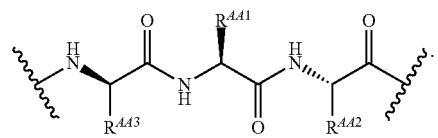

In some of these examples, $R^{AA1}$ is an amino acid side chain, $R^{AA2}$ is an amino acid side chain, and $R^{AA3}$ is an amino acid side chain that is bonded directly or indirectly to a hydrophilic moiety.

In some examples, $R^{AA1}$ is a valine sidechain.

In some examples $R^{AA2}$ is an alanine sidechain.

In some examples, $R^{AA2}$ is a citrulline sidechain.

In some examples, $AA^1$-$AA^2$ is

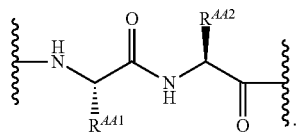

In some of these examples, $R^{AA1}$ is an amino acid side chain, and wherein $R^{AA2}$ is an amino acid side chain.

In some examples, AA² is

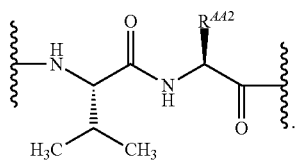

In some examples, AA² is

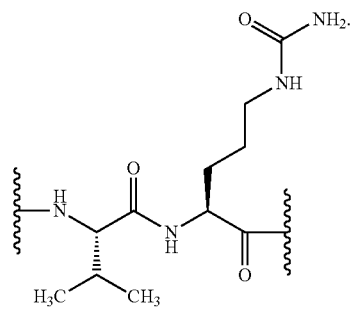 [SMILES: *N[C@H](C(=O)N[C@@H](CCCNC(N)=O)C(*)=O)C(C)C]

In some examples, AA² is

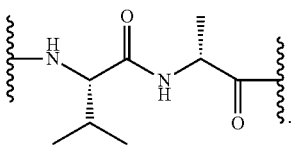 [SMILES: *N[C@H](C(=O)N[C@H](C)C(*)=O)C(C)C]

In some examples, set forth herein is a linker-payload comprising a compound set forth herein.

In some examples, set forth herein is a linker-payload comprising a compound set forth herein bonded to an oxygen or a primary or secondary nitrogen of any compound described herein.

In some examples, set forth herein is an antibody-drug-conjugate comprising the compound or linker-payload set forth herein bonded to an antibody, or an antigen binding fragment thereof.

Conjugates provided here can be prepared from reactive linker-payloads with reactive groups RG as described above and in the Examples section and figures. The reactive linker payloads can be linked to hydrophilic groups and/or binding agents according to the methods described herein, e.g., in the Examples section and figures.

In some embodiments, the reactive linker-payload is:

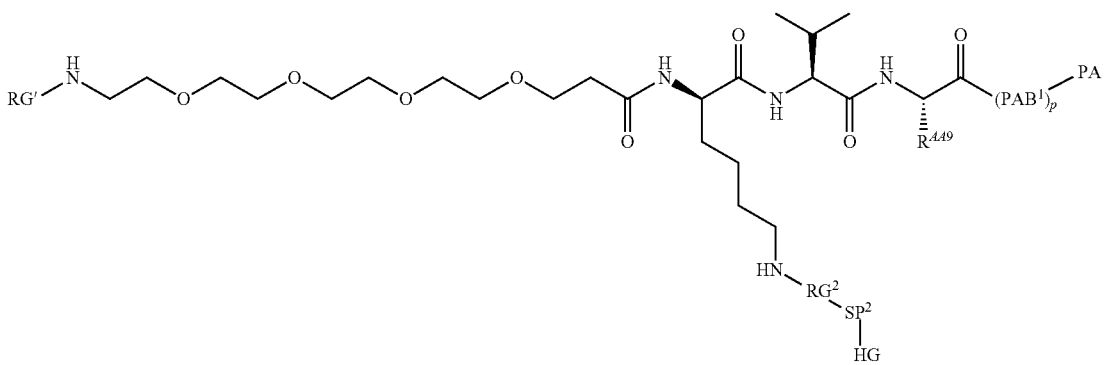

or a pharmaceutically acceptable salt, solvate, or stereoisomeric form thereof, or a regioisomer thereof, wherein PAB¹ is PAB or PABC as described herein; p is 0 or 1; $R^{A49}$ is methyl or —(CH$_2$)$_3$—NH—C(═O)—NH$_2$; and RG', RG², PA, SP² and HG are as defined herein.

In some embodiments, RG' is

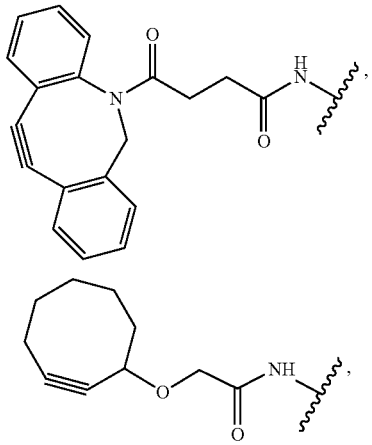

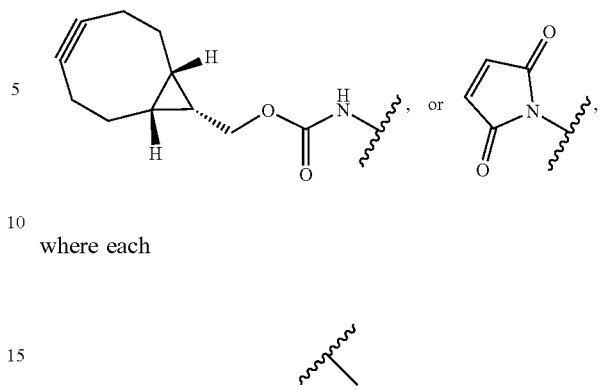

where each indicates the atom through which the group is attached to the rest of the molecule.

In some embodiments, a reactive linker payload is:

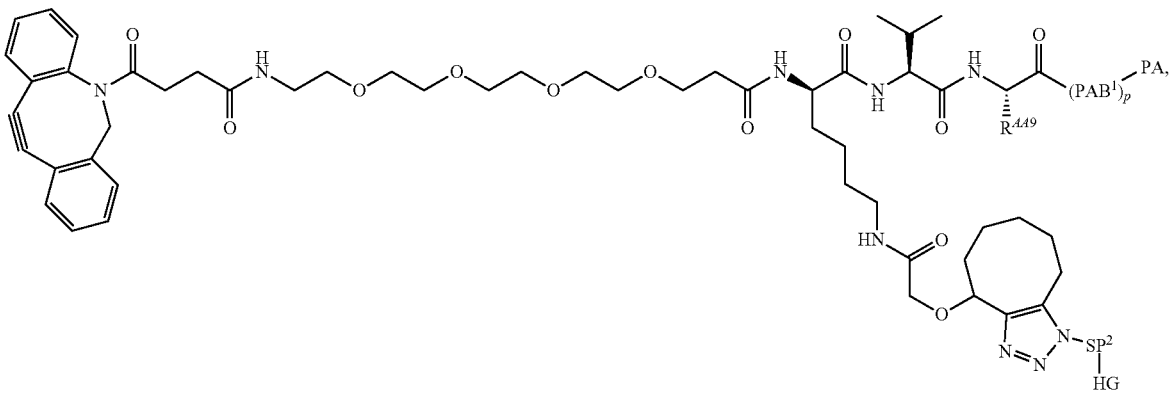

or a pharmaceutically acceptable salt, solvate, or stereoisomeric form thereof, or a regioisomer thereof, wherein $PAB^1$ is PAB or PABC as described herein; p is 0 or 1; $R^{A49}$ is methyl or —$(CH_2)_3$—NH—C(=O)—$NH_2$; and PA, $SP^2$ and HG are as defined herein. In some of these embodiments, HG is a taurine or dualtaurine as defined herein and PA is payload A of FIG. 1. In some of these embodiments, HG is a taurine or dualtaurine as defined herein and PA is payload B of FIG. 1. In some of these embodiments, HG is a taurine or dualtaurine as defined herein and PA is payload C of FIG. 1. In some of these embodiments, HG is a taurine or dualtaurine as defined herein and PA is payload D of FIG. 1. In some of these embodiments, HG is a taurine or dualtaurine as defined herein and PA is payload E of FIG. 1.

In some embodiments, a reactive linker payload is:

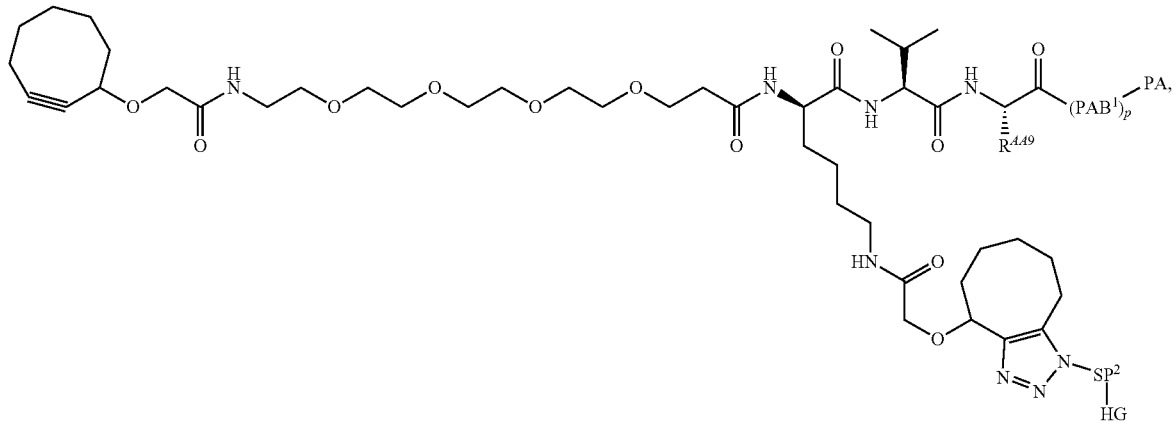

or a pharmaceutically acceptable salt, solvate, or stereoisomeric form thereof, or a regioisomer thereof, wherein $PAB^1$ is PAB or PABC as described herein; p is 0 or 1; $R^{AA9}$ is methyl or $—(CH_2)_3—NH—C(=O)—NH_2$; and PA, $SP^2$ and HG are as defined herein. In some of these embodiments, HG is a taurine or dualtaurine as defined herein and PA is payload A of FIG. 1. In some of these embodiments, HG is a taurine or dualtaurine as defined herein and PA is payload B of FIG. 1. In some of these embodiments, HG is a taurine or dualtaurine as defined herein and PA is payload C of FIG. 1. In some of these embodiments, HG is a taurine or dualtaurine as defined herein and PA is payload D of FIG. 1. In some of these embodiments, HG is a taurine or dualtaurine as defined herein and PA is payload E of FIG. 1.

In some embodiments, a reactive linker payload is:

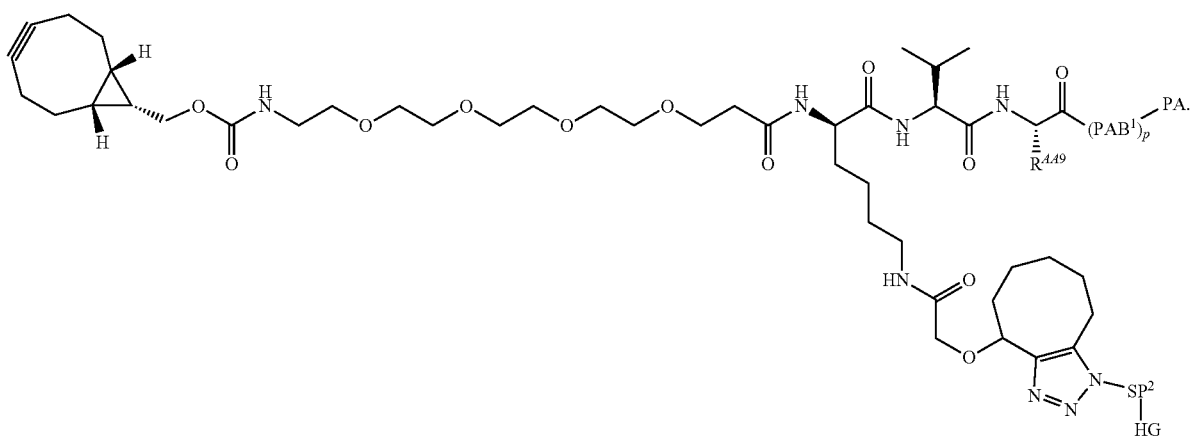

or a pharmaceutically acceptable salt, solvate, or stereoisomeric form thereof, or a regioisomer thereof, wherein $PAB^1$ is PAB or PABC as described herein; p is 0 or 1; $R^{AA9}$ is methyl or $—(CH_2)_3—NH—C(=O)—NH_2$; and PA, $SP^2$ and HG are as defined herein. In some of these embodiments, HG is a taurine or dualtaurine as defined herein and PA is payload A of FIG. 1. In some of these embodiments, HG is a taurine or dualtaurine as defined herein and PA is payload B of FIG. 1. In some of these embodiments, HG is a taurine or dualtaurine as defined herein and PA is payload C of FIG. 1. In some of these embodiments, HG is a taurine or dualtaurine as defined herein and PA is payload D of FIG. 1. In some of these embodiments, HG is a taurine or dualtaurine as defined herein and PA is payload E of FIG. 1.

In some embodiments, a reactive linker payload is:

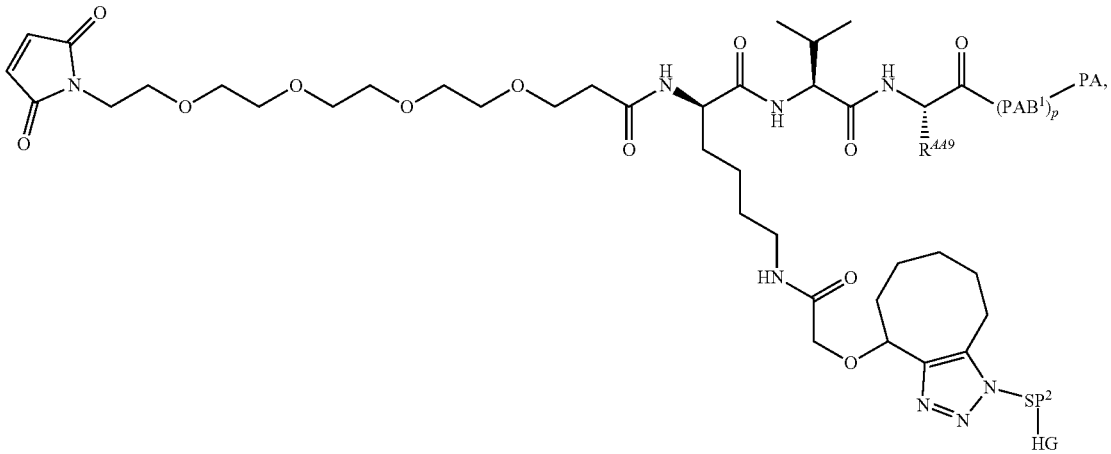

or a pharmaceutically acceptable salt, solvate, or stereoisomeric form thereof, or a regioisomer thereof, wherein $PAB^1$ is PAB or PABC as described herein; p is 0 or 1; $R^{AA9}$ is methyl or —$(CH_2)_3$—NH—C(=O)—$NH_2$; and PA, $SP^2$ and HG are as defined herein. In some of these embodiments, HG is a taurine or dualtaurine as defined herein and PA is payload A of FIG. 1. In some of these embodiments, HG is a taurine or dualtaurine as defined herein and PA is payload B of FIG. 1. In some of these embodiments, HG is a taurine or dualtaurine as defined herein and PA is payload C of FIG. 1. In some of these embodiments, HG is a taurine or dualtaurine as defined herein and PA is payload D of FIG. 1. In some of these embodiments, HG is a taurine or dualtaurine as defined herein and PA is payload E of FIG. 1.

In some embodiments, a reactive linker payload is:

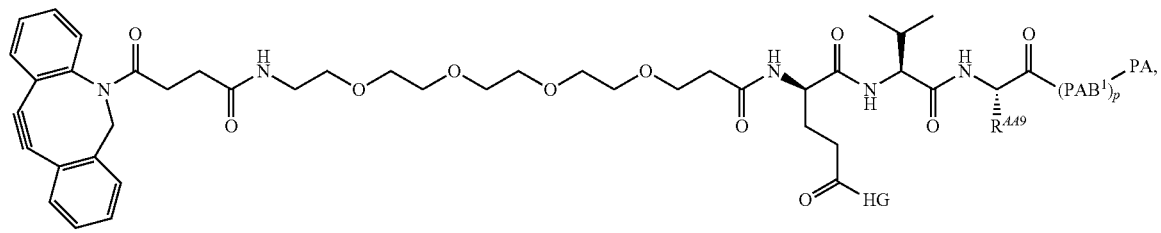

or a pharmaceutically acceptable salt, solvate, or stereoisomeric form thereof, or a regioisomer thereof, wherein $PAB^1$ is PAB or PABC as described herein; p is 0 or 1; $R^{AA9}$ is methyl or —$(CH_2)_3$—NH—C(=O)—$NH_2$; and PA, and HG are as defined herein. In some of these embodiments, HG is a taurine or dualtaurine as defined herein and PA is payload A of FIG. 1. In some of these embodiments, HG is a taurine or dualtaurine as defined herein and PA is payload B of FIG. 1. In some of these embodiments, HG is a taurine or dualtaurine as defined herein and PA is payload C of FIG. 1. In some of these embodiments, HG is a taurine or dualtaurine as defined herein and PA is payload D of FIG. 1. In some of these embodiments, HG is a taurine or dualtaurine as defined herein and PA is payload E of FIG. 1.

In some embodiments, a reactive linker payload is:

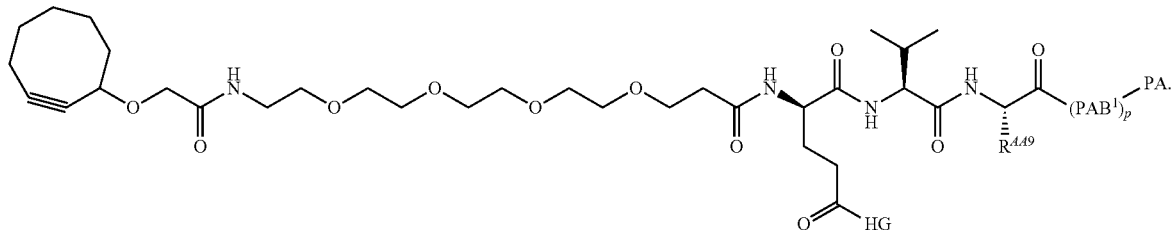

or a pharmaceutically acceptable salt, solvate, or stereoisomeric form thereof, or a regioisomer thereof, wherein PAB$^1$ is PAB or PABC as described herein; p is 0 or 1; R$^{AA9}$ is methyl or —(CH$_2$)$_3$—NH—C(=O)—NH$_2$; and PA, and HG are as defined herein. In some of these embodiments, HG is a taurine or dualtaurine as defined herein and PA is payload A of FIG. 1. In some of these embodiments, HG is a taurine or dualtaurine as defined herein and PA is payload B of FIG. 1. In some of these embodiments, HG is a taurine or dualtaurine as defined herein and PA is payload C of FIG. 1. In some of these embodiments, HG is a taurine or dualtaurine as defined herein and PA is payload D of FIG. 1. In some of these embodiments, HG is a taurine or dualtaurine as defined herein and PA is payload E of FIG. 1.

In some embodiments, a reactive linker payload is:

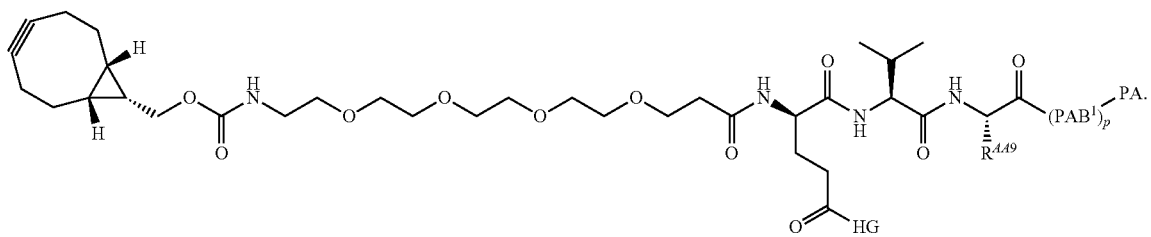

or a pharmaceutically acceptable salt, solvate, or stereoisomeric form thereof, or a regioisomer thereof, wherein PAB$^1$ is PAB or PABC as described herein; p is 0 or 1; R$^{AA9}$ is methyl or —(CH$_2$)$_3$—NH—C(=O)—NH$_2$; and PA, and HG are as defined herein. In some of these embodiments, HG is a taurine or dualtaurine as defined herein and PA is payload A of FIG. 1. In some of these embodiments, HG is a taurine or dualtaurine as defined herein and PA is payload B of FIG. 1. In some of these embodiments, HG is a taurine or dualtaurine as defined herein and PA is payload C of FIG. 1. In some of these embodiments, HG is a taurine or dualtaurine as defined herein and PA is payload D of FIG. 1. In some of these embodiments, HG is a taurine or dualtaurine as defined herein and PA is payload E of FIG. 1.

In some embodiments, a reactive linker payload is:

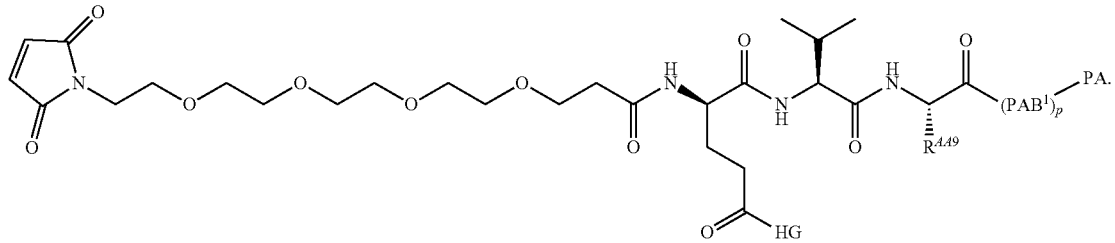

or a pharmaceutically acceptable salt, solvate, or stereoisomeric form thereof, or a regioisomer thereof, wherein $PAB^1$ is PAB or PABC as described herein; p is 0 or 1; $R^{A49}$ is methyl or —$(CH_2)_3$—NH—C(=O)—$NH_2$; and PA, and HG are as defined herein. In some of these embodiments, HG is a taurine or dualtaurine as defined herein and PA is payload A of FIG. 1. In some of these embodiments, HG is a taurine or dualtaurine as defined herein and PA is payload B of FIG. 1. In some of these embodiments, HG is a taurine or dualtaurine as defined herein and PA is payload C of FIG. 1. In some of these embodiments, HG is a taurine or dualtaurine as defined herein and PA is payload D of FIG. 1. In some of these embodiments, HG is a taurine or dualtaurine as defined herein and PA is payload E of FIG. 1.

In any instance of the reactive linker payloads described herein, the reactive linker payload is linked to a binding agent (e.g., Ab or Ab-1 as defined herein) via reaction of an azide (e.g., by click chemistry) with a strained alkyne. In other embodiments, the reactive linker payload is linked to a binding agent (e.g., Ab or Ab-1 as defined herein) via a nucleophilic attack on the succinimide moiety in the reactive linker payload.

In some embodiments, a reactive linker payload is:

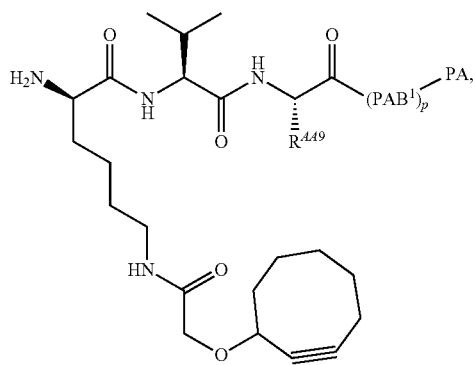

or a pharmaceutically acceptable salt, solvate, or stereoisomeric form thereof, or a regioisomer thereof, wherein $PAB^1$ is PAB or PABC as described herein; p is 0 or 1; $R^{A49}$ is methyl or —$(CH_2)_3$—NH—C(=O)—$NH_2$; and PA is as defined herein. In such instances, a hydrophilic linker comprising an azide is linked to the reactive linker payload via reaction of an azide (e.g., by click chemistry) with a strained alkyne.

Methods of Preparing Compounds

The compounds provided herein can be prepared, isolated, or obtained by any method apparent to those of skill in the art. Exemplary methods of preparation are described in detail in the examples below. In certain embodiments, compounds provided herein can be prepared according to methods described in the Examples and in FIGS. 1-19.

The conjugates described herein can be synthesized by coupling the linker-payloads described herein with a binding agent, for example, an antibody under standard conjugation conditions (see, e.g., Doronina et al. *Nature Biotechnology* 2003, 21, 7, 778, which is incorporated herein by reference in its entirety). When the binding agent is an antibody, the antibody may be coupled to a linker-payload via one or more cysteine or lysine residues of the antibody. Linker-payloads can be coupled to cysteine residues, for example, by subjecting the antibody to a reducing agent, for example, dithiotheritol, to cleave the disulfide bonds of the antibody, purifying the reduced antibody, for example, by gel filtration, and subsequently treating the antibody with a linker-payload containing a suitable reactive moiety, for example, a maleimido group. Suitable solvents include, but are not limited to water, DMA, DMF, and DMSO. Linker-payloads containing a reactive group, for example, an activated ester or acid halide group, can be coupled to lysine residues of the antibody. Suitable solvents include, but are not limited to water, DMA, DMF, and DMSO. Conjugates can be purified using known protein techniques, including, for example, size exclusion chromatography, dialysis, and ultrafiltration/diafiltration.

Binding agents, for example antibodies, can also be conjugated via click chemistry reactions. In some embodiments of said click chemistry reactions, the linker-payload includes a reactive group, for example an alkyne, that is capable of undergoing a 1,3-cycloaddition reaction with an azide. Such suitable reactive groups are described above. The antibody includes one includes one or more azide groups. Such antibodies include antibodies functionalized with, for example, azido-polyethylene glycol groups. In certain embodiments, such functionalized antibody is derived by treating an antibody having at least one glutamine residue, for example, heavy chain Gln295, with a primary amine compound in the presence of the enzyme transglutaminase. Such antibodies may also include Asn297Gln (N297Q) mutants. In certain embodiments, such functionalized antibody is derived by treating an antibody having at least two glutamine residues, for example, heavy chain Gln295 and heavy chain Gln297, with a primary amine compound in the presence of the enzyme transglutaminase. Such antibodies include Asn297Gln (N297Q) mutants. In certain embodiments, the antibody has two heavy chains as described in this paragraph for a total of two or a total of four glutamine residues. In certain instances, antibodies to be conjugated contain one or more additional naturally occurring Glutamine residues in their variable regions, which can be accessible to transglutaminase and therefore are able to be conjugated, for instance Gln55 (Q55). In these instances, the antibodies after conjugation via transglutaminase may have a DAR value higher than 4. Such antibodies include Asn297Gln (N297Q) mutants. In some embodiments, the antibody has two heavy chains as described in this paragraph for a total of two or a total of four or a total of five or six glutamine residues.

In certain embodiments, the antibody comprises a glutamine residue at one or more heavy chain positions numbered 295 in the EU numbering system. In the present disclosure, this position is referred to as glutamine 295, or as Gln295, or as Q295. Those of skill will recognize that this is a conserved glutamine residue in the wild type sequence of many antibodies. In other useful embodiments, the antibody can be engineered to comprise a glutamine residue. Techniques for modifying an antibody sequence to include a glutamine residue are within the skill of those in the art (see, e.g., Ausubel et al. *Current Protoc. Mol. Biol.*).

In certain embodiments, the antibody comprises two glutamine residues, one in each heavy chain. In particular embodiments, the antibody comprises a Q295 residue in each heavy chain. In further embodiments, the antibody comprises one, two, three, four, five, six, seven, eight, or more glutamine residues. These glutamine residues can be in heavy chains, light chains, or in both heavy chains and light chains. These glutamine residues can be wild-type residues, or engineered residues. The antibodies can be prepared according to standard techniques. In certain embodiments, the antibodies comprise a Q55 residue.

Those of skill will recognize that antibodies are often glycosylated at residue N297, near residue Q295 in a heavy chain sequence. Glycosylation at residue N297 can interfere with a transglutaminase at residue Q295 (Dennler et al., supra). Accordingly, in advantageous embodiments, the antibody is not glycosylated. In certain embodiments, the antibody is deglycoslated or aglycosylated. In particular embodiments, an antibody heavy chain has an N297 mutation. Alternatively stated, the antibody is mutated to no longer have an asparagine residue at position 297. In particular embodiments, an antibody heavy chain has an N297Q mutation. Such an antibody can be prepared by site-directed mutagenesis to remove or disable a glycosylation sequence or by site-directed mutagenesis to insert a glutamine residue at a site apart from any interfering glycosylation site or any other interfering structure. Such an antibody also can be isolated from natural or artificial sources.

The antibody without interfering glycosylation is then treated with a primary amine compound. In certain embodiments, an aglycosylated antibody is treated with a primary amine compound to produce a glutaminyl-modified antibody. In certain embodiments, a deglycosylated antibody is reacted with a primary amine compound to produce a glutaminyl-modified antibody.

The primary amine can be any primary amine that is capable of forming a covalent bond with a glutamine residue in the presence of a transglutaminase. Useful primary amines are described herein. The transglutaminase can be any transglutaminase deemed suitable by those of skill in the art. In certain embodiments, the transglutaminase is an enzyme that catalyzes the formation of an isopeptide bond between a free amine group on the primary amine compound and the acyl group on the side chain of a glutamine residue. Transglutaminase is also known as protein-glutamine-γ-glutamyltransferase. In particular embodiments, the transglutaminase is classified as EC 2.3.2.13. The transglutaminase can be from any source deemed suitable. In certain embodiments, the transglutaminase is microbial. Useful transglutaminases have been isolated from *Streptomyces mobaraense, Streptomyces cinnamoneum, Streptomyces griseo-carneum, Streptomyces lavendulae*, and *Bacillus subtilis*. Non-microbial transglutaminases, including mammalian transglutaminases, can also be used. In certain embodiments, the transglutaminase can be produced by any technique or obtained from any source deemed suitable by the practitioner of skill. In particular embodiments, the transglutaminase is obtained from a commercial source.

In particular embodiments, the primary amine compound comprises a reactive group capable of further reaction after transglutamination. In these embodiments, the glutaminyl-modified antibody can be reacted or treated with a reactive payload compound or a reactive linker-payload compound to form an antibody-payload conjugate. In certain embodiments, the primary amine compound comprises an azide as described herein.

In certain embodiments, the glutaminyl-modified antibody is reacted or treated with a reactive linker-payload to form an antibody-payload conjugate. The reaction can proceed under conditions deemed suitable by those of skill in the art. In certain embodiments, the glutaminyl-modified antibody is contacted with the reactive linker-payload compound under conditions suitable for forming a bond between the glutaminyl-modified antibody and the linker-payload compound. Suitable reaction conditions are well known to those in the art.

Examples of such reactions are provided in the Examples below.

In some examples, set forth herein is a method of making a conjugate comprising treating or contacting a compound with a binding agent under coupling conditions, wherein the compound comprises a reactive linker bonded to at least one payload moiety and linked to at least one cyclodextrin moiety via a covalent linker, wherein said covalent linker is bonded directly or indirectly to each of the reactive linker, the payload moiety, the cyclodextrin moiety. In some examples, the compound which reacts with a binding agent is a compound according to Formula (VI):

(VI)

or a pharmaceutically acceptable salt, solvate, stereoisomer, or derivative thereof,
wherein RG' is a reactive group; L is a trivalent linker; HL is a hydrophilic residue; and PA is a payload residue.

In some examples, the binding agent that reacts with a compound of Formula (II) is an antibody or an antigen binding fragment thereof.

In some examples, herein, the D-Lys can be replaced with a reagent set forth in FIG. 20.

In some examples, the cyclodextrin-containing moieties may react in a bioorthogonal reaction selected from a [3+2] click reaction, a Diels-Alder reaction, a reductive-amination, a photoclick reaction, or other reactions.

Other useful bioorthogonal reactions suitable for use with the methods herein include, but are not limited to, the Staudinger ligation, a click reaction, a tetrazine ligation, and a photoclick reaction.

The following reference shows example reactions and reagents that may be used with the bioorthogonal reactions set forth herein: Zheng, Mengmeng, et al., *Molecules* 2015, 20, 3190-3205, the contents of which are herein incorporated by reference in their entirety for all purposes.

Pharmaceutical Compositions and Methods of Treatment

Provided herein are methods of treating and preventing diseases, conditions, or disorders comprising administering a therapeutically or prophylactically effective amount of one or more of the compounds disclosed herein, for example, one or more of the compounds of a formula provided herein. A person of skill will appreciate that the diseases, disorders, and/or conditions include, but are not limited to, those associated with the antigens listed herein.

The compounds described herein can be administered alone or together with one or more additional therapeutic agents. The one or more additional therapeutic agents can be administered just prior to, concurrent with, or shortly after the administration of the compounds described herein. The present disclosure also includes pharmaceutical compositions comprising any of the compounds described herein in combination with one or more additional therapeutic agents, and methods of treatment comprising administering such combinations to subjects in need thereof.

Suitable additional therapeutic agents include, but are not limited to: a second glucocorticoid, an autoimmune therapeutic agent, a hormone, a biologic, or a monoclonal antibody. Suitable therapeutic agents also include, but are not limited to any pharmaceutically acceptable salts, acids, or derivatives of a compound set forth herein.

In some embodiments of the methods described herein, multiple doses of a compound described herein (or a pharmaceutical composition comprising a combination of a compound described herein and any of the additional therapeutic agents mentioned herein) may be administered to a subject over a defined time course. The methods according to this aspect of the disclosure comprise sequentially administering to a subject multiple doses of a compound described herein. As used herein, "sequentially administering" means that each dose of the compound is administered to the subject at a different point in time, e.g., on different days separated by a predetermined interval (e.g., hours, days, weeks or months).

The present disclosure includes methods which comprise sequentially administering to the patient a single initial dose of a compound described herein, followed by one or more secondary doses of the compound, and optionally followed by one or more tertiary doses of the compound.

The terms "initial dose," "secondary doses," and "tertiary doses," refer to the temporal sequence of administration of the compounds described herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses can all contain the same amount the compound described herein, but generally can differ from one another in terms of frequency of administration. In certain embodiments, the amount of the compound contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose the compound which is administered to a patient prior to the administration of the very next dose in the sequence with no intervening doses.

The methods according to this aspect of the disclosure may comprise administering to a patient any number of secondary and/or tertiary doses of the compound. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the disclosure, if the loading doses are administered at a frequency of once a month, then the maintenance doses may be administered to the patient once every six weeks, once every two months, once every three months, etc.

The present disclosure includes pharmaceutical compositions of the compounds and/or conjugates described herein, e.g., the compounds of Formula (I), Formula (II), Formula (III), Formula (IV), Formula (IVa), Formula (IVb), Formula (IVc), Formula (Va), Formula (Vb), Formula (Vc), or Formula (Vd), e.g., compositions comprising a compound described herein, a salt, stereoisomer, polymorph thereof, and a pharmaceutically acceptable carrier, diluent, and/or excipient. Examples of suitable carriers, diluents and excipients include, but are not limited to, buffers for maintenance of proper composition pH (e.g., citrate buffers, succinate buffers, acetate buffers, phosphate buffers, lactate buffers, oxalate buffers, and the like), carrier proteins (e.g., human serum albumin), saline, polyols (e.g., trehalose, sucrose, xylitol, sorbitol, and the like), surfactants (e.g., polysorbate 20, polysorbate 80, polyoxolate, and the like), antimicrobials, and antioxidants.

In some examples, set forth herein is a method of treating a disease, disorder or condition comprising administering to a patient having said disorder a therapeutically effective amount of a compound of Formula (I), Formula (II), Formula (III), Formula (IV), Formula (IVa), Formula (IVb), Formula (IVc), Formula (Va), Formula (Vb), Formula (Vc), or Formula (Vd), or a pharmaceutical composition thereof.

In some examples, set forth herein is a method of preventing a disease, disorder or condition comprising administering to a patient having said disorder a prophylactically effective amount of a compound of Formula (I), Formula (II), Formula (III), Formula (IV), Formula (IVa), Formula (IVb), Formula (IVc), Formula (Va), Formula (Vb), Formula (Vc), or Formula (Vd), or a pharmaceutical composition thereof.

In some examples, set forth herein is a method of treating or preventing a disease, disorder, or condition selected from the group consisting of a proliferative disorder, a neurodegenerative disorder, an immunological disorder, an autoimmune disease, an inflammatory disorder, a dermatological disease, a metabolic disease, cardiovascular disease, and a gastrointestinal disease.

Provided herein are methods for modulating LDLR (low-density lipoprotein receptor) protein expression or cholesterol efflux in a cell comprising contacting said cell with an antibody drug conjugate (ADC), wherein the ADC comprises an antibody targeting said cell, hydrophilic residue, and LXR agonist.

The proliferative disorder can be any proliferative disorder known to those of skill. In certain embodiments, proliferative disorders include, without limitation, oncology disorders, where the oncology disorder can be any cancer disorder known to those of skill. In certain embodiments, provided herein are methods of treating or preventing a melanoma. In certain embodiments, provided herein are methods of treating or preventing metastatic melanoma. In certain embodiments, provided herein are methods of treating or preventing lung cancer. In certain embodiments, provided herein are methods of treating or preventing EGFR-tyrosine kinase inhibitor resistant lung cancer. In certain embodiments, provided herein are methods of treating or preventing oral cancer. In certain embodiments, provided herein are methods of treating or preventing oral squamous cell carcinoma. In certain embodiments, provided herein are methods of treating or preventing prostate cancer. In certain embodiments, provided herein are methods of treating or preventing Hodgkin's lymphoma. In certain embodiments, provided herein are methods of treating or preventing breast cancer.

The neurodegenerative disorder can be any neurodegenerative disorder known to those of skill. In certain embodiments, provided herein are methods of treating or preventing Alzheimer's disease. In certain embodiments, provided herein are methods of treating or preventing Parkinson's disease. In certain embodiments, provided herein are methods of treating or preventing Huntington's disease. In certain embodiments, provided herein are methods of treating or preventing amyotrophic lateral sclerosis. In certain embodiments, provided herein are methods of treating or preventing myelin gene expression. In certain embodiments, provided herein are methods of treating or preventing myelination and remyelination conditions, diseases, or disorders.

The immunological disorder can be any immunological disorder known to those of skill. In certain embodiments, provided herein are methods of treating or preventing inflammatory bowel disease. In certain embodiments, provided herein are methods of treating or preventing ulcerative colitis. In certain embodiments, provided herein are methods of treating or preventing Crohn's disease.

The inflammatory disorder can be any inflammatory disorder known to those of skill. In certain embodiments, provided herein are methods of treating or preventing arthritis. In certain embodiments, provided herein are methods of treating or preventing rheumatoid arthritis.

The metabolic disease can be any metabolic disease known to those of skill. In certain embodiments, dyslipidemia is selected from the group consisting of hyperlipidemia, hypercholesterolemia, hypertriglyceridemia, hyperlipoproteinemia, HDL deficiency, ApoA-I deficiency, and cardiovascular disease such as coronary artery disease (including, for example, treatment and prevention of angina, myocardial infarction and sudden cardiac death); atherosclerosis (including, for example, treatment and prevention of atherosclerosis); and restenosis (including, for example, preventing or treating atherosclerotic plaques which develop as a consequence of medical procedures such as balloon angioplasty). In certain embodiments, provided herein are methods of treating or preventing diabetes.

The cardiovascular disease can be any cardiovascular disease known to those of skill. In certain embodiments, provided herein are methods of treating or preventing atherosclerosis. In certain embodiments, provided herein are methods of treating or preventing atherosclerosis derived from abnormal macrophage processing. In certain embodiments, provided herein are methods of treating or preventing atherosclerosis derived from the formation of oxidized low-density lipoproteins (oxLDLs), where marcrophages fail to process oxLDLs. In certain embodiments, provided herein are methods of treating or preventing ischemic heart disease. In certain embodiments, provided herein are methods of treating or preventing stroke. In certain embodiments, provided herein are methods of treating or preventing hypertensive heart disease. In certain embodiments, provided herein are methods of treating or preventing aortic aneurysm. In certain embodiments, provided herein are methods of treating or preventing endocarditis. In certain embodiments, provided herein are methods of treating or preventing peripheral artery disease. In certain embodiments, provided herein are methods of treating or preventing combinations of any of the diseases provided in this paragraph.

In some examples, set forth herein is a method for modulating the function of a nuclear receptor. By way of non-limiting example, the function may be selected from expression/secretion of inflammatory mediators (e.g. cytokines, chemokines), cholesterol regulation, cholesterol intake, cholesterol efflux, cholesterol oxidation, migration, chemotaxis, apoptosis and necrosis, an inflammatory activity, lipid regulation, apoptosis, migration, chemotaxis, gene transcription, and protein expression.

In some examples, set forth herein is a method of treating a disease or disorder in a patient in need thereof comprising administering to the patient a compound or pharmaceutical composition set forth herein. In some examples, the administered compound is an antibody-drug conjugate set forth herein.

In some examples, set forth herein is a method of an antibody-drug conjugate comprising the step of contacting a binding agent with a linker-payload compound under conditions suitable for forming a bond between the binding agent and the compound.

In some examples, set forth herein is a method of treating a proliferative disease, a metabolic disease, inflammation, or a neurodegenerative disease in a subject comprising administering to the subject of an effective treatment amount of a compound or pharmaceutical composition set forth herein. In some examples, the administered compound is an antibody-drug conjugate set forth herein.

In some examples, set forth herein is a method of treating a disease, disorder, or condition in a subject comprising administering to the subject of an effective treatment amount of a compound or pharmaceutical composition set forth herein. In some examples, the administered compound is an antibody-drug conjugate set forth herein.

In some examples, set forth herein is a method of treating a proliferative disease in a subject comprising administering to the subject of an effective treatment amount of a compound or pharmaceutical composition set forth herein. In some examples, the administered compound is an antibody-drug conjugate set forth herein.

In some examples, set forth herein is a method of treating a metabolic disease in a subject comprising administering to the subject of an effective treatment amount of a compound or pharmaceutical composition set forth herein. In some examples, the administered compound is an antibody-drug conjugate set forth herein.

In some examples, set forth herein is a method of treating inflammation in a subject comprising administering to the subject of an effective treatment amount of a compound or pharmaceutical composition of set forth herein. In some examples, the administered compound is an antibody-drug conjugate set forth herein.

In some examples, set forth herein is a method of treating a neurodegenerative disease in a subject comprising administering to the subject of an effective treatment amount of a compound or pharmaceutical composition set forth herein. In some examples, the administered compound is an antibody-drug conjugate set forth herein.

EXAMPLES

Reagents and solvents were obtained from commercial sources such as Sinopharm Chemical Reagent Co. (SCRC), Sigma-Aldrich, Alfa, or other vendors, unless explicitly stated otherwise.

1H NMR and other NMR spectra were recorded on a Bruker AVIII 400 or Bruker AVIII 500. The data were processed with Nuts software or MestReNova software, measuring proton shifts in parts per million (ppm) downfield from an internal standard tetramethylsilane (TMS).

HPLC-MS measurements were run on an Agilent 1200 HPLC/6100 SQ System using the follow conditions:

Method A for HPLC-MS measurements included, as the Mobile Phase: A: Water (0.01% trifluoroacetic acid (TFA)), B: acetonitrile (0.01% TFA); Gradient Phase: 5% of B increased to 95% of B within 15 minutes (min); Flow Rate: 1.0 mL/min; Column: SunFire C18, 4.6×50 mm, 3.5 µm; Column Temperature: 50° C. Detectors: Analog to Digital Converter (ADC) Evaporative Light-scattering Detector (ELSD), Diode array detector (DAD) (214 nm and 254 nm), electrospray ionization-atmospheric ionization (ES-API).

Method B for HPLC-MS measurements included, as the Mobile Phase: A: Water (10 mM $NH_4HCO_3$), B: acetonitrile; Gradient Phase: 5% to 95% of B within 15 min; Flow Rate: 1.0 mL/min; Column: XBridge C18, 4.6×50 mm, 3.5 µm; Column Temperature: 50° C. Detectors: ADC ELSD, DAD (214 nm and 254 nm), mass selective detector (MSD) (ES-API).

LC-MS measurements were run on an Agilent 1200 HPLC/6100 SQ System using the following conditions:

Method A for LC-MS measurements included, as the Instrument: WATERS 2767; column: Shimadzu Shim-Pack, PRC-ODS, 20×250 mm, 15 µm, two connected in series; Mobile Phase: A: Water (0.01% TFA), B: acetonitrile (0.01% TFA); Gradient Phase: 5% of B increased to 95% of B within 3 min; Flow Rate: 1.8-2.3 mL/min; Column: SunFire C18, 4.6×50 mm, 3.5 µm; Column Temperature: 50° C. Detectors: ADC ELSD, DAD (214 nm and 254 nm), ES-API.

Method B for LC-MS measurement included, as the Instrument: Gilson GX-281; column: Xbridge Prep C18 10 µm OBD, 19×250 mm; Mobile Phase: A: Water (10 mM NH4HCO3), B: Acetonitrile; Gradient Phase: 5% to 95% of B within 3 min; Flow Rate: 1.8-2.3 mL/min; Column: XBridge C18, 4.6×50 mm, 3.5 µm; Column Temperature: 50° C. Detectors: ADC ELSD, DAD (214 nm and 254 nm), MSD (ES-API).

Preparative high-pressure liquid chromatography (Prep-HPLC) in an acidic (Method A) or basic (Method B) solvent system was utilized on a Gilson GX-281 instrument. The acidic solvent system used a Waters SunFire 10 µm C18 column (100 Å, 250×19 mm), and solvent A for prep-HPLC was water/0.05% TFA and solvent B was acetonitrile. The elution conditions were a linear gradient increase of solvent B from 5% to 100% over a time period of 20 min at a flow rate of 30 mL/min. The basic solvent system included a Waters Xbridge 10 µm C18 column (100 Å, 250×19 mm), and solvent A used for prep-HPLC was water/10 mM ammonium bicarbonate ($NH_4HCO_3$) and solvent B was acetonitrile. The elution conditions were a linear gradient increase of solvent B from 5% to 100% over a time period of 20 min at a flow rate of 30 mL/min.

Flash chromatography was performed on a Biotage instrument, with Agela Flash Column silica-CS cartridges; Reversed phase flash chromatography was performed on Biotage instrument, with Boston ODS or Agela C18 cartridges.

Analytical chiral HPLC method—SFC conditions
Instrument: SFC Method Station (Thar, Waters)
Column: CHIRALPAK AD-H/AS-H/OJ-H/OD-H 4.6× 100 mm, 5 µm (Daicel)
Column temperature: 40° C.
Mobile phase: CO2/IPA (0.1% DEA)=55/45
Flow: 4.0 ml/min
Back Pressure: 120 Bar
Injection volume: 2 µL
Preparative chiral HPLC method—SFC conditions
Instrument: SFC-80 (Thar, Waters)
Column: CHIRALPAK AD-H/AS-H/OJ-H/OD-H 20×250 mm, 10 µm (Daicel)
Column temperature: 35° C.
Mobile phase: CO2/IPA (0.2% Methanol Ammonia)=30/70
Flow rate: 80 g/min
Back pressure: 100 bar
Detection wavelength: 214 nm
Cycle time: 6.0 min
Sample solution: 1500 mg dissolved in 70 mL Methanol
Injection volume: 2 mL (loading: 42.86 mg/injection)

As used herein, the symbols and conventions used in these processes, schemes, and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the Examples and throughout the specification:

Specifically, but without limitation, the following abbreviations may be used in the Examples and throughout the specification:

| Abbreviation | Term |
| --- | --- |
| ADC | Antibody-drug conjugate |
| Aglycosylated antibody | Antibody does not have any glycan |
| aq | Aqueous |
| Boc | N-tert-butoxycarbonyl |
| BupH ™ | Thermo Scientific Prod# 28372, containing 100 mM sodium phosphate and 150 mM sodium chloride, potassium free, pH was adjusted from 7.2 to 7.6-7.8 MQ, unless otherwise noted. |
| COT | Cyclooctynol |
| Da | Dalton |
| DAR | Drug to antibody ratio. |
| DCM | Dichloromethane |
| DIBAC | Dibenz[b,f]azocine, 11,12-didehydro-5,6-dihydro- or Dibenzocyclooctyne or Dibenz[b,f]azocine-5(6H)-butanoic acid, 11,12-didehydro |
| DIBAC-Suc | Dibenz[b,f]azocine-5(6H)-butanoic acid, 11,12-didehydro |
| BCN | Bicyclo[6.1.0]nonyne |
| MAL | Maleimide |
| COT | Cyclooctynol |
| DIBACT | 3H-Benzo[c]-1,2,3-triazolo[4,5-e][1]benzazocine, 8,9-dihydro- |

-continued

| Abbreviation | Term |
|---|---|
| DIPEA | Diisopropylethylamine |
| DMF | N,N-dimethylformamide |
| DMSO | Dimethylsulfoxide |
| ESI | Electrospray ionization |
| Fmoc | Fluorenylmethyloxycarbonyl |
| Fmoc-vcPAB-PNP | N-Fmoc-L-valine-L-citrulline-p-aminobenzyl alcohol p-nitrophenyl carbonate |
| g | Gram |
| HATU | 2-(7-Aza-1H-benzotriazole-1-yl)-1,1,3,3-tetramethyluronium hexafluorophosphate |
| HC | Heavy chain of immunoglobulin |
| HEK | Human embryonic kidney (cells) |
| HPLC | High performance liquid chromatography |
| hr or hrs | Hours |
| LC | Light chain of immunoglobulin |
| LC | Liquid chromatography |
| MC | Maleimidocaproyl |
| mg | milligrams |
| min | minutes |
| mL | milliliters |
| mM | millimolar |
| MMAE | Monomethyl auristatin E |
| MS | Mass spectrometry |
| MSD | Mass-selective detector |
| MTG | Microbial transglutaminase (MTG EC 2.3.2.13, Zedira, Darmstadt, Germany) |
| MW | Molecular weight |
| ncADC | Non-Cytotoxic antibody drug conjugation |
| NHS | N-hydroxy succinimide |
| nM | nanomolar |
| NMR | Nuclear magnetic resonance |
| NOESY | Nuclear Overhauser effect spectroscopy |
| PAB | Para-aminobezyloxy(carbonyl) |
| PBS | 10 mM sodium phosphate buffer and 150 mM sodium chloride |
| PBSg | 10 mM phosphate, 150 mM sodium chloride, 5% glycerol |
| PEG | Polyethyleneglycol |
| ppm | Parts per million (chemical shift) |
| RP | Reversed phase |
| RT | Room temperature |
| SDS-PAGE | Sodium dodecylsulfate polyacrylamide gel electrophoresis |
| SEC | Size exclusion chromatography |
| Suc | Succinic acid |
| TCEP | Tris(2-carboxyethyl)phosphine hydrochloride |
| TEA | Triethylamine |
| TFA | Trifluoroacetic acid |
| TG | Transglutaminase |
| THF | Tetrahydrofuran |
| TOF | Time-of-flight |
| UPLC | Ultra Performance Liquid Chromatography |
| UV | Ultraviolet |
| VA | Valine-Aniline |
| VC | Valine-citrulline |
| μL | microliters |
| μM | micromolar |

Preparation Methods

TABLE 1

List of payloads

Figure 4:
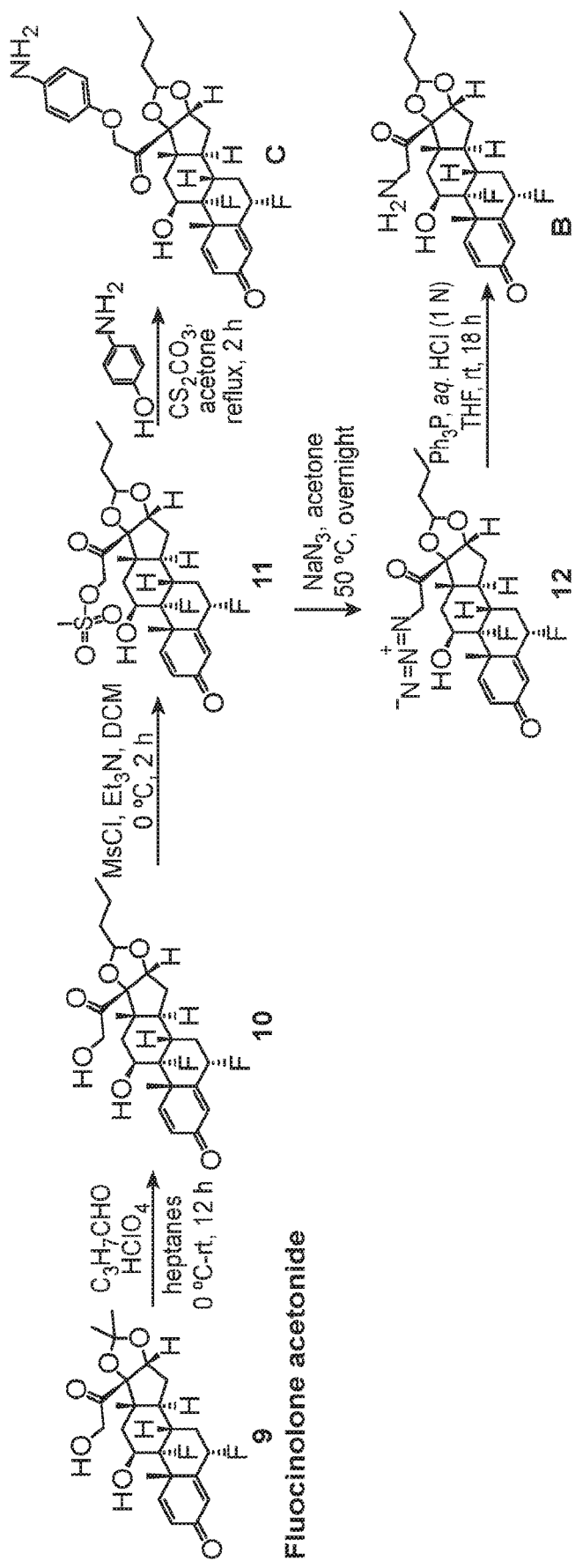
FIG. 4 shows a synthetic process for preparing payloads B and C.

| # | Structure | HPLC purity | cLogP | MF | MW (Cal.) | MS (M+H) | Synthesis |
|---|---|---|---|---|---|---|---|
| A | 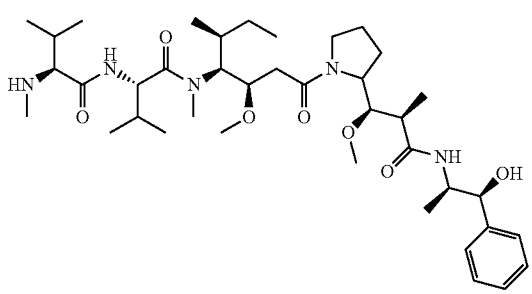 [SMILES: CC[C@H](C)[C@@H]([C@@H](CC(=O)N1CCCC1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C] | >95 | 3.51 | $C_{39}H_{67}N_5O_7$ | 717.98 | N.D. | Commercial |
| B | 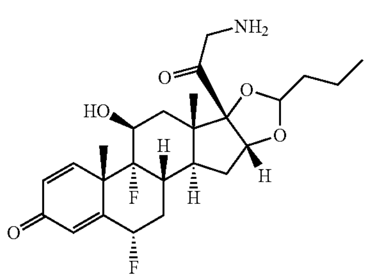 | 98 | 2.33 | $C_{25}H_{33}F_2NO_5$ | 465.54 | 466.2 | FIG. 4 |

TABLE 1-continued

List of payloads

Figure 5:
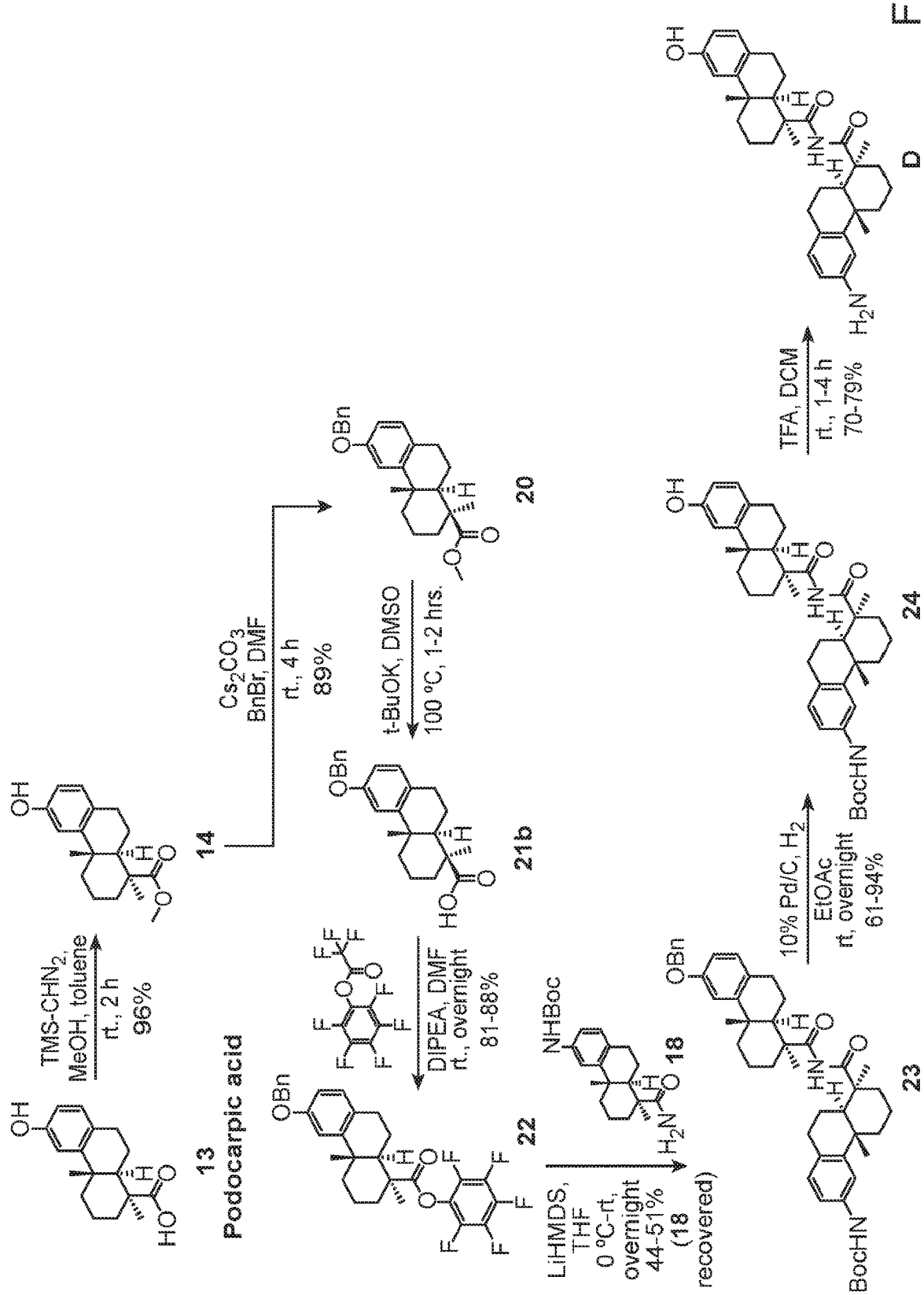
FIG. 5 shows a synthetic process for preparing payload D.

| # | Structure | HPLC purity | cLogP | MF | MW (Cal.) | MS (M +H) | Synthesis |
|---|---|---|---|---|---|---|---|
| C | 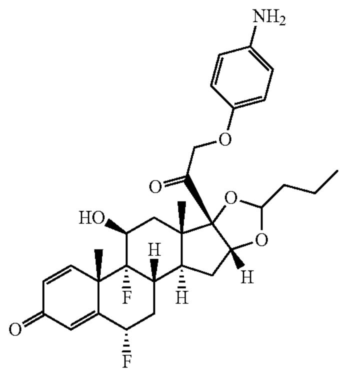 | 97 | 3.94 | $C_{31}H_{37}F_2NO_6$ | 557.63 | 558.2 | FIG. 4 |
| D | 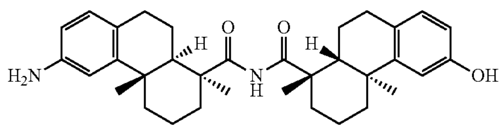 [SMILES: C[C@]1(C(=O)NC(=O)[C@@]2(C)CCC[C@]3(C)c4cc(O)ccc4CC[C@@H]23)CCC[C@]2(C)c3cc(N)ccc3CC[C@@H]12] | >95 | 7.28 | $C_{34}H_{44}N_2O_3$ | 528.72 | 529.3 | FIG. 5 |
| E | 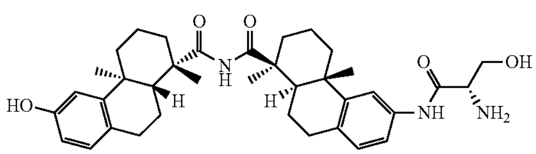 [SMILES: C[C@]1(C(=O)NC(=O)[C@@]2(C)CCC[C@]3(C)c4cc(NC(=O)[C@@H](N)CO)ccc4CC[C@@H]23)CCC[C@]2(C)c3cc(O)ccc3CC[C@@H]12] | 92 | 5.94 | $C_{37}H_{49}N_3O_4$ | 615.8 | 616.3 | FIG. 5 |

TABLE 2

List of charged linker payloads

| LP | Ex | Payload | Linker name | Structure |
|---|---|---|---|---|
| Ia | 17 | MMAE | DIBAC-PEG$_4$-dLys(COT-PEG$_6$)-vcPAB | |
| Ib | 17A | MMAE | DIBAC-PEG$_4$-dLys(COT-PEG$_4$-N$^+$Me$_3$)-vcPAB | 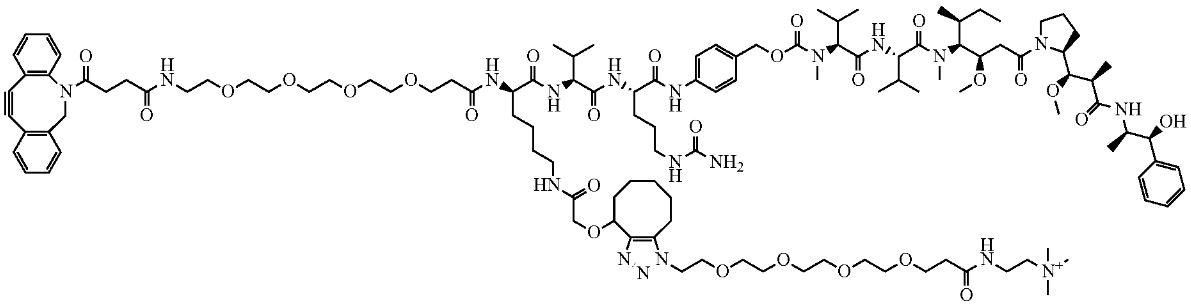 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCCCNC(=O)COC2CCCCCc3c2nnn3CCOCCOCCOCCOCCC(=O)NCC[N+](C)(C)C)NC(=O)CCOCCOCCOCCOCCNC(=O)CCC(=O)N2Cc3ccccc3C#Cc3ccccc32)C(C)C)cc1)C(C)C] |
| Ic | 18 | MMAE | DIBAC-PEG$_4$-dLys(COT-PEG$_4$-taurine)-vcPAB | 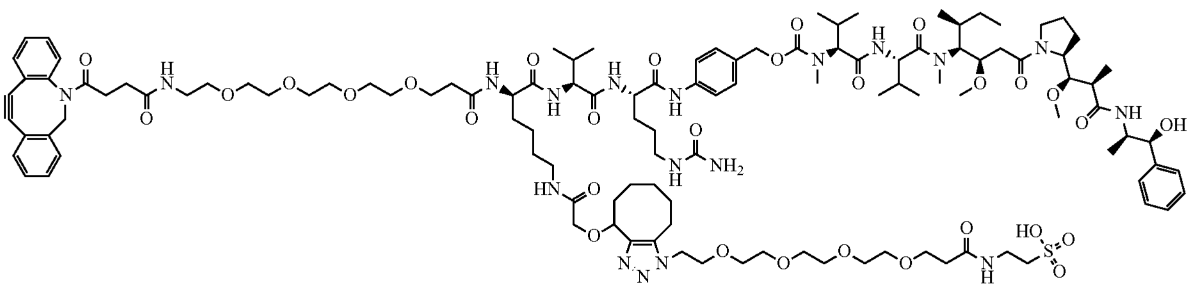 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCCCNC(=O)COC2CCCCCc3c2nnn3CCOCCOCCOCCOCCC(=O)NCCS(=O)(=O)O)NC(=O)CCOCCOCCOCCOCCNC(=O)CCC(=O)N2Cc3ccccc3C#Cc3ccccc32)C(C)C)cc1)C(C)C] |

TABLE 2-continued

List of charged linker payloads

| LP Id | Ex | Payload | Linker name | Structure |
|---|---|---|---|---|
| Id-1 | 18A | MMAE | DIBAC-PEG$_4$-dLys(COT-PEG$_6$-phosphate)-vcPAB | |
| Ie-1 | 18B | MMAE | DIBAC-PEG-hd 4-dLys(COT-galactose)-vcPAB | 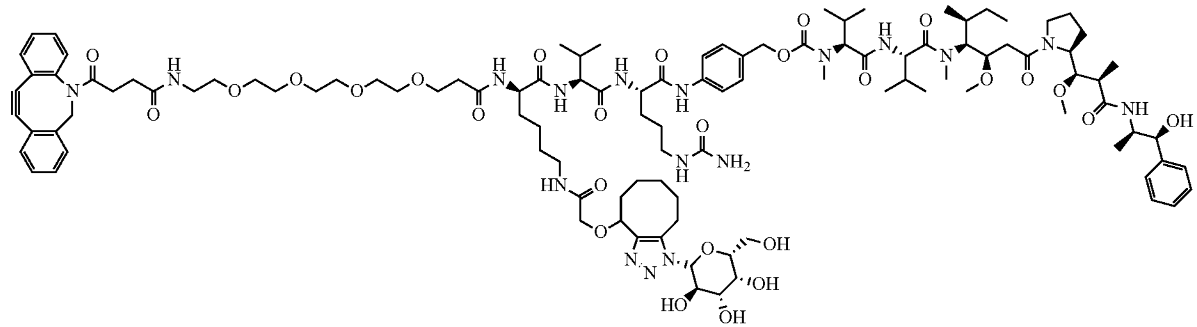 |
| If-1 | 18C | MMAE | MAL-PEG$_4$-dLys(COT-galactose)-vcPAB | 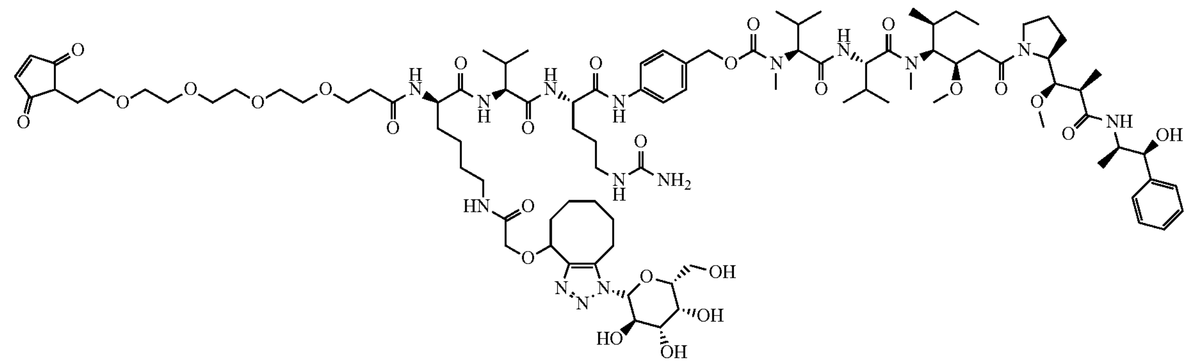 |

TABLE 2-continued

List of charged linker payloads

| LP | Ex | Payload | Linker name | Structure |
|---|---|---|---|---|
| Ig | 18D | MMAE | DIBAC-PEG$_4$-dGlu(glucamide)-vcPAB | 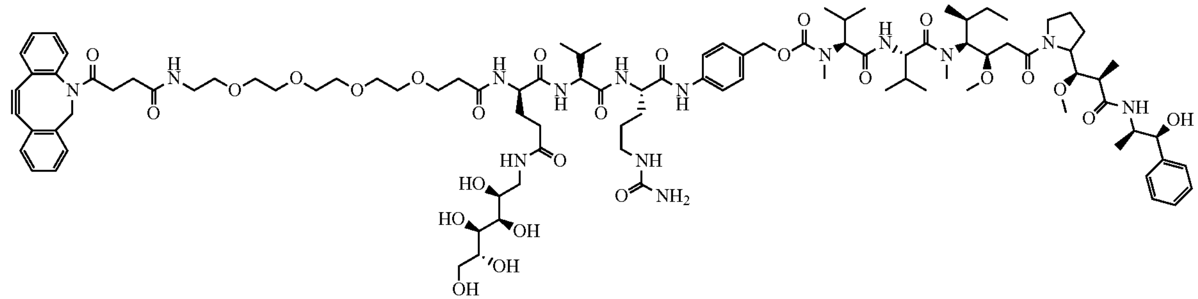 [SMILES: CC[C@H](C)[C@@H]([C@@H](CC(=O)N1CCCC1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCC(=O)NC[C@H](O)[C@@H](O)[C@H](O)[C@H](O)CO)NC(=O)CCOCCOCCOCCOCCNC(=O)CCC(=O)N2Cc3ccccc3C#Cc3ccccc32)C(C)C)cc1)C(C)C] |
| Ih-1 | 18E | MMAE | MAL-PEG$_4$-dGlu(glucamide)-vcPAB | 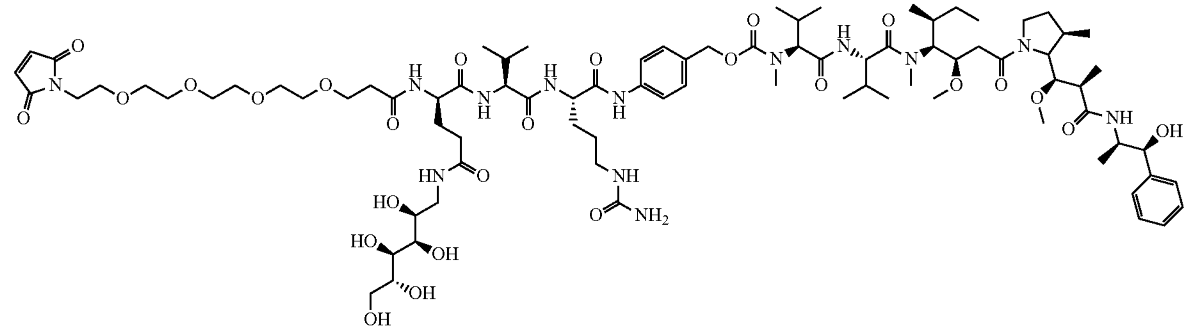 [SMILES: CC[C@H](C)[C@@H]([C@@H](CC(=O)N1CC[C@@H](C)C1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCC(=O)NC[C@H](O)[C@@H](O)[C@H](O)[C@H](O)CO)NC(=O)CCOCCOCCOCCOCCN2C(=O)C=CC2=O)C(C)C)cc1)C(C)C] |
| 1e | 19 | B | DIBAC-PEG$_4$-dLys(COT-PEG$_4$-taurine)-vcPAB | 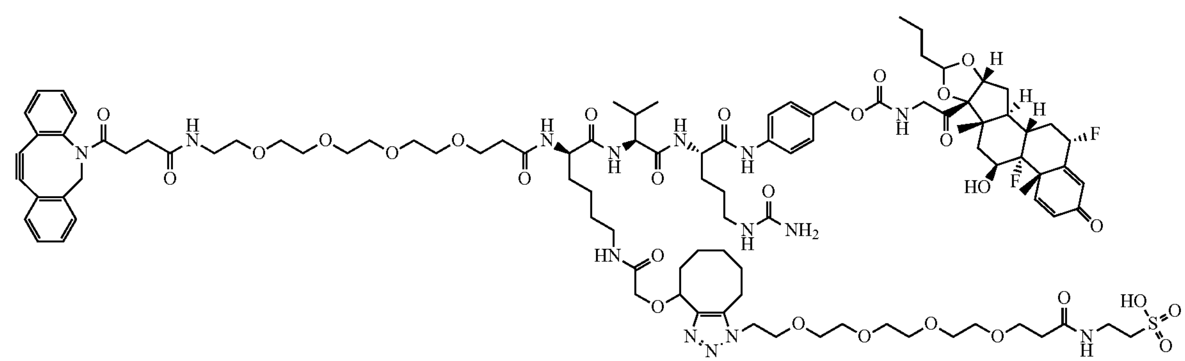 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@@H](CCCCNC(=O)COC3CCCCCc4c3nnn4CCOCCOCCOCCOCCC(=O)NCCS(=O)(=O)O)NC(=O)CCOCCOCCOCCOCCNC(=O)CCC(=O)N3Cc4ccccc4C#Cc4ccccc43)C(C)C)cc2)O1] |

TABLE 2-continued
List of charged linker payloads
| LP | Ex | Payload | Linker name | Structure |
|---|---|---|---|---|
| IIb | 19A | B | DIBAC-PEG4-dLys(COT-PEG4-N+Me3)-vcPAB | 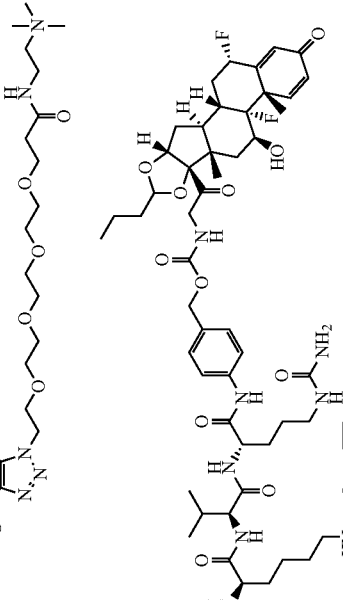 |
| 1f | 20 | B | DIBAC-PEG4-dLys(COT-dualtaurine)-vcPAB | 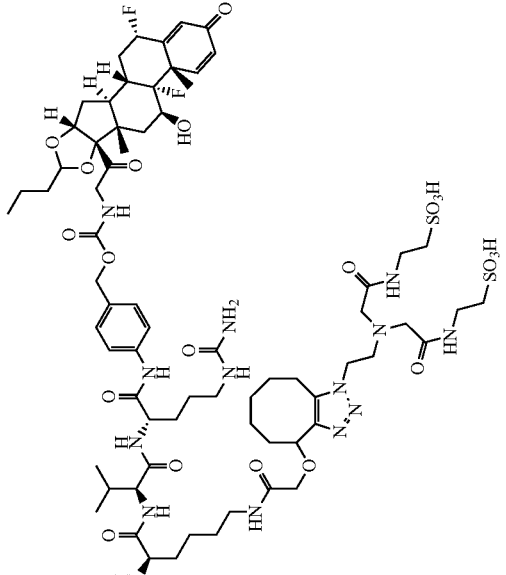 |

TABLE 2-continued

List of charged linker payloads

| LP | Ex | Payload | Linker name | Structure |
|---|---|---|---|---|
| 1h | 21 | B | DIBAC-PEG$_4$-dGlu(taurine)-vcPAB | 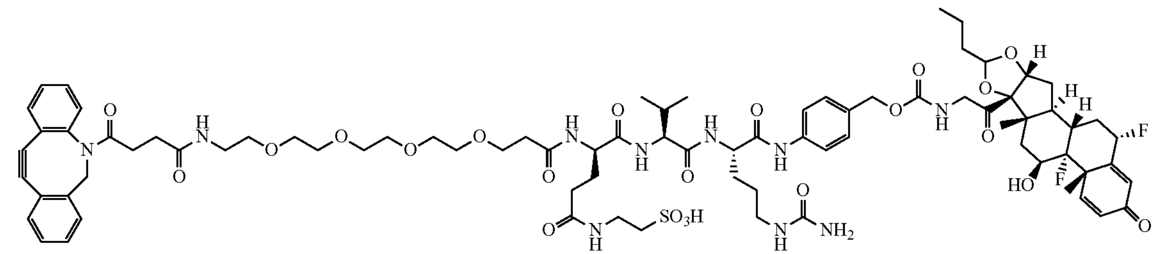 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@@H](CCC(=O)NCCS(=O)(=O)O)NC(=O)CCOCCOCCOCCOCCNC(=O)CCC(=O)N3Cc4ccccc4C#Cc4ccccc43)C(C)C)cc2)O1] |
| 1i | 22 | C | DIBAC-PEG$_4$-dLys(COT-PEG$_4$-taurine)-vcPAB | 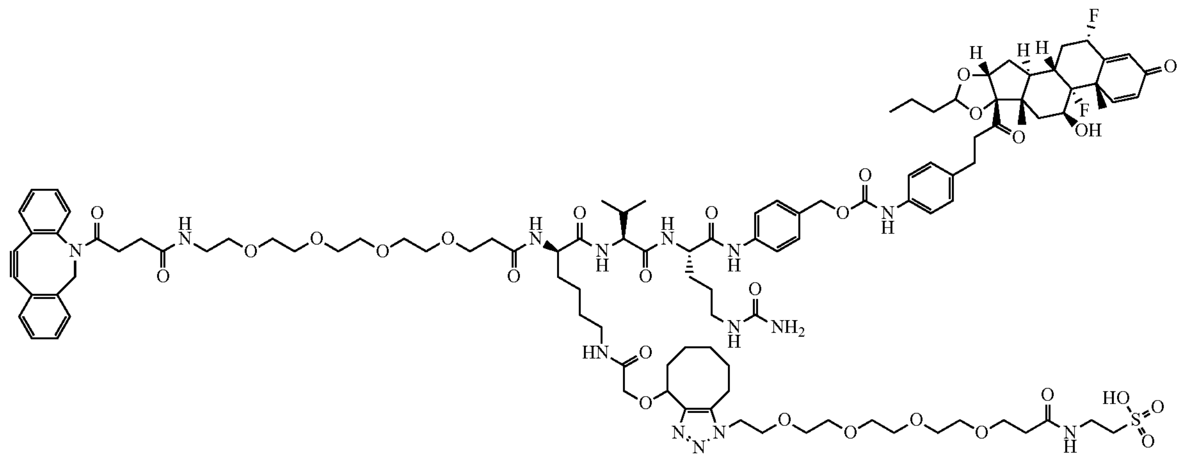 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CCc2ccc(NC(=O)OCc3ccc(NC(=O)[C@H](CCCNC(N)=O)NC(=O)[C@@H](NC(=O)[C@@H](CCCCNC(=O)COC4CCCCCc5c4nnn5CCOCCOCCOCCOCCC(=O)NCCS(=O)(=O)O)NC(=O)CCOCCOCCOCCOCCNC(=O)CCC(=O)N4Cc5ccccc5C#Cc5ccccc54)C(C)C)cc3)cc2)O1] |

TABLE 2-continued

List of charged linker payloads

| LP | Ex | Payload | Linker name | Structure |
|---|---|---|---|---|
| 1j | 23 | C | DIBAC-PEG$_4$-dLys(COT-PEG$_4$-taurine)-VA | 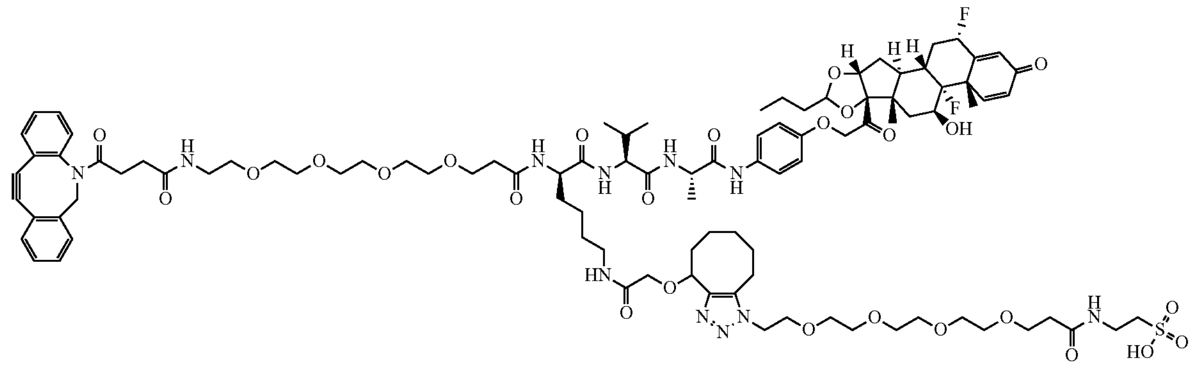 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](C)NC(=O)[C@@H](NC(=O)[C@@H](CCCCNC(=O)COC3CCCCCc4c3nnn4CCOCCOCCOCCOCCC(=O)NCCS(=O)(=O)O)NC(=O)CCOCCOCCOCCOCCNC(=O)CCC(=O)N3Cc4ccccc4C#Cc4ccccc43)C(C)C)cc2)O1] |
| 1k | 24 | C | DIBAC-PEG$_4$-dLys(COT-PEG$_4$-taurine)-vc | 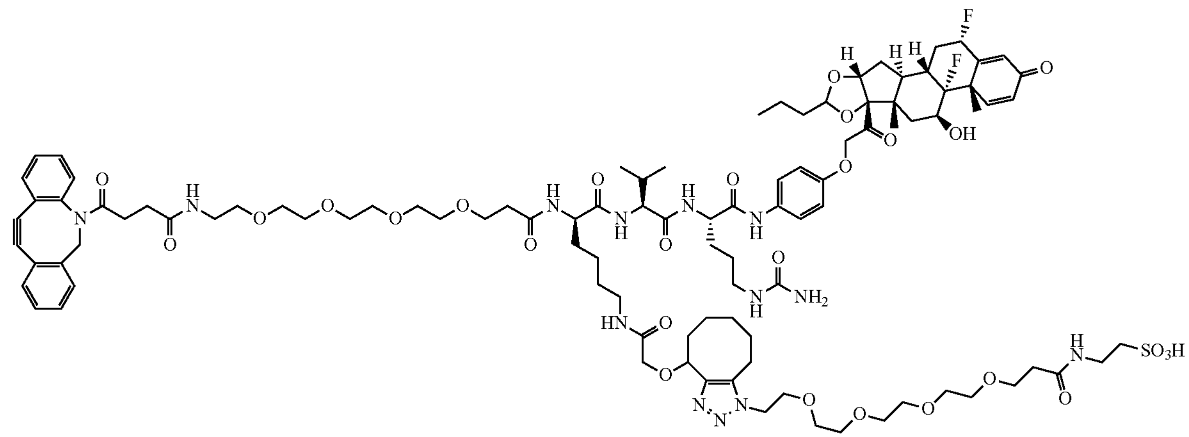 |

TABLE 2-continued

List of charged linker payloads

| LP | Ex | Payload | Linker name | Structure |
|---|---|---|---|---|
| IIId | 24A | C | COT-PEG$_4$-dLys(COT-PEG$_4$-N$^+$Me$_3$)-vcPAB | 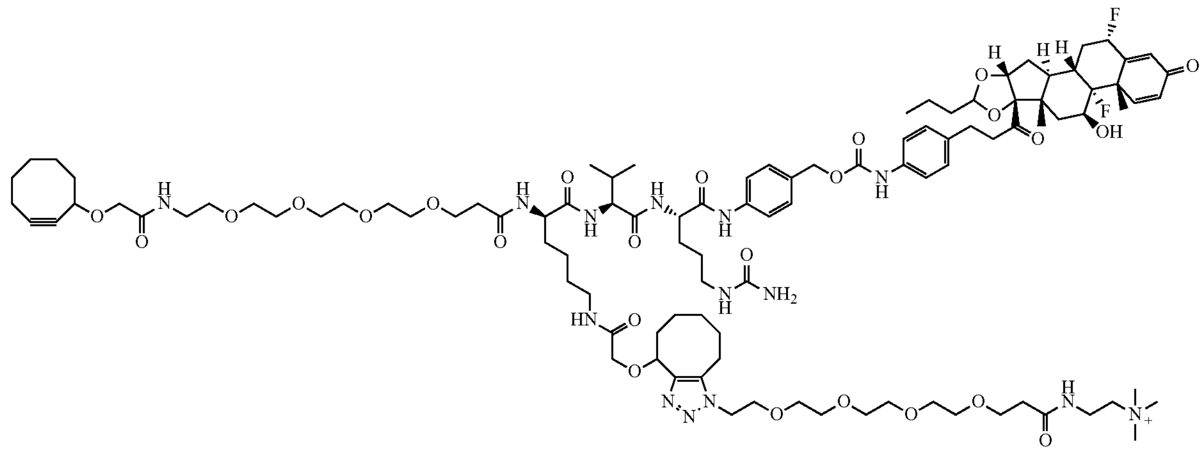 |
| IIIe | 24B | C | BCN-PEG$_4$-dLys(COT-PEG$_4$-N$^+$Me3)-vcPAB | 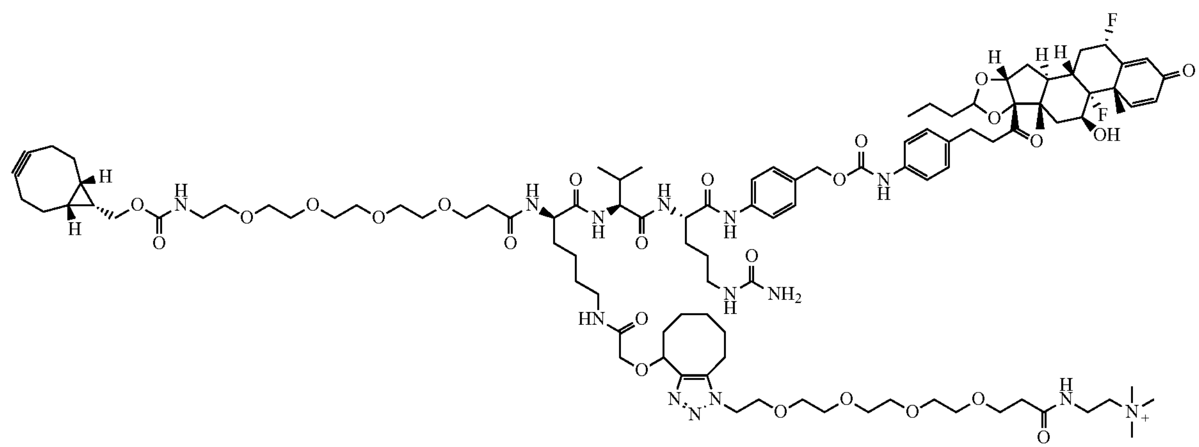 |

TABLE 2-continued

List of charged linker payloads

| LP | Ex | Payload | Linker name | Structure |
|---|---|---|---|---|
| 11 | 25 | C | DIBAC-PEG4-dGlut(taurine)-vc | |
| 1m | 26 | D | DIBAC-PEG4-dLys(COT-PEG4-taurine)-VA | 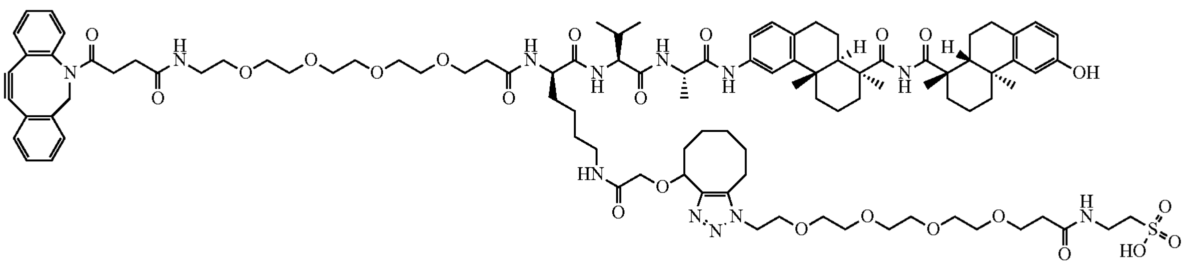 [SMILES: CC(C)[C@H](NC(=O)[C@@H](CCCCNC(=O)COC1CCCCCc2c1nnn2CCOCCOCCOCCOCCC(=O)NCCS(=O)(=O)O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2] |
| IVb | 26A | D | DIBAC-PEG4-dLys(COT-PEG4-N+Me3)-VA | 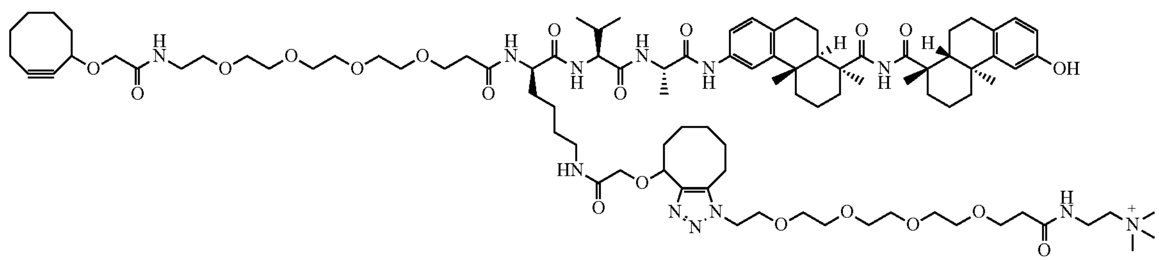 |

TABLE 2-continued
List of charged linker payloads
| LP | Ex | Payload | Linker name | Structure |
|---|---|---|---|---|
| 1q | 27 | E | DIBAC-PEG$_4$-dLys(COT-PEG$_4$-taurine)-vc | 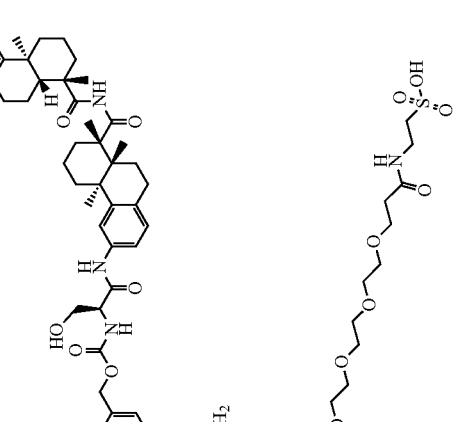 |

Example 1

Figure 2:
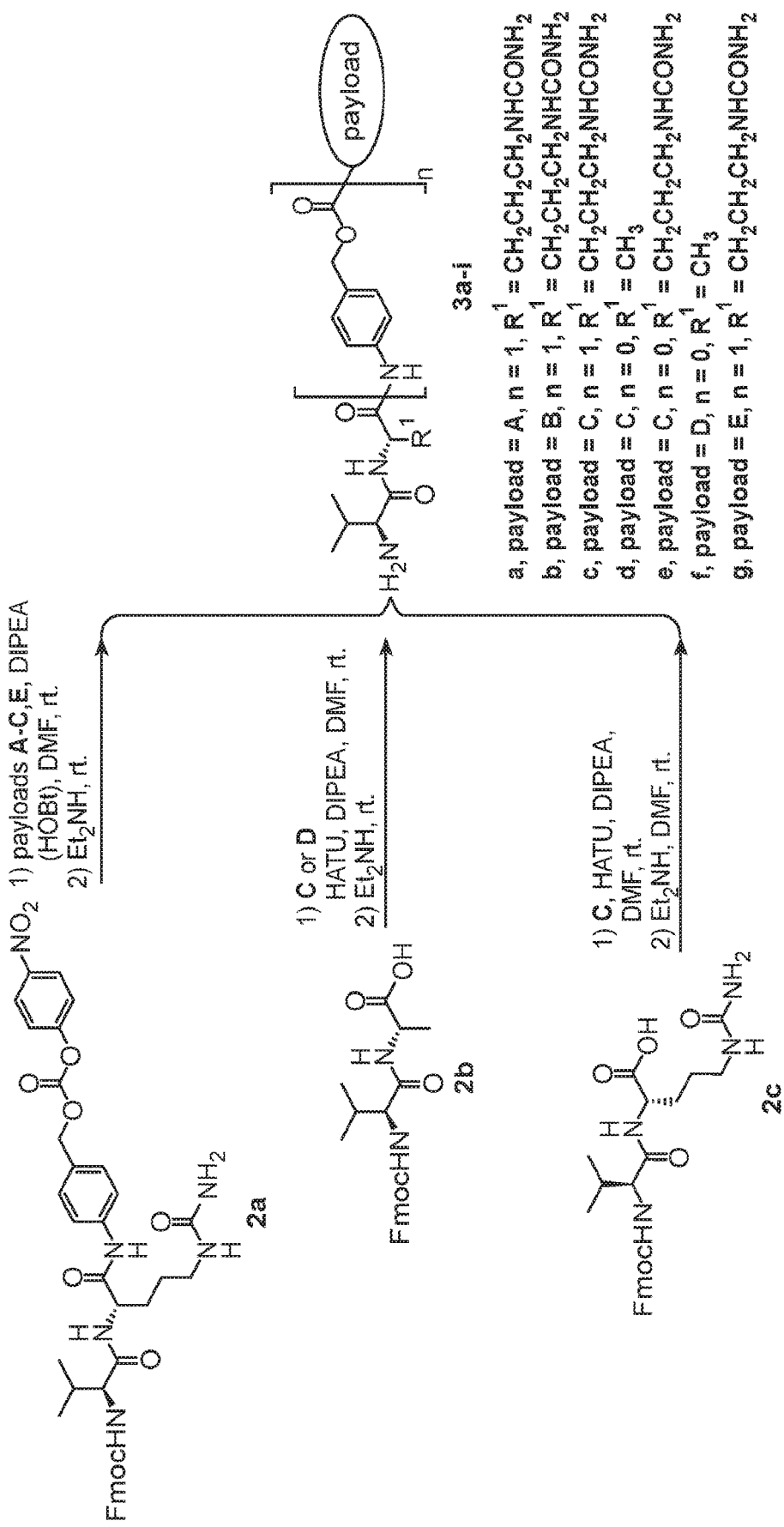
FIG. 2 shows a synthetic process for preparing compounds 1a, 1c, 1e, 1f, 1i, 1j, 1k, 1m, 1q, Ib, Id, Ie-1, If-1, IIb, IIId, IIIe, and IVb.
Figure 2:
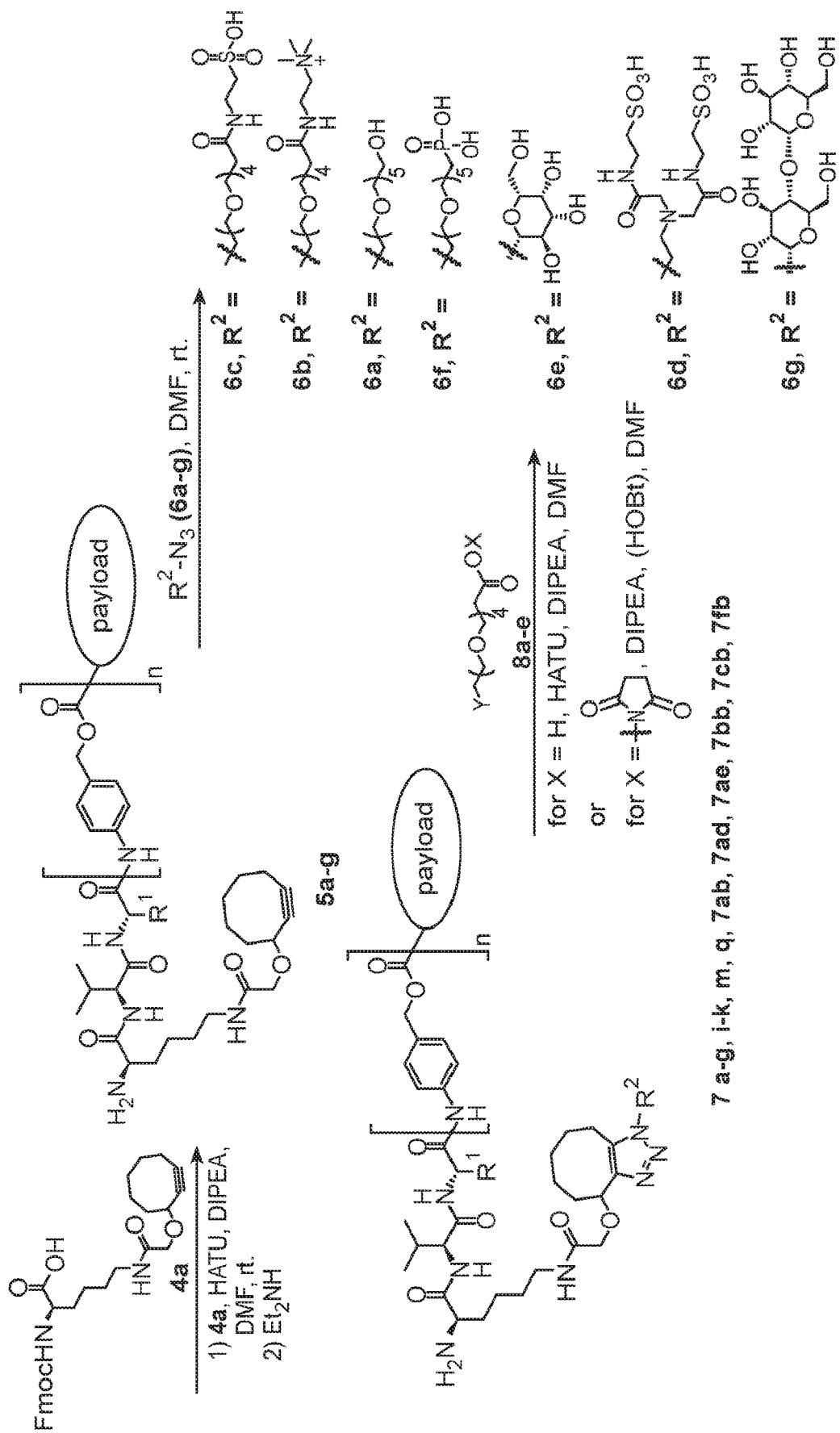

General Preparation of Linker Payloads (See FIG. 2)

Synthesis of Linker-Payloads 1 (except 1h and 1l) started from Fmoc-vcPAB-PNP (2a), Fmoc-Val-Ala-OH (2b) and Fmoc-Val-Cit-OH (2c) with payloads A-D gave the carbamates (3a-g). Amides (5a-h) were synthesized from 3a-f with Fmoc-D-Lys-COT (4a). 5a-f were cyclized with azides (6a-d) to afford 7. Finally 7 reacted with acid 8a or its active ester 8b to give Linker-Payloads 1 (except 1h and 1l).

Synthesis of Linker-Payloads I, II, III and IV (except Ig-1, Ih-1, 1h and 1l) started from Fmoc-vcPAB-PNP (2a), Fmoc-Val-Ala-OH (2b) and Fmoc-Val-Cit-OH (2c) with payloads A-E, gave the carbamates (3a-g). Amides (5a-g) were synthesized from 3a-g with Fmoc-D-Lys-COT (4a). 5a-g were cyclized with azides (6a-g) to afford 7. Finally 7 reacted with acid 8a or active esters 8b-e to give Linker-Payloads I, II, III and IV (except Ig-1, Ih-1).

Example 2

Figure 3:
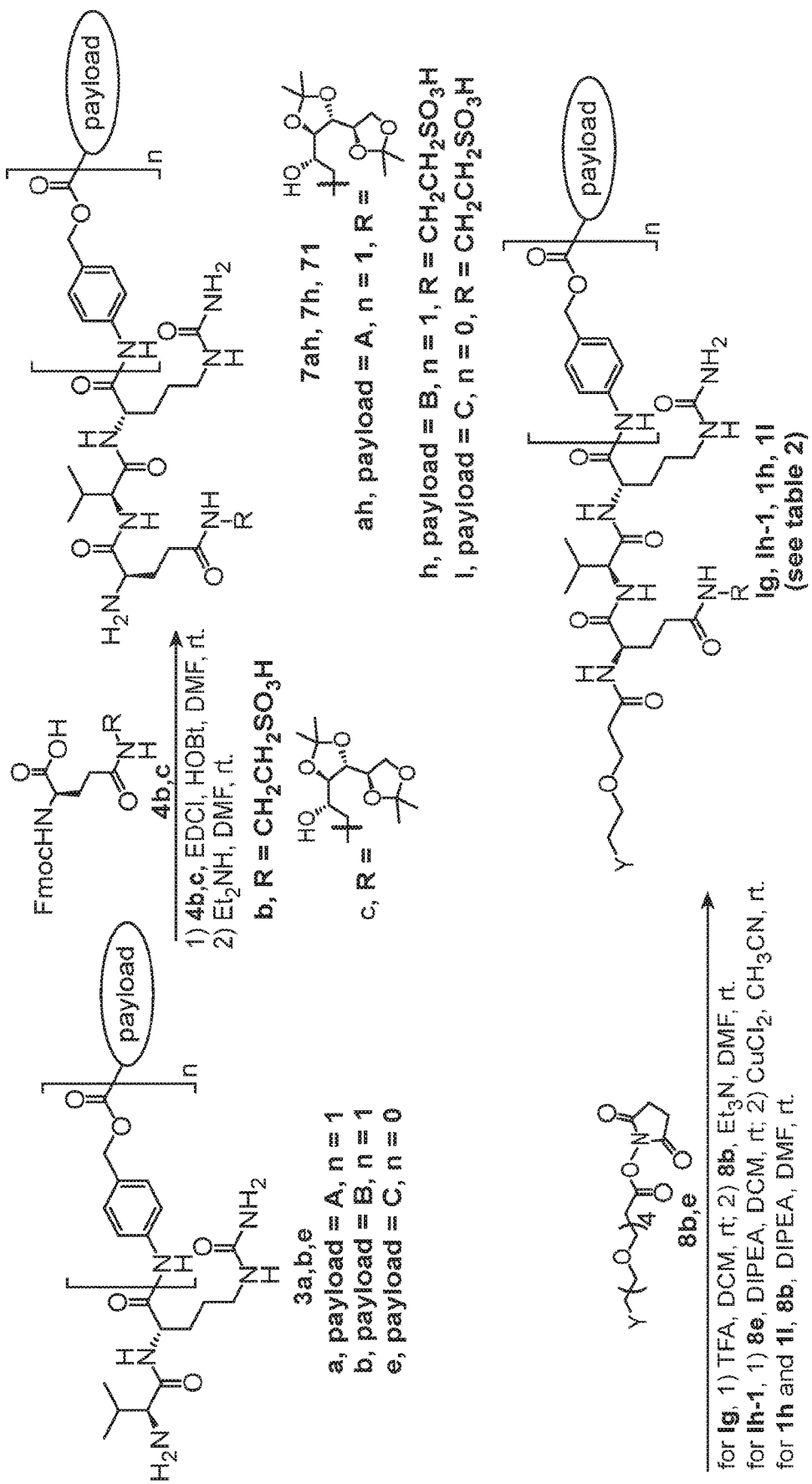
FIG. 3 shows shows a synthetic process for preparing compounds 1h, 1l, Ig, and Ih-1.

Preparation of Payloads 1h and 1l (See FIG. 3)

Synthesis of linker-payloads 1h and 1l started from 3b and 3e with Fmoc-dGlu-taurine (4b) under the condensation condition of EDCI followed by the de-Fmoc reaction and finally amidation with active ester 8b. Synthesis of linker-payloads 1h and 1l started from condensation of 3b and 3e with Fmoc-dGlu-taurine (4b), separately, followed by a reaction removing Fmoc and finally amidation with active ester 8b.

Synthesis of linker-payloads Ig-1 and Ih-1 was started from amide coupling reactions of 3a with Fmoc-dGlu-acetal glucamide (4c), followed by the condensation with 8e, and finally de-protection by TFA and then condensation with 8b.

Example 3

Preparation of Linker Payloads B and C (See FIG. 4)

MMAE (A) was commercially available with CAS 474645-27-7. Steroidal payloads B and C were prepared according to FIG. 4 starting from commercial fluocinolone acetonide 9 (CAS: 67-73-2). Compound 10, obtained from 9 by ketal-exchange with butyraldehyde in the presence of perchloric acid, was converted to mesylate 11 followed by replacement of the mesylate group with azide moiety to form 12 that were further reduced to amine B. Otherwise, the mesylate moiety in 11 was also replaced by 4-amino-phenol to afford aniline C.

(1S,2S,4R,8S,9S,11S,12R,13S,19S)-12,19-Difluoro-11-hydroxy-8-(2-hydroxyacetyl)-9,13-dimethyl-6-propyl-5,7-dioxapentacyclo[10.8.0.0$^{2,9}$.0$^{4,8}$.0$^{13,18}$]icosa-14,17-dien-16-one (10)

To a mixture of fluocinolone acetonide (9, 0.90 g, 2.0 mmol) and silica gel (18 g) in heptanes (90 mL) was added butyraldehyde (0.27 mL, 3.0 mmol) at 10° C. and the suspension was stirred at 10-20° C. for 10 minutes. To the mixture was added perchloric acid (70%, 0.68 mL, 8.3 mmol) dropwise at 0° C. The reaction mixture was then stirred at 10-20° C. overnight. Most of fluocinolone acetonide 9 was consumed according to TLC and LCMS. The reaction mixture was diluted with petroleum ether and quenched with sat. aq. Na$_2$CO$_3$. The suspension was filtered and the solid was washed with DCM/methanol (v/v=1). The combined filtrate was concentrated in vacuo. The residue was purified by flash chromatography on silica gel (0-100% ethyl acetate in petroleum ether) to give compound 10 (0.15 g, 16% yield) as a white solid. ESI m/z: 467.1 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl methanesulfonate (11)

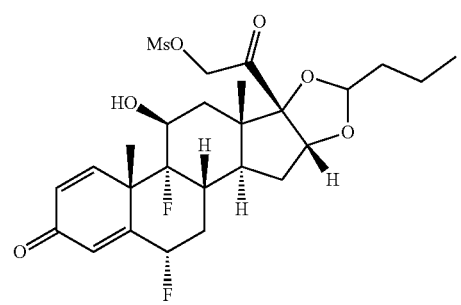

To a solution of compound 10 (0.28 g, 0.65 mmol)) and triethylamine (0.13 g, 1.3 mmol) in DCM (3 mL) was added methanesulfonyl chloride (89 mg, 0.78 mmol) at 0° C. After stirred at 0° C. for 0.5 h, the reaction mixture was diluted with DCM (20 mL). The mixture was washed with H$_2$O (20 mL×2), dried over anhydrous Na$_2$SO$_4$, filtered and concentrated in vacuo. The residue was purified by silica gel column chromatography on silica gel (0-50% ethyl acetate in petroleum ether) to give compound 11 (0.26 g, >99% yield) as a white solid. ESI m/z: 545 (M+H)$^+$.

(1S,2S,4R,8S,9S,11S,12R,13S,19S)-8-(2-Azidoacetyl)-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (12)

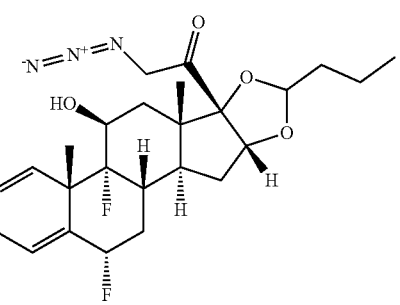

A suspension of compound 11 (1.0 g, 1.8 mmol) and sodium azide (1.2 g, 18 mmol) in acetone (15 mL) was stirred at 50° C. overnight. The mixture was cooled to RT and poured into water (80 mL). The aqueous mixture was extracted with ethyl acetate (50 mL×3). The combined organic layer was washed with brine (30 mL), dried over anhydrous $Na_2SO_4$, filtered and concentrated in vacuo to afford crude compound 12 (0.90 g, >99% yield) as a yellow solid, which was used for the next step without further purification. ESI m/z: 492 (M+H)+.

Payload B (1S,2S,4R,6R,8S,9S,11S,12R,13S,19S)-8-(2-Amino-acetyl)-12,19-difluoro-11-hydroxy-9,13-dimethyl-6-propyl-5,7-dioxapentacyclo[10.8.0.0$^{2,9}$0.0$^{4,8}$0.0$^{13,18}$]icosa-14,17-dien-16-one; trifluoroacetic acid salt (Compound B)

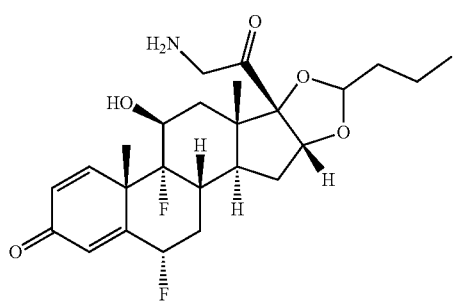

To a solution of compound 12 (0.85 g, 1.7 mmol) in THF (20 mL) was added aq. hydrochloride (1N, 10 mL). The mixture was stirred at 28-32° C. until it turned clear, to the mixture was then added triphenylphosphine (0.68 g, 2.6 mmol). The resulting yellow clear solution was stirred at RT for 18 h. The mixture was concentrated in vacuo and the residue was purified by reversed phase flash chromatography (0-50% acetonitrile in aq. TFA (0.05%)) to give compound B (0.56 g, 57% yield, TFA salt) as an off-white solid. ESI m/z: 466 (M+H)+. $^1$H NMR (400 MHz, MeOD$_{d4}$) δ 7.33 (d, J=9.9 Hz, 1H), 6.40-6.29 (m, 2H), 5.69-5.45 (m, 1H), 4.93-4.92 (m, 1H), 4.71 (t, J=4.3 Hz, 1H), 4.35-4.27 (m, 2H), 3.90-3.84 (m, 1H), 2.81-2.54 (m, 1H), 2.42-2.06 (m, 3H), 1.82-1.32 (m, 11H), 1.09-0.87 (m, 6H) ppm. $^{19}$F NMR (376 MHz, CD$_3$OD) δ −77.01, −166.24, −166.92, −188.81, −188.83 ppm. Anal. HPLC: 100%, Retention time: 6.86 min (method A).

Payload C (1S,2S,4R,8S,9S,11S,12R,13S,19S)-8-[2-(4-Amino-phenoxy)acetyl]-12,19-difluoro-11-hydroxy-9,13-dimethyl-6-propyl-5,7-dioxapentacyclo[10.8.0.0$^{2,9}$0.0$^{4,8}$0.0$^{13,18}$]icosa-14,17-dien-16-one (C)

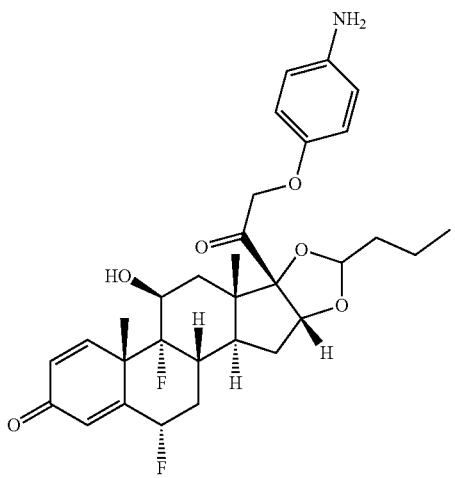

A mixture of compound 11 (93 mg, 0.17 mmol), 4-aminophenol (37 mg, 0.34 mmol) and cesium carbonate (0.11 g, 0.34 mmol) in acetone (0.5 mL) was refluxed for 2 hours. The mixture was cooled to RT and diluted with $H_2O$ (10 mL). The mixture was extracted with ethyl acetate (10 mL×3). The combined organic layer was washed with water (20 mL) and brine (20 mL), dried over $Na_2SO_4$, filtered and concentrated in vacuo. The residue was purified by prep-HPLC to give payload C (6.0 mg, 6.3% yield) as a white solid. ESI m/z: 298 (M/2+H)+, 558 (M+H)+ (10%). $^1$H NMR (500 MHz, MeOD$_{d4}$) δ 7.34 (d, J=10.0 Hz, 1H), 6.78-6.71 (m, 4H), 6.37-6.33 (m, 2H), 5.63-5.49 (m, 1H), 5.10-4.99 (m, 1H), 4.77-4.63 (m, 2H), 4.33 (d, J=9.1 Hz, 1H), 2.74-2.57 (m, 1H), 2.39-2.13 (m, 3H), 1.98-1.31 (m, 12H), 1.03-0.93 (m, 6H) ppm. Anal. HPLC: purity 97.4%, Retention time: 7.55 min (method B).

Example 4

Preparation of Payload D (See FIG. 5)

Methyl (1S,4aS,10aR)-6-hydroxy-1,4a-dimethyl-1,2,3,4,4a,9,10,10a-octahydrophenanthrene-1-carboxylate (14)

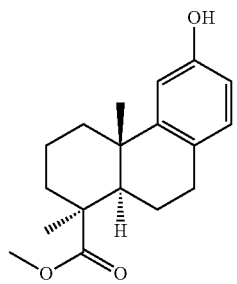 [SMILES: COC(=O)[C@@]1(C)CCC[C@]2(C)c3cc(O)ccc3CC[C@@H]12]

To a solution of podocarpic acid (13, 90 g, 0.33 mol) in methanol (200 mL) and toluene (600 mL) was added with (trimethylsilyl)diazomethane (2 M in hexane, 200 mL). The reaction mixture was stirred at room temperature for 2 hours. The podocarpic acid was then totally consumed according to LCMS. The volatiles were removed in vacuo, and the residue was triturated from petroleum ether (2 L) to give compound 14 (91 g, 96% yield) as a white solid. ESI m/z: 289 (M+H)$^+$. $^1$H NMR (400 MHz, DMSO$_{d6}$) δ 8.95 (s, 1H), 6.79 (d, J=8.2 Hz, 1H), 6.63 (d, J=2.4 Hz, 1H), 6.48 (dd, J=8.2, 2.4 Hz, 1H), 3.58 (s, 3H), 2.80-2.55 (m, 2H), 2.20-2.02 (m, 3H), 1.96-1.71 (m, 2H), 1.56-1.45 (m, 2H), 1.27 (t, J=13.5 Hz, 1H), 1.21 (s, 3H), 1.09 (td, J=13.5, 4.1 Hz, 1H), 0.91 (s, 3H) ppm.

Methyl (1S,4aS,10aR)-6-(benzyloxy)-1,4a-dimethyl-1,2,3,4,4a,9,10,10a-octahydrophenanthrene-1-carboxylate (20)

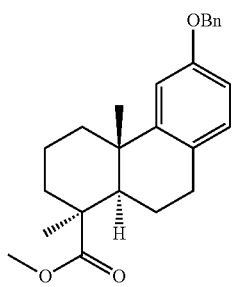 [SMILES: COC(=O)[C@@]1(C)CCC[C@]2(C)c3cc(OCc4ccccc4)ccc3CC[C@@H]12]

A mixture of compound 14 (12 g, 40 mmol) and cesium carbonate (14 g, 44 mmol) in DMF (100 mL) was stirred at 20-25° C. for 15 minutes. To the mixture was added benzyl bromide (7.1 mL, 60 mmol) at room temperature. After stirred at room temperature for 4 hours, the resulting mixture was poured into cold water and extracted with ethyl acetate. The combined organic solution was washed with water and brine, dried over sodium sulfate and concentrated in vacuo. The crude product was purified by flash chromatography (0-10% ethyl acetate in petroleum ether) to give the title compound 20 (13 g, 89% yield) as a white solid. ESI m/z: 379 (M+H)$^+$. $^1$H NMR (500 MHz, MeOD$_{d4}$) δ 7.60-7.20 (m, 5H), 7.00-6.82 (m, 2H), 6.73 (d, J=7.1 Hz, 1H), 5.03 (s, 2H), 3.66 (s, 3H), 2.95-2.58 (m, 2H), 2.36-2.10 (m, 3H), 2.10-1.85 (m, 2H), 1.70-1.48 (m, 2H), 1.44-1.21 (m, 4H), 1.15 (t, J=17.2 Hz, 1H), 1.01 (s, 3H) ppm.

(1S,4aS,10aR)-6-(Benzyloxy)-1,4a-dimethyl-1,2,3,4,4a,9,10,10a-octahydrophenanthrene-1-carboxylic acid (21)

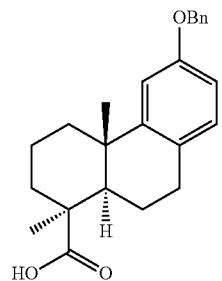 [SMILES: C[C@]1(C(=O)O)CCC[C@]2(C)c3cc(OCc4ccccc4)ccc3CC[C@@H]12]

A mixture of compound 20 (11 g, 29 mmol) and potassium tert-butoxide (33 g, 0.29 mol) in DMSO (0.19 L) was stirred at 100° C. for an hour until the methyl group was totally removed, which was monitored by LCMS and TLC. After cooled to 25° C., the mixture was quenched with aqueous hydrochloride (1N) and extracted with ethyl acetate. The combined organic solution was washed with brine, dried over sodium sulfate and concentrated in vacuo. The residue was purified by silica gel column chromatography (0-24% ethyl acetate in petroleum ether) to give compound 21 (7.5 g, 71% yield) as a white solid. ESI m/z: 365 (M+H)$^+$. $^1$H NMR (500 MHz, MeOD$_{d4}$) δ 7.42 (d, J=7.4 Hz, 2H), 7.36 (t, J=7.5 Hz, 2H), 7.30 (t, J=7.3 Hz, 1H), 6.92 (d, J=8.4 Hz, 1H), 6.87 (d, J=2.5 Hz, 1H), 6.72 (dd, J=8.4, 2.5 Hz, 1H), 5.02 (s, 2H), 2.82 (dd, J=16.3, 4.4 Hz, 1H), 2.77-2.65 (m, 1H), 2.24 (d, J=13.2 Hz, 2H), 2.19 (dd, J=13.8, 6.0 Hz, 1H), 2.11-1.96 (m, 2H), 1.64-1.56 (m, 1H), 1.53 (d, J=11.0 Hz, 1H), 1.35 (td, J=13.3, 3.7 Hz, 1H), 1.30 (s, 3H), 1.13 (s, 3H), 1.11-1.05 (m, 1H) ppm.

Pentafluorophenyl (1S,4aS,10aR)-6-(benzyloxy)-1,4a-dimethyl-1,2,3,4,4a,9,10,10a-octahydrophenanthrene-1-carboxylate (22)

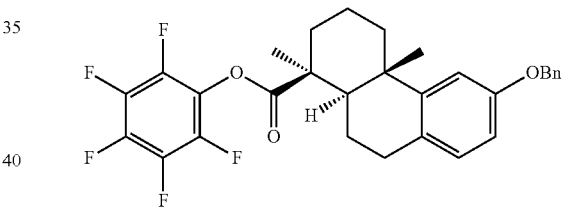

To a solution of 21 (9.6 g, 26 mmol) in DMF (100 mL) was added DIPEA (14 mL, 79 mmol), and perfluorophenyl 2,2,2-trifluoroacetate (15 g, 53 mmol). This mixture was stirred at room temperature overnight, which was monitored by LCMS. The reaction mixture was then diluted with ether (200 mL) and washed with water (300 mL) and brine (200 mL). The organic solution was dried over sodium sulfate, and concentrated in vacuo. The residue was purified by flash chromatography (0-10% ethyl acetate in petroleum ether) to give compound 22 (12 g, 88% yield) as a white solid. ESI m/z: 531 (M+H)$^+$. $^1$H NMR (500 MHz, DMSO$_{d6}$) δ 7.43 (d, J=7.1 Hz, 2H), 7.38 (t, J=7.4 Hz, 2H), 7.31 (t, J=7.2 Hz, 1H), 6.93 (dd, J=10.2, 5.5 Hz, 2H), 6.76 (dd, J=8.4, 2.5 Hz, 1H), 5.05 (s, 2H), 2.81 (dd, J=16.3, 4.5 Hz, 1H), 2.77-2.68 (m, 1H), 2.28-2.19 (m, 2H), 2.18 (dd, J=13.4, 5.6 Hz, 1H), 2.00-1.83 (m, 2H), 1.74 (d, J=11.8 Hz, 1H), 1.65 (d, J=14.1 Hz, 1H), 1.47 (s, 3H), 1.38-1.27 (m, 2H), 1.08 (s, 3H) ppm.

tert-Butyl N-[(4bS,8S,8aR)-8-({[(1S,4aS,10aR)-6-(benzyloxy)-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (23)

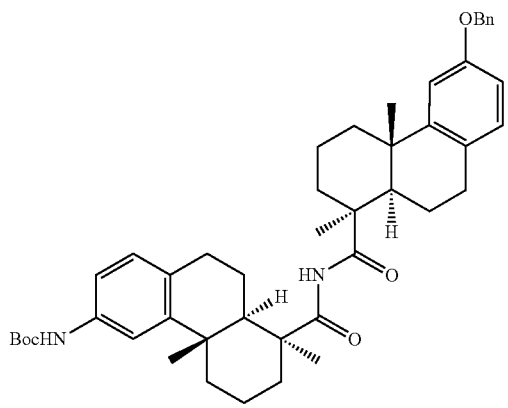 [SMILES: CC(C)(C)OC(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of compound 18 (2.3 g, 6.2 mmol) in THF (20 mL) was added dropwise n-BuLi (2.5 M in hexane, 5.5 mL, 14 mmol) at −78° C. The reaction was stirred at this temperature for 1 hour. To the mixture was added a solution of 22 (3.0 g, 5.6 mmol) in THF (20 mL), and the resulting mixture was then stirred at 10-20° C. overnight until compound 22 was consumed, which was monitored by LCMS. The reaction was quenched with sat. aq. ammonium chloride and extracted with ethyl acetate. The combined organic solution was washed with water and brine, dried over sodium sulfate and concentrated in vacuo. The residue was purified by flash chromatography (0-30% ethyl acetate in petroleum ether) to give compound 23 (1.59 g, 51% yield) as a white solid. ESI m/z: 719 (M+1)$^+$.

tert-Butyl N-[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (24)

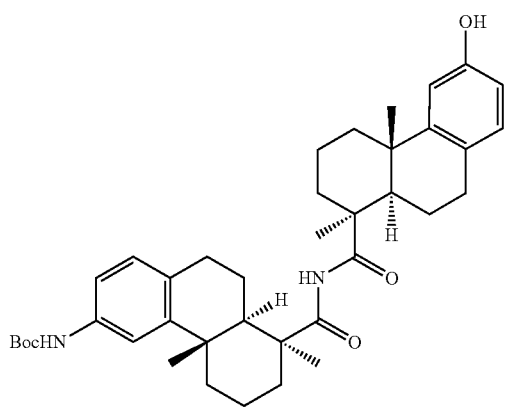

To a solution of 23 (2.0 g, 2.78 mmol) in ethyl acetate (40 mL) was added wet palladium on carbon (10% Pd, 0.9 g) under nitrogen protection. The mixture was degassed and fulfilled with hydrogen and stirred at room temperature under hydrogen balloon overnight until 23 was totally consumed, which was monitored by LCMS. The mixture was filtered through Celite and the filtration was concentrated in vacuo. The residue was purified by silica gel column chromatography (0-55% ethyl acetate in petroleum ether) to give 24 (1.06 g, 61% yield) as a white solid. ESI m/z: 629 (M+H)$^+$. $^1$H NMR (500 MHz, DMSO$_{d6}$) δ 9.10 (s, 1H), 8.98 (s, 1H), 8.11 (s, 1H), 7.40 (s, 1H), 7.15 (d, J=7.5 Hz, 1H), 6.90 (d, J=8.4 Hz, 1H), 6.81 (d, J=8.3 Hz, 1H), 6.63 (d, J=2.3 Hz, 1H), 6.50 (dd, J=8.2, 2.4 Hz, 1H), 2.84 (td, J=16.3, 3.8 Hz, 2H), 2.77-2.64 (m, 2H), 2.30-2.22 (m, 2H), 2.14 (t, J=10.9 Hz, 4H), 2.00-1.80 (m, 4H), 1.65-1.54 (m, 4H), 1.45 (s, 9H), 1.34-1.28 (m, 2H), 1.27 (d, J=2.5 Hz, 6H), 1.15-1.08 (m, 2H), 0.99 (s, 6H) ppm.

Payload D

(1S,4aS,10aR)—N-[(1S,4aS,10aR)-6-Amino-1,4a-dimethyl-1,2,3,4,4a,9,10,10a-octahydrophenanthrene-1-carbonyl]-6-hydroxy-1,4a-dimethyl-1,2,3,4,4a,9,10,10a-octahydrophenanthrene-1-carboxamide (D)

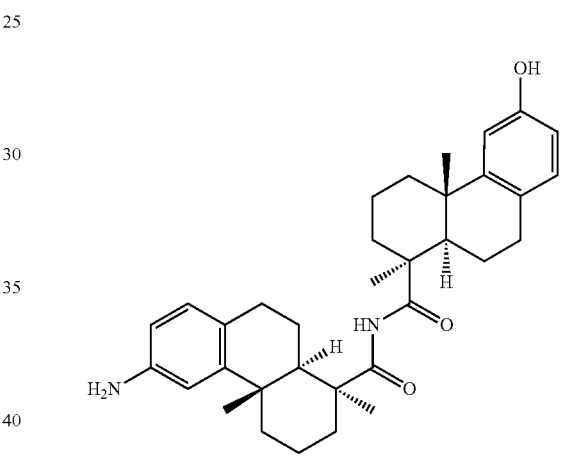

To the solution of compound 24 (0.17 g, 0.27 mmol) in DCM (10 mL) was added dropwise TFA (3 mL) at room temperature. The reaction mixture was stirred at room temperature for an hour until Boc was removed according to LCMS. The volatiles were removed in vacuo and the residue was purified by prep-HPLC (method B) to give D (0.10 g, 70% yield) as a white solid.

ESI m/z: 529.3 (M+1)$^+$.

$^1$H NMR (400 MHz, CDCl$_3$) δ 8.14 (s, 1H), 6.92 (d, J=8.3 Hz, 1H), 6.86 (d, J=8.1 Hz, 1H), 6.73 (d, J=2.5 Hz, 1H), 6.65-6.57 (m, 2H), 6.50 (dd, J=8.1, 2.3 Hz, 1H), 4.75 (s, 1H), 3.49 (s, 1H), 2.99-2.85 (m, 2H), 2.79 (tt, J=11.6, 5.8 Hz, 2H), 2.34-2.14 (m, 6H), 2.15-1.95 (m, 4H), 1.74-1.51 (m, 5H), 1.46-1.34 (m, 2H), 1.30 (s, 6H), 1.21-1.06 (m, 8H) ppm.

$^1$H NMR (400 MHz, DMSO$_{d6}$) δ 8.99 (s, 1H), 8.09 (s, 1H), 6.81 (d, J=8.0 Hz, 1H), 6.68 (d, J=8.0 Hz, 1H), 6.63 (d, J=2.5 Hz, 1H), 6.50 (dd, J=8.0, 2.5 Hz, 1H), 6.48 (d, J=2.5 Hz, 1H), 6.34 (dd, J=8.0, 2.5 Hz, 1H), 4.69 (s, 2H), 2.86-2.60 (m, 4H), 2.28-2.10 (m, 6H), 1.94-1.75 (m, 4H), 1.65-1.53 (m, 4H), 1.35-1.20 (m, 8H), 1.20-1.06 (m, 2H), 0.98 (s, 6H) ppm.

$^{13}$C NMR (100 MHz, DMSO$_{d6}$) δ 174.03, 173.92, 155.34, 148.39, 147.63, 146.43, 129.56, 129.09, 124.60, 121.65, 113.23, 112.58, 111.81, 110.77, 52.32, 52.09, 45.56, 45.52, 39.20, 39.36, 38.23, 38.17, 37.18, 37.12, 31.08, 31.00, 27.65, 27.64, 23.08, 23.03, 21.43, 21.27, 19.64, 19.61 ppm.

HPLC (method B): Retention time: 8.92 min, purity: 99.4%. chiral HPLC: >99.9% (in column AD, AS, OD and OJ).

Optical rotation (α): +2.53° (1.7 g/100 mL THF, 25° C.).

Payload E (1S,4aS,10aR)-6-((S)-2-Amino-3-hydroxypropanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (E)

To a solution of Fmoc-Ser-OH (30 mg, 0.1 mmol) in DMF (1 mL) were added HATU (38 mg, 0.1 mmol), and DIPEA (39 mg, 0.3 mmol) at 25° C. The resulting mixture was stirred at this temperature for an hour. To the mixture was then added D (30 mg, 0.06 mmol), and the reaction mixture was stirred at 25° C. for 16 h. To the mixture was added piperidine (0.2 mL), and the resulting mixture was stirred for additional 30 min at rt. The volatiles were removed in vacuo and the residue was directly purified by prep-HPLC (method B) to give the desired product (18 mg, 51% yield) as a white solid. ESI m/z: 616 (M+1)$^+$. $^1$H NMR (500 MHz, DMSO-$d_6$) δ 9.74 (br s, 1H, CONH-Ph), 9.00 (s, 1H, OH), 8.11 (s, 1H, NH of imidine), 7.58 (s, 1H), 7.41 (dd, J=8.2, 2.0 Hz, 1H), 6.96 (d, J=8.4 Hz, 1H), 6.82 (d, J=8.3 Hz, 1H), 6.63 (d, J=2.3 Hz, 1H), 6.50 (dd, J=8.2, 2.4 Hz, 1H), 4.82 (t, J=5.5 Hz, 1H, OH on Ser), 3.62-3.45 (m, 3H), 2.97-2.61 (m, 4H), 2.33-2.21 (m, 2H), 2.21-2.03 (m, 4H), 1.96-1.77 (m, 4H), 1.70-1.50 (m, 4H), 1.36-1.20 (m, 8H), 1.23-1.06 (m, 2H), 1.06-0.93 (m, 6H) ppm.

Example 5

Figure 6:
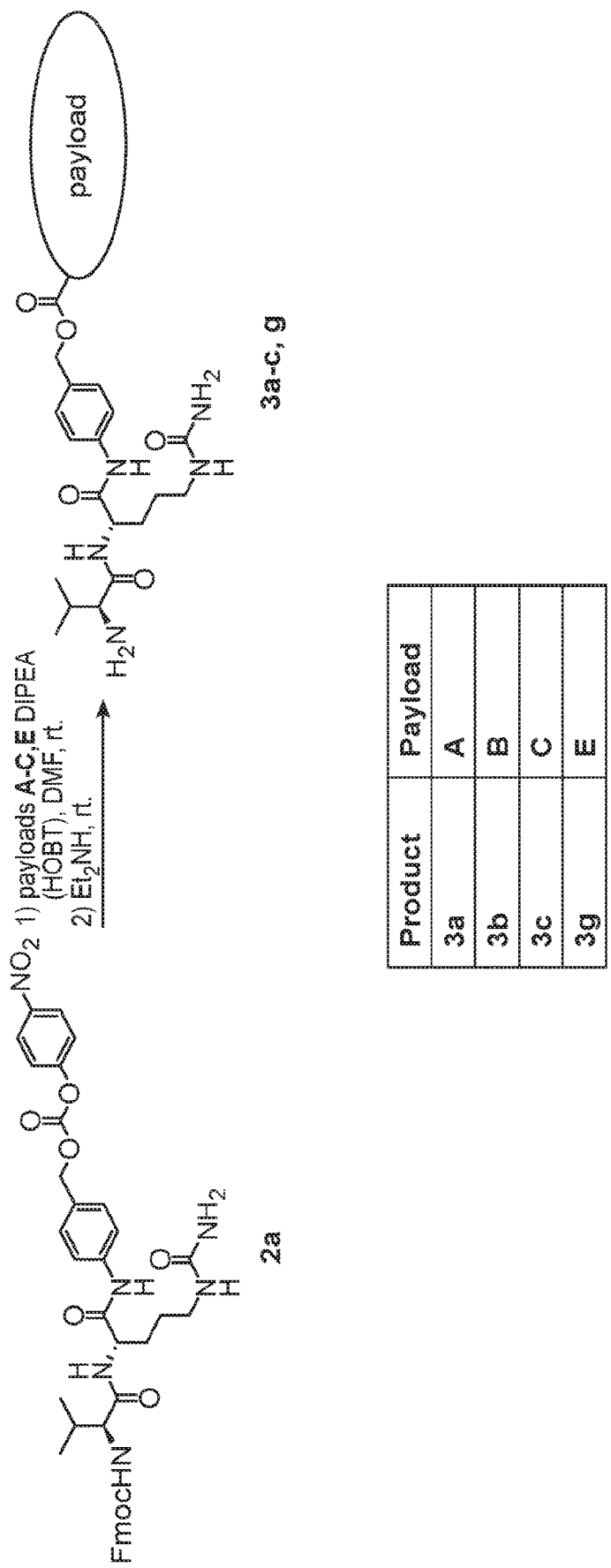
FIG. 6 shows a general synthetic procedure A for preparing intermediates 3a, 3b, 3c, and 3g.
Figure 7:
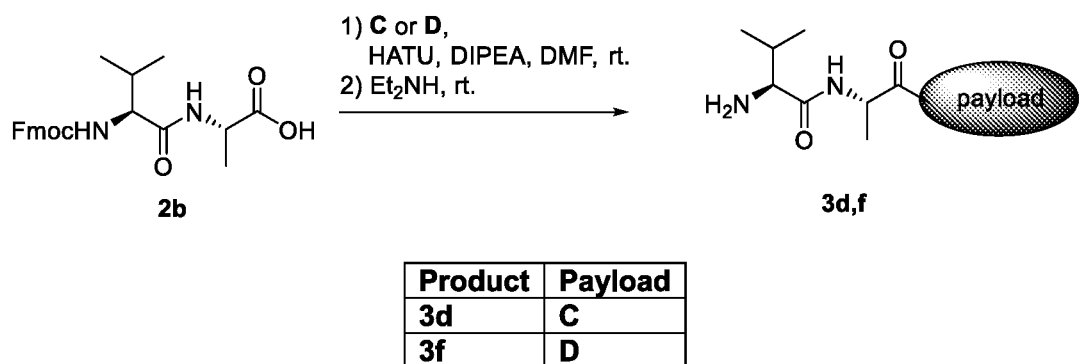
FIG. 7 shows a general synthetic procedure for preparing intermediates 3d, and 3f.

Preparation of Intermediates 3a-c, 3g (See FIG. 6)

General Procedure A:

To a solution of payload (A, B, C, or E 1.0 eq.) in DMF (0.3 mL per 10 mg of payload) were added Fmoc-vcPAB-PNP 2a (1.1 eq.), HOBt (1.5 eq.) and DIPEA (2.0 eq.) at RT. The mixture was stirred at RT for 3 hours until payload was totally consumed, which was monitored by LCMS. To the reaction mixture was added diethyl amine (0.03 mL per 10 mg of payload) and the mixture was stirred at RT (18-30° C.) for one hour until Fmoc was removed. The mixture was filtered and the filtrate was concentrated in vacuo. The residue was purified by reversed phase flash chromatography or prep-HPLC to titled compound (3a, 3b, 3c or 3g).

4-((S)-2-((S)-2-Amino-3-methylbutanamido)-5-ureidopentanamido)benzyl (S)-1-((S)-1-(((3R,4S,5S)-1-((S)-2-((1R,2R)-3-((1S,2R)-1-hydroxy-1-phenylpropan-2-ylamino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-ylamino)-3-methyl-1-oxobutan-2-yl(methyl)carbamate (3a) (vcPAB-MMAE)

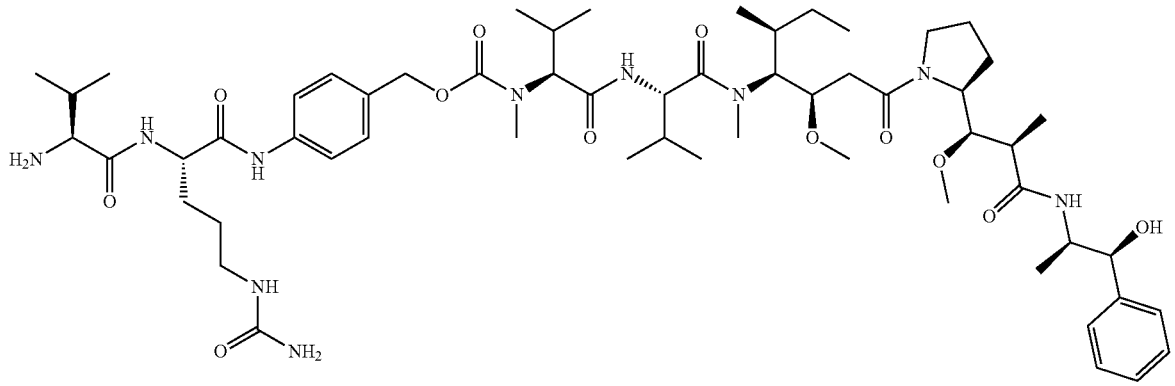 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](N)C(C)C)cc1)C(C)C]

[Ref: WO2012/166560] Following the general procedure A from compound 2a (90 mg, purity 75%, 88 μmol) with payload A (45 mg, 63 μmol), compound 3a (28 mg, 40% yield) as a white powder was obtained. ESI m/z: 1123.5 (M+H)$^+$. $^1$H NMR (DMSO-$d_6$, 500 MHz): δ 10.12 (br s, 1H), 8.25-8.05 (m, 2H), 7.89-7.58 (m, 3H), 7.34-7.16 (m, 7H), 5.98 (t, J=5.5 Hz, 1H), 5.42-5.34 (m, 3H), 5.06-4.95 (m, 2H), 4.78-4.57 (m, 1H), 4.51-4.26 (m, 3H), 3.80-3.40 (m, 2H), 3.28-3.18 (m, 7H), 3.12-2.84 (m, 10H), 2.43-2.40 (m, 1H), 2.30-2.27 (m, 1H), 2.15-1.91 (m, 5H), 1.96-1.68 (m, 4H), 1.59-1.34 (m, 6H), 1.06-0.93 (m, 6H), 0.90-0.70 (m, 26H) ppm.

{4-[(2S)-2-[(2S)-2-Amino-3-methylbutanamido]-5-(carbamoylamino)pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}carbamate (3b)

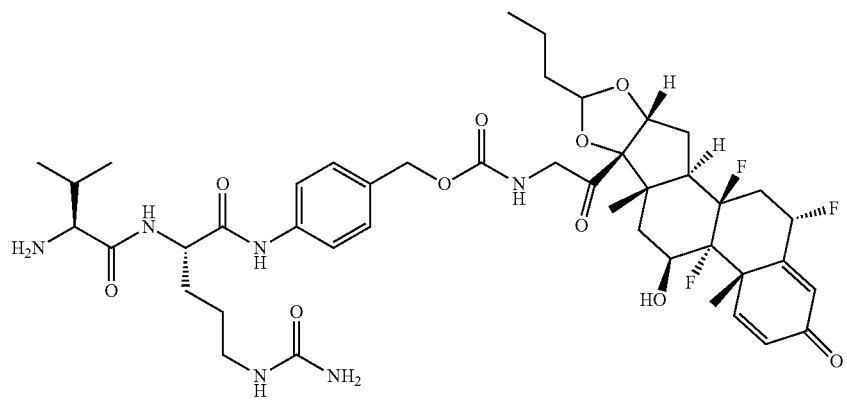 [SMILES: CCCC1O[C@@H]2C[C@@H]3[C@](C)(C[C@H](O)[C@]4(F)[C@@]5(C)C=CC(=O)C=C5[C@@H](F)C[C@@]34F)[C@]2(C(=O)CNC(=O)OCc2ccc(NC(=O)[C@H](CCCNC(N)=O)NC(=O)[C@@H](N)C(C)C)cc2)O1]

Following the general procedure A from compound 2a (93 mg, 0.20 mmol) with payload B, compound 3b was obtained after purification by reversed phase flash chromatography (50-80% acetonitrile in aq. ammonium bicarbonate (10 mM)) as a white solid. ESI m/z: 871 (M+H)$^+$.

{4-[(2S)-2-[(2S)-2-Amino-3-methylbutanamido]-5-(carbamoylamino)pentanamido]phenyl}methyl N-(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$0.0$^{4,8}$0.0$^{13,18}$]icosa-14,17-dien-8-yl]-2-oxoethoxy}phenyl)carbamate (3c)

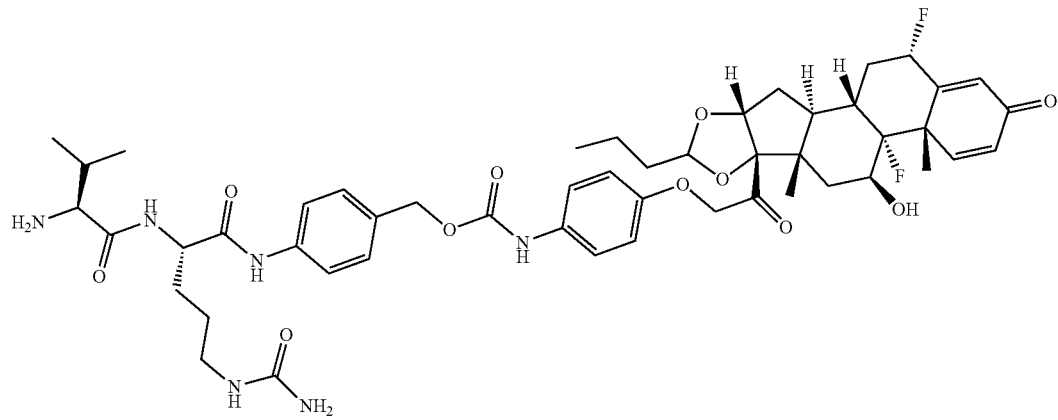 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)OCc3ccc(NC(=O)[C@H](CCCNC(N)=O)NC(=O)[C@@H](N)C(C)C)cc3)cc2)O1]

Following the general procedure A from compound 2a (0.10 g, 0.22 mmol) with payload C, compound 3c (160 mg, 76% yield) was obtained after purification by reversed phase flash chromatography (50-80% acetonitrile in aq. ammonium bicarbonate (10 mM)) as a white solid. ESI m/z: 963.4 (M+H)$^+$.

{4-[(2S)-2-[(2S)-2-Amino-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (3g)

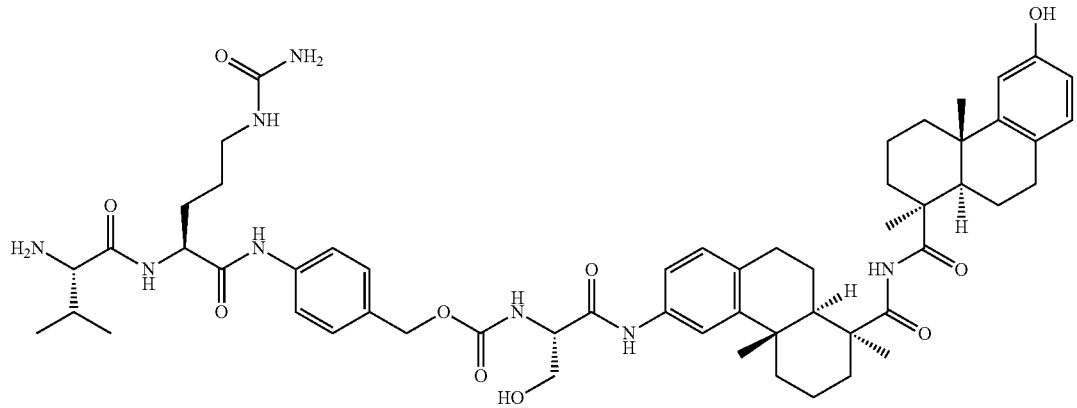 [SMILES: CC(C)[C@H](N)C(=O)N[C@@H](CCCNC(N)=O)C(=O)Nc1ccc(COC(=O)N[C@@H](CO)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

To a solution of Fmoc-vc-PAB-PNP (58 mg, 76 µmol) and E (36 mg, 58 µmol) in DMF (3 mL) were added HOBt (7.9 mg, 58 µmol) and DIPEA (15 mg, 0.12 mmol), and the mixture was stirred at 30° C. for 16 hours. Compound E was then totally consumed according to LCMS. To the resulting mixture was added diethylamine (0.1 mL) and it was stirred at RT for an hour until Fmoc was removed, which was monitored by LCMS. After filtered, the filtrate was directly purified by prep-HPLC (method B) to give compound 3g (36 mg, 48% yield) as a light yellow solid. ESI m/z: 1021 (M+1)$^+$. $^1$H NMR (400 MHz, DMSO$_{d6}$) δ 10.02 (s, 1H), 9.82 (s, 1H), 9.00 (s, 1H), 8.69-8.65 (m, 1H), 8.11-8.00 (m, 4H), 7.65-7.53 (m, 3H), 7.40-7.30 (m, 3H), 7.30-7.20 (m, 1H), 6.96 (d, J=8.0 Hz, 1H), 6.81 (d, J=8.0 Hz, 1H), 6.65-6.61 (m, 1H), 6.50 (dd, J=8.0 Hz, 2.0 Hz, 1H), 6.00-5.95 (m, 1H), 5.48 (s, 2H), 5.00-4.95 (m, 3H), 4.60-4.40 (m, 1H), 4.25-4.20 (m, 1H), 3.65-3.55 (m, 4H), 3.15-2.55 (m, 10H), 2.40-2.20 (m, 3H), 2.20-2.00 (m, 5H), 2.00-1.80 (m, 4H), 1.86-1.55 (m, 6H), 1.27 (d, J=4.8 Hz, 9H), 1.20-1.10 (m, 2H), 0.97-0.90 (m, 6H) ppm.

Example 6

Preparation of Intermediates 3d and 3f (See FIG. 7)
General Procedure B:

To a solution of Fmoc-Val-Ala-OH (2b, 1.2 eq.) in DMF (25 mL per gram of payload) were added HATU (1.5 eq.) and DIPEA (3.0 eq.) at RT. The mixture was stirred at RT for 5 minutes followed by addition of payload (C or D, 1.0 eq.). The mixture was stirred for additional 2 hours and LCMS showed the completion of reaction. To the reaction mixture was added diethyl amine (5 eq.). The mixture was stirred at RT for 2 hours, until the Fmoc was totally removed according to LCMS. The mixture was filtered and the filtrate was concentrated in vacuo. The residue was purified by reversed phase flash chromatography (0-100% acetonitrile in aq. ammonium bicarbonate (10 mM)) or prep-HPLC (Method B) to give the desired product (3d or 3f, 64-72% yield from payload).

(2S)-2-Amino-N-[(1S)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$0.0$^{4,8}$0.0$^{13,18}$]icosa-14,17-dien-8-yl]-2-oxoethoxy}phenyl)carbamoyl]ethyl]-3-methylbutanamide (3d)

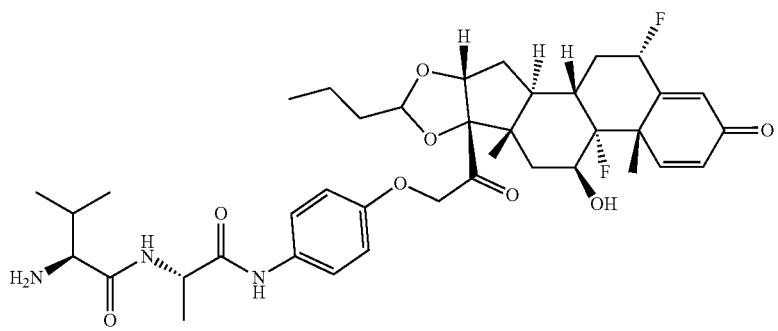 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](C)NC(=O)[C@@H](N)C(C)C)cc2)O1]

Following the general procedure B from compound 2b (0.50 g, 0.90 mmol) with payload C, compound 3d (0.69 g, 72% yield) was obtained after purification by reversed phase flash chromatography (0-100% acetonitrile in aq. ammonium bicarbonate (10 mM)) as viscous yellow oil. ESI m/z: 728 (M+H)+.

(1S,4aS,10aR)-6-((S)-2-((S)-2-Amino-3-methylbutanamido)propanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (3f)

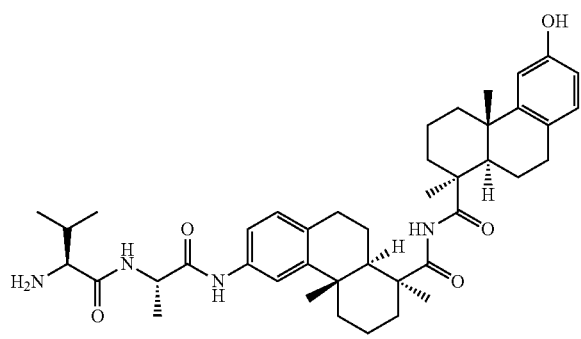 [SMILES: CC(C)[C@H](N)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

Following the general procedure B from compound 2b with payload D (53 mg, 0.10 mmol), compound 3f (45 mg, 64% yield) was obtained after purification by prep-HPLC (method B) as a white solid. ESI m/z: 699 (M+1)+. 1H NMR (500 MHz, MeOD$_{d4}$) δ 8.40 (s, 1H), 7.47 (s, 1H), 7.32 (d, J=8.0 Hz, 1H), 7.03 (d, J=8.3 Hz, 1H), 6.88 (d, J=8.2 Hz, 1H), 6.72 (d, J=2.4 Hz, 1H), 6.56 (dd, J=8.3, 2.4 Hz, 1H), 4.60-4.48 (m, 1H), 3.22-3.11 (m, 1H), 3.02-2.93 (m, 1H), 2.92-2.76 (m, 3H), 2.74-2.70 (m, 1H), 2.43-2.31 (m, 3H), 2.28 (d, J=14.1 Hz, 3H), 2.16-1.96 (m, 3H), 1.81 (s, 1H), 1.78-1.65 (m, 4H), 1.53-1.42 (m, 4H), 1.38 (d, J=5.3 Hz, 6H), 1.33-1.22 (m, 2H), 1.14 (d, J=6.6 Hz, 6H), 1.09 (d, J=18.6 Hz, 6H) ppm.

Example 7

Figure 8:
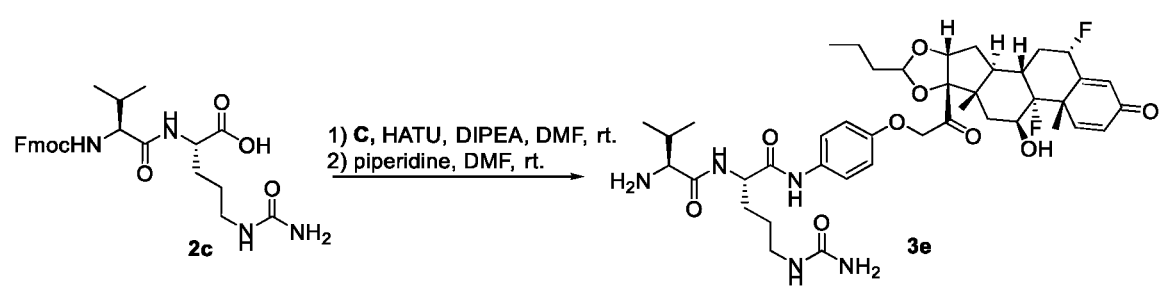
FIG. 8 shows a synthetic process for preparation of intermediate 3e.

Preparation of Intermediate 3e (See FIG. 8)

(2S)-2-[(2S)-2-Amino-3-methylbutanamido]-5-(carbamoylamino)-N-(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$0.0$^{4,8}$0.0$^{13,18}$]icosa-14,17-dien-8-yl]-2-oxoethoxy}phenyl)pentanamide (3e)

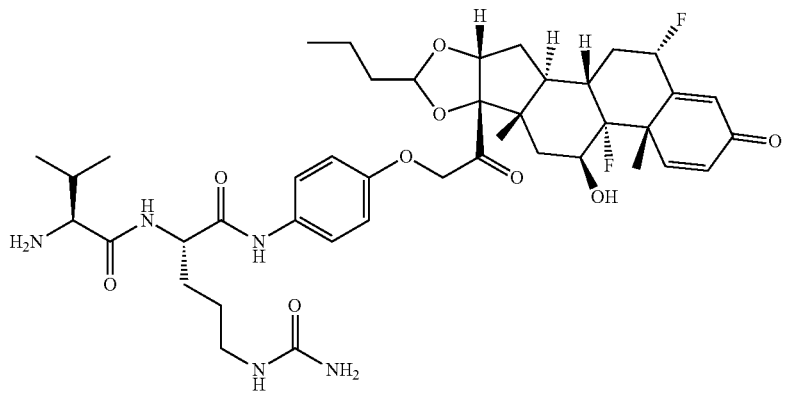 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](CCCNC(N)=O)NC(=O)[C@@H](N)C(C)C)cc2)O1]

To a solution of Fmoc-Val-Cit-OH (0.23 g, 0.43 mmol) in DMF (5 mL) were added HATU (0.38 g, 0.43 mmol) and DIPEA (93 mg, 0.72 mmol) at RT. The mixture was stirred at RT for 5 minutes followed by addition of payload C (0.20 g, 0.36 mmol). The mixture was stirred for additional 2 hours and LCMS showed the completion of reaction. To the reaction mixture was added diethylamine (0.5 mL). The mixture was stirred at RT for an hour, until the Fmoc was totally removed according to LCMS. The mixture was filtered and the filtrate was concentrated in vacuo. The residue was purified by reversed phase flash chromatography (0-100% acetonitrile in aq. ammonium bicarbonate (10 mM)) and then methanol) to give compound 3e (38% yield from payload C). ESI m/z: 814 (M+1)+.

Example 8

Figure 9:
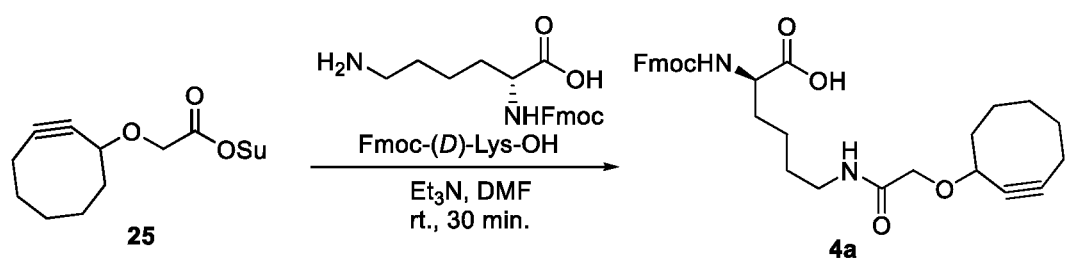

Preparation of Intermediate 4 (See FIG. 9)

Intermediate 4a was synthesized by the amidation from Fmoc-(D)-Lys-OH with commercial activated ester 25.

(2R)-6-[2-(Cycloct-2-yn-1-yloxy)acetamido]-2-{[(9H-fluoren-9-ylmethoxy)carbonyl]amino}hexanoic acid (4a)

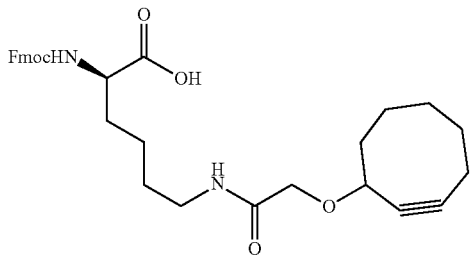

To a mixture of compound 25 (65 mg, 0.23 mmol, CAS: 1425803-45-7) in DMF (2 mL) were added Fmoc-D-Lys-OH (85 mg, 0.23 mmol) and triethylamine (52 mg, 0.51 mmol). The reaction mixture was stirred at room temperature for 30 minutes. The mixture was directly separated by reversed phase flash chromatography (0-100% acetonitrile in water (0.05% TFA)) to give intermediate 4a (85 mg, yield 70%) as a white solid. ESI m/z: 533 (M+H)+. 1H NMR (MeOD$_{d4}$, 500 MHz): δ 7.70 (d, J=7.5 Hz, 2H), 7.59 (t, J=8.0 Hz, 2H), 7.30 (t, J=7.5 Hz, 2H), 7.22 (t, J=7.4 Hz, 2H), 4.35-4.22 (m, 2H), 4.22-4.09 (m, 2H), 4.09-3.99 (m, 1H), 3.94-3.81 (m, 1H), 3.79-3.67 (m, 1H), 3.15 (t, J=6.9 Hz, 2H), 2.17-1.96 (m, 3H), 1.96-1.86 (m, 1H), 1.85-1.66 (m, 4H), 1.66-1.41 (m, 5H), 1.41-1.25 (m, 3H) ppm.

Example 9

Figure 10:
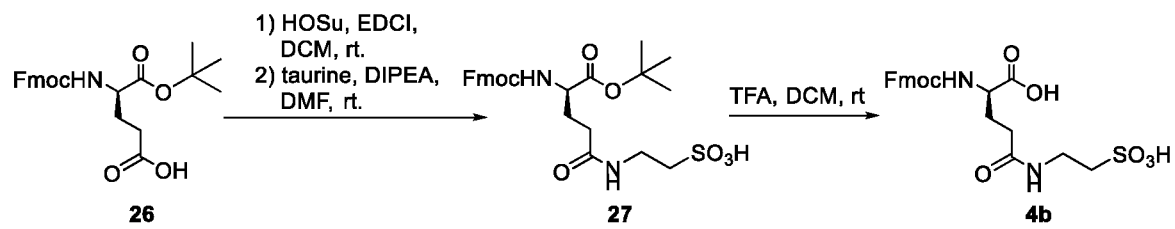
FIG. 10 shows a synthetic process for preparation of intermediate 4b.

Preparation of Intermediate 4b (See FIG. 10)

Intermediate 4b was synthesized from Fmoc-(D)-Glu-O$^t$Bu (26). Compound 26 was activated with HOSu and then amidated by taurine to provide compound 27, which was hydrolyzed by TFA to give intermediate 4b.

2-[(4R)-5-(tert-Butoxy)-4-{[(9H-fluoren-9-ylmethoxy)carbonyl]amino}-5-oxopentanamido]ethane-1-sulfonic acid (27)

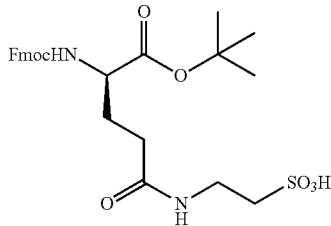

To a solution of Fmoc-(D)-Glu-O$^t$Bu (26) (2.0 g, 4.7 mmol) in DCM (20 mL) were added HOSu (1.1 g, 9.6 mmol) and EDCI (1.8 g, 9.4 mmol) at RT. The mixture was stirred at RT overnight, which was monitored by LCMS. The reaction mixture was diluted with DCM (100 mL), washed with water (50 mL×2) and brine (50 mL), dried over anhydrous sodium sulfate and concentrated in vacuo. The residue was dissolved in DMF (2 mL) and to the solution were added taurine (1.2 g, 9.6 mmol) and DIPEA (1.4 g, 14 mmol). The resulting mixture was stirred at RT overnight until the reaction was completed according to LCMS. The reaction mixture was directly purified by prep-HPLC (method B) to give compound 27 (2.0 g, 81% yield) as a white solid. ESI m/z: 477 (M−55+H)+.

(2R)-2-{[(9H-Fluoren-9-ylmethoxy)carbonyl]amino}-4-[(2-sulfoethyl)carbamoyl]butanoic acid (4b)

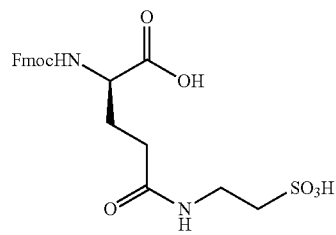

To a solution of compound 27 (0.52 g, 0.98 mmol) in DCM (2 mL) was added TFA (2 mL). The reaction mixture was stirred at RT for 3 hours until hydrolysis was completed according to LCMS. The volatiles were removed in vacuo and the residue was purified by reversed phase flash chromatography (0-100% acetonitrile in aq. ammonium bicarbonate (10 mM)) to give intermediate 4b (0.45 g, 97% yield) as a white solid. ESI m/z: 477 (M+H)+. 1H NMR (DMSO$_{d6}$, 500 MHz) δ 7.89 (d, J=7.5 Hz, 2H), 7.72 (d, J=7.5 Hz, 2H), 7.42 (t, J=7.5 Hz, 2H), 7.34 (t, J=7.5 Hz, 2H), 7.21-7.17 (br s, 1H), 4.27-4.23 (m, 2H), 3.82-3.79 (m, 1H), 3.27-3.19 (m, 1H), 2.71-2.67 (m, 1H), 2.54 (t, J=7.5 Hz, 2H), 2.13-1.89 (m, 2H), 1.80-1.75 (m, 1H), 1.07-1.06 (m, 4H) ppm (the proton COOH was not revealed).

Compound 4c was prepared by following the synthetic procedures outlined in *J. Org. Chem.* 2010, 75, 3685-3691, the compound 4c was obtained with 25% total yield. ESI m/z: 613.3 (M+H)+.

Example 10

Figure 11:
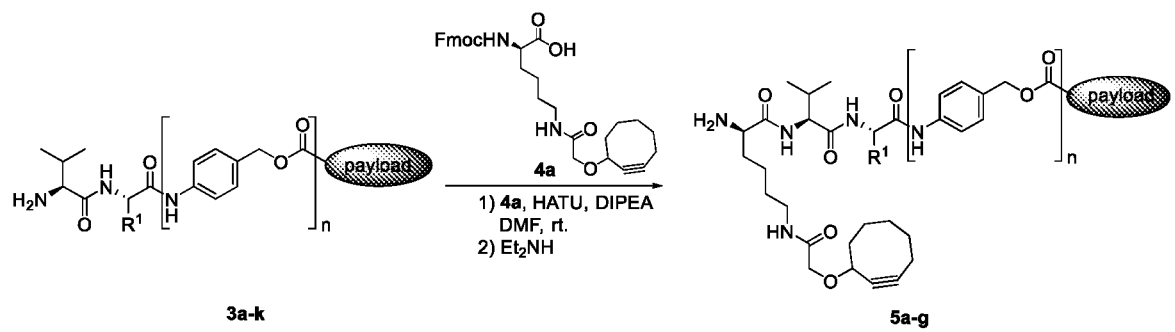
FIG. 11 shows a synthetic process for preparation of intermediates 5a-g.

Preparation of Intermediates 5a-g (See FIG. 11)

General Procedure D:

To a solution of compound 4a (1.2 eq.) in DMF (0.2 mL per 10 mg of 4a) were added HATU (1.4 eq.) and DIPEA (3 eq.) at RT. The mixture was stirred at RT for 5 minutes before the addition of compound 3 (1.0 eq.). The reaction mixture was then stirred at RT for 2 hours until compound 3a-g was totally consumed, which was monitored by LCMS. To the reaction mixture was added diethyl amine (5.0 eq.). The mixture was stirred at RT for 2 hours. The mixture was filtered and the filtrate was concentrated. The residue was purified by reversed phase flash chromatography (0-100% acetonitrile in aq. ammonium bicarbonate (10 mM)) or prep-HPLC (Method B) to give compound 5a-g.

4-((2S)-2-((2S)-2-((2R)-2-Amino-6-(2-(cyclooct-2-ynyloxy)acetamido)hexanamido)-3-methylbutanamido)-5-ureidopentanamido)benzyl (S)-1-((S)-1-(((3R,4S,5S)-1-((S)-2-((1R,2R)-3-((1S,2R)-1-hydroxy-1-phenylpropan-2-ylamino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-ylamino)-3-methyl-1-oxobutan-2-yl (methyl)carbamate (5a)

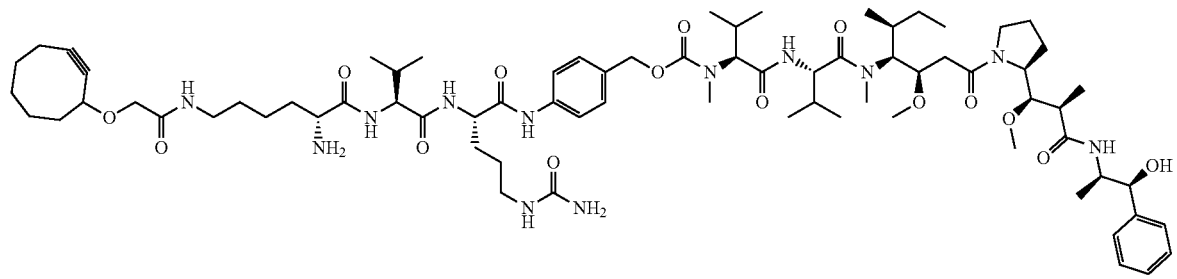 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@H](N)CCCCNC(=O)COC2C#CCCCCC2)C(C)C)cc1)C(C)C]

Following the general procedure D from compound 3a (38 mg, 34 µmol) with compound 4 (34 mg, 64 µmol), compound 5a (17 mg, 35% yield) was obtained as a white solid. ESI m/z: 1415 (M+1)+. 1H NMR (DMSO$_{d6}$, 400 MHz) δ 10.09-10.02 (m, 1H), 8.54 (d, J=8.4 Hz, 1H), 8.38 (d, J=7.5 Hz, 1H), 8.35-8.26 (m, 0.5H), 8.12-8.02 (m, 3H), 7.94-7.85 (m, 0.5H), 7.66-7.54 (m, 3H), 7.34-7.23 (m, 6H), 7.20-7.13 (m, 1H), 6.08-5.97 (m, 1H), 5.54-5.37 (m, 3H), 5.13-4.94 (m, 2H), 4.52-4.21 (m, 6H), 4.03-3.70 (m, 4H), 3.63-3.51 (m, 1H), 3.25-3.17 (m, 8H), 3.13-2.82 (m, 10H), 2.31-1.91 (m, 10H), 1.85-1.64 (m, 9H), 1.64-1.25 (m, 15H), 1.07-0.96 (m, 6H), 0.90-0.74 (m, 26H) ppm.

{4-[(2S)-2-[(2S)-2-[(2S)-2-Amino-6-[2-(cyclooct-2-yn-1-yloxy)acetamido]hexanamido]-3-methylbutanamido]-5-(carbamoylamino)pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$0.0$^{4,8}$.0$^{13,18}$]icosa-14,17-dien-8-yl]-2-oxoethyl}carbamate (5b)

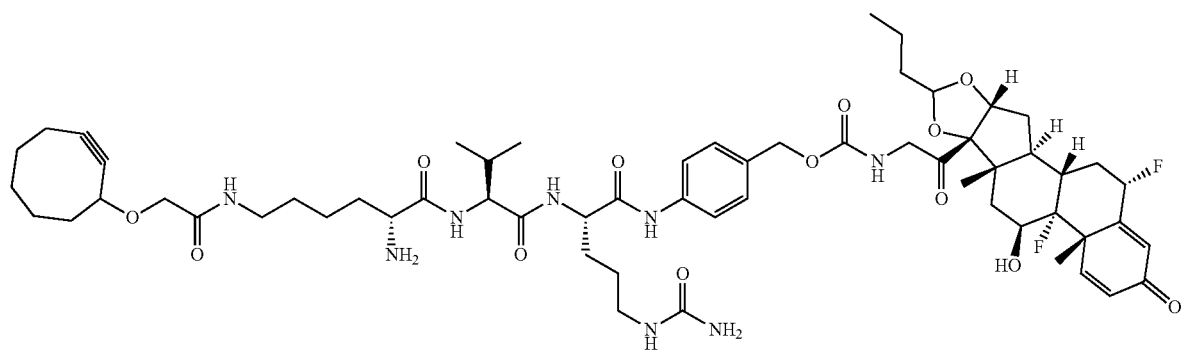 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@H](N)CCCCNC(=O)COC3C#CCCCCC3)C(C)C)cc2)O1]

Following the general procedure D from 3b (0.20 g, 0.23 mmol), the compound 5b (0.12 g, 45% yield) was obtained as a white solid after prep-HPLC (method B). ESI m/z: 1385 (M+1)+. 1H NMR (400 MHz, MeOD$_{d4}$) δ 7.65-7.55 (m, 2H), 7.40-7.26 (m, 3H), 6.39-6.27 (m, 2H), 5.65-5.45 (m, 1H), 5.13-5.01 (m, 2H), 4.71-4.50 (m, 2H), 4.40-4.14 (m, 4H), 4.11-3.82 (m, 3H), 3.46-3.39 (m, 1H), 3.29-3.09 (m, 4H), 2.76-2.54 (m, 1H), 2.41-2.10 (m, 7H), 2.09-1.99 (m, 1H), 1.96-1.80 (m, 5H), 1.78-1.21 (m, 23H), 1.06-0.82 (m, 12H) ppm.

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹0.0⁴,⁸0.0¹³,¹⁸]icosa-14,17-dien-8-yl]-2-oxoethoxy}phenyl)carbamate (5c)

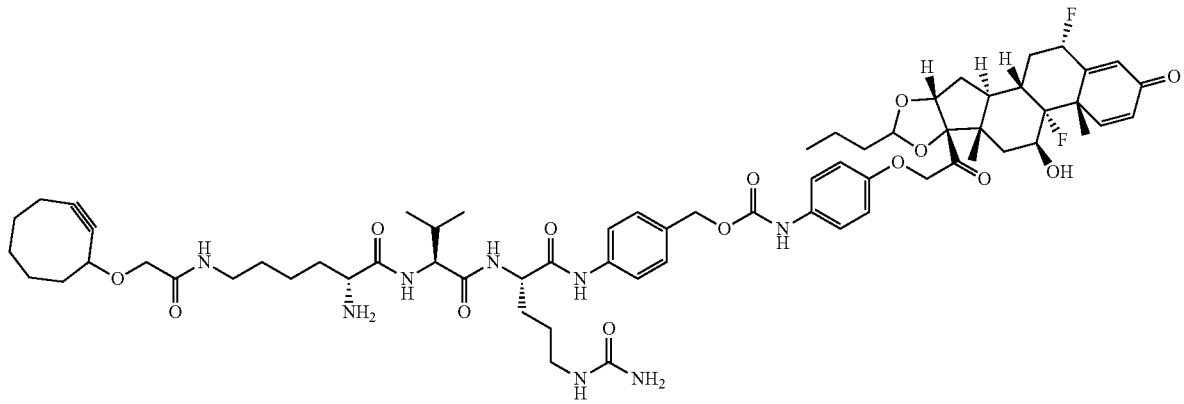 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)OCc3ccc(NC(=O)[C@H](CCCNC(N)=O)NC(=O)[C@@H](NC(=O)[C@H](N)CCCCNC(=O)COC4C#CCCCCC4)C(C)C)cc3)cc2)O1]

Following the general procedure D from 3c (55 mg, 54 μmol) with 4a, compound 5c (0.10 g, yield 57%) was obtained as a white solid. ESI m/z: 1255.5 (M+1)⁺. ¹H NMR (400 MHz, MeOD$_{d4}$) δ 7.61 (d, J=8.4 Hz, 2H), 7.32-7.39 (m, 5H), 6.84-6.88 (m, 2H), 6.31-6.36 (m, 2H), 5.05-5.16 (m, 3H), 4.71-4.83 (m, 1H), 4.50-4.54 (m, 1H), 4.18-4.33 (m, 3H), 3.00-2.85 (m, 2H), 3.40-3.51 (m, 1H), 3.00-3.29 (m, 6H), 1.31-2.35 (m, 34H), 1.29 (t, J=7.2 Hz, 2H), 0.93-1.02 (m, 12H) ppm.

(2R)-2-Amino-6-[2-(cyclooct-2-yn-1-yloxy)acetamido]-N-[(1S)-1-{[(1S)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹0.0⁴,⁸0.0¹³,¹⁸]icosa-14,17-dien-8-yl]-2-oxoethoxy}phenyl)carbamoyl]ethyl]carbamoyl}-2-methylpropyl]hexanamide (5d)

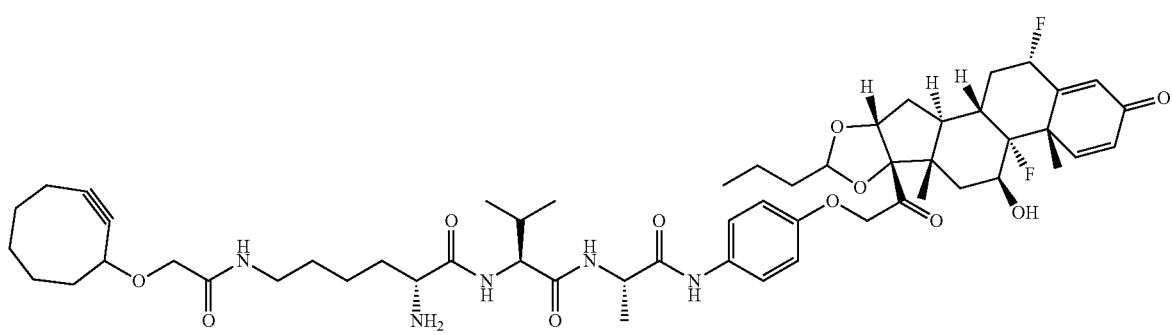 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](C)NC(=O)[C@@H](NC(=O)[C@H](N)CCCCNC(=O)COC3C#CCCCCC3)C(C)C)cc2)O1]

Following the general procedure D from 3d (0.28 g, 0.38 mmol), compound 5d (0.21 g, 46% yield) was obtained as a white solid after prep-HPLC (method B). ESI m/z: 1021.5 (M+1)⁺. ¹H NMR (400 MHz, MeOD$_{d4}$) δ 7.33-7.60 (m, 3H), 6.87-6.91 (m, 2H), 6.32-6.37 (m, 2H), 5.47-5.65 (m, 1H), 5.07-5.30 (m, 1H), 4.72-4.86 (m, 3H), 4.34-4.51 (m, 3H), 3.83-4.20 (m, 3H), 3.33-3.49 (m, 1H), 3.14-3.27 (m, 3H), 2.59-2.75 (m, 1H), 1.31-2.39 (m, 33H), 0.93-1.05 (m, 12H) ppm.

(2R)-2-Amino-N-[(1S)-1-{[(1S)-4-(carbamoylamino)-1-[(4-{2-[(1S,2S,4R,8S,9S,11S,12R,13S, 19S)-12,19-difluoro-11-hydroxy-9,13-dimethyl-16-oxo-6-propyl-5,7-dioxapentacyclo[10.8.0.0$^{2,5}$0.0$^{4,8}$.0$^{13,18}$]icosa-14,17-dien-8-yl]-2-oxoethoxy}phenyl)carbamoyl]butyl]carbamoyl}-2-methylpropyl]-6-[2-(cyclooct-2-yn-1-yloxy)acetamido]hexanamide (5e)

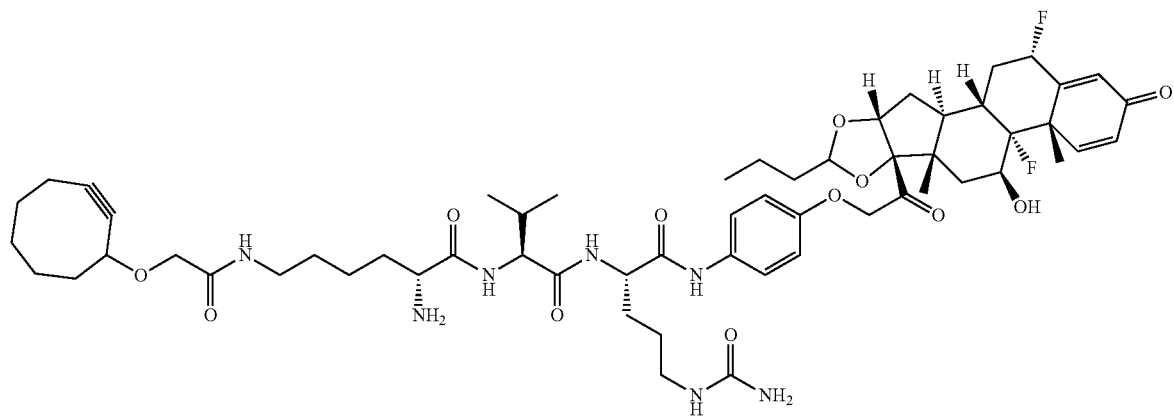 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](CCCNC(N)=O)NC(=O)[C@@H](NC(=O)[C@H](N)CCCCNC(=O)COC3C#CCCCCC3)C(C)C)cc2)O1]

Following the general procedure D from 3e (0.10 g, 0.12 mmol), compound 5d (0.12 g, 88% yield) was obtained as a white solid after purification by reversed phase flash chromatography (0-100% acetonitrile in aq. ammonium bicarbonate (10 mM)). ESI m/z: 553.7 (M/2+1)$^+$.

(1S,4aS,10aR)-6-((2S)-2-((2S)-2-((2R)-2-Amino-6-(2-(cyclooct-2-ynyloxy)acetamido)hexanamido)-3-methylbutanamido)propanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (5f)

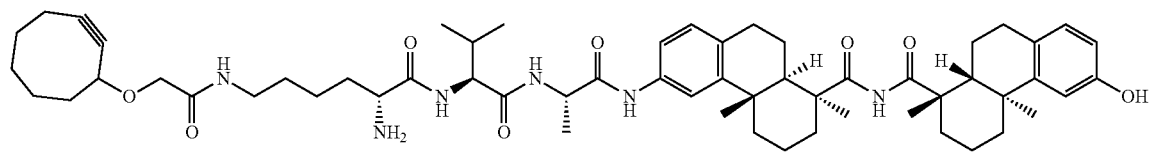 [SMILES: CC(C)[C@H](NC(=O)[C@H](N)CCCCNC(=O)COC1C#CCCCCC1)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

Following the general procedure D from 3f (80 mg, 0.11 mmol), compound 5f (48 mg, 84% yield) was obtained as a white solid after prep-HPLC (method B). ESI m/z: 991.5 (M+1)$^+$.

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (5g)

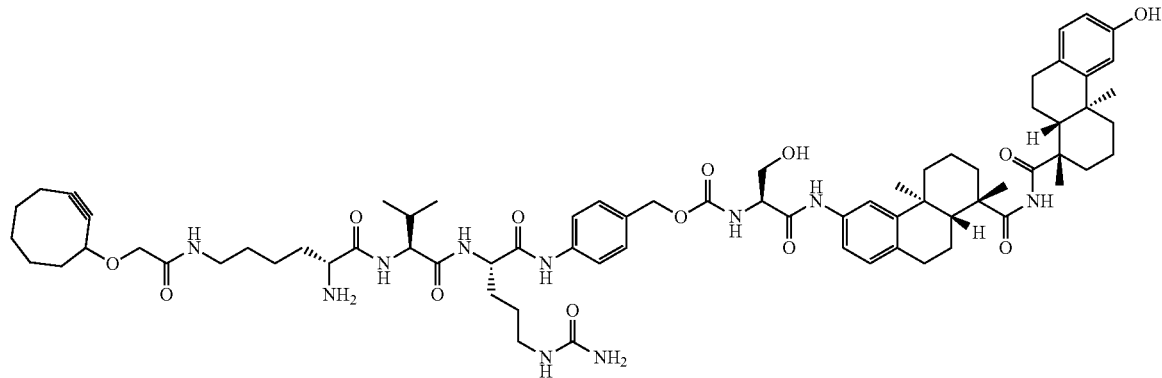 [SMILES: CC(C)[C@H](NC(=O)[C@H](N)CCCCNC(=O)COC1C#CCCCCC1)C(=O)N[C@@H](CCCNC(N)=O)C(=O)Nc1ccc(COC(=O)N[C@@H](CO)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

To a solution of compound 4a (24 mg, 44 μmol) in DMF (2 mL) were added HATU (17 mg, 44 μmol) and compound 3g (35 mg, 34 μmol) subsequently at RT. The mixture was stirred for a few minutes at RT until the mixture was homogenous. To this mixture was added DIPEA (8.8 mg, 68 μmol) at RT by syringe. The resulting mixture was stirred at RT for 2 hours until the 3g was mostly consumed according to LCMS. To this reaction mixture was then added diethylamine or piperidine (0.1 mL, excess)[1] dropwise at RT and the mixture was stirred for an hour until Fmoc group was removed, which was monitored by LCMS. The reaction mixture was directly purified by prep-HPLC (method B) to give compound 5g (15 mg, 33% yield) as a white solid. ESI m/z: 1313.6 (M+H)+. $^1$H NMR (500 MHz, MeOD$_{d4}$) δ 7.59 (d, J=8.5 Hz, 2H), 7.51 (s, 1H), 7.36-7.26 (m, 3H), 7.01 (d, J=8.5 Hz, 1H), 6.88 (d, J=8.0 Hz, 1H), 6.72-6.71 (m, 1H), 6.57-6.54 (m, 1H), 5.09 (s, 2H), 4.64-4.52 (m, 1H), 4.35-4.28 (m, 2H), 4.21 (d, J=7.0 Hz, 1H), 4.01-3.98 (m, 1H), 3.88-3.84 (m, 3H), 3.43 (t, J=6.5 Hz, 1H), 3.26-3.10 (m, 4H), 3.00-2.76 (m, 3H), 2.38-2.24 (m, 7H), 2.19-2.02 (m, 9H), 1.98-1.78 (m, 4H), 1.74-1.54 (m, 12H), 1.45-1.26 (m, 14H), 1.13 (s, 6H), 1.00 (t, J=7.5 Hz, 6H) ppm.

Example 10-1

Figure 11A:
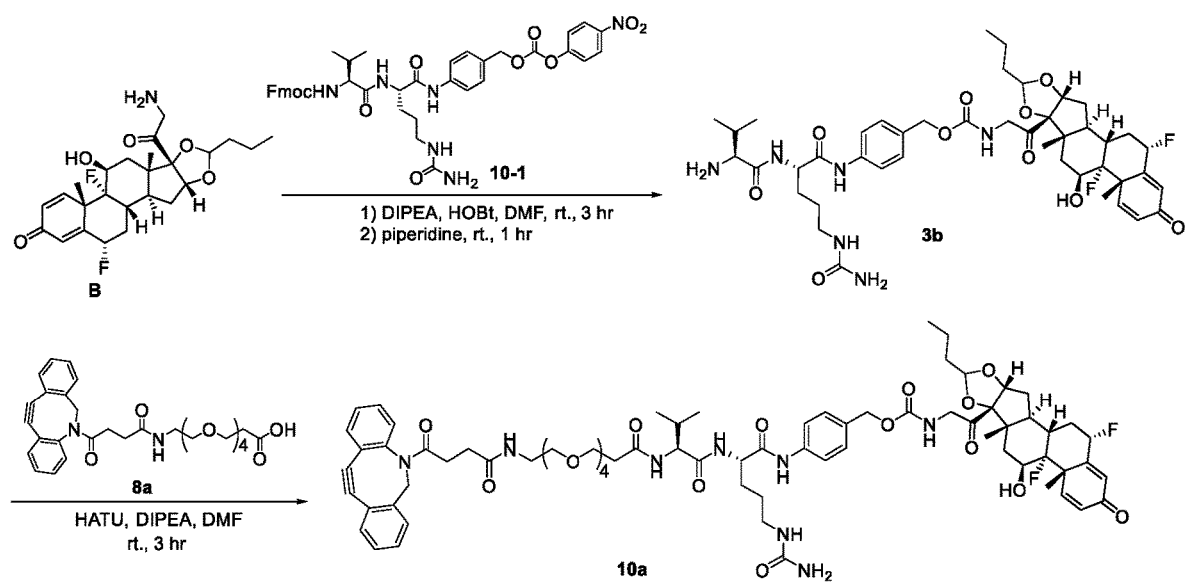
Figure 11B:
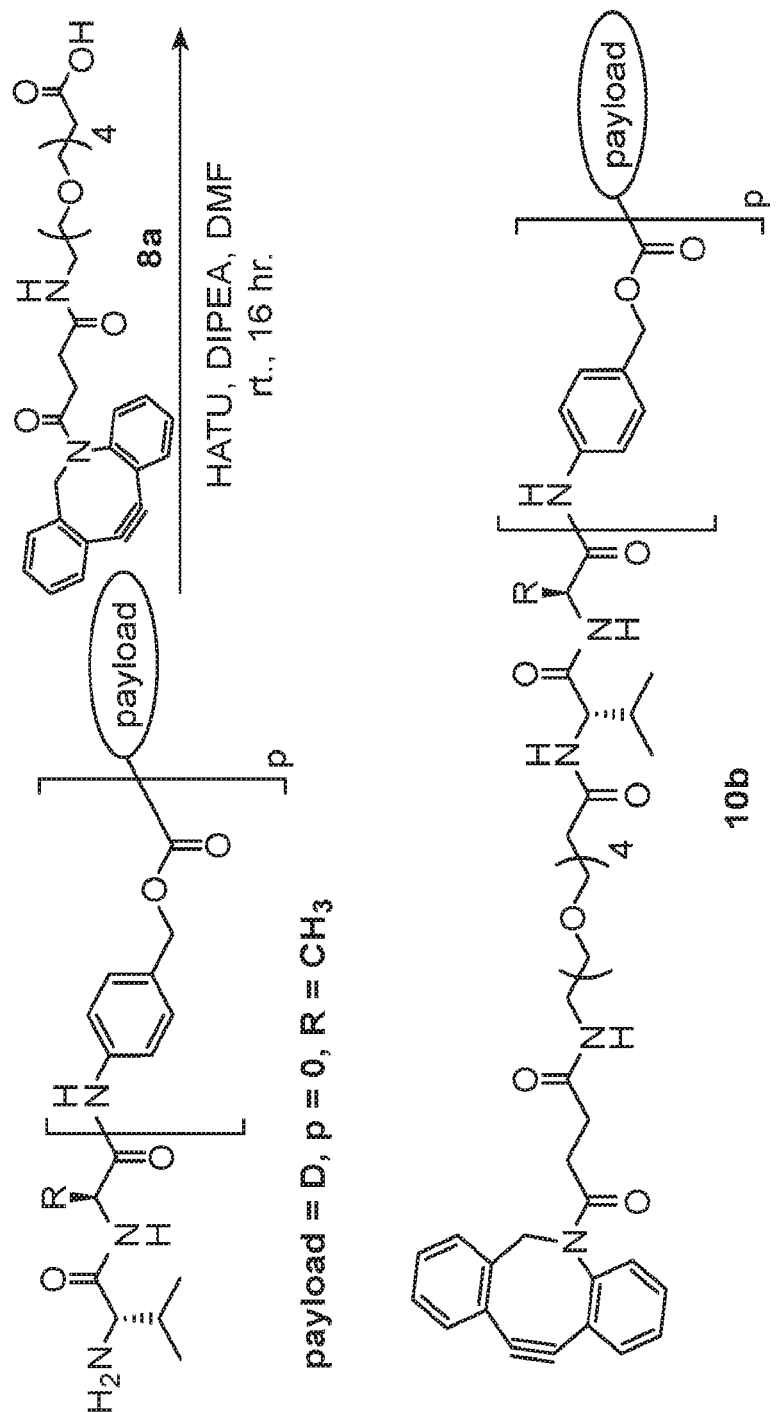
FIG. 11B shows a synthetic process for preparation of intermediate 10b.
Figure 11C:
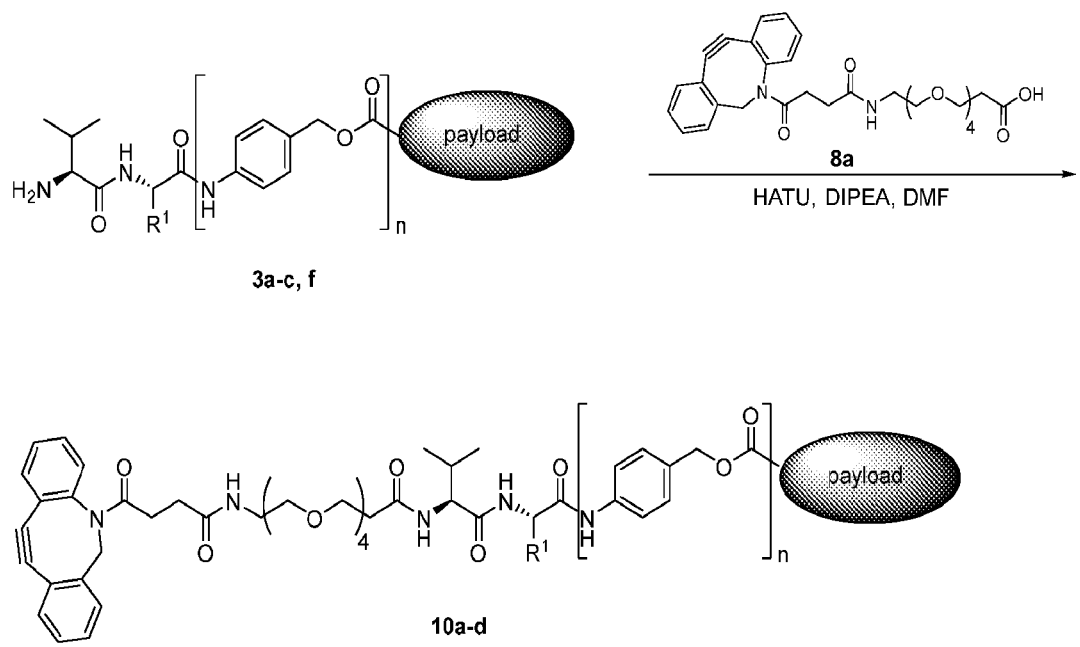
FIG. 11C shows a synthetic process for preparation of intermediates 10a, 10b, 10c, and 10d.

Preparation of Compounds 10a-d (FIG. 11C)

Compounds 10a-d were prepared by an amide coupling procedure according to FIG. 11C.

General Procedure D2 for Compounds 10a-d:

To a solution of DIBAC-suc-PEG$_4$-acid 8a (1.1-1.3 eq.) in DMF (1 mL per 5-10 mg of 8a) were added HATU (1.5 eq.) and DIPEA (5.0 eq.) at RT. The mixture was stirred at RT for half an hour followed by addition of compound 3 (1.0 eq.). The resulting mixture was stirred at RT until compound 3 was consumed, which was monitored by LCMS. After filtration, the filtrate was directly purified by prep-HPLC to give compound 10a-d.

Example 10A

Preparation of Compound 10a (See FIG. 11A)

{4-[(2S)-2-[(2S)-2-Amino-3-methylbutanamido]-5-(carbamoylamino)pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}carbamate 10a

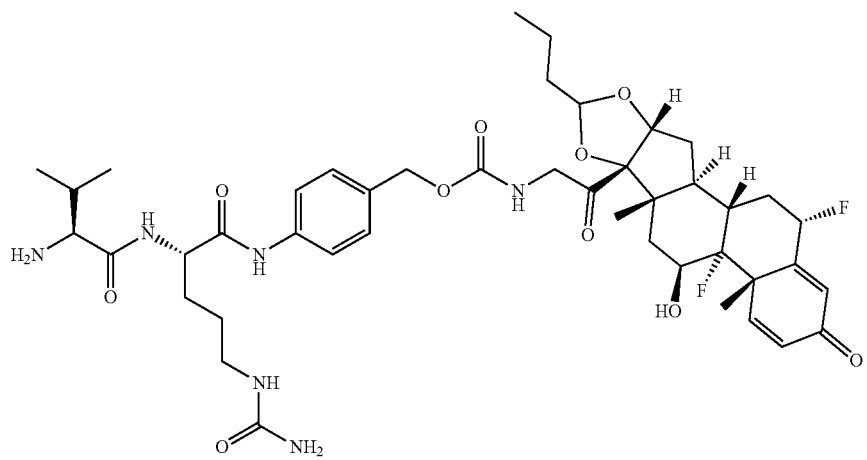

925

To a solution of Fmoc-VC-PAB-PNP (10-1, 0.17 g, 0.22 mmol) and compound B, (93 mg, 0.20 mmol) in DMF (3 mL) was added with DIPEA (51 mg, 0.40 mmol) at RT by syringe. The mixture was stirred at RT for 3 hours and most of materials were consumed according to LCMS. To the resulting mixture was added piperidine (0.3 mL, excess) and it was stirred at RT for an hour until Fmoc was totally removed, which was monitored by LCMS. After filtering through a membrane, the filtrate was directly purified by prep-HPLC (method B) to give compound 3b (0.13 g, 73% yield) as a white solid. ESI m/z: 871 (M+1)$^+$.

926

{4-[(2S)-2-[(2S)-2-[1-(4-{2-Azatricyclo[10.4.0.0$^{4,9}$] hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino) pentanamido]phenyl}methyl N-{2-[(1S,2S,4R,8S, 9S,11S,12R,13S,19S)-12,19-difluoro-11-hydroxy-9, 13-dimethyl-16-oxo-6-propyl-5,7-dioxapentacyclo [10.8.0.0$^{2,9}$0.0$^{4,8}$0.0$^{13,18}$]icosa-14,17-dien-8-yl]-2-oxoethyl}carbamate 10a

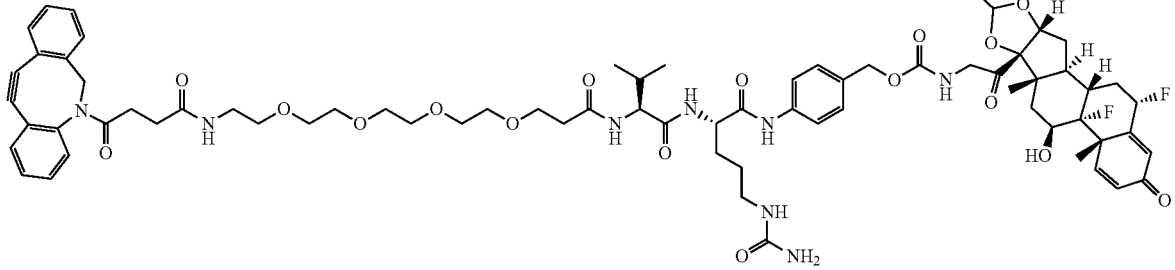

To a solution of acid 8a (30 mg, 54 μmol) in DMF (5 mL) were added DIPEA (13 mg, 0.10 mmol) and HATU (31 mg, 81 μmol) at RT successively. The resulting mixture was stirred at this temperature for 0.5 hour before the amine 3b (43 mg, 50 μmol) was added. The reaction mixture was stirred at RT for 3 hours until the amine was totally consumed, which was monitored by LCMS. The reaction mixture was filtered through membrane and the filtrate was then separated by prep-HPLC (method B) to give compound 10a (16 mg, 23% yield) as a white solid. ESI m/z: 1406 (M+H)$^+$. $^1$H NMR (500 MHz, DMSO$_{d6}$) δ 9.99 (s, 1H), 8.11 (d, J=7.5 Hz, 1H), 7.88 (d, J=8.5 Hz, 1H), 7.80-7.75 (m, 1H), 7.70-7.66 (m, 1H), 7.65-7.60 (m, 3H), 7.53-7.33 (m, 6H), 7.33-7.28 (m, 3H), 6.30 (dd, J=10.0 Hz, 1.5 Hz, 1H), 6.11 (s, 1H), 6.10-6.00 (m, 1H), 5.72-5.55 (m, 2H), 5.41 (s, 2H), 5.05-5.01 (m, 1H), 4.97 (s, 2H), 4.80-4.72 (m, 1H), 4.60-4.58 (m, 1H), 4.43-4.33 (m, 1H), 4.25-4.10 (m, 3H), 3.88-3.80 (m, 1H), 3.65-3.55 (m, 3H), 3.50-3.40 (m, 12H), 3.30-3.25 (m, 2H), 3.12-2.90 (m, 4H), 2.70-2.55 (m, 2H), 2.48-2.35 (m, 2H), 2.30-2.20 (m, 2H), 2.15-1.95 (m, 4H), 1.86-1.65 (m, 3H), 1.64-1.54 (m, 5H), 1.49 (s, 4H), 1.46-1.34 (m, 5H), 0.90-0.80 (m, 12H) ppm. Anal. HPLC: 100%, Retention time: 7.40 min (method B). Solubility: 0.02 mg/mL water.

Example 10B

Preparation of 1-(4-{2-Azatricyclo[10.4.0.0$^{4,9}$]hexadeca-1(12),4(9),5,7,13,15-hexaen-10-yn-2-yl}-4-oxobutanamido)-N-[(1S)-1-{[(1S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]-3,6,9,12-tetraoxapentadecan-15-amide 10b (See FIG. 11B)

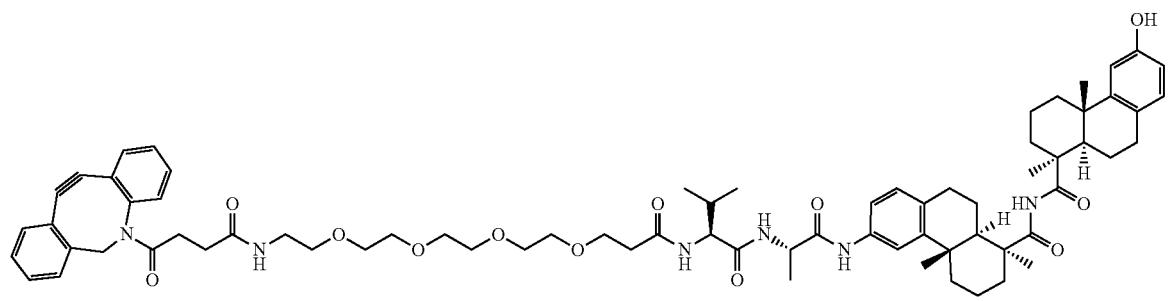 [SMILES: CC(C)[C@H](NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

Prepared by an amide coupling procedure according to FIG. 11B. Following general procedure D2, amine 3f (20 mg, 29 μmol), acid 8a (18 mg, 33 μmop, HATU (33 mg, 87 μmol), and DIPEA (33 mg, 87 μmop, were stirred in 1 mL of DMF at 15-20° C. for 16 hours, purified by prep-HPLC (method B). Yield of 10b: 10 mg, 28%. ESI m/z: 1234 (M+H)$^+$.

$^1$H NMR (500 MHz, methanol$_{d4}$) δ 7.65 (d, J=7.4 Hz, 1H), 7.62-7.51 (m, 2H), 7.48-7.28 (m, 6H), 7.27-7.21 (m, 1H), 7.00 (d, J=8.5 Hz, 1H), 6.88 (d, J=8.0 Hz, 1H), 6.72 (d, J=2.4 Hz, 1H), 6.56 (dd, J=8.3, 2.4 Hz, 1H), 5.15-5.10 (m, 1H), 4.52-4.43 (m, 1H), 4.20 (d, J=6.5 Hz, 0.5H), 4.04 (d, J=7.9 Hz, 0.5H), 3.77-3.64 (m, 3H), 3.63-3.49 (m, 12H), 3.47-3.39 (m, 2H), 3.24 (t, J=5.5 Hz, 2H), 2.99-2.66 (m, 5H), 2.57-2.42 (m, 2H), 2.42-1.94 (m, 14H), 1.76-1.63 (m, 4H), 1.48-1.21 (m, 13H), 1.14-1.10 (m, 6H), 1.05-0.97 (m, 6H) ppm.

Anal. HPLC: >99%, Retention time: 9.21 min (method B).

Solubility: <0.1 mg/mL water.

Example 10C

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$0.0$^{4,8}$0.0$^{13,18}$]icosa-14,17-dien-8-yl]-2-oxoethoxy}phenyl)carbamate (10c)

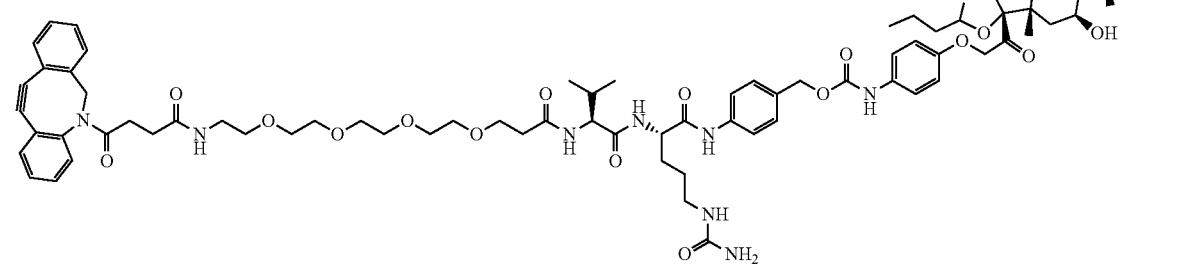

Following the general procedure D2 from compound 3c (58 mg, 60 μmol) with compound 8a, compound 10c (20 mg, 22% yield) was obtained as a white solid. ESI m/z: 1499 (M+H)$^+$. $^1$H NMR (400 MHz, DMSO$_{d6}$) δ 10.02 (s, 1H), 9.59 (s, 1H), 8.14 (d, J=7.6 Hz, 1H), 7.88 (d, J=8.8 Hz, 1H), 7.80-7.75 (m, 1H), 7.70-7.66 (m, 1H), 7.65-7.60 (m, 3H), 7.53-7.45 (m, 3H), 7.40-7.28 (m, 7H), 6.84 (d, J=9.2 Hz, 2H), 6.30 (dd, J=10.4 Hz, 1.6 Hz, 1H), 6.11 (s, 1H), 6.10-6.00 (m, 1H), 5.72-5.55 (m, 1H), 5.52 (s, 1H), 5.43 (s, 2H), 5.16-5.05 (m, 4H), 4.88-4.70 (m, 3H), 4.43-4.33 (m, 1H), 4.25-4.20 (m, 2H), 3.65-3.55 (m, 3H), 3.50-3.40 (m, 12H), 3.30-3.25 (m, 2H), 3.12-2.90 (m, 4H), 2.70-2.55 (m, 2H), 2.48-2.43 (m, 1H), 2.40-2.35 (m, 1H), 2.30-2.20 (m, 2H), 2.15-1.95 (m, 4H), 1.86-1.75 (m, 2H), 1.64-1.54 (m, 5H), 1.49 (s, 4H), 1.46-1.34 (m, 4H), 1.23 (s, 2H), 0.90-0.80 (m, 12H) ppm. Solubility: <0.01 mg/mL water.

Example 10D

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (10d)

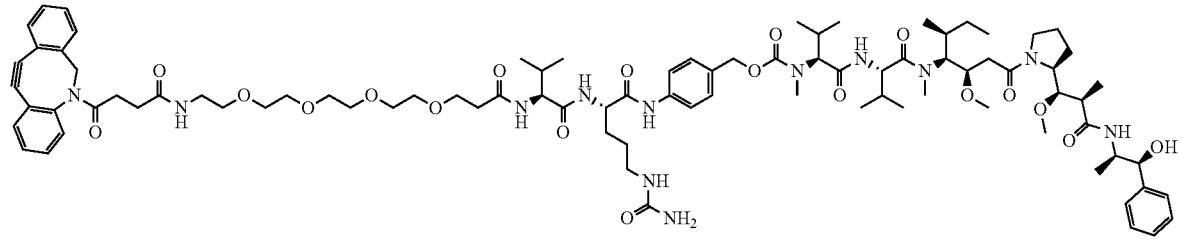 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCOCCOCCOCCOCCNC(=O)CCC(=O)N2Cc3ccccc3C#Cc3ccccc32)C(C)C)cc1)C(C)C]

Following the general procedure D2 from vcPAB-MMAE 3a (6.9 mg, 6.1 μmol) with compound 8a, compound 10d (2.0 mg, 20% yield) was obtained as a white solid. ESI m/z: 830 (M/2+H)$^+$. $^1$H NMR (500 MHz, DMSO$_{d6}$) δ 9.98 (s, 1H), 8.29 (s, 1H), 8.11 (d, J=7.3 Hz, 1H), 8.04 (s, 1H), 7.92-7.82 (m, 2H), 7.75 (t, J=5.1 Hz, 1H), 7.68 (d, J=7.2 Hz, 1H), 7.65-7.53 (m, 3H), 7.53-7.42 (m, 3H), 7.41-7.22 (m, 9H), 7.22-7.10 (m, 1H), 6.06-5.91 (m, 1H), 5.75 (s, 1H), 5.40 (s, 2H), 5.33 (d, J=4.8 Hz, 1H), 5.15-4.91 (m, 3H), 4.79-4.57 (m, 1H), 4.54-4.46 (m, 1H), 4.46-4.32 (m, 2H), 4.32-4.17 (m, 2H), 4.08-3.88 (m, 2H), 3.67-3.53 (m, 4H), 3.50-3.40 (m, 12H), 3.27-3.15 (m, 8H), 3.14-2.91 (m, 8H), 2.91-2.80 (m, 3H), 2.62-2.53 (m, 1H), 2.41-2.33 (m, 2H), 2.32-2.19 (m, 2H), 2.17-2.05 (m, 2H), 2.05-1.90 (m, 4H), 1.86-1.65 (m, 5H), 1.64-1.52 (m, 2H), 1.52-1.40 (m, 2H), 1.39-1.27 (m, 2H), 1.07-0.95 (m, 6H), 0.90-0.67 (m, 26H) ppm.

Example 11

Figure 12:
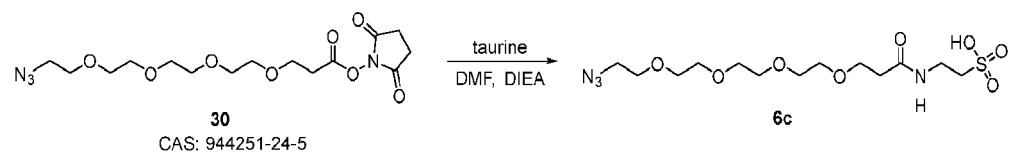
FIG. 12 shows a synthetic process for preparation of intermediate 6c.

Preparation of Intermediate 6c (See FIG. 12)

Azido-intermediate 6c was synthesized by the amidation from the activated ester 30 with taurine as described in FIG. 12.

1-Azido-15-oxo-3,6,9,12-tetraoxa-16-azaoctadecane-18-sulfonic acid (6c)

To a solution of 2,5-dioxopyrrolidin-1-yl 1-azido-3,6,9,12-tetraoxapentadecan-15-oate 30 (0.10 g, 0.26 mmol) and taurine (39 mg, 0.31 mmol) in anhydrous DMF (4 mL) was added diisopropylethylamine (15 mg, 0.52 mmol). The mixture was stirred at 25° C. overnight. The reaction mixture was filtered and the solution was purified by prep-HPLC (method A) to give intermediate 6c (0.80 g, yield 78%) as colorless oil. ESI m/z: 399.1 (M+H)$^+$. $^1$H NMR (500 MHz, D$_2$O) δ 3.69 (t, J=6.0 Hz, 2H), 3.64-3.59 (m, 14H), 3.49 (t, J=6.5 Hz, 2H), 3.41 (t, J=4.5 Hz, 2H), 3.00 (t, J=7.0 Hz, 2H), 2.45 (t, J=6.0 Hz, 2H) ppm.

Example 11A

Figure 13:
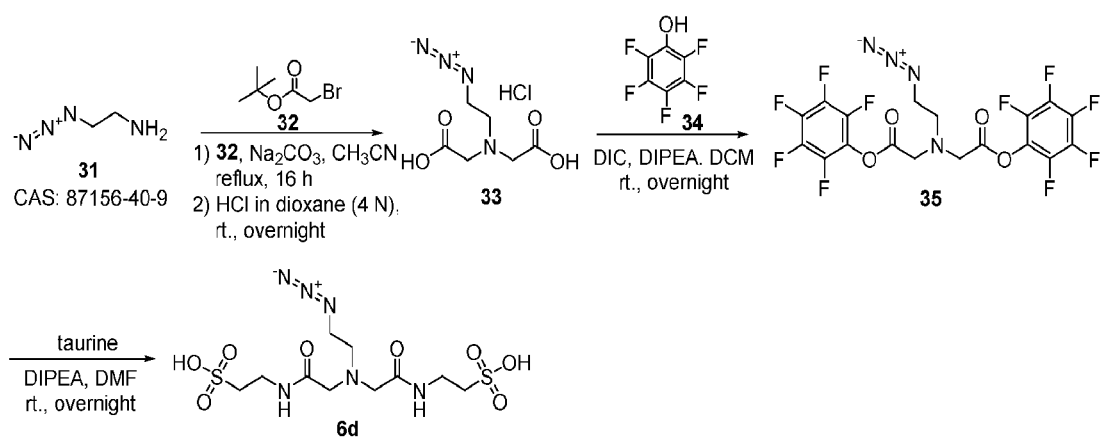
FIG. 13 shows a synthetic process for preparation of intermediate 6d.
Figure 13A:
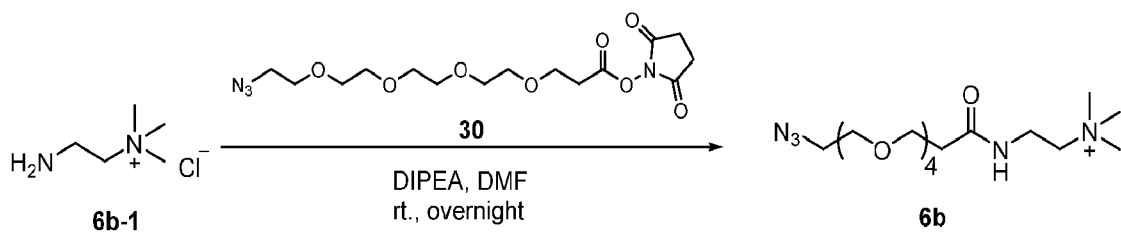
FIG. 13A shows a synthetic process for preparation of intermediate 6b.

Azido-intermediate 6b was synthesized by the amidation from the activated ester 30 with compound 6b-1 as described in FIG. 13A.

[2-(1-Azido-3,6,9,12-tetraoxapentadecan-15-amido)ethyl]trimethylazanium chloride (6b)

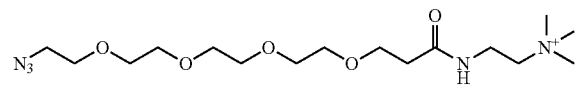 [SMILES: C[N+](C)(C)CCNC(=O)CCOCCOCCOCCOCCN=[N+]=[N-]]

To a solution of azido-PEG$_4$-NHS 30 (0.19 g, 0.50 mmol) in anhydrous DMF (4 mL) were added compound 6b-1 (83 mg, 0.60 mmol) and DIPEA (19 g, 1.5 mmol). The mixture was stirred at 25° C. overnight. The mixture was filtered and the filtrate was purified by prep-HPLC (method A) to give compound 6b (0.13 g, 64% yield) as colorless oil. ESI m/z: 376 (M+H)$^+$. $^1$H NMR (500 MHz, DMSO$_{d6}$) δ 3.65-3.58 (m, 4H), 3.58-3.45 (m, 16H), 3.45-3.30 (m, 12H), 2.35 (t, J=6.5 Hz, 2H) ppm.

Example 11B

Azido-intermediate 6a was commercially available with CAS 86770-69-6.

Example 11C

[2-(1-Azido-3,6,9,12-tetraoxapentadecan-15

Azido-intermediate 6f was synthesized from compound 6d-1 by substitution of the bromine with azide moiety followed by the hydrolysis.

Figure 13B:
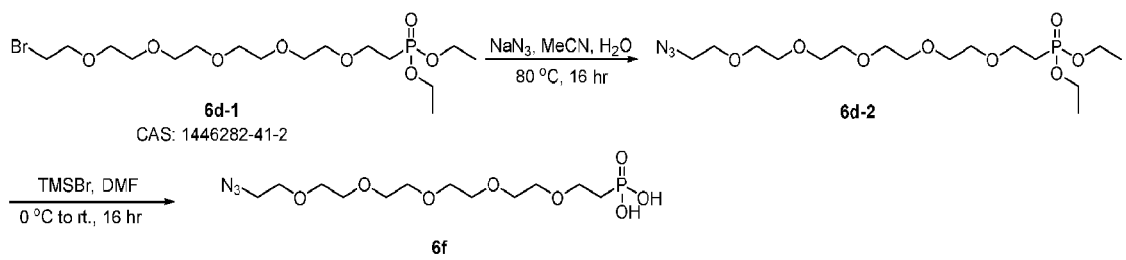
FIG. 13B shows a synthetic process for preparation of intermediate 6f

17-Azido-3,6,9,12,15-pentaoxaheptadecylphosphonic acid (6f) (See FIG. 13B)

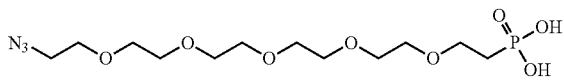 [SMILES: [N-]=[N+]=NCCOCCOCCOCCOCCOCCP(=O)(O)O]

To a 10 mL round bottom flask were added 6d-1 (50 mg, 0.11 mmol), sodium azide (28 mg, 0.43 mmol), acetonitrile (2 mL) and water (2 mL). The mixture was stirred at 80° C. for 16 hours. LCMS showed 6d-1 was completely consumed. The reaction was cooled to RT and acetonitrile was removed in vacuo. The residue was partitioned between ethyl acetate (20 mL) and H$_2$O (20 mL). The organic layer was washed with H$_2$O (15 mL×2), brine (15 mL), dried over anhydrous Na$_2$SO$_4$, filtered and concentrated to give 6d-2 (35 mg, yield: 76%, ESI m/z: 428.2 (M+H)$^+$) as red oil, which was dissolved in anhydrous DMF (2 mL). To the solution was added bromotrimethylsilane (TMSBr, 0.12 g, 0.32 mmol) at 0° C. The mixture was stirred at 0° C. for 30 minutes, and then at RT for 16 hours. The volatiles were removed in vacuo and the residue was co-evaporated with dry toluene (3 times). The residue was dissolved in water and lyophilized to afford crude 6f (crude yield >100%) as oil for the next step without further purification.

Example 11E

Azido-intermediate 6e was commercially available with CAS 35899-89-9.

Example 11F

Azido intermediate maltose-N$_3$ (6g) was synthesized according to Tetrahedron Letters, 2001, 42 (7), 1325-1328.

Example 12

Preparation of Intermediate 6d (See FIG. 13)

Azido-intermediate 6d with dual-sulfonate was synthesized as described in FIG. 13. Azidoethanamine 31 reacted with 2 equivalents of bromoacetate 32, followed by hydrolysis to give dual acid 33, which was converted to activated ester 35 with pentafluorophenol 34. Compound 35 was amidated with taurine to provide the intermediate 6d.

2-{2-[(2-Azidoethyl)({[(2-sulfoethyl)carbamoyl]methyl})amino]acetamido}ethane-1-sulfonic acid (6d)

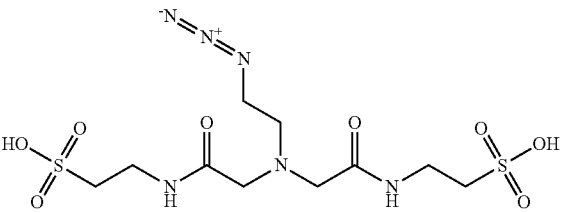

To the solution of 2-azidoethanamine 31 (0.52 g, 6.0 mmol) in acetonitrile (50 mL) were added tert-butyl 2-bromoacetate 32 (2.6 g, 13 mmol) and sodium carbonate (3.2 g, 30 mmol). The suspension was refluxed for 16 hr. After cooled to RT, the mixture was filtered and the filtrate was concentrated in vacuo to give yellow oil (1.6 g, ESI m/z: 315 (M+H)$^+$). 0.62 g of the oily product was dissolved in a solution of hydrochloride in dioxane (4N, 10 mL). The mixture was stirred at 25° C. overnight and LCMS showed the reaction completion. The volatiles were removed in vacuo to give compound 33 (0.39 g, ESI m/z: 203 (M+H)$^+$) as hydrochloride salt, 0.20 g of which was dissolved in DCM (5 mL) for the next step without further purification. To the solution were added DIC (0.38 g, 3.0 mmol), DIPEA (0.77 g, 6.0 mmol) and pentafluorophenol 34 (0.55 g, 3.0 mol). The reaction mixture was stirred at RT overnight. LCMS indicated the reaction was completed. The mixture was concentrated in vacuo to give crude 35 (ESI m/z: 289 (M/2+Na)$^+$), which was dissolved in DMF (5 mL). To the solution were added taurine (0.38 g, 3.0 mmol) and DIPEA (0.52 g, 4.0 mmol). The mixture was stirred at 25° C. overnight and the resulting mixture was directly purified by reversed phase flash chromatography (0-10% acetonitrile in water (with 0.01% TFA)) to give compound 6d (0.18 g, 34% yield from 2-azidoethanamine) as a white solid. ESI m/z: 417 (M+H)$^+$.

Example 13

Figure 14:
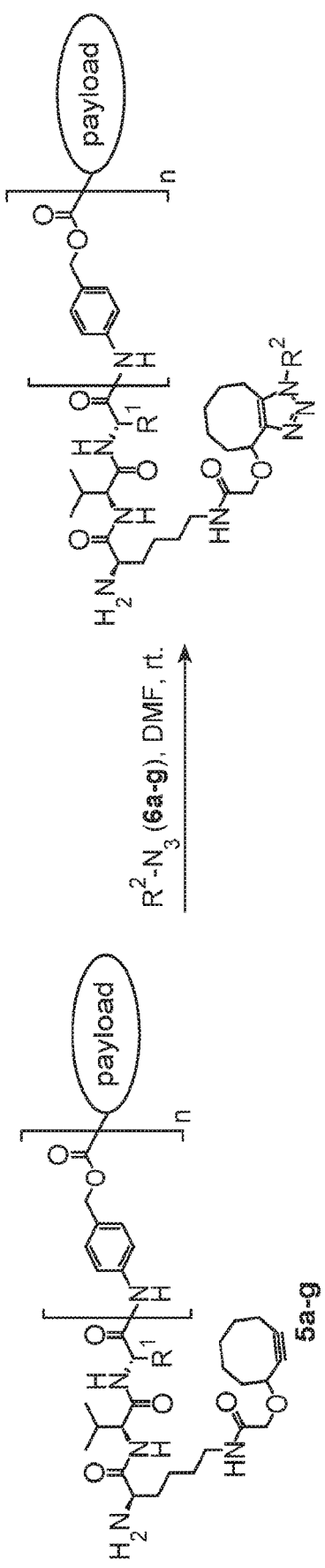
FIG. 14 shows a general synthetic procedure E for preparing intermediates 7a, 7c, 7e, 7f, 7i, 7k, 7m, 7q, 7ab, 7ad, 7ae, 7bb, 7cb, and 7fb.

Preparation of Intermediates 7a, 7c, 7e, 7f, 7j, 7k, 7l, 7m, 7q, 7ab, 7ad, 7ae, 7bb, 7cb, 7th (See FIG. 14)

General Procedure E:

To a solution of compound 5 in DMF (0.5 mL per 10 mg of 5) were added azido intermediate 6 (1.5 eq) and DIPEA (0.1 mL per 10 mg of 5) at RT. The reaction was stirred at RT for 24 hours, LCMS showed the completion of reaction. The reaction mixture was directly purified by prep-HPLC to give compound 7 as a white solid.

{4-[(2S)-2-[(2S)-2-[(2R)-2-Amino-6-(2-{[1-(17-hydroxy-3,6,9,12,15-pentaoxaheptadecan-1-yl)-1H,4H,5H,6H,7H,8H,9H-cycloocta[d][1,2,3]triazol-4-yl]oxy}acetamido)hexanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (7a)

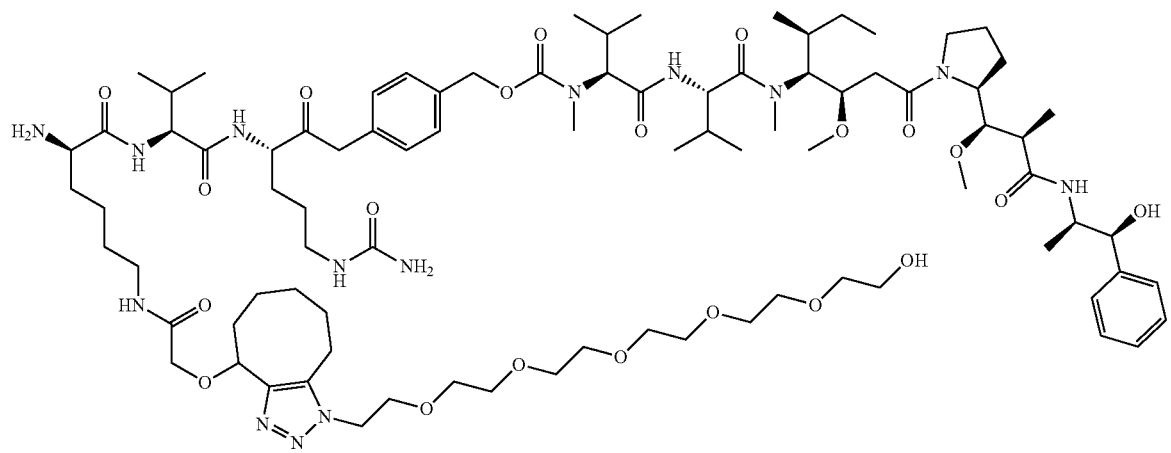 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(CC(=O)[C@H](CCCNC(N)=O)NC(=O)[C@@H](NC(=O)[C@H](N)CCCCNC(=O)COC2CCCCCc3c2nnn3CCOCCOCCOCCOCCOCCO)C(C)C)cc1)C(C)C]

Following the general procedure E from compound 5a (30 mg, 21 μmol) with compound 6a (20 mg, 64 μmol), compound 7a (30 mg, 74% yield) was obtained as a white solid. ESI m/z: 862 (M/2+H)$^+$. $^1$H NMR (MeOD$_{d4}$, 500 MHz): δ7.66-7.57 (m, 2H), 7.44-7.29 (m, 6H), 7.26-7.18 (m, 1H), 5.25-5.04 (m, 2H), 4.88-4.74 (m, 2H), 4.70-4.47 (m, 2H), 4.59-4.48 (m, 4H), 4.29-4.17 (m, 4H), 4.00-3.95 (m, 2H), 3.93-3.88 (m, 2H), 3.76-3.70 (m, 1H), 3.69-3.64 (m, 10H), 3.62-3.59 (m, 2H), 3.59-3.55 (m, 8H), 3.49-3.42 (m, 2H), 3.38-3.36 (m, 4H), 3.31-3.28 (m, 3H), 3.27-3.17 (m, 3H), 3.15-3.06 (m, 3H), 3.00-2.87 (m, 4H), 2.57-2.46 (m, 2H), 2.41-2.18 (m, 2H), 2.17-1.99 (m, 5H), 1.98-1.86 (m, 3H), 1.85-1.68 (m, 6H), 1.67-1.54 (m, 9H), 1.50-1.36 (m, 4H), 1.34-1.25 (m, 1H), 1.22-1.12 (m, 6H), 1.06-0.98 (m, 11H), 0.96-0.93 (m, 3H), 0.92-0.84 (m, 9H), 0.79 (m, 2H). ppm.

2-{1-[4-({[(5R)-5-Amino-5-{[(1S)-1-{[(1S)-4-(car-
bamoylamino)-1-({4-[({[(1S)-1-{[(1S)-1-{[(3R,4S,
5S)-1-[(2S)-2-[(1R,2R)-2-{[(1S,2R)-1-hydroxy-1-
phenylpropan-2-yl]carbamoyl}-1-methoxy-2-
methylethyl]pyrrolidin-1-yl]-3-methoxy-5-methyl-1-
oxoheptan-4-yl](methyl)carbamoyl}-2-methyl
propyl]carbamoyl}-2-methyl propyl](methyl)
carbamoyl}oxy)methyl]phenyl}carbamoyl)butyl]
carbamoyl}-2-methyl propyl]carbamoyl}pentyl]
carbamoyl}methoxy)-1H,4H,5H,6H,7H,8H,9H-
cycloocta[d][1,2,3]triazol-1-yl]-3,6,9,12-
tetraoxapentadecan-15-amido}ethane-1-sulfonic
acid (7c)

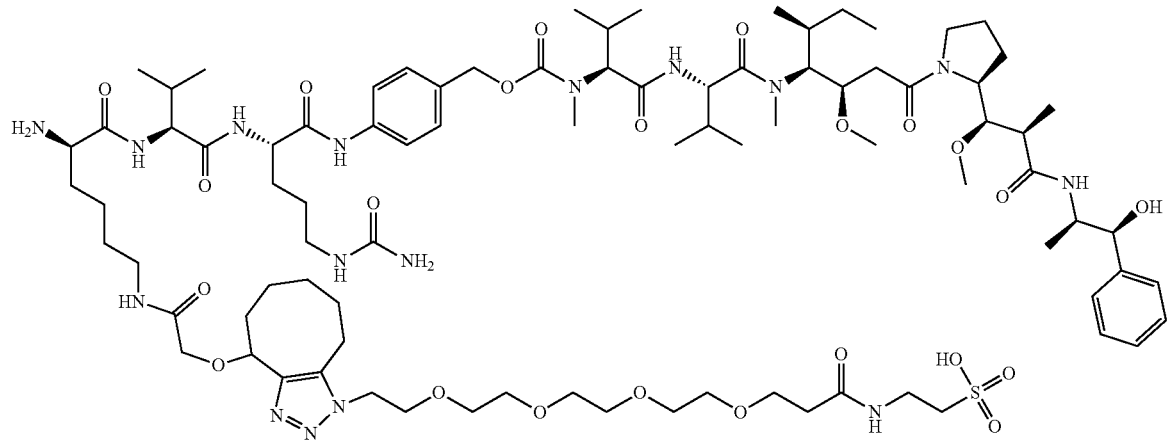 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@H](N)CCCCNC(=O)COC2CCCCCc3c2nnn3CCOCCOCCOCCOCCC(=O)NCCS(=O)(=O)O)C(C)C)cc1)C(C)C]

Following the general procedure E from compound 5a (28 mg, 20 μmol) with compound 6c (20 mg, 50 μmol), compound 7c (20 mg, 56% yield) was obtained as a white solid. ESI m/z: 907.3 (M/2+H)+.

2-{1-[4-({[(5R)-5-Amino-5-{[(1S)-1-{[(1S)-4-(car-
bamoylamino)-1-[(4-{[({2-[(1S,2S,4R,8S,9S,11S,
12R,13S,19S)-12,19-difluoro-11-hydroxy-9,13-dim-
ethyl-16-oxo-6-propyl-5,7-dioxapentacyclo
[10.8.0.0$^{2,9}$.0$^{4,8}$.0$^{13,18}$]icosa-14,17-dien-8-yl]-2-
oxoethyl}carbamoyl)oxy]methyl}phenyl)carbamoyl]
butyl]carbamoyl}-2-methylpropyl]
carbamoyl}pentyl]carbamoyl}methoxy)-1H,4H,5H,
6H,7H,8H,9H-cycloocta[d][1,2,3]triazol-1-yl]-3,6,9,
12-tetraoxapentadecan-15-amido}ethane-1-sulfonic
acid (7e)

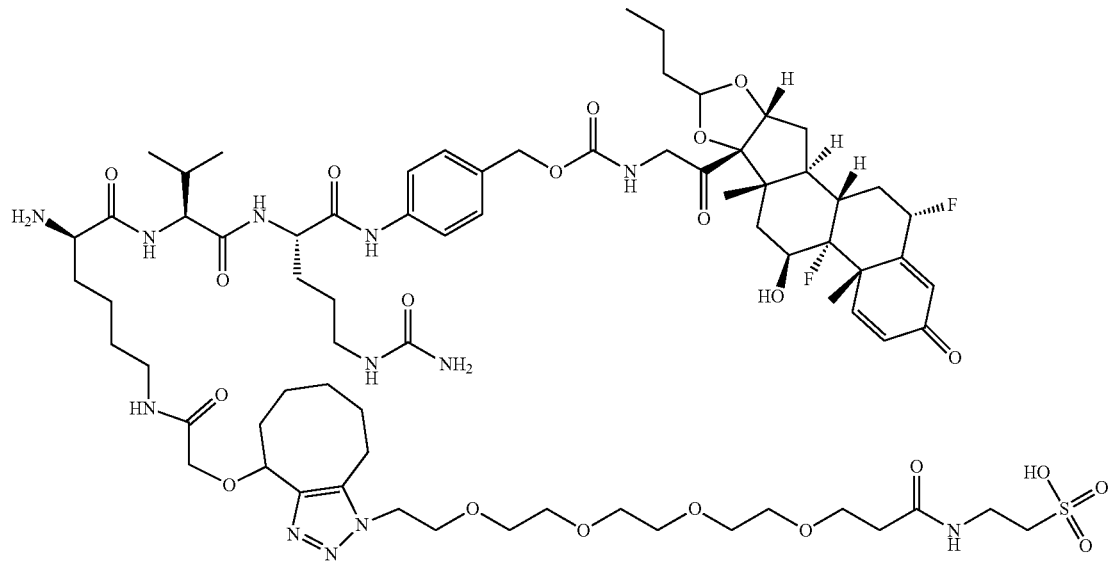 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@H](N)CCCCNC(=O)COC3CCCCCc4c3nnn4CCOCCOCCOCCOCCC(=O)NCCS(=O)(=O)O)C(C)C)cc2)O1]

Following the general procedure E from 5b (60 mg, 52 μmol) with 6c, compound 7e (60 mg, 74% yield) was obtained as a white solid. ESI m/z: 781 (M/2+H)⁺. ¹H NMR (400 MHz, MeOD$_{d4}$) δ 7.61 (d, J=8.5 Hz, 2H), 7.39-7.28 (m, 3H), 6.39-6.30 (m, 2H), 5.66-5.46 (m, 1H), 5.29-5.13 (m, 1H), 5.12-5.04 (m, 3H), 4.72-4.60 (m, 2H), 4.56-4.49 (m, 2H), 4.36-3.84 (m, 8H), 3.76-3.70 (m, 2H), 3.66-3.54 (m, 14H), 3.30-3.23 (m, 2H), 3.21-3.04 (m, 3H), 3.03-2.97 (m, 2H), 2.96-2.84 (m, 1H), 2.75-2.52 (m, 1H), 2.50-2.42 (m, 2H), 2.39-2.01 (m, 6H), 1.99-1.78 (m, 6H), 1.74-1.22 (m, 22H), 1.03-0.87 (m, 12H) ppm.

2-[2-({2-[4-({[(5R)-5-Amino-5-{[(1S)-1-{[(1S)-4-(carbamoylamino)-1-[(4-{[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethyl}carbamoyl)oxy]methyl}phenyl)carbamoyl]butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]ethyl}({[(2-sulfoethyl)carbamoyl]methyl})amino)acetamido]ethane-1-sulfonic acid (7f)

obtained as a white solid. ESI m/z: 790 (M/2+H)⁺. ¹H NMR (500 MHz, DMSO$_{d6}$) δ 10.1-10.0 (m, 1H), 8.60-8.50 (m, 1H), 8.40-8.30 (m, 1H), 8.30-8.20 (m, 2H), 8.15-8.00 (m, 4H), 7.60-7.55 (m, 2H), 7.50-7.40 (m, 1H), 7.30-7.20 (m, 4H), 6.30 (d, J=10.5 Hz, 1H), 6.15-6.00 (m, 2H), 5.70-5.55 (m, 3H), 4.98 (s, 2H), 4.80-4.70 (m, 1H), 4.59 (t, J=4.0 Hz, 1H), 4.50-4.45 (m, 1H), 4.40-4.35 (m, 2H), 4.25-4.10 (m, 2H), 3.95-3.80 (m, 4H), 3.20-2.90 (m, 10H), 2.85-2.75 (m, 2H), 2.70-2.60 (m, 4H), 2.31-2.10 (m, 3H), 2.10-1.95 (m, 6H), 1.80-1.65 (m, 6H), 1.65-1.55 (m, 7H), 1.40-1.20 (m, 12H), 1.20-1.10 (m, 1H), 1.06 (t, J=7.0 Hz, 1H), 1.02-1.00 (m, 1H), 0.90-0.80 (m, 16H) ppm.

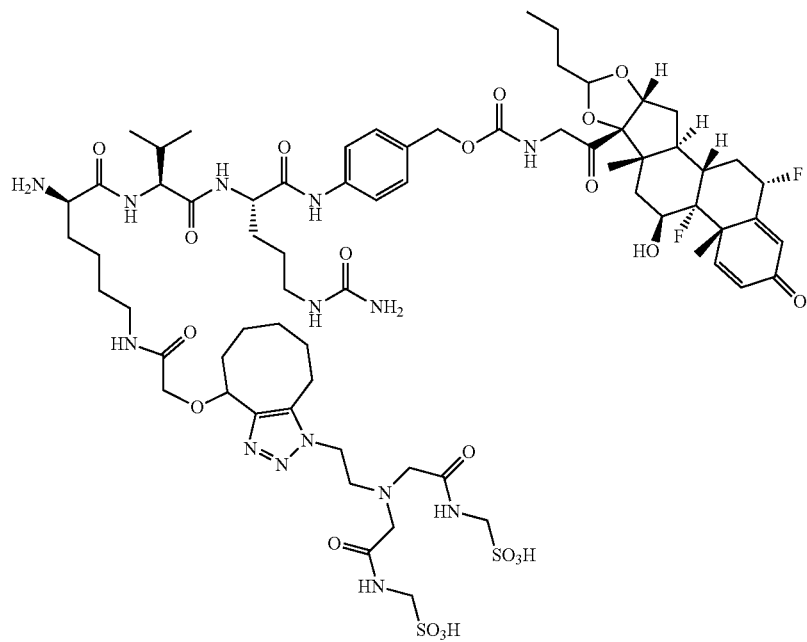 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@H](N)CCCCNC(=O)COC3CCCCCc4c3nnn4CCN(CC(=O)NCS(=O)(=O)O)CC(=O)NCS(=O)(=O)O)C(C)C)cc2)O1]

Following the general procedure E from 5b (0.10 g, 86 μmol) with 6d, compound 7f (65 mg, 48% yield) was 2-{1-[4-({[(5R)-5-Amino-5-{[(1S)-1-{[(1S)-4-(car-bamoylamino)-1-{[4-({[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]oxy}methyl)phenyl]carbamoyl}butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (7i)

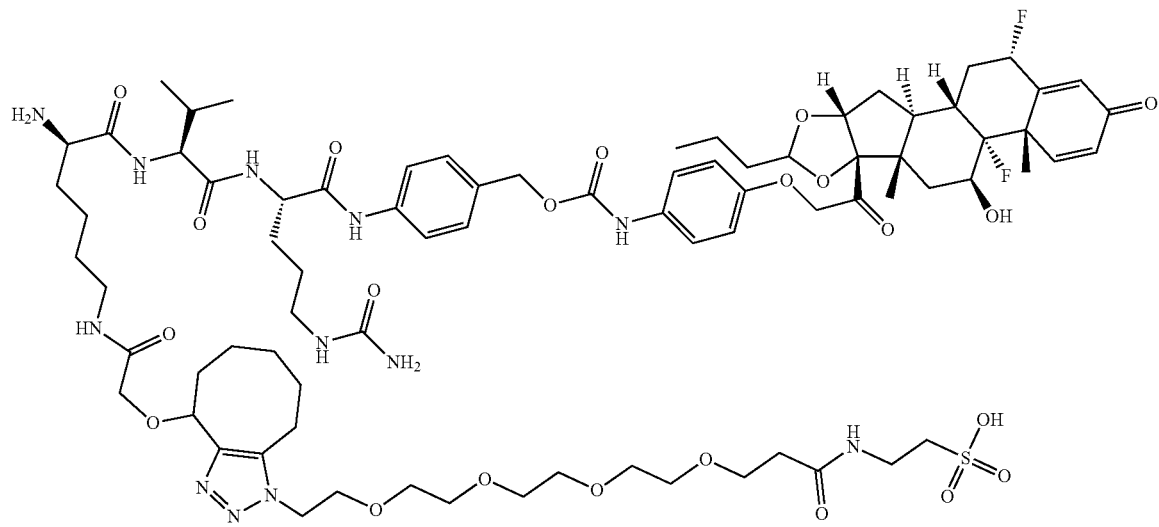 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)OCc3ccc(NC(=O)[C@H](CCCNC(N)=O)NC(=O)[C@@H](NC(=O)[C@H](N)CCCCNC(=O)COC4CCCCCc5c4nnn5CCOCCOCCOCCOCCC(=O)NCCS(=O)(=O)O)C(C)C)cc3)cc2)O1]

Following the general procedure E from 5c (55 mg, 54 µmol) with 6c, compound 7i (53 mg, yield 43%) was obtained as a white solid. ESI m/z: 827.6 (m/2+H)$^+$. $^1$HNMR (400 MHz, MeOD$_{d4}$) δ 7.63-7.61 (m, 2H), 7.40-7.29 (m, 5H), 6.89-6.85 (m, 2H), 6.38-6.33 (m, 2H), 5.65-5.48 (m, 1H), 5.31-5.06 (m, 4H), 4.91-4.70 (m, 4H), 4.65-4.22 (m, 5H), 4.07-3.86 (m, 5H), 3.74-3.63 (m, 16H), 3.33-2.82 (m, 4H), 2.76-1.21 (m, 39H), 1.06-0.93 (m, 12H) ppm.

2-{1-[4-({[(5R)-5-Amino-5-{[(1S)-1-{[(1S)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (7j)

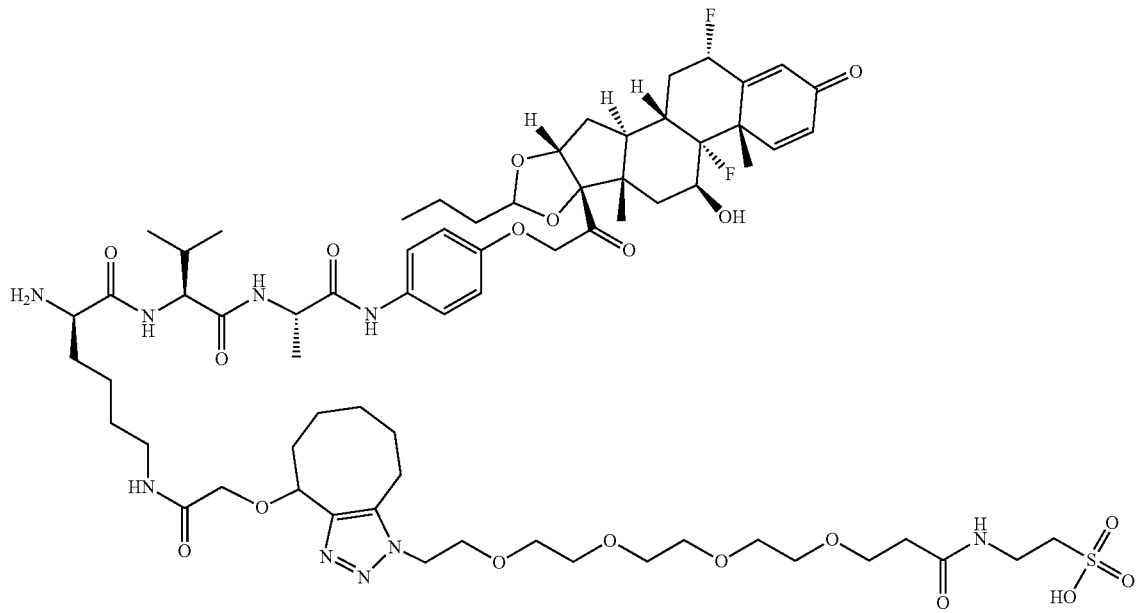 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](C)NC(=O)[C@@H](NC(=O)[C@H](N)CCCCNC(=O)COC3CCCCCc4c3nnn4CCOCCOCCOCCOCCC(=O)NCCS(=O)(=O)O)C(C)C)cc2)O1]

Following the general procedure E from 5d (55 mg, 54 µmol) with 6c, compound 7j (70 mg, 67% yield) was obtained as a white solid. ESI m/z: 709.9 (M/2+H)+. $^1$H NMR (400 MHz, MeOD$_{d4}$) δ 7.58-7.48 (m, 2H), 7.35 (d, J=8.8 Hz, 1H), 6.92-6.88 (m, 2H), 6.38-6.34 (m, 1H), 6.33 (s, 1H), 5.65-5.46 (m, 1H), 5.31-5.07 (m, 2H), 4.87-4.44 (m, 7H), 4.36-4.13 (m, 2H), 4.06-3.87 (m, 5H), 3.75-3.55 (m, 16H), 3.33-2.60 (m, 6H), 2.47-1.79 (m, 13H), 1.72-1.43 (m, 21H), 1.03-0.94 (m, 12H) ppm.

2-{1-[4-({[(5R)-5-Amino-5-{[(1S)-1-{[(1S)-4-(carbamoylamino)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$0.0$^{4,8}$0.0$^{13,18}$]icosa-14,17-dien-8-yl]-2-oxoethoxy}phenyl)carbamoyl]butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (7k)

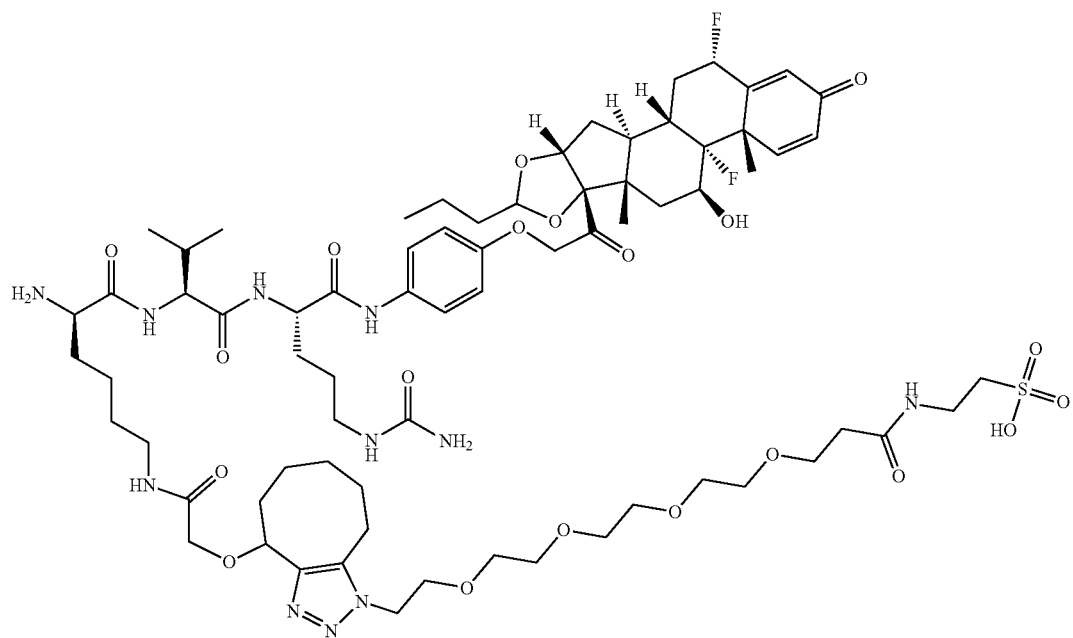 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](CCCNC(N)=O)NC(=O)[C@@H](NC(=O)[C@H](N)CCCCNC(=O)COC3CCCCCc4c3nnn4CCOCCOCCOCCOCCC(=O)NCCS(=O)(=O)O)C(C)C)cc2)O1]

Following the general procedure E from 5e (60 mg, 54 µmol) with 6c, compound 7k (50 mg, 61% yield) was obtained as a white solid. ESI m/z: 753 (M/2+H)+.

1-(4-(2-((R)-5-Amino-6-((S)-1-((S)-1-((4bS,8S,8aR)-8-((1S,4aS,10aR)-6-hydroxy-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-1-oxopropan-2-ylamino)-3-methyl-1-oxobutan-2-ylamino)-6-oxohexylamino)-2-oxoethoxy)-4,5,6,7,8,9-hexahydro-1H-cycloocta[d][1,2,3]triazol-1-yl)-15-oxo-3,6,9,12-tetraoxa-16-azaoctadecane-18-sulfonic acid (7m)

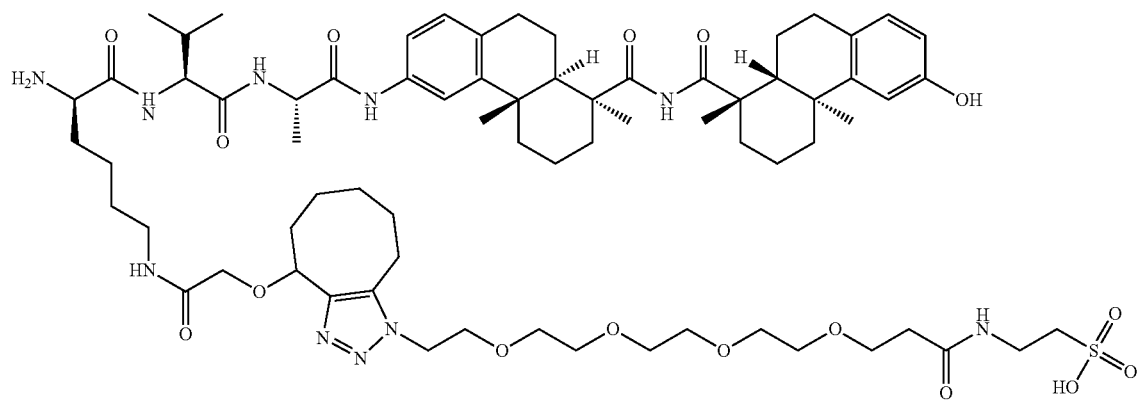 [SMILES: CC(C)[C@H](NC(=O)[C@H](N)CCCCNC(=O)COC1CCCCCc2c1nnn2CCOCCOCCOCCOCCC(=O)NCCS(=O)(=O)O)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

Following the general procedure E from 5f (40 mg, 40 μmol) with 6c, compound 7m (52 mg, 77% yield) was obtained as a white solid. ESI m/z: 695.4 (M/2+H)⁺.

2-{1-[4-({[(5R)-5-Amino-5-{[(1S)-1-{[(1S)-1-({4-[({[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamoyl}oxy)methyl]phenyl}carbamoyl)-4-(carbamoylamino)butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (7q)

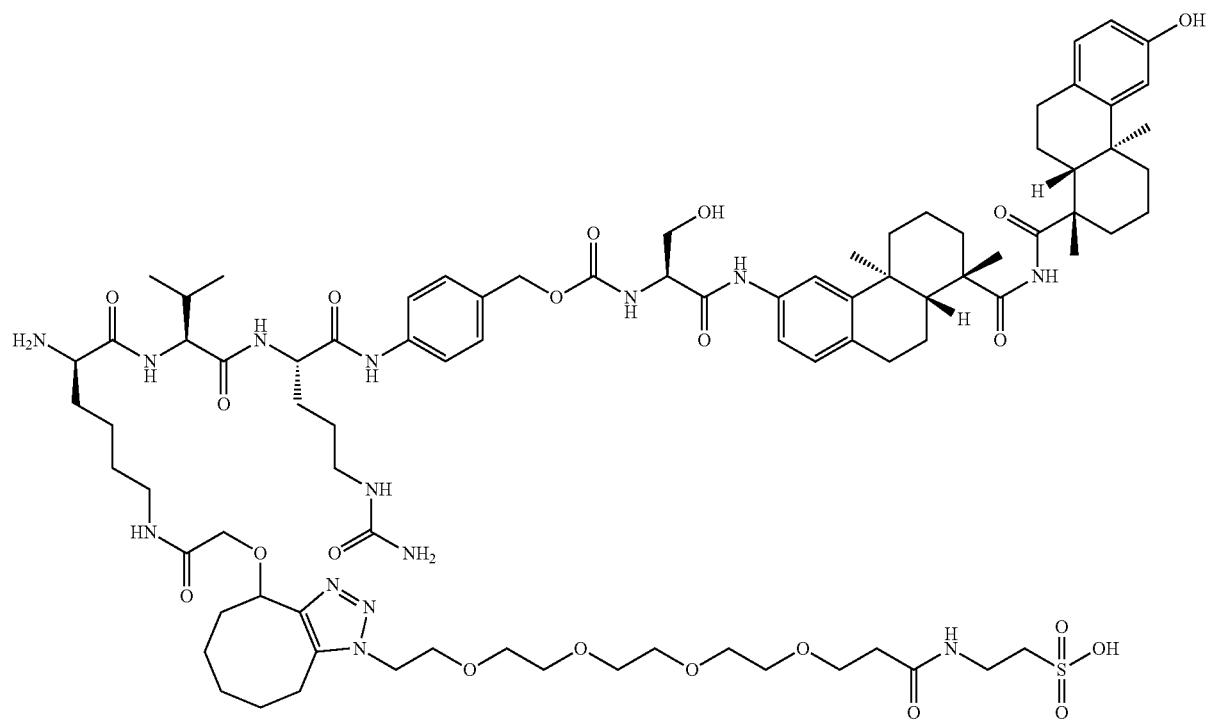 [SMILES: CC(C)[C@H](NC(=O)[C@H](N)CCCCNC(=O)COC1CCCCCc2c1nnn2CCOCCOCCOCCOCCC(=O)NCCS(=O)(=O)O)C(=O)N[C@@H](CCCNC(N)=O)C(=O)Nc1ccc(COC(=O)N[C@@H](CO)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

To a solution of compound 6c (20 mg, 50 µmol) in water (1 mL) was added dropwise sat. aq. sodium bicarbonate solution at 0° C. until pH~7. To the stirred solution was then added a solution of compound 5? (28 mg, 21 µmol) in acetonitrile (1 mL) by syringe. The mixture was stirred at 25° C. overnight. The reaction mixture was monitored by LCMS until compound 5? was totally consumed. The reaction mixture was filtered and purified by prep-HPLC (method A) to give compound 7q (15 mg, 41% yield) as a white solid. ESI m/z: 856.5 (M/2+1)$^+$.

(2-{1-[4-({[(5R)-5-Amino-5-{[(1S)-1-{[(1S)-4-(car-bamoylamino)-1-({4-[({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl}oxy)methyl]phenyl}carbamoyl)butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethyl)trimethylazanium chloride (7ab)

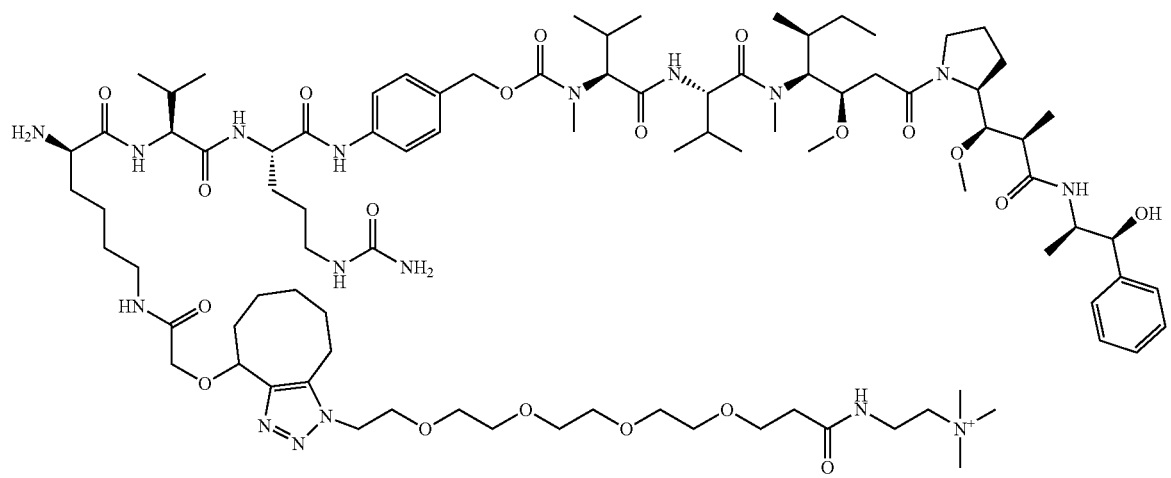 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@H](N)CCCCNC(=O)COC2CCCCCc3c2nnn3CCOCCOCCOCCOCCC(=O)NCC[N+](C)(C)C)C(C)C)cc1)C(C)C]

Following the general procedure from 5a (55 mg, 39 μmol) with 6b except stirring at 50° C. overnight, compound 7ab (50 mg, 70% yield) was obtained as a white solid. ESI m/z: 896 [(M+H)/2]$^+$. $^1$H NMR (400 MHz, DMSO$_{d4}$) δ 9.35 (s, 1H), 8.95 (s, 1H), 8.43-8.34 (m, 1H), 8.07-8.00 (m, 1H), 7.91-7.83 (m, 1H), 7.79-7.60 (m, 4H), 7.33-7.23 (m, 6H), 7.20-7.13 (m, 1H), 6.30-5.80 (m, 1H), 5.49-5.34 (m, 1H), 5.12-4.83 (m, 3H), 4.77-4.71 (m, 1H), 4.54-4.38 (m, 4H), 4.27 (t, J=11.6 Hz, 1H), 4.03-3.93 (m, 4H), 3.85-3.75 (m, 5H), 3.59 (t, J=6.2 Hz, 3H), 3.50-3.40 (m, 15H), 3.38-3.35 (m, 2H), 3.26-3.16 (m, 7H), 3.13-3.03 (m, 14H), 2.99-2.92 (m, 4H), 2.89-2.78 (m, 4H), 2.44-2.38 (m, 1H), 2.34 (t, J=6.2 Hz, 2H), 2.30-2.22 (m, 2H), 2.15-1.93 (m, 6H), 1.85-1.42 (m, 19H), 1.37-1.23 (m, 3H), 1.06-0.96 (m, 7H), 0.94-0.71 (m, 27H) ppm.

{17-[4-({[(5R)-5-Amino-5-{[(1S)-1-{[(1S)-4-(carbamoylamino)-1-({4-[({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methyl propyl]carbamoyl}-2-methyl propyl](methyl)carbamoyl}oxy)methyl]phenyl}carbamoyl)butyl]carbamoyl}-2-methyl propyl]carbamoyl}pentyl]carbamoyl}methoxy)-1H,4H,5H,6H,7H,8H,9H-cycloocta[d][1,2,3]triazol-1-yl]-3,6,9,12,15-pentaoxaheptadecan-1-yl}phosphonic acid (7ad)

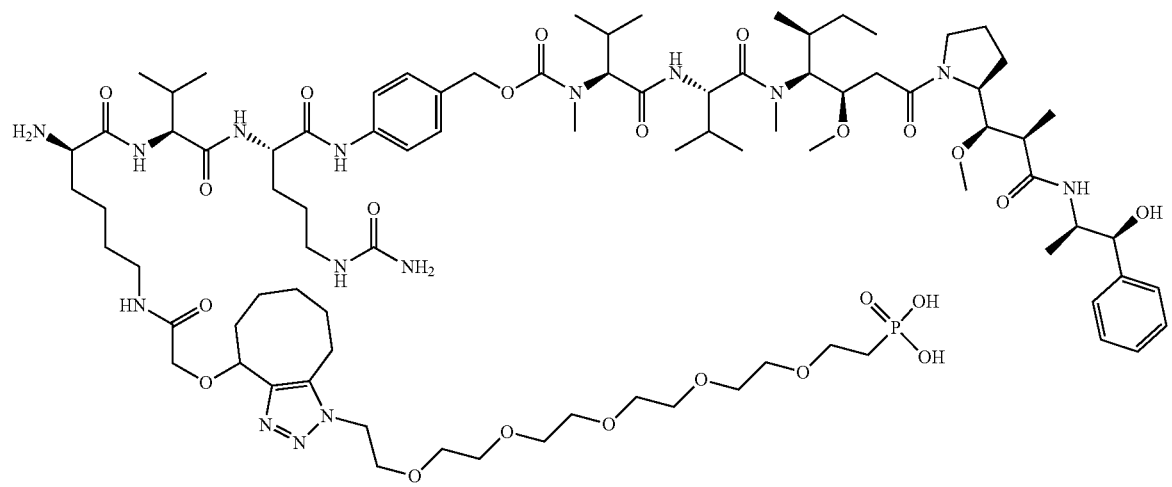 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@H](N)CCCCNC(=O)COC2CCCCCc3c2nnn3CCOCCOCCOCCOCCOCCP(=O)(O)O)C(C)C)cc1)C(C)C]

Following the general procedure from compound 5a (18 mg, 13 μmol) with compound 6f (14 mg, 38 μmol), compound 7ad (15 mg, 58% yield) was obtained as a white solid. ESI m/z: 893.9 (M/2+H)$^+$. $^1$H NMR (MeOD$_{d4}$, 500 MHz): δ 7.98-7.91 (m, 1H), 7.79-7.59 (m, 2H), 7.41-7.20 (m, 6H), 5.51-5.06 (m, 2H), 4.78-4.53 (m, 6H), 4.29-3.88 (m, 9H), 3.78-3.75 (m, 3H), 3.64-3.58 (m, 16H), 3.47-3.36 (m, 6H), 3.29-3.07 (m, 8H), 3.01-2.80 (m, 4H), 2.58-2.05 (m, 10H), 1.96-1.32 (m, 26H), 1.21-1.14 (m, 6H), 1.02-0.71 (m, 25H) ppm.

{4-[(2S)-2-[(2S)-2-[(2R)-2-Amino-6-[2-({1-[(2R,3R,4S,5R,6R)-3,4,5-trihydroxy-6-(hydroxymethyl)oxan-2-yl]-1H,4H,5H,6H,7H,8H,9H-cycloocta[d][1,2,3]triazol-4-yl}oxy)acetamido]hexanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methyl propyl]carbamoyl}-2-methyl propyl]-N-methylcarbamate (7ae)

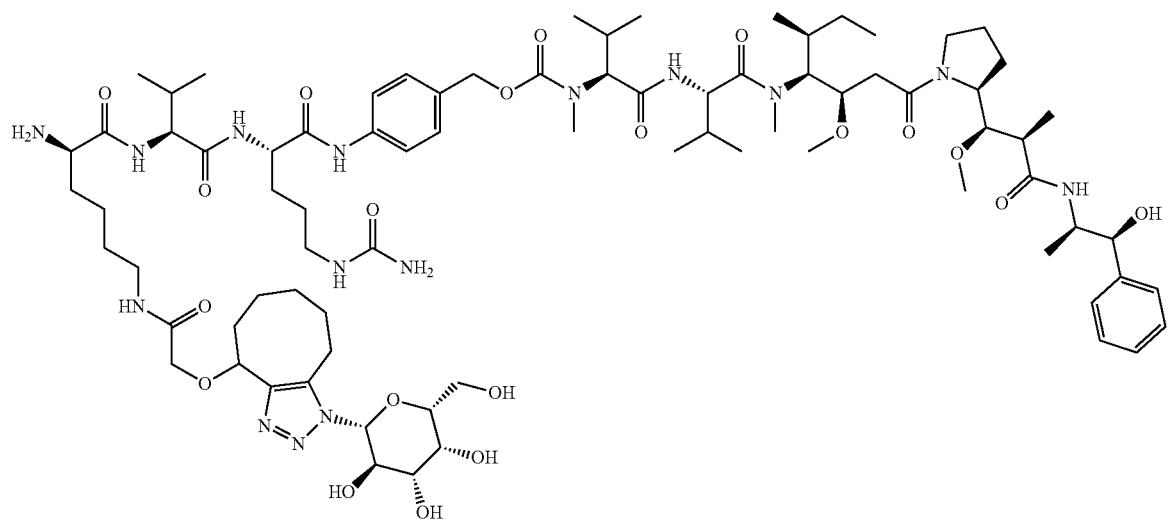 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@H](N)CCCCNC(=O)COC2CCCCCc3c2nnn3[C@@H]2O[C@H](CO)[C@H](O)[C@H](O)[C@H]2O)C(C)C)cc1)C(C)C]

Following the general procedure from compound 5a (6.0 mg, 4.2 μmol) with compound 6e (3.0 mg, 15 μmol), the reaction solution of compound 7ae was obtained and used directly for the next step. ESI m/z: 811 (M/2+H)$^+$.

(2-{1-[4-({[(5R)-5-Amino-5-{[(1S)-1-{[(1S)-4-(car-bamoylamino)-1-[(4-{[({2-[(1S,2S,4R,8S,9S,11S, 12R,13S,19S)-12,19-difluoro-11-hydroxy-9,13-dim-ethyl-16-oxo-6-propyl-5,7-dioxapentacyclo [10.8.0.0²,⁹.0⁴,⁸.0¹³,¹⁸]icosa-14,17-dien-8-yl]-2-oxoethyl}carbamoyl)oxy]methyl}phenyl)carbamoyl] butyl]carbamoyl}-2-methylpropyl] carbamoyl}pentyl]carbamoyl}methoxy)-1H,4H,5H, 6H,7H,8H,9H-cycloocta[d][1,2,3]triazol-1-yl]-3,6,9, 12-tetraoxapentadecan-15-amido}ethyl) trimethylazanium chloride (7bb)

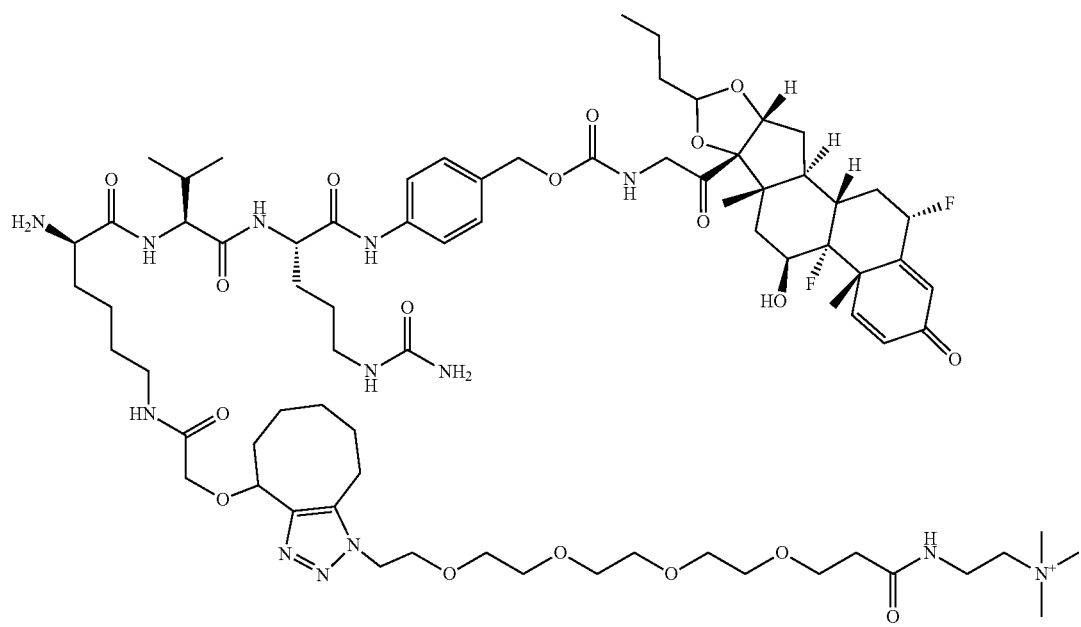 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@H](N)CCCCNC(=O)COC3CCCCCc4c3nnn4CCOCCOCCOCCOCCC(=O)NCC[N+](C)(C)C)C(C)C)cc2)O1]

Following the general procedure E from 5b (40 mg, 34 μmol) with 6b except stirring at 50° C. overnight, compound 7bb (40 mg, 76% yield) was obtained as a white solid after purified by prep-HPLC (method B). ESI m/z: 770 [(M+18)/ 2]⁺. ¹H NMR (400 MHz, DMSO$_{d6}$) δ 10.13-8.87 (m, 2H), 8.58-8.21 (m, 2H), 8.09-7.85 (m, 2H), 7.82-7.64 (m, 3H), 7.63-7.55 (m, 1H), 7.49-7.37 (m, 1H), 7.34-7.16 (m, 3H), 6.34-6.21 (m, 1H), 6.15-5.99 (m, 2H), 5.78-5.42 (m, 3H), 5.01-4.83 (m, 3H), 4.81-4.69 (m, 2H), 4.63-4.47 (m, 2H), 4.45-4.34 (m, 2H), 4.27-4.07 (m, 3H), 4.04-3.96 (m, 1H), 3.91-3.70 (m, 6H), 3.60 (t, J=6.2 Hz, 2H), 3.53-3.40 (m, 14H), 3.15-3.01 (m, 11H), 3.00-2.88 (m, 3H), 2.83-2.73 (m, 1H), 2.68-2.56 (m, 1H), 2.38-2.19 (m, 4H), 2.13-1.93 (m, 4H), 1.87-1.74 (m, 2H), 1.71-1.64 (m, 2H), 1.62-1.18 (m, 22H), 1.14-1.02 (m, 1H), 0.97-0.70 (m, 12H) ppm.

(2-{1-[4-({[(5R)-5-Amino-5-{[(1S)-1-{[(1S)-4-(car-bamoylamino)-1-{[4-({[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethoxy}phenyl)carbamoyl]oxy}methyl)phenyl]carbamoyl}butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethyl)trimethylazanium (7cb)

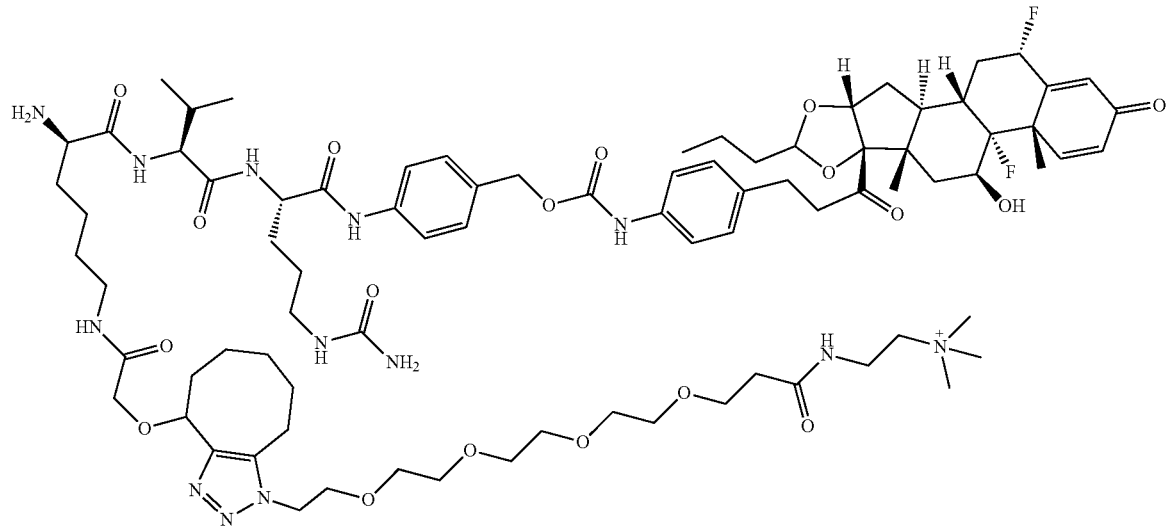

Following the general procedure from 6b (44 mg, 35 μmol) stirring at RT for 24 hours, compound 7cb (44 mg, yield 77%) was obtained as a white solid after purification by reversed phase flash chromatography (0-100% acetonitrile in aq. TFA (0.03%)). ESI m/z: 816.0 (m/2+H)⁺; 544.5 (M/3+H)⁺.

1-(4-(2-(((R)-5-Amino-6-(((S)-1-(((S)-1-(((4bS,8S,8aR)-8-(((1S,4aS,10aR)-6-hydroxy-1,4a-dimethyl-1,2,3,4,4a,9,10,10a-octahydrophenanthrene-1-carbo-nyl)carbamoyl)-4b,8-dimethyl-4b,5,6,7,8,8a,9,10-octahydrophenanthren-3-yl)amino)-1-oxopropan-2-yl)amino)-3-methyl-1-oxobutan-2-yl)amino)-6-oxohexyl)amino)-2-oxoethoxy)-4,5,6,7,8,9-hexahydro-1H-cycloocta[d][1,2,3]triazol-1-yl)-N,N,N-trimethyl-15-oxo-3,6,9,12-tetraoxa-16-azaoctadecan-18-aminium (7fb)

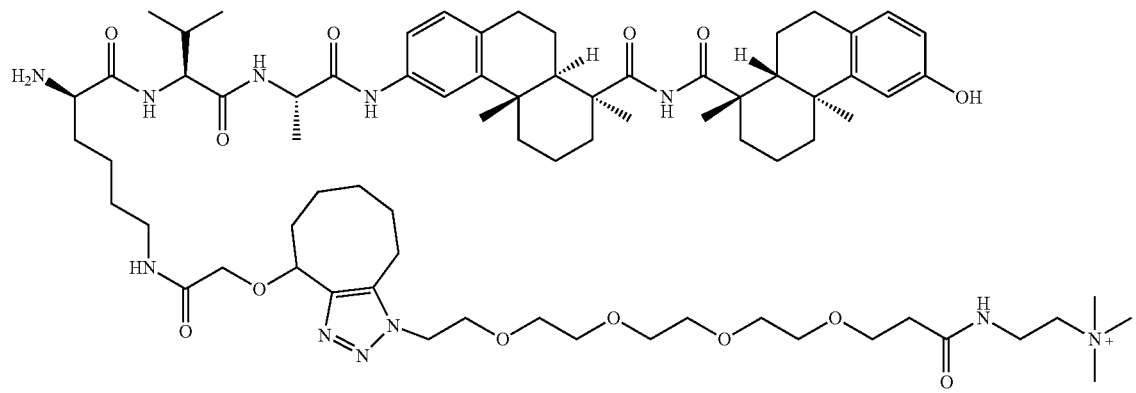

Following the general procedure from 6b (50 mg, 50 μmol) stirring at RT for 24 hours, compound 7fb (50 mg, 73% yield) was obtained as a white solid after purification by reversed phase flash chromatography (0-30% acetonitrile in aq. TFA (0.03%)). ESI m/z: 684 (M/2+H)⁺.

Example 14

Preparation of Intermediates 7h, 7l (See FIG. 15)
General Procedure F:

To a solution of compound 4b (1.2 eq.) in DMF (40 mL per gram of compound 3) were added EDCI (1.5 eq.), HOBt (2.0 eq.), compound 3 (3b or 3e, 1.0 eq.) and triethylamine (3.0 eq.) successively at RT. The resulting mixture was stirred at RT overnight. LCMS showed compound 4b was totally consumed (compound 3 was not consumed). To the reaction was added diethylamine (6 mL per gram of compound 3, excess). The reaction mixture was stirred at RT for 2 hours until Fmoc was removed according to LCMS. The reaction mixture was directly purified by reversed phase flash chromatography (0-100% acetonitrile in aq. ammonium bicarbonate (10 mM)) to give compound 7 (7h or 7l, 25-26% yield) as a white solid and unreacted compound 3 could be recovered.

2-[(4R)-4-Amino-4-{[(1S)-1-{[(1S)-4-(carbamoylamino)-1-[(4-{[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹0.0⁴,⁸ 0.0¹³,¹⁸]icosa-14,17-dien-8-yl]-2-oxoethyl}carbamoyl)oxy]methyl}phenyl)carbamoyl] butyl]carbamoyl}-2-methylpropyl] carbamoyl}butanamido]ethane-1-sulfonic acid (7h)

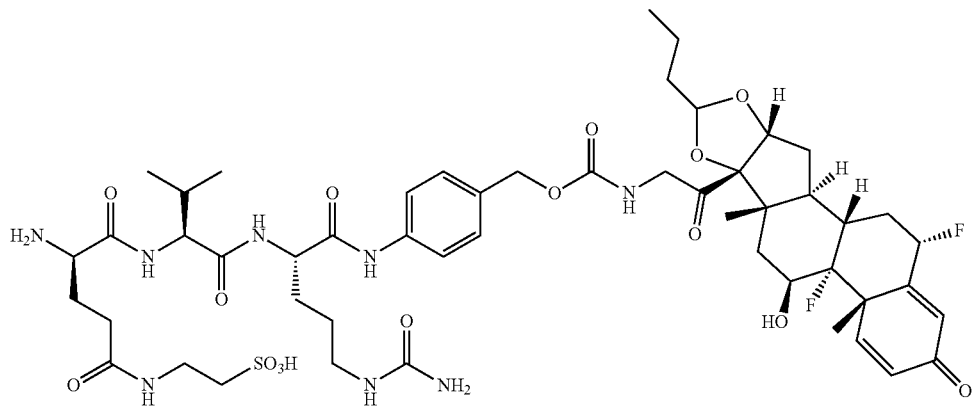 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@H](N)CCC(=O)NCCS(=O)(=O)O)C(C)C)cc2)O1]

Following the general procedure F from 3b (50 mg, 57 μmol) with 4b, compound 7h (17 mg, 26% yield) was obtained as a white solid after purification by reversed phase flash chromatography (0-100% acetonitrile in water, 17 mg of compound 3b was recycled (34% recycled yield)). ESI m/z: 1107 (M+H)⁺. ¹H NMR (500 MHz, DMSO$_{d6}$) δ 10.07 (s, 1H), 8.31 (d, J=7.0 Hz, 2H), 7.81 (t, J=5.5 Hz, 1H), 7.61-7.60 (m, 2H), 7.45-7.42 (m, 1H), 7.30-7.27 (m, 3H), 6.30 (d, J=10 Hz, 1H), 6.11-6.03 (m, 2H), 5.86-5.82 (m, 1H), 5.70-5.57 (m, 2H), 5.46 (s, 2H), 4.97 (s, 2H), 4.78-4.76 (m, 1H), 4.59 (t, J=4.5 Hz, 1H), 4.41-4.12 (m, 4H), 3.86-3.80 (m, 1H), 3.64-3.58 (m, 1H), 3.21-3.16 (m, 1H), 3.01-2.90 (m, 6H), 2.56 (t, J=7.5 Hz, 2H), 2.35-2.32 (m, 2H), 2.17-2.14 (m, 2H), 2.09-1.28 (m, 18H), 1.17-1.14 (m, 1H), 0.97 (t, J=6.5 Hz, 2H), 0.89-0.84 (m, 10H) ppm.

2-[(4R)-4-Amino-4-{[(1S)-1-{[(1S)-4-(carbamoylamino)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]butyl]carbamoyl}-2-methylpropyl]carbamoyl}butanamido]ethane-1-sulfonic acid (71)

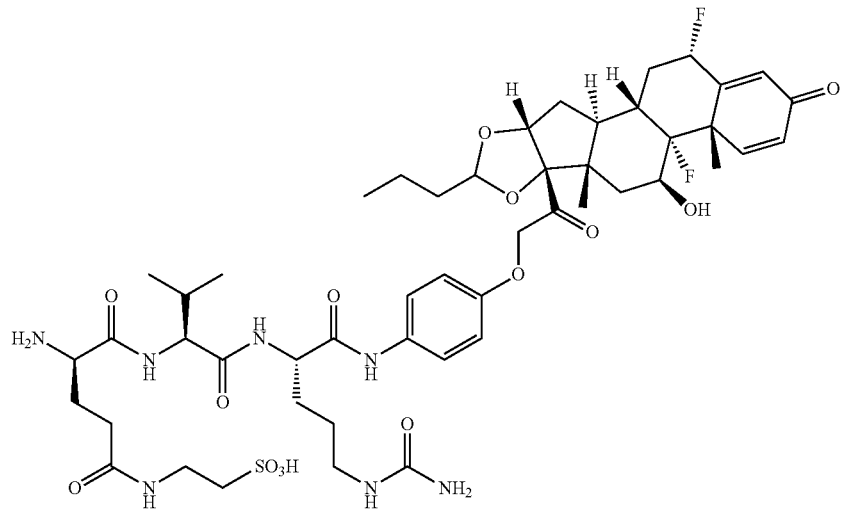 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](CCCNC(N)=O)NC(=O)[C@@H](NC(=O)[C@H](N)CCC(=O)NCCS(=O)(=O)O)C(C)C)cc2)O1]

Following the general procedure F from 3e (80 mg, 98 μmol) with 4b, compound 71 (26 mg, 25% yield) was obtained as a white solid after purification by reversed phase flash chromatography (0-100% acetonitrile in water). ESI m/z: 525.8 (M/2+H)$^+$.

Figure 15:
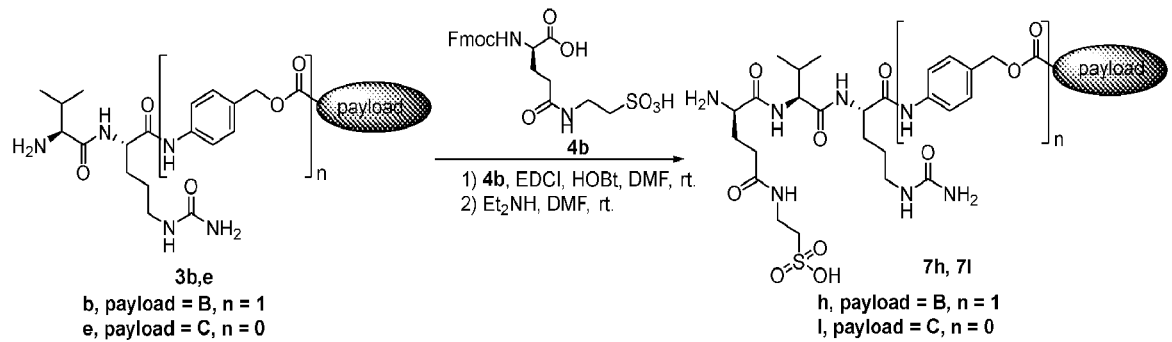
FIG. 15 shows a general synthetic procedure F for preparing intermediates 7h and 7l.
Figure 15A:
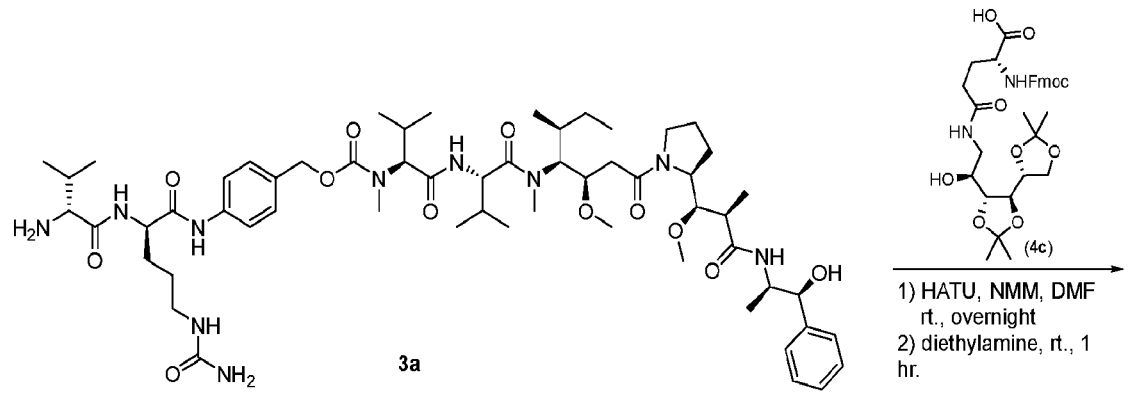
FIG. 15A shows a general synthetic procedure for preparing intermediate 7ah.
Figure 15A:
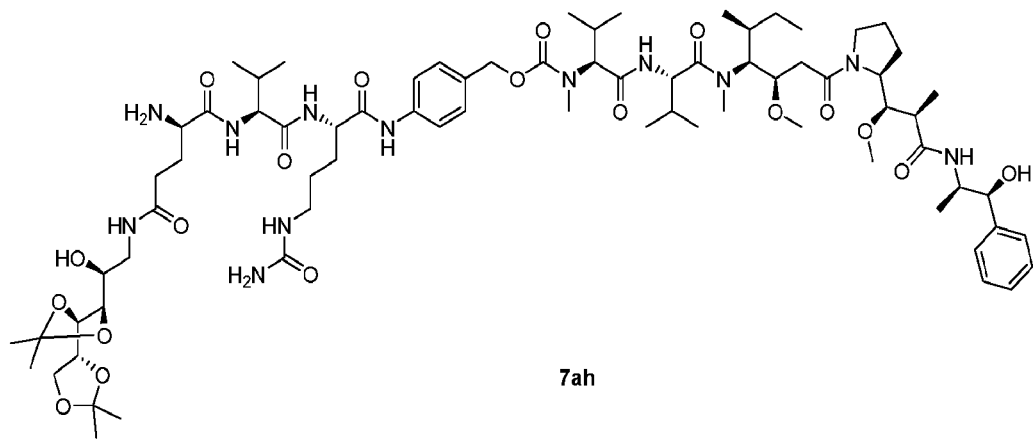

Preparation of Intermediate 7ah (See FIG. 15A)

{4-[(2S)-2-[(2S)-2-[(2R)-2-Amino-4-{[(2S)-2-[(4R,5R)-5-[(4R)-2,2-dimethyl-1,3-dioxolan-4-yl]-2,2-dimethyl-1,3-dioxolan-4-yl]-2-hydroxyethyl]carbamoyl}butanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (7ah)

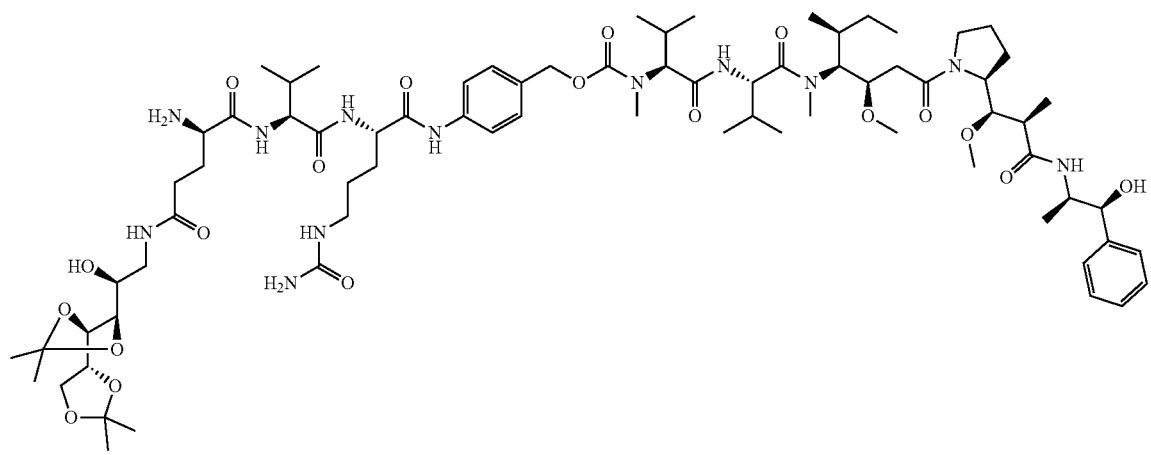

To a solution of intermediate 4c (25 mg, 41 μmol) in DMF (1 mL) was added HATU (23 mg, 61 μmol) at RT. The solution obtained was stirred at RT for an hour. To this suspension were added a solution of vcPAB-MMAE 3a (28 mg, 25 μmol) in DMF (1 mL) and subsequently NMM (1 drop, excess). The reaction mixture was stirred at RT for 3 hours and turned clear. The reaction was monitored by LCMS until compound 3a was totally consumed. To the reaction mixture was then added diethylamine (excess), and the resulting mixture was then stirred at RT overnight. The reaction was completed according to LCMS. The volatiles were removed in vacuo and the residue was purified by reversed phase flash chromatography (0-100% acetonitrile in aq. TFA (0.5%)) to give compound 7ah (25 mg, 67% yield) as a white solid. ESI m/z: 1495 (M+H)$^+$. $^1$H NMR (MeOD$_{d4}$, 500 MHz): δ 7.65-7.55 (m, 2H), 7.46-7.28 (m, 6H), 7.23 (t, J=7.1 Hz, 1H), 5.27-5.02 (m, 2H), 4.72-4.47 (m, 4H), 4.30-4.05 (m, 6H), 4.03-3.78 (m, 4H), 3.78-3.65 (m, 1H), 3.61-3.40 (m, 4H), 3.39-3.27 (m, 5H), 3.26-3.16 (m, 2H), 3.17-3.08 (m, 3H), 3.00-2.91 (m, 3H), 2.58-2.11 (m, 7H), 2.10-1.52 (m, 12H), 1.50-1.25 (m, 15H), 1.24-1.11 (m, 6H), 1.05-0.69 (m, 26H) ppm.

Example 14A

Figure 15B:
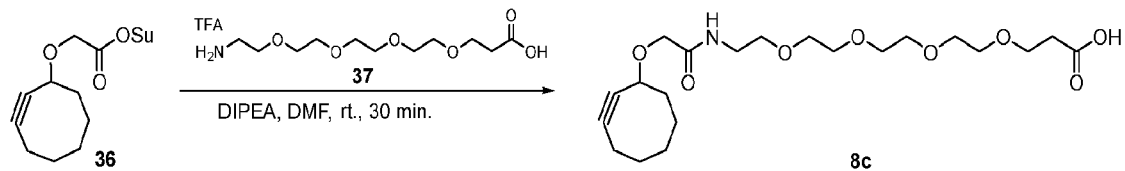
FIG. 15B shows a synthetic procedure for preparing intermediate 8c.

Preparation of Intermediate 8c (See FIG. 15B)

1-[2-(Cyclooct-2-yn-1-yloxy)acetamido]-3,6,9,12-tetraoxapentadecan-15-oic acid (8c)

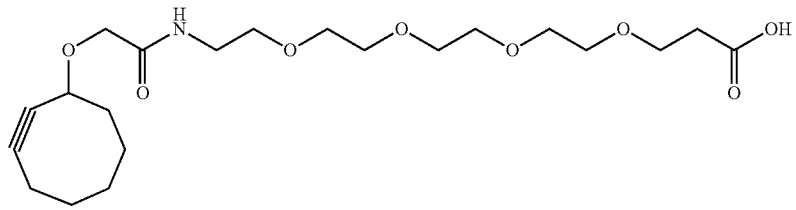 [SMILES: O=C(O)CCOCCOCCOCCOCCNC(=O)COC1C#CCCCCC1]

To a mixture of compound 36 (0.50 g, 1.8 mmol) and 37 (0.65 g, 1.8 mmol) in DMF (3 mL) was added DIPEA (1.2 g, 9.0 mmol) at RT. The mixture was stirred at RT for 30 minutes. The reaction mixture was directly purified by prep-HPLC (method A) to give OCT-PEG$_4$-acid (8c) (0.70 g, 91% yield) as light yellow oil. ESI m/z: 430 (M+H)$^+$.

8d and 8e were prepared using methods similar to the method of preparation of 8c, using suitable starting materials known to one of skill in the art.

Example 15

Figure 16:
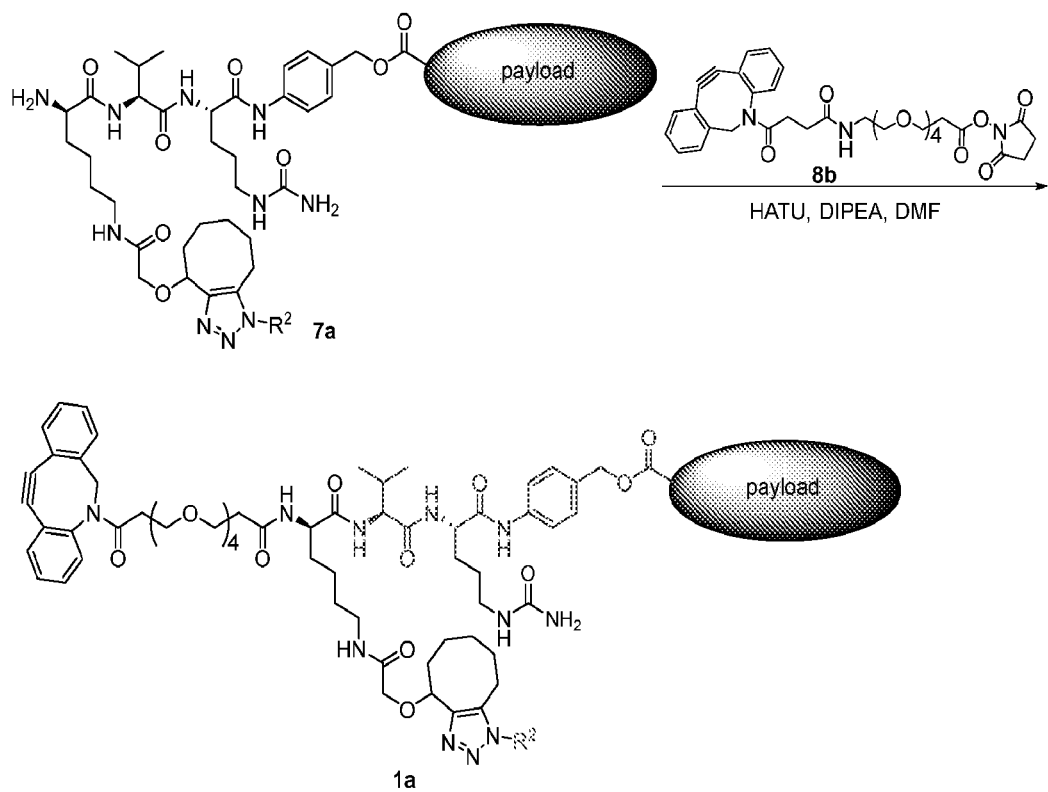

Preparation of 1a (See FIG. 16)

To a solution of DIBAC-suc-PEG$_4$-acid 8a (1.2-1.3 eq.) in DMF (1 mL per 10 mg of 8a) were added HATU (1.3 eq.) and DIPEA (5.0 eq.) at RT. The mixture was stirred at RT for half an hour followed by addition of a solution of compound 7a (1.0 eq.) in DMF (0.6 mg per 10 mg of 7a). The resulting mixture was stirred at RT until compound 7 was consumed, which was monitored by LCMS. After filtration, the filtrate was directly purified by prep-HPLC to give compound 1a.

General Procedure G (from 8a, 8c or 8d):

To a solution of acid 8 (8a, 8c or 8d, 1.2-1.3 eq.) in DMF (1 mL per 10 mg of 8) were added HATU (1.3 eq.) and DIPEA (5.0 eq.) at RT. The mixture was stirred at RT for half an hour followed by addition of a solution of compound 7 (1.0 eq.) in DMF (0.6 mg per 10 mg of 7). The resulting mixture was stirred at RT until compound 7 was consumed, which was monitored by LCMS. After filtration, the filtrate was directly purified by prep-HPLC to give linker-payloads 1, and II-V.

Example 16

Figure 17:
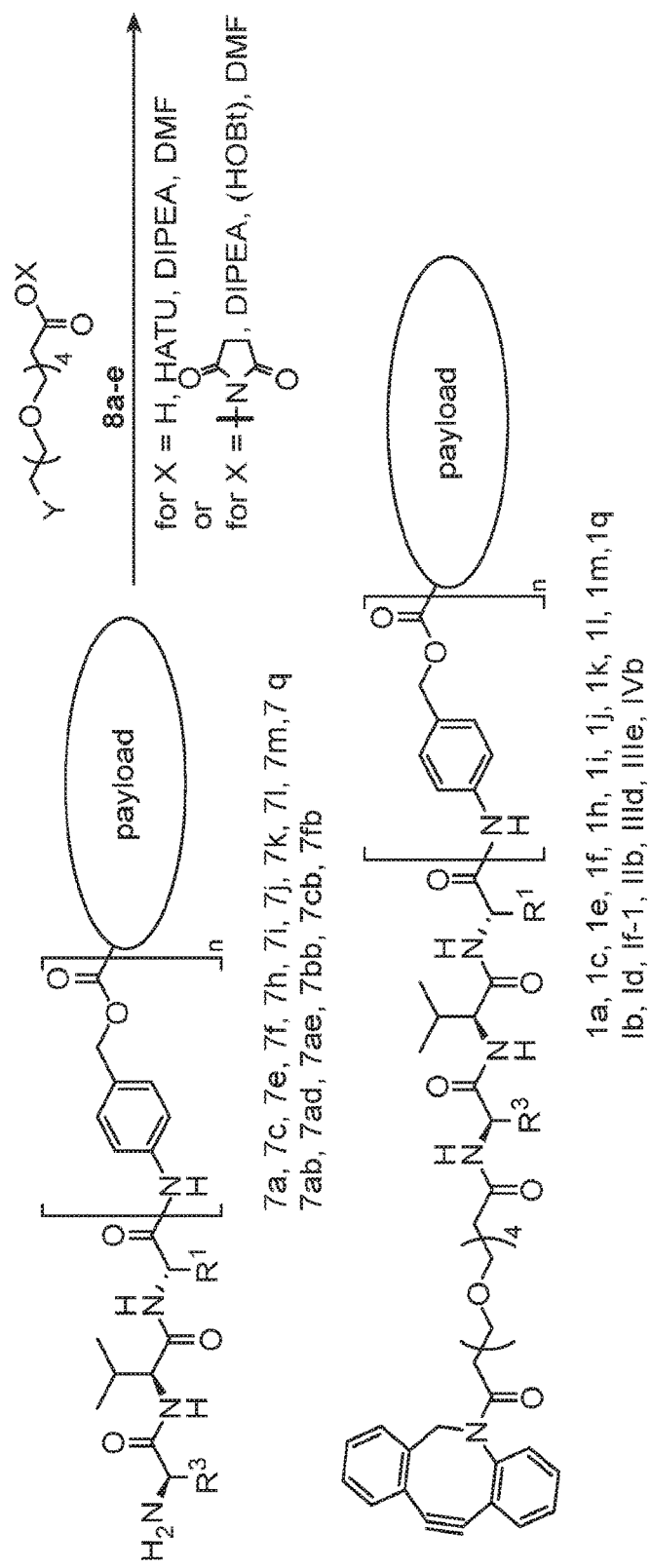
FIG. 17 shows a general synthetic procedure H for preparing compounds 1a, 1c, 1e, 1f, 1h, 1i, 1j, 1k, 1l, 1m, 1q, Ib, Id, If-1, IIb, IIId, IIIe, and IVb.

Preparation of 1a, 1c, 1e, 1f, 1h, 1i, 1j, 1k, 1l, 1m 1q (See FIG. 17)

General Procedure H (from 8b or 8e):

To a solution of compound 7 (1.0 eq.) in DMF (1 mL per 50 mg) were added compound DIBAC-PEG$_4$-NHS 8b (1.1-1.2 eq.) and DIPEA (5.0 eq.) at RT. The reaction mixture was stirred at RT for 3 hours. The reaction mixture was directly purified by prep-HPLC to give compound 1.

Example 17

Preparation of 1a (See FIG. 17)

{4-[(2S)-2-[(2S)-2-[(2R)-2-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-6-(2-([1-(17-hydroxy-3,6,9,12,15-pentaoxaheptadecan-1-yl)-1H,4H,5H,6H,7H,8H,9H-cycloocta[d][1,2,3]triazol-4-yl]oxy}acetamido)hexanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (1a)

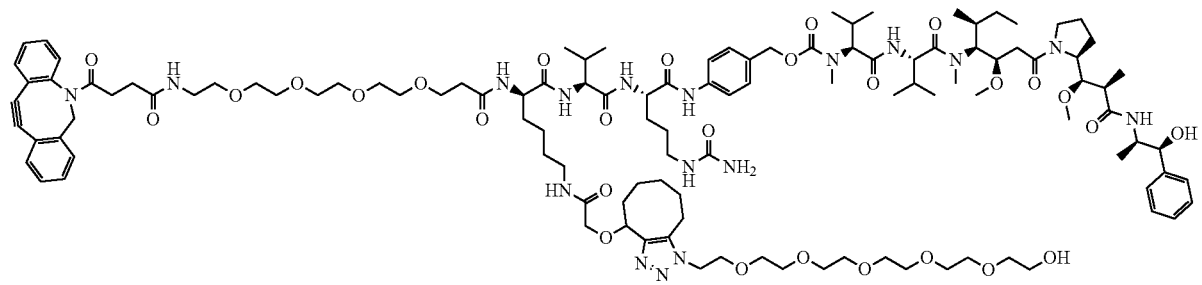 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCCCNC(=O)COC2CCCCCc3c2nnn3CCOCCOCCOCCOCCOCCO)NC(=O)CCOCCOCCOCCOCCNC(=O)CCC(=O)N2Cc3ccccc3C#Cc3ccccc32)C(C)C)cc1)C(C)C]

Following the general procedure G from compound 7a (25 mg, 15 μmol) with compound 8a (10 mg, 18 μmol), linker-payload 1a (24 mg, 73% yield) was obtained as a white solid. ESI: 753 (M/3+H)⁺. $^1$H NMR (500 MHz, MeOD$_{d4}$) δ 7.74-7.69 (m, 2H), 7.67-7.64 (m, 1H), 7.63-7.59 (m, 1H), 7.53-7.45 (m, 3H), 7.42-7.29 (m, 9H), 7.25-7.20 (m, 1H), 5.22-5.05 (m, 3H), 4.70-4.49 (m, 4H), 4.47-4.43 (m, 1H), 4.33-4.29 (m, 1H), 4.27-4.16 (m, 4H), 4.00-3.95 (m, 2H), 3.92-3.87 (m, 2H), 3.77-3.69 (m, 2H), 3.68-3.63 (m, 10H), 3.61-3.52 (m, 21H), 3.49-3.41 (m, 5H), 3.38-3.36 (m, 4H), 3.30-3.27 (m, 3H), 3.27-3.22 (m, 3H), 3.20-3.14 (m, 2H), 3.12 (s, 1H), 3.10-3.03 (m, 1H), 2.99-2.86 (m, 4H), 2.82-2.68 (m, 2H), 2.56-2.12 (m, 10H), 2.11-1.97 (m, 5H), 1.91-1.79 (m, 5H), 1.76-1.53 (m, 10H), 1.48-1.37 (m, 3H), 1.34-1.26 (m, 1H), 1.21-1.12 (m, 14H), 1.06-0.93 (m, 14H), 0.92-0.81 (m, 10H) ppm.

Example 17A

Preparation of Ib (See FIG. 17)

(2-{1-[4-({[(5R)-5-[1-(4-{2-Azatricyclo[10.4.0.0⁴¹ hexadeca-1(12),4(9),5,7,13,15-hexaen-10-yn-2-yl}-4-oxobutanamido)-3,6,9,12-tetraoxapentadecan-15-amido]-5-{[(1S)-1-{[(1S)-4-(carbamoylamino)-1-({4-[({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methyl propyl]carbamoyl}-2-methyl propyl](methyl)carbamoyl}oxy)methyl]phenyl}carbamoyl)butyl]carbamoyl}-2-methyl propyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethyl)trimethylazanium (Ib)

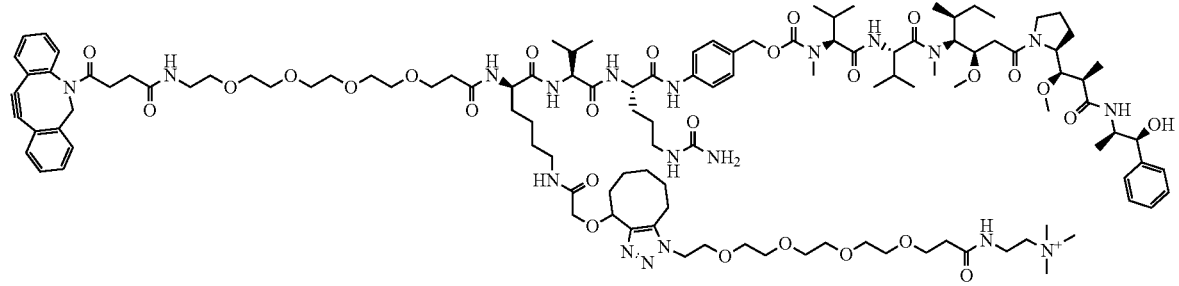 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCCCNC(=O)COC2CCCCCc3c2nnn3CCOCCOCCOCCOCCC(=O)NCC[N+](C)(C)C)NC(=O)CCOCCOCCOCCOCCNC(=O)CCC(=O)N2Cc3ccccc3C#Cc3ccccc32)C(C)C)cc1)C(C)C]

Following the general procedure G from compound 7ab (45 mg, 25 µmol) with compound 8a (16 mg, 29 µmol), linker-payload Ib (16 mg, 27% yield) was obtained as a white solid. ESI m/z: 766 [(M+H)/3]+. ¹H NMR (500 MHz, DMSO$_{d6}$): δ 9.78 (s, 1H), 8.34-8.04 (m, 5H), 7.95-7.83 (m, 2H), 7.79-7.74 (m, 1H), 7.70-7.56 (m, 5H), 7.52-7.43 (m, 3H), 7.40-7.11 (m, 12H), 6.08 (s, 1H), 5.43 (s, 2H), 5.06-5.00 (m, 2H), 4.76-4.71 (m, 1H), 4.54-4.39 (m, 4H), 4.35-4.15 (m, 4H), 4.03-3.92 (m, 2H), 3.85-3.73 (m, 5H), 3.64-3.55 (m, 5H), 3.46-3.43 (m, 20H), 3.25-3.16 (m, 11H), 3.13-3.05 (m, 15H), 3.00-2.93 (m, 5H), 2.89-2.82 (m, 4H), 2.80-2.73 (m, 2H), 2.61-2.55 (m, 1H), 2.42-2.32 (m, 5H), 2.31-2.20 (m, 4H), 2.15-2.04 (m, 4H), 2.03-1.95 (m, 4H), 1.83-1.65 (m, 8H), 1.57-1.38 (m, 11H), 1.30-1.19 (m, 10H), 1.06-0.96 (m, 7H), 0.87-0.76 (m, 20H) ppm.

Example 18

Preparation of 1c (See FIG. 17)

2-{1-[4-({[(5R)-5-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-5-{[(1S)-1-{[(1S)-4-(carbamoylamino)-1-({4-[({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methyl propyl]carbamoyl}-2-methyl propyl](methyl)carbamoyl}oxy)methyl]phenyl}carbamoyl)butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (1c)

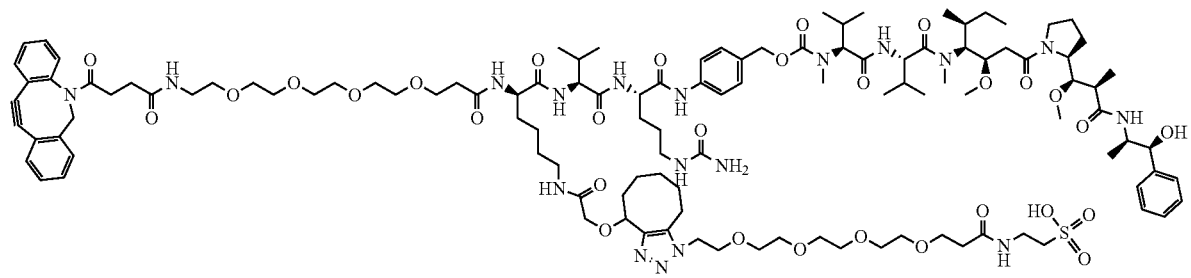 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCCCNC(=O)COC2CCCCCc3c2nnn3CCOCCOCCOCCOCCC(=O)NCCS(=O)(=O)O)NC(=O)CCOCCOCCOCCOCCNC(=O)CCC(=O)N2Cc3ccccc3C#Cc3ccccc32)C(C)C)cc1)C(C)C]

Following the general procedure H from compound 7c (20 mg, 11 μmol) with compound 8b (7.1 mg, 11 μmol), compound 1c (5.0 mg, 19% yield) was obtained as a white solid. ESI m/z: 1174.7 (M/2+H)$^+$. $^1$H NMR (MeOD$_{d4}$, 500 MHz): δ 8.38-8.17 (m, 2H), 7.99-7.87 (m, 2H), 7.77-7.56 (m, 4H), 7.49-7.20 (m, 9H), 5.36 (t, J=4.5 Hz, 1H), 5.21-5.07 (m, 4H), 4.71-4.18 (m, 9H), 3.98-3.88 (m, 5H), 3.74-3.43 (m, 37H), 3.37-3.36 (m, 6H), 3.29-3.12 (m, 6H), 3.00-2.88 (m, 6H), 2.75-2.33 (m, 5H), 2.32-1.78 (m, 17H), 1.64-1.34 (m, 15H), 1.20-1.13 (m, 6H), 1.03-0.76 (m, 30H) ppm.

Example 18A

Preparation of Id (FIG. 17)

{4-[(2S)-2-[(2S)-2-[(2R)-2-[1-(4-{2-Azatricyclo[10.4.0.0^{4,9}]hexadeca-1(12),4(9),5,7,13,15-hexaen-10-yn-2-yl}-4-oxobutanamido)-3,6,9,12-tetraoxapentadecan-15-amido]-6-(2-0-(14-{[(1S)-1-{[(1S)-4-(carbamoylamino)-1-({4-[({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl}oxy)methyl]phenyl}carbamoyl)butyl]carbamoyl}-2-methylpropyl]carbamoyl}-3,6,9,12-tetraoxatetradecan-1-yl)-1H,4H,5H,6H,7H,8H,9H-cycloocta[d][1,2,3]triazol-4-yl]oxy}acetamido)hexanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (Id)

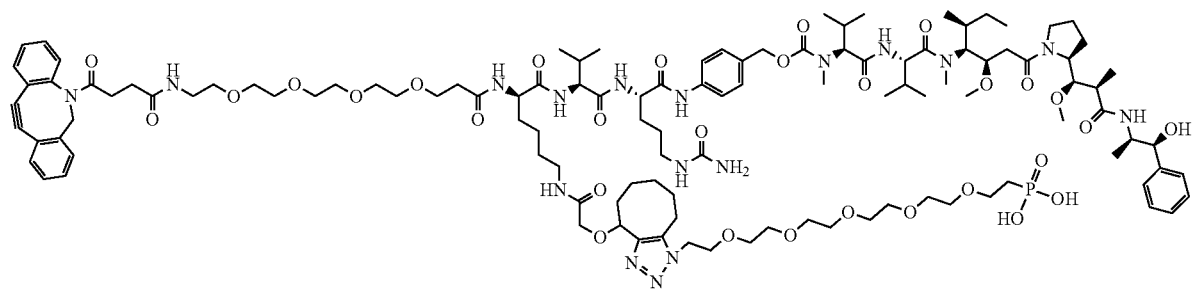 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCCCNC(=O)COC2CCCCCc3c2nnn3CCOCCOCCOCCOCCOCCP(=O)(O)O)NC(=O)CCOCCOCCOCCOCCNC(=O)CCC(=O)N2Cc3ccccc3C#Cc3ccccc32)C(C)C)cc1)C(C)C]

Following the general procedure G from compound 7ad (12 mg, 6.7 µmol) with compound 8a (4.4 mg, 8.0 µmol), linker-payload Id (3.0 mg, 19% yield) was obtained as a white solid. ESI m/z: 774.7 (M/3+H)+. $^1$H NMR (MeOD$_{d4}$, 500 MHz): δ 8.00-7.90 (m, 1H), 7.94-7.61 (m, 4H), 7.49-7.47 (m, 3H), 7.41-7.14 (m, 9H), 5.37-5.03 (m, 5H), 4.70-4.44 (m, 6H), 4.34-3.90 (m, 7H), 3.77-3.42 (m, 38H), 3.37-3.35 (m, 4H), 3.29 (s, 3H), 3.27-3.01 (m, 9H), 2.97-2.87 (m, 6H), 2.75-2.59 (m, 2H), 2.53-2.16 (m, 9H), 2.06-1.81 (m, 12H), 1.64-1.32 (m, 19H), 1.20-1.13 (m, 6H), 1.03-0.79 (m, 21H) ppm. Anal. HPLC: 95%, Retention time: 5.56 and 6.64 min (method B).

Example 18B

Preparation of 1e-1 (FIG. 17)

{4-[(2S)-2-[(2S)-2-[(2R)-2-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-6-[2-({1-[(2R,3R,4S,5R,6R)-3,4,5-trihydroxy-6-(hydroxymethyl)oxan-2-yl]-1H,4H,5H,6H,7H,8H,9H-cycloocta[d][1,2,3]triazol-4-yl}oxy)acetamido]hexanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (1e-1) (with triazole isomers)

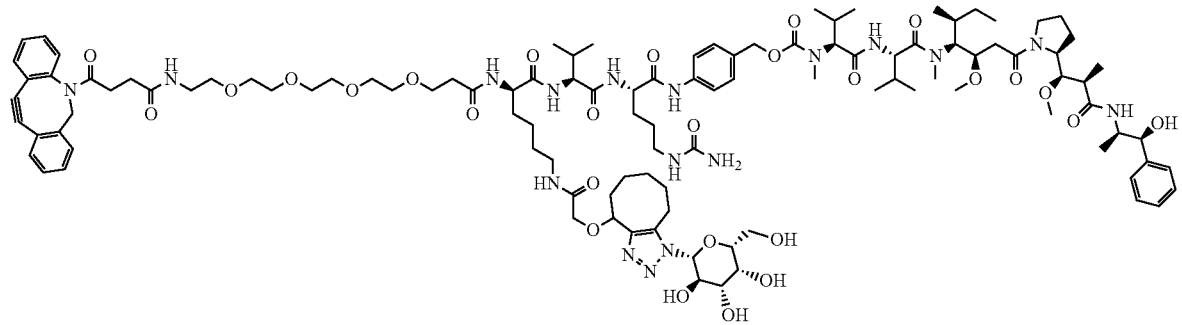 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCCCNC(=O)COC2CCCCCc3c2nnn3[C@@H]2O[C@H](CO)[C@H](O)[C@H](O)[C@H]2O)NC(=O)CCOCCOCCOCCOCCNC(=O)CCC(=O)N2Cc3ccccc3C#Cc3ccccc32)C(C)C)cc1)C(C)C]

Following the general procedure H from 7ae (reaction solution) and 8b, the compound 1e-1 with triazole isomers (with the ratio 3/2 by HPLC) (13 mg, 30% yield from 5a) was obtained as a white solid after purification by prep-HPLC (method B). ESI m/z: 1078 (M/2+H)⁺ (100%), 2156.9 (M+H)⁺ (10%). ¹H NMR (DMSO$_{d6}$, 500 MHz): δ 9.69 (m, 1H), 8.08-8.30 (m, 4H), 7.84-7.89 (m, 1H), 7.61-7.75 (m, 6H), 7.45-7.49 (m, 2H), 7.16-7.37 (m, 10H), 5.96 (m, 1H), 5.34-5.51 (m, 4H), 4.97-5.16 (m, 5H), 4.62-4.75 (m, 4H), 3.92-4.49 (m, 9H), 3.77-3.80 (m, 3H), 3.40-3.72 (m, 18H), 3.24 (s, 3H), 3.23 (s, 2H), 3.18-3.20 (m, 4H), 2.88-3.17 (m, 17H), 2.54-2.83 (m, 2H), 2.35-2.42 (m, 2H), 2.22-2.29 (m, 3H), 1.96-2.15 (m, 7H), 1.72-1.82 (m, 5H), 1.28-1.65 (m, 16H), 0.87-1.05 (m, 6H), 0.75-0.87 (m, 27H). Anal. HPLC: isomer 1: 60.3%, Retention time: 7.34 min; isomer 2: 39.7%, Retention time: 7.41 min (method B).

Example 18C

Preparation of If-1 (FIG. 17)

{4-[(2S)-5-(Carbamoylamino)-2-[(2S)-2-[(2R)-2-[1-(2,5-dioxo-2,5-dihydro-1H-pyrrol-1-yl)-3,6,9,12-tetraoxapentadecan-15-amido]-6-[2-({1-[(2R,3R,4S,5R,6R)-3,4,5-trihydroxy-6-(hydroxymethyl)oxan-2-yl]-1H,4H,5H,6H,7H,8H,9H-cycloocta[d][1,2,3]triazol-4-yl}oxy)acetamido]hexanamido]-3-methylbutanamido]pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (If-1)

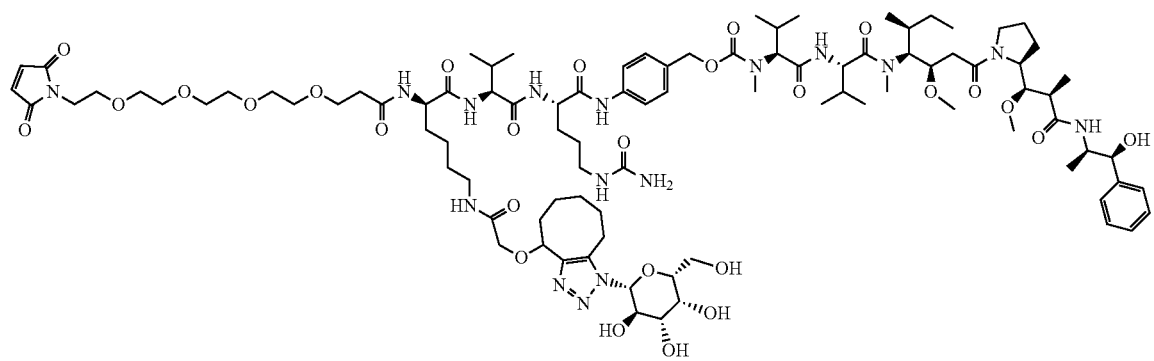 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCCCNC(=O)COC2CCCCCc3c2nnn3[C@@H]2O[C@H](CO)[C@H](O)[C@H](O)[C@H]2O)NC(=O)CCOCCOCCOCCOCCN2C(=O)C=CC2=O)C(C)C)cc1)C(C)C]

Following the general procedure H from 7ae (reaction solution) and 8e, the compound 1f-1 with triazole isomers (with the ratio 3/2 by HPLC) (1.5 mg, 18% yield from 5a) was obtained as a white solid after purification by prep-HPLC (method A). ESI m/z: 974.7 (M/2+H)$^+$ (100%), 1972 (M+Na)' (20%). $^1$H NMR (DMSO$_{d6}$, 500 MHz): δ 9.69 (s, 1H), 8.19-7.97 (m, 4H), 7.92-7.83 (m, 1H), 7.66-7.54 (m, 3H), 7.36-7.23 (m, 6H), 7.22-7.12 (m, 2H), 7.01 (s, 2H), 6.87 (s, 2H), 6.68-6.59 (m, 2H), 6.03-5.93 (m, 1H), 5.47-5.26 (m, 5H), 5.20-5.11 (m, 1H), 5.07-4.95 (m, 2H), 4.80-4.58 (m, 3H), 4.53-4.38 (m, 2H), 4.36-4.12 (m, 5H), 4.04-3.94 (m, 2H), 3.84-3.76 (m, 3H), 3.68-3.37 (m, 21H), 3.26-3.17 (m, 7H), 3.13-2.96 (m, 7H), 2.90-2.81 (m, 3H), 2.44-2.34 (m, 2H), 2.31-2.21 (m, 2H), 2.18 (s, 3H), 2.15-1.94 (m, 9H), 1.77-1.74 (m, 2H), 1.69-1.59 (m, 4H), 1.56-1.42 (m, 9H), 1.32-1.27 (m, 2H), 1.06-0.96 (m, 6H), 0.90-0.72 (m, 26H) ppm. Anal. HPLC: isomer 1: 76.0%, Retention time: 7.19 min; isomer 2: 24.0%, Retention time: 7.28 min (method A).

Example 18D

Figure 18:
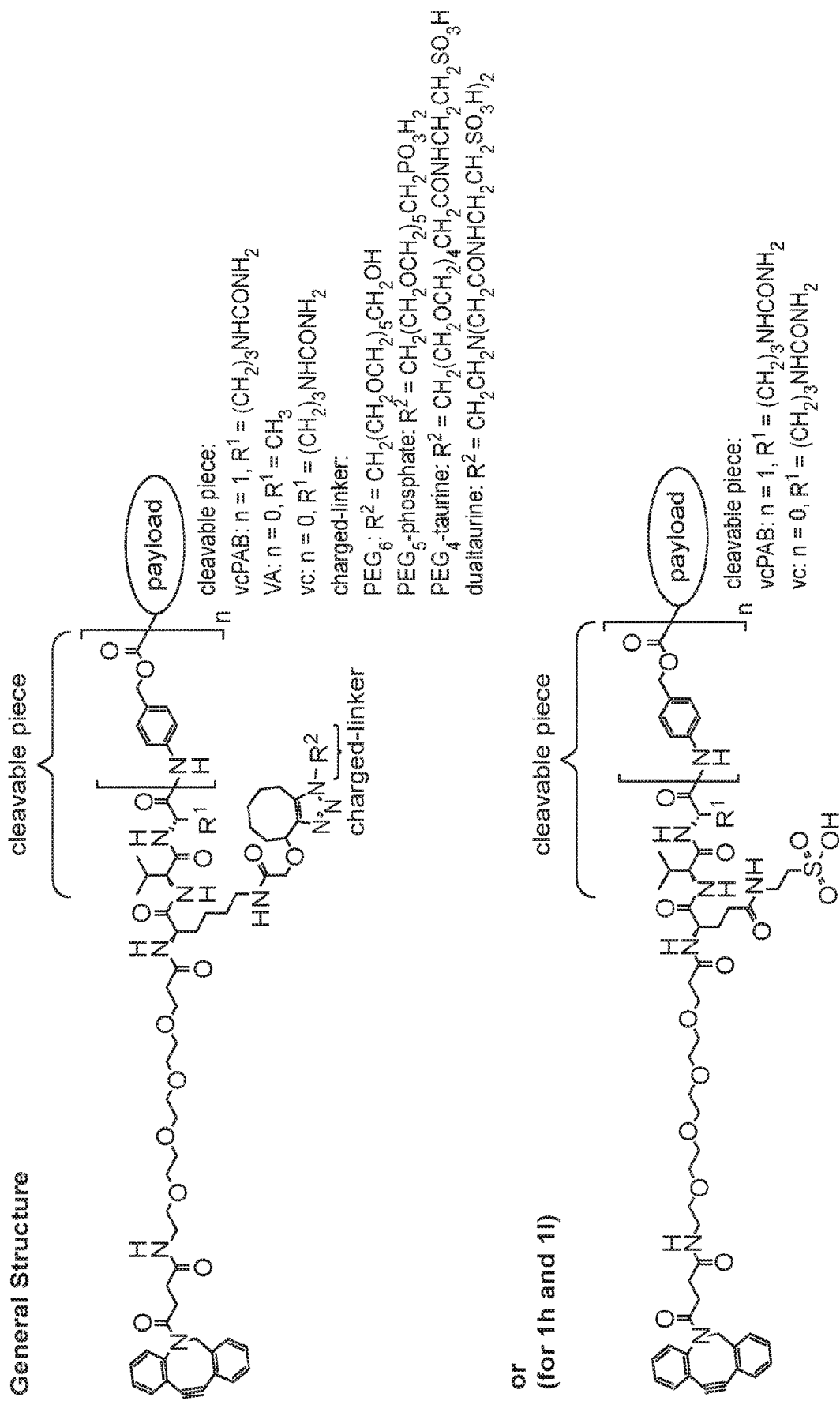
FIG. 18 shows cleavable pieces for Cathepsin B cleavage of linker-payload to release free payload.
Figure 18A:
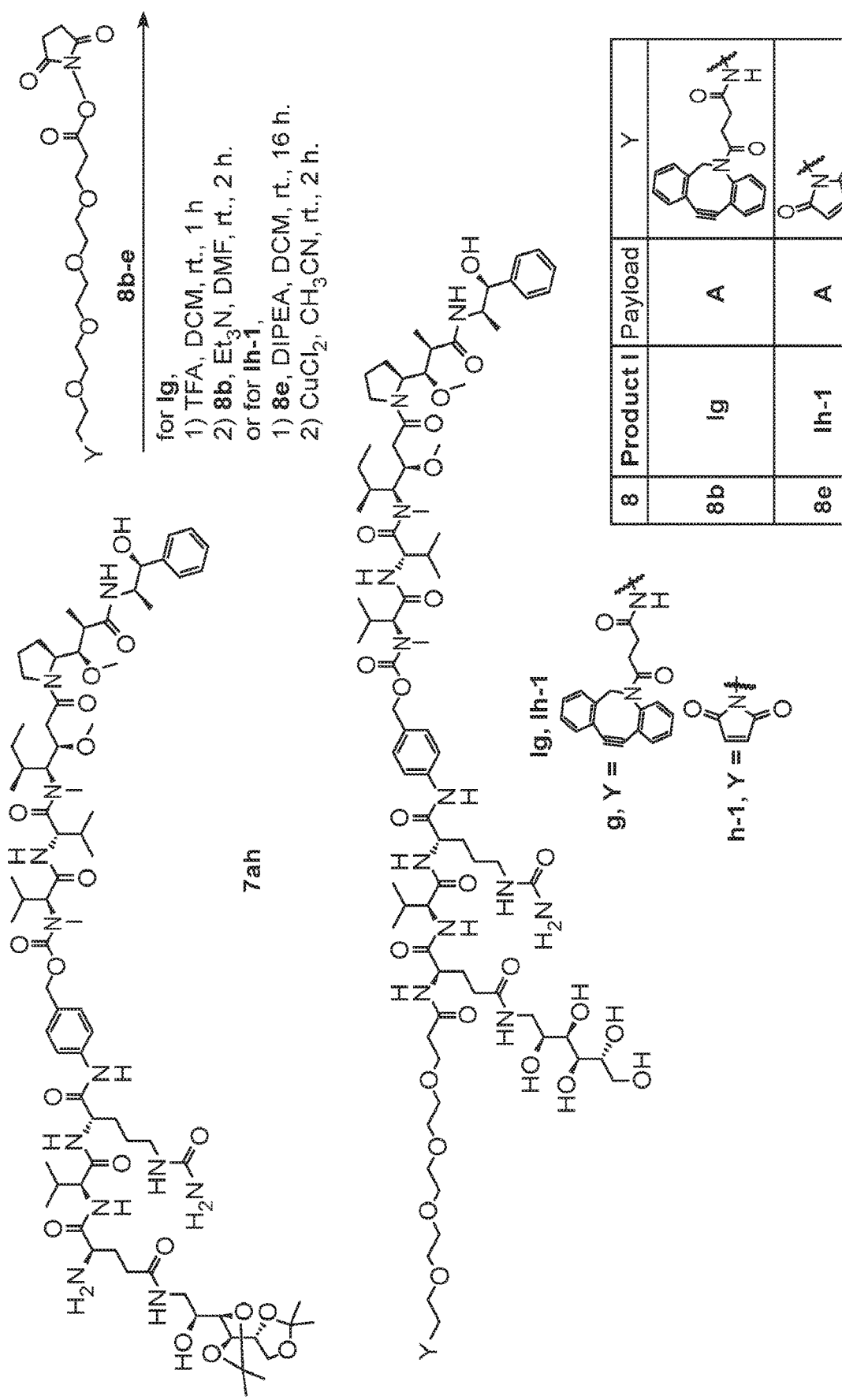
FIG. 18A shows a synthetic procedure for preparing Ig and Ih-1.
Figure 18B:
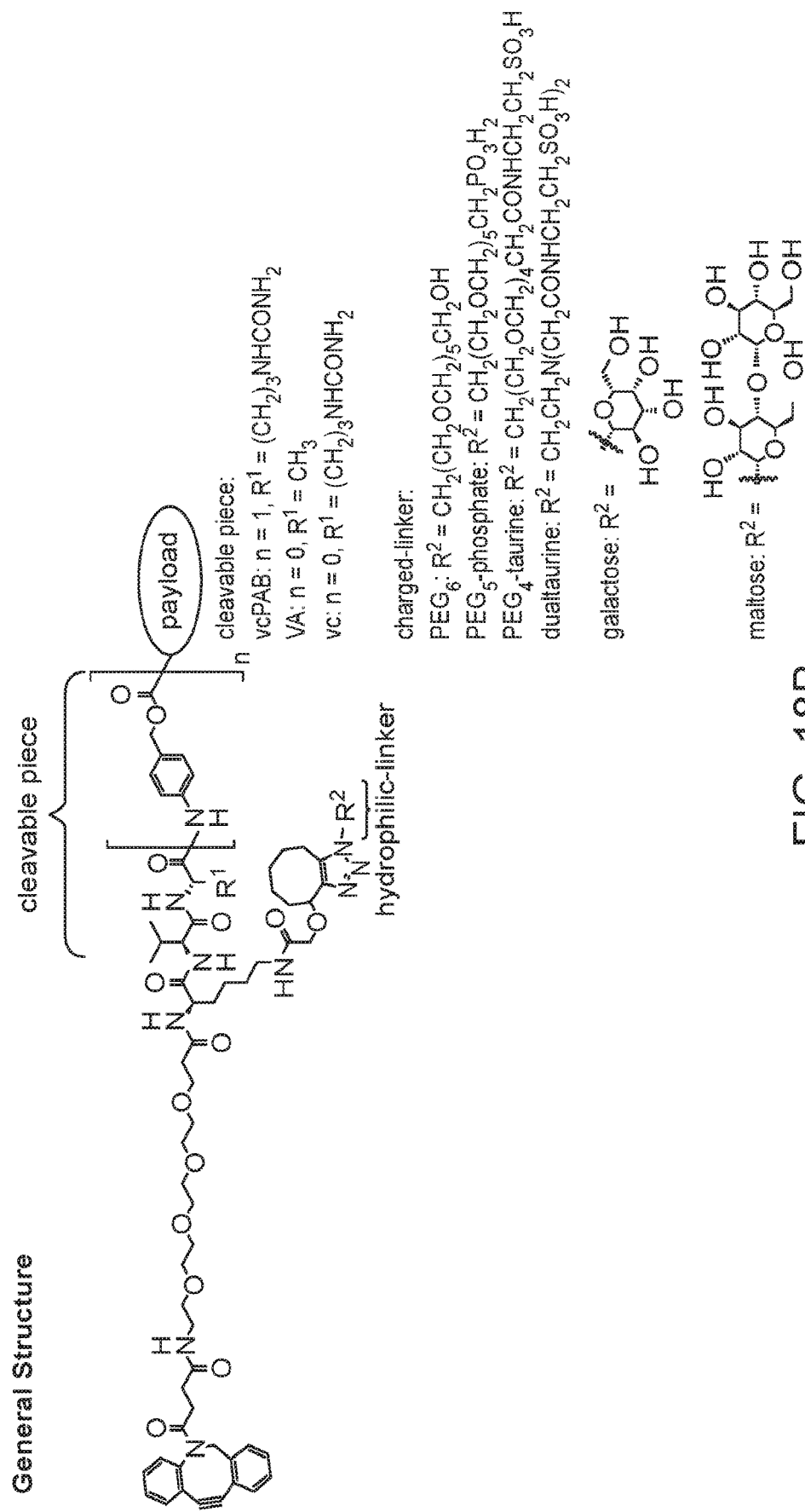
FIG. 18B shows cleavable pieces for Cathepsin B cleavage of linker-payload to release free payload.
Figure 18B:
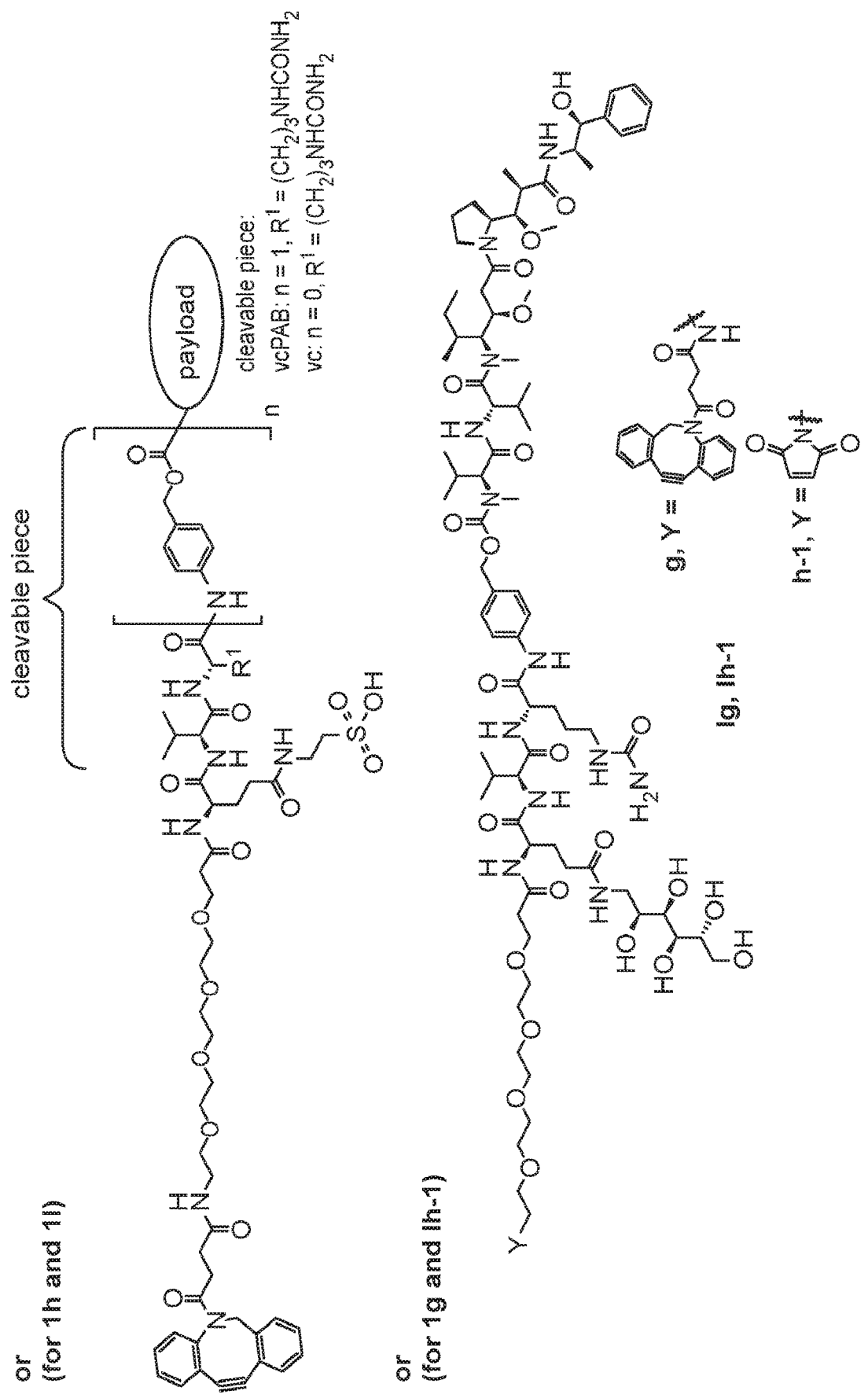

Preparation of Ig (FIG. 18)

{4-[(2S)-2-[(2S)-2-[(2R)-2-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-4-{[(2S,3R,4R,5R)-2,3,4,5,6-pentahydroxyhexyl]carbamoyl}butanamido]-3-methylbutanamido]-5-(carbamoylamino)pentanamido]phenyl) methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (Ig)

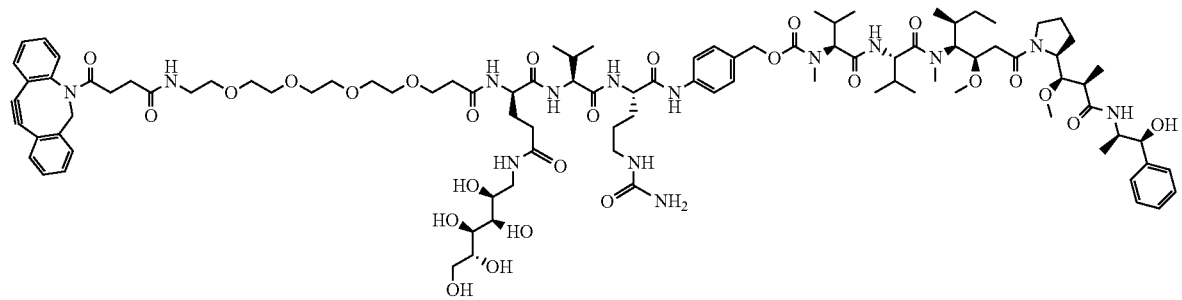 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCC(=O)NC[C@H](O)[C@@H](O)[C@H](O)[C@H](O)CO)NC(=O)CCOCCOCCOCCOCCNC(=O)CCC(=O)N2Cc3ccccc3C#Cc3ccccc32)C(C)C)cc1)C(C)C]

To a mixture of intermediate 7ah (40 mg, 27 μmol) in DCM (3 mL) was added TFA (0.25 mL) dropwise at 0° C. The mixture was stirred at RT for an hour until 7ah was consumed. The de-protection was completed according to LCMS. The volatiles were removed in vacuo and the residue (ESI m/z: 708 (M/2+H)$^+$) was dissolved in DMF (2 mL). To the solution were added intermediate 8b (17 mg, 27 μmol) and triethylamine (8.2 mg, 81 μmol). The mixture stirred at RT overnight. The reaction mixture was directly purified by prep-HPLC (method B) to give Ig (8.0 mg, 15% yield in two steps from 7ah) as a white solid. ESI m/z: 650.8 (M/3+H)$^+$ (100%), 975 (M/2+H)$^+$ (40%). $^1$H NMR (DMSO$_{d6}$, 500 MHz): δ 9.75 (s, 1H), 8.31-8.06 (m, 5H), 7.91-7.88 (m, 1H), 7.75-7.74 (m, 2H), 7.68-7.61 (m, 5H), 7.50-7.46 (m, 3H), 7.39-7.24 (m, 11H), 7.17-7.15 (m, 1H), 5.99 (s, 1H), 5.41-5.34 (m, 3H), 5.04-5.01 (m, 2H), 4.77-4.75 (m, 1H), 4.48-4.18 (m, 11H), 4.05-3.95 (m, 3H), 3.62-3.55 (m, 7H), 3.47-3.17 (m, 14H), 3.12-2.97 (m, 10H), 2.88-2.83 (m, 3H), 2.60-2.54 (m, 1H), 2.53-2.51 (m, 2H), 2.42-2.36 (m, 2H), 2.29-2.21 (m, 3H), 2.17-1.99 (m, 8H), 1.79-1.71 (m, 7H), 1.54-1.44 (m, 3H), 1.36-1.28 (m, 2H), 1.05-0.97 (m, 8H), 0.88-0.75 (m, 28H) ppm. Anal. HPLC: 96.9%, Retention time: 7.58 min (method B).

Example 18E

Preparation of Ih-1 (FIG. 18)

{4-[(2S)-5-(Carbamoylamino)-2-[(2S)-2-[(2R)-2-[1-(2,5-dioxo-2,5-dihydro-1H-pyrrol-1-yl)-3,6,9,12-tetraoxapentadecan-15-amido]-4-{[(2R,3S,4S,5S)-2,3,4,5,6-pentahydroxyhexyl]carbamoyl}butanamido]-3-methylbutanamido]pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methyl propyl]carbamoyl}-2-methyl propyl]-N-methylcarbamate (Ih-1)

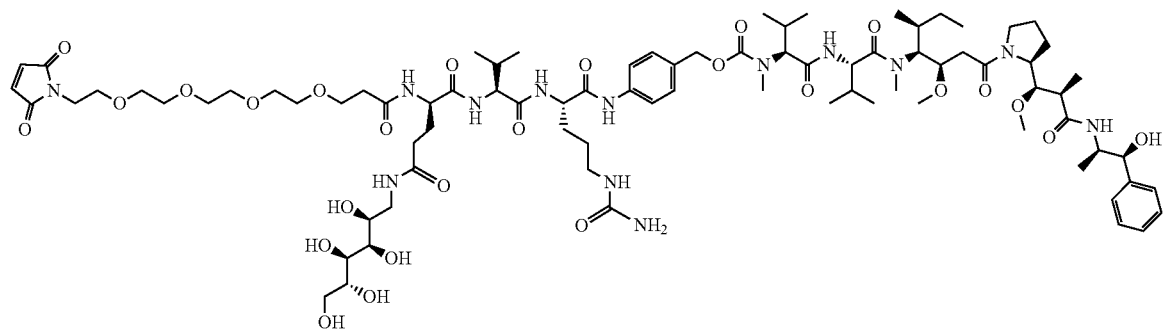 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@@H](CCC(=O)NC[C@H](O)[C@@H](O)[C@H](O)[C@H](O)CO)NC(=O)CCOCCOCCOCCOCCN2C(=O)C=CC2=O)C(C)C)cc1)C(C)C]

To a solution of intermediate 7ah (10 mg, 6.7 μmol) in DMF (1 mL) was added intermediate 8e (5.9 mg, 13 μmol) and DIPEA (1.7 mg, 13 μmol). The mixture was stirred at RT for 24 hours until most of 10a was consumed according to LCMS. The reaction mixture was filtered through membrane and the filtration was purified by prep-HPLC (Method A) (ESI m/z: 912 (M/2+H)$^+$). The residue after lyophilization was dissolved in acetonitrile (2 mL) and the solution was added copper(II) chloride dehydrate (19 mg, 0.12 mmol). The mixture was stirred at RT for two days. Desired mass of 1h was detected by LCMS as major product. After filtered to remove inorganic salts, the solution was directly purified by prep-HPLC (Method A) to give Ih-1 (2.0 mg, 17% yield in two steps from 7ah) as a white solid. ESI m/z: 1742.7 (M+H)$^+$, 1764.8 (M+Na)$^+$. $^1$H NMR (DMSO$_{d6}$, 500 MHz): δ 9.75 (s, 1H), 8.42-7.84 (m, 5H), 7.79-7.70 (m, 1H), 7.68-7.52 (m, 3H), 7.44-7.11 (m, 8H), 7.02 (s, 2H), 6.04-5.93 (m, 1H), 5.45-5.31 (m, 3H), 5.15-4.57 (m, 5H), 4.53-3.91 (m, 14H), 3.84-3.74 (m, 1H), 3.63-3.53 (m, 8H), 3.52-3.09 (m, 9H), 3.04-2.92 (m, 4H), 2.90-2.82 (m, 3H), 2.42-2.36 (m, 2H), 2.32-2.21 (m, 2H), 2.19-1.92 (m, 8H), 1.90-1.15 (m, 23H), 1.06-0.97 (m, 6H), 0.90-0.71 (m, 26H) ppm. Anal. HPLC: 99.4%, Retention time: 6.09 min (method A).

Example 19

Preparation of 1e (See FIG. 17)

2-{1-[4-({[(5R)-5-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-5-{[(1S)-1-{[(1S)-4-(carbamoylamino)-1-[(4-{[({2-[(1S,2S,4R,8S,9S,11S,12R,13S, 19S)-12, 19-difluoro-11-hydroxy-9,13-dimethyl-16-oxo-6-propyl-5,7-dioxapentacyclo[10.8.0.0²,⁹0.0⁴,⁸0.0¹³,¹⁸]icosa-14,17-dien-8-yl]-2-oxoethyl}carbamoyl)oxy]methyl}phenyl)carbamoyl]butyl]carbamoyl}-2-methyl propyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (1e)

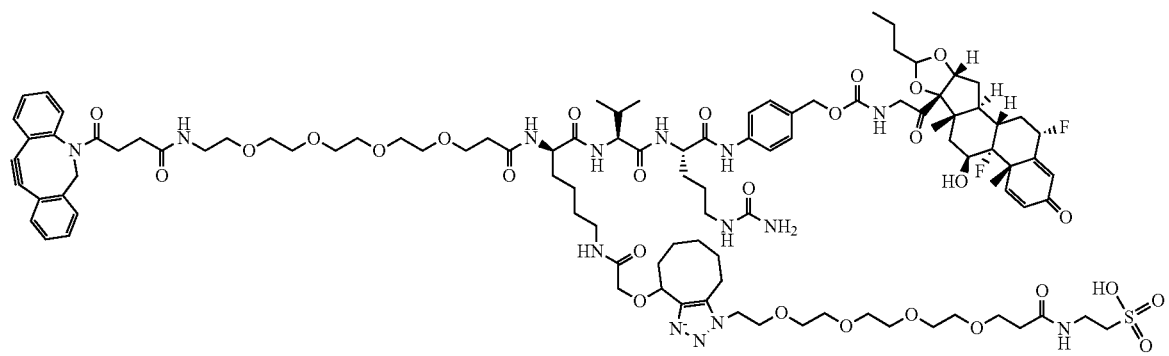

Following the general procedure H from compound 7e (47 mg, 30 μmol) with 8b, compound 1e (28 mg, 45% yield) was obtained as a white solid. ESI m/z: 1049 (M/2+H)⁺. 1H NMR (500 MHz, MeODd4) δ 7.75-7.57 (m, 4H), 7.48-7.43 (m, 3H), 7.38-7.23 (m, 6H), 6.37-6.28 (m, 2H), 5.65-5.43 (m, 1H), 5.17-5.03 (m, 3H), 4.69-4.59 (m, 2H), 4.52-4.47 (m, 1H), 4.45-4.41 (m, 1H), 4.34-4.25 (m, 2H), 4.23-4.13 (m, 2H), 4.07-3.86 (m, 5H), 3.77-3.68 (m, 4H), 3.64-3.54 (m, 22H), 3.52-3.47 (s, 3H), 3.46-3.40 (m, 4H), 3.29-3.21 (m, 4H), 3.20-3.14 (m, 2H), 3.10-3.01 (m, 1H), 3.00-2.95 (m, 2H), 2.92-2.84 (m, 1H), 2.76-2.60 (m, 2H), 2.47-2.42 (m, 2H), 2.40-2.25 (m, 5H), 2.23-2.13 (m, 3H), 2.07-1.97 (m, 3H), 1.90-1.79 (m, 4H), 1.71-1.55 (m, 14H), 1.52-1.42 (m, 3H), 1.40-1.29 (m, 8H), 1.07-0.85 (m, 12H) ppm. Anal. HPLC: 98%, Retention time: 5.88 min (method B).

Example 19A

Preparation of IIb (FIG. 17)

(2-{1-[4-({[(5R)-5-[1-(4-{2-Azatricyclo[10.4.0.0^{4,9}]hexadeca-1(12),4(9),5,7,13,15-hexaen-10-yn-2-yl}-4-oxobutanamido)-3,6,9,12-tetraoxapentadecan-15-amido]-5-{[(1S)-1-{[(1S)-4-(carbamoylamino)-1-[(4-{[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0^{2,9}0.0^{4,8}0.0^{13,18}]icosa-14,17-dien-8-yl]-2-oxoethyl}carbamoyl)oxy]methyl}phenyl)carbamoyl]butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethyl)trimethylazanium chloride (11b)

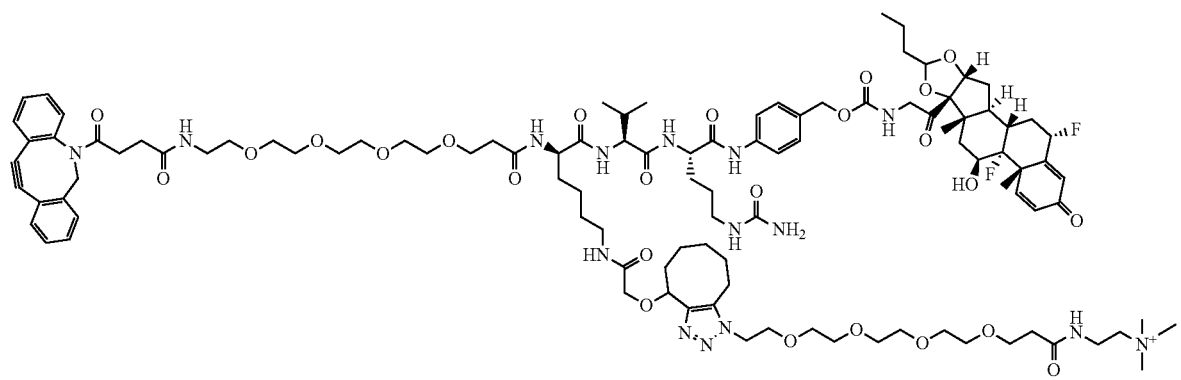 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@@H](CCCCNC(=O)COC3CCCCCc4c3nnn4CCOCCOCCOCCOCCC(=O)NCC[N+](C)(C)C)NC(=O)CCOCCOCCOCCOCCNC(=O)CCC(=O)N3Cc4ccccc4C#Cc4ccccc43)C(C)C)cc2)O1]

Following the general procedure G from compound 7bb (35 mg, 23 µmol) with 8a, compound IIb (25 mg, 52% yield) was obtained as a white solid after purified by reversed phase flash chromatography 0-100% acetonitrile in aq. ammonium bicarbonate (10 mM) and then 100% methanol). ESI m/z: 1037 [(M+18)/2]+. $^1$H NMR (400 MHz, DMSO$_{d6}$) δ 9.82-9.74 (m, 1H), 8.30 (s, 1H), 8.21-8.08 (m, 2H), 7.92-7.82 (m, 1H), 7.76 (t, J=5.5 Hz, 1H), 7.69-7.58 (m, 3H), 7.53-7.18 (m, 9H), 6.34-6.26 (m, 1H), 6.15-6.03 (m, 2H), 5.71-5.53 (m, 1H), 5.43 (s, 2H), 5.31 (t, J=12.4, 7.8 Hz, 1H), 5.10-4.90 (m, 3H), 4.79-4.72 (m, 1H), 4.58 (t, J=4.2 Hz, 1H), 4.52 (t, 1H), 4.44-4.28 (m, 3H), 4.25-4.11 (m, 3H), 3.88-3.74 (m, 4H), 3.64-3.55 (m, 3H), 3.49-3.42 (m, 20H), 3.13-3.02 (m, 12H), 3.00-2.91 (m, 3H), 2.81-2.73 (m, 1H), 2.61-2.54 (m, 1H), 2.41-2.32 (m, 3H), 2.29-2.19 (m, 3H), 2.12-1.93 (m, 7H), 1.83-1.73 (m, 3H), 1.70-1.62 (m, 3H), 1.60-1.31 (m, 20H), 1.31-1.19 (m, 17H), 1.15-1.04 (m, 3H), 0.89-0.79 (m, 12H) ppm.

Example 20

Preparation of 1f (See FIG. 17)

2-[2-({2-[4-({[(5R)-5-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxa-pentadecan-15-amido]-5-{[(1S)-1-{[(1S)-4-(carbamoylamino)-1-[(4-{[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹0.0⁴,⁸0¹³,¹⁸]icosa-14,17-dien-8-yl]-2-oxoethyl}carbamoyl)oxy]methyl}phenyl)carbamoyl]butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]ethyl}({[(2-sulfoethyl)carbamoyl]methyl})amino)acetamido]ethane-1-sulfonic acid (1f)

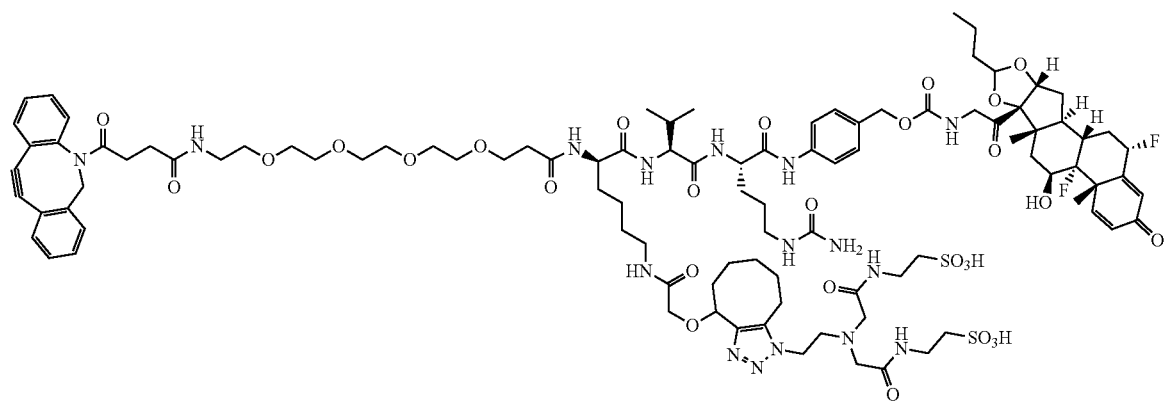 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@@H](CCCCNC(=O)COC3CCCCCc4c3nnn4CCN(CC(=O)NCCS(=O)(=O)O)CC(=O)NCCS(=O)(=O)O)NC(=O)CCOCCOCCOCCOCCNC(=O)CCC(=O)N3Cc4ccccc4C#Cc4ccccc43)C(C)C)cc2)O1]

Following the general procedure H from compound 7f (60 mg, 38 µmol) with 8b, compound 1f (25 mg, 31% yield) was obtained as a white solid. ESI m/z: 1058 (M/2+H)⁺. ¹H NMR (500 MHz, DMSO$_{d6}$) δ 9.62-9.58 (m, 1H), 8.25-8.00 (m, 6H), 7.90-7.80 (m, 1H), 7.77 (t, J=5.5 Hz, 1H), 7.70-7.60 (m, 4H), 7.55-7.25 (m, 12H), 6.30 (d, J=10.5 Hz, 1H), 6.10 (s, 1H), 6.05-5.95 (m, 1H), 5.70-5.55 (m, 2H), 5.40 (s, 2H), 5.10-4.90 (m, 4H), 4.80-4.70 (m, 1H), 4.59 (t, J=4.0 Hz, 1H), 4.50-4.35 (m, 2H), 4.35-4.25 (m, 2H), 4.25-4.10 (m, 3H), 3.90-3.75 (m, 3H), 3.65-3.50 (m, 5H), 3.50-3.40 (m, 16H), 3.20-3.05 (m, 12H), 3.00-2.80 (m, 6H), 2.65-2.55 (m, 6H), 2.40-2.35 (m, 1H), 2.30-2.20 (m, 5H), 2.10-1.95 (m, 5H), 1.85-1.70 (m, 4H), 1.65-1.30 (m, 18H), 0.90-0.80 (m, 12H) ppm. Anal. HPLC: 97%, Retention time: 6.82 min (method B).

Example 21

Preparation of 1h (See FIG. 17)

2-[(4R)-4-[1-(4-{2-Azatricyclo[10.4.0.0⁴,⁹]hexa-deca-1(12),4(9),5,7,13,15-hexaen-10-yn-2-yl}-4-oxobutanamido)-3,6,9,12-tetraoxapentadecan-15-amido]-4-{[(1S)-1-{[(1S)-4-(carbamoylamino)-1-[(4-{[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹0.0⁴,⁸0¹³,¹⁸]icosa-14,17-dien-8-yl]-2-oxoethyl}carbamoyl)oxy]methyl}phenyl)carbamoyl]butyl]carbamoyl}-2-methyl propyl]carbamoyl}butanamido]ethane-1-sulfonic acid (1h)

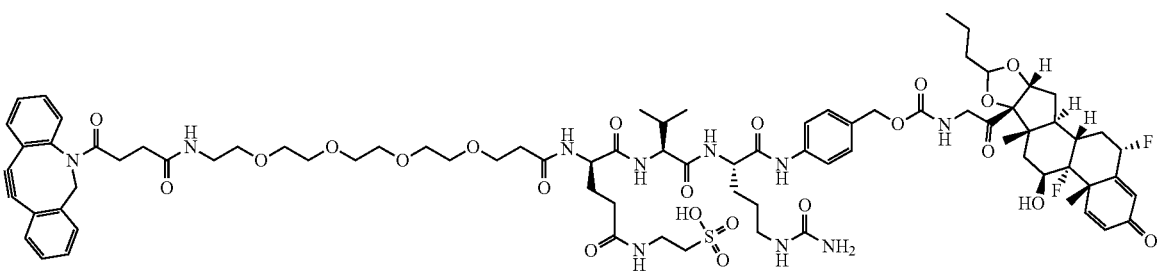 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@@H](CCC(=O)NCCS(=O)(=O)O)NC(=O)CCOCCOCCOCCOCCNC(=O)CCC(=O)N3Cc4ccccc4C#Cc4ccccc43)C(C)C)cc2)O1]

Following the general procedure H from compound 7h (20 mg, 18 μmol) with 8b, compound 1h (11 mg, 37% yield) was obtained as a white solid after purified by reversed phase flash chromatography 0-100% acetonitrile in aq. ammonium bicarbonate (10 mM)). ESI m/z: 821.3 (M/2+H)$^+$. $^1$H NMR (500 MHz, DMSO$_{d6}$) δ 9.70 (s, 1H), 8.22 (d, J=7.0 Hz, 1H), 8.10 (d, J=7.0 Hz, 2H), 7.95-7.61 (m, 7H), 7.51-7.26 (m, 11H), 6.30 (d, J=10 Hz, 1H), 6.11 (s, 1H), 6.01-5.99 (m, 1H), 5.69-5.57 (m, 2H), 5.41 (s, 2H), 5.22-4.92 (m, 4H), 4.78-4.58 (m, 1H), 4.35-4.13 (m, 5H), 3.86-3.80 (m, 1H), 3.62-3.40 (m, 14H), 3.30-3.28 (m, 4H), 3.10-2.73 (m, 5H), 2.63-2.53 (m, 2H), 2.41-2.20 (m, 3H), 2.09-1.57 (m, 13H), 1.48-1.12 (m, 15H), 0.90-0.84 (m, 10H) ppm. Anal. HPLC: 96%, Retention time: 7.28 min (method B).

Example 22

Preparation of 1i (See FIG. 17)

2-(1-{4-[({5-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-5-{[(1S)-1-{[(1S)-4-(carbamoylamino)-1-{[4-({[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$0.0$^{4,8}$0.0$^{13,18}$]icosa-14,17-dien-8-yl]-2-oxoethoxy}phenyl)carbamoyl]oxy}methyl)phenyl]carbamoyl}butyl]carbamoyl}-2-methyl propyl]carbamoyl}pentyl}carbamoyl)methoxy]-1H,4H,5H,6H,7H,8H,9H-cyclooctal[d][1,2,3]triazol-1-yl}-3,6,9,12-tetraoxapentadecan-15-amido)ethane-1-sulfonic acid (1i)

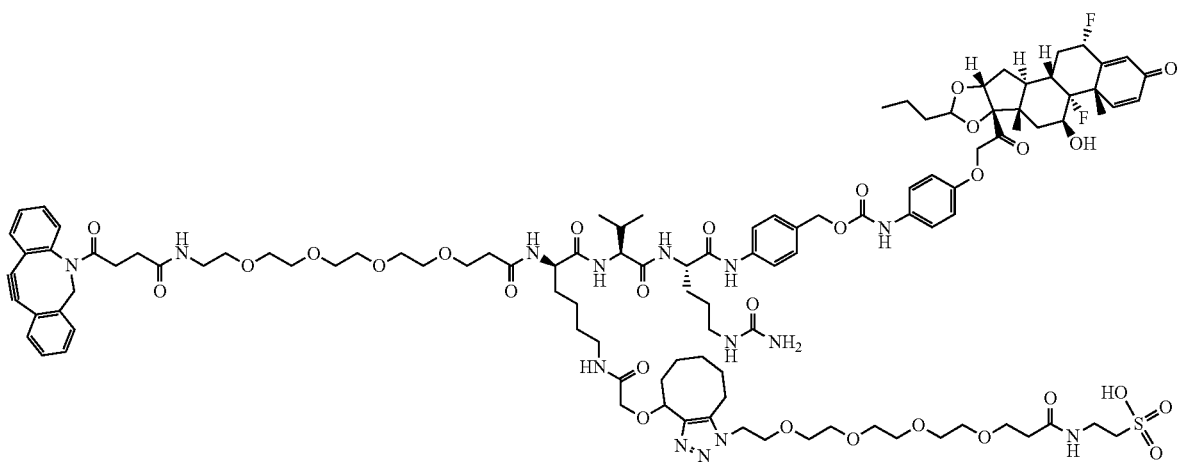 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)OCc3ccc(NC(=O)[C@H](CCCNC(N)=O)NC(=O)[C@@H](NC(=O)[C@@H](CCCCNC(=O)COC4CCCCC/C(NCCOCCOCCOCCOCCC(=O)NCCS(=O)(=O)O)=C\4N=N)NC(=O)CCOCCOCCOCCOCCNC(=O)CCC(=O)N4Cc5ccccc5C#Cc5ccccc54)C(C)C)cc3)cc2)O1]

Following the general procedure H from compound 7i (46 mg, 28 μmol) with compound 8b, compound 1i (28 mg, 46% yield) was obtained as a white solid. ESI m/z: 1095.0 (M/2+H)$^+$. $^1$H NMR (400 MHz, MeOD$_{d4}$) δ 7.42-7.23 (m, 15H), 6.87-6.83 (m, 2H), 6.36-6.31 (m, 2H), 5.64-5.47 (m, 1H), 5.29-5.05 (m, 5H), 4.94-4.90 (m, 1H), 4.84-4.59 (m, 2H), 4.49-4.41 (m, 2H), 4.34-4.26 (m, 2H), 4.16-4.13 (m, 1H), 4.02-3.86 (m, 4H), 3.72-3.68 (m, 3H), 3.66-3.34 (m, 31H), 3.24-3.14 (m, 5H), 3.08-2.83 (m, 4H), 2.73-2.60 (m, 2H), 2.46-2.36 (m, 9H), 2.12-1.19 (m, 32H), 1.05-0.90 (m, 12H) ppm. Anal. HPLC: 100%, Retention time: 7.62 min (method B).

Example 23

Preparation of 1j (See FIG. 17)

2-{1-[4-({[(5R)-5-[1-(4-{2-Azatricyclo[10.4.0.0$^{4,9}$]
hexadeca-1(12),4(9),5,7,13,15-hexaen-10-yn-2-yl}-
4-oxobutanamido)-3,6,9,12-tetraoxapentadecan-15-
amido]-5-{[(1S)-1-{[(1S)-1-[(4-{2-[(1S,2S,4R,8S,
9S,11S,12R,13S,19S)-12,19-difluoro-11-hydroxy-9,
13-dimethyl-16-oxo-6-propyl-5,7-dioxapentacyclo
[10.8.0.0$^{2,9}$0.0$^{4,8}$0.0$^{13,18}$]icosa-14,17-dien-8-yl]-2-
oxoethoxy}phenyl)carbamoyl}methyl]carbamoyl}-
2-methylpropyl]carbamoyl}pentyl]
carbamoyl}methoxy)-1H,4H,5H,6H,7H,8H,9H-
cycloocta[d][1,2,3]triazol-1-yl]-3,6,9,12-
tetraoxapentadecan-15-amido}ethane-1-sulfonic
acid (1j)

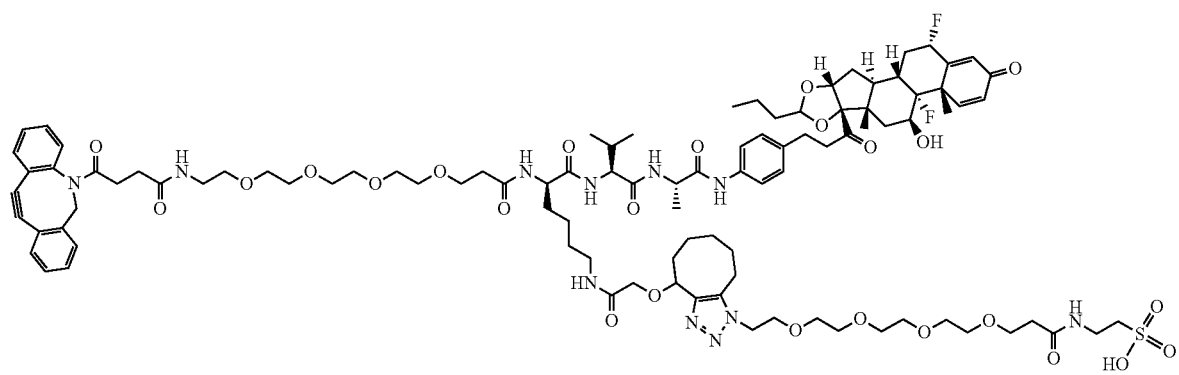 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CCc2ccc(NC(=O)[C@H](C)NC(=O)[C@@H](NC(=O)[C@@H](CCCCNC(=O)COC3CCCCCc4c3nnn4CCOCCOCCOCCOCCC(=O)NCCS(=O)(=O)O)NC(=O)CCOCCOCCOCCOCCNC(=O)CCC(=O)N3Cc4ccccc4C#Cc4ccccc43)C(C)C)cc2)O1]

Following the general procedure H from compound 7j (66 mg, 47 µmol) with compound 8b, compound 1j (40 mg, 44% yield) was obtained as a white solid. ESI m/z: 977.5 (M/2+H)$^+$. $^1$H NMR (400 MHz, MeOD$_{d4}$) δ 7.66-7.55 (m, 4H), 7.48-7.24 (m, 7H), 6.90-6.85 (m, 2H), 6.35 (d, J=10.0 Hz, 1H), 6.32 (s, 1H), 5.64-5.47 (m, 1H), 5.28-5.07 (m, 3H), 4.85-4.60 (m, 3H), 4.50-4.44 (m, 2H), 4.34-4.25 (m, 2H), 4.12-3.88 (m, 5H), 3.73-3.49 (m, 29H), 3.45-3.39 (m, 3H), 3.25-3.20 (m, 3H), 3.14-2.86 (m, 5H), 2.74-2.63 (m, 2H), 2.46-1.27 (m, 41H), 1.05-0.92 (m, 12H) ppm. Anal. HPLC: 95%, Retention time: 7.55 min (method B).

Example 24

Preparation of 1k (See FIG. 17)

2-{1-[4-({[(5R)-5-[1-(4-{2-Azatricyclo[10.4.0.0$^{4,9}$]
hexadeca-1(12),4(9),5,7,13,15-hexaen-10-yn-2-yl}-
4-oxobutanamido)-3,6,9,12-tetraoxapentadecan-15-
amido]-5-{[(1S)-1-{[(1S)-4-(carbamoylamino)-1-
[(4-{2-[(1S,2S,4R,8S,9S,11S,12R,13S,19S)-12,19-
difluoro-11-, hydroxy-9,13-dimethyl-16-oxo-6-
propyl-5,7-dioxapentacyclo[10.8.0.0$^{2,9}$0.0$^{4,8}$0$^{13,18}$]
icosa-14,17-dien-8-yl]-2-oxoethoxy}phenyl)
carbamoyl]butyl]carbamoyl}-2-methylpropyl]
carbamoyl}pentyl]carbamoyl}methoxy)-1H,4H,5H,
6H,7H,8H,9H-cycloocta[d][1,2,3]triazol-1-yl]-3,6,9,
12-tetraoxapentadecan-15-amido}ethane-1-sulfonic
acid (1k)

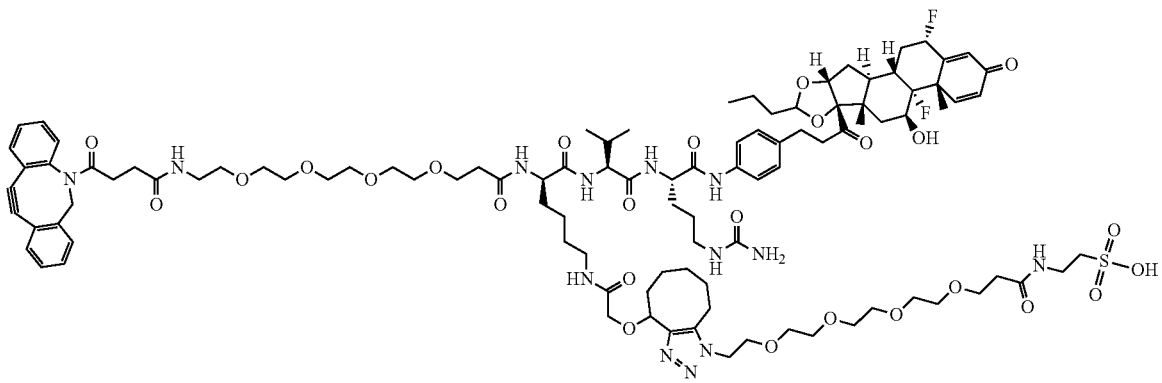 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CCc2ccc(NC(=O)[C@H](CCCNC(N)=O)NC(=O)[C@@H](NC(=O)[C@@H](CCCCNC(=O)COC3CCCCC/C(NCCOCCOCCOCCOCCC(=O)NCCS(=O)(=O)O)=C\3N=N)NC(=O)CCOCCOCCOCCOCCNC(=O)CCC(=O)N3Cc4ccccc4C#Cc4ccccc43)C(C)C)cc2)O1]

Following the general procedure H from compound 7k (50 mg, 33 μmol) with compound 8b, compound 1k (30 mg, 44% yield) was obtained as a white solid. ESI m/z: 680 (M/3+H)$^+$. $^1$H NMR (500 MHz, DMSO$_{d6}$) δ 9.51 (s, 1H), 8.30-7.97 (m, 3H), 7.92-7.84 (m, 1H), 7.80-7.73 (m, 2H), 7.68 (d, J=7.5 Hz, 1H), 7.62 (d, J=7.9 Hz, 1H), 7.50-7.45 (m, 4H), 7.38-7.26 (m, 4H), 7.08 (br s, 3H), 6.90-6.78 (m, 2H), 6.30 (d, J=10.5 Hz, 1H), 6.11 (s, 1H), 6.01-5.94 (m, 1H), 5.72-5.55 (m, 1H), 5.52 (s, 1H), 5.39 (s, 2H), 5.12 (d, J=18.5 Hz, 1H), 5.03 (d, J=14.5 Hz, 1H), 4.84 (d, J=18.5 Hz, 1H), 4.80-4.71 (m, 2H), 4.55-4.49 (m, 1H), 4.42 (t, J=5.5 Hz, 1H), 4.38-4.12 (m, 4H), 3.81-3.76 (m, 4H), 3.62-3.53 (m, 4H), 3.46-3.39 (m, 21H), 3.33-3.25 (m, 4H), 3.09-2.93 (m, 7H), 2.81-2.78 (m, 1H), 2.64-2.52 (m, 8H), 2.40-2.36 (m, 2H), 2.27-2.20 (m, 5H), 2.09-1.98 (m, 5H), 1.61-1.35 (m, 29H), 0.89-0.83 (m, 11H) ppm.

Example 24A

Preparation of IIId (FIG. 17)

(2-{1-[4-({[(5R)-5-{[(1S)-1-{[(1S)-4-(Carbamoylamino)-1-{[4-({[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$0.0$^{4,8}$0.0$^{13,18}$]icosa-14,17-dien-8-yl]-2-oxoethoxy}phenyl)carbamoyl]oxy}methyl)phenyl]carbamoyl}butyl]carbamoyl}-2-methylpropyl]carbamoyl}-5-{1-[2-(cyclooct-2-yn-1-yloxy)acetamido]-3,6,9,12-tetraoxapentadecan-15-amido}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethyl)trimethylazanium (IIId)

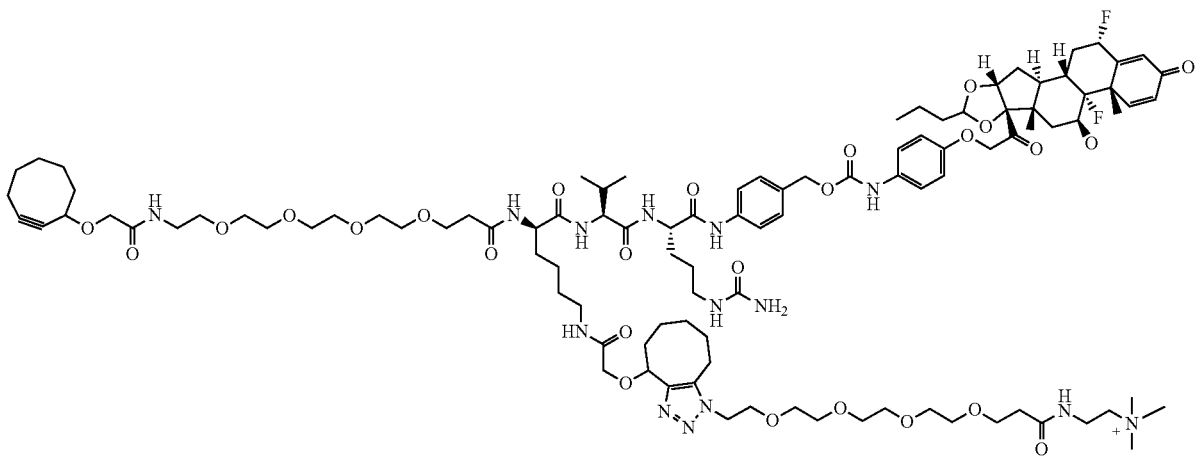

Following the general procedure G from compound 7cb (20 mg, 12 μmol) with compound 8c (5.2 mg, 12 μmol), compound IIId (8 mg, 32% yield) was obtained as a yellow solid after purification by reversed phase flash chromatography (0-100% acetonitrile in aq. TFA (0.01%)). ESI m/z: 681.7 (M/3+H)$^+$; 1021.7 (M/2+H)$^+$. $^1$H NMR (400 MHz, DMSO$_{d6}$) δ 9.73-9.67 (m, 1H), 9.61-9.54 (m, 1H), 8.26-8.20 (m, 1H), 8.19-8.04 (m, 2H), 7.91-7.77 (m, 1H), 7.66-7.57 (m, 3H), 7.40-7.26 (m, 4H), 6.84-6.78 (m, 2H), 6.30 (d, J=10 Hz, 1H), 6.12 (s, 1H), 6.01-5.99 (m, 1H), 5.72-5.42 (m, 4H), 5.24-5.06 (m, 3H), 4.91-4.73 (m, 3H), 4.55-4.16 (m, 7H), 3.89-3.73 (m, 5H), 3.58 (t, J=10.4 Hz, 3H), 3.49-3.41 (m, 29H), 3.26-3.22 (m, 4H), 3.08 (s, 9H), 3.04-2.93 (m, 4H), 2.77-2.62 (m, 3H), 2.40-1.98 (m, 13H), 1.89-1.02 (m, 41H), 0.89-0.84 (m, 9H) ppm.

Example 24B

Preparation of IIIe (FIG. 17)

(2-{1-[4-({[(5R)-5-[1-({[(1R,8S,9S)-Bicyclo[6.1.0]non-4-yn-9-ylmethoxy]carbonyl}amino)-3,6,9,12-tetraoxapentadecan-15-amido]-5-{[(1S)-1-{[(1S)-4-(carbamoylamino)-1-{[4-({[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$0.0$^{4,8}$0.0$^{13,18}$]icosa-14,17-dien-8-yl]-2-oxoethoxy}phenyl)carbamoyl]oxy}methyl) phenyl]carbamoyl}butyl]carbamoyl}-2-methyl propyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethyl) trimethylazanium (IIIe)

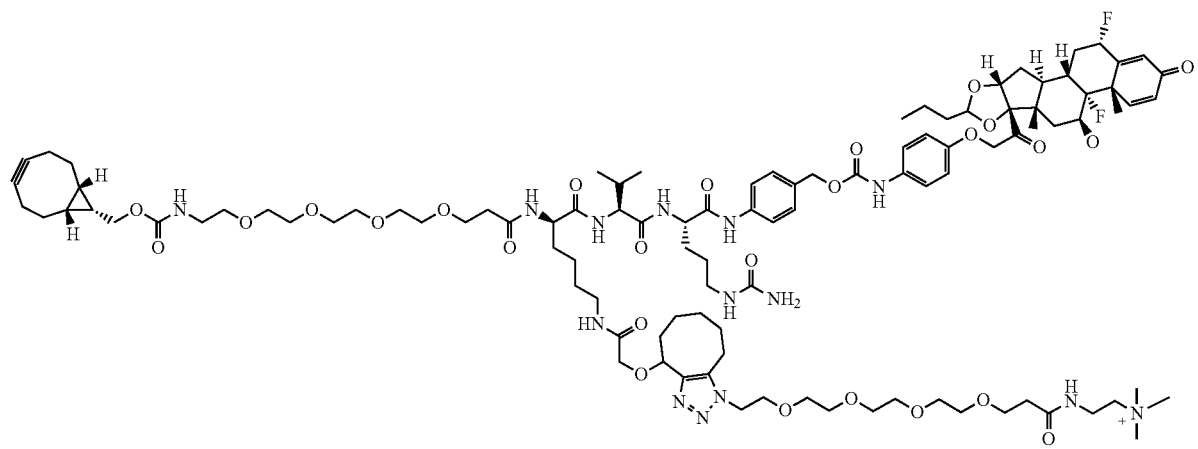

Following the general procedure G from compound 7cb (25 mg, 15 μmol) with compound 8d (6.8 mg, 15 μmol), compound IIIe (4 mg, 13% yield) was obtained as a yellow solid after purification by reversed phase flash chromatography (0-100% acetonitrile in aq. TFA (0.01%)). ESI m/z: 685.6 (M/3+H)$^+$. $^1$H NMR (400 MHz, MeOD$_{d4}$) δ 7.77-7.71 (m, 2H), 7.40-7.34 (m, 5H), 6.90-6.86 (m, 2H), 6.38-6.33 (m, 2H), 5.66-5.47 (m, 1H), 5.38-5.24 (m, 1H), 5.14-5.02 (m, 2H), 4.76-4.58 (m, 4H), 4.52-4.27 (m, 6H), 4.19-4.11 (m, 3H), 3.99-3.86 (m, 4H), 3.75-3.42 (m, 37H), 3.30-3.27 (m, 3H), 3.17 (s, 9H), 3.16-3.00 (m, 2H), 3.0-2.84 (m, 1H), 2.72-2.46 (m, 4H), 2.38-2.04 (m, 15H), 1.83-1.31 (m, 27H), 1.06-0.90 (m, 13H) ppm.

Example 25

Preparation of 1l (See FIG. 17)

2-[(4R)-4-[1-(4-{2-Azatricyclo[10.4.0.0⁴,⁹]hexa-deca-1(12),4(9),5,7,13,15-hexaen-10-yn-2-yl}-4-oxobutanamido)-3,6,9,12-tetraoxapentadecan-15-amido]-4-{[(1S)-1-{[(1S)-4-(carbamoylamino)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹0.0⁴,⁸0.0¹³,¹⁸] icosa-14,17-dien-8-yl]-2-oxoethoxy}phenyl) carbamoyl]butyl]carbamoyl}-2-methylpropyl] carbamoyl}butanamido]ethane-1-sulfonic acid (1l)

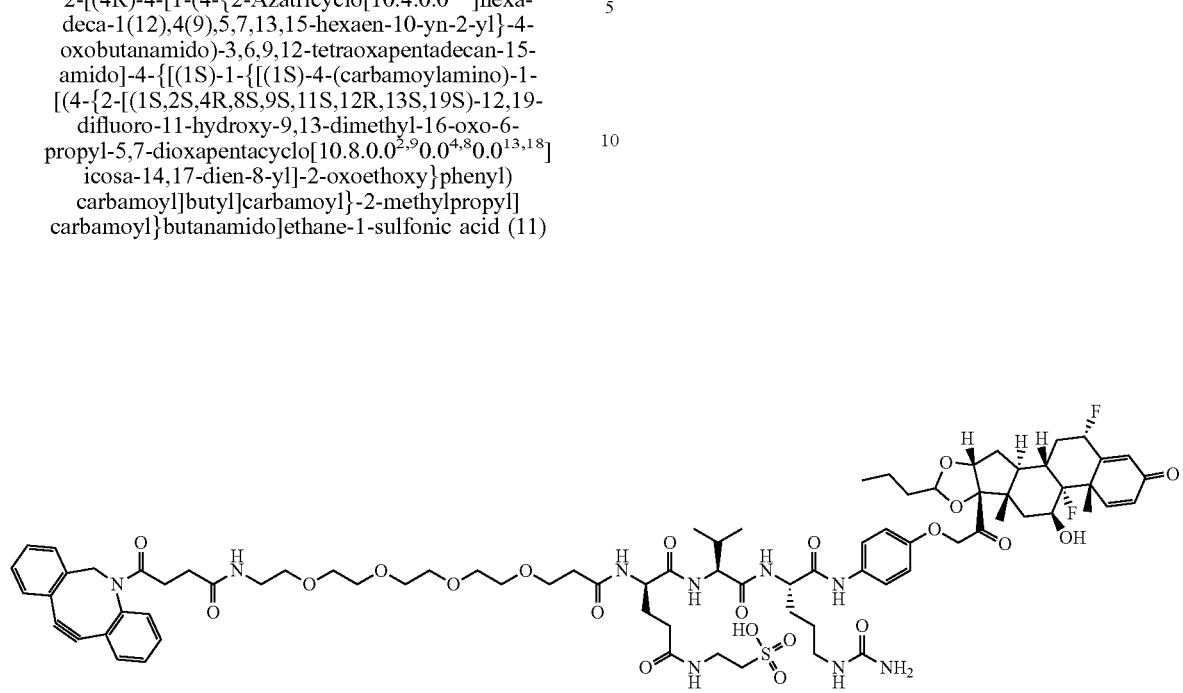

Following the general procedure H from compound 7l (20 mg, 19 μmol) with compound 8b, compound 1l (6.0 mg, 20% yield) was obtained as a white solid. ESI m/z: 793 (M/2+H)⁺. ¹H NMR (400 MHz, DMSO$_{d6}$) δ 9.81-9.48 (m, 1H), 8.32-8.18 (m, 1H), 8.12-7.96 (m, 2H), 7.81-7.60 (m, 4H), 7.58-7.43 (m, 5H), 7.41-7.25 (m, 5H), 7.18-6.98 (m, 2H), 6.88-6.81 (m, 2H), 6.30 (d, J=10.3 Hz, 1H), 6.11 (s, 1H), 6.02-5.95 (m, 1H), 5.71-5.52 (m, 2H), 5.40 (s, 2H), 5.15-5.00 (m, 2H), 4.86-4.74 (m, 2H), 4.34-4.13 (m, 4H), 3.63-3.54 (m, 2H), 3.48-3.42 (m, 9H), 3.30-3.28 (m, 2H), 3.12-3.05 (m, 2H), 3.01-2.92 (m, 2H), 2.62-2.56 (m, 1H), 2.42-2.37 (m, 1H), 2.29-2.20 (m, 3H), 2.12-1.95 (m, 7H), 1.86-1.70 (m, 5H), 1.64-1.56 (m, 4H), 1.52-1.22 (m, 14H), 0.92-0.81 (m, 14H) ppm.

Example 26

Preparation of 1m (See FIG. 17)

2-{1-[4-({[(5R)-5-[1-(4-{2-Azatricyclo[10.4.0.0⁴,⁹] hexadeca-1(12),4(9),5,7,13,15-hexaen-10-yn-2-yl}-4-oxobutanamido)-3,6,9,12-tetraoxapentadecan-15-amido]-5-{[(1S)-1-{[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl] formamido}carbonyl)-4b,8-dimethyl-4b,5,6,7,8,8a,9,10-octahydrophenanthren-3-yl]carbamoyl}ethyl] carbamoyl}-2-methylpropyl]carbamoyl}pentyl] carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (1m)

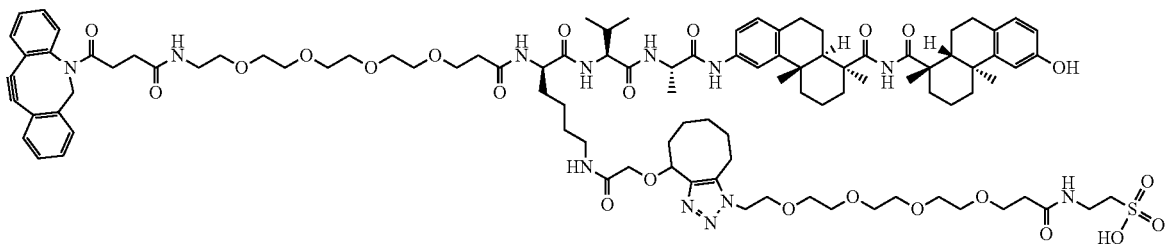 [SMILES: CC(C)[C@H](NC(=O)[C@@H](CCCCNC(=O)COC1CCCCCc2c1nnn2CCOCCOCCOCCOCCC(=O)NCCS(=O)(=O)O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

Following the general procedure H from compound 7m (30 mg, 22 µmol) with compound 8b, compound 1m (15 mg, 37% yield) was obtained as a white solid. ESI m/z: 642 (M/3+H)⁺. ¹H NMR (400 MHz, DMSO$_{d6}$) δ 9.68-9.27 (m, 1H), 8.99 (s, 1H), 8.23-7.85 (m, 4H), 7.79-7.71 (m, 2H), 7.76-7.42 (m, 6H), 7.39-7.28 (m, 3H), 7.21 (s, 1H), 7.09 (s, 1H), 6.96-6.93 (m, 2H), 6.81 (d, J=8.4 Hz, 1H), 6.63 (d, J=2.4 Hz, 1H), 6.50 (dd, J=8.4 Hz, 2.4 Hz, 1H), 5.02 (d, J=14.0 Hz, 1H), 4.93-4.72 (m, 1H), 4.53-4.09 (m, 5H), 3.82-3.75 (m, 4H), 3.62-3.53 (m, 3H), 3.51-3.38 (m, 23H), 3.30-3.27 (m, 6H), 3.12-2.67 (m, 10H), 2.61-2.54 (m, 4H), 2.39-1.52 (m, 31H), 1.45-1.08 (m, 18H), 1.01-0.98 (m, 6H), 0.90-0.82 (m, 6H) ppm.

Example 26A

Preparation of IVb (FIG. 17)

(2-{1-[4-({[(5R)-5-{[(1S)-1-{[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}-5-{1-[2-(cycloocт-2-yn-1-yloxy)acetamido]-3,6,9,12-tetraoxapentadecan-15-amido}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethyl)trimethylazanium (IVb)

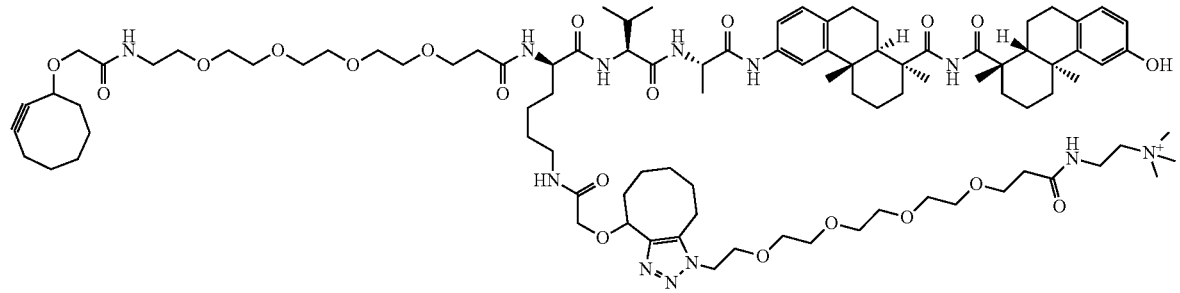 [SMILES: CC(C)[C@H](NC(=O)[C@@H](CCCCNC(=O)COC1CCCCCc2c1nnn2CCOCCOCCOCCOCCC(=O)NCC[N+](C)(C)C)NC(=O)CCOCCOCCOCCOCCNC(=O)COC1C#CCCCCC1)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

Following the general procedure G from compound 7fb (20 mg, 15 µmol) with compound 8c, compound IVb (6 mg, 23% yield) was obtained as a yellow solid after purification by prep-HPLC (method A). ESI m/z: 889.8 (M/2+H)⁺, 593.5 (M/3+H)⁺. ¹H NMR (500 MHz, DMSO$_{d6}$) δ 9.30 (d, J=8.5 Hz, 1H), 9.02 (s, 1H), 8.76 (d, J=5.5 Hz, 1H), 8.54-8.48 (m, 1H), 8.32-7.76 (m, 6H), 7.62-7.60 (m, 2H), 7.53-7.51 (m, 2H), 7.44 (d, J=8.0 Hz, 1H), 6.95 (d, J=8.5 Hz, 1H), 6.81 (d, J=8.5 Hz, 1H), 6.63 (s, 1H), 6.50 (d, J=8.0 Hz, 1H), 5.33-4.71 (m, 2H), 4.55-4.05 (m, 7H), 3.88-3.74 (m, 6H), 3.61-3.58 (m, 4H), 3.50-3.42 (m, 44H), 3.26-3.24 (m, 4H), 3.08 (s, 9H), 2.84-2.65 (m, 3H), 2.44 (t, J=6.5 Hz, 2H), 2.35-1.26 (m, 35H), 1.16-1.13 (m, 2H), 1.02-0.98 (m, 6H), 0.89-0.84 (m, 6H) ppm.

Example 27

Preparation of 1q (See FIG. 17)

2-{1-[4-({[(5R)-5-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-5-{[(1S)-1-{[(1S)-1-({4-[({[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamoyl}oxy)methyl]phenyl}carbamoyl)-4-(carbamoylamino)butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (1q)

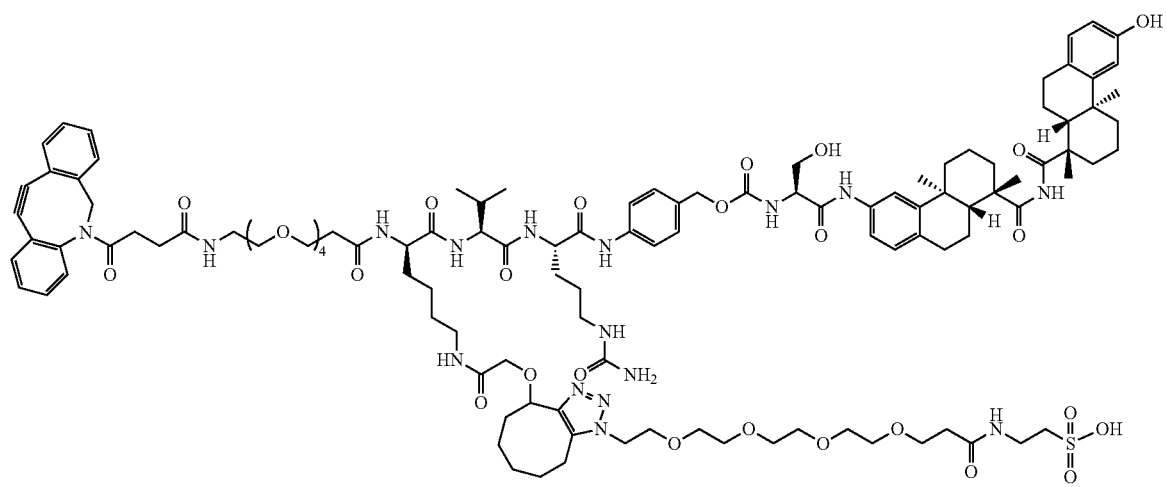

To a solution of compound 7q (15 mg, 8.8 μmol) and commercial DIBAC-Suc-PEG$_4$-OSu (5.7 mg, 8.8 μmol, CAS 1427004-19-0) in DMF (1 mL) was added DIPEA (2.3 mg, 18 μmol) and the mixture was stirred at RT for 2 hours. Most of The volatiles were removed in vacuo and the residue was purified by prep-HPLC (method B) to give 1q (6.0 mg, 30% yield) as a white solid. ESI m/z: 1123.8 (M/2+H)$^+$, 749.5 (M/3+H)$^+$. $^1$H NMR (500 MHz, MeOD$_{d4}$) δ 7.76-7.16 (m, 14H), 7.06-7.00 (m, 1H), 6.88 (d, J=8.5 Hz, 1H), 6.72-6.71 (m, 1H), 6.56-6.55 (m, 1H), 5.39-5.33 (m, 1H), 5.14-5.09 (m, 5H), 4.61 (s, 18H), 4.50-4.43 (m, 2H), 4.33-4.30 (m, 1H), 3.99 (s, 2H), 3.89-3.85 (m, 3H), 3.73-3.42 (m, 28H), 3.25-2.72 (m, 8H), 2.45 (t, J=7.5 Hz, 2H), 2.36-1.96 (m, 18H), 1.81-1.51 (m, 12H), 1.45-1.32 (m, 15H), 1.12-0.89 (m, 12H) ppm.

Table 2B and Table 2B-1 summarize the results for the Linker-Payloads: HPLC purity and LC retention time on HPLC, M/Z from mess spectra. The analytical HPLC and MS methods are described in General procedures.

TABLE 2B

Chemical-physical properties of Linker-Payloads

| LP | Ex | cLogP | MF | MW | HPLC purity (%) | HPLC RT (min)[1] | MS (m/z) 100% | Highest m/z peak |
|---|---|---|---|---|---|---|---|---|
| 1a | 17 | 5.07 | $C_{116}H_{177}N_{17}O_{28}$ | 2257.74 | 95 | 6.89 | 753.3 (M/3 + H) | 1029.3 (M/2 + H) (30%) |
| 1c | 18 | 2.75 | $C_{117}H_{178}N_{18}O_{30}S$ | 2348.83 | 100 | 7.17 | 783.7 (M/3 + H) | 1174.7 (M/2 + H) (20%) |
| 1e | 19 | 2.98 | $C_{103}H_{144}F_2N_{14}O_{28}S$ | 2096.38 | 98 | 5.88 | 699.6 (M/3 + H) | 1049.0 (M/2 + H) (67%) |

TABLE 2B-continued

Chemical-physical properties of Linker-Payloads

| LP | Ex | cLogP | MF | MW | HPLC purity (%) | HPLC RT (min)[1] | MS (m/z) 100% | Highest m/z peak |
|---|---|---|---|---|---|---|---|---|
| 1f | 20 | −1.43 | $C_{100}H_{138}F_2N_{16}O_{28}S_2$ | 2114.38 | 97 | 6.82 | 1057.6 (M/2 + H) | 1057.6 (M/2 + H) |
| 1h | 21 | 1.94 | $C_{81}H_{106}F_2N_{10}O_{22}S$ | 1641.82 | 96 | 7.28 | 821.4 (M/2 + H) | 821.4 (M/2 + H) |
| 1i | 22 | 3.75 | $C_{109}H_{148}F_2N_{14}O_{29}S$ | 2188.48 | 100 | 7.62 | 1095.0 (M/2 + H) | 1095.0 (M/2 + H) |
| 1j | 23 | 3.15 | $C_{98}H_{135}F_2N_{11}O_{26}S$ | 1953.24 | 95 | 7.55 | 977.5 (M/2 + H) | 977.5 (M/2 + H) |
| 1k | 24 | 2.06 | $C_{101}H_{141}F_2N_{13}O_{27}S$ | 2039.33 | 100 | 5.97 | 1020.3 (M/2 + H) | 1020.3 (M/2 + H) |
| 1l | 25 | 2.22 | $C_{79}H_{103}F_2N_9O_{21}S$ | 1584.77 | 100 | 5.89 | 792.8 (M/2 + H) | 792.8 (M/2 + H) |
| 1m | 26 | 6.49 | $C_{101}H_{142}N_{12}O_{23}S$ | 1924.34 | 97 | 7.57 | 642.2 (M/3 + H) | 962.5 (M/2 + H) (70%) |
| 1q | 27 | 6.59 | $C_{115}H_{160}N_{16}O_{28}S$ | 2245.13 | 99 | 7.24 | 749.5 (M/3 + H) | 1123.8 (M/2 + H)⁺ |

[1]There might be COT-isomers.

TABLE 2B-1

Chemical-physical properties of Linker-Payloads

| LP | Ex | cLogP | MF | MW | HPLC purity (%) | HPLC RT (min)[1] | MS (m/z) 100% | Highest m/z peak |
|---|---|---|---|---|---|---|---|---|
| 1a | 17 | 2.75 | $C_{117}H_{178}N_{18}O_{30}S$ | 2348.83 | 100 | 7.17 | 783.7 (M/3 + H) | 1174.7 (M/2 + H) (20%) |
| Ib | 17A | 0.79 | $C_{120}H_{186}N_{19}O_{27}^+$ | 2326.87 | 91 | 8.08 | 776.0 (M/3 + H) | 776.0 (M/3 + H) |
| 1c | 18 | 5.07 | $C_{116}H_{177}N_{17}O_{28}$ | 2257.74 | 95 | 6.89 | 753.3 (M/3 + H) | 1029.3 (M/2 + H) (30%) |
| Id | 18A | 3.50 | $C_{116}H_{178}N_{17}O_{30}P$ | 2321.72 | 95 | 5.56, 5.64 | 774.7 (M/3 + H) | 774.7 (M/3 + H) |
| Ie-1 | 18B | 3.58 | $C_{110}H_{163}N_{17}O_{27}$ | 2155.57 | 100 | 7.34 | 1078.3 [M/2 + H] | 2156.9 [M + H] (10%) |
| If-1 | 18C | 0.98 | $C_{95}H_{150}N_{16}O_{27}$ | 1948.3 | 100 | 7.19 (A) | 974.7 [M/2 + H] | 1971.8 [M + Na] (20%) |
| Ig | 18D | 0.68 | $C_{99}H_{148}N_{14}O_{26}$ | 1950.31 | 97 | 7.58 | 650.8 [M/3 + H] | 975.8 [M/2 + H] (40%) |
| Ih-1 | 18E | −1.92 | $C_{84}H_{135}N_{13}O_{26}$ | 1743.04 | >97 | 6.09 (A) | 1742.7 [M + H] | 1764.8 [M + Na] (90%) |
| 1e | 19 | 2.98 | $C_{103}H_{144}F_2N_{14}O_{28}S$ | 2096.38 | 98 | 5.88 | 699.6 (M/3 + H) | 1049.0 (M/2 + H) (67%) |
| IIb | 19A | −0.18 | $C_{106}H_{152}F_2N_{15}O_{25}^+$ | 2074.42 | 96 | 8.36 | 1037.6 (M/2 + H) | 692.2 (M/3 + H) |
| 1f | 20 | −1.43 | $C_{100}H_{138}F_2N_{16}O_{28}S_2$ | 2114.38 | 97 | 6.82 | 1057.6 (M/2 + H) | 1057.6 (M/2 + H) |
| 1h | 21 | 1.94 | $C_{81}H_{106}F_2N_{10}O_{22}S$ | 1641.82 | 96 | 7.28 | 821.4 (M/2 + H) | 821.4 (M/2 + H) |
| 1i | 22 | 3.75 | $C_{109}H_{148}F_2N_{14}O_{29}S$ | 2188.48 | 100 | 7.62 | 1095.0 (M/2 + H) | 1095.0 (M/2 + H) |
| 1j | 23 | 3.15 | $C_{98}H_{135}F_2N_{11}O_{26}S$ | 1953.24 | 95 | 7.55 | 977.5 (M/2 + H) | 977.5 (M/2 + H) |
| 1k | 24 | 2.06 | $C_{101}H_{141}F_2N_{13}O_{27}S$ | 2039.33 | 100 | 5.97 | 1020.3 (M/2 + H) | 1020.3 (M/2 + H) |
| IIId | 24A | 0.94 | $C_{103}H_{155}F_2N_{14}O_{26}^+$ | 2043.41 | 96 | 6.86 (A) | 681.7 (M/3 + H) | 1021.7 (M/2 + H) (33%) |
| IIIe | 24B | 1.55 | $C_{104}H_{155}F_2N_{14}O_{26}^+$ | 2055.42 | 100 | 7.15 (A) | 685.7 (M/3 + H) | 685.7 (M/3 + H) |
| 1l | 25 | 2.22 | $C_{79}H_{103}F_2N_9O_{21}S$ | 1584.77 | 100 | 5.89 | 792.8 (M/2 + H) | 792.8 (M/2 + H) |

TABLE 2B-1-continued

Chemical-physical properties of Linker-Payloads

| LP | Ex | cLogP | MF | MW | HPLC purity (%) | HPLC RT (min)[1] | MS (m/z) 100% | Highest m/z peak |
|---|---|---|---|---|---|---|---|---|
| 1m | 26 | 6.49 | $C_{101}H_{142}N_{12}O_{23}S$ | 1924.34 | 97 | 7.57 | 642.2 (M/3 + H) | 962.5 (M/2 + H) (70%) |
| IVb | 26A | 3.78 | $C_{95}H_{149}N_{12}O_{20}^+$ | 1779.27 | 92 | 6.20 (A) | 593.7 (M/3 + H) | 889.8 (M/2 + H) |
| 1q | 27 | 6.59 | $C_{115}H_{160}N_{16}O_{28}S$ | 2245.13 | 99 | 7.24 | 749.5 (M/3 + H) | 1123.8 (M/2 + H)$^+$ |
| 10a | 10A | 4.39 | $C_{74}H_{94}F_2N_8O_{17}$ | 1405.58 | 100 | 7.40 | 703.5 (M/2 + H) | 1405.7 (M + H) (5%) |
| 10b | 10B | 9.10 | $C_{72}H_{92}N_6O_{12}$ | 1233.53 | 100 | 9.21 | 617.3 (M/2 + H) | 1233.6 (M + H) (80%) |
| 10c | 10C | 6.25 | $C_{80}H_{98}F_2N_8O_{18}$ | 1497.67 | 100 | 7.99 | 749.5 (M/2 + H) | 1497.7 (M + H) (5%) |
| 10d | 10D | 5.37 | $C_{88}H_{128}N_{12}O_{19}$ | 1658.03 | >95 | 8.25 | 829.7 (M/2 + H) | 1659.7 (M + H) (20%) |

[1]There might be two regioisomers.

Example 28

This Example illustrates the activity of anti-MSR1 antibody steroid non-cytotoxic ADCs comprising an SO$_3$H moiety, in an in vitro lipopolysaccharide (LPS) mediated IL-1β release assay For the assay, THP-1 cells were seeded onto 96 well plates at 40,000 cells/well in media containing RPMI supplemented with 10% FBS and pencillin/streptomycinin, and were differentiated with 200 nM Phorbol Myristate Acetate (PMA) for 3 days. After the 3 day differentiation, three-fold serial dilutions of the antibody drug conjugates and unconjugated antibody fresh media were added to the cells at final concentration ranging from 100 nM to 0.01 nM. The last well was left as blank control containing only the media. Seventy-two hours later, cells were treated with 5 µg/mL of LPS (InVivoGen, Cat #tlrl-eklps) for 5 hours. The cell media was then collected and the IL-1f3 was measured using a V-PLEX Proinflammatory Panel 1 human kit (Meso Scale Diagnostics, Cat #15049D-2) as per manufacturer's instructions. Subsequently, the plate was read on a MSD plate reader (Meso Scale Discovery). The IC$_{50}$ values were determined from a four-parameter logistic equation over a 10-point response curve (GraphPad Prism). All IC$_{50}$ values are expressed in molar (M) concentration.

As shown in Table 1A, H1H21234N-N297Q conjugated with the steroid linker payload without SO$_3$H moiety (H1H21234N-N297Q-Example 10A) demonstrated inhibition of LPS mediated IL-1β release from THP1 cells with an IC$_{50}$ value of 1.73 nM and having a reduction of IL-1β released down to 97.2 µg/mL. H1H21234N-N297Q conjugated with the steroid linker payload with a SO$_3$H moiety (H1H21234N-N297Q-Example 19) demonstrated similar inhibition of LPS mediated IL-1β release from THP1 cells with an IC$_{50}$ value of 1.97 nM and having a reduction of IL-1β released down to 97.17 µg/mL. The unconjugated antibody demonstrated inhibition of LPS mediated IL-1β release from THP1 cells with an IC$_{50}$ value of 22.9 nM and having a reduction of IL-1β released down to 343.7 µg/mL showing the lack of efficacy compared to the conjugated antibodies.

TABLE 1A

Activity of anti-MSR1 Ab-steroid ncADCs on LPS-induced IL-1β release from THP1 cells

| Payload Type | Linker Modification | ncADC | 72 hour IC$_{50}$ (M) | IL1beta released at max concentration tested (pg/mL) |
|---|---|---|---|---|
| Steroid | N/A | H1H21234N-N297Q-Example 10A | 1.73E– | 97.24 |
|  | SO$_3$H | H1H21234N-N297Q-Example 19 | 1.97E– | 97.17 |
| N/A | N/A | H1H21234N-N297Q | 2.29E– | 343.7 | pH Stability pH stability was assessed as follows. 0.1 mg of sample was dissolved into 0.2-0.3 mL of DMSO, and the resulting solution was added dropwise into different pH buffers (1 mL) while maintain clear solutions during testing time period. The samples were collected from several time points (e.g., over 72 hours), and pH stability was determined by LC-MS. pH buffer was prepared as follows: pH 8.0 sodium borate buffer: Add 9.534 g Sodium borate decahydrate, 1.461 g Sodium chloride, and 0.393 g DTPA to 900 mL distilled water, make sure all powers dissolve completely, then make final volume to 1 L by adding water. pH 7.4 sodium borate buffer: Add 900 ml Milli-Q water, 9.534 g Sodium borate decahydrate, 1.461 g Sodium chloride, and 0.393 g DTPA to 900 mL distilled water, make sure all powers dissolve completely, then make final volume to 1 L by adding water. pH 5.0 succinate acid buffer: Add 10 mM succinate acid to 150 mL distilled water, and then change the pH to pH5.0 by adding 0.5M NaOH, then make final volume to 250 mL by adding water. pH 7.4 PBS buffer: commercially available. Stability was assessed at 72 hours by LCMS.

Solubility

Procedure for the solubility test: Dissolve 1 mg of testing sample into 1 mL DMSO, and prepare standard solutions A (4.5 mL, 100 µg/mL), B (4.5 mL, 10 µg/mL), C (4.5 mL, 1 µg/mL), D (5 mL, 0.1 µg/mL).

| Standard solution | Sample amount (mg) | DMSO (%) | Total volume (mL) | Conc (mg/mL) |
|---|---|---|---|---|
| DMSO | 1 | 100% | 1 | 1 |
| A | 0.5 | 10% | 5 | 0.1 |
| B | 0.05 | 1% | 5 | 0.01 |
| C | 0.005 | 0.10% | 5 | 0.001 |
| D | 0.0005 | 0.01% | 5 | 0.0001 |

The DMSO solution (1 mg/mL, 0.5 mL) was diluted with water (4.5 mL) to generate solution A (0.1 mg/mL, 5 mL, 0.5 mg). Solution A (0.1 mg/mL, 0.5 mL) was diluted with water (4.5 mL) to generate solution B (0.01 mg/mL, 5 mL, 0.05 mg). Solution B (0.01 mg/mL, 0.5 mL) was diluted with water (4.5 mL) to generate solution C (1 µg/mL, 5 mL, 5 µg). Solution C (1 µg/mL, 0.5 mL) was diluted with water (4.5 mL) to generate solution D (0.1 µg/mL, 5 mL, 0.5 µg). The testing sample (0.05 mg) was suspended in water (1 mL), and was sonicated for 5-30 min to dissolve the sample. 1f no clear solution was observed, the resulting suspension was centrifuged and the clear supernatant solution was collected for analysis. All the standard solutions A, B, C, D and sample solutions were tested using same method on the same LC-MS instrument. Solubility was assessed by LCMS and calculated based on a standard curve. Table 3 and Table 3-1 show data from these experiments.

TABLE 3 pH stability, solubility data for linker-payloads

| LP | Ex | Payload | cLogP | cLogD (pH 5.07) | Solubility (mg/mL) | pH Stability |
|---|---|---|---|---|---|---|
| 1e | 19 | B | 2.98 | 0.61 | >10 | Y |
| 1j | 23 | C | 3.15 | 1.97 | >10 | Y |
| 1k | 24 | C | 2.06 | 0.88 | >1 | Y |

Y: stable in pH7.4 or 8 buffer at room temperature for more than 3 days;

TABLE 3-1 pH stability, solubility data for linker-payloads

| LP | Ex | Payload | cLogP | cLogD (pH 5.07) | Solubility (mg/mL) | pH Stability |
|---|---|---|---|---|---|---|
| 10d | 10D | A | 5.37 | 5.37 | <0.1 | Y |
| 1a | 17 | A | 2.75 | 1.58 | 0.17 | Y |
| 1c | 19 | A | 5.07 | 5.07 | 0.16 | |
| Id | 18A | A | 3.50 | 1.23 | 0.25 | Y |
| Ie-1 | 18B | A | 3.58 | 3.58 | 0.4 | Y |
| Ig | 18D | A | 0.68 | 0.68 | 0.28 | Y |
| Ih-1 | 18E | A | -1.92 | -1.92 | 0.5 | |
| 10a | 10A | B | 4.39 | 4.39 | 0.02 | Y |
| 1e | 19 | B | 2.98 | 0.61 | >10 | Y |
| 10c | 10C | C | 6.25 | 6.25 | <0.1 | Y |
| 1i | 22 | C | 3.75 | 2.46 | >10 | |
| 1j | 23 | C | 3.15 | 1.97 | >10 | Y |
| 1k | 24 | C | 2.06 | 0.88 | >1 | Y |
| IIIe | 24B | C | 2.22 | -0.16 | >10 | Y |
| 10d | 10D | D | 9.10 | 9.10 | <0.1 | Y |
| 1q | 27 | E | 6.59 | 4.22 | 0.17 | Y |

Y: stable in pH7.4 and 8 buffer at RT for more than 3 days

Example 29

Figure 19:
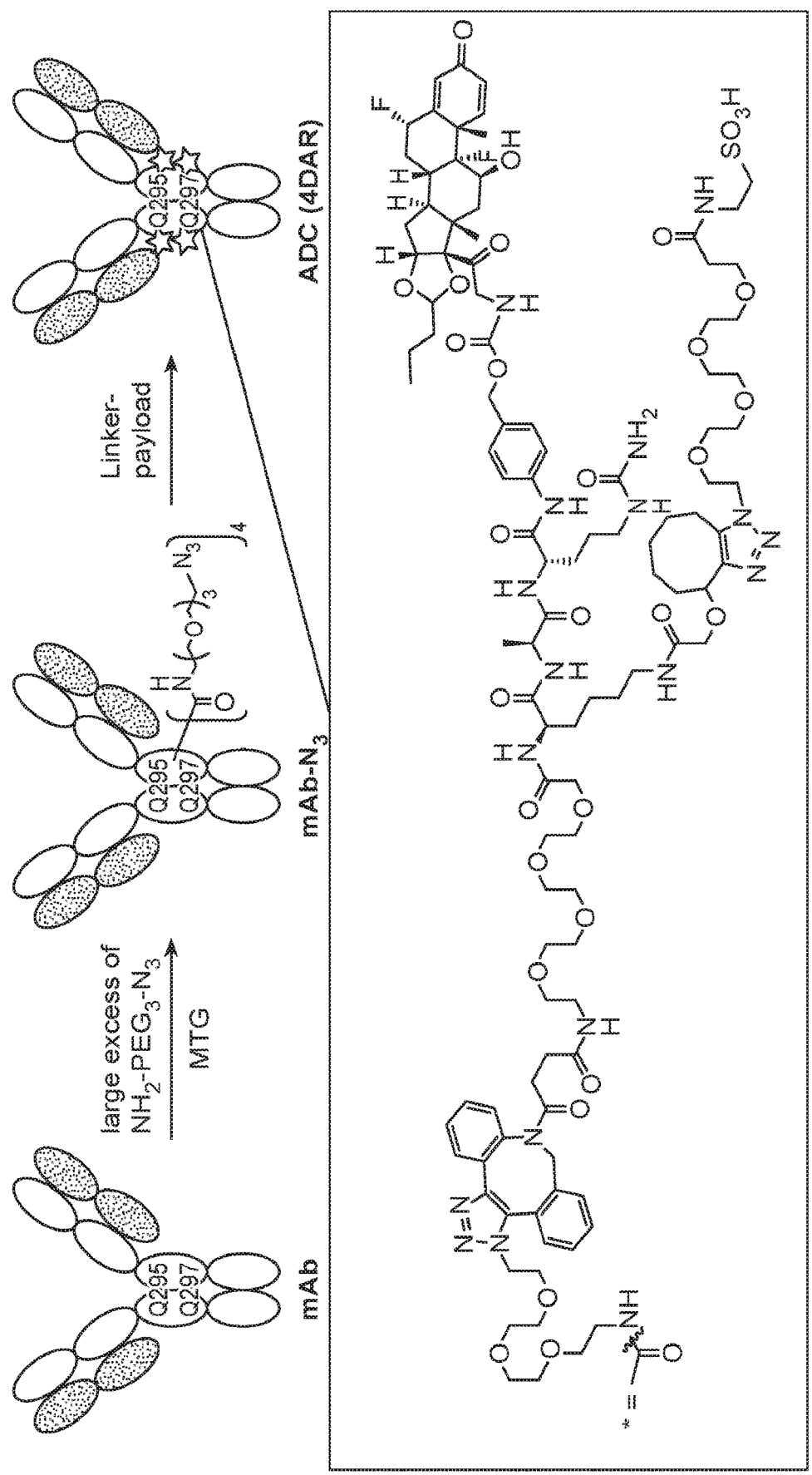
FIG. 19 shows an example of a general synthetic procedure for antibody drug conjugations.

ADC Conjugations (See FIG. 19)

This example demonstrates a method for site-specific conjugation, generally, of a payload to an antibody or antigen-binding fragment thereof.

The following example demonstrates a method for making the conjugates. Aglycosylated antibody with a human IgG1 isotype in BupH™ (pH 7-8) was mixed with 200 molar equivalents of azido-dPEG$_3$-amine (MW. 218.26 g/mol). The resulting solution was mixed with transglutaminase (25 U/mL; 5U MTG per mg of antibody) resulting in a final concentration of the antibody at 0.5-10 mg/mL, and the solution was then incubated at 37° C. for 4-24 hours while gently shaking. The reaction was monitored by SDS-PAGE or ESI-MS. Upon the completion, the excess amine and MTG were removed by Size Exclusion Chromatography (SEC) to generate the azido-functionalized antibody (mAb-N$_3$). This product was analyzed on SDS-PAGE and ESI-MS. The azido-dPEG$_3$-amine added to two sites —Q295 and Q297-of the antibody resulting in an 804 Da increase for the 4DAR aglycosylated antibody-PEG$_3$-azide conjugate. The conjugation sites were identified and confirmed at EEQ$^{Link}_{er}$YQ$^{Linker}$STYR for the 4DAR azido-functionalized antibody via peptide sequence mapping of trypsin digested heavy chains.

The site-specific aglycosylated antibody drug conjugates (ADCs) with a human IgG1 or IgG4 generated against MSR1, HER2 (or PRLR) and containing an N297Q mutation were prepared by a [2+3] click reaction between the azido-functionalized antibody (mAb-N$_3$) with an alkyne containing linker-payload (LP). FelD1 is a non-binding control antibody.

As shown in Table 5, the site-specific aglycosylated antibodies containing an N297Q mutation were conjugated with amine-PEG$_3$-N$_3$ to generate the azido-functionalized antibody conjugates (mAb-N$_3$), including anti MSR1 Ab-PEG$_3$-N$_3$, anti Fel D1 Ab-PEG$_3$-N$_3$, anti HER2 Ab-PEG$_3$-N$_3$, anti PRLR Ab-PEG$_3$-N$_3$.

A site-specific antibody conjugate with linker-payload (LP) was prepared by incubating mAb-PEG$_3$-N$_3$ (1-12 mg/mL) in an aqueous medium (e.g., PBS, PBS containing 5% glycerol, HBS) with ≥6 molar equivalents of an LP dissolved in a suitable organic solvent, such as DMSO, DMF or DMA (i.e., the reaction mixture contains 5-20% organic solvent, v/v) at 24° C. to 37° C. for 30 min to 24 hr. The progress of the reaction was monitored by ESI-MS and the absence of mAb-PEG$_3$-N$_3$ indicated the completion of the conjugation. The excess amount of the LP and organic solvent were removed by SEC via elution with PBS, or via protein A column chromatography via elution with acidic buffer followed by neutralization with Tris (pH8.0). The purified conjugates were analyzed by SEC, SDS-PAGE, and ESI-MS. Shown in Table 5 is a list of the MMAE antibody conjugates, steroid antibody conjugates, and LXR agonist antibody conjugates from the corresponding LPs, their molecular weights and ESI-DAR values.

In a specific example, the azido-functionalized antibody (1 mg) in 0.800 mL PBSg (PBS, 5% glycerol, pH 7.4) was treated with six molar equivalents of of a linker payload (LP) from Table 2 (conc. 10 mg/mL in DMSO) for 2 hours at RT and the excess linker payload (LP) was removed by size exclusion chromatography (SEC, Superdex 200 HR, GE Healthcare). The final product was concentrated by ultracentrifugation and characterized by UV, SEC, SDS-PAGE and ESI-MS.

Characterization of ADC by LC-ESI-MS

Measurement of intact mass for the ADC samples by LC-ESI-MS was performed to determine drug-payload distribution profile and to calculate the average DAR. Each testing sample (20-50 ng, 5 μL) was loaded onto an Acquity UPLC Protein BEH C4 column (10K psi, 300 Å, 1.7 μm, 75 μm×100 mm; Cat No. 186003810). After 3 min desalting, the protein was eluted and mass spectra were acquired by a Waters Synapt G2-Si mass spectrometer. The MWs of the naked antibodies, the azido-functionalized antibody conjugates (mAb-$N_3$), the LPs, and the ADCs were listed in Table 5. As summarized in Table 5, most site-specific ADCs have 3.9-4DAR for the site specific conjugates.

TABLE 5

List of conjugates

| LP | Ex | MW (LP) | Ab, Ab-$N_3$, or ncADC | Target | MS m/z (ncADC) | DAR (ESI-MS) |
|---|---|---|---|---|---|---|
| 1q | 27 | 2246.7 | H1H21234N-EX 27 | MSR1 | 155570 | 3.9 |
| 1e | 19 | 2096.4 | H1H21234N-EX 19 | MSR1 | 154964 | 3.9 |
| 1q | 27 | 2246.2 | H1H1238N-N297Q-EX 27 | FelD1(isotype control) | 155245 | 4 |
| 1e | 19 | 2096.4 | H1H1238N-N297Q-Ex 19 | FelD1(isotype control) | 154641 | 3.9 |
| 1j | 23 | 1953.2 | H1H6958N2-N297Q -Ex 23 | Anti-PRLRmAb1 | 154070 | 4 |
| 1i | 22 | 2188.5 | H1H6958N2-N297Q -Ex 22 | Anti-PRLRmAb2 | 155011 | 3.9 |
| 1e | 19 | 2096.4 | H1H6958N2-N297Q -Ex 19 | Anti-PRLRmAb3 | 153792 | 4 |
| 1f | 20 | 2114.4 | H1H6958N2-N297Q -Ex 20 | Anti-PRLRmAb4 | 152301 | 3.7 |
| 1j | 23 | 1953.2 | H1H6958N2-N297Q -Ex 23 | Anti-PRLRmAb5 | 153227 | 3.9 |
| 1i | 22 | 2188.5 | H1H6958N2-N297Q -Ex 22 | Anti-PRLRmAb6 | 154168 | 3.9 |
| 1k | 24 | 2039.3 | H1H6958N2-N297Q-EX 24 | Anti-PRLRmAb7 | 153555 | 3.9 |
| 1c | 18 | 2348.9 | Anti-HER-N297Q-Ex 18 | HER2 | 155358 | 3.9 |
| 1q | 27 | 2246.7 | Anti-HER-N297Q-Ex 27 | HER2 | 154945 | 3.9 |

Example 30

This example demonstrates the effect on the cleavage efficiency for a steroid or LXR agonist payload when a $SO_3H$ moiety, $N^+Me_3$ moiety, phosphate moiety, or galactose moiety, present on a linker using a Cathepsin B cleavage assay.

For the assay, the linker-payload stock solution (10 mM of linker-payload in DMSO) was added into a solution of 100 mM NaOAc, 10 mM dithiothreitol, at pH5 to obtain a 50 μM substrate solution. Human liver Cathepsin B (Athens Research & Technology, Cat #16-12-030102) in 50 mM NaOAc, 1 mM EDTA, at pH 5, was added to the substrate solution. The Cathepsin B and substrate solution was mixed with and without 10 mM of a Cathepsin B inhibitor (CA074; APE Bio, Cat #A1926), and incubated at 37° C. for 4 hours. Following the 4 hour incubation, acetic acid and then acetonitrile were added to stop the reaction. The quenched samples then underwent centrifugation at 14,000 rpm. Aliquots of the resultant supernatants were then diluted with equal volume of water and analyzed by LC/MS to determine the amount of payload released. The stability and activity of Cathepsin B was confirmed by incubating with 200 μM fluorogenic substrate for Cathepsin B (Santa Cruz Biotechnology, Cat #207975) (fluorescence at excitation of 340 nm/emission of 425 nm).

As shown in Table 1B, the LXR agonist linker payload without the $SO_3H$ moiety had 13.6% of the free payload release when treated with Cathepsin B for 4 hours, whereas the LXR agonist linker payload with the $SO_3H$ moiety had 44.2% of the free payload release when treated with Cathepsin B for 4 hours. The steroid linker payload without the $SO_3H$ moiety had between 7.5-17.2% of the free payload released when treated with Cathepsin B for 4 hours, whereas the steroid linker payload with $SO_3H$ moiety had 79.6% of the free payload release when treated with Cathepsin B for 4 hours. Table 1C and Table 1D show additional data for free payload release when linker payloads are treated with Cathepsin B.

TABLE 1B

Amount of payload released from linker-payloads with and without $SO_3H$ moiety in a Cathepsin B assay (See FIG. 18)

| Payload | Payload Type | Linker-Payload (LP) | Linker Modification | Percent of payload released at 4 hrs |
|---|---|---|---|---|
| D | LXR Agonist | Ex 10B | N/A | 13.6% |
|   |   | Ex 26 | $SO_3H$ | 44.2% |
| B | Steroid | Ex 10A | N/A | 7.5-17.2% |
|   |   | Ex 19 | $SO_3H$ | 79.6% |

TABLE 1C

Amount of payload released from linker-payloads with different $SO_3H$ linkers in a Cathepsin B assay. (See FIG. 18)

| # | Ex | Payload | Cleaved piece | Linker | CapB cleavage rate (%) at 4 hrs |
|---|---|---|---|---|---|
| 1e | 19 | B | vcPAB | $PEG_4$-taurine | 79.6 |
| 1f | 20 | B | vcPAB | Dual taurine | 63.0 |
| 1i | 22 | C | vcPAB | $PEG_4$-taurine | 57.8 |
| 1j | 23 | C | VA | $PEG_4$-taurine | 30.8 |
| 1k | 24 | C | vc | $PEG_4$-taurine | 31.0 |
| 1m | 26 | D | VA | $PEG_4$-taurine | 44.2 |

TABLE 1D

% of Payload released from linker-payloads (FIG. 19) in a Cathepsin B assay.

| # | Ex | Payload | Cleaved piece | Linker | CapB cleavage rate (%) at 4 hrs |
|---|---|---|---|---|---|
| 10b | 10B | A | vcPAB | — | 63 |
| Ib | 17A | A | vcPAB | $PEG_4$-$N^+Me_3$ | 65 |
| Id | 18A | A | vcPAB | $PEG_5$-phosphate | 50 |
| Ie-1 | 18B | A | vcPAB | galactose | 72 |
| Ig | 18D | A | vcPAB | glucamide | 70 |

TABLE 1D-continued

% of Payload released from linker-payloads (FIG. 19) in a Cathepsin B assay.

| # | Ex | Payload | Cleaved piece | Linker linker | CapB cleavage rate (%) at 4 hrs |
|---|---|---|---|---|---|
| Ih-1 | 18E | A | vcPAB | glucamide | 42 |
| 10a | 10A | B | vcPAB | — | 18.6 |
| 1e | 19 | B | vcPAB | PEG$_4$-taurine | 79.6 |
| 1f | 20 | B | vcPAB | Dual taurine | 63.0 |
| 10c | 10C | C | vcPAB | — | <5 |
| 1i | 22 | C | vcPAB | PEG$_4$-taurine | 57.8 |
| 1j | 23 | C | VA | PEG$_4$-taurine | 30.8 |
| 1k | 24 | C | vc | PEG$_4$-taurine | 31.0 |
| 10b | 10B | D | VA | — | 13.6 |
| 1m | 26 | D | VA | PEG$_4$-taurine | 44.2 |
| 1q | 27 | E | vcPAB | PEG$_4$-taurine | 30.4 |

Example 31

This experiment demonstrates the effect on the cleavage efficiency of a steroid payload when a hydrophilic linker is present in an anti-MSR1 antibody steroid non-cytotoxic ADC (ncADC), by measuring lysosomal cleavage over time.

For the assay, The ncADCs were added to a freshly prepared lysosome working solution containing 1× catabolic buffer (Xenotech Cat #K5200) and 0.125 mg/mL human liver lysosome proteins (Xenotech Cat #H0610.L). 200 µL of the resulting mixture, which contains 0.25 µM ncADC, was incubated at 37° C. with gentle shaking over a 24-hour period. 20 µL aliquots were taken at 0, 0.5, 1.0, 2.0, 4.0, 8.0 and 24 hours and then transferred to a plate containing 80 µL cold acetonitrile to deactivate the lysosome and precipitate the proteins. After the centrifugation at 2,000 rpm for 5 minutes, aliquots of the supernatant were diluted with an equal volume of water before subjecting to analysis by LC-MS to determine the amount of payload release.

As shown in Table 1E, ncADC steroid conjugate without the hydrophilic linker (H1H21234N-N297Q-Example 10A) released 548 nM steroid at the 24-hour time point. The ncADC steroid conjugate with the hydrophilic linker (H1H21234N-N297Q-Example 19) released 760 nM at 24-hour time point.

TABLE 1E

Amount of steroid released with and without hydrophilic linker

| ncADC | Payload | Payload Type | Linker Modification | Released Payload Concentration (nM) | | | | | | |
|---|---|---|---|---|---|---|---|---|---|---|
| | | | | 0 hour | 0.5 hour | 1.0 hour | 2.0 hour | 4.0 hour | 8.0 hour | 24 hour |
| H1H21234 N-N297Q- Example 10A | B | Steroid | N/A | 0 | 43.1 | 105 | 265 | 628 | 719 | 548 |
| H1H21234 N-N297Q- Example 19 | B | Steroid | SO$_3$H | 12.6 | 13.8 | 40.4 | 175 | 680 | 961 | 760 |

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A compound, pharmaceutically acceptable salt, stereoisomer, regioisomer, or a mixture of regioisomers thereof of Formula (Va), (Vb), (Vc) or (Vd) respectively:

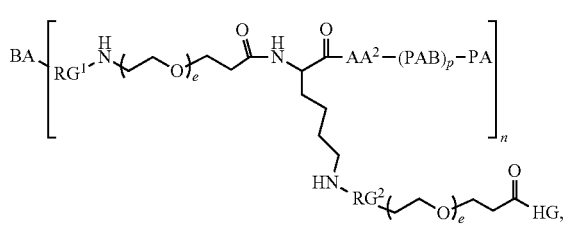

(Va)

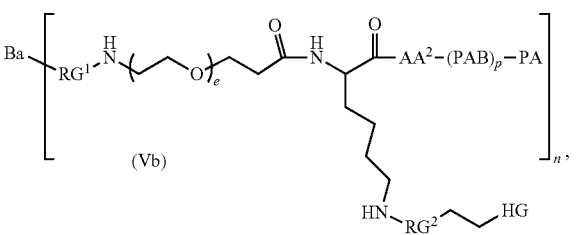

(Vb)

(Vc)

or

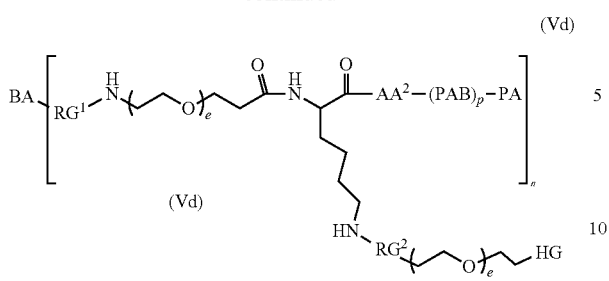

(Vd)

wherein:

BA is an antibody or antigen binding fragment thereof;

RG¹ and RG² are independently a reactive group residue selected from the group consisting of

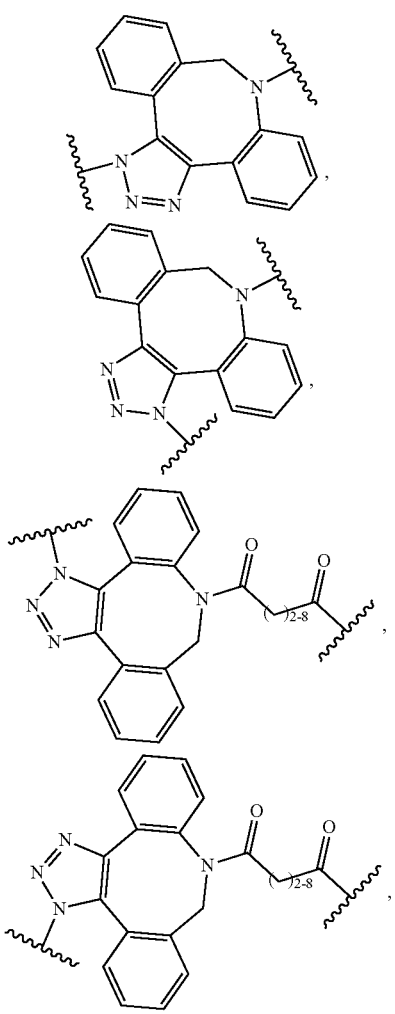

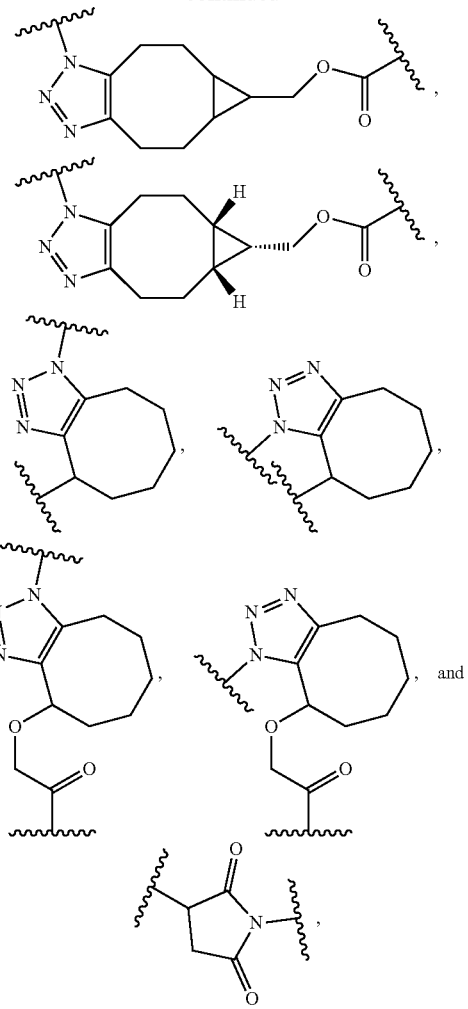

wherein the

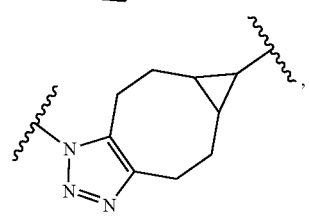

indicates the atom through which the RG¹ or RG² is bonded to the adjacent groups in the formula;

PA is a payload residue;

AA² is a dipeptide, tripeptide, or tetrapeptide residue comprising amino acid residues selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, and citrulline;

PAB is wherein the

indicates the atom through which the PAB is bonded to the adjacent groups in the formula;

subscript e is an integer from 0 to 6;
subscript n is an integer from 1 to 30;
subscript p is 0 or 1;
subscript q is 0 or 1; and
HG is selected from the following:

(a)

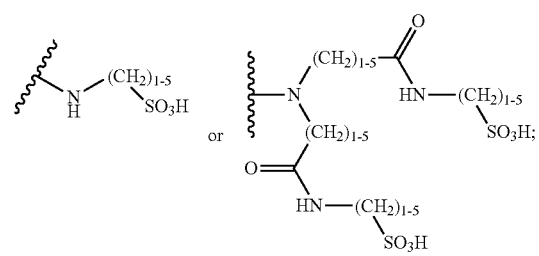 [SMILES: *NCS(=O)(=O)O ; *N(CC(=O)NCS(=O)(=O)O)CC(=O)NCS(=O)(=O)O]

(b)

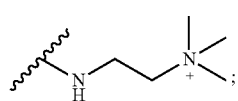

(c)

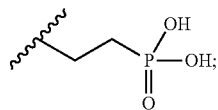 [SMILES: *CCP(=O)(O)O]

or (d)

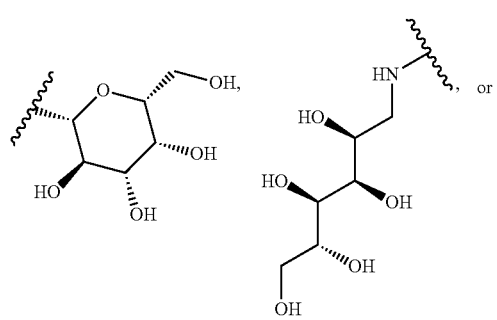

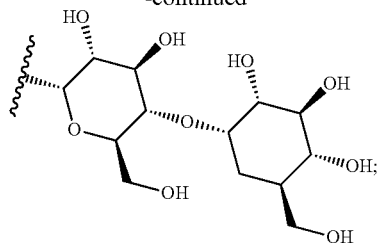

wherein the

indicates the atom through which the HG is bonded to the adjacent groups in the formula.

2. The compound of claim 1, wherein subscript n is 1, 2, 3 or 4.

3. The compound of claim 1, wherein $RG^1$ and $RG^2$ are independently, in each instance, selected from the group consisting of

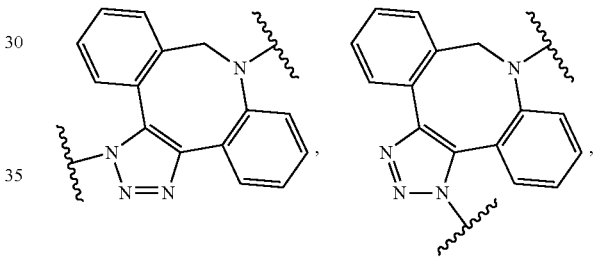

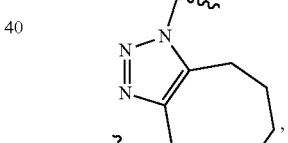

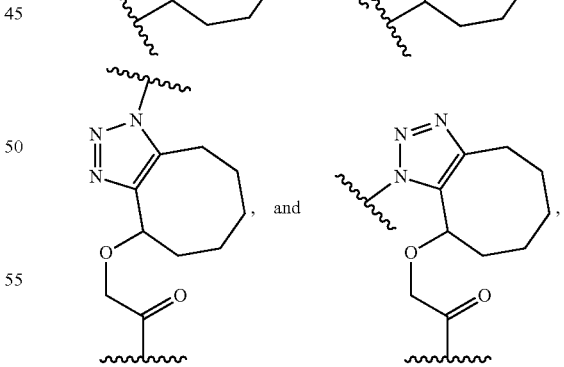

wherein the

indicates the atom through which the RG¹ or RG² is bonded to the adjacent groups in the formula.

4. The compound of claim 1, wherein HG is

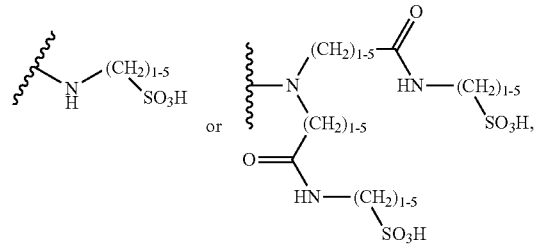 [SMILES: *NCS(=O)(=O)O ; *N(CC(=O)NCS(=O)(=O)O)CC(=O)NCS(=O)(=O)O]

wherein the

indicates the atom through which the HG is bonded to the adjacent groups in the formula.

5. The compound of claim 1, wherein HG is

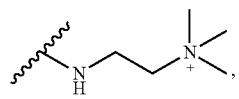

wherein the

indicates the atom through which the HG is bonded to the adjacent groups in the formula.

6. The compound of claim 1, wherein HG is

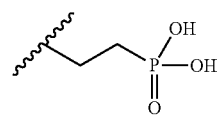 [SMILES: *CCP(=O)(O)O]

wherein the

indicates the atom through which the HG is bonded to the adjacent groups in the formula.

7. The compound of claim 1, wherein HG is

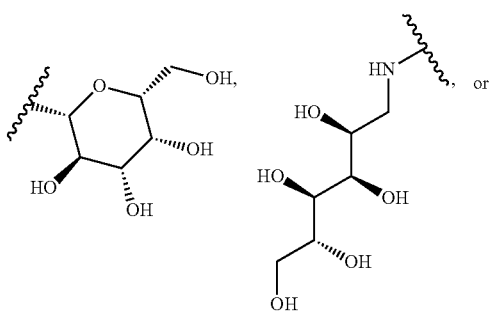

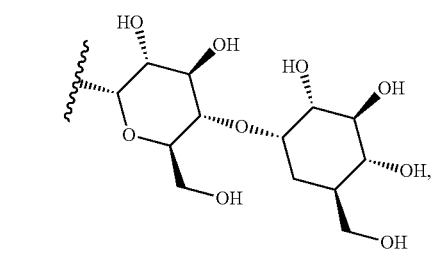

wherein the

indicates the atom through which the HG is bonded to the adjacent groups in the formula.

8. The compound of claim 1, having a structure selected from the group consisting of:

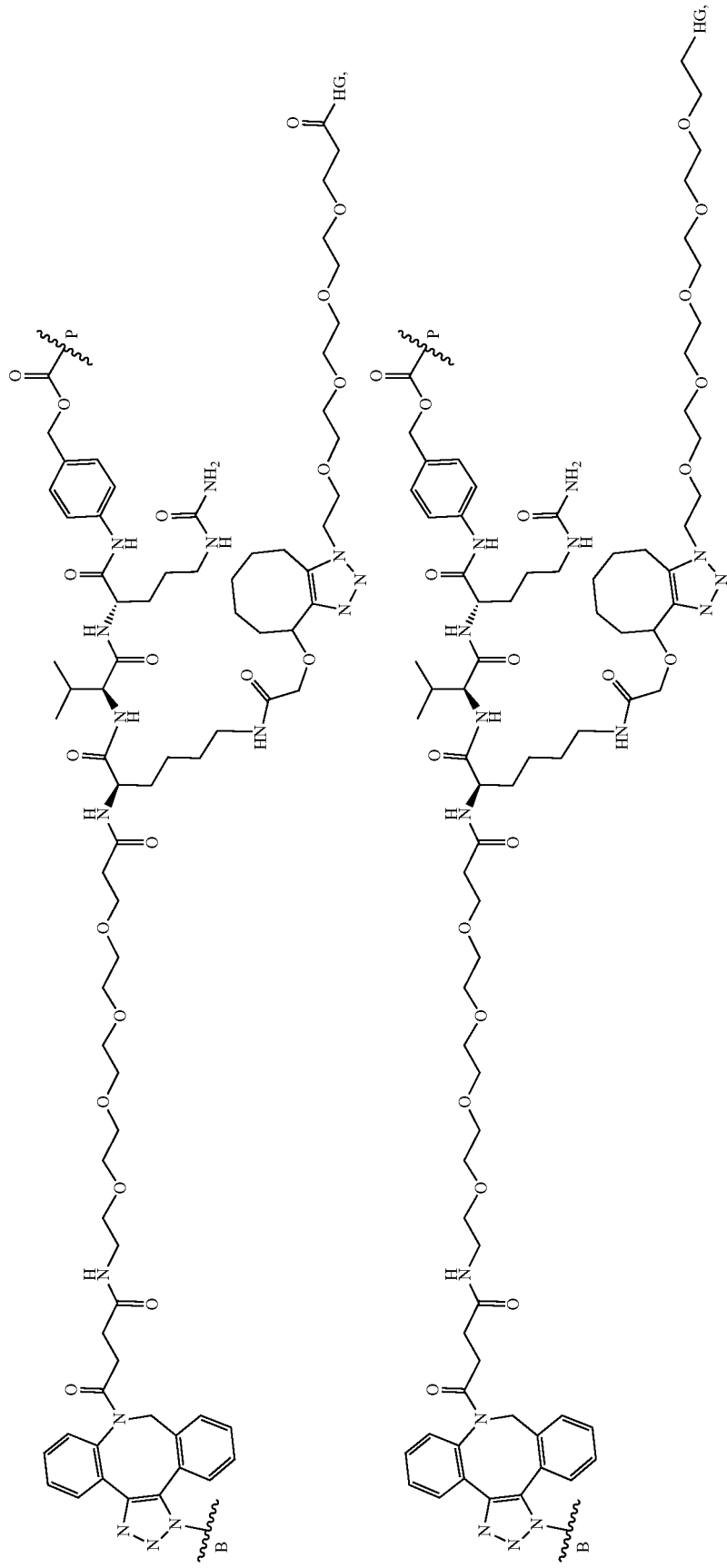
1015 1016

1017
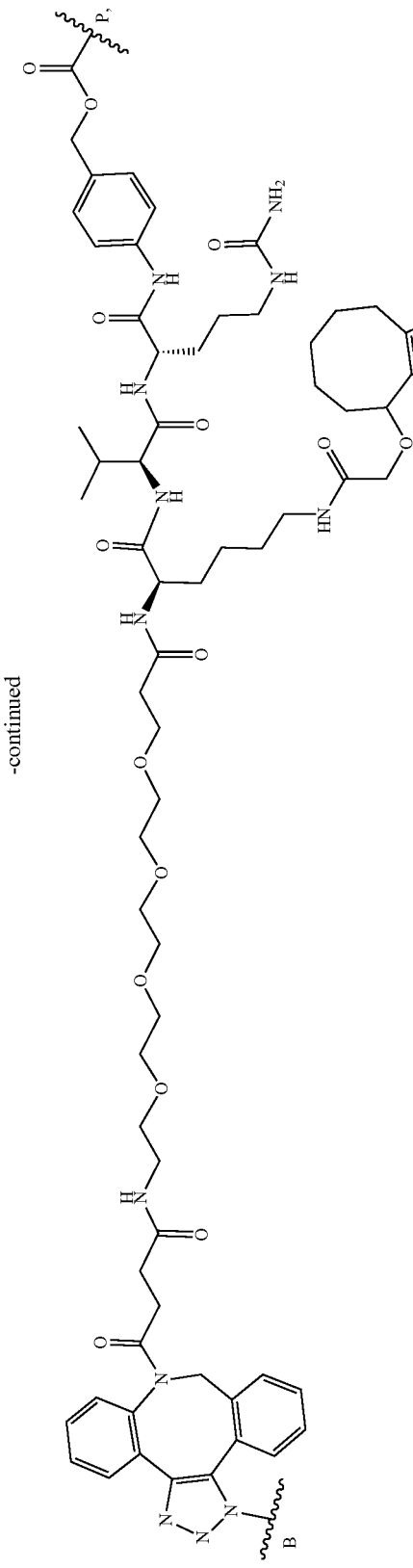
1018
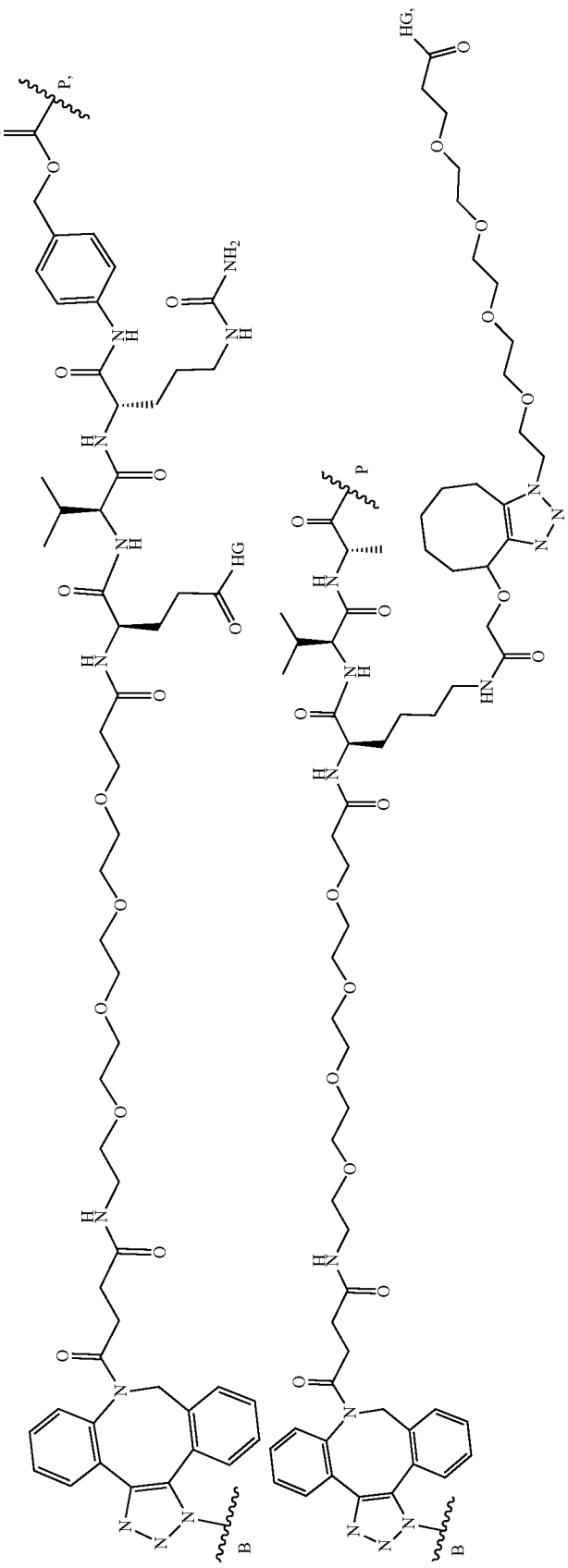

1019
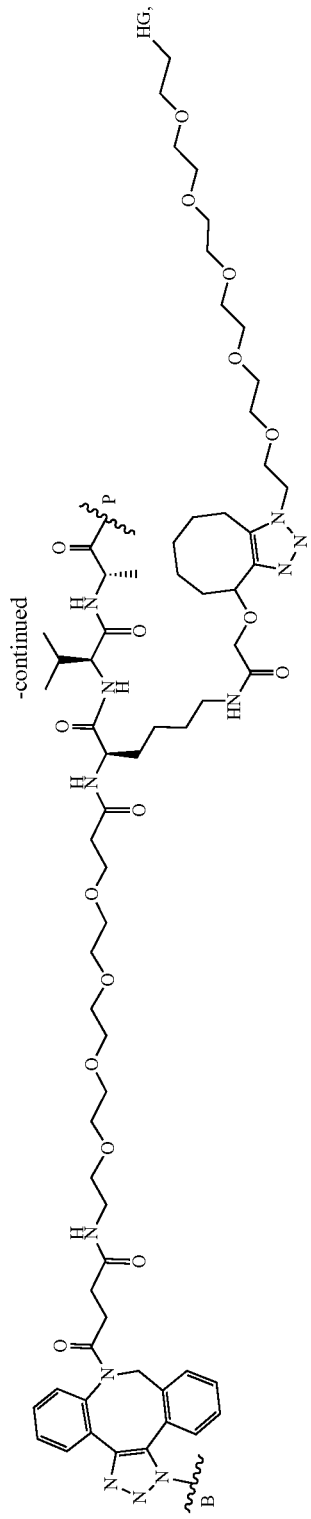
1020
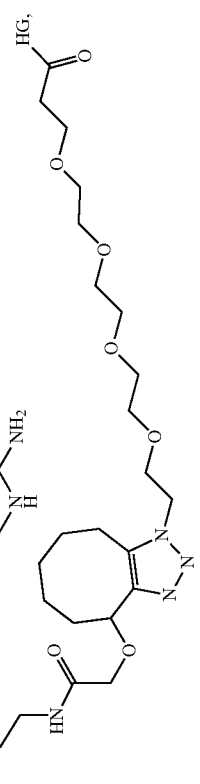
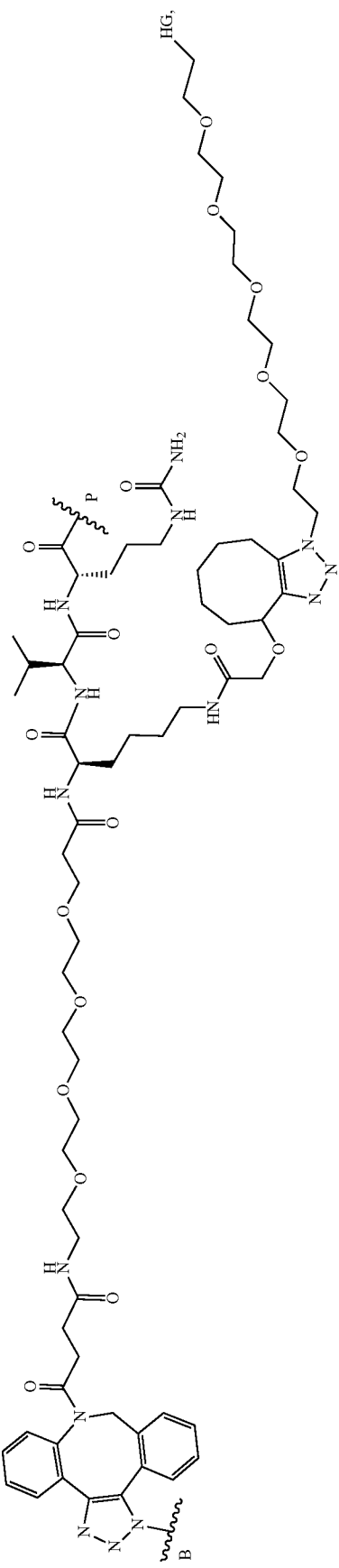

1021 1022
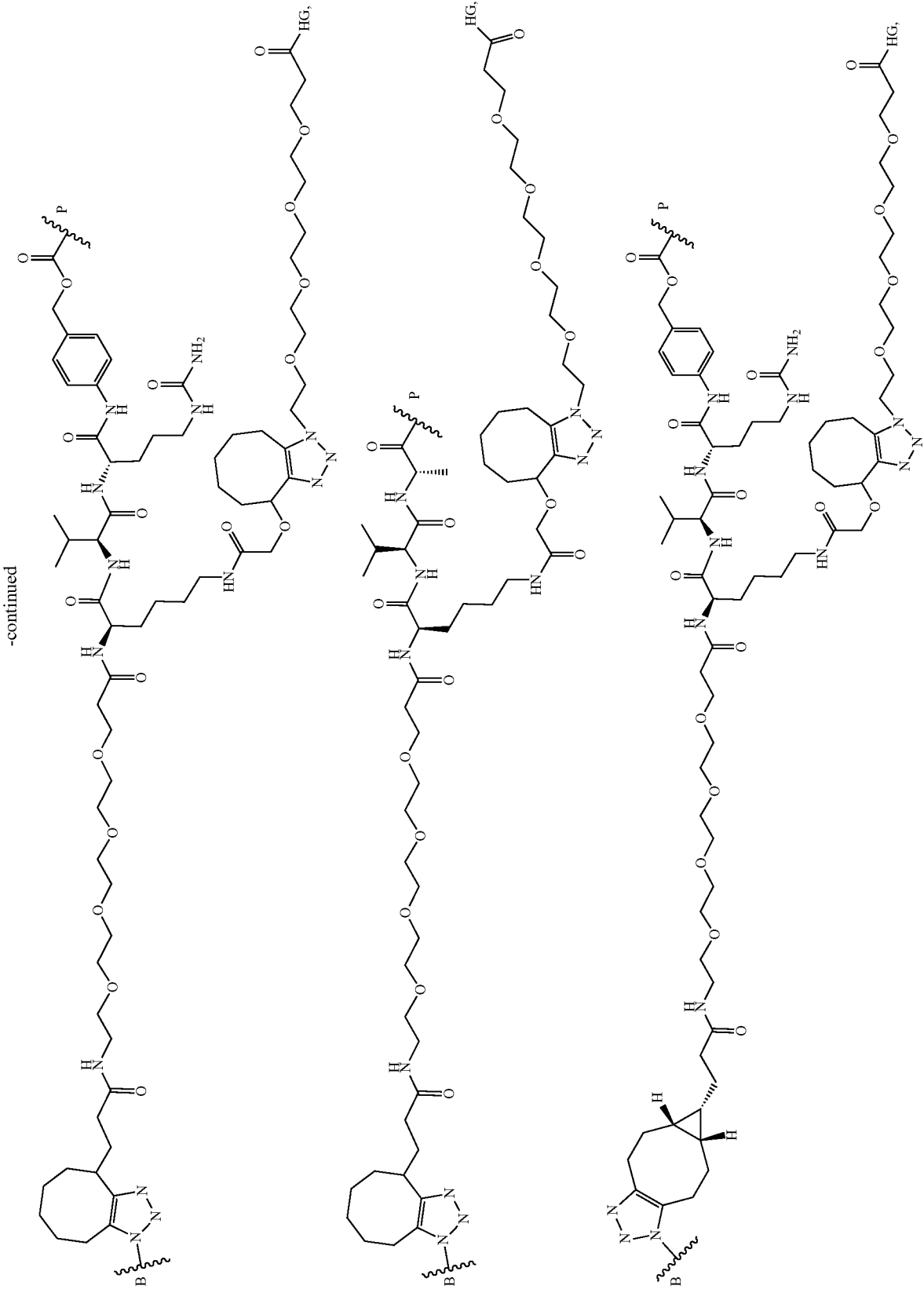

1023 1024
-continued
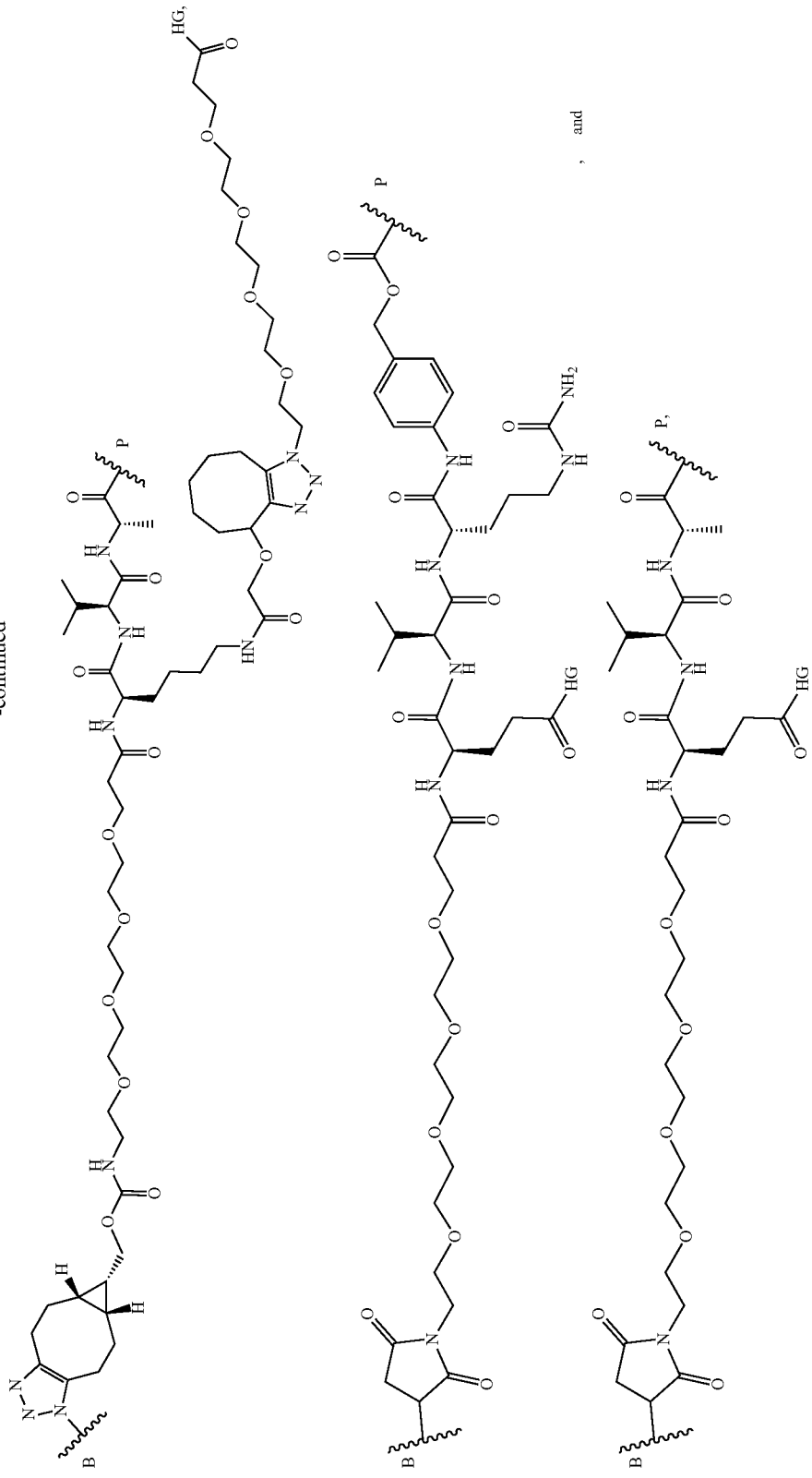
, and or a stereoisomeric form thereof, or a regioisomer thereof, or a mixture of regioisomers thereof, wherein each
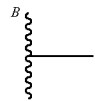
is a bond to the antibody or antigen binding fragment thereof; and
each
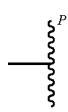
is a bond to the payload residue.
9. The compound of claim 1, having a structure selected from the group consisting of:

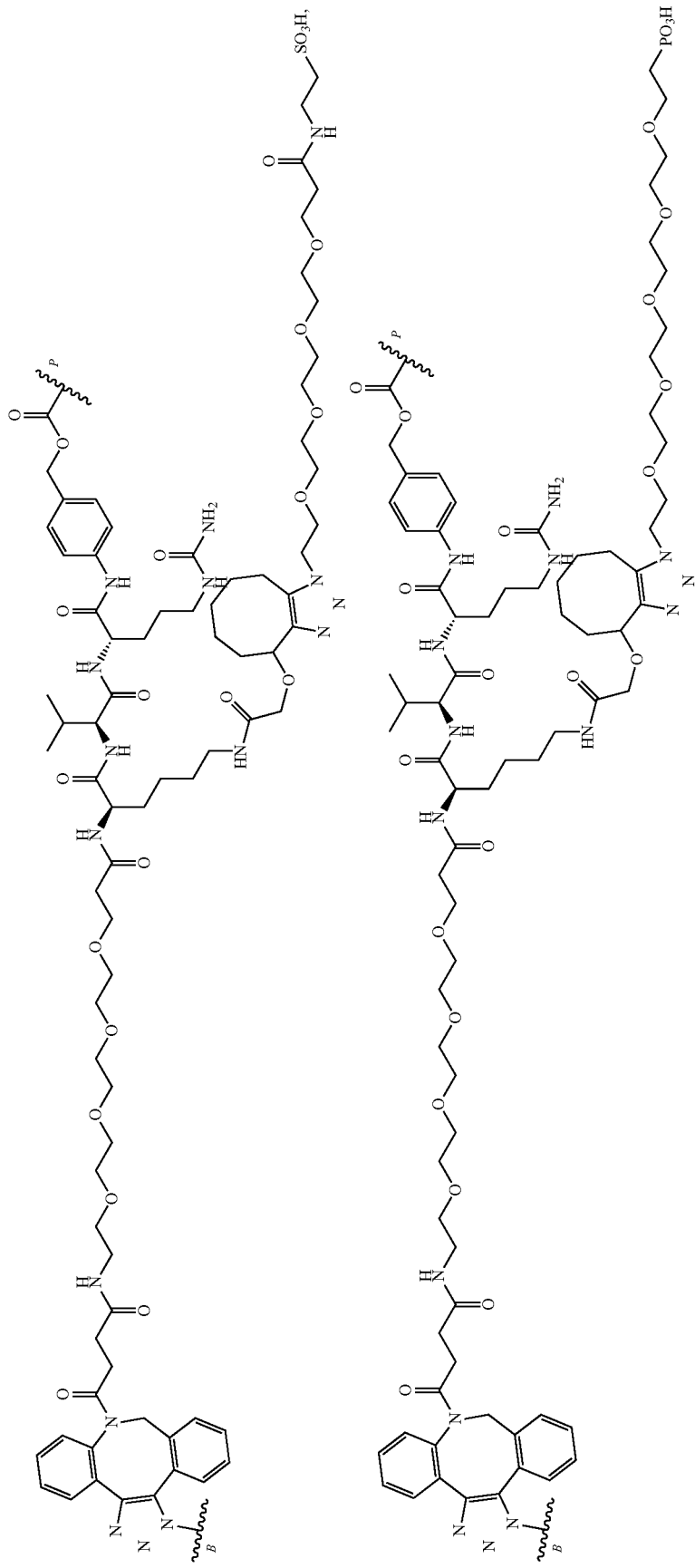

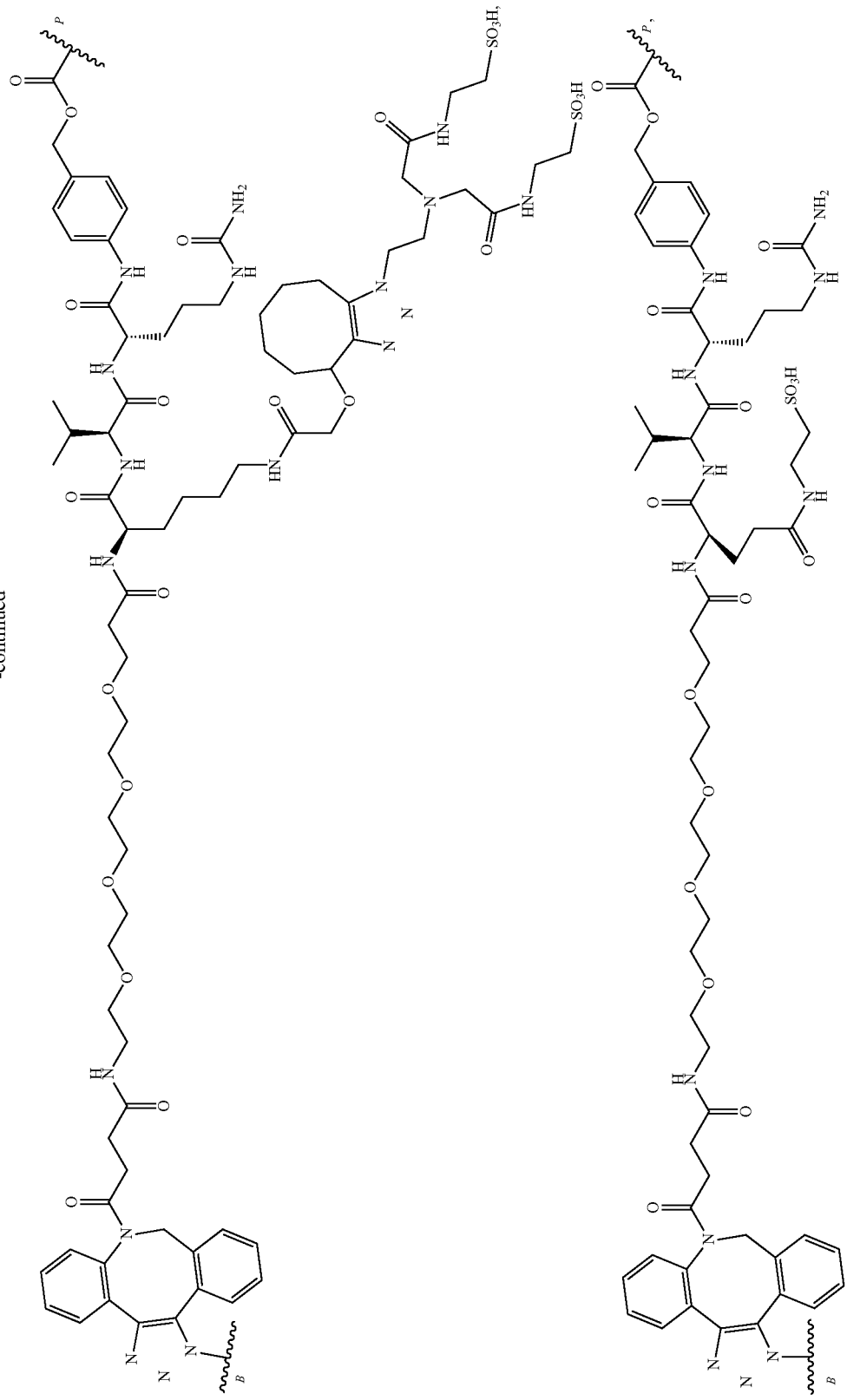

1031 1032
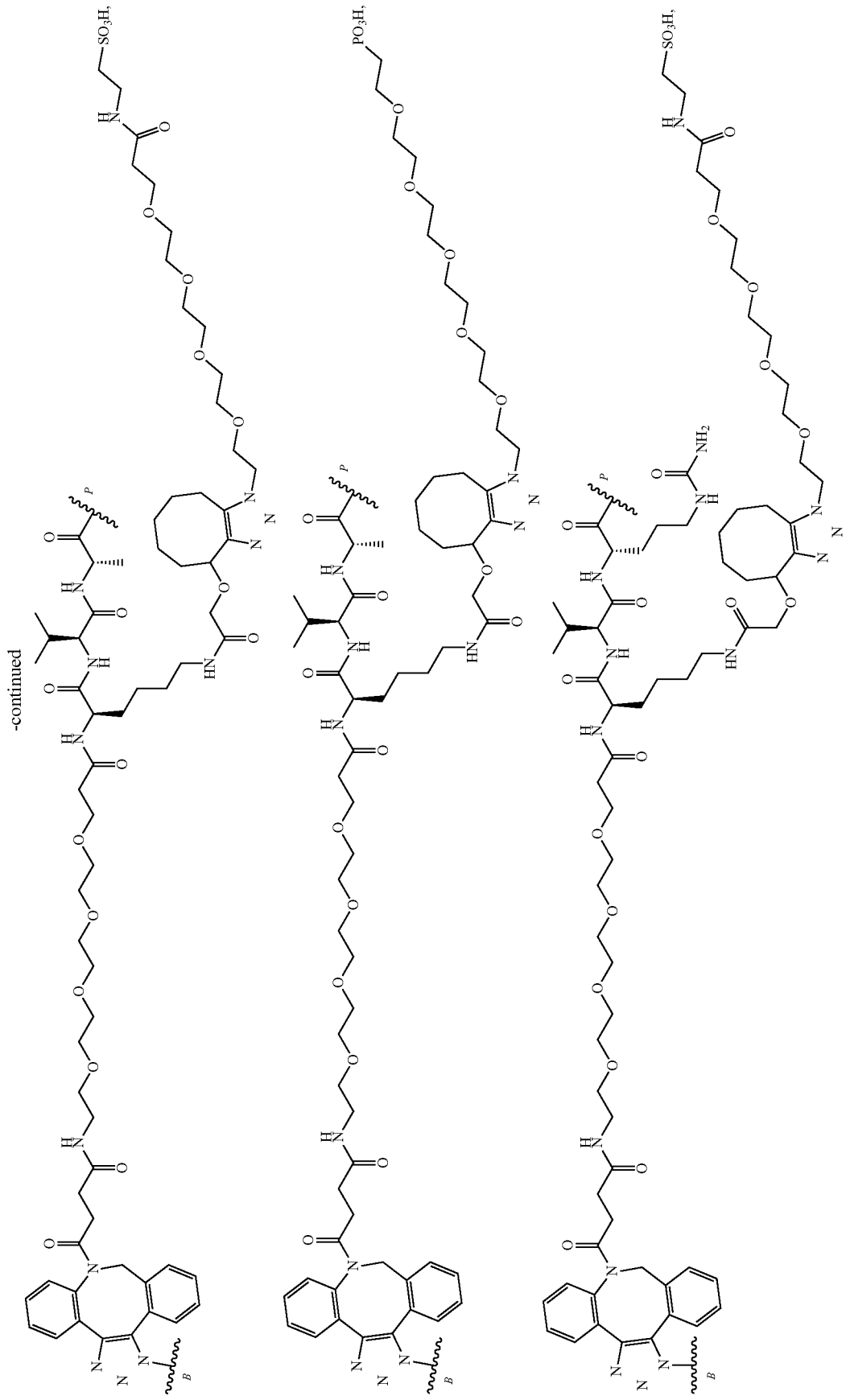

1033            1034
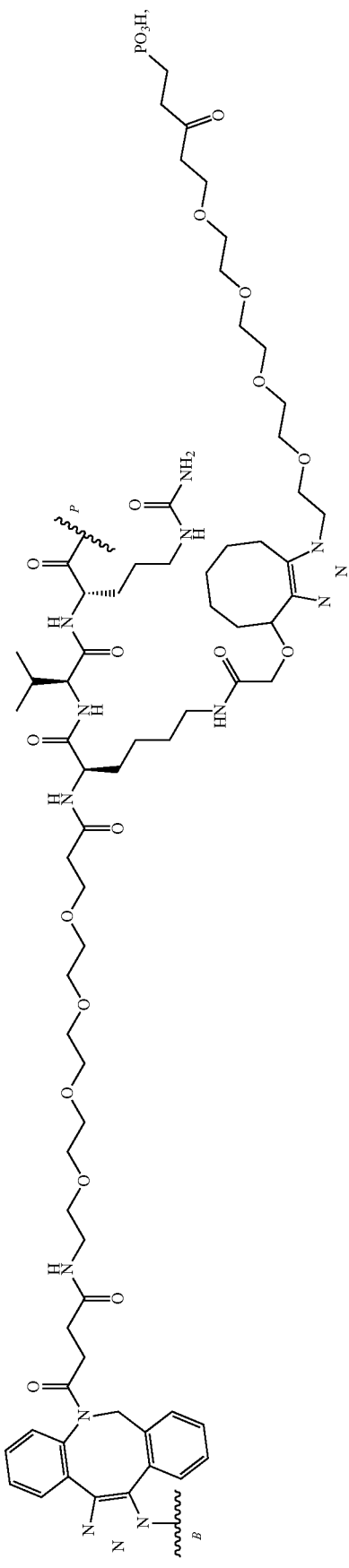
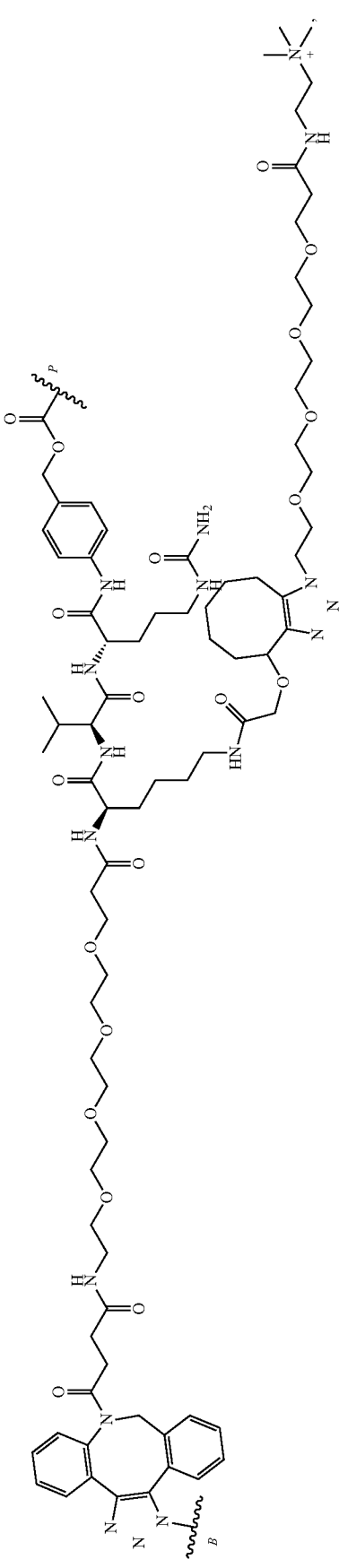

1035      1036
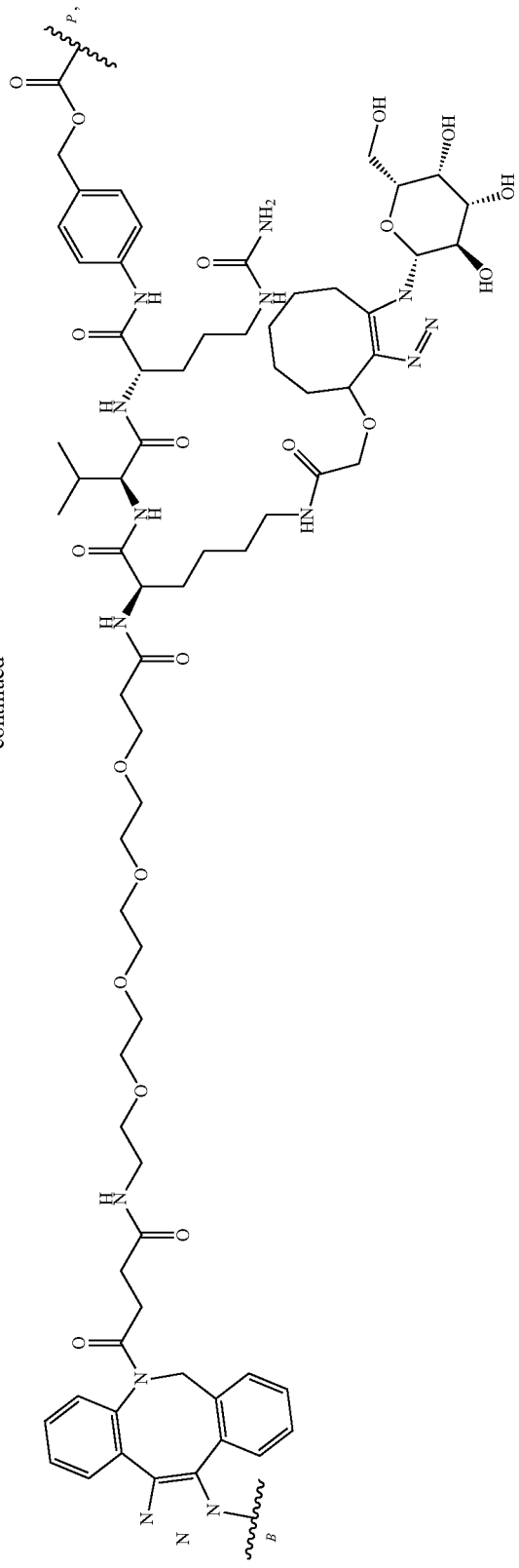
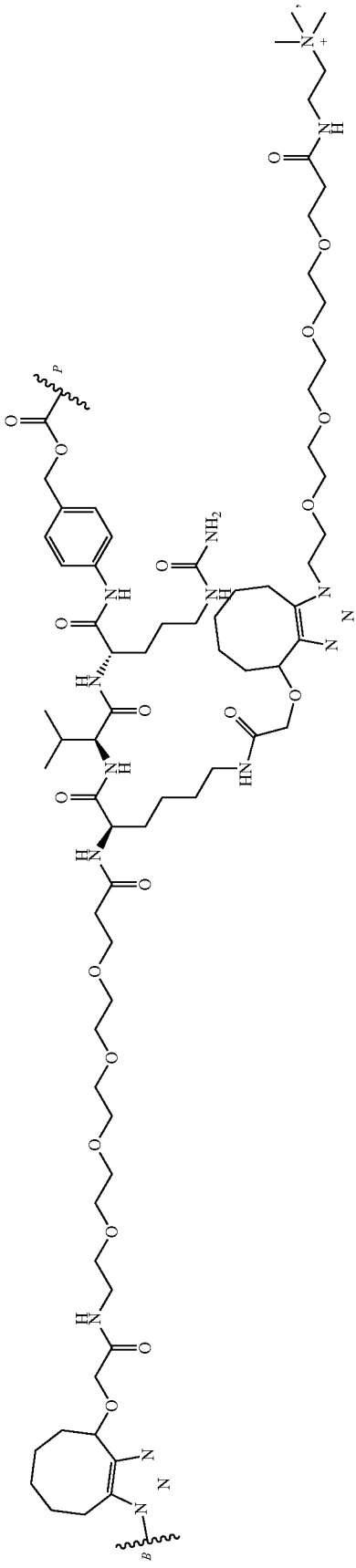

1037 1038
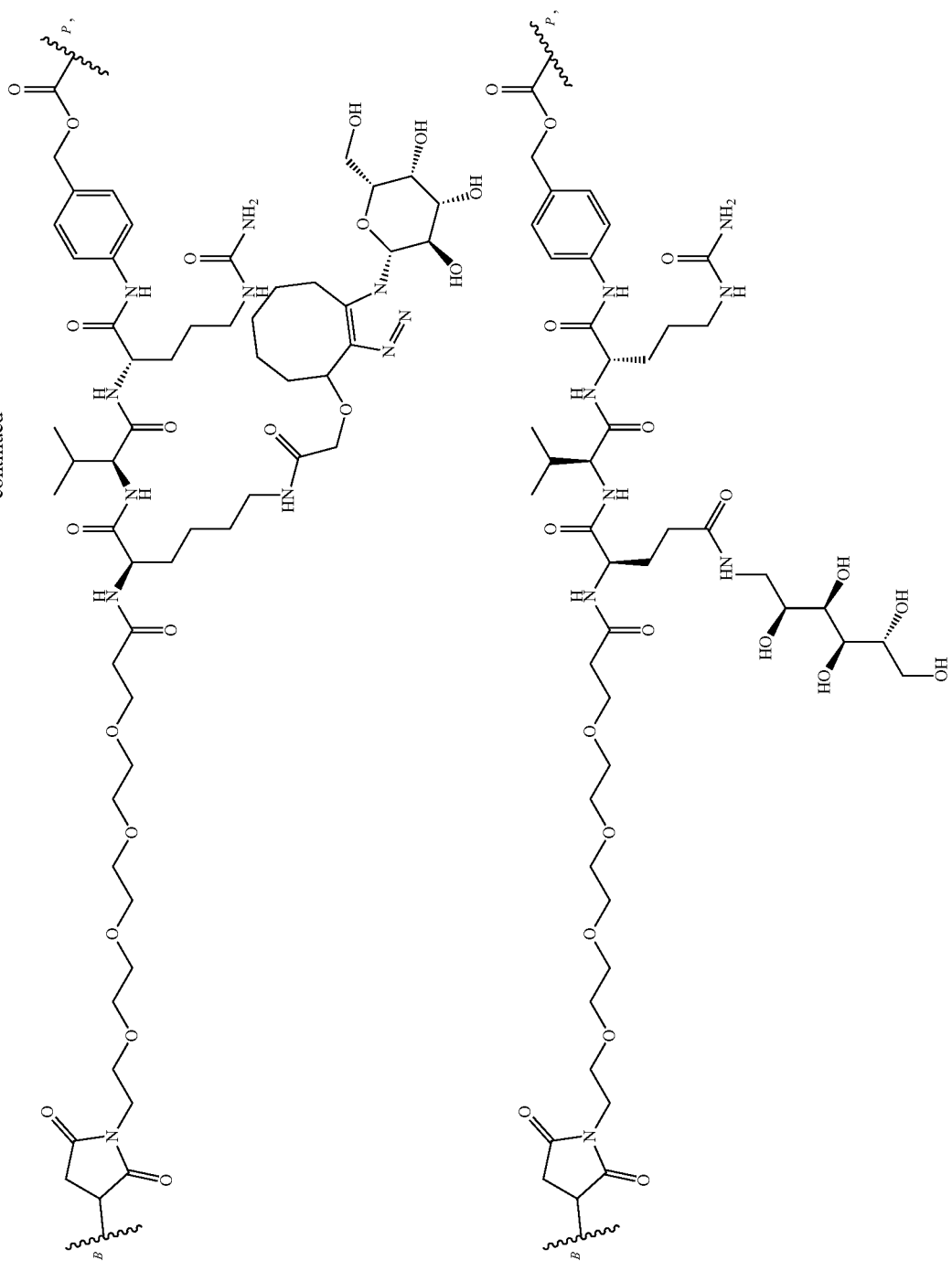

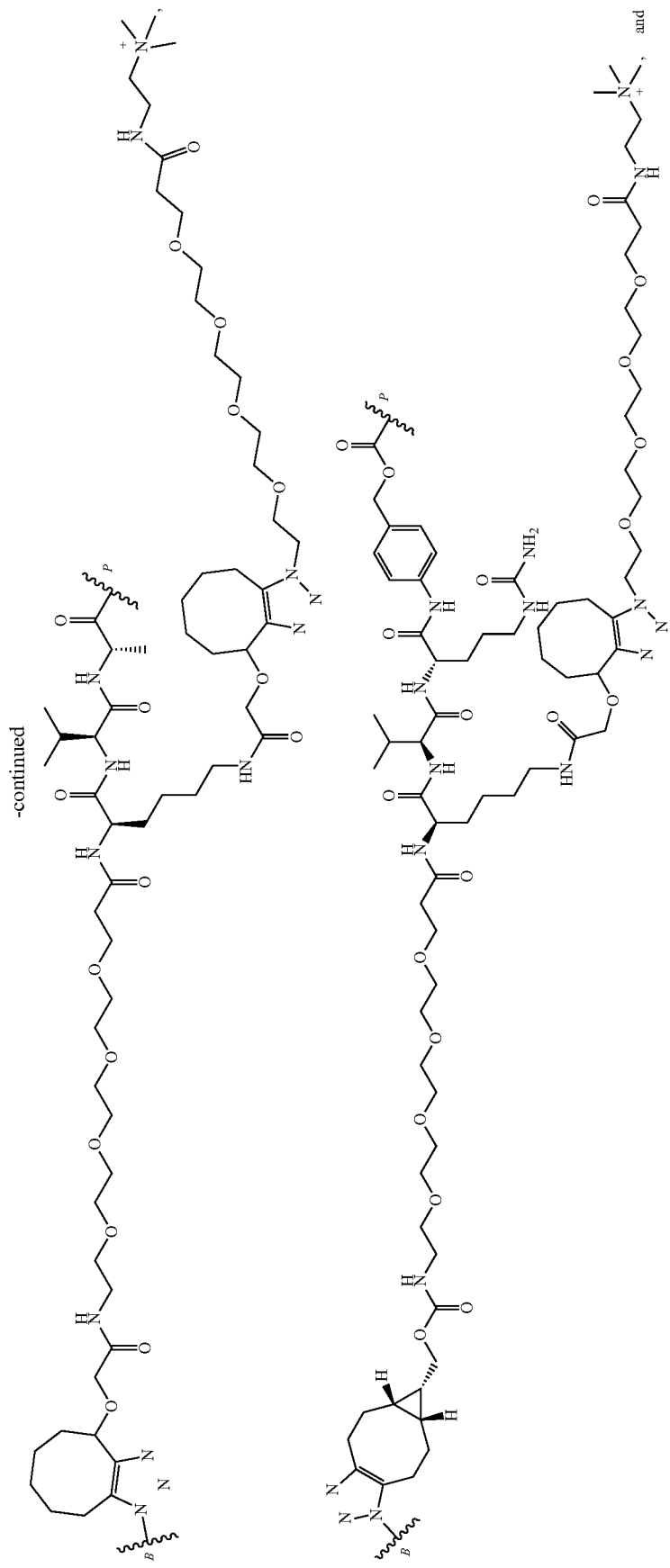

-continued
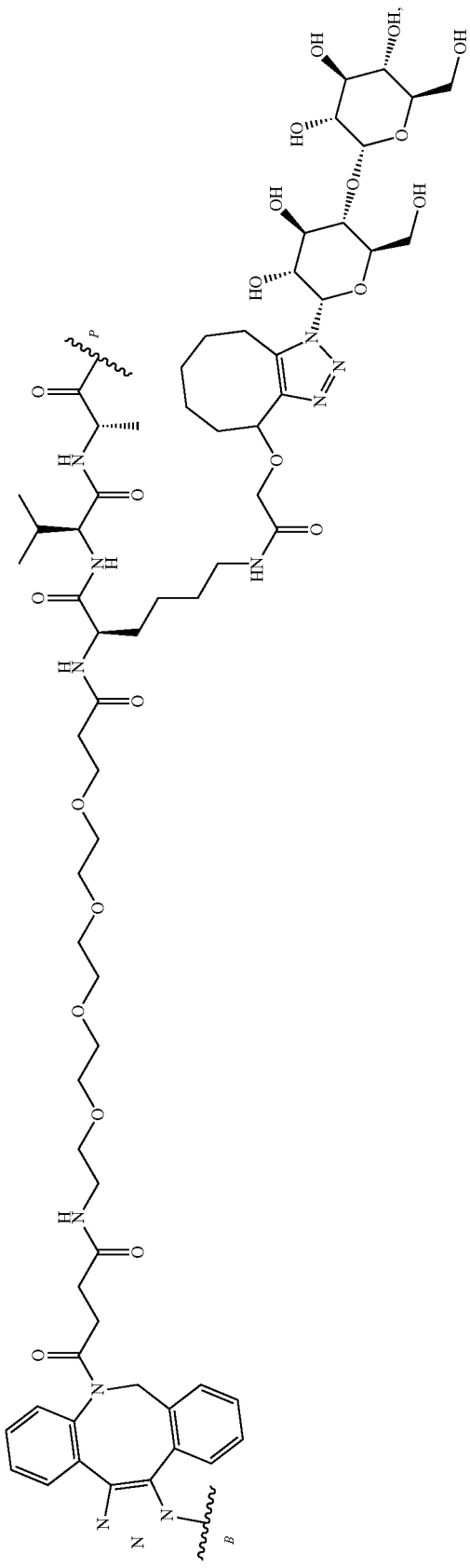

or a stereoisomeric form thereof, or a regioisomer thereof, or a mixture of regioisomers thereof, wherein each

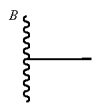

is a bond to the antibody or antigen binding fragment thereof; and each

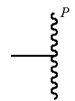

is a bond to the payload residue.

10. The compound of claim 1, wherein AA² is

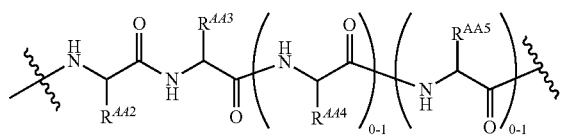

wherein $R^{AA2}$, $R^{AA3}$, $R^{AA4}$, and $R^{AA5}$ are each, independently, an amino acid side chain residue selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, and citrulline, wherein the

indicates the atom through which AA² is bonded to the adjacent groups in the formula.

11. The compound of claim 1, wherein AA² is

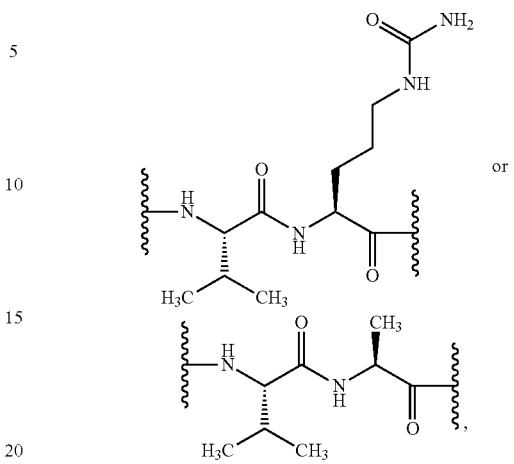

wherein the

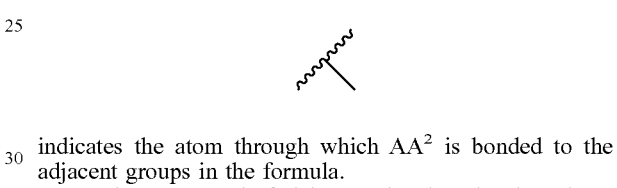

indicates the atom through which AA² is bonded to the adjacent groups in the formula.

12. The compound of claim 1, wherein subscript e is 4.
13. The compound of claim 1, wherein BA is an antibody.
14. The compound of claim 1, wherein the binding agent (BA) is an antibody, or an antigen-binding fragment thereof, selective for an antigen selected from the group consisting of AXL, BAFFR, BCMA, BCR-list components, BDCA2, BDCA4, BTLA, BTNL2, BTNL3, BTNL8, BTNL9, C10 or f54, CCR1, CCR3, CCR4, CCR5, CCR6, CCR7, CCR9, CCR10, CD11c, CD137, CD138, CD14, CD168, CD177, CD19, CD20, CD209, CD209L, CD22, CD226, CD248, CD25, CD27, CD274, CD276, CD28, CD30, CD300A, CD33, CD37, CD38, CD4, CD40, CD44, CD45, CD46, CD48, CD5, CD52, CD55, CD56, CD59, CD62E, CD68, CD69, CD70, CD74, CD79a, CD79b, CD8, CD80, CD86, CD90.2, CD96, CLEC12A, CLEC12B, CLEC7A, CLEC9A, CR1, CR3, CRTAM, CSFIR, CTLA4, CXCR1/2, CXCR4, CXCR5, DDR1, DDR2, DEC-205, DLL4, DR6, FAP, FCamR, FCMR, FcR's, Fire, GITR, HER2, HHLA2, HLA class II, HVEM, ICOSLG, IFNLR1, IL10R1, IL10R2, IL12R, IL13RA1, IL13RA2, IL15R, IL17RA, IL17RB, IL17RC, IL17RE, IL20R1, IL20R2, IL21R, IL22R1, IL22RA, IL23R, IL27R, IL29R, IL2Rg, IL31R, IL36R, IL3RA, IL4R, IL6R, IL5R, IL7R, IL9R, Integrins, LAG3, LIFR, MAG/Siglec-4, MMR, MSR1, NCR3LG1, NKG2D, NKp30, NKp46, PDCD1, PROKR1, PVR, PVRIG, PVRL2, PVRL3, RELT, SIGIRR, Siglec-1, Siglec-10, Siglec-5, Siglec-6, Siglec-7, Siglec-8, Siglec-9, SIRPA, SLAMF7, TACI, TCR-list components/assoc, PTCRA, TCRb, CD3z, CD3, TEK, TGFBR1, TGFBR2, TGFBR3, TIGIT, TLR2, TLR4, TROY, TSLPR, TYRO, VLDLR, VSIG4, and VTCN1.

15. The compound of claim 1, wherein PA is the residue of a compound selected from the group consisting of a dolastatin, an auristatin, a maytansinoid, a plant alkaloid, a taxane, a *vinca* alkaloid, a steroid, and a liver X receptor (LXR) modulator.

16. The compound of claim 1, selected from the group consisting of:

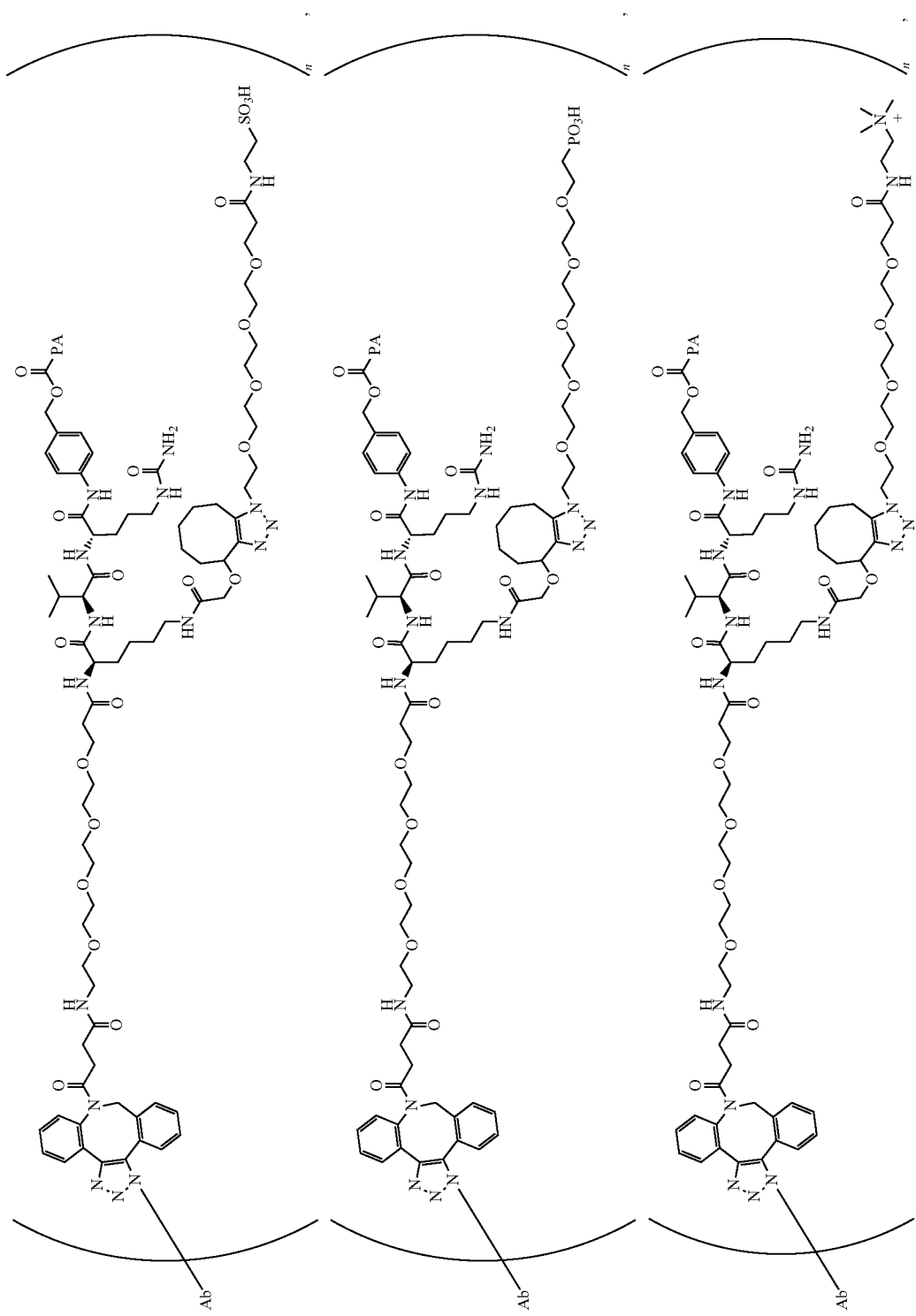

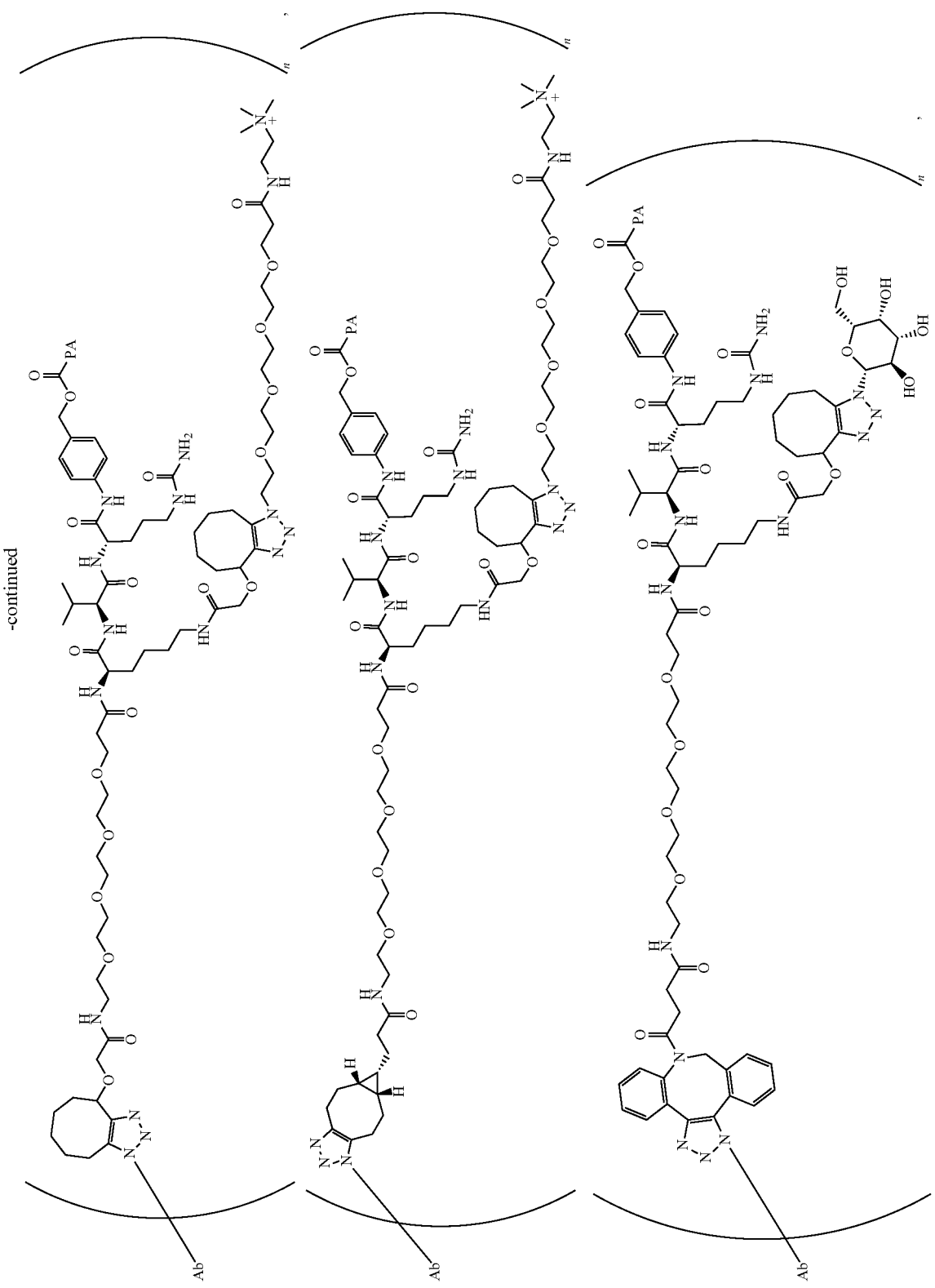

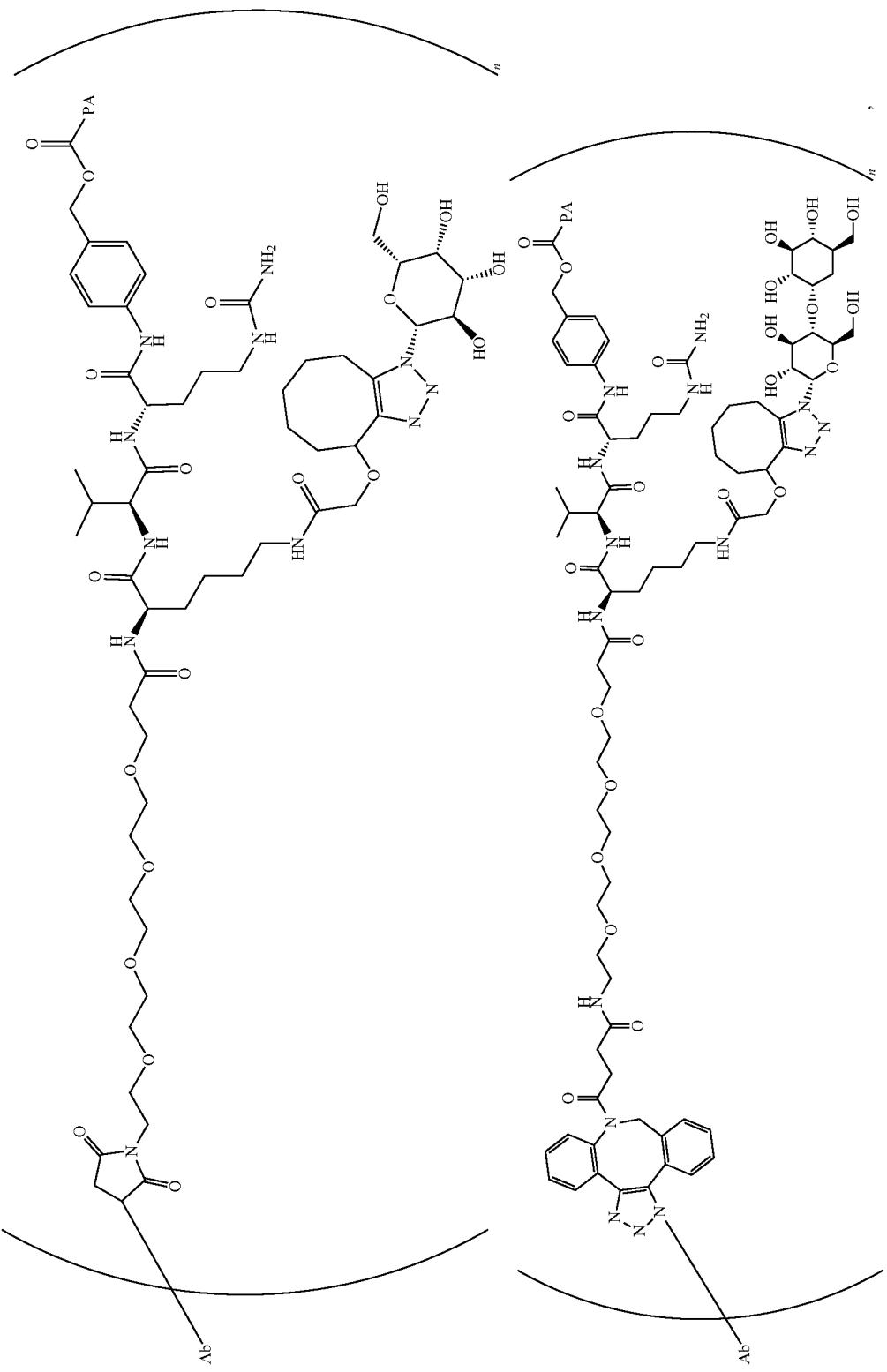

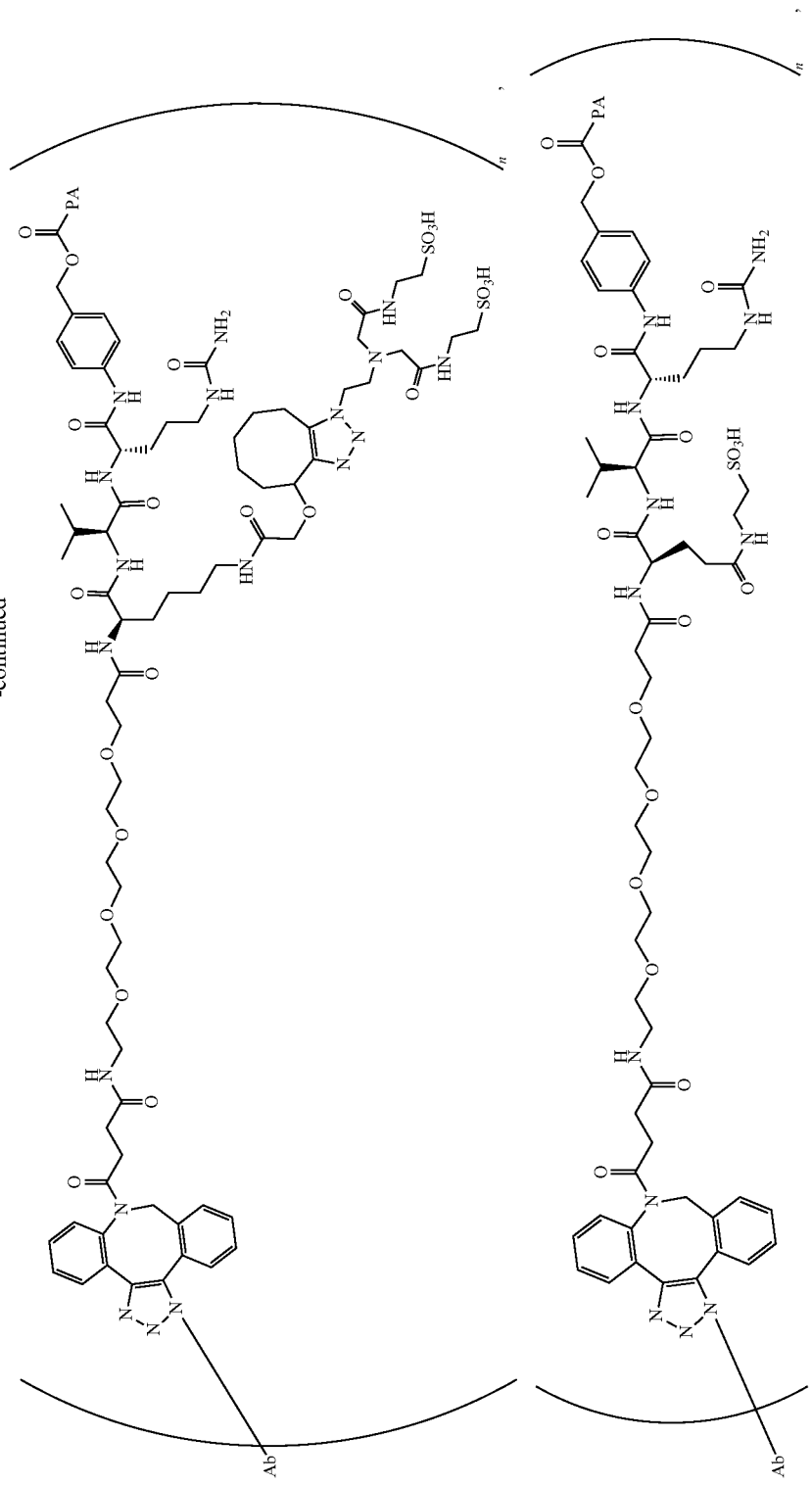

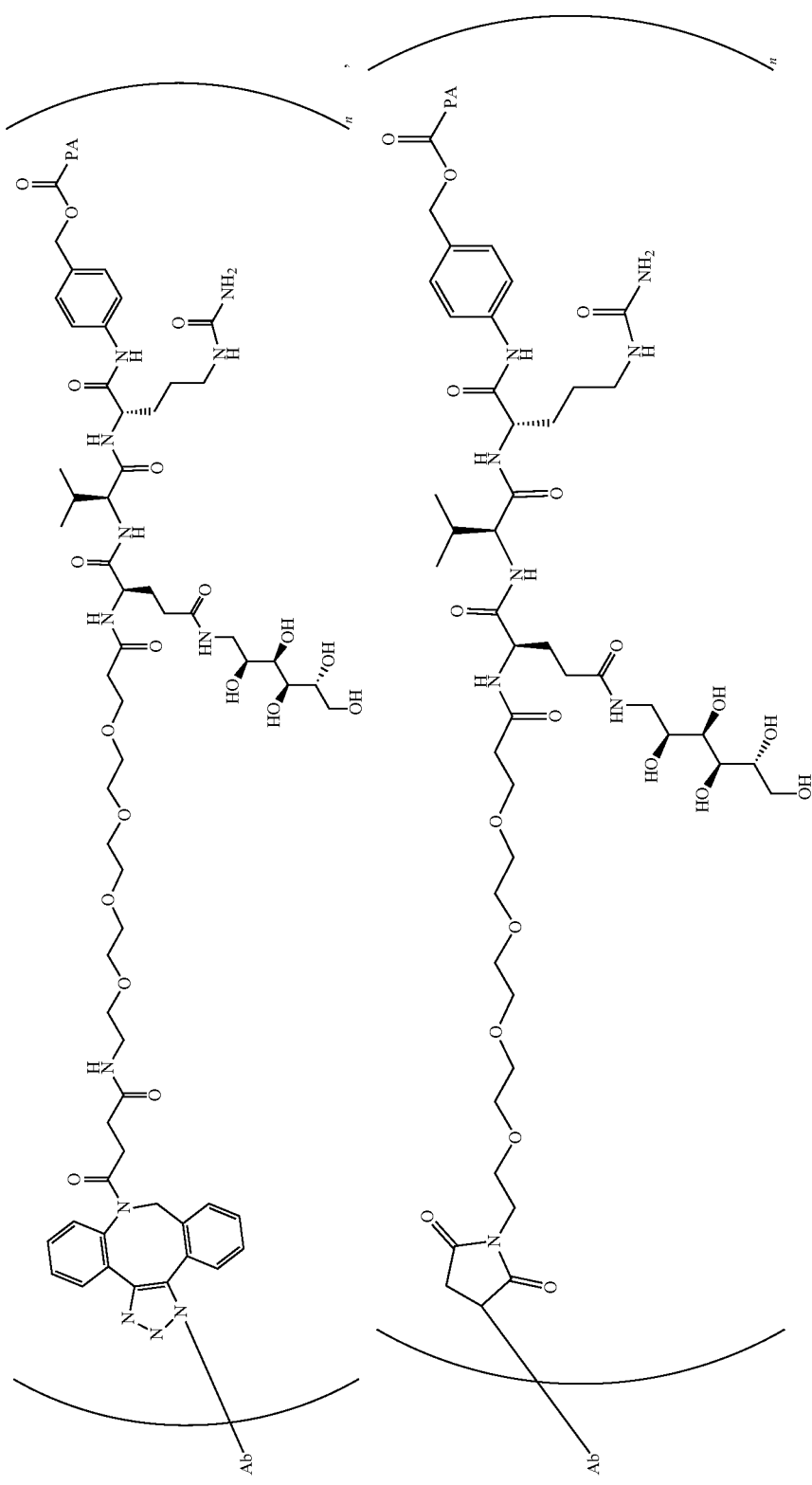

-continued
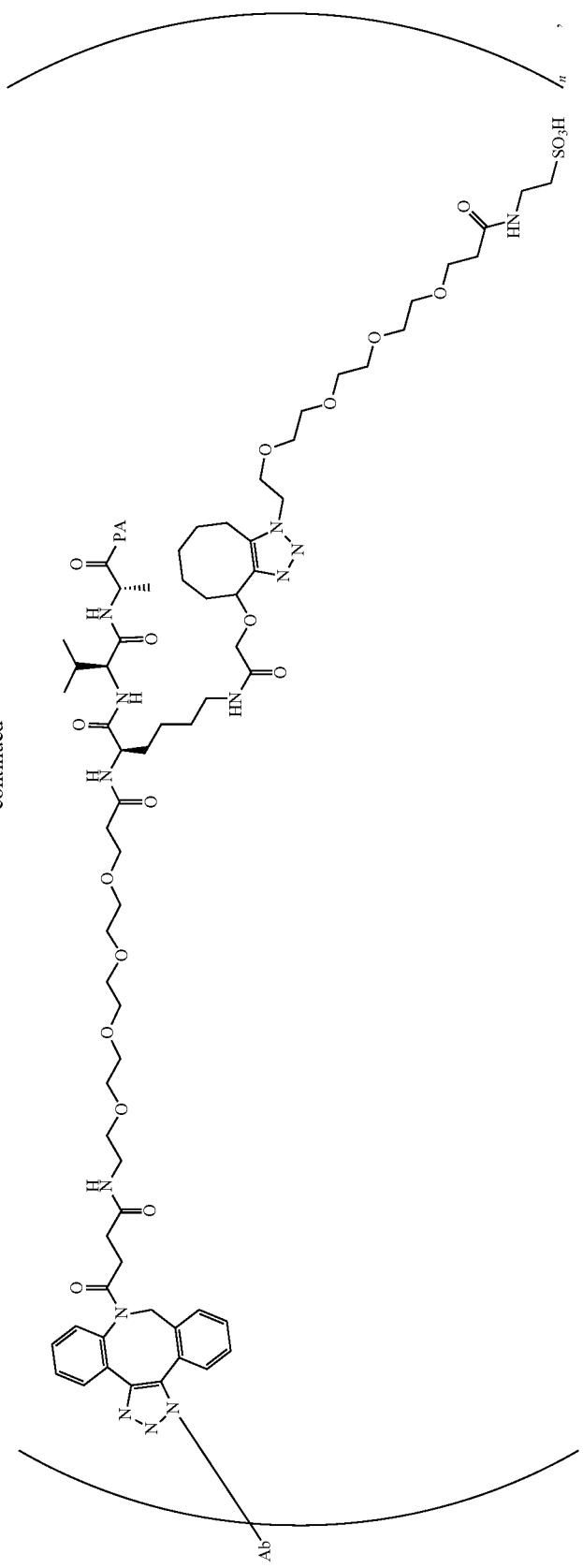

-continued
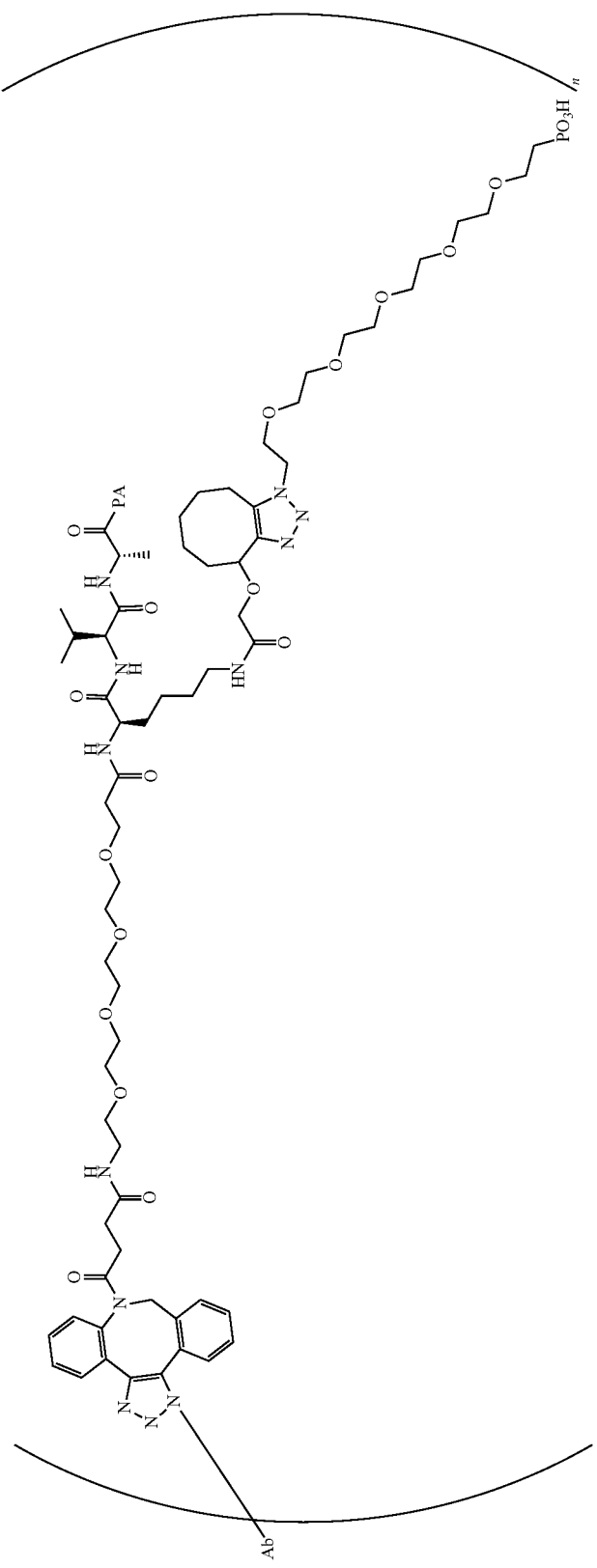

-continued
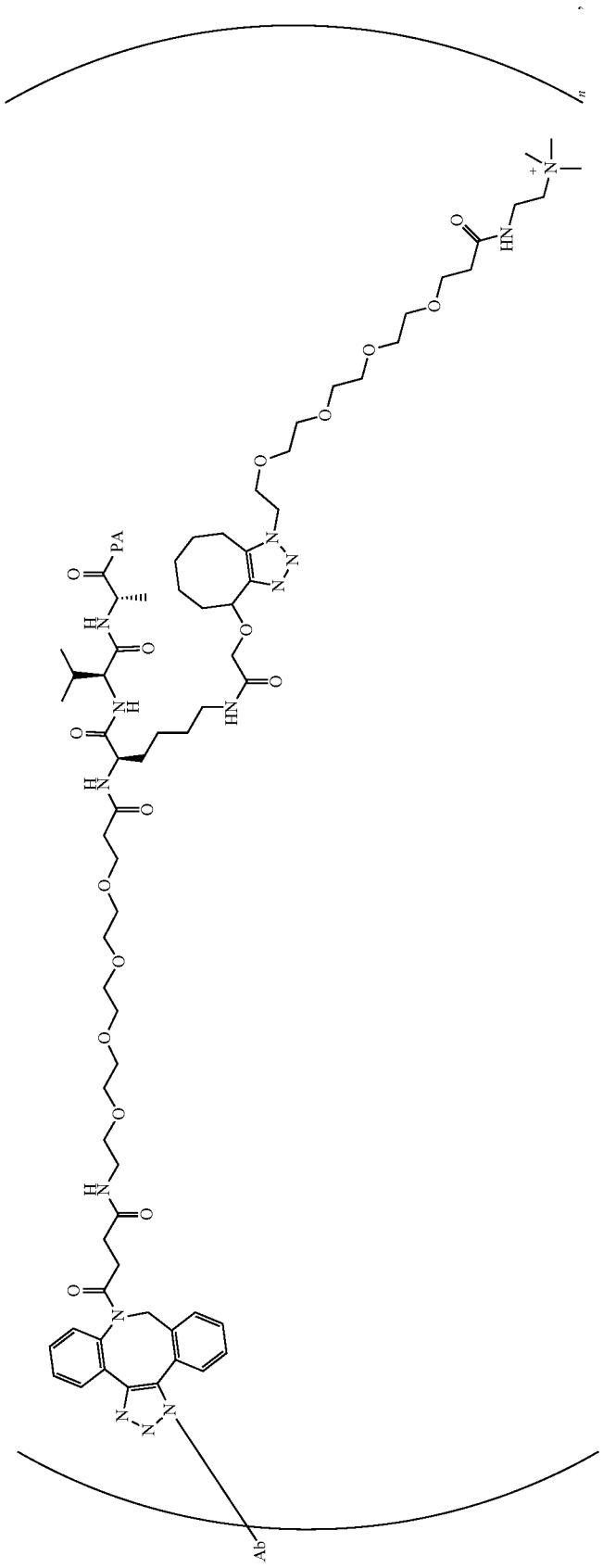

-continued
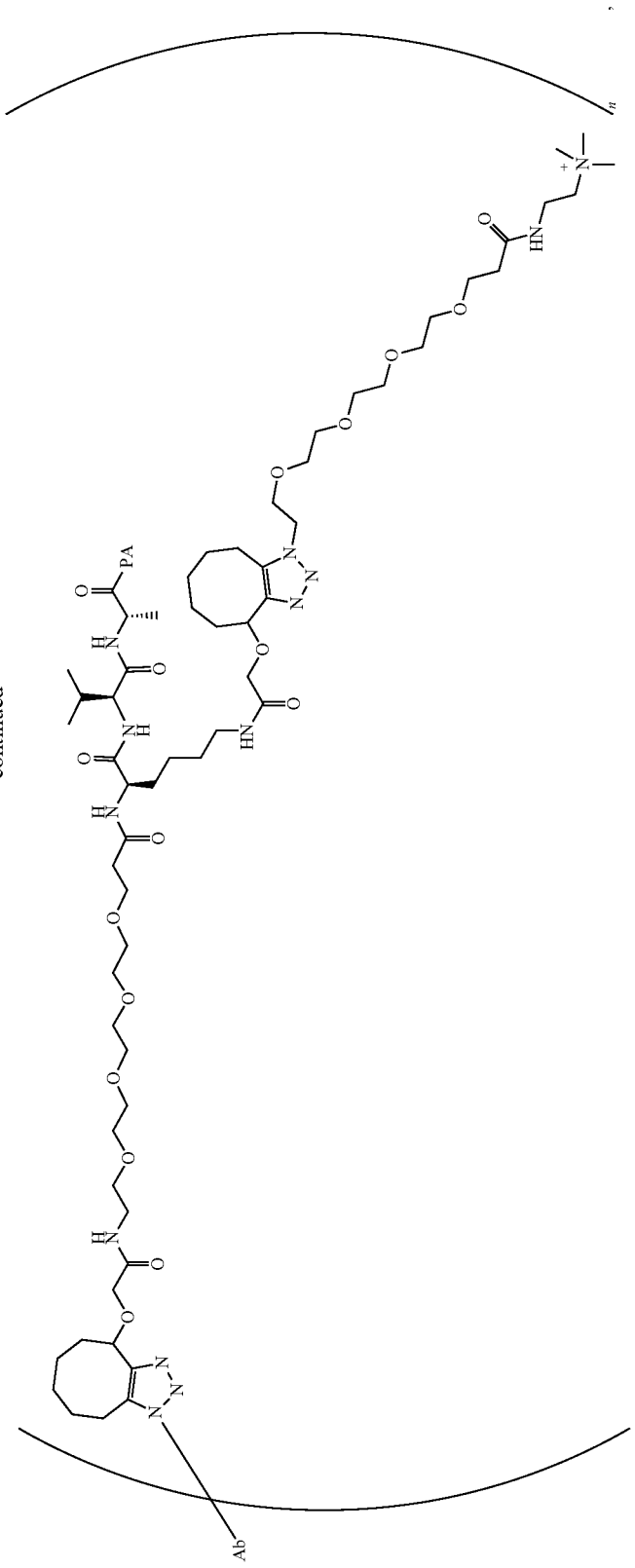

1063 1064
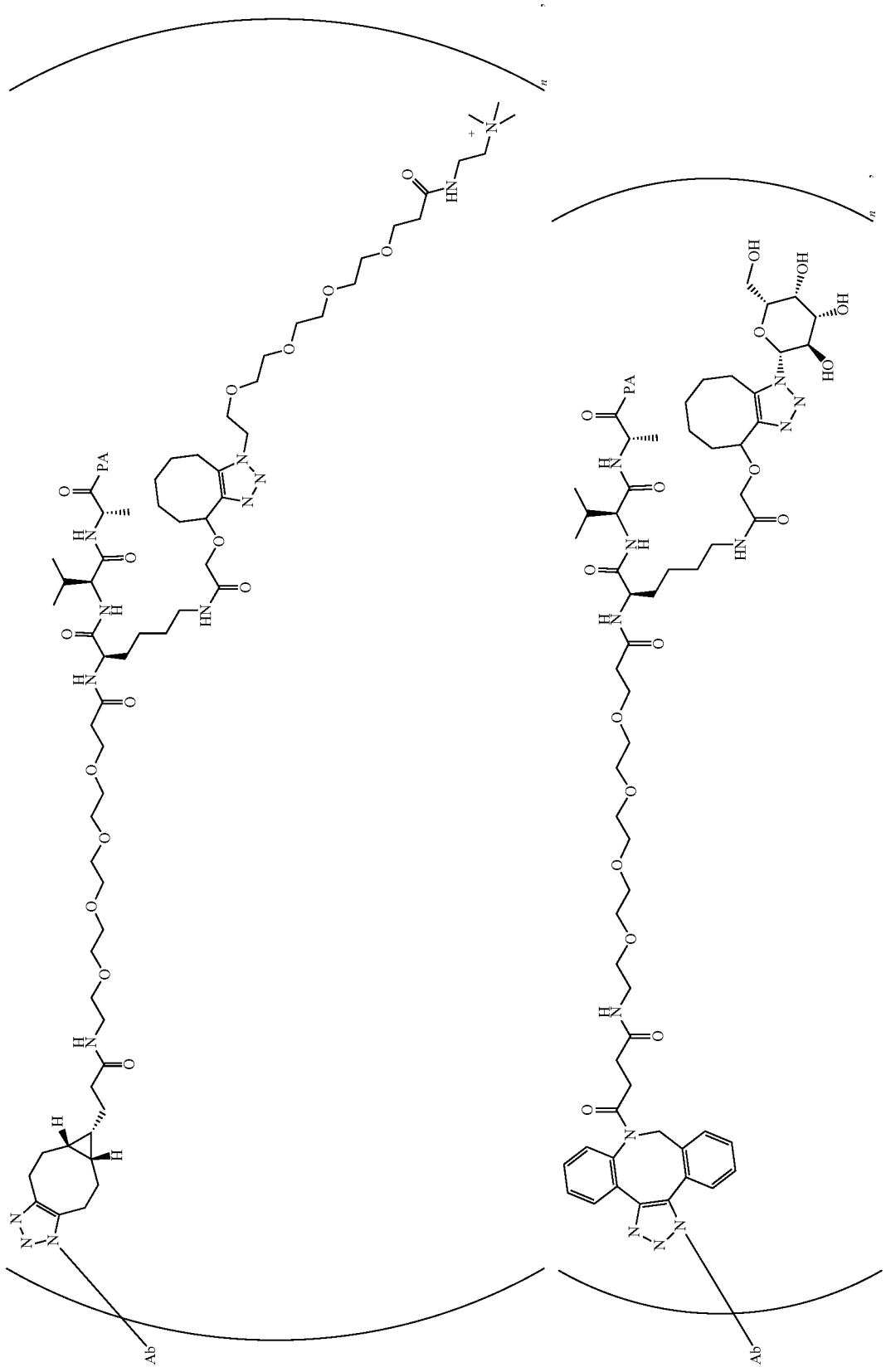

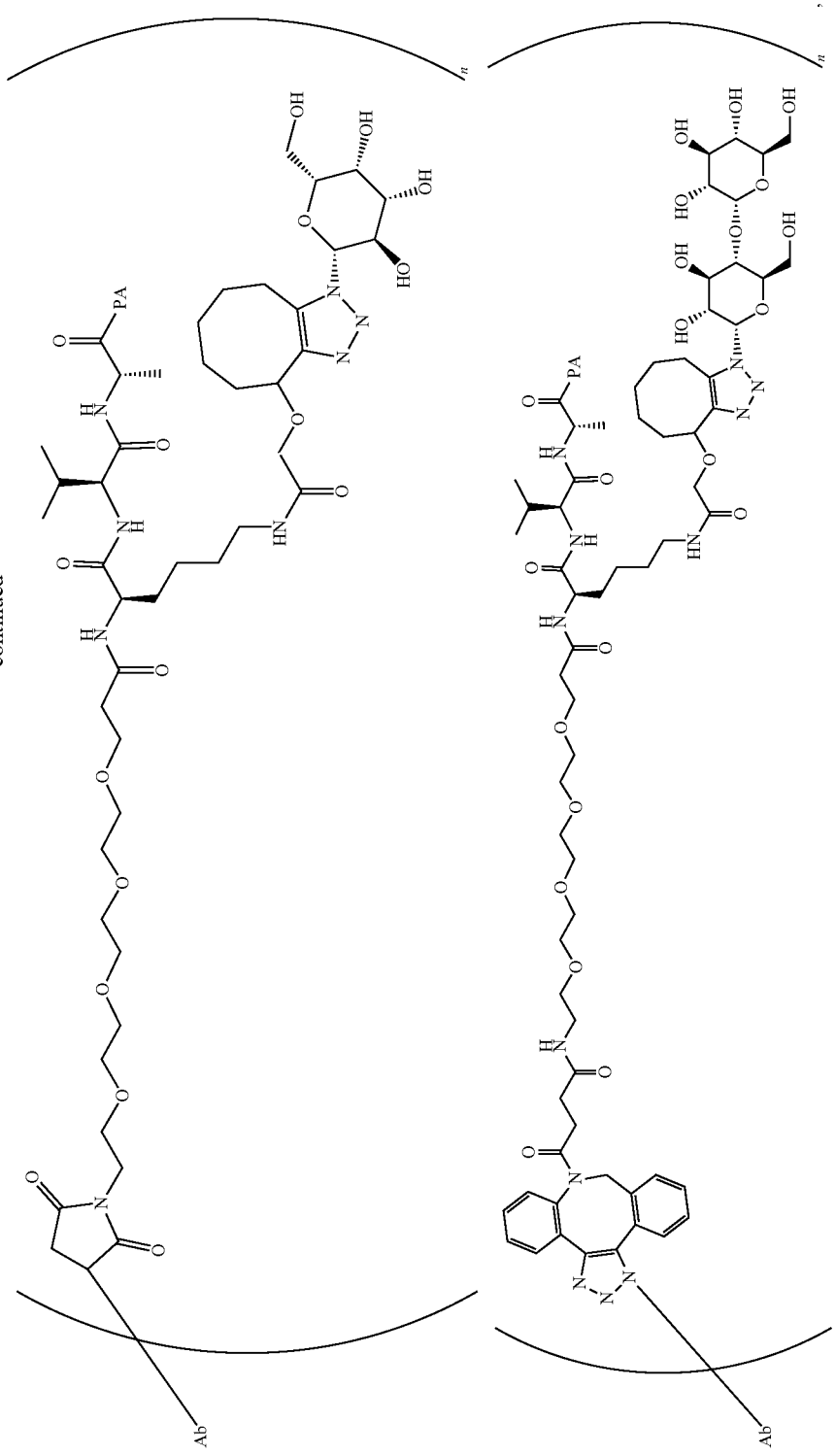

-continued
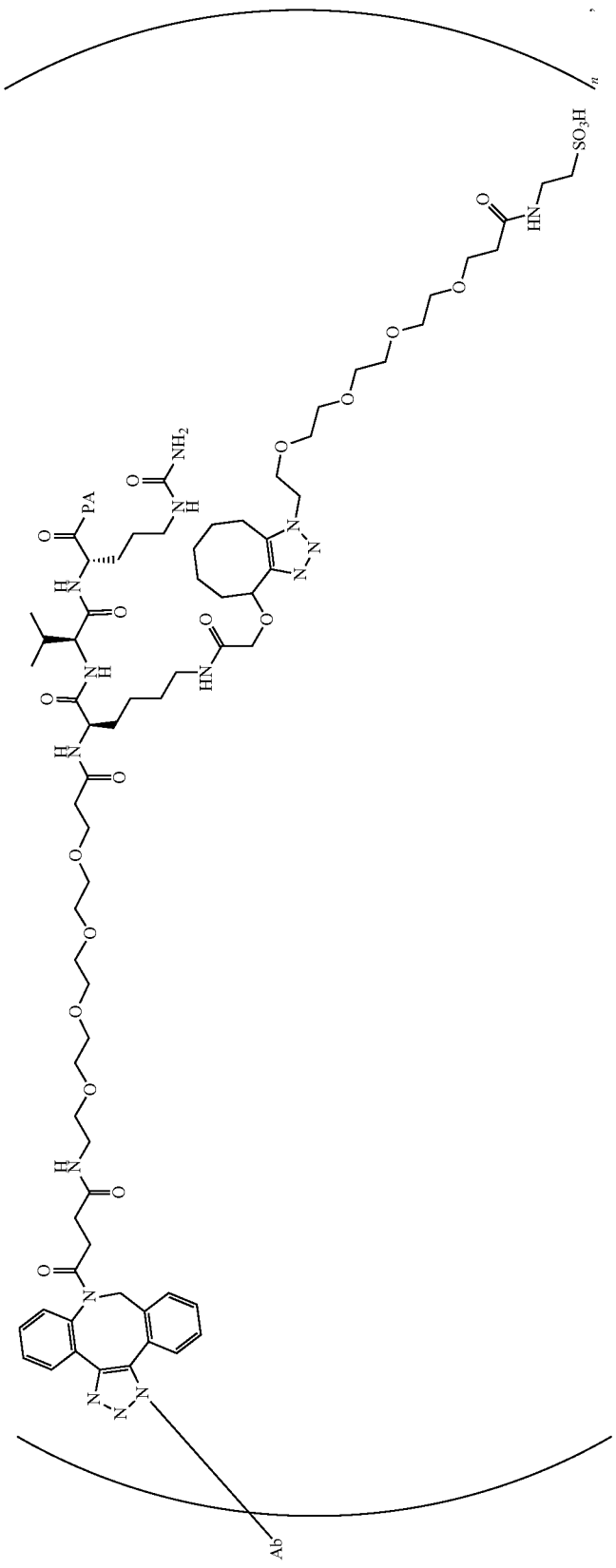

-continued
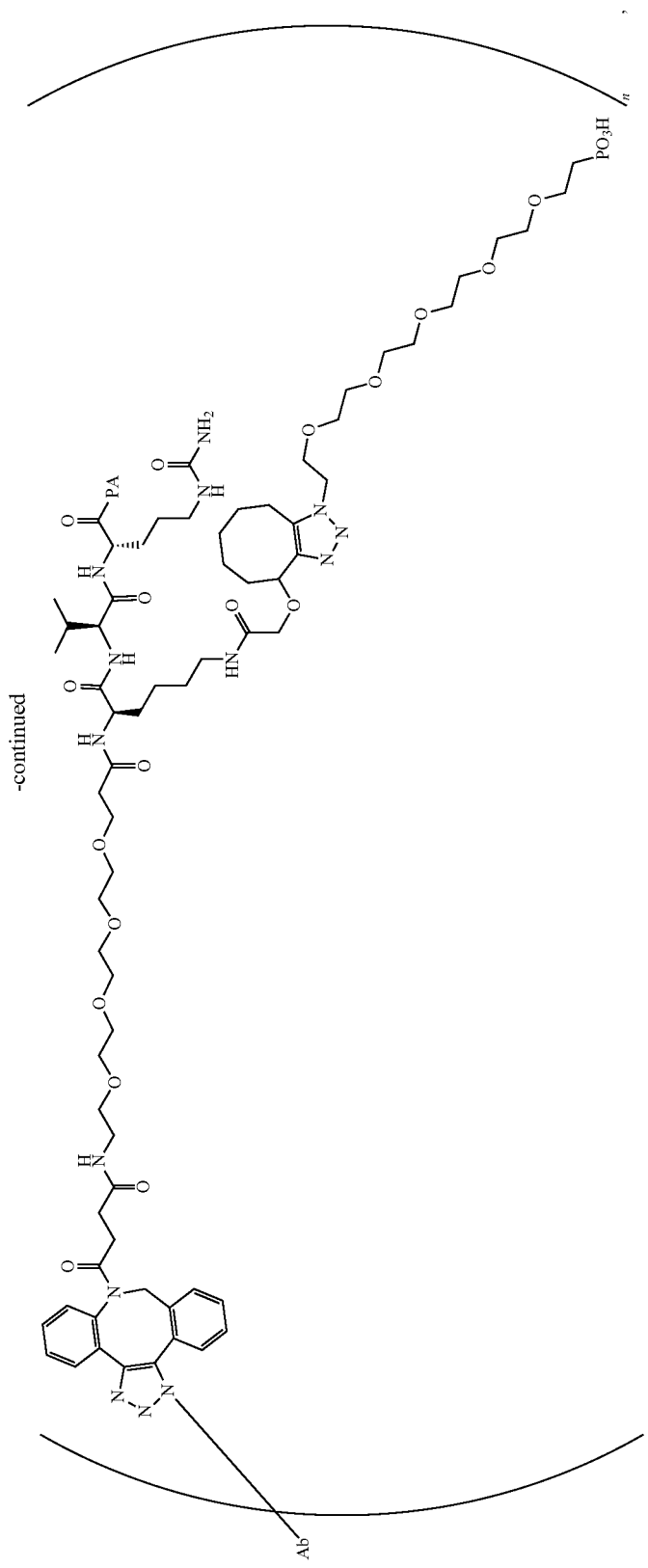

-continued
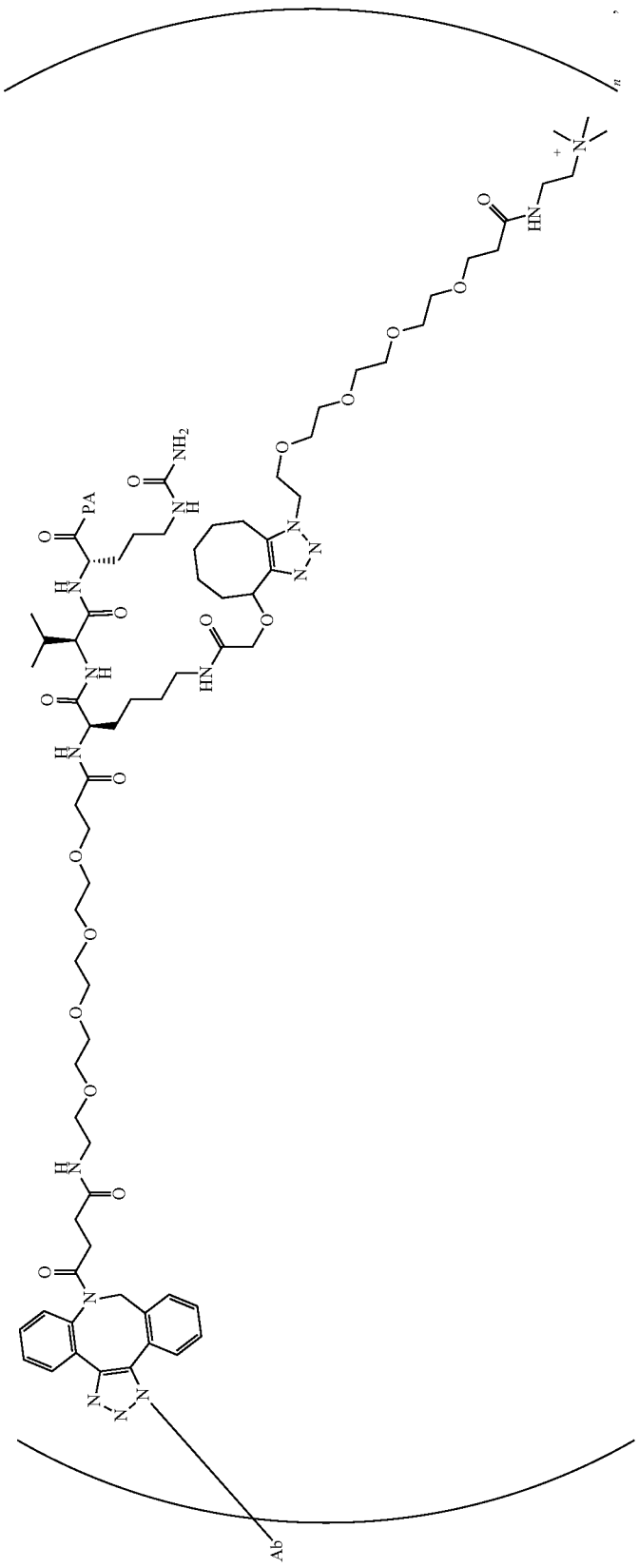

-continued
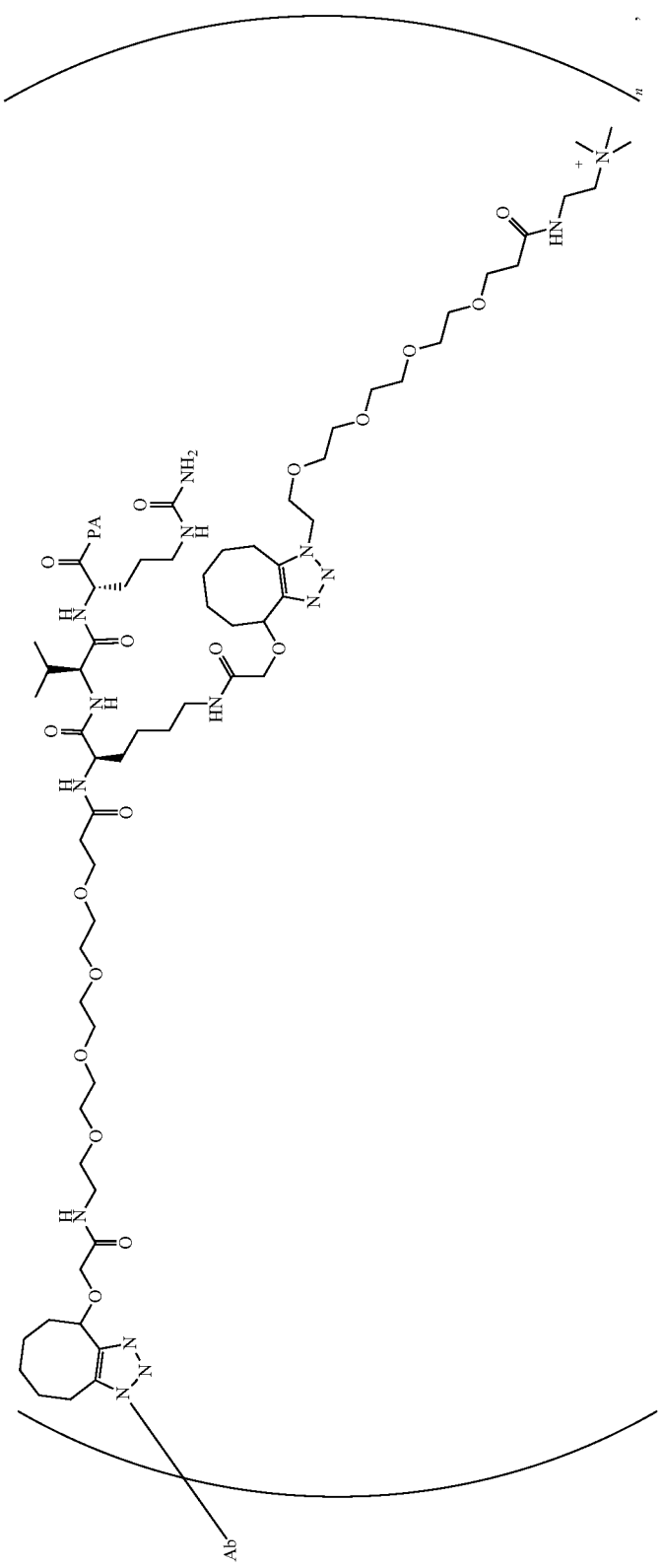

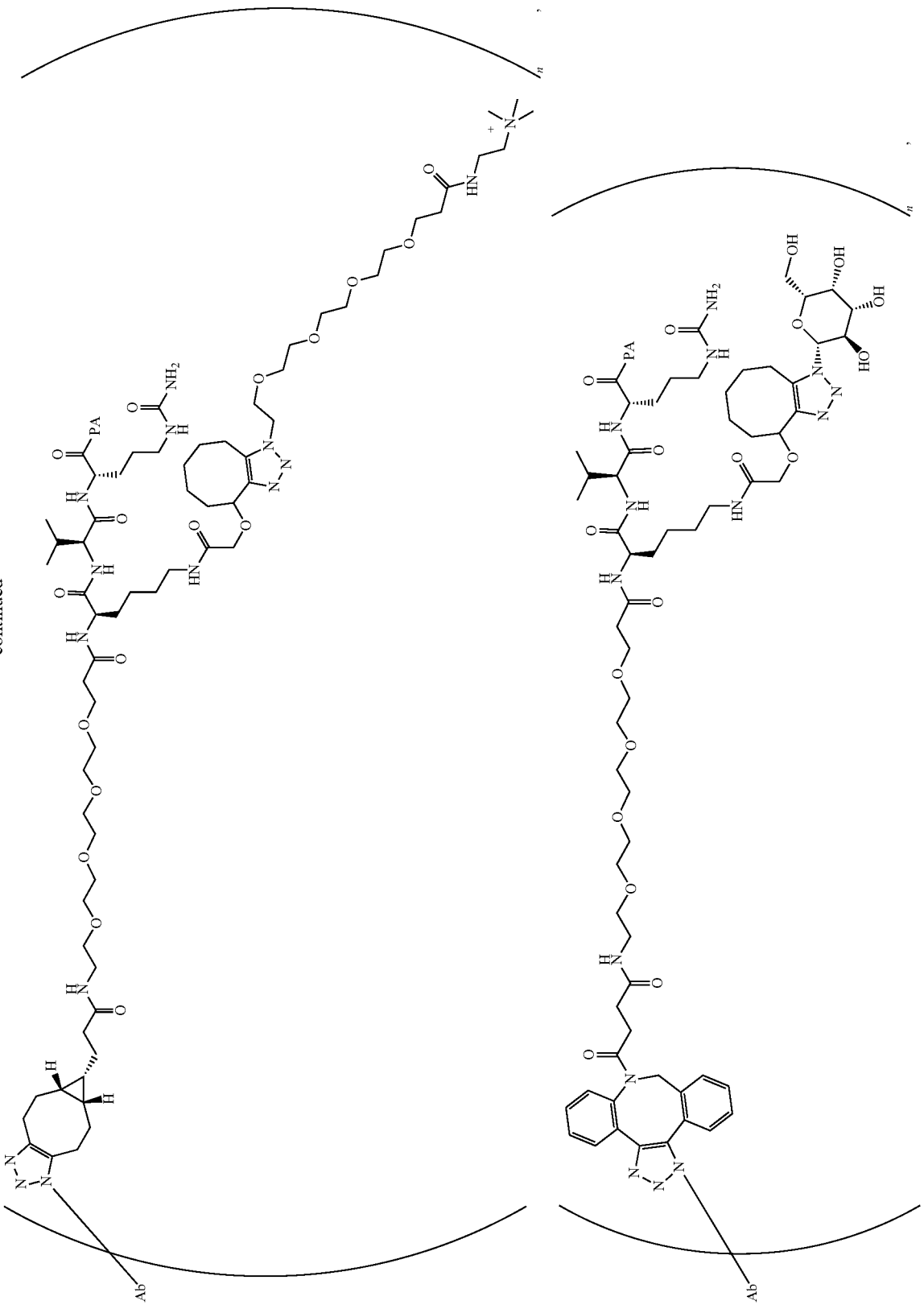

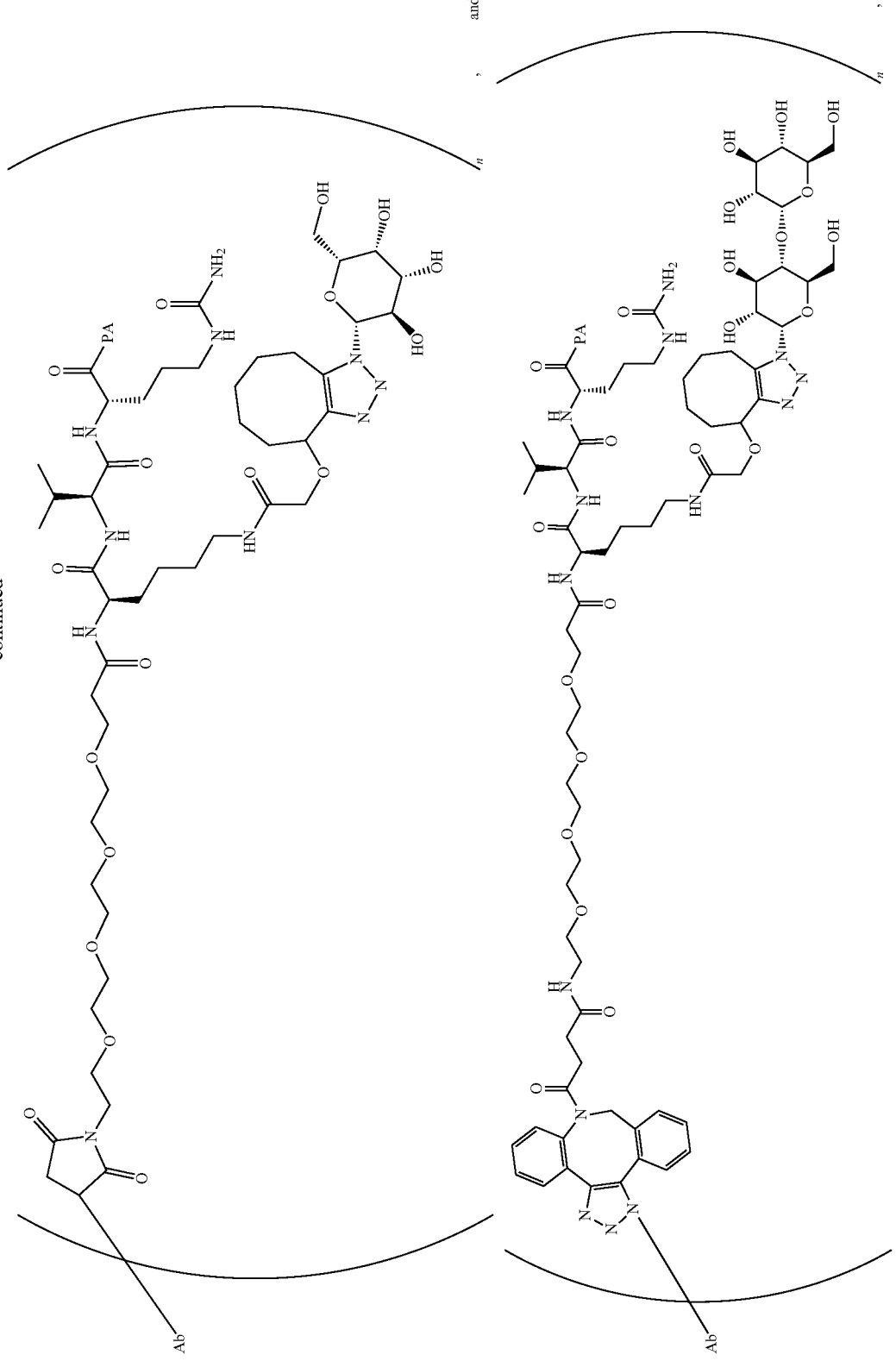

or a stereoisomeric form thereof, or a regioisomer thereof, or a mixture of regioisomers thereof, wherein each Ab is the antibody, or an antigen-binding fragment thereof;
PA is the payload residue; and
subscript n is an integer from 1 to 30.

17. The compound of claim 1, selected from the group consisting of:

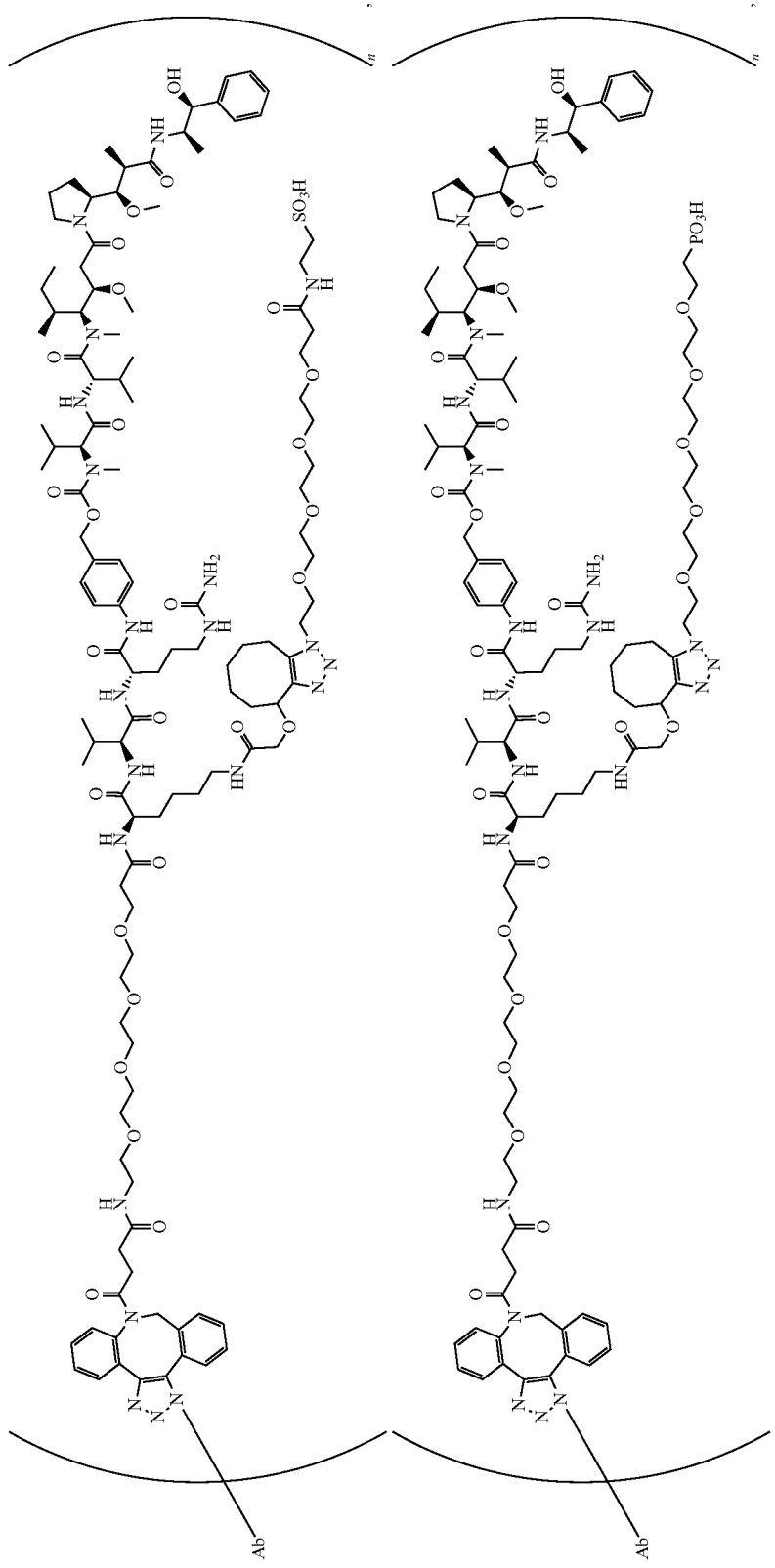

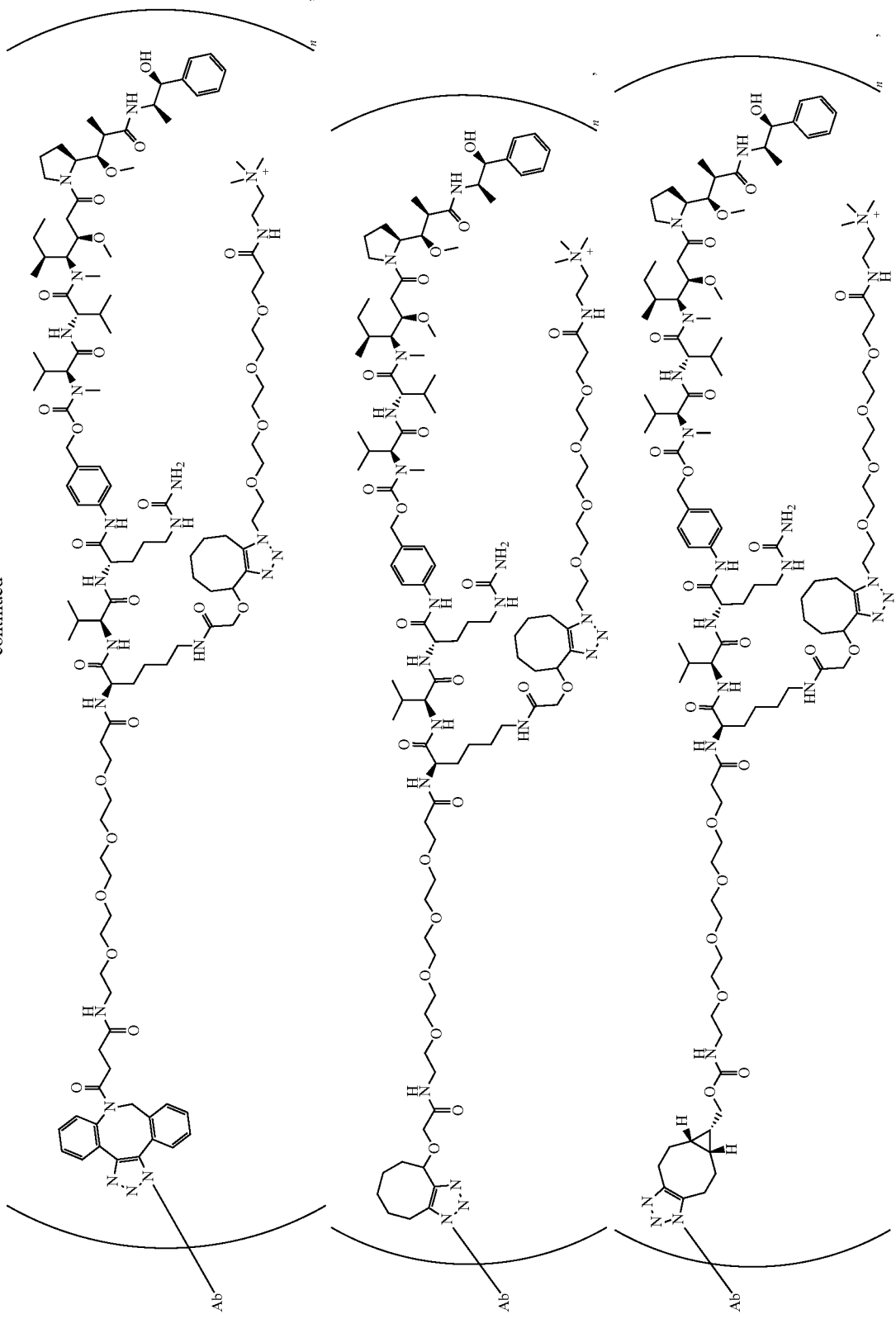

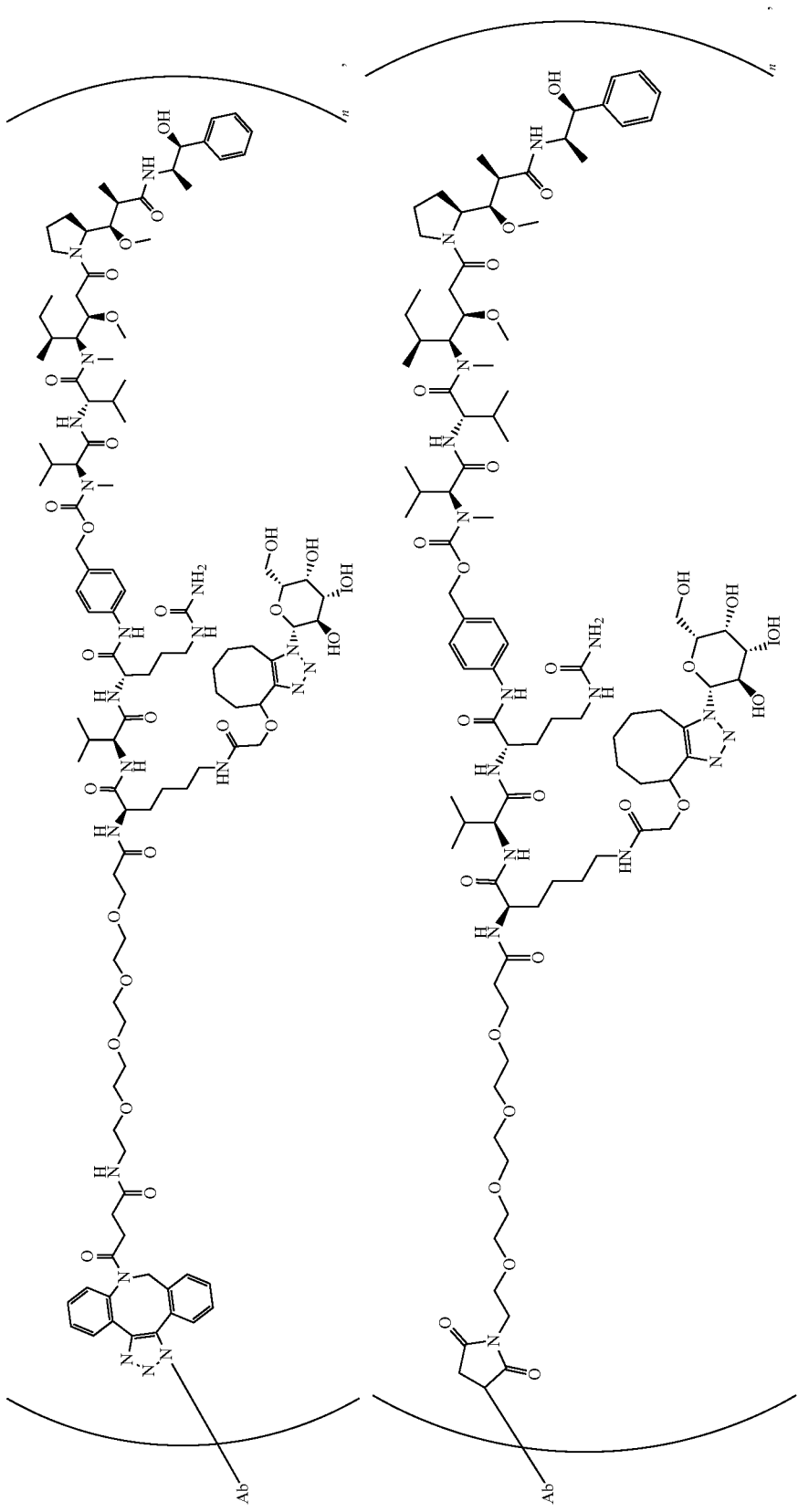

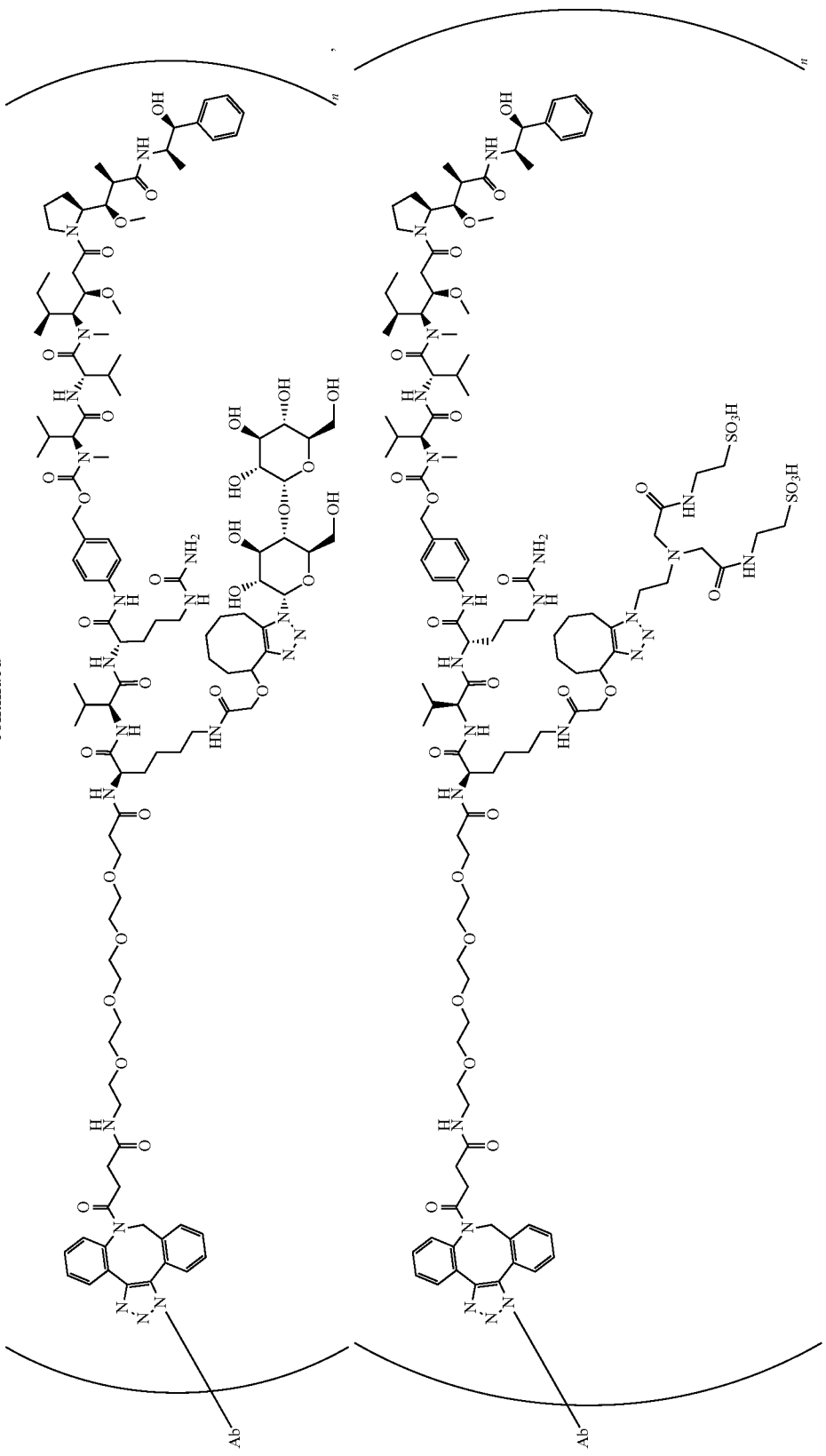

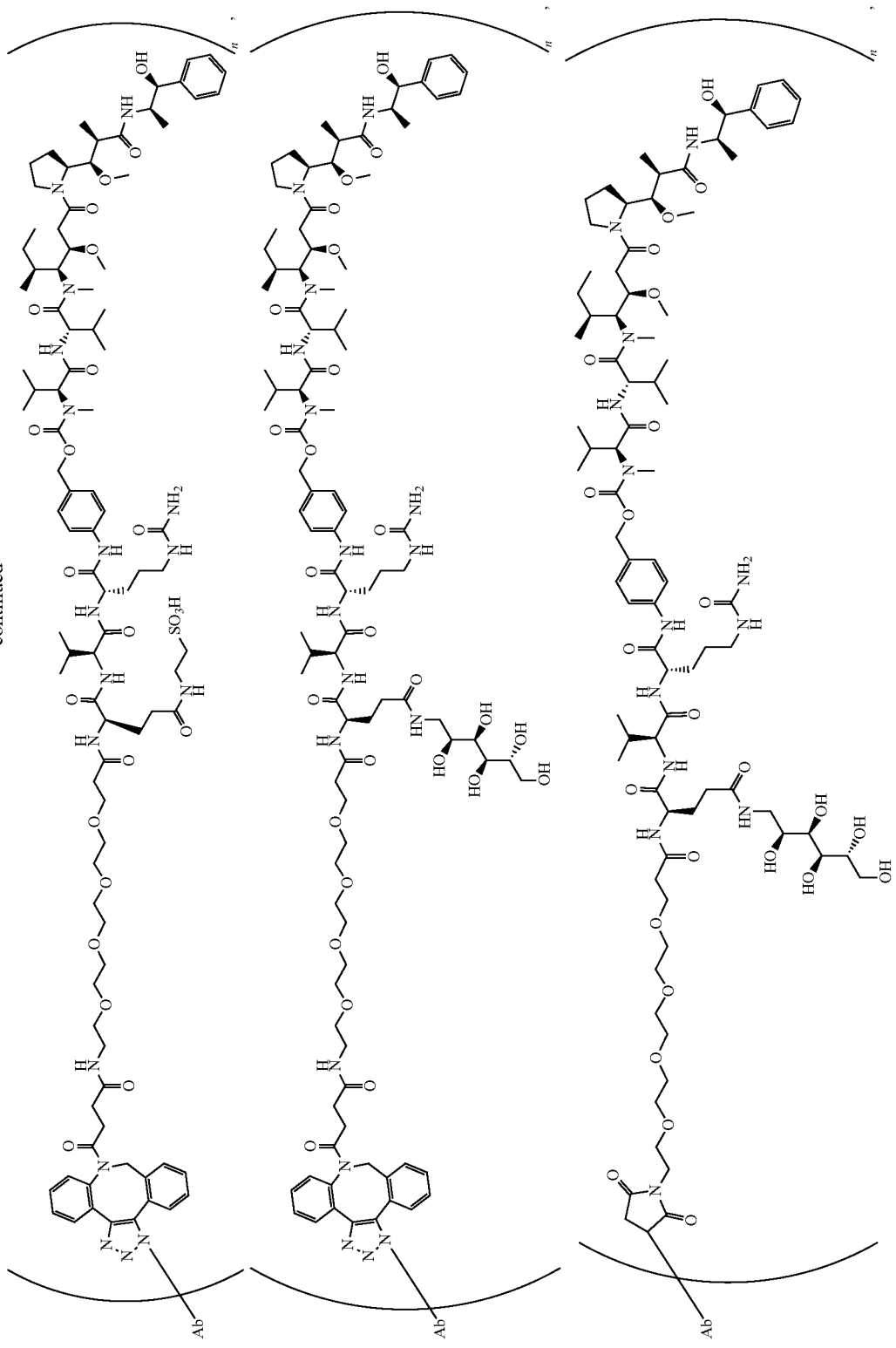

1091 1092
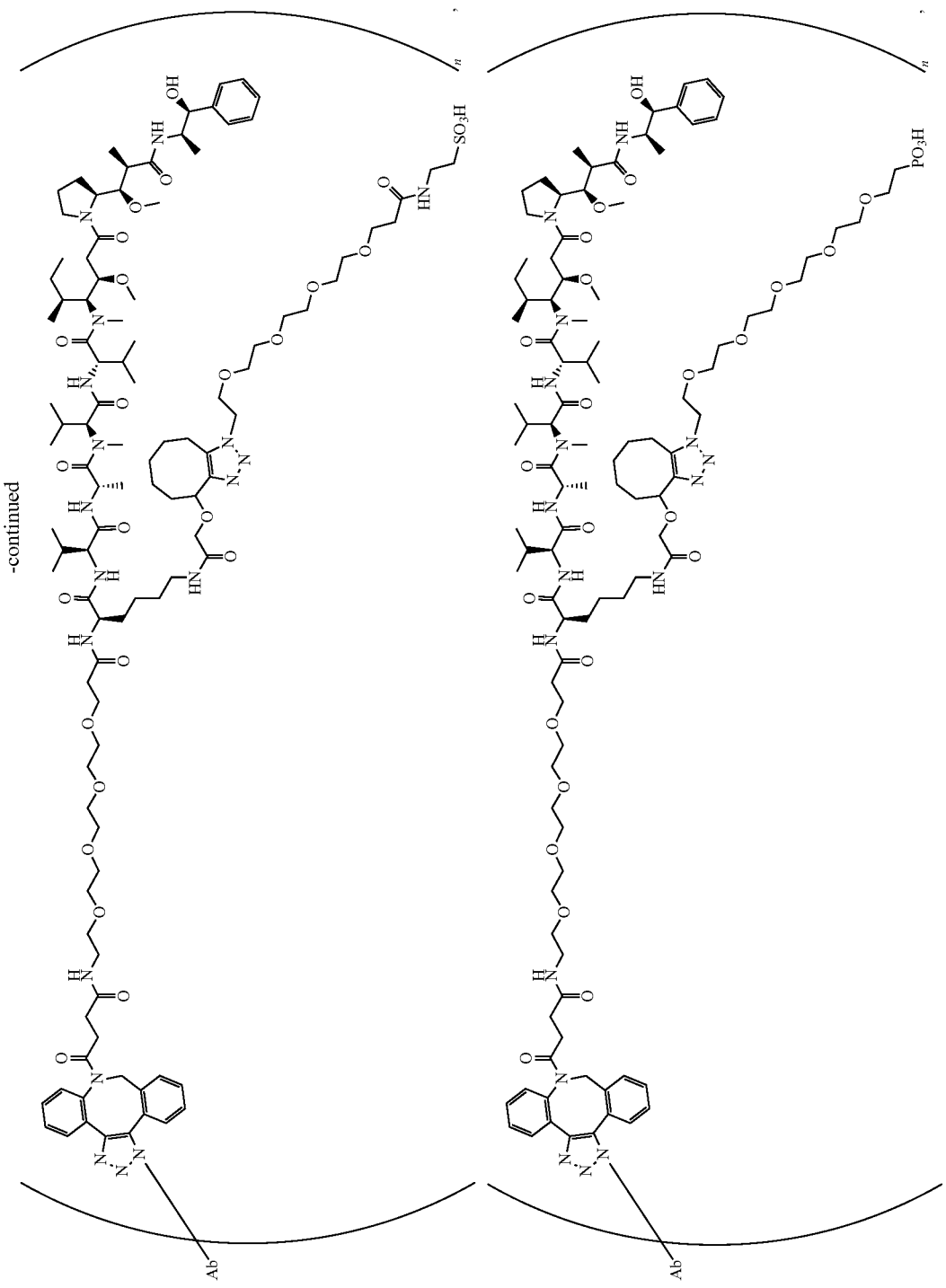

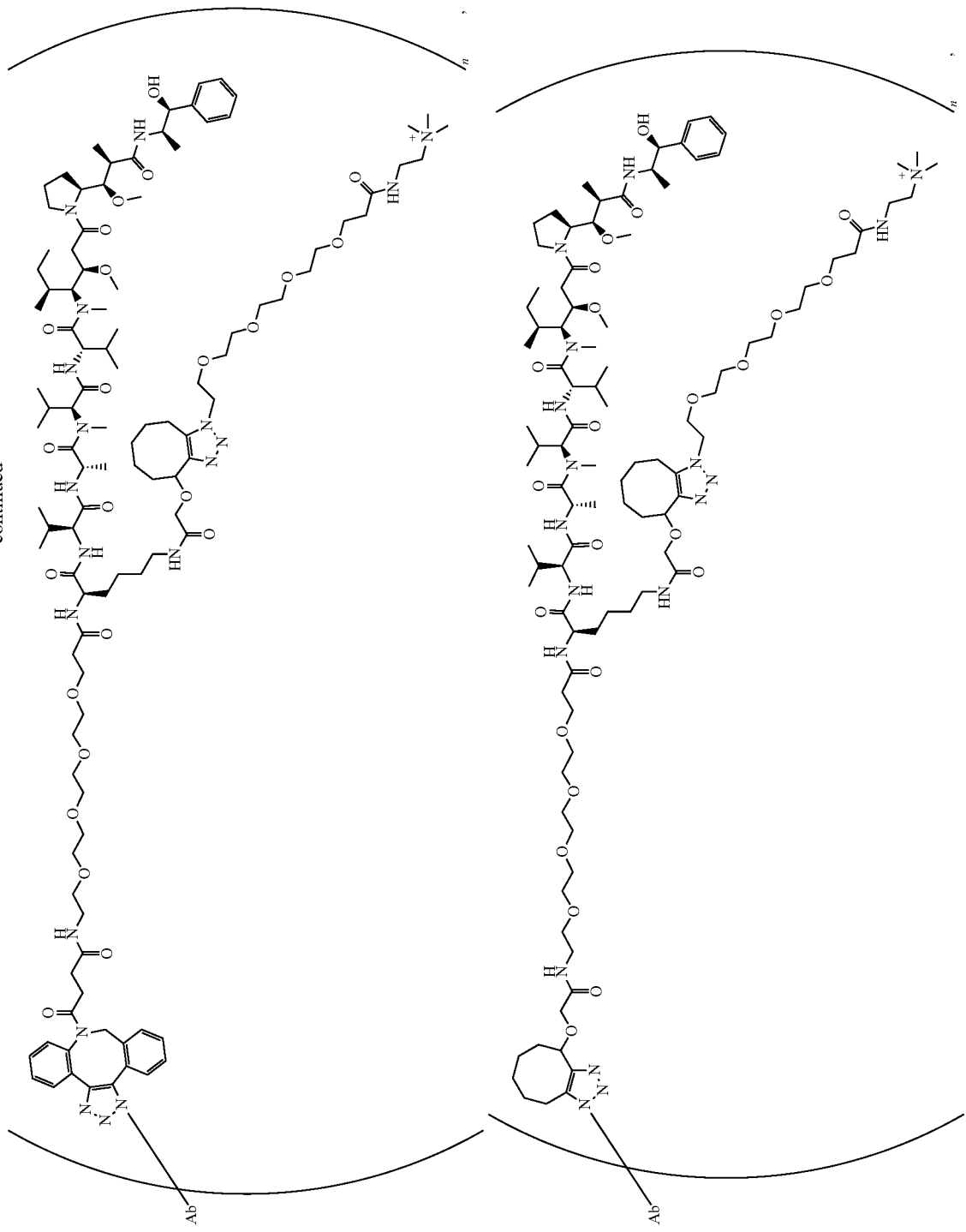

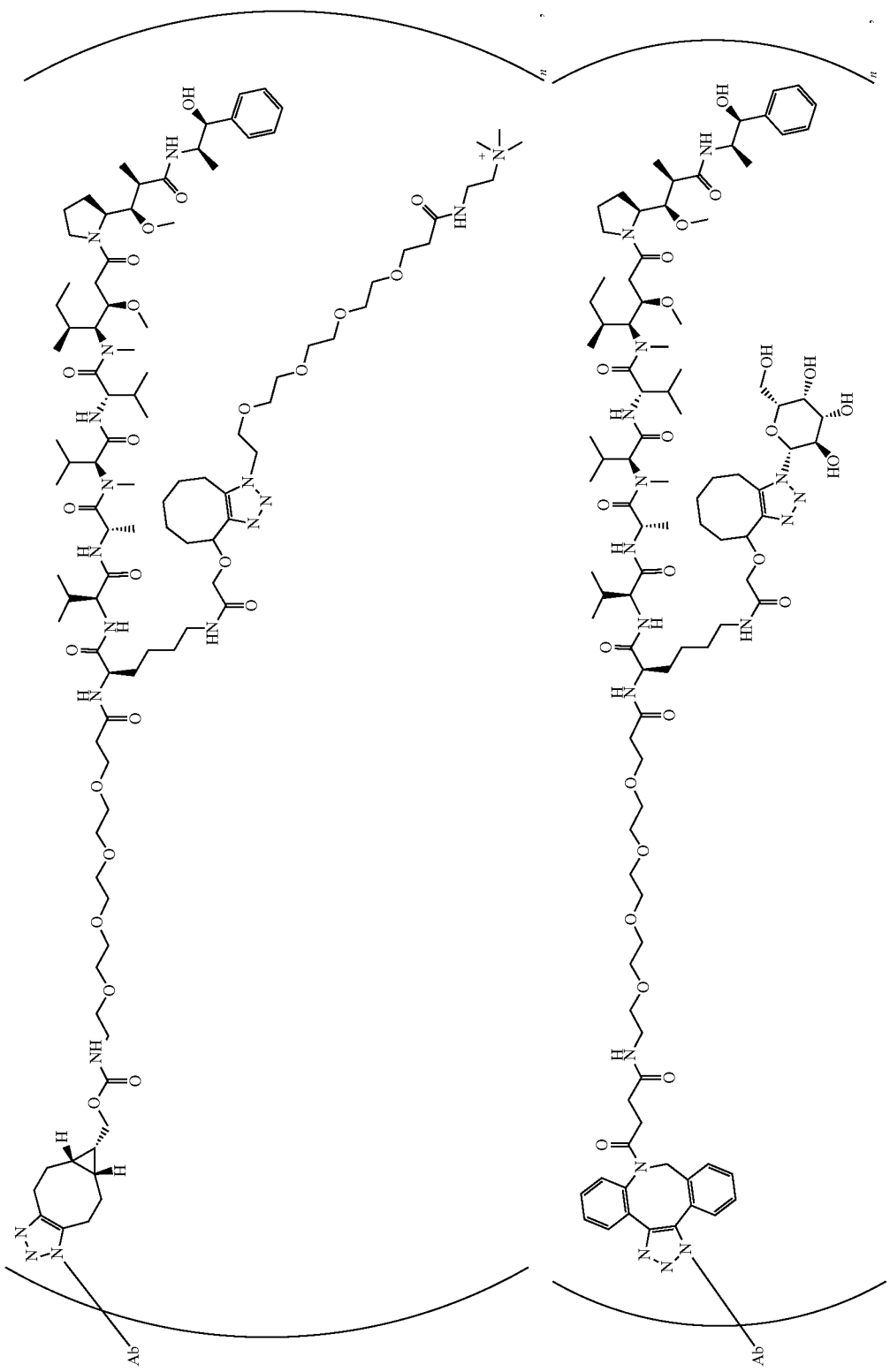

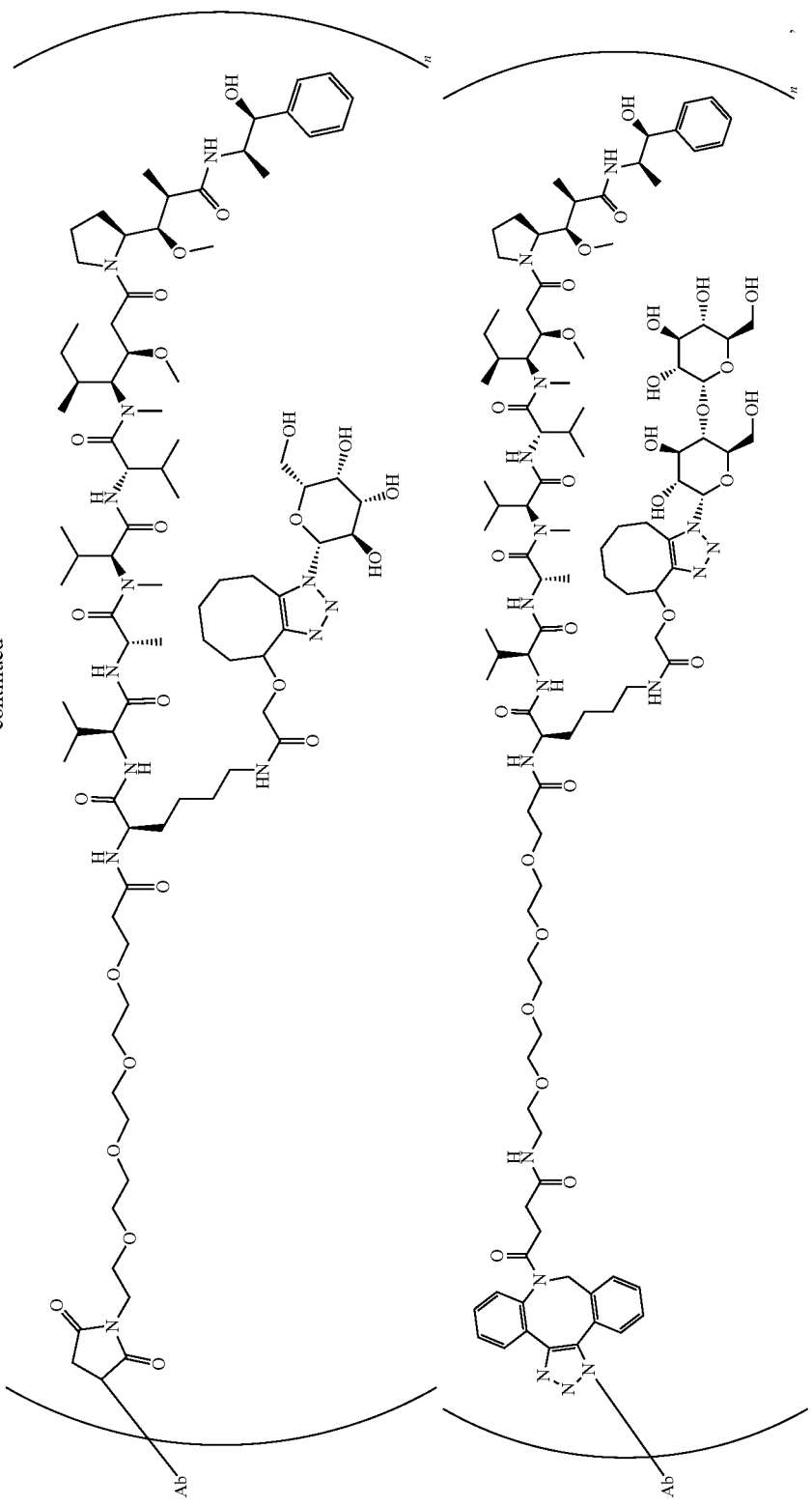

-continued
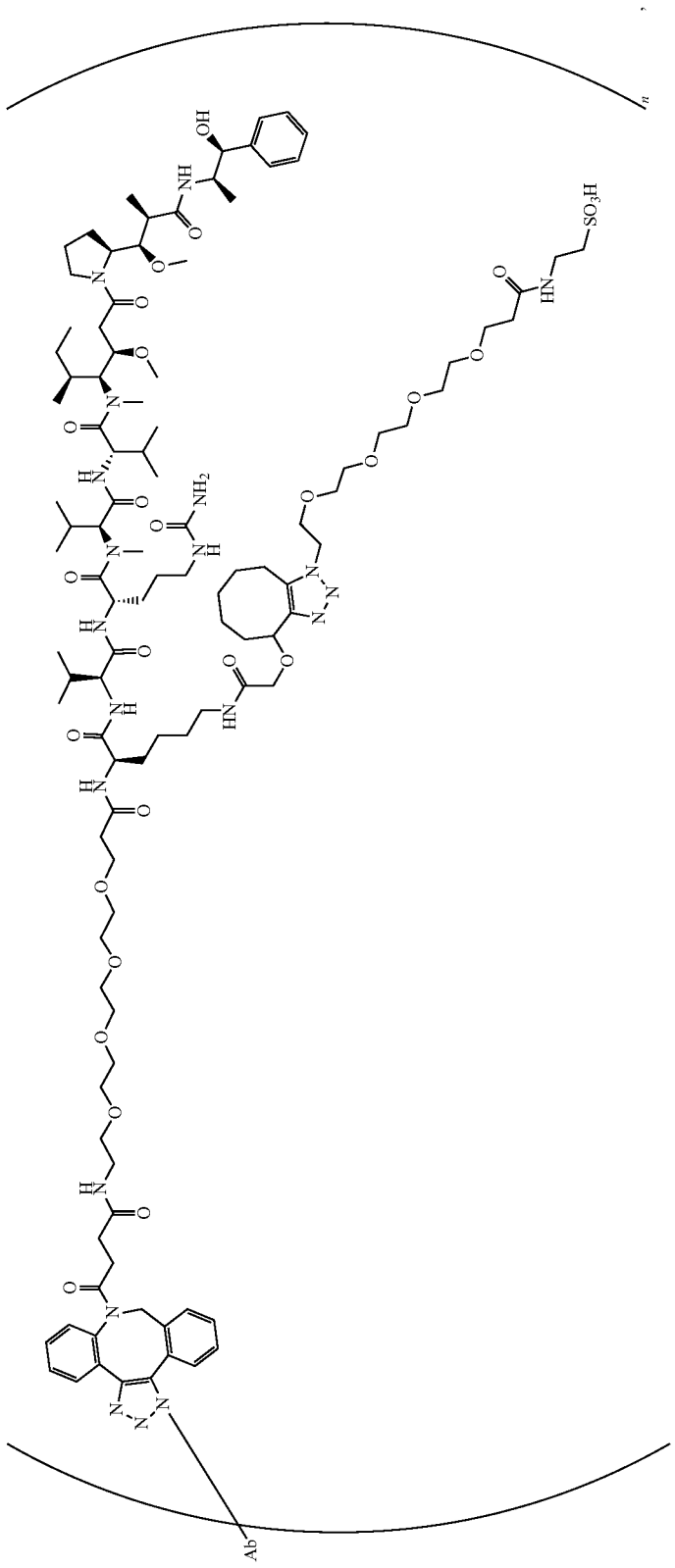

-continued
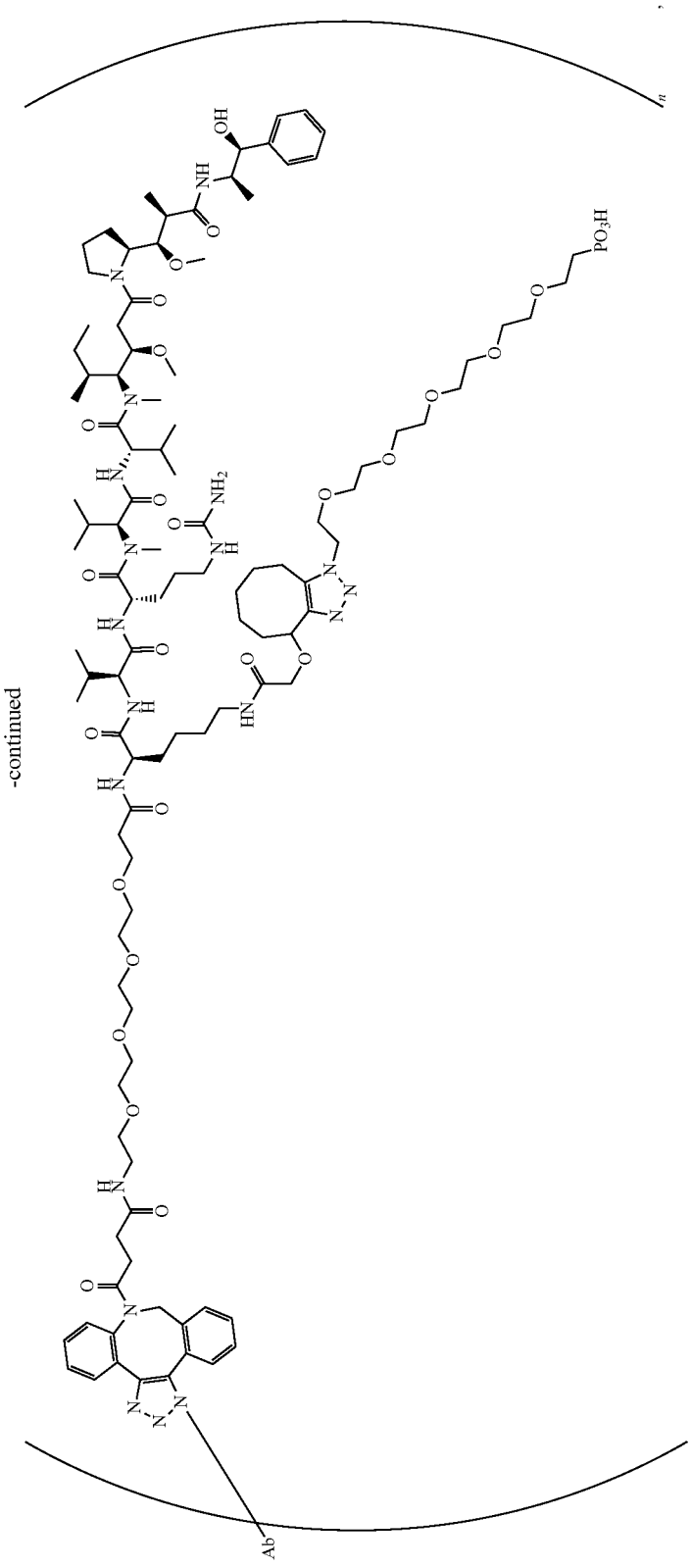
1101 1102

-continued
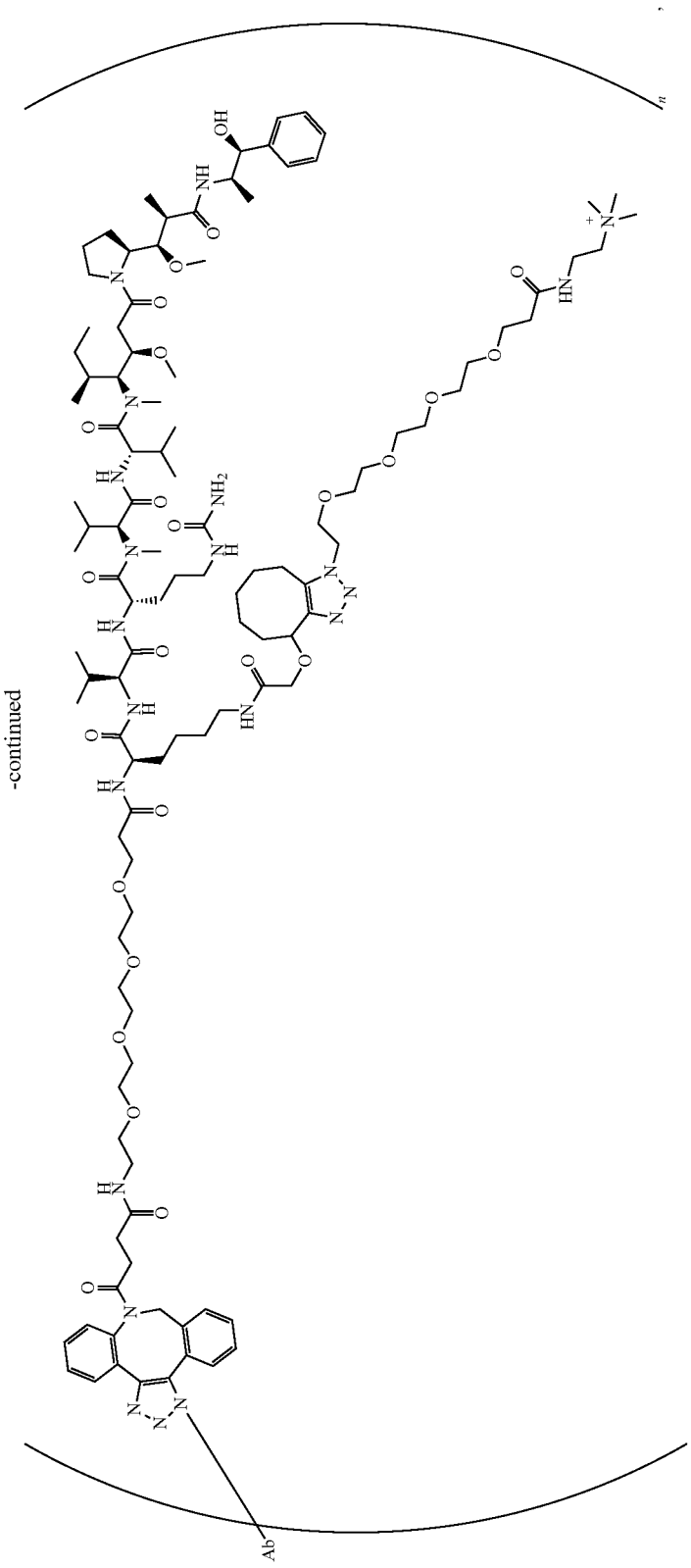

-continued
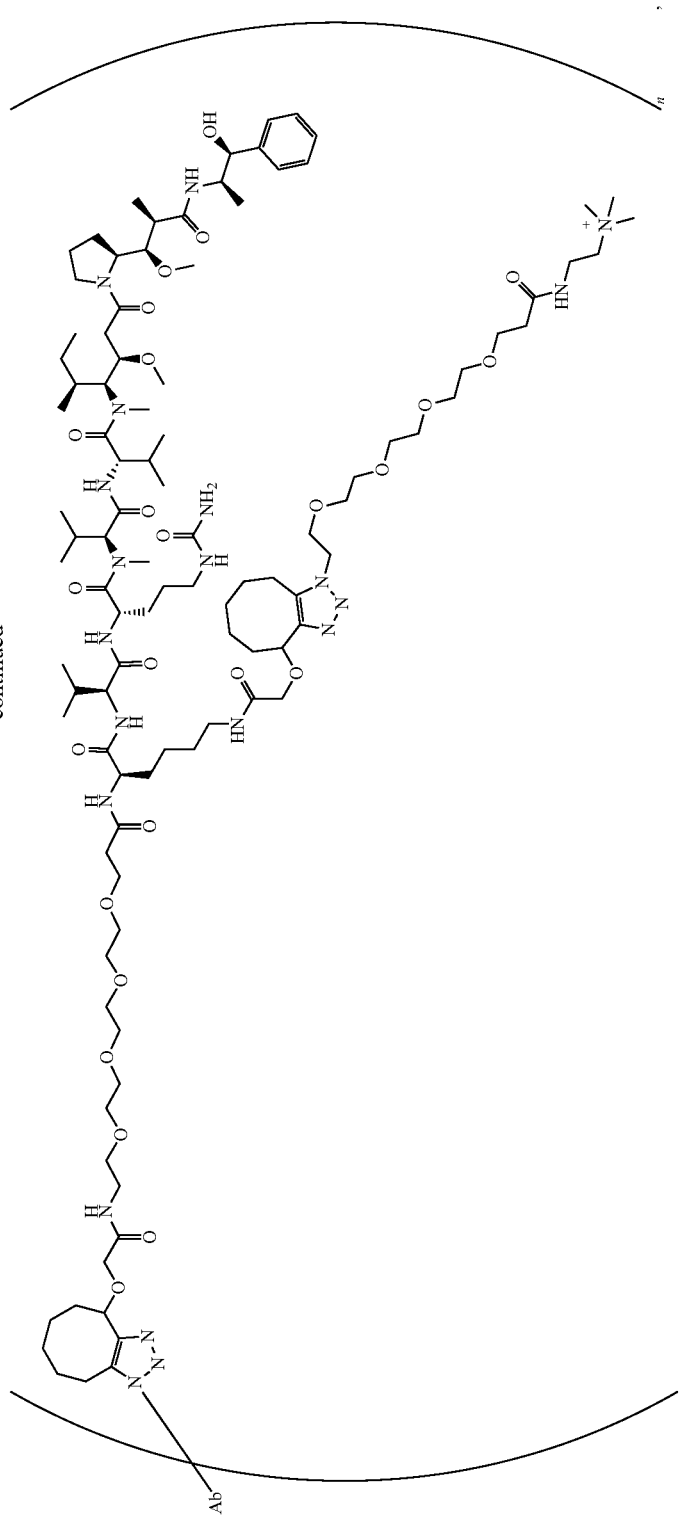

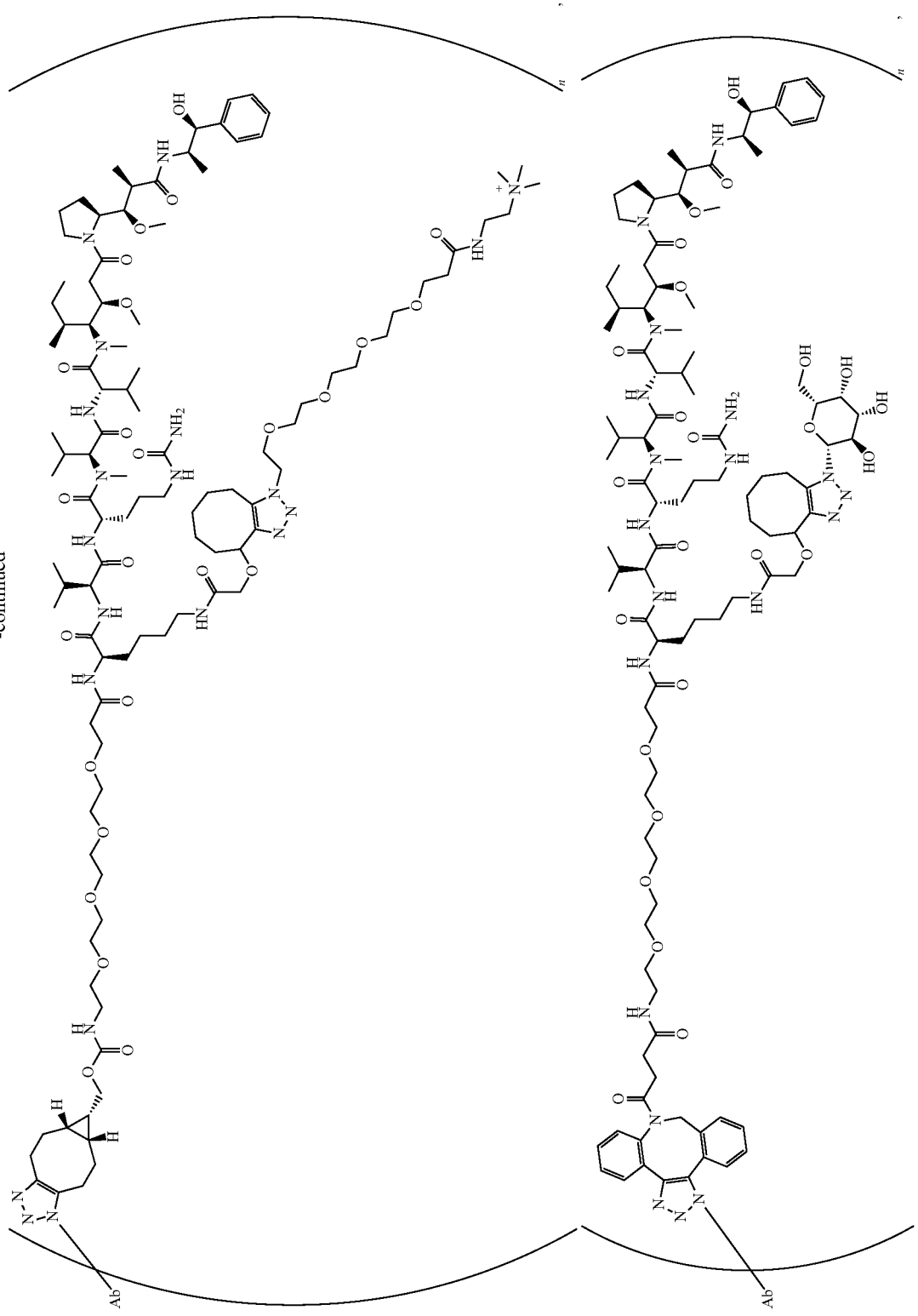

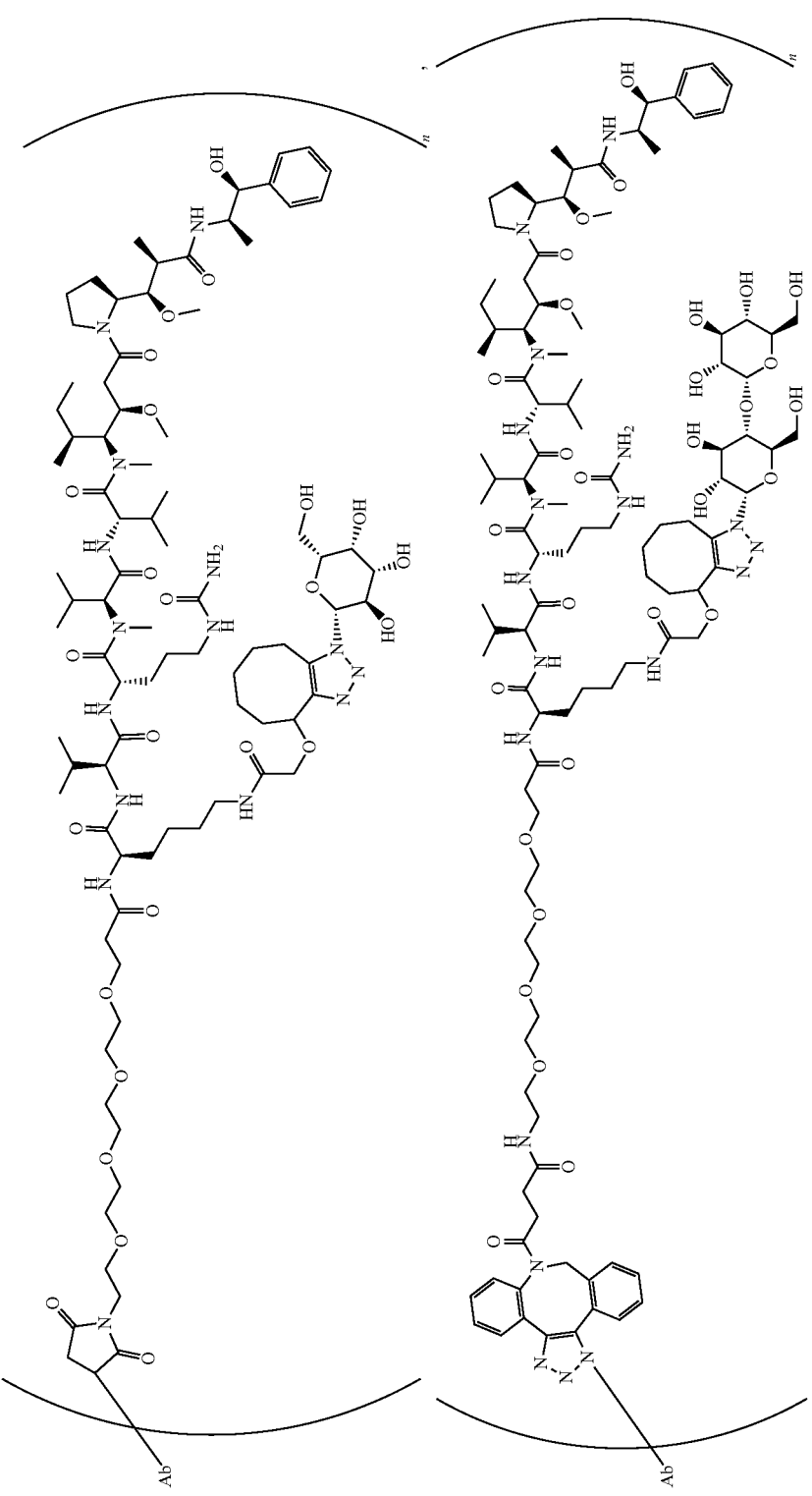

1111　　　　　　　　　　　1112
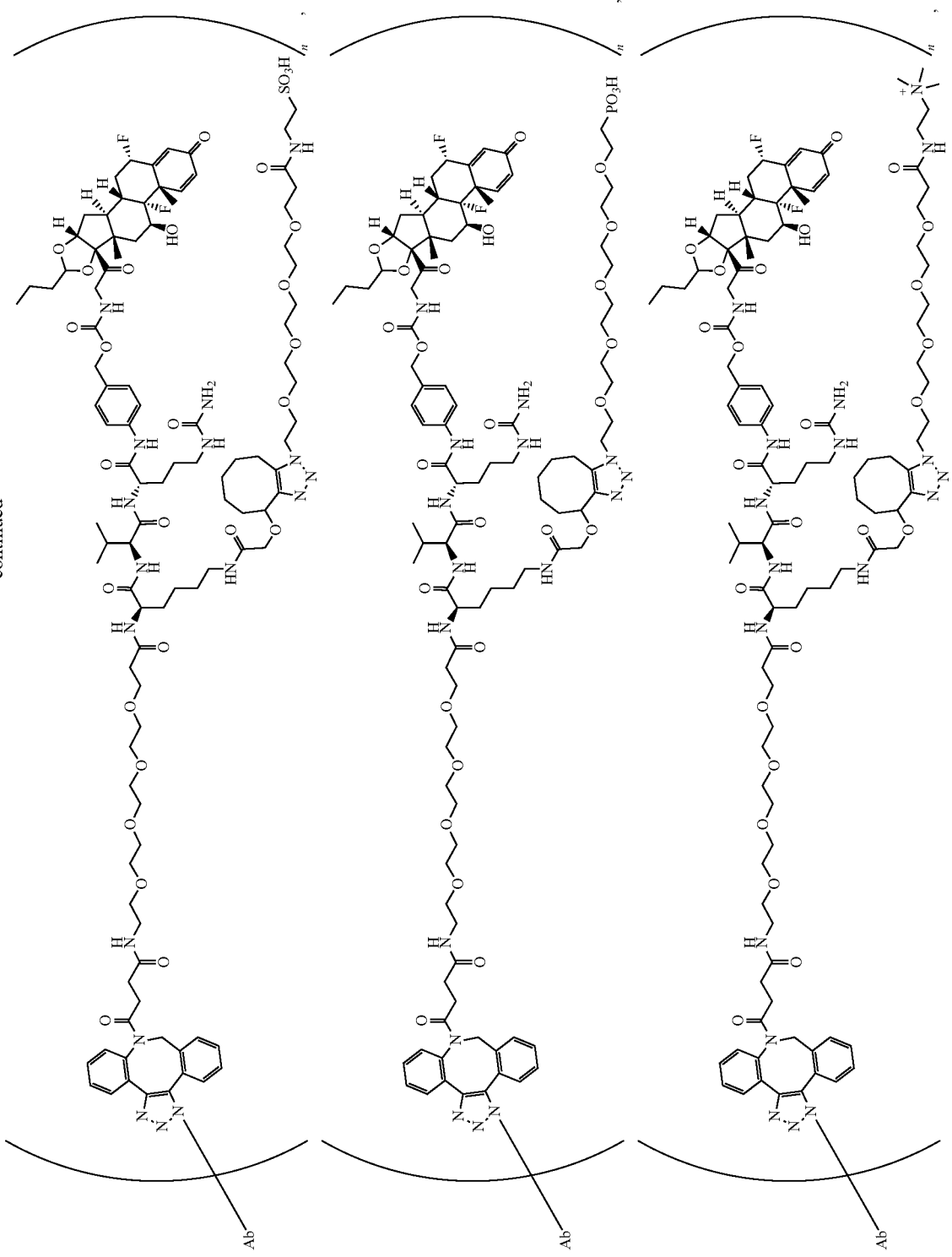

-continued
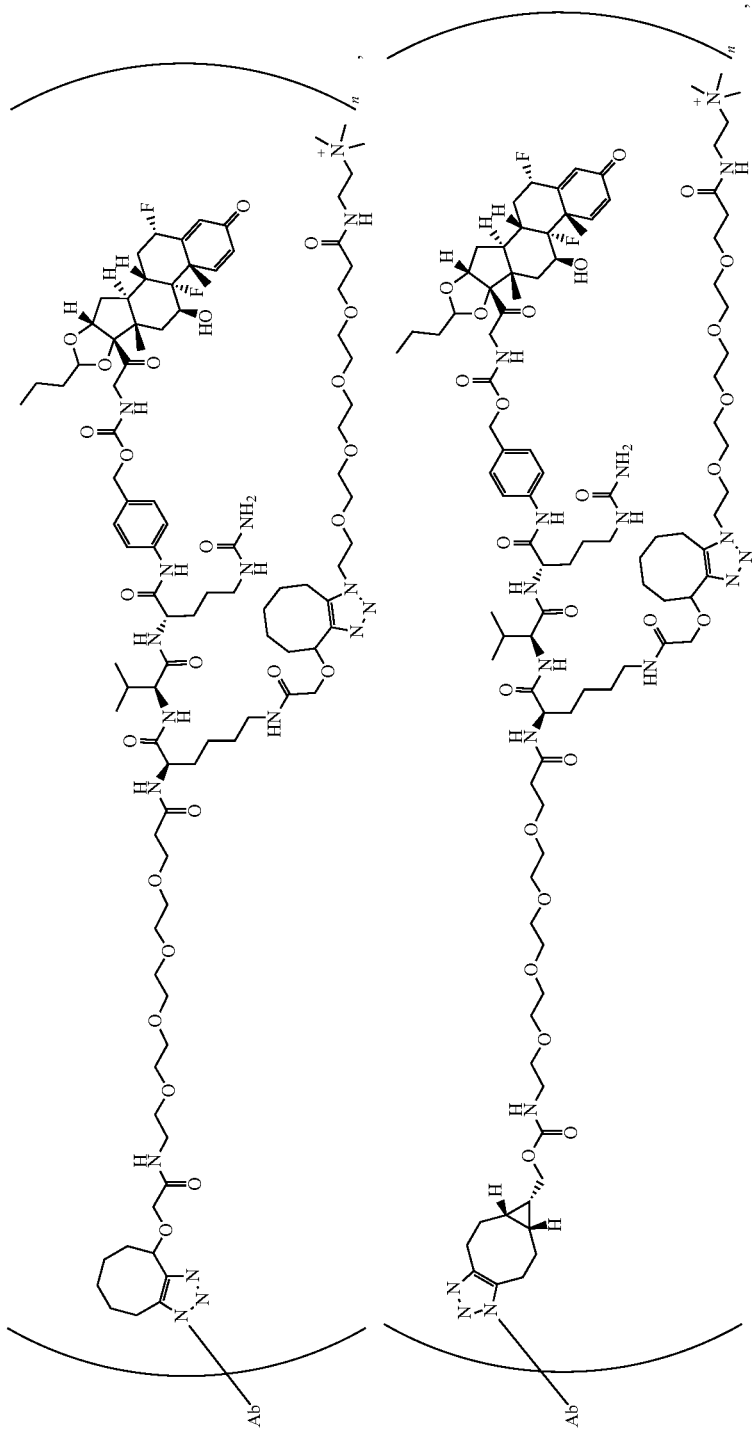

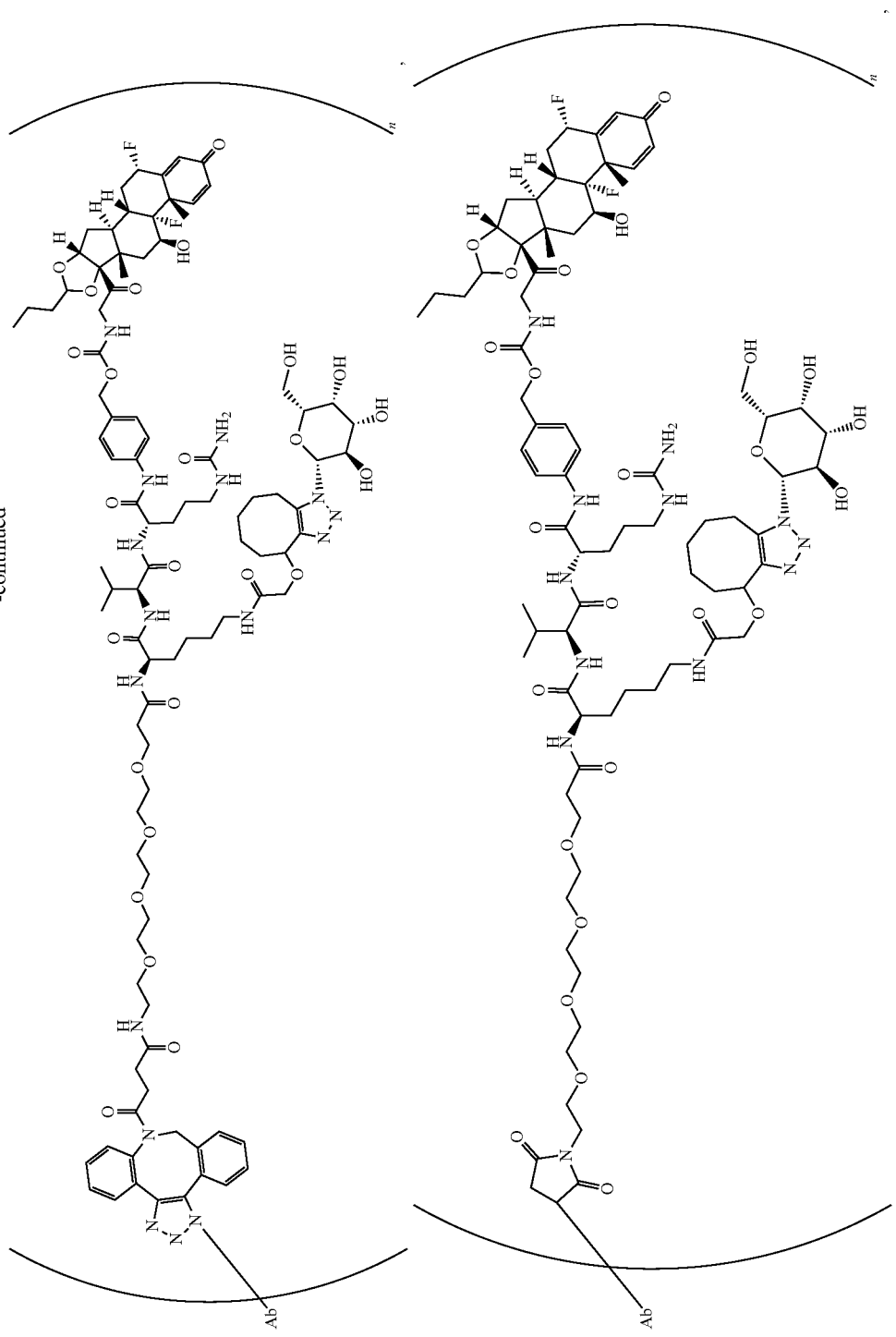

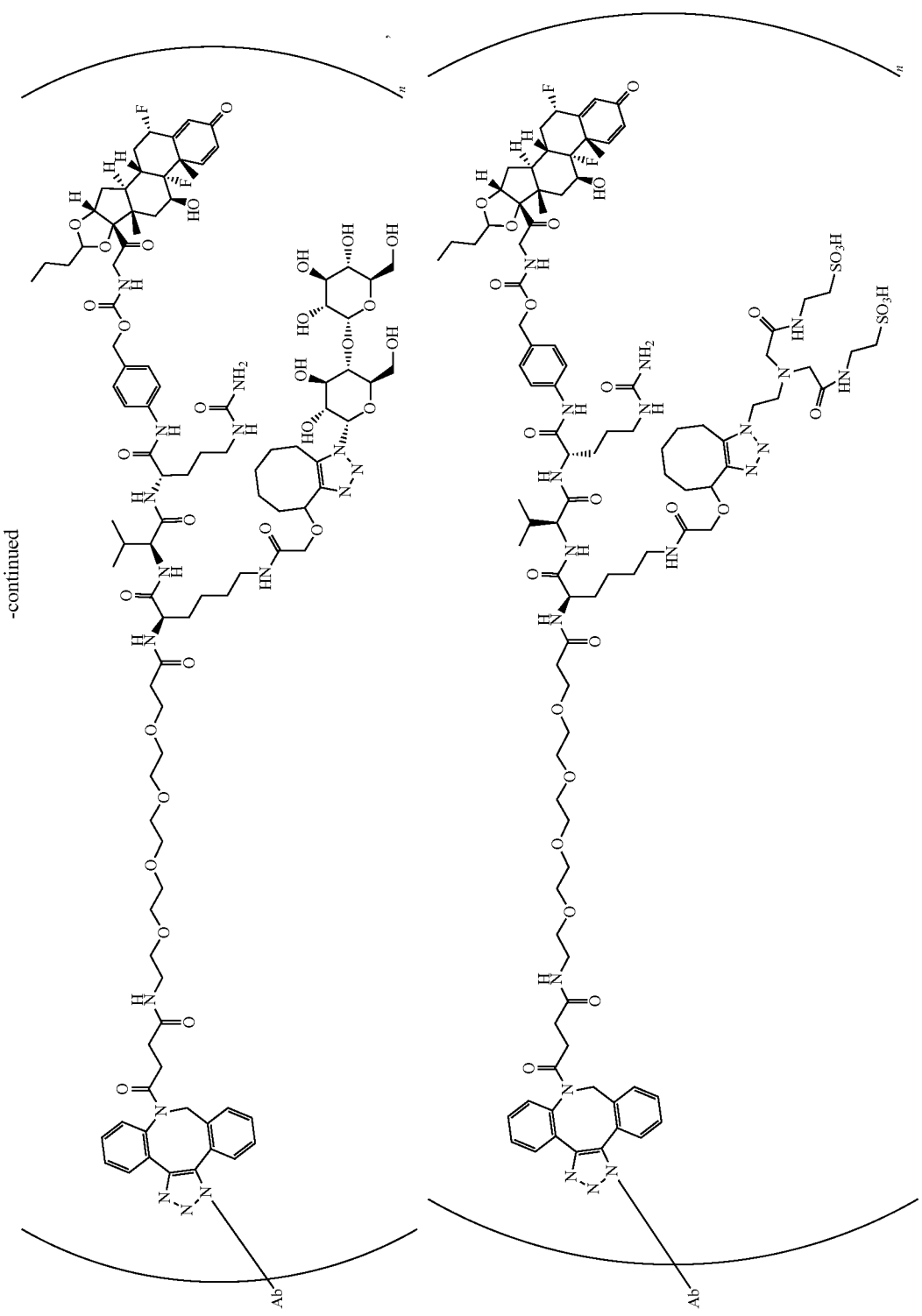

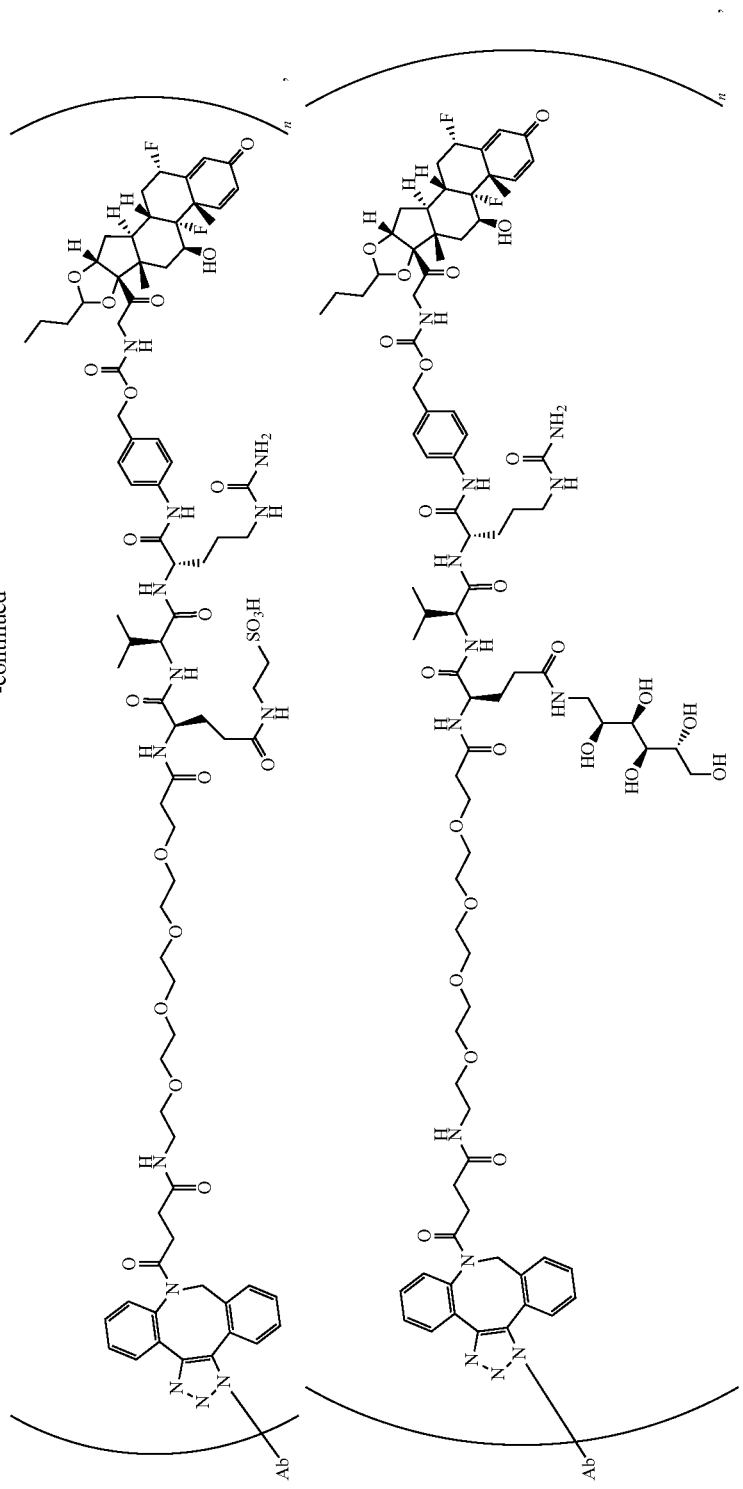

1121 1122
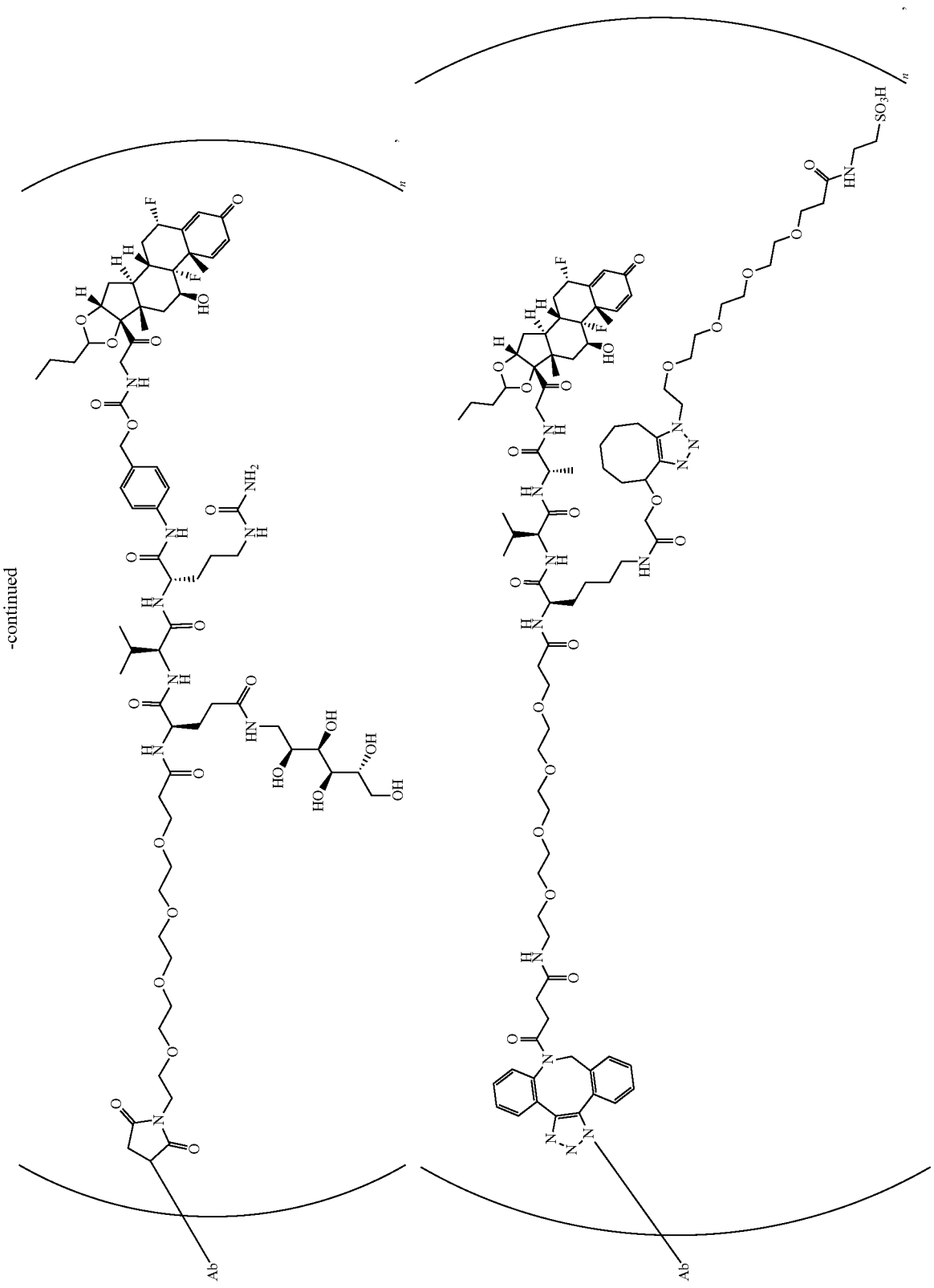

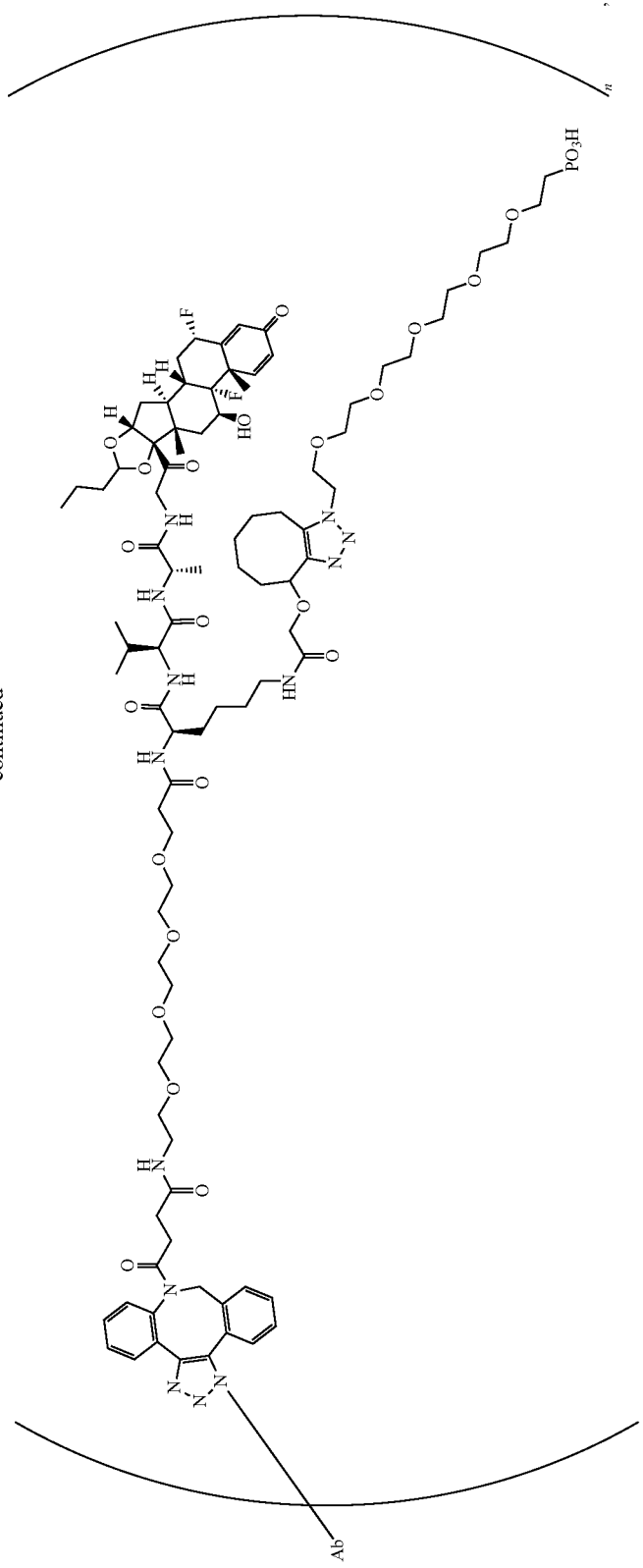

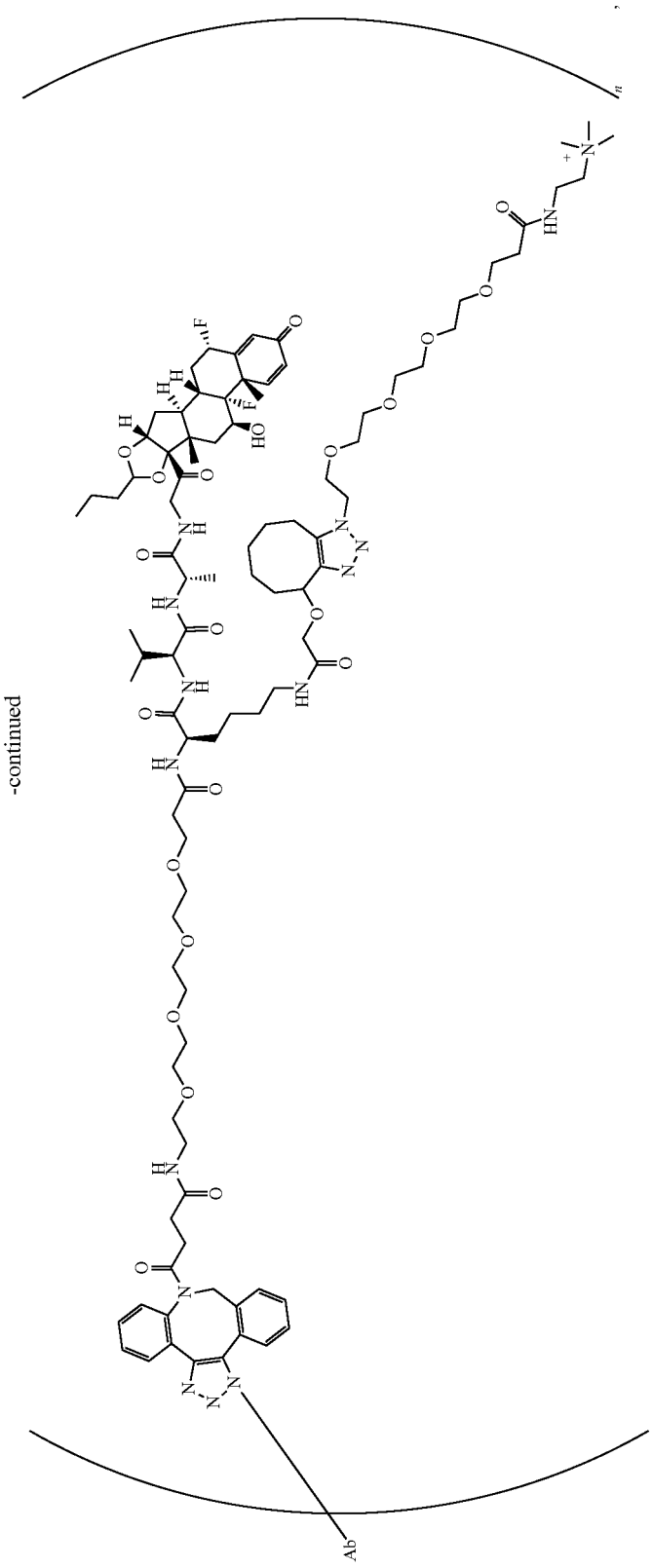

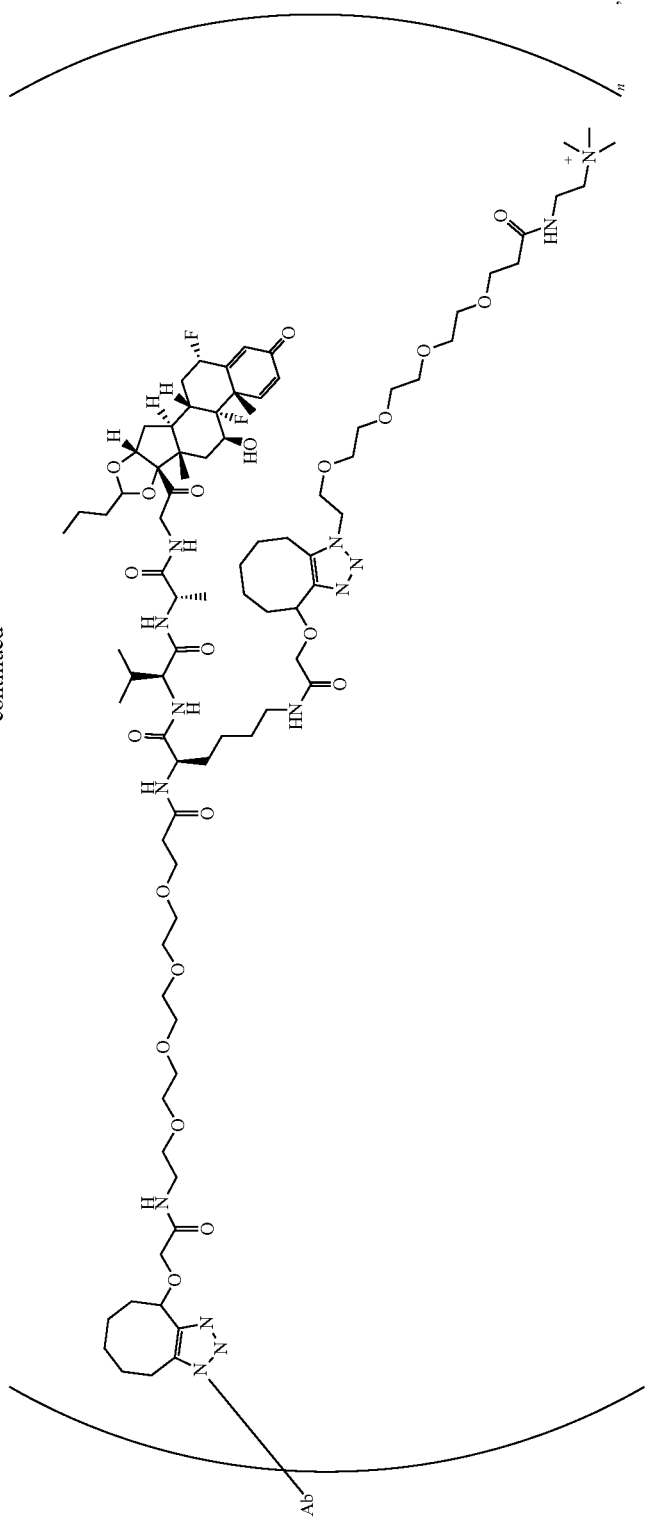

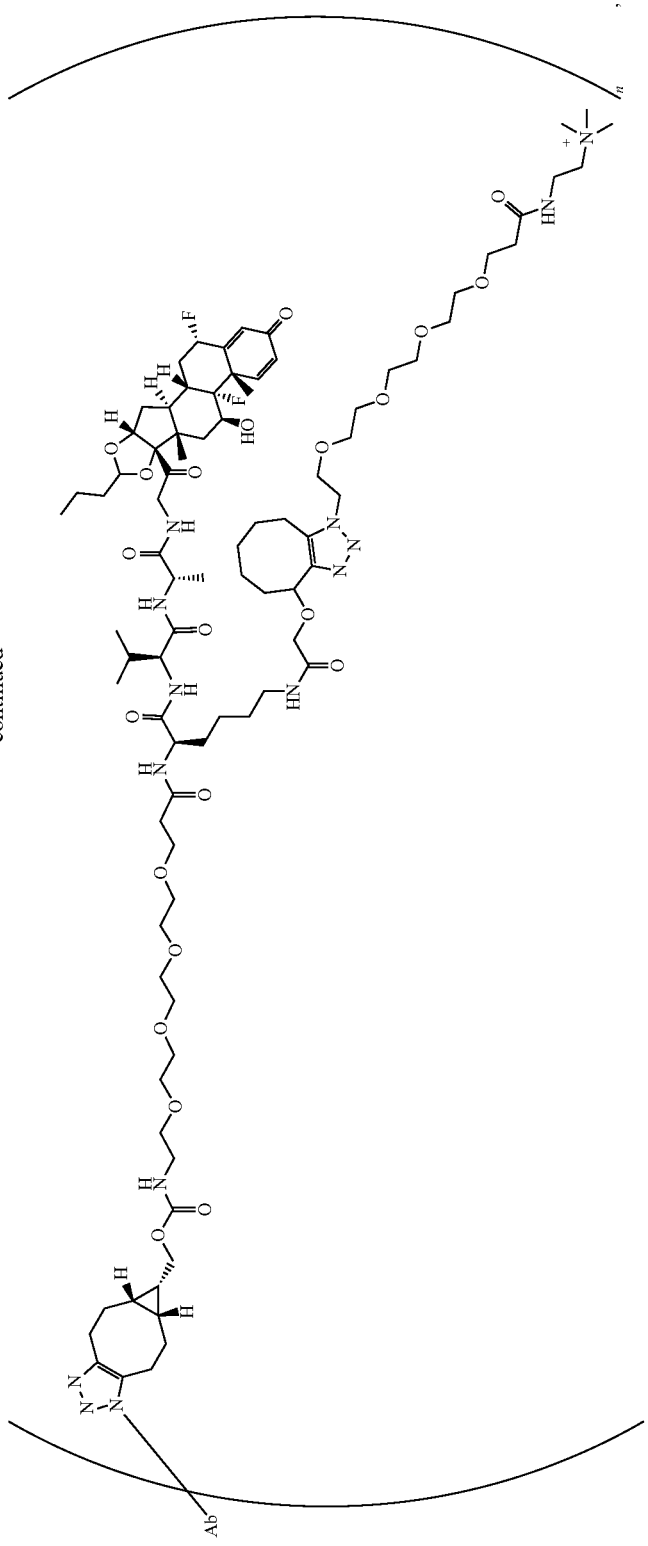

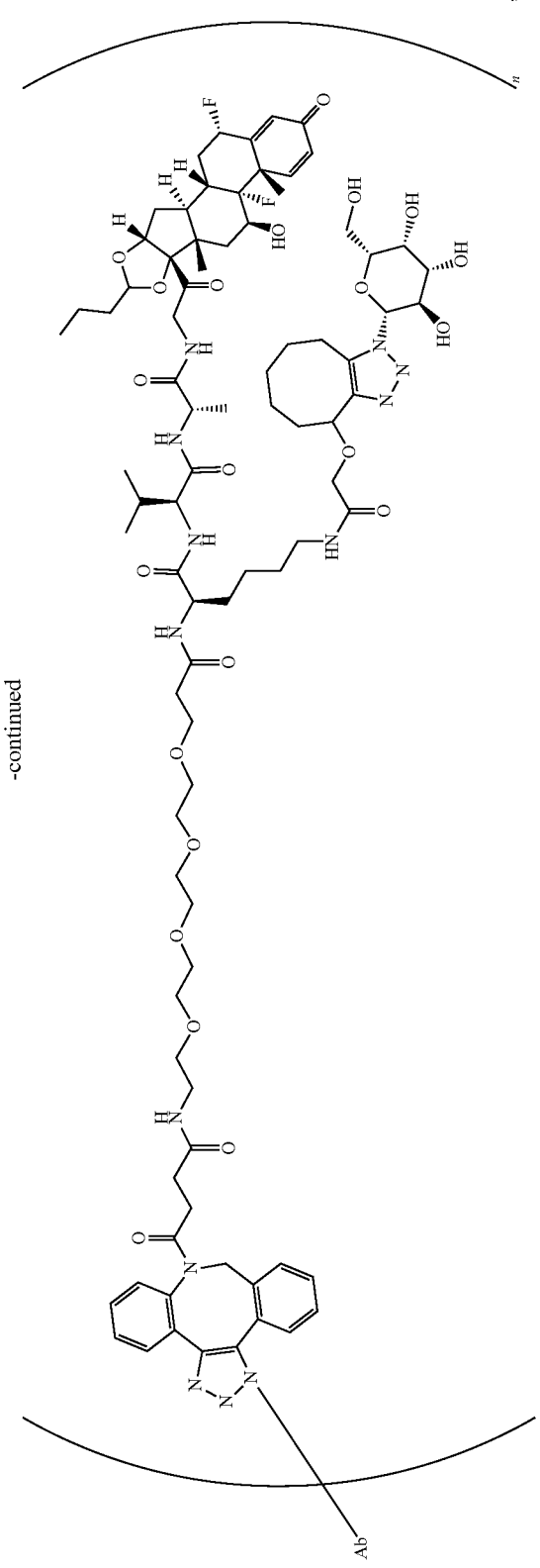

-continued
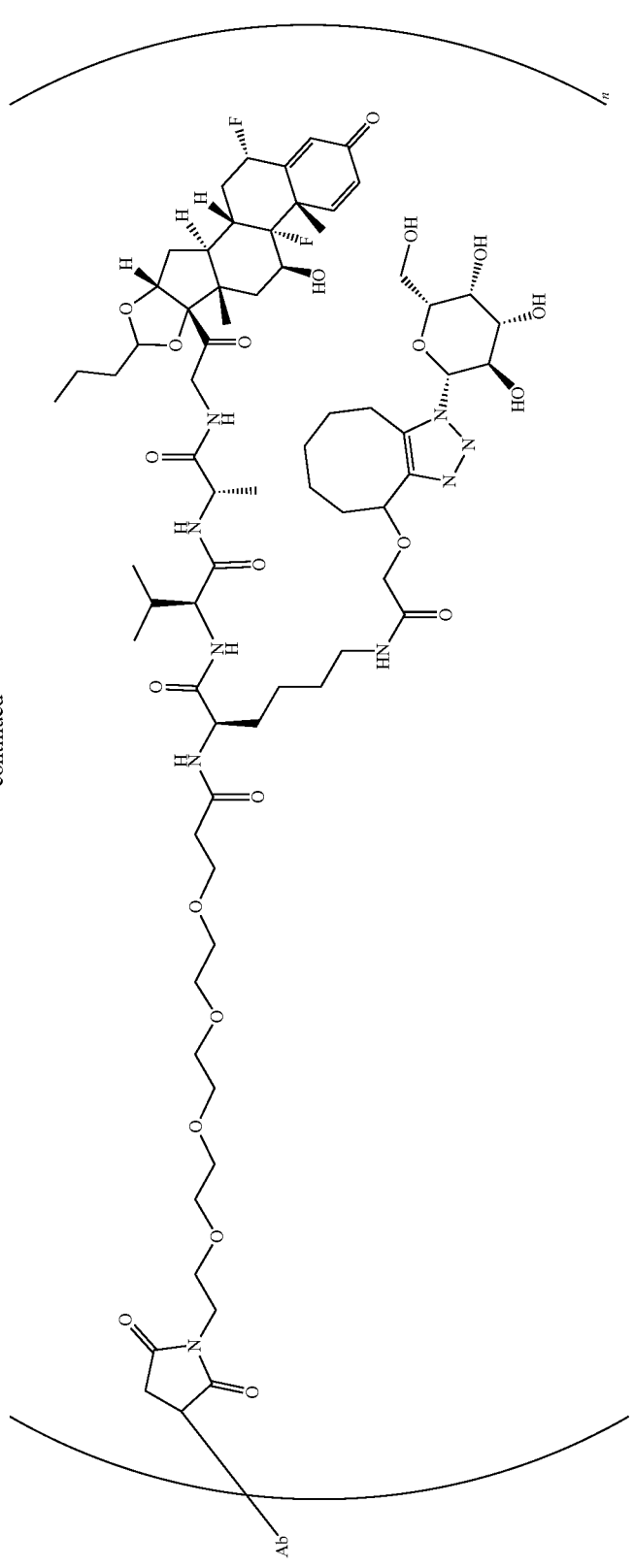

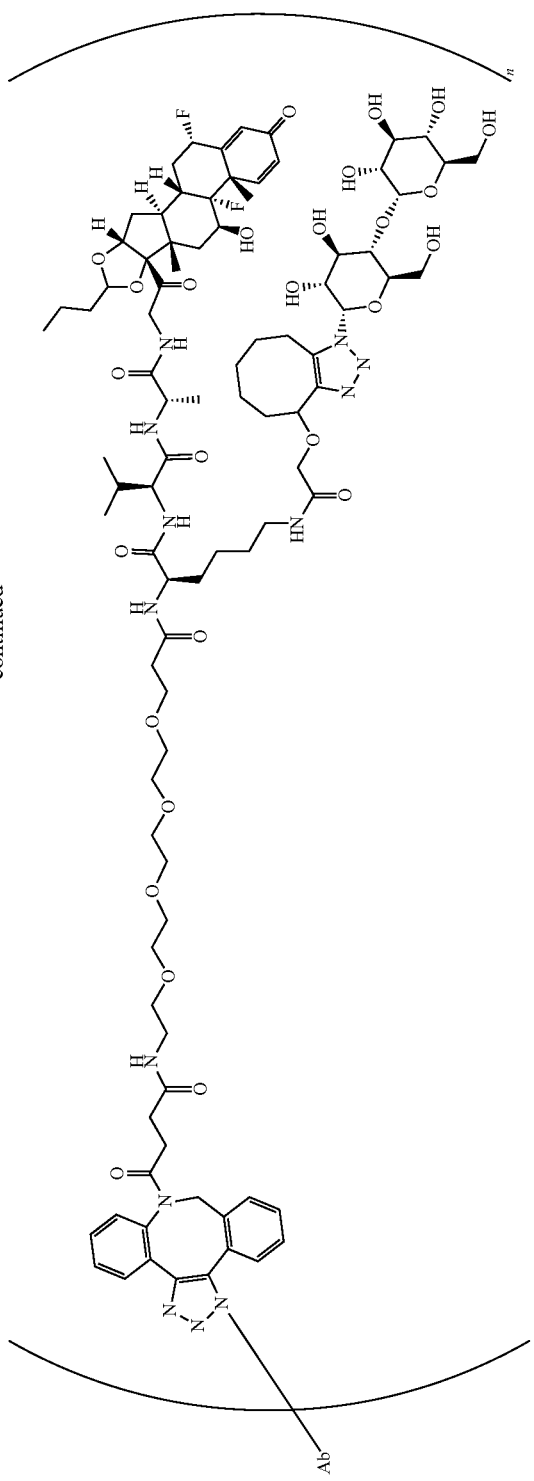

-continued
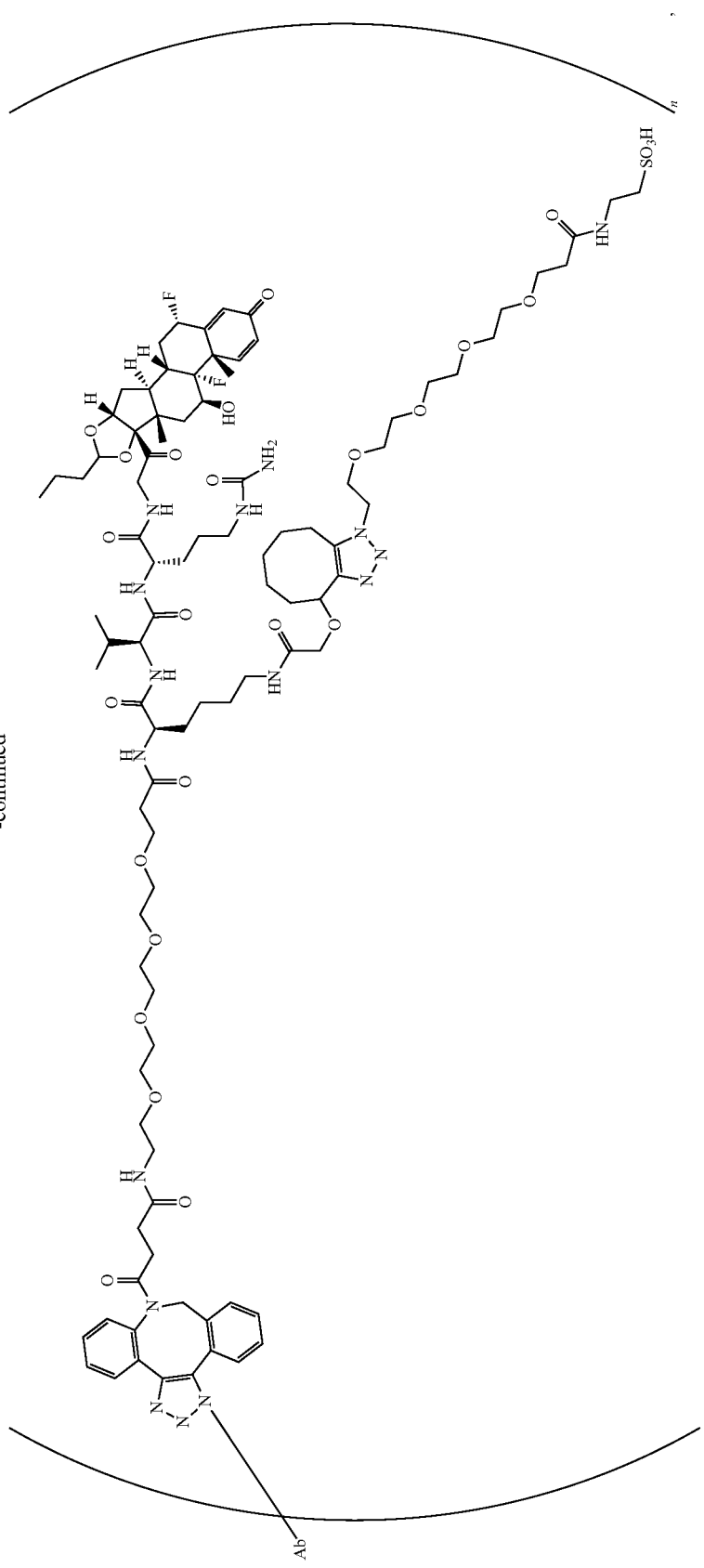

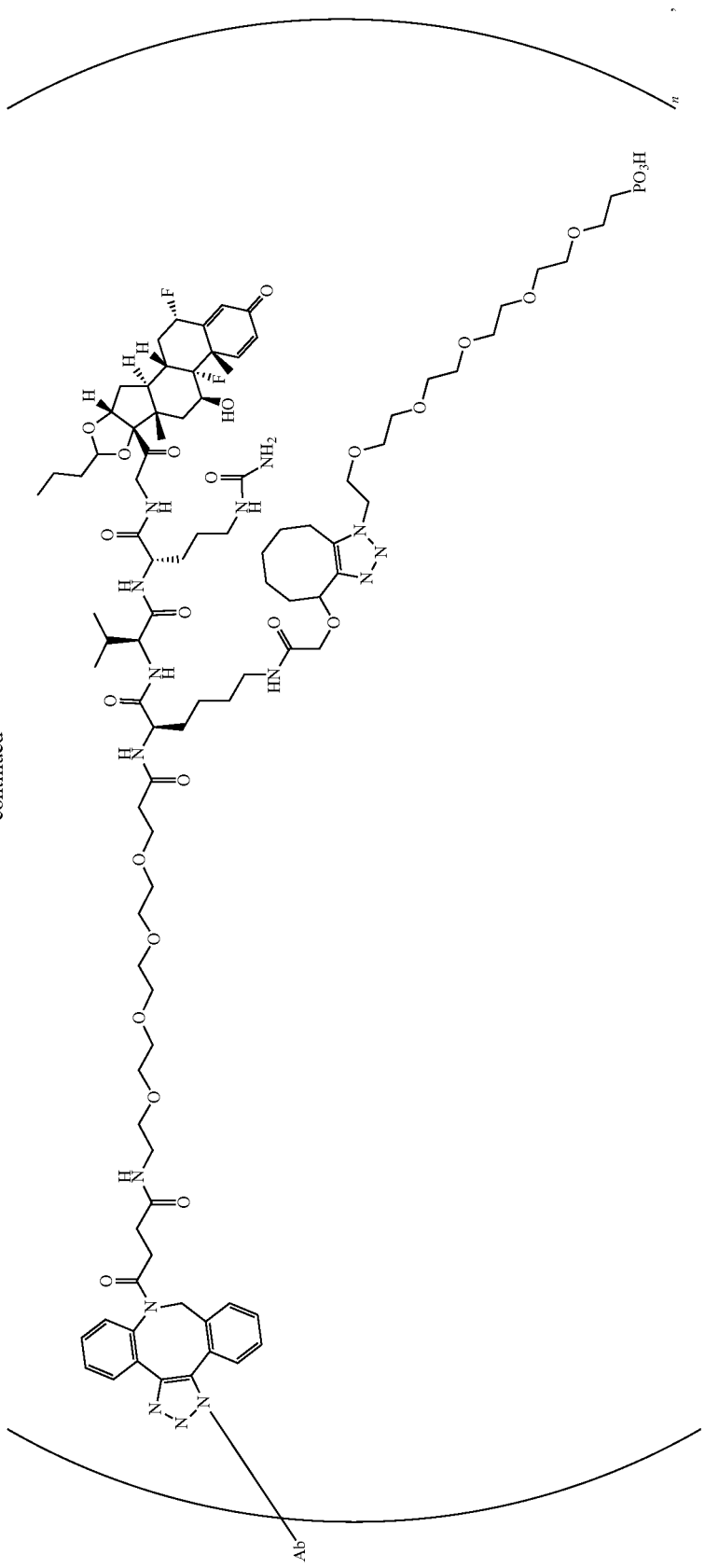

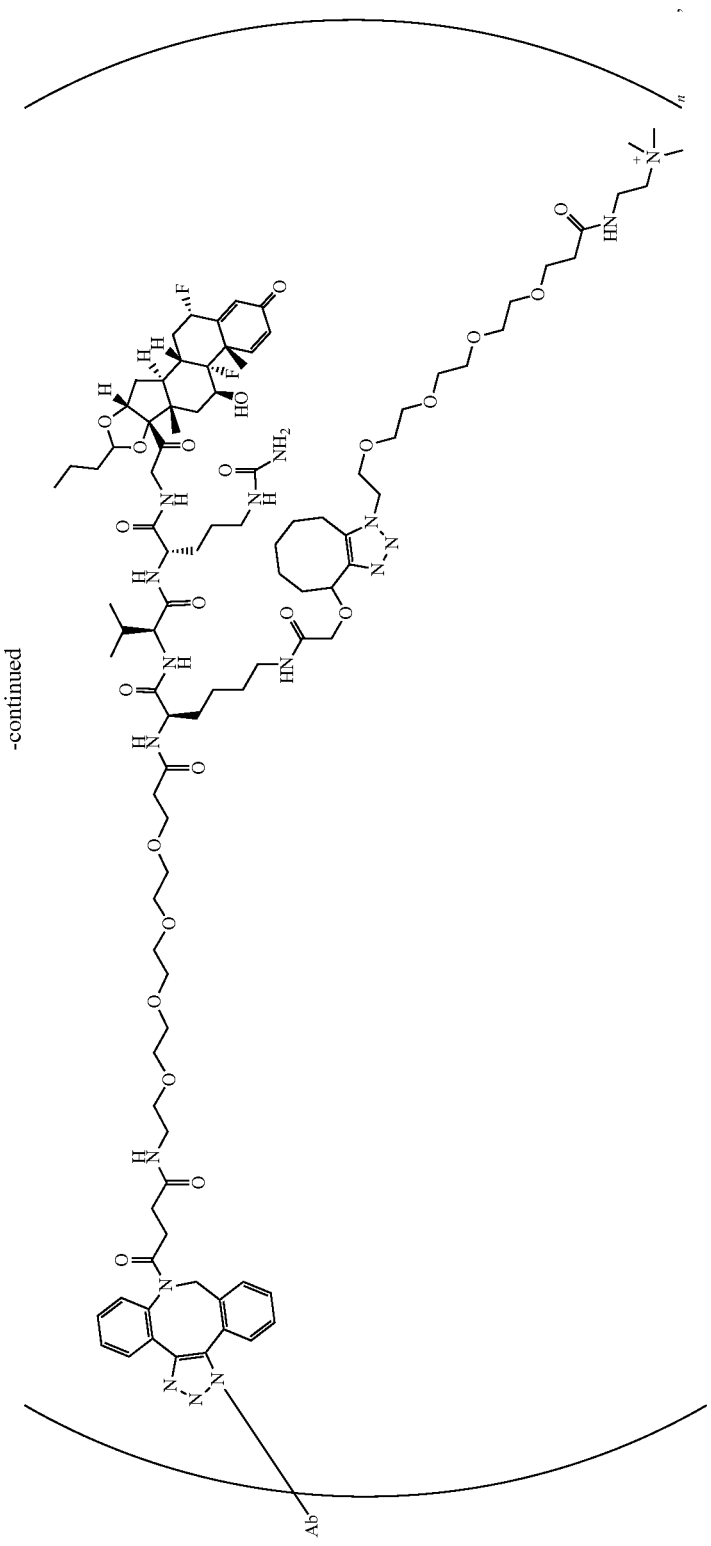

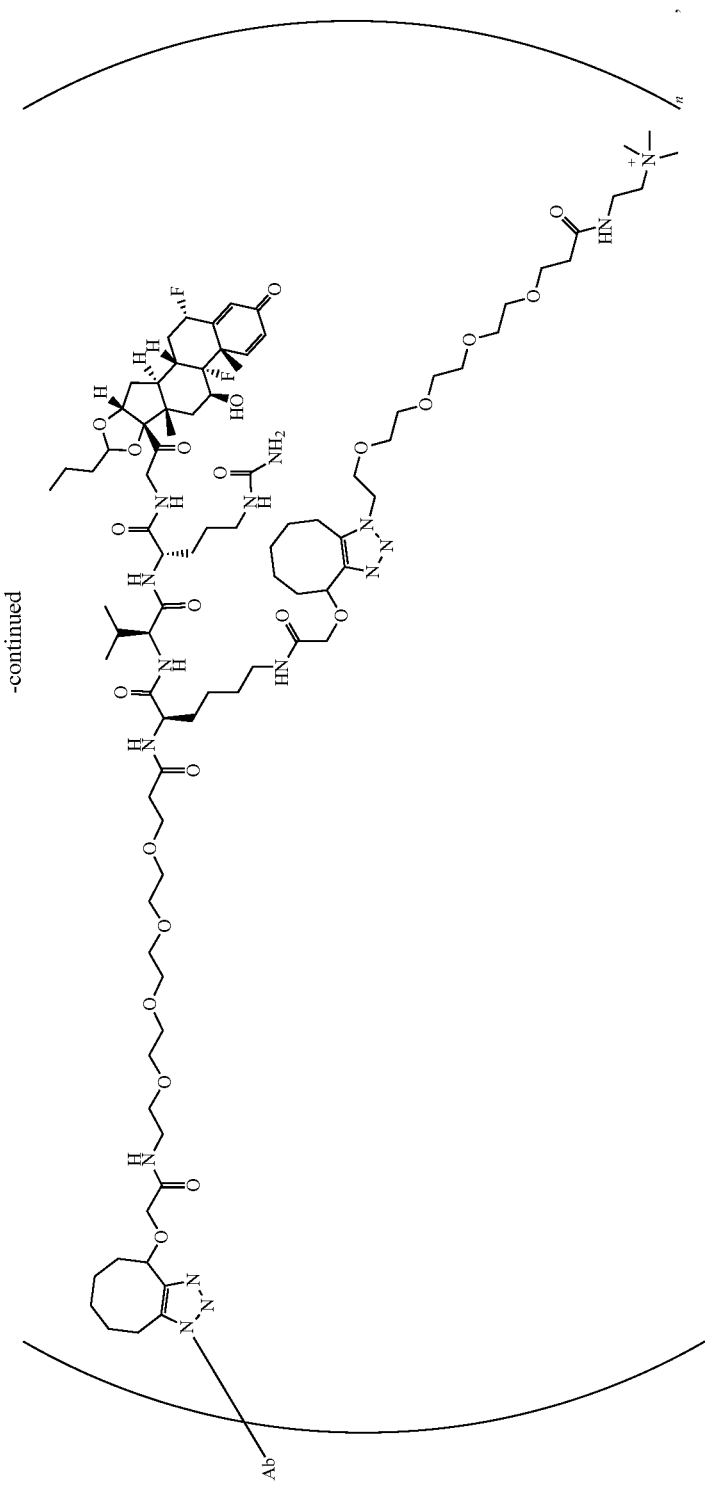

-continued
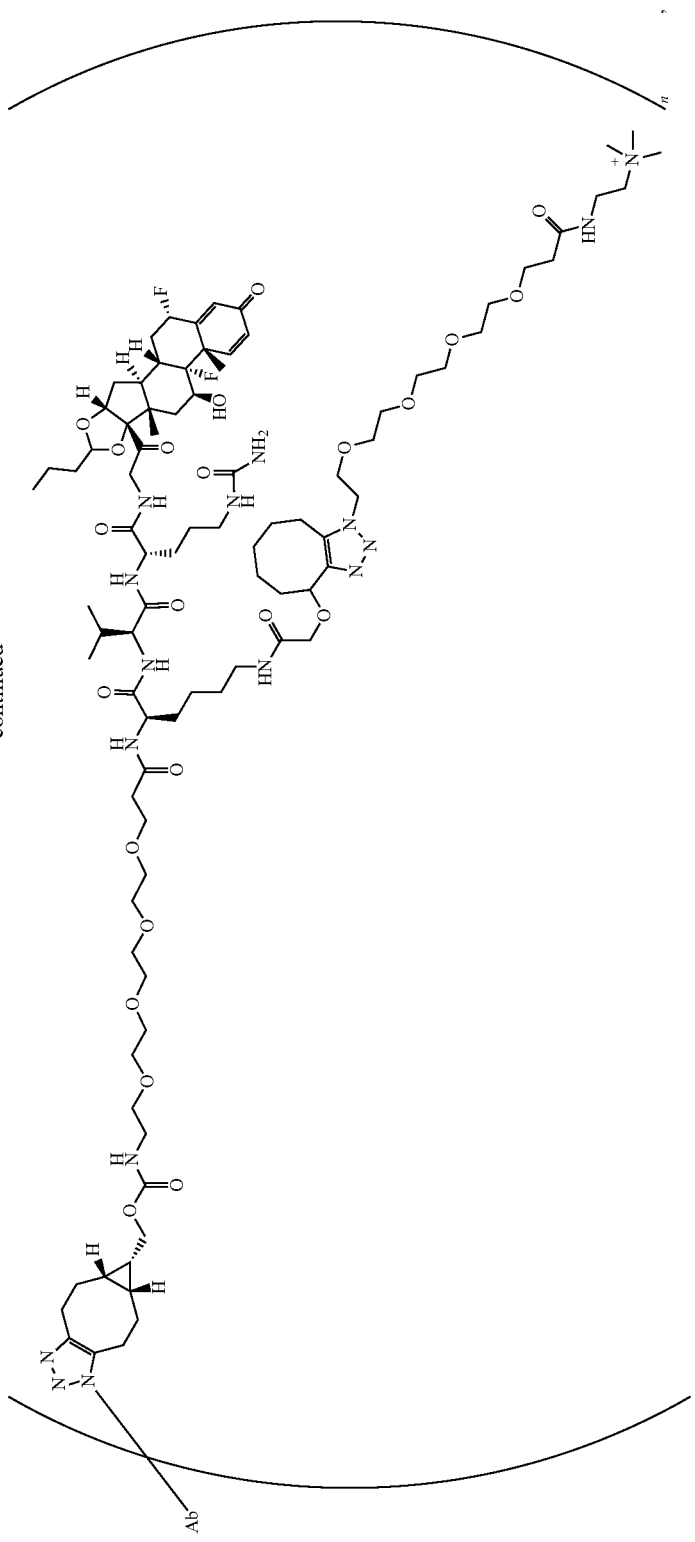

-continued
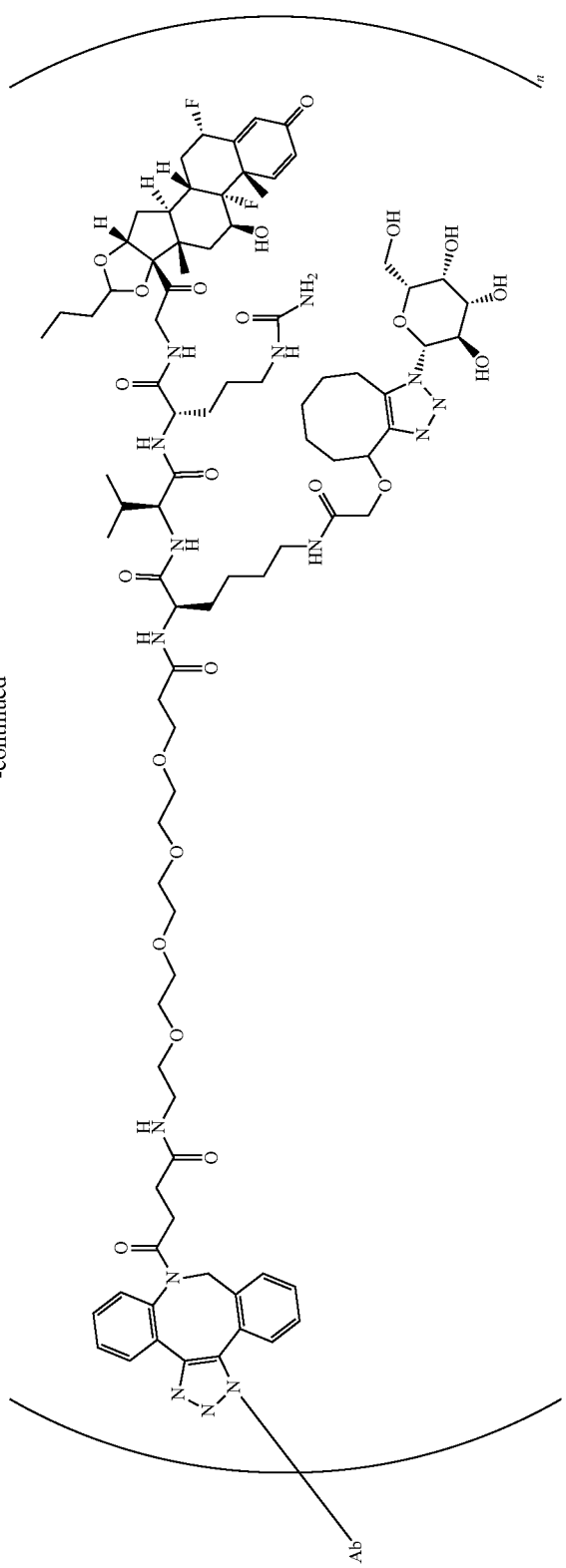

-continued
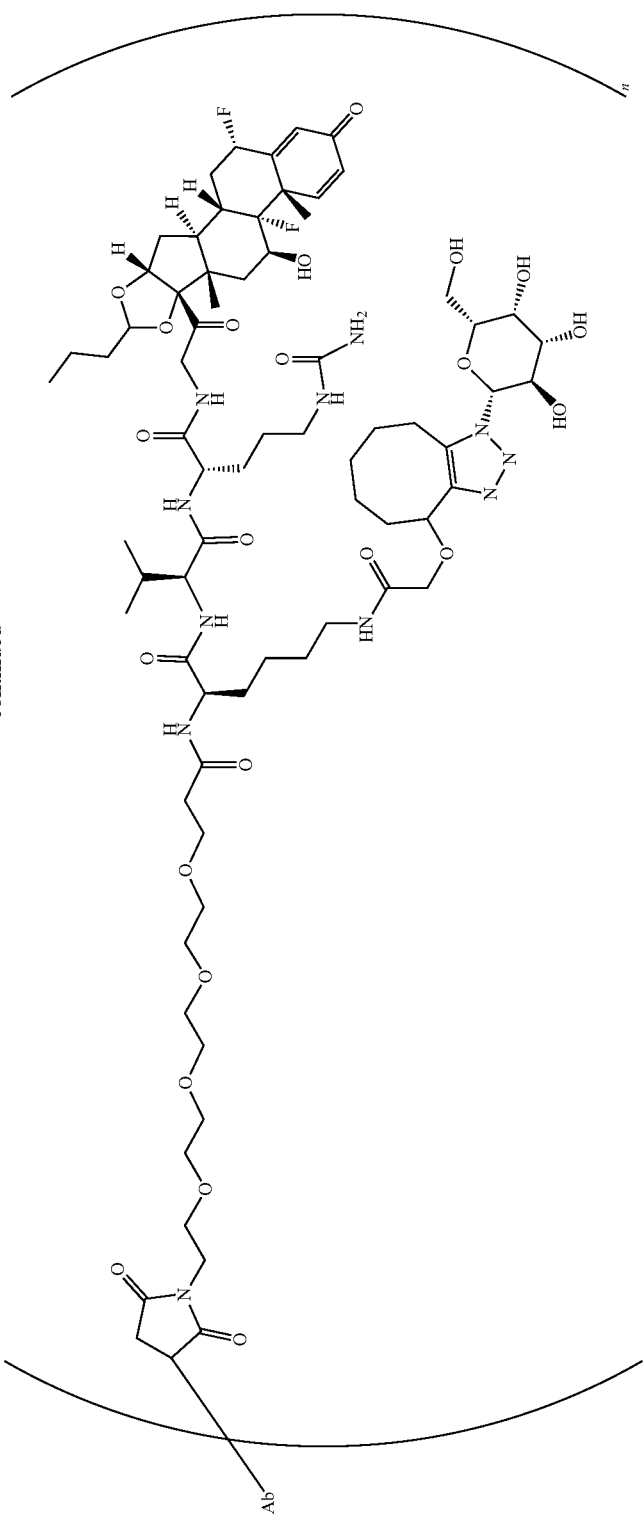

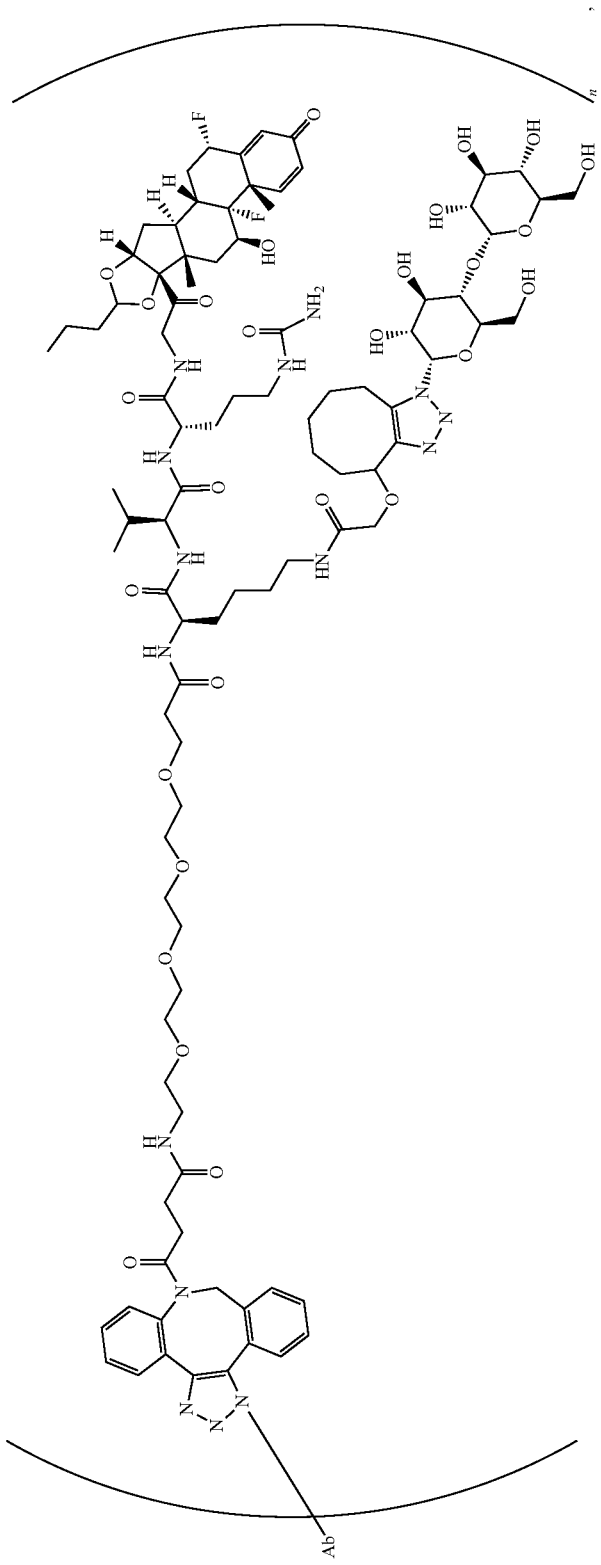

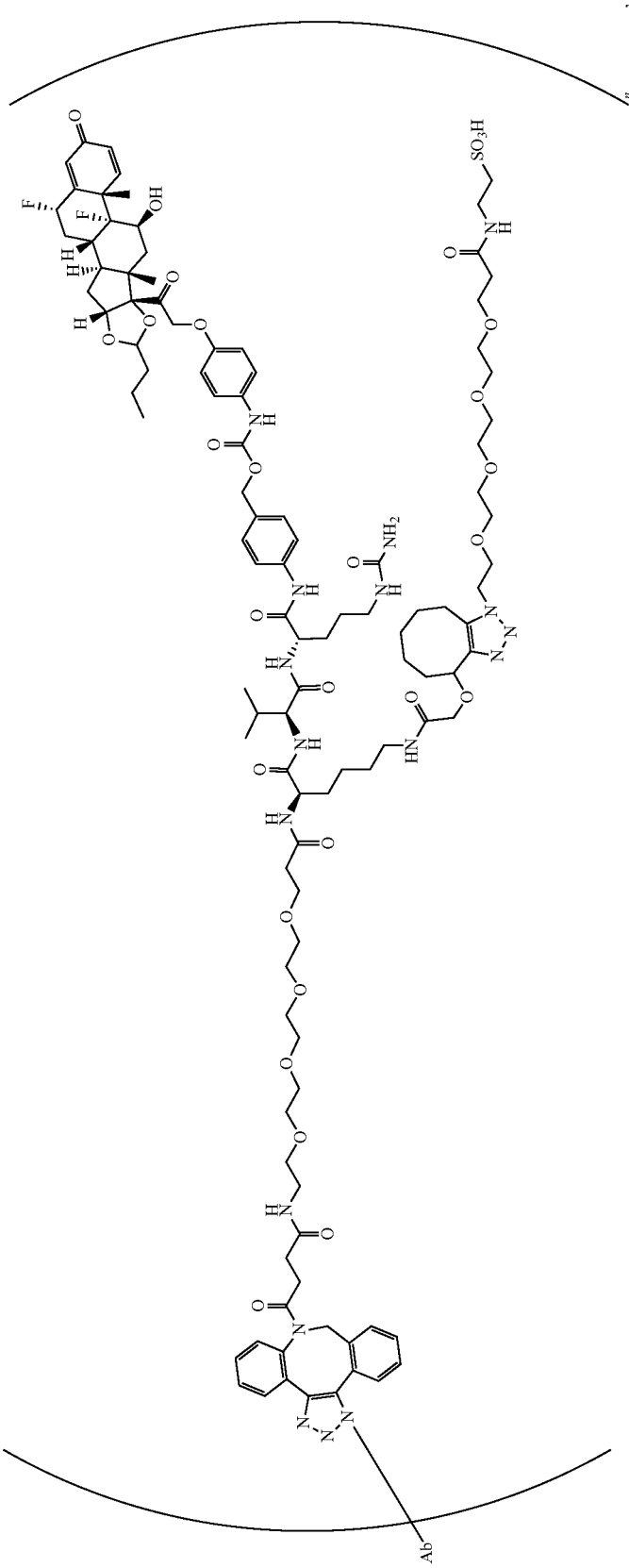

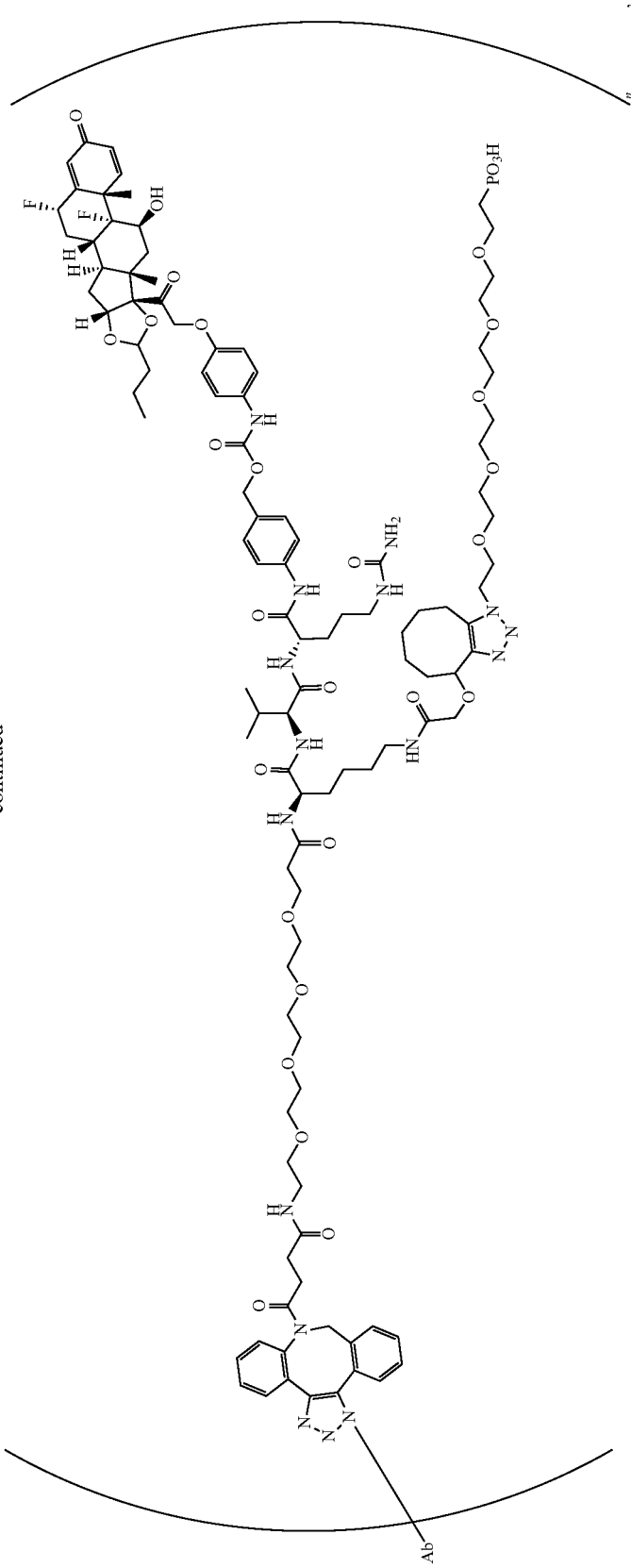

1157
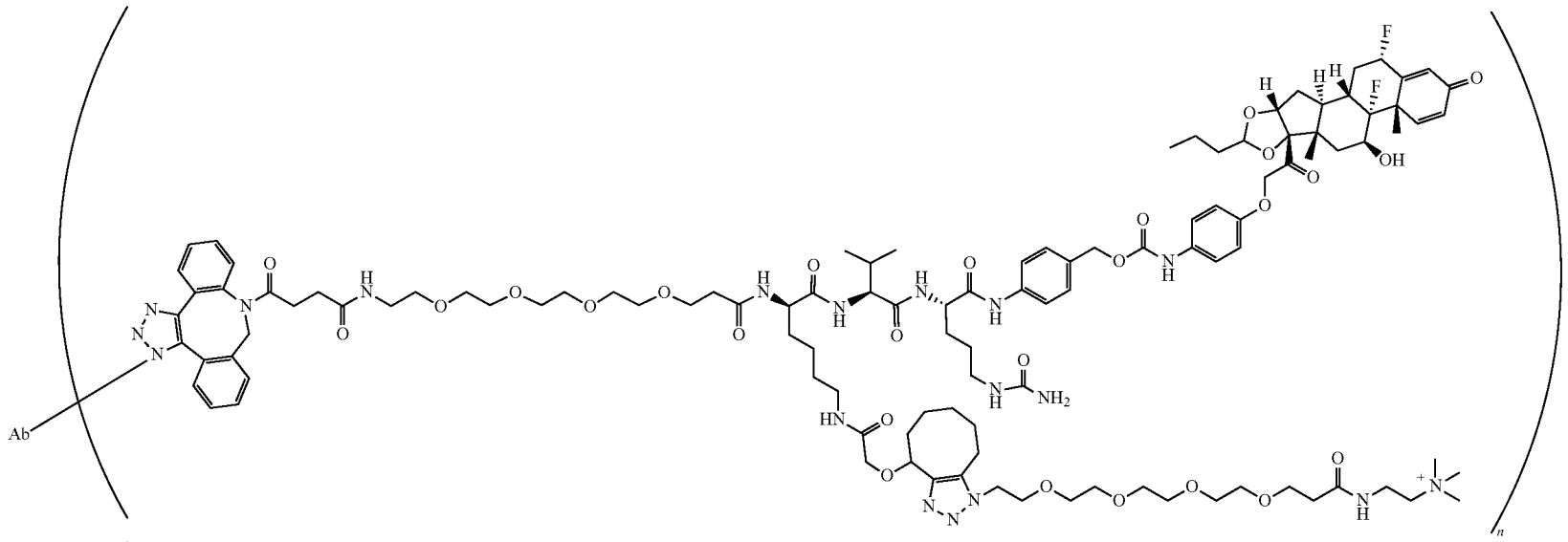
1158
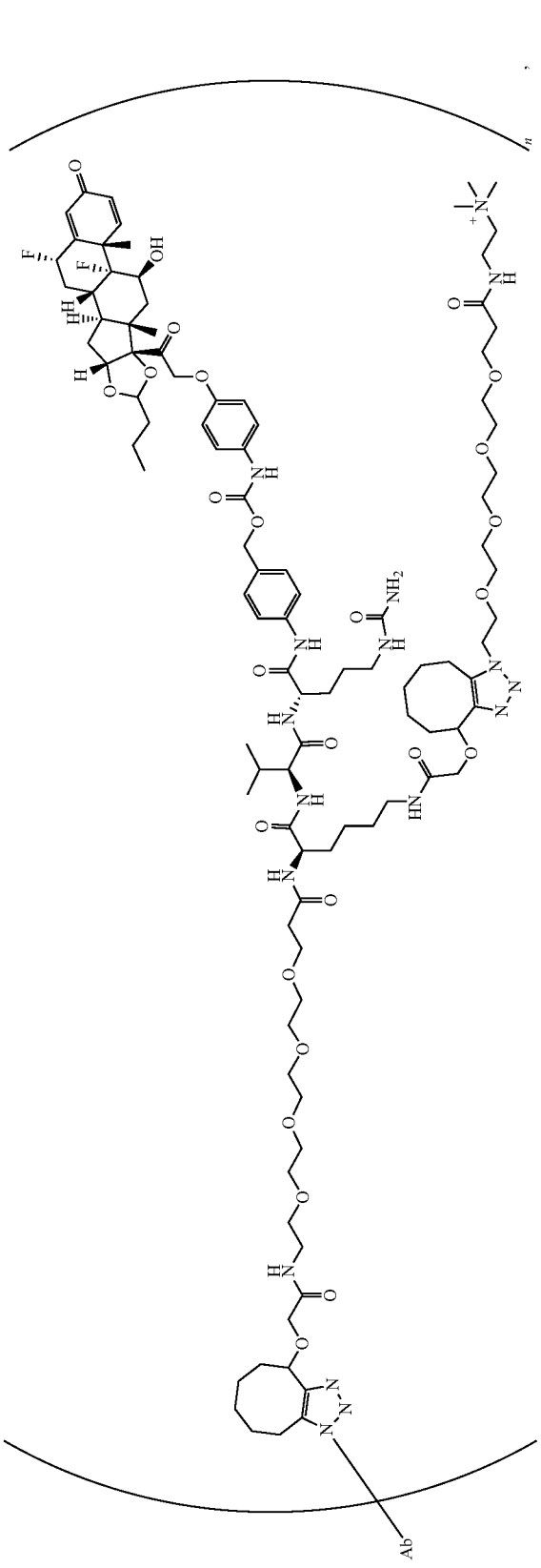

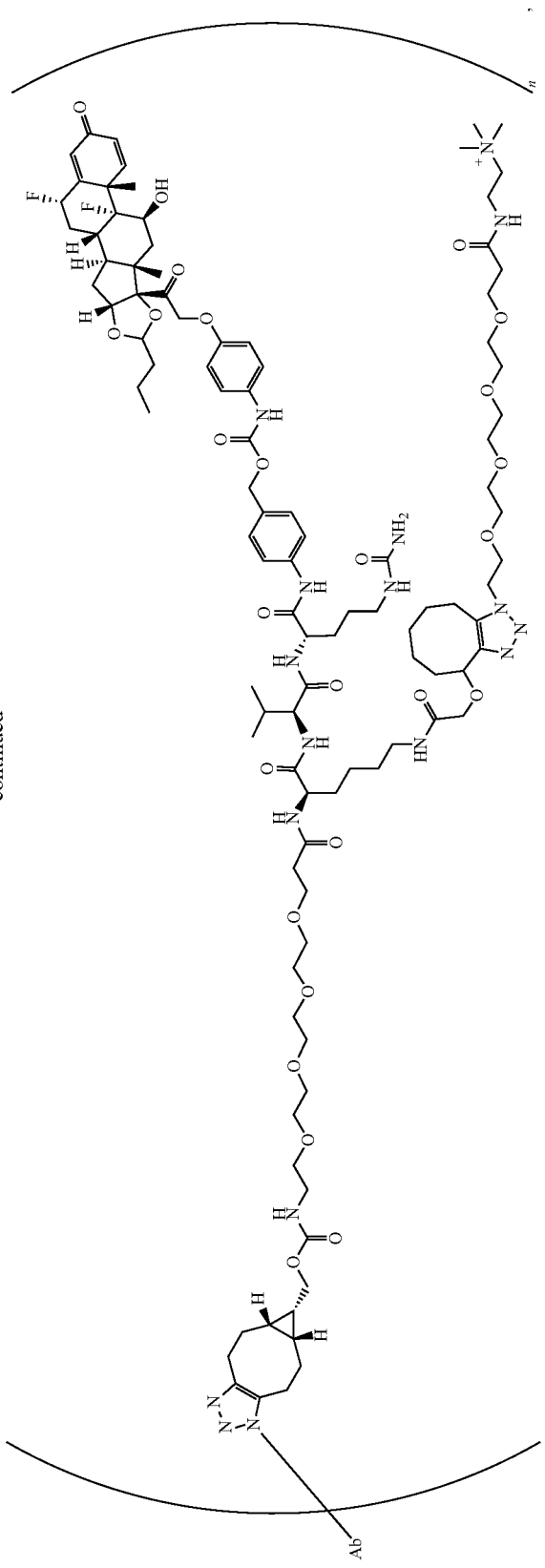

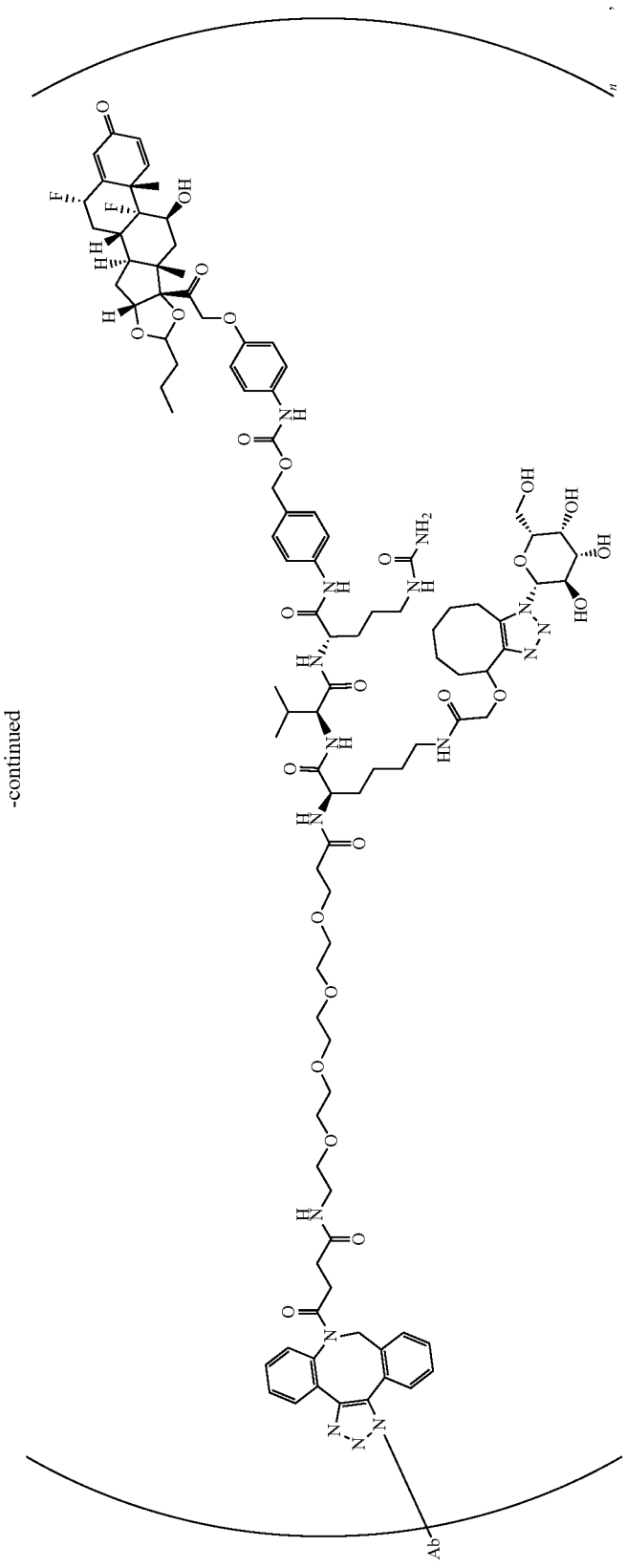

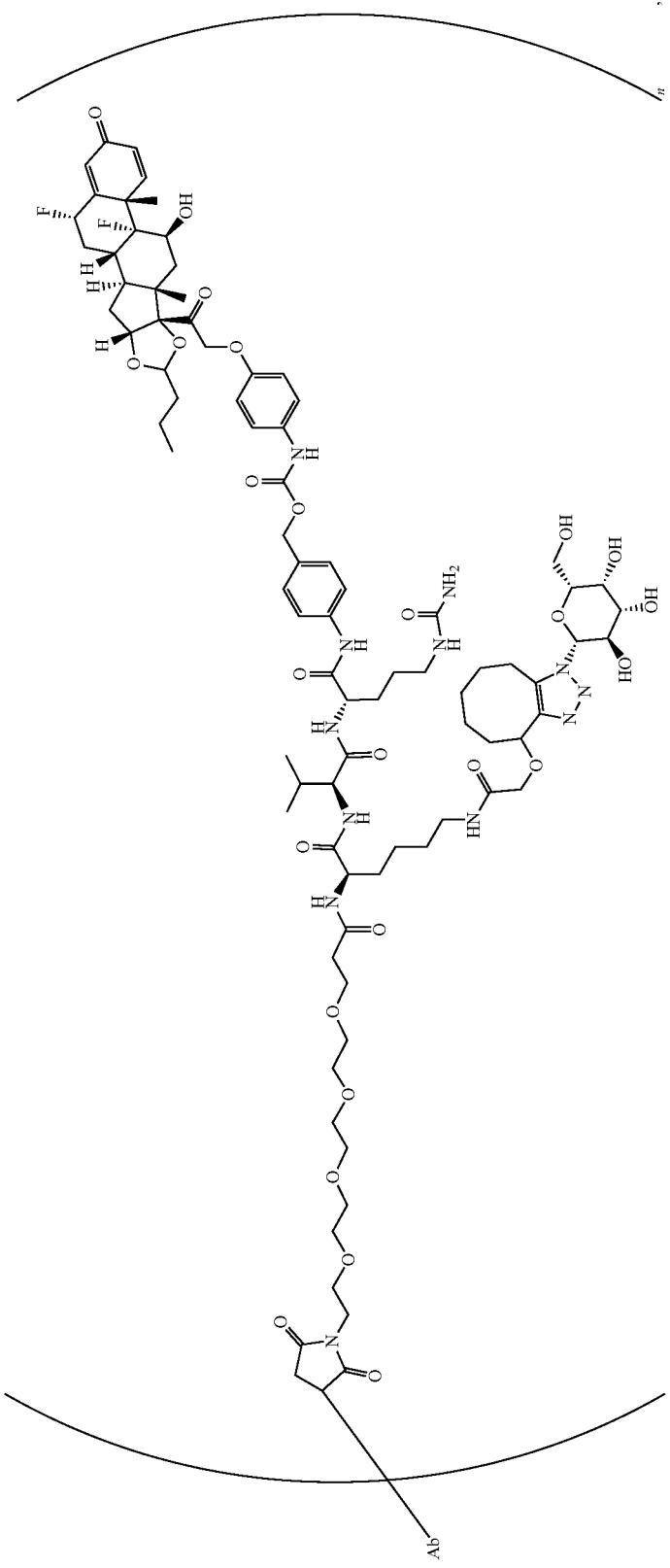

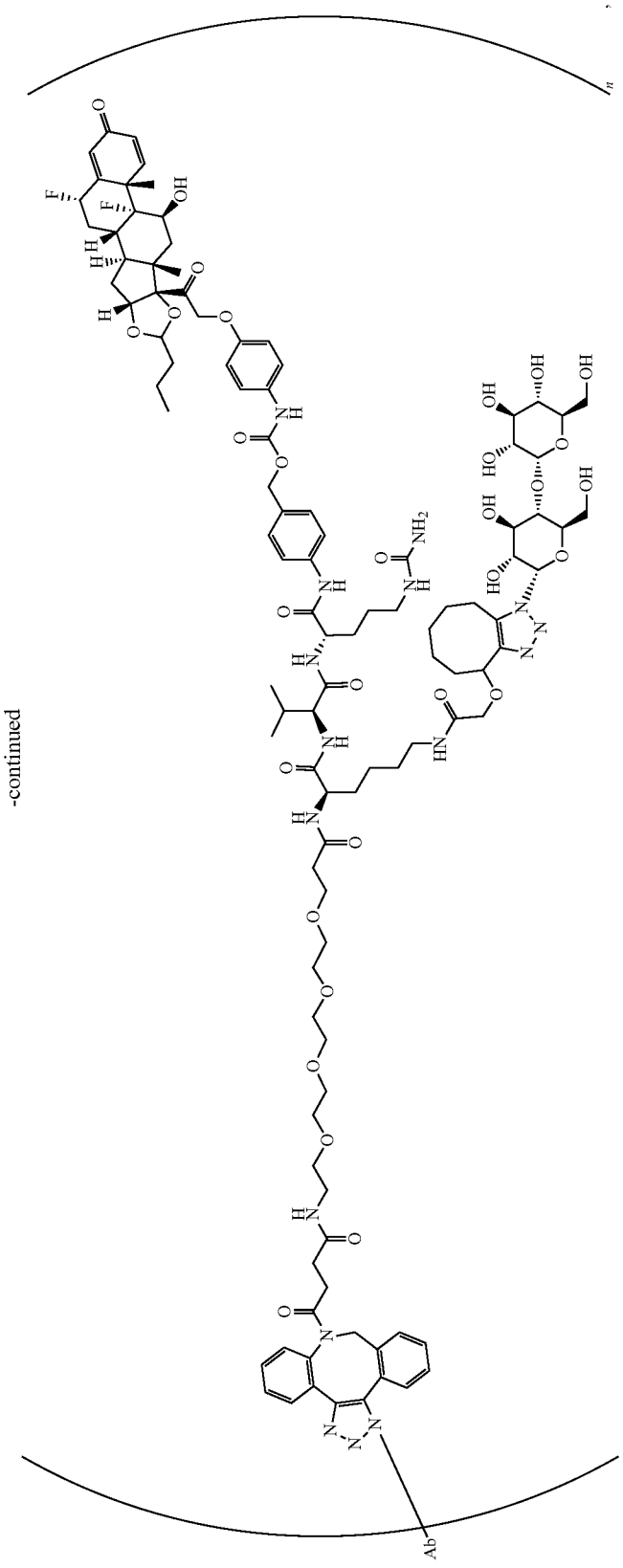

-continued
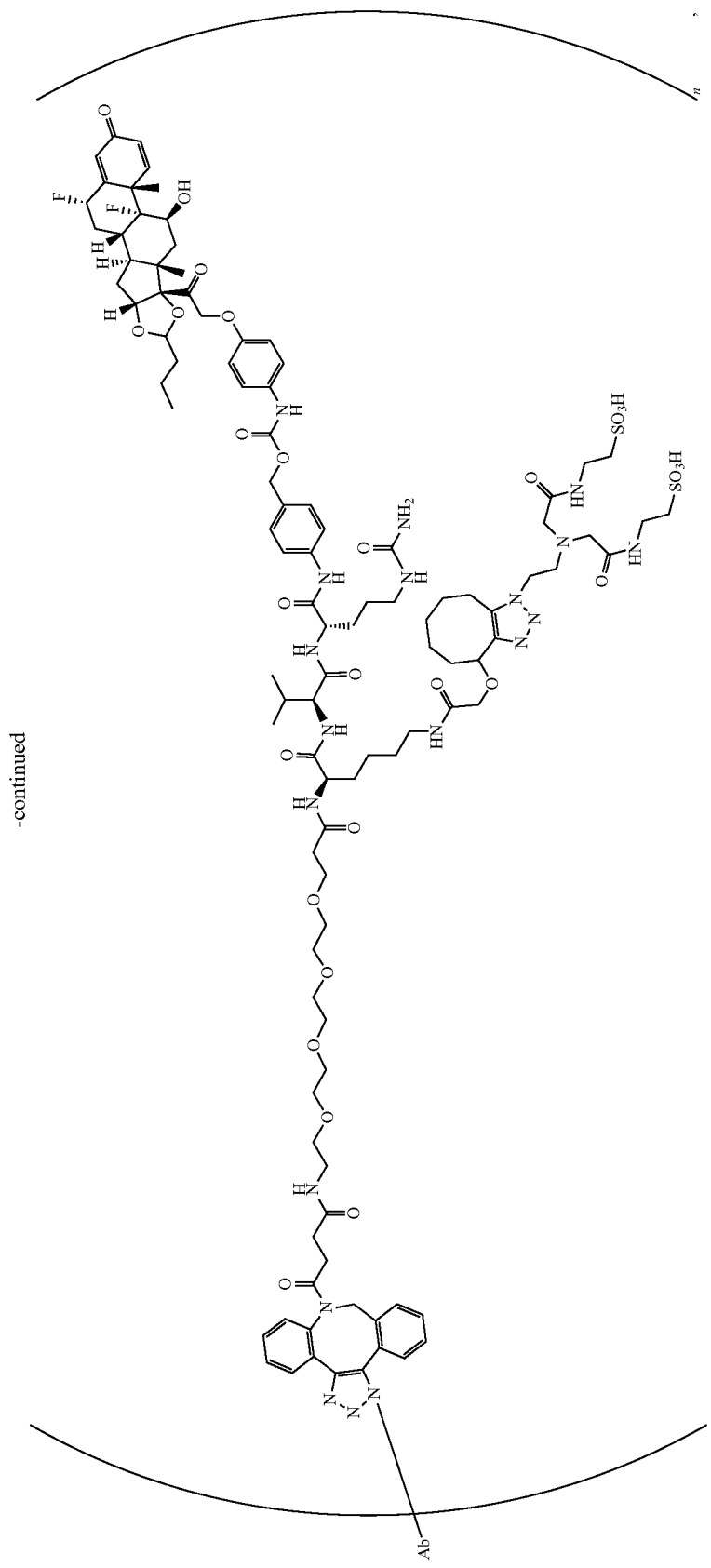

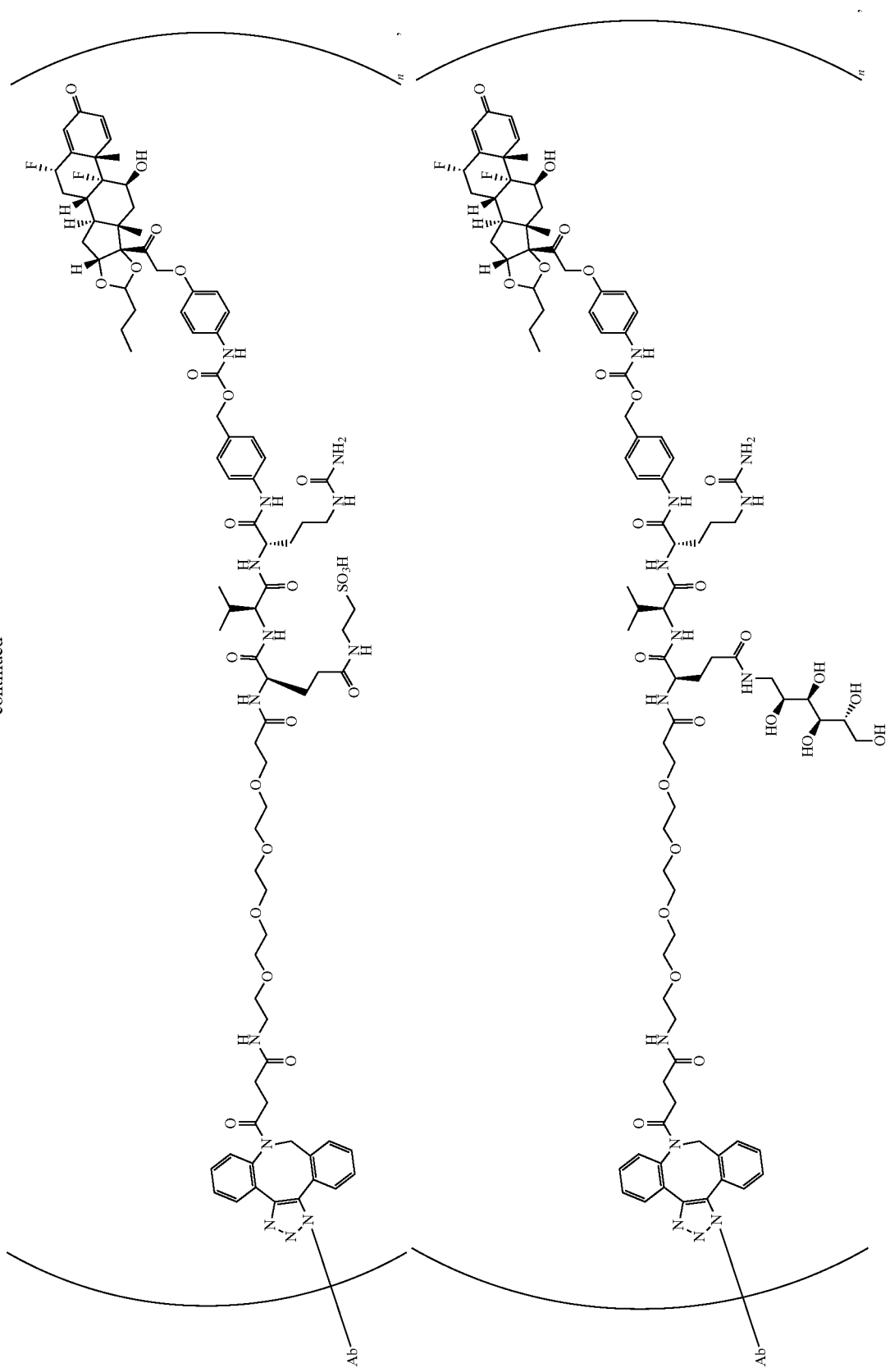

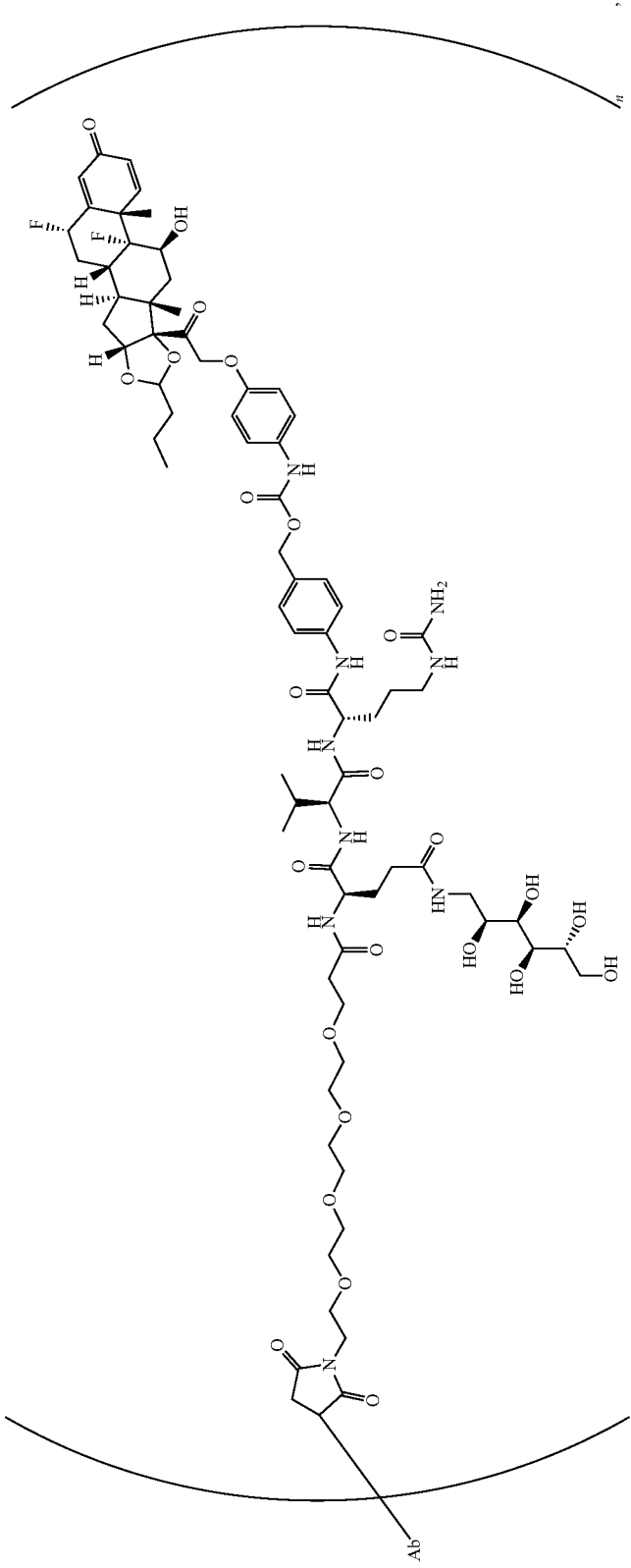

-continued
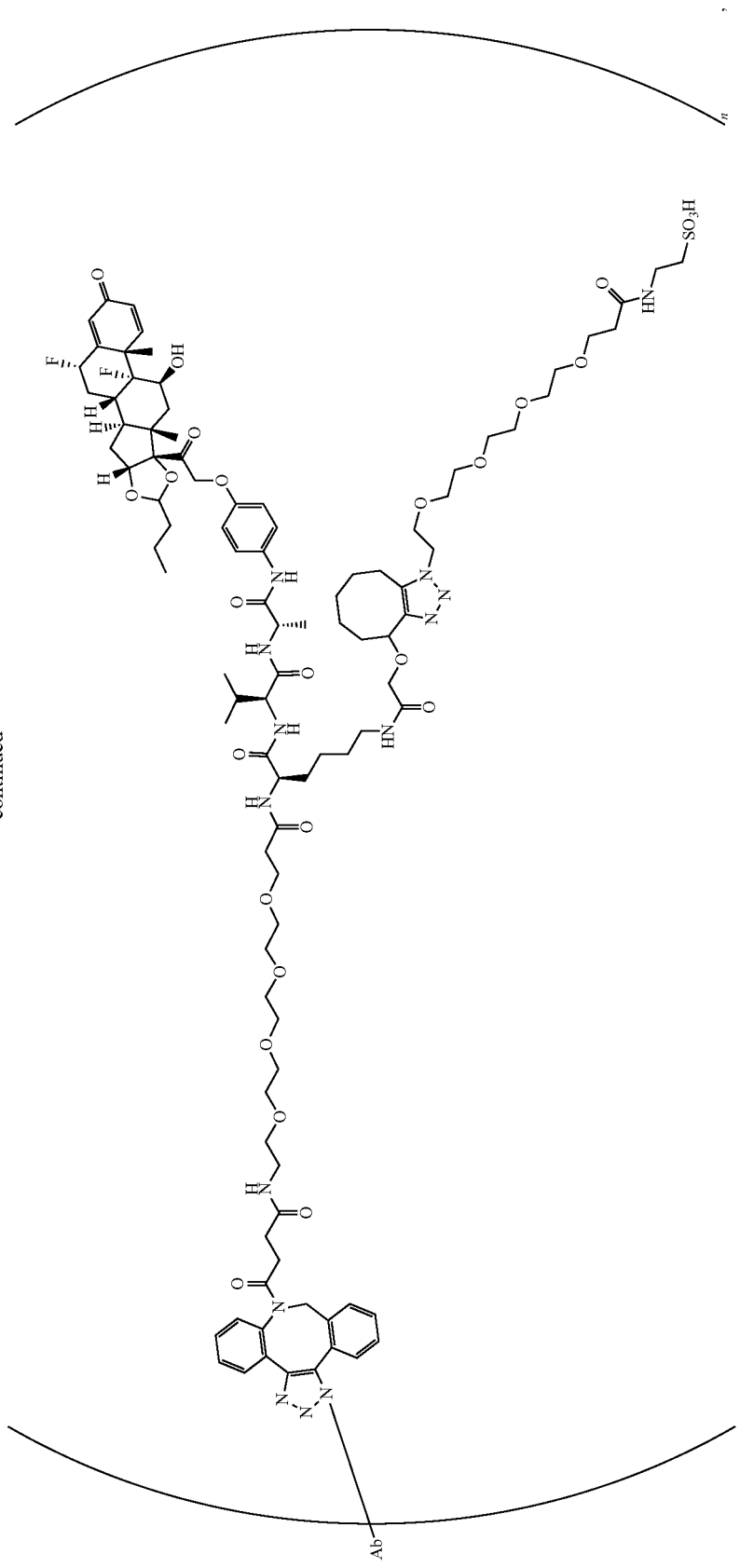

-continued
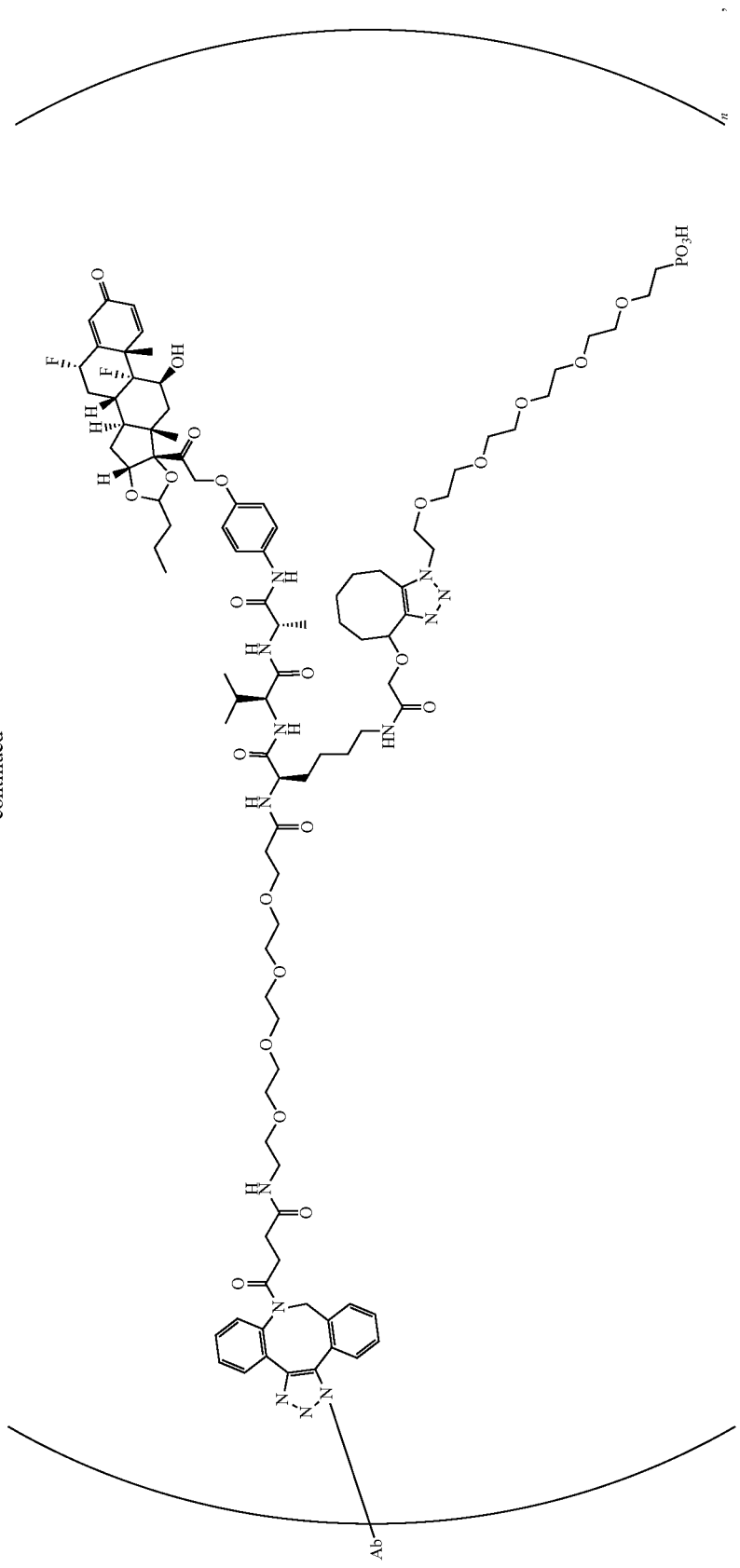

-continued
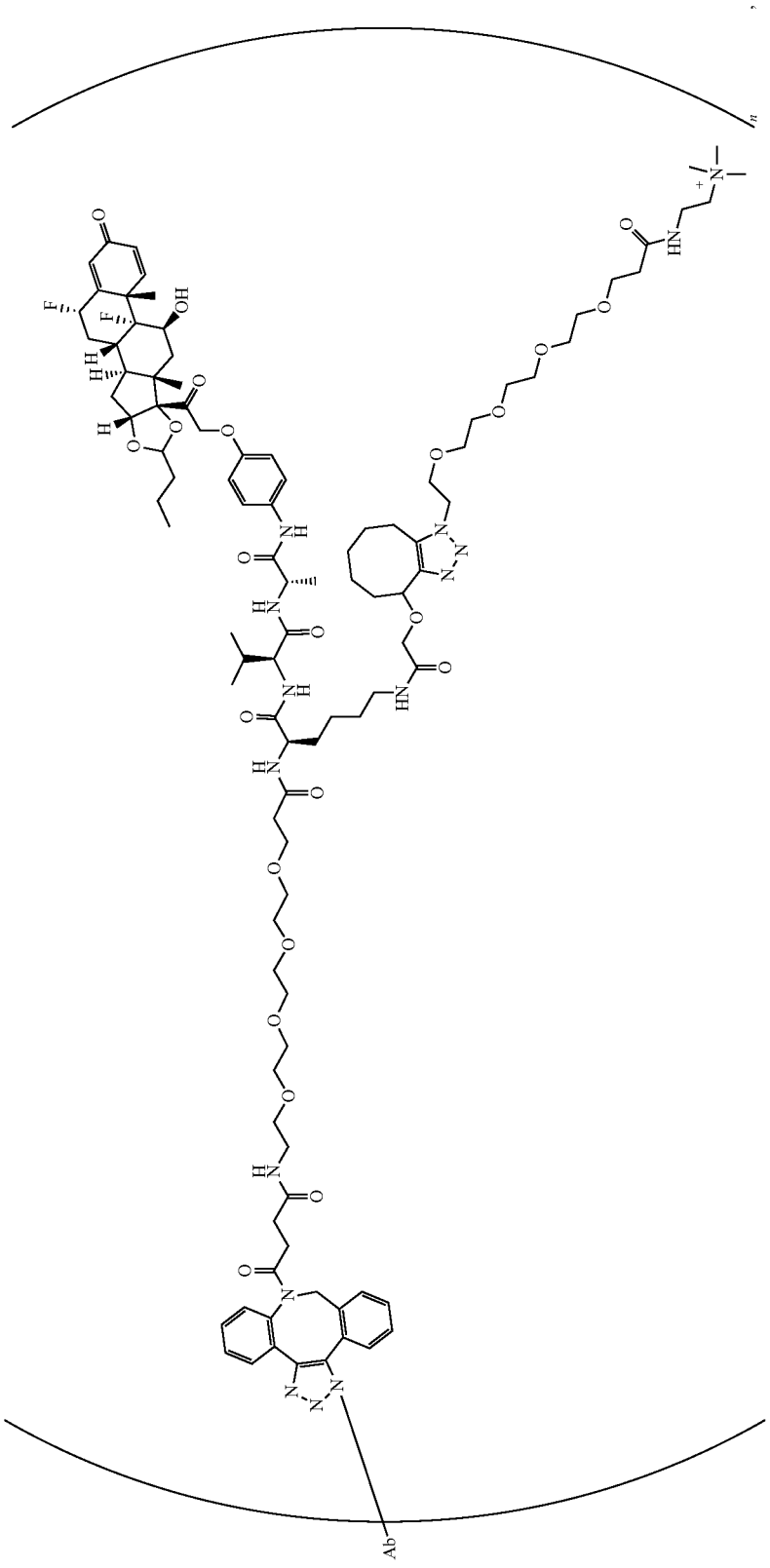

-continued
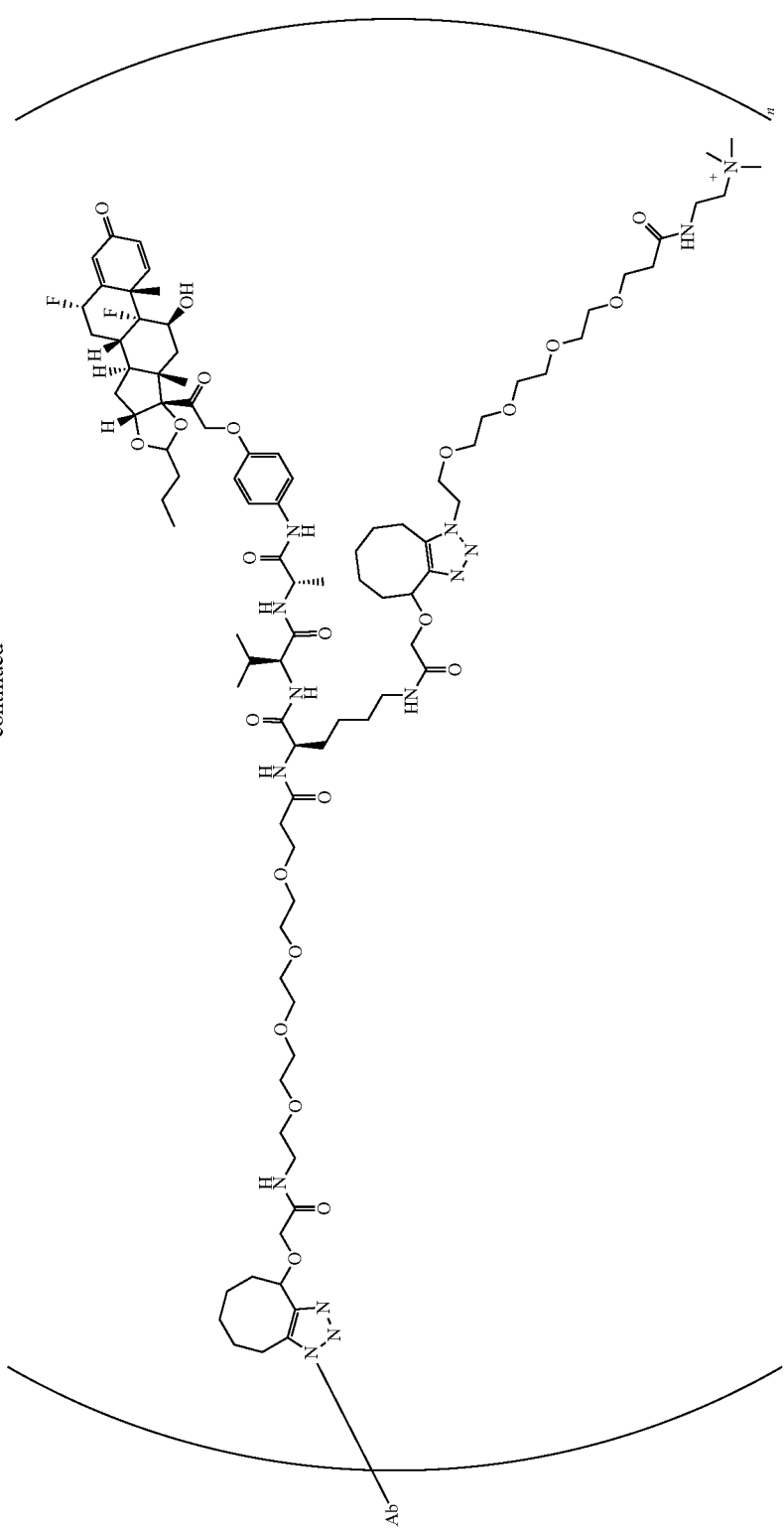

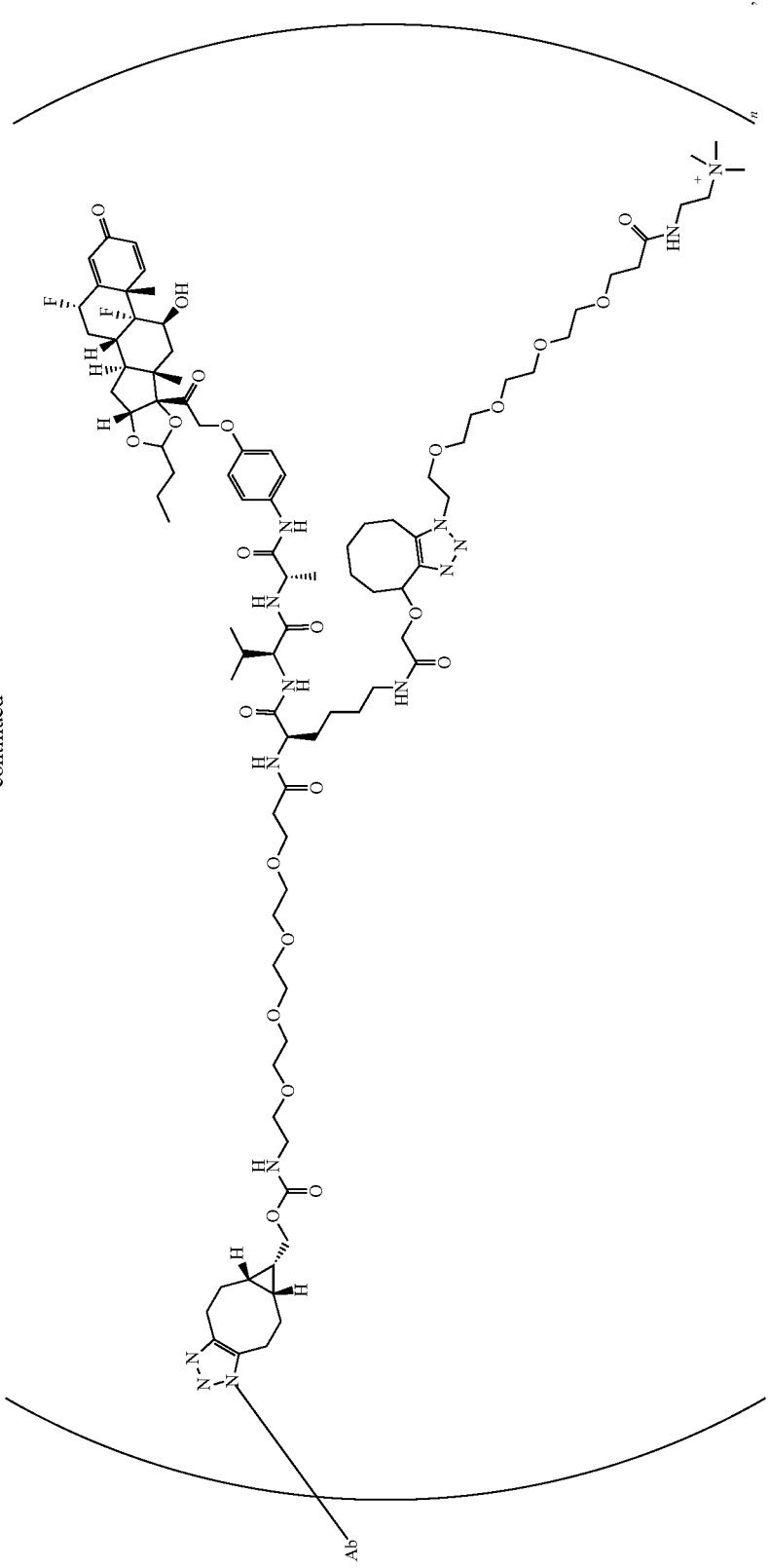

1183 1184
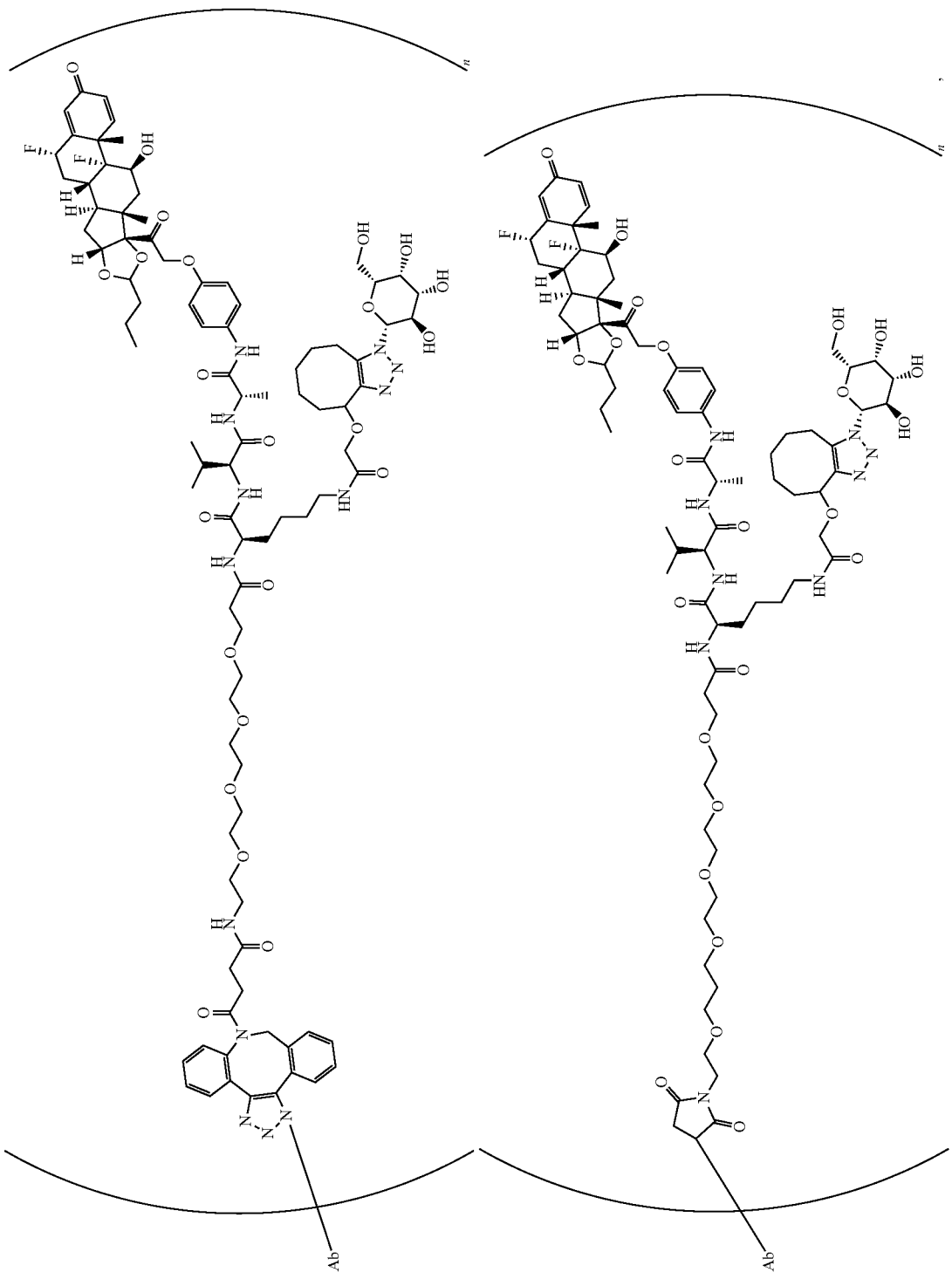

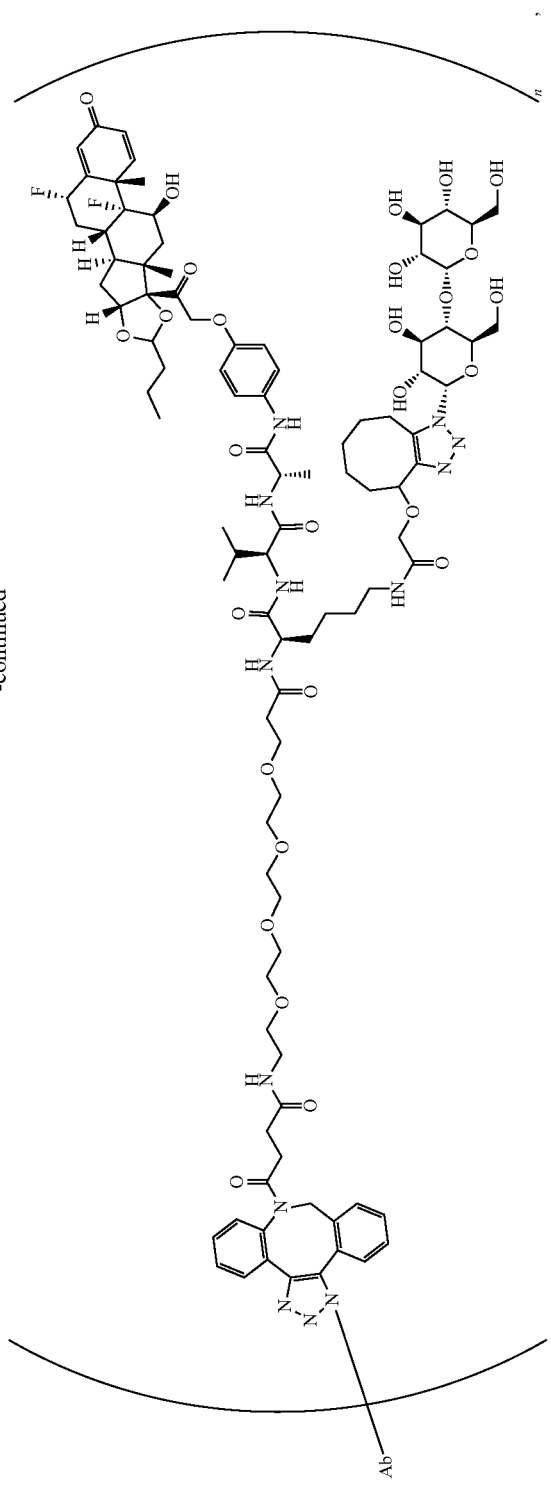

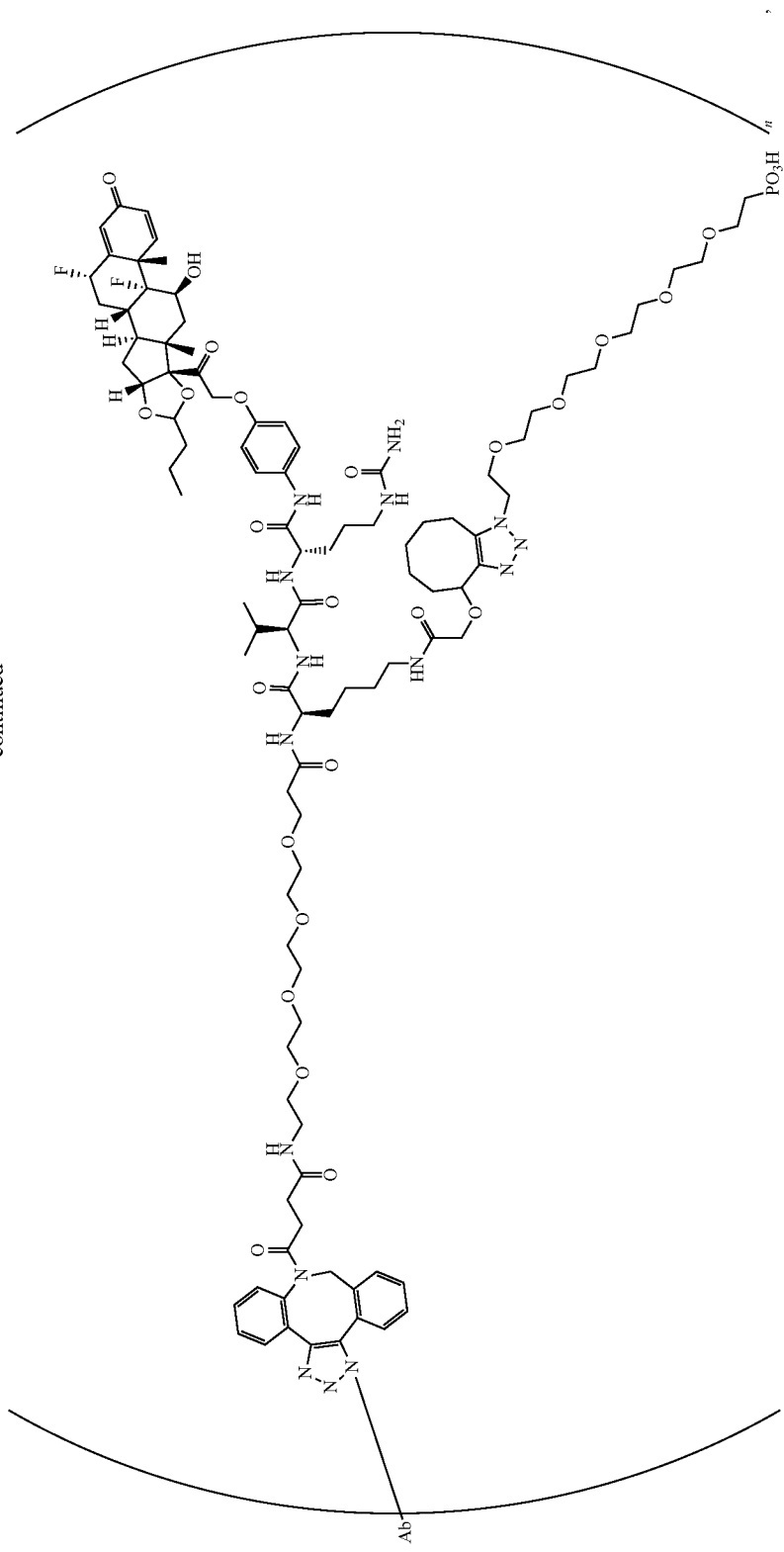

-continued
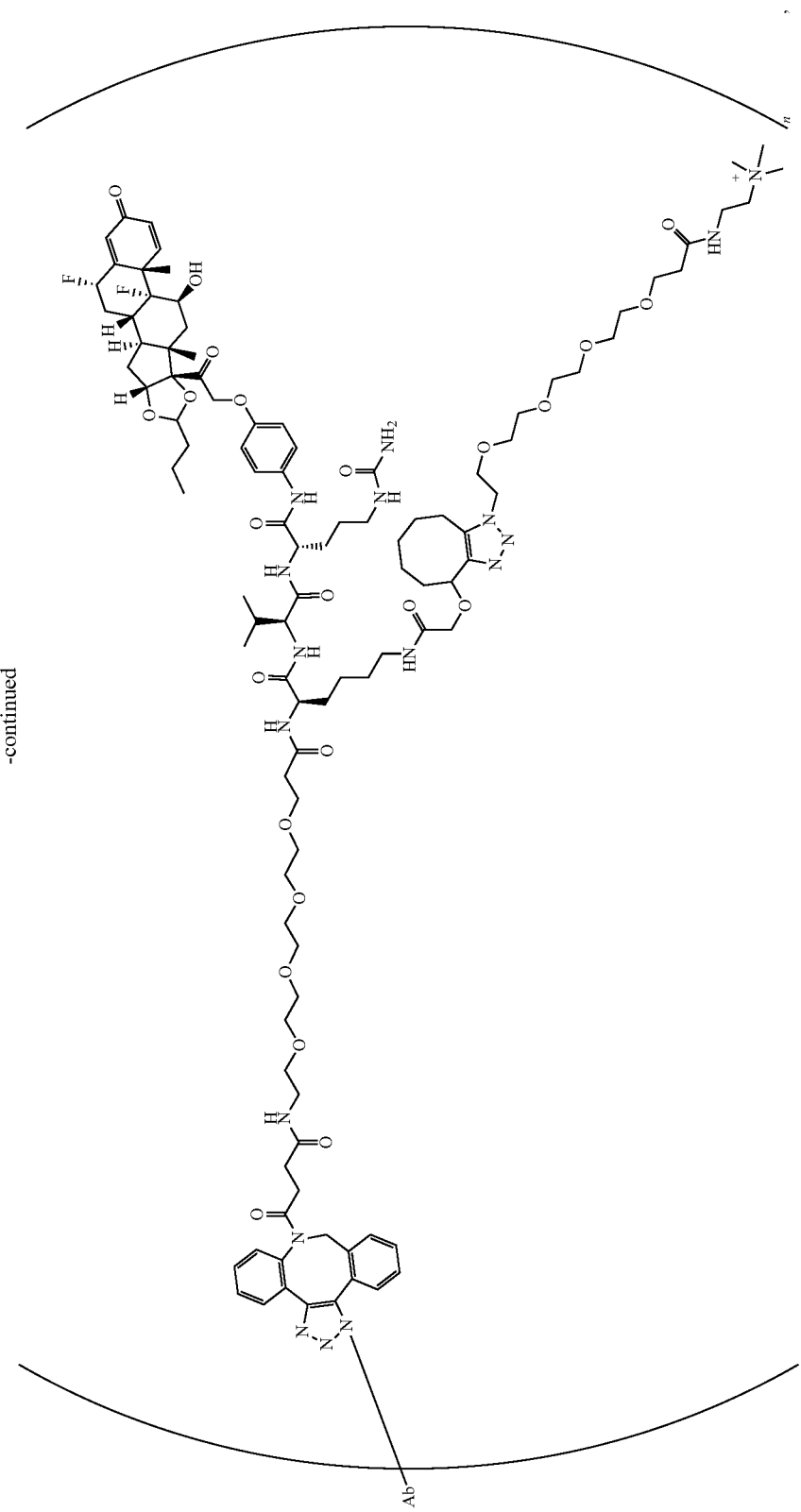

-continued
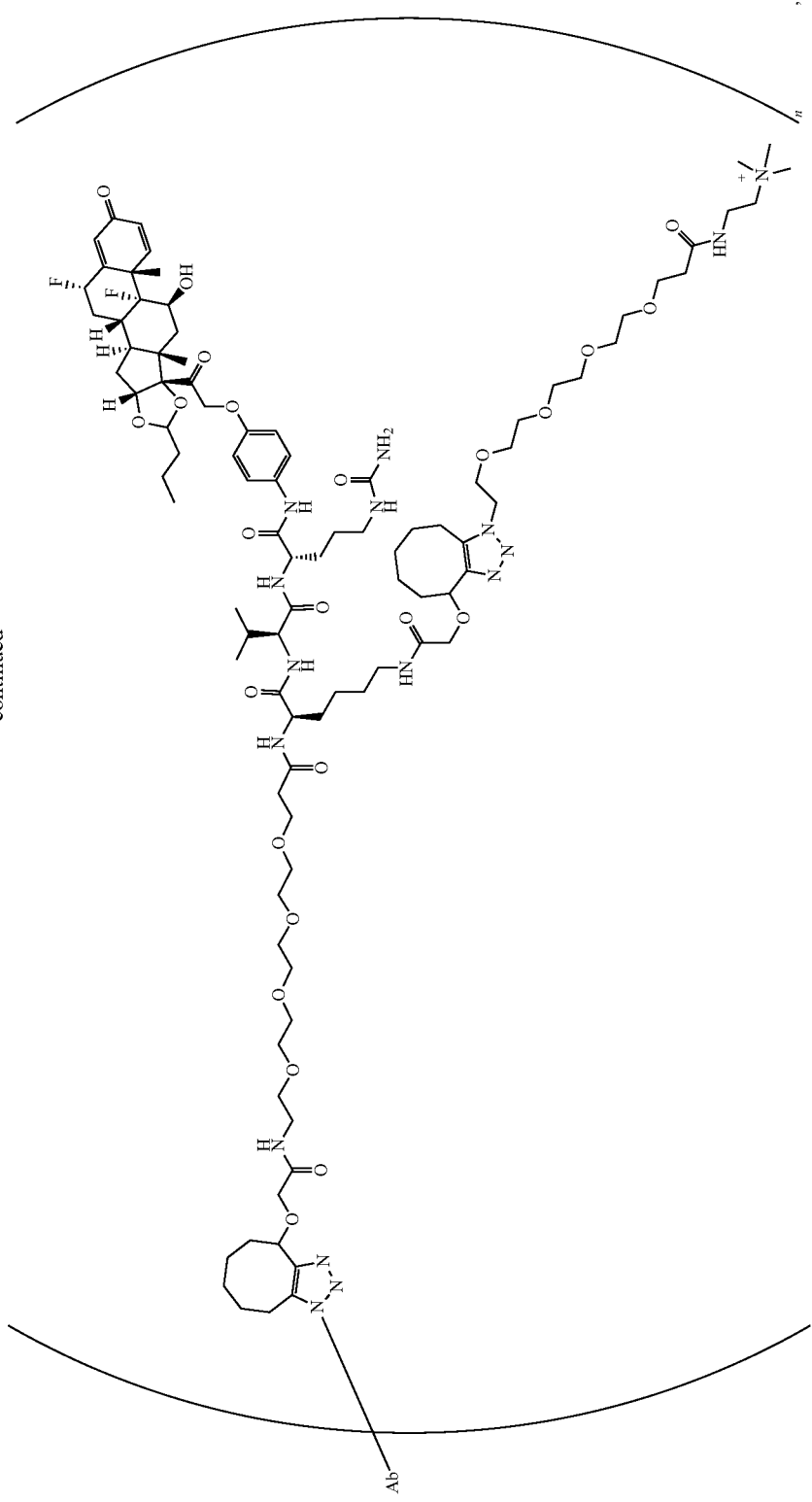

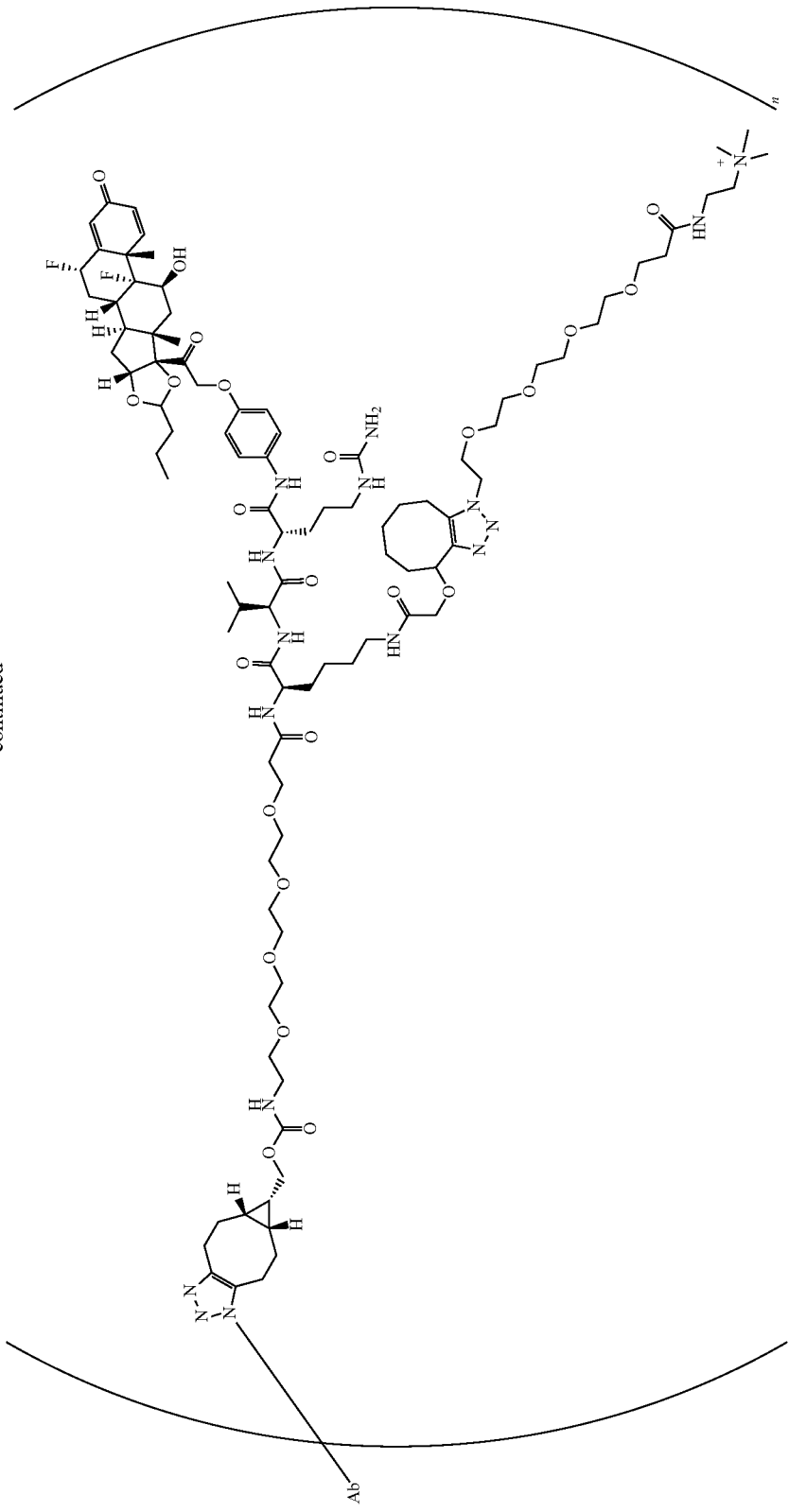

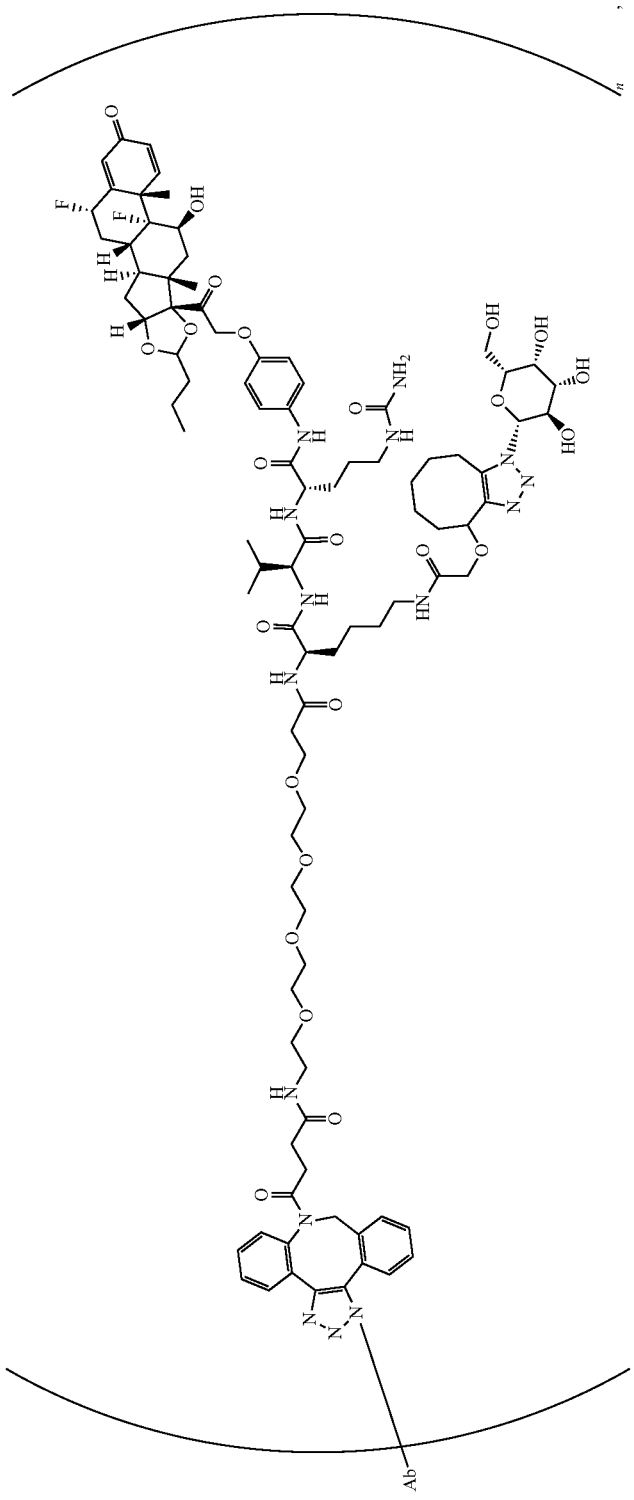

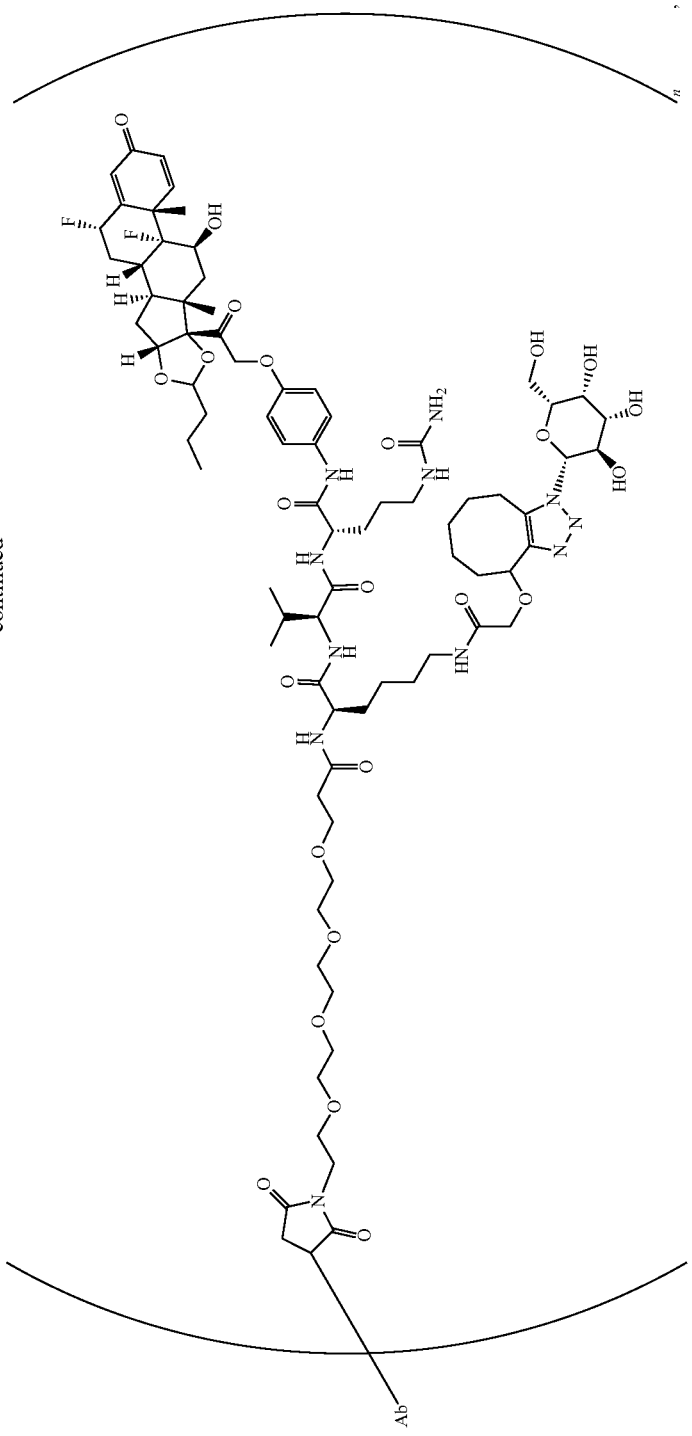

1199 1200
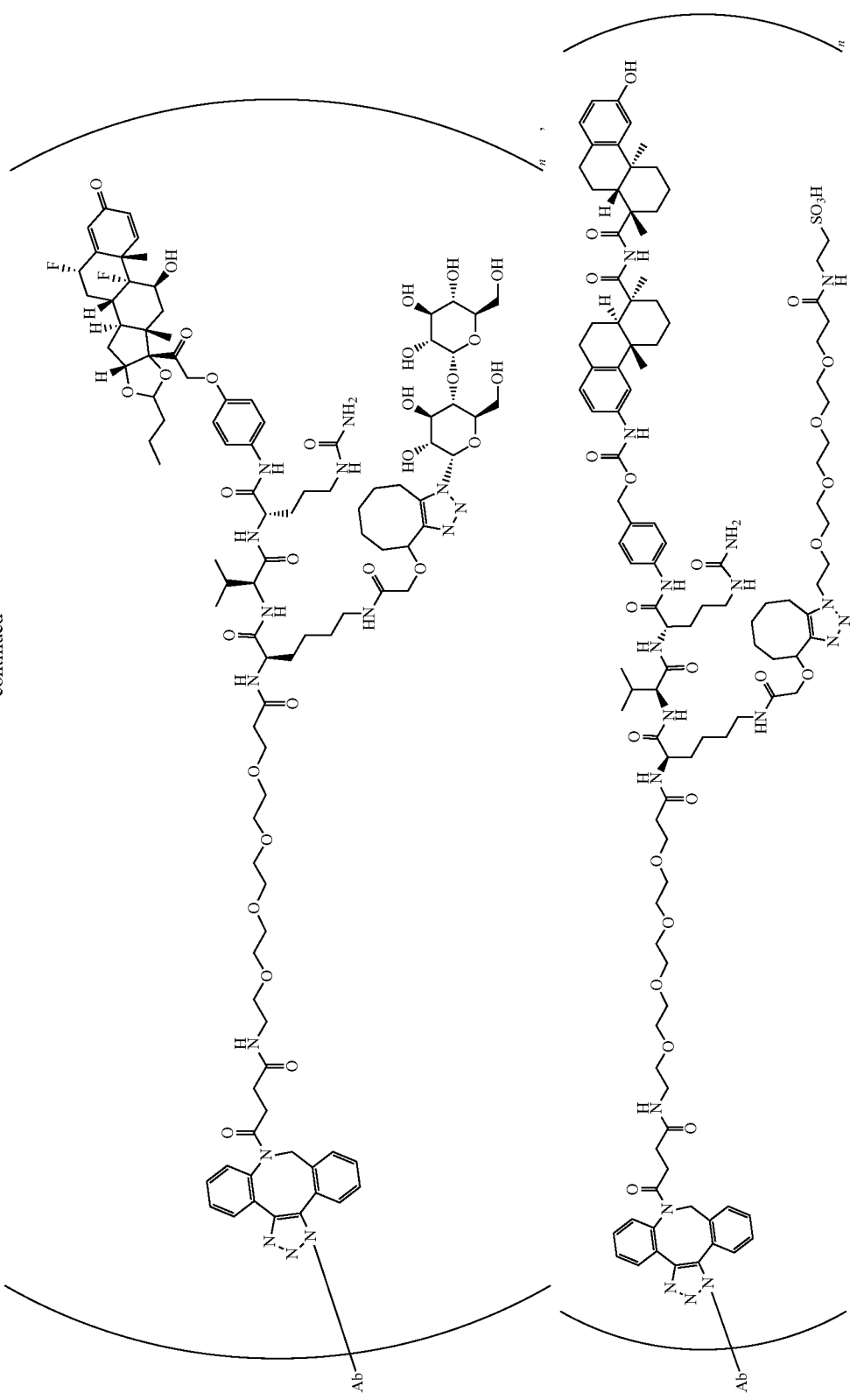

1201 1202
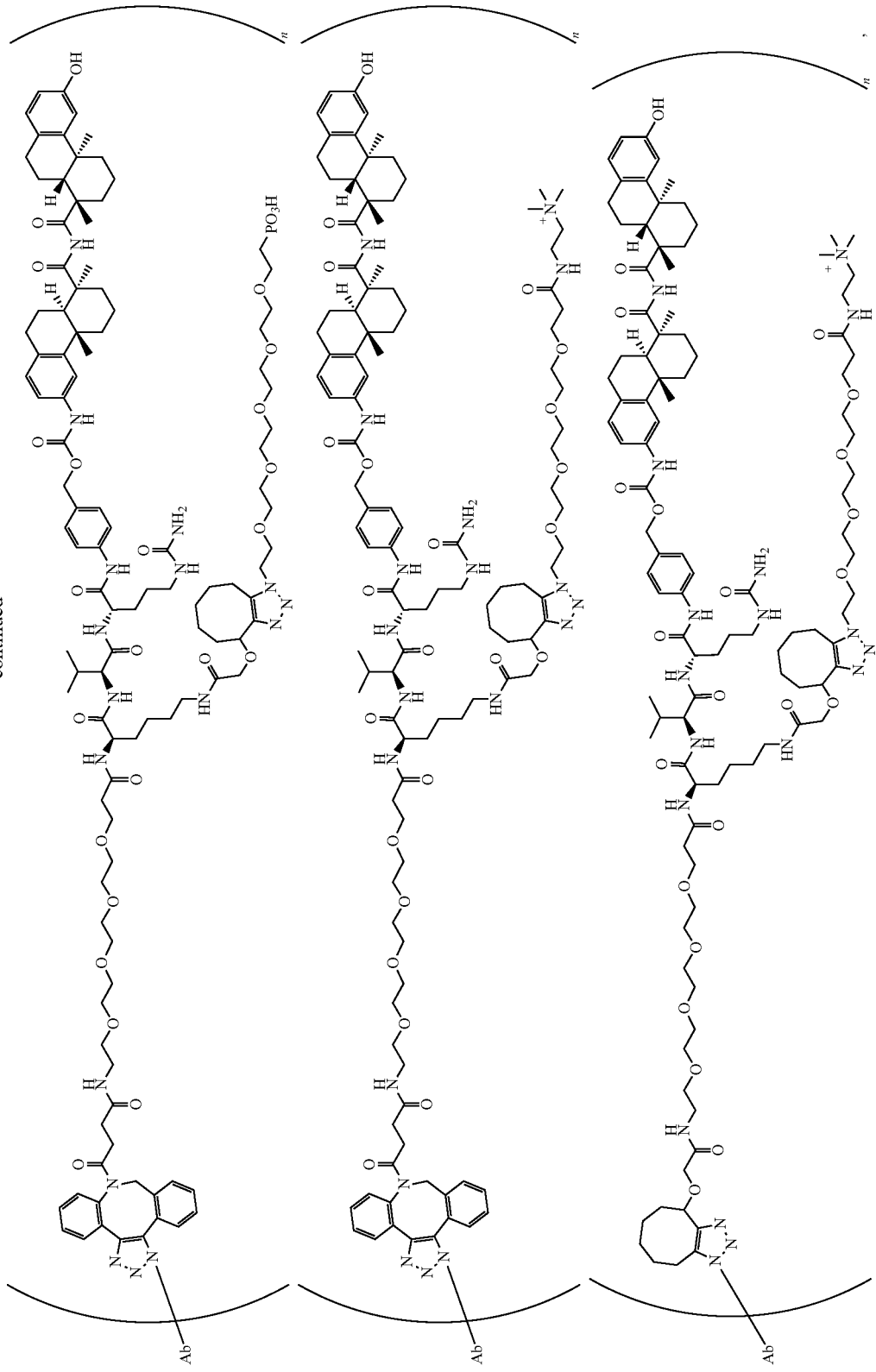
-continued

1203
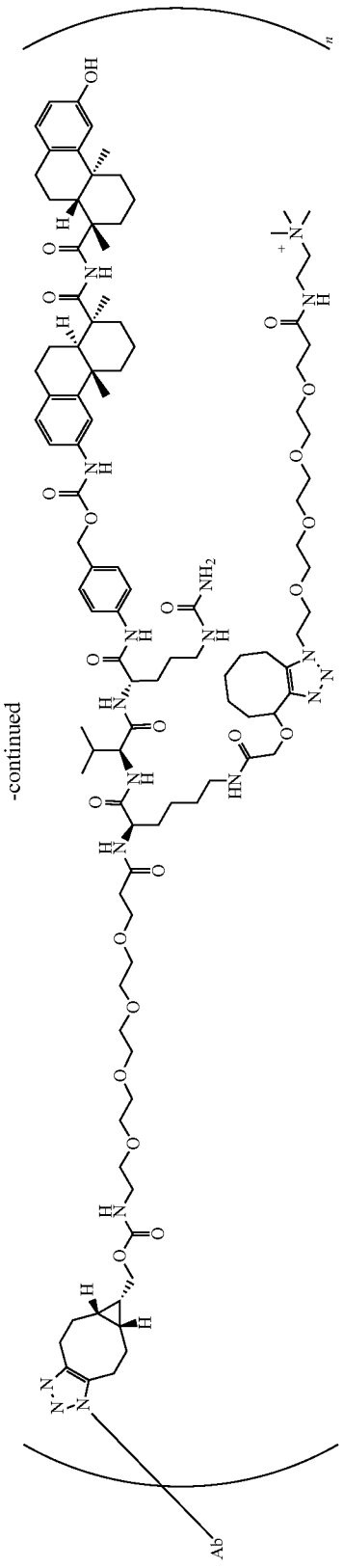
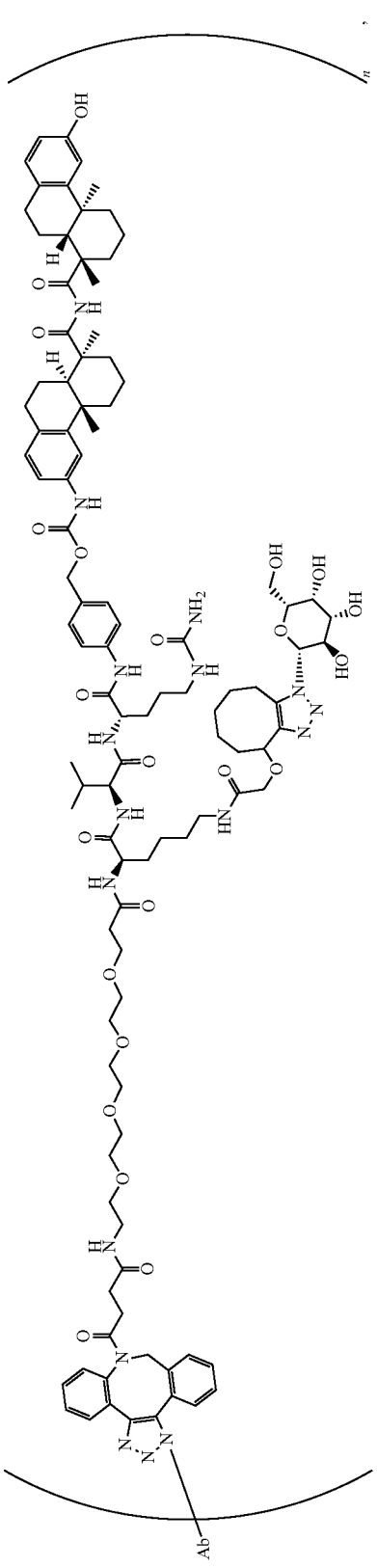
1204
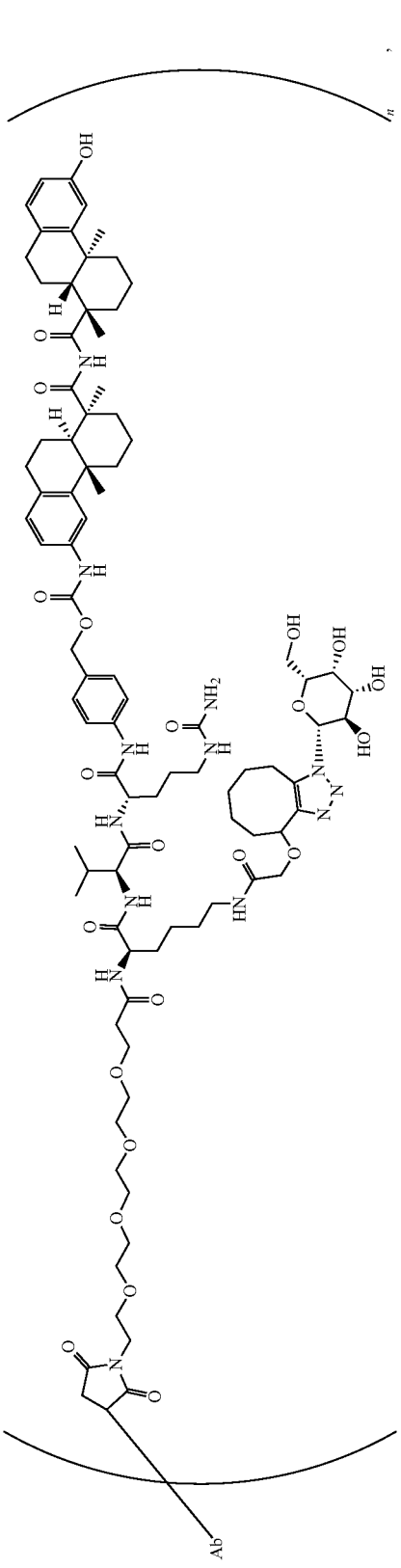

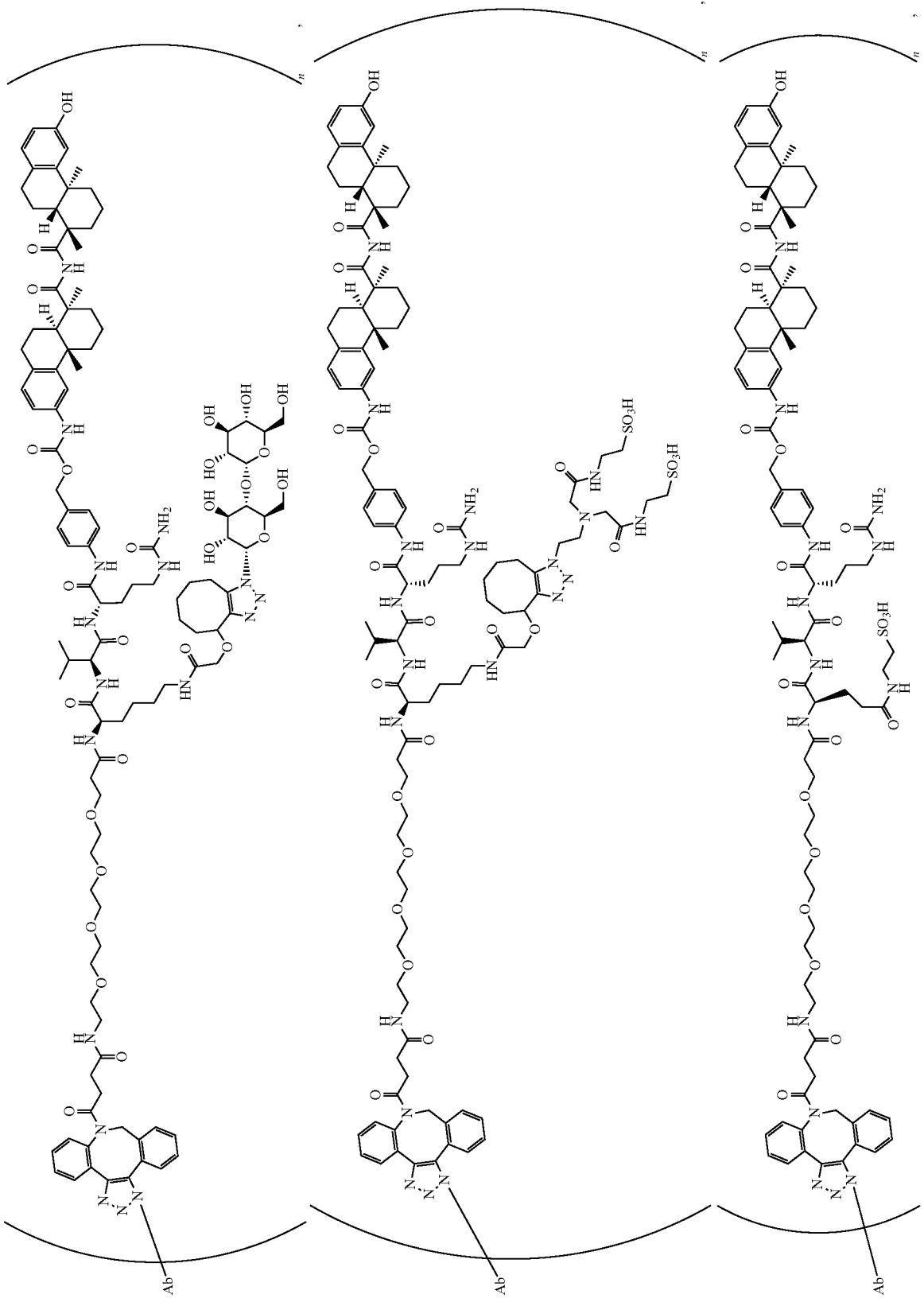

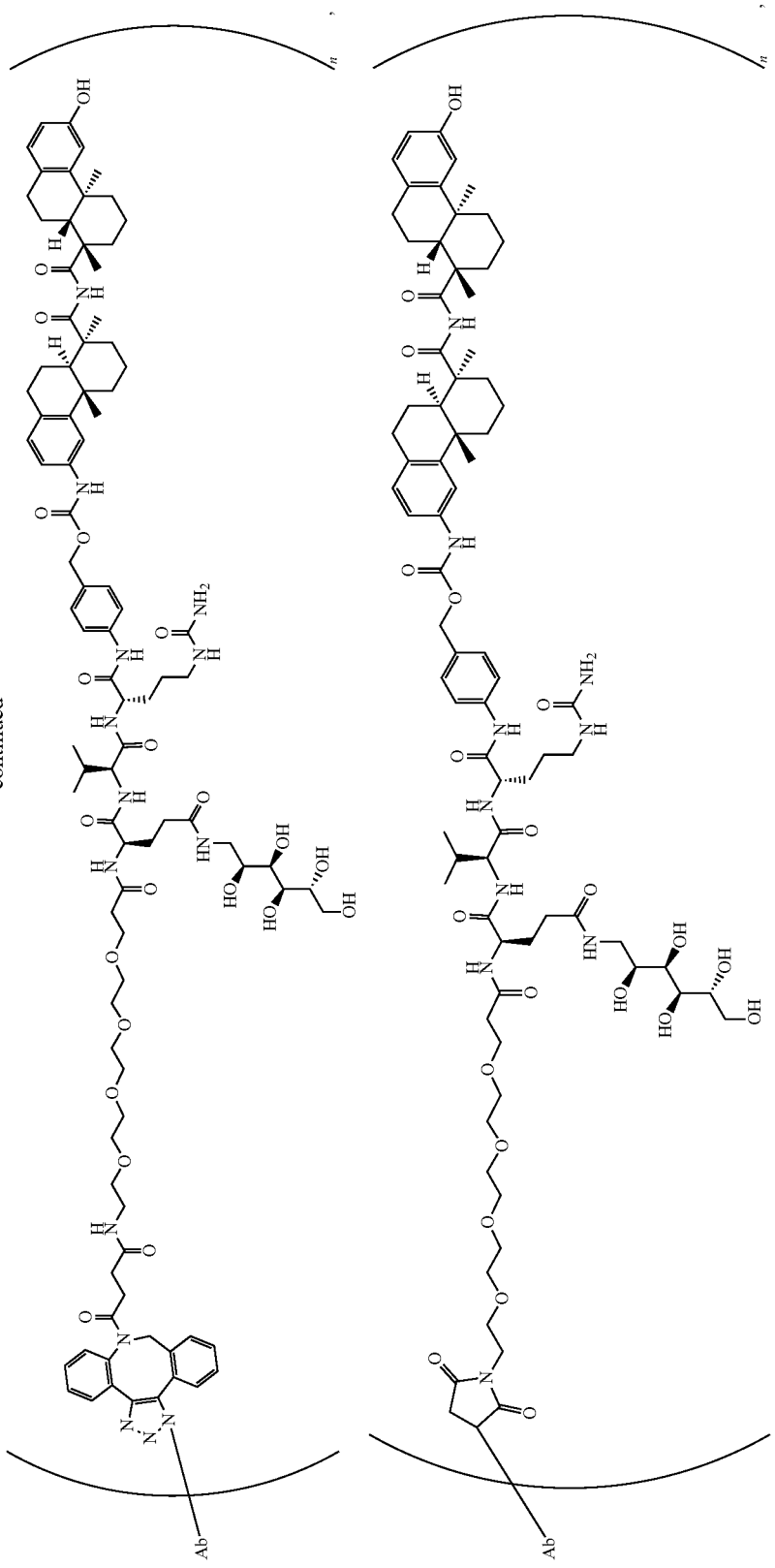

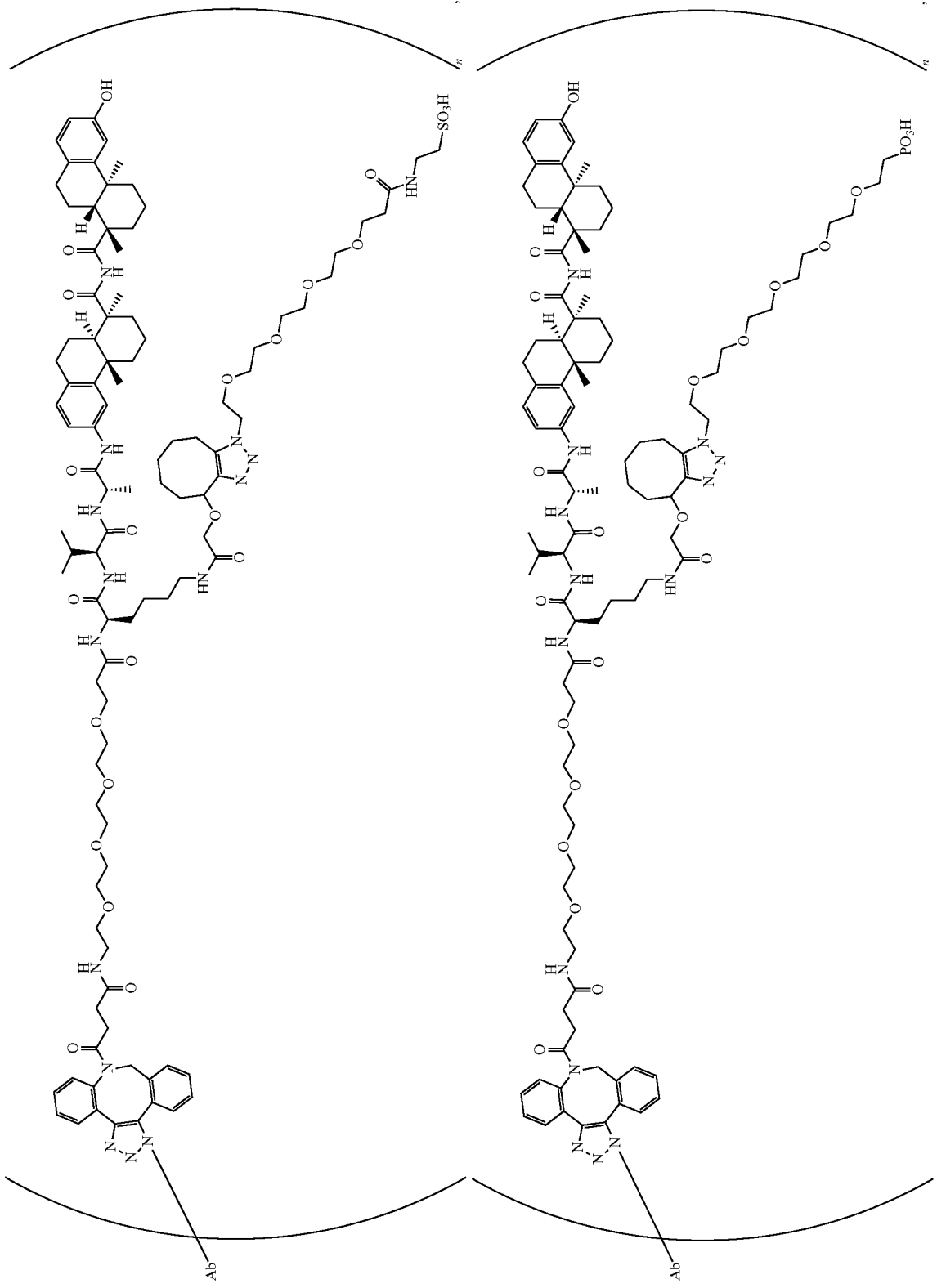

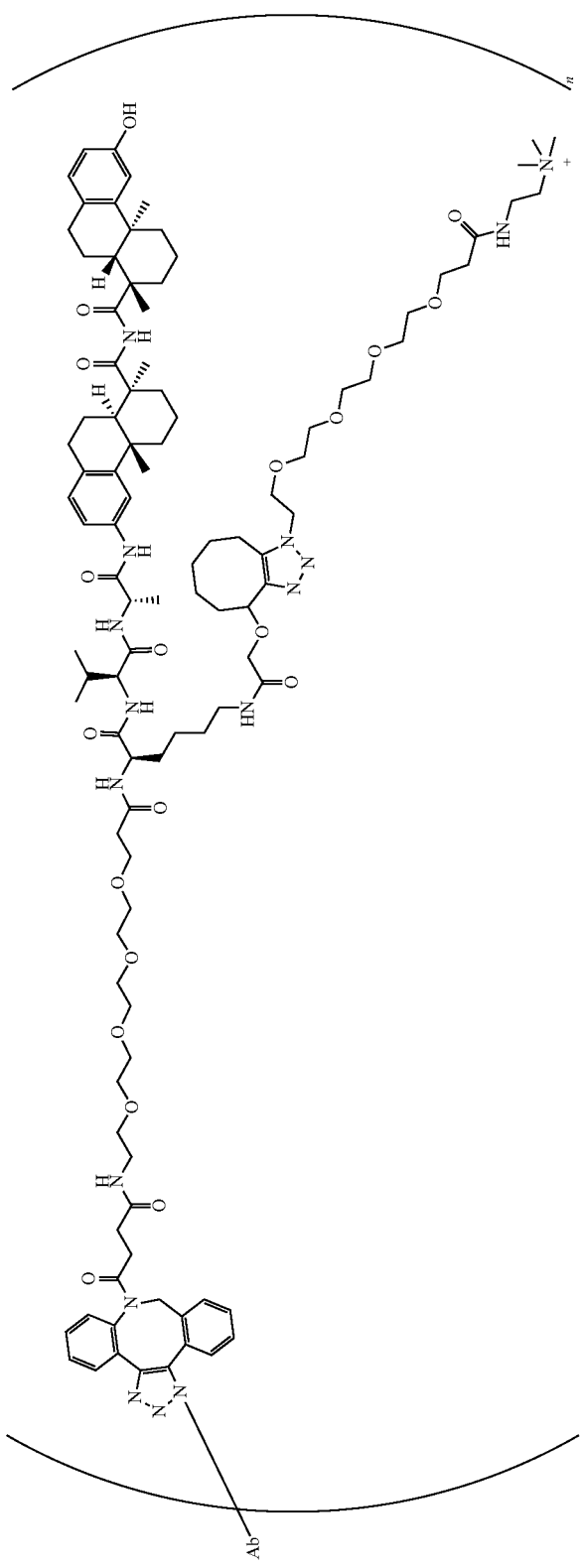

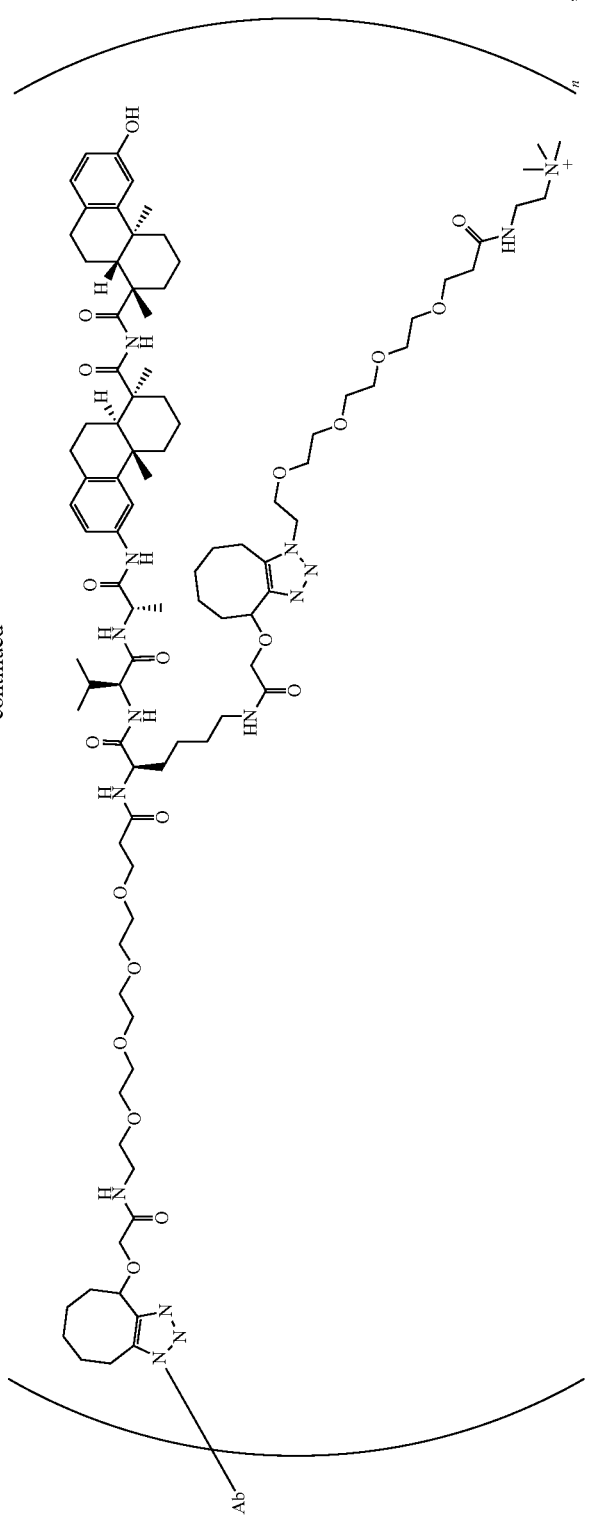

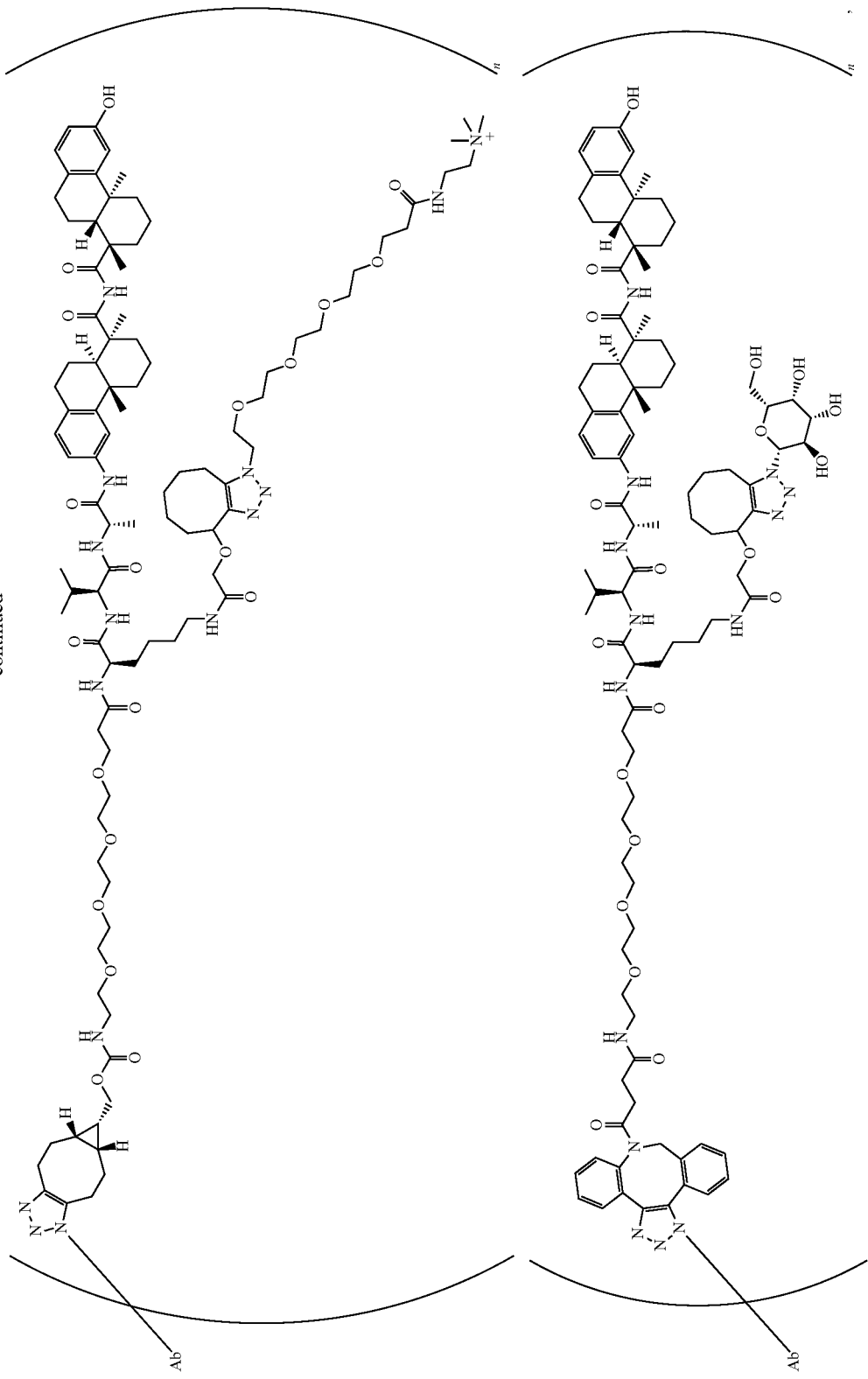

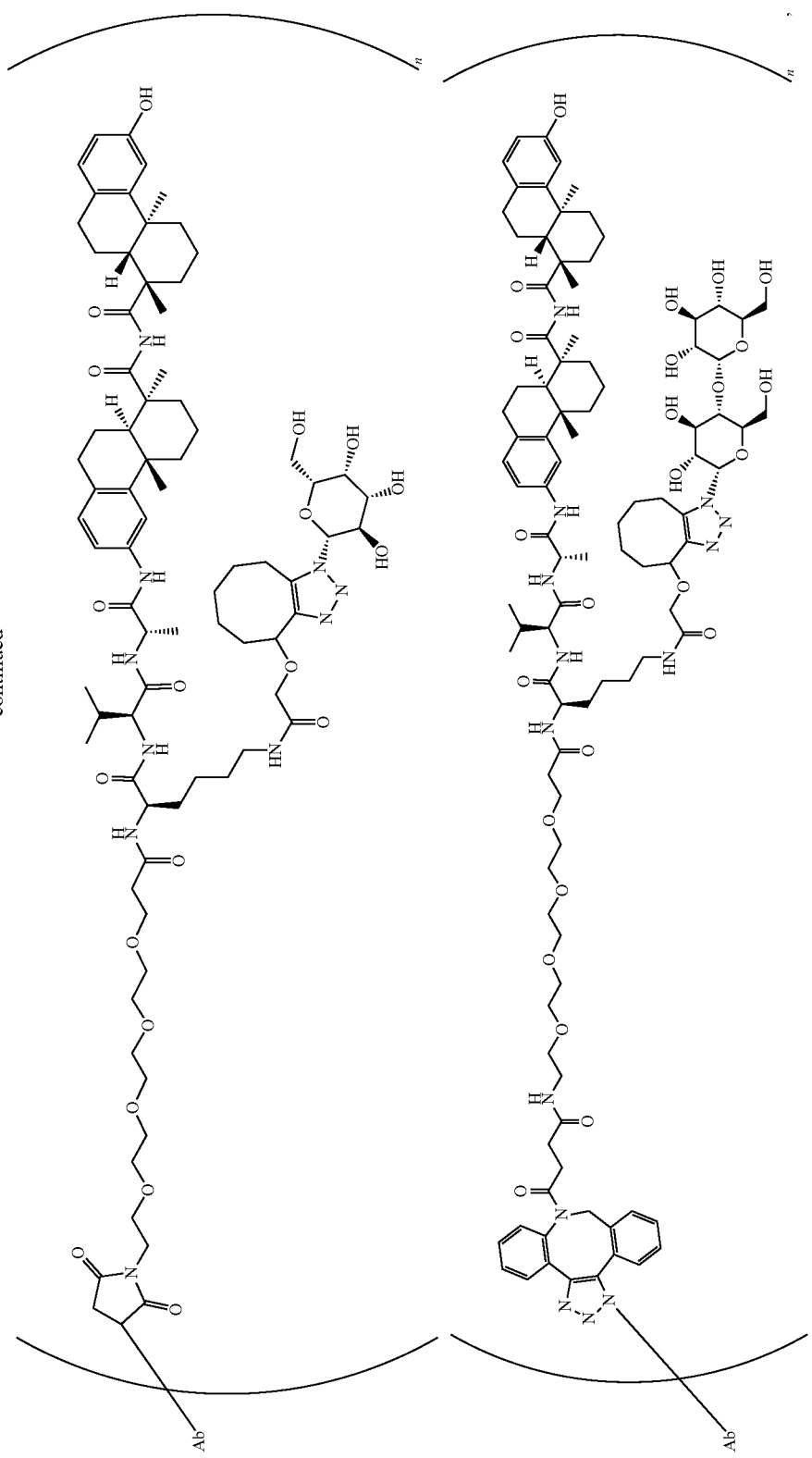

-continued
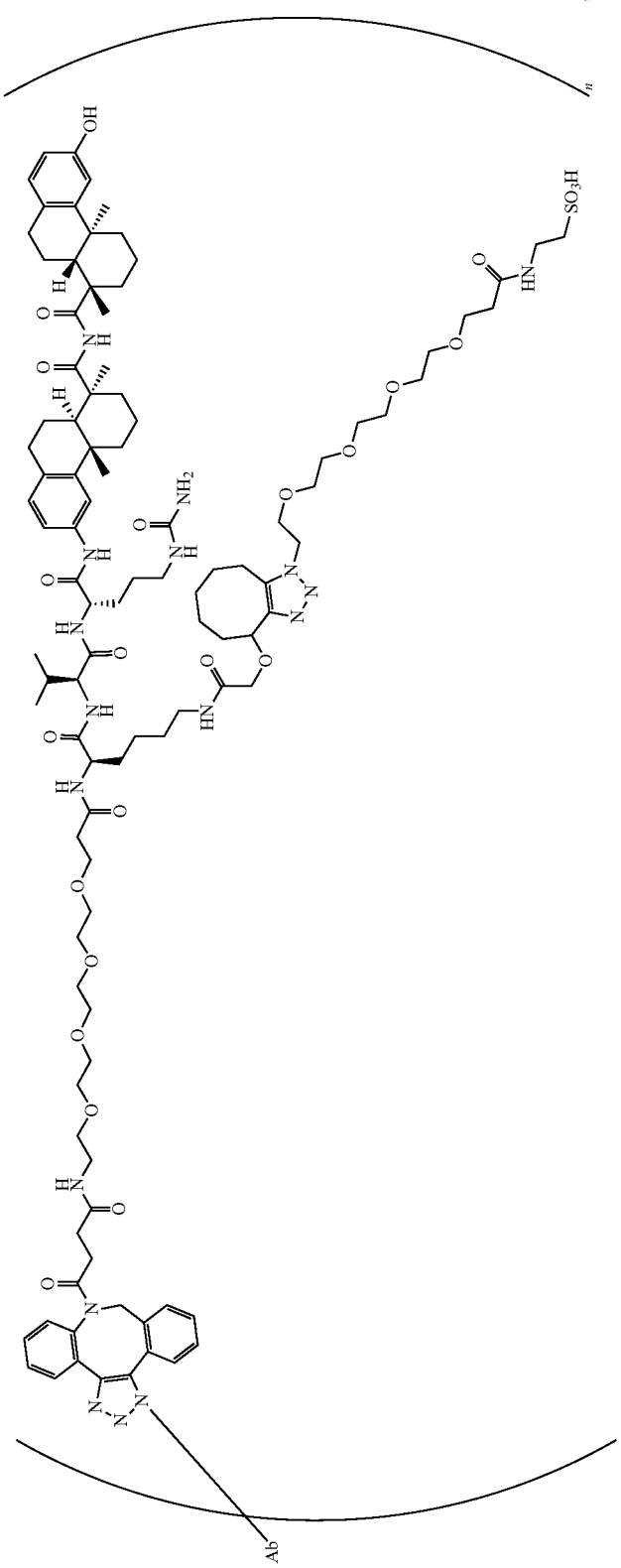

-continued
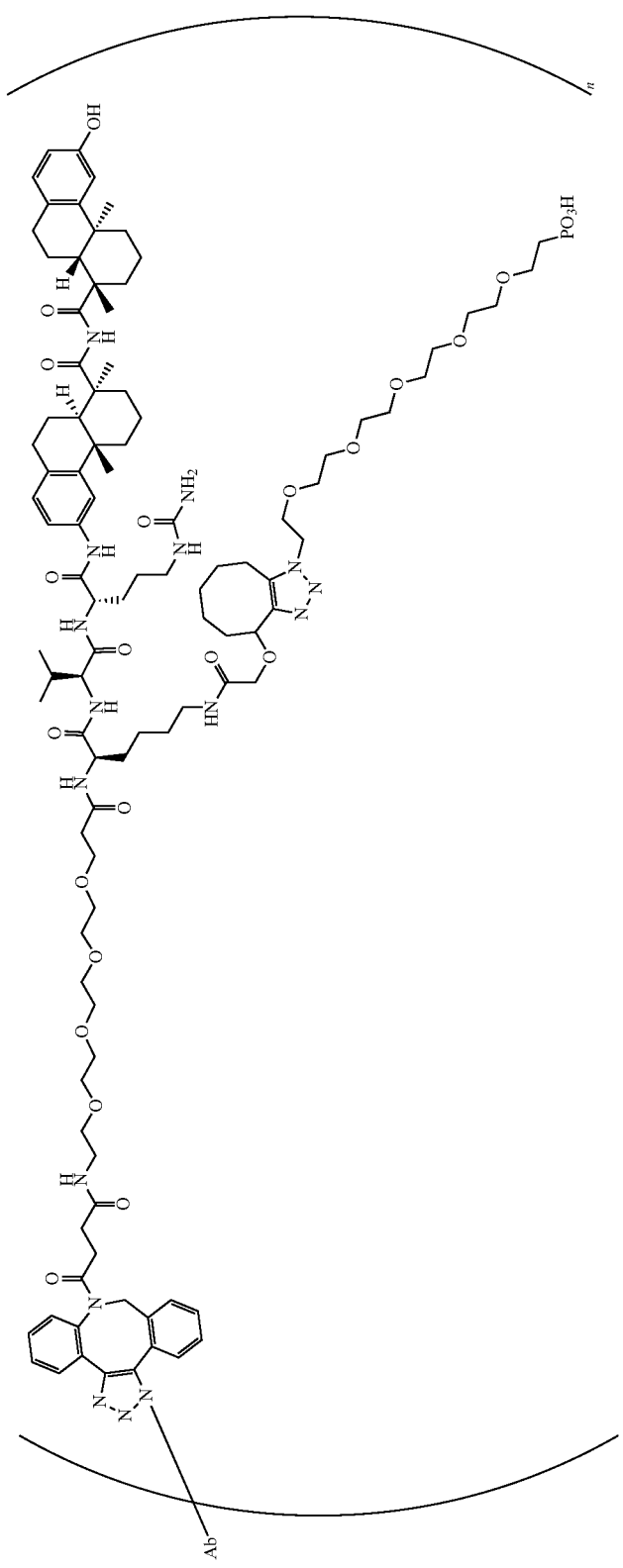

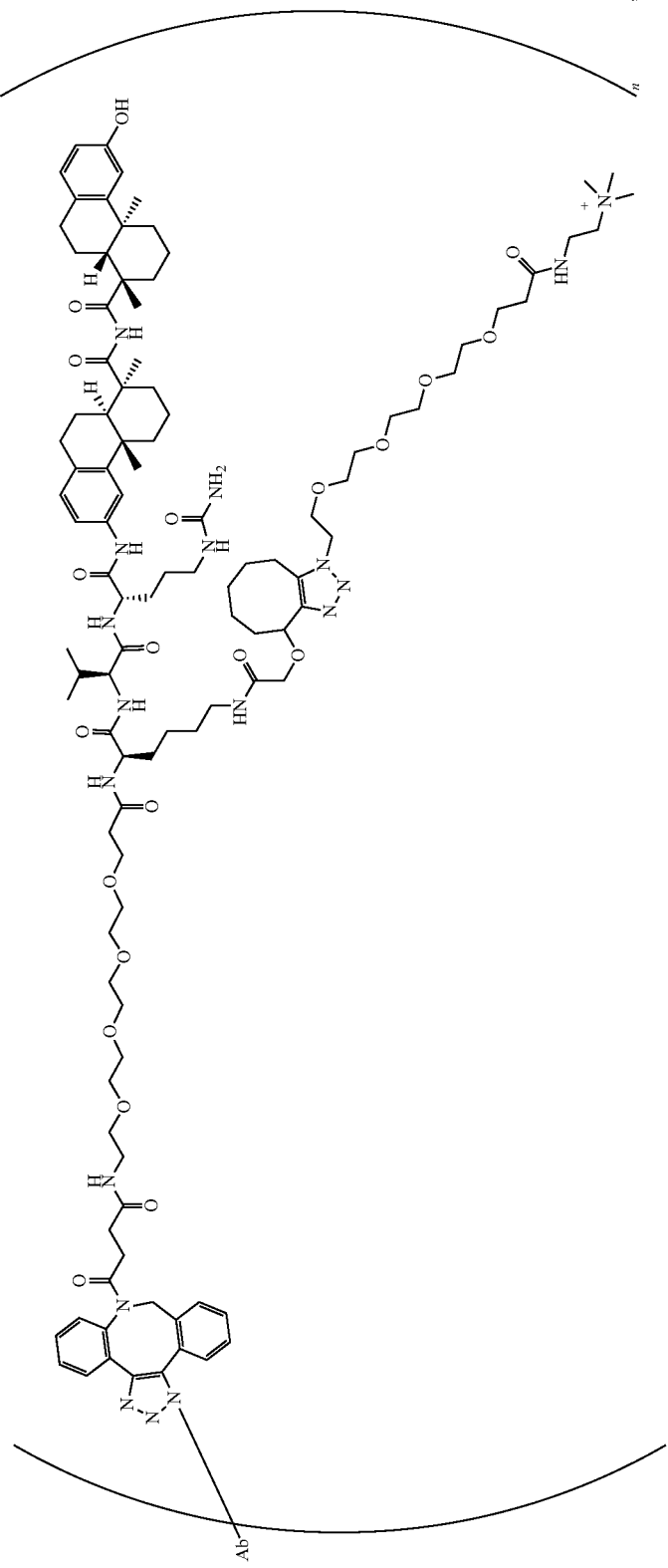

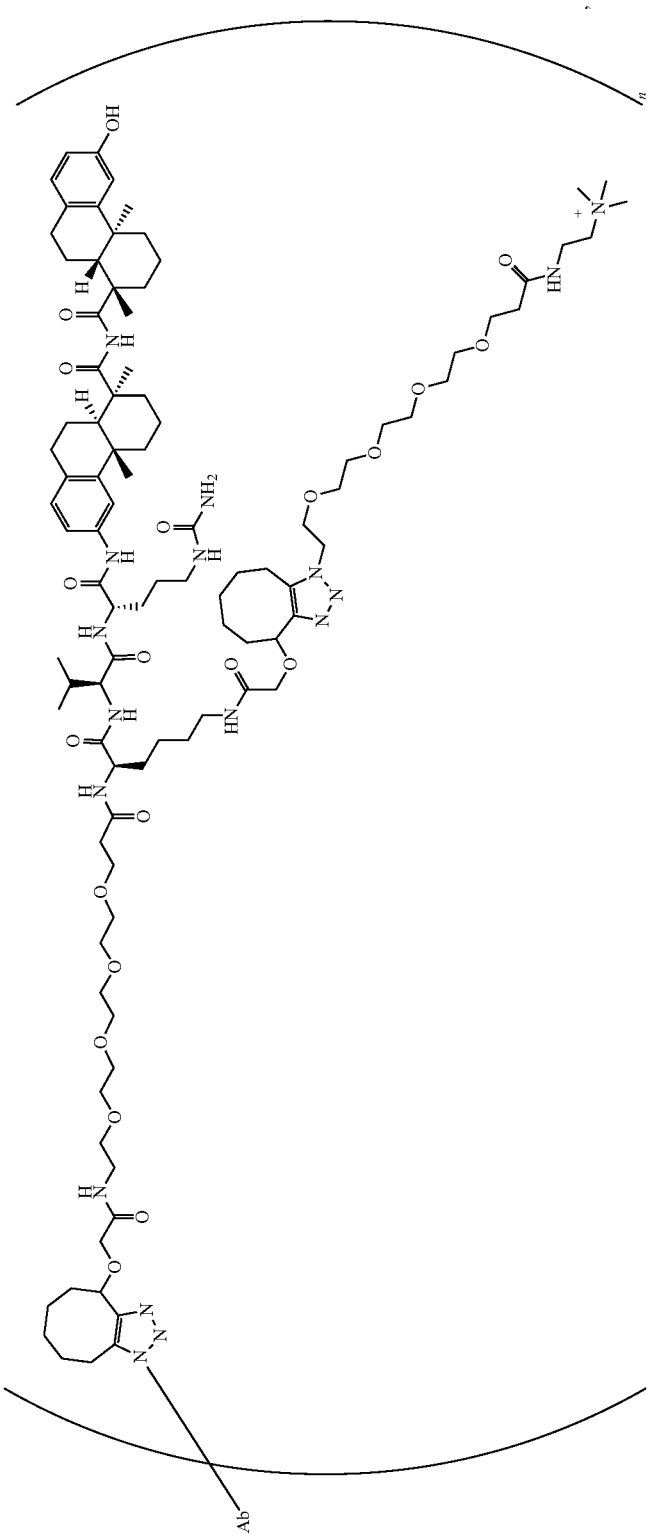

1227 1228
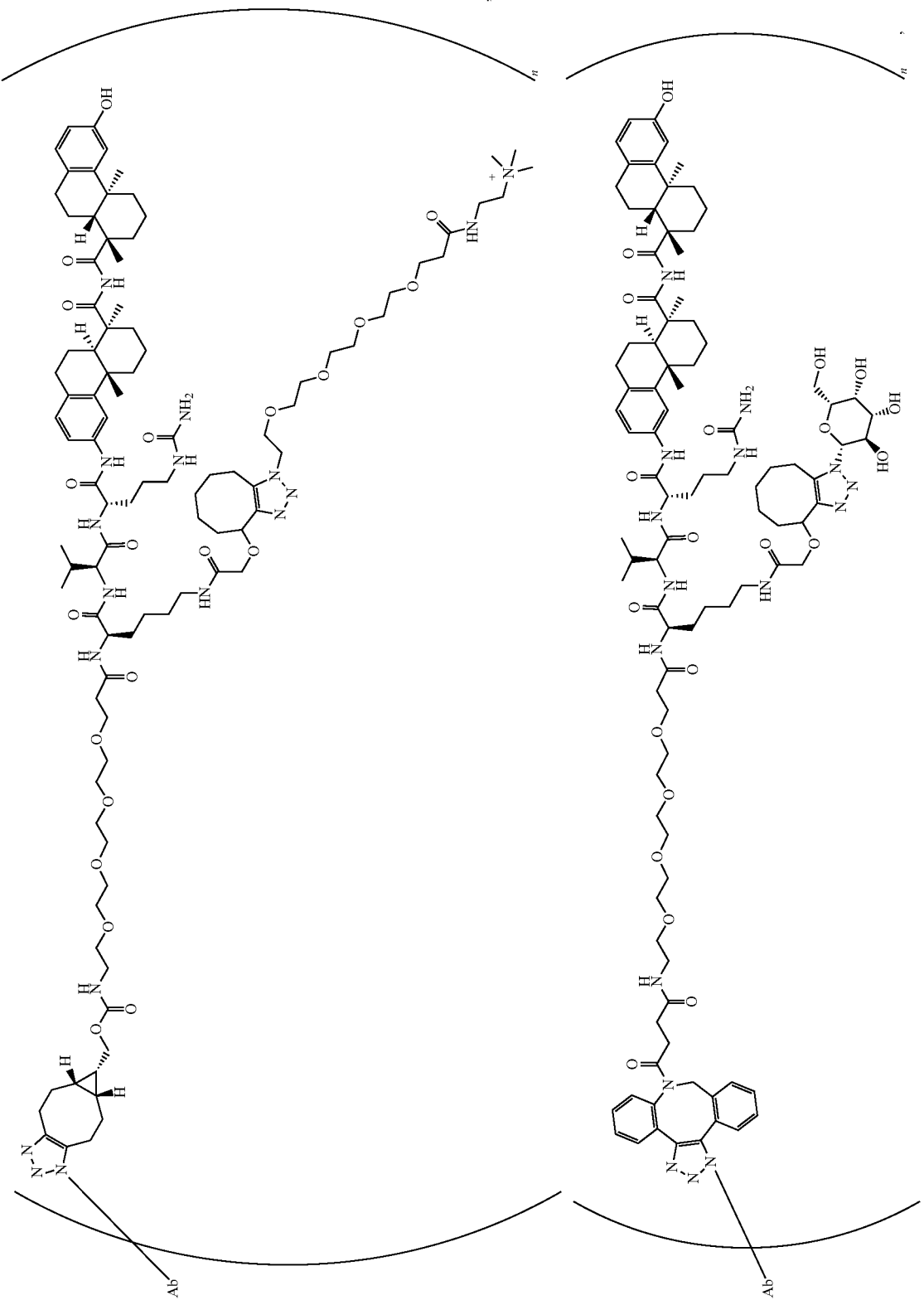
-continued

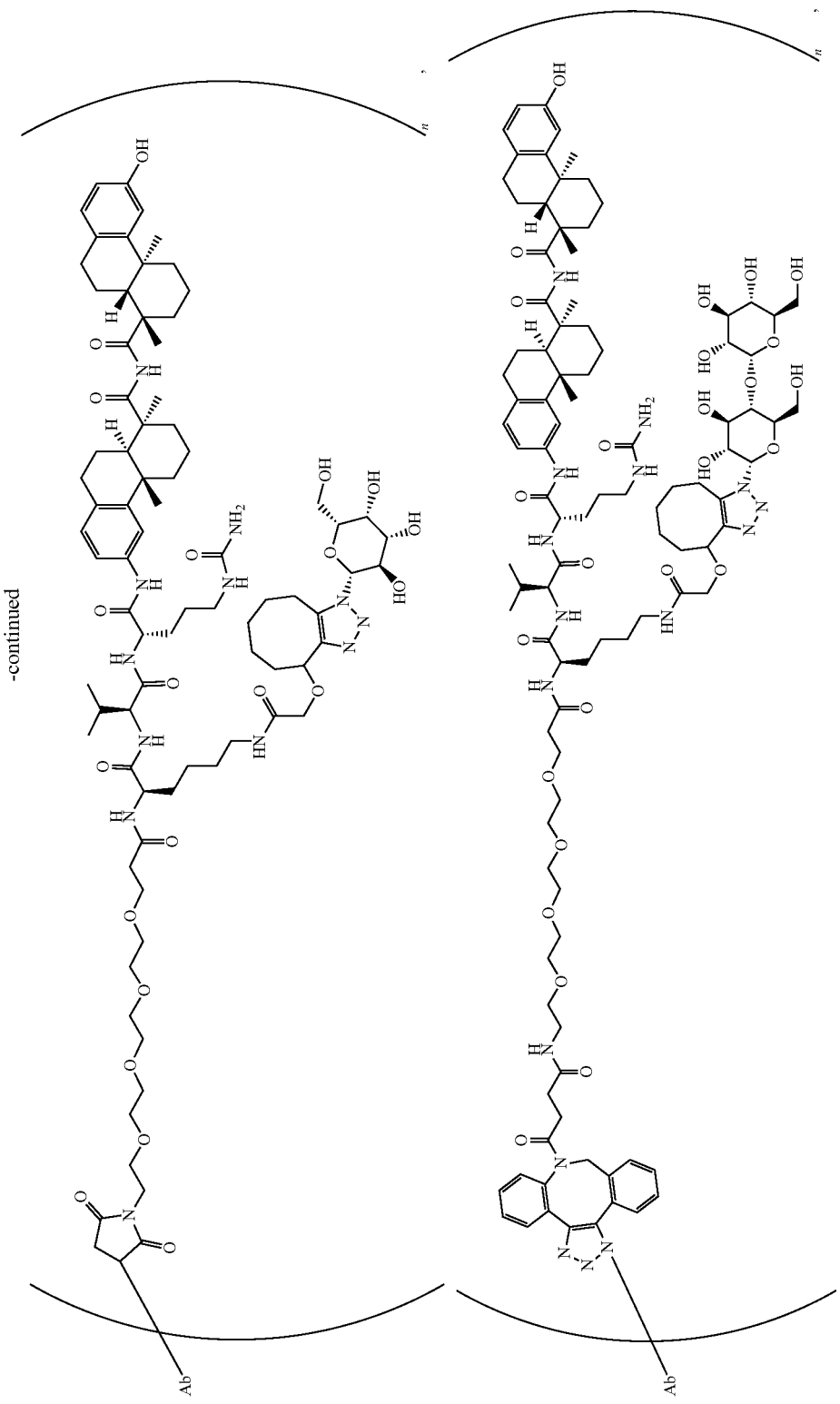

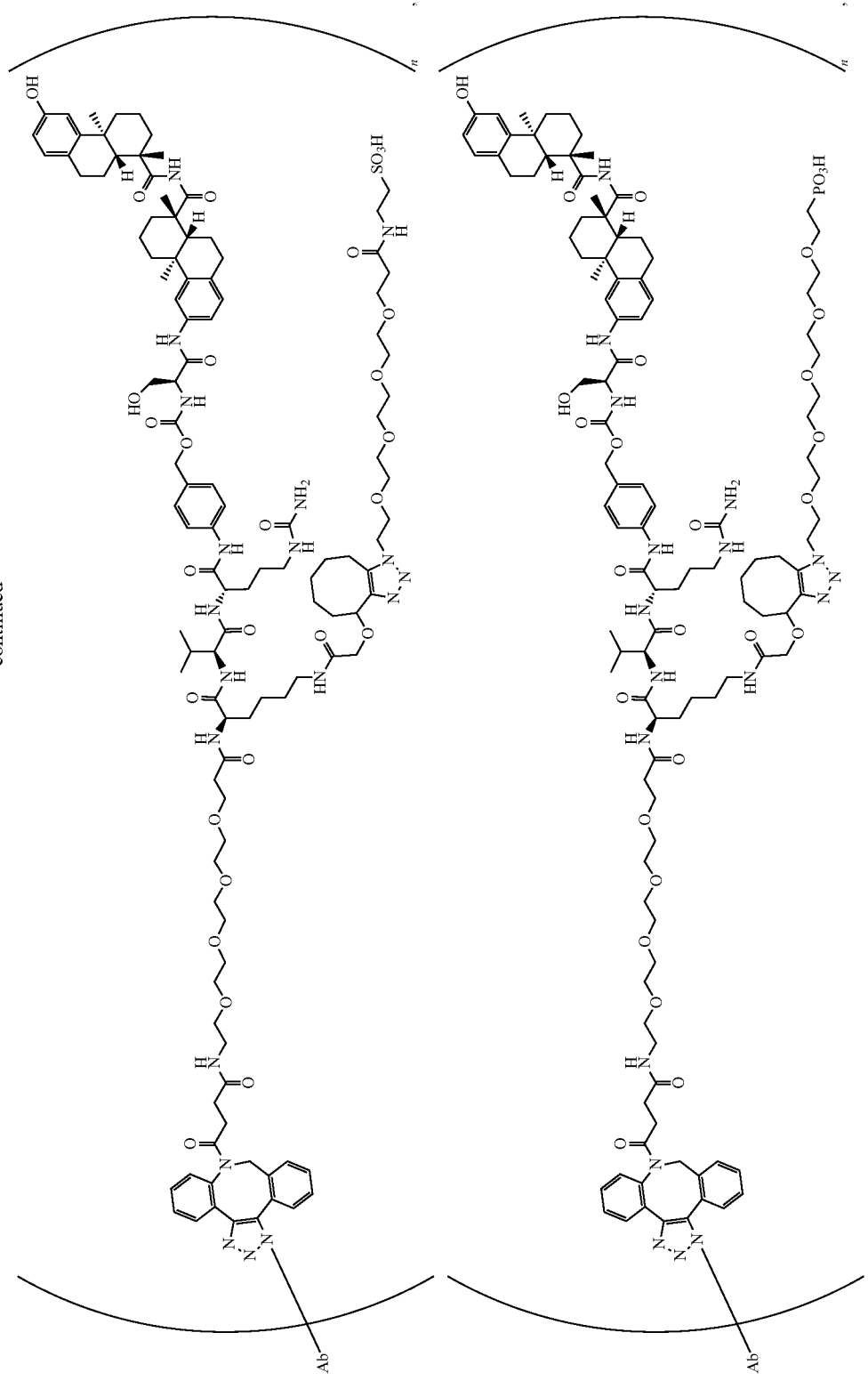

1233 1234
-continued
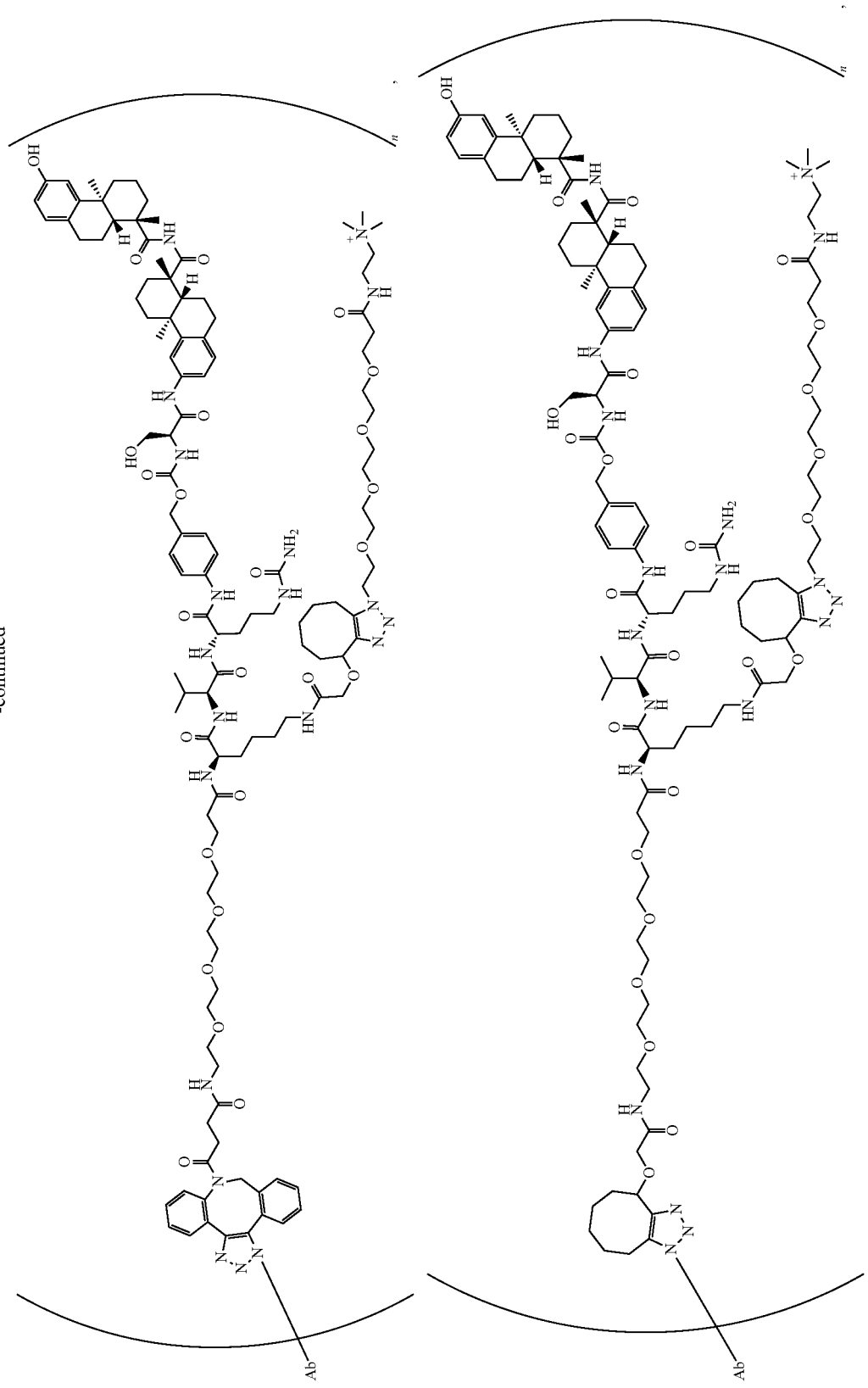

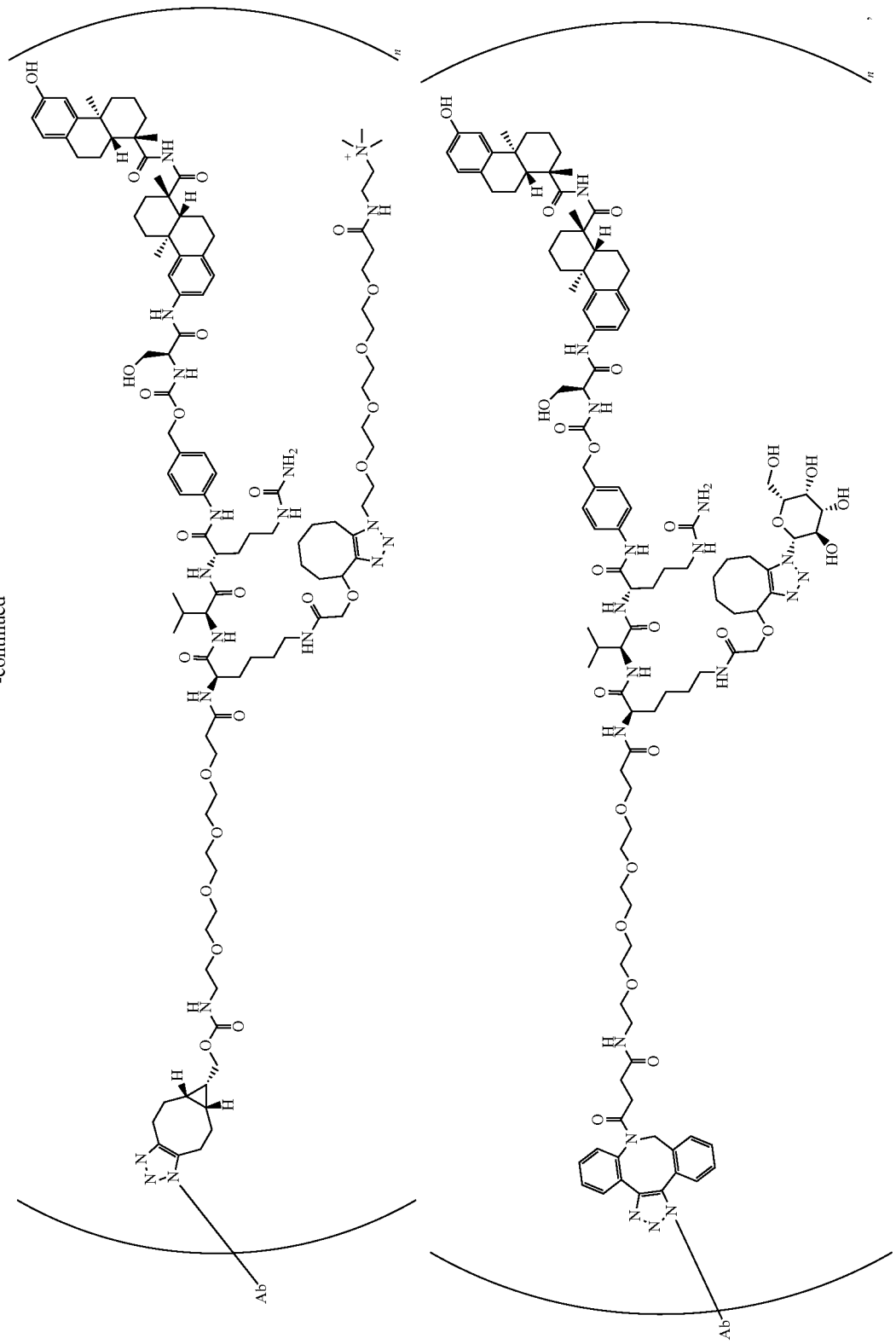

1237
1238
-continued
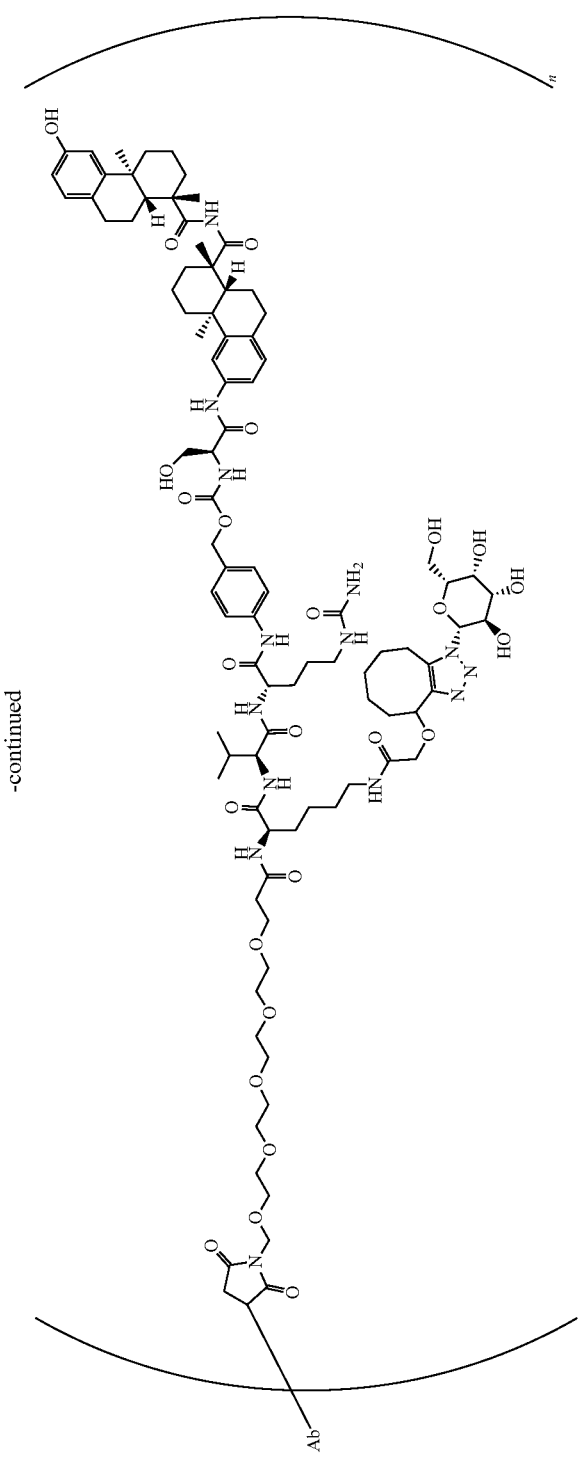
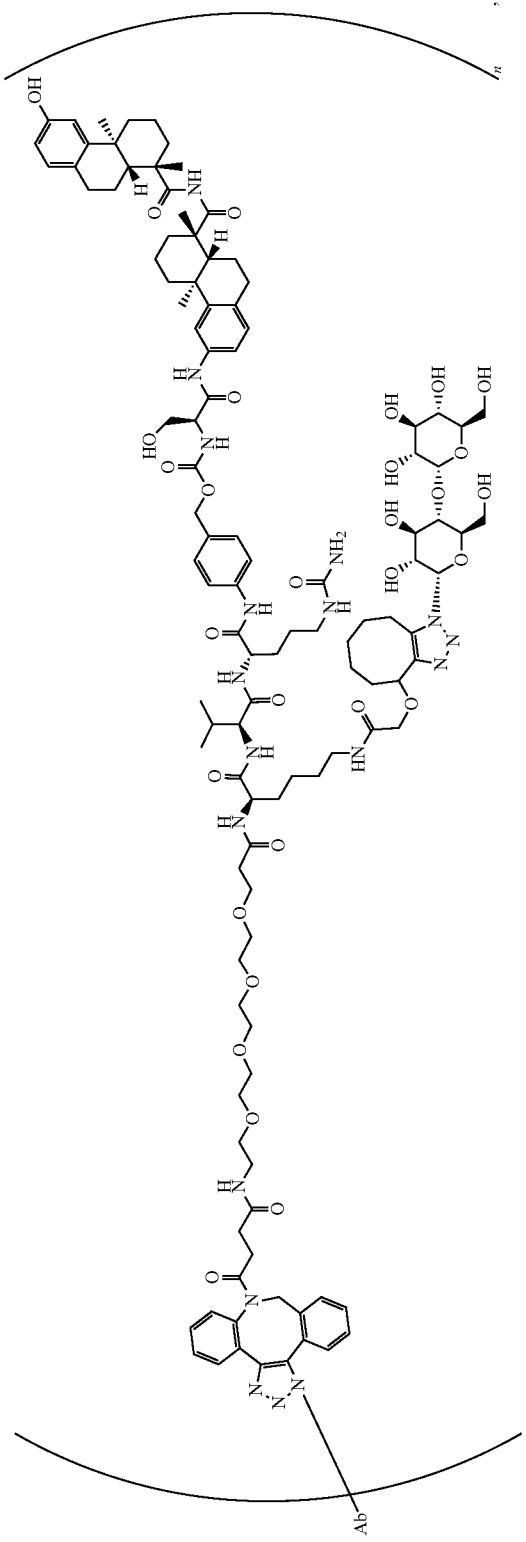

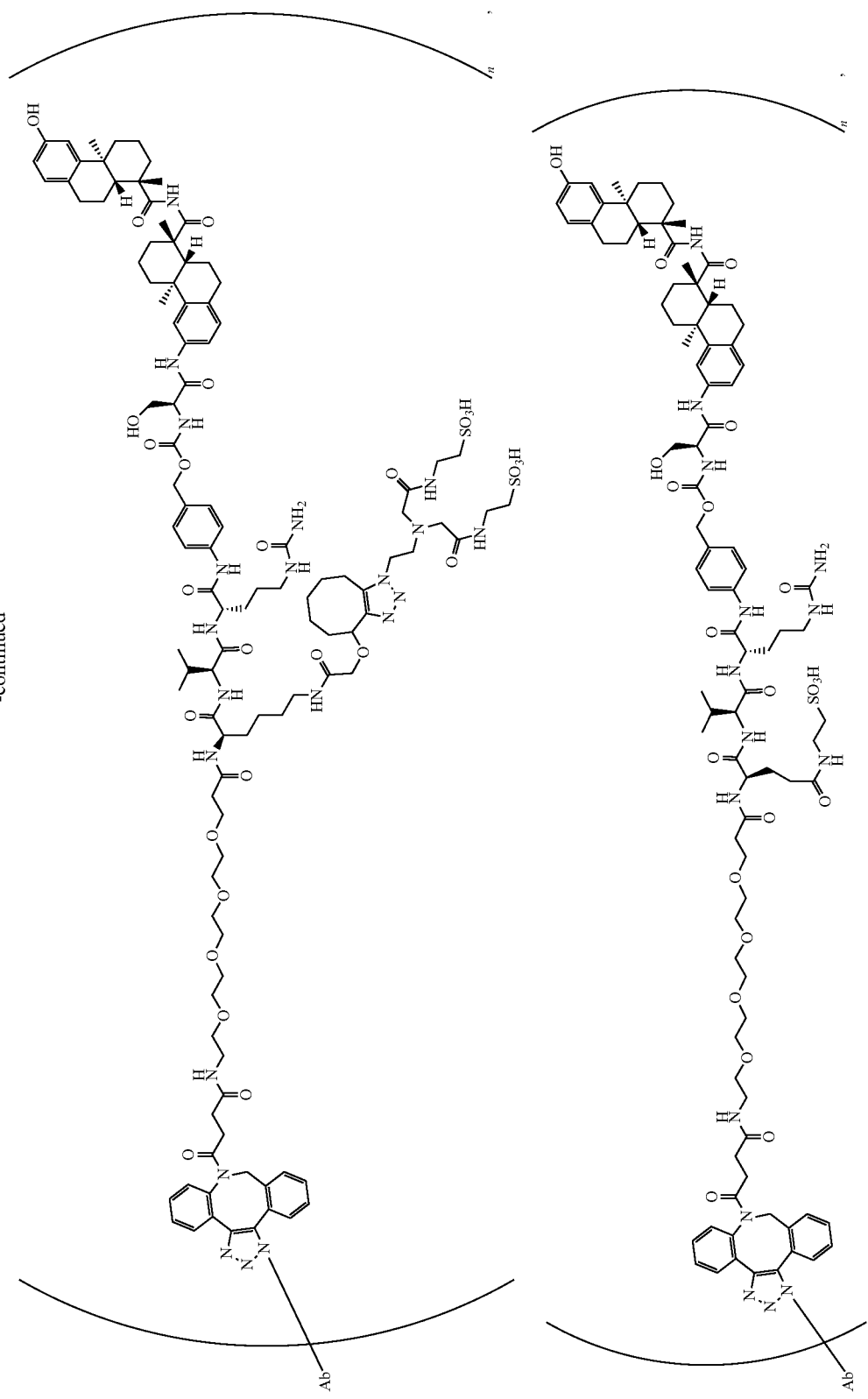

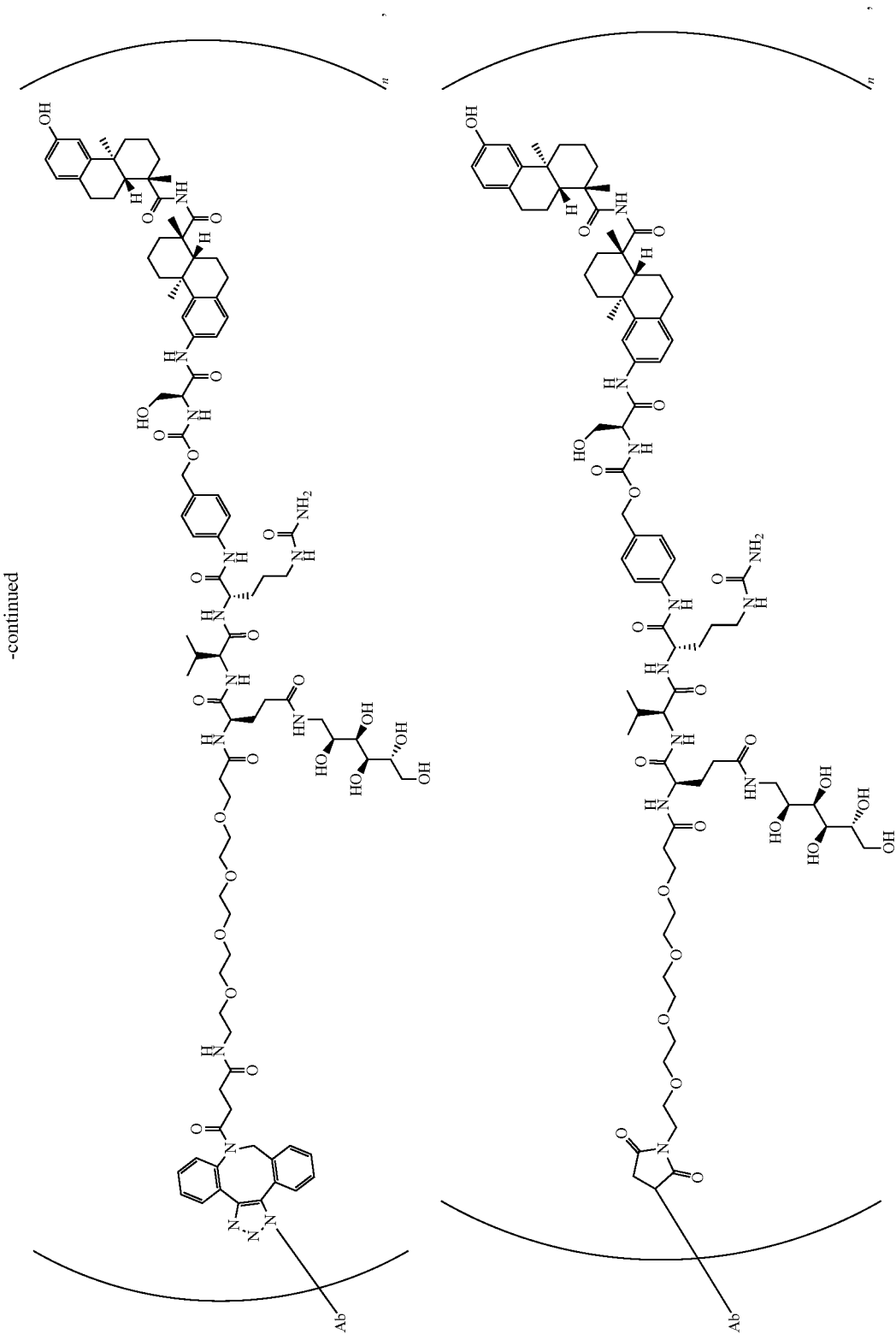

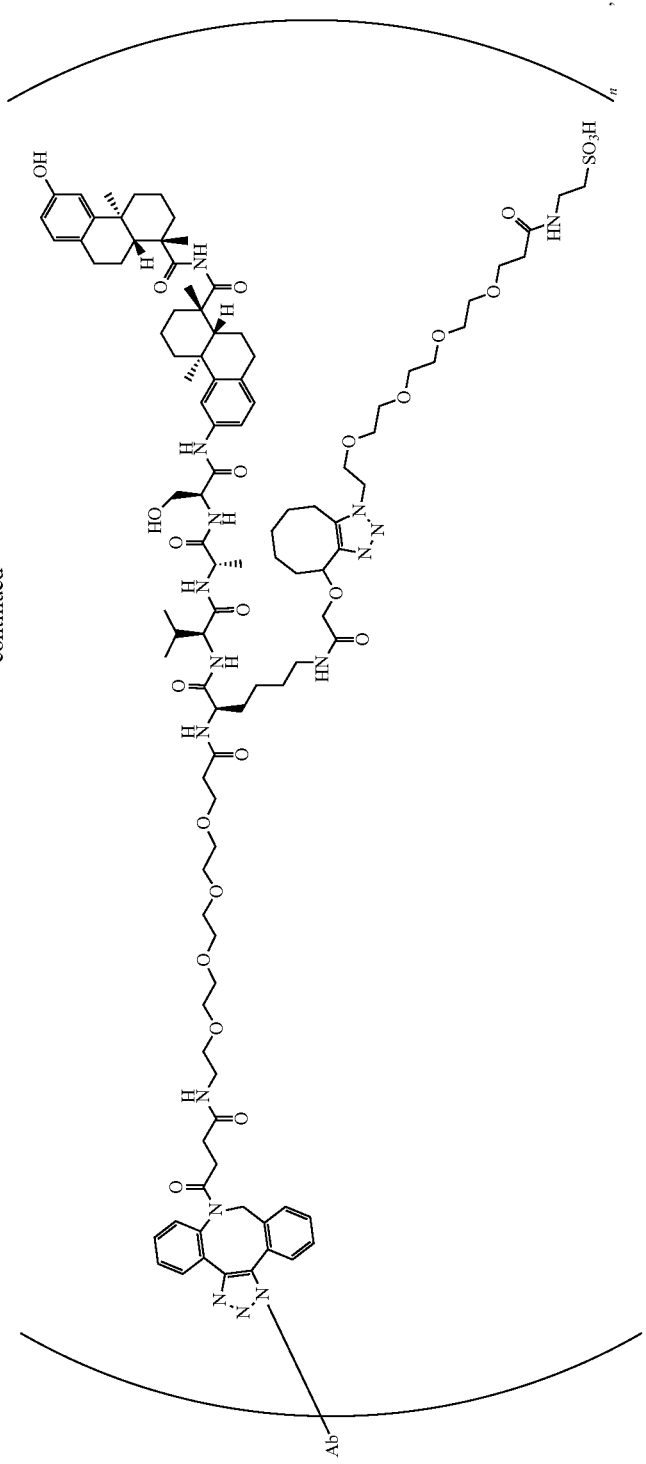

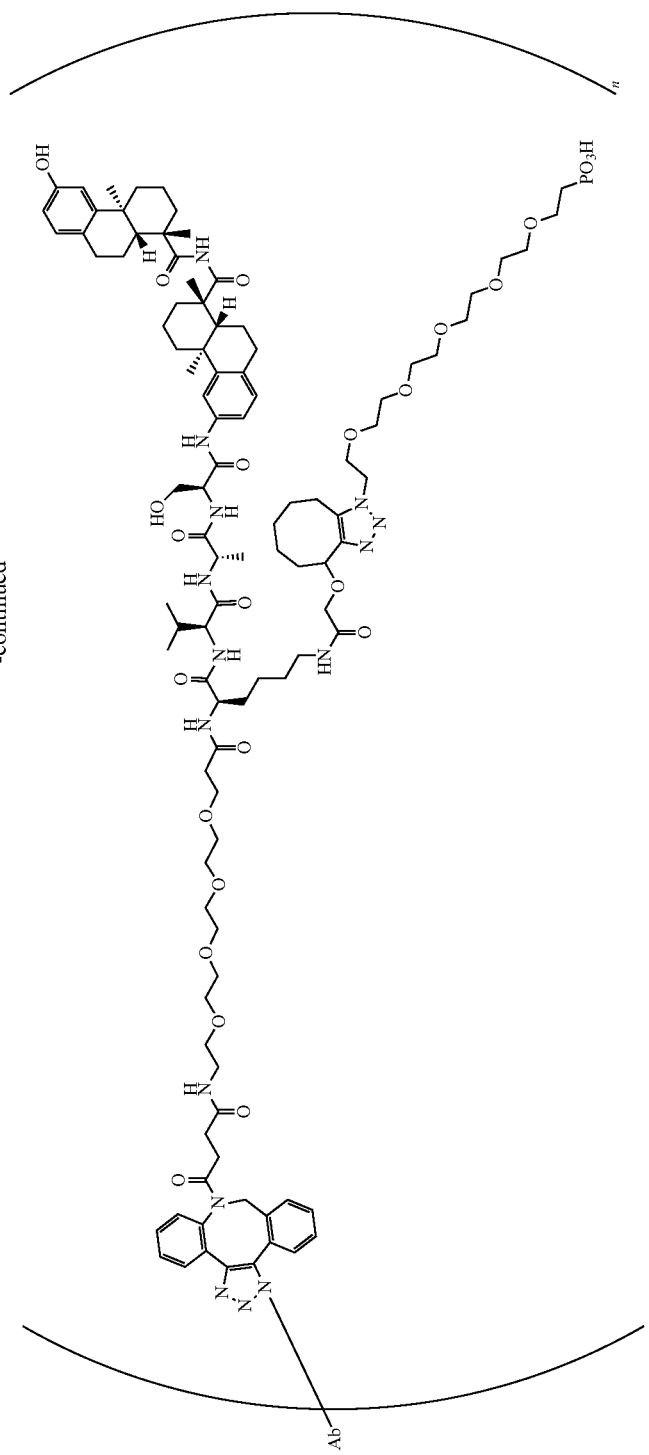

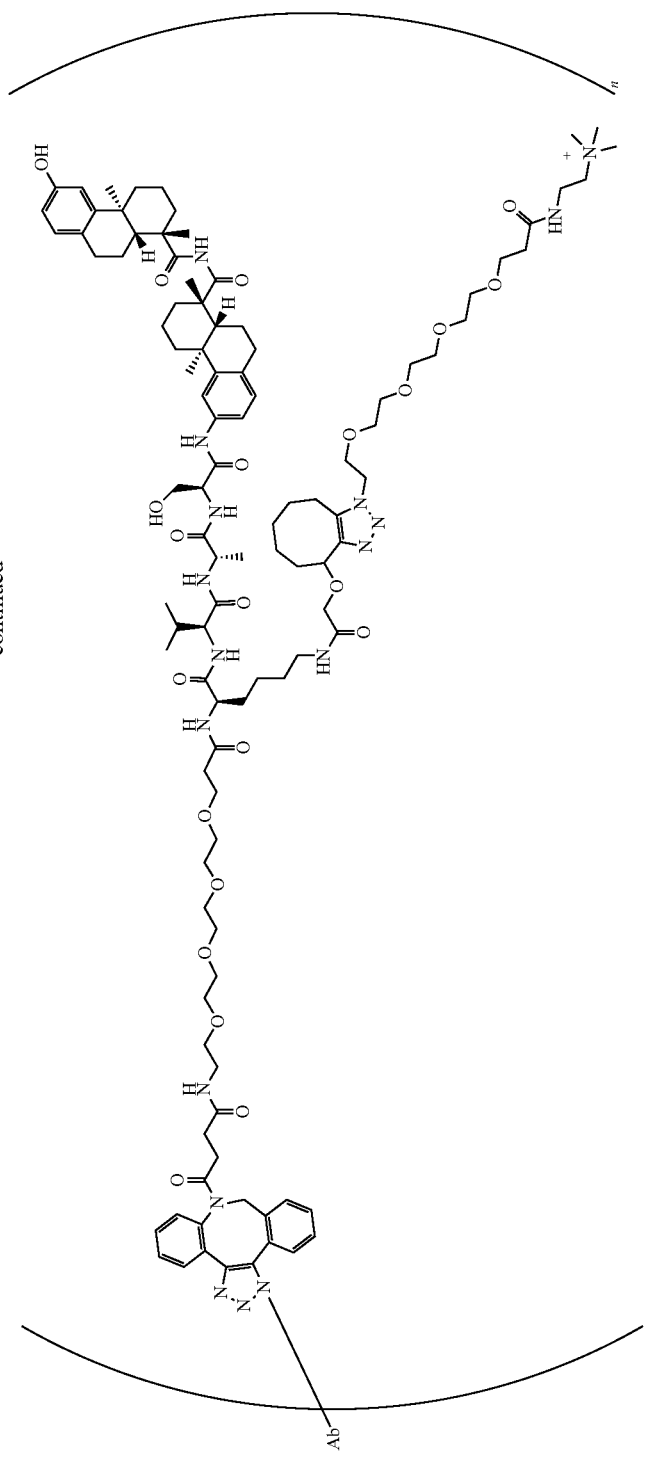

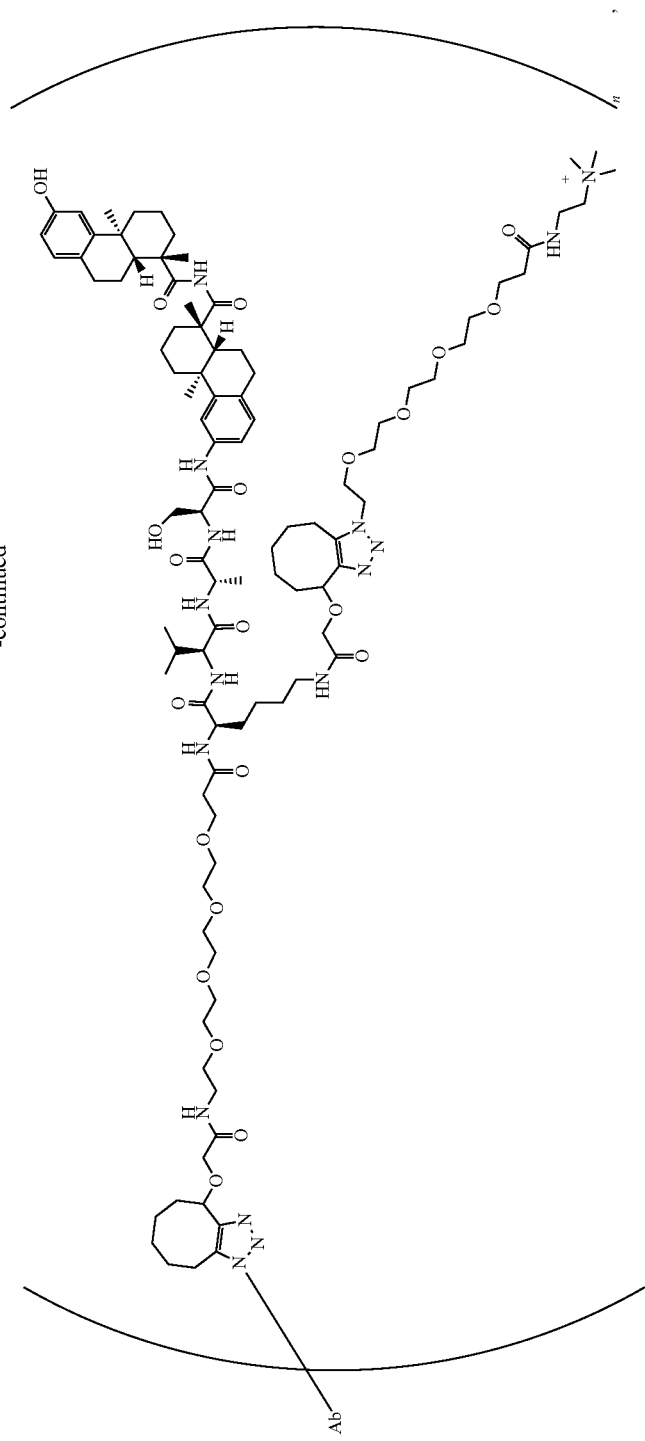

1251 1252
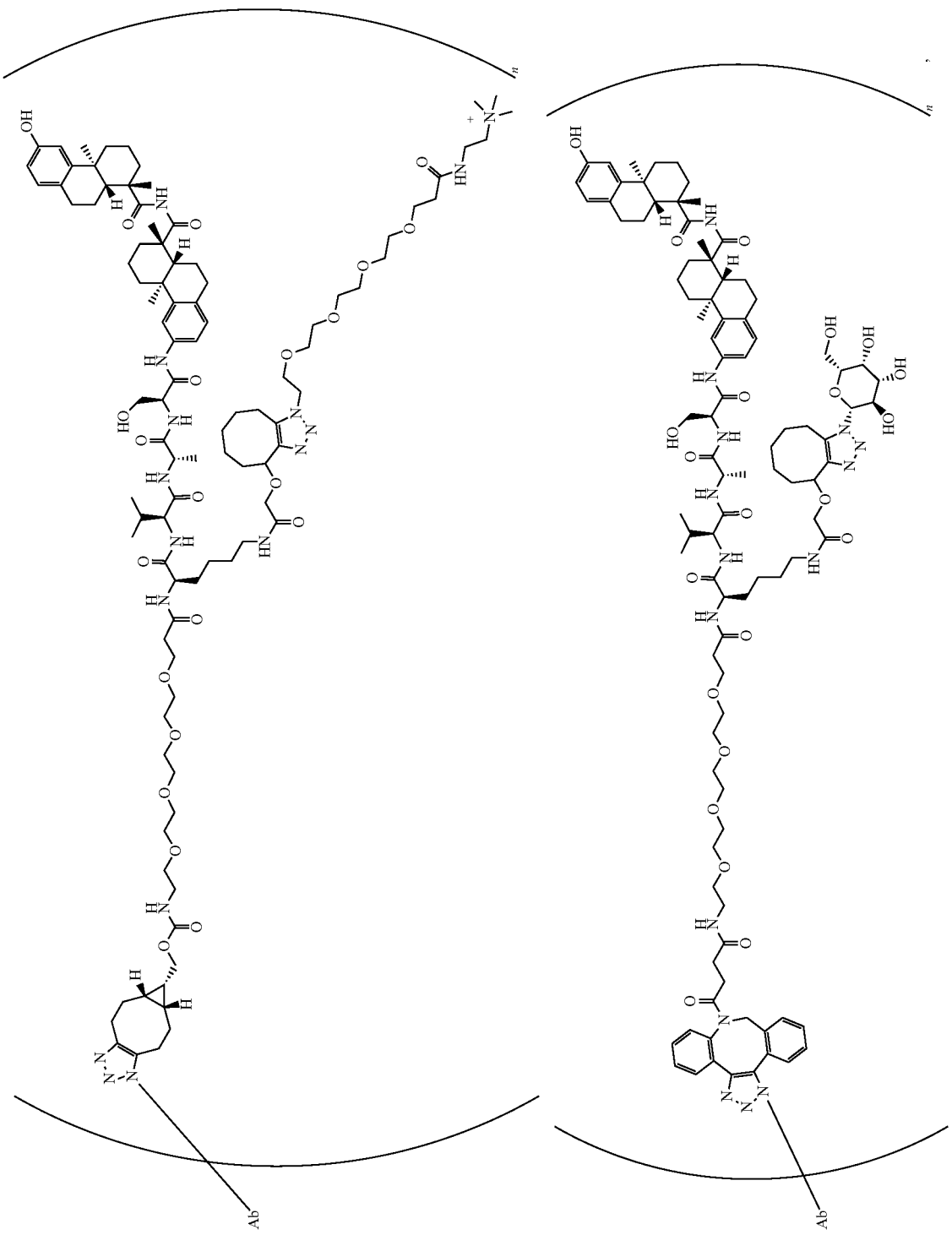

1253 1254
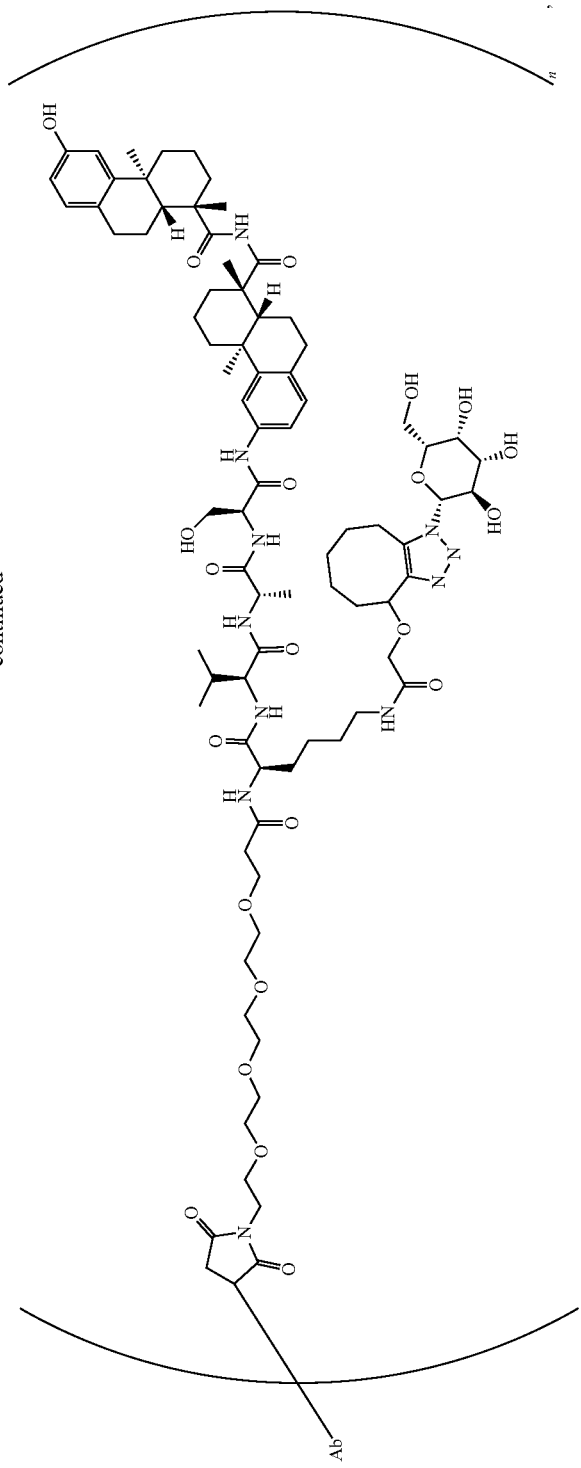
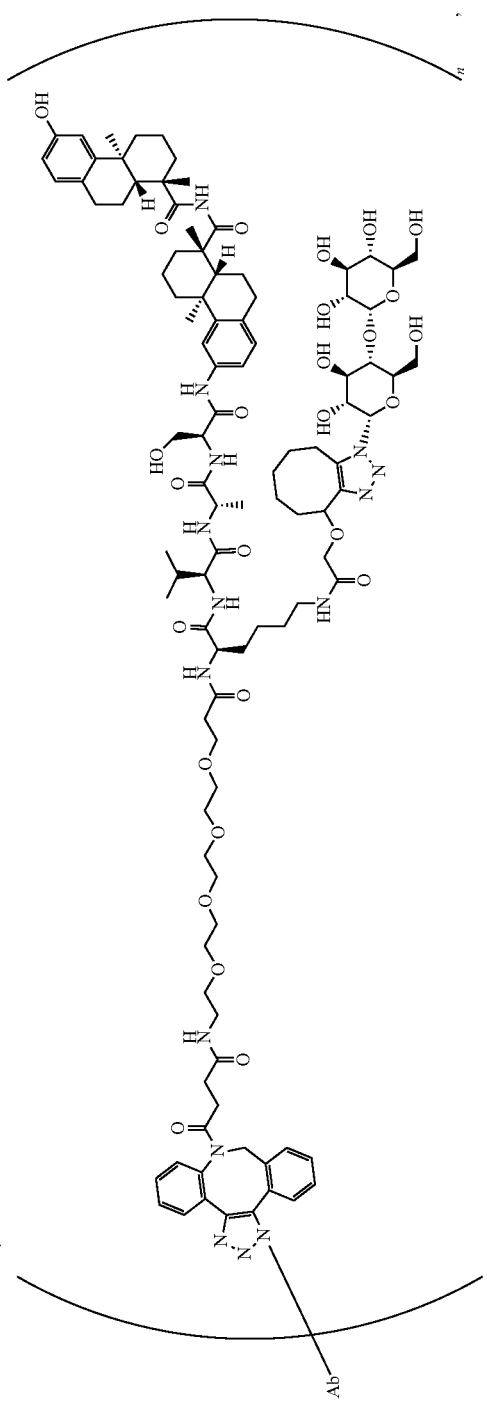

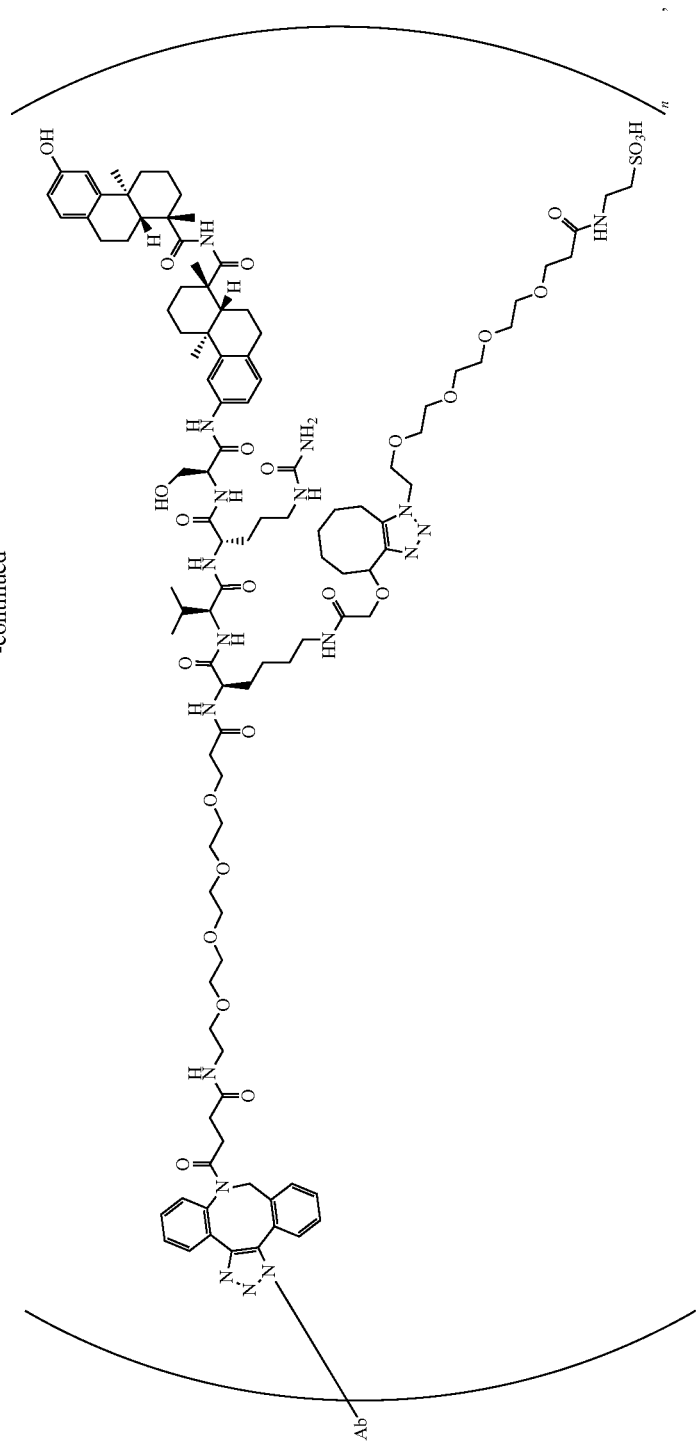

-continued
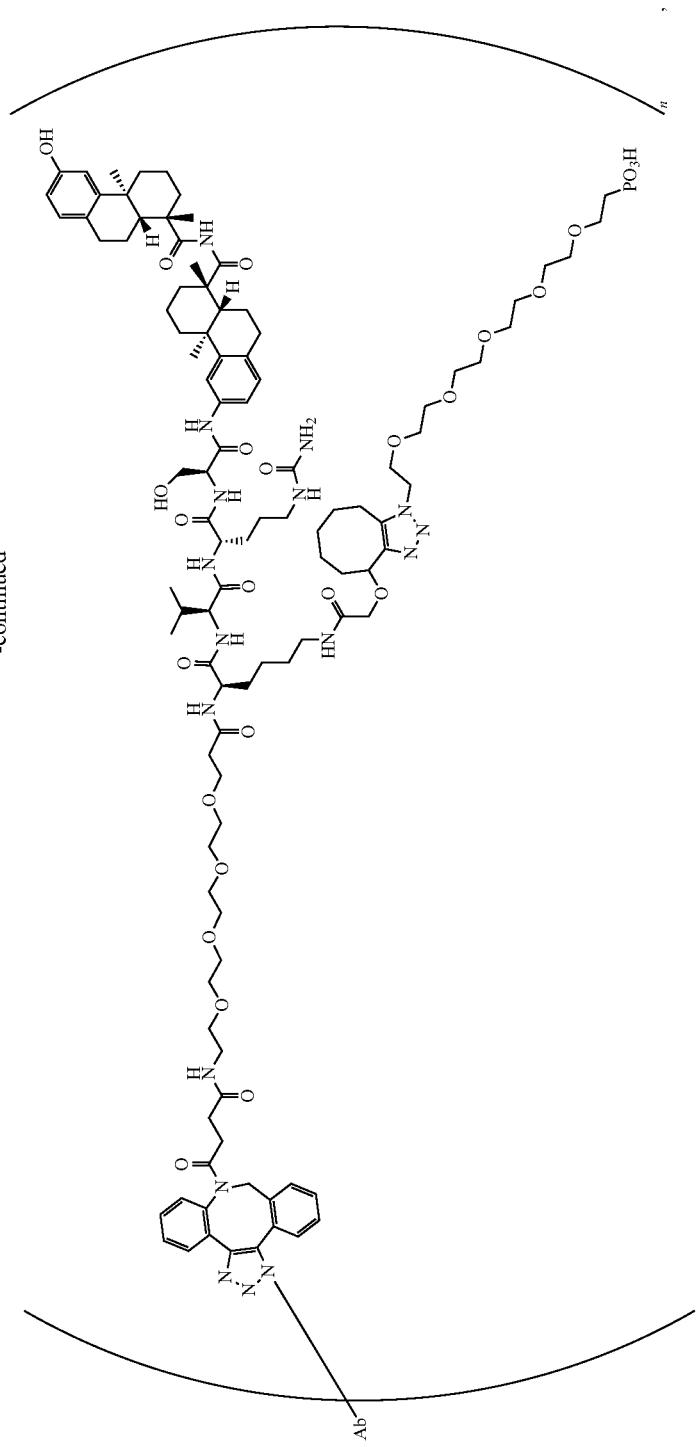

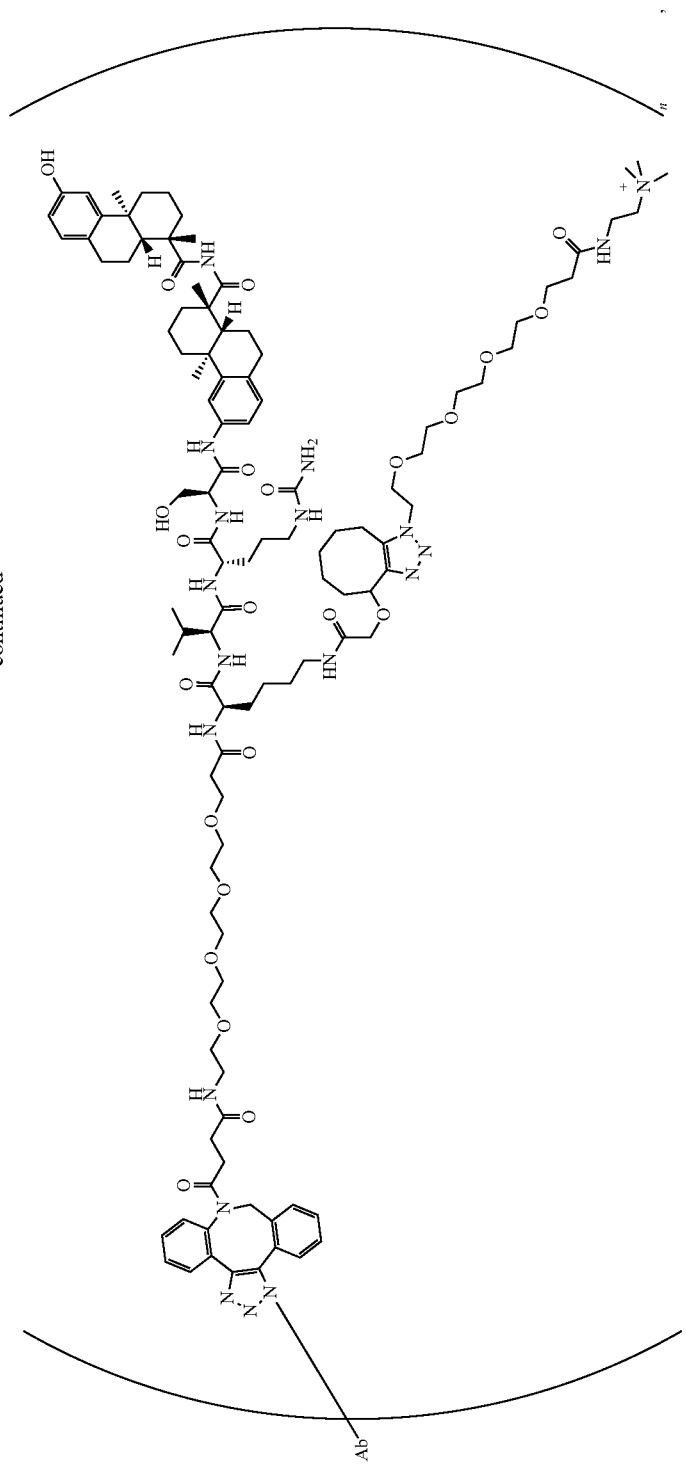

-continued
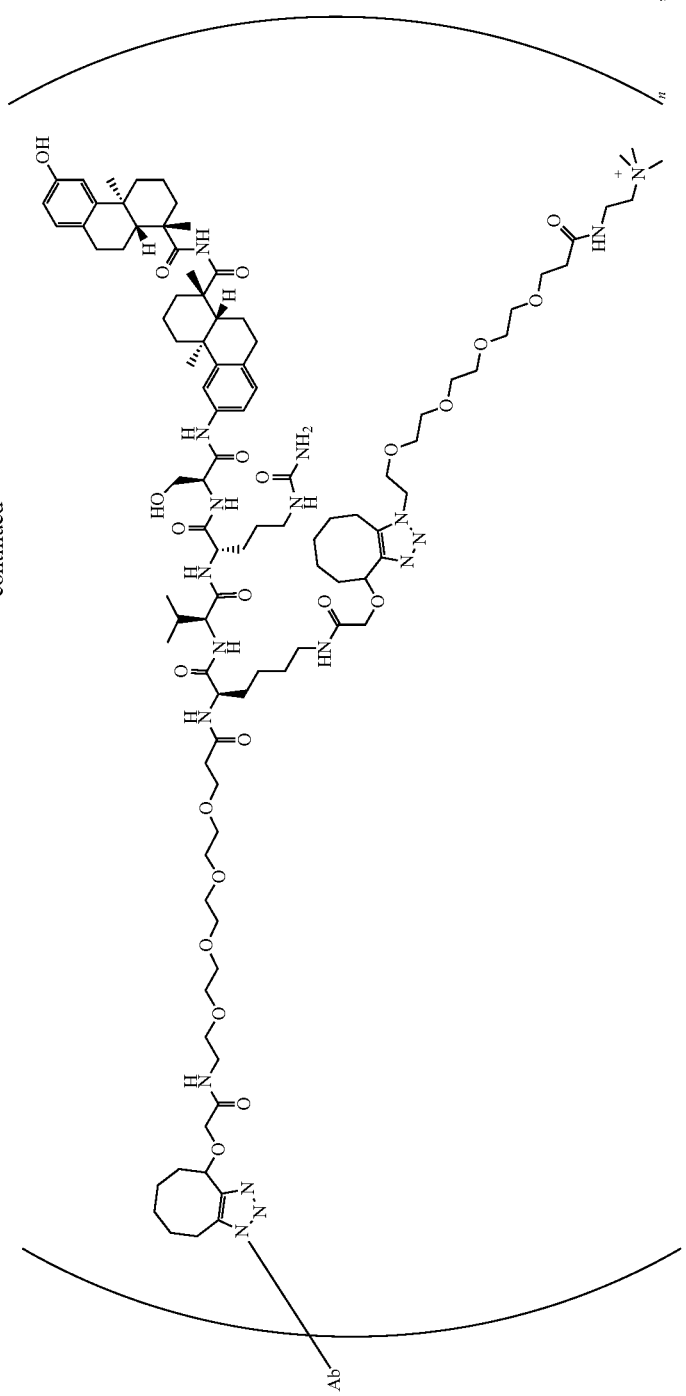

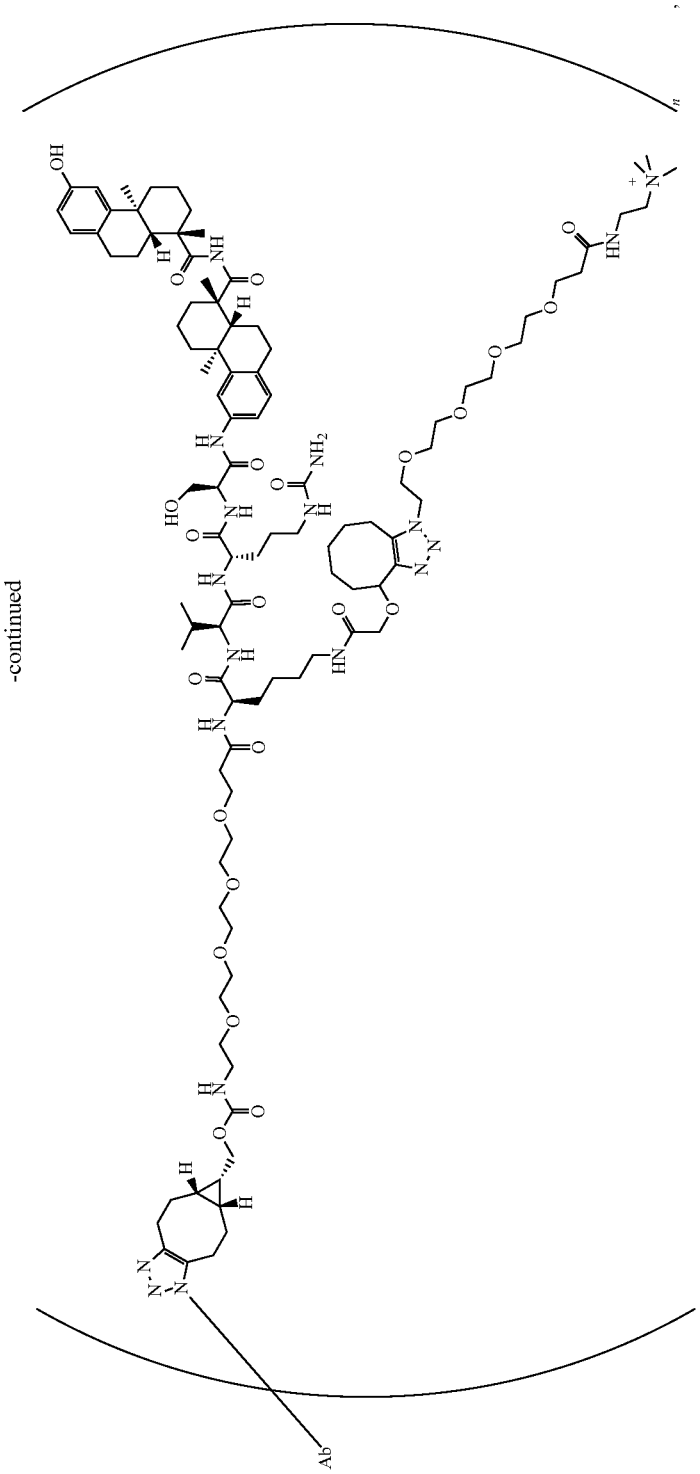

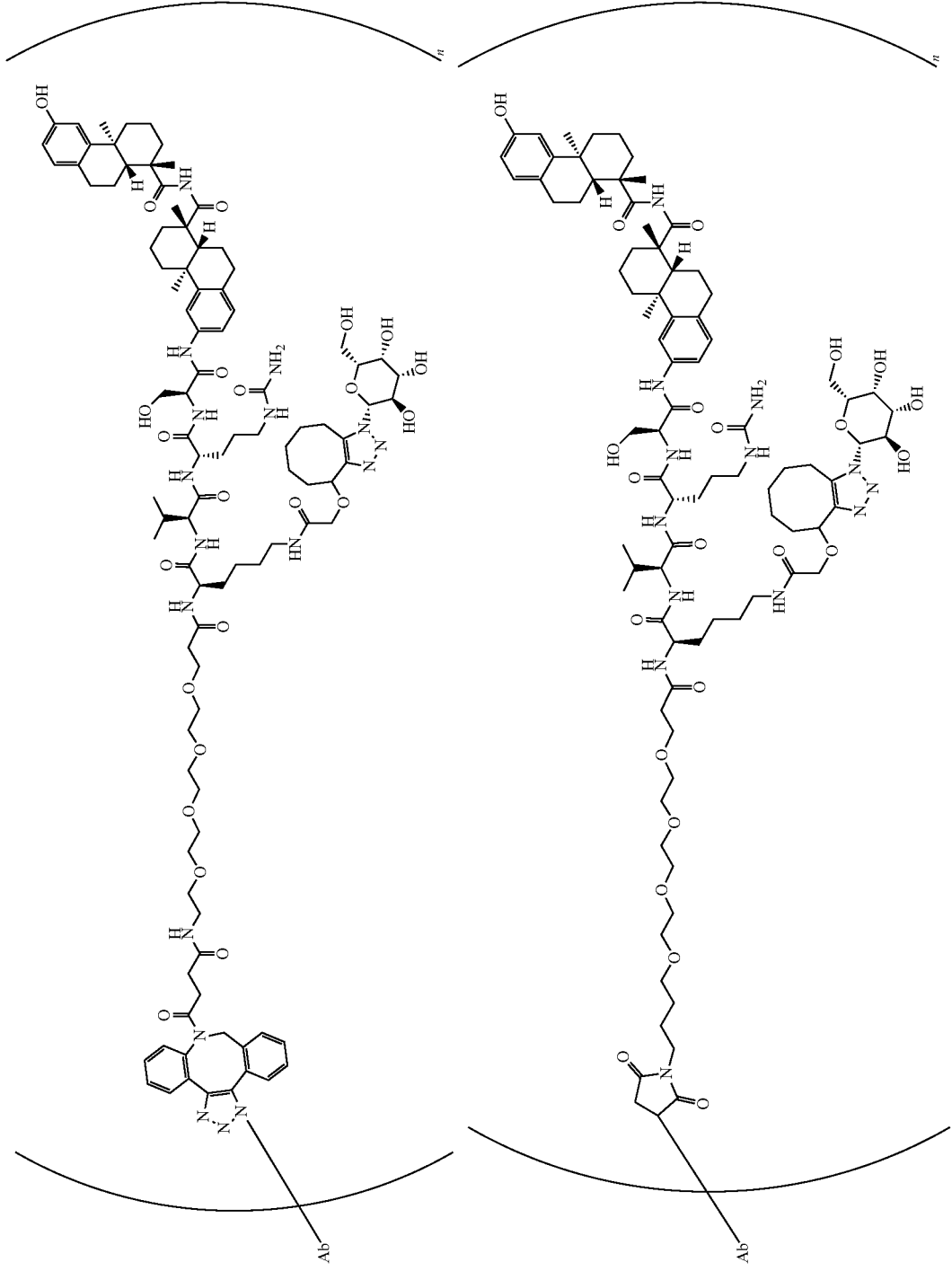

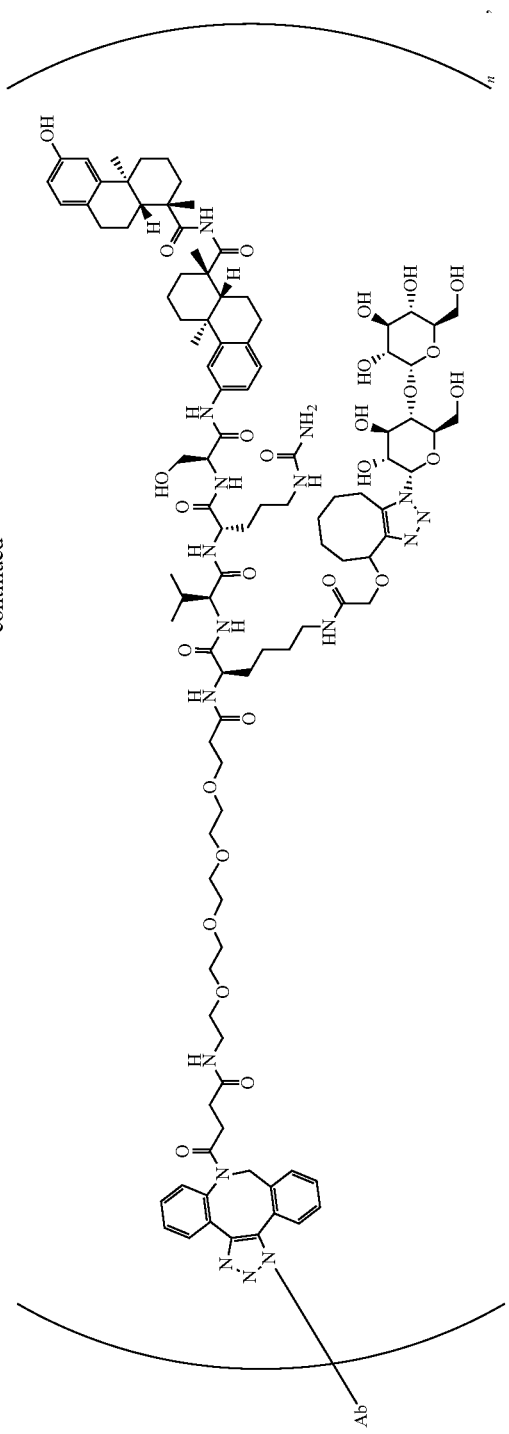

or a stereoisomeric form thereof, or a regioisomer thereof, or a mixture of regioisomers thereof, wherein
each Ab is the antibody, or an antigen-binding fragment thereof; and
subscript n is an integer from 1 to 30.

18. The compound of claim 1, wherein BA is a modified antibody of formula (Ab-1)

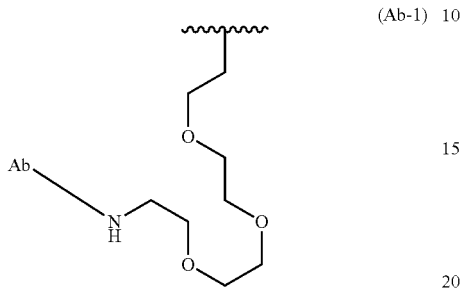

(Ab-1)

wherein the

indicates the atom through which Ab-1 is bonded to the adjacent groups in the formula.

19. A compound selected from the group consisting of:

1271 1272
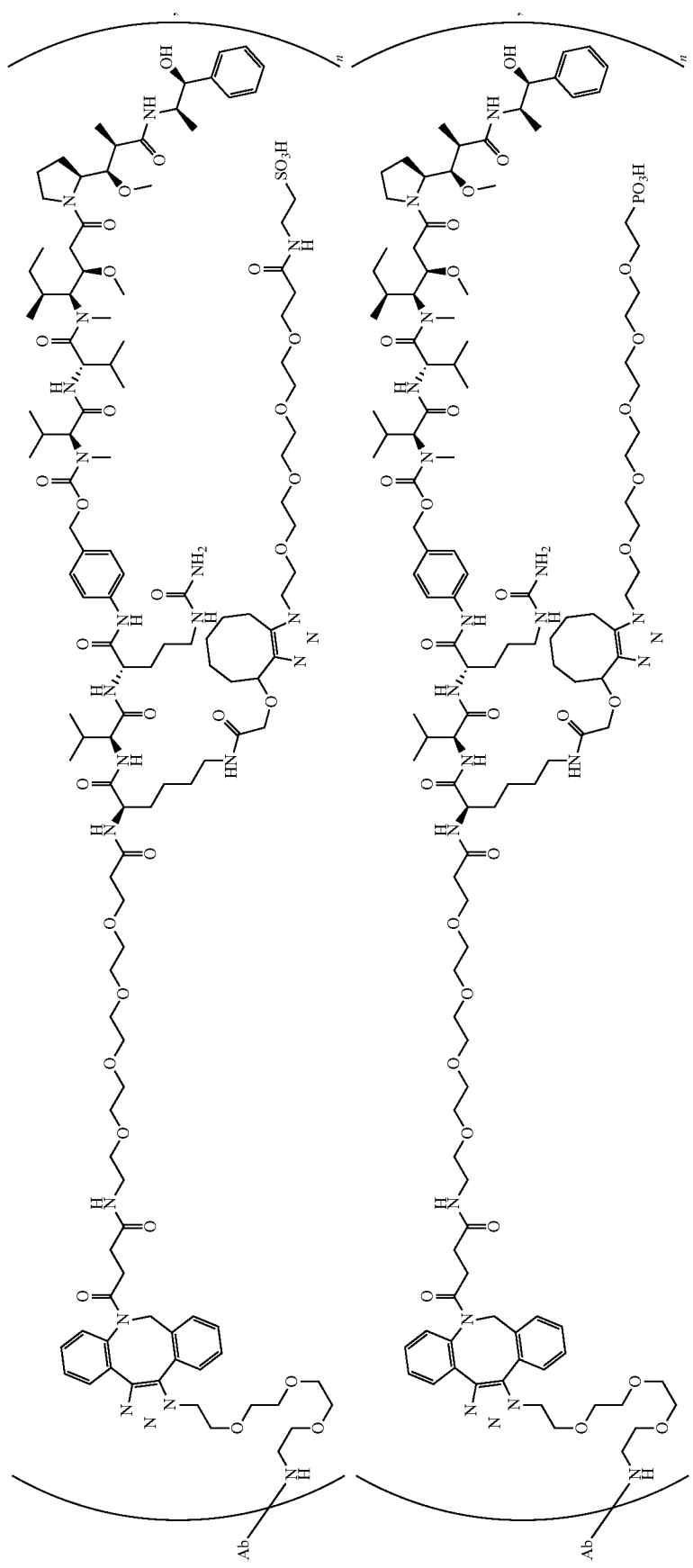

1273 1274
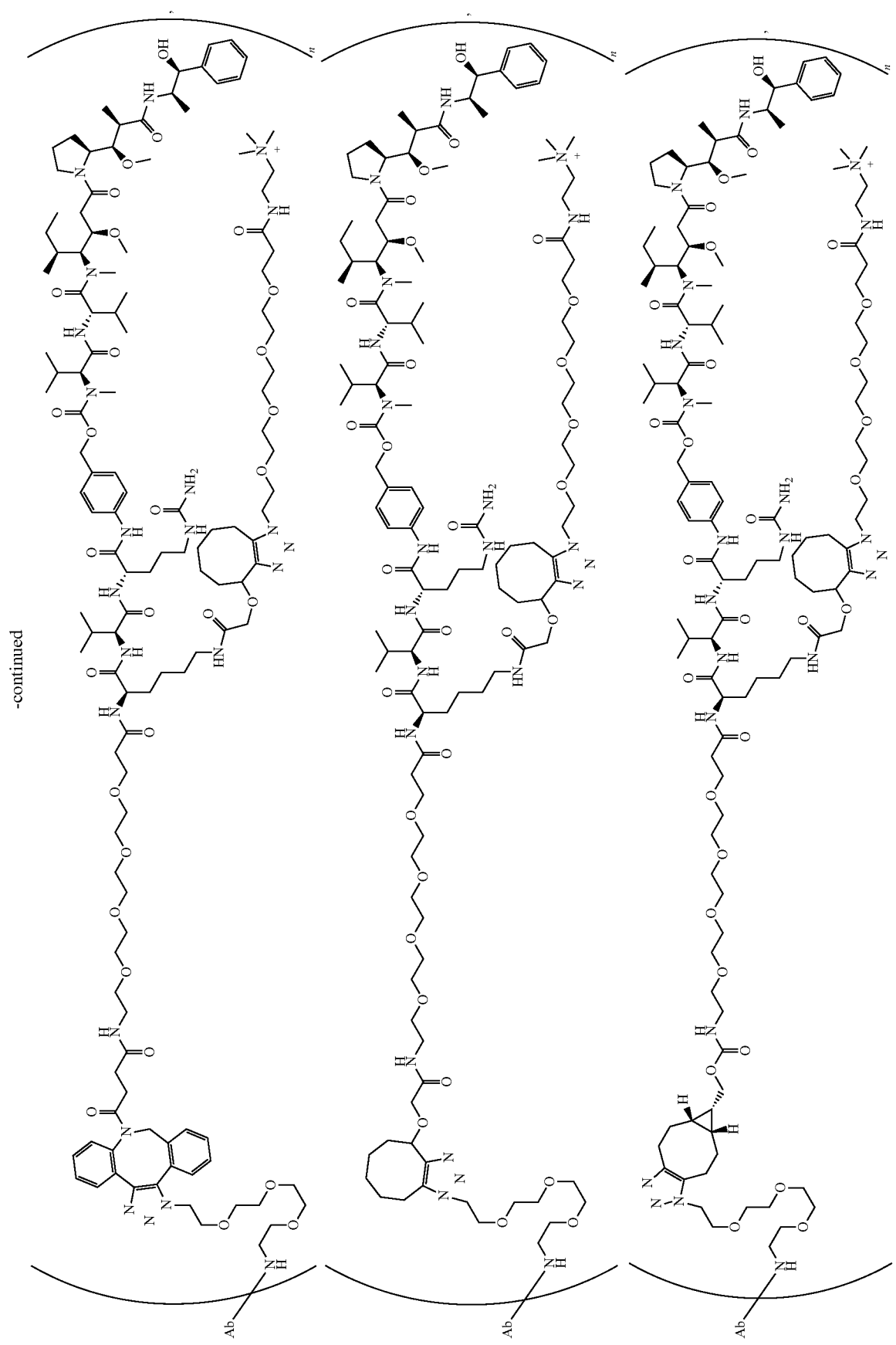

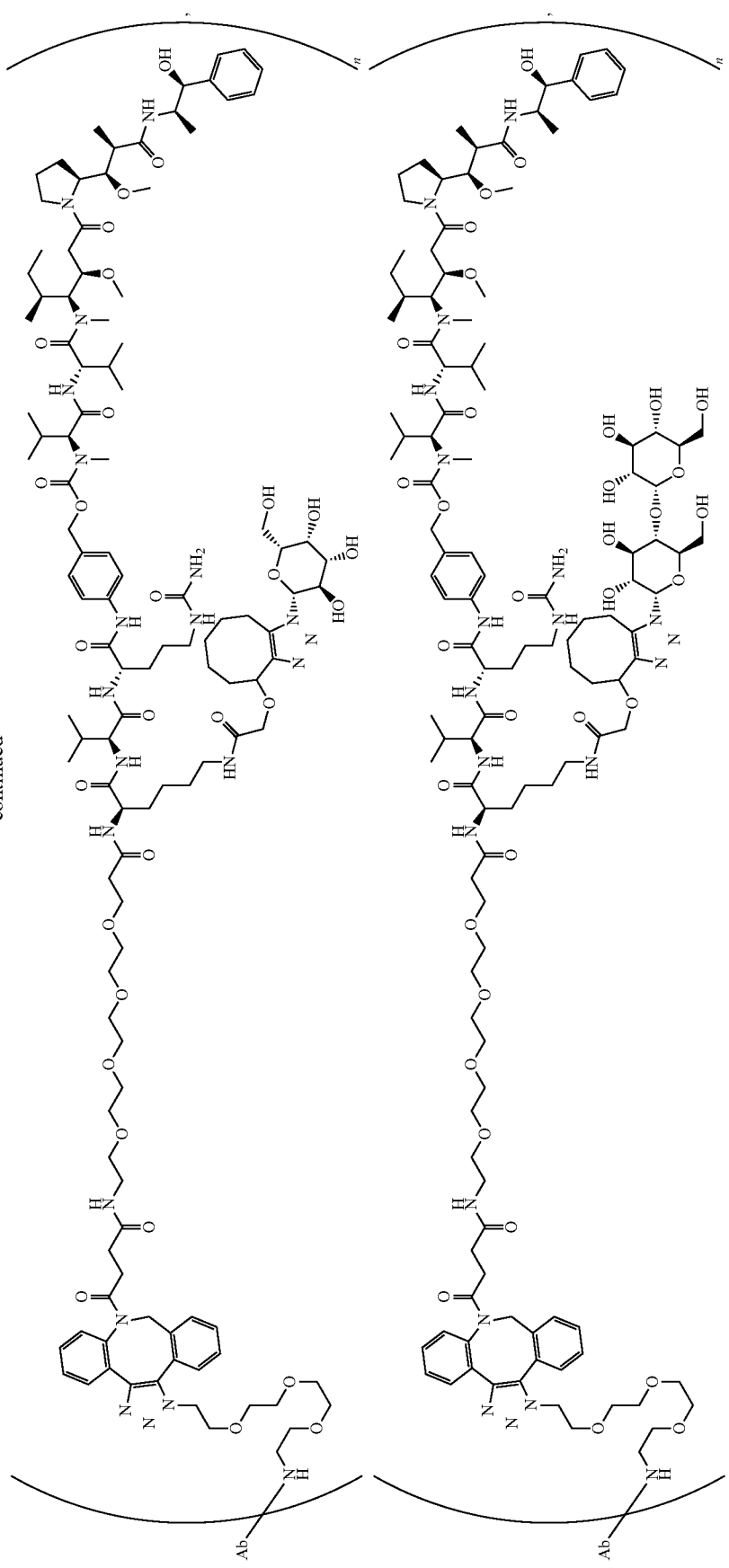

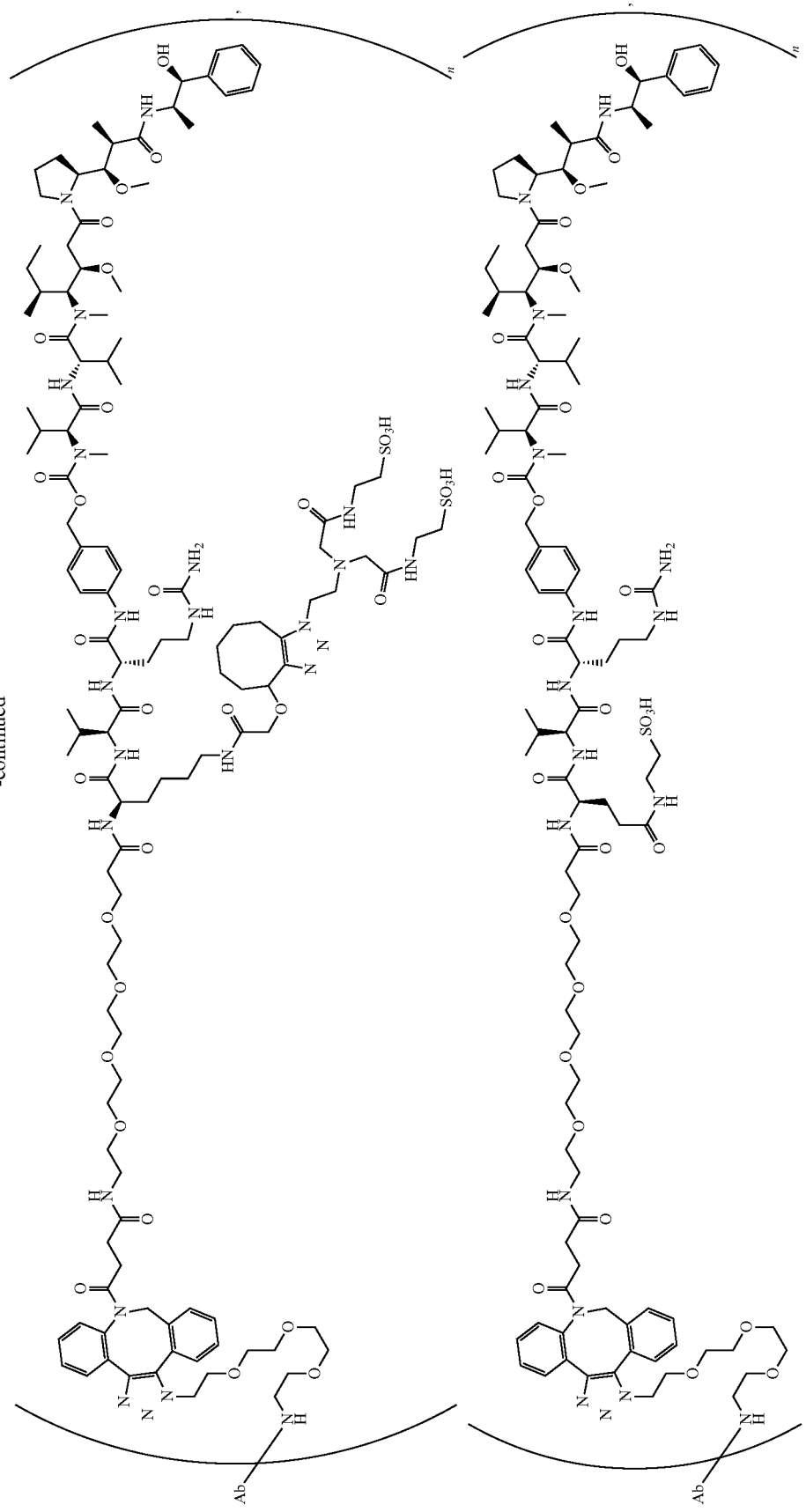

1279 1280
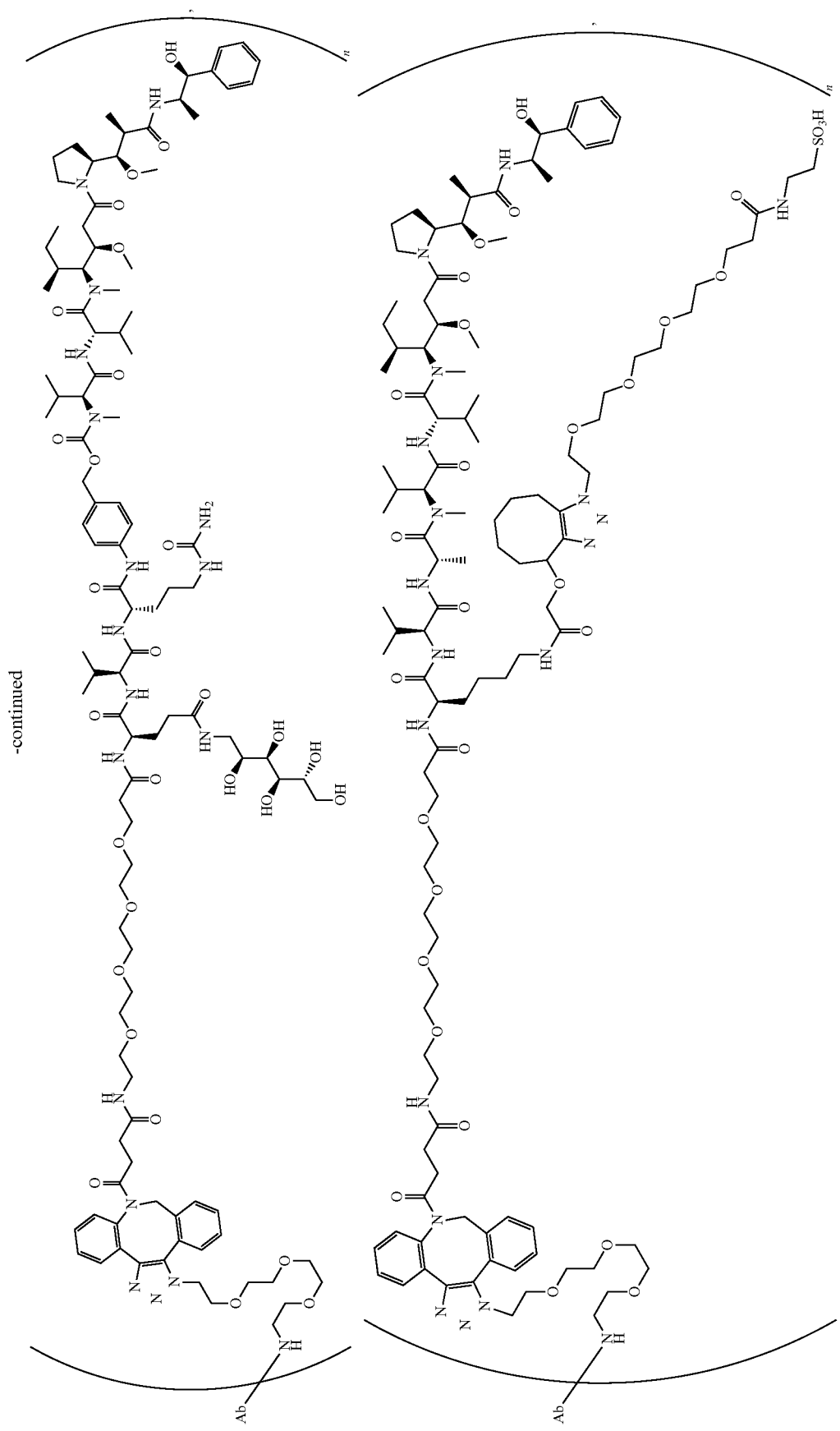

1281
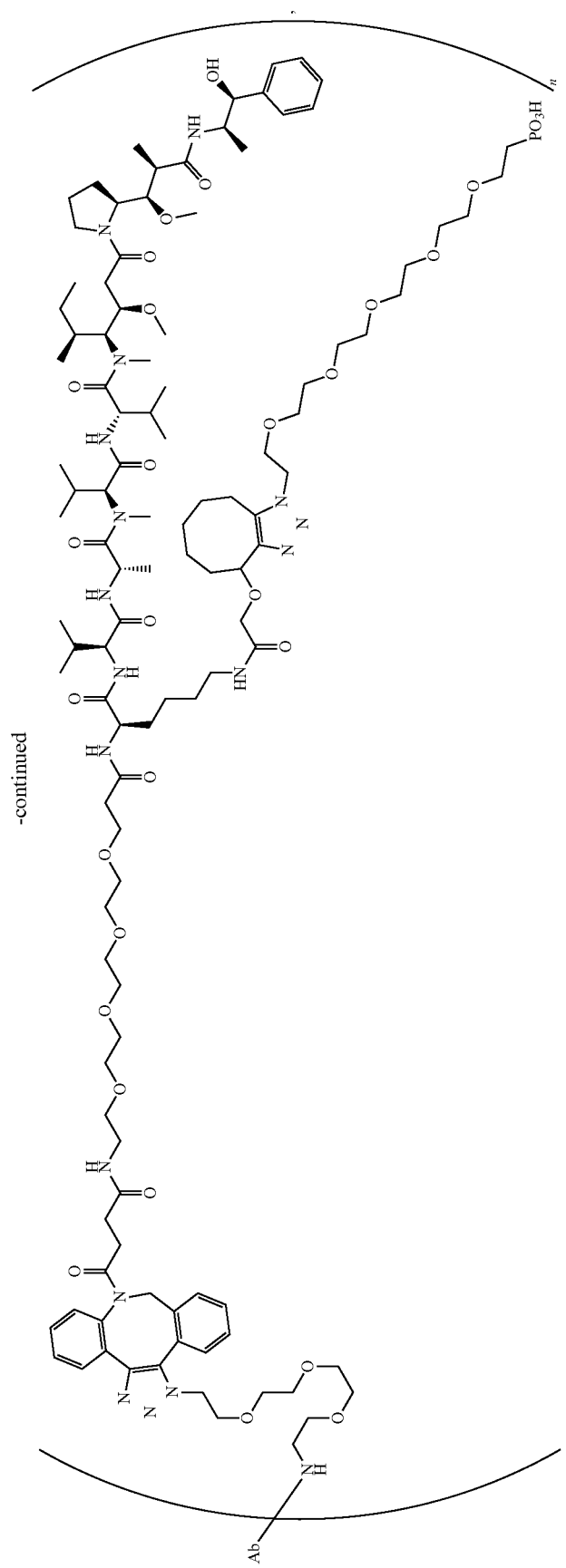
1282

1283 1284
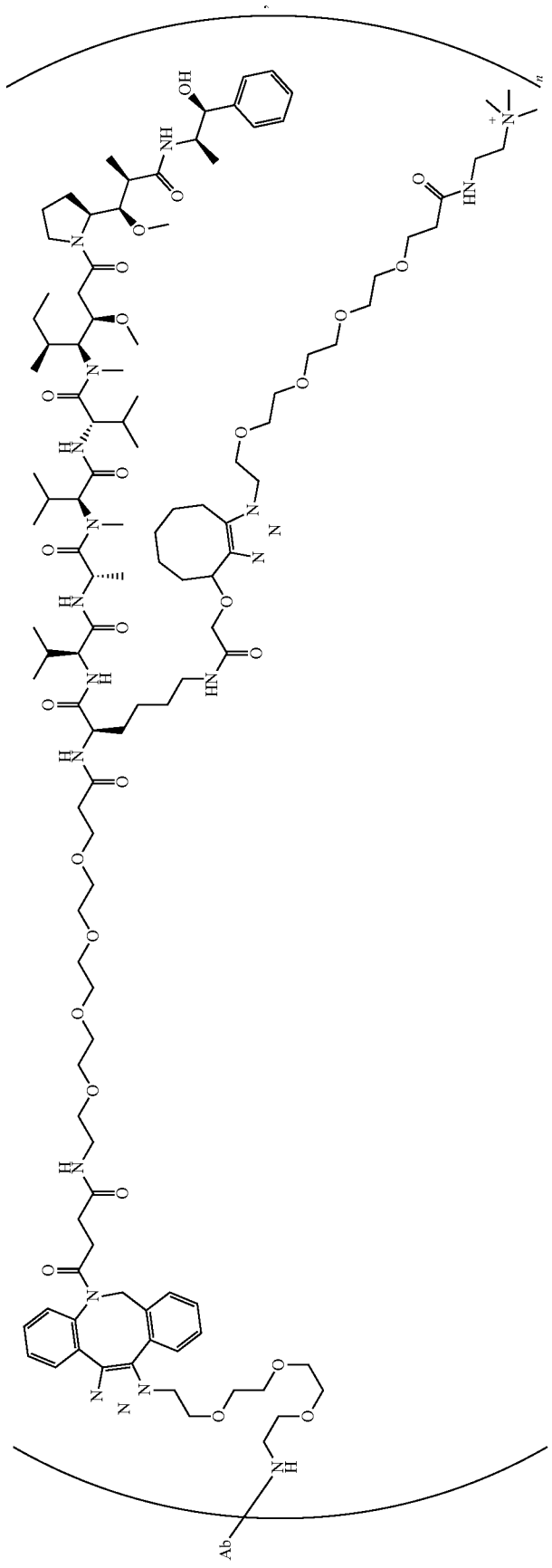

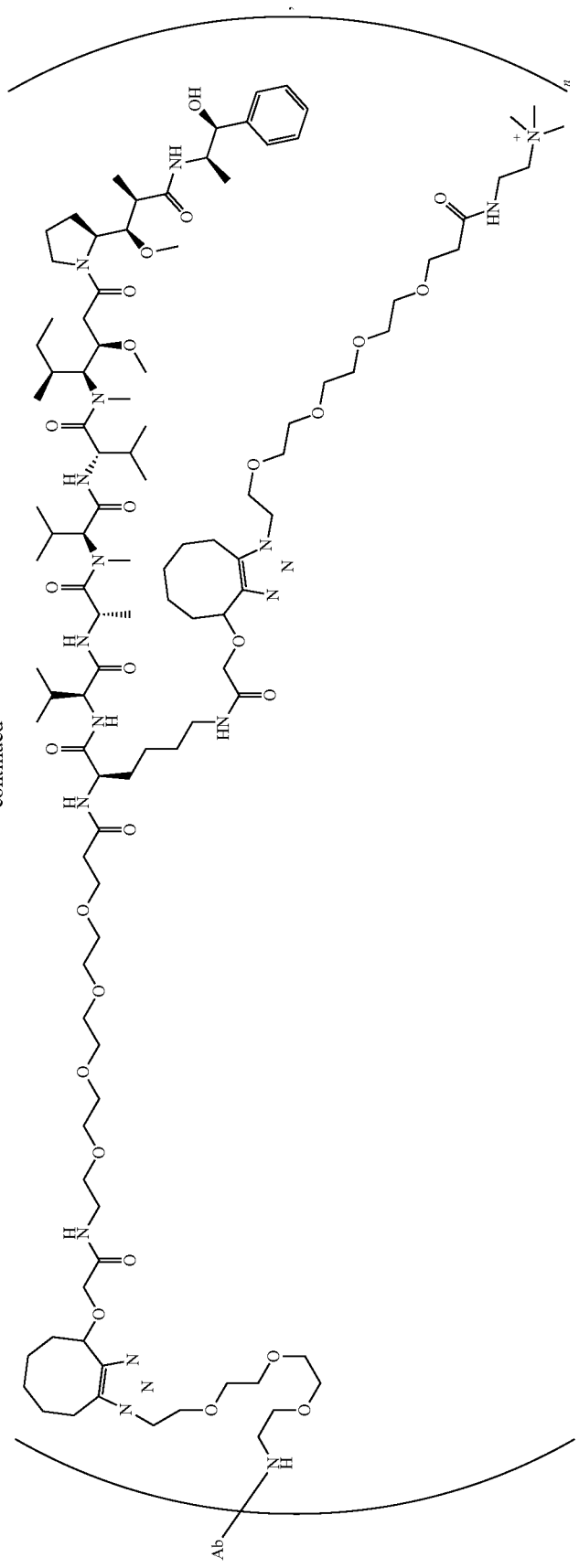

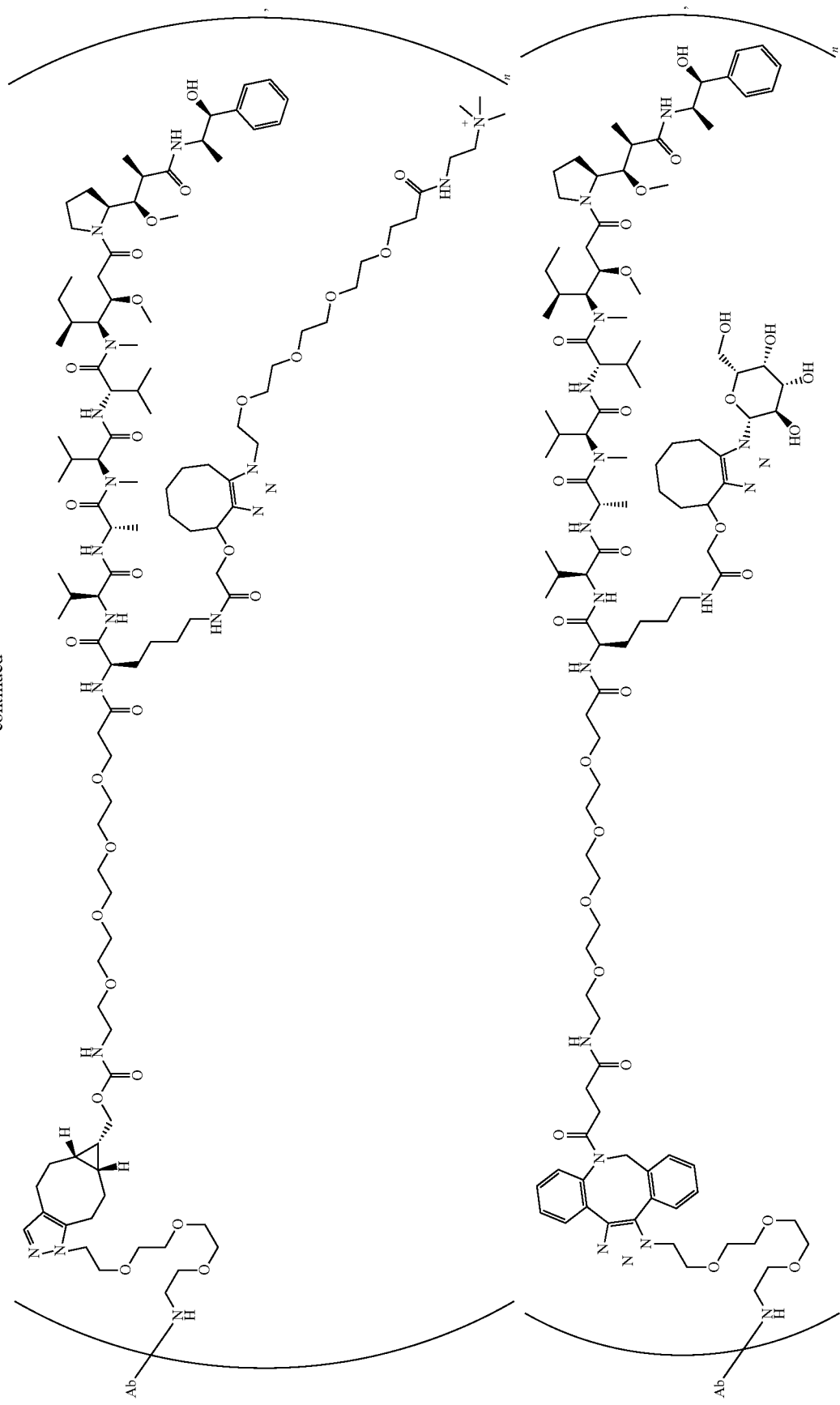

1289      1290
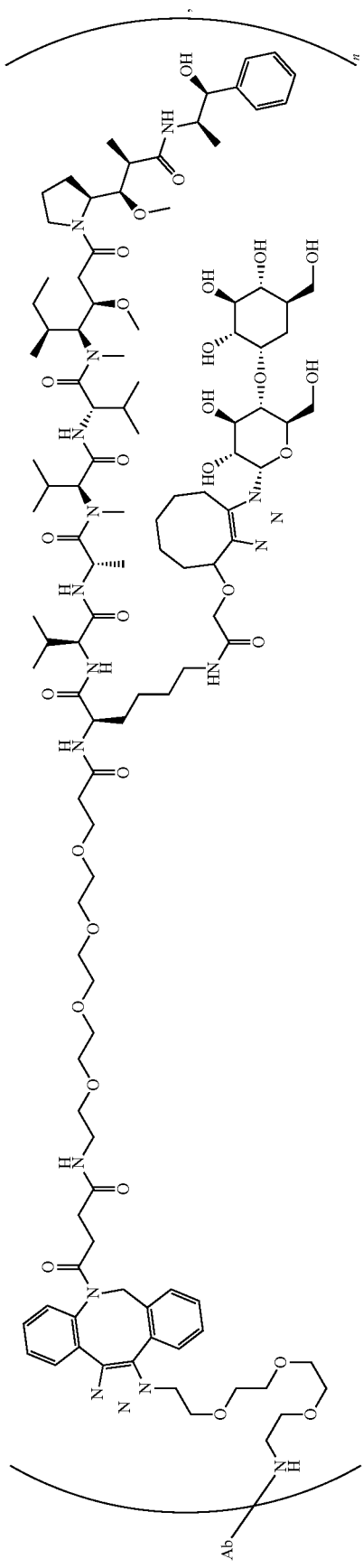
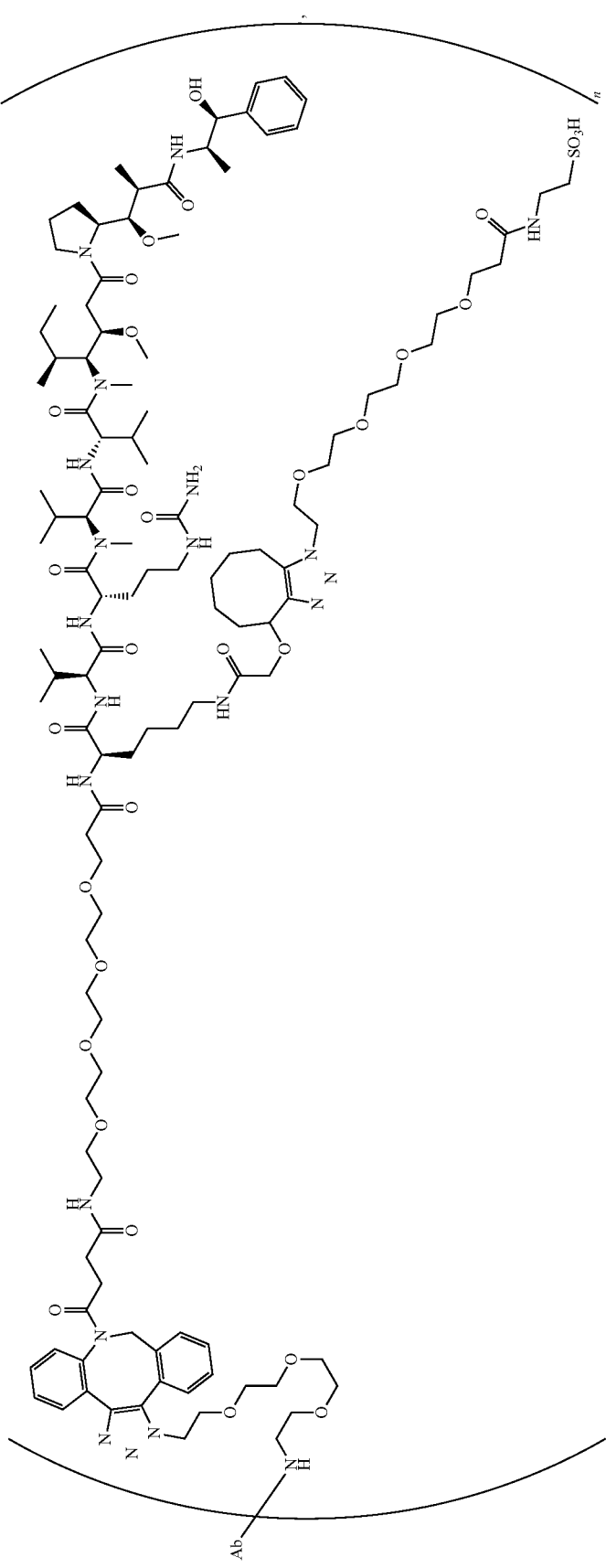

1291                    1292
-continued
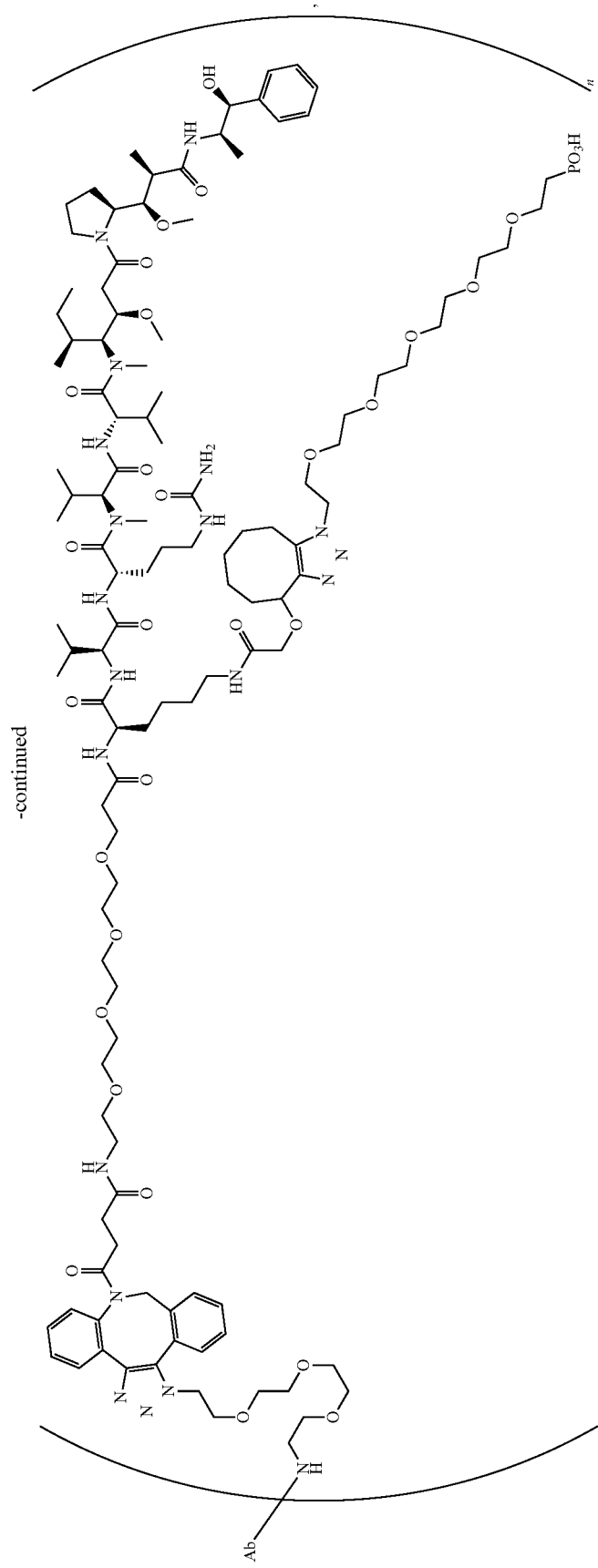

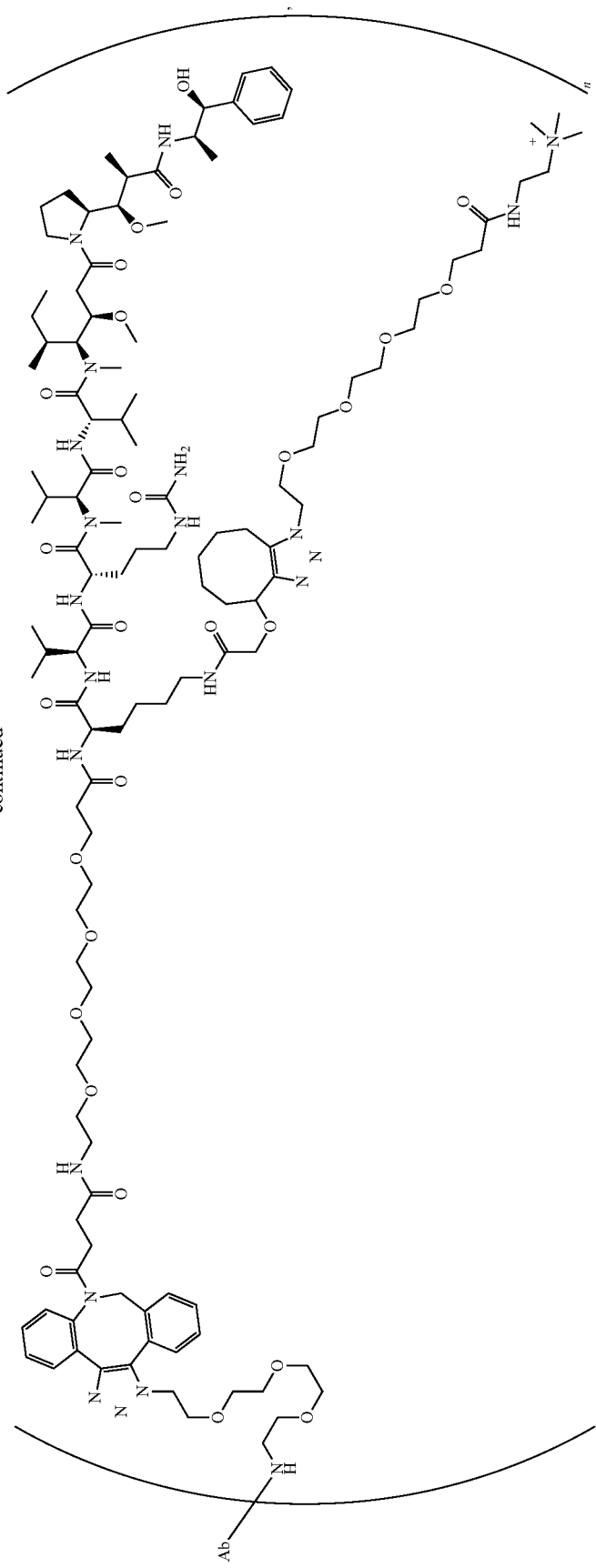

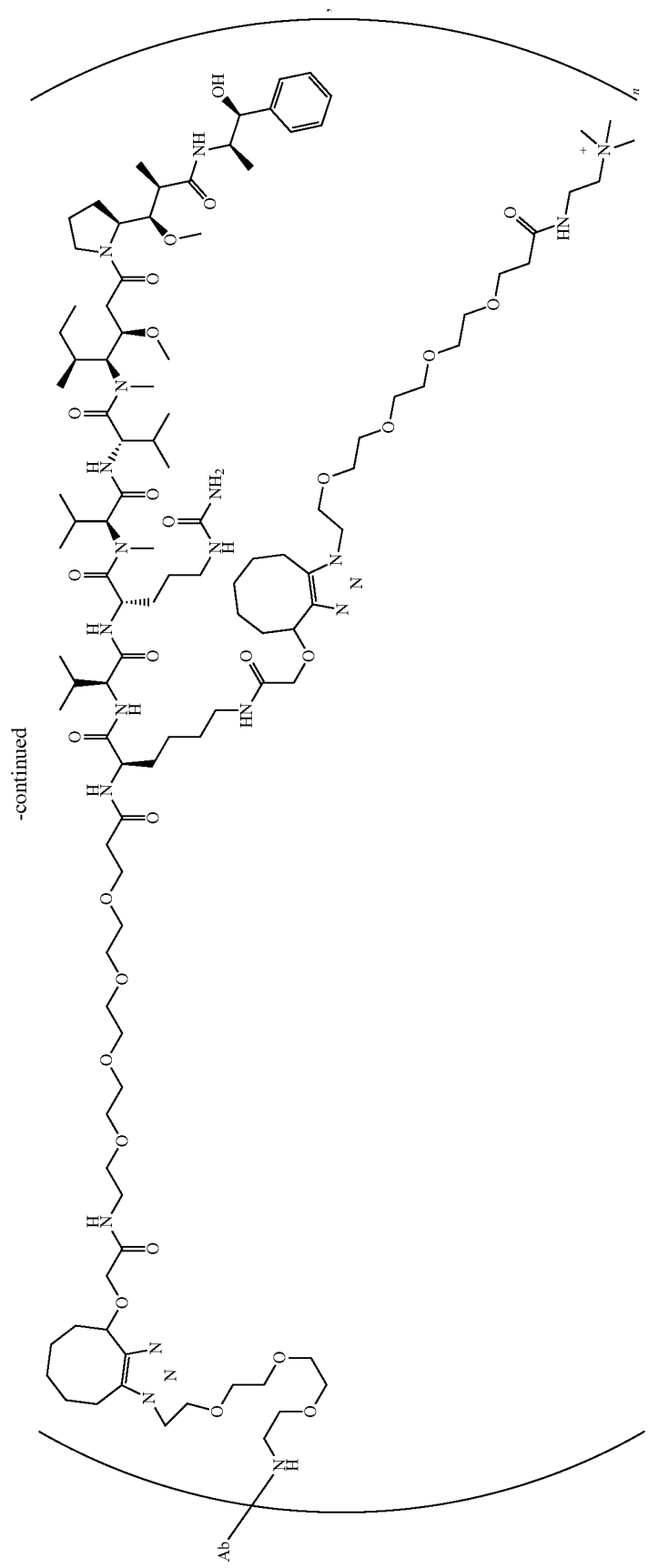

1297 1298
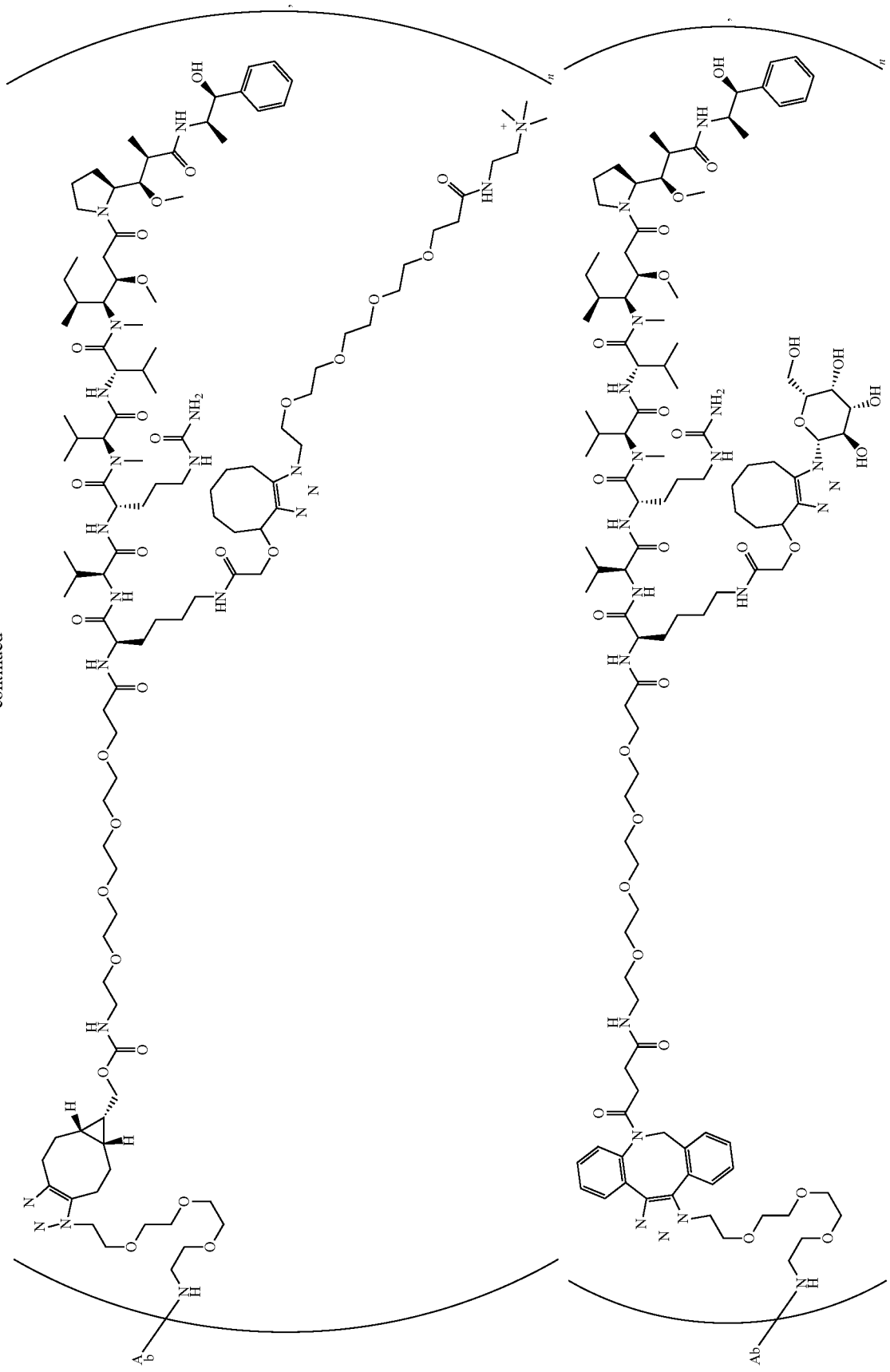

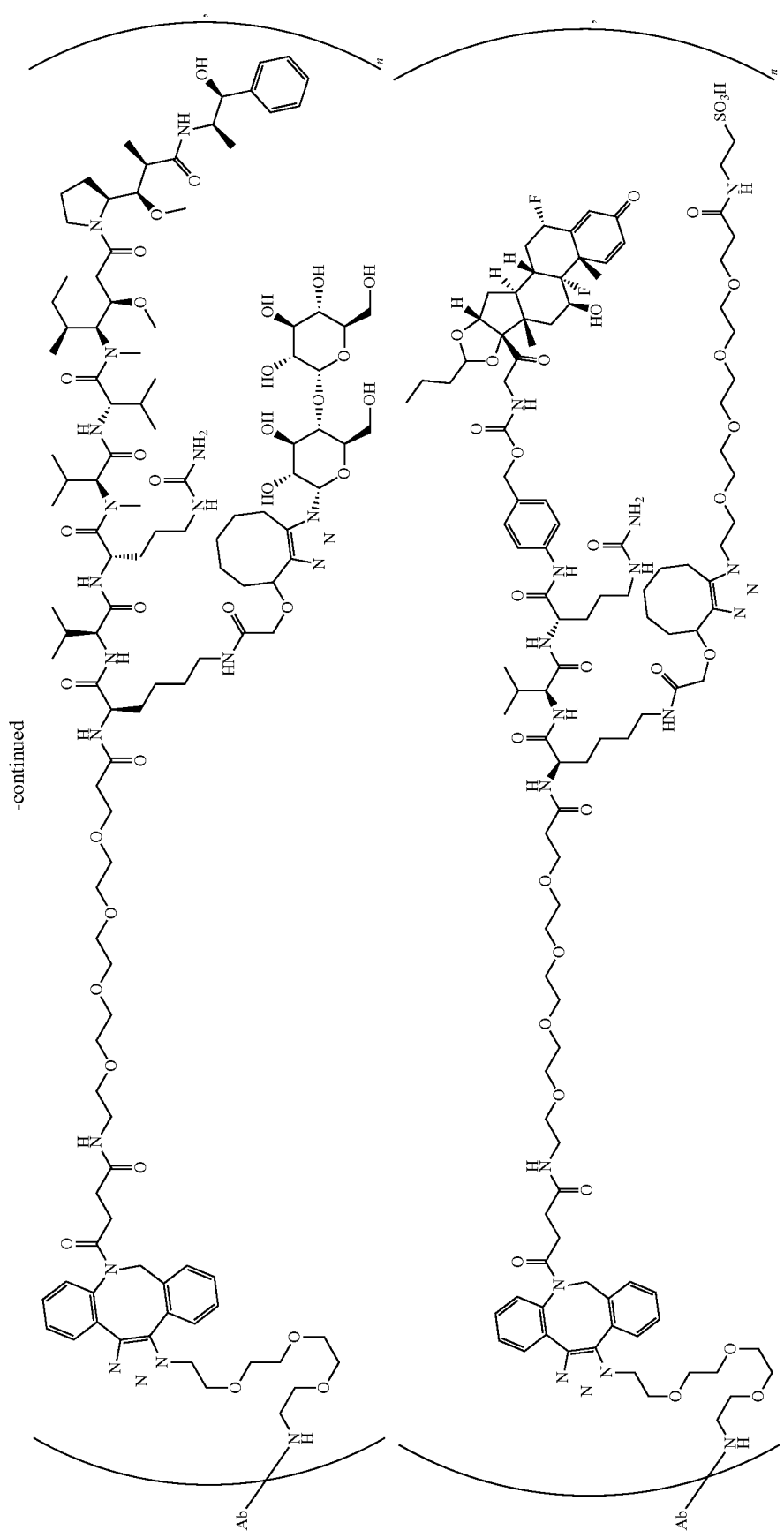

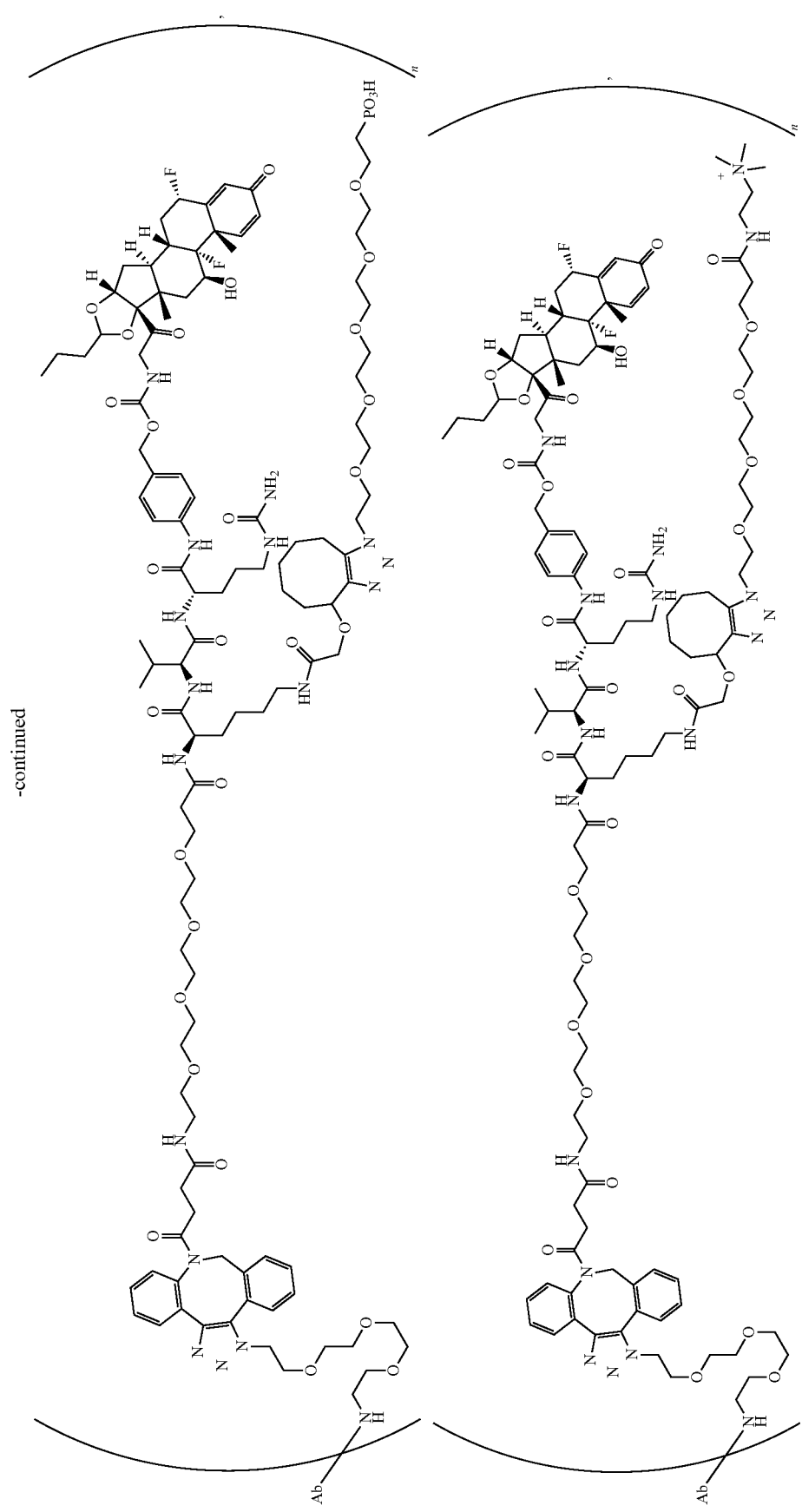
1301 1302

1303 1304
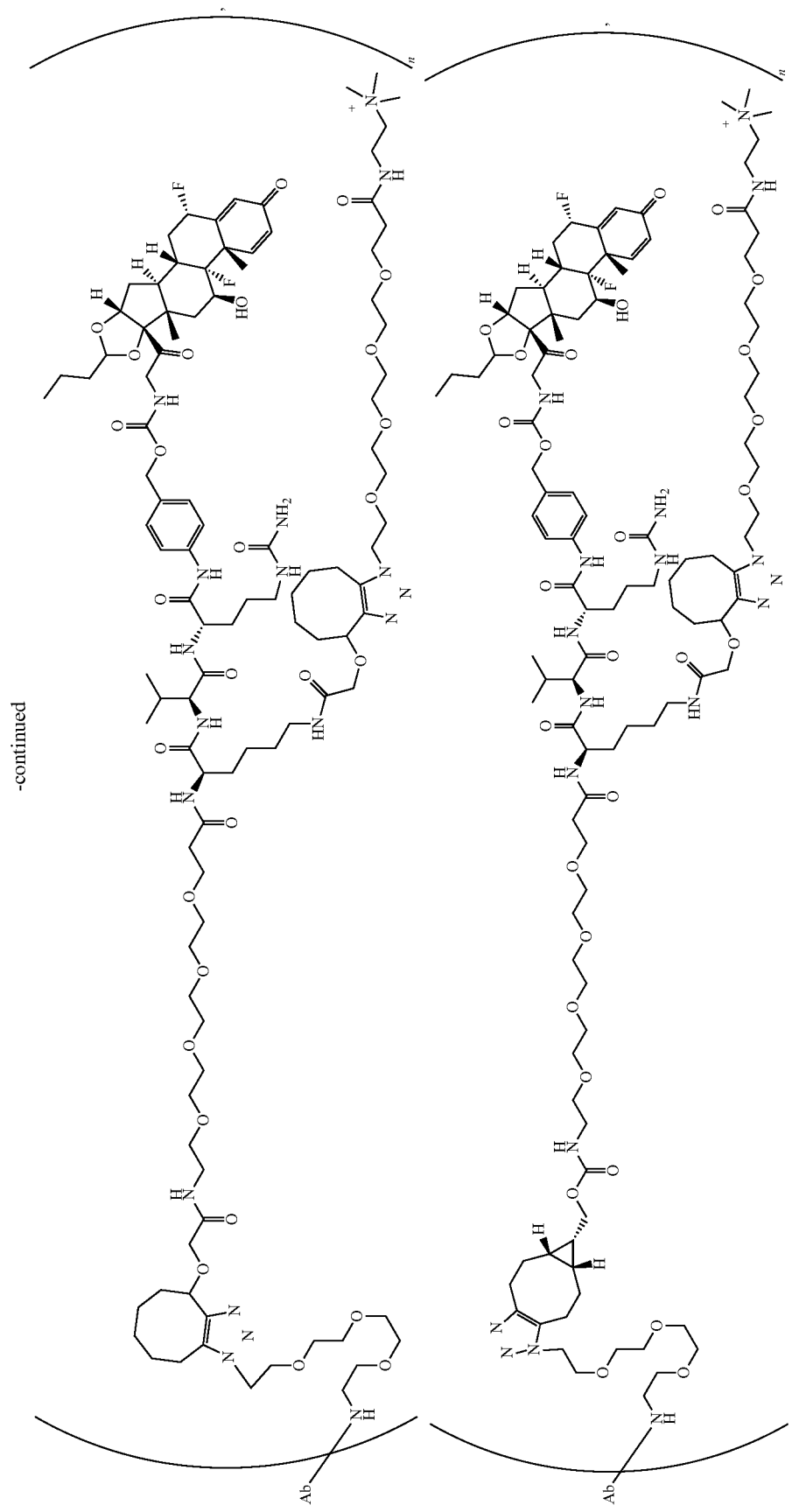

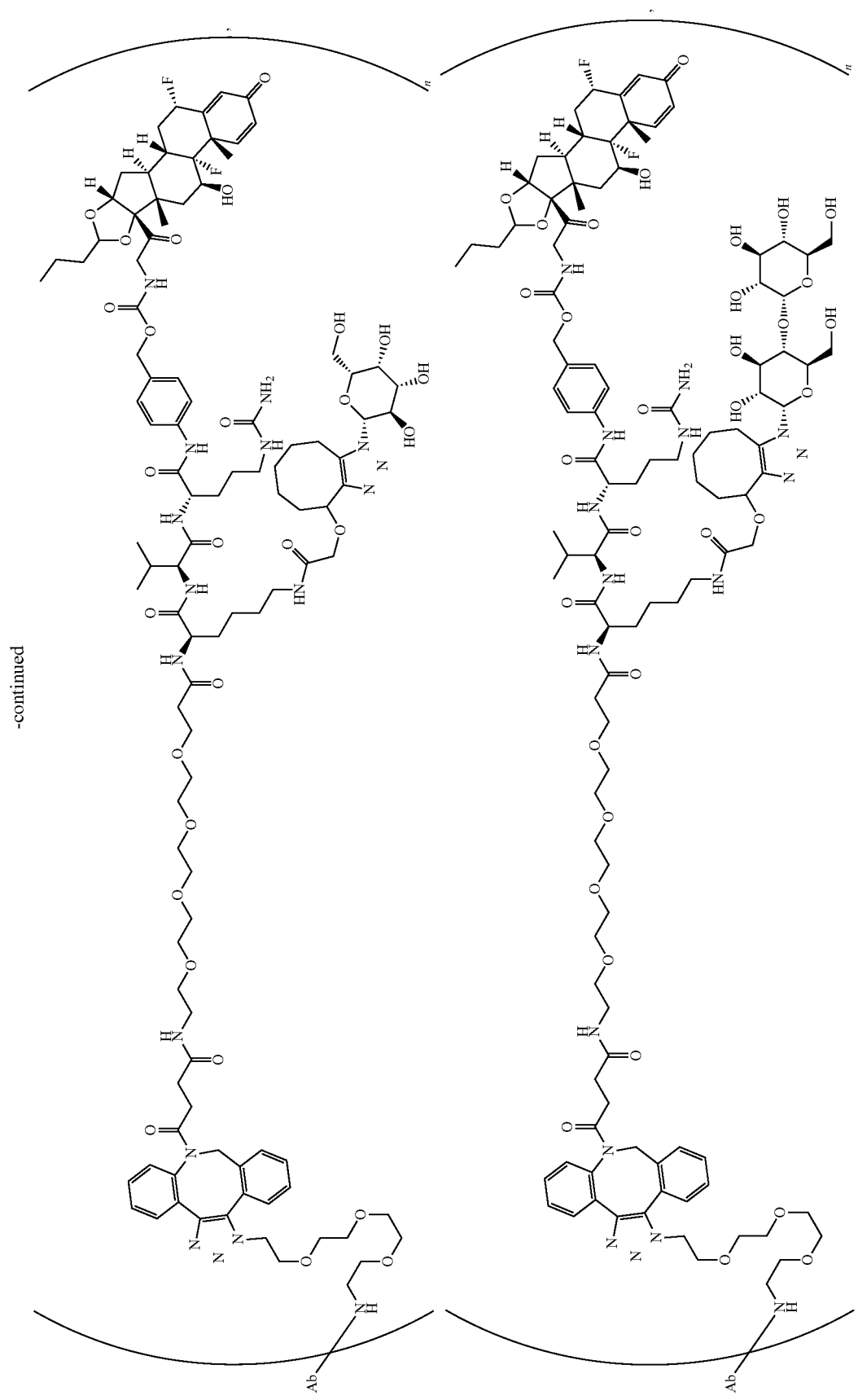

1307 1308
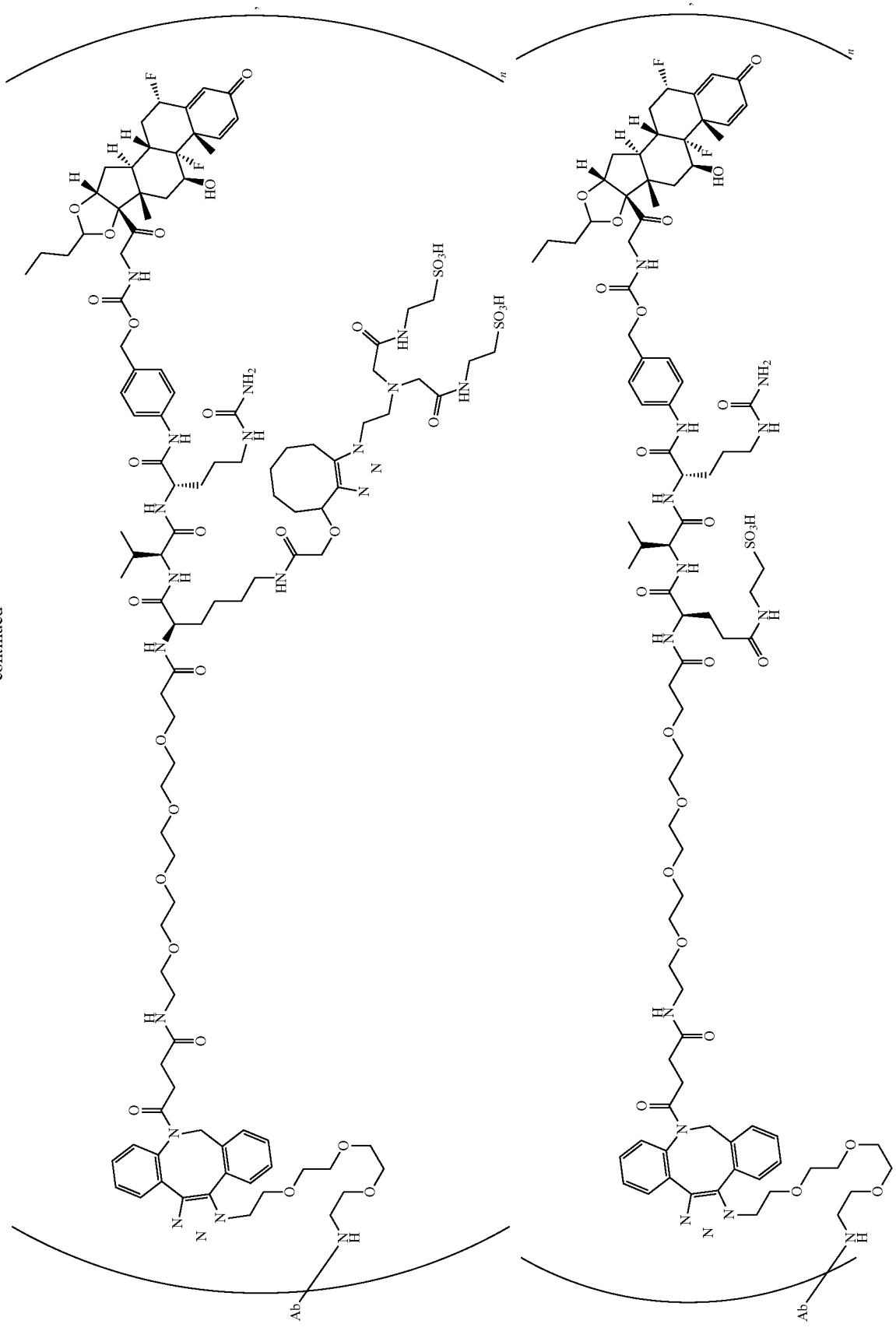

1309 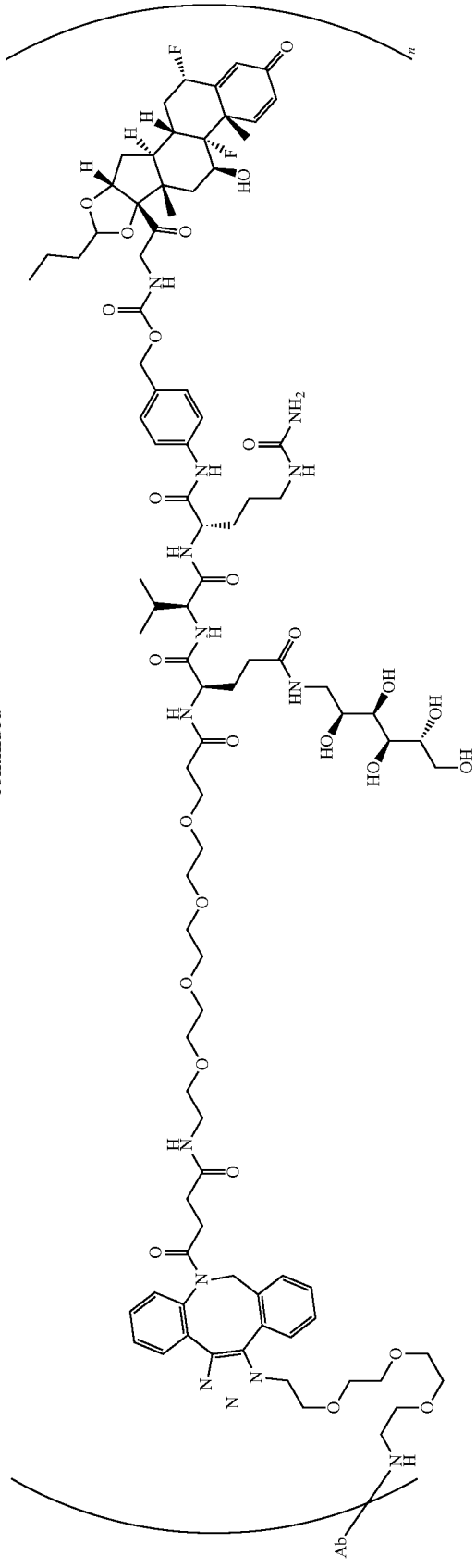 1310 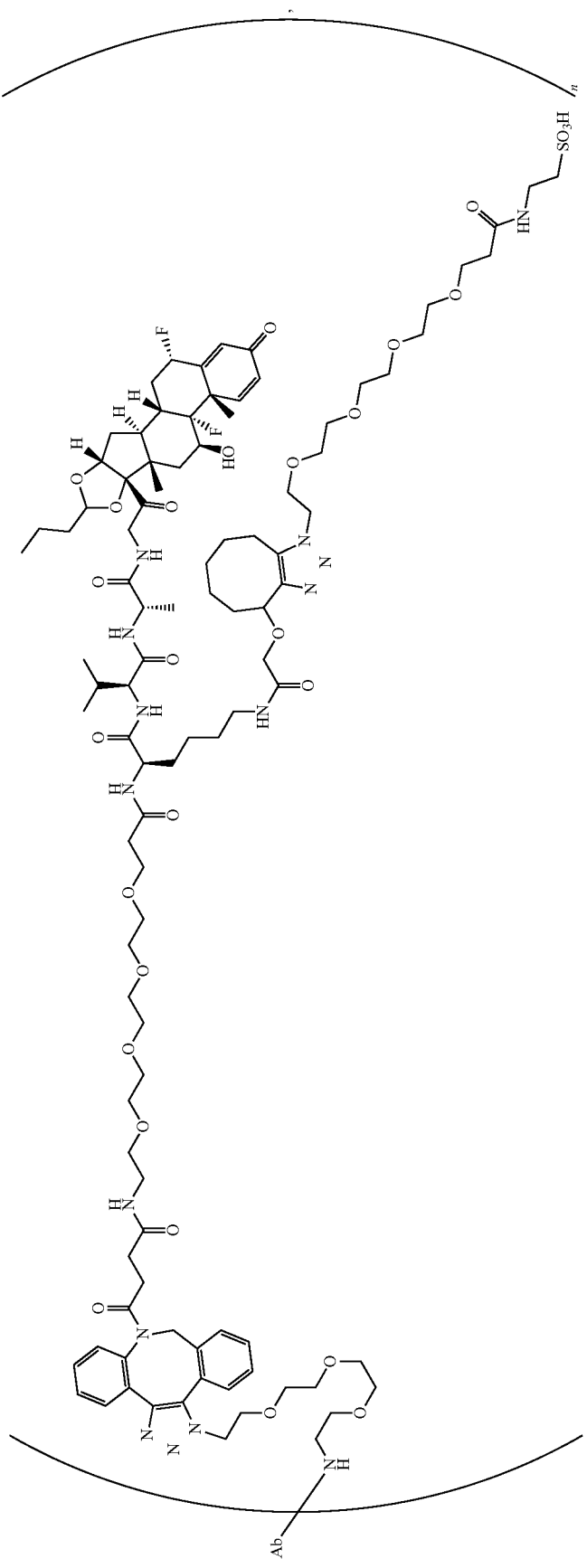

1311 1312
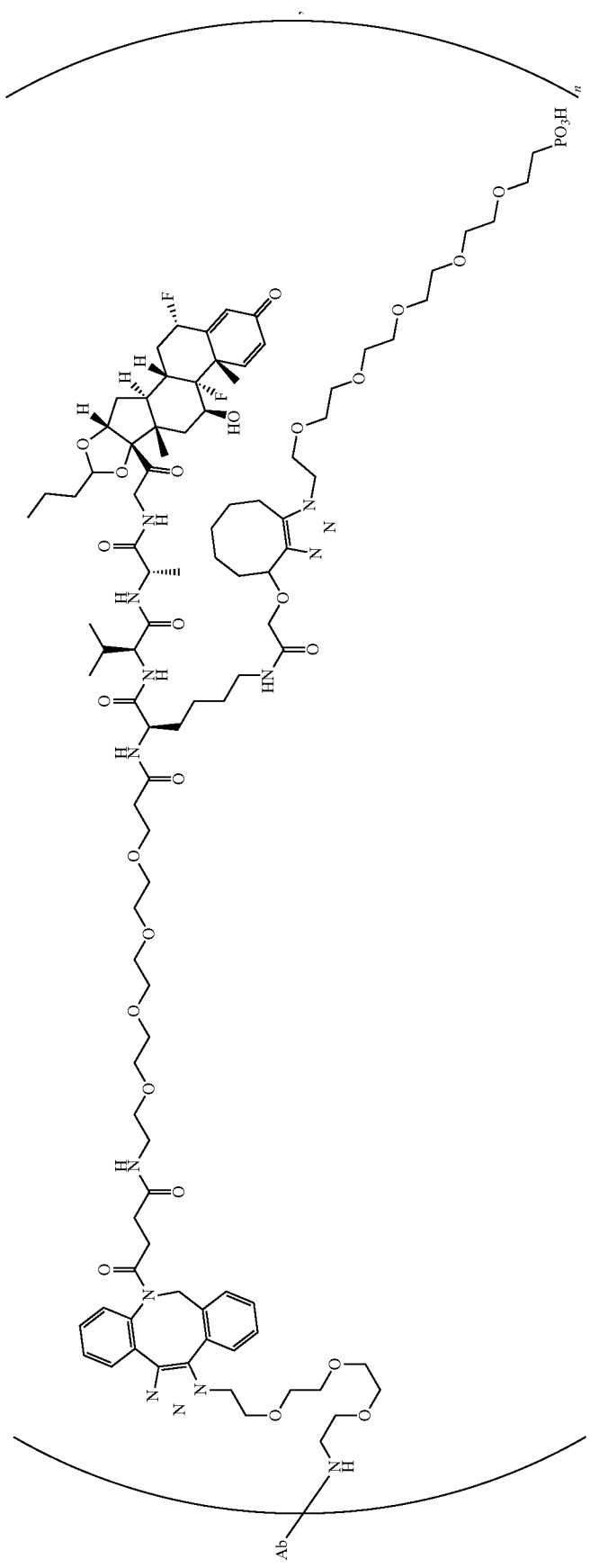

1313 1314
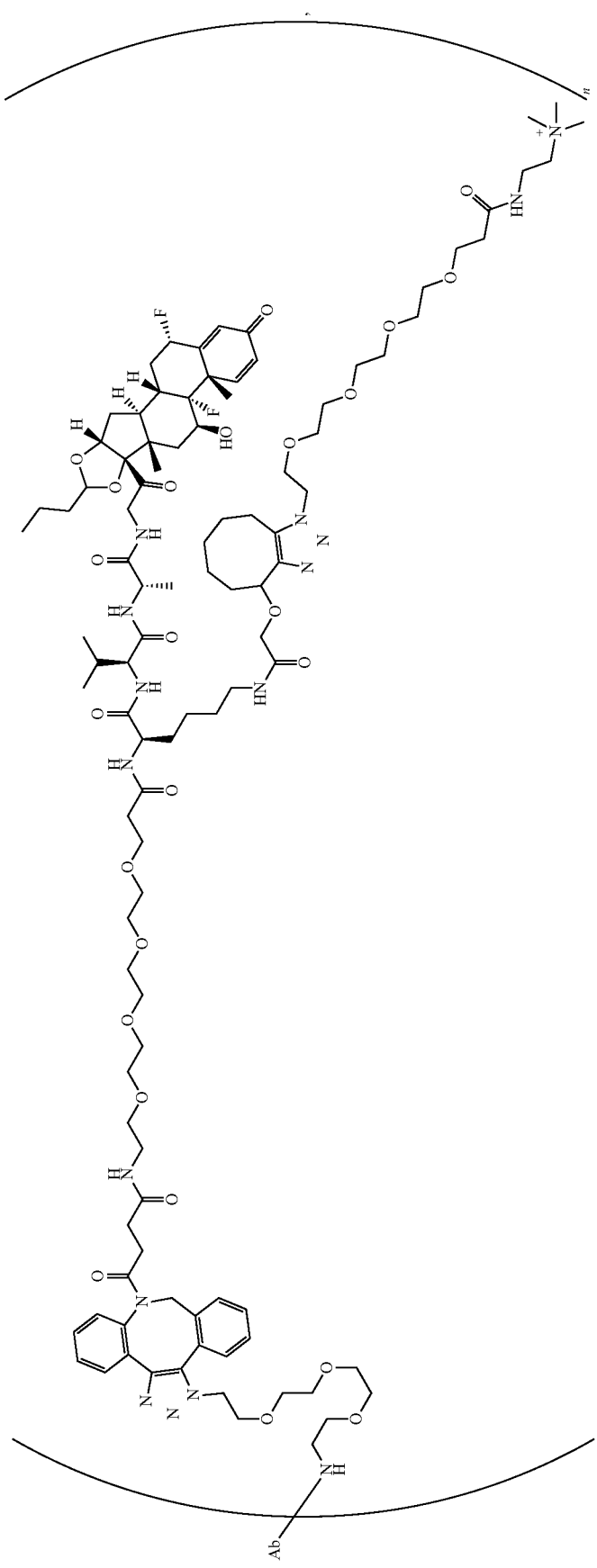
-continued

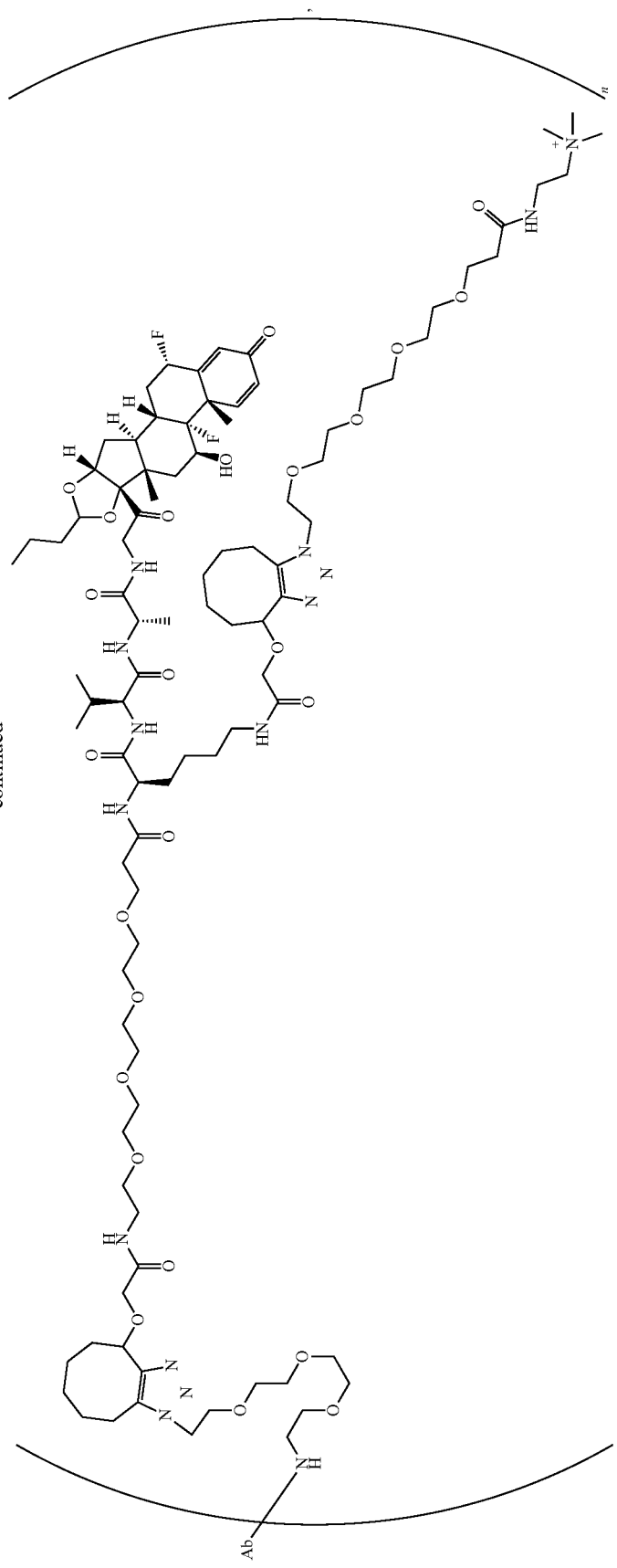

1317 1318
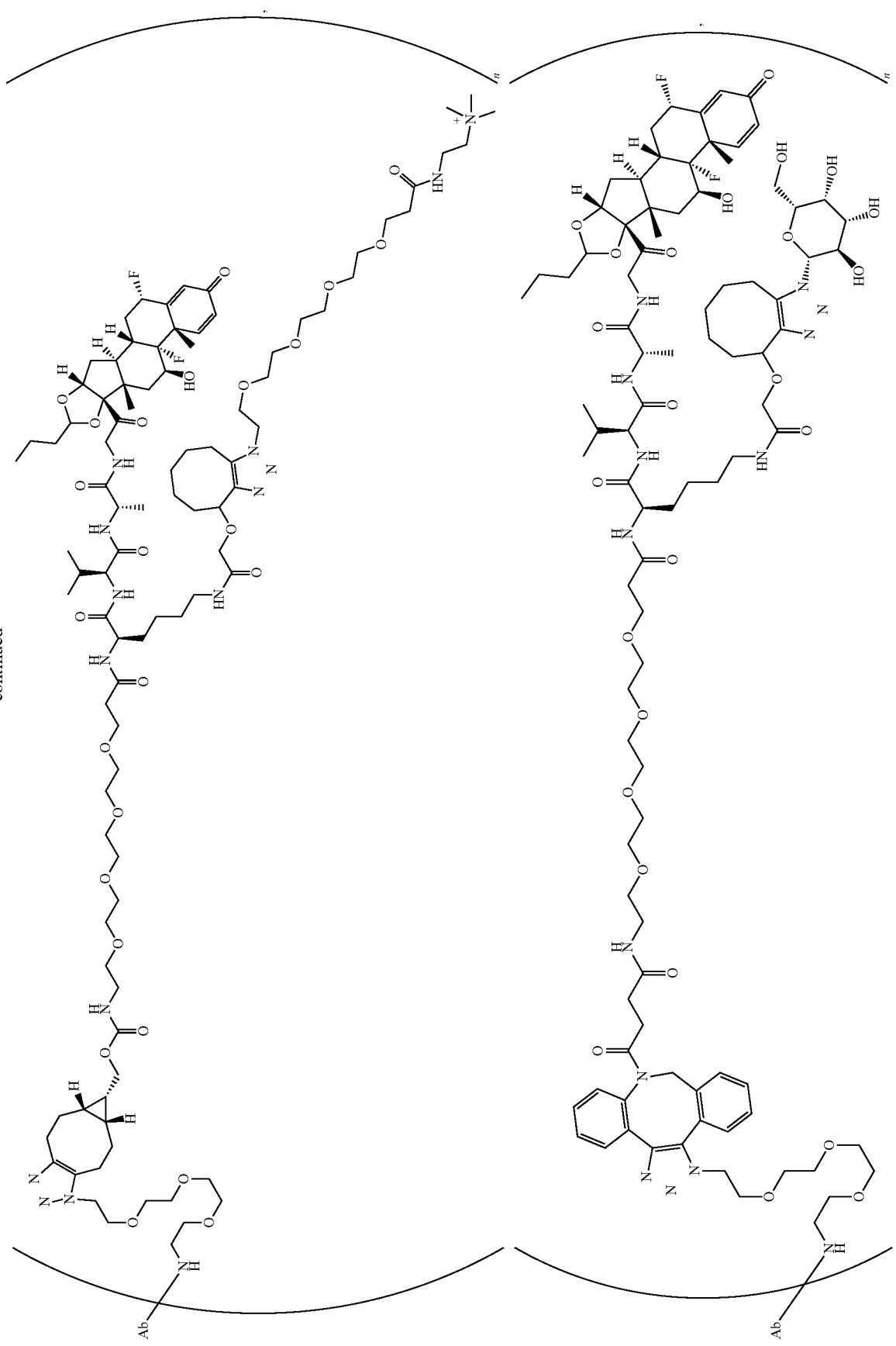

1319          1320
-continued
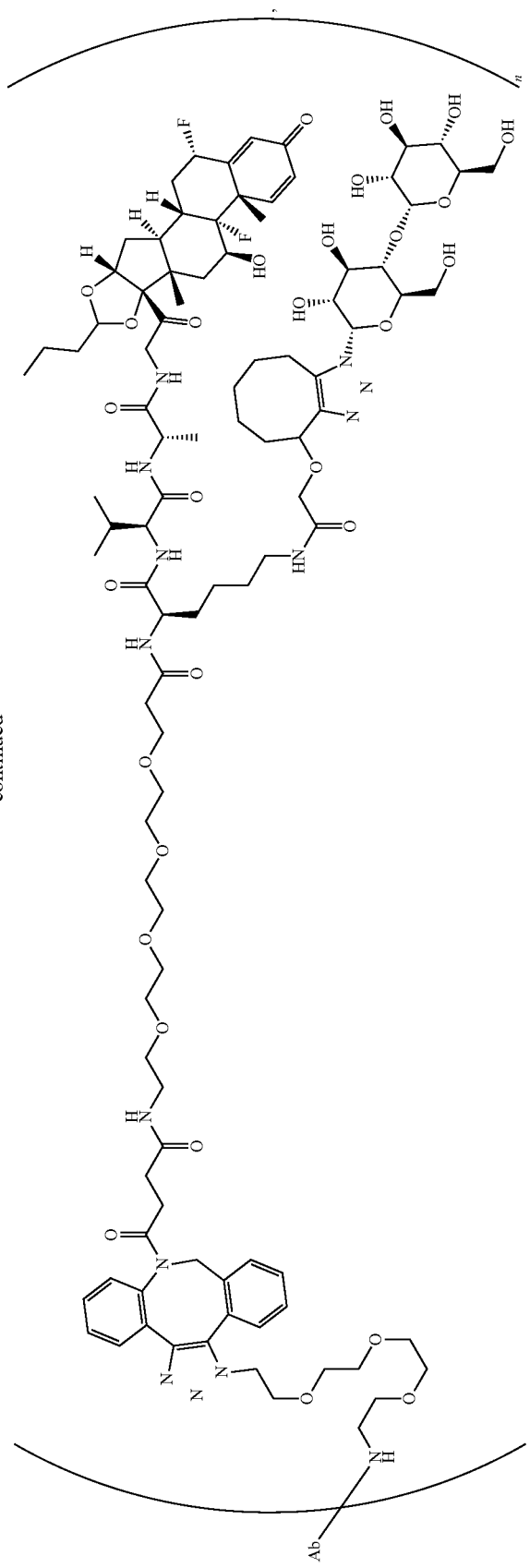

1321 -continued 1322
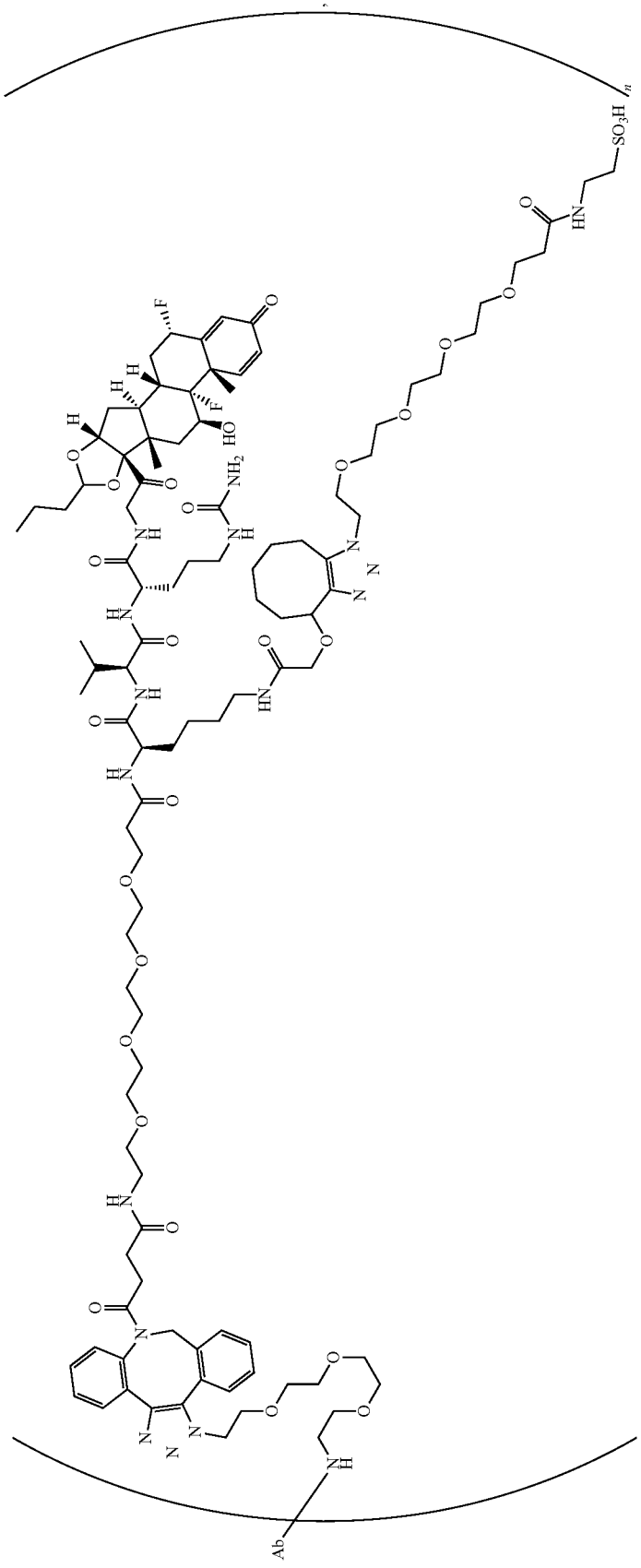

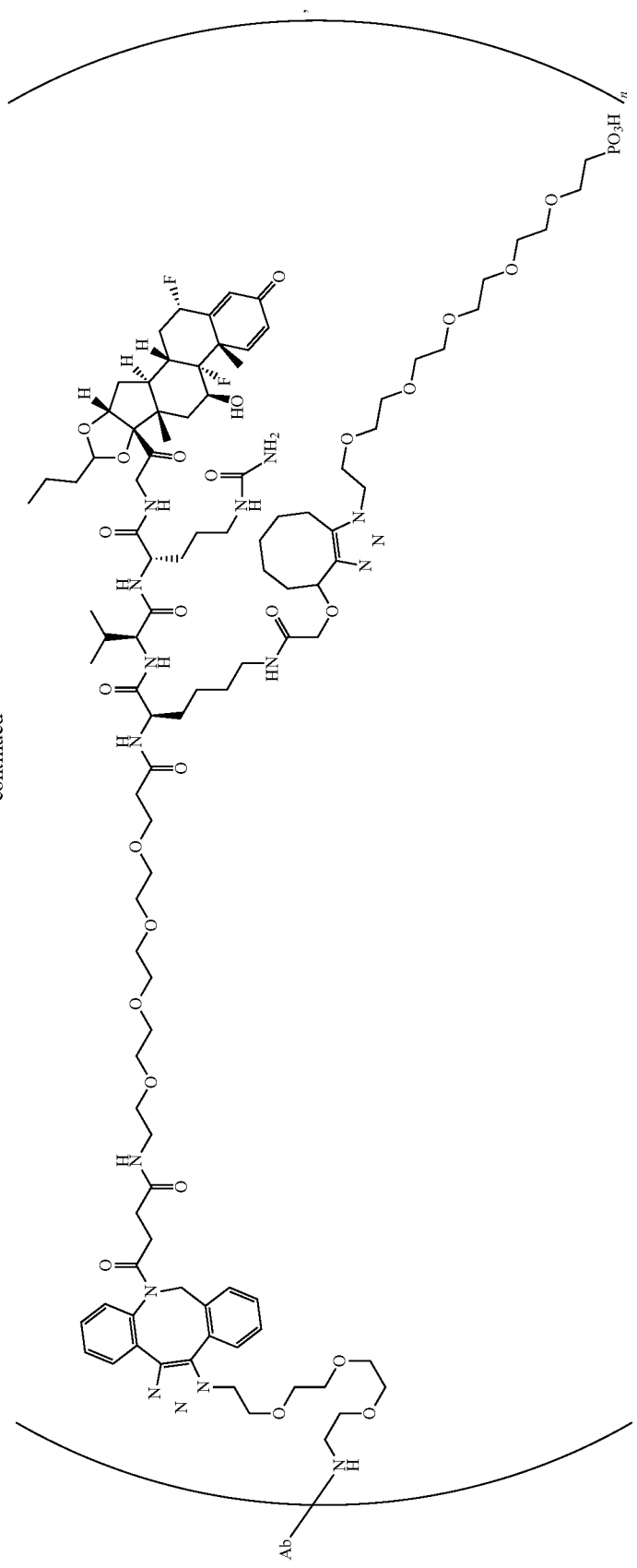

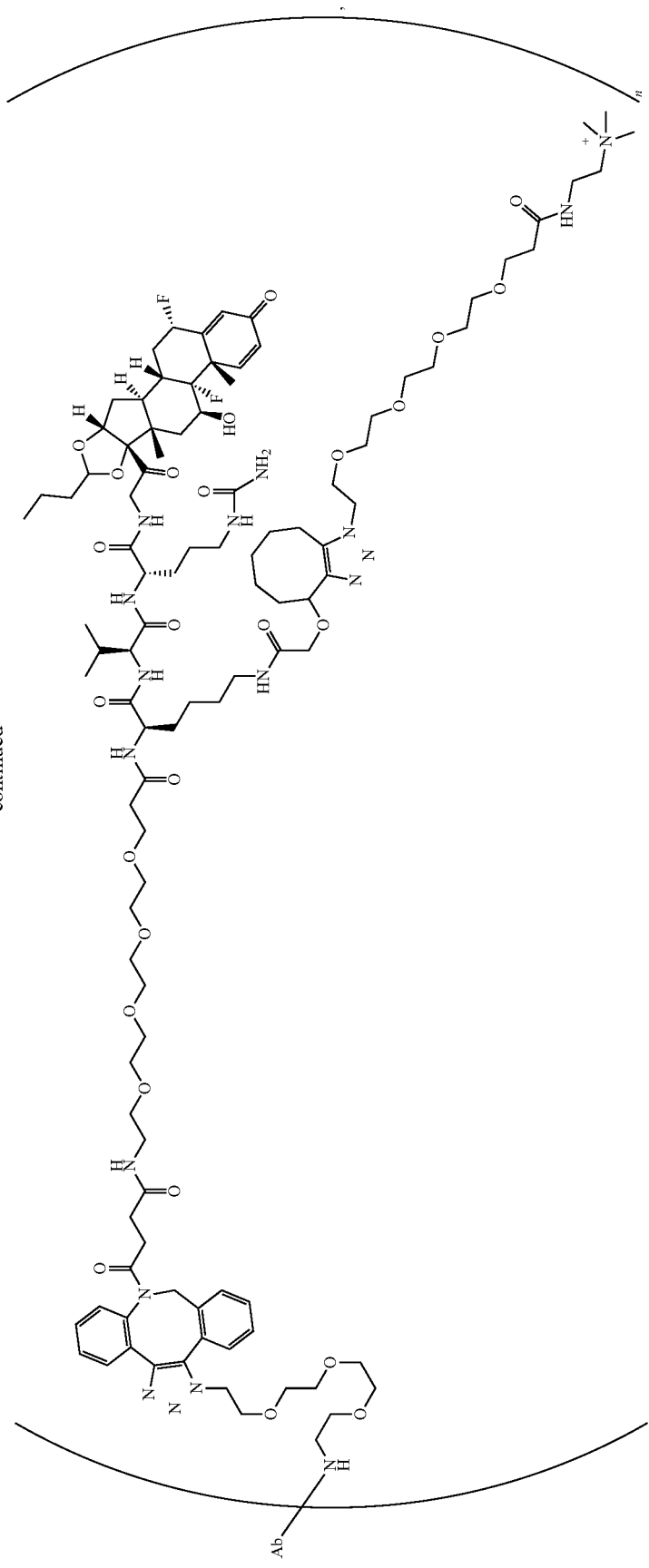

-continued
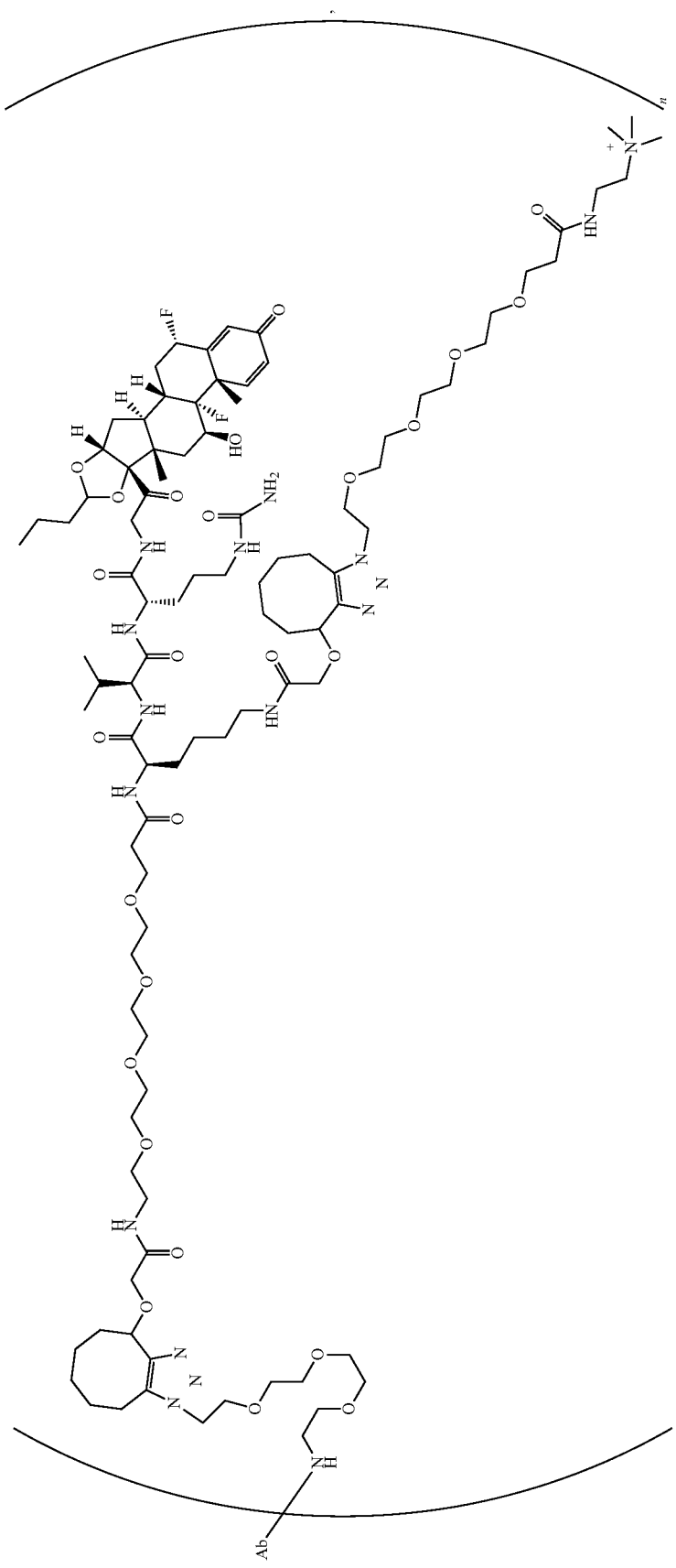

1329    1330
-continued
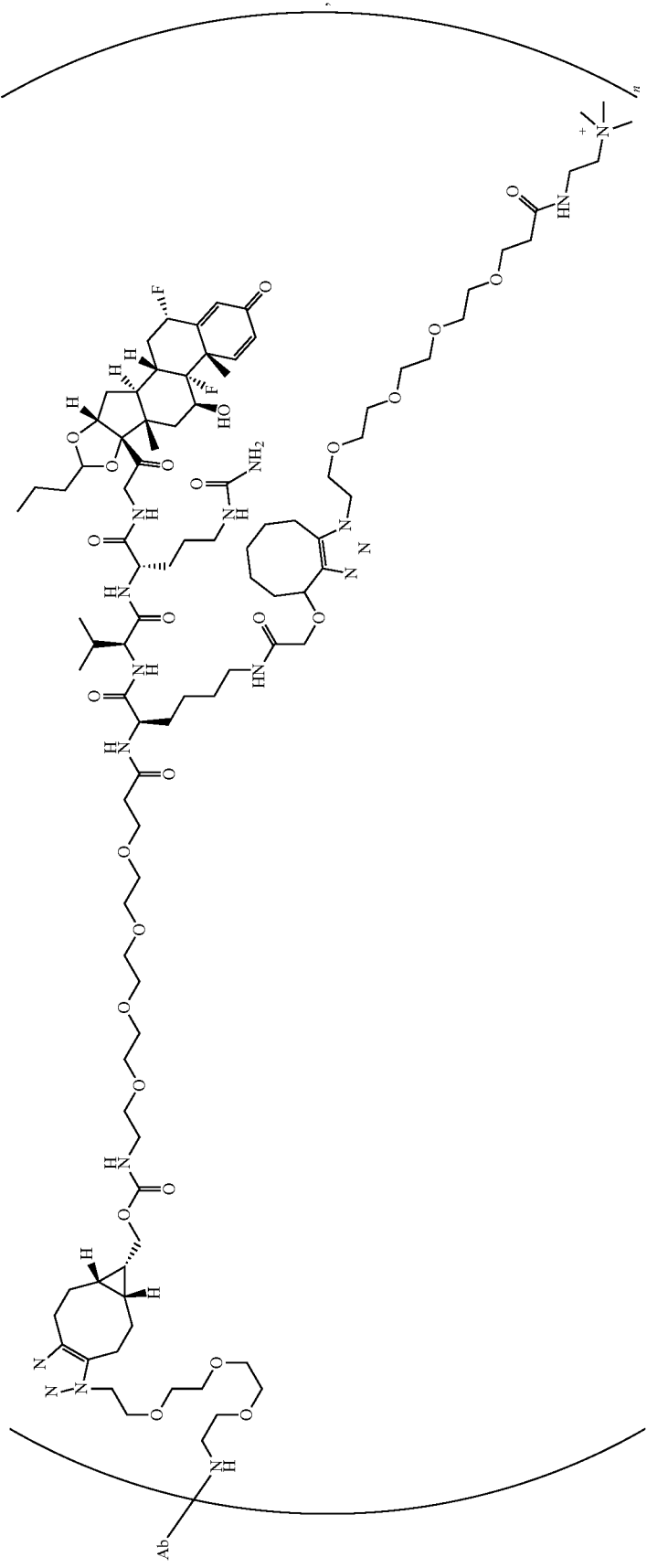

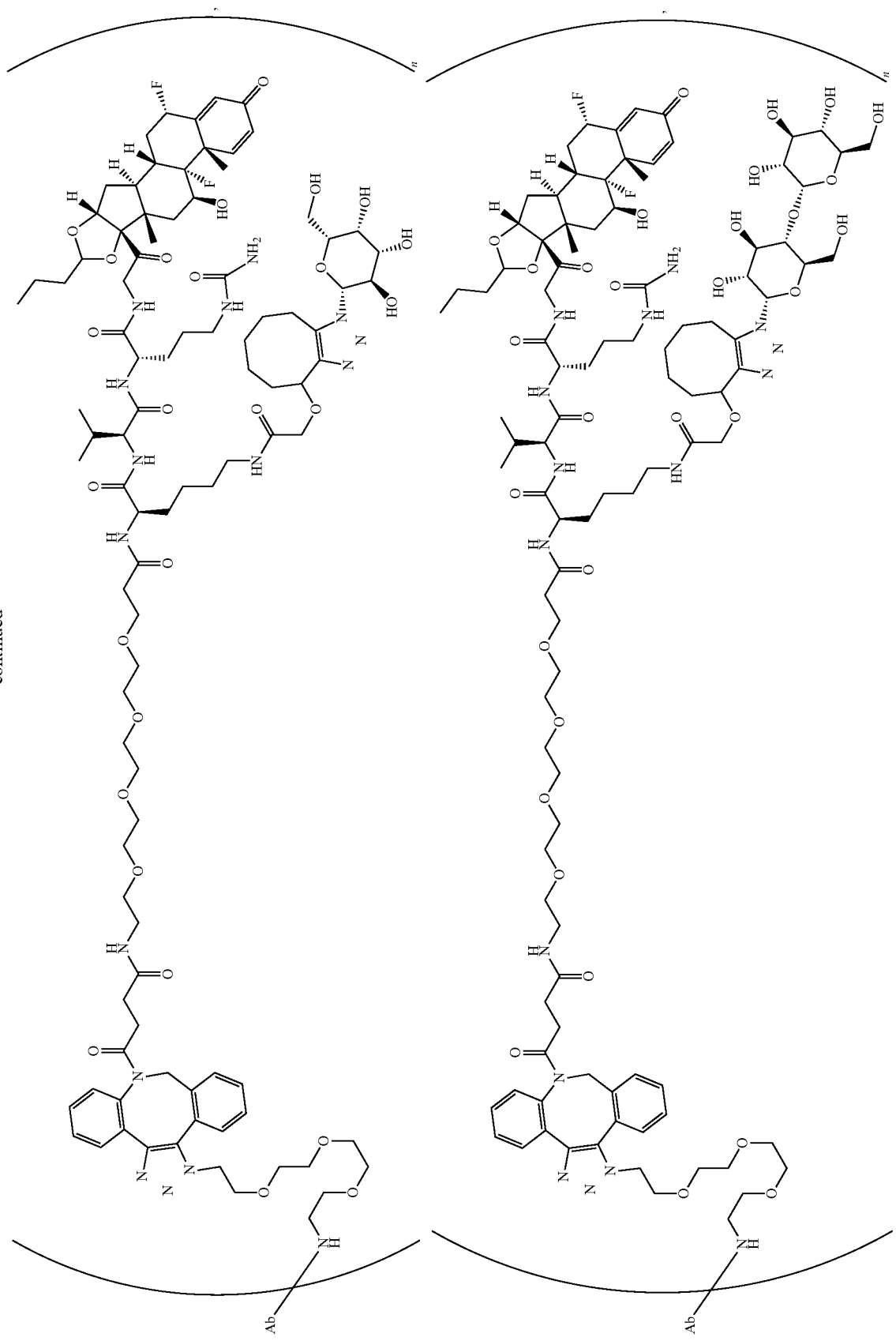
1331 1332

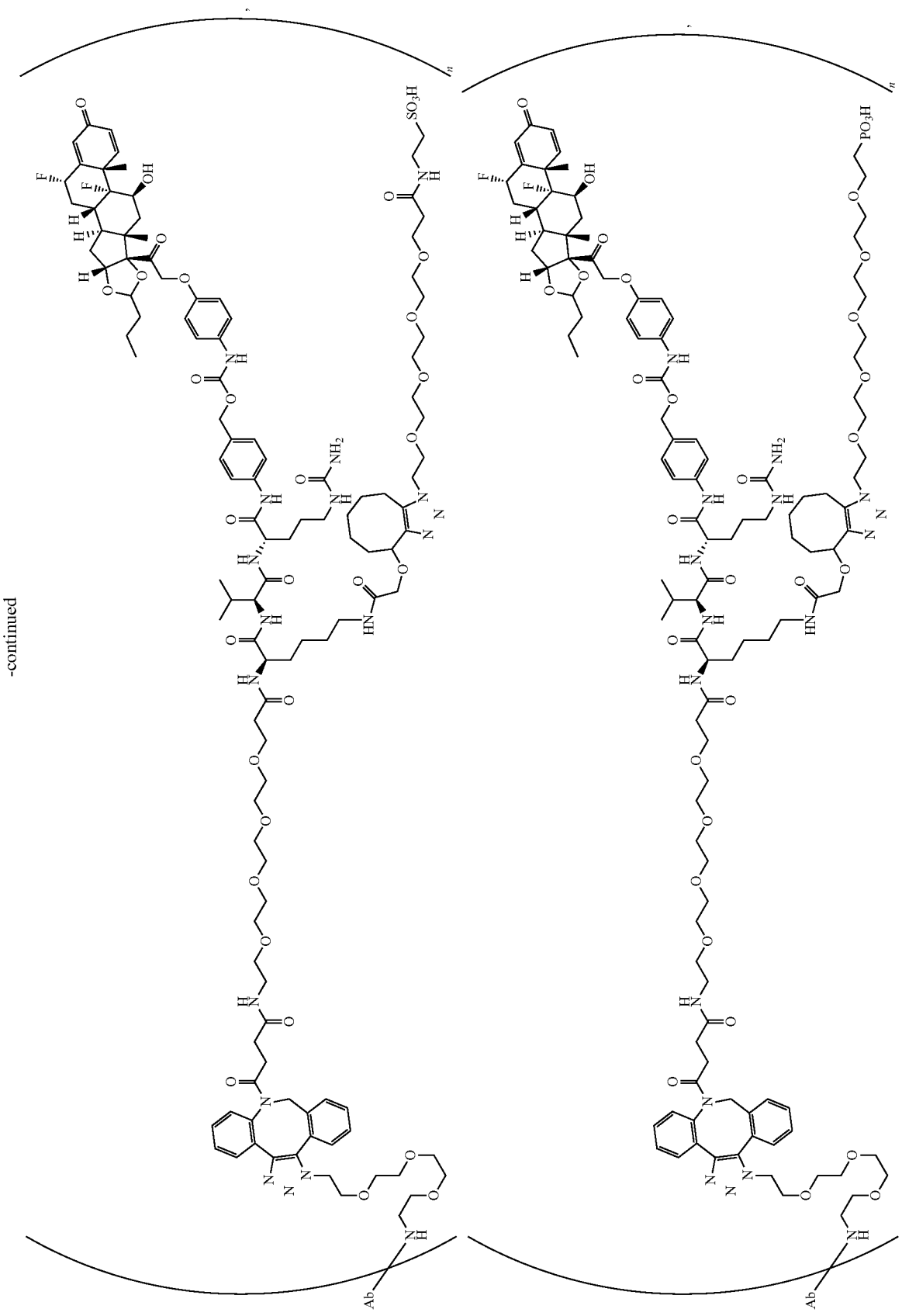

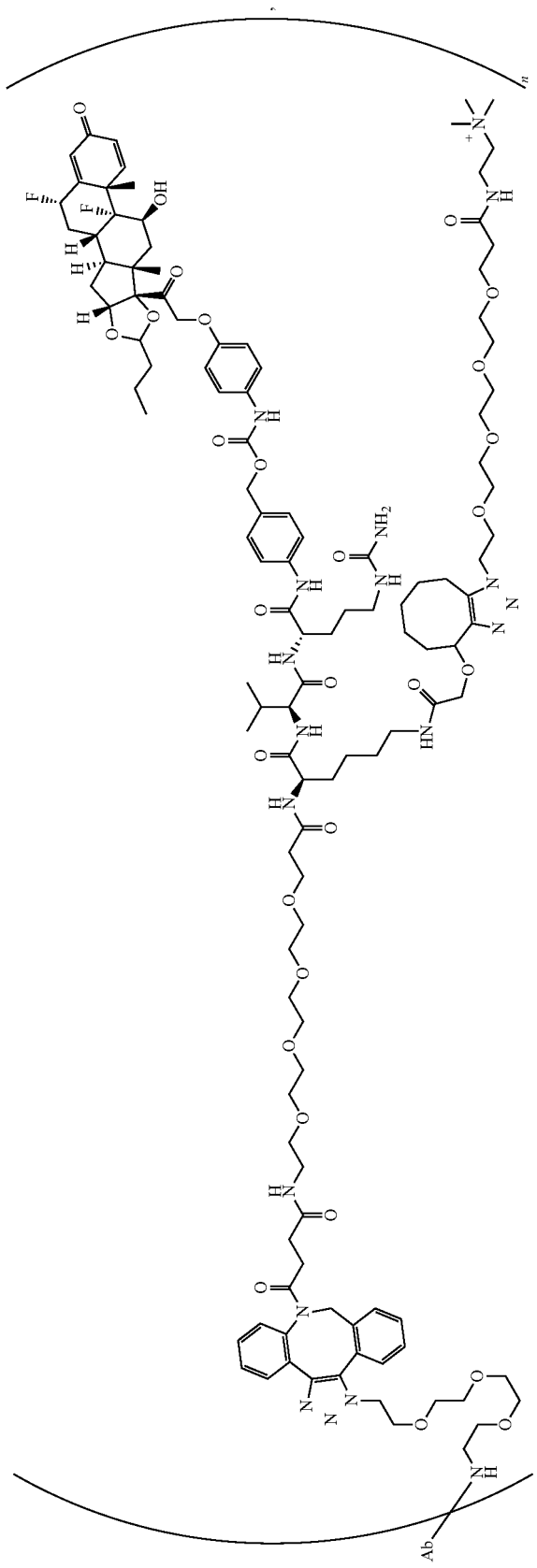

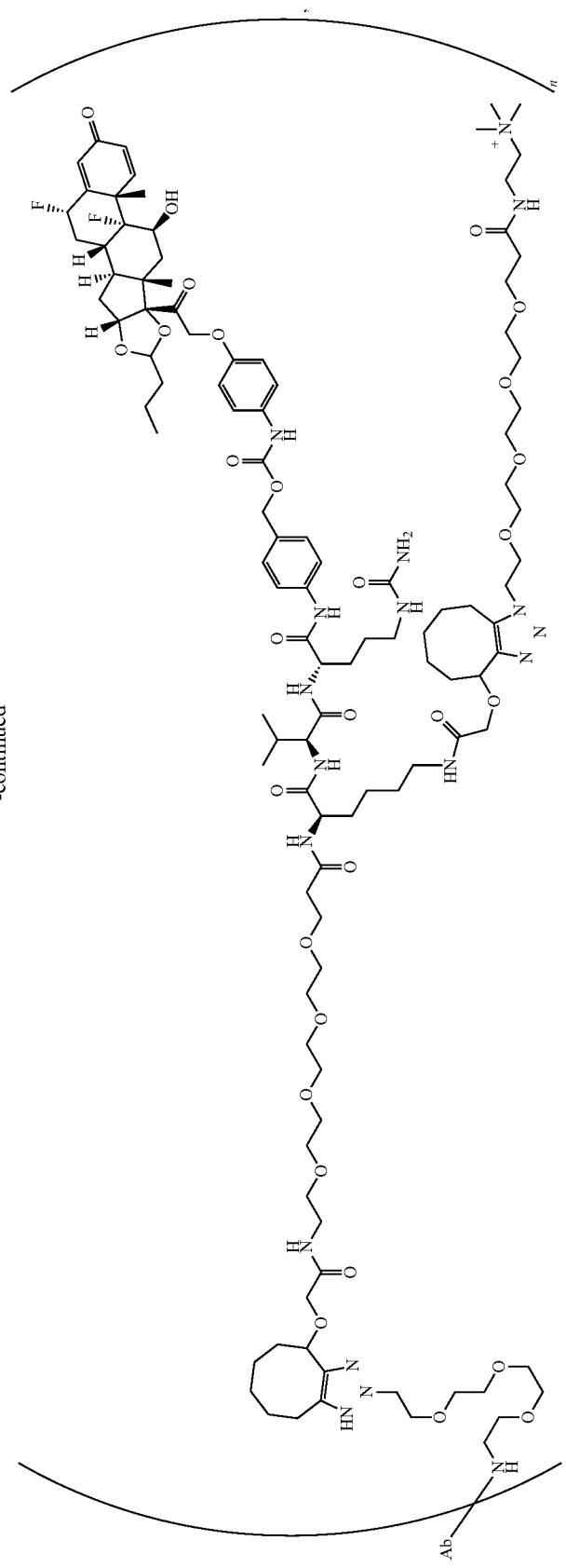

1339 1340
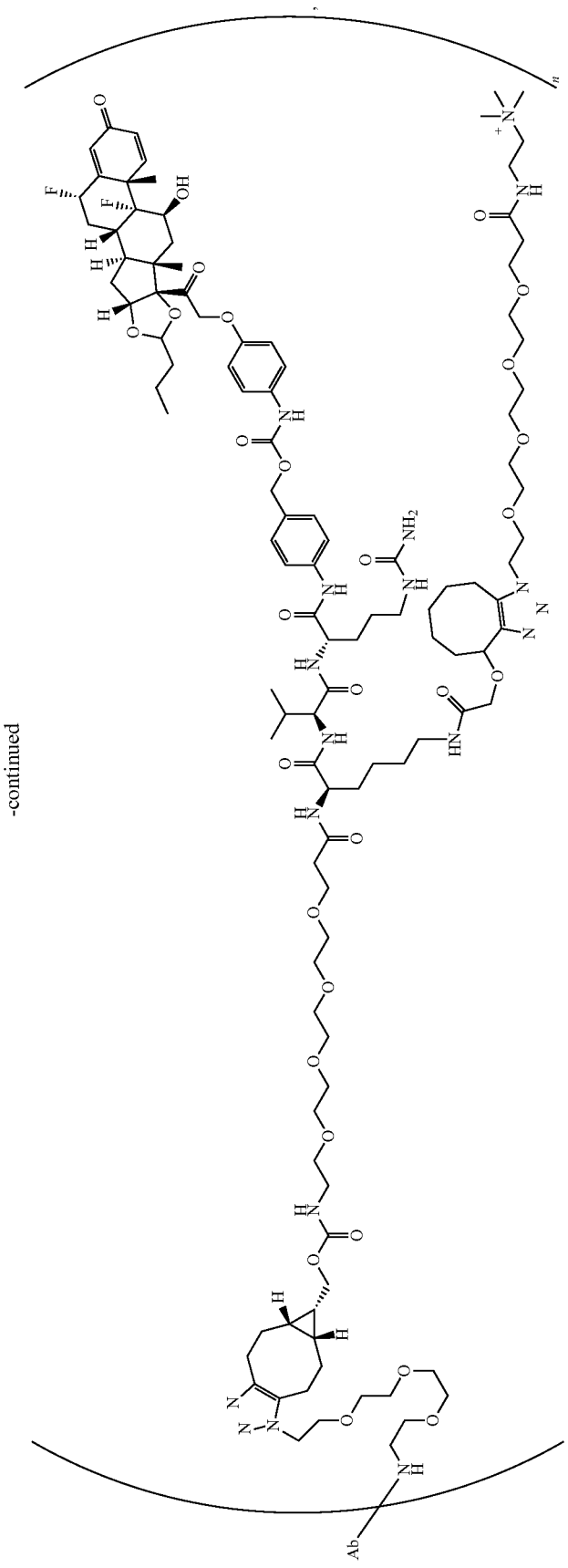

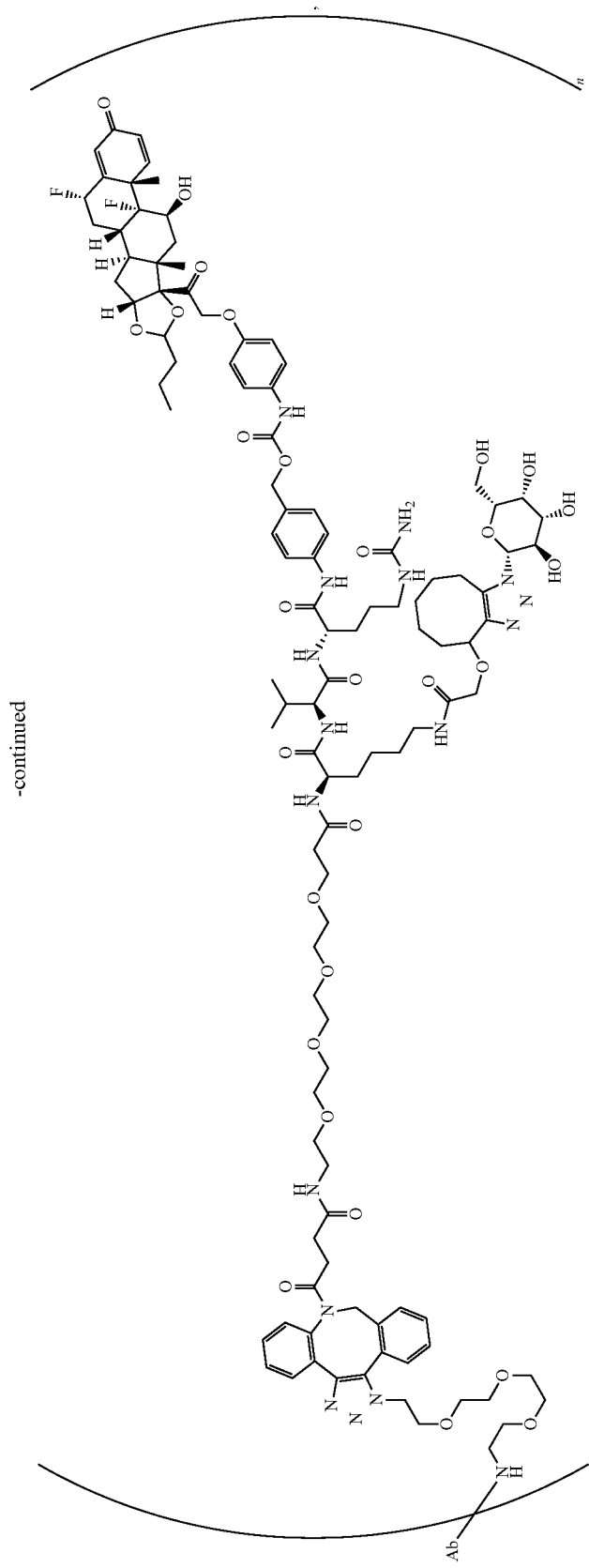

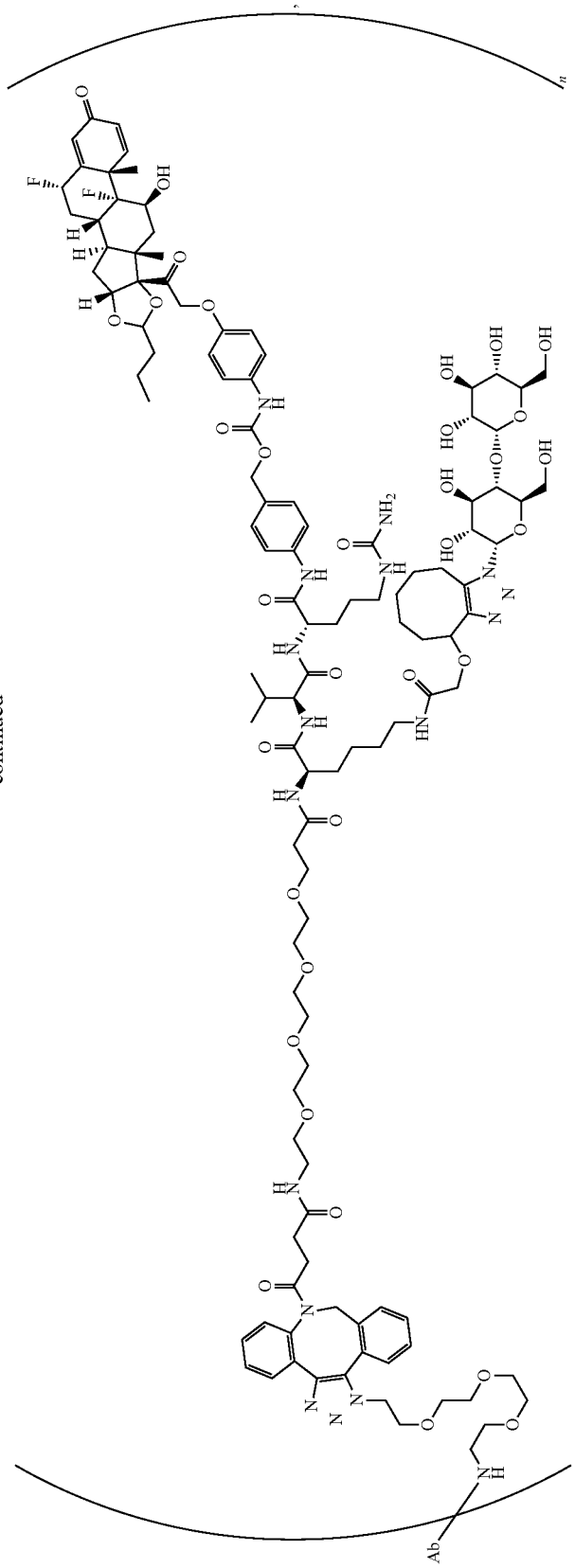

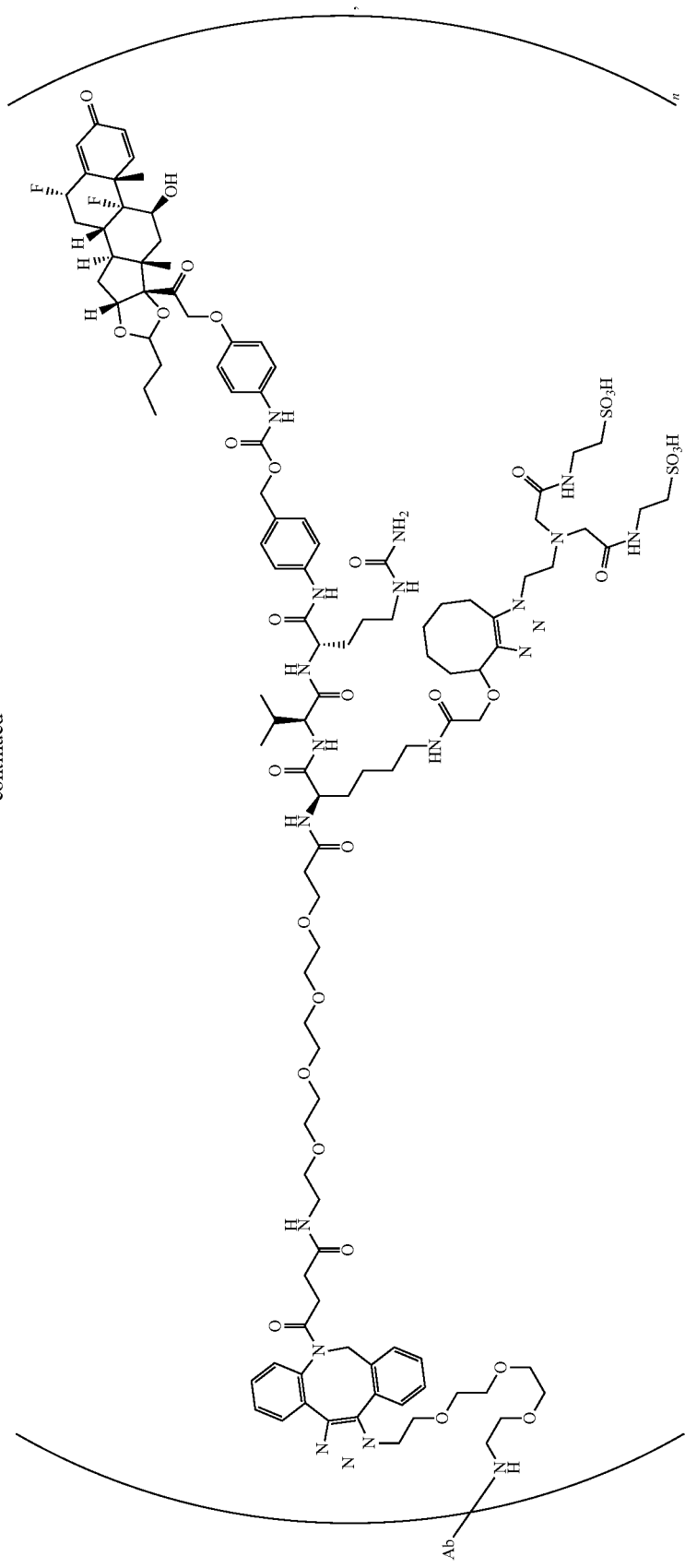

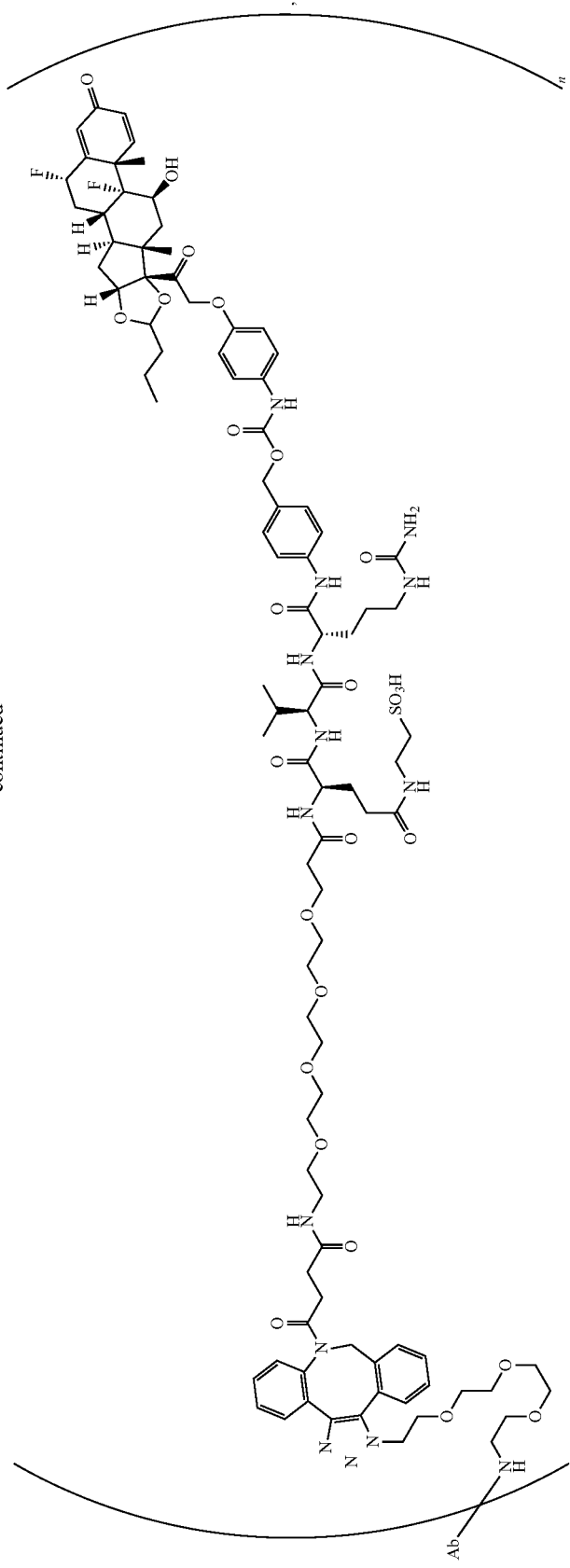

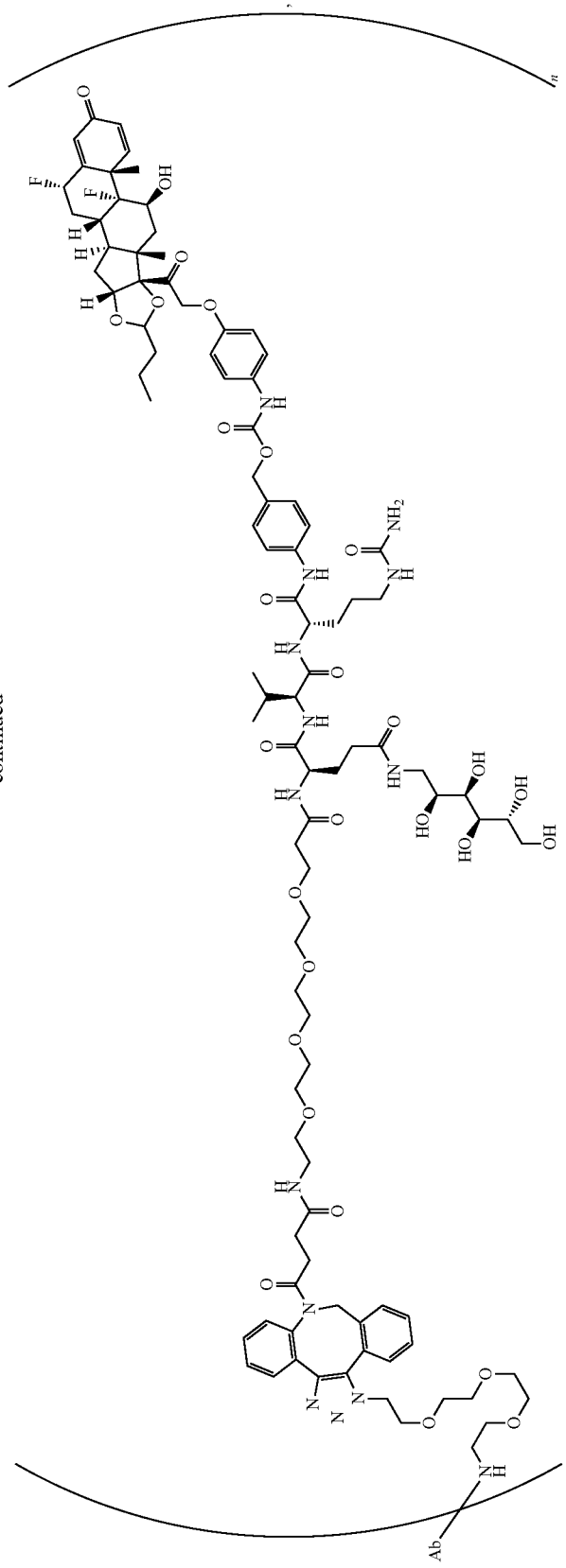

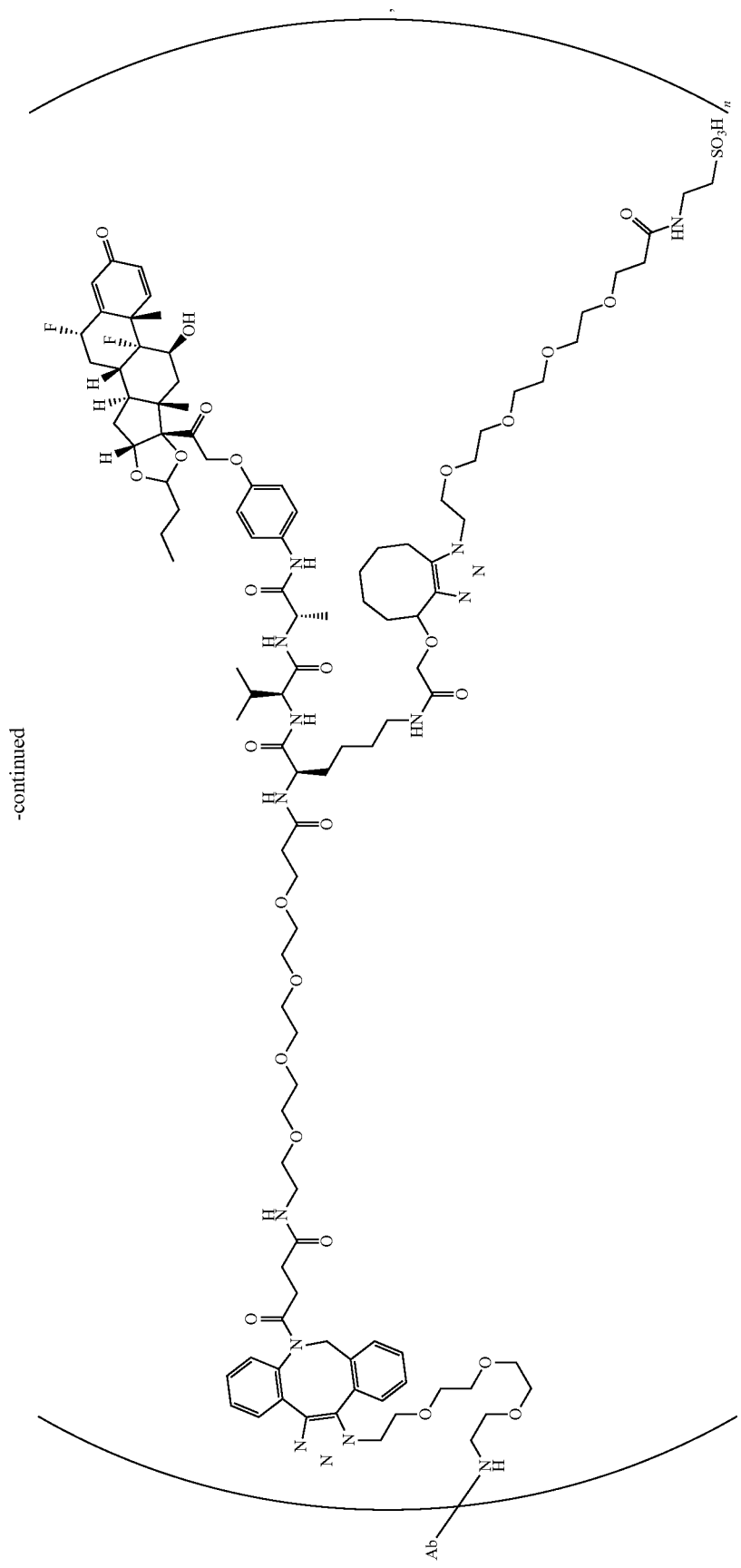
-continued

1353
-continued
1354
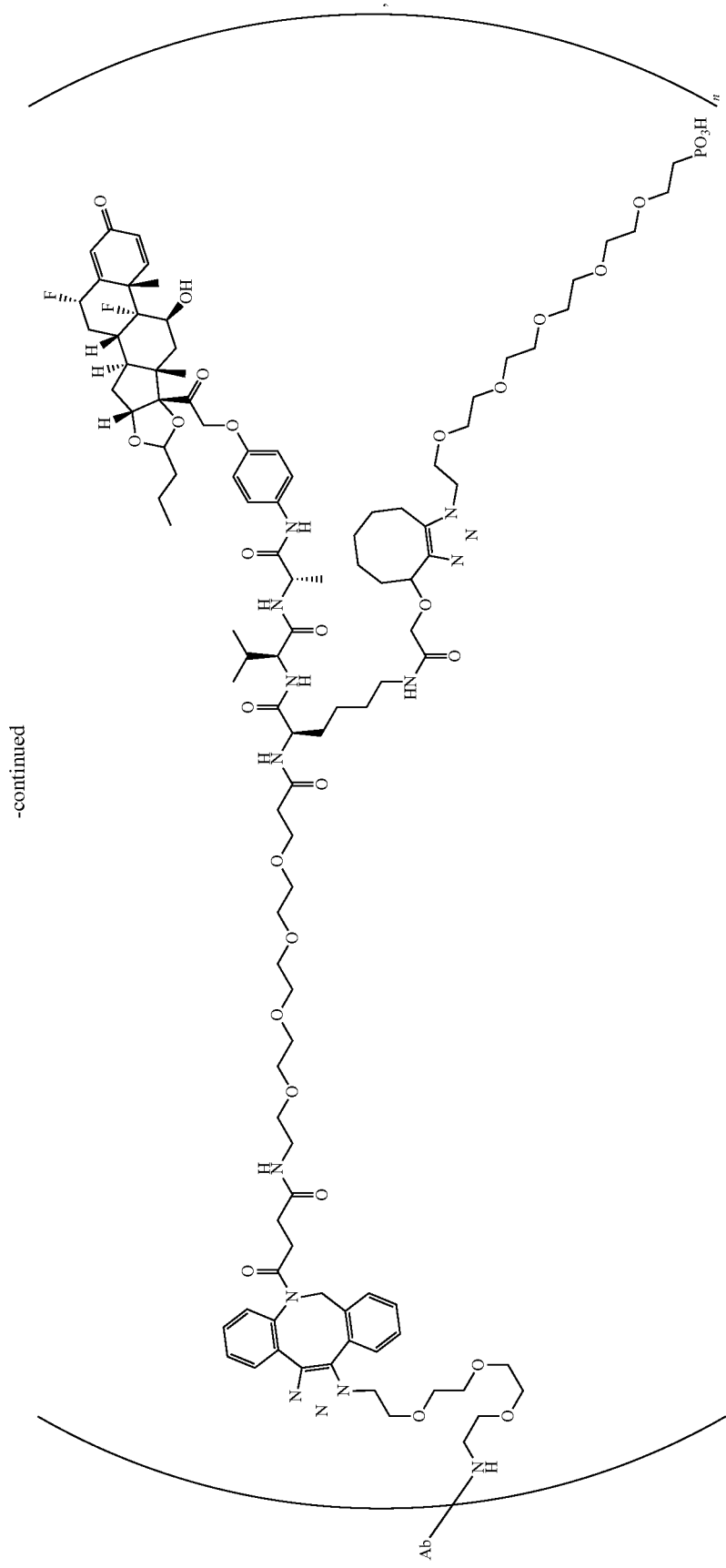

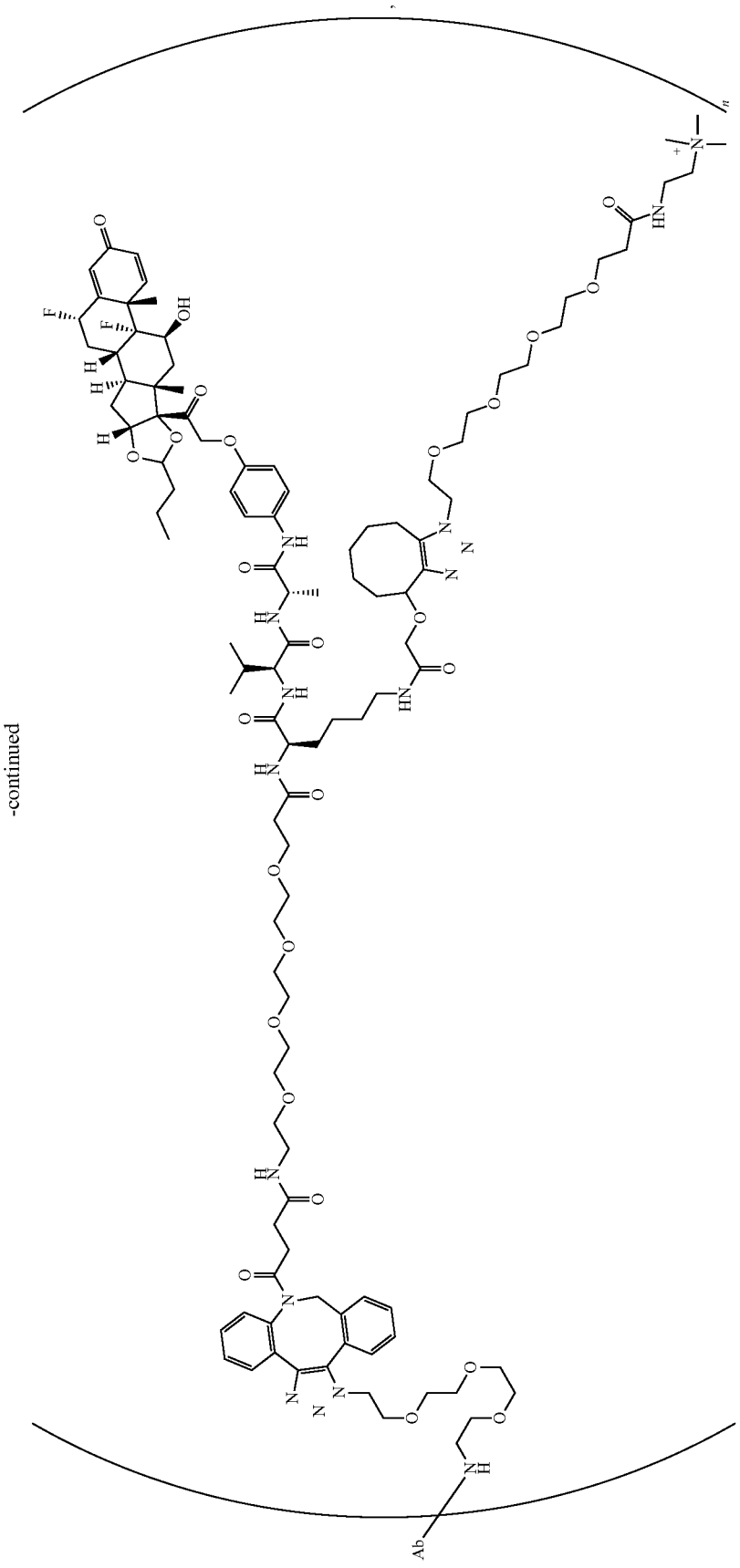

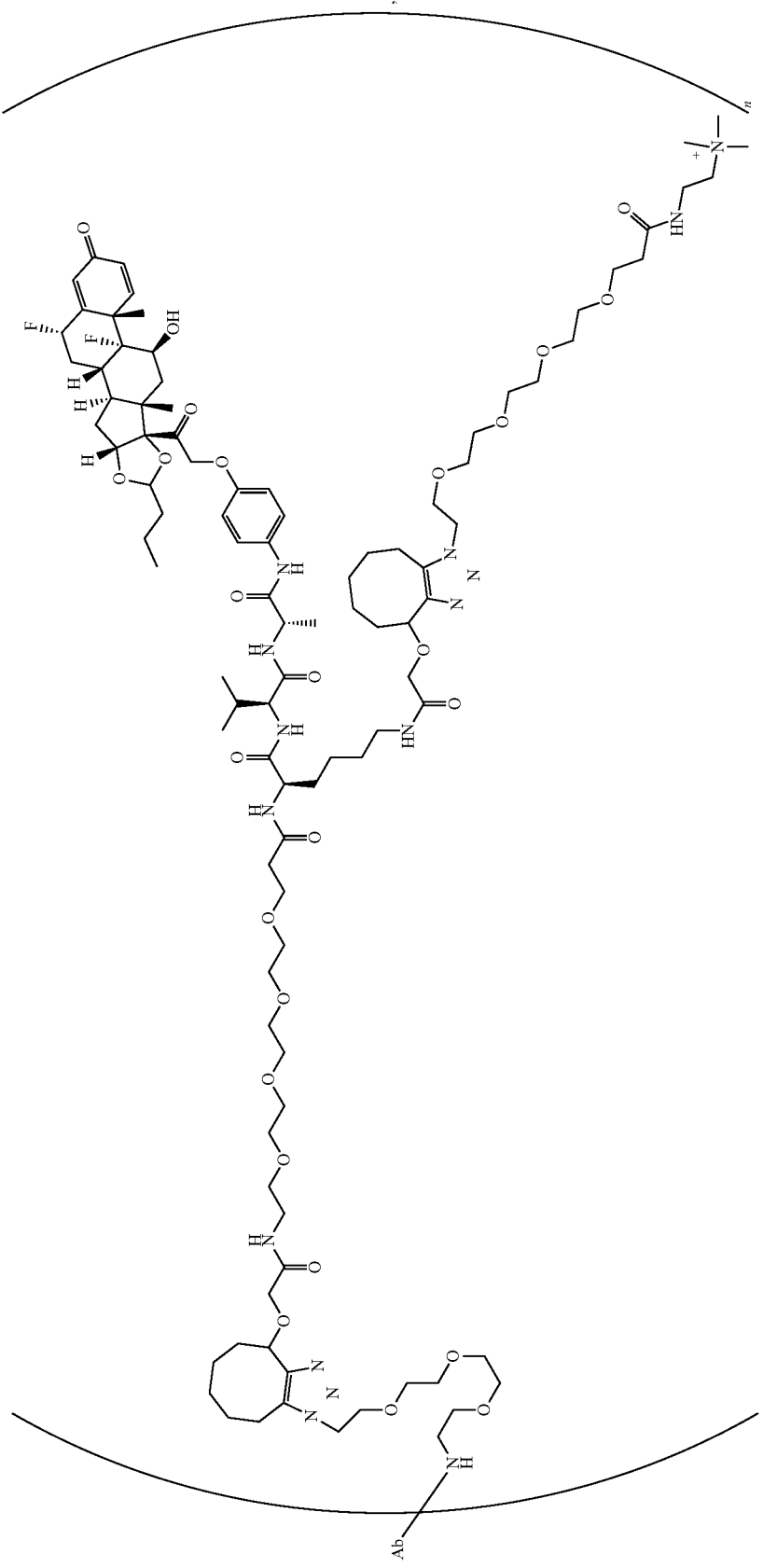

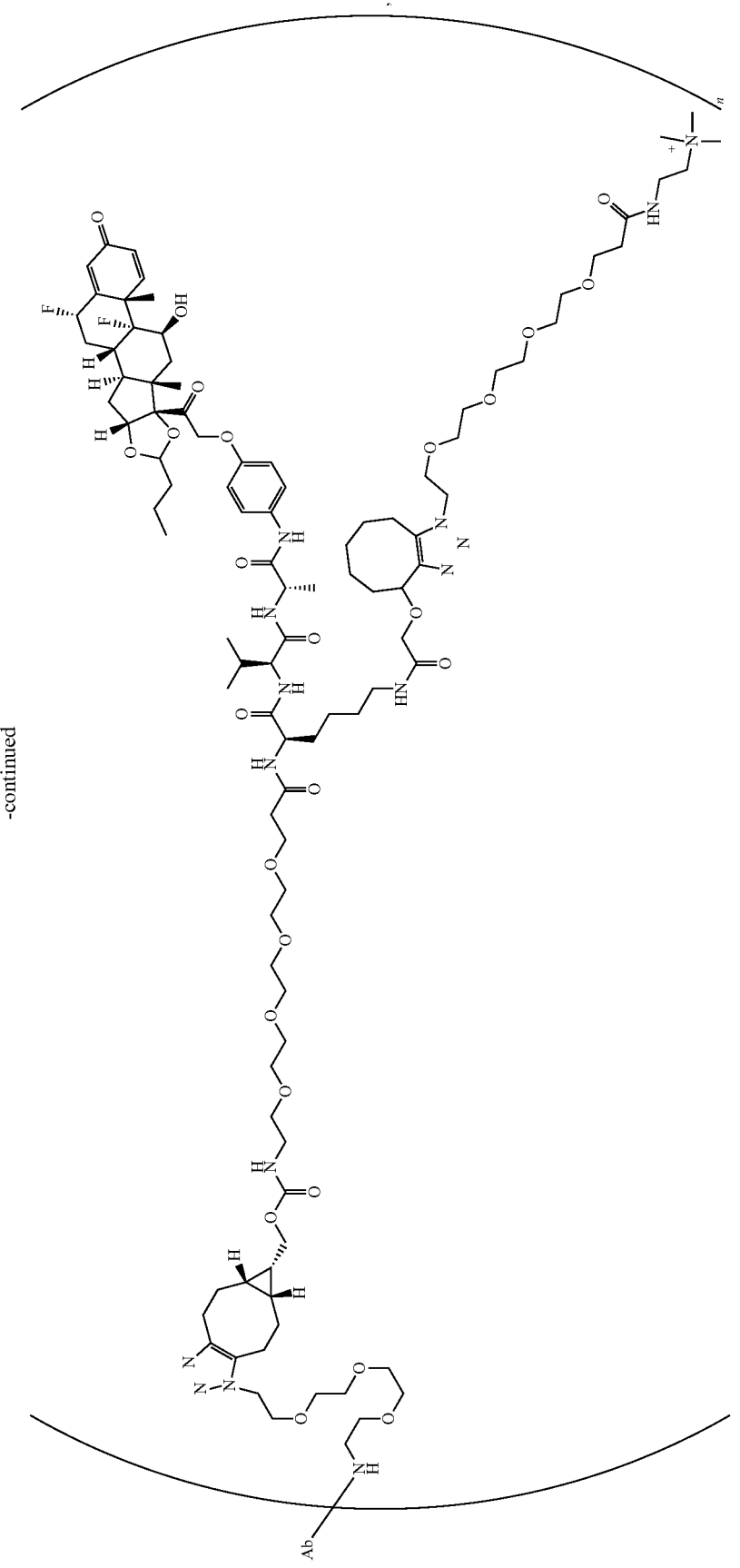

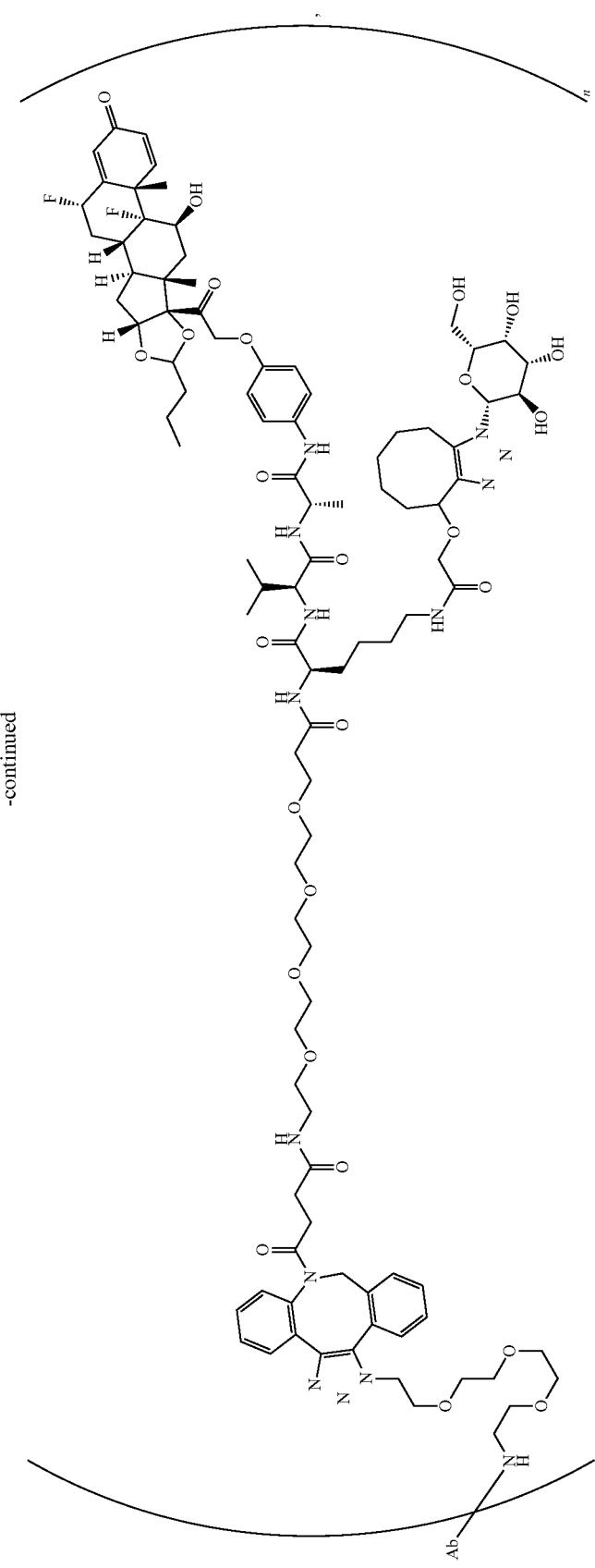

1363
-continued
1364
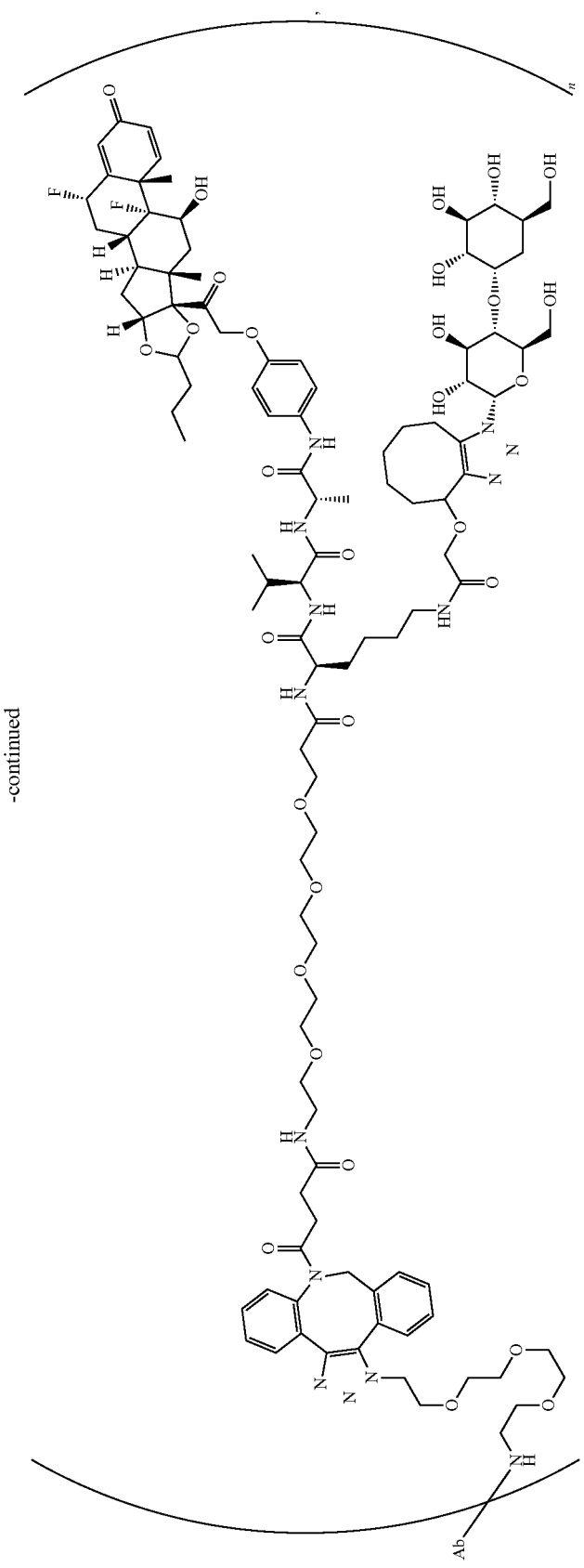

-continued
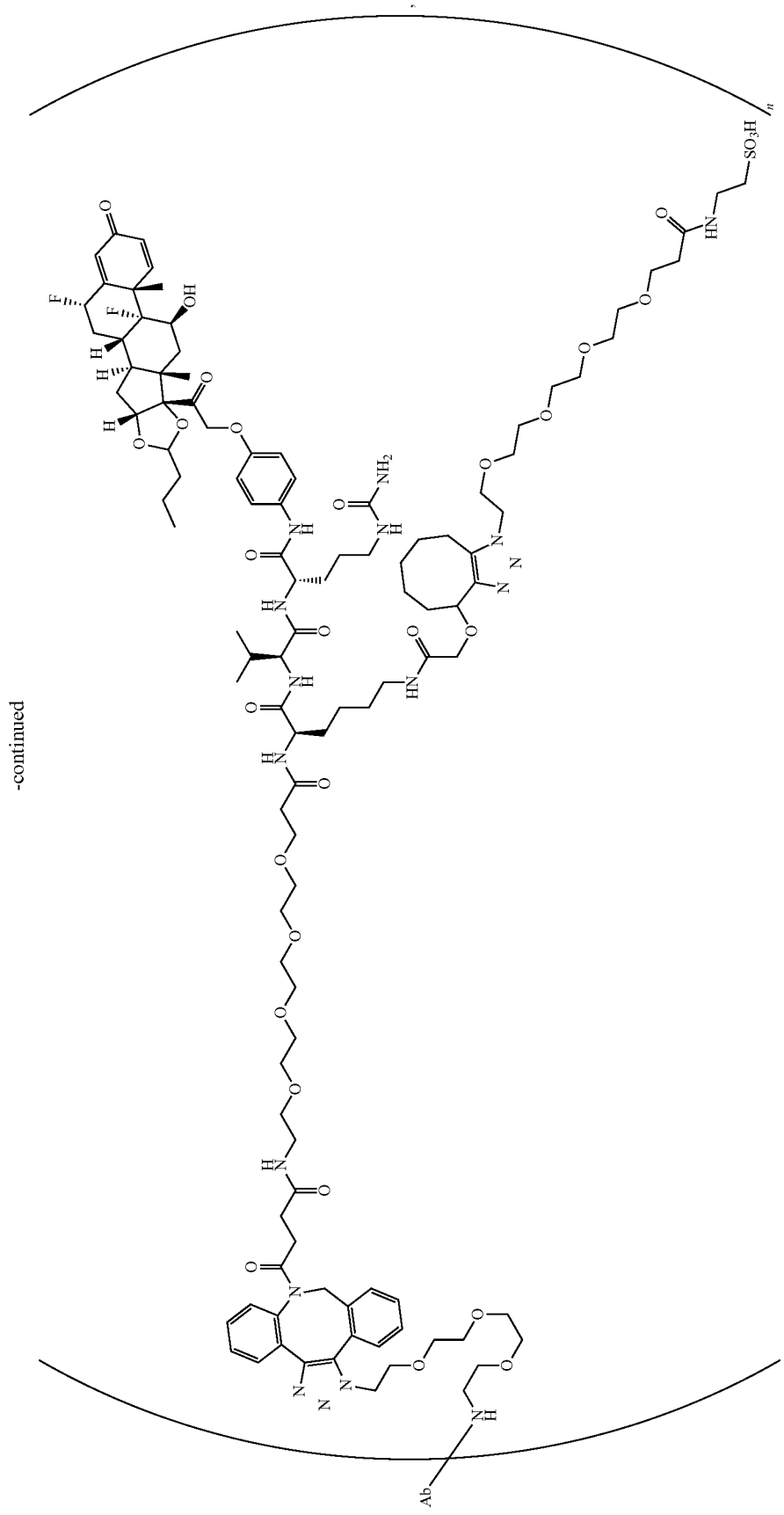

-continued
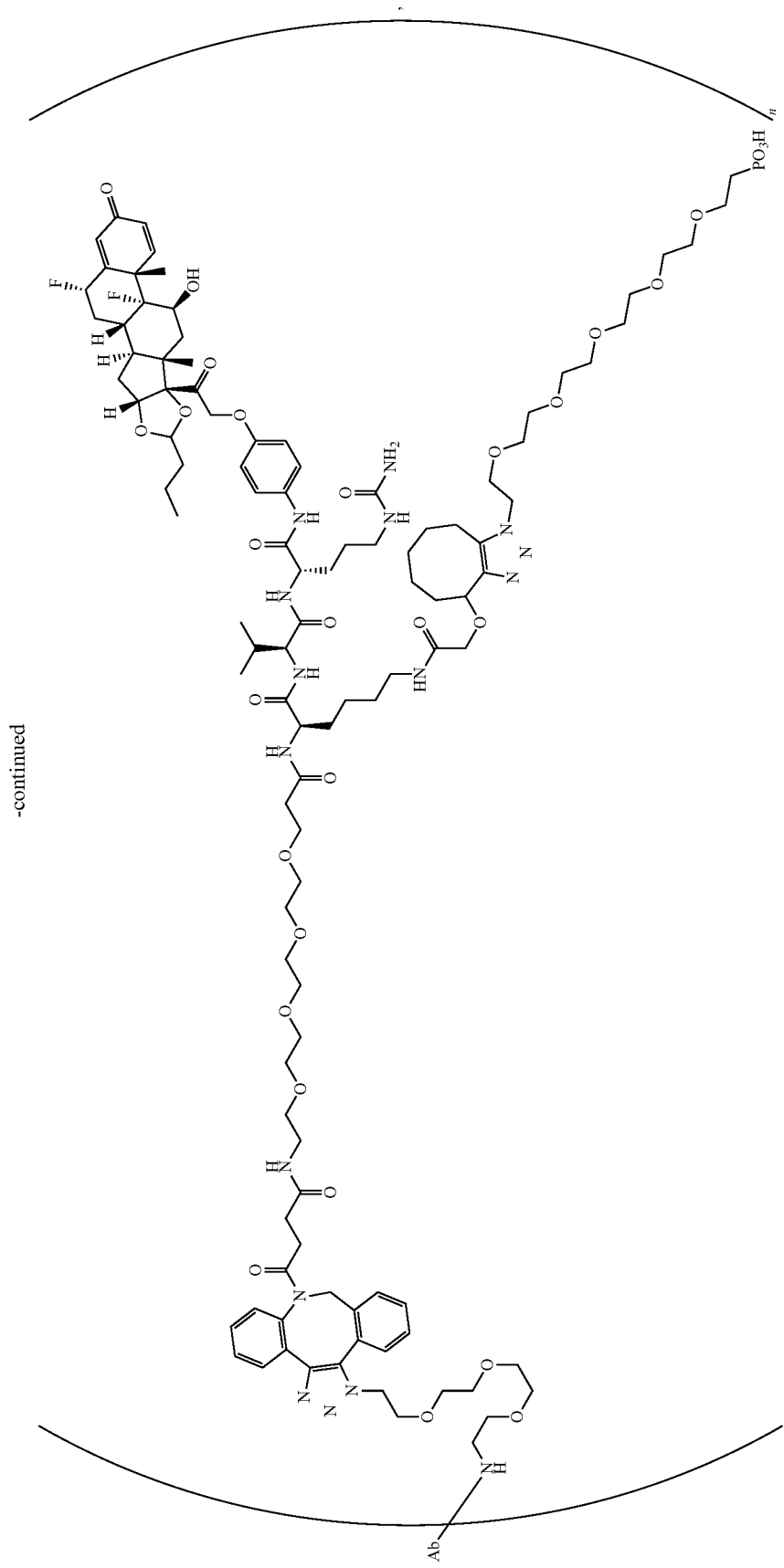

-continued
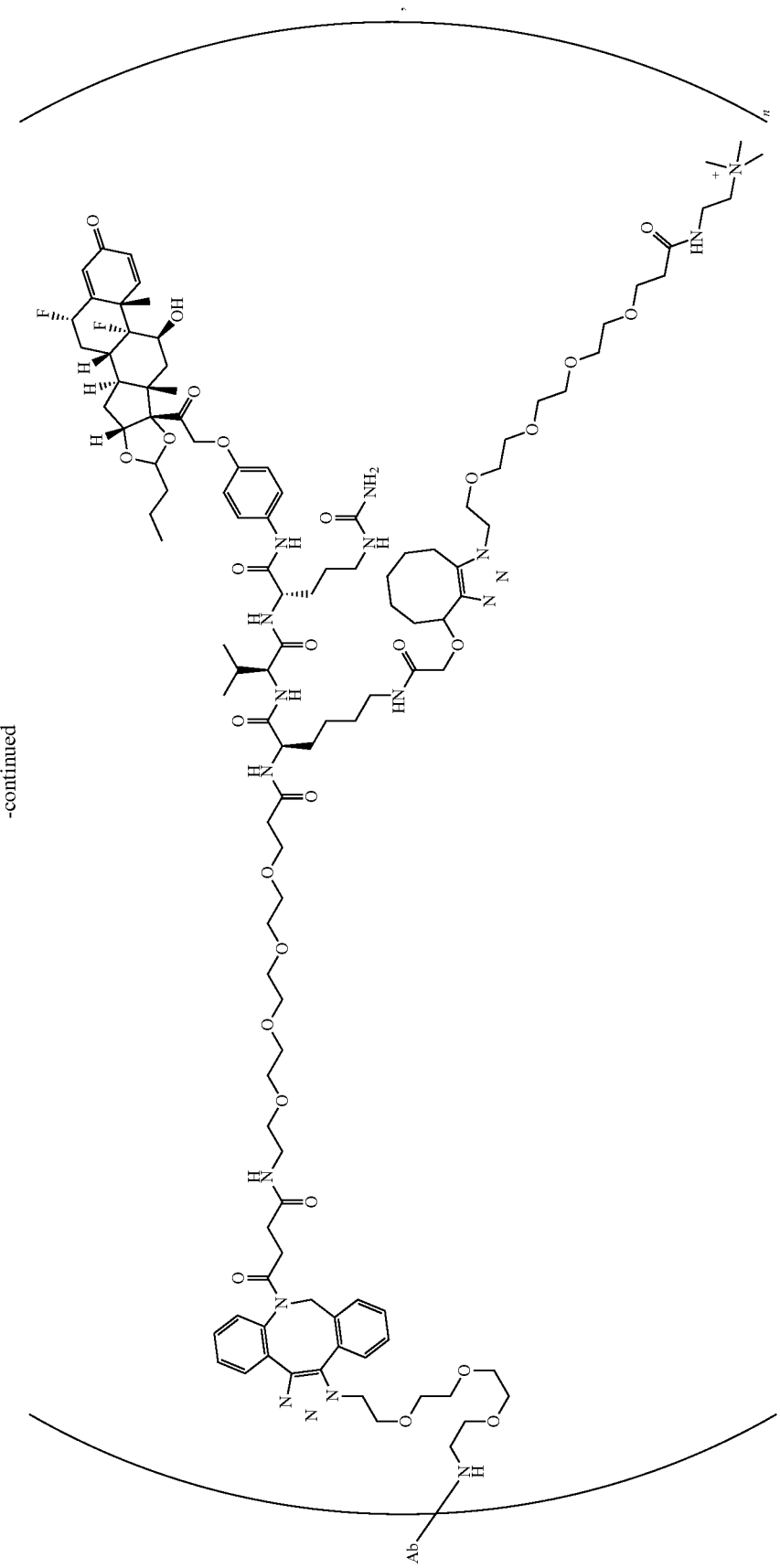

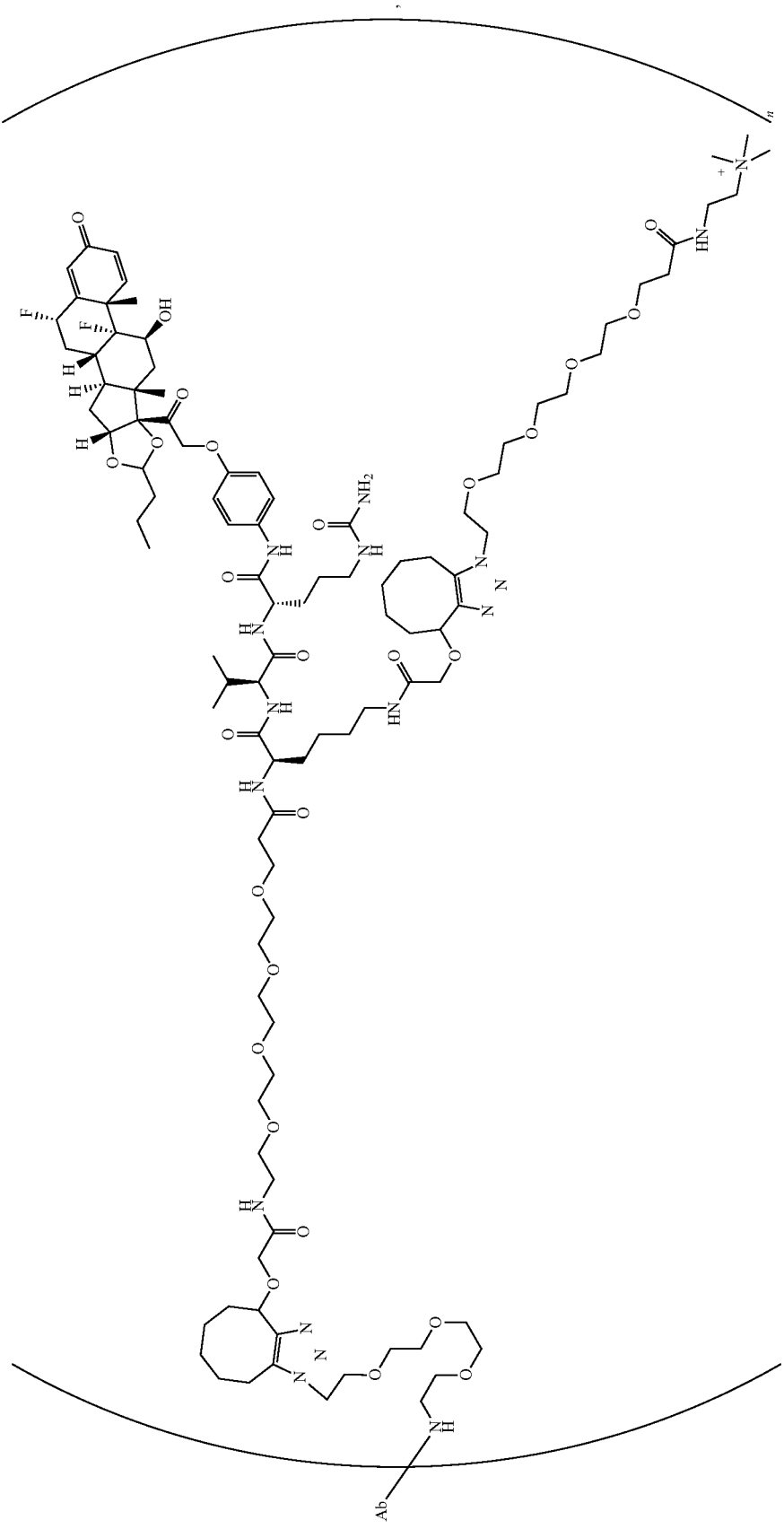

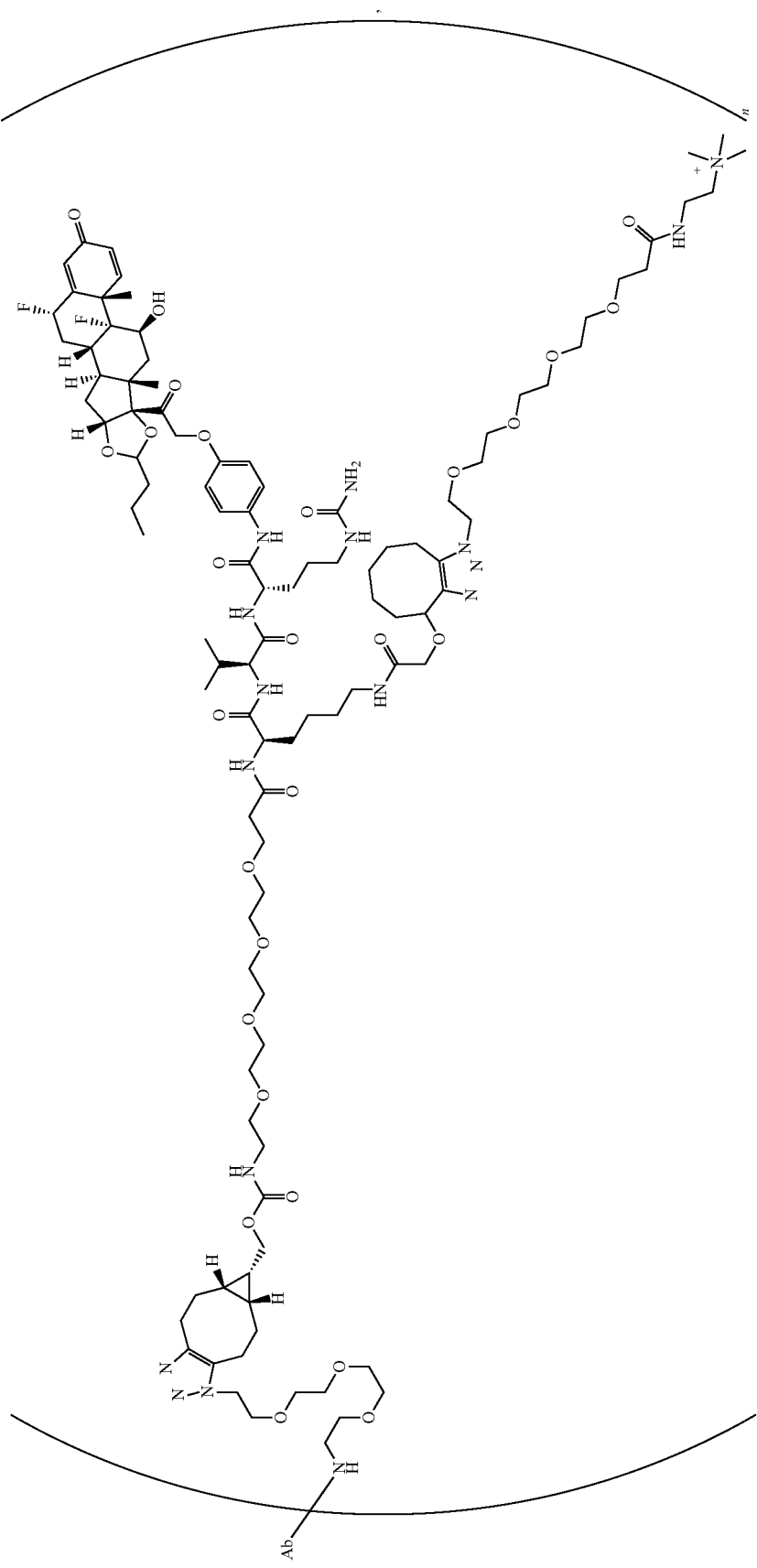

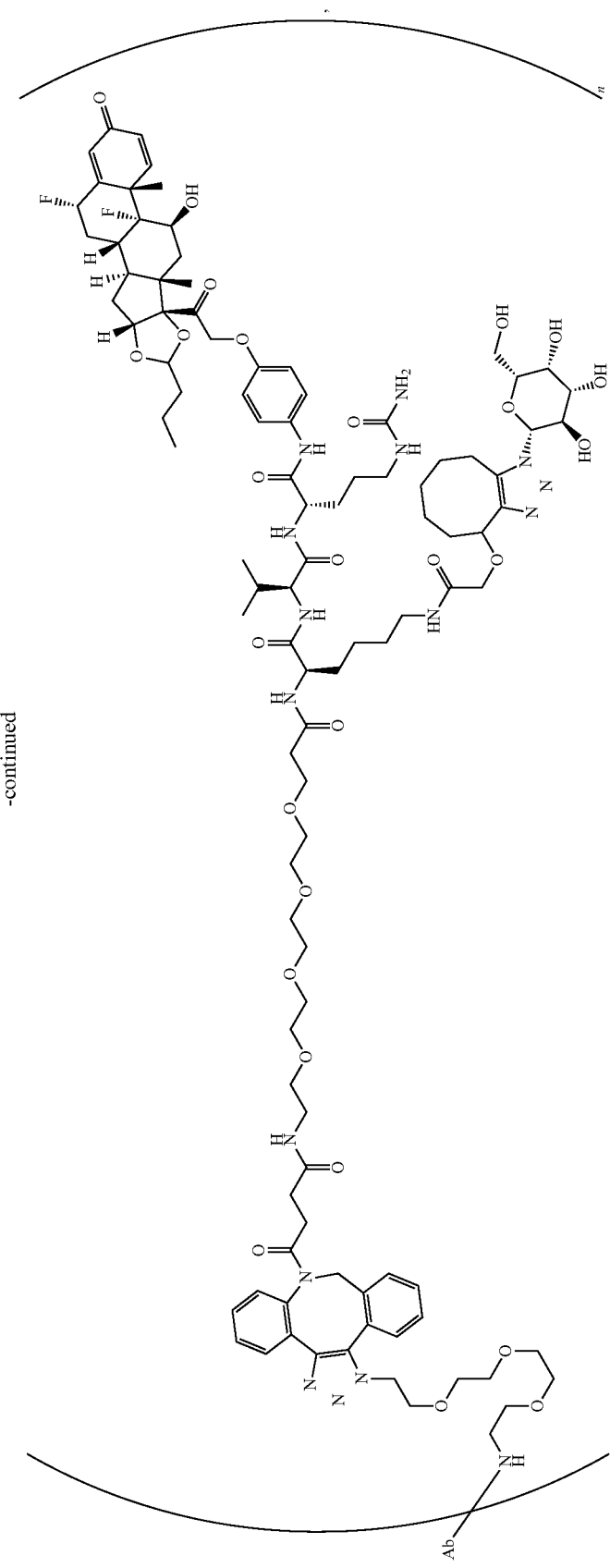

1377 1378
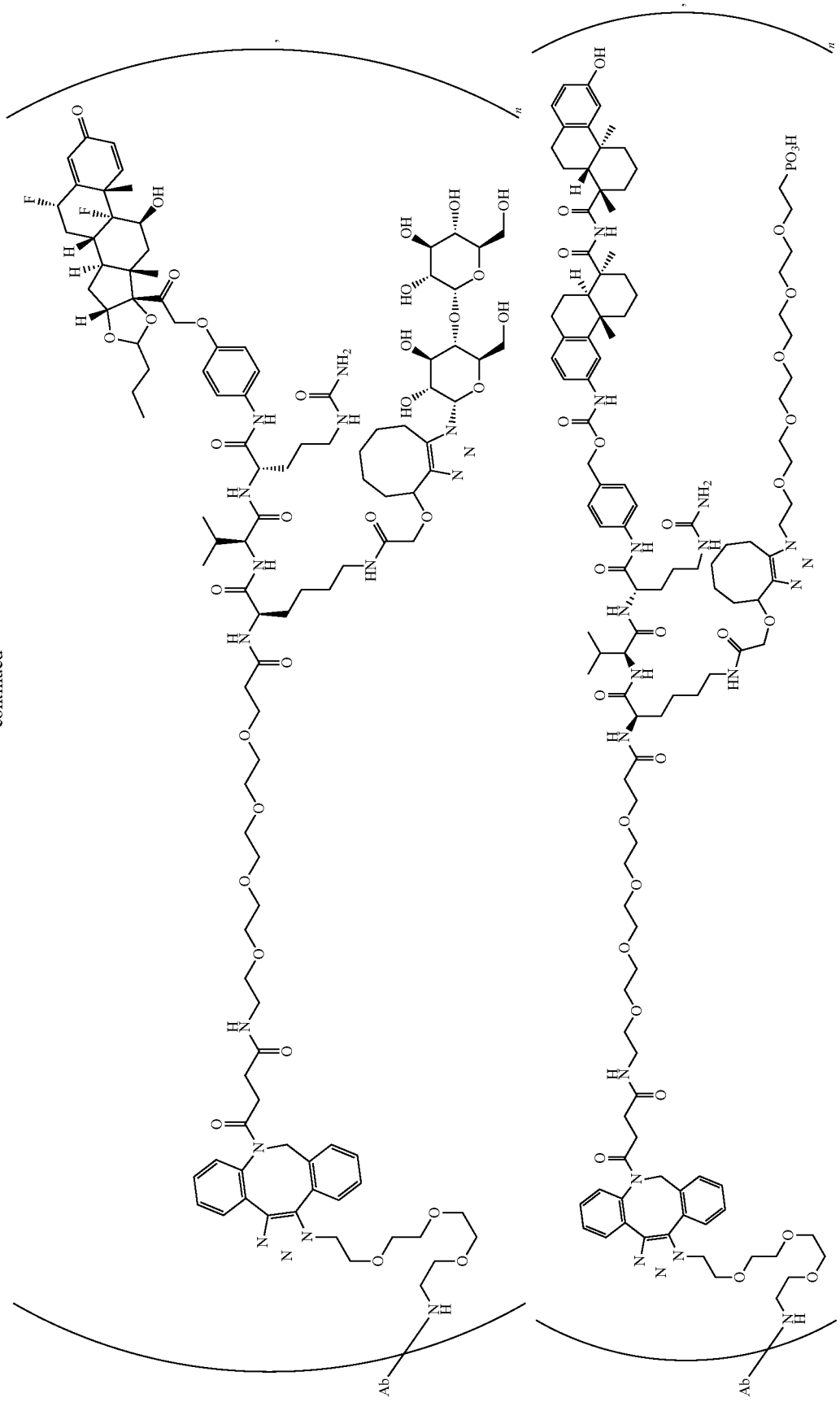

1379 1380
-continued
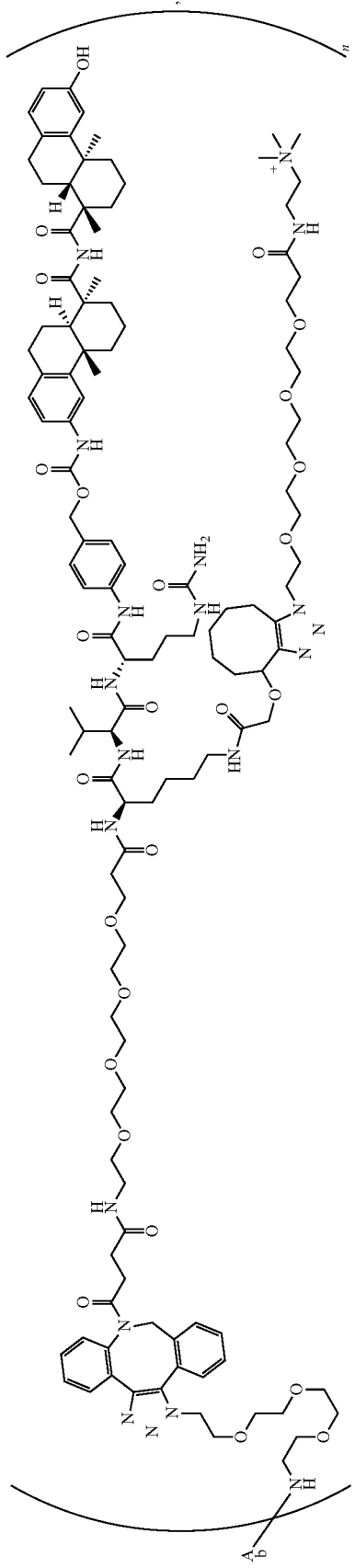
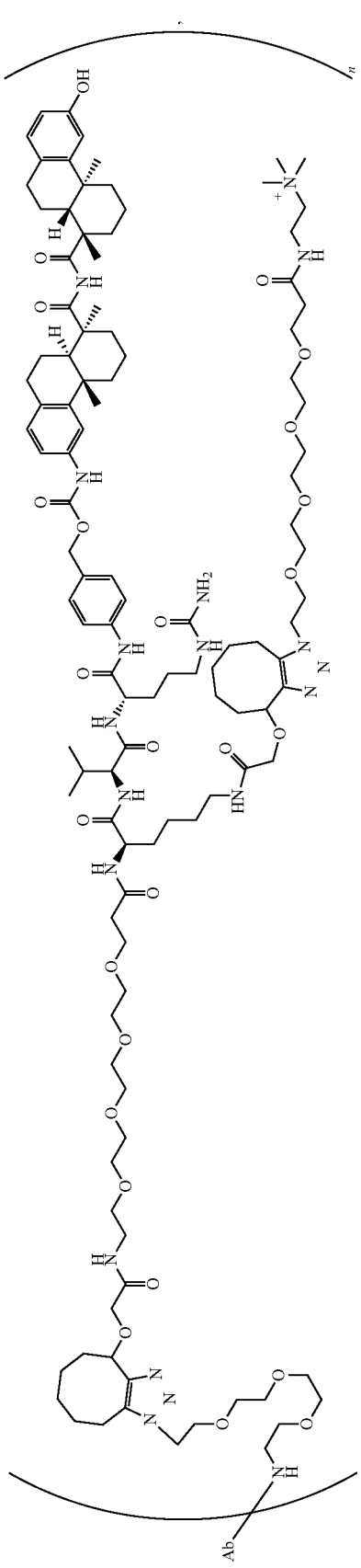
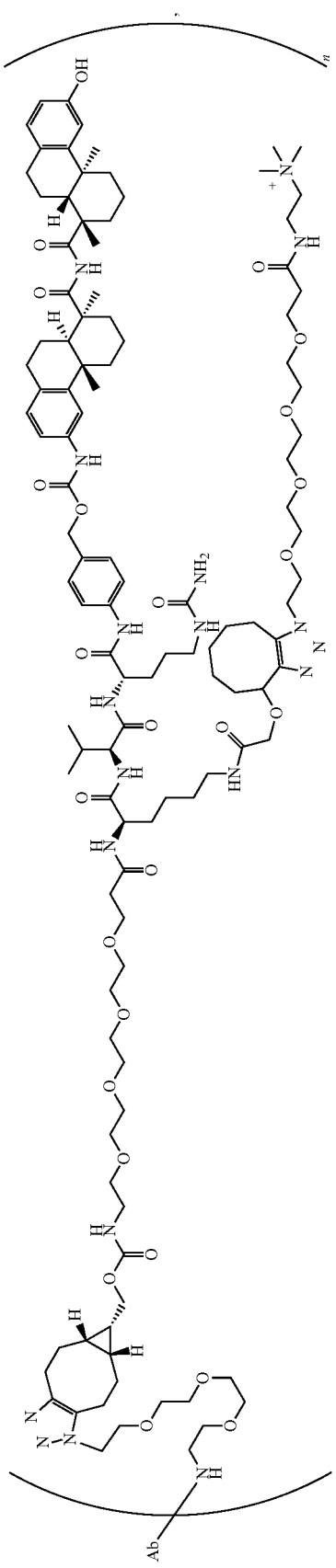

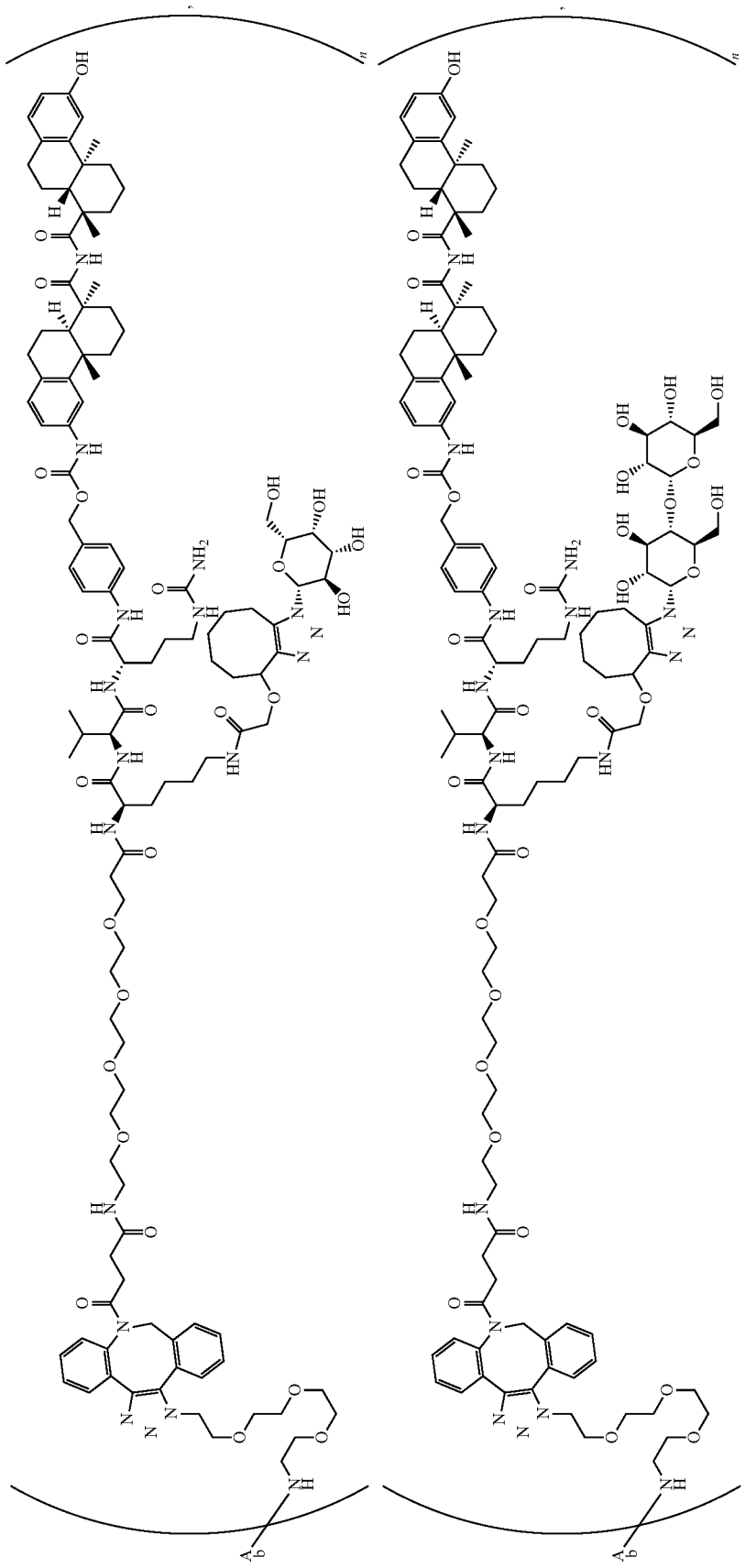

1383
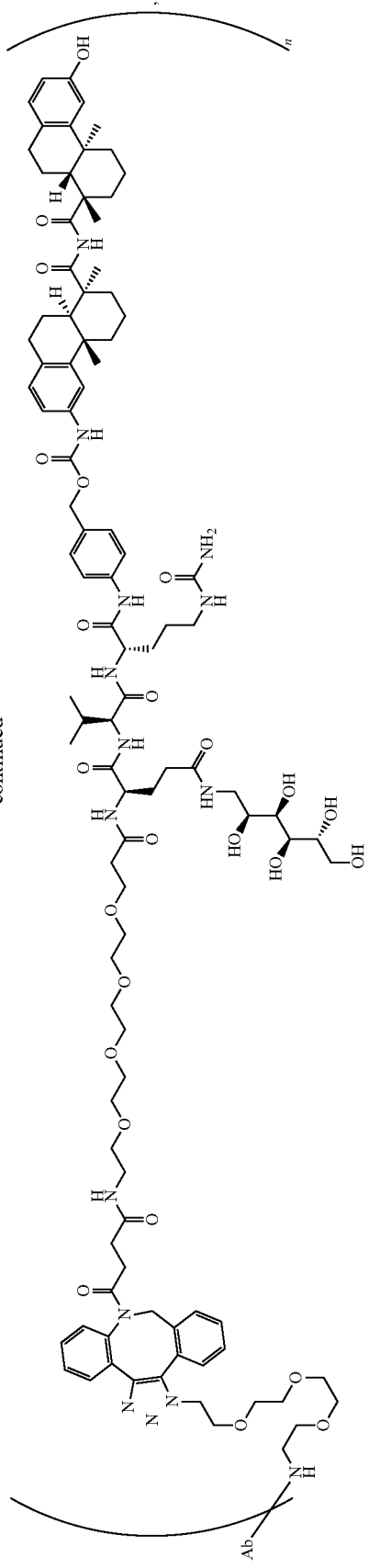
1384
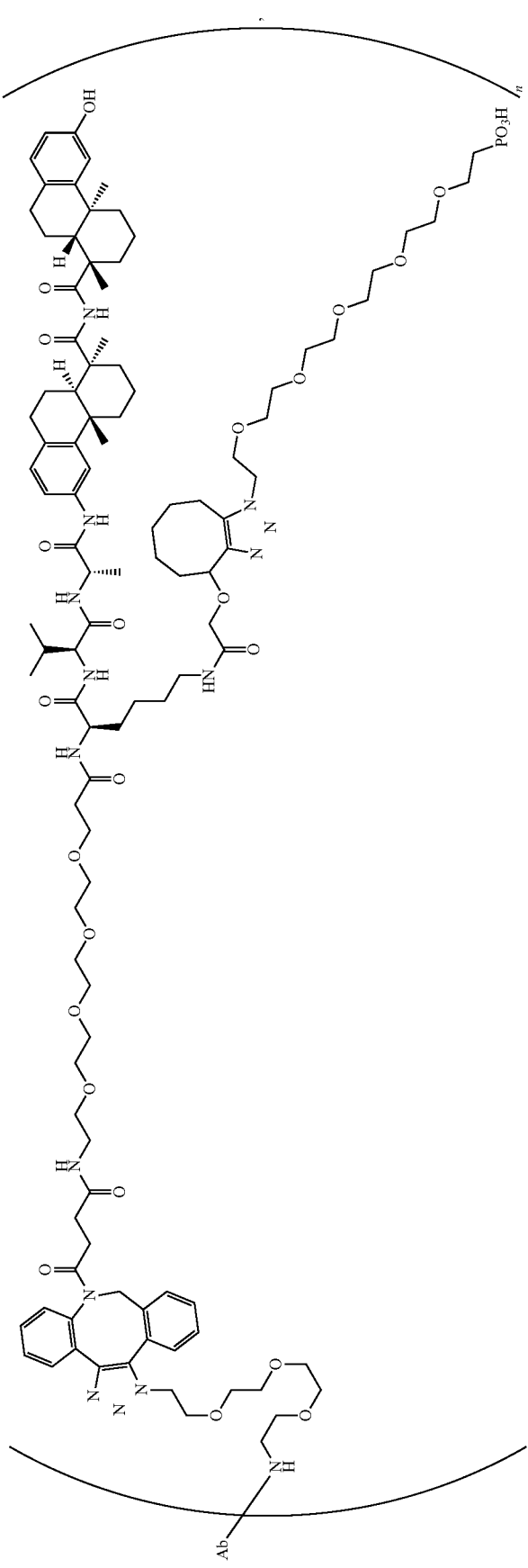

-continued
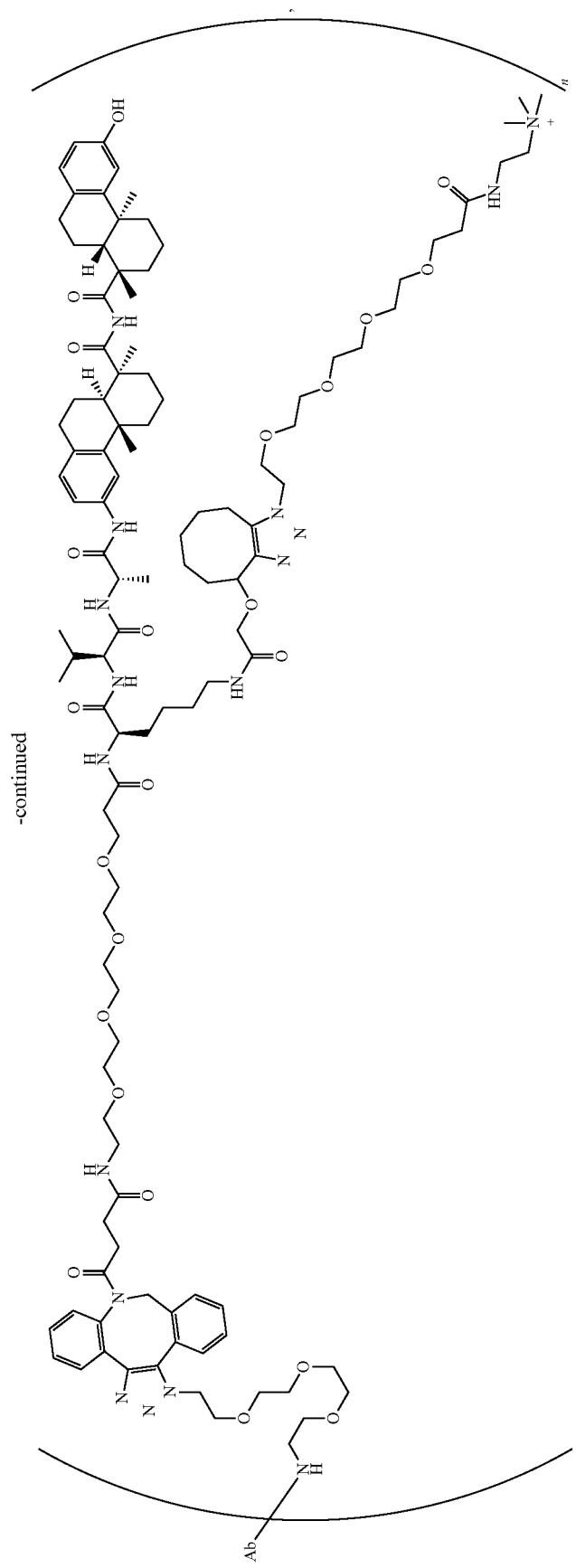

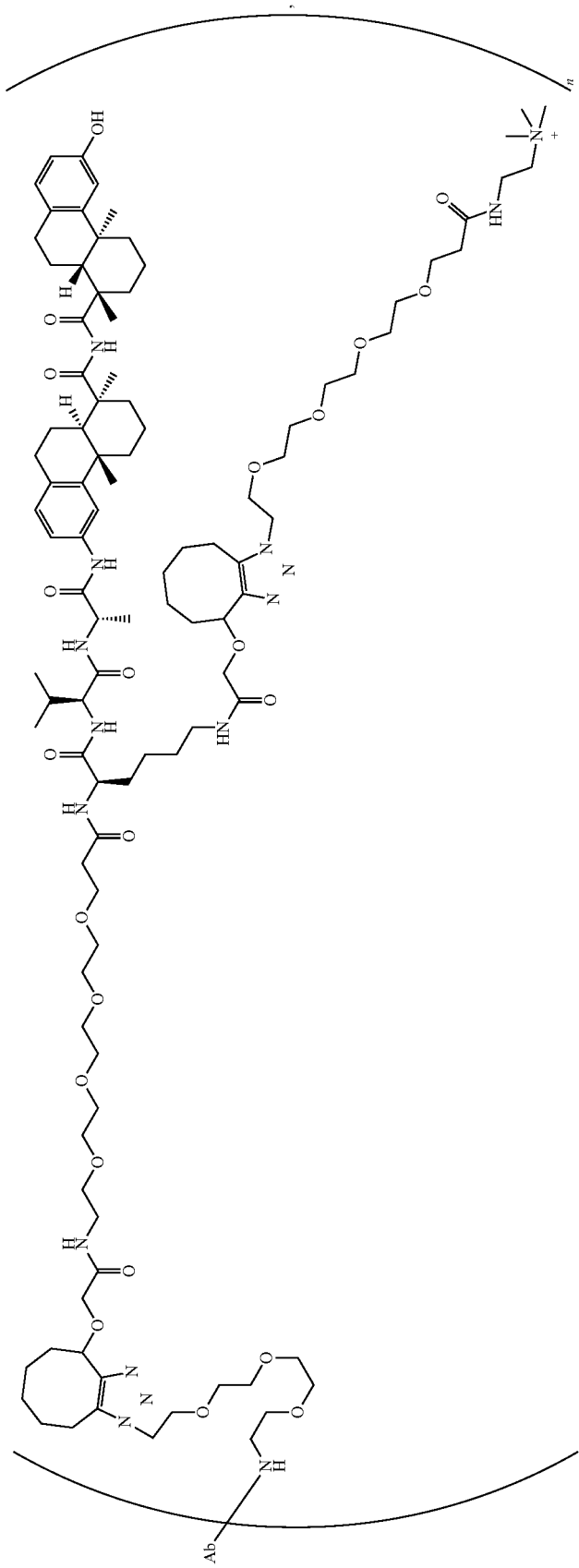

1389 1390
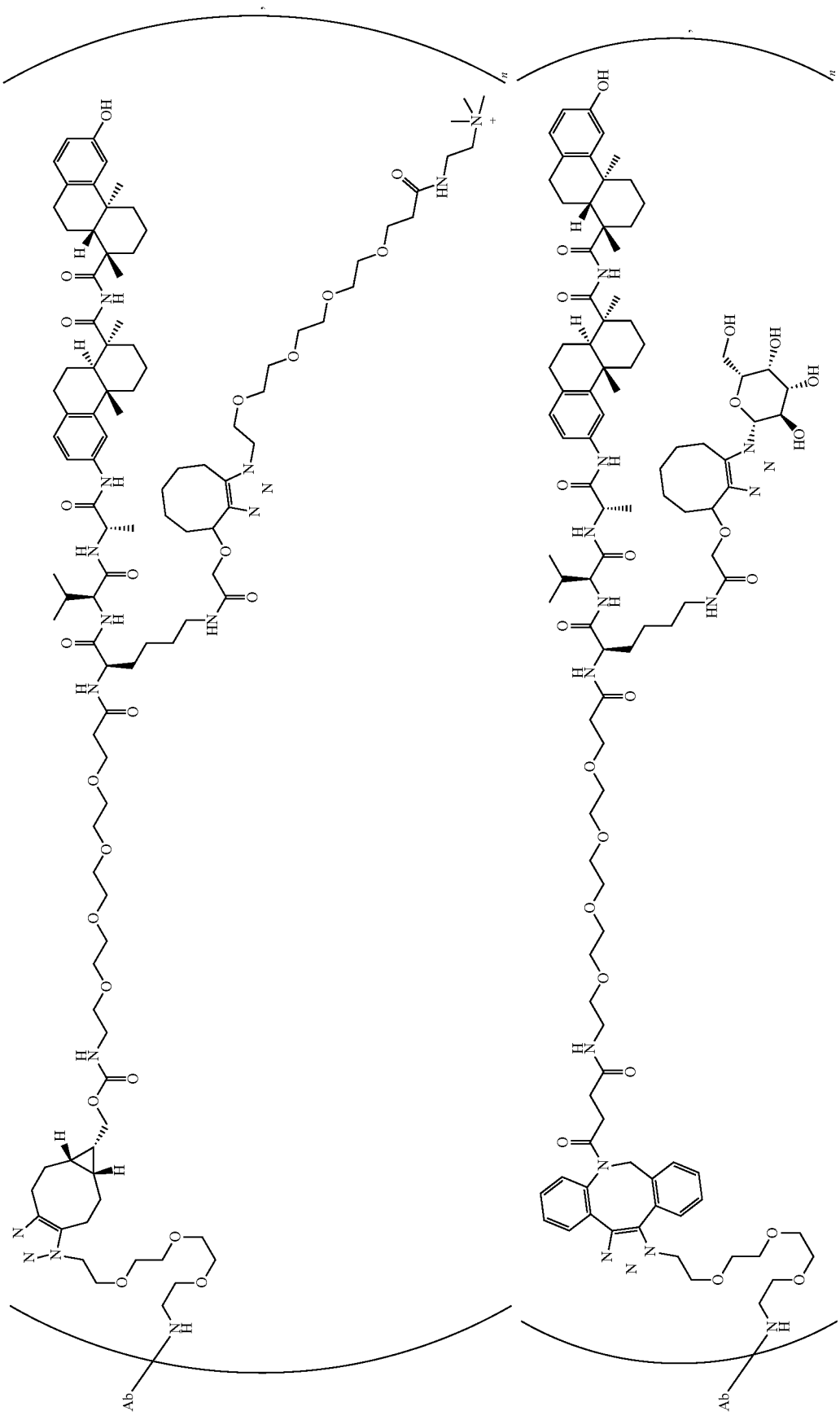

1391 1392
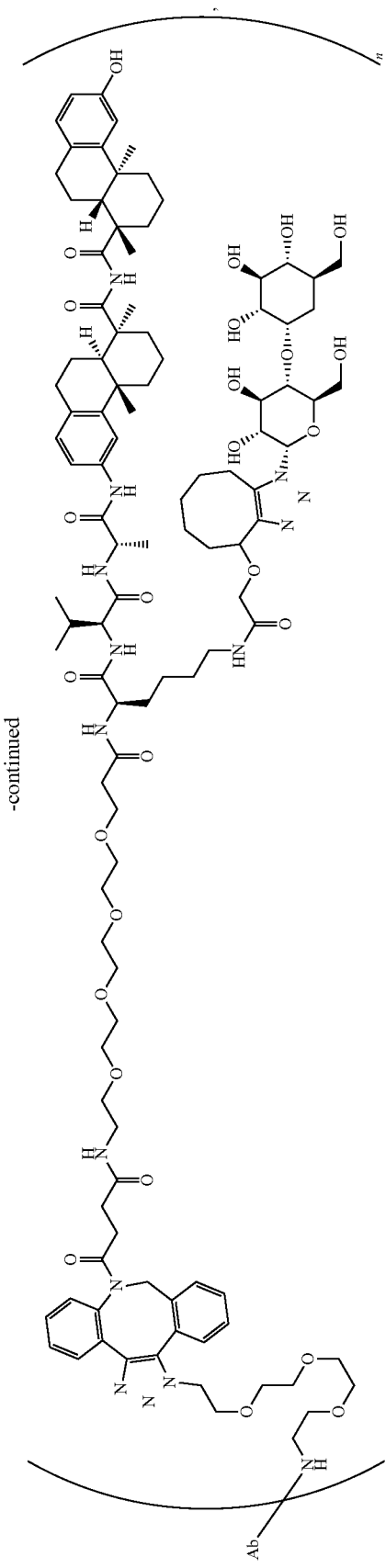
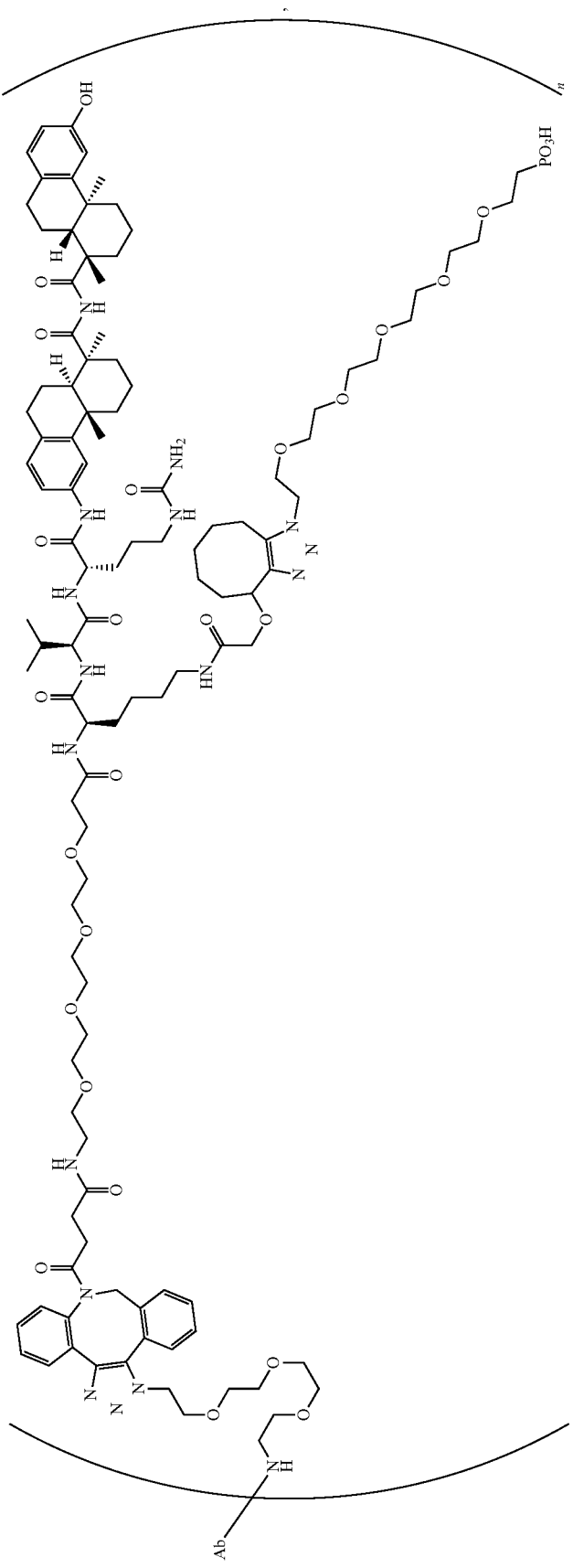

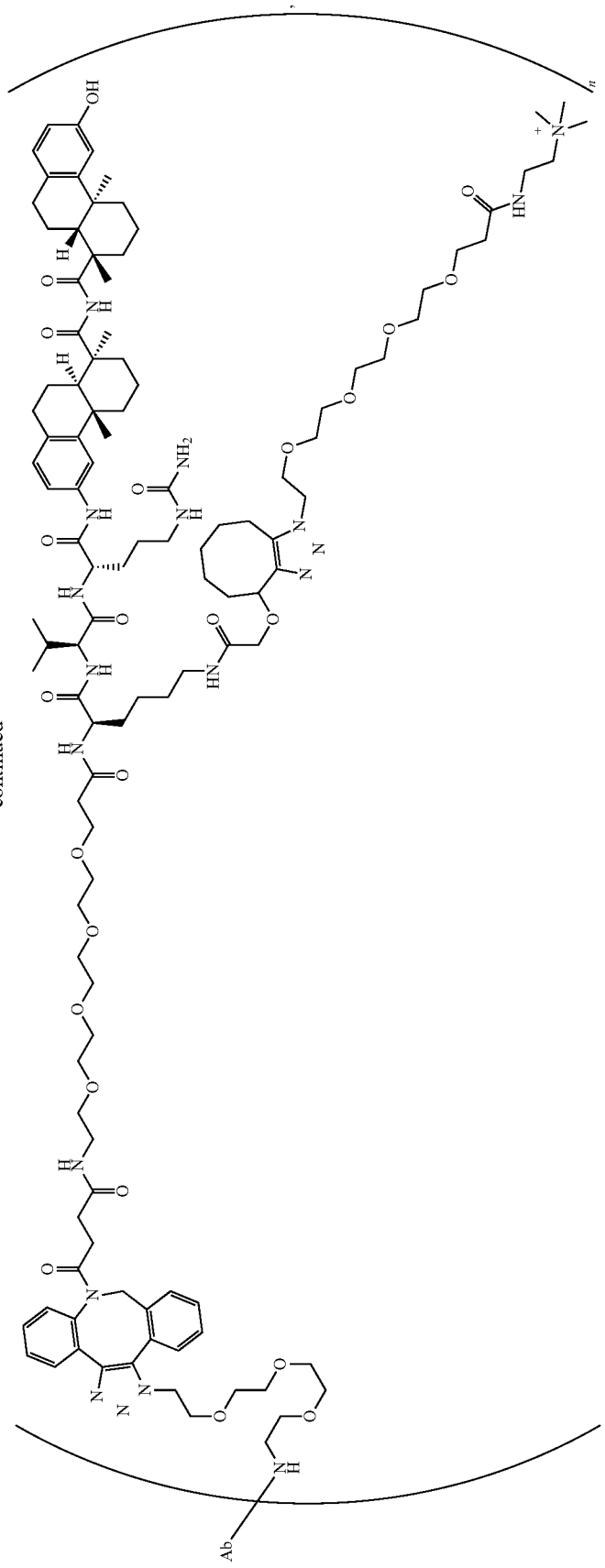

-continued
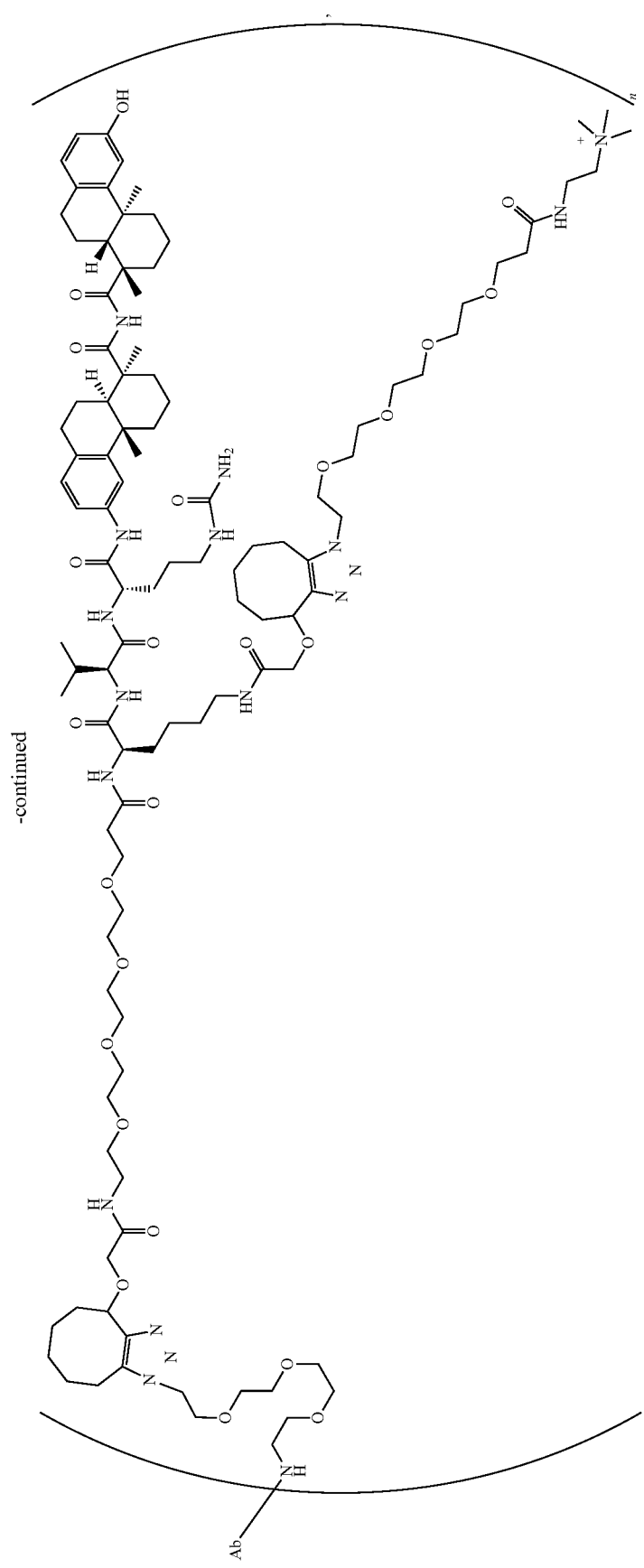

1397 1398
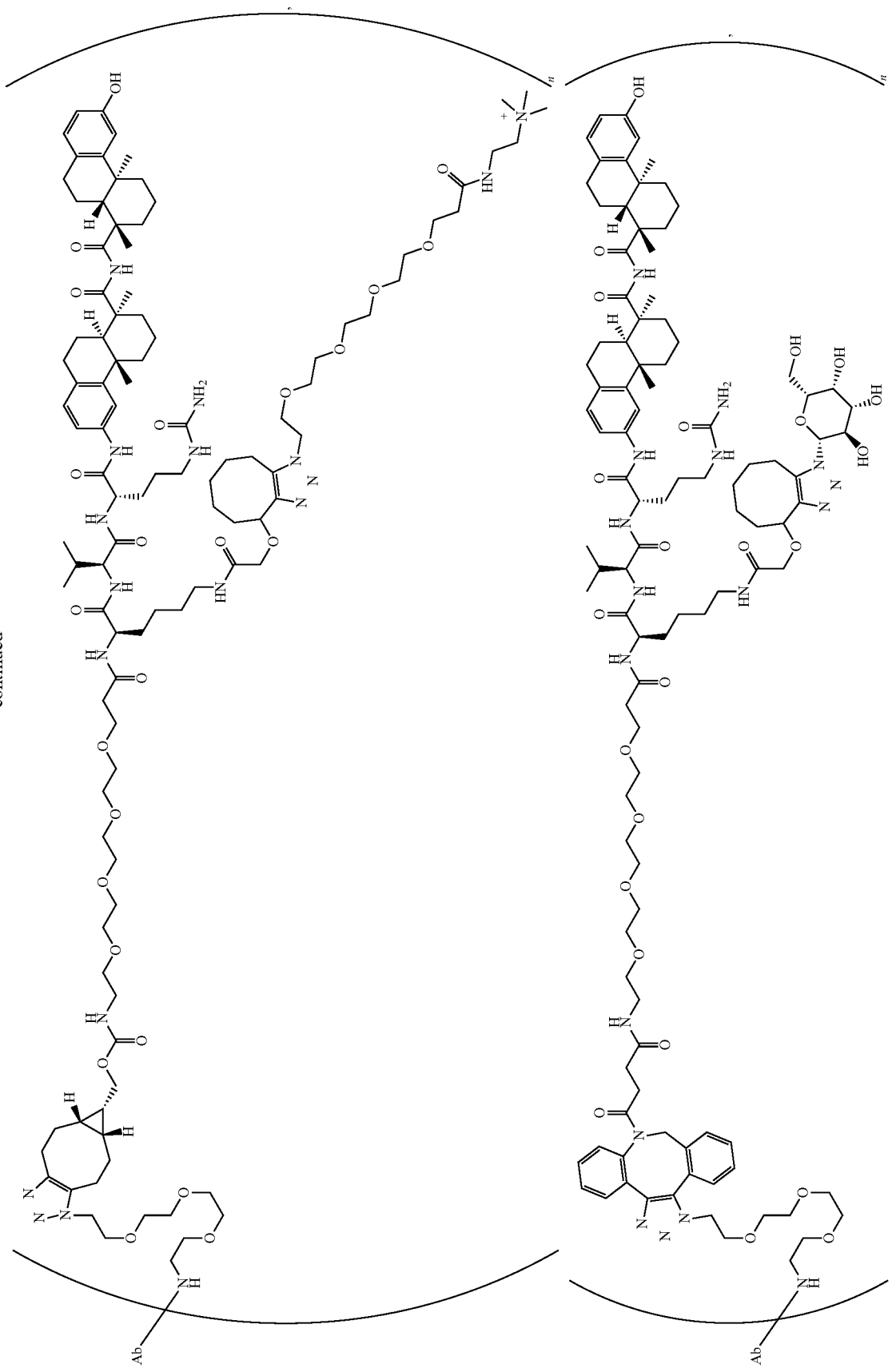

1399 1400
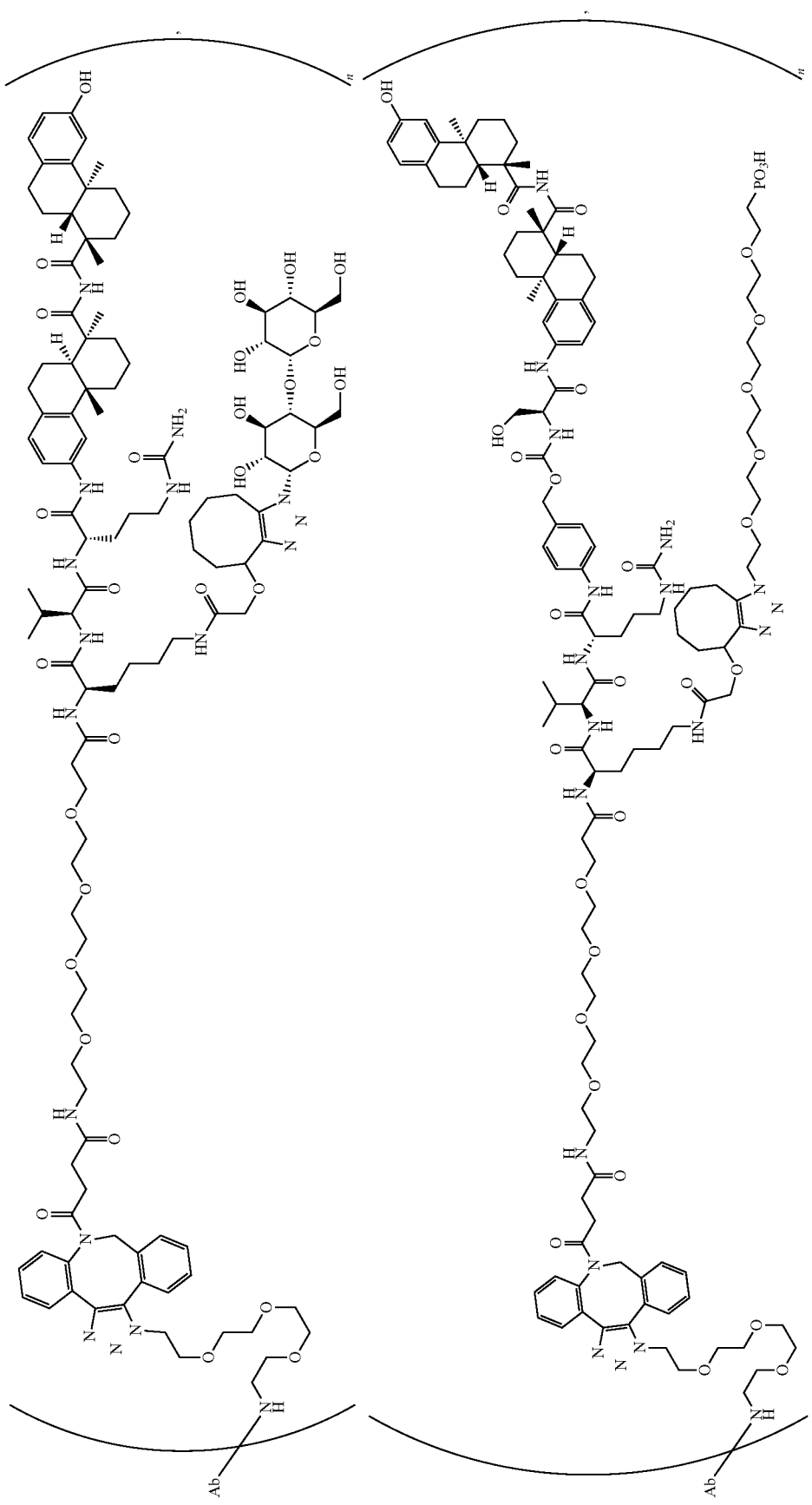
-continued 1401 1402
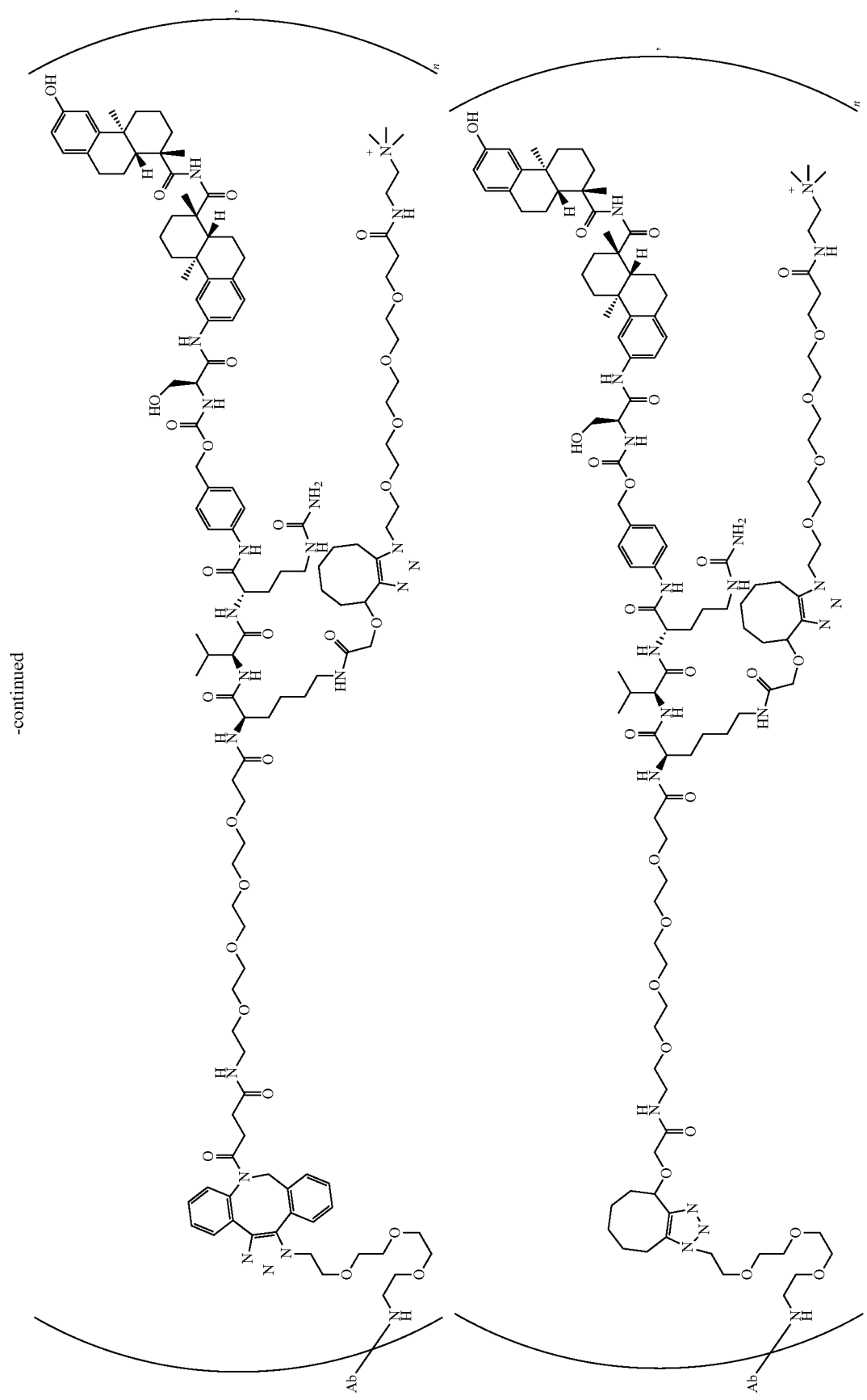

1403 1404
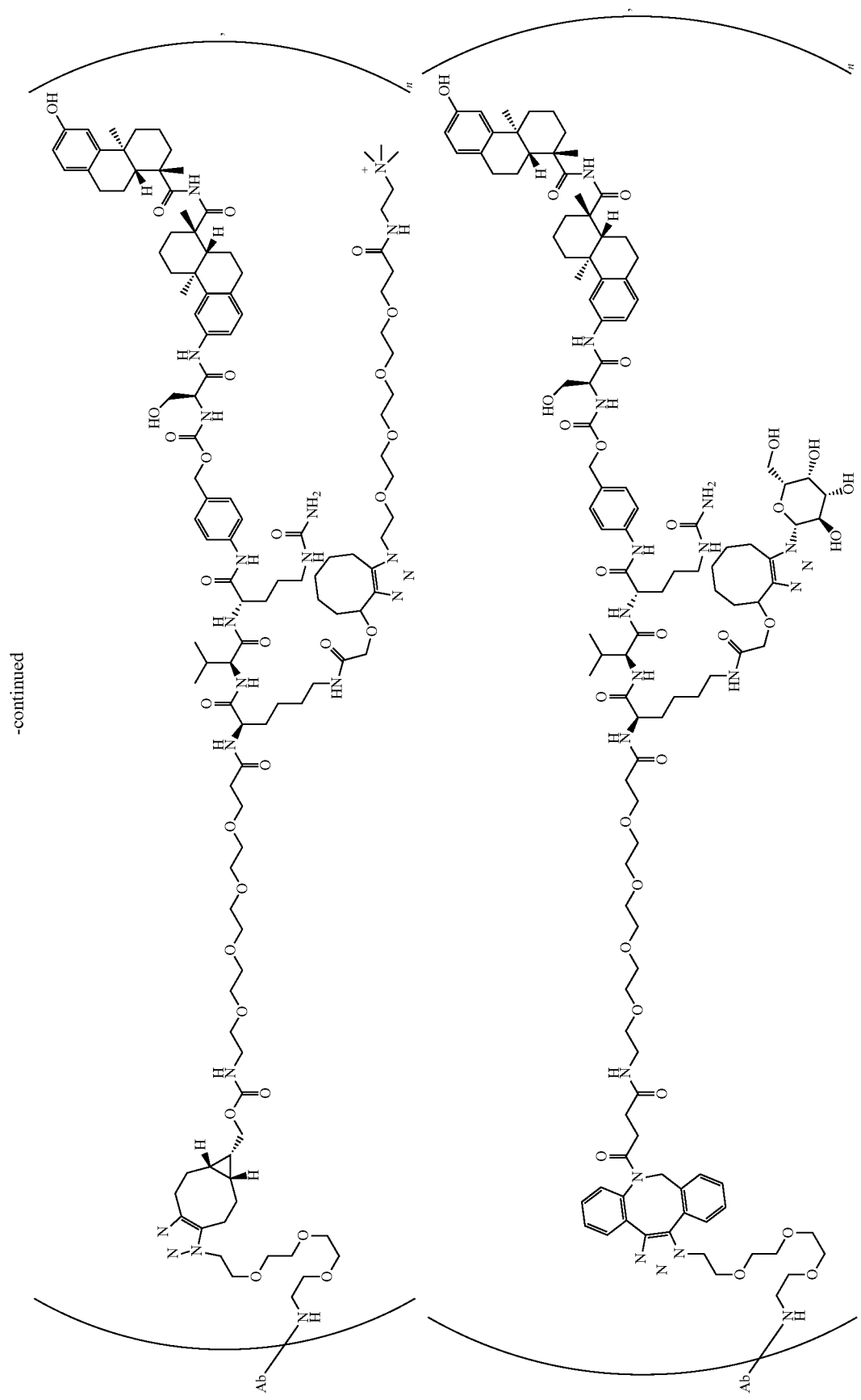

1405 1406
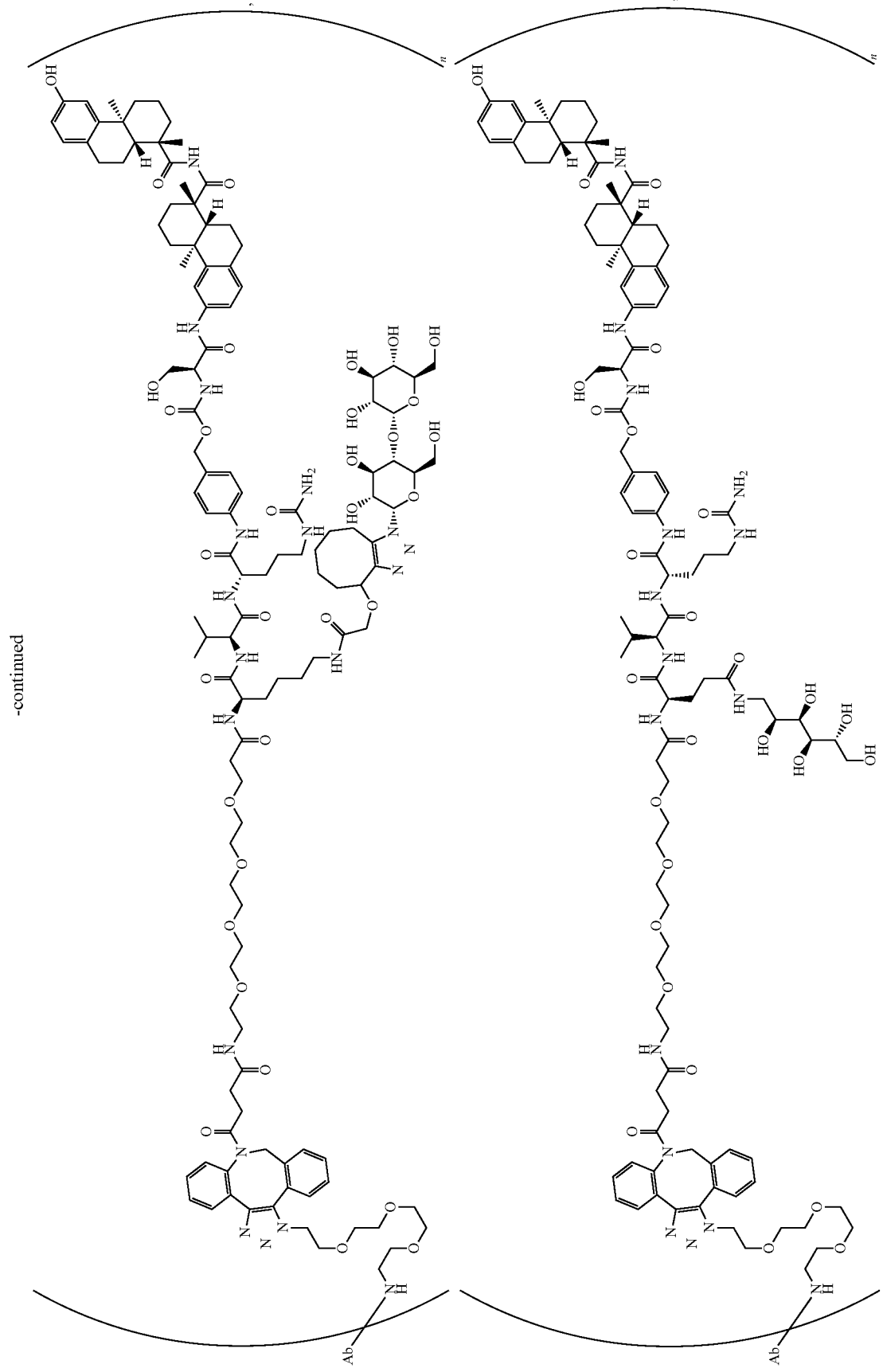

1407 1408
-continued
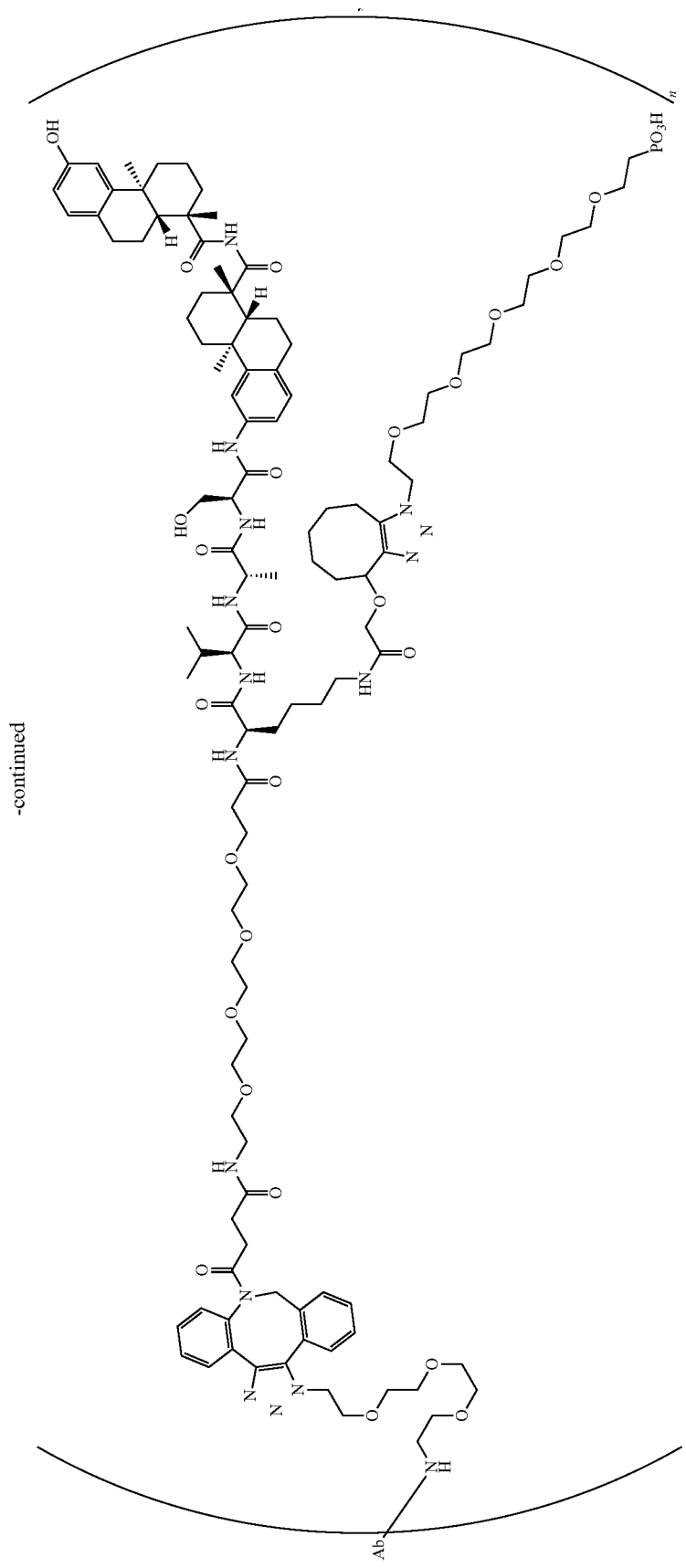

-continued
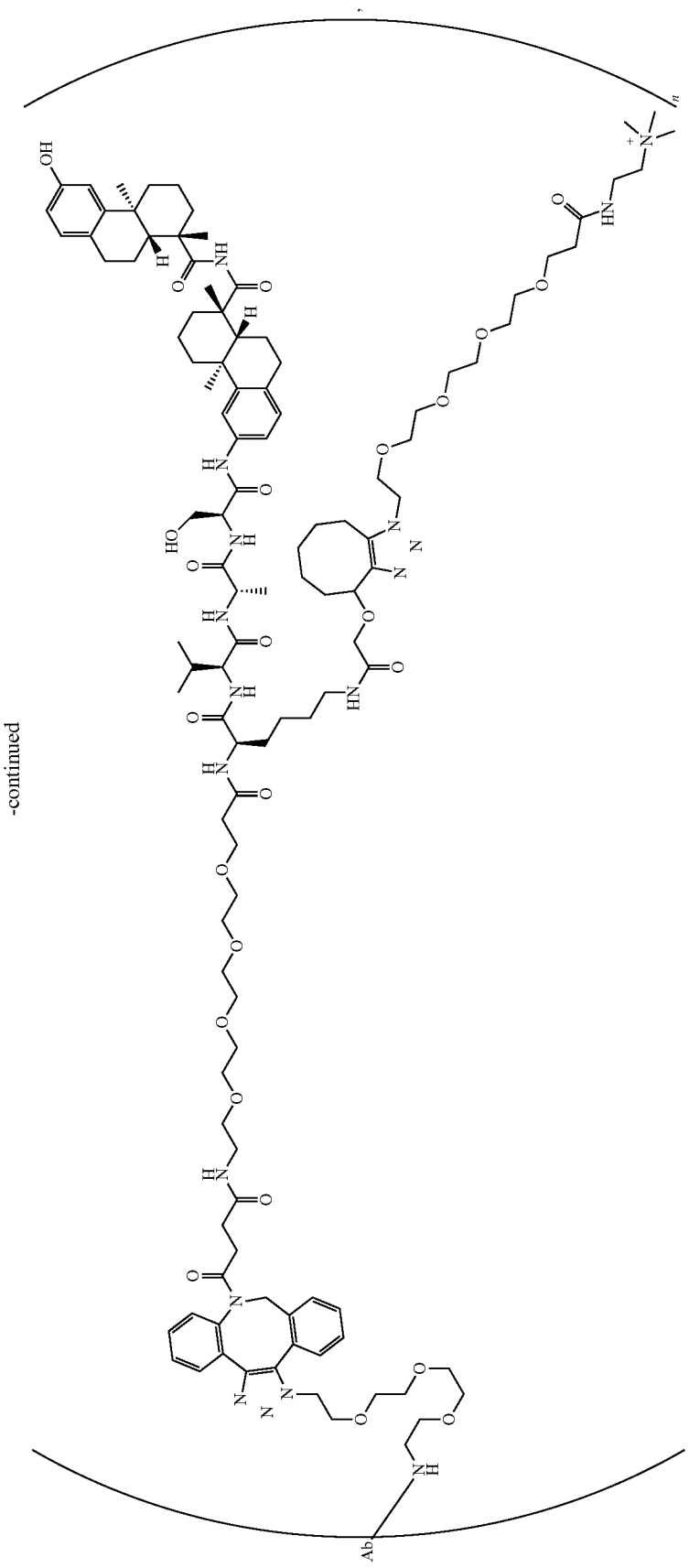

1411 1412
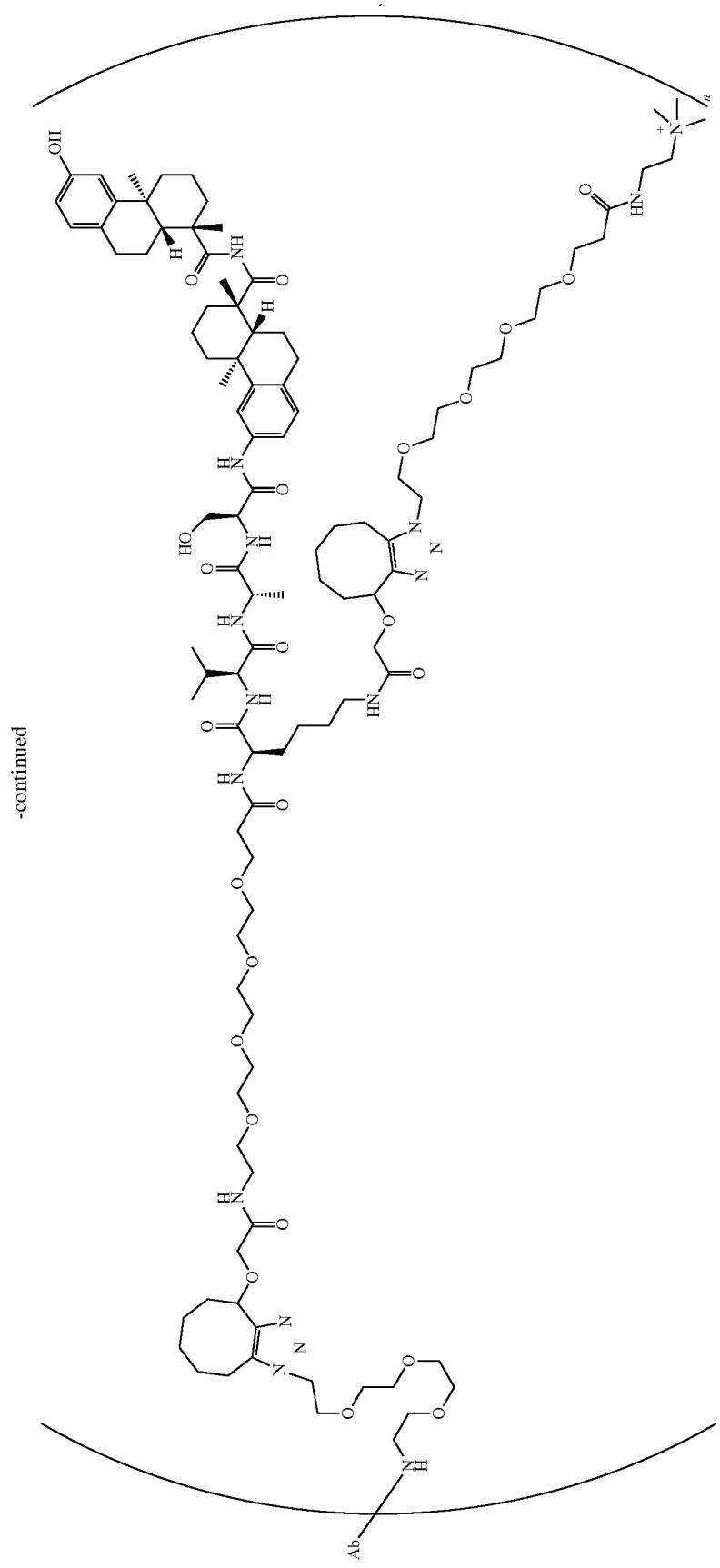

1413   1414
-continued
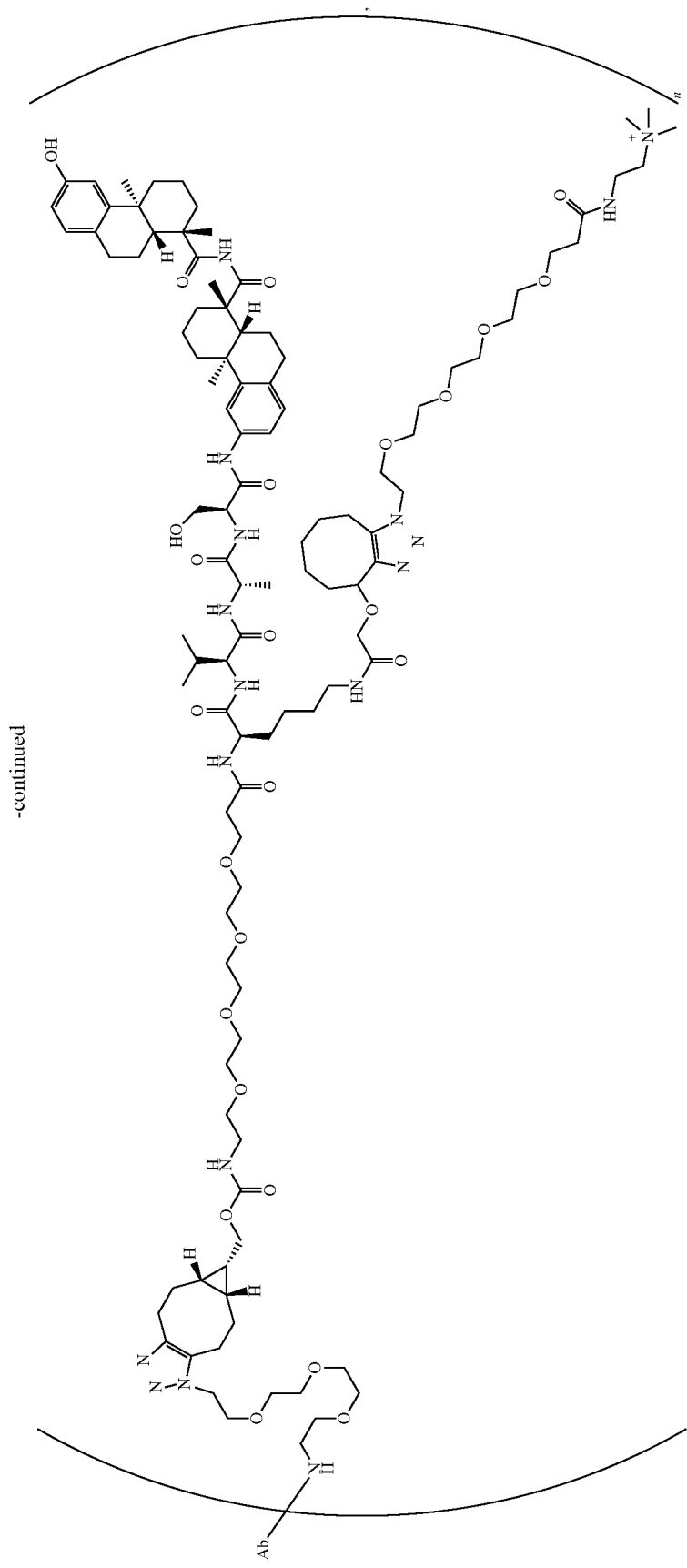

1415 1416
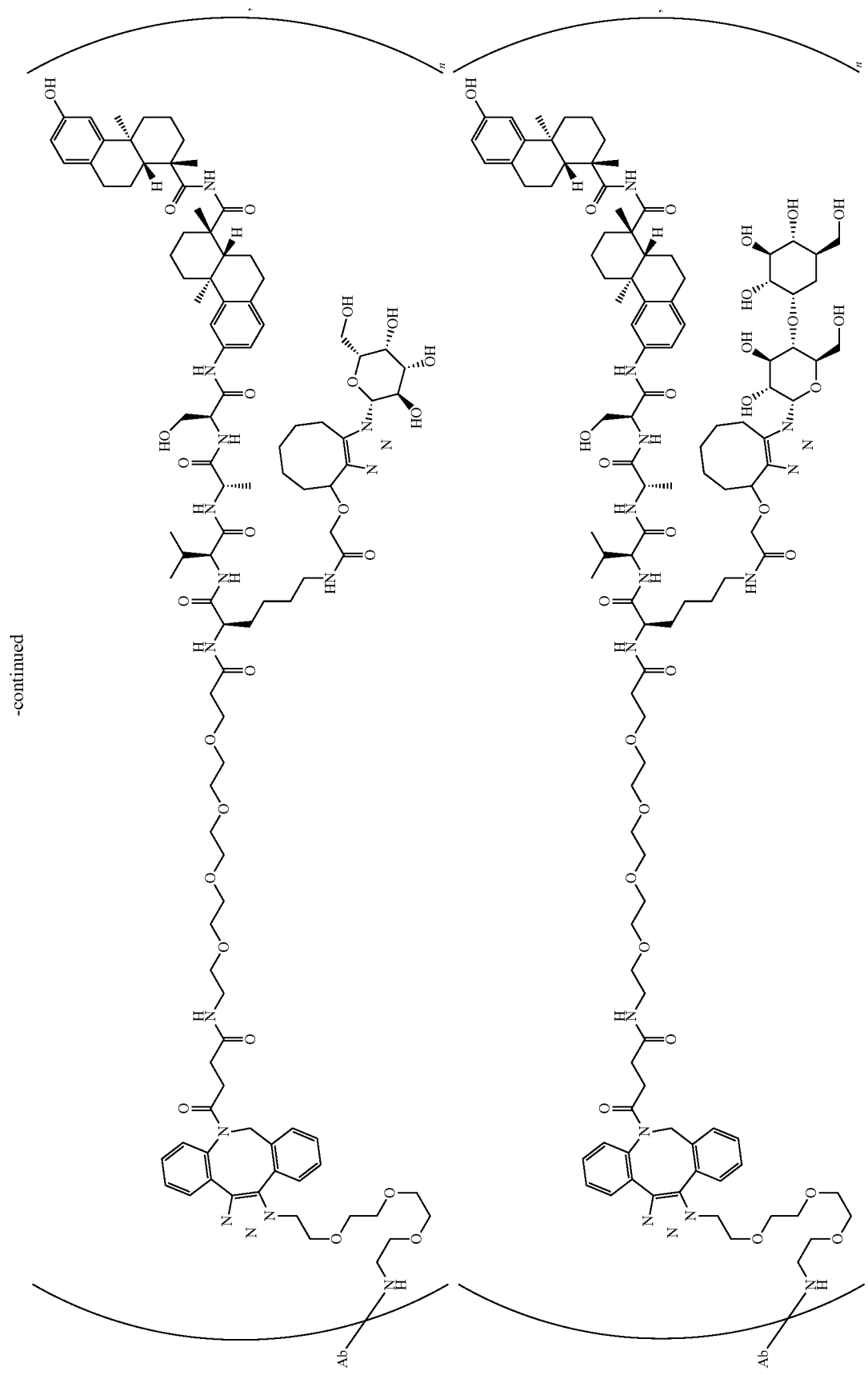

1417 1418
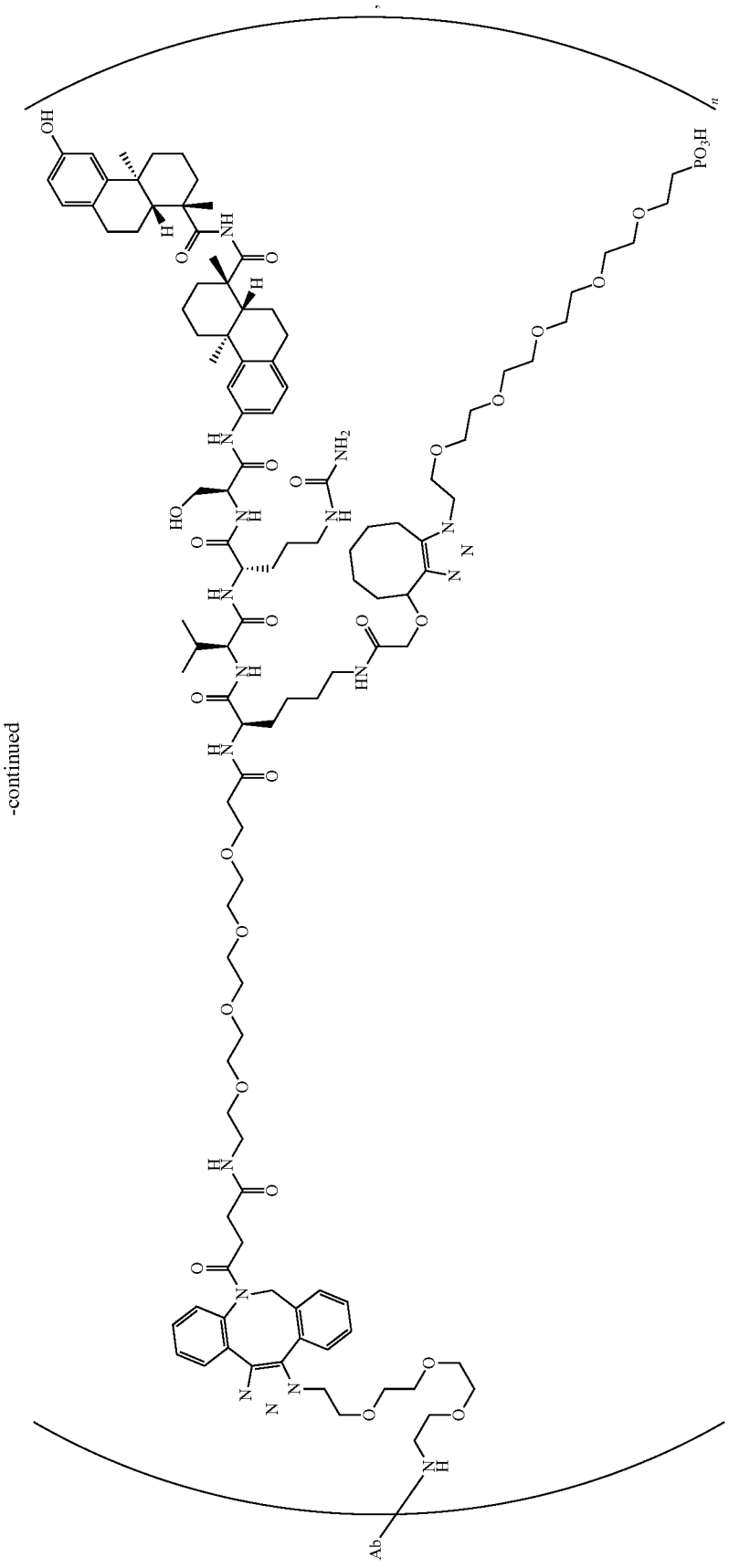

1419 1420
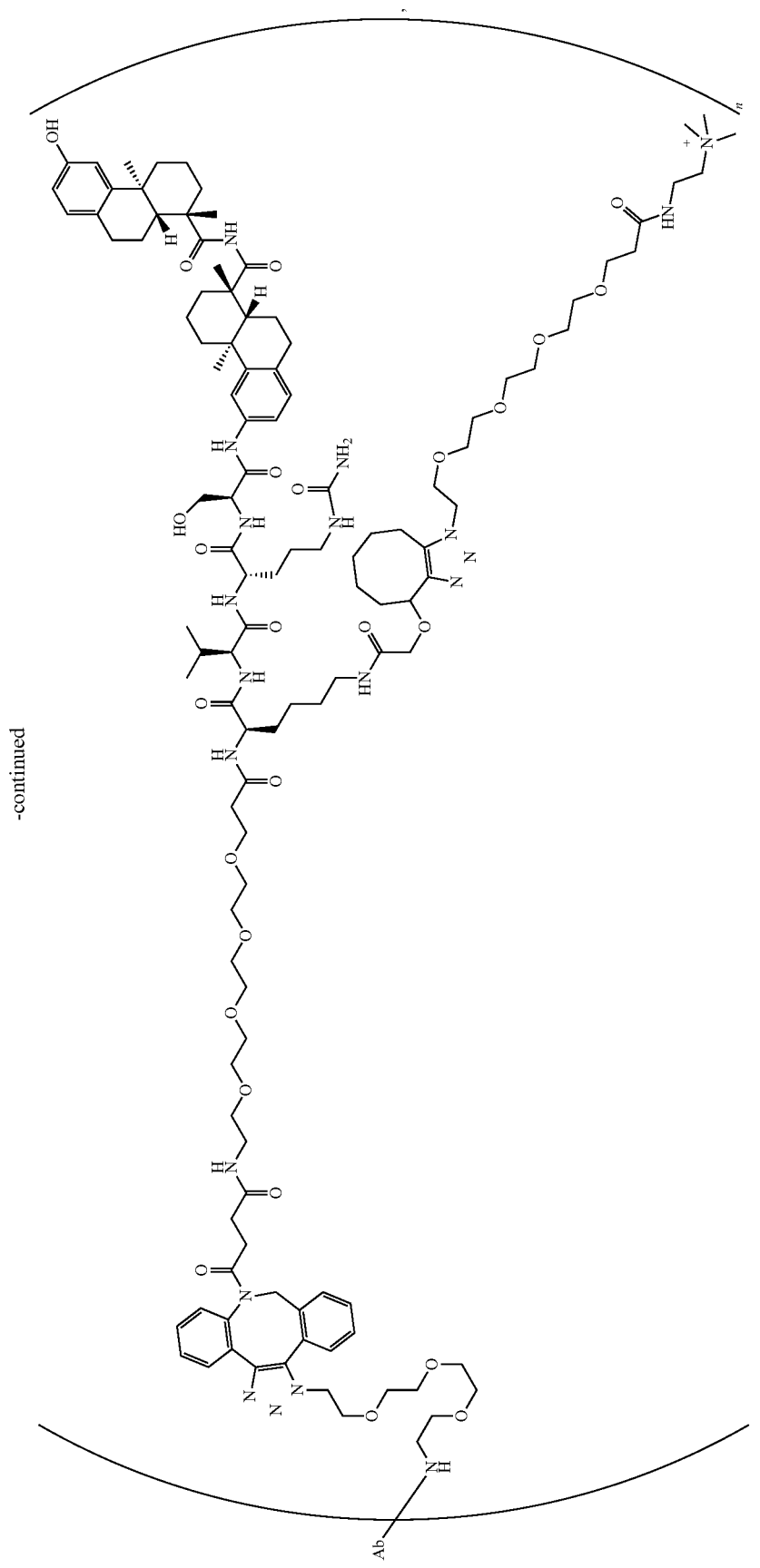

1421 1422
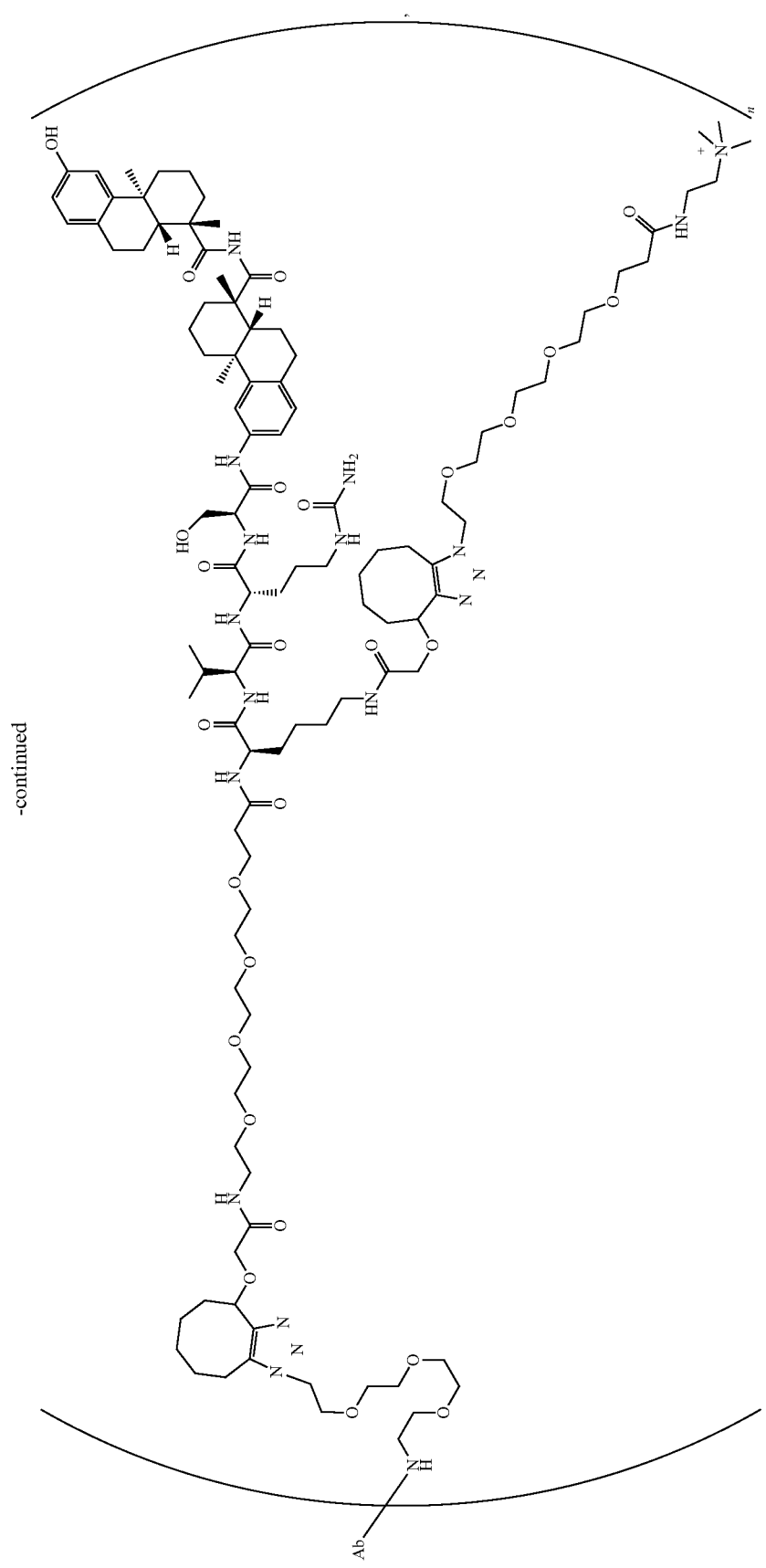

1423 1424
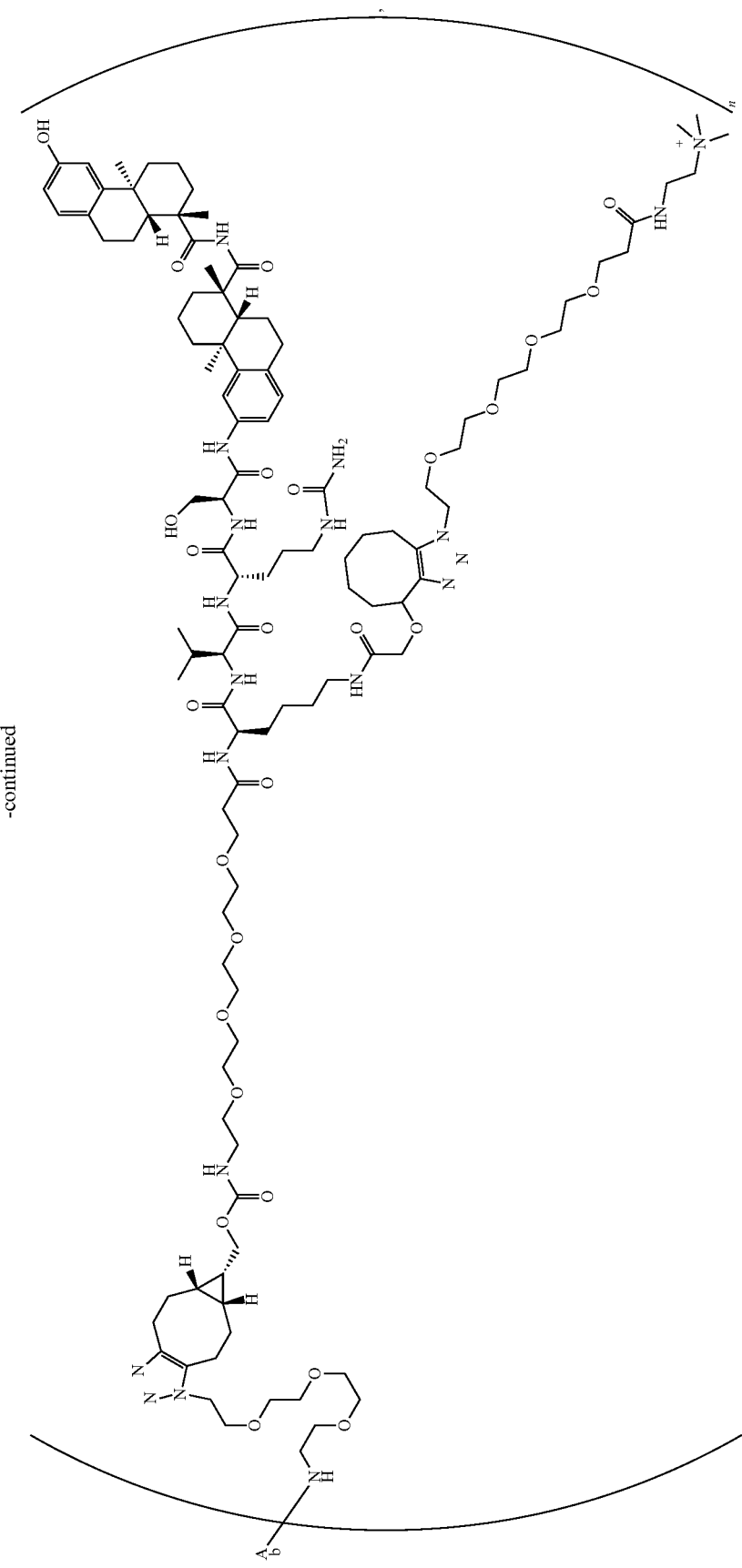
-continued

-continued
1425 1426
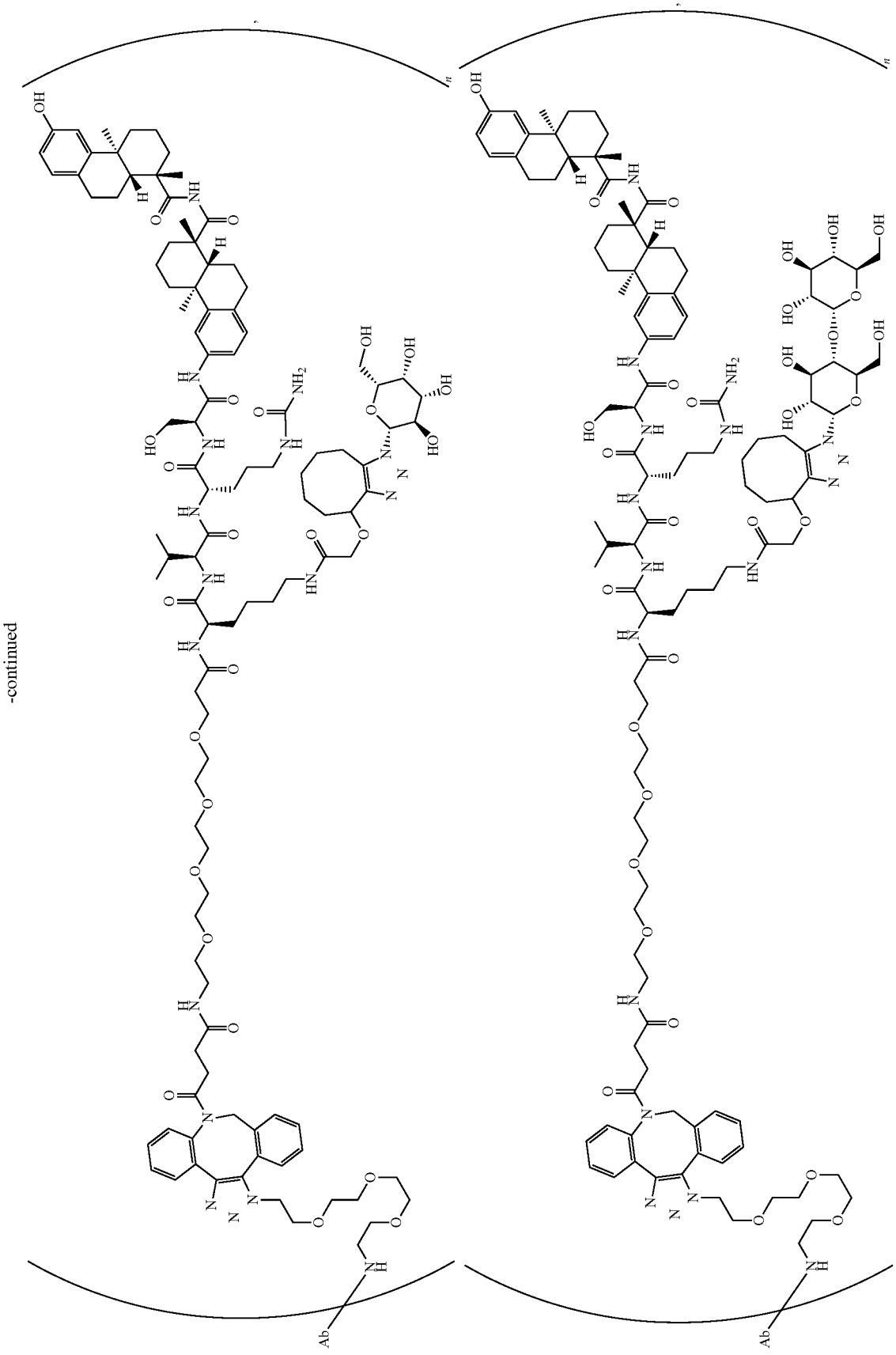

or a stereoisomeric form thereof, or a regioisomer thereof, or a mixture of regioisomers thereof, wherein each Ab is an antibody, or an antigen-binding fragment thereof; and subscript n is an integer from 1 to 30.

20. A pharmaceutical composition comprising a compound of claim 1, or pharmaceutically acceptable salt thereof, and a pharmaceutically acceptable excipient.

21. The compound of claim 1, wherein BA is an antigen binding fragment thereof.

22. The compound of claim 13, wherein the antibody is the anti HER2 antibody.

23. The compound of claim 1, wherein p is 1.

24. The compound of claim 1, wherein $AA^1$ is L-lysine.

25. The compound of claim 1, wherein $AA^1$ is D-lysine.

26. The compound of claim 1, wherein $AA^1$ is L-glutamic acid.

27. The compound of claim 1, wherein $AA^1$ is D-glutamic acid.

28. The compound of claim 1, wherein $AA^1$ is L-aspartic acid.

29. The compound of claim 1, wherein $AA^1$ is D-aspartic acid.

* * * * *